US011447762B2

(12) United States Patent
Alekseyev et al.

(10) Patent No.: US 11,447,762 B2
(45) Date of Patent: Sep. 20, 2022

(54) BACILLUS LENTUS SUBTILISIN PROTEASE VARIANTS AND COMPOSITIONS COMPRISING THE SAME

(71) Applicant: DANISCO US INC, Palo Alto, CA (US)

(72) Inventors: Viktor Yuryevich Alekseyev, Palo Alto, CA (US); Neelam S. Amin, Palo Alto, CA (US); Luis G. Cascao-Pereira, Redwood City, CA (US); Katherine D. Collier, Loomis, CA (US); David A. Estell, Palo Alto, CA (US); James T. Kellis, Jr., Palo Alto, CA (US); Ayrookaran J. Poulose, Belmont, CA (US); Philip F. Souter, Newcastle upon Tyne (GB); Glenn S. Ward, Newcastle upon Tyne (GB); Katherine Augustyn, Palo Alto, CA (US); Jian Yao, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 16/030,994

(22) Filed: Jul. 10, 2018

(65) Prior Publication Data
US 2019/0136217 A1    May 9, 2019

Related U.S. Application Data

(63) Continuation of application No. 15/831,913, filed on Dec. 5, 2017, now abandoned, which is a continuation of application No. 13/696,512, filed as application No. PCT/US2011/035389 on May 5, 2011, now abandoned.

(60) Provisional application No. 61/332,006, filed on May 6, 2010, provisional application No. 61/332,151, filed on May 6, 2010, provisional application No. 61/392,188, filed on Oct. 12, 2010, provisional application No. 61/392,364, filed on Oct. 12, 2010.

(51) Int. Cl.
*C12N 9/54* (2006.01)
*C11D 3/386* (2006.01)

(52) U.S. Cl.
CPC ............. *C12N 9/54* (2013.01); *C11D 3/386* (2013.01); *C11D 3/38681* (2013.01)

(58) Field of Classification Search
CPC ................... C11D 3/386; C12Y 304/21062
USPC ........................................................ 435/221
See application file for complete search history.

(56) References Cited

U.S. PATENT DOCUMENTS

| 4,302,544 A | 11/1981 | Young et al. |
| 4,430,243 A | 2/1984 | Bragg |
| 4,435,307 A | 3/1984 | Barbesgaard et al. |
| 4,450,235 A | 5/1984 | Dean et al. |
| 4,515,705 A | 5/1985 | Moeddel |
| 4,515,707 A | 5/1985 | Brooks |
| 4,537,706 A | 8/1985 | Severson, Jr. |
| 4,550,862 A | 11/1985 | Barker et al. |
| 4,561,998 A | 12/1985 | Wertz et al. |
| 4,597,898 A | 7/1986 | Vander Meer |
| 4,683,195 A | 7/1987 | Mullis et al. |
| 4,683,202 A | 7/1987 | Mullis |
| 4,760,025 A | 7/1988 | Estell et al. |
| 4,765,916 A | 8/1988 | Ogar, Jr. et al. |
| 4,810,410 A | 3/1989 | Diakun et al. |
| 4,965,188 A | 10/1990 | Mullis et al. |
| 4,968,451 A | 11/1990 | Scheibel et al. |
| 4,972,017 A | 11/1990 | Smith et al. |
| 4,977,252 A | 12/1990 | Chiu |
| 5,227,084 A | 7/1993 | Martens et al. |
| 5,264,366 A | 11/1993 | Ferrari et al. |
| RE34,606 E | 5/1994 | Estell et al. |
| 5,340,735 A | 8/1994 | Christianson et al. |
| 5,352,603 A | 10/1994 | Vetter et al. |
| 5,354,559 A | 10/1994 | Morehouse |
| 5,427,936 A | 6/1995 | Moeller et al. |
| 5,486,303 A | 1/1996 | Capeci et al. |
| 5,489,392 A | 2/1996 | Capeci et al. |
| 5,500,364 A | 3/1996 | Christianson et al. |
| 5,516,448 A | 5/1996 | Capeci et al. |
| 5,565,145 A | 10/1996 | Watson et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,595,967 A | 1/1997 | Miracle et al. |
| 5,597,936 A | 1/1997 | Perkins et al. |
| 5,646,101 A | 7/1997 | MacBeath |

(Continued)

FOREIGN PATENT DOCUMENTS

| CA | 2162459 | 11/1994 |
| CA | 2162460 | 11/1994 |

(Continued)

OTHER PUBLICATIONS

U.S. Appl. No. 07/573,802, filed Aug. 29, 1990, Vetter et al.

(Continued)

*Primary Examiner* — Sheridan Swope

(57) ABSTRACT

The present invention provides serine protease variants produced there from. Specifically, the present invention provides serine protease variants having one or more substitutions as compared to a reference serine protease. In addition, the present invention provides compositions comprising these serine protease variants. In some embodiments, the present invention provides cleaning compositions comprising at least one of these serine protease variants.

14 Claims, 4 Drawing Sheets

Specification includes a Sequence Listing.

(56) References Cited

U.S. PATENT DOCUMENTS

| | | | |
|---|---|---|---|
| 5,686,014 | A | 11/1997 | Baillely et al. |
| 5,691,297 | A | 11/1997 | Nassano et al. |
| 5,695,679 | A | 12/1997 | Christie et al. |
| 5,698,504 | A | 12/1997 | Christie et al. |
| 5,700,676 | A | 12/1997 | Bott et al. |
| 5,705,464 | A | 1/1998 | Scheper et al. |
| 5,710,115 | A | 1/1998 | Patel et al. |
| 5,801,039 | A | 9/1998 | Maurer et al. |
| 5,855,625 | A | 1/1999 | Maurer et al. |
| 5,874,276 | A | 2/1999 | Fowler et al. |
| 5,879,584 | A | 3/1999 | Bianchetti et al. |
| 5,929,022 | A | 7/1999 | Velazquez |
| 5,935,826 | A | 8/1999 | Blue et al. |
| 5,955,340 | A | 9/1999 | Bott et al. |
| 6,225,464 | B1 | 5/2001 | Hiler, II et al. |
| 6,294,514 | B1 | 9/2001 | Welling |
| 6,306,812 | B1 | 10/2001 | Perkins et al. |
| 6,312,936 | B1 | 11/2001 | Poulose et al. |
| 6,326,348 | B1 | 12/2001 | Vinson et al. |
| 6,376,445 | B1 | 4/2002 | Bettiol et al. |
| 6,376,450 | B1 | 4/2002 | Ghosh et al. |
| 6,440,991 | B1 | 8/2002 | Zhu et al. |
| 6,472,184 | B1 | 10/2002 | Hegemann |
| 6,482,628 | B1 | 11/2002 | Poulose et al. |
| 6,509,021 | B1 | 1/2003 | Weiss et al. |
| 6,566,112 | B2 | 5/2003 | Jones et al. |
| 6,566,114 | B1 | 5/2003 | Kaupinnen et al. |
| 6,602,842 | B2 | 8/2003 | Cuperus et al. |
| 6,605,458 | B1 | 8/2003 | Hansen et al. |
| 6,610,642 | B2 | 8/2003 | Ghosh et al. |
| 8,224,578 | B2 | 7/2012 | Raab et al. |
| 2003/0228995 | A1 | 12/2003 | Poulose et al. |
| 2005/0202535 | A1 | 9/2005 | Collier et al. |
| 2006/0089284 | A1 | 4/2006 | Miracle et al. |
| 2008/0090747 | A1 | 4/2008 | Augustinus et al. |
| 2010/0192985 | A1 | 8/2010 | Aehle et al. |

FOREIGN PATENT DOCUMENTS

| | | |
|---|---|---|
| EP | 0134048 | 3/1985 |
| EP | 0200362 | 12/1986 |
| EP | 0201184 | 12/1986 |
| EP | 0214761 | 3/1987 |
| EP | 0218272 | 4/1987 |
| EP | 0238023 | 9/1987 |
| EP | 0258068 | 3/1988 |
| EP | 0305216 | 3/1989 |
| EP | 0331376 | 9/1989 |
| EP | 0415296 | 8/1990 |
| EP | 0495257 | 7/1992 |
| EP | 2100947 | 9/2009 |
| EP | 2100949 | 9/2009 |
| GB | 1296839 | 11/1972 |
| GB | 1372034 | 10/1974 |
| JP | 64/074992 | 3/1989 |
| WO | WO88/09367 | 12/1988 |
| WO | WO89/06270 | 7/1989 |
| WO | WO90/09446 | 8/1990 |
| WO | WO91/00345 | 1/1991 |
| WO | WO92/21760 | 12/1992 |
| WO | WO94/12621 | 6/1994 |
| WO | WO95/01426 | 1/1995 |
| WO | WO95/23221 | 8/1995 |
| WO | WO97/11151 | 3/1997 |
| WO | WO99/06521 | 2/1999 |
| WO | WO99/20726 | 4/1999 |
| WO | WO99/20727 | 4/1999 |
| WO | WO99/20771 | 4/1999 |
| WO | WO99/34011 | 7/1999 |
| WO | WO00/24924 | 5/2000 |
| WO | WO00/32601 | 6/2000 |
| WO | WO02/014490 | 2/2002 |
| WO | WO02/102955 | 12/2002 |
| WO | WO04/041979 | 5/2004 |
| WO | WO04/111178 | 12/2004 |
| WO | WO05/056782 | 6/2005 |
| WO | WO07/006305 | 1/2007 |
| WO | WO07/044993 | 4/2007 |
| WO | WO07/145964 | 12/2007 |
| WO | WO09/149144 | 12/2009 |
| WO | WO09/149200 | 12/2009 |
| WO | WO/2011/072099 | 6/2011 |
| WO | WO11/140364 | 11/2011 |

OTHER PUBLICATIONS

Altschul, S.F., et al., "Basic Local Alignment Search Tool." *J. Mol. Biol.* 215: 403-410, 1990.

Altschul, S.F., et al., "Basic Local Alignment Statistics." *Meth. Enzymol.* 266: 460-480, 1996.

Altschul, S.F., et al., "Gapped BLAST and PSI-BLAST: a new generation of protein database search programs." *Nucleic Acids Res.* 25(17): 3389-3402, 1997.

Arigoni, F., et al., "The SpoIIE phosphatase, the sporulation septum and the establishment of forespore-specific transcription in *Bacillus subtilis*: a reassessment." *Mol. Microbiol.* 31: 1407-1415, 1999.

Babé, L., et al., "Heterologous expression of human granzyme K in *Bacillus subtills* and characterization of its hydrolytic activity In vitro." *Biotech. Appl. Biochem.* 27: 117-124, 1998.

Beaucage, S.L., et al. "Deoxynucleoside Phosphoramioites—A New Class of Key Intermediates For Deoxypolynucleotide Synthesis." *Tetrahedron Letters* 22: 1859-69, 1981.

Bittker, J.A., et al., "Nucleic acid evolution and minimization by nonhomologous random recombination." *Nat. Biotechnol.* 20: 1024-1029, 2002.

Bittker, J.A., et al., "Directed evolution of protein enzymes using nonhomologous random recombination." *Proc Natl. Acad. Sci. USA* 101: 7011-7016, 2004.

Bron, S., "Plasmids." In *Molecular Biological Methods for Bacillus*, Chapter 3, pp. 140-145, Harwood, C.R., et al. (eds.), John Wiley & Sons; Chichester, England; 1990.

Caldwell, R., et al., "Correlation between *Bacillus subtilis* scoC Phenotype and Gene Expression Determined Using Microarrays for Transcriptome Analysis." *J. Bacteriol.* 183: 7329-7340, 2001.

Chang, S., et al., "High Frequency Transformation of *Bacillus subtilis* Protoplasts by Plasmid DNA." *Mol. Gen. Genet.* 168: 111-115, 1979.

Christianson, T., et al., "Peptide Mapping of Subtilisins as a Practical Tool for Locating Protein Sequence Errors during Extensive Protein Engineering Projects." *Anal. Biochem.* 223: 119-129, 1994.

Coco, W.M., et al., "Growth factor engineering by degenerate homoduplex gene family recombination." *Nat. Biotechnol.* 20: 1246-1250, 2002.

Contente, S., et al., "Marker Rescue Transformation by Linear Plasmid DNA in *Bacillus subtilis.*" *Plasmid* 2: 555-571, 1979.

Dartois, V., et al., "Cloning, nucleotide sequence and expression in *Escherichia coli* of a lipase gene from Bacillus subtilis 168." *Biochem. Biophys. Acta* 1131: 253-260, 1992.

Del Mar, E.G., et al., "A Sensitive New Substrate for Chymotrypsin." *Anal. Biochem.* 99: 316-320, 1979.

Devereux, J., et al., "A comprehensive set of sequence analysis programs for the VAX." *Nucl. Acid Res.* 12: 387-395, 1984.

Fahnestock, S.R., et al., "Expression of the Staphylococcal Protein A Gene in Bacillus subtilis by Gene Fusions Utilizing the Promoter from a Bacillus amyloliquefaciens α-Amylase Gene."*J. Bacteriol.* 165: 796-804, 1986.

Feng. D.-F., "Progressive Sequence Alignment as a Prerequisite to Correct Phylogenetic Trees." *J. Mol. Evol.* 25: 351-360, 1987.

Ferrari, E., et al., "Genetics." In Bacillus, Hardwood (ed.), Plenum Publishing Corp., pp. 57-72, 1989.

Fisher, H.M., et al., "Introduction of plasmid pC194 into *Bacillus thuringiensis* by protoplast transformation and plasmid transfer." *Arch. Microbiol.* 139: 213-217, 1981.

Glaser, S.M., et al., "Antibody Engineering By Codon-Based Mutagenesis in a Filamentous Phage Vector System." *J. Immunol.* 149(12): 3903-3913, 1992.

(56) References Cited

OTHER PUBLICATIONS

Haima, P., et al., "Novel plasmid marker rescue transformation system for molecular cloning in *Bacillus subtilis* enabling direct selection of recombinants." *Mol. Gen. Genet.* 223: 185-191, 1990.
Haas, M.J., et al., "Cloning, expression and characterization of a cDNA encoding a lipase from *Rhizopus delemar.*" *Gene* 109: 117-113, 1991.
Henikoff, S., et al., "Amino acid substitution matrices from protein blocks." *Proc. Natl. Acad. Sci. USA* 89: 10915-10919, 1992.
Higgins, D.G., et al., "Fast and sensitive multiple sequence alignments on a microcomputer." *CABIOS* 5: 151-153, 1989.
Hoch, J.A., et al., "Chromosomal Location of Pleiotropic Negative Sporulation Mutations in *Bacillus subtilis.*" *Genetics* 73: 215-228, 1973.
Hoch, J.A., et al., "Transformation and Transduction in Recombination—Defective Mutants of *Bacillus subtilis*" *J. Bacteriol.* 93: 1925-1937, 1967.
Holubova, I., et al., "Transfer of Liposome-Encapsulated Plasmid DNA to *Bacillus subtilis* Protoplasts and Calcium-Treated *Escherichia coli* Cells." *Folia Microbiol.* 30: 97-109, 1985.
Hsia, C.Y., et al., "Active-Site Titration of Serine Proteases Using a Fluoride Ion Selective Electrode and Sulfonyl Fluoride Inhibitors." *Anal. Biochem.* 242: 221-227, 1999.
Itakura, K., et al., "Synthesis and Use of Synthetic Oligonucleotides." *Ann. Rev. Biochem.* 53: 323-326, 1984.
Itakura, K., et al., "Expression in *Escherichia coli* of a Chemically Synthesized Gene for the Hormone Somatostatin." *Science* 198: 1056-1063, 1977.
Kalisz, "Microbial Proteinases." In *Advances in Biochemical Engineering/Biotechnology*, vol. 36, Fiechter, A. (ed.), pp. 2-65, 1988.
Karlin, S., et al., "Applications and statistics for multiple high-scoring segment s in molecular sequences." *Proc. Natl. Acad. Sci. USA* 90: 5873-5877, 1993.
Kroll, D.J., et al., "A Multifunctional Prokaryotic Protein Expression System: Overproduction, Affinity Purjfication, and Selective Detection." *DNA Cell Biol.* 12(5) :441-453, 1993.
Kugimiya, W., et al., "Cloning and Sequence Analysis of cDNA encoding *Rhizopus niveus* Lipase." *Biosci. Biotech. Biochem.* 56(5): 716-719, 1992.
Lutz, S., et al. "Creating multiple-crossover DNA libraries independent of sequence identity." *Proc. Natl. Acad. Sci. USA* 98: 11248-11253, 2001.
Maddox, D.E., et al., "Elevated Serum Levels in Human Pregnancy of a Molecule Immunochemically Similar to Eosinophil Granule Major Basic Protein." *J. Exp. Med.* 158: 1211-1226, 1983.
Mann, S.P., et al., "Transformation of *Bacillus* Spp.: an Examination of the Transformation of Bacillus Protoplast by Plasmids pUB 110 and pHV33." *Current Microbiol.* 13: 191-195, 1986.
Matthes, H.W.D., et al., "Simultaneous rapid chemical synthesis of over one hundred oligonucleotides on a microscale." *EMBO J.* 3(4): 801-805, 1984.
McDonald, K.O., et al., "Plasmid Transformation of *Bacillus sphaericus* 1593." *J. Gen. Microbiol.* 130: 203-208, 1984.
McKenzie, T., et al., "The Nucleotide Sequence of pUB110: Some Salient Features in Relation to Replication and Its Regulation." *Plasmid* 15: 93-103, 1986.
Msadek, T., et al., "Signal Transduction Pathway Controlling Synthesis of a Class of Degradative Enzymes in *Bacillus subtilis*: Expression of the Regulatory Genes and Analysis of Mutations in degS and deqU." *J. Bacteriol.* 172(2): 824-834, 1990.
Needleman, S.B., et al., "A General Method Applicable to the Search for Similarities in the Amino Add Sequence of Two Proteins." *J. Mol. Biol.* 48: 443-453, 1970.
Neidhardt, F.C., et al., "Culture Medium for Enterobacteria." *J. Bacteriol.*, 119: 736-747, 1974.
Ness, J.E., et al., "Synthetic shuffling expands functional protein diversity by allowing amino acids to recombine independently." *Nat. Biotechnol.* 20: 1251-1255, 2002.

Olmos, J., et al., "Effects of the sinR and degtU32 (Hy) mutations on the regulation of the aprE gene in *Bacillus subtilis.*" *Mol. Gen. Genet.* 253: 562-567, 1997.
Ostermeier, M., et al., "Incremental Truncation as a Strategy in the Engineering of Novel Biocatalysts." *Bioorg. Med. Chem.* 7: 2139-2144, 1999.
Palmeros, B., et al., "A family of removable cassettes designed to obtain antibiotic-resistance-free genomic modifications of *Escherichia coli* and other bacteria." *Gene* 247: 255-264, 2000.
Palva , I., , "Molecular cloning of α-amylase gene from *Bacillus amyloliquefaciens* and its expression in *B. subtilis.*" *Gene* 19: 81-87, 1982.
Pearson, W.R., et al., "Improved tools for biological sequence comparison." *Proc. Natl. Acad. Sci. USA* 85: 2444-2448, 1988.
Perego, M., et al., "The oligopeptide transport system of *Bacillus subtilis* plays a role in the initiation of sporulation." *Mol. Microbiol.* 5(1): 173-185, 1991.
Perego, M., "Integrational Vectors for Genetic Manipulations in *Bacillus subtilis.*" In *Bacillus Subtilis and Other Gram-Positive Bacteria*; Biochemistry, Physiology and Molecular Genetics, American Society for Microbiology, Sonenshein et al., (eds.) Washington, D.C., Chapter 42, pp. 615-624, 1993.
Porath, J., "Immobilized Metal Ion Affinity Chromatography." *Protein Expr. Purif.* 3: 263-281, 1992.
Rawlings, N.D., "Evolutionary families of peptidases." *Biochem J.*, 290: 205-218, 1993.
Rawlings, N.D., et al., "MEROPS: the peptidase database." *Nucl Acids Res*, 34: D270-D272, 2006.
Saunders, C.W., et al., "Use of Chromosomal Integration in the Establishment and Expression of blaZ, a *Staphylococcus aureus* β-Lactamase Gene, in *Bacillus subtilis.*" *J. Bacteriol.* 157: 718-726, 1984.
Schimada, Y., et al., "cDNA Molecular Cloning of *Geotrichum candidum* Lipase." *J. Biochem.* 106: 383-388, 1989.
Sieber, V., et al., "Libraries of hybrid proteins from distantly related sequences." *Nat. Biotechnol.* 19: 456-460, 2001.
Smith, T.F., et al., "Comparison of Biosequences." *Adv. Appl. Math.* 2: 482-489, 1981.
Smith, M.D., et al., "Protoplast Transformation in Coryneform Bacteria and Introduction of an α-Amylase Gene from *Bacillus amyloliquefaciens* into *Brevibacterium lactofermentum.*" *Appl. Env. Microbiol.* 51: 634-639, 1986.
Stahl, M.L., et al., "Replacement of the *Bacillus subtilis* Subtilisin Structural Gene with an In Vitro-Derived Deletion Mutation." *J. Bacteriol.* 158: 411-418, 1984.
Vorobjeva, I.P., et al., "Transformation of *Bacillus megaterium* Protoplasts By Plasmid DNA." *FEMS Microbiol. Lett.* 7: 261-263, 1980.
Wang, L.-F., et al., "Expression and secretion of human atrial natriuretic α-factor in *Bacillus subtilis* using the subtilisin signal peptide." *Gene* 69: 39-47, 1988.
Ward, "Proteinases." In *Microbial Enzymes and Biotechnology*, Fogarty, W.M., (ed.), Applied Science Publishers, London, Chapter 6, pp. 251-317, 1983.
Weinrauch, Y., et al., "Plasmid Marker Rescue Transformation in *Bacillus subtilis.*"*J. Bacteriol.* 154(3): 1077-1087, 1983.
Weinrauch, Y., et al., "Plasmid Marker Rescue Transformation Proceeds by Breakage-Reunion in *Bacillus subtilis.*" *J. Bacteriol.* 169(3): 1205-1211, 1987.
Wells, J.A., et al., "Cloning, sequencing, and secretion of Bacillus amyloliquefaciens subtilisin in Bacillus subtilis." *Nucleic Acids Res.* 11: 7911-7925, 1983.
Yamaguchi, S., et al., "Cloning and structure of the mono- and diacylglycerol lipase-encoding gene from *Penicillium camembertii* U-150." *Gene* 103: 61-67, 1991.
Zha, D., et al., "Assembly of Designed Oligonucleotides as an Efficient Method for Gene Recombination: A New Tool in Directed Evolution." *Chembiochem.* 4: 34-39, 2003.
International Search Report and the Written Opinion of the International Searching Authority for PCT/US2011/035389 dated Sep. 16, 2011.
International Preliminary Report on Patentability for PCT/US2011/035389 dated Nov. 6, 2012.

(56) References Cited

OTHER PUBLICATIONS

Alekseyev et al., SEQ ID No. 1, from the sequence listing filed in 13696512 on Nov. 6, 2012.
USPTO in house BLAST alignment SEQ ID No. 1 vs SEQ Id No. 2 herein. Performed Jun. 30, 2015.
A_Geneseq_201406 database Acc# AZK14016 from WO2011072099 Basler et al., Jun. 16, 2011. Alignment with SEQ ID No. 2.
Bryan, P.N., "Protein Engineering of Subtilisin." *Biochimica et Biophysica Acta* 1543(2): 203-222, 2000.
Sif7en, R.J et al., "Subtilases: the Superfamily of Subtilisin-like Serine Proteases." *Protein Science* 6(3): 501-523, 1997.

FIG. 1

```
              10         20         30         40         50         60
BPN'   1  AQSVPYGVSQ IKAPALHSQG YTGSNVKVAV IDSGIDSSHP DLKVAGGASM VPSETNPFQD  60
GG36   1  AQSVPWGISR VQAPAAHNRG LTGSGVKVAV LDTGIS-THP DLNIRGGASF VPGEPST-QD  58
              10         20         30         40         50         49

70         80         90        100        110        120
BPN'  61  NNSHGTHVAG TVAALNNSIG VLGVAPSASL YAVKVLGADG SGQYSWIING IEWAIANNMD 120
GG36  59  GNGHGTHVAG TIAALNNSIG VLGVAPSAEL YAVKVLGASG SGSVSSIAQG LEWAGNNGMH 118
              68         78         88         98        108        118

130        140        150        160        170        180
BPN' 121  VINMSLGGPS GSAALKAAVD KAVASGVVVV AAAGNEGTSG SSSTVGYPGK YPSVIAVGAV 180
GG36 119  VANLSLGSPS PSATLEQAVN SATSRGVLVV AASGNSGAGS -----ISYPAR YANAMAVGAT 174
             128        138        148        158        164

190        200        210        220        230        240
BPN' 181  DSSNQRASFS SVGPELDVMA PGVSIQSTLP GNKYGAYNGT SMASPHVAGA AALILSKHPN 240
GG36 175  DQNNNRASFS QYGAGLDIVA PGVNVQSTYP GSTYASLNGT SMATPHVAGA AALVKQKNPS 234
             184        194        204        214        224        234

250        260        270        275
BPN' 241  WTNTQVRSSL ENTTTKLGDS FYYGKGLINV QAAAQ 275
GG36 235  WSNVQIRNHL KNTATSLGST NLYGSGLVNA EAATR 269
             244        254        264        269
```

BACILLUS LENTUS SUBTILISIN PROTEASE VARIANTS AND COMPOSITIONS COMPRISING THE SAME

CROSS-REFERENCE TO RELATED APPLICATION

This application is a Continuation of U.S. application Ser. No. 15/831,913, filed Dec. 5, 2017, which is a Continuation of U.S. application Ser. No. 13/696,512, filed Jun. 11, 2013, which is a 371 of PCT/US11/35389, filed May 5, 2011, which claims the benefit of U.S. Provisional Application Nos. 61/332,151, filed May 6, 2010; 61/332,006, filed May 6, 2010; 61/392,364, filed Oct. 12, 2010, and 61/392,188, filed Oct. 12, 2010, all of which are incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named 20180709_NB31528USCNT4_SeqLst.txt created on Jul. 9, 2018, and having a size of 33 kilobytes and is filed concurrently with the specification. The sequence listing contained in this ASCII formatted document is part of the specification and is herein incorporated by reference in its entirety.

FIELD OF THE INVENTION

The present invention provides serine protease variants. Specifically, the present invention provides serine protease variants having one or more substitutions as compared to a reference serine protease. In addition, the present invention provides compositions comprising these serine protease variants. In some embodiments, the present invention provides cleaning compositions comprising at least one of these serine protease variants.

BACKGROUND OF THE INVENTION

Although serine proteases have long been known in the art of industrial enzymes, there remains a need for engineered proteases that are suitable for particular conditions and uses.

SUMMARY OF THE INVENTION

The present invention provides serine protease variants. Specifically, the present invention provides serine protease variants having one or more substitutions as compared to a reference serine protease. In addition, the present invention provides compositions comprising these serine protease variants. In some embodiments, the present invention provides cleaning compositions comprising at least one of these serine protease variants.

The present invention provides isolated subtilisin variants, wherein the subtilisin variants are mature forms having proteolytic activity and comprise amino acid sequences comprising a combination of amino acid substitutions selected from: X1R, X2W, X2M, X2R, X2A, X2S, X3R, X4R, X4C, X4S, X8A, X9F, X9W, X9A, X10S, X10M, X10H, X10A, X12R, X12F, X14K, X14F, X14Q, X15R, X15F, X16S, X17R, X17M, X17F, X18R, X18K, X20F, X20R, X20K, X22Y, X22A, X22R, X22V, X22Q, X22W, X22L, X23F, X23S, X23A, X24W, X24R, X24H, X24F, X24Q, X24L, X25V, X25F, X25R, X26F, X27V, X27F, X27L, X27R, X28N, X28E, X28A, X29T, X30E, X31F, X33D, X33G, X33S, X34P, X35M, X36F, X36R, X36T, X38L, X38F, X38R, X40L, X40W, X40N, X40R, X40T, X40H, X42I, X43D, X43I, X43R, X43M, X43F, X43W, X43S, X43A, X45T, X46R, X48X, X50C, X51H, X51W, X51F, X52F, X52E, X52N, X55Y, X57R, X59R, X59A, X59F, X60A, X60Q, X60P, X62E, X62Q, X63I, X63V, X63T, X63P, X63D, X63M, X63H, X63Q, X63E, X63A, X63S, X64F, X64T, X68C, X68A, X69N, X69P, X69W, X69T, X71G, X72C, X74C, X75F, X75A, X75R, X75E, X76D, X78I, X78R, X78N, X79W, X79Q, X81R, X82V, X82T, X82F, X82M, X82R, X85M, X86L, X86I, X86W, X89P, X89T, X89V, X89G, X89W, X89H, X89F, X89L, X89I, X91N, X91F, X92F, X94N, X99G, X99F, X99M, X99T, X99P, X100I, X100S, X100N, X100Q, X101N, X101A, X101G, X101P, X101F, X101E, X101T, X101D, X102H, X102N, X102E, X102T, X102A, X103G, X103D, X103N, X104D, X104E, X104I, X104L, X105Q, X105E, X105T, X106F, X106V, X106G, X106E, X106T, X106D, X106A, X107F, X107M, X108G, X108I, X109M, X111V, X111I, X112V, X112L, X112Q, X114G, X115K, X115R, X116A, X116K, X116L, X117F, X118I, X118R, X119C, X120F, X120A, X120R, X121E, X121F, X123G, X123E, X124S, X128F, X128H, X128I, X128L, X128Q, X128N, X128M, X128D, X129E, X132E, X132A, X138G, X144R, X147L, X148I, X158E, X158E, X159E, X159C, X160D, X166D, X166E, X167W, X175V, X177C, X181A, X182R, X183F, X183I, X183D, X183R, X183M, X185E, X185I, X185V, X186H, X186K, X188R, X188E, X188D, X192H, X192W, X194V, X194F, X194E, X197F, X198L, X198F, X203E, X203C, X208S, X209N, X209F, X209E, X209S, X209H, X209G, X209T, X209L, X210R, X210V, X210L, X211R, X211Q, X212I, X212M, X212F, X213A, X214F, X215F, X215N, X215D, X215H, X215E, X216F, X216A, X217N, X217E, X217D, X218P, X218D, X218E, X224A, X224G, X227I, X230E, X231I, X231C, X233C, X234F, X235F, X236F, X236N, X238L, X238K, X238R, X239K, X239S, X239T, X239G, X239H, X239R, X239N, X239F, X240R, X241R, X242L, X242R, X243R, X243F, X244R, X246S, X248I, X248V, X248R, X249R, X249T, X250I, X251S, X251R, X252I, X252F, X252H, X252R, X253F, X253I, X253R, X254C, X256N, X258R, X260V, X260I, X262H, X262D, X263F, X265F, X267N, X267V, X267M, X269I, X269R, X270C, X271F, X271V, X271I, X271P, X271H, X271M, X271T, X271L, X271A, X272F, X272R, X272F, X273I, X273F, and X274G, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants wherein the subtilisin variants are mature forms having proteolytic activity and comprise amino acid sequences comprising a combination of amino acid substitutions selected from: X16S, X18R, X20R, X22A, X24R, X43R/D, X45T, X76D, X101A, X103G, X104L, X111V, X128N, X148I, X230E, X242R, and X249R, wherein the amino acid positions of the subtilisin variant are numbered by correspondence with the amino acid sequence of *B. amyloliquefaciens* subtilisin BPN' set forth as SEQ ID NO:1.

The present invention further provides isolated subtilisin variants, wherein the subtilisin variants are mature forms having proteolytic activity and comprise amino acid sequences comprising a combination of amino acid substitutions selected from: X1R, X230E, X271L, X115R, X20R, X249R, X235F, X27V/F/L, X75E, X82R, X18R, X269R, X43D, X43R, X76D, X45T, X212F, X242R, X24R, X78R, X9A, X22R, X121E, X244R, X28E, X30E, X4R, and X241R, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X062E-X158E, X103G-X158E, X128N-X158E, X016S-X158E, X104L-X158E, X089P-X158E, X111V-X158E, X022A-X158E, X101A-X158E, X148I-X158E, X129E-X158E, X022A-X089P, X016S-X089P, X062E-X089P, X062E-X271F, X158E-X271F, X186H-X271F, X129E-X271F, X111V-X271F, X209E-X271F, X016S-X271F, X188D-X271F, X022A-X271F, X159E-X271F, X104L-X271F, X101A-X271F, X089P-X271F, X128N-X271F, X103G-X271F, X148I-X271F, X249R-X271F, X062E-X159E, X016S-X159E, X128N-X159E, X148I-X159E, X111V-X159E, X089P-X159E, X022A-X159E, X129E-X159E, X103G-X159E, X104L-X159E, X158E-X159E, X101A-X159E, X158E-X249R, X111V-X249R, X129E-X249R, X062E-X249R, X016S-X249R, X186H-X249R, X148I-X249R, X159E-X249R, X101A-X249R, X188D-X249R, X104L-X249R, X209E-X249R, X022A-X249R, X128N-X249R, X103G-X249R, X089P-X249R, X022A-X111V, X101A-X111V, X016S-X111V, X104L-X111V, X062E-X111V, X103G-X111V, X089P-X111V, X016S-X148I, X062E-X148I, X022A-X148I, X129E-X148I, X104L-X148I, X103G-X148I, X128N-X148I, X101A-X148I, X089P-X148I, X111V-X148I, X016S-X062E, X022A-X062E, X062E-X129E, X022A-X129E, X128N-X129E, X016S-X129E, X101A-X129E, X104L-X129E, X089P-X129E, X103G-X129E, X111V-X129E, X062E-X186H, X128N-X186H, X101A-X186H, X022A-X186H, X016S-X186H, X158E-X186H, X089P-X186H, X129E-X186H, X159E-X186H, X103G-X186H, X104L-X186H, X111V-X186H, X148I-X186H, X062E-X101A, X022A-X101A, X016S-X101A, X089P-X101A, X062E-X103G, X022A-X103G, X016S-X103G, X101A-X103G, X089P-X103G, X062E-X128N, X016S-X128N, X022A-X128N, X101A-X128N, X104L-X128N, X089P-X128N, X103G-X128N, X111V-X128N, X111V-X188D, X062E-X188D, X016S-X188D, X148I-X188D, X022A-X188D, X128N-X188D, X101A-X188D, X104L-X188D, X089P-X188D, X129E-X188D, X159E-X188D, X186H-X188D, X103G-X188D, X158E-X188D, X016S-X022A, X016S-X104L, X022A-X104L, X101A-X104L, X062E-X104L, X103G-X104L, X089P-X104L, X159E-X209E, X111V-X209E, X101A-X209E, X016S-X209E, X128N-X209E, X148I-X209E, X129E-X209E, X062E-X209E, X022A-X209E, X103G-X209E, X158E-X209E, X188D-X209E, X104L-X209E, X089P-X209E, and X186H-X209E, wherein the amino acid positions of the subtilisin variant are numbered by correspondence with the amino acid sequence of B. amyloliquefaciens subtilisin BPN' set forth as SEQ ID NO:1.

The present invention further provides isolated subtilisin variants, wherein the subtilisin variants are mature forms having proteolytic activity and comprise amino acid sequences comprising a combination of amino acid substitutions selected from: X018R-X241R, X020R-X241R, X024R-X241R, X009A-X241R, X020R-X241R, X004R-X241R, X043R-X241R, X078R-X241R, X022R-X241R, X115R-X241R, X001R-X241R, X212F-X241R, X082R-X241R, X018R-X244R, X024R-X244R, X078R-X244R, X020R-X244R, X212F-X244R, X009A-X244R, X082R-X244R, X001R-X244R, X043R-X244R, X022R-X244R, X004R-X244R, X115R-X244R, X241R-X244R, X242R-X244R, X001R-X004R, X009A-X022R, X018R-X022R, X020R-X022R, X004R-X022R, X001R-X022R, X024R-X242R, X018R-X242R, X004R-X242R, X020R-X242R, X212F-X242R, X082R-X242R, X078R-X242R, X001R-X242R, X009A-X242R, X022R-X242R, X115R-X242R, X043R-X242R, X241R-X242R, X018R-X212F, X022R-X212F, X004R-X212F, X024R-X212F, X001R-X212F, X115R-X212F, X020R-X212F, X009A-X212F, X043R-X212F, X078R-X212F, X082R-X212F, X009A-X078R, X020R-X078R, X024R-X078R, X022R-X078R, X018R-X078R, X004R-X078R, X001R-X078R, X043R-X078R, X022R-X024R, X020R-X024R, X018R-X024R, X001R-X024R, X004R-X024R, X009A-X024R, X004R-X009A, X001R-X009A, X242R-X269R, X024R-X269R, X020R-X269R, X022R-X269R, X249R-X269R, X212F-X269R, X043R-X269R, X244R-X269R, X001R-X269R, X018R-X269R, X078R-X269R, X009A-X269R, X115R-X269R, X241R-X269R, X004R-X269R, X082R-X269R, X018R-X043R, X020R-X043R, X004R-X043R, X022R-X043R, X009A-X043R, X001R-X043R, X024R-X043R, X009A-X018R, X004R-X018R, X001R-X018R, X024R-X018R, X009A-X082R, X018R-X082R, X001R-X082R, X078R-X082R, X020R-X082R, X022R-X082R, X004R-X082R, X043R-X082R, X043R-X249R, X020R-X249R, X004R-X249R, X018R-X249R, X009A-X249R, X212F-X249R, X022R-X249R, X024R-X249R, X115R-X249R, X001R-X249R, X082R-X249R, X242R-X249R, X241R-X249R, X244R-X249R, X078R-X249R, X018R-X115R, X020R-X115R, X022R-X115R, X078R-X115R, X009A-X115R, X004R-X115R, X001R-X115R, X082R-X115R, X043R-X115R, X024R-X115R, X009A-X020R, X018R-X020R, X004R-X020R, X001R-X020R, X009A-X271L, X020R-X271L, X024R-X271L, X244R-X271L, X241R-X271L, X043R-X271L, X022R-X271L, X249R-X271L, X212F-X271L, X115R-X271L, X242R-X271L, X078R-X271L, X004R-X271L, X269R-X271L, X001R-X271L, X018R-X271L, and X082R-X271L, wherein the amino acid positions of the subtilisin variant are numbered by correspondence with the amino acid sequence of B. amyloliquefaciens subtilisin BPN' set forth as SEQ ID NO:1.

The present invention further provides isolated subtilisin variants, wherein the subtilisin variants are mature forms having proteolytic activity and comprise amino acid sequences comprising a combination of amino acid substitutions selected from: X020R-X-43R, X020K-X062E, X024F-X116L, X020K-X024F, X024R-X174T, X024R-X118R, X024R-X235F, X024R-X086R, X024R-X086W, X078R-X118R, X033 S-X118R, X033 S-X235F, X209A-X241R, X020R-X076D, X018R-X245R, X024R-X045T, X232V-X245R, X118R-X172V, X118R-X194T, X008T-X024R, X235F-X243F, X018R-X103A, X018R-X104I, X086W-X118R, X086W-X243F, X086W-X209A, X024C-X033S, X024R-X232V, X024R-X243F, X024R-X239Q, X024R-X101G, X024R-X141G, X024R-X033S, X024R-X274I, X024R-X209A, X078R-X086W, X101G-X232V, X033S-X148F, X033S-X086W, X033S-X201S, X033S-X078R, X033S-X241R, X033S-X209A, X230E-X249R, X232V-X249R, X118R-X235F, X076D-X245R, X086W-X235F, X024R-X247H, X024R-X104A, X078R-X235F, X101G-X249R, X103A-X232V, X033S-X048T, X033S-X239T, X033S-X253A, X143A-X209A, X209A-X235F, X018R-X045T, X209A-X243F, X024R-X272P, X024R-X269C, X101G-X104I, X104I-X232V, X076D-X249R, and X024R-X076D wherein the amino acid positions of the subtilisin variant are numbered by correspondence with the amino acid sequence of *B. amyloliquefaciens* subtilisin BPN' set forth as SEQ ID NO:1.

The present invention further provides isolated subtilisin variants, wherein the subtilisin variants are mature forms having proteolytic activity and comprise amino acid sequences comprising a combination of amino acid substitutions selected from: X020R-X076D, X024R-X045T, X230E-X249R, X018R-X045T, X018R-X245R, X101G-X232V, X024R-X232V, X232V-X245R, X024R-X101G, X018R-X104I, X018R-X103A, X101G-X249R, X232V-X249R, X103A-X232V, X076D-X245R, X101G-X104I, X104I-X232V, X076D-X249R, X024R-X076D, X024F-X116L, X020K-X024F, X020K-X062E, X033S-X118R, X024R-X086W, X024R-X118R, X024R-X086R, X209A-X241R, X024R-X241R, X024R-X235F, X118R-X209A, X078R-X118R, X033S-X235F, X024R-X174T, X086W-X209A, X008T-X024R, X086W-X118R, X033S-X241R, X024R-X243F, X024R-X209A, X033S-X086W, X024R-X033S, X086W-X243F, X033S-X201S, X024R-X239Q, X078R-X086W, X235F-X243F, X118R-X172V, X033S-X148F, X033S-X078R, X033S-X243F, X024C-X033S, X118R-X194T, X033S-X209A, X024R-X141G, X024R-X274I, X086W-X235F, X015T-X033S, X209A-X235F, X024R-X247H, X078R-X235F, X024R-X104A, X033S-X048T, X118R-X235F, X033S-X253A, X143A-X209A, X033S-X239T, X209A-X243F, X024R-X272P, and X024R-X269C, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X004R-X009A-X020R-X242R, X020R-X043R-X241R, X020R-X242R-X269R, X004R-X009A-X020R-X043R, X004R-X020R-X249R, X018R-X024R-X244R, X009A-X022R-X212F-X241R, X020R-X043R-X269R, X018R-X024R-X242R, X004R-X009A-X043R-X241R, X020R-X043R-X244R, X020R-X022R-X242R, X004R-X020R-X043R, X004R-X009A-X020R-X043R-X242R, X020R-X043R-X242R, X020R-X043R-X242R-X249R, X020R-X212F-X249R, X004R-X009A-X241R, X001R-X009A-X043R, X020R-X043R-X249R, X009A-X020R-X043R-X241R, X020R-X022R-X043R, X020R-X249R-X269R, X020R-X022R-X241R, X004R-X009A-X024R-X043R-X241R, X009A-X043R-X078R, X004R-X020R-X024R-X244R, X020R-X022R-X078R-X242R, X020R-X024R-X242R-X249R, X004R-X009A-X078R-X241R, X009A-X043R-X078R-X242R, X004R-X020R-X024R, X009A-X043R-X212F, X020R-X043R-X212F, X024R-X078R-X212F, X009A-X020R-X024R-X043R, X009A-X022R-X043R-X078R, X020R-X022R-X212F-X241R, X020R-X043R-X212F-X241R, X009A-X043R-X241R, X020R-X043R-X271L, X020R-X022R-X078R-X241R, X020R-X024R-X043R-X242R, X020R-X022R-X043R-X241R, X009A-X020R-X043R-X212F, X004R-X009A-X020R-X024R-X242R, X020R-X043R-X249R-X271L, X020R-X022R-X024R-X242R, X009A-X022R-X078R-X212F, X020R-X043R-X242R-X271L, X009A-X022R-X078R-X212F-X241R, X004R-X020R-X024R-X249R, X020R-X022R-X271L, X020R-X022R-X043R-X212F, X004R-X020R-X024R-X043R-X242R, X004R-X020R-X024R-X043R, X004R-X009A-X022R-X078R-X212F, X020R-X022R-X078R-X212F-X241R, and X020R-X022R-X269R, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: X018R-X020R-X043D-X045T-X230E, X018R-X043R-X045T-X242R-X249R, X024R-X043D-X249R, X018R-X020R-X045T, X020R-X024R-X076D-X249R, X024R-X043R-X230E-X242R, X018R-X024R-X043D-X230E, X020R-X076D, X018R-X024R-X043D-X076D-X249R, X024R-X043R-X076D-X249R, X018R-X024R-X045T-X242R, X020R-X043D-X076D-X230E-X249R, X020R-X043R-X045T-X242R, X018R-X024R-X076D-X249R, X018R-X020R-X024R-X043D-X045T-X233I-X242R, X024R-X043R-X230E, X018R-X020R-X043D, X043R-X242R-X249R, X020R-X043R-X045T-X230E, X043R-X076D-X242R-X249R, X020R-X024R-X045T-X230E-X242R, X024R-X045T-X076D-X230E-X242R-X249R, X024R-X045T, X024R-X043R-X045T-X076D-X230E-X249R, X018R-X024R-X043D-X045T-X249R, X018R-X043R-X045T-X249R, X024R-X043R-X242R, X018R-X020R-X043R-X076D-X249R, X020R-X024R-X043D-X249R, X020R-X043R-X230E-X242R, X020R-X043R-X242R, X018R-X043R-X076D-X230E, X020R-X024R-X043D-X242R, X020R-X043R-X230E, X018R-X020R-X043R-X076D-X242R-X249R, X043D-X045T-X076D-X249R, X018R-X043R-X242R-X249R, X018R-X020R-X043R-X045T-X242R, X018R-X020R-X043D-X230E-X242R, X020R-X024R-X043R-X045T-X249R, X024R-X043R-X249R, X020R-X024R-X27E-X043R-X076D-X230E, X024R-X043R-X045T-X242R, X018R-X020R-X024R-X043R-X045T-X076D-X230E, X020R-X043R-X076D-X230E-X249R, X018R-X043R-X045T-X242R, X020R-X242R-X249R, X018R-X043R-X076D-X230E-X242R-X249R, X018R-X024R-X076D, X020R-X024R-X27R-X043D-X242R-X249R, X018R-X020R-X024R-X043D-X076D-X242R, X018R-X043R-X076D-X242R-X249R, X018R-X024R-X043D-X230E-X249R, X018R-X020R-X043D-X249R, X018R-X020R-X043D-X045T-X076D-X242R, X024R-X043R-X076D-X230E-X242R, X020R-X024R-X381-X043R-X045T-X076D-X242R-X249R, X018R-X020R-X043R, X018R-X024R-X045T-X230E-X242R, X018R-X020R-X249R, X024R-X043R-X076D, X018R-X020R-X024R-X043R-X045T-X076D-X249R, X018R-X043D-X045T-X076D-X242R-X249R, X024R-X043D-X242R-X249R, X018R-X020R-X024R-X043D-X045T-X242R, X020R-X024R-X043R-X076D, X018R-X020R-X043D-X045T-X230E-X242R, X020R-X024R-X043R-X045T-X076D-X242R-X249R, X018R-X043R-X045T-X076D-X242R, X018R-X020R-X043R-X076D-X230E-X242R, X018R-X024R-X043D-X249R, X018R-X024R-X043R-X045T-X230E-X249R, X018R-X020R-X043R-X045T-X076D-X249R, X018R-X024R-X242R, X018R-X043R-X045T-X076D-X230E-X242R, X045T-X242R-X249R, X018R-X024R-X043D-X242R, X018R-X020R-X043D-X045T-X240P, X024R-X043R-X045T-X242R-X249R, X018R-X024R-X30S-X31S-X321-X33Q-X34V-X35F, X018R-X020R-X043D-X076D, X020R-X043D-X045T-X076D-X242R-X249R, X018R-X024R-X043D-X230E-X242R, X018R-X024R-X043D-X242R-X249R, X024R-X043D-X045T-X242R-X249R, X043R-X230E-X249R, X024R-X043R-X076D-X230E-X249R, X020R-X024R-X043D-X076D-X249R, X024R-X045T-X242R-X273V, X020R-X024R-X045T-X076D-X242R-X249R, X018R-X024R-

X043D-X076D-X242R, X018R-X043R-X076D-X230E-X249R, X018R-X020R-X043R-X045T-X249R, X018R-X043R-X045T-X230E-X242R, X020R-X024R-X043D-X045T-X230E-X242R, X018R-X043D-X230E-X249R, X018R-X043R-X076D-X242R, X018R-X020R-X076D, X018R-X020R-X043D-X076D-X242R-X249R, X020R-X024R-X043D-X076D-X242R-X249R, X043D-X242R-X249R, X018R-X020R-X024R-X043R-X076D, X018R-X020R-X043D-X045T-X076D-X249R, X018R-X020R-X043R-X045T-X076D-X230E-X249R, X018R-X076D-X242R, X020R-X043R-X249R, X018R-X076D-X242R-X249R, X018R-X024R-X045T-X230E-X249R, X230E-X249R, X018R-X045T-X249R, X020R-X043R-X076D, X043R-X045T-X249R, X018R-X043D-X076D-X242R-X249R, X043R-X076D-X249R, X018R-X045T, X020R-X076D-X230E-X242R, X020R-X024R-X043D-X045T, X024R-X043D-X076D-X242R-X249R, X020R-X045T-X249R, X043R-X076D-X153A-X249R, X043R-X076D-X230E-X249R, X018R-X043D-X076D-X249R, and X020R-X043R-X076D-X227I, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X101G-X103A-X104I-X232V-X236H-X245R-X252K, X101G-X103A-X104I-X232V-X245R-X248R, X101G-X103A-X104I-X159R-X232V-X245R-X248D, X101G-X103A-X104I-X159D-X232V-X245R-X248R, X101G-X103A-X104I-X232V-X245R, X101G-X103A-X104I-X159D-X232V-X245R, and X101G-X103A-X104I-X232V-X245R-X248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X101G-X103A-X104I-X129E-X188D-X232V-X238R-X245R-X248D, X024R-X101G-X103A-X104I-X129E-X158E-X188D-X232V-X245R-X248D-X249R, X022A-X101G-X103A-X104I-X129E-X158E-X188D-X232V-X245R-X248D-X249R, X022A-X024R-X101G-X103A-X104I-X129E-X158E-X188D-X232V-X245R-X248D-X249R, X024R-X101G-X103A-X104I-X129E-X188D-X232V-X245R-X248D-X249R, X024R-X101G-X103A-X104I-X129E-X159E-X188D-X232V-X245R-X248D-X249R, X024R-X101G-X103A-X104I-X128N-X129E-X158E-X232V-X245R-X248D-X249R, X024R-X101G-X103A-X104I-X148I-X158E-X188D-X232V-X245R-X248D, X022A-X024R-X101G-X103A-X104I-X129E-X159E-X188D-X232V-X245R-X248D-X249R, X024R-X101G-X103A-X104I-X128N-X129E-X232V-X245R-X248D, X101G-X103A-X104I-X129E-X188D-X232V-X245R-X248D-X249R, X024R-X101G-X103A-X104I-X129E-X158E-X232V-X245R-X248D-X249R, X022A-X024R-X101G-X103A-X104I-X158E-X159E-X188D-X232V-X245R-X248D-X249R, X022A-X024R-X101G-X103A-X104I-X129E-X158E-X159E-X232V-X238R-X245R-X248D, X024R-X101G-X103A-X104I-X129E-X148I-X158E-X232V-X245R-X248D, X016S-X024R-X101G-X103A-X104I-X158E-X188D-X232V-X245R-X248D-X249R, X101G-X103A-X104I-X158E-X159E-X232V-X245R-X248D-X249R, X022A-X101G-X103A-X104I-X129E-X158E-X159E-X232V-X238R-X245R-X248D, X022A-X024R-X101G-X103A-X104I-X129E-X158E-X159E-X232V-X245R-X248D-X249R, X022A-X024R-X101G-X103A-X104I-X128N-X158E-X188D-X232V-X245R-X248D, X022A-X024R-X101G-X103A-X104I-X104I-X128N-X158E-X188D-X232V-X245R-X248D, X024R-X101G-X103A-X104I-X129E-X188D-X232V-X245R-X248D, X022A-X024R-X101G-X103A-X104I-X129E-X158E-X232V-X245R-X248D, X022A-X024R-X101G-X103A-X104I-X129E-X188D-X232V-X245R-X248D, X024R-X101G-X103A-X104I-X158E-X188D-X232V-X238R-X245R-X248D, X022A-X101G-X103A-X104I-X128N-X129E-X188D-X232V-X238R-X245R-X248D, X024R-X101G-X103A-X104I-X129E-X188D-X232V-X238R-X245R-X248D, X024R-X101G-X103A-X104I-X158E-X159E-X188D-X232V-X245R-X248D, X022A-X024R-X101G-X103A-X104I-X128N-X188D-X232V-X245R-X248D, X024R-X101G-X103A-X104I-X129E-X158E-X188D-X232V-X245R-X248D, X022A-X024R-X101G-X103A-X104I-X128N-X129E-X158E-X232V-X245R-X248D, X024R-X101G-X103A-X104I-X159E-X188D-X232V-X245R-X248D, X022A-X101G-X103A-X104I-X128N-X129E-X232V-X238R-X245R-X248D, X024R-X101G-X103A-X104I-X129E-X159E-X232V-X245R-X248D, X022A-X024R-X101G-X103A-X104I-X129E-X158E-X188D-X232V-X238R-X245R-X248D, X022A-X024R-X101G-X103A-X104I-X158E-X159E-X188D-X232V-X245R-X248D, X024R-X101G-X103A-X104I-X159E-X188D-X232V-X245R-X248D-X249R, X022A-X101G-X103A-X104I-X129E-X158E-X232V-X238R-X245R-X248D, X022A-X024R-X101G-X103A-X104I-X129E-X158E-X232V-X245R-X248D-X249R, X024R-X101G-X103A-X104I-X148I-X158E-X232V-X245R-X248D, X022A-X101G-X103A-X104I-X158E-X159E-X188D-X232V-X245R-X248D-X249R, X022A-X101G-X103A-X104I-X158E-X188D-X232V-X245R-X248D, X022A-X101G-X103A-X104I-X129E-X188D-X232V-X238R-X245R-X248D, X024R-X101G-X103A-X104I-X129E-X158E-X159E-X188D-X232V-X245R-X248D-X249R, X022A-X024R-X101G-X103A-X104I-X158E-X159E-X188D-X232V-X238R-X245R-X248D, X101G-X103A-X104I-X129E-X158E-X188D-X232V-X245R-X248D-X249R, X024R-X101G-X103A-X104I-X128N-X158E-X232V-X245R-X248D, X022A-X024R-X101G-X103A-X104I-X128N-X129E-X188D-X232V-X245R-X248D, X022A-X101G-X103A-X104I-X129E-X159E-X232V-X238R-X245R-X248D, X101G-X103A-X104I-X129E-X159E-X232V-X245R-X248D-X249R, X022A-X101G-X103A-X104I-X129E-X158E-X232V-X245R-X248D-X249R, X024R-X101G-X103A-X104I-X129E-X148I-X158E-X188D-X232V-X245R-X248D, X022A-X101G-X103A-X104I-X129E-X159E-X232V-X245R-X248D-X249R, X024R-X101G-X103A-X104I-X159E-X188D-X232V-X238R-X245R-X248D, X024R-X101G-X103A-X104I-X129E-X158E-X159E-X232V-X245R-X248D-X249R, X024R-X101G-X103A-X104I-X129E-X158E-X159E-X232V-X238R-X245R-X248D, X024R-X101G-X103A-X104I-X128N-X159E-X188D-X232V-X245R-X248D, X022A-X101G-X103A-X104I-X159E-X188D-X232V-X245R-X248D-X249R, X024R-X101G-X103A-X104I-X129E-X159E-X188D-X232V-X238R-X245R-X248D, X101G-X103A-X104I-X158E-X232V-X238R-X245R-X248D, X022A-X101G-X103A-X104I-X129E-X159E-X188D-X232V-X245R-X248D-X249R, X024R-X101G-X103A-X104I-X129E-X148I-X188D-X232V-X245R-X248D, X024R-X101G-X103A-X104I-X158E-X232V-X245R-

X248D-X249R, X022A-X101G-X103A-X104I-X158E-X159E-X232V-X238R-X245R-X248D, X024R-X101G-X103A-X104I-X158E-X159E-X232V-X238R-X245R-X248D, X022A-X101G-X103A-X104I-X129E-X158E-X159E-X232V-X245R-X248D-X249R, X101G-X103A-X104I-X129E-X158E-X188D-X232V-X238R-X245R-X248D, X022A-X024R-X101G-X103A-X104I-X129E-X158E-X159E-X232V-X245R-X248D, X101G-X103A-X104I-X188D-X232V-X238R-X245R-X248D, X022A-X024R-X101G-X103A-X104I-X158E-X232V-X245R-X248D-X249R, X022A-X024R-X101G-X103A-X104I-X148I-X158E-X232V-X245R-X248D, X101G-X103A-X104I-X129E-X158E-X159E-X232V-X238R-X245R-X248D, X022A-X101G-X103A-X104I-X159E-X188D-X232V-X238R-X245R-X248D, X022A-X024R-X101G-X103A-X104I-X129E-X158E-X159E-X188D-X232V-X245R-X248D-X249R, X022A-X101G-X103A-X104I-X129E-X232V-X238R-X245R-X248D, X022A-X024R-X101G-X103A-X104I-X188D-X232V-X245R-X248D-X249R, X101G-X103A-X104I-X129E-X158E-X159E-X232V-X245R-X248D-X249R, X022A-X101G-X103A-X104I-X158E-X159E-X232V-X245R-X248D-X249R, X101G-X103A-X104I-X129E-X188D-X232V-X245R-X248D, X024R-X101G-X103A-X104I-X129E-X159E-X232V-X238R-X245R-X248D, X101G-X103A-X104I-X128N-X129E-X232V-X245R-X248D, X101G-X103A-X104I-X158E-X188D-X232V-X245R-X248D, X022A-X024R-X101G-X103A-X104I-X129E-X232V-X245R-X248D-X249R, X101G-X103A-X104I-X129E-X159E-X232V-X238R-X245R-X248D, X101G-X103A-X104I-X158E-X159E-X188D-X232V-X238R-X245R-X248D, X024R-X101G-X103A-X104I-X232V-X245R-X248D-X249R, X022A-X024R-X101G-X103A-X104I-X129E-X148I-X232V-X245R-X248D, X022A-X024R-X101G-X103A-X104I-X158E-X232V-X238R-X245R-X248D, X101G-X103A-X104I-X128N-X129E-X232V-X238R-X245R-X248D, X022A-X101G-X103A-X104I-X128N-X159E-X232V-X245R-X248D, X022A-X101G-X103A-X104I-X128N-X129E-X158E-X232V-X238R-X245R-X248D, X101G-X103A-X104I-X128N-X129E-X188D-X232V-X245R-X248D-X249R, X022A-X024R-X101G-X103A-X104I-X128N-X129E-X158E-X188D-X232V-X245R-X248D-X249R, X024R-X101G-X103A-X104I-X128N-X158E-X159E-X188D-X232V-X245R-X248D, X022A-X024K-X101G-X103A-X104I-X128N-X158E-X159E-X232V-X245R-X248D, X101G-X103A-X104I-X129E-X148I-X188D-X232V-X245R-X248D, X024R-X101G-X103A-X104I-X148I-X232V-X245R-X248D, X022A-X101G-X103A-X104I-X148I-X188D-X232V-X245R-X248D, X024R-X101G-X103A-X104I-X128N-X129E-X188D-X232V-X245R-X248D, X101G-X103A-X104I-X128N-X129E-X158E-X232V-X238R-X245R-X248D, X022A-X024R-X101G-X103A-X104I-X129E-X148I-X158E-X188D-X232V-X245R-X248D, X022A-X024R-X101G-X103A-X104I-X148I-X158E-X188D-X232V-X245R-X248D, X101G-X103A-X104I-X148I-X159E-X232V-X245R-X248D, X022A-X024R-X101G-X103A-X104I-X158E-X188D-X232V-X245R-X248D, and X101G-X103A-X104I-X128N-X129E-X158E-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X022A-X024R-X101G-X103A-X104I-X158E-X232V-X245R-X248D-X249R, X022A-X024R-X101G-X103A-X104I-X129E-X232V-X245R-X248D-X249R, X024R-X101G-X103A-X104I-X158E-X159E-X232V-X238R-X245R-X248D, X024R-X101G-X103A-X104I-X232V-X245R-X248D-X249R, X101G-X103A-X104I-X158E-X232V-X245R-X248D-X249R, X101G-X103A-X104I-X188D-X232V-X245R-X248D-X249R, X024R-X101G-X103A-X104I-X159E-X188D-X232V-X245R-X248D-X249R, X022A-X024R-X101G-X103A-X104I-X158E-X232V-X238R-X245R-X248D, X024R-X101G-X103A-X104I-X159E-X188D-X232V-X238R-X245R-X248D, X022A-X024R-X101G-X103A-X104I-X129E-X232V-X245R-X248D, X024R-X101G-X103A-X104I-X148I-X232V-X245R-X248D, X024R-X101G-X103A-X104I-X129E-X158E-X232V-X245R-X248D-X249R, X024R-X101G-X103A-X104I-X148I-X158E-X232V-X245R-X248D, X022A-X024R-X101G-X103A-X104I-X129E-X158E-X232V-X245R-X248D-X249R, X016S-X024R-X101G-X103A-X104I-X158E-X188D-X232V-X245R-X248D-X249R, X024R-X101G-X103A-X104I-X129E-X159E-X232V-X238R-X245R-X248D, X024R-X101G-X103A-X104I-X129E-X188D-X232V-X245R-X248D-X249R, X022A-X101G-X103A-X104I-X129E-X232V-X238R-X245R-X248D, X022A-X024R-X101G-X103A-X104I-X148I-X158E-X232V-X245R-X248D, X024R-X101G-X103A-X104I-X129E-X188D-X232V-X238R-X245R-X248D, X022A-X024R-X101G-X103A-X104I-X158E-X159E-X188D-X232V-X238R-X245R-X248D, X022A-X101G-X103A-X104I-X158E-X159E-X232V-X238R-X245R-X248D, X022A-X024R-X101G-X103A-X104I-X129E-X158E-X232V-X245R-X248D, X101G-X103A-X104I-X158E-X188D-X232V-X245R-X248D-X249R, X022A-X101G-X103A-X104I-X158E-X159E-X232V-X245R-X248D-X249R, and X024R-X101G-X103A-X104I-X158E-X159E-X232V-X245R-X248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X104L-X128N-X158E-X186H-X249R, X128N-X158E-X188D-X249R, X062E-X128N-X158E-X159E-X271F, X062E-X158E-X188D-X249R-X271F, X062E-X158E-X186H-X249R-X271F, X128N-X158E-X188D-X209E-X271F, X062E-X159E-X188D-X249R, X016S-X062E-X158E-X186H-X249R, X062E-X158E-X159E-X249R, X101A-X128N-X158E-X209E-X249R, X128N-X158E-X186H-X271F, X062E-X158E-X188D-X249R, X062E-X158E-X186H-X271F, X062E-X158E-X186H-X249R, X062E-X101A-X186H-X249R, X062E-X101A-X158E-X186H-X271F, X062E-X104L-X158E-X188D-X249R-X271F, X062E-X159E-X186H-X249R, X062E-X159E-X249R, X128N-X158E-X186H-X249R, X128N-X158E-X188D-X271F, X062E-X158E-X249R, X062E-X186H-X188D-X249R-X271F, X128N-X158E-X209E-, X062E-X101A-X158E-X249R, X104L-X128N-X158E-X186H-X271F, X062E-X101A-X158E-X186H-X249R-X271F, X016S-X062E-X158E-X249R, X062E-X101A-X159E-X249R, X128N-X158E-X186H-X188D-X271F, X101A-X128N-X158E-X186H-X271F, X062E-X101A-X188D-X249R, X101A-X104L-X158E-X186H-X188D-X249R, X062E-X159E-X249R-X271F, X128N-X158E-X159E-X271F, X016S-X062E-X104L-

X158E-X186H-X271F, X022A-X128N-X158E-X249R, X128N-X158E-X249R, X062E-X101A-X104L-X158E-X186H-X271F, X016S-X062E-X158E-X186H-X271F, X104L-X128N-X158E-X249R, X104L-X128N-X158E-X188D-X249R, X022A-X062E-X158E, X062E-X101A-X188D-X249R-X271F, X062E-X158E-X249R-X271F, X104L-X128N-X158E-X186H-X188D-X271F, X062E-X101A-X186H-X271F, X062E-X104L-X159E-X249R, X062E-X186H-X249R, X062E-X101A-X186H-X249R-X271F, X101A-X158E-X186H-X188D-X249R, X062E-X101A-X186H, X101A-X128N-X129E-X186H-X249R, X101A-X103G-X158E-X186H-X249R, X016S-X062E-X104L-X186H-X188D-X271F, X104L-X158E-X186H-X249R, X101A-X128N-X158E-X188D-X209E-X271F, X062E-X101A-X186H-X188D-X271F, X016S-X062E-X158E-X249R-X271F, X062E-X128N-X158E, X062E-X128N-X159E-X249R, X062E-X101A-X158E-X188D-X249R, X101A-X128N-X158E-X249R, X062E-X158E-X186H-X188D-X249R, X016S-X104L-X158E-X186H-X271F, X062E-X148I-X159E, X062E-X101A-X158E-X186H-X249R, X062E-X101A-X186H-X188D-X249R, X104L-X158E-X186H-X188D-X249R, X062E-X101A-X104L-X186H-X188D-X271F, X022A-X101A-X158E-X186H-X249R, X101A-X128N-X158E-X209E, X158E-X186H-X188D-X249R-X271F, X104L-X158E-X186H-X188D-X249R-X271F, X101A-X104L-X158E-X186H-X249R, X104L-X158E-X249R, X101A-X104L-X128N-X158E-X186H-X271F, X016S-X104L-X188D-X249R, X101A-X104L-X158E-X186H-X188D-X271F, X104L-X128N-X159E-X271F, X104L-X158E-X186H-X249R-X271F, X158E-X186H-X249R, X101A-X158E-X186H-X249R, X104L-X158E-X188D-X249R-X271F, X016S-X128N-X158E-X186H, X104L-X128N-X186H-X188D-X249R, X016S-X101A-X128N-X186H, X016S-X062E-X128N-X186H-X271F, X016S-X128N-X186H-X271F, X128N-X129E-X186H, X158E-X186H-X249R-X271F, X016S-X158E-X249R, X016S-X158E-X186H-X249R, X016S-X022A-X158E-X186H-X271F, X089P-X101A-X129E-X186H, X022A-X128N-X158E-X186H, X101A-X104L-X128N-X158E-X186H, X022A-X128N-X186H-X188D-, X062E-X104L-X158E-X186H-X188D-X249R, X022A-X158E-X186H-X249R-X271F, X022A-X104L-X158E-X249R, X101A-X111V-X129E, X016S-X158E-X249R-X271F, X016S-X111V-X188D-, X022A-X104L-X186H-X188D-X249R, and X104L-X148I-X188D-X249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X001R-X101G-X103A-X104I-X232V-X245R, X004R-X101G-X103A-X104I-X232V-X245R, X043R-X101G-X103A-X104I-X232V-X245R-X271L, X078R-X101G-X103A-X104I-X232V-X245R, X004R-X043R-X101G-X103A-X104I-X232V-X245R, X018R-X043R-X101G-X103A-X104I-X232V-X245R, X020R-X101G-X103A-X104I-X232V-X245R, X101G-X103A-X104I-X232V-X245R-X271L, X020R-X043R-X101G-X103A-X104I-X232V-X245R, X024R-X043R-X101G-X103A-X104I-X232V-X245R, X020R-X025R-X116A-X167W, X018R-X101G-X103A-X104I-X232V-X245R, X022R-X101G-X103A-X104I-X232V-X245R, X078R-X103N-X106G-X167W-X236N, X018R-X043D-X101G-X103A-X104I-X232V-X245R-X269R, X043R-X101G-X103A-X104I-X232V-X245R-X269R, X024R-X101A-X120E-X194F-X249R, X020R-X043D-X101G-X103A-X104I-X232V-X245R-X269R, X101G-X103A-X104I-X212F-X232V-X245R, X020R-X144R-X185I-X233C-X236N, X023A-X078R-X216F-X236N-X249R, X101G-X103A-X104I-X232V-X245R-X269R, X101G-X103A-X104I-X115R-X232V-X245R, X052N-X078R-X103N-X148I-X213A, X018R-X043D-X101G-X103A-X104I-X232V-X245R-X249R, X024R-X043D-X101G-X103A-X104I-X232V-X245R-X249R, X024R-X043D-X101G-X103A-X104I-X232V-X245R-X269R, X025R-X089I-X116A-X239S-X270C, X024R-X101G-X103A-X104I-X232V-X245R, X148I-X213A-X252R, X024R-X025R-X183D-X192W-X239S, X046R-X194F-X212M, X104L-X217E-X224A-X249R-X252R, X023A-X091F-X121F-X192W-X236N, X101G-X103A-X104I-X232V-X244R-X245R, X099F-X144R-X167W-X252R, X101G-X103A-X104I-X232V-X245R-X249R, X043R-X101G-X103A-X104I-X232V-X245R, X022W-X078R-X167W-X212M-X270C, X121F-X252R-X270C, X020R-X103N-X216F-X236N-X252R, X043R-X101G-X103A-X104I-X232V-X245R-X249R, X023A-X052N-X192W-X198L-X252R, X025R-X046R-X121F, X024R-X078R-X104L-X116A-X183D, X046R-X059A-X103N-X211Q-X212M, X020R-X052N-X062Q-X091F-X192W, X023A-X052N-X144R-X192W-X216F, X101G-X103A-X104I-X232V-X242R-X245R, X052N-X103N-X116A-X148I-X192W, X089I-X116A-X117F-X224A-X249R, X144R-X211Q-X238L-X239S-X249R, X043A-X062Q-X194F-X211Q, X020R-X024R-X052N-X059A-X216F, X024R-X167W-X224A-X249R, X057R-X167W-X249R, X025R-X103N-X186K-X194F-X224A, X105T-X128N-X144R-X148I-X212M, X020R-X059A-X144R-X192W-X224A, X024R-X043A-X117F-X194F-X211Q, X117F-X194F-X213A-X270C, X078R-X091F-X121F-X233C-X252R, X057R-X099F-X105T-X198L-X213A, X023A-X091F-X101A-X198L-X252R, X062Q-X103N-X121F-X144R-X249R, X043R-X101G-X103A-X104I-X232V-X242R-X245R, X023A-X024R-X117F-X212M-X216F, X104L-X213A-X216F, X194F-X211Q-X236N, X062Q-X103N-X117F-X194F, X024R-X062Q-X104L-X106G-X249R, X057R-X089I-X198L, X046R-X059A-X106G-X217E-X249R, X117F-X213A-X215F, X101A-X120E-X192W-X215F-X224A, X043-X057R-X117F-X144R-X183D, X046R-X183D-X238L, X025R-X043A-X089I-X117F, X078R-X104L-X213A-X215F-X224A, X091F-X099F-X101A-X105T-X167W, X106G-X117F-X238L, X046R-X089I-X091F-X101A-X116A, X020R-X062Q-X089I-X186K-X212M, X057R-X099F-X121F-X185I-X192W, X046R-X089I-X192W-X233C-X270C, X089I-X117F-X185I-X215F-X233C, X052N-X104L-X183D-X216F-X249R, X078R-X099F-X116A-X186K-X224A, X025R-X105T-X128N-X144R-X270C, X105T-X211Q-X216F, X024R-X046R-X091F-X121F, X106G-X185I-X216F-X236N, X062Q-X101A-X236N-X252R-X270C, X025R-X043A-X091F-X198L-X270C, X020R-X023A-X104L-X192W-X233C, X024R-X043A-X105T-X106G-X198L, X020R-X089I-X217E, X024R-X091F-X198L-X215F-X239S, X046R-X089I-X099F-X186K-X212M, X104L-X120E-X186K-X216F-X252R, X022W-X194F-X213A-X233C-X238L, X099F-X105T-X106G-X194F-X212M, X089I-X105T-X116A-X215F-X216F, X025R-X116A-X120E-X224A-X270C, X043A-X059A-X101A-X216F-X224A, X057R-X183D-X236N, X025R-X062Q-X128N-X144R-X185I, X103N-X120E-X167W-X198L-X233C, X022W-X089I-X216F, X024R-X106G-X116A-X212M-X224A, X020R-X052N-X101A-X198L-X233C, X089I-X091F-

X185I-X211Q-X270C, X111I-X215F-X239S, X024R-X116A-X186K-X233C-X236N, and X023A-X103N-X106G-X212M-X215F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X020R-X022W-X078R-X101A-X103A-X104I-X116S-X213A-X215F-X232V-X245R, X018R-X078R-X101G-X103A-X104I-X232V-X245R, X024R-X045T-X101G-X103A-X104I-X232V-X245R-X269R, X020R-X022W-X078R-X101G-X103A-X104I-X116A-X232V-X245R, X020R-X22W-X101G-X103A-X104I-X232V-X245R, X018R-X043R-X101G-X103A-X104I-X232V-X245R, X018R-X022W-X024R-X076D-X101A-X116A-X232V-X245R, X018R-X104I-X232V-X249R, X018R-X024R-X076D-X101A-X116A-X211Q-X249R, X018R-X043D-X078R-X101G-X103A-X104I-X217E-X232V-X245R, X018R-X043R-X101G-X103A-X104I-X232V-X245R-X269R, X018R-X045T-X076D-X101G-X103A-X104I-X232V-X245R-X269R, X076D-X078R-X101G-X103A-X104I-X232V-X245R-X269R, X020R-X043D-X078R-X101G-X103A-X104I-X232V-X245R, X018R-X043D-X076D-X101G-X103A-X104I-X232V-X245R-X269R, X024R-X045T-X076D-X078R-X101G-X103A-X104I-X232V-X245R-X269R, X018R-X103A-X232V-X249R, X018R-X101G-X104I-X232V-X245R, X020R-X024R-X101G-X103A-X104I-X217E-X232V-X245R-X249R, X018R-X22K-X043D-X101G-X103A-X104I-X232V-X245R, X043R-X045T-X101G-X103A-X104I-X232V-X245R-X269R, X020R-X22W-X101G-X103A-X104I-X211Q-X232V-X245R, X024R-X076D-X078R-X101G-X103A-X104I-X232V-X245R-X269R, X020R-X22W-X078R-X101A-X103A-X104I-X116A-X183D-X232V, X018R-X024R-X076D-X116A-X215F-X249R, X018R-X043R-X045T-X101G-X103A-X104I-X232V-X245R, X024R-X043R-X076D-X101G-X103A-X104I-X232V-X245R, X020R-X022W-X101G-X103A-X104I-X232V-X245R, X020R-X022W-X103A-X104I-X211Q-X232V-X245R, X020R-X022W-X078R-X101G-X103A-X104I-X116A-X213A-X215F-X232V-X245R, X043D-X076D-X078R-X101G-X103A-X104I-X232V-X245R-X269R, X018R-X024R-X076D-X101A-X116A-X213A-X249R, X018R-X024R-X076D-X116A-X211Q-X249R, X043R-X045T-X076D-X078R-X101G-X103A-X104I-X232V-X245R, X018R-X101G-X245R, X020R-X22W-X101A-X103A-X104I-X211Q-X213A-X232V-X245R, X020R-X024R-X043D-X076D-X078R-X101G-X103A-X104I-X232V-X245R, X018R-X045T-X076D-X078R-X101G-X103A-X104I-X232V-X245R, X020R-X078R-X101G-X103A-X104I-X211Q-X213A-X215F-X232V-X245R, X045T-X078R-X101G-X103A-X104I-X232V-X245R-X269R, X024R-X043D-X101G-X103A-X104I-X232V-X245R-X269R, X018R-X101G-X103A-X249R, X018R-X22W-X024R-X076D-X101A-X116A-X232V-X245R, X018R-X101G-X104I-X232V-X249R, X020R-X22W-X101A-X103A-X104I-X215F-X232V-X245R, X018R-X024R-X076D-X211Q-X213A-X249R, X018R-X022W-X024R-X076D-X101A-X198L-X249R, X024R-X101G-X103A-X104I-X232V-X245R, X020R-X076D-X101G-X103A-X104I-X232V-X245R-X269R, X020R-X101G-X103A-X104I-X232V-X245R-X269R, X043D-X078R-X101G-X103A-X104I-X232V-X245R, X020R-X101G-X104I-X213A-X215F-X232V-X245R, X020R-X101G-X103A-X104I-X116A-X215F-X232V-X245R, X024R-X103A-X104I-X249R, X018R-X076D-X078R-X101G-X103A-X104I-X232V-X245R, X045T-X076D-X078R-X101G-X103A-X104I-X232V-X245R-X269R, X024R-X101G-X104I-X245R, X020R-X101G-X103A-X104I-X211Q-X213A-X215F-X232V-X245R, X024R-X103A-X104I-X232V-X249R, X018R-X024R-X076D-X116A-X211Q-X215F-X249R, X018R-X245R, X024R-X103A-X245R, X024R-X103A-X104I-X245R, X020R-X078R-X101G-X232V-X245R, X018R-X024R-X076D-X104I-X249R, X018R-X024R-X104I-X249R, X024R-X101G-X103A-X104I-X232V-X245R, X018R-X024R-X076D-X211Q-X215F-X249R, X019H-X020R-X022W-X078R-X101G-X103A-X104I-X211Q-X232V-X245R, X018R-X024R-X076D-X101A-X198L-X211Q-X213A-X249R, X018R-X024R-X043D-X101G-X103A-X104I-X232V-X245R, X020R-X22W-X103A-X104I-X232V-X245R, X018R-X103A-X104I-X249R, X018R-X022W-X024R-X076D-X101A-X198L-X215F-X249R, X018R-X024R-X101G-X104I-X232V, X078R-X101G-X103A-X104I-X232V-X245R-X269R, X024R-X043R-X076D-X078R-X101G-X103A-X104I-X232V-X245R, X018R-X020R-X043D-X076D-X101G-X103A-X104I-X232V-X245R, X018R-X22W-X024R-X076D-X116A-X213A-X249R, X018R-X024R-X101G-X104I, X020R-X101A-X103A-X104I-X215F-X232V-X245R, X018R-X045T-X078R-X101G-X103A-X104I-X232V-X245R, X018R-X101G-X103A-X245R, X043R-X076D-X078R-X101G-X103A-X104I-X232V-X245R, X020R-X022W-X101A-X103A-X104I-X211Q-X215F-X232V-X245R, X020R-X22W-X078R-X101G-X103A-X104I-X116A-X213A-X215F-X232V-X245R, X020R-X078R-X101G-X103A-X104I-X215F-X232V-X245R, X020R-X022W-X078R-X101G-X103A-X104I-X116A-X183D-X232V-X245R, X076D-X101G-X103A-X104I-X232V-X245R, X076D-X101G-X103A-X104I-X232V-X245R-X269R, X020R-X22W-X101A-X103A-X104I-X232V-X245R, X020R-X101G-X103A-X232V-X245R, X020R-X022W-X078R-X101A-X103A-X104I-X116A-X183D-X232V-X245R, X018R-X020R-X024R-X045T-X076D-X101G-X103A-X104I-X232V-X245R-X269R, X043R-X045T-X078R-X101G-X103A-X104I-X232V-X245R, X018R-X101G-X104I-X249R, X020R-X22W-X078R-X101G-X103A-X104I-X116A-X183D-X232V-X245R, X020R-X022W-X101G-X103A-X104I-X198L-X211Q-X213A-X232V-X245R, X020R-X078R-X101A-X103A-X104I-X116A-X183D-X213A-X232V-X245R, X024R-X076D-X104I-X232V-X245R, X018R-X020R-X076D-X101G-X103A-X104I-X232V-X245R, X018R-X024R-X076D-X101G-X104I-X232V-X249R, X018R-X043D-X078R-X101G-X103A-X104I-X232V-X245R, X001T-X018R-X024R-X076D-X116A-X213A-X249R, X076D-X078R-X101G-X103A-X104I-X232V-X245R, X020R-X078R-X101G-X103A-X104I-X116A-X232V-X245R, X043R-X076D-X101G-X103A-X104I-X232V-X245R, X018R-X045T-X101G-X103A-X104I-X232V-X245R, X018R-X076D-X101G-X104I-X232V-X245R, X020R-X078R-X101G-X103A-X104I-X116A-X183D-X232V-X245R, X018R-X024R-X076D-X101A-X211Q-X213A-X215F-X249R, X045T-X078R-X101G-X103A-X104I-X232V-X245R, X043R-X076D-X101G-X103A-X104I-X232V-X245R-X269R, X020R-X022W-X078R-X101G-X103A-X104I-X116A-X183D-X213A-X232V-X245R, X020R-X022W-X101G-X103A-X104I-X116A-X183D-X213A-X232V-X245R, X020R-X101G-X198L-X215F-X232V-X245R, X018R-X024R-X076D-X213A-X215F-X249R, X020R-X078R-X101G-X103A-X104I-

X116A-X211Q-X232V-X245R, X020R-X022W-X078R-X101A-X103A-X104I-X116A-X183D-X215F-X232V-X245R, X020R-X022W-X078R-X101A-X103A-X104I-X116A-X183D-X213A-X232V-X245R, X024R-X232V-X245R, X018R-X024R-X043D-X101G-X103A-X104I-X232V-X245R-X269R, X018R-X024R-X076D-X101A-X215F-X249R, X018R-X022W-X024R-X076D-X116A-X213A-X249R, X101G-X103A-X104I-X232V-X245R, X018R-X024R-X076D-X211Q-X213A-X215F-X249R, X018R-X024R-X076D-X116A-X213A-X215F-X249R, X043D-X076D-X078R-X101G-X103A-X104I-X232V-X245R-X269R, X043D-X078R-X101G-X103A-X104I-X232V-X245R-X249R, X020R-X022W-X078R-X101G-X103A-X104I-X116A-X183D-X211Q-X232V-X245R, X018R-X024R-X076D-X101A-X198L-X211Q-X215V-X249R, X018R-X022W-X024R-X076D-X116A-X211Q-X249R, X020R-X103A-X104I-X232V-X245R, X020R-X22W-X101A-X103A-X104I-X211Q-X215F-X232V-X245R, X024R-X076D-X101G-X103A-X104I-X232V-X245R, X020R-X101G-X103A-X104I-X116A-X232V-X245R, X018R-X22W-X024R-X076D-X198L-X215F-X249R, X020R-X022W-X103A-X104I-X232V-X245R, X020R-X022W-X101A-X103A-X104I-X211Q-X213A-X232V-X245R, X020R-X022W-X101G-X103A-X104I-X211Q-X213A-X215F-X232V-X245R, X018R-X043R-X045T-X076D-X101G-X103A-X104I-X232V-X245R, X018R-X022W-X024R-X076D-X101A-X198L-X213A-X215F-X249R, X018R-X22W-X024R-X076D-X101A-X215F-X249R, X020R-X045T-X101G-X103A-X104I-X232V-X245R, X020R-X078R-X101G-X103A-X104I-X180A-X232V-X245R, X020R-X022W-X078R-X101G-X103A-X104I-X116A-X183D-X215F-X232V-X245R, X018R-X101G-X103A-X104I, X020R-X22W-X101A-X103A-X104I-X116A-X211Q-X213A-X215F-X232V-X245R, X018R-X024R-X076D-X103A-X232V-X245R, X020R-X078R-X101A-X103A-X104I-X116A-X183D-X232V-X245R, X018R-X024R-X076D-X211Q-X249R, X020R-X101A-X103A-X104I-X213A-X215F-X232V-X245R, X018R-X020R-X043D-X101G-X103A-X104I-X232V-X245R, X020R-X022W-X101A-X103A-X104I-X211Q-X232V-X245R, X020R-X022W-X101A-X103A-X104I-X116A-X211Q-X215F-X232V-X245R, X020R-X022W-X101A-X103A-X104I-X116A-X211Q-X232V-X245R, X018R-X024R-X076D-X232V-X249R, X018R-X024R-X045T-X076D-X101G-X103A-X104I-X232V-X245R-X269R, X018R-X076D-X245R, X024R-X104I-X245R, X101G-X232V, X020R-X22W-X101A-X103A-X104I-X116A-X211Q-X215F-X232V-X245R, X018R-X020R-X022W-X024R-X076D-X116A-X183D-X198L-X213A-X249R, X020R-X022W-X078R-X101A-X103A-X104I-X232V-X245R, X020R-X022W-X078R-X101A-X103A-X104I-X198L-X232V-X245R, X024R-X245R-X249R, X020R-X101G-X103A-X104I-X116A-X211Q-X232V-X245R, X018R-X22W-X024R-X076D-X116A-X211Q-X249R, X024R-X101G-X104I-X249R, X018R-X024R-X076D-X116A-X198L-X211Q-X213A-X215F-X249R, X018R-X024R-X104I, X020R-X022W-X078R-X101A-X103A-X104I-X183D-X198L-X213A-X215F-X232V-X245R, X018R-X020R-X22W-X024R-X076D-X116A-X183D-X198L-X213A-X249R, X020R-X022W-X101A-X103A-X104I-X232V-X245R, X012H-X020R-X078R-X101G-X103A-X104I-X198L-X211Q-X213A-X232V-X245R, X018R-X024R-X076D-X101A-X211Q-X215F-X249R, X018R-X024R-X076D-X213A-X249R, X024R-X104I-X249R, X018R-X022W-X024R-X076D-X211Q-X249R, X018R-X076D-X103A-X104I-X249R, X043R-X076D-X101G-X103A-X104I-X217E-X232V-X245R, X020R-X078R-X101G-X103A-X104I-X183D-X211Q-X213A-X232V-X245R-X271G, X018R-X022W-X024R-X076D-X101A-X116A-X198L-X215F-X249R, X018R-X024R-X043D-X076D-X101G-X103A-X104I-X232V-X245R, X018R-X024R-X076D-X101A-X198L-X215F-X249R, X018R-X022W-X024R-X076D-X116A-X198L-X211Q-X213A-X249R, X018R-X024R-X076D-X101A-X116A-X213A-X215F-X249R, X020R-X043D-X045T-X078R-X101G-X103A-X104I-X232V-X245R, X045T-X078R-X101G-X103A-X104I-X232V-X245R-X249R, X018R-X22W-X024R-X076D-X101A-X116A-X215F-X249R, X043D-X101G-X103A-X104I-X232V-X245R-X269R, X020R-X022W-X078R-X101A-X103A-X104I-X116A-X183D-X213A-X215F-X232V-X245R, X018R-X024R-X076D-X116A-X211Q-X213A-X215F-X249R, X024R-X103A-X175L-X232V-X249R, X018R-X024R-X076D-X116A-X213A-X249R, X020R-X045T-X076D-X101G-X103A-X104I-X232V-X245R, X020R-X078R-X101A-X103A-X104I-X116A-X183D-X211Q-X213A-X215F-X232V-X245R, X024R-X043R-X045T-X076D-X078R-X101G-X103A-X104I-X232V-X245R, X018R-X024R-X076D-X101A-X116A-X198L-X213A-X215F-X249R, X043R-X045T-X101G-X103A-X104I-X232V-X245R, X018R-X022W-X024R-X076D-X101A-X198L-X211Q-X245R, X020R-X024R-X043D-X076D-X078R-X101G-X103A-X104I-X232V-X245R-X269R, X024R-X232V, X020R-X078R-X101A-X103A-X104I-X116A-X183D-X211Q-X232V-X245R, X024R-X076D-X101G-X232V-X245R, X018R-X076D-X101G-X103A-X104I-X249R, X018R-X024R-X076D-X198M-X211Q-X213A-X215F-X249R, X018R-X22W-X024R-X076D-X101A-X198L-X215F-X249R, X018R-X043R-X076D-X101G-X103A-X104I-X232V-X245R-X269R, X020R-X022W-X103A-X211Q-X213A-X215F-X232V-X245R, X020R-X078R-X101A-X103A-X104I-X116A-X183D-X211Q-X213A-X232V-X245R, X045T-X076D-X101G-X103A-X104I-X232V-X245R-X269R, X018R-X22W-X024R-X076D-X101A-X211Q-X213A-X249R, X018R-X024R-X076D-X116A-X198L-X215F-X249R-X268G, X018R-X022W-X024R-X076D-X101A-X211Q-X249R, X018R-X022W-X024R-X076D-X101A-X116A-X198L-X211Q-X249R, X101G-X103A-X104I-X245R, X018R-X076D-X101G-X232V-X245R, X018R-X020R-X045T-X101G-X103A-X104I-X232V-X245R, X018R-X022W-X024R-X076D-X101A-X116A-X198L-X249R, X018R-X022W-X024R-X076D-X116A-X198L-X213A-X249R, X078R-X101G-X103A-X104I-X232V-X245R-X249R, X018R-X078R-X101G-X103A-X104I-X217E-X232V-X245R, X020R-X043R-X076D-X101G-X103A-X104I-X232V-X245R-X269R, X018R-X043D-X076D-X101G-X103A-X104I-X232V-X245R-X249R, X045T-X101G-X103A-X104I-X232V-X245R-X269R, X024R-X103A-X232V, X018R-X024R-X076D-X101A-X211Q-X249R, X043D-X101G-X103A-X104I-X232V-X245R-X249R, X018R-X043R-X045T-X076D-X076T-X101G-X103A-X104I-X232V-X245R-X273T, X018R-X020R-X043D-X078R-X101G-X103A-X104I-X232V-X245R, X020R-X078R-X101A-X103A-X104I-X183D-X215F-X232V-X245R, X018R-X024R-X076D-X101G-X232V, X232V-X245R, X043R-X045T-X076D-X078R-X101G-X103A-X104I-X232V-X234I-X245R, X024R-X076D-X103A-X104I-X245R, X020R-X078R-X101A-X103A-X104I-X211Q-X213A-X232V-X245R, X043D-X078R-X101G-X103A-X104I-X232V-X245R-X269R-X272V, X018R-X020R-X024R-X076D-X116A-X183D-X198L-X211Q-X249R, X018R-X103A-X104I-X232V, X020R-X022W-X101G-X103A-X104I-X116A-X183D-X213A-X215F-

X232V-X245R, X024R-X043R-X076D-X101G-X103A-X104I-X232V-X245R-X269R, X018R-X022R-X024R-X076D-X213A-X215F-X249R, X018R-X024R-X076D-X101A-X116A-X198L-X211Q-X213A-X249R, X020R-X22W-X078R-X101A-X103A-X104I-X116A-X183D-X213A-X232V-X245R, X020R-X022W-X078R-X101G-X103A-X104I-X211Q-X213A-X232V-X245R, X020R-X022W-X101A-X103A-X104I-X215F-X232V-X245R, X018R-X020R-X024R-X076D-X116A-X183D-X215F-X249R, X018R-X024R-X076D-X116A-X117I-X183D-X213A-X249R, X018R-X022W-X024R-X076D-X101A-X116A-X198L-X213A-X249R, X018R-X22W-X024R-X076D-X101A-X198L-X213A-X215F-X249R, X018R-X043D-X078R-X101G-X103A-X104I-X232V-X245R-X249R, X018R-X076D-X101G-X103A-X104I-X232V-X245R-X249R, X020R-X022W-X101G-X103A-X104I-X116A-X183D-X198L-X232V-X245R, X018R-X043R-X045T-X076D-X101G-X103A-X104I-X232V-X245R-X269R, X018R-X024R-X076D-X116A-X198L-X209H-X213A-X249R, X020R-X022W-X101A-X103A-X104I-X116A-X183D-X211Q-X213A-X232V-X245R, X024R-X076D-X101G-X175L-X232V-X245R, X018R-X043D-X045T-X101G-X103A-X104I-X232V-X245R, X045T-X076D-X078R-X101G-X103A-X104I-X232V-X245R, X020R-X078R-X101A-X103A-X104I-X116A-X183D-X198L-X215F-X232V-X245R, X043R-X076D-X101G-X103A-X104I-X232V-X245R-X249R, X018R-X024R-X076D-X198L-X213A-X215F-X249R, X018R-X022W-X024R-X076D-X198L-X215F-X249R, X018R-X022W-X024R-X076D-X116A-X213A-X215F-X249R, X018R-X022W-X024R-X076D-X101A-X116A-X198L-X213A-X215F-X249R, X018R-X022W-X024R-X076D-X116A-X211Q-X213A-X249R, X018R-X024R-X245R, X018R-X022W-X024R-X076D-X101A-X116A-X215F-X249R, X024R-X076D-X104I-X245R, X027R-X043R-X101G-X103A-X104I-X232V-X245R-X269R, X018R-X024R-X076D-X116A-X198L-X211Q-X213A-X249R, X018R-X024R-X076D-X116A-X198L-X249R, X018R-X024R-X076D-X183D-X198L-X211Q-X213A-X215F-X249R, X020R-X022W-X101A-X103A-X104I-X116A-X211Q-X213A-X215F-X232V-X245R, X018R-X043D-X045T-X078R-X101G-X103A-X104I-X232V-X245R, X043R-X045T-X076D-X078R-X101G-X103A-X104I-X232V-X245R-X269R, X018R-X22W-X024R-X076D-X116A-X213A-X215F-X249R, X018R-X022W-X024R-X076D-X116A-X211Q-X215F-X249R, X020R-X078R-X101G-X103A-X104I-X116A-X183D-X213A-X232V-X245R, X018R-X076D-X101G-X103A-X104I-X232V-X245R, X018R-X101G-X104I, X020R-X078R-X101G-X103A-X104I-X116A-X183D-X211Q-X213A-X215F-X232V-X245R, X020R-X078R-X101A-X103A-X104I-X232V-X245R, X018R-X024R-X076D-X101A-X198L-X211Q-X249R, X018R-X024R-X076D-X198L-X211Q-X213A-X249R, X018R-X022W-X024R-X076D-X101A-X116A-X198L-X211Q-X213A-X249R, X018R-X076D-X249R, X018R-X020R-X024R-X076D-X101A-X116A-X183D-X198L-X249R, X018R-X024R-X076D-X101A-X116A-X211Q-X213A-X249R, X020R-X022W-X078R-X101A-X103A-X104I-X116A-X183D-X211Q-X213A-X215F-X232V-X245R, X020R-X022W-X101G-X103A-X104I-X114T-X213A-X215F-X232V-X245R, X018R-X22W-X024R-X076D-X116A-X211Q-X213A-X249R, X018R-X020R-X022W-X024R-X076D-X101A-X116A-X183D-X249R, X020R-X101A-X103A-X104I-X116A-X183D-X213A-X232V-X245R, X018R-X022W-X024R-X076D-X101A-X211Q-X213A-X249R, X018R-X022K-X043D-X101G-X103A-X104I-X232V-X245R, X018R-X101G-X103A-X104I-X232V-X245R-X269R, X020R-X078R-X101G-X103A-X104I-X116A-X183D-X211Q-X213A-X215F-X232V, X018R-X024R-X076D-X116A-X249R, X020R-X024R-X076D-X101G-X103A-X104I-X232V-X245R, X043D-X076D-X101G-X103A-X104I-X232V-X245R-X269R, X018R-X024R-X076D-X101A-X116A-X198L-X211Q-X249R, X018R-X022W-X024R-X076D-X198L-X213A-X215F-X249R, X018R-X043D-X076D-X078R-X101G-X103A-X104I-X232V-X245R-X269R, X020R-X22W-X101G-X103A-X104I-X116A-X183D-X213A-X215F-X232V-X245R, X020R-X101G-X103A-X104I-X183D-X211Q-X232V-X245R-, X018R-X024R-X076D-X101A-X198L-X213A-X249R, X018R-X024R-X076D-X101A-X198L-X249R, X018R-X024R-X045T-X076D-X101G-X103A-X104I-X232V-X245R-X249R, X018R-X024R-X076D-X101A-X183D-X213A-X249R, X018R-X043D-X076D-X078R-X101G-X103A-X104I-X232V-X245R, X020R-X078R-X101G-X103A-X104I-X116A-X131V-X183D-X213A-X232V-X245R, X018R-X045T-X076D-X101G-X103A-X104I-X232V-X245R, X018R-X024R-X076D-X101A-X183D-X211Q-X249R, X076D-X101G-X103A-X104I-X232V-X245R-X249R, X024R-X101G-X245R, X024R-X076D-X101G-X245R, X076D-X078R-X101G-X103A-X104I-X232V-X245R-X249R, X018R-X020R-X024R-X076D-X101A-X183D-X211Q-X215F-X249R, X024R-X101G, X018R-X22W-X024R-X076D-X213A-X215F-X249R, X020R-X043D-X101G-X103A-X104I-X232V-X245R, X020R-X022W-X101G-X103A-X104I-X183D-X198L-X213A-X215F-X232V-X245R, X018R-X043D-X045T-X101G-X103A-X104I-X232V-X245R-X269R, X043D-X076D-X078R-X101G-X103A-X104I-X232V-X245R, X024R-X045T-X076D-X101G-X103A-X104I-X232V-X245R-X269R, X020R-X022W-X101A-X103A-X104I-X198L-X211Q-X215F-X232V-X245R, X020R-X022W-X101G-X103A-X104I-X116A-X183D-X215F-X232V-X245R, X018R-X020R-X076D-X101G-X103A-X104I-X232V-X245R-X249R, X018R-X022W-X024R-X076D-X101A-X215F-X249R, X018R-X104I, X018R-X024R-X076D-X116A-X198L-X215F-X249R, X018R-X024R-X076D-X088I-X101A-X116A-X198L-X211Q-X215F-X249R, X018R-X022W-X024R-X076D-X101A-X116A-X211Q-X213A-X249R, X043R-X045T-X076D-X101G-X103A-X104I-X232V-X245R-X269R, X018R-X076D-X101G-X104I-X249R, X018R-X022W-X024R-X076D-X101A-X213A-X215F-X249R, X018R-X22W-X024R-X076D-X101A-X116A-X198L-X215F-X249R, X018R-X020R-X101G-X103A-X104I-X232V-X245R-X249R, X101G-X103A-X104I-X232V-X245R-X249R-X269R, X024R-X076D-X245R, X018R-X020R-X043R-X045T-X076D-X101G-X103A-X104I-X232V-X245R, X018R-X020R-X024R-X076D-X215F-X249R, X018R-X024R-X076D-X101A-X116A-X183D-X198L-X213A-X249R, X018R-X020R-X024R-X076D-X211Q-X215F-X249R, X043D-X101G-X103A-X104I-X232V-X245R, X020R-X22W-X078R-X101A-X103A-X104I-X116A-X183D-X215F-X232V-X245R, X018R-X024R-X076D-X198L-X211Q-X215F-X249R, X043R-X076D-X078R-X101G-X103A-X104I-X232V-X245R-X269R, X043R-X078R-X101G-X103A-X104I-X232V-X245R-X269R, X020R-X043D-X101G-X103A-X104I-X232V-X245R-X249R, X018R-X022W-X024R-X076D-X101A-X213A-X249R, X020R-X022W-X101A-X116A-X198L-X211Q-X213A-X215F-X249R, X043R-X045T-X078R-X101G-X103A-X104I-X218S-X232V-X245R, X018R-X103A, X020R-X22W-X101G-X103A-X104I-X116A-X183D-X215F-X232V-X245R, X018R-X024R-X076D-X101A-X249R, X018R-X022W-

X024R-X076D-X211Q-X213A-X249R, X024R-X043R-X045T-X076D-X101G-X103A-X104I-X232V-X245R, X020R-X022W-X101A-X103A-X104I-X116A-X183D-X232V-X245R, X020R-X101A-X103A-X104I-X116A-X183D-X211Q-X213A-X215F-X232V-X245R, X027R-X045T-X076D-X078R-X101G-X103A-X104I-X232V-X245R-X269R, X020R-X045T-X076D-X101G-X103A-X104I-X232V-X245R-X249R, X018R-X020R-X024R-X076D-X116A-X183D-X213A-X215F-X249R, X018R-X024R-X076D-X104I, X101G-X103A-X104I-X232V-X249R, X018R-X024R-X076D-X116A-X183D-X211Q-X249R, X018R-X020R-X024R-X076D-X116A-X215F-X249R, X018R-X024R-X076D-X183D-X213A-X215F-X249R, X018R-X022W-X024R-X076D-X198L-X211Q-X249R, X043D-X078R-X101G-X103A-X104I-X232V-X245R-X269R-X275S, X020R-X022W-X101A-X103A-X104I-X116A-X183D-X211Q-X232V-X245R, X018R-X022W-X024R-X076D-X101A-X198L-X211Q-X213A-X215F-X249R, X018R-X022W-X024R-X076D-X101A-X116A-X198L-X211Q-X213A-X215F-X249R, X018R-X020R-X024R-X076D-X183D-X249R, X018R-X024R-X076D-X116A-X198L-X213A-X249R, X018R-X022W-X024R-X076D-X101A-X116A-X211Q-X249R, X004M-X018R-X024R-X076D-X116A-X198L-X211Q-X213A-X249R, X104I-X232V-X249R, X020R-X022W-X101G-X103A-X104I-X116A-X183D-X211Q-X215F-X232V-X245R, X020R-X101A-X103A-X104I-X116A-X183D-X211Q-X232V-X245R-X274I, X020R-X101A-X103A-X104I-X213A-X232V-X245R, X020R-X101G-X103A-X104I-X116A-X183D-X211Q-X213A-X232V-X245R, X020R-X024R-X043D-X078R-X101G-X103A-X104I-X232V-X245R, X018R-X024R-X076D-X103A-X249R, X018R-X020R-X024R-X076D-X101A-X116A-X183D-X211Q-X215F-X249R, X018R-X020R-X024R-X076D-X116A-X183D-X198L-X249R, X018R-X022W-X024R-X076D-X116A-X198L-X215F-X249R, X018R-X024R-X076D-X101A-X211Q-X213A-X215F-X249R-X270V, X018R-X043D-X045T-X076D-X078R-X101G-X103A-X104I-X232V-X245R-X269R, X020R-X022W-X101G-X103A-X104I-X183D-X232V-X245R, X018R-X020R-X022W-X024R-X076D-X101A-X116A-X213A-X249R, X018R-X022W-X024R-X076D-X198L-X211Q-X215F-X249R, X018R-X022W-X024R-X076D-X198L-X213A-X249R, X020R-X022W-X101G-X103A-X104I-X116A-X183D-X232V-X245R, X018R-X22W-X024R-X076D-X116A-X198L-X213A-X249R, X043R-X045T-X078R-X101G-X103A-X104I-X232V-X245R-X269R, X018R-X024R-X076D-X101G-X103A-X104I-X232V, X101G-X249R, X024R-X076D-X101G-X103A-X104I-X175L-X249R, X020R-X022W-X101A-X103A-X104I-X116A-X183D-X232V-X245R-X269S, X018R-X024R-X076D-X101A-X116A-X198L-X249R, X018R-X022W-X024R-X076D-X116A-X249R, X018R-X020R-X024R-X076D-X101A-X183D-X198L-X215F-X249R, X018R-X024R-X076D-X213A-X215F-X249R-X260K, X018R-X024R-X076D-X116A-X211Q-X213A-X249R, X018R-X020R-X022W-X024R-X076D-X116A-X198L-X249R, X024R-X076D-X101G-X103A-X104I-X245R, X024R-X076D-X103A-X249R, X018R-X101G-X103A-X104I-X232V-X245R-X249R, X018R-X024R-X076D-X198L-X211Q-X249R, X018R-X022W-X024R-X076D-X101A-X198L-X211Q-X213A-X249R, X020R-X024R-X045T-X101G-X103A-X104I-X232V-X245R, X018R-X020R-X024R-X076D-X183D-X211Q-X213A-X249R, X018R-X043D-X045T-X078R-X101G-X103A-X104I-X232V-X245R-X272D, X018R-X024R-X076D-X116A-X198L-X213A-X215F-X249R, X018R-X22W-X024R-X076D-X101A-X198L-X249R, X018R-X022W-X024R-X076D-X116A-X198L-X249R, X024R-X076D-X101G-X103A-X232V, X024R-X103A-X104I, X018R-X024R-X076D-X101A-X116A-X183D-X211Q-X215F-X249R, X024R-X045T-X076D-X101G-X103A-X104I-X232V-X245R-X249R, X020R-X101G-X103A-X104I-X116A-X183D-X232V-X245R, X024R-X043D-X076D-X101G-X103A-X104I-X232V-X245R-X269R, X020R-X022W-X101A-X103A-X104I-X183D-X211Q-X213A-X215F-X232V-X245R, X020R-X045T-X076D-X078R-X101G-X103A-X104I-X232V-X245R-X269R, X018R-X024R-X076D-X101A-X116A-X198L-X211Q-X215F-X249R, X020R-X101A-X103A-X104I-X116A-X183D-X215F-X232V-X245R, X018R-X043R-X101G-X103A-X104I-X232V-X245R-X249R, X018R-X024R-X076D-X198L-X213A-X249R, X018R-X024R-X076D-X116A-X183D-X213A-X249R, X020R-X043D-X101G-X103A-X104I-X232V-X245R-X269R, X024R-X076D-X103A-X245R, X018R-X022W-X024R-X076D-X101A-X116A-X211Q-X213A-X215F-X249R, X103A-X104I-X245R, X018R-X022W-X024R-X076D-X211Q-X215F-X249R, X018R-X022W-X024R-X076D-X116A-X183D-X198L-X249R, X018R-X022W-X024R-X076D-X198L-X211Q-X213A-X249R, X018R-X024R-X076D-X116A-X183D-X211Q-X213A-X215F-X249R, X018R-X020R-X043D-X045T-X076D-X101G-X103A-X104I-X232V-X245R-X269R, X018R-X020R-X022W-X024R-X076D-X101A-X211Q-X213A-X215F-X249R, X016T-X043R-X045T-X076D-X101G-X103A-X104I-X232V-X245R-X269R, X018R-X022W-X024R-X076D-X116A-X215F-X249R, X043R-X076D-X101G-X103T-X104I-X232V-X245R-X249R-X269R, X020R-X078R-X101A-X103A-X104I-X115E-X116A-X183D-X211Q-X213A-X232V-X245R, X018R-X024R-X076D-X198L-X249R, X018R-X024R-X076D-X101A-X116A-X183D-X249R, X020R-X101G-X103A-X104I-X116A-X183D-X211Q-X232V-X245R, X018R-X024R-X076D-X101G, X076D-X101G-X232V-X245R, X018R-X076D-X101G-X103A-X104I-X245R, X018R-X045T-X101G-X103A-X104I-X232V-X245R-X249R, X018R-X024R-X076D-X215F-X249R, X018R-X104I-X232V, X043D-X045T-X076D-X078R-X101G-X103A-X104I-X232V-X245R, X024R-X076D-X101G-X232V-X249R, X103A-X232V-X245R, X020R-X101G-X103A-X104I-X116A-X183D-X211Q-X213A-X215F-X232V-X245R, X018R-X020R-X024R-X076D-X116A-X183D-X198L-X211Q-X215F-X249R, X018R-X022W-X024R-X076D-X101A-X198L-X211Q-X215F-X249R, X024R-X076D-X103A-X104I-X249R, X024R-X101G-X103A-X104I, X020R-X101G-X103A-X104I-X116A-X183D-X211Q-X215F-X232V-X245R, X018R-X022W-X024R-X076D-X101A-X116A-X183D-X215F-X249R, X020R-X022W-X101G-X103A-X104I-X116A-X183D-X211Q-X213A-X215F-X232V-X245R, X020R-X024R-X045T-X076D-X101G-X103A-X104I-X232V-X245R, X018R-X022W-X024R-X076D-X116A-X183D-X213A-X249R, X018R-X020R-X024R-X076D-X131T-X215F-X249R, X018R-X024R-X076D-X101A-X116A-X183D-X211Q-X213A-X215F-X249R, X018R-X024R-X076D-X101A-X116A-X211Q-X213A-X215F-X249R, X018R-X024R-X076D-X198L-X215F-X249R, X018R-X022W-X024R-X076D-X183D-X211Q-X249R, X018R-X022W-X024R-X076D-X101A-X116A-X213A-X215F-X249R, X018R-X020R-X024R-X045T-X076D-X101G-X103A-X104I-X232V-X245R, X043R-X101G-X103A-X104I-X245R-X249R, X018R-X076D-X232V-X249R, X018K-X076D-X078R-X101G-X103A-X104I-X217E-X232V-X245R-X269R, X018R-X020R-X024R-X043D-X076D-X078R-X101G-X103A-

X104I-X232V-X245R, X018R-X022W-X024R-X076D-X101A-X116A-X213A-X215F-X249R-X267I, X232V-X249R, X018R-X020R-X024R-X076D-X116A-X211Q-X213A-X215F-X249R, X076D-X104I-X245R, X018R-X020R-X024R-X076D-X183D-X198L-X211Q-X215F-X249R, X018R-X024R-X076D-X101A-X211Q-X213A-X249R, X024R-X101G-X103A-X232V, X018R-X020R-X022W-X024R-X076D-X116A-X183D-X198L-X213A-X215F-X249R, X018R-X020R-X024R-X076D-X116A-X183D-X198L-X211Q-X213A-X249R, X018R-X020R-X022W-X024R-X076D-X101A-X215F-X249R, X020R-X022W-X101A-X103A-X104I-X116A-X183D-X211Q-X215F-X232V-X245R, X018R-X024R-X076D-X116A-X198L-X211Q-X249R, X103A-X232V-X249R, X018R-X020R-X024R-X076D-X116A-X183D-X198L-X215F-X249R, X018R-X024R-X076D-X116A-X183D-X198L-X213A-X249R, X018R-X022W-X024R-X076D-X183D-X213A-X249R, X018R-X024R-X076D-X101A-X213A-X215F-X249R, X018R-X022W-X024R-X076D-X101A-X116A-X183D-X211Q-X249R, X018R-X045T-X101G-X103A-X104I-X232V-X245R-X269R, X018R-X020R-X045T-X076D-X078R-X101G-X103A-X104I-X232V-X245R, X018R-X022W-X024R-X076D-X116A-X198L-X213A-X215F-X249R, X020R-X022W-X101G-X103A-X104I-X116A-X183D-X211Q-X213A-X232V-X245R, X018R-X020R-X024R-X076D-X198L-X249R, X018R-X020R-X022W-X024R-X076D-X101A-X116A-X211Q-X249R, X020R-X022W-X101A-X103A-X104I-X116A-X183D-X232V-X245R-X274I, X024R-X103A-X245R-X249R, X018R-X022W-X024R-X076D-X101A-X116A-X249R, X018R-X024R-X076D-X101A-X198L-X211Q-X215F-X249R, X018R-X022W-X024R-X076D-X116A-X198L-X211Q-X215F-X249R, X018R-X020R-X022W-X024R-X076D-X116A-X183D-X213A-X249R, X018R-X043D-X045T-X076D-X101G-X103A-X104I-X232V-X245R-X269R, X018R-X022W-X024R-X076D-X116A-X211Q-X213A-X215F-X249R, X018R-X024R-X076D-X101A-X183D-X198L-X213A-X249R, X043D-X076D-X101G-X103A-X104I-X232V-X245R-X249R, X018R-X024R-X076D-X198L-X211Q-X213A-X215F-X249R, X018R-X020R-X024R-X076D-X116A-X183D-X213A-X249R, X103A-X232V, X018R-X022W-X024R-X076D-X116A-X183D-X215F-X249R, X018R-X024R-X076D-X101A-X116A-X249R, X018R-X043R-X078R-X101G-X103A-X104I-X232V-X245R, X018R-X020R-X022W-X024R-X076D-X101A-X183D-X211Q-X215F-X249R, X043R-X076D-X078R-X101G-X103A-X104I-X232V-X245R-X249R, X018R-X020R-X024R-X076D-X101A-X116A-X183D-X198L-X213A-X249R, X018R-X024R-X076D-X183D-X198L-X213A-X249R, X018R-X022W-X024R-X076D-X101A-X183D-X211Q-X249R, X018R-X020R-X024R-X076D-X198L-X213A-X215F-X249R, X018R-X020R-X022W-X024R-X076D-X183D-X211Q-X213A-X249R, X018R-X022W-X024R-X076D-X198L-X249R, X018R-X024R-X076D-X183D-X198L-X211Q-X249R, X020R-X022W-X101A-X103A-X104I-X116A-X183D-X213A-X232V-X245R, X018R-X020R-X024R-X076D-X116A-X183D-X211Q-X213A-X249R, X018R-X024R-X076D-X116A-X183D-X198L-X211Q-X213A-X215F-X249R, X020R-X022W-X101A-X103A-X104I-X116A-X183D-X215F-X232V-X245R, X018R-X024R-X076D-X101A-X183D-X249R, X018R-X024R-X076D-X232V, X018R-X022W-X024R-X076D-X101A-X116A-X249R, X020R-X101A-X103A-X104I-X116A-X183D-X198L-X211Q-X213A-X215F-X232V-X245R, X020R-X022W-X101G-X103A-X104I-X116A-X183D-X211Q-X232V-X245R-X263S, X024R-X076D-X101G-X104I-X232V-X249R, X043R-X078R-X101G-X103A-X104I-X232V-X245R, X024R-X076D-X078R-X101G-X103A-X104I-X232V-X245R-X249R, X018R-X024R-X076D-X101A-X183D-X198L-X213A-X215F-X249R, X018R-X020R-X024R-X076D-X198L-X215F-X249R, X018R-X020R-X024R-X076D-X101A-X116A-X213A-X249R, X018R-X024R-X076D-X101A-X197A-X213A-X215F-X249R, X024R-X101G-X103A, X018R-X024R-X076D-X101A-X116A-X211Q-X215F-X249R, X043R-X076D-X078R-X101G-X103A-X104I-X217E-X232V-X245R, X024R-X104I-X232V, X018R-X024R-X076D-X183D-X211Q-X249R, X020R-X043R-X045T-X078R-X101G-X103A-X104I-X232V-X245R, X018R-X020R-X022W-X024R-X076D-X101A-X116A-X183D-X213A-X249R, X018R-X024R-X076D-X116A-X150T-X213A-X249R, X018R-X024R-X076D-X183D-X213A-X249R, X018R-X020R-X024R-X076D-X116A-X183D-X211Q-X215F-X249R, X018R-X020R-X024R-X076D-X211Q-X249R, X018R-X024R-X076D-X101A-X116A-X183D-X198L-X249R, X024R-X076D-X232V-X249R, X018R-X020R-X022W-X024R-X076D-X101A-X116A-X183D-X198L-X211Q-X213A-X249R, X018R-X022W-X024R-X076D-X101A-X116T-X198L-X215F-X249R, X018R-X024R-X076D-X183D-X198L-X211Q-X215F-X249R, X018R-X022R-X024R-X076D-X101A-X116A-X183D-X211Q-X249R, X045T-X101G-X103A-X104I-X232V-X245R, X018R-X020R-X024R-X076D-X101A-X183D-X211Q-X249R, X020R-X101G-X103A-X104I-X116A-X183D-X213A-X232V-X245R, X076D-X101G-X103A-X245R, X020R-X043D-X078R-X101G-X103A-X104I-X232V-X245R-X249R, X018R-X024R-X076D-X116A-X183D-X249R, X018R-X024R-X076D-X101A-X183D-X211Q-X213A-X215F-X249R, X018R-X020R-X022W-X024R-X076D-X101A-X116A-X198L-X249R, X018R-X22W-X024R-X076D-X211Q-X213A-X249R, X018R-X020R-X024R-X076D-X183D-X211Q-X249R, X018R-X020R-X024R-X076D-X101A-X116A-X183D-X213A-X249R, X043R-X078R-X101G-X103A-X104I-X217E-X232V-X245R, X018R-X022W-X024R-X076D-X101A-X215F-X249R, X018R-X020R-X024R-X076D-X101A-X183D-X198L-X211Q-X213A-X249R, X076D-X101G-X104I-X249R, X018R-X022W-X024R-X076D-X101A-X116A-X183D-X213A-X249R, X018R-X024R-X076D-X183D-X249R, X018R-X024R-X076D-X101A-X183D-X198L-X215F-X249R, X018R-X022W-X024R-X076D-X183D-X198L-X215F-X249R, X018R-X022W-X024R-X076D-X101A-X198L-X211Q-X249R, X020R-X101A-X103A-X104I-X116A-X183D-X232V-X245R, X018R-X024R-X076D-X116A-X183D-X198L-X211Q-X249R, X018R-X020R-X024R-X101G-X103A-X104I-X232V-X245R, X018R-X076D-X078R-X101G-X103A-X104I-X217E-X232V-X245R, X020R-X101A-X103A-X104I-X116A-X183D-X211Q-X232V-X245R, X018R-X022W-X024R-X076D-X101A-X183D-X198L-X209H-X249R, X018R-X024R-X076D-X183D-X198L-X213A-X215F-X249R, X018R-X024R-X076D-X101A-X116A-X183D-X211Q-X213A-X249R, X018R-X022W-X024R-X076D-X101A-X116A-X183D-X211Q-X213A-X249R, X018R-X024R-X076D-X183D-X198L-X249R, X018R-X024R-X076D-X183D-X215F-X249R, X018R-X020R-X024R-X076D-X211Q-X213A-X215F-X249R, X076D-X245R, X076D-X101G-X104I-X245R, X018R-X022W-X024R-X076D-X101A-X211Q-X215F-X249R, X018R-X022W-X024R-X076D-X101A-X116A-X183D-X211Q-X215F-X249R, X018R-X020R-X022W-X024R-X076D-X101A-X211Q-X213A-X249R, X020R-X024R-X043R-X101G-X103A-X104I-X232V-X245R, X018R-X024R-

X076D-X116A-X183D-X211Q-X215F-X249R, X020R-X101A-X103A-X104I-X116A-X183D-X213A-X215F-X232V-X245R, X101G-X103A-X104I, X018R-X020R-X024R-X076D-X101A-X116A-X183D-X211Q-X213A-X249R, X018R-X020R-X024R-X076D-X204D-X213A-X249R, X018R-X022W-X024R-X076D-X183D-X198L-X249R, X018R-X024R-X076D-X101A-X116A-X183D-X215F-X249R, X018R-X022W-X024R-X076D-X116A-X183D-X198L-X211Q-X213A-X209V-X249R, X018R-X022W-X024R-X076D-X101A-X116A-X183D-X211Q-X213A-X215F-X249R, X018R-X024R-X076D-X101A-X116A-X198L-X213A-X249R, X018R-X020R-X024R-X076D-X101A-X116A-X211Q-X213A-X249R, X018R-X020R-X022W-X024R-X076D-X101A-X116A-X183D-X211Q-X213A-X215F-X249R, X018R-X024R-X076D-X101A-X116A-X183D-X213A-X215F-X249R, X018R-X024R-X076D-X101A-X183D-X198L-X211Q-X213A-X215F-X249R, X018R-X024R-X076D-X101A-X183D-X198L-X211Q-X213A-X249R, X018R-X043R-X045T-X078R-X101G-X103A-X104I-X217E-X232V-X245R, X018R-X024R-X076D-X183D-X211Q-X213A-X215F-X249R, X018R-X022W-X024R-X076D-X116A-X183D-X198L-X215F-X249R, X018R-X020R-X024R-X076D-X116A-X249R, X018R-X020R-X022W-X024R-X076D-X101A-X211Q-X215F-X249R, X018R-X020R-X024R-X076D-X183D-X211Q-X213A-X215F-X249R, X018R-X020R-X022W-X024R-X076D-X198L-X213A-X249R, X018R-X020R-X024R-X076D-X101A-X211Q-X215F-X249R-X269D, X018R-X020R-X043D-X101G-X103A-X104I-X232V-X245R-X269R, X018R-X022W-X024R-X076D-X101A-X183D-X198L-X213A-X249R, X020R-X022W-X101G-X103A-X104I-X183D-X215F-X232V-X245R, X018R-X022W-X024R-X076D-X116A-X183D-X198L-X209H-X211Q-X249R, X018R-X020R-X022W-X024R-X076D-X101A-X116A-X183D-X211Q-X249R, X076D-X232V-X245R, X043D-X045T-X078R-X101G-X103A-X104I-X232V-X245R, X018R-X020R-X024R-X076D-X116A-X198L-X211Q-X215F-X245R, X018R-X020R-X022W-X024R-X076D-X213A-X249R, X020R-X024R-X043D-X078R-X101G-X103A-X104I-X232V-X245R-X249R, X018R-X020R-X022W-X024R-X076D-X101A-X198L-X215F-X249R, X020R-X090S-X101G-X103A-X104I-X116A-X183D-X213A-X215F-X232V-X245R, X018R-X020R-X022W-X024R-X076D-X101A-X198L-X211Q-X213A-X215F-X249R, X018R-X020R-X024R-X076D-X101A-X183D-X213A-X215F-X249R, X018R-X024R-X076D-X116A-X183D-X198L-X211Q-X213A-X249R, X043D-X045T-X078R-X101G-X103A-X104I-X232V-X245R-X269R, X018R-X024R-X076D-X101A-X183D-X215F-X249R, X018R-X020R-X024R-X076D-X101A-X183D-X198L-X213A-X249R, X020R-X022W-X101A-X103A-X104I-X116A-X183D-X198L-X211Q-X213A-X215F-X232V-X245R, X018R-X020R-X024R-X043D-X076D-X101G-X103A-X104I-X232V-X245R-X269R, X018R-X024R-X076D-X101A-X183D-X213A-X215F-X249R, X018R-X020R-X022W-X024R-X076D-X101A-X116A-X198L-X211Q-X213A-X215F-X249R, X018R-X020R-X043D-X101G-X103A-X104I-X217E-X232V-X245R, X076D-X103A-X104I-X232V-X245R, X045T-X076D-X078R-X101G-X103A-X104I-X232V-X245R-X249R, X018R-X022W-X024R-X076D-X101A-X183D-X211Q-X215F-X249R, X018R-X022W-X024R-X076D-X101A-X116A-X183D-X249R, X018R-X024R-X076D-X116A-X183D-X198L-X211Q-X215F-X249R, X018R-X020R-X043D-X076D-X078R-X101G-X103A-X104I-X217E-X232V-X245R, X076D-X103A-X104I-X245R, X018R-X020R-X024R-X076D-X101A-X116A-X211Q-X213A-X215F-X249R, X018R-X024R-X076D-X101A-X183D-X198L-X249R, X018R-X022W-X024R-X076D-X116A-X183D-X198L-X211Q-X215F-X249R, X018R-X024R-X076D-X116A-X183D-X213A-X215F-X249R, X018R-X022W-X024R-X076D-X116A-X183D-X198L-X211Q-X249R, X018R-X024R-X076D-X101G-X245R, X018R-X024R-X076D-X101A-X116A-X183D-X198L-X213A-X215F-X249R, X043R-X045T-X076D-X101G-X103A-X104I-X232V-X245R, X018R-X020R-X022W-X024R-X076D-X116A-X198L-X213A-X215F-X249R, X076D-X104I-X232V-X245R, X027R-X043R-X045T-X076D-X101G-X103A-X104I-X232V-X245R, X018R-X022W-X024R-X076D-X101A-X183D-X213A-X215F-X249R, X018R-X024R-X076D-X103A-X104I-X135I-X232V, X018R-X020R-X022W-X024R-X076D-X183D-X198L-X211Q-X249R, X018R-X020R-X022W-X024R-X076D-X101A-X116A-X183D-X198L-X215F-X249R, X018R-X024R-X076D-X101A-X116A-X183D-X211Q-X249R, X018R-X022W-X024R-X076D-X183D-X211Q-X213A-X215F-X249R, X076D-X101G-X103A-X104I-X232V-X249R, X005S-X018R-X022W-X024R-X076D-X101A-X213A-X215F-X249R, X018R-X024R-X076D-X116A-X183D-X215F-X249R, X018R-X024R-X076D-X183D-X198L-X215F-X249R, X018R-X020R-X024R-X076D-X101A-X116A-X183D-X249R, X018R-X022W-X024R-X076D-X116A-X183D-X211Q-X249R, X018R-X020R-X022W-X024R-X076D-X101A-X116A-X249R, X018R-X022W-X024R-X076D-X101A-X116A-X183D-X198L-X213A-X249R, X018R-X022W-X024R-X076D-X101A-X183D-X211Q-X213A-X249R, X018R-X020R-X024R-X076D-X116A-X198L-X249R, X018R-X024R-X076D-X183D-X211Q-X213A-X249R, X018R-X024R-X076D-X101A-X116A-X183D-X213A-X249R, X018R-X024R-X076D-X116A-X183D-X198L-X215F-X249R, X018R-X022W-X024R-X076D-X183D-X198L-X211Q-X215F-X249R, X018R-X022W-X024R-X076D-X183D-X249R, X018R-X022W-X024R-X076D-X101A-X183D-X198L-X215F-X249R, X018R-X020R-X043D-X045T-X076D-X101G-X103A-X104I-X232V-X245R, X020R-X022W-X101A-X103A-X104I-X183D-X198L-X215F-X232V-X245R, X076D-X101G-X103A-X104I-X249R, X018R-X020R-X024R-X076D-X183D-X198L-X215F-X249R, X018R-X020R-X022W-X024R-X076D-X101A-X183D-X215F-X249R, X018R-X020R-X024R-X076D-X211Q-X213A-X249R, X018R-X024R-X076D-X116A-X183D-X211Q-X213A-X249R, X018R-X024R-X076D-X116A-X183D-X198L-X249R, X018R-X020R-X024R-X076D-X211Q-X243D-X249R, X018R-X020R-X045T-X076D-X101G-X103A-X104I-X232V-X245R-X249R, X018R-X022W-X024R-X076D-X183D-X198L-X211Q-X213A-X249R, X018R-X024R-X076D-X101A-X116A-X183D-X198L-X211Q-X213A-X249R, X018R-X022W-X024R-X076D-X116A-X198L-X211Q-X213A-X215F-X249R, X024R-X076D-X101G, X018R-X020R-X024R-X076D-X101A-X198L-X213A-X215F-X249R, X018R-X022W-X024R-X076D-X116A-X183D-X211Q-X213A-X249R, X018R-X020R-X024R-X076D-X183D-X215F-X249R, X018R-X043D-X076D-X078R-X101G-X103A-X104I-X232V-X245R-X249R, X018R-X022W-X024R-X076D-X116A-X183D-X211Q-X213A-X245R, X020R-X024R-X076D-X078R-X101G-X103A-X104I-X232V-X245R-X249R, X018R-X020R-X045T-X101G-X103A-X104I-X232V-X245R-X249R, X018R-X024R-X076D-X101A-X183D-X198L-X211Q-X249R, X018R-X022W-X024R-X076D-X183D-X211Q-X213A-X249R, X018R-X020R-X024R-X076D-X116A-X198L-X211Q-X215F-X249R-X269S, X018R-X020R-X022W-

X024R-X076D-X101A-X116A-X183D-X198L-X211Q-X215F-X249R, X020R-X022W-X101A-X103A-X104I-X183D-X213A-X215F-X232V-X245R, X018R-X024R-X076D-X086V-X101A-X183D-X198L-X211Q-X249R, X018R-X076D-X101G-X198T-X232V, X018R-X020R-X024R-X076D-X101A-X116A-X183D-X198L-X211Q-X215F-X249R, X018R-X022W-X024R-X076D-X101A-X116A-X183D-X213A-X215F-X249R, X018R-X022W-X024R-X076D-X101A-X183D-X211Q-X213A-X215F-X249R, X018R-X024R-X076D-X183D-X249R-X248T, X018R-X076D-X104I-X245R-X249R, X018R-X022W-X024R-X076D-X101A-X116A-X183D-X198L-X215F-X249R, X018R-X022W-X024R-X076D-X116A-X183D-X213A-X215F-X249R, X018R-X020R-X022W-X024R-X076D-X116A-X183D-X211Q-X213A-X215F-X249R, X018R-X020R-X024R-X076D-X101A-X249R, X018R-X020R-X024R-X076D-X101A-X116A-X213A-X215F-X249R, X018R-X022W-X024R-X076D-X116A-X183D-X211Q-X215F-X249R, X018R-X022W-X024R-X076D-X116A-X183D-X198L-X211Q-X213A-X249R, X043R-X045T-X078R-X101G-X103A-X104I-X217E-X232V-X245R, X043R-X045T-X101G-X103A-X104I-X232V-X245R-X249R, X018R-X076D-X101G-X104I, X020R-X045T-X076D-X078R-X101G-X103A-X104I-X232V-X245R-X249R, X043D-X076D-X101G-X103A-X104I-X232V-X245R, X018R-X020R-X022W-X024R-X076D-X101A-X116A-X183D-X198L-X249R, X018R-X076D-X104I, X018R-X020R-X043D-X101G-X103A-X104I-X232V-X245R-X249R, X018R-X020R-X022W-X024R-X076D-X183D-X211Q-X249R, X018R-X024R-X076D-X101A-X183D-X198L-X211Q-X215F-X249R, X101G-X104I, X018R-X022W-X024R-X076D-X116A-X183D-X198L-X211Q-X213A-X215F-X249R, X018R-X020R-X024R-X076D-X101A-X183D-X211Q-X213A-X215F-X249R, X018R-X020R-X024R-X076D-X116A-X183D-X215F-X249R-X263D, X018R-X022W-X024R-X076D-X101A-X183D-X249R, X018R-X024R-X076D-X101A-X116A-X183D-X198L-X215F-X249R, X018R-X022W-X024R-X076D-X116A-X198L-X215F-X249R-X269H, X018R-X043D-X045T-X076D-X078R-X101G-X103A-X104I-X232V-X245R, X018R-X024R-X045T-X076D-X078R-X101G-X103A-X104I-X232V-X245R-X269R, X078R-X101G-X103A-X104I-X217E-X232V-X245R, X018R-X020R-X022W-X024R-X076D-X101A-X183D-X198L-X213A-X215F-X249R, X018R-X020R-X024R-X076D-X183D-X198L-X213A-X249R, X018R-X020R-X022W-X024R-X076D-X116A-X198L-X211Q-X215F-X249R, X018R-X020R-X022W-X024R-X076D-X116A-X183D-X211Q-X249R, X018R-X020R-X022W-X024R-X076D-X101A-X198L-X211Q-X213A-X249R, X018R-X020R-X022W-X024R-X076D-X249R, X020R-X022W-X101G-X103A-X104I-X116A-X183D-X198L-X211Q-X213A-X215F-X232V-X245R, X104I-X232V, X018R-X020R-X022W-X024R-X076D-X101A-X116A-X183D-X211Q-X215F-X249R, X018R-X020R-X022W-X024R-X076D-X101A-X116A-X183D-X198L-X211Q-X213A-X215F-X249R, X018R-X020R-X022W-X024R-X076D-X101A-X183D-X213A-X215F-X249R, X018R-X022W-X024R-X076D-X101A-X183D-X198L-X211Q-X213A-X249R, X018R-X022W-X024R-X076D-X101A-X183D-X198L-X249R, X043D-X045T-X101G-X103A-X104I-X232V-X245R-X269R, X018R-X020R-X024R-X076D-X101A-X183D-X198L-X211Q-X249R, X018R-X020R-X043R-X101G-X103A-X104I-X217E-X232V-X245R, X024R-X043R-X076D-X078R-X101G-X103A-X104I-X232V-X245R-X269R, X043R-X045T-X076D-X078R-X101G-X103A-X104I-X166F-X176P-X179V-X184T-X187P-X194P, X018R-X022W-X024R-X041E-X076D-X101A-X160T-X183D-X211Q-X213A-X249R, X018R-X020R-X022W-X024R-X076D-X116A-X183D-X198L-X211Q-X215F-X249R, X018R-X020R-X022W-X024R-X076D-X101A-X116A-X198L-X213A-X249R, X018R-X022W-X024R-X076D-X101A-X116A-X183D-X198L-X211Q-X213A-X249R, X018R-X020R-X024R-X076D-X198L-X213A-X249R, X018R-X020R-X022W-X024R-X076D-X116A-X183D-X198L-X211Q-X249R, X018R-X020R-X024R-X076D-X183D-X211Q-X215F-X249R, X024R-X076D-X104I, X018R-X076D-X101G-X232V, X018R-X024R-X076D-X101A-X116A-X183D-X198L-X211Q-X213A-X215F-X249R, X018R-X020R-X022W-X024R-X076D-X116A-X183D-X215F-X249R, X018R-X024R-X031F-X076D-X116A-X183D-X211Q-X213A-X215F-X249R, X018R-X024R-X076D-X101A-X116A-X183D-X198L-X213A-X249R-X269S, X018R-X020R-X024R-X076D-X101A-X116A-X198L-X215F-X249R, X018R-X043R-X076D-X078R-X101G-X103A-X104I-X232V-X245R-X269R, X018R-X020R-X024R-X076D-X101A-X114T-X198L-X211Q-X215F-X249R, X024R-X043R-X078R-X101G-X103A-X104I-X217E-X232V-X245R, X024R-X076D-X103A-X104I-X232V, X018R-X020R-X022W-X024R-X076D-X101A-X198L-X211Q-X215F-X249R, X101G-X104I-X232V, X018R-X022W-X024R-X076D-X183D-X198L-X213A-X215F-X249R, X018R-X022W-X024R-X076D-X183D-X198L-X211Q-X249R, X018R-X020R-X024R-X076D-X183D-X213A-X249R, X018R-X024R-X076D-X101A-X183D-X211Q-X215F-X249R, X018R-X020R-X022W-X024R-X076D-X116A-X211Q-X213A-X249R, X018R-X078R-X101G-X103A-X104I-X232V-X245R-X269R, X018R-X022W-X024R-X076D-X101A-X116A-X183D-X211Q-X215F-X249R-X260A, X076D-X249R, X018R-X022W-X024R-X076D-X183D-X211Q-X215F-X249R, X018R-X020R-X024R-X076D-X116A-X211Q-X215F-X249R, X018R-X020R-X024R-X076D-X213A-X249R, X018R-X020R-X022W-X024R-X076D-X116A-X183D-X198L-X249R, X018R-X020R-X022W-X024R-X076D-X101A-X183D-X249R, X076D-X104I-X249R, X020R-X022W-X101A-X103A-X104I-X116A-X183D-X211Q-X213A-X215F-X232V-X245R, X024R-X043R-X045T-X078R-X101G-X103A-X104I-X217E-X232V-X245R, X018R-X020R-X022W-X024R-X076D-X183D-X198L-X215F-X249R, X018R-X076D-X101G-X103A, X020R-X024R-X101G-X103A-X104I-X232V-X245R-X269R, X018R-X020R-X024R-X076D-X101A-X116A-X183D-X211Q-X249R, X101G-X103A-X232V, X024R-X076D-X101G-X232V, X018R-X022W-X024R-X076D-X101A-X183D-X198L-X211Q-X249R, X018R-X020R-X024R-X076D-X101A-X183D-X198L-X211Q-X215F-X249R, X018R-X020R-X024R-X076D-X183D-X198L-X249R, X018R-X022W-X024R-X076D-X101A-X116A-X183D-X198L-X211Q-X249R, X018R-X020R-X024R-X076D-X116A-X156V-X183D-X211Q-X215F-X249R-X269S, X045T-X076D-X101G-X103A-X104I-X232V-X245R-X249R, X018R-X020R-X024R-X076D-X101A-X183D-X198L-X249R, X018R-X020R-X022W-X024R-X076D-X198L-X211Q-X215F-X249R, X018R-X020R-X022W-X024R-X076D-X101A-X116A-X198L-X211Q-X215F-X249R, X018R-X020R-X022W-X024R-X076D-X116A-X249R, X018R-X076D-X101G, X018R-X024R-X076D-X116A-X183D-X198L-X213A-X215F-X249R, X018R-X020R-X022W-X024R-X076D-X101A-X116A-X198L-X213A-X215F-X249R, X018R-X024R-X076D-X101A-X116A-X183D-X198L-X211Q-X249R, X018R-X076D-X232V, X018R-X020R-X024R-X076D-X101A-X232V-X245R, X018R-

X043D-X045T-X076D-X101G-X103A-X104I-X232V-X245R, X018R-X022W-X024R-X076D-X183D-X213A-X215F-X249R, X018R-X024R-X076D-X101A-X116A-X211Q-X213A-X237D-X249R, X018R-X020R-X024R-X076D-X101A-X116A-X183D-X211Q-X249R-X275S, X018R-X022W-X024R-X076D-X101A-X116A-X183D-X198L-X211Q-X213A-X215F-X249R, X024R-X076D, X018R-X024R-X076D-X183D-X211Q-X215F-X249R, X018R-X022W-X024R-X076D-X116A-X183D-X198L-X213A-X215F-X249R, X076D-X104I-X232V-X249R, X018R-X076D-X103A-X232V, X018R-X020R-X024R-X076D-X101A-X116A-X183D-X198L-X211Q-X213A-X249R, X018R-X020R-X024R-X076D-X101A-X183D-X213A-X249R, X018R-X020R-X024R-X076D-X101A-X175E-X183D-X211Q-X215F-X249R, X018R-X020R-X043D-X078R-X101G-X103A-X104I-X217E-X232V-X245R-X273E, X020R-X024R-X043D-X045T-X076D-X101G-X103A-X104I-X232V-X245R, X005S-X101G-X103A-X104I-X232V-X245R-X249R, X103A-X104I-X232V, X018R-X020R-X024R-X068A-X076D-X101A-X116A-X213A-X215F-X249R, X018R-X022W-X024R-X076D-X101A-X198L-X215F-X249R-X275S, X018R-X024R-X076D-X183D-X198L-X211Q-X213A-X249R, and X043D-X045T-X101G-X103A-X104I-X232V-X245R, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: X018R-X024R-X043R-X076D-X249R-X269R, X018R-X022R-X024R-X043R-X076D-X249R, X018R-X043D-X101G-X103A-X104I-X232V-X245R, X020R-X043D-X101G-X103A-X104I-X232V-X245R, X043D-X101G-X103A-X104I-X232V-X245R-X269R, X043D-X078R-X101G-X103A-X104I-X232V-X245R, X043R-X076D-X101G-X103A-X104I-X232V-X245R, X022R-X043R-X101G-X103A-X104I-X232V-X245R, X043R-X078R-X101G-X103A-X104I-X232V-X245R, X020R-X076D-X101G-X103A-X104I-X232V-X245R, X043R-X076D-X101G-X103A-X104I-X232V-X245R, X022R-X076D-X101G-X103A-X104I-X232V-X245R, X076D-X078R-X101G-X103A-X104I-X232V-X245R, X018R-X024R-X043R-X076D-X249R, X018R-X024R-X076D-X242R-X249R, X018R-X024R-X076D-X249R-X269R, X018R-X022R-X024R-X076D-X249R, X018R-X024R-X076D-X078R-X249R, X018R-X024R-X043D-X076D-X249R-X269R, X018R-X022R-X024R-X043D-X076D-X249R, X018R-X024R-X043D-X076D-X078R-X249R, X020R-X101G-X103G-X104I-X232V-X245R, X020R-X101G-X103A-X104L-X232V-X245R, X020R-X101G-X103A-X104V-X232V-X245R, X020R-X101G-X103S-X104I-X232V-X245R, X020R-X101G-X103S-X104L-X232V-X245R, X020R-X101S-X103S-X104I-X232V-X245R, X020R-X101S-X103S-X104L-X232V-X245R, X020R-X101A-X103A-X104L-X232V-X245R, X020R-X101S-X103S-X104V-X232V-X245R, X020R-X101S-X103A-X104I-X232V-X245R, X020R-X101S-X103A-X104V-X232V-X245R, X020R-X101S-X103G-X104I-X232V-X245R, X020R-X101S-X103G-X104V-X232V-X245R, X020R-X101A-X103A-X104V-X232V-X245R, X020R-X101A-X103S-X104I-X232V-X245R, X020R-X101A-X103 S-X104V-X232V-X245R, X018R-X024R-X043R-X076D-X078R-X249R, X024R-X043D-X101G-X103A-X104I-X232V-X245R, X043D-X101G-X103A-X104I-X232V-X245R-X249R, X024R-X076D-X101G-X103A-X104I-X232V-X245R, X076D-X101G-X103A-X104I-X232V-X242R-X245R, X018R-X020R-X024R-X076D-X217E-X249R, X018R-X024R-X043R-X076D-X217E-X249R, X018R-X024R-X043D-X076D-X242R-X249R, X018R-X020R-X024R-X043R-X076D-X249R, X020R-X101A-X103G-X104V-X232V-X245R, X043D-X101G-X103A-X104I-X232V-X245R, X018R-X024R-X076D-X217E-X249R-X269R, and X018R-X024R-X076D-X217E-X242R-X249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X020R-X101A-X103A-X104I-X118R-X232V-X245R, X020R-X024R-X116A-X213A, X043R-X101A-X116A-X215F-X269R, X024R-X043R-X101A-X116A, X024R-X043R-X101A-X116A-X215F-X269R, X020R-X101G-X103A-X104I-X215F-X232V-X245R, X043R-X101A-X269R, X024R-X043R-X116A-X213A-X269R, X020R-X024R-X043R-X045T-X101A-X213A, X024R-X043R-X116A-X215F-X269R, X020R-X024R-X213A-X215F, X020R-X116A-X269R, X024R-X116A-X213A-X269R, X043R-X101A-X116A-X269R, X101G-X103A-X104I-X116A-X213A-X232V-X245R-X269R, X024R-X043R-X045T-X101A-X116A-X215F-X269R, X020R-X043R-X101A-X269R, X101A-X103A-X104I-X213A-X232V-X245R-X269R, X024R-X215F-X269R, X043R-X101A-X116A-X213A-X215F-X269R, X043R-X101A-X213A-X269R, X020R-X024R-X043R-X045T-X116A-X213A, X101G-X103A-X104I-X232V-X245R-X269R, X024R-X043R-X045T-X101A-X116A-X213A-X269R, X024R-X043R-X045T-X269R, X020R-X043R-X045T-X101A-X269R, X024R-X043R-X116A-X269R, X020R-X024R-X043R-X045T, X043R-X116A-X269R, X024R-X043R-X101A-X215F-X269R, X024R-X043R-X045T-X213A-X215F-X269R, X020R-X024R-X045T-X269R, X020R-X043R-X101A-X116A-X213A-X215F, X020R-X101G-X103A-X104I-X213A-X215F-X232V-X245R, X020R-X024R-X045T-X116A-X269R, X020R-X101A-X116A-X269R, X024R-X043R-X215F, X020R-X024R-X213A, X024R-X043R-X101A-X215F, X020R-X024R-X043R-X045T-X116A, X020R-X024R-X043R-X045T-X101A-X269R, X020R-X024R-X101A-X215F, X020R-X024R-X116A-X213A-X215F, X020R-X024R-X116A, X020R-X024R-X101A-X116A, X043R-X213A-X215F-X269R, X024R-X101A-X269R, X024R-X043R-X116A-X215F, X020R-X038A-X043R-X101A, X020R-X024R-X116A-X215F, X024R-X043R-X101A-X213A, X014L-X020R-X024R-X043R-X045T-X101A-X215F, X020R-X024R-X215F, X020R-X116A-X215F-X269R, X020R-X045T-X116A-X269R, X020R-X024R-X043R-X045T-X215F, and X020R-X024R-X043R-X045T-X116A-X213A-X215F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X043R-X076D-X101A-X103A-X104I-X158E-X188D-X232V-X245R-X248D-X249R-X271F, X024R-X043R-X076D-X101A-X103A-X104I-

X158E-X188D-X217E-X232V-X245R-X248D-X249R, X101A-X103A-X104I-X158E-X188D-X232V-X245R-X248D-X249R-X271F-X271F, X101A-X103A-X104I-X158E-X188D-X217E-X232V-X245R-X248D-X249R-X271F, X076D-X101G-X103A-X104I-X114V-X158E-X188D-X232V-X245R-X248D-X249R-X271F, X024R-X076D-X101G-X103A-X104I-X158E-X188D-X232V-X245R-X248D-X249R-X271F, X024R-X043R-X101A-X103A-X104I-X158E-X188D-X217E-X232V-X245R-X248D-X249R, X024R-X043R-X101A-X103A-X104I-X158E-X188D-X232V-X245R-X248D-X249R, X024R-X101A-X103A-X104I-X158E-X166D-X188D-X217E-X232V-X245R-X248D-X249R, X076D-X101G-X103A-X104I-X128L-X158E-X188D-X232V-X245R-X248D-X249R-X271F, and X043R-X076D-X101G-X103A-X104I-X158E-X166D-X188D-X232V-X245R-X248D-X249R-X271F, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X022A-X101G-X103A-X104I-X159D-X217E-X232V-X245R-X248D-X271F, X022A-X043R-X101G-X103A-X104I-X159D-X188D-X217E-X232V-X245R-X248D-X271F, X022A-X101G-X103A-X104I-X159D-X188D-X232V-X245R-X248D-X271F, X043R-X101A-X103A-X104I-X158E-X188D-X217E-X232V-X245R-X248D-X249R, X043R-X076D-X101A-X103A-X104I-X158E-X188D-X217E-X232V-X245R-X248D-X249R-X271F, X024R-X101G-X103A-X104I-X158E-X188D-X217E-X232V-X245R-X248D-X249R, X024R-X101G-X103A-X104I-X158E-X188D-X232V-X245R-X248D-X249R, X101G-X103A-X104I-X158E-X188D-X232V-X245R-X248D-X249R, X024R-X101G-X103A-X104I-X158E-X183D-X188D-X232V-X245R-X248D-X249R, X022A-X076D-X101G-X103A-X104I-X159D-X188D-X232V-X245R-X248D-X271F, X022A-X043R-X076D-X101G-X103A-X104I-X159D-X188D-X232V-X245R-X248D-X271F, X022A-X076D-X101G-X103A-X104I-X159D-X232V-X245R-X248D-X271F, X022A-X101G-X103A-X104I-X159D-X232V-X245R-X248D-X271F, X076D-X101A-X103A-X104I-X158E-X188D-X232V-X245R-X248D-X249R-X271F, X043R-X101A-X103A-X104I-X158E-X166D-X188D-X232V-X245R-X248D-X249R, X024R-X076D-X101A-X103A-X104I-X158E-X166D-X188D-X232V-X245R-X248D-X249R-X271F, X076D-X101A-X103A-X104I-X158E-X188D-X232V-X245R-X248D-X249R, X101A-X103A-X104I-X158E-X166D-X188D-X232V-X245R-X248D-X249R-X271F, X043R-X076D-X101A-X103A-X104I-X158E-X166D-X188D-X232V-X245R-X248D-X249R-X271F, X101G-X103A-X104I-X158E-X166D-X188D-X232V-X245R-X248D-X249R-X271F, X101A-X103A-X104I-X158E-X188D-X232V-X245R-X248D-X249R-X271F, X101A-X103A-X104I-X158E-X188D-X217E-X232V-X245R-X248D-X249R, X076D-X101A-X103A-X104I-X158E-X166D-X188D-X232V-X245R-X248D-X249R-X271F, X101G-X103A-X104I-X158E-X183D-X188D-X232V-X245R-X248D-X249R, X024R-X101G-X103A-X104I-X128L-X158E-X188D-X232V-X245R-X248D-X249R, X076D-X101G-X103A-X104I-X158E-X166D-X188D-X232V-X245R-X248D-X249R-X271F, X043R-X076D-X101A-X103A-X104I-X158E-X166D-X188D-X232V-X245R-X248D-X249R, and X076D-X101A-X103A-X104I-X158E-X188D-X217E-X232V-X245R-X248D-X249R-X271F, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X017R-X022A-X076D-X101G-X103A-X104I-X159D-X188D-X232V-X245R-X248D-X271F, X022A-X043R-X101G-X103A-X104I-X159D-X232V-X245R-X248D-X271F, X022A-X101G-X103A-X104I-X159D-X188D-X232V-X245R-X248D-X249R-X271F, X017R-X022A-X076D-X101G-X103A-X104I-X159D-X232V-X245R-X248D-X271F, X022A-X076D-X101G-X103A-X104I-X159D-X232V-X245R-X248D-X249R-X271F, X022A-X101G-X102A-X103A-X104I-X159D-X188D-X232V-X245R-X248D-X271F, and X022A-X043R-X076D-X101G-X103A-X104I-X159D-X232V-X245R-X248D-X249R-X271F, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X101S-X103A-X104I-X158E-X188D-X232V-X245R-X248D-X249R, X101 S-X103G-X104V-X158E-X188D-X232V-X245R-X248D-X249R, X101G-X103S-X104I-X158E-X188D-X232V-X245R-X248D-X249R, X101A-X103A-X104I-X158E-X188D-X232V-X245R-X248D-X249R, X101A-X103A-X104L-X158E-X188D-X232V-X245R-X248D-X249R, X101G-X103G-X104I-X158E-X188D-X232V-X245R-X248D-X249R, X101 S-X103G-X104I-X158E-X188D-X232V-X245R-X248D-X249R, X101S-X103S-X104I-X158E-X188D-X232V-X245R-X248D-X249R, X101 S-X103 S-X104V-X158E-X188D-X232V-X245R-X248D-X249R, X101A-X103S-X104I-X158E-X188D-X232V-X245R-X248D-X249R, X101A-X103S-X104I-X159E-X232V-X245R-X248D-X249R, X101S-X103A-X104I-X159E-X232V-X245R-X248D-X249R, X101G-X103A-X104L-X158E-X188D-X232V-X245R-X248D-X249R, X101A-X103A-X104L-X159E-X232V-X245R-X248D-X249R, X101A-X103S-X104L-X159E-X232V-X245R-X248D-X249R, X101G-X103S-X104L-X159E-X232V-X245R-X248D-X249R, X101 S-X103A-X104L-X159E-X232V-X245R-X248D-X249R, X101A-X103G-X104V-X159E-X232V-X245R-X248D-X249R, and X101S-X103A-X104V-X159E-X232V-X245R-X248D-X249R, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X026F-X051W-X104L-X106E, X026F-X031F-X078N-X102A-X160D, X020K-X100S-X116L-X158E-X166D-X243F, X033S-X043W-X218D-X239G-X243F, X022L-X038F-X048R-X062E-X100S-X186K, X101D-X103N-X116L-X144R-X215D, X104L-X105T-X213A-X217E-X256N, X043W-X101D-X212M-X243F, X026F-X048R-X105T-X213A-X218D-X224A, X024F-X101D-X118R-X215D-X250I-X272F, X121F-

X185E-X224A-X239G, X022L-X031F-X102A-X128D-X224A-X243F, X062E-X078N-X102A-X116L-X144R-X250I, X022L-X038F-X121F-X160D-X272F, X026F-X078N-X159C-X186K-X243F, X024F-X048R-X118R-X166D-X217E, X023A-X038F-X078N-X100S-X212M-X215D, X100S-X116L-X158E-X213A, X078N-X104L-X118R-X128D, X102A-X103N-X105T-X194E, X022L-X078N-X128D-X213A, X027R-X100S-X118R-X160D-X188D-X243F, X024F-X102A-X186K-X213A-X217E-X243F, X033S-X105T-X188D-X216F, X023A-X100S-X194E-X212M, X048R-X128D-X185E-X239G, X020K-X024F-X033S-X129E-X194E, X020K-X027R-X129E-X166D-X239G, X022L-X023A-X027R-X101D-X104L-X216F, X033S-X118R-X129E-X194E-X239G, X022L-X078N-X116L-X129E-X256N, X027R-X101D-X103N-X105T-X272F, X048R-X078N-X116L-X185E-X217E-X239G, X023A-X024F-X027R-X062E, X024F-X103N-X104L-X118R-X188D, X026F-X104L-X256N-X272F, X024F-X043W-X104L-X121F-X129E, X062E-X078N-X116L-X224A, X023A-X024F-X051W-X158E, X027R-X038F-X102A-X116L, X062E-X078N-X144R-X212M, X031F-X116L-X256N-X272F, X022L-X033S-X104L-X116L-X160D-X186K, X024F-X118R-X129E-X186K-X213A, X043W-X105T-X213A-X215D-X216F, X031F-X105T-X186K-X188D, X026F-X194E-X213A-X256N, and X103N-X160D-X250I-X256N, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X022A-X024R-X101D-X103A-X104I-X118R-X159D-X188D-X232V-X248D-X271F, X022A-X024R-X103A-X104I-X129E-X159D-X188D-X232V-X248D-X271F, X022A-X024R-X103A-X104I-X118R-X159D-X188D-X217D-X232V-X248D, X022A-X024R-X101D-X103A-X104I-X118R-X129E-X159D-X188D-X232V-X245R-X248D, X022A-X024R-X101D-X103A-X104I-X159D-X188D-X232V-X245R-X248D, X022A-X043R-X103A-X104I-X118R-X129E-X159D-X188D-X232V-X245R-X248D, X022A-X043R-X103A-X104I-X118R-X128I-X129E-X159D-X188D-X232V-X248D, X022A-X043R-X101D-X103A-X104I-X118R-X129E-X159D-X188D-X232V-X248D-X271F, X022A-X024R-X043R-X101D-X103A-X104I-X159D-X188D-X232V-X245R-X248D, X022A-X103A-X104I-X159D-X188D-X232V-X248D, X022A-X024R-X103A-X104I-X118R-X129E-X159D-X188D-X232V-X248D-X271F, X022A-X024R-X103A-X104I-X159D-X188D-X217D-X232V-X245R-X248D-X271F, X022A-X043R-X062E-X103A-X104I-X159D-X188D-X232V-X245R-X248D-X271F, X022A-X043R-X103A-X104I-X129E-X159D-X188D-X232V-X245R-X248D, X022A-X024R-X103A-X104I-X159D-X188D-X217D-X232V-X248D-X271F, X022A-X103A-X104I-X118R-X159D-X188D-X217D-X232V-X245R-X248D, X022A-X024R-X101D-X103A-X104I-X118R-X128I-X159D-X188D-X232V-X245R-X248D, X022A-X024R-X043R-X103A-X104I-X159D-X188D-X217D-X232V-X248D-X271F, X022A-X043R-X103A-X104I-X118R-X159D-X188D-X217D-X232V-X248D-X271F, X022A-X043R-X103A-X104I-X118R-X159D-X188D-X232V-X248D-X271F, X022A-X103A-X104I-X128I-X129E-X159D-X188D-X232V-X248D-X271F, X022A-X103A-X104I-X159D-X188D-X217D-X232V-X245R-X248D-X271F, X022A-X043R-X103A-X104I-X128I-X159D-X188D-X232V-X245R-X248D, X022A-X101D-X103A-X104I-X118R-X159D-X188D-X217D-X232V-X245R-X248D-X271F, X022A-X103A-X104I-X118R-X129E-X159D-X188D-X232V-X245R-X248D-X271F, X022A-X024R-X043R-X103A-X104I-X118R-X159D-X188D-X217D-X232V-X248D, X022A-X062E-X103A-X104I-X118R-X159D-X188D-X232V-X245R-X248D, X022A-X043R-X101D-X103A-X104I-X118R-X129E-X159D-X188D-X217D-X232V, X022A-X024R-X103A-X104I-X159D-X188D-X217D-X232V-X248D, X022A-X024R-X043R-X103A-X104I-X118R-X128I-X129E-X159D-X188D-X217D-X232V-X248D-X271F, and X022A-X103A-X104I-X118R-X159D-X188D-X217D-X232V-X245R-X248D-X271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X020K-X024F-X062E-X188D-X239G, X024F-X062E-X116L-X239G, X020K-X023A-X062E-X188D, X020K-X023A-X024F-X062E-X118R-X188D-X213A, X020K-X043W-X062E-X116L-X188D-X213A-X239G, X023A-X062E-X116L-X118R, X023A-X024F-X062E-X116L-X118R, X024F-X116L, X024F-X062E-X188D-X213A, X023A-X062E-X116L-X118R-X188D-X239G, X020K-X024F-X062E, X020K-X043W-X062E-X116L-X239G, X024F-X062E-X116L-X213A-X239G, X020K-X024F-X043W-X062E-X116L-X213A, X020K-X023A-X024F-X062E-X116L-X188D-X213A, X024F-X062E-X188D-X239G, X023A-X043W-X062E-X116L-X118R-X213A, X062E-X188D-X239G, X020K-X024F-X062E-X239G, X024F-X116L-X118R-X188D-X239G, X020K-X023A-X062E-X116L-X118R-X213A, X020K-X023A-X024F-X062E-X188D-X213A-X239G, X024F-X043W-X118R-X188D, X023A-X024F-X116L-X118R-X188D-X213A, X020K-X023A-X043W-X116L-X188D-X213A-X239G, X023A-X024F-X116L-X188D-X239G, X023A-X043W-X116L-X118R-X188D, X023A-X024F-X118R-X188D-X239G, X023A-X024F-X043W-X062E-X116L-X118R, X020K-X043W-X188D-X213A, X024F-X062E-X118R-X239G, X023A-X043W-X188D-X213A, X020K-X024F-X043W-X062E-X116L-X118R-X188D-X239G, X020K-X116L-X188D-X239G, X020K-X043W-X062E-X118R, X020K-X043W-X116L-X188D-X213A, X020K-X024F, X023A-X043W-X116L-X239G, X023A-X024F-X043W-X116L-X118R-X188D-X239G, X020K-X023A-X043W-X213A, and X023A-X024F-X062E-X118R-X213A-X239G, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X020K-X023A-X043W-X118R-X128I-X129E-X159D-X188D, X024F-X118R-X128I-X129E-X159D, X020K-X024F-X062E-X116L-X118R-X188D, X020K-X062E-X116L-X188D, X062E-X116L-X118R-X213A, X020K-X023A-X062E-X116L-X188D, X062E-X116L-X118R-X188D, X020K-X062E-X116L-X213A, X020K-X023A-X062E-X116L, X020K-X062E-X188D-X213A, X020K-X062E, X020K-X024F-X062E-X116L-X188D, X020K-X043W-X062E-X116L-X188D, X020K-X024F-X062E-X188D-X213A, X062E-X116L-X188D-X213A, X020K-X062E-X116L, X020K-X023A-X062E-X116L-X188D-X213A, X023A-X024F-X062E-X116L-X213A, X022A-X043R-X103A-X104I-X128I-X129E-X159D-X188D-X232V-X245R-X248D, X022A-X043R-X103A-X104I-X118R-X128I-X129E-X159D-X188D-X232V-X248D-X271F, X024F-X062E-X116L-X188D, X022A-X024R-X103A-X104I-X118R-X128I-X129E-X159D-X188D-X232V-X248D, X023A-X062E-X116L-X188D, X043W-X062E-X116L, X020K-X023A-X116L-X188D, X043W-X062E-X116L-X188D, X024F-X062E-X116L, X062E-X116L-X188D, and X022A-X024R-X103A-X104I-X128I-X159D-X188D-X232V-X248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X087R-X101G-X103A-X104I-X109R-X212P-X232V-X245R-X271V, X101G-X103A-X104I-X109R-X232V-X245R, X101G-X103A-X104I-X109R-X212P-X232V-X245R-X271V, X101G-X103A-X104I-X109R-X212P-X232V-X245R, X076D-587R-X103A-X104I-X212P-X271V, X076D-X103A-X104I-X109R, X076D-X103A-X104I-X212P-X271V, X076D-X103A-X104I-X109R-X245R, and X076D-X103A-X104I-X212P-X245L-X271V, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X024R-X086W-X118R, X024R-X078R-X086W-X243F, X024R-X033S-X086S-X087N-X209A, X033S-X118R, X024R-X078R-X086W-X118R-X270T, X024R-X033S-X086W-X118R, X078R-X086W-X243F, X033S-X078R-X086W-X118R-X209A, X033S-X078R-X209A, X086W-X118R-X243F, X024R-X086W, X078R-X086W-X235F, X024R-X118R, X024R-X086R, X101G-X103A-X104I-X232V, X024R-X033S-X078R-X086W-X118R, X024R-X118R-X209A, X209A-X241R, X033S-X086W-X243F, X033S-X172V-X209A, X118R-X209A-X243F, X024R-X086S-X141G, X024R-X118R-X209A-X243F, X024R-X033S-X086S-X085N-X235F, X024R-X033S-X133V, X024R-X033S-X078R-X086W, X024R-X086W-X209A, X024R-X241R, X033S-X118R-X243F, X024R-X235F, X024R-X078R-X086W, X024R-X118R-X209A-X235F, X024R-X209A-X241R, X033S-X118R-X241R, X086W-X118R-X209A, X033S-X118R-X159D-X209A, X033S-X078R-X086W, X024R-X086W-X243F, X118R-X209A, X024R-X086W-X118R-X203I, X078R-X209A-X235F, X024R-X033S-X241R, X078R-X118R, X033S-X118R-X209A-X243F, X021M-X024R-X033S, X024R-X033S-X086W, X033S-X235F, X078R-X086W-X209A, X024R-X033S-X209A-X235F, X033S-X086W-X118R, X024R-X033S-X078R-X209A, X033S-X086W-X118R-X209A-X243F, X086W-X209A-X243F, X005S-X078R-X118R-X241R, X024R-X174T, X033S-X209A-X243F, X086W-X118R-X133V, X024R-X033S-X118R, X024R-X086W-X209A-X235F, X086W-X209A, X008T-X024R, X086W-X118R, X033S-X241R, X005S-X024R-X033S-X243F, X024R-X209A-X242P, X024R-X033S-X078R-X118R, X024R-X033S-X194T, X024R-X243F, X024R-X209A, X024R-X033S-X118R-X209A, X033S-X086W, X024R-X033S, X024R-X033S-X078R-X243F, X086W-X243F, X033S-X118D-X138V-X209A, X033S-X209A-X235F, X024R-X086R-X118R, X033S-X201S, X024R-X239Q, X033S-X118R-X209A-, X078R-X086W, X235F-X243F, X024R-X209A-X235F, X118R-X172V, X017Y-X024R-X033S-X086W, X033S-X148F, X024R-X118R-X235F, X033S-X078R, X033S-X243F, X024C-X033S, X118R-X194T, X033S-X209A, X118R-X209A-X235F, X024R-X033S-X209A-X243F, X024R-X033S-X235F, X024R-X033S-X118R-X235F, X024R-X141G, X024R-X274I, X024R-X033S-X209A, X086W-X235F, X024R-X209A-X243F, X004E-X033S-X078R, X086W-X209A-X235F, X015T-X033S, X033S-X086W-X156L-X209A, X024R-X118R-X243F-X269H, X209A-X235F, X024R-X247H, X024R-X033S-X228T, X078R-X235F, X024R-X033S-X174V-X235F, X024R-X235F-X243F, X024R-X033S-X235F-X241R, X024R-X033S-X151V, X024R-X104A, X033S-X048T, X012H-X104A-X118R, X118R-X235F, X033S-X253A, X143A-X209A, X024R-X033S-X243F, X033S-X239T, X209A-X243F, X024R-X033S-X129H-X184D-X253M, X024R-X085V-X086W-X118R-X235F, X024R-X272P, and X024R-X269C, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X020R-X087D-X101G-X103A-X104I-X232V-X245R, X020R-X101G-X103A-X104I-X150L-X232V-X245R, X018R-X020R-X024R-X076D-X087D-X249R, X018R-X020R-X024R-X076D-X150L-X249R, X018R-X024R-X043R-X076D-X087D-X249R, X018R-X024R-X043R-X076D-X150L-X249R, X018R-X024R-X076D-X078R-X087D-X249R, X018R-X024R-X076D-X078R-X150L-X249R, X018R-X024R-X076D-X087D-X249R-X269R, X018R-X024R-X076D-X087D-X242R-X249R, X018R-X024R-X076D-X087D-X150L-X249R, X018R-X024R-X076D-X150L-X249R, X018R-X087D-X101G-X103A-X104I-X232V-X245R, X018R-X101G-X103A-X104I-X150L-X232V-X245R, X018R-X022R-X024R-X076D-X087D-X249R, X018R-X022R-X024R-X076D-X150L-X249R, X043R-X087D-X101G-X103A-X104I-X232V-X245R-X269R, X043R-X101G-X103A-X104I-X150L-X232V-X245R, X024R-X087D-X101G-X103A-X104I-X232V-X245R, X024R-X101G-X103A-X104I-X150L-X232V-X245R, X078R-X087D-X101G-X103A-X104I-X232V-X245R, X078R-X101G-X103A-X104I-X150L-X232V-X245R, X087D-X101G-X103A-X104I-X232V-X245R-X269R, X101G-X103A-X104I-X150L-X232V-X245R-X249R, X101G-X103A-X104I-X150L-X232V-X245R-X269R, X022R-X087D-X101G-X103A-X104I-X232V-X245R, X018R-X024R-X043D-X076D-X150L-X249R, X043R-X087D-X101G-X103A-X104I-X232V-X245R, X022R-X101G-X103A-X104I-X150L-X232V-X245R, X018R-X024R-X043D-X076D-X087D-X249R, X018R-X024R-X076D-X087D-X249R, X018R-X024R-X076D-X150L-X242R-X249R, X043R-X101G-X103A-X104I-X150L-X232V-X245R-X269R, X076D-X101G-X103A-X104I-X150L-X232V-X245R, X087D-X101G-X103A-X104I-X232V-X242R-X245R, X101G-X103A-X104I-X150L-X232V-X245R, X076D-X087D-X101G-X103A-X104I-X232V-X245R, X087D-X101G-X103A-X104I-X232V-X245R, and X101G-X103A-X104I-X150L-X232V-X242R-X245R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X024R-X101G-X103A-X104I-X129Q-X158E-X188D-X217E-X232V-X245R-X248D-X249R, X024R-X101G-X103A-X104I-X130A-X158E-X183D-X188D-X232V-X245R-X248D-X249R, X024R-X101G-X103A-X104I-X129Q-X158E-X183D-X188D-X232V-X245R-X248D-X249R, X101G-X103A-X104I-X130A-X158E-X188D-X232V-X245R-X248D-X249R, X024R-X101G-X103A-X104I-X129Q-X158E-X188D-X232V-X245R-X248D-X249R, X024R-X101G-X103A-X104I-X130A-X158E-X188D-X232V-X245R-X248D-X249R, X024R-X101G-X103A-X104I-X129Q-X130A-X158E-X183D-X188D-X232V-X245R-X248D-X249R, X024R-X101G-X103A-X104I-X128L-X129Q-X158E-X188D-X232V-X245R-X248D-X249R, X024R-X101G-X103A-X104I-X129Q-X130A-X158E-X188D-X232V-X245R-X248D-X249R, X101G-X103A-X104I-X129Q-X158E-X188D-X232V-X245R-X248D-X249R, X101G-X103A-X104I-X129Q-X130A-X158E-X188D-X232V-X245R-X248D-X249R, X024R-X101G-X103A-X104I-X128L-X129Q-X130A-X158E-X188D-X232V-X245R-X248D-X249R, X101G-X103A-X104I-X128L-X129Q-X158E-X188D-X232V-X245R-X248D-X249R, and X024R-X027R-X101G-X103A-X104I-X128L-X129Q-X130A-X158E-X188D-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X101G-X103A-X104I-X232V-X222Q-X245R, X101G-X103A-X104I-X158E-X188D-X222S-X232V-X245R-X248D-X249R, X101G-X103A-X104I-X158E-X188D-X222Q-X232V-X245R-X248D-X249R, X076D-X101G-X103A-X104I-X232V-X222Q-X245R, X101G-X103A-X104I-X232V-X222S-X245R, X076D-X101G-X103A-X104I-X232V-X222S-X245R, and X076D-X101G-X103A-X104I-X158E-X188D-X222S-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X024R-X101G-X103A-X104I-X128L-X129Q-X158E-X188D-X232V-X245R-X248D-X249R, X101G-X103A-X104I-X130A-X158E-X188D-X232V-X245R-X248D-X249R, X024R-X101G-X103A-X104I-X158E-X188D-X232V-X245R-X248D-X249R, X101G-X103A-X104I-X128L-X129Q-X158E-X188D-X232V-X245R-X248D-X249R, X101G-X103A-X104I-X129Q-X130A-X158E-X188D-X232V-X245R-X248D-X249R, X101G-X103A-X104I-X130A-X158E-X183D-X188D-X217E-X232V-X245R-X248D-X249R, X024R-X101G-X103A-X104I-X128L-X129Q-X130A-X158E-X188D-X232V-X245R-X248D-X249R, X024R-X101G-X103A-X104I-X129Q-X158E-X188D-X217E-X232V-X245R-X248D-X249R, X101G-X103A-X104I-X128L-X130A-X158E-X188D-X217E-X232V-X245R-X248D-X249R, X024R-X101G-X103A-X104I-X128L-X129Q-X158E-X183D-X188D-X232V-X245R-X248D-X249R, X024R-X101G-X103A-X104I-X128L-X129Q-X130A-X158E-X183D-X188D-X232V-X245R-X248D-X249R, X024R-X101G-X103A-X104I-X128L-X129Q-X158E-X188D-X232V-X245R-X248D-X249R-X271G, X101G-X103A-X104I-X129Q-X158E-X183D-X188D-X232V-X245R-X248D-X249R, X024R-X101G-X103A-X104I-X130A-X158E-X188D-X217E-X232V-X245R-X248D-X249R, X024R-X101G-X103A-X104I-X128L-X158E-X183D-X188D-X232V-X245R-X248D-X249R, X101G-X103A-X104I-X129Q-X158E-X188D-X217E-X232V-X245R-X248D-X249R, and X024R-X101G-X103A-X104I-X128L-X130A-X158E-X188D-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention further provides isolated subtilisin variants, wherein the subtilisin variants are mature forms having proteolytic activity and comprise amino acid sequences comprising a combination of amino acid substitutions selected from: X101G-X103A-X104I, X22A-X101A-X209E, S103G-L111V-G159E, X22A-X103G-X159E, X22A-X111V-X159E, X22A-X128N-X271F-X209E, X22A-X103G-X111V, X62E-X111V-X128N, X22A-X111V-X128N, X22A-X62E-X111V, X101A-X103G-X104L-X188D, X101G-X103A-X104I-X159D, X101A-X103G-X104L-X128N, X22A-X101A-X159E, X101A-X103G-X104L, X101A-X103G-X104L-X159E, X22A-X101A-X103G-X104L, X101A-X103G-X104L-X209E, X22A-X209E-X271F, X22A-X101A-X271F, and X101A-X209E-X271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X103A-X104I-X159D-X232V-X236H-X245R-X248D-X252K, X101G-X104I-X159D-X232V-X236H-X245R-X248D-X252K, X101G-X103A-X159D-X232V-X236H-X245R-X248D-X252K, X101G-X103A-X104L-X232V-X236H-X245R-X248D-X252K, X101G-X103A-X104L-X159D-X236H-X245R-X248D-X252K, X101G-X103A-X104L-X159D-X232V-X245R-X248D-X252K, X101G-X103A-X104L-X159D-X232V-X236H-X248D-X252K, X101G-X103A-X104L-X159D-X232V-X236H-X245R-X252K, and X101G-X103A-X104L-X159D-X232V-X236H-X245R-X248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X101G-X103A-X104I-X159D-X232V-X245R-X248D, X101G-X103A-X104I-X159D-X232V-X245R-X248D-X271F, X101G-X103A-X104I-

X159D-X232V-X245R-X248D-X238R, X101G-X103A-X104I-X159D-X232V-X245R-X248D-X248R, X101G-X103A-X104I-X159D-X232V-X245R-X248D-X253R, X101G-X103A-X104I-X159D-X232V-X245R-X248D-X24R, X101G-X103A-X104I-X159D-X232V-X245R-X248D-X76D, X101G-X103A-X104I-X159E-X232V-X245R-X248D-X249R, X101G-X103A-X104I-X159E-X232V-X245R-X248D-X271F, X101G-X103A-X104I-X158E-X232V-X245R-X248D-X249R, X101G-X103A-X104I-X158E-X232V-X245R-X248D-X271F, X22A-X101G-X103A-X104I-X159D-X232V-X245R-X248D-X249R, X22A-X101G-X103A-X104I-X159D-X232V-X245R-X248D-X271F, X62E-X101G-X103A-X104I-X159D-X232V-X245R-X248D-X249R, and X62E-X101G-X103A-X104I-X159D-X232V-X245R-X248D-X271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X20R-X43R-X249R, X20R-X22R-X43R, X20R-X43R-X242R, X20R-X43R-X271L, X20R-X43R-X244R, X20R-X24R-X43R-X242R, X9A-X22R-X78R-X212F-X241R, X9A-X20R-X43R-X212F, X9A-X43R-X212F, X20R-X43R-X212F, X20R-X22R-X43R-X212F, X24R-X78R-X212F, X9A-X43R-X78R, X9A-X43R-X78R-X242R, X9A-X20R-X43R-X78R, X20R-X24R-X43R-X78R-X242R, X22R-X24R-X78R-X212F, X9A-X20R-X43R-X78R-X242R, X20R-X43R-X78R-X249R, X20R-X43R-X78R, X9A-X78R-X212F, X9A-X22R-X43R-X78R, X9A-X20R-X24R-X43R, X9A-X22R-X78R-X212F, X4R-X9A-X22R-X78R-X212F, X20R-X24R-X43R, X1R-X9A-X43R, X20R-X24R-X43R-X115R, X9A-X24R-X43R, X20R-X22R-X24R-X43R, X1R-X24R-X43R, X9A-X20R-X24R-X43R-X242R, X9A-X20R-X22R-X78R-X212F, X9A-X24R-X43R-X244R, X9A-X24R-X43R-X242R, X4R-X9A-X22R-X24R-X212F, and X22R-X24R-X43R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X101G-X103A-X104I-X232V-X245R-X248D, X101G-X103A-X104I-X159D-X232V-X245R, X101G-X103A-X104I-X159R-X232V-X245R-X248D, X101G-X103A-X104I-X159D-X232V-X245R-X248R, X101G-X103A-X104I-X232V-X245R, X101G-X103A-X104I-X232V-X245R-X248R, X101G-X103A-X104I-X159R-X232V-X245R-X248R, and X101G, X103A, X104I, X232V, X236H, X245R, and X252K, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X16S, X22A, X24R, X62E, X76D, X89P, X101A/G, X103G/A, X104L/I, X111V, X128N, X129E, X232V, X148I, X158E, X159D/E, X166D, X186H, X188D, X209E, X236H, X238R, X245R, X248D/R, X249R, X252K/R, X253R, and X271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: N062E-A158E, S103G-A158E, S128N-A158E, A016S-A158E, V104L-A158E, E089P-A158E, L111V-A158E, T022A-A158E, S101A-A158E, L148I-A158E, P129E-A158E, T022A-E089P, A016S-E089P, N062E-E089P, N062E-E271F, A158E-E271F, R186H-E271F, P129E-E271F, L111V-E271F, Y209E-E271F, A016S-E271F, S188D-E271F, T022A-E271F, G159E-E271F, V104L-E271F, S101A-E271F, E089P-E271F, S128N-E271F, S103G-E271F, L148I-E271F, H249R-E271F, N062E-G159E, A016S-G159E, S128N-G159E, L148I-G159E, L111V-G159E, E089P-G159E, T022A-G159E, P129E-G159E, S103G-G159E, V104L-G159E, A158E-G159E, S101A-G159E, A158E-H249R, L111V-H249R, P129E-H249R, N062E-H249R, A016S-H249R, R186H-H249R, L148I-H249R, G159E-H249R, S101A-H249R, S188D-H249R, V104L-H249R, Y209E-H249R, T022A-H249R, S128N-H249R, S103G-H249R, E089P-H249R, T022A-L111V, S101A-L111V, A016S-L111V, V104L-L111V, N062E-L111V, S103G-L111V, E089P-L111V, A016S-L148I, N062E-L148I, T022A-L148I, P129E-L148I, V104L-L148I, S103G-L148I, S128N-L148I, S101A-L148I, E089P-L148I, L111V-L148I, A016S-N062E, T022A-N062E, N062E-P129E, T022A-P129E, S128N-P129E, A016S-P129E, S101A-P129E, V104L-P129E, E089P-P129E, S103G-P129E, L111V-P129E, N062E-R186H, S128N-R186H, S101A-R186H, T022A-R186H, A016S-R186H, A158E-R186H, E089P-R186H, P129E-R186H, G159E-R186H, S103G-R186H, V104L-R186H, L111V-R186H, L148I-R186H, N062E-S101A, T022A-S101A, A016S-S101A, E089P-S101A, N062E-S103G, T022A-S103G, A016S-S103G, S101A-S103G, E089P-S103G, N062E-S128N, A016S-S128N, T022A-S128N, S101A-S128N, V104L-S128N, E089P-S128N, S103G-S128N, L111V-S128N, L111V-S188D, N062E-S188D, A016S-S188D, L148I-S188D, T022A-S188D, S128N-S188D, S101A-S188D, V104L-S188D, E089P-S188D, P129E-S188D, G159E-S188D, R186H-S188D, S103G-S188D, A158E-S188D, A016S-T022A, A016S-V104L, T022A-V104L, S101A-V104L, N062E-V104L, S103G-V104L, E089P-V104L, G159E-Y209E, L111V-Y209E, S101A-Y209E, A016S-Y209E, S128N-Y209E, L148I-Y209E, P129E-Y209E, N062E-Y209E, T022A-Y209E, S103G-Y209E, A158E-Y209E, S188D-Y209E, V104L-Y209E, E089P-Y209E, and R186H-Y209E, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: N018R-W241R, G020R-W241R, S024R-W241R, S009A-W241R, G020R-W241R, V004R-W241R, N043R-W241R, S078R-W241R, T022R-W241R, G115R-W241R, A001R-W241R, S212F-W241R, L082R-W241R, N018R-V244R, S024R-V244R, S078R-V244R, G020R-V244R, S212F-V244R, S009A-V244R, L082R-V244R, A001R-V244R, N043R-V244R, T022R-V244R, V004R-V244R, G115R-V244R, W241R-V244R, S242R-V244R, A001R-V004R, S009A-T022R, N018R-T022R, G020R-T022R, V004R-T022R, A001R-T022R, S024R-S242R, N018R-S242R, V004R-S242R, G020R-S242R, S212F-S242R, L082R-S242R, S078R-S242R, A001R-S242R, S009A-S242R, T022R-S242R, G115R-S242R, N043R-S242R, W241R-S242R, N018R-S212F, T022R-S212F, V004R-S212F, S024R-S212F, A001R-S212F, G115R-S212F, G020R-S212F, S009A-S212F, N043R-S212F, S078R-S212F, L082R-S212F, S009A-S078R, G020R-S078R, S024R-S078R, T022R-S078R, N018R-S078R, V004R-S078R, A001R-S078R, N043R-S078R, T022R-S024R, G020R-S024R, N018R-S024R, A001R-S024R, V004R-S024R, S009A-S024R, V004R-S009A, A001R-S009A, S242R-N269R, S024R-N269R, G020R-N269R, T022R-N269R, H249R-N269R, S212F-N269R, N043R-N269R, V244R-N269R, A001R-N269R, N018R-N269R, S078R-N269R, S009A-N269R, G115R-N269R, W241R-N269R, V004R-N269R, L082R-N269R, N018R-N043R, G020R-N043R, V004R-N043R, T022R-N043R, S009A-N043R, A001R-N043R, S024R-N043R, S009A-N018R, V004R-N018R, A001R-N018R, S024R-L082R, S009A-L082R, N018R-L082R, A001R-L082R, S078R-L082R, G020R-L082R, T022R-L082R, V004R-L082R, N043R-L082R, N043R-H249R, G020R-H249R, V004R-H249R, N018R-H249R, S009A-H249R, S212F-H249R, T022R-H249R, S024R-H249R, G115R-H249R, A001R-H249R, L082R-H249R, S242R-H249R, W241R-H249R, V244R-H249R, S078R-H249R, N018R-G115R, G020R-G115R, T022R-G115R, S078R-G115R, S009A-G115R, V004R-G115R, A001R-G115R, L082R-G115R, N043R-G115R, S024R-G115R, S009A-G020R, N018R-G020R, V004R-G020R, A001R-G020R, S009A-E271L, G020R-E271L, S024R-E271L, V244R-E271L, W241R-E271L, N043R-E271L, T022R-E271L, H249R-E271L, S212F-E271L, G115R-E271L, S242R-E271L, S078R-E271L, V004R-E271L, N269R-E271L, A001R-E271L, N018R-E271L, and L082R-E271L, wherein the amino acid positions of the subtilisin variant are numbered by correspondence with the amino acid sequence of *B. amyloliquefaciens* subtilisin BPN' set forth as SEQ ID NO:1.

The present invention further provides isolated subtilisin variants, wherein said subtilisin variant is a mature form having proteolytic activity and comprises an amino acid sequence comprising a combination of amino acid substitutions selected from: G020R-N043R, N062E-A158E, S103G-A158E, S128N-A158E, A016S-A158E, V104L-A158E, E089P-A158E, L111V-A158E, T022A-A158E, S101A-A158E, L148I-A158E, P129E-A158E, T022A-E089P, A016S-E089P, N062E-E089P, N062E-E271F, A158E-E271F, R186H-E271F, P129E-E271F, L111V-E271F, Y209E-E271F, A016S-E271F, S188D-E271F, T022A-E271F, G159E-E271F, V104L-E271F, S101A-E271F, E089P-E271F, S128N-E271F, S103G-E271F, L148I-E271F, H249R-E271F, N062E-G159E, A016S-G159E, S128N-G159E, L148I-G159E, L111V-G159E, E089P-G159E, T022A-G159E, P129E-G159E, S103G-G159E, V104L-G159E, A158E-G159E, S101A-G159E, A158E-H249R, L111V-H249R, P129E-H249R, N062E-H249R, A016S-H249R, R186H-H249R, L148I-H249R, G159E-H249R, S101A-H249R, S188D-H249R, V104L-H249R, Y209E-H249R, T022A-H249R, S128N-H249R, S103G-H249R, E089P-H249R, T022A-L111V, S101A-L111V, A016S-L111V, V104L-L111V, N062E-L111V, S103G-L111V, E089P-L111V, A016S-L148I, N062E-L148I, T022A-L148I, P129E-L148I, V104L-L148I, S103G-L148I, S128N-L148I, S101A-L148I, E089P-L148I, L111V-L148I, A016S-N062E, T022A-N062E, N062E-P129E, T022A-P129E, S128N-P129E, A016S-P129E, S101A-P129E, V104L-P129E, E089P-P129E, S103G-P129E, L111V-P129E, N062E-R186H, S128N-R186H, S101A-R186H, T022A-R186H, A016S-R186H, A158E-R186H, E089P-R186H, P129E-R186H, G159E-R186H, S103G-R186H, V104L-R186H, L111V-R186H, L148I-R186H, N062E-S101A, T022A-S101A, A016S-S101A, E089P-S101A, N062E-S103G, T022A-S103G, A016S-S103G, S101A-S103G, E089P-S103G, N062E-S128N, A016S-S128N, T022A-S128N, S101A-S128N, V104L-S128N, E089P-S128N, S103G-S128N, L111V-S128N, L111V-S188D, N062E-S188D, A016S-S188D, L148I-S188D, T022A-S188D, S128N-S188D, S101A-S188D, V104L-S188D, E089P-S188D, P129E-S188D, G159E-S188D, R186H-S188D, S103G-S188D, A158E-S188D, A016S-T022A, A016S-V104L, T022A-V104L, S101A-V104L, N062E-V104L, S103G-V104L, E089P-V104L, G159E-Y209E, L111V-Y209E, S101A-Y209E, A016S-Y209E, S128N-Y209E, L148I-Y209E, P129E-Y209E, N062E-Y209E, T022A-Y209E, S103G-Y209E, A158E-Y209E, S188D-Y209E, V104L-Y209E, E089P-Y209E, R186H-Y209E, N018R-W241R, G020R-W241R, S024R-W241R, S009A-W241R, G020R-W241R, V004R-W241R, N043R-W241R, S078R-W241R, T022R-W241R, G115R-W241R, A001R-W241R, S212F-W241R, L082R-W241R, N018R-V244R, S024R-V244R, S078R-V244R, G020R-V244R, S212F-V244R, S009A-V244R, L082R-V244R, A001R-V244R, N043R-V244R, T022R-V244R, V004R-V244R, G115R-V244R, W241R-V244R, S242R-V244R, A001R-V004R, S009A-T022R, N018R-T022R, G020R-T022R, V004R-T022R, A001R-T022R, S024R-S242R, N018R-S242R, V004R-S242R, G020R-S242R, S212F-S242R, L082R-S242R, S078R-S242R, A001R-S242R, S009A-S242R, T022R-S242R, G115R-S242R, N043R-S242R, W241R-S242R, N018R-S212F, T022R-S212F, V004R-S212F, S024R-S212F, A001R-S212F, G115R-S212F, G020R-S212F, S009A-S212F, N043R-S212F, S078R-S212F, L082R-S212F, S009A-S078R, G020R-S078R, S024R-S078R, T022R-S078R, N018R-S078R, V004R-S078R, A001R-S078R, N043R-S078R, T022R-S024R, G020R-S024R, N018R-S024R, A001R-S024R, V004R-S024R, S009A-S024R, V004R-S009A, A001R-S009A, S242R-N269R, S024R-N269R, G020R-N269R, T022R-N269R, H249R-N269R, S212F-N269R, N043R-N269R, V244R-N269R, A001R-N269R, N018R-N269R, S078R-N269R, S009A-N269R, G115R-N269R, W241R-N269R, V004R-N269R, L082R-N269R, N018R-N043R, G020R-N043R, V004R-N043R, T022R-N043R, S009A-N043R, A001R-N043R, S024R-N043R, S009A-N018R, V004R-N018R, A001R-N018R, S024R-L082R, S009A-L082R, N018R-L082R, A001R-L082R, S078R-L082R, G020R-L082R, T022R-L082R, V004R-L082R, N043R-L082R, N043R-H249R, G020R-H249R, V004R-H249R, N018R-H249R, S009A-H249R, S212F-H249R, T022R-H249R, S024R-H249R, G115R-H249R, A001R-H249R, L082R-H249R, S242R-H249R, W241R-H249R, V244R-H249R, S078R-H249R, N018R-G115R, G020R-G115R, T022R-G115R, S078R-G115R, S009A-G115R, V004R-G115R, A001R-G115R, L082R-G115R, N043R-G115R, S024R-G115R, S009A-G020R, N018R-G020R, V004R-G020R, A001R-G020R, S009A-E271L, G020R-E271L, S024R-E271L, V244R-E271L, W241R-E271L, N043R-E271L, T022R-E271L, H249R-E271L, S212F-E271L, G115R-E271L, S242R-E271L, S078R-E271L, V004R-E271L, N269R-E271L, A001R-E271L, N018R-E271L, and L082R-E271L, and wherein the total net charge of the variant is 0, +1, +2, +3, +4, +5, −1, −2, −3, −4, or −5 relative to the total net charge of the *Bacillus lentus* subtilisin GG36 protease, and wherein the total net charge is obtained by one or more substitutions selected from: N43D, R45T, N62E, N76D, S101D, P129E, A158E, G159D, G159E, S166D, S188D, A230E, N18R, G20K, G20R, T22R, S24R, N43R, G118R, Q245R, H249R, N269R, E271F, and E271L, and wherein amino acid positions of the protease variant are numbered according to the numbering of corresponding amino acid positions in the amino acid sequence of *Bacillus amyloliquefaciens* subtilisin BPN' shown in SEQ ID NO:1

In one aspect, said protease variant comprises:

a) two or more of the following mutations: X1R, X2S, V4R, V4S, X9A, X10S, X14K, X16S, X22A, X22R, X24R, X25V, X26F, X42I, X52F, X52E, X52N, X62E, X62Q, X68A, X68C, X71G, X72C, X74C, X75A, X75F, X78R, X89P, X89T, X89G, X89H, X89W, X91N, X94N, X100S, X101A, X101N, X101G, X101D, X103G, X103N, X104L, X104I, X108I, X111V, X112V, X115K, X117F, X121F, X128D, X128F, X128L, X128N, X129E, X148I, X158E, X159E, X160D, X166D, X185E, X186H, X188E, X188D, X203E, X209S, X209N, X209F, X209T, X209E, X209H, X209G, X210R, X212I, X212F, X214F, X215N, X215D, X215E, X217E, X217N, X224A, X230E, X231I, X236F, X238R, X238K, X239K, X239G, X239R, X248V, X249R, X250I, X262D, X263F, X265F, X267V, X267N, X269I, X269R, X271F, X271I, X271H and X272F; and/or b) one or more of the following sets of mutations: X062E-X129E, X062E-X159E, X016S-X148I, X158E-X249R, X016S-X062E, X111V-X188D, X022A-X062E, X062E-X148I, X022A-X129E, X062E-X271F, X062E-X158E, X016S-X159E, X062E-X186H, X128N-X159E, X062E-X188D, X062E-X128N, X148I-X159E, X103G-X158E, X111V-X159E, X158E-X271F, X016S-X188D, X022A-X111V, X128N-X158E, X016S-X158E, X104L-X158E, X128N-X186H, X159E-X209E, X062E-X101A, X111V-X209E, X148I-X188D, X101A-X209E, X022A-X188D, X016S-X022A, X128N-X129E, X016S-X209E, X016S-X128N, X022A-X089P, X128N-X209E, X089P-X158E, X062E-X103G, X186H-X271F, X016S-X129E, X089P-X159E, X111V-X249R, X101A-X129E, X148I-X209E, X022A-X159E, X129E-X249R, X129E-X209E, X104L-X129E, X128N-X188D, X111V-X158E, X022A-X158E, X062E-X209E, X062E-X249R, X101A-X186H, X089P-X129E, X129E-X271F, X22A-X111V-X159E, X101A-X103G-X104L-X209E, X101A-X103G-X104L-X159E, X101A-X103G-X104L-X188D, X101G-X103A-X104I-X159D, X22A-X103G-X159E, X22A-X128N-X271F-X209E, X22A-X209E-X271F, X22A-X101A-X209E, X101A-X209E-X271F, X22A-X111V-X128N, X22A-X101A-X159E, X101A-X103G-X104L, X22A-X101A-X103G-X104L, X101A-X103G-X104L, X101G-X103A-X104I, X101A-X103G-X104L-X128N, X103A-X104I-X159D-X232V-X236H-X245R-X248D-X252K, X101G-X104I-X159D-X232V-X236H-X245R-X248D-X252K, X101G-X103A-X159D-X232V-X236H-X245R-X248D-X252K, X101G-X103A-X104L-X232V-X236H-X245R-X248D-X252K, X101G-X103A-X104L-X159D-X236H-X245R-X248D-X252K, X101G-X103A-X104L-X159D-X232V-X245R-X248D-X252K, X101G-X103A-X104L-X159D-X232V-X236H-X248D-X252K, X101G-X103A-X104L-X159D-X232V-X236H-X245R-X252K, X101G-X103A-X104L-X159D-X232V-X236H-X245R-X248D, X62E-X101G-X103A-X104I-X159D-X232V-X245R-X248D-X271F, X62E-X101G-X103A-X104I-X159D-X232V-X245R-X248D-X249R, X22A-X101G-X103A-X104I-X159D-X232V-X245R-X248D-X249R, X101G-X103A-X104I-X159D-X232V-X245R-X248D-X24R, X101G-X103A-X104I-X159D-X232V-X245R-X248D-X253R, X101G-X103A-X104I-X158E-X232V-X245R-X248D-X249R, X22A-X101G-X103A-X104I-X159D-X232V-X245R-X248D-X271F, X101G-X103A-X104I-X159E-X232V-X245R-X248D-X249R, X101G-X103A-X104I-X159D-X232V-X245R-X248D-X238R, X101G-X103A-X104I-X158E-X232V-X245R-X248D-X271F, X101G-X103A-X104I-X159D-X232V-X245R-X248D, X101G-X103A-X104I-X159D-X232V-X245R-X248D-X271F, X101G-X103A-X104I-X159D-X232V-X245R-X248D-X76D and X101G-X103A-X104I-X159E-X232V-X245R-X248D-X271F; said variant having a total net charge of 0, −1, −2, −3, −4 or −5, preferably 0, −1, −2 or −3, relative to the *B. lentus* subtilisin GG36 protease having the amino acid sequence of SEQ ID NO:2. These protease variants may be particularly preferred in an aqueous wash liquor with low ionic strength or low detergent concentrations.

In one aspect, said protease variant comprises:

a) two or more of the following mutations X4R, X17R, X18R, X20R, X22R, X24R, X24W, X25R, X43R, X43A, X46R, X52F, X52N, X57R, X59A, X62Q, X71G, X75R, X76D, X78R, X82R, X86W, X89P, X89W, X89T, X89I, X89H, X89V, X104L, X106V, X106G, X115R, X118I, X121F, X144R, X185I, X197F, X209N, X209S, X217E, X231I, X239R, X239S, X241R, X242R, X242L, X243R, X244R, X248I, X249R, X252R, X253R, X271T, X271V, X271L, X271H, X271F, X271P, X1R, X9A, X212F and X269R; and/or b) one or more of the following sets of mutations X022R-X024R, X009A-X271L, X018R-X241R, X018R-X115R, X043R-X249R, X020R-X249R, X004R-X249R, X020R-X024R, X018R-X249R, X009A-X020R, X020R-X241R, X009A-X078R, X020R-X115R, X018R-X024R, X024R-X242R, X022R-X115R, X018R-X043R, X020R-X043R, X018R-X242R, X242R-X269R, X018R-X244R, X024R-X269R, X020R-X271L, X024R-X271L, X004R-X009A, X020R-X269R, X001R-X024R, X244R-X271L, X009A-X018R, X241R-X271L, X004R-X024R, X009A-X249R, X009A-X022R, X101G-X103A-X104I-X159D-X232V-X245R-X248D-X271F, X101G-X103A-X104I-X158E-X232V-X245R-X248D-X271F, X101G-X103A-X104I-X158E-X232V-X245R-X248D-X249R, X101G-X103A-X104I-X159D-X232V-X245R-X248D-X24R, X101G-X103A-X104L-X159D-X232V-X236H-X245R-X252K, X101G-X103A-X104L-X232V-X236H-X245R-X248D-X252K; said protease variant having a total net charge of 0, +1, +2, +3, +4 or +5, preferably having a positive total net charge, most preferably +1, +2 or +3, relative to the *B. lentus* subtilisin GG36 protease having the amino acid sequence of SEQ ID NO:2. These protease variants may be particularly preferred in an aqueous wash liquor with high ionic strength or high detergent concentrations.

The present invention further provides isolated subtilisin variants, wherein the subtilisin variants are mature forms having proteolytic activity and comprise amino acid sequences comprising a combination of amino acid substitutions selected from: G020R-N043R, G020K-N062E, S024F-N116L, G020K-S024F, S024R-A174T, S024R-G118R, S024R-K235F, S024R-P086R, S024R-P086W, S078R-G118R, T033S-G118R, T033S-K235F, Y209A-W241R, G020R-N076D, N018R-Q245R, S024R-R045T, A232V-Q245R, G118R-A172V, G118R-A194T, I008T-S024R, K235F-N243F, N018R-S103A, N018R-V104I, P086W-G118R, P086W-N243F, P086W-Y209A, S024C-T033S, S024R-A232V, S024R-N243F, S024R-P239Q, S024R-S101G, S024R-S141G, S024R-T033S, S024R-T274I, S024R-Y209A, S078R-P086W, S101G-A232V, T033S-L148F, T033S-P086W, T033S-P201S, T033S-S078R, T033S-W241R, T033S-Y209A, A230E-H249R, A232V-H249R, G118R-K235F, N076D-Q245R, P086W-K235F, S024R-R247H, S024R-V104A, S078R-K235F, S101G-H249R, S103A-A232V, T033S-A048T, T033S-P239T, T033S-T253A, T143A-Y209A, Y209A-K235F, N018R-R045T, Y209A-N243F, S024R-A272P, S024R-R269C, S101G-V104I, V104I-A232V, N076D-H249R, and S024R-N076D wherein the amino acid positions of the subtilisin variant are numbered by correspondence with the amino acid sequence of *B. amyloliquefaciens* subtilisin BPN' set forth as SEQ ID NO:1.

The present invention further provides isolated subtilisin variants, wherein the subtilisin variants are mature forms having proteolytic activity and comprise amino acid sequences comprising a combination of amino acid substitutions selected from: G020R-N076D, S024R-R045T, A230E-H249R, N018R-R045T, N018R-Q245R, S101G-A232V, S024R-A232V, A232V-Q245R, S024R-S101G, N018R-V104I, N018R-S103A, S101G-H249R, A232V-H249R, S103A-A232V, N076D-Q245R, S101G-V104I, V104I-A232V, N076D-H249R, S024R-N076D, S024R-N116L, G020K-S024F, G020K-N062E, T033S-G118R, S024R-P086W, S024R-G118R, S024R-P086R, Y209A-W241R, S024R-W241R, S024R-K235F, G118R-Y209A, S078R-G118R, T033S-K235F, S024R-A174T, P086W-Y209A, I008T-S024R, P086W-G118R, T033S-W241R, S024R-N243F, S024R-Y209A, T033S-P086W, S024R-T033S, P086W-N243F, T033S-P201S, S024R-P239Q, S078R-P086W, K235F-N243F, G118R-A172V, T033S-L148F, T033S-S078R, T033S-N243F, S024C-T033S, G118R-A194T, T033S-Y209A, S024R-S141G, S024R-T274I, P086W-K235F, A015T-T033S, Y209A-K235F, S024R-R247H, S078R-K235F, S024R-V104A, T033S-A048T, G118R-K235F, T033S-T253A, T143A-Y209A, T033S-P239T, Y209A-N243F, S024R-A272P, and S024R-R269C, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: V004R-S009A-G020R-S242R, G020R-N043R-W241R, G020R-S242R-N269R, V004R-S009A-G020R-N043R, V004R-G020R-H249R, N018R-S024R-V244R, S009A-T022R-S212F-W241R, G020R-N043R-N269R, N018R-S024R-S242R, V004R-S009A-N043R-W241R, G020R-N043R-V244R, G020R-T022R-S242R, V004R-G020R-N043R, V004R-S009A-G020R-N043R-S242R, G020R-N043R-S242R, G020R-N043R-S242R-H249R, G020R-S212F-H249R, V004R-S009A-W241R, A001R-S009A-N043R, G020R-N043R-H249R, S009A-G020R-N043R-W241R, G020R-T022R-N043R, G020R-H249R-N269R, G020R-T022R-W241R, V004R-S009A-S024R-N043R-W241R, S009A-N043R-S078R, V004R-G020R-S024R-V244R, G020R-T022R-S078R-S242R, G020R-S024R-S242R-H249R, V004R-S009A-S078R-W241R, S009A-N043R-S078R-S242R, V004R-G020R-S024R, S009A-N043R-S212F, G020R-N043R-S212F, S024R-S078R-S212F, S009A-G020R-S024R-N043R, S009A-T022R-N043R-S078R, G020R-T022R-S212F-W241R, G020R-N043R-S212F-W241R, S009A-N043R-W241R, G020R-N043R-E271L, G020R-T022R-S078R-W241R, G020R-S024R-N043R-S242R, G020R-T022R-N043R-W241R, S009A-G020R-N043R-S212F, V004R-S009A-G020R-S024R-S242R, G020R-N043R-H249R-E271L, G020R-T022R-S024R-S242R, S009A-T022R-S078R-S212F, G020R-N043R-S242R-E271L, S009A-T022R-S078R-S212F-W241R, V004R-G020R-S024R-H249R, G020R-T022R-E271L, G020R-T022R-N043R-S212F, V004R-G020R-S024R-N043R-S242R, V004R-G020R-S024R-N043R, V004R-S009A-T022R-S078R-S212F, G020R-T022R-S078R-S212F-W241R, and G020R-T022R-N269R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: N018R-G020R-N043D-R045T-A230E, N018R-N043R-R045T-S242R-H249R, S024R-N043D-H249R, N018R-G020R-R045T, G020R-S024R-N076D-H249R, S024R-N043R-A230E-S242R, N018R-S024R-N043D-A230E, G020R-N076D, N018R-S024R-N043D-N076D-H249R, S024R-N043R-N076D-H249R, N018R-S024R-R045T-S242R, G020R-N043D-N076D-A230E-H249R, G020R-N043R-R045T-S242R, N018R-S024R-N076D-H249R, N018R-G020R-S024R-N043D-R045T-L233I-S242R, S024R-N043R-A230E, N018R-G020R-N043D, N043R-S242R-H249R, G020R-N043R-R045T-A230E, N043R-N076D-S242R-H249R, G020R-S024R-R045T-A230E-S242R, S024R-R045T-N076D-A230E-S242R-H249R, S024R-R045T, S024R-N043R-R045T-N076D-A230E-H249R, N018R-S024R-N043D-R045T-H249R, N018R-N043R-R045T-H249R, S024R-N043R-S242R, N018R-G020R-N043R-N076D-H249R, G020R-S024R-N043D-H249R, G020R-N043R-A230E-S242R, G020R-N043R-S242R, N018R-N043R-N076D-A230E, G020R-S024R-N043D-S242R, G020R-N043R-A230E, N018R-G020R-N043R-N076D-S242R-H249R, N043D-R045T-N076D-H249R, N018R-N043R-S242R-H249R, N018R-G020R-N043R-R045T-S242R, N018R-G020R-N043D-A230E-S242R, G020R-S024R-N043R-R045T-H249R, S024R-N043R-H249R, G020R-S024R-K27E-N043R-N076D-A230E, S024R-N043R-R045T-S242R, N018R-G020R-S024R-N043R-R045T-N076D-A230E, G020R-N043R-N076D-A230E-H249R, N018R-N043R-R045T-S242R, G020R-S242R-H249R, N018R-N043R-N076D-A230E-S242R-H249R, N018R-S024R-N076D, G020R-S024R-K27R-N043D-S242R-H249R, N018R-G020R-S024R-N043D-N076D-S242R, N018R-N043R-N076D-S242R-H249R, N018R-S024R-N043D-A230E-H249R, N018R-G020R-N043D-H249R, N018R-G020R-N043D-R045T-N076D-S242R, S024R-N043R-N076D-A230E-S242R, G020R-S024R-T381-N043R-R045T-N076D-S242R-H249R, N018R-G020R-N043R, N018R-S024R-R045T-A230E-S242R, N018R-G020R-H249R, S024R-N043R-N076D, N018R-G020R-S024R-N043R-R045T-N076D-H249R, N018R-N043D-R045T-N076D-S242R-H249R, S024R-N043D-S242R-H249R, N018R-G020R-S024R-N043D-R045T-S242R, G020R-S024R-N043R-N076D, N018R-G020R-N043D-R045T-A230E-S242R, G020R-S024R-N043R-R045T-N076D-S242R-H249R, N018R-N043R-R045T-N076D-S242R, N018R-G020R-N043R-N076D-A230E-S242R, N018R-S024R-N043D-H249R, N018R-S024R-N043R-R045T-A230E-H249R, N018R-G020R-N043R-R045T-N076D-H249R, N018R-S024R-S242R, N018R-N043R-R045T-

N076D-A230E-S242R, R045T-S242R-H249R, N018R-S024R-N043D-S242R, N018R-G020R-N043D-R045T-S240P, S024R-N043R-R045T-S242R-H249R, N018R-S024R-V30S-L31S-D321-T33Q-G34V-I35F, N018R-G020R-N043R-N076D, G020R-N043R-R045T-N076D-S242R-H249R, N018R-S024R-N043D-A230E-S242R, N018R-S024R-N043D-S242R-H249R, S024R-N043D-R045T-S242R-H249R, N043R-A230E-H249R, S024R-N043R-N076D-A230E-H249R, G020R-S024R-N043D-N076D-H249R, S024R-R045T-S242R-A273V, G020R-S024R-R045T-N076D-S242R-H249R, N018R-S024R-N043D-N076D-S242R, N018R-N043R-N076D-A230E-H249R, N018R-G020R-N043R-R045T-H249R, N018R-N043R-R045T-A230E-S242R, G020R-S024R-N043D-R045T-A230E-S242R, N018R-N043D-A230E-H249R, N018R-N043R-N076D-S242R, N018R-G020R-N076D, N018R-G020R-N043D-N076D-S242R-H249R, G020R-S024R-N043D-N076D-S242R-H249R, N043D-S242R-H249R, N018R-G020R-S024R-N043R-N076D, N018R-G020R-N043D-R045T-N076D-H249R, N018R-G020R-N043R-R045T-N076D-A230E-H249R, N018R-N076D-S242R, G020R-N043R-H249R, N018R-N076D-S242R-H249R, N018R-S024R-R045T-A230E-H249R, A230E-H249R, N018R-R045T-H249R, G020R-N043R-N076D, N043R-R045T-H249R, N018R-N043D-N076D-S242R-H249R, N043R-N076D-H249R, N018R-R045T, G020R-N076D-A230E-S242R, G020R-S024R-N043D-R045T, S024R-N043D-N076D-S242R-H249R, G020R-R045T-H249R, N043R-N076D-S153A-H249R, N043R-N076D-A230E-H249R, N018R-N043D-N076D-H249R, and G020R-N043R-N076D-V227I, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101G-S103A-V104I-A232V-Q236H-Q245R-N252K, S101G-S103A-V104I-A232V-Q245R-N248R, S101G-S103A-V104I-G159R-A232V-Q245R-N248D, S101G-S103A-V104I-G159D-A232V-Q245R-N248D, S101G-S103A-V104I-A232V-Q245R, S101G-S103A-V104I-G159D-A232V-Q245R, and S101G-S103A-V104I-A232V-Q245R-N248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101G-S103A-V104I-P129E-S188D-A232V-N238R-Q245R-N248D, S024R-S101G-S103A-V104I-P129E-A158E-S188D-A232V-Q245R-N248D-H249R, T022A-S101G-S103A-V104I-P129E-A158E-S188D-A232V-Q245R-N248D-H249R, T022A-S024R-S101G-S103A-V104I-P129E-A158E-S188D-A232V-Q245R-N248D-H249R, S024R-S101G-S103A-V104I-P129E-S188D-A232V-Q245R-N248D-H249R, S024R-S101G-S103A-V104I-P129E-G159E-S188D-A232V-Q245R-N248D-H249R, S024R-S101G-S103A-V104I-S128N-P129E-A158E-A232V-Q245R-N248D-H249R, S024R-S101G-S103A-V104I-L148I-A158E-S188D-A232V-Q245R-N248D, T022A-S024R-S101G-S103A-V104I-P129E-G159E-S188D-A232V-Q245R-N248D-H249R, S024R-S101G-S103A-V104I-S128N-P129E-A232V-Q245R-N248D, S101G-S103A-V104I-P129E-S188D-A232V-Q245R-N248D-H249R, S024R-S101G-S103A-V104I-P129E-A158E-S188D-A232V-Q245R-N248D, H249R, T022A-S024R-S101G-S103A-V104I-A158E-G159E-S188D-A232V-Q245R-N248D-H249R, T022A-S024R-S101G-S103A-V104I-P129E-A158E-G159E-S188D-A232V-N238R-Q245R-N248D, S024R-S101G-S103A-V104I-P129E-L148I-A158E-A232V-Q245R-N248D, A016S-S024R-S101G-S103A-V104I-A158E-S188D-A232V-Q245R-N248D-H249R, S101G-S103A-V104I-A158E-G159E-A232V-Q245R-N248D-H249R, T022A-S101G-S103A-V104I-P129E-A158E-G159E-A232V-N238R-Q245R-N248D, T022A-S024R-S101G-S103A-V104I-P129E-A158E-G159E-A232V-Q245R-N248D-H249R, T022A-S024R-S101G-S103A-V104I-S128N-A158E-S188D-A232V-Q245R-N248D, S024R-S101G-S103A-V104I-P129E-S188D-A232V-Q245R-N248D, T022A-S024R-S101G-S103A-V104I-P129E-A158E-A232V-Q245R-N248D, T022A-S024R-S101G-S103A-V104I-P129E-A232V-Q245R-N248D, T022A-S024R-S101G-S103A-V104I-P129E-S188D-A232V-Q245R-N248D, S024R-S101G-S103A-V104I-A158E-S188D-A232V-N238R-Q245R-N248D, T022A-S101G-S103A-V104I-S128N-P129E-S188D-A232V-N238R-Q245R-N248D, S024R-S101G-S103A-V104I-P129E-S188D-A232V-N238R-Q245R-N248D, S024R-S101G-S103A-V104I-A158E-G159E-S188D-A232V-Q245R-N248D, T022A-S024R-S101G-S103A-V104I-S128N-S188D-A232V-Q245R-N248D, S024R-S101G-S103A-V104I-P129E-A158E-S188D-A232V-Q245R-N248D, T022A-S024R-S101G-S103A-V104I-S128N-P129E-A158E-A232V-Q245R-N248D, S024R-S101G-S103A-V104I-G159E-S188D-A232V-Q245R-N248D, T022A-S101G-S103A-V104I-S128N-P129E-A232V-N238R-Q245R-N248D, S024R-S101G-S103A-V104I-P129E-G159E-A232V-Q245R-N248D, T022A-S024R-S101G-S103A-V104I-P129E-A158E-S188D-A232V-N238R-Q245R-N248D, T022A-S024R-S101G-S103A-V104I-A158E-G159E-S188D-A232V-Q245R-N248D, S024R-S101G-S103A-V104I-G159E-S188D-A232V-Q245R-N248D-H249R, T022A-S101G-S103A-V104I-P129E-A158E-A232V-N238R-Q245R-N248D, T022A-S024R-S101G-S103A-V104I-P129E-A158E-A232V-Q245R-N248D-H249R, S024R-S101G-S103A-V104I-L148I-A158E-A232V-Q245R-N248D, T022A-S101G-S103A-V104I-A158E-G159E-S188D-A232V-Q245R-N248D-H249R, T022A-S101G-S103A-V104I-A158E-S188D-A232V-Q245R-N248D, T022A-S101G-S103A-V104I-P129E-S188D-A232V-N238R-Q245R-N248D, S024R-S101G-S103A-V104I-P129E-A158E-G159E-S188D-A232V-Q245R-N248D-H249R, T022A-S024R-S101G-S103A-V104I-A158E-G159E-S188D-A232V-N238R-Q245R-N248D, S101G-S103A-V104I-P129E-A158E-S188D-A232V-Q245R-N248D-H249R, S024R-S101G-S103A-V104I-S128N-A158E-A232V-Q245R-N248D, T022A-S024R-S101G-S103A-V104I-S128N-P129E-S188D-A232V-Q245R-N248D, T022A-S101G-S103A-V104I-P129E-G159E-A232V-N238R-Q245R-N248D, S101G-S103A-V104I-P129E-G159E-A232V-Q245R-N248D-H249R, T022A-S101G-S103A-V104I-P129E-A158E-A232V-Q245R-N248D-H249R, S024R-S101G-S103A-V104I-P129E-L148I-A158E-S188D-A232V-Q245R-N248D, T022A-S101G-S103A-V104I-P129E-G159E-A232V-Q245R-N248D-H249R, S024R-S101G-S103A-V104I-G159E-S188D-A232V-N238R-Q245R-N248D, S024R-S101G-S103A-V104I-P129E-A158E-G159E-A232V-Q245R-N248D-H249R, S024R-S101G-

S103A-V104I-P129E-A158E-G159E-A232V-N238R-Q245R-N248D, S024R-S101G-S103A-V104I-S128N-G159E-S188D-A232V-Q245R-N248D, T022A-S101G-S103A-V104I-G159E-S188D-A232V-Q245R-N248D-H249R, S024R-S101G-S103A-V104I-P129E-G159E-S188D-A232V-N238R-Q245R-N248D, S101G-S103A-V104I-A158E-A232V-N238R-Q245R-N248D, T022A-S101G-S103A-V104I-P129E-G159E-S188D-A232V-Q245R-N248D-H249R, S024R-S101G-S103A-V104I-P129E-L148I-S188D-A232V-Q245R-N248D, S024R-S101G-S103A-V104I-A158E-A232V-Q245R-N248D-H249R, T022A-S101G-S103A-V104I-A158E-G159E-A232V-N238R-Q245R-N248D, S024R-S101G-S103A-V104I-A158E-G159E-A232V-N238R-Q245R-N248D, T022A-S101G-S103A-V104I-P129E-A158E-G159E-A232V-Q245R-N248D-H249R, S101G-S103A-V104I-P129E-A158E-S188D-A232V-N238R-Q245R-N248D, T022A-S024R-S101G-S103A-V104I-P129E-A158E-G159E-A232V-Q245R-N248D, S101G-S103A-V104I-S188D-A232V-N238R-Q245R-N248D, T022A-S024R-S101G-S103A-V104I-A158E-A232V-Q245R-N248D-H249R, T022A-S024R-S101G-S103A-V104I-L148I-A158E-A232V-Q245R-N248D, S101G-S103A-V104I-P129E-A158E-G159E-A232V-N238R-Q245R-N248D, T022A-S101G-S103A-V104I-G159E-S188D-A232V-N238R-Q245R-N248D, T022A-S024R-S101G-S103A-V104I-P129E-A158E-G159E-S188D-A232V-Q245R-N248D-H249R, T022A-S101G-S103A-V104I-P129E-A232V-N238R-Q245R-N248D, T022A-S024R-S101G-S103A-V104I-S188D-A232V-Q245R-N248D-H249R, S101G-S103A-V104I-P129E-A158E-G159E-A232V-Q245R-N248D-H249R, T022A-S101G-S103A-V104I-A158E-G159E-A232V-Q245R-N248D-H249R, S101G-S103A-V104I-P129E-S188D-A232V-Q245R-N248D, S024R-S101G-S103A-V104I-P129E-G159E-A232V-N238R-Q245R-N248D, S101G-S103A-V104I-S128N-P129E-A232V-Q245R-N248D, S101G-S103A-V104I-A158E-S188D-A232V-Q245R-N248D, T022A-S024R-S101G-S103A-V104I-P129E-A232V-Q245R-N248D-H249R, S101G-S103A-V104I-P129E-G159E-A232V-N238R-Q245R-N248D, S101G-S103A-V104I-A158E-G159E-S188D-A232V-N238R-Q245R-N248D, S024R-S101G-S103A-V104I-A232V-Q245R-N248D-H249R, T022A-S024R-S101G-S103A-V104I-P129E-L148I-A232V-Q245R-N248D, T022A-S024R-S101G-S103A-V104I-A158E-A232V-N238R-Q245R-N248D, S101G-S103A-V104I-S128N-P129E-A232V-N238R-Q245R-N248D, T022A-S101G-S103A-V104I-S128N-G159E-A232V-Q245R-N248D, T022A-S101G-S103A-V104I-S128N-P129E-A158E-A232V-N238R-Q245R-N248D, S101G-S103A-V104I-S128N-P129E-S188D-A232V-Q245R-N248D-H249R, T022A-S024R-S101G-S103A-V104I-S128N-P129E-A158E-S188D-A232V-Q245R-N248D-H249R, S024R-S101G-S103A-V104I-S128N-A158E-G159E-S188D-A232V-Q245R-N248D, T022A-S024K-S101G-S103A-V104I-S128N-A158E-G159E-A232V-Q245R-N248D, S101G-S103A-V104I-P129E-L148I-S188D-A232V-Q245R-N248D, S024R-S101G-S103A-V104I-L148I-A232V-Q245R-N248D, T022A-S101G-S103A-V104I-L148I-S188D-A232V-Q245R-N248D, S024R-S101G-S103A-V104I-S128N-P129E-S188D-A232V-Q245R-N248D, S101G-S103A-V104I-S128N-P129E-A158E-A232V-N238R-Q245R-N248D, T022A-S024R-S101G-S103A-V104I-P129E-L148I-A158E-S188D-A232V-Q245R-N248D, T022A-S024R-S101G-S103A-V104I-L148I-A158E-S188D-A232V-Q245R-N248D, S101G-S103A-V104I-L148I-G159E-A232V-Q245R-N248D, T022A-S024R-S101G-S103A-V104I-A158E-S188D-A232V-Q245R-N248D, and S101G-S103A-V104I-S128N-P129E-A158E-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: T022A-S024R-S101G-S103A-V104I-A158E-A232V-Q245R-N248D-H249R, T022A-S024R-S101G-S103A-V104I-P129E-A232V-Q245R-N248D-H249R, S024R-S101G-S103A-V104I-A158E-G159E-A232V-N238R-Q245R-N248D, S024R-S101G-S103A-V104I-A232V-Q245R-N248D-H249R, S101G-S103A-V104I-A158E-A232V-Q245R-N248D-H249R, S101G-S103A-V104I-S188D-A232V-Q245R-N248D-H249R, S024R-S101G-S103A-V104I-G159E-S188D-A232V-Q245R-N248D-H249R, T022A-S024R-S101G-S103A-V104I-A158E-A232V-N238R-Q245R-N248D, S024R-S101G-S103A-V104I-G159E-S188D-A232V-N238R-Q245R-N248D, T022A-S024R-S101G-S103A-V104I-P129E-A232V-Q245R-N248D, S024R-S101G-S103A-V104I-L148I-A232V-Q245R-N248D, S024R-S101G-S103A-V104I-P129E-A158E-A232V-Q245R-N248D-H249R, S024R-S101G-S103A-V104I-L148I-A158E-A232V-Q245R-N248D, T022A-S024R-S101G-S103A-V104I-P129E-A158E-A232V-Q245R-N248D-H249R, A016S-S024R-S101G-S103A-V104I-A158E-S188D-A232V-Q245R-N248D-H249R, S024R-S101G-S103A-V104I-P129E-G159E-A232V-N238R-Q245R-N248D, S024R-S101G-S103A-V104I-P129E-S188D-A232V-Q245R-N248D-H249R, T022A-S101G-S103A-V104I-P129E-A232V-N238R-Q245R-N248D, T022A-S024R-S101G-S103A-V104I-L148I-A158E-A232V-Q245R-N248D, S024R-S101G-S103A-V104I-P129E-S188D-A232V-N238R-Q245R-N248D, T022A-S024R-S101G-S103A-V104I-A158E-G159E-S188D-A232V-N238R-Q245R-N248D, T022A-S101G-S103A-V104I-A158E-G159E-A232V-N238R-Q245R-N248D, T022A-S024R-S101G-S103A-V104I-P129E-A158E-A232V-Q245R-N248D, S101G-S103A-V104I-A158E-S188D-A232V-Q245R-N248D-H249R, T022A-S101G-S103A-V104I-A158E-G159E-A232V-Q245R-N248D-H249R, and S024R-S101G-S103A-V104I-A158E-G159E-A232V-Q245R-N248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: V104L-S128N-A158E-R186H-H249R, S128N-A158E-S188D-H249R, N062E-S128N-A158E-G159E-E271F, N062E-A158E-S188D-H249R-E271F, N062E-A158E-R186H-H249R-E271F, S128N-A158E-S188D-Y209E-E271F, N062E-G159E-S188D-H249R, A016S-N062E-A158E-R186H-H249R, N062E-A158E-G159E-H249R, S101A-S128N-A158E-Y209E-H249R, S128N-A158E-R186H-E271F, N062E-A158E-S188D-H249R, N062E-A158E-R186H-E271F, N062E-A158E-R186H-H249R, N062E-S101A-R186H-H249R, N062E-S101A-A158E-R186H-E271F, N062E-V104L-A158E-S188D-H249R-E271F, N062E-G159E-R186H-

H249R, N062E-G159E-H249R, S128N-A158E-R186H-H249R, S128N-A158E-S188D-E271F, N062E-A158E-H249R, N062E-R186H-S188D-H249R-E271F, S128N-A158E-Y209E-, N062E-S101A-A158E-H249R, V104L-S128N-A158E-R186H-E271F, N062E-S101A-A158E-R186H-H249R-E271F, A016S-N062E-A158E-H249R, N062E-S101A-G159E-H249R, S128N-A158E-R186H-S188D-E271F, S101A-S128N-A158E-R186H-E271F, N062E-S101A-S188D-H249R, S101A-V104L-A158E-R186H-S188D-H249R, N062E-G159E-H249R-E271F, S128N-A158E-G159E-E271F, A016S-N062E-V104L-A158E-R186H-E271F, T022A-S128N-A158E-H249R, S128N-A158E-H249R, N062E-S101A-V104L-A158E-R186H-E271F, A016S-N062E-A158E-R186H-E271F, V104L-S128N-A158E-H249R, V104L-S128N-A158E-S188D-H249R, T022A-N062E-A158E, N062E-S101A-S188D-H249R-E271F, N062E-A158E-H249R-E271F, V104L-S128N-A158E-R186H-S188D-E271F, N062E-S101A-R186H-E271F, N062E-V104L-G159E-H249R, N062E-R186H-H249R, N062E-S101A-R186H-H249R-E271F, S101A-A158E-R186H-S188D-H249R, N062E-S101A-R186H, S101A-S128N-P129E-R186H-H249R, S101A-S103G-A158E-R186H-H249R, A016S-N062E-V104L-R186H-S188D-E271F, V104L-A158E-R186H-H249R, S101A-S128N-A158E-S188D-Y209E-E271F, N062E-S101A-R186H-S188D-E271F, A016S-N062E-A158E-H249R-E271F, N062E-S128N-A158E, N062E-S128N-G159E-H249R, N062E-S101A-A158E-S188D-H249R, S101A-S128N-A158E-H249R, N062E-A158E-R186H-S188D-H249R, A016S-V104L-A158E-R186H-E271F, N062E-L148I-G159E, N062E-S101A-A158E-R186H-H249R, N062E-S101A-R186H-S188D-H249R, V104L-A158E-R186H-S188D-H249R, N062E-S101A-V104L-R186H-S188D-E271F, T022A-S101A-A158E-R186H-H249R, S101A-S128N-A158E-Y209E, A158E-R186H-S188D-H249R-E271F, V104L-A158E-R186H-S188D-H249R-E271F, S101A-V104L-A158E-R186H-H249R, V104L-A158E-H249R, S101A-V104L-S128N-A158E-R186H-E271F, A016S-V104L-S188D-H249R, S101A-V104L-A158E-R186H-S188D-E271F, V104L-S128N-G159E-E271F, V104L-A158E-R186H-H249R-E271F, A158E-R186H-H249R, S101A-A158E-R186H-H249R, V104L-A158E-S188D-H249R-E271F, A016S-S128N-A158E-R186H, V104L-S128N-R186H-S188D-H249R, A016S-S101A-S128N-R186H, A016S-N062E-S128N-R186H-E271F, A016S-S128N-R186H-E271F, S128N-P129E-R186H, A158E-R186H-H249R-E271F, A016S-A158E-H249R, A016S-A158E-R186H-H249R, A016S-T022A-A158E-R186H-E271F, E089P-S101A-P129E-R186H, T022A-S128N-A158E-R186H, S101A-V104L-S128N-A158E-R186H, T022A-S128N-R186H-S188D-, N062E-V104L-A158E-R186H-S188D-H249R, T022A-A158E-R186H-H249R-E271F, T022A-V104L-A158E-H249R, S101A-L111V-P129E, A016S-A158E-H249R-E271F, A016S-L111V-S188D-, T022A-V104L-R186H-S188D-H249R, and V104L-L148I-S188D-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: A001R-S101G-S103A-V104I-A232V-Q245R, V004R-S101G-S103A-V104I-A232V-Q245R, N043R-S101G-S103A-V104I-A232V-Q245R-E271L, S078R-S101G-S103A-V104I-A232V-Q245R, V004R-N043R-S101G-S103A-V104I-A232V-Q245R, N018R-N043R-S101G-S103A-V104I-A232V-Q245R, G020R-S101G-S103A-V104I-A232V-Q245R, S101G-S103A-V104I-A232V-Q245R-E271L, G020R-N043R-S101G-S103A-V104I-A232V-Q245R, S024R-N043R-S101G-S103A-V104I-A232V-Q245R, G020R-G025R-N116A-Y167W, N018R-S101G-S103A-V104I-A232V-Q245R, T022R-S101G-S103A-V104I-A232V-Q245R, S078R-S103N-S106G-Y167W-Q236N, N018R-N043D-S101G-S103A-V104I-A232V-Q245R-N269R, N043R-S101G-S103A-V104I-A232V-Q245R-N269R, S024R-S101A-H120E-A194F-H249R, G020R-N043D-S101G-S103A-V104I-A232V-Q245R-N269R, S101G-S103A-V104I-S212F-A232V-Q245R, G020R-S144R-N185I-L233C-Q236N, G023A-S078R-S216F-Q236N-H249R, S101G-S103A-V104I-A232V-Q245R-N269R, S101G-S103A-V104I-G115R-A232V-Q245R, P052N-S078R-S103N-L148I-T213A, N018R-N043D-S101G-S103A-V104I-A232V-Q245R-H249R, S024R-N043D-S101G-S103A-V104I-A232V-Q245R-H249R, S024R-N043D-S101G-S103A-V104I-A232V-Q245R-N269R, G025R-E089I-N116A-P239S-A270C, S024R-S101G-S103A-V104I-A232V-Q245R, L148I-T213A-N252R, S024R-G025R-N183D-Y192W-P239S, G046R-A194F-S212M, V104L-L217E-T224A-H249R-N252R, G023A-Y091F-V121F-Y192W-Q236N, S101G-S103A-V104I-A232V-V244R-Q245R, S099F-S144R-Y167W-N252R, S101G-S103A-V104I-A232V-Q245R-H249R, N043R-S101G-S103A-V104I-A232V-Q245R, T022W-S078R-Y167W-S212M-A270C, V121F-N252R-A270C, G020R-S103N-S216F-Q236N-N252R, N043R-S101G-S103A-V104I-A232V-Q245R-H249R, G023A-P052N-Y192W-I198L-N252R, G025R-G046R-V121F, S024R-S078R-V104L-N116A-N183D, G046R-Q059A-S103N-G211Q-S212M, G020R-P052N-N062Q-Y091F-Y192W, G023A-P052N-S144R-Y192W-S216F, S101G-S103A-V104I-A232V-S242R-Q245R, P052N-S103N-N116A-L148I-Y192W, E089I-N116A-N117F-T224A-H249R, S144R-G211Q-N238L-P239S-H249R, N043A-N062Q-A194F-G211Q, G020R-S024R-P052N-Q059A-S216F, S024R-Y167W-T224A-H249R, T057R-Y167W-H249R, G025R-S103N-R186K-A194F-T224A, S105T-S128N-S144R-L148I-S212M, G020R-Q059A-S144R-Y192W-T224A, S024R-N043A-N117F-A194F-G211Q, N117F-A 194F-T213A-A270C, S078R-Y091F-V121F-L233C-N252R, T057R-S099F-S105T-I198L-T213A, G023A-Y091F-S101A-I198L-N252R, N062Q-S103N-V121F-S144R-H249R, N043R-S101G-S103A-V104I-A232V-S242R-Q245R, G023A-S024R-N117F-S212M-S216F, V104L-T213A-S216F, A194F-G211Q-Q236N, N062Q-S103N-N117F-A194F, S024R-N062Q-V104L-S106G-H249R, T057R-E089I-I198L, G046R-Q059A-S106G-L217E-H249R, N117F-T213A-A215F, S101A-H120E-Y192W-A215F-T224A, N043A-T057R-N117F-S144R-N183D, G046R-N183D-N238L, G025R-N043A-E089I-N117F, S078R-V104L-T213A-A215F-T224A, Y091F-S099F-S101A-S105T-Y167W, S106G-N117F-N238L, G046R-E089I-Y091F-S101A-N116A, G020R-N062Q-E089I-R186K-S212M, T057R-S099F-V121F-N185I-Y192W, G046R-E089I-Y192W-L233C-A270C, E089I-N117F-N185I-A215F-L233C, P052N-V104L-N183D-S216F-H249R, S078R-S099F-N116A-R186K-T224A, G025R-S105T-S128N-S144R-A270C, S105T-G211Q-S216F, S024R-G046R-Y091F-V121F, S106G-N185I-S216F-Q236N, N062Q-S101A-Q236N-N252R-A270C, G025R-N043A-Y091F-I198L-A270C, G020R-G023A-V104L-Y192W-

L233C, S024R-N043A-S105T-S106G-I198L, G020R-E089I-L217E, S024R-Y091F-I198L-A215F-P239S, G046R-E089I-S099F-R186K-S212M, V104L-H120E-R186K-S216F-N252R, T022W-A194F-T213A-L233C-N238L, S099F-S105T-S106G-A194F-S212M, E089I-S105T-N116A-A215F-S216F, G025R-N116A-H120E-T224A-A270C, N043A-Q059A-S101A-S216F-T224A, T057R-N183D-Q236N, G025R-N062Q-S128N-S144R-N185I, S103N-H120E-Y167W-I198L-L233C, T022W-E089I-S216F, S024R-S106G-N116A-S212M-T224A, G020R-P052N-S101A-I198L-L233C, E089I-Y091F-N185I-G211Q-A270C, L111I-A215F-P239S, S024R-N116A-R186K-L233C-Q236N, and G023A-S103N-S106G-S212M-A215F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: G020R-T022W-S078R-S101A-S103A-V104I-N116S-T213A-A215F-A232V-Q245R, N018R-S078R-S101G-S103A-V104I-A232V-Q245R, S024R-R045T-S101G-S103A-V104I-A232V-Q245R-N269R, G020R-T022W-S078R-S101G-S103A-V104I-N116A-A232V-Q245R, G020R-T22W-S101G-S103A-V104I-A232V-Q245R, N018R-N043R-S101G-S103A-V104I-A232V-Q245R, N018R-T022W-S024R-N076D-S101A-N116A-A232V-Q245R, N018R-V104I-A232V-H249R, N018R-S024R-N076D-S101A-N116A-G211Q-H249R, N018R-N043D-S078R-S101G-S103A-V104I-L217E-A232V-Q245R, N018R-N043R-S101G-S103A-V104I-A232V-Q245R-N269R, N018R-R045T-N076D-S101G-S103A-V104I-A232V-Q245R-N269R, N076D-S078R-S101G-S103A-V104I-A232V-Q245R-N269R, G020R-N043D-S078R-S101G-S103A-V104I-A232V-Q245R, N018R-N043D-N076D-S101G-S103A-V104I-A232V-Q245R-N269R, S024R-R045T-N076D-S078R-S101G-S103A-V104I-A232V-Q245R-N269R, N018R-S103A-A232V-H249R, N018R-S101G-V104I-A232V-Q245R, G020R-S024R-S101G-S103A-V104I-L217E-A232V-Q245R-H249R, N018R-T22K-N043D-S101G-S103A-V104I-A232V-Q245R, N043R-R045T-S101G-S103A-V104I-A232V-Q245R-N269R, G020R-T22W-S101G-S103A-V104I-G211Q-A232V-Q245R, S024R-N076D-S078R-S101G-S103A-V104I-A232V-Q245R-N269R, G020R-T22W-S078R-S101A-S103A-V104I-N116A-N183D-A232V, N018R-S024R-N076D-N116A-A215F-H249R, N018R-N043R-R045T-S101G-S103A-V104I-A232V-Q245R, S024R-N043R-N076D-S101G-S103A-V104I-A232V-Q245R, G020R-T022W-S101G-S103A-V104I-A232V-Q245R, G020R-T022W-S101G-S103A-V104I-G211Q-A232V-Q245R, G020R-T022W-S078R-S101G-S103A-V104I-N116A-T213A-A215F-A232V-Q245R, N043D-N076D-S078R-S101G-S103A-V104I-A232V-Q245R-N269R, N018R-S024R-N076D-S101A-N116A-T213A-H249R, N018R-S024R-N076D-N116A-G211Q-H249R, N043R-R045T-N076D-S078R-S101G-S103A-V104I-A232V-Q245R, N018R-S101G-Q245R, G020R-T22W-S101A-S103A-V104I-G211Q-T213A-A232V-Q245R, G020R-S024R-N043D-N076D-S078R-S101G-S103A-V104I-A232V-Q245R, N018R-R045T-N076D-S078R-S101G-S103A-V104I-A232V-Q245R, G020R-S078R-S101G-S103A-V104I-G211Q-T213A-A215F-A232V-Q245R, R045T-S078R-S101G-S103A-V104I-A232V-Q245R-N269R, S024R-N043D-S101G-S103A-V104I-A232V-Q245R-N269R, N018R-S101G-S103A-H249R, N018R-T22W-S024R-N076D-S101A-N116A-A232V-Q245R, N018R-S101G-V104I-A232V-H249R, G020R-T22W-S101A-S103A-V104I-A215F-A232V-Q245R, N018R-S024R-N076D-G211Q-T213A-H249R, N018R-T022W-S024R-N076D-S101A-I198L-H249R, S024R-S101G-S103A-V104I-A232V-Q245R, G020R-N076D-S101G-S103A-V104I-A232V-Q245R-N269R, G020R-S101G-S103A-V104I-A232V-Q245R-N269R, N043D-S078R-S101G-S103A-V104I-A232V-Q245R, G020R-S101G-V104I-T213A-A215F-A232V-Q245R, G020R-S101G-S103A-V104I-N116A-A215F-A232V-Q245R, S024R-S103A-V104I-H249R, N018R-N076D-S078R-S101G-S103A-V104I-A232V-Q245R, R045T-N076D-S078R-S101G-S103A-V104I-A232V-Q245R-N269R, S024R-S101G-V104I-Q245R, G020R-S101G-S103A-V104I-G211Q-T213A-A215F-A232V-Q245R, S024R-S103A-V104I-A232V-H249R, N018R-S024R-N076D-N116A-G211Q-A215F-H249R, N018R-Q245R, S024R-S103A-Q245R, S024R-S103A-V104I-Q245R, G020R-S078R-S101G-A232V-Q245R, N018R-S024R-N076D-V104I-H249R, N018R-S024R-V104I-H249R, S024R-S101G-S103A-V104I-A232V-Q245R, N018R-S024R-N076D-G211Q-A215F-H249R, R019H-G020R-T022W-S078R-S101G-S103A-V104I-G211Q-A232V-Q245R, N018R-S024R-N076D-S101A-I198L-G211Q-T213A-H249R, N018R-S024R-N043D-S101G-S103A-V104I-A232V-Q245R, G020R-T22W-S103A-V104I-A232V-Q245R, N018R-S103A-V104I-H249R, N018R-T022W-S024R-N076D-S101A-I198L-A215F-H249R, N018R-S024R-S101G-V104I-A232V, S078R-S101G-S103A-V104I-A232V-Q245R-N269R, S024R-N043R-N076D-S078R-S101G-S103A-V104I-A232V-Q245R, N018R-G020R-N043D-N076D-S101G-S103A-V104I-A232V-Q245R, N018R-T22W-S024R-N076D-N116A-T213A-H249R, N018R-S024R-S101G-V104I, G020R-S101A-S103A-V104I-A215F-A232V-Q245R, N018R-R045T-S078R-S101G-S103A-V104I-A232V-Q245R, N018R-S101G-S103A-Q245R, N043R-N076D-S078R-S101G-S103A-V104I-A232V-Q245R, G020R-T022W-S101A-S103A-V104I-G211Q-A215F-A232V-Q245R, G020R-T22W-S078R-S101G-S103A-V104I-N116A-T213A-A215F-A232V-Q245R, G020R-S078R-S101G-S103A-V104I-A215F-A232V-Q245R, G020R-T022W-S078R-S101G-S103A-V104I-N116A-N183D-A232V-Q245R, N076D-S101G-S103A-V104I-A232V-Q245R, N076D-S101G-S103A-V104I-A232V-Q245R-N269R, G020R-T22W-S101A-S103A-V104I-A232V-Q245R, G020R-S101G-S103A-A232V-Q245R, G020R-T022W-S078R-S101A-S103A-V104I-N116A-N183D-A232V-Q245R, N018R-G020R-S024R-R045T-N076D-S101G-S103A-V104I-A232V-Q245R-N269R, N043R-R045T-S078R-S101G-S103A-V104I-A232V-Q245R, N018R-S101G-V104I-H249R, G020R-T22W-S078R-S101G-S103A-V104I-N116A-N183D-A232V-Q245R, G020R-T022W-S101G-S103A-V104I-I198L-G211Q-T213A-A232V-Q245R, G020R-S078R-S101A-S103A-V104I-N116A-N183D-T213A-A232V-Q245R, S024R-N076D-V104I-A232V-Q245R, N018R-G020R-N076D-S101G-S103A-V104I-A232V-Q245R, N018R-S024R-N076D-S101G-V104I-A232V-H249R, N018R-N043D-S078R-S101G-S103A-V104I-A232V-Q245R, A001T-N018R-S024R-N076D-N116A-T213A-H249R, N076D-S078R-S101G-S103A-V104I-A232V-Q245R, G020R-S078R-S101G-S103A-V104I-N116A-A232V-Q245R, N043R-N076D-S101G-S103A-V104I-A232V-Q245R, N018R-R045T-S101G-S103A-V104I-A232V-

Q245R, N018R-N076D-S101G-V104I-A232V-Q245R, G020R-S078R-S101G-S103A-V104I-N116A-N183D-A232V-Q245R, N018R-S024R-N076D-S101A-G211Q-T213A-A215F-H249R, R045T-S078R-S101G-S103A-V104I-A232V-Q245R, N043R-N076D-S101G-S103A-V104I-A232V-Q245R-N269R, G020R-T022W-S078R-S101G-S103A-V104I-N116A-N183D-T213A-A232V-Q245R, G020R-T022W-S101G-S103A-V104I-N116A-N183D-T213A-A232V-Q245R, G020R-S101G-I198L-A215F-A232V-Q245R, N018R-S024R-N076D-T213A-A215F-H249R, G020R-S078R-S101G-S103A-V104I-N116A-G211Q-A232V-Q245R, G020R-T022W-S078R-S101A-S103A-V104I-N116A-N183D-A215F-A232V-Q245R, G020R-T022W-S078R-S101A-S103A-V104I-N116A-N183D-T213A-A232V-Q245R, S024R-A232V-Q245R, N018R-S024R-N043D-S101G-S103A-V104I-A232V-Q245R-N269R, N018R-S024R-N076D-S101A-A215F-H249R, N018R-T022W-S024R-N076D-N116A-T213A-H249R, S101G-S103A-V104I-A232V-Q245R, N018R-S024R-N076D-G211Q-T213A-A215F-H249R, N018R-S024R-N076D-N116A-T213A-A215F-H249R, N043D-N076D-S078R-S101G-S103A-V104I-A232V-Q245R-N269R, N043D-S078R-S101G-S103A-V104I-A232V-Q245R-H249R, G020R-T022W-S078R-S101G-S103A-V104I-N116A-N183D-G211Q-A232V-Q245R, N018R-S024R-N076D-S101A-I198L-G211Q-A215V-H249R, N018R-T022W-S024R-N076D-N116A-G211Q-H249R, G020R-S103A-V104I-A232V-Q245R, G020R-T22W-S101A-S103A-V104I-G211Q-A215F-A232V-Q245R, S024R-N076D-S101G-S103A-V104I-A232V-Q245R, G020R-S101G-S103A-V104I-N116A-A232V-Q245R, N018R-T22W-S024R-N076D-I198L-A215F-H249R, G020R-T022W-S103A-V104I-A232V-Q245R, G020R-T022W-S101A-S103A-V104I-G211Q-T213A-A232V-Q245R, G020R-T022W-S101G-S103A-V104I-G211Q-T213A-A215F-A232V-Q245R, N018R-N043R-R045T-N076D-S101G-S103A-V104I-A232V-Q245R, N018R-T022W-S024R-N076D-S101A-I198L-T213A-A215F-H249R, N018R-T22W-S024R-N076D-S101A-A215F-H249R, G020R-R045T-S101G-S103A-V104I-A232V-Q245R, G020R-S078R-S101G-S103A-V104I-T180A-A232V-Q245R, G020R-T022W-S078R-S101G-S103A-V104I-N116A-N183D-A215F-A232V-Q245R, N018R-S101G-S103A-V104I, G020R-T22W-S101A-S103A-V104I-N116A-G211Q-T213A-A215F-A232V-Q245R, N018R-S024R-N076D-S103A-A232V-Q245R, G020R-S078R-S101A-S103A-V104I-N116A-N183D-A232V-Q245R, N018R-S024R-N076D-G211Q-H249R, G020R-S101A-S103A-V104I-T213A-A215F-A232V-Q245R, N018R-G020R-N043D-S101G-S103A-V104I-A232V-Q245R, G020R-T022W-S101A-S103A-V104I-G211Q-A232V-Q245R, G020R-T022W-S101A-S103A-V104I-N116A-G211Q-A215F-A232V-Q245R, G020R-T022W-S101A-S103A-V104I-N116A-G211Q-A232V-Q245R, N018R-S024R-N076D-A232V-H249R, N018R-S024R-R045T-N076D-S101G-S103A-V104I-A232V-Q245R-N269R, N018R-N076D-Q245R, S024R-V104I-Q245R, S101G-A232V, G020R-T22W-S101A-S103A-V104I-N116A-G211Q-A215F-A232V-Q245R, N018R-G020R-T022W-S024R-N076D-N116A-N183D-I198L-T213A-H249R, G020R-T022W-S078R-S101A-S103A-V104I-A232V-Q245R, G020R-T022W-S078R-S101A-S103A-V104I-I198L-A232V-Q245R, S024R-Q245R-H249R, G020R-S101G-S103A-V104I-N116A-G211Q-A232V-Q245R, N018R-T22W-S024R-N076D-N116A-G211Q-H249R, S024R-S101G-V104I-H249R, N018R-S024R-N076D-N116A-I198L-G211Q-T213A-A215F-H249R, N018R-S024R-V104I, G020R-T022W-S078R-S101A-S103A-V104I-N183D-I198L-T213A-A215F-A232V-Q245R, N018R-G020R-T22W-S024R-N076D-N116A-N183D-I198L-T213A-H249R, G020R-T022W-S101A-S103A-V104I-A232V-Q245R, Q012H-G020R-S078R-S101G-S103A-V104I-I198L-G211Q-T213A-A232V-Q245R, N018R-S024R-N076D-S101A-G211Q-A215F-H249R, N018R-S024R-N076D-T213A-H249R, S024R-V104I-H249R, N018R-T022W-S024R-N076D-G211Q-H249R, N018R-N076D-S103A-V104I-H249R, N043R-N076D-S101G-S103A-V104I-L217E-A232V-Q245R, G020R-S078R-S101G-S103A-V104I-N183D-G211Q-T213A-A232V-Q245R-E271G, N018R-T022W-S024R-N076D-S101A-N116A-I198L-A215F-H249R, N018R-S024R-N043D-N076D-S101G-S103A-V104I-A232V-Q245R, N018R-S024R-N076D-S101A-I198L-A215F-H249R, N018R-T022W-S024R-N076D-N116A-I198L-G211Q-T213A-H249R, N018R-S024R-N076D-S101A-N116A-T213A-A215F-H249R, G020R-N043D-R045T-S078R-S101G-S103A-V104I-A232V-Q245R, R045T-S078R-S101G-S103A-V104I-A232V-Q245R-H249R, N018R-T22W-S024R-N076D-S101A-N116A-A215F-H249R, N043D-S101G-S103A-V104I-A232V-Q245R-N269R, G020R-T022W-S078R-S101A-S103A-V104I-N116A-N183D-T213A-A215F-A232V-Q245R, N018R-S024R-N076D-N116A-G211Q-T213A-A215F-H249R, S024R-S103A-M175L-A232V-H249R, N018R-S024R-N076D-N116A-T213A-H249R, G020R-R045T-N076D-S101G-S103A-V104I-A232V-Q245R, G020R-S078R-S101A-S103A-V104I-N116A-N183D-G211Q-T213A-A215F-A232V-Q245R, S024R-N043R-R045T-N076D-S078R-S101G-S103A-V104I-A232V-Q245R, N018R-S024R-N076D-S101A-N116A-I198L-T213A-A215F-H249R, N043R-R045T-S101G-S103A-V104I-A232V-Q245R, N018R-T022W-S024R-N076D-S101A-I198L-G211Q-Q245R, G020R-S024R-N043D-N076D-S078R-S101G-S103A-V104I-A232V-Q245R-N269R, S024R-A232V, G020R-S078R-S101A-S103A-V104I-N116A-N183D-G211Q-A232V-Q245R, S024R-N076D-S101G-A232V-Q245R, N018R-N076D-S101G-S103A-V104I-H249R, N018R-S024R-N076D-I198M-G211Q-T213A-A215F-H249R, N018R-T22W-S024R-N076D-S101A-I198L-A215F-H249R, N018R-N043R-N076D-S101G-S103A-V104I-A232V-Q245R-N269R, G020R-T022W-S103A-G211Q-T213A-A215F-A232V-Q245R, G020R-S078R-S101A-S103A-V104I-N116A-N183D-G211Q-T213A-A232V-Q245R, R045T-N076D-S101G-S103A-V104I-A232V-Q245R-N269R, N018R-T22W-S024R-N076D-S101A-G211Q-T213A-H249R, N018R-S024R-N076D-N116A-I198L-A215F-H249R-V268G, N018R-T022W-S024R-N076D-S101A-G211Q-H249R, N018R-T022W-S024R-N076D-S101A-N116A-I198L-G211Q-H249R, S101G-S103A-V104I-Q245R, N018R-N076D-S101G-A232V-Q245R, N018R-G020R-R045T-S101G-S103A-V104I-A232V-Q245R, N018R-T022W-S024R-N076D-S101A-N116A-I198L-H249R, N018R-T022W-S024R-N076D-N116A-I198L-T213A-H249R, S078R-S101G-S103A-V104I-A232V-Q245R-H249R, N018R-S078R-S101G-S103A-V104I-L217E-A232V-Q245R, G020R-N043R-N076D-S101G-S103A-V104I-A232V-Q245R-N269R, N018R-N043D-N076D-S101G-S103A-V104I-A232V-Q245R-H249R, R045T-S101G-S103A-V104I-A232V-Q245R-N269R, S024R-S103A-A232V, N018R-S024R-N076D-S101A-G211Q-H249R, N043D-S101G-S103A-V104I-A232V-Q245R-H249R, N018R-N043R-R045T-N076D-S076T-S101G-S103A-V104I-A232V-Q245R-A273T, N018R-G020R-N043D-

S078R-S101G-S103A-V104I-A232V-Q245R, G020R-S078R-S101A-S103A-V104I-N183D-A215F-A232V-Q245R, N018R-S024R-N076D-S101G-A232V, A232V-Q245R, N043R-R045T-N076D-S078R-S101G-S103A-V104I-A232V-V234I-Q245R, S024R-N076D-S103A-V104I-Q245R, G020R-S078R-S101A-S103A-V104I-G211Q-T213A-A232V-Q245R, N043D-S078R-S101G-S103A-V104I-A232V-Q245R-N269R-A272V, N018R-G020R-S024R-N076D-N116A-N183D-I198L-G211Q-H249R, N018R-S103A-V104I-A232V, G020R-T022W-S101G-S103A-V104I-N116A-N183D-T213A-A215F-A232V-Q245R, S024R-N043R-N076D-S101G-S103A-V104I-A232V-Q245R-N269R, N018R-T022W-S024R-N076D-T213A-A215F-H249R, N018R-S024R-N076D-S101A-N116A-I198L-G211Q-T213A-H249R, G020R-T22W-S078R-S101A-S103A-V104I-N116A-N183D-T213A-A232V-Q245R, G020R-T022W-S078R-S101G-S103A-V104I-G211Q-T213A-A232V-Q245R, G020R-T022W-S101A-S103A-V104I-A215F-A232V-Q245R, N018R-G020R-S024R-N076D-N116A-N183D-A215F-H249R, N018R-S024R-N076D-N116A-M117I-N183D-T213A-H249R, N018R-T022W-S024R-N076D-S101A-N116A-I198L-T213A-H249R, N018R-T22W-S024R-N076D-S101A-I198L-T213A-A215F-H249R, N018R-N043D-S078R-S101G-S103A-V104I-A232V-Q245R-H249R, N018R-N076D-S101G-S103A-V104I-A232V-Q245R-H249R, G020R-T022W-S101G-S103A-V104I-N116A-N183D-I198L-A232V-Q245R, N018R-N043R-R045T-N076D-S101G-S103A-V104I-A232V-Q245R-N269R, N018R-S024R-N076D-N116A-I198L-Y209H-T213A-H249R, G020R-T022W-S101A-S103A-V104I-N116A-N183D-G211Q-T213A-A232V-Q245R, S024R-N076D-S101G-M175L-A232V-Q245R, N018R-N043D-R045T-S101G-S103A-V104I-A232V-Q245R, R045T-N076D-S078R-S101G-S103A-V104I-A232V-Q245R, G020R-S078R-S101A-S103A-V104I-N116A-N183D-I198L-A215F-A232V-Q245R, N043R-N076D-S101G-S103A-V104I-A232V-Q245R-H249R, N018R-S024R-N076D-I198L-T213A-A215F-H249R, N018R-T022W-S024R-N076D-I198L-A215F-H249R, N018R-T022W-S024R-N076D-N116A-T213A-A215F-H249R, N018R-T022W-S024R-N076D-S101A-N116A-I198L-T213A-A215F-H249R, N018R-T022W-S024R-N076D-N116A-G211Q-T213A-H249R, N018R-S024R-Q245R, N018R-T022W-S024R-N076D-S101A-N116A-A215F-H249R, S024R-N076D-V104I-Q245R, K027R-N043R-S101G-S103A-V104I-A232V-Q245R-N269R, N018R-S024R-N076D-N116A-I198L-G211Q-T213A-H249R, N018R-S024R-N076D-N116A-I198L-H249R, N018R-S024R-N076D-N183D-I198L-G211Q-T213A-A215F-H249R, G020R-T022W-S101A-S103A-V104I-N116A-G211Q-T213A-A215F-A232V-Q245R, N018R-N043D-R045T-S078R-S101G-S103A-V104I-A232V-Q245R, N043R-R045T-N076D-S078R-S101G-S103A-V104I-A232V-Q245R-N269R, N018R-T22W-S024R-N076D-N116A-T213A-A215F-H249R, N018R-T022W-S024R-N076D-N116A-G211Q-A215F-H249R, G020R-S078R-S101G-S103A-V104I-N116A-N183D-T213A-A232V-Q245R, N018R-N076D-S101G-S103A-V104I-A232V-Q245R, N018R-S101G-V104I, G020R-S078R-S101G-S103A-V104I-N116A-N183D-G211Q-T213A-A215F-A232V-Q245R, G020R-S078R-S101A-S103A-V104I-A232V-Q245R, N018R-S024R-N076D-S101A-I198L-G211Q-H249R, N018R-S024R-N076D-I198L-G211Q-T213A-H249R, N018R-T022W-S024R-N076D-S101A-N116A-I198L-G211Q-T213A-H249R, N018R-N076D-H249R, N018R-G020R-S024R-N076D-S101A-N116A-N183D-I198L-H249R, N018R-S024R-N076D-S101A-N116A-G211Q-T213A-H249R, G020R-T022W-S078R-S101A-S103A-V104I-N116A-N183D-G211Q-T213A-A215F-A232V-Q245R, G020R-T022W-S101G-S103A-V104I-A114T-T213A-A215F-A232V-Q245R, N018R-T22W-S024R-N076D-N116A-G211Q-T213A-H249R, N018R-G020R-T022W-S024R-N076D-S101A-N116A-N183D-H249R, G020R-S101A-S103A-V104I-N116A-N183D-T213A-A232V-Q245R, N018R-T022W-S024R-N076D-S101A-G211Q-T213A-H249R, N018R-T022K-N043D-S101G-S103A-V104I-A232V-Q245R, N018R-S101G-S103A-V104I-A232V-Q245R-N269R, G020R-S078R-S101G-S103A-V104I-N116A-N183D-G211Q-T213A-A215F-A232V, N018R-S024R-N076D-N116A-H249R, G020R-S024R-N076D-S101G-S103A-V104I-A232V-Q245R, N043D-N076D-S101G-S103A-V104I-A232V-Q245R-N269R, N018R-S024R-N076D-S101A-N116A-I198L-G211Q-H249R, N018R-T022W-S024R-N076D-I198L-T213A-A215F-H249R, N018R-N043D-N076D-S078R-S101G-S103A-V104I-A232V-Q245R-N269R, G020R-T22W-S101G-S103A-V104I-N116A-N183D-T213A-A215F-A232V-Q245R, G020R-S101G-S103A-V104I-N183D-G211Q-A232V-Q245R-, N018R-S024R-N076D-S101A-I198L-T213A-H249R, N018R-S024R-N076D-S101A-I198L-H249R, N018R-S024R-R045T-N076D-S101G-S103A-V104I-A232V-Q245R-H249R, N018R-S024R-N076D-S101A-N183D-T213A-H249R, N018R-N043D-N076D-S078R-S101G-S103A-V104I-A232V-Q245R, G020R-S078R-S101G-S103A-V104I-N116A-A131V-N183D-T213A-A232V-Q245R, N018R-R045T-N076D-S101G-S103A-V104I-A232V-Q245R, N018R-S024R-N076D-S101A-N183D-G211Q-H249R, N076D-S101G-S103A-V104I-A232V-Q245R-H249R, S024R-S101G-Q245R, S024R-N076D-S101G-Q245R, N076D-S078R-S101G-S103A-V104I-A232V-Q245R-H249R, N018R-G020R-S024R-N076D-S101A-N183D-G211Q-A215F-H249R, S024R-S101G, N018R-T22W-S024R-N076D-T213A-A215F-H249R, G020R-N043D-S101G-S103A-V104I-A232V-Q245R, G020R-T022W-S101G-S103A-V104I-N183D-I198L-T213A-A215F-A232V-Q245R, N018R-N043D-R045T-S101G-S103A-V104I-A232V-Q245R-N269R, N043D-N076D-S078R-S101G-S103A-V104I-A232V-Q245R, S024R-R045T-N076D-S101G-S103A-V104I-A232V-Q245R-N269R, G020R-T022W-S101A-S103A-V104I-I198L-G211Q-A215F-A232V-Q245R, G020R-T022W-S101G-S103A-V104I-N116A-N183D-A215F-A232V-Q245R, N018R-G020R-N076D-S101G-S103A-V104I-A232V-Q245R-H249R, N018R-T022W-S024R-N076D-S101A-A215F-H249R, N018R-V104I, N018R-S024R-N076D-N116A-I198L-A215F-H249R, N018R-S024R-N076D-L088I-S101A-N116A-I198L-G211Q-A215F-H249R, N018R-T022W-S024R-N076D-S101A-N116A-G211Q-T213A-H249R, N043R-R045T-N076D-S101G-S103A-V104I-A232V-Q245R-N269R, N018R-N076D-S101G-V104I-H249R, N018R-T022W-S024R-N076D-S101A-T213A-A215F-H249R, N018R-T22W-S024R-N076D-S101A-N116A-I198L-A215F-H249R, N018R-G020R-S101G-S103A-V104I-A232V-Q245R-H249R, S101G-S103A-V104I-A232V-Q245R-H249R-N269R, S024R-N076D-Q245R, N018R-G020R-N043R-R045T-N076D-S101G-S103A-V104I-A232V-Q245R, N018R-G020R-S024R-N076D-A215F-H249R, N018R-S024R-N076D-S101A-N116A-N183D-I198L-T213A-H249R, N018R-G020R-S024R-N076D-G211Q-A215F-H249R, N043D-S101G-S103A-V104I-A232V-Q245R, G020R-T22W-S078R-S101A-S103A-V104I-N116A-N183D-A215F-A232V-

Q245R, N018R-S024R-N076D-I198L-G211Q-A215F-H249R, N043R-N076D-S078R-S101G-S103A-V104I-A232V-Q245R-N269R, N043R-S078R-S101G-S103A-V104I-A232V-Q245R-N269R, G020R-N043R-S101G-S103A-V104I-A232V-Q245R-H249R, N018R-T022W-S024R-N076D-S101A-T213A-H249R, G020R-T022W-S101A-N116A-I198L-G211Q-T213A-A215F-H249R, N043R-R045T-S078R-S101G-S103A-V104I-N218S-A232V-Q245R, N018R-S103A, G020R-T22W-S101G-S103A-V104I-N116A-N183D-A215F-A232V-Q245R, N018R-S024R-N076D-S101A-H249R, N018R-T022W-S024R-N076D-G211Q-T213A-H249R, S024R-N043R-R045T-N076D-S101G-S103A-V104I-A232V-Q245R, G020R-T022W-S101A-S103A-V104I-N116A-N183D-A232V-Q245R, G020R-S101A-S103A-V104I-N116A-N183D-G211Q-T213A-A215F-A232V-Q245R, K027R-R045T-N076D-S078R-S101G-S103A-V104I-A232V-Q245R-N269R, G020R-R045T-N076D-S101G-S103A-V104I-A232V-Q245R-H249R, N018R-G020R-S024R-N076D-N116A-N183D-T213A-A215F-H249R, N018R-S024R-N076D-V104I, S101G-S103A-V104I-A232V-H249R, N018R-S024R-N076D-N116A-N183D-G211Q-H249R, N018R-G020R-S024R-N076D-N116A-A215F-H249R, N018R-S024R-N076D-N183D-T213A-A215F-H249R, N018R-T022W-S024R-N076D-I198L-G211Q-H249R, N043D-S078R-S101G-S103A-V104I-A232V-Q245R-N269R-R275S, G020R-T022W-S101A-S103A-V104I-N116A-N183D-G211Q-A232V-Q245R, N018R-T022W-S024R-N076D-S101A-I198L-G211Q-T213A-A215F-H249R, N018R-T022W-S024R-N076D-S101A-N116A-I198L-G211Q-T213A-A215F-H249R, N018R-G020R-S024R-N076D-N183D-H249R, N018R-S024R-N076D-N116A-I198L-T213A-H249R, N018R-T022W-S024R-N076D-S101A-N116A-G211Q-H249R, V004M-N018R-S024R-N076D-N116A-I198L-G211Q-T213A-H249R, V104I-A232V-H249R, G020R-T022W-S101G-S103A-V104I-N116A-N183D-G211Q-A215F-A232V-Q245R, G020R-S101A-S103A-V104I-N116A-N183D-G211Q-A232V-Q245R-T274I, G020R-S101A-S103A-V104I-T213A-A232V-Q245R, G020R-S101G-S103A-V104I-N116A-N183D-G211Q-T213A-A232V-Q245R, G020R-S024R-N043D-S078R-S101G-S103A-V104I-A232V-Q245R, N018R-S024R-N076D-S103A-H249R, N018R-G020R-S024R-N076D-S101A-N116A-N183D-G211Q-A215F-H249R, N018R-G020R-S024R-N076D-N116A-N183D-I198L-H249R, N018R-T022W-S024R-N076D-N116A-I198L-A215F-H249R, N018R-S024R-N076D-S101A-G211Q-T213A-A215F-H249R-A270V, N018R-N043D-R045T-N076D-S078R-S101G-S103A-V104I-A232V-Q245R-N269R, G020R-T022W-S101G-S103A-V104I-N183D-A232V-Q245R, N018R-G020R-T022W-S024R-N076D-S101A-N116A-T213A-H249R, N018R-T022W-S024R-N076D-I198L-G211Q-A215F-H249R, N018R-T022W-S024R-N076D-I198L-T213A-H249R, G020R-T022W-S101G-S103A-V104I-N116A-N183D-A232V-Q245R, N018R-T22W-S024R-N076D-N116A-I198L-T213A-H249R, N043R-R045T-S078R-S101G-S103A-V104I-A232V-Q245R-N269R, N018R-S024R-N076D-S101G-S103A-V104I-A232V, S101G-H249R, S024R-N076D-S101G-S103A-V104I-M175L-H249R, G020R-T022W-S101A-S103A-V104I-N116A-N183D-A232V-Q245R-N269S, N018R-S024R-N076D-S101A-N116A-I198L-H249R, N018R-T022W-S024R-N076D-N116A-H249R, N018R-G020R-S024R-N076D-S101A-N183D-I198L-A215F-H249R, N018R-S024R-N076D-T213A-A215F-H249R-T260K, N018R-S024R-N076D-N116A-G211Q-T213A-H249R, N018R-G020R-T022W-S024R-N076D-N116A-I198L-H249R, S024R-N076D-S101G-S103A-V104I-Q245R, S024R-N076D-S103A-H249R, N018R-S101G-S103A-V104I-A232V-Q245R-H249R, N018R-S024R-N076D-I198L-G211Q-H249R, N018R-T022W-S024R-N076D-S101A-I198L-G211Q-T213A-H249R, G020R-S024R-R045T-S101G-S103A-V104I-A232V-Q245R, N018R-G020R-S024R-N076D-N183D-G211Q-T213A-H249R, N018R-N043D-R045T-S078R-S101G-S103A-V104I-A232V-Q245R-A272D, N018R-S024R-N076D-N116A-I198L-T213A-A215F-H249R, N018R-T22W-S024R-N076D-S101A-I198L-H249R, N018R-T022W-S024R-N076D-N116A-I198L-H249R, S024R-N076D-S101G-S103A-A232V, S024R-S103A-V104I, N018R-S024R-N076D-S101A-N116A-N183D-G211Q-A215F-H249R, S024R-R045T-N076D-S101G-S103A-V104I-A232V-Q245R-H249R, G020R-S101G-S103A-V104I-N116A-N183D-A232V-Q245R, S024R-N043D-N076D-S101G-S103A-V104I-A232V-Q245R-N269R, G020R-T022W-S101A-S103A-V104I-N183D-G211Q-T213A-A215F-A232V-Q245R, G020R-R045T-N076D-S078R-S101G-S103A-V104I-A232V-Q245R-N269R, N018R-S024R-N076D-S101A-N116A-I198L-G211Q-A215F-H249R, G020R-S101A-S103A-V104I-N116A-N183D-A215F-A232V-Q245R, N018R-N043R-S101G-S103A-V104I-A232V-Q245R-H249R, N018R-S024R-N076D-I198L-T213A-H249R, N018R-S024R-N076D-N116A-N183D-T213A-H249R, G020R-N043D-S101G-S103A-V104I-A232V-Q245R-N269R, S024R-N076D-S103A-Q245R, N018R-T022W-S024R-N076D-S101A-N116A-G211Q-T213A-A215F-H249R, S103A-V104I-Q245R, N018R-T022W-S024R-N076D-G211Q-A215F-H249R, N018R-T022W-S024R-N076D-N116A-N183D-I198L-H249R, N018R-T022W-S024R-N076D-I198L-G211Q-T213A-H249R, N018R-S024R-N076D-N116A-N183D-G211Q-T213A-A215F-H249R, N018R-G020R-N043D-R045T-N076D-S101G-S103A-V104I-A232V-Q245R-N269R, N018R-G020R-T022W-S024R-N076D-S101A-G211Q-T213A-A215F-H249R, A016T-N043R-R045T-N076D-S101G-S103A-V104I-A232V-Q245R-N269R, N018R-T022W-S024R-N076D-N116A-A215F-H249R, N043R-N076D-S101G-S103T-V104I-A232V-Q245R-H249R-N269R, G020R-S078R-S101A-S103A-V104I-G115E-N116A-N183D-G211Q-T213A-A232V-Q245R, N018R-S024R-N076D-I198L-H249R, N018R-S024R-N076D-S101A-N116A-N183D-H249R, G020R-S101G-S103A-V104I-N116A-N183D-G211Q-A232V-Q245R, N018R-S024R-N076D-S101G, N076D-S101G-A232V-Q245R, N018R-N076D-S101G-S103A-V104I-Q245R, N018R-R045T-S101G-S103A-V104I-A232V-Q245R-H249R, N018R-S024R-N076D-A215F-H249R, N018R-V104I-A232V, N043D-R045T-N076D-S078R-S101G-S103A-V104I-A232V-Q245R, S024R-N076D-S101G-A232V-H249R, S103A-A232V-Q245R, G020R-S101G-S103A-V104I-N116A-N183D-G211Q-T213A-A215F-A232V-Q245R, N018R-G020R-S024R-N076D-N116A-N183D-I198L-G211Q-A215F-H249R, N018R-T022W-S024R-N076D-S101A-I198L-G211Q-A215F-H249R, S024R-N076D-S103A-V104I-H249R, S024R-S101G-S103A-V104I, G020R-S101G-S103A-V104I-N116A-N183D-G211Q-A215F-A232V-Q245R, N018R-T022W-S024R-N076D-S101A-N116A-N183D-A215F-H249R, G020R-T022W-S101G-S103A-V104I-N116A-N183D-G211Q-T213A-A215F-A232V-Q245R, G020R-S024R-R045T-N076D-S101G-S103A-V104I-A232V-Q245R, N018R-T022W-S024R-N076D-N116A-N183D-T213A-H249R, N018R-G020R-S024R-N076D-A131T-A215F-H249R, N018R-S024R-

N076D-S101A-N116A-N183D-G211Q-T213A-A215F-H249R, N018R-S024R-N076D-S101A-N116A-G211Q-T213A-A215F-H249R, N018R-S024R-N076D-I198L-A215F-H249R, N018R-T022W-S024R-N076D-N183D-G211Q-H249R, N018R-T022W-S024R-N076D-S101A-N116A-T213A-A215F-H249R, N018R-G020R-S024R-R045T-N076D-S101G-S103A-V104I-A232V-Q245R, N043R-S101G-S103A-V104I-Q245R-H249R, N018R-N076D-A232V-H249R, NO 18K-N076D-S078R-S101G-S103A-V104I-L217E-A232V-Q245R-N269R, N018R-G020R-S024R-N043D-N076D-S078R-S101G-S103A-V104I-A232V-Q245R, N018R-T022W-S024R-N076D-S101A-N116A-T213A-A215F-H249R-L267I, A232V-H249R, N018R-G020R-S024R-N076D-N116A-G211Q-T213A-A215F-H249R, N076D-V104I-Q245R, N018R-G020R-S024R-N076D-N183D-I198L-G211Q-A215F-H249R, N018R-S024R-N076D-S101A-G211Q-T213A-H249R, S024R-S101G-S103A-A232V, N018R-G020R-T022W-S024R-N076D-N116A-N183D-I198L-T213A-A215F-H249R, N018R-G020R-S024R-N076D-N116A-N183D-I198L-G211Q-T213A-H249R, N018R-G020R-T022W-S024R-N076D-S101A-A215F-H249R, G020R-T022W-S101A-S103A-V104I-N116A-N183D-G211Q-A215F-A232V-Q245R, N018R-S024R-N076D-N116A-I198L-G211Q-H249R, S103A-A232V-H249R, N018R-G020R-S024R-N076D-N116A-N183D-I198L-A215F-H249R, N018R-S024R-N076D-N116A-N183D-I198L-T213A-H249R, N018R-T022W-S024R-N076D-N183D-T213A-H249R, N018R-S024R-N076D-S101A-T213A-A215F-H249R, N018R-T022W-S024R-N076D-S101A-N116A-N183D-G211Q-H249R, N018R-R045T-S101G-S103A-V104I-A232V-Q245R-N269R, N018R-G020R-R045T-N076D-S078R-S101G-S103A-V104I-A232V-Q245R, N018R-T022W-S024R-N076D-N116A-I198L-T213A-A215F-H249R, G020R-T022W-S101G-S103A-V104I-N116A-N183D-G211Q-T213A-A232V-Q245R, N018R-G020R-S024R-N076D-I198L-H249R, N018R-G020R-T022W-S024R-N076D-S101A-N116A-G211Q-H249R, G020R-T022W-S101A-S103A-V104I-N116A-N183D-A232V-Q245R-T274I, S024R-S103A-Q245R-H249R, N018R-T022W-S024R-N076D-S101A-N116A-N183D-I198L-H249R, N018R-S024R-N076D-S101A-I198L-G211Q-A215F-H249R, N018R-T022W-S024R-N076D-N116A-I198L-G211Q-A215F-H249R, N018R-G020R-T022W-S024R-N076D-N116A-N183D-T213A-H249R, N018R-N043D-R045T-N076D-S101G-S103A-V104I-A232V-Q245R-N269R, N018R-T022W-S024R-N076D-N116A-G211Q-T213A-A215F-H249R, N018R-S024R-N076D-S101A-N183D-I198L-T213A-H249R, N043D-N076D-S101G-S103A-V104I-A232V-Q245R-H249R, N018R-S024R-N076D-I198L-G211Q-T213A-A215F-H249R, N018R-G020R-S024R-N076D-N116A-N183D-T213A-H249R, S103A-A232V, N018R-T022W-S024R-N076D-N116A-N183D-A215F-H249R, N018R-S024R-N076D-S101A-N116A-H249R, N018R-N043R-S078R-S101G-S103A-V104I-A232V-Q245R, N018R-G020R-T022W-S024R-N076D-S101A-N183D-G211Q-A215F-H249R, N043R-N076D-S078R-S101G-S103A-V104I-A232V-Q245R-H249R, N018R-G020R-S024R-N076D-S101A-N116A-N183D-I198L-T213A-H249R, N018R-S024R-N076D-N183D-I198L-T213A-H249R, N018R-T022W-S024R-N076D-S101A-N183D-G211Q-H249R, N018R-G020R-S024R-N076D-I198L-T213A-A215F-H249R, N018R-G020R-T022W-S024R-N076D-N183D-G211Q-T213A-H249R, N018R-T022W-S024R-N076D-I198L-H249R, N018R-S024R-N076D-N183D-I198L-G211Q-H249R, G020R-T022W-S101A-S103A-V104I-N116A-N183D-T213A-A232V-Q245R, N018R-G020R-S024R-N076D-N116A-N183D-G211Q-T213A-H249R, N018R-S024R-N076D-N116A-N183D-I198L-G211Q-T213A-A215F-H249R, G020R-T022W-S101A-S103A-V104I-N116A-N183D-A215F-A232V-Q245R, N018R-S024R-N076D-S101A-N183D-H249R, N018R-S024R-N076D-A232V, N018R-T022W-S024R-N076D-S101A-N116A-H249R, G020R-S101A-S103A-V104I-N116A-N183D-I198L-G211Q-T213A-A215F-A232V-Q245R, G020R-T022W-S101G-S103A-V104I-N116A-N183D-G211Q-A232V-Q245R-N263S, S024R-N076D-S101G-V104I-A232V-H249R, N043R-S078R-S101G-S103A-V104I-A232V-Q245R, S024R-N076D-S078R-S101G-S103A-V104I-A232V-Q245R-H249R, N018R-S024R-N076D-S101A-N183D-I198L-T213A-A215F-H249R, N018R-G020R-S024R-N076D-I198L-A215F-H249R, N018R-G020R-S024R-N076D-S101A-N116A-T213A-H249R, N018R-S024R-N076D-S101A-V197A-T213A-A215F-H249R, S024R-S101G-S103A, N018R-S024R-N076D-S101A-N116A-G211Q-A215F-H249R, N043R-N076D-S078R-S101G-S103A-V104I-L217E-A232V-Q245R, S024R-V104I-A232V, N018R-S024R-N076D-N183D-G211Q-H249R, G020R-N043R-R045T-S078R-S101G-S103A-V104I-A232V-Q245R, N018R-G020R-T022W-S024R-N076D-S101A-N116A-N183D-T213A-H249R, N018R-S024R-N076D-N116A-A150T-T213A-H249R, N018R-S024R-N076D-N183D-T213A-H249R, N018R-G020R-S024R-N076D-N116A-N183D-G211Q-A215F-H249R, N018R-G020R-S024R-N076D-G211Q-H249R, N018R-S024R-N076D-S101A-N116A-N183D-I198L-H249R, S024R-N076D-A232V-H249R, N018R-G020R-T022W-S024R-N076D-S101A-N116A-N183D-I198L-G211Q-T213A-H249R, N018R-T022W-S024R-N076D-S101A-N116T-I198L-A215F-H249R, N018R-S024R-N076D-N183D-I198L-G211Q-A215F-H249R, N018R-T022R-S024R-N076D-S101A-N116A-N183D-G211Q-H249R, R045T-S101G-S103A-V104I-A232V-Q245R, N018R-G020R-S024R-N076D-S101A-N183D-G211Q-H249R, G020R-S101G-S103A-V104I-N116A-N183D-T213A-A232V-Q245R, N076D-S101G-S103A-Q245R, G020R-N043D-S078R-S101G-S103A-V104I-A232V-Q245R-H249R, N018R-S024R-N076D-N116A-N183D-H249R, N018R-S024R-N076D-S101A-N183D-G211Q-T213A-A215F-H249R, N018R-G020R-T022W-S024R-N076D-S101A-N116A-I198L-H249R, N018R-T22W-S024R-N076D-G211Q-T213A-H249R, N018R-G020R-S024R-N076D-N183D-G211Q-H249R, N018R-G020R-S024R-N076D-S101A-N116A-N183D-T213A-H249R, N043R-S078R-S101G-S103A-V104I-L217E-A232V-Q245R, N018R-T022W-S024R-N076D-S101A-A215F-H249R, N018R-G020R-S024R-N076D-S101A-N183D-I198L-G211Q-T213A-H249R, N076D-S101G-V104I-H249R, N018R-T022W-S024R-N076D-S101A-N116A-N183D-T213A-H249R, N018R-S024R-N076D-N183D-H249R, N018R-S024R-N076D-S101A-N183D-I198L-A215F-H249R, N018R-T022W-S024R-N076D-N183D-I198L-A215F-H249R, N018R-T022W-S024R-N076D-S101A-I198L-G211Q-H249R, G020R-S101A-S103A-V104I-N116A-N183D-A232V-Q245R, N018R-S024R-N076D-N116A-N183D-I198L-G211Q-H249R, N018R-G020R-S024R-S101G-S103A-V104I-A232V-Q245R, N018R-N076D-S078R-S101G-S103A-V104I-L217E-A232V-Q245R, G020R-S101A-S103A-V104I-N116A-N183D-G211Q-A232V-Q245R, N018R-T022W-S024R-N076D-S101A-N183D-I198L-Y209H-H249R, N018R-S024R-N076D-N183D-I198L-T213A-A215F-H249R, N018R-S024R-N076D-S101A-N116A-

N183D-G211Q-T213A-H249R, N018R-T022W-S024R-N076D-S101A-N116A-N183D-G211Q-T213A-H249R, N018R-S024R-N076D-N183D-I198L-H249R, N018R-S024R-N076D-N183D-A215F-H249R, N018R-G020R-S024R-N076D-G211Q-T213A-A215F-H249R, N076D-Q245R, N076D-S101G-V104I-Q245R, N018R-T022W-S024R-N076D-S101A-G211Q-A215F-H249R, N018R-T022W-S024R-N076D-S101A-N116A-N183D-G211Q-A215F-H249R, N018R-G020R-T022W-S024R-N076D-S101A-G211Q-T213A-H249R, G020R-S024R-N043R-S101G-S103A-V104I-A232V-Q245R, N018R-S024R-N076D-N116A-N183D-G211Q-A215F-H249R, G020R-S101A-S103A-V104I-N116A-N183D-T213A-A215F-A232V-Q245R, S101G-S103A-V104I, N018R-G020R-S024R-N076D-S101A-N116A-N183D-G211Q-T213A-H249R, N018R-G020R-S024R-N076D-N204D-T213A-H249R, N018R-T022W-S024R-N076D-N183D-I198L-H249R, N018R-S024R-N076D-S101A-N116A-N183D-A215F-H249R, N018R-T022W-S024R-N076D-N116A-N183D-I198L-G211Q-T213A-A209V-H249R, N018R-T022W-S024R-N076D-S101A-N116A-N183D-G211Q-T213A-A215F-H249R, N018R-S024R-N076D-S101A-N116A-I198L-T213A-H249R, N018R-G020R-S024R-N076D-S101A-N116A-G211Q-T213A-H249R, N018R-G020R-T022W-S024R-N076D-S101A-N116A-N183D-G211Q-T213A-A215F-H249R, N018R-S024R-N076D-S101A-N116A-N183D-T213A-A215F-H249R, N018R-S024R-N076D-S101A-N183D-I198L-G211Q-T213A-A215F-H249R, N018R-S024R-N076D-S101A-N183D-I198L-G211Q-T213A-H249R, N018R-N043R-R045T-S078R-S101G-S103A-V104I-L217E-A232V-Q245R, N018R-S024R-N076D-N183D-G211Q-T213A-A215F-H249R, N018R-T022W-S024R-N076D-N116A-N183D-I198L-A215F-H249R, N018R-G020R-S024R-N076D-N116A-H249R, N018R-G020R-T022W-S024R-N076D-S101A-G211Q-A215F-H249R, N018R-G020R-S024R-N076D-N183D-G211Q-T213A-A215F-H249R, N018R-G020R-T022W-S024R-N076D-I198L-T213A-H249R, N018R-G020R-S024R-N076D-S101A-G211Q-A215F-H249R-N269D, N018R-G020R-N043D-S101G-S103A-V104I-A232V-Q245R-N269R, N018R-T022W-S024R-N076D-S101A-N183D-I198L-T213A-H249R, G020R-T022W-S101G-S103A-V104I-N183D-A215F-A232V-Q245R, N018R-T022W-S024R-N076D-N116A-N183D-I198L-Y209H-G211Q-H249R, N018R-G020R-T022W-S024R-N076D-S101A-N116A-N183D-G211Q-H249R, N076D-A232V-Q245R, N043D-R045T-S078R-S101G-S103A-V104I-A232V-Q245R, N018R-G020R-S024R-N076D-N116A-I198L-G211Q-A215F-Q245R, N018R-G020R-T022W-S024R-N076D-T213A-H249R, G020R-S024R-N043D-S078R-S101G-S103A-V104I-A232V-Q245R-H249R, N018R-G020R-T022W-S024R-N076D-S101A-I198L-A215F-H249R, G020R-A090S-S101G-S103A-V104I-N116A-N183D-T213A-A215F-A232V-Q245R, N018R-G020R-T022W-S024R-N076D-S101A-I198L-G211Q-T213A-A215F-H249R, N018R-G020R-S024R-N076D-S101A-N183D-T213A-A215F-H249R, N018R-S024R-N076D-N116A-N183D-I198L-G211Q-T213A-H249R, N043D-R045T-S078R-S101G-S103A-V104I-A232V-Q245R-N269R, N018R-S024R-N076D-S101A-N183D-A215F-H249R, N018R-G020R-S024R-N076D-S101A-N183D-I198L-T213A-H249R, G020R-T022W-S101A-S103A-V104I-N116A-N183D-I198L-G211Q-T213A-A215F-A232V-Q245R, N018R-G020R-S024R-N043D-N076D-S101G-S103A-V104I-A232V-Q245R-N269R, N018R-S024R-N076D-S101A-N183D-T213A-A215F-H249R, N018R-G020R-T022W-S024R-N076D-S101A-N116A-I198L-G211Q-T213A-A215F-H249R, N018R-G020R-N043D-S101G-S103A-V104I-L217E-A232V-Q245R, N076D-S103A-V104I-A232V-Q245R, R045T-N076D-S078R-S101G-S103A-V104I-A232V-Q245R-H249R, N018R-T022W-S024R-N076D-S101A-N183D-G211Q-A215F-H249R, N018R-T022W-S024R-N076D-S101A-N116A-N183D-H249R, N018R-S024R-N076D-N116A-N183D-I198L-G211Q-A215F-H249R, N018R-G020R-N043D-N076D-S078R-S101G-S103A-V104I-L217E-A232V-Q245R, N076D-S103A-V104I-Q245R, N018R-G020R-S024R-N076D-S101A-N116A-G211Q-T213A-A215F-H249R, N018R-S024R-N076D-S101A-N183D-I198L-H249R, N018R-T022W-S024R-N076D-N116A-N183D-I198L-G211Q-A215F-H249R, N018R-S024R-N076D-N116A-N183D-T213A-A215F-H249R, N018R-T022W-S024R-N076D-N116A-N183D-I198L-G211Q-H249R, N018R-S024R-N076D-S101G-Q245R, N018R-S024R-N076D-S101A-N116A-N183D-I198L-T213A-A215F-H249R, N043R-R045T-N076D-S101G-S103A-V104I-A232V-Q245R, N018R-G020R-T022W-S024R-N076D-N116A-I198L-T213A-A215F-H249R, N076D-V104I-A232V-Q245R, K027R-N043R-R045T-N076D-S101G-S103A-V104I-A232V-Q245R, N018R-T022W-S024R-N076D-S101A-N183D-T213A-A215F-H249R, N018R-S024R-N076D-S103A-V104I-L135I-A232V, N018R-G020R-T022W-S024R-N076D-N183D-I198L-G211Q-H249R, N018R-G020R-T022W-S024R-N076D-S101A-N116A-N183D-I198L-A215F-H249R, N018R-S024R-N076D-S101A-N116A-N183D-G211Q-H249R, N018R-T022W-S024R-N076D-N183D-G211Q-T213A-A215F-H249R, N076D-S101G-S103A-V104I-A232V-H249R, P005S-N018R-T022W-S024R-N076D-S101A-T213A-A215F-H249R, N018R-S024R-N076D-N116A-N183D-A215F-H249R, N018R-S024R-N076D-N183D-I198L-A215F-H249R, N018R-G020R-S024R-N076D-S101A-N116A-N183D-H249R, N018R-T022W-S024R-N076D-N116A-N183D-G211Q-H249R, N018R-G020R-T022W-S024R-N076D-S101A-N116A-H249R, N018R-T022W-S024R-N076D-S101A-N116A-N183D-I198L-T213A-H249R, N018R-T022W-S024R-N076D-S101A-N183D-G211Q-T213A-H249R, N018R-G020R-S024R-N076D-N116A-I198L-H249R, N018R-S024R-N076D-N183D-G211Q-T213A-H249R, N018R-S024R-N076D-S101A-N116A-N183D-T213A-H249R, N018R-S024R-N076D-N116A-N183D-I198L-A215F-H249R, N018R-T022W-S024R-N076D-N183D-I198L-G211Q-A215F-H249R, N018R-T022W-S024R-N076D-N183D-H249R, N018R-T022W-S024R-N076D-S101A-N183D-I198L-A215F-H249R, N018R-G020R-N043D-R045T-N076D-S101G-S103A-V104I-A232V-Q245R, G020R-T022W-S101A-S103A-V104I-N183D-I198L-A215F-A232V-Q245R, N076D-S101G-S103A-V104I-H249R, N018R-G020R-S024R-N076D-N183D-I198L-A215F-H249R, N018R-G020R-T022W-S024R-N076D-S101A-N183D-A215F-H249R, N018R-G020R-S024R-N076D-G211Q-T213A-H249R, N018R-S024R-N076D-N116A-N183D-G211Q-T213A-H249R, N018R-S024R-N076D-N116A-N183D-I198L-H249R, N018R-G020R-S024R-N076D-G211Q-N243D-H249R, N018R-G020R-R045T-N076D-S101G-S103A-V104I-A232V-Q245R-H249R, N018R-T022W-S024R-N076D-N183D-I198L-G211Q-T213A-H249R, N018R-S024R-N076D-S101A-N116A-N183D-I198L-G211Q-T213A-H249R, N018R-T022W-S024R-N076D-N116A-I198L-G211Q-T213A-A215F-H249R, S024R-N076D-S101G, N018R-G020R-S024R-N076D-S101A-I198L-T213A-A215F-H249R, N018R-T022W-S024R-N076D-N116A-N183D-

G211Q-T213A-H249R, N018R-G020R-S024R-N076D-N183D-A215F-H249R, N018R-N043D-N076D-S078R-S101G-S103A-V104I-A232V-Q245R-H249R, N018R-T022W-S024R-N076D-N116A-N183D-G211Q-T213A-Q245R, G020R-S024R-N076D-S078R-S101G-S103A-V104I-A232V-Q245R-H249R, N018R-G020R-R045T-S101G-S103A-V104I-A232V-Q245R-H249R, N018R-S024R-N076D-S101A-N183D-I198L-G211Q-H249R, N018R-T022W-S024R-N076D-N183D-G211Q-T213A-H249R, N018R-G020R-S024R-N076D-N116A-I198L-G211Q-A215F-H249R-N269S, N018R-G020R-T022W-S024R-N076D-S101A-N116A-N183D-I198L-G211Q-A215F-H249R, G020R-T022W-S101A-S103A-V104I-N183D-T213A-A215F-A232V-Q245R, N018R-S024R-N076D-A086V-S101A-N183D-I198L-G211Q-H249R, N018R-N076D-S101G-I198T-A232V, N018R-G020R-S024R-N076D-S101A-N116A-N183D-I198L-G211Q-A215F-H249R, N018R-T022W-S024R-N076D-S101A-N116A-N183D-T213A-A215F-H249R, N018R-T022W-S024R-N076D-S101A-N183D-G211Q-T213A-A215F-H249R, N018R-S024R-N076D-N183D-H249R-A248T, N018R-N076D-V104I-Q245R-H249R, N018R-T022W-S024R-N076D-S101A-N116A-N183D-I198L-A215F-H249R, N018R-T022W-S024R-N076D-N116A-N183D-T213A-A215F-H249R, N018R-G020R-T022W-S024R-N076D-N116A-N183D-G211Q-T213A-A215F-H249R, N018R-G020R-S024R-N076D-S101A-H249R, N018R-G020R-S024R-N076D-S101A-N116A-T213A-A215F-H249R, N018R-T022W-S024R-N076D-N116A-N183D-G211Q-A215F-H249R, N018R-T022W-S024R-N076D-N116A-N183D-I198L-G211Q-T213A-H249R, N043R-R045T-S078R-S101G-S103A-V104I-L217E-A232V-Q245R, N043R-R045T-S101G-S103A-V104I-A232V-Q245R-H249R, N018R-N076D-S101G-V104I, G020R-R045T-N076D-S078R-S101G-S103A-V104I-A232V-Q245R-H249R, N043D-N076D-S101G-S103A-V104I-A232V-Q245R, N018R-G020R-T022W-S024R-N076D-S101A-N116A-N183D-I198L-H249R, N018R-N076D-V104I, N018R-G020R-N043D-S101G-S103A-V104I-A232V-Q245R-H249R, N018R-G020R-T022W-S024R-N076D-N183D-G211Q-H249R, N018R-S024R-N076D-S101A-N183D-I198L-G211Q-A215F-H249R, S101G-V104I, N018R-T022W-S024R-N076D-N116A-N183D-I198L-G211Q-T213A-A215F-H249R, N018R-G020R-S024R-N076D-S101A-N183D-G211Q-T213A-A215F-H249R, N018R-G020R-S024R-N076D-N116A-N183D-A215F-H249R-N263D, N018R-T022W-S024R-N076D-S101A-N183D-H249R, N018R-S024R-N076D-S101A-N116A-N183D-I198L-A215F-H249R, N018R-T022W-S024R-N076D-N116A-I198L-A215F-H249R-R269H, N018R-N043D-R045T-N076D-S078R-S101G-S103A-V104I-A232V-Q245R, N018R-S024R-R045T-N076D-S078R-S101G-S103A-V104I-A232V-Q245R-N269R, S078R-S101G-S103A-V104I-L217E-A232V-Q245R, N018R-G020R-T022W-S024R-N076D-S101A-N183D-I198L-T213A-A215F-H249R, N018R-G020R-S024R-N076D-N183D-I198L-T213A-H249R, N018R-G020R-T022W-S024R-N076D-N116A-I198L-G211Q-A215F-H249R, N018R-G020R-T022W-S024R-N076D-N116A-N183D-G211Q-H249R, N018R-G020R-T022W-S024R-N076D-S101A-I198L-G211Q-T213A-H249R, N018R-G020R-T022W-S024R-N076D-H249R, G020R-T022W-S101G-S103A-V104I-N116A-N183D-I198L-G211Q-T213A-A215F-A232V-Q245R, V104I-A232V, N018R-G020R-T022W-S024R-N076D-S101A-N116A-N183D-G211Q-A215F-H249R, N018R-G020R-T022W-S024R-N076D-S101A-N116A-N183D-I198L-G211Q-T213A-

A215F-H249R, N018R-G020R-T022W-S024R-N076D-S101A-N183D-T213A-A215F-H249R, N018R-T022W-S024R-N076D-S101A-N183D-I198L-G211Q-T213A-H249R, N018R-T022W-S024R-N076D-S101A-N183D-I198L-H249R, N043D-R045T-S101G-S103A-V104I-A232V-Q245R-N269R, N018R-G020R-S024R-N076D-S101A-N183D-I198L-G211Q-H249R, N018R-G020R-N043R-S101G-S103A-V104I-L217E-A232V-Q245R, S024R-N043R-N076D-S078R-S101G-S103A-V104I-A232V-Q245R-N269R, N043R-R045T-N076D-S078R-S101G-S103A-V104I-Y166F-A176P-A179V-N184T-A187P-A194P, N018R-T022W-S024R-D041E-N076D-S101A-S160T-N183D-G211Q-T213A-H249R, N018R-G020R-T022W-S024R-N076D-N116A-N183D-I198L-G211Q-A215F-H249R, N018R-G020R-T022W-S024R-N076D-S101A-N116A-I198L-T213A-H249R, N018R-T022W-S024R-N076D-S101A-N116A-N183D-I198L-G211Q-T213A-H249R, N018R-G020R-S024R-N076D-I198L-T213A-H249R, N018R-G020R-T022W-S024R-N076D-N116A-N183D-I198L-G211Q-H249R, N018R-G020R-S024R-N076D-N183D-G211Q-A215F-H249R, S024R-N076D-V104I, N018R-N076D-S101G-A232V, N018R-S024R-N076D-S101A-N116A-N183D-I198L-G211Q-T213A-A215F-H249R, N018R-G020R-T022W-S024R-N076D-N116A-N183D-A215F-H249R, N018R-S024R-L031F-N076D-N116A-N183D-G211Q-T213A-A215F-H249R, N018R-S024R-N076D-S101A-N116A-N183D-I198L-T213A-H249R-N269S, N018R-G020R-S024R-N076D-S101A-N116A-I198L-A215F-H249R, N018R-N043R-N076D-S078R-S101G-S103A-V104I-A232V-Q245R-N269R, N018R-G020R-S024R-N076D-S101A-N114T-I198L-G211Q-A215F-H249R, S024R-N043R-S078R-S101G-S103A-V104I-L217E-A232V-Q245R, S024R-N076D-S103A-V104I-A232V, N018R-G020R-T022W-S024R-N076D-S101A-I198L-G211Q-A215F-H249R, S101G-V104I-A232V, N018R-T022W-S024R-N076D-N183D-I198L-T213A-A215F-H249R, N018R-T022W-S024R-N076D-N183D-I198L-G211Q-H249R, N018R-G020R-S024R-N076D-N183D-T213A-H249R, N018R-S024R-N076D-S101A-N183D-G211Q-A215F-H249R, N018R-G020R-T022W-S024R-N076D-N116A-G211Q-T213A-H249R, N018R-S078R-S101G-S103A-V104I-A232V-Q245R-N269R, N018R-T022W-S024R-N076D-S101A-N116A-N183D-G211Q-A215F-H249R-T260A, N076D-H249R, N018R-T022W-S024R-N076D-N183D-G211Q-A215F-H249R, N018R-G020R-S024R-N076D-N116A-G211Q-A215F-H249R, N018R-G020R-S024R-N076D-T213A-H249R, N018R-G020R-T022W-S024R-N076D-N116A-N183D-I198L-H249R, N018R-G020R-T022W-S024R-N076D-S101A-N183D-H249R, N076D-V104I-H249R, G020R-T022W-S101A-S103A-V104I-N116A-N183D-G211Q-T213A-A215F-A232V-Q245R, S024R-N043R-R045T-S078R-S101G-S103A-V104I-L217E-A232V-Q245R, N018R-G020R-T022W-S024R-N076D-N183D-I198L-A215F-H249R, N018R-N076D-S101G-S103A, G020R-S024R-S101G-S103A-V104I-A232V-Q245R-N269R, N018R-G020R-S024R-N076D-S101A-N116A-N183D-G211Q-H249R, S101G-S103A-A232V, S024R-N076D-S101G-A232V, N018R-T022W-S024R-N076D-S101A-N183D-I198L-G211Q-H249R, N018R-G020R-S024R-N076D-S101A-N183D-I198L-G211Q-A215F-H249R, N018R-G020R-S024R-N076D-N183D-I198L-H249R, N018R-T022W-S024R-N076D-S101A-N116A-N183D-I198L-G211Q-H249R, N018R-G020R-S024R-N076D-N116A-A156V-N183D-G211Q-A215F-H249R-N269S, R045T-N076D-S101G-S103A-V104I-A232V-Q245R-H249R, N018R-

G020R-S024R-N076D-S101A-N183D-I198L-H249R, N018R-G020R-S024R-N076D-I198L-G211Q-A215F-H249R, N018R-G020R-T022W-S024R-N076D-S101A-N116A-I198L-G211Q-A215F-H249R, N018R-G020R-T022W-S024R-N076D-N116A-H249R, N018R-N076D-S101G, N018R-S024R-N076D-N116A-N183D-I198L-T213A-A215F-H249R, N018R-G020R-T022W-S024R-N076D-S101A-N116A-I198L-T213A-A215F-H249R, N018R-S024R-N076D-S101A-N116A-N183D-I198L-G211Q-H249R, N018R-N076D-A232V, N018R-G020R-S024R-N076D-S101A-A232V-Q245R, N018R-N043D-R045T-N076D-S101G-S103A-V104I-A232V-Q245R, N018R-T022W-S024R-N076D-N183D-T213A-A215F-H249R, N018R-S024R-N076D-S101A-N116A-G211Q-T213A-N237D-H249R, N018R-G020R-S024R-N076D-S101A-N116A-N183D-G211Q-H249R-R275S, N018R-T022W-S024R-N076D-S101A-N116A-N183D-I198L-G211Q-T213A-A215F-H249R, S024R-N076D, N018R-S024R-N076D-N183D-G211Q-A215F-H249R, N018R-T022W-S024R-N076D-N116A-N183D-I198L-T213A-A215F-H249R, N076D-V104I-A232V-H249R, N018R-N076D-S103A-A232V, N018R-G020R-S024R-N076D-S101A-N116A-N183D-I198L-G211Q-T213A-H249R, N018R-G020R-S024R-N076D-S101A-N183D-T213A-H249R, N018R-G020R-S024R-N076D-S101A-D175E-N183D-G211Q-A215F-H249R, N018R-G020R-N043D-S078R-S101G-S103A-V104I-L217E-A232V-Q245R-A273E, G020R-S024R-N043D-R045T-N076D-S101G-S103A-V104I-A232V-Q245R, P005S-S101G-S103A-V104I-A232V-Q245R-H249R, S103A-V104I-A232V, N018R-G020R-S024R-V068A-N076D-S101A-N116A-T213A-A215F-H249R, N018R-T022W-S024R-N076D-S101A-I198L-A215F-H249R-R275S, N018R-S024R-N076D-N183D-I198L-G211Q-T213A-H249R, and N043D-R045T-S101G-S103A-V104I-A232V-Q245R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: N018R-S024R-N043R-N076D-H249R-N269R, N018R-T022R-S024R-N043R-N076D-H249R, N018R-N043D-S101G-S103A-V104I-A232V-Q245R, G020R-N043D-S101G-S103A-V104I-A232V-Q245R, N043D-S101G-S103A-V104I-A232V-Q245R-N269R, N043D-S078R-S101G-S103A-V104I-A232V-Q245R, N043R-N076D-S101G-S103A-V104I-A232V-Q245R, T022R-N043R-S101G-S103A-V104I-A232V-Q245R, N043R-S078R-S101G-S103A-V104I-A232V-Q245R, G020R-N076D-S101G-S103A-V104I-A232V-Q245R, N043R-N076D-S101G-S103A-V104I-A232V-Q245R, T022R-N076D-S101G-S103A-V104I-A232V-Q245R, N076D-S078R-S101G-S103A-V104I-A232V-Q245R, N018R-S024R-N043R-N076D-H249R, N018R-S024R-N076D-S242R-H249R, N018R-S024R-N076D-H249R-N269R, N018R-T022R-S024R-N076D-H249R, N018R-S024R-N076D-S078R-H249R, N018R-S024R-N043D-N076D-H249R-N269R, N018R-T022R-S024R-N043D-N076D-H249R, N018R-S024R-N043D-N076D-S078R-H249R, G020R-S101G-S103G-V104I-A232V-Q245R, G020R-S101G-S103A-V104L-A232V-Q245R, G020R-S101G-S103A-V104V-A232V-Q245R, G020R-S101G-S103S-V104I-A232V-Q245R, G020R-S101G-S103S-V104L-A232V-Q245R, G020R-S101S-S103S-V104I-A232V-Q245R, G020R-S101S-S103S-V104L-A232V-Q245R, G020R-S101A-S103A-V104L-A232V-Q245R, G020R-S101S-S103S-V104V-A232V-Q245R, G020R-S101S-S103A-V104I-A232V-Q245R, G020R-S101S-S103A-V104V-A232V-Q245R, G020R-S101S-S103G-V104I-A232V-Q245R, G020R-S101S-S103G-V104V-A232V-Q245R, G020R-S101A-S103A-V104V-A232V-Q245R, G020R-S101A-S103S-V104I-A232V-Q245R, G020R-S101A-S103S-V104V-A232V-Q245R, N018R-S024R-N043R-N076D-S078R-H249R, S024R-N043D-S101G-S103A-V104I-A232V-Q245R, N043D-S101G-S103A-V104I-A232V-Q245R-H249R, S024R-N076D-S101G-S103A-V104I-A232V-Q245R, N076D-S101G-S103A-V104I-A232V-S242R-Q245R, N018R-G020R-S024R-N076D-L217E-H249R, N018R-S024R-N043R-N076D-L217E-H249R, N018R-S024R-N043D-N076D-S242R-H249R, N018R-G020R-S024R-N043R-N076D-H249R, G020R-S101A-S103G-V104V-A232V-Q245R, N043D-S101G-S103A-V104I-A232V-Q245R, N018R-S024R-N076D-L217E-H249R-N269R, and N018R-S024R-N076D-L217E-S242R-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: G020R-S101A-S103A-V104I-G118R-A232V-Q245R, G020R-S024R-N116A-T213A, N043R-S101A-N116A-A215F-N269R, S024R-N043R-S101A-N116A, S024R-N043R-S101A-N116A-A215F-N269R, G020R-S101G-S103A-V104I-A215F-A232V-Q245R, N043R-S101A-N269R, S024R-N043R-N116A-T213A-N269R, G020R-S024R-N043R-R045T-S101A-T213A, S024R-N043R-N116A-A215F-N269R, G020R-S024R-T213A-A215F, G020R-N116A-N269R, S024R-N116A-T213A-N269R, N043R-S101A-N116A-N269R, S101G-S103A-V104I-N116A-T213A-A232V-Q245R-N269R, S024R-N043R-R045T-S101A-N116A-A215F-N269R, G020R-N043R-S101A-N269R, S101A-S103A-V104I-T213A-A232V-Q245R-N269R, S024R-A215F-N269R, N043R-S101A-N116A-T213A-A215F-N269R, N043R-S101A-T213A-N269R, G020R-S024R-N043R-R045T-N116A-T213A, S101G-S103A-V104I-A232V-Q245R-N269R, S024R-N043R-R045T-S101A-N116A-T213A-N269R, S024R-N043R-R045T-N269R, G020R-N043R-R045T-S101A-N269R, S024R-N043R-N116A-N269R, G020R-S024R-N043R-R045T, N043R-N116A-N269R, S024R-N043R-S101A-A215F-N269R, S024R-N043R-R045T-T213A-A215F-N269R, G020R-S024R-R045T-N269R, G020R-N043R-S101A-N116A-T213A-A215F, G020R-S101G-S103A-V104I-T213A-A215F-A232V-Q245R, G020R-S024R-R045T-N116A-N269R, G020R-S101A-N116A-N269R, S024R-N043R-A215F, G020R-S024R-T213A, S024R-N043R-S101A-A215F, G020R-S024R-N043R-R045T-N116A, G020R-S024R-N043R-R045T-S101A-N269R, G020R-S024R-S101A-A215F, G020R-S024R-N116A-T213A-A215F, G020R-S024R-N116A, G020R-S024R-S101A-N116A, N043R-T213A-A215F-N269R, S024R-S101A-N269R, S024R-N043R-N116A-A215F, G020R-T038A-N043R-S101A, G020R-S024R-N116A-A215F, S024R-N043R-S101A-T213A, P014L-G020R-S024R-N043R-R045T-S101A-A215F, G020R-S024R-A215F, G020R-N116A-A215F-N269R, G020R-R045T-N116A-N269R, G020R-S024R-N043R-R045T-A215F, and G020R-S024R-N043R-R045T-

N116A-T213A-A215F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: N043R-N076D-S101A-S103A-V104I-A158E-S188D-A232V-Q245R-N248D-H249R-E271F, S024R-N043R-N076D-S101A-S103A-V104I-A158E-S188D-L217E-A232V-Q245R-N248D-H249R, S101A-S103A-V104I-A158E-S188D-A232V-Q245R-N248D-H249R-E271F-E271F, S101A-S103A-V104I-A158E-S188D-L217E-A232V-Q245R-N248D-H249R-E271F, N076D-S101G-S103A-V104I-A114V-A158E-S188D-A232V-Q245R-N248D-H249R-E271F, S024R-N076D-S101G-S103A-V104I-A158E-S188D-A232V-Q245R-N248D-H249R-E271F, S024R-N043R-S101A-S103A-V104I-A158E-S188D-L217E-A232V-Q245R-N248D-H249R, S024R-N043R-S101A-S103A-V104I-A158E-S188D-A232V-Q245R-N248D-H249R, S024R-S101A-S103A-V104I-A158E-S166D-S188D-L217E-A232V-Q245R-N248D-H249R, N076D-S101G-S103A-V104I-S128L-A158E-S188D-A232V-Q245R-N248D-H249R-E271F, and N043R-N076D-S101G-S103A-V104I-A158E-S166D-S188D-A232V-Q245R-N248D-H249R-E271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: T022A-S101G-S103A-V104I-G159D-L217E-A232V-Q245R-N248D-E271F, T022A-N043R-S101G-S103A-V104I-G159D-S188D-L217E-A232V-Q245R-N248D-E271F, T022A-S101G-S103A-V104I-G159D-S188D-A232V-Q245R-N248D-E271F, N043R-S101A-S103A-V104I-A158E-S188D-L217E-A232V-Q245R-N248D-H249R, N043R-N076D-S101A-S103A-V104I-A158E-S188D-L217E-A232V-Q245R-N248D-H249R-E271F, S024R-S101G-S103A-V104I-A158E-S188D-L217E-A232V-Q245R-N248D-H249R, S024R-S101G-S103A-V104I-A158E-S188D-A232V-Q245R-N248D-H249R, S101G-S103A-V104I-A158E-S188D-A232V-Q245R-N248D-H249R, S024R-S101G-S103A-V104I-A158E-N183D-S188D-A232V-Q245R-N248D-H249R, T022A-N076D-S101G-S103A-V104I-G159D-S188D-A232V-Q245R-N248D-E271F, T022A-N043R-N076D-S101G-S103A-V104I-G159D-S188D-A232V-Q245R-N248D-E271F, T022A-N076D-S101G-S103A-V104I-G159D-A232V-Q245R-N248D-E271F, T022A-S101G-S103A-V104I-G159D-A232V-Q245R-N248D-E271F, N076D-S101A-S103A-V104I-A158E-S188D-A232V-Q245R-N248D-H249R-E271F, N043R-S101A-S103A-V104I-A158E-S166D-S188D-A232V-Q245R-N248D-H249R, S024R-N076D-S101A-S103A-V104I-A158E-S166D-S188D-A232V-Q245R-N248D-H249R-E271F, N076D-S101A-S103A-V104I-A158E-S188D-A232V-Q245R-N248D-H249R, S101A-S103A-V104I-A158E-S166D-S188D-A232V-Q245R-N248D-H249R-E271F, N043R-N076D-S101A-S103A-V104I-A158E-S166D-S188D-A232V-Q245R-N248D-H249R-E271F, S101G-S103A-V104I-A158E-S166D-S188D-A232V-Q245R-N248D-H249R-E271F, S101A-S103A-V104I-A158E-S188D-A232V-Q245R-N248D-H249R-E271F, S101A-S103A-V104I-A158E-S188D-L217E-A232V-Q245R-N248D-H249R, N076D-S101A-S103A-V104I-A158E-S166D-S188D-A232V-Q245R-N248D-H249R-E271F, S101G-S103A-V104I-A158E-N183D-S188D-A232V-Q245R-N248D-H249R, S024R-S101G-S103A-V104I-S128L-A158E-S188D-A232V-Q245R-N248D-H249R, N076D-S101G-S103A-V104I-A158E-S166D-S188D-A232V-Q245R-N248D-H249R-E271F, N043R-N076D-S101A-S103A-V104I-A158E-S166D-S188D-A232V-Q245R-N248D-H249R, and N076D-S101A-S103A-V104I-A158E-S188D-L217E-A232V-Q245R-N248D-H249R-E271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: H017R-T022A-N076D-S101G-S103A-V104I-G159D-S188D-A232V-Q245R-N248D-E271F, T022A-N043R-S101G-S103A-V104I-G159D-A232V-Q245R-N248D-E271F, T022A-S101G-S103A-V104I-G159D-S188D-A232V-Q245R-N248D-H249R-E271F, H017R-T022A-N076D-S101G-S103A-V104I-G159D-A232V-Q245R-N248D-E271F, T022A-N076D-S101G-S103A-V104I-G159D-A232V-Q245R-N248D-H249R-E271F, T022A-S101G-G102A-S103A-V104I-G159D-S188D-A232V-Q245R-N248D-E271F, and T022A-N043R-N076D-S101G-S103A-V104I-G159D-A232V-Q245R-N248D-H249R-E271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101S-S103A-V104I-A158E-S188D-A232V-Q245R-N248D-H249R, S101S-S103G-V104V-A158E-S188D-A232V-Q245R-N248D-H249R, S101G-S103S-V104I-A158E-S188D-A232V-Q245R-N248D-H249R, S101A-S103A-V104I-A158E-S188D-A232V-Q245R-N248D-H249R, S101A-S103A-V104L-A158E-S188D-A232V-Q245R-N248D-H249R, S101G-S103G-V104I-A158E-S188D-A232V-Q245R-N248D-H249R, S101S-S103G-V104I-A158E-S188D-A232V-Q245R-N248D-H249R, S101S-S103S-V104I-A158E-S188D-A232V-Q245R-N248D-H249R, S101S-S103S-V104V-A158E-S188D-A232V-Q245R-N248D-H249R, S101A-S103S-V104I-A158E-S188D-A232V-Q245R-N248D-H249R, S101A-S103S-V104I-G159E-A232V-Q245R-N248D-H249R, S101S-S103A-V104I-G159E-A232V-Q245R-N248D-H249R, S101G-S103A-V104L-A158E-S188D-A232V-Q245R-N248D-H249R, S101A-S103A-V104L-G159E-A232V-Q245R-N248D-H249R, S101A-S103S-V104L-G159E-A232V-Q245R-N248D-H249R, S101G-S103S-V104L-G159E-A232V-Q245R-N248D-H249R, S101S-S103A-V104L-G159E-A232V-Q245R-N248D-H249R, S101A-S103G-V104V-G159E-A232V-Q245R-N248D-H249R, and S101S-S103A-V104V-G159E-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: V026F-V051W-V104L-S106E, V026F-L031F-S078N-G102A-S160D, G020K-G100S-N116L-A158E-S166D-N243F, T033S-N043W-N218D-P239G-N243F, T022L-T038F-A048R-N062E-G100S-R186K, S101D-S103N-N116L-S144R-A215D, V104L-S105T-T213A-L217E-S256N, N043W-S101D-S212M-N243F, V026F-A048R-S105T-T213A-N218D-T224A, S024F-S101D-G118R-A215D-L250I-A272F, V121F-N185E-T224A-P239G, T022L-L031F-G102A-S128D-T224A-N243F, N062E-S078N-G102A-N116L-S144R-L250I, T022L-T038F-V121F-S160D-A272F, V026F-S078N-G159C-R186K-N243F, S024F-A048R-G118R-S166D-L217E, G023A-T038F-S078N-G100S-S212M-A215D, G100S-N116L-A158E-T213A, S078N-V104L-G118R-S128D, G102A-S103N-S105T-A194E, T022L-S078N-S128D-T213A, K027R-G100S-G118R-S160D-S188D-N243F, S024F-G102A-R186K-T213A-L217E-N243F, T033S-S105T-S188D-S216F, G023A-G100S-A194E-S212M, A048R-S128D-N185E-P239G, G020K-S024F-T033S-P129E-A194E, G020K-K027R-P129E-S166D-P239G, T022L-G023A-K027R-S101D-V104L-S216F, T033S-G118R-P129E-A194E-P239G, T022L-S078N-N116L-P129E-S256N, K027R-S101D-S103N-S105T-A272F, A048R-S078N-N116L-N185E-L217E-P239G, G023A-S024F-K027R-N062E, S024F-S103N-V104L-G118R-S188D, V026F-V104L-S256N-A272F, S024F-N043W-V104L-V121F-P129E, N062E-S078N-N116L-T224A, G023A-S024F-V051W-A158E, K027R-T038F-G102A-N116L, N062E-S078N-S144R-S212M, L031F-N116L-S256N-A272F, T022L-T033S-V104L-N116L-S160D-R186K, S024F-G118R-P129E-R186K-T213A, N043W-S105T-T213A-A215D-S216F, L031F-S105T-R186K-S188D, V026F-A194E-T213A-S256N, and S103N-S160D-L250I-S256N, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: T022A-S024R-S101D-S103A-V104I-G118R-G159D-S188D-A232V-N248D-E271F, T022A-S024R-S103A-V104I-P129E-G159D-S188D-A232V-N248D-E271F, T022A-S024R-S103A-V104I-G118R-G159D-S188D-L217D-A232V-N248D, T022A-S024R-S101D-S103A-V104I-G118R-P129E-G159D-S188D-A232V-Q245R-N248D, T022A-S024R-S101D-S103A-V104I-G159D-S188D-A232V-Q245R-N248D, T022A-N043R-S103A-V104I-G118R-P129E-G159D-S188D-A232V-Q245R-N248D, T022A-N043R-S103A-V104I-G118R-S128I-P129E-G159D-S188D-A232V-N248D, T022A-N043R-S101D-S103A-V104I-G118R-P129E-G159D-S188D-A232V-N248D-E271F, T022A-S024R-N043R-S101D-S103A-V104I-G159D-S188D-A232V-Q245R-N248D, T022A-S103A-V104I-G159D-S188D-A232V-N248D, T022A-S024R-S103A-V104I-G118R-P129E-G159D-S188D-A232V-N248D-E271F, T022A-S024R-S103A-V104I-G159D-S188D-L217D-A232V-Q245R-N248D-E271F, T022A-N043R-N062E-S103A-V104I-G159D-S188D-A232V-Q245R-N248D-E271F, T022A-N043R-S103A-V104I-P129E-G159D-S188D-A232V-Q245R-N248D, T022A-S024R-S103A-V104I-G159D-S188D-L217D-A232V-N248D-E271F, T022A-S103A-V104I-G118R-G159D-S188D-L217D-A232V-Q245R-N248D, T022A-S024R-S101D-S103A-V104I-G118R-S128I-G159D-S188D-A232V-Q245R-N248D, T022A-S024R-N043R-S103A-V104I-G159D-S188D-L217D-A232V-N248D-E271F, T022A-N043R-S103A-V104I-G118R-G159D-S188D-L217D-A232V-N248D-E271F, T022A-N043R-S103A-V104I-G118R-G159D-S188D-A232V-N248D-E271F, T022A-S103A-V104I-S128I-P129E-G159D-S188D-A232V-N248D-E271F, T022A-S103A-V104I-G159D-S188D-L217D-A232V-Q245R-N248D-E271F, T022A-N043R-S103A-V104I-S128I-G159D-S188D-A232V-Q245R-N248D, T022A-S101D-S103A-V104I-G118R-G159D-S188D-L217D-A232V-Q245R-N248D-E271F, T022A-S103A-V104I-G118R-P129E-G159D-S188D-A232V-Q245R-N248D-E271F, T022A-S024R-N043R-S103A-V104I-G118R-G159D-S188D-L217D-A232V-N248D, T022A-N062E-S103A-V104I-G118R-G159D-S188D-A232V-Q245R-N248D, T022A-N043R-S101D-S103A-V104I-G118R-P129E-G159D-S188D-L217D-A232V, T022A-S024R-S103A-V104I-G159D-S188D-L217D-A232V-N248D, T022A-S024R-N043R-S103A-V104I-G118R-S128I-P129E-G159D-S188D-L217D-A232V-N248D-E271F, and T022A-S103A-V104I-G118R-G159D-S188D-L217D-A232V-Q245R-N248D-E271F, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: G020K-S024F-N062E-S188D-P239G, S024F-N062E-N116L-P239G, G020K-G023A-N062E-S188D, G020K-G023A-S024F-N062E-G118R-S188D-T213A, G020K-N043W-N062E-N116L-S188D-T213A-P239G, G023A-N062E-N116L-G118R, G023A-S024F-N062E-N116L-G118R, S024F-N116L, S024F-N062E-S188D-T213A, G023A-N062E-N116L-G118R-S188D-P239G, G020K-S024F-N062E, G020K-N043W-N062E-N116L-P239G, S024F-N062E-N116L-T213A-P239G, G020K-S024F-N043W-N062E-N116L-T213A, G020K-G023A-S024F-N062E-N116L-S188D-T213A, S024F-N062E-S188D-P239G, G023A-N043W-N062E-N116L-G118R-T213A, N062E-S188D-P239G, G020K-S024F-N062E-P239G, S024F-N116L-G118R-S188D-P239G, G020K-G023A-N062E-N116L-G118R-T213A, G020K-G023A-S024F-N062E-S188D-T213A-P239G, S024F-N043W-G118R-S188D, G023A-S024F-N116L-G118R-S188D-T213A, G020K-G023A-N043W-N116L-S188D-T213A-P239G, G023A-S024F-N116L-S188D-P239G, G023A-N043W-N116L-G118R-S188D, G023A-S024F-G118R-S188D-P239G, G023A-S024F-N043W-N062E-N116L-G118R, G020K-N043W-S188D-T213A, S024F-N062E-G118R-P239G, G023A-N043W-S188D-T213A, G020K-S024F-N043W-N062E-N116L-G118R-S188D-P239G, G020K-N116L-S188D-P239G, G020K-N043W-N062E-G118R, G020K-N043W-N116L-S188D-T213A, G020K-S024F, G023A-N043W-N116L-P239G, G023A-S024F-N043W-N116L-G118R-S188D-P239G, G020K-G023A-N043W-T213A, and G023A-S024F-N062E-G118R-T213A-P239G, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: G020K-G023A-N043W-G118R-S128I-P129E-G159D-S188D, S024F-G118R-S128I-P129E-G159D, G020K-S024F-N062E-N116L-G118R-S188D, G020K-N062E-N116L-S188D, N062E-N116L-G118R-T213A, G020K-G023A-N062E-N116L-S188D, N062E-N116L-G118R-S188D, G020K-N062E-N116L-T213A, G020K-G023A-N062E-N116L, G020K-N062E-S188D-T213A, G020K-N062E, G020K-S024F-N062E-N116L-S188D, G020K-N043W-N062E-N116L-S188D, G020K-S024F-N062E-S188D-T213A, N062E-N116L-S188D-T213A, G020K-N062E-N116L, G020K-G023A-N062E-N116L-S188D-T213A, G023A-S024F-N062E-N116L-T213A, T022A-N043R-S103A-V104I-S128I-P129E-G159D-S188D-A232V-Q245R-N248D, T022A-N043R-S103A-V104I-G118R-S128I-P129E-G159D-S188D-A232V-N248D-E271F, S024F-N062E-N116L-S188D, T022A-S024R-S103A-V104I-G118R-S128I-P129E-G159D-S188D-A232V-N248D, G023A-N062E-N116L-S188D, N043W-N062E-N116L, G020K-G023A-N116L-S188D, N043W-N062E-N116L-S188D, S024F-N062E-N116L, N062E-N116L-S188D, and T022A-S024R-S103A-V104I-S128I-G159D-S188D-A232V-N248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S087R-S101G-S103A-V104I-Q109R-S212P-A232V-Q245R-E271V, S101G-S103A-V104I-Q109R-A232V-Q245R, S101G-S103A-V104I-Q109R-S212P-A232V-Q245R-E271V, S101G-S103A-V104I-Q109R-S212P-A232V-Q245R, N076D-587R-S103A-V104I-S212P-E271V, N076D-S103A-V104I-Q109R, N076D-S103A-V104I-S212P-E271V, N076D-S103A-V104I-Q109R-Q245R, and N076D-S103A-V104I-S212P-Q245L-E271V, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S024R-P086W-G118R, S024R-S078R-P086W-N243F, S024R-T033S-P086S-S087N-Y209A, T033S-G118R, S024R-S078R-P086W-G118R-A270T, S024R-T033S-P086W-G118R, S078R-P086W-N243F, T033S-S078R-P086W-G118R-Y209A, T033S-S078R-Y209A, P086W-G118R-N243F, S024R-P086W, S078R-P086W-K235F, S024R-G118R, S024R-P086R, S101G-S103A-V104I-A232V, S024R-T033S-S078R-P086W-G118R, S024R-G118R-Y209A, Y209A-W241R, T033S-P086W-N243F, T033S-A172Y-Y209A, G118R-Y209A-N243F, S024R-P086S-S141G, S024R-G118R-Y209A-N243F, S024R-T033S-P086S-S085N-K235F, S024R-T033S-A133V, S024R-T033S-S078R-P086W, S024R-P086W-Y209A, S024R-W241R, T033S-G118R-N243F, S024R-K235F, S024R-S078R-P086W, S024R-G118R-Y209A-K235F, S024R-Y209A-W241R, T033S-G118R-W241R, P086W-G118R-Y209A, T033S-G118R-G159D-Y209A, T033S-S078R-P086W, S024R-P086W-N243F, G118R-Y209A, S024R-P086W-G118R-V203I, S078R-Y209A-K235F, S024R-T033S-W241R, S078R-G118R, T033S-G118R-Y209A-N243F, L021M-S024R-T033S, S024R-T033S-P086W, T033S-K235F, S078R-P086W-Y209A, S024R-T033S-Y209A-K235F, T033S-P086W-G118R, S024R-T033S-S078R-Y209A, T033S-P086W-G118R-Y209A-N243F, P086W-Y209A-N243F, P005S-S078R-G118R-W241R, S024R-A174T, T033S-Y209A-N243F, P086W-G118R-A133V, S024R-T033S-G118R, S024R-P086W-Y209A-K235F, P086W-Y209A, I008T-S024R, P086W-G118R, T033S-W241R, P005S-S024R-T033S-N243F, S024R-Y209A-S242P, S024R-T033S-S078R-G118R, S024R-T033S-A194T, S024R-N243F, S024R-Y209A, S024R-T033S-G118R-Y209A, T033S-P086W, S024R-T033S, S024R-T033S-S078R-N243F, P086W-N243F, T033S-G118D-A138V-Y209A, T033S-Y209A-K235F, S024R-P086R-G118R, T033S-P201S, S024R-P239Q, T033S-G118R-Y209A-, S078R-P086W, K235F-N243F, S024R-Y209A-K235F, G118R-A172V, H017Y-S024R-T033S-P086W, T033S-L148F, S024R-G118R-K235F, T033S-S078R, T033S-N243F, S024C-T033S, G118R-A194T, T033S-Y209A, G118R-Y209A-K235F, S024R-T033S-Y209A-N243F, S024R-T033S-K235F, S024R-T033S-G118R-K235F, S024R-S141G, S024R-T274I, S024R-T033S-Y209A, P086W-K235F, S024R-Y209A-N243F, V004E-T033S-S078R, P086W-Y209A-K235F, A015T-T033S, T033S-P086W-S156L-Y209A, S024R-G118R-N243F-R269H, Y209A-K235F, S024R-R247H, S024R-T033S-A228T, S078R-K235F, S024R-T033S-A174V-K235F, S024R-K235F-N243F, S024R-T033S-K235F-W241R, S024R-T033S-A151V, S024R-V104A, T033S-A048T, Q012H-V104A-G118R, G118R-K235F, T033S-T253A, T143A-Y209A, S024R-T033S-N243F, T033S-P239T, Y209A-N243F, S024R-T033S-P129H-N184D-T253M, S024R-A085V-P086W-G118R-K235F, S024R-A272P, and S024R-R269C, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: G020R-S087D-S101G-S103A-V104I-A232V-Q245R, G020R-S101G-S103A-V104I-V150L-A232V-Q245R, N018R-G020R-S024R-N076D-S087D-H249R, N018R-G020R-S024R-N076D-V150L-H249R, N018R-S024R-N043R-N076D-S087D-H249R, N018R-S024R-N043R-N076D-V150L-H249R, N018R-S024R-N076D-S078R-S087D-H249R, N018R-S024R-N076D-S078R-V150L-H249R, N018R-S024R-N076D-S087D-H249R-N269R, N018R-S024R-N076D-S087D-S242R-H249R, N018R-S024R-N076D-S087D-V150L-H249R, N018R-S024R-N076D-V150L-H249R, N018R-S087D-S101G-S103A-V104I-A232V-Q245R, N018R-S101G-S103A-V104I-V150L-A232V-Q245R, N018R-T022R-S024R-N076D-S087D-H249R, N018R-T022R-S024R-N076D-V150L-H249R, N043R-S087D-S101G-S103A-V104I-A232V-Q245R-N269R, N043R-S101G-S103A-V104I-V150L-A232V-Q245R, S024R-S087D-S101G-S103A-V104I-A232V-Q245R, S024R-S101G-S103A-V104I-A232V-Q245R, S078R-S087D-S101G-S103A-V104I-A232V-Q245R, S078R-S101G-S103A-V104I-V150L-A232V-Q245R, S087D-S101G-S103A-V104I-A232V-Q245R-N269R, S101G-S103A-

V104I-V150L-A232V-Q245R-H249R, S101G-S103A-V104I-V150L-A232V-Q245R-N269R, T022R-S087D-S101G-S103A-V104I-A232V-Q245R, N018R-S024R-N043D-N076D-V150L-H249R, N043R-S087D-S101G-S103A-V104I-A232V-Q245R, T022R-S101G-S103A-V104I-V150L-A232V-Q245R, N018R-S024R-N043D-N076D-S087D-H249R, N018R-S024R-N076D-S087D-H249R, N018R-S024R-N076D-V150L-S242R-H249R, N043R-S101G-S103A-V104I-V150L-A232V-Q245R-N269R, N076D-S101G-S103A-V104I-V150L-A232V-Q245R, S087D-S101G-S103A-V104I-A232V-S242R-Q245R, S101G-S103A-V104I-V150L-A232V-Q245R, N076D-S087D-S101G-S103A-V104I-A232V-Q245R, S087D-S101G-S103A-V104I-A232V-Q245R, and S101G-S103A-V104I-V150L-A232V-S242R-Q245R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S024R-S101G-S103A-V104I-P129Q-A158E-S188D-L217E-A232V-Q245R-N248D-H249R, S024R-S101G-S103A-V104I-S130A-A158E-N183D-S188D-A232V-Q245R-N248D-H249R, S024R-S101G-S103A-V104I-P129Q-A158E-N183D-S188D-A232V-Q245R-N248D-H249R, S101G-S103A-V104I-S130A-A158E-S188D-A232V-Q245R-N248D-H249R, S024R-S101G-S103A-V104I-P129Q-A158E-S188D-A232V-Q245R-N248D-H249R, S024R-S101G-S103A-V104I-S130A-A158E-S188D-A232V-Q245R-N248D-H249R, S024R-S101G-S103A-V104I-P129Q-S130A-A158E-N183D-S188D-A232V-Q245R-N248D-H249R, S024R-S101G-S103A-V104I-S128L-P129Q-A158E-S188D-A232V-Q245R-N248D-H249R, S024R-S101G-S103A-V104I-P129Q-S130A-A158E-S188D-A232V-Q245R-N248D-H249R, S101G-S103A-V104I-P129Q-A158E-S188D-A232V-Q245R-N248D-H249R, S101G-S103A-V104I-P129Q-S130A-A158E-S188D-A232V-Q245R-N248D-H249R, S024R-S101G-S103A-V104I-S128L-P129Q-S130A-A158E-S188D-A232V-Q245R-N248D-H249R, S101G-S103A-V104I-S128L-P129Q-A158E-S188D-A232V-Q245R-N248D-H249R, and S024R-K027R-S101G-S103A-V104I-S128L-P129Q-S130A-A158E-S188D-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101G-S103A-V104I-A232V-M222Q-Q245R, S101G-S103A-V104I-A158E-S188D-M222S-A232V-Q245R-N248D-H249R, S101G-S103A-V104I-A158E-S188D-M222Q-A232V-Q245R-N248D-H249R, N076D-S101G-S103A-V104I-A232V-M222Q-Q245R, S101G-S103A-V104I-A232V-M222S-Q245R, N076D-S101G-S103A-V104I-A232V-M222S-Q245R, and N076D-S101G-S103A-V104I-A158E-S188D-M222S-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S024R-S101G-S103A-V104I-S128L-P129Q-A158E-S188D-A232V-Q245R-N248D-H249R, S101G-S103A-V104I-S130A-A158E-S188D-A232V-Q245R-N248D-H249R, S024R-S101G-S103A-V104I-A158E-S188D-A232V-Q245R-N248D-H249R, S101G-S103A-V104I-S128L-P129Q-A158E-S188D-A232V-Q245R-N248D-H249R, S101G-S103A-V104I-P129Q-S130A-A158E-S188D-A232V-Q245R-N248D-H249R, S101G-S103A-V104I-S130A-A158E-N183D-S188D-L217E-A232V-Q245R-N248D-H249R, S024R-S101G-S103A-V104I-S128L-P129Q-S130A-A158E-S188D-A232V-Q245R-N248D-H249R, S024R-S101G-S103A-V104I-P129Q-A158E-S188D-L217E-A232V-Q245R-N248D-H249R, S101G-S103A-V104I-S128L-S130A-A158E-S188D-L217E-A232V-Q245R-N248D-H249R, S024R-S101G-S103A-V104I-S128L-P129Q-A158E-N183D-S188D-A232V-Q245R-N248D-H249R, S024R-S101G-S103A-V104I-S128L-P129Q-S130A-A158E-N183D-S188D-A232V-Q245R-N248D-H249R, S024R-S101G-S103A-V104I-S128L-P129Q-A158E-S188D-A232V-Q245R-N248D-H249R-E271G, S101G-S103A-V104I-P129Q-A158E-N183D-S188D-A232V-Q245R-N248D-H249R, S024R-S101G-S103A-V104I-S130A-A158E-S188D-L217E-A232V-Q245R-N248D-H249R, S024R-S101G-S103A-V104I-S128L-A158E-N183D-S188D-A232V-Q245R-N248D-H249R, S101G-S103A-V104I-P129Q-A158E-S188D-L217E-A232V-Q245R-N248D-H249R, and S024R-S101G-S103A-V104I-S128L-S130A-A158E-S188D-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101G-S103A-V104I, T22A-S101A-Y209E, S103G-L111V-G159E, T22A-S103G-G159E, T22A-L111V-G159E, T22A-S128N-E271F-Y209E, T22A-S103G-L111V, N62E-L111V-S128N, T22A-L111V-S128N, T22A-N62E-L111V, S101A-S103G-V104L-S188D, S101G-S103A-V104I-G159D, S101A-S103G-V104L-S128N, T22A-S101A-G159E, S101A-S103G-V104L, S101A-S103G-V104L-G159E, T22A-S101A-S103G-V104L, S101A-S103G-V104L-Y209E, T22A-Y209E-E271F, T22A-S101A-E271F, and S101A-Y209E-E271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, and S101G-S103A-

V104L-G159D-A232V-Q236H-Q245R-N248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N238R, S101G-S103A-V104I-G159D-A232V-Q245R-N248D-N248R, S101G-S103A-V104I-G159D-A232V-Q245R-N248D-T253R, S101G-S103A-V104I-G159D-A232V-Q245R-N248D-S24R, S101G-S103A-V104I-G159D-A232V-Q245R-N248D-N76D, S101G-S103A-V104I-G159E-A232V-Q245R-N248D-H249R, S101G-S103A-V104I-G159E-A232V-Q245R-N248D-E271F, S101G-S103A-V104I-A158E-A232V-Q245R-N248D-H249R, S101G-S103A-V104I-A158E-A232V-Q245R-N248D-E271F, T22A-S101G-S103A-V104I-G159D-A232V-Q245R-N248D-H249R, T22A-S101G-S103A-V104I-G159D-A232V-Q245R-N248D-E271F, N62E-S101G-S103A-V104I-G159D-A232V-Q245R-N248D-H249R, and N62E-S101G-S103A-V104I-G159D-A232V-Q245R-N248D-E271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, W241R, G20R-N43R-H249R, G20R-T22R-N43R, G20R-N43R-S242R, G20R-N43R-E271L, G20R-N43R-V244R, G20R-S24R-N43R-S242R, S9A-T22R-S78R-S212F-W241R, S9A-G20R-N43R-S212F, S9A-N43R-S212F, G20R-N43R-S212F, G20R-T22R-N43R-S212F, S24R-S78R-S212F, S9A-N43R-S78R, S9A-N43R-S78R-S242R, S9A-G20R-N43R-S78R, G20R-S24R-N43R-S78R-S242R, T22R-S24R-S78R-S212F, S9A-G20R-N43R-S78R-S242R, G20R-N43R-S78R-H249R, G20R-N43R-S78R, S9A-S78R-S212F, S9A-T22R-N43R-S78R, S9A-G20R-S24R-N43R, S9A-T22R-S78R-S212F, V4R-S9A-T22R-S78R-S212F, G20R-S24R-N43R, A1R-S9A-N43R, G20R-S24R-N43R-G115R, S9A-S24R-N43R, G20R-T22R-S24R-N43R, A1R-S24R-N43R, S9A-G20R-S24R-N43R-S242R, S9A-G20R-T22R-S78R-S212F, S9A-S24R-N43R-V244R, S9A-S24R-N43R-S242R, V4R-S9A-T22R-S24R-S212F, and T22R-S24R-N43R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101G-S103A-V104I-A232V-Q245R-N248D, S101G-S103A-V104I-G159D-A232V-Q245R, S101G-S103A-V104I-G159R-A232V-Q245R-N248D, S101G-S103A-V104I-G159D-A232V-Q245R-N248R, S101G-S103A-V104I-A232V-Q245R, S101G-S103A-V104I-A232V-Q245R-N248R, S101G-S103A-V104I-G159R-A232V-Q245R-N248R, S101G, S103A, V104I, A232V, Q236H, and Q245R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, and E271F wherein amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: A1R, Q2S, Q2M, Q2A, Q2R, Q2W, S3R, V4R, V4S, V4C, I8A, S9A, S9F, S9W, R10S, R10A, R10H, R10M, Q12F, Q12R, P14K, P14F, P14Q, A15R, A15F, A16S, H17R, H17M, H17F, N18R, N18K, G20F, G20K, G20R, T22A, T22R, T22Y, T22V, T22Q, T22L, T22W, G23A, G23S, G23F, S24R, S24F, S24W, S24Q, S24H, S24L, G25V, G25F, G25R, V26F, K27L, K27F, K27R, K27V, V28A, V28N, V28E, A29T, V30E, L31F, T33S, T33G, T33D, G34P, I35M, S36T, S36F, S36R, T38L, T38F, T38R, P40N, P40L, P40T, P40W, P40H, P40R, L42I, N43A, N43F, N43I, N43S, N43R, N43M, N43W, N43D, R45T, G46R, A48R, F50C, V51W, V51F, V51H, P52F, P52E, P52N, P55Y, T57R, Q59A, Q59F, Q59R, D60P, D60Q, D60A, N62E, N62Q, G63V, G63M, G63T, G63I, G63A, G63S, G63H, G63Q, G63D, G63E, G63P, H64F, H64T, V68A, V68C, A69N, A69T, A69P, A69W, T71G, T71G, I72C, A74C, L75A, L75F, L75E, L75R, N76D, S78R, S78N, S78I, S78R, I79W, I79Q, V81R, L82F, L82T, L82V, L82R, L82M, A85M, P86W, P86L, P86I, E89P, E89T, E89G, E89H, E89W, E89L, E89V, E89W, E89F, E89I, Y91N, Y91F, A92F, K94N, S99F, S99T, S99P, S99G, S99M, G100S, G100N, G100Q, G100I, S101A, S101N, S101G, S101D, S101T, S101D, S101E, S101P, S101F, G102A, G102T, G102N, G102H, G102E, S103G, S103N, S103D, S103A, V104L, V104I, V104E, V104D, S105T, S105E, S105Q, S106G, S106T, S106E, S106D, S106A, S106V, S106F, I107M, I107F, A108I, A108G, Q109M, L111V, L111I, E112V, E112L, E112Q, A114G, G115K, G115R, N116K, N116A, N116L, N117F, G118R, G118I, M119C, H120A, H120F, H120R, V121F, V121F, V121E, N123G, N123E, L124S, S128D, S128F, S128L, S128N, S128H, S128M, S128I, S128Q, P129E, S132A, S132E, A138G, S144R, V147L, L148I, A158E, G159D, G159E, G159C, S160D, S166D, S166E, Y167W, M175V, V177C, D181A, Q182R, N183I, N183D, N183M, N183R, N183F, N183R, N185E, N185V, N185I, R186H, R186K, S188E, S188D, S188R, Y192H, Y192W, A194E, A194V, A194F, D197F, D197F, I198L, I198F, V203E, V203C, T208S, Y209S, Y209N, Y209F, Y209T, Y209E, Y209H, Y209G, Y209L, P210R, P210V, P210L, G211Q, G211R, S212I, S212M, S212F, T213A, Y214F, A215N, A215D, A215E, A215H, A215F, S216F, S216A, L217E, L217N, L217D, N218D, N218P, N218E, T224A, T224G, V227I, A230E, A231I, A231C, A232V, L233C, V234F, K235F, Q236F, Q236N, Q236H, N238R, N238K, N238L, P239K, P239G, P239R, P239R, P239H, P239T, P239N, P239S, P239F, S240R, W241R, S242L, S242R, N243F, N243R, V244R, Q245R, I246S, N248D, N248V, N248I, N248R, H249R, H249T, L250I, K251R, K251S, N252I, N252F, N252R, N252K, N252H, T253I, T253R, T253F, A254C, S256N, G258R, T260V, T260I, L262D, L262H, Y263F, S265F, L267V, L267N, L267M, N269I, N269R, A270C, E271I, E271H, E271V, E271H, E271M, E271L, E271P, E271A, E271F, E271T, A272F, A272F, A272R, A273F, A273I, and T274G, wherein the amino acid positions of the subtilisin variant are numbered by correspondence with the amino acid sequence of *B. amyloliquefaciens* subtilisin BPN' set forth as SEQ ID NO:1.

The present invention also provides protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations at amino acid positions selected from amino acid 1, 2, 3, 4, 8, 9, 10, 12, 14, 15, 16, 17, 18, 20, 22, 23, 24, 25, 26, 27, 28, 29, 30, 31, 33, 34, 35, 36, 38, 40, 42, 43, 45, 46, 48, 50, 51, 52, 55, 57, 59, 60, 62, 63, 64, 68, 69, 71, 72, 74, 75, 76, 78, 79, 81, 82, 85, 86, 89, 91, 92, 94, 99, 100, 101, 102, 103, 104, 105, 106, 107, 108, 109, 111, 112, 114, 115, 116, 117, 118, 119, 120, 121, 123, 124, 128, 129, 132, 138, 44, 147, 148, 158, 159, 160, 166, 167, 175, 177, 181, 182, 183, 185, 186, 188, 192, 194, 197, 198, 203, 208, 209, 210, 211, 212, 213, 214, 215, 216, 217, 218, 224, 227, 230, 231, 233, 234, 235, 236, 236, 238, 238, 239, 240, 241, 242, 243, 244, 246, 248, 249, 250, 251, 252, 253, 254, 256, 258, 260, 262, 263, 265, 267, 269, 270, 271, 272, 273, and 274, wherein the amino acid positions of the subtilisin variant are numbered by correspondence with the amino acid sequence of *B. amyloliquefaciens* subtilisin BPN' set forth as SEQ ID NO:1, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the variant protease amino acid sequence with the *Bacillus amyloliquefaciens* subtilisin BPN' amino acid sequence.

The present invention also provides protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2, in no more than two, three, four, five, six, seven, eight, nine, 10, 11, 12, 13, 14, 15, 16, 17, 18, 19, 20, 21, 22, 23, 24, or 25 mutations selected from the group of A1R, Q2S, Q2M, Q2A, Q2R, Q2W, S3R, V4R, V4S, V4C, I8A, S9A, S9F, S9W, R10S, R10A, R10H, R10M, Q12F, Q12R, P14K, P14F, P14Q, A15R, A15F, A16S, H17R, H17M, H17F, N18R, N18K, G20F, G20K, G20R, T22A, T22R, T22Y, T22V, T22Q, T22L, T22W, G23A, G23S, G23F, S24R, S24F, S24W, S24Q, S24H, S24L, G25V, G25F, G25R, V26F, K27L, K27F, K27R, K27V, V28A, V28N, V28E, A29T, V30E, L31F, T33S, T33G, T33D, G34P, I35M, S36T, S36F, S36R, T38L, T38F, T38R, P40N, P40L, P40T, P40W, P40H, P40R, L42I, N43A, N43F, N43I, N43S, N43R, N43M, N43W, N43D, R45T, G46R, A48R, F50C, V51W, V51F, V51H, P52F, P52E, P52N, P55Y, T57R, Q59A, Q59F, Q59R, D60P, D60Q, D60A, N62E, N62Q, G63V, G63M, G63T, G63I, G63A, G63S, G63H, G63Q, G63D, G63E, G63P, H64F, H64T, V68A, V68C, A69N, A69T, A69P, A69W, T71G, T71G, I72C, A74C, L75A, L75F, L75E, L75R, N76D, S78R, S78N, S78I, S78R, 179W, 179Q, V81R, L82F, L82T, L82V, L82R, L82M, A85M, P86W, P86L, P86I, P86P, E89T, E89G, E89H, E89W, E89L, E89V, E89W, E89F, E89I, Y91N, Y91F, A92F, K94N, S99F, S99T, S99P, S99G, S99M, G100S, G100N, G100Q, G100I, S101A, S101N, S101G, S101D, S101T, S101D, S101E, S101P, S101F, G102A, G102T, G102N, G102H, G102E, S103G, S103N, S103D, S103A, V104L, V104I, V104E, V104D, S105T, S105E, S105Q, S106G, S106T, S106E, S106D, S106A, S106V, S106F, I107M, I107F, A108I, A108G, Q109M, L111V, L111I, E112V, E112L, E112Q, A114G, G115K, G115R, N116K, N116A, N116L, N117F, G118R, G118I, M119C, H120A, H120F, H120R, V121F, V121F, V121E, N123G, N123E, L124S, S128D, S128F, S128L, S128N, S128H, S128M, S128I, S128Q, P129E, S132A, S132E, A138G, S144R, V147L, L148I, A158E, G159D, G159E, G159C, S160D, S166D, S166E, Y167W, M175V, V177C, D181A, Q182R, N183I, N183D, N183M, N183R, N183F, N183R, N185E, N185V, N185I, R186H, R186K, S188E, S188D, S188R, Y192H, Y192W, A194E, A194V, A194F, D197F, D197F, I198L, I198F, V203E, V203C, T208S, Y209S, Y209N, Y209F, Y209T, Y209E, Y209H, Y209G, Y209L, P210R, P210V, P210L, G211Q, G211R, S212I, S212M, S212F, T213A, Y214F, A215N, A215D, A215E, A215H, A215F, S216F, S216A, L217E, L217N, L217D, N218D, N218P, N218E, T224A, T224G, V227I, A230E, A231I, A231C, A232V, L233C, V234F, K235F, Q236F, Q236N, Q236H, N238R, N238K, N238L, P239K, P239G, P239R, P239R, P239H, P239T, P239N, P239S, P239F, S240R, W241R, S242L, S242R, N243F, N243R, V244R, Q245R, I246S, N248D, N248V, N248I, N248R, H249R, H249T, L250I, K251R, K251S, N252I, N252F, N252R, N252K, N252H, T253I, T253R, T253F, A254C, S256N, G258R, T260V, T260I, L262D, L262H, Y263F, S265F, L267V, L267N, L267M, N269I, N269R, A270C, E271I, E271H, E271V, E271H, E271M, E271L, E271P, E271A, E271F, E271T, A272F, A272F, A272R, A273F, A273I, and T274G, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E, G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N, N269I, N269R, E271F, E271I, E271H, E271P, E271T, E271V, E271L and A272F, and optionally comprises at least one mutation selected from the group of S103A, G159D, Q236H, Q245R, N248D and N252K, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, and E271F, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of G20K, G20R, G23A, S24F, S24R, N43R, N43W, R45T, N62E, N76D, S101A, N116A, N116L, G118R, S128I, P129E, S166D, S188D, T213A, A215F, L217E, P239G, and N269R, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, and W241R, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, and W241R, and optionally comprises at least one mutation selected from the group of S103A, G159D, Q236H, Q245R, N248D and N252K, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants comprising amino acid sequence which differs from the amino acid sequence of SEQ ID NO:2, and wherein the total net charge of the protease variant is 0, +1, +2, +3, +4, +5, −1, −2, −3, −4, or −5 relative to the total net charge of the *Bacillus lentus* subtilisin GG36 protease, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence. In some instances, the the total net charge of the protease variant is 0 relative to the total net charge of the *Bacillus lentus* subtilisin GG36 protease. In some instances, the the total net charge of the protease variant is −5 relative to the total net charge of the *Bacillus lentus* subtilisin GG36 protease. In some instances, the the total net charge of the protease variant is −4 relative to the total net charge of the *Bacillus lentus* subtilisin GG36 protease. In some instances, the the total net charge of the protease variant is −3 relative to the total net charge of the *Bacillus lentus* subtilisin GG36 protease. In some instances, the the total net charge of the protease variant is −2 relative to the total net charge of the *Bacillus lentus* subtilisin GG36 protease. In some instances, the the total net charge of the protease variant is −1 relative to the total net charge of the *Bacillus lentus* subtilisin GG36 protease. In some instances, the the total net charge of the protease variant is +1 relative to the total net charge of the *Bacillus lentus* subtilisin GG36 protease. In some instances, the the total net charge of the protease variant is +2 relative to the total net charge of the *Bacillus lentus* subtilisin GG36 protease. In some instances, the the total net charge of the protease variant is +3 relative to the total net charge of the *Bacillus lentus* subtilisin GG36 protease. In some instances, the the total net charge of the protease variant is +4 relative to the total net charge of the *Bacillus lentus* subtilisin GG36 protease. In some instances, the the total net charge of the protease variant is +5 relative to the total net charge of the *Bacillus lentus* subtilisin GG36 protease. In some instances, the the total net charge of the protease variant differs from 0 (i.e, the total net charge of the protease is not neutral).

The present invention also provides protease variants having one or more of the following characteristics: a) a Test Method 2 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; b) a Test Method 3 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; c) a Test Method 4 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or d) a Test Method 6 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5.

The present invention also provides isolated nucleic acids comprising polynucleotide sequences that encode the subtilisin variants provided herein. The present invention further provides expression vectors comprising the nucleic acid sequences encoding the subtilisin variants provided herein. In some further embodiments, the nucleic acid in the expression vector operably linked to a promoter. The present invention also provides host cells comprising the expression vectors provided herein. In some embodiments, the host cells are Bacillus host cells. In some further embodiments, the host cells are B. subtilis host cells.

The present invention also provides methods for producing at least one subtilisin variant, comprising: transforming a host cell with an expression vector comprising at least one nucleic acid encoding at least one subtilisin variant provided herein to produce a transformed host cell; and cultivating the transformed host cell under conditions suitable for the production of at least one subtilisin variant, to produce at least one subtilisin variant. In some embodiments, the methods further comprise harvesting the produced subtilisin variant. In some further embodiments, the nucleic acid in the expression vector operably linked to a promoter. In some further embodiments, the nucleic acid in the expression vector operably linked to a promoter. The present invention also provides host cells comprising the expression vectors provided herein. In some embodiments, the host cells are Bacillus host cells. In some further embodiments, the host cells are B. subtilis host cells.

The protease variants of the present invention can also be used in fabric and home care products comprising at least one subtilisin variant provided herein. In some embodiments, the fabric and home care product is a cleaning composition. In some further embodiments, the cleaning composition is a granular, powder, solid, bar, liquid, tablet, gel, or paste composition. In some additional embodiments, the cleaning composition is a detergent composition. In some further additional embodiments, the cleaning composition is a cold water detergent composition, a low pH detergent composition, or a compact detergent composition. In some additional embodiments, the cleaning composition is a laundry detergent composition, a dish detergent composition and/or a hard surface cleaning composition. In some embodiments, the dish detergent composition is a hand dishwashing detergent composition or an automatic dishwashing detergent composition. In some additional embodiments, the fabric and home care product further comprises at least one bleaching agent. In some further additional embodiments, the cleaning composition is phosphate-free, while in other embodiments, the cleaning composition contains phosphate. In some further embodiments, the fabric and home care product further comprises at least one additional enzyme. In still some additional embodiments, the at least one additional enzyme is selected from hemicellulases, cellulases, peroxidases, proteases, metalloproteases, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidases, chondroitinases, laccases, and amylases, or any combination thereof. In some embodiments, the fabric and home care products comprise at least one subtilisin variant that is not a cold water protease.

The present invention also provides cleaning compositions comprising at least one subtilisin variant. In some embodiments, the cleaning compositions are a granular, powder, solid, bar, liquid, tablet, gel, or paste compositions. In some further embodiments, the cleaning compositions are detergent compositions. In some still additional embodiments, the cleaning compositions are cold water detergent compositions, low pH detergent compositions, and/or compact detergent compositions. In some additional embodiments, the cleaning compositions are laundry detergent compositions, dish detergent compositions, and/or a hard surface cleaning compositions. In some further embodiments, the dish detergents are hand dishwashing detergent compositions or automatic dishwashing detergent compositions. In some additional embodiments, the cleaning compositions are laundry detergent compositions. In still some further embodiments, the cleaning compositions further comprise at least one bleaching agent. In some additional embodiments, the cleaning compositions are phosphate-free, while in other embodiments the cleaning compositions contain phosphate. In some further embodiments, the cleaning compositions further comprise at least one additional enzyme. In still some additional embodiments, the cleaning compositions the at least one additional enzyme is selected from the group consisting of hemicellulases, cellulases, peroxidases, proteases, metalloproteases, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidases, chondroitinases, laccases, and amylases, or any combination thereof. In some embodiments, the cleaning compositions comprise at least one subtilisin variant that is not a cold water protease. Such composition may be a fabric and home care product or such composition may not be a fabric and home care product.

The present invention also provides methods of cleaning, comprising contacting a surface or an item with a cleaning composition comprising at least one subtilisin variant provided herein. In some embodiments, the methods of cleaning comprise contacting a surface or an item with at least one cleaning composition provided herein. In some embodiments, the methods further comprise rinsing the surface or item after contacting the surface or item, respectively, with the cleaning composition. In some embodiments, the item is dishware, while in other embodiments, the item is fabric. In some embodiments, the methods further comprise the step of rinsing the surface or item after contacting the surface or item with the cleaning composition. In some additional embodiments, the methods further comprise the step of drying the surface or item after rinsing the surface or item.

In some embodiments, the cleaning compositions comprise at least one subtilisin variant that is not a cold water protease.

The present invention provides methods of cleaning a surface or item, comprising: providing the cleaning composition provided herein and a surface or item in need of cleaning; and contacting the cleaning composition with the surface or item in need of cleaning under conditions suitable for the cleansing of the surface of the surface or item, to produce a cleansed surface or item. In some embodiments, the methods of the present invention further comprise the step of rinsing the cleansed surface or item to produce a rinsed surface or item. In some further embodiments, the methods further comprise the step of drying the rinsed surface or item. In some embodiments, the cleaning compositions comprise at least one subtilisin variant that is not a cold water protease.

BRIEF DESCRIPTION OF THE DRAWINGS

FIG. 1 provides an alignment of the mature reference proteases including: BPN' (SEQ ID NO:1) and GG36 (SEQ ID NO:2). Each amino acid position of each protease variant described herein, including each cold water protease variant, is numbered according to the numbering of the corresponding amino acid position in the amino acid sequence of *Bacillus amyloliquefaciens* subtilisin protease BPN' (SEQ ID NO:1), as shown in FIG. 1, as determined by alignment of the protease variant amino acid sequence with the *Bacillus amyloliquefaciens* subtilisin protease BPN' amino acid sequence. Thus, unless otherwise specified herein, substitution positions are given in relationship to BPN'.

DESCRIPTION OF THE INVENTION

Figure 2:
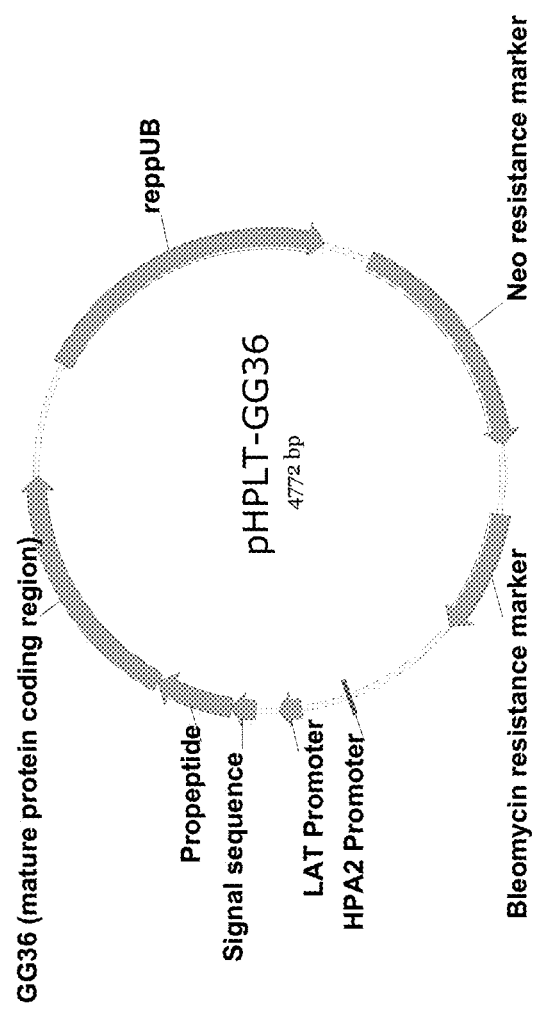
FIG. 2 provides a map of pHPLT-GG36.

The present invention provides serine protease variants. Specifically, the present invention provides serine protease variants having one or more substitutions as compared to a reference serine protease. In addition, the present invention provides compositions comprising these serine protease variants. In some embodiments, the present invention provides cleaning compositions comprising at least one of these serine protease variants.

Definitions

Unless otherwise indicated, the practice of the present invention involves conventional techniques commonly used in molecular biology, protein engineering, microbiology, and recombinant DNA, which are within the skill of the art. Such techniques are known to those of skill in the art and are described in numerous texts and reference works well known to those of skill in the art. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. Many technical dictionaries are known to those of skill in the art. Although any methods and materials similar or equivalent to those described herein find use in the practice of the present invention, some suitable methods and materials are described herein. Accordingly, the terms defined immediately below are more fully described by reference to the Specification as a whole. Also, as used herein, the singular "a", "an" and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

The practice of the present invention employs, unless otherwise indicated, conventional techniques of protein purification, molecular biology, microbiology, recombinant DNA techniques and protein sequencing, all of which are within the skill of those in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

As used herein, the terms "protease" and "proteinase" refer to an enzyme protein that has the ability to break down other proteins. A protease has the ability to conduct "proteolysis," which begins protein catabolism by hydrolysis of peptide bonds that link amino acids together in a peptide or polypeptide chain forming the protein. This activity of a protease as a protein-digesting enzyme is referred to as "proteolytic activity." Many well known procedures exist for measuring proteolytic activity (See e.g., Kalisz, "Microbial Proteinases," In: Fiechter (ed.), *Advances in Biochemical Engineering/Biotechnology*, (1988)). For example, proteolytic activity may be ascertained by comparative assays which analyze the respective protease's ability to hydrolyze a commercial substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011 and U.S. Pat. No. 6,376,450, both of which are incorporated herein by reference). The pNA assay (See e.g., Del Mar et al., Anal. Biochem. 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration. The active enzyme/total protein ratio gives the enzyme purity.

As used herein, the term "subtilisin" refers any member of the S8 serine protease family as described in MEROPS—The Peptidase Data base (See, Rawlings et al., MEROPS: the peptidase database, Nucl Acids Res, 34 Database issue, D270-272 [2006]). As described therein, the peptidase family S8 contains the serine endopeptidase subtilisin and its homologues (Rawlings and Barrett, Biochem J., 290:205-218, [1993]). Family S8, also known as the subtilase family, is the second largest family of serine peptidases. The tertiary structures for several members of family S8 have now been determined. A typical S8 protein structure consists of three layers with a seven-stranded β sheet sandwiched between two layers of helices. Subtilisin (S08.001) is the type structure for clan SB (SB). Despite the different structure, the active sites of subtilisin and chymotrypsin (S01.001) can be superimposed, which suggests the similarity is the result of convergent rather than divergent evolution.

As used herein, the terms "protease variant," "variant protease," "variant serine protease," "serine protease variant", "subtilisin variant", "mutant protease," are used in reference to proteases that are similar to a reference protease (which may be a wild-type subtilisin protease), particularly in their function, but have mutations in their amino acid sequence that make them different in sequence from the wild-type protease or any starting reference protease (i.e., "parent" protease) from which the variant protease is derived. In some embodiments, the present invention provides "GG36 variants," (or "GG36 subtilisin variants") wherein the mutations are present in the mature GG36 sequence set forth in SEQ ID NO:2. However, it is not intended that the reference protease be limited to any particular amino acid sequence. In addition, it is intended that the term encompass variants of a parent protease wherein the parent protease's sequence is at least 90%, at least 95%, at least 96%, at least 97%, at least 98%, at least 99%, or 100% identical to the amino acid sequence of SEQ ID NO:2.

As used herein, the term "cold water protease variant" means a protease variant of a parent protease, wherein the *B. lentus* subtilisin GG36 protease has the amino acid sequence of SEQ ID NO:2, wherein said protease variant has one or more of the following characteristics: a) a Test Method 2 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; b) a Test Method 3 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; c) a Test Method 4 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or d) a Test Method 6 performance index of at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5. Test Method 2, Test Method 3, Test Method 4, and Test Method 6 are explicitly described infra in the section of Example 1 entitled "Test_Methods". In addition, it is intended that the term encompass variants of a parent protease wherein the parent protease's sequence is at least 90%, at least 95%, at least 96%, at least 97%, at least 98%, at least 99%, or 100% identical to the amino acid sequence of SEQ ID NO:2.

In some embodiments of the present invention, the parent protease (i.e., "reference" or "starting" protease) is a commercially available protease, including but not limited to the proteases sold under the tradenames SAVINASE®, POLARZYME®, KANNASE®, LIQUINASE®, LIQUINASE ULTRA®, SAVINASE ULTRA®, OVOZYME®, (by Novozymes A/S); MAXACAL®, PROPERASE®, PURAFECT®, FN3®, FN4® and PURAFECT OXP®, PURAFAST™, PURAFECT® PRIME, PURAMAX® (by Danisco US, Genencor Division); and those available from Henkel/Kemira, namely BLAP (sequence shown in FIG. 29 of U.S. Pat. No. 5,352,604 with the following mutations S99D+S101R+S103A+V104I+G159S, hereinafter referred to as BLAP) and BLAP X (BLAP with S3T+V4I+V205I).

As used herein, the term "variant polypeptide" refers to a polypeptide comprising an amino acid sequence that differs in at least one amino acid residue from the amino acid sequence of a parent or reference polypeptide (including but not limited to wild-type polypeptides).

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulars, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

The terms "polynucleotide" and "nucleic acid," which are used interchangeably herein, refer to a polymer of any length of nucleotide monomers covalently bonded in a chain. DNA (deoxyribonucleic acid), a polynucleotide comprising deoxyribonucleotides, and RNA (ribonucleic acid), a polymer of ribonucleotides, are examples of polynucleotides or nucleic acids having distinct biological function. Polynucleotides or nucleic acids include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, expressed sequence tag(s) (EST(s)), exons, introns, messenger RNA (mRNA), transfer RNA (tRNA), ribosomal RNA (rRNA), ribozymes, complementary DNA (cDNA), recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracyl, other sugars and linking groups such as fluororibose and thioate, and nucleotide branches. In a particular embodiment, a sequence of nucleotides is interrupted by non-nucleotide components.

As used herein, the term "mutation" refers to changes made in a starting amino acid or nucleic acid sequence. It is intended that the term encompass substitutions, insertions and deletions.

As used herein, the term "vector" refers to a nucleic acid construct or polynucleotide construct used to introduce or transfer nucleic acid(s) or polynucleotide(s) into a target cell or tissue. A vector is typically used to introduce foreign DNA into another cell or tissue. A vector generally comprises a DNA sequence that is a transgene and a larger polynucleotide sequence that serves as the "backbone" of the vector. The vector typically serves to transfers genetic information, such as the inserted transgene, to a target cell or tissue so as to isolate, multiply, or express the insert in the target cell or tissue. Vectors include plasmids, cloning vectors, bacteriophages, viruses (e.g., viral vector), cosmids, expression vectors, shuttle vectors, cassettes, and the like. A vector typically includes an origin of replication, a multi-cloning site, and a selectable marker. The process of inserting a vector into a target cell is typically referred to as transfection. The transfection of a cell with a viral vector is typically referred to as transduction. The present invention includes, in some embodiments, a vector that comprises a DNA sequence encoding a variant protease (e.g., precursor or mature variant protease) that is operably linked to a suitable prosequence (e.g., secretory, signal peptide sequence, etc.) capable of effecting the expression of the DNA sequence in a suitable host.

As used herein, the term "expression cassette," "expression plasmid" or "expression vector" refers to a nucleic acid construct or vector generated recombinantly or synthetically for the expression of a nucleic acid of interest (e.g., a foreign nucleic acid or transgene) in a target cell. The nucleic acid of interest typically expresses a protein of interest. An expression vector or expression cassette typically comprises a promoter nucleotide sequence that drives or promotes expression of the foreign nucleic acid. The expression vector or cassette also typically includes any other specified nucleic acid elements that permit transcription of a particular nucleic acid in a target cell. A recombinant expression cassette can be incorporated into a plasmid, chromosome, mitochondrial DNA, plastid DNA, virus, or nucleic acid fragment. Some expression vectors have the ability to incorporate and express heterologous DNA fragments in a host cell. Many prokaryotic and eukaryotic expression vectors are commercially available. Selection of appropriate expression vectors is within the knowledge of those of skill in the art. Selection of appropriate expression vectors for expression of a protein from a nucleic acid sequence incorporated into the expression vector is within the knowledge of those of skill in the art.

A DNA construct is an artificially constructed segment of nucleic acid that may be introduced into a target cell or tissue. A DNA construct typically comprises a DNA insert comprising a nucleotide sequence encoding a protein of interest that has been subcloned into a vector. The vector may contain bacterial resistance genes for growth in bacteria and a promoter for expression of the protein of interest in an organism. The DNA may be generated in vitro by PCR or any other suitable technique(s) known to those in the art. In some embodiments, the DNA construct comprises a nucleic acid sequence of interest. In some embodiments, the sequence is operably linked to additional elements such as control elements (e.g., promoters, etc.). The DNA construct may further comprise a selectable marker and may further comprise an incoming sequence flanked by homology boxes. The construct may comprise other non-homologous sequences, added to the ends (e.g., stuffer sequences or flanks). In some embodiments, the ends of the sequence are closed such that the DNA construct forms a closed circle. The nucleic acid sequence of interest, which is incorporated into the DNA construct, using techniques well known in the art, may be a wild-type, mutant, or modified nucleic acid. In some embodiments, the DNA construct comprises one or more nucleic acid sequences homologous to the host cell chromosome. In other embodiments, the DNA construct comprises one or more non-homologous nucleotide sequences. Once the DNA construct is assembled in vitro, it may be used, for example, to: 1) insert heterologous sequences into a desired target sequence of a host cell; and/or 2) mutagenize a region of the host cell chromosome (i.e., replace an endogenous sequence with a heterologous sequence); 3) delete target genes; and/or 4) introduce a replicating plasmid into the host. "DNA construct" is used interchangeably herein with "expression cassette."

As used herein, a "plasmid" refers to an extrachromosomal DNA molecule which is capable of replicating independently from the chromosomal DNA. A plasmid is double stranded (ds) and may be circular and is typically used as a cloning vector.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction (See e.g., Ferrari et al., "Genetics," in Hardwood et al. (eds.), *Bacillus*, Plenum Publishing Corp., pp. 57-72 [1989]).

Transformation refers to the genetic alteration of a cell which results from the uptake, genomic incorporation, and expression of genetic material (e.g., DNA).

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

As used herein the term "gene" refers to a polynucleotide (e.g., a DNA segment), that encodes a polypeptide and includes regions preceding and following the coding regions as well as intervening sequences (introns) between individual coding segments (exons).

As used herein, "recombinant" when used with reference to a cell typically indicates that the cell has been modified by the introduction of a heterologous nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) but which has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination," "recombining," and "recombined" of polynucleotides or nucleic acids refer generally to the assembly or combining of two or more nucleic acid or polynucleotide strands or fragments to generate a new polynucleotide or nucleic acid. The recombinant polynucleotide or nucleic acid is sometimes referred to as a chimera. A nucleic acid or polypeptide is "recombinant" when it is artificial or engineered, or derived from an artificial or engineered protein or nucleic acid.

As used herein, the term nucleic acid or gene "amplification" refers to a process by which specific DNA sequences are disproportionately replicated such that the amplified nucleic acid or gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this nucleic acid or gene product or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide (a polymer of nucleotide residues), whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent such as DNA polymerase and at a suitable temperature and pH). A primer is preferably single stranded for maximum efficiency in amplification, but may alternatively be double stranded. If double stranded, the primer is first treated to separate its strands before being used to prepare extension products. In some embodiments, the primer is an oligodeoxyribonucleotide. The primer must be sufficiently long to prime the synthesis of extension products in the presence of the inducing agent. The exact length of a primer depends on a variety of factors, including temperature, source of primer, and the use of the method.

As used herein, the term "probe" refers to an oligonucleotide, whether occurring naturally as in a purified restriction digest or produced synthetically, recombinantly or by PCR amplification, which is typically capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A nucleotide "segment" is a region of a nucleic acid within the target nucleic acid sequence.

As used herein, the term "polymerase chain reaction" (PCR) refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence is well known in the art.

As used herein, the term "amplification reagents" refers to those reagents (e.g., deoxyribonucleotide triphosphates, buffer, etc.) needed for amplification except for primers, nucleic acid template, and the amplification enzyme. Typically, amplification reagents along with other reaction components are placed and contained in a reaction vessel (test tube, microwell, etc.).

As used herein, the term "restriction endonuclease" or "restriction enzyme" refers to an enzyme (e.g., bacterial enzyme) that is capable of cutting double-stranded or single-stranded DNA at or near a specific sequence of nucleotides known as a restriction site. The nucleotide sequence comprising the restriction site is recognized and cleaved by a given restriction endonuclease or restriction enzyme and is frequently the site for insertion of DNA fragments. A restriction site can be engineered into an expression vector or DNA construct.

"Homologous recombination" refers to the exchange of DNA fragments between two DNA molecules or paired chromosomes at the site of identical or nearly identical nucleotide sequences. In some embodiments, chromosomal integration is homologous recombination.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

As is known in the art, a DNA sequence can be transcribed by an RNA polymerase to produce an RNA sequence, but an RNA sequence can be reverse transcribed by reverse transcriptase to produce a DNA sequence.

"Host strain" or "host cell" refers to a suitable host for an expression vector comprising a DNA sequence of interest. The DNA sequence of interest may express a protein of interest in the host strain or host cell.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used through out this disclosure. The single letter X refers to any of the twenty amino acids. It is also understood that a polypeptide may be coded for by more than one nucleotide sequence due to the degeneracy of the genetic code. Mutations are named by the one letter code for the parent amino acid, followed by a three or two digit position number and then the one letter code for the variant amino acid. For example, mutating glycine (G) at position 87 to serine (S) is represented as "G087S" or "G87S". Multiple mutations are indicated by inserting a "−" between the mutations. Mutations at positions 87 and 90 are represented as either "G087S−A090Y" or "G87S−A90Y" or "G87S+A90Y" or "G087S+A090Y". For deletions, the one letter code "Z" is used. For an insertion relative to the parent sequence, the one letter code "Z" is on the left side of the position number. For a deletion, the one letter code "Z" is on the right side of the position number. For insertions, the position number is the position number before the inserted amino acid(s), plus 0.01 for each amino acid. For example, an insertion of three amino acids alanine (A), serine (S) and tyrosine (Y) between position 87 and 88 is shown as "Z087.01A−Z087.02S−Z087.03Y." Thus, combining all the mutations above plus a deletion at position 100 is: "G087S−Z087.01A−Z087.02S−Z087.03Y−A090Y−A100Z."

A "prosequence" or "propetide sequence" refers to an amino acid sequence between the signal peptide sequence and mature protease sequence that is necessary for the secretion of the protease. Cleavage of the prosequence or propeptide sequence results in a mature active protease.

The term "signal sequence" or "signal peptide" refers to a sequence of amino acid residues that may participate in the secretion or direct transport of the mature or precursor form of a protein. The signal sequence is typically located N-terminal to the precursor or mature protein sequence. The signal sequence may be endogenous or exogenous. One exemplary exogenous signal sequence comprises the first seven amino acid residues of the signal sequence from *Bacillus subtilis* subtilisin fused to the remainder of the signal sequence of the subtilisin from *Bacillus lentus* (ATCC 21536). A signal sequence is normally absent from the mature protein. A signal sequence is typically cleaved from the protein by a signal peptidase after the protein is transported.

The term "hybrid signal sequence" refers to signal sequences in which part of sequence is obtained from the expression host fused to the signal sequence of the gene to be expressed. In some embodiments, synthetic sequences are utilized.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polynucleotides that are involved in post-translational activity (e.g., polynucleotides cleaved therefrom to leave the mature form of a protein or peptide).

The term "wild-type" in reference to an amino acid sequence or nucleic acid sequence indicates that the amino acid sequence or nucleic acid sequence is native or naturally occurring sequence. As used herein, the term "naturally-occurring" refers to anything (e.g., proteins, amino acids, or nucleic acid sequences) that are found in nature (i.e., have not been manipulated by means of recombinant methods).

As used herein, the term "non-naturally occurring" refers to anything that is not found in nature (e.g., recombinant nucleic acids produced in the laboratory).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position along related proteins or a reference protein.

The terms "derived from" and "obtained from" refer to not only a protease produced or producible by a strain of the organism in question, but also a protease encoded by a DNA sequence isolated from such strain and produced in a host organism containing such DNA sequence. Additionally, the term refers to a protease which is encoded by a DNA sequence of synthetic and/or cDNA origin and which has the identifying characteristics of the protease in question. To exemplify, "proteases derived from *Bacillus*" refers to those enzymes having proteolytic activity which are naturally produced by *Bacillus*, as well as to serine proteases like those produced by *Bacillus* sources but which through the use of genetic engineering techniques are produced by non-*Bacillus* organisms transformed with a nucleic acid encoding the serine proteases.

The term "identical" in the context of two nucleic acids or polypeptide sequences refers to the residues in the two sequences that are the same when aligned for maximum correspondence, as measured using one of the following sequence comparison or analysis algorithms.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "homology" refers to sequence similarity or identity, with identity being preferred. Homology may be determined using standard techniques known in the art (See e.g., Smith and Waterman, Adv. Appl. Math. 2:482 [1981]; Needleman and Wunsch, J. Mol. Biol. 48:443 [1970\; Pearson and Lipman, Proc. Natl. Acad. Sci. USA 85:2444 [1988]; software programs such as GAP, BESTFIT, FASTA, and TFASTA in the Wisconsin Genetics Software Package (Genetics Computer Group, Madison, Wis.); and Devereux et al., Nucl. Acid Res. 12:387-395 [1984]). One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (See, Feng and Doolittle, J. Mol. Evol. 35:351-360 [1987]). The method is similar to that described by Higgins and Sharp (See, Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (See, Altschul et al., J. Mol. Biol. 215:403-410 [1990]; and Karlin and Altschul, Proc. Natl. Acad. Sci. USA 90:5873-5787 [1993]). A particularly useful BLAST program is the WU-BLAST-2 program (See, Altschul et al., Meth. Enzymol. 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity.

The percent sequence identity between a reference sequence and a test sequence of interest may be readily determined by one skilled in the art. The percent identity shared by polynucleotide or polypeptide sequences is determined by direct comparison of the sequence information between the molecules by aligning the sequences and determining the identity by methods known in the art. An example of an algorithm that is suitable for determining sequence similarity is the BLAST algorithm, (See, Altschul, et al., J. Mol. Biol., 215:403-410 [1990]). Software for performing BLAST analyses is publicly available through the National Center for Biotechnology Information. This algorithm involves first identifying high scoring sequence pairs (HSPs) by identifying short words of length W in the query sequence that either match or satisfy some positivevalued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1992]) alignments (B) of 50, expectation (E) of 10, M'S, N'-4, and a comparison of both strands.

The BLAST algorithm then performs a statistical analysis of the similarity between two sequences (See e.g., Karlin and Altschul, supra). One measure of similarity provided by the BLAST algorithm is the smallest sum probability (P(N)), which provides an indication of the probability by which a match between two nucleotide or amino acid sequences would occur by chance. For example, a nucleic acid is considered similar to a serine protease nucleic acid of this invention if the smallest sum probability in a comparison of the test nucleic acid to a serine protease nucleic acid is less than about 0.1, more preferably less than about 0.01, and most preferably less than about 0.001. Where the test nucleic acid encodes a serine protease polypeptide, it is considered similar to a specified serine protease nucleic acid if the comparison results in a smallest sum probability of less than about 0.5, and more preferably less than about 0.2.

Percent "identical" or "identity" in the context of two or more nucleic acid or polypeptide sequences refers to two or more sequences that are the same or have a specified percentage of nucleic acid residues or amino acid residues, respectively, that are the same, when compared and aligned for maximum similarity, as determined using a sequence comparison algorithm or by visual inspection. "Percent sequence identity" or "% identity" or "% sequence identity or "% amino acid sequence identity" of a subject amino acid sequence to a reference (i.e., query) amino acid sequence means that the subject amino acid sequence is identical (i.e., on an amino acid-by-amino acid basis) by a specified percentage to the query amino acid sequence over a comparison length when the sequences are optimally aligned. Thus, 80% amino acid sequence identity or 80% identity with respect to two amino acid sequences means that 80% of the amino acid residues in two optimally aligned amino acid sequences are identical.

"Percent sequence identity" or "% identity" or "% sequence identity or "% nucleotide sequence identity" of a subject nucleic acid sequence to a reference (i.e. query) nucleic acid sequence means that the subject nucleic acid sequence is identical (i.e., on a nucleotide-by-nucleotide basis for a polynucleotide sequence) by a specified percentage to the query sequence over a comparison length when the sequences are optimally aligned. Thus, 80% nucleotide sequence identity or 80% identity with respect to two nucleic acid sequences means that 80% of the nucleotide residues in two optimally aligned nucleic acid sequences are identical.

In some embodiments, the "percent sequence identity" or "% sequence identity" or "% identity" of a subject sequence to a query sequence can be calculated by optimally aligning the two sequences and comparing the two optimally aligned sequences over the comparison length. The number of positions in the optimal alignment at which identical residues occur in both sequences is determined, thereby providing the number of matched positions, and the number of matched positions is then divided by the total number of positions of the comparison length (which, unless otherwise specified, is the length of the query sequence). The resulting number is multiplied by 100 to yield the percent sequence identity of the subject sequence to the query sequence.

"Optimal alignment" or "optimally aligned" refers to the alignment of two (or more) sequences giving the highest percent identity score. For example, optimal alignment of two protein sequences can be achieved by manually aligning the sequences such that the maximum number of identical amino acid residues in each sequence are aligned together or by using software programs or procedures described herein or known in the art. Optimal alignment of two nucleic acid sequences can be achieved by manually aligning the sequences such that the maximum number of identical nucleotide residues in each sequence are aligned together or by using software programs or procedures described herein or known in the art.

In some embodiments, two polypeptide sequences are deemed "optimally aligned" when they are aligned using defined parameters, such as a defined amino acid substitution matrix, gap existence penalty (also termed gap open penalty), and gap extension penalty, so as to achieve the highest similarity score possible for that pair of sequences. The BLOSUM62 scoring matrix (See, Henikoff and Henikoff, supra) is often used as a default scoring substitution matrix in polypeptide sequence alignment algorithms (e.g., BLASTP). The gap existence penalty is imposed for the introduction of a single amino acid gap in one of the aligned sequences, and the gap extension penalty is imposed for each residue position in the gap. Exemplary alignment parameters employed are: BLOSUM62 scoring matrix, gap existence penalty=11, and gap extension penalty=1. The alignment score is defined by the amino acid positions of each sequence at which the alignment begins and ends (e.g., the alignment window), and optionally by the insertion of a gap or multiple gaps into one or both sequences, so as to achieve the highest possible similarity score.

Optimal alignment between two or more sequences can be determined manually by visual inspection or by using a computer, such as, but not limited to for example, the BLASTP program for amino acid sequences and the BLASTN program for nucleic acid sequences (See e.g., Altschul et al., Nucleic Acids Res. 25(17):3389-3402 (1997); See also, the National Center for Biotechnology Information (NCBI) website).

A polypeptide of interest may be said to be "substantially identical" to a reference polypeptide if the polypeptide of interest comprises an amino acid sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the reference polypeptide. The percent identity between two such polypeptides can be determined manually by inspection of the two optimally aligned polypeptide sequences or by using software programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative amino acid substitution or one or more conservative amino acid substitutions.

A nucleic acid of interest may be said to be "substantially identical" to a reference nucleic acid if the nucleic acid of interest comprises a nucleotide sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the nucleotide sequence of the reference nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the two nucleic acid molecules hybridize to each other under stringent conditions (e.g., within a range of medium to high stringency).

A nucleic acid or polynucleotide is "isolated" when it is partially or completely separated from other components, including but not limited to for example, other proteins, nucleic acids, cells, etc. Similarly, a polypeptide, protein or peptide is "isolated" when it is partially or completely separated from other components, including but not limited to for example, other proteins, nucleic acids, cells, etc. On a molar basis, an isolated species is more abundant than are other species in a composition. For example, an isolated species may comprise at least about 50%, about 70%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a protein or nucleic acid sample, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, the invention provides methods of enriching compositions for one or more molecules of the invention, such as one or more polypeptides or polynucleotides of the invention. A composition is enriched for a molecule when there is a substantial increase in the concentration of the molecule after application of a purification or enrichment technique. A substantially pure polypeptide or polynucleotide of the invention (e.g., substantially pure variant protease or polynucleotide encoding a variant protease of the invention, respectively) will typically comprise at least about 55%, about 60%, about 70%, about 80%, about 85%, about 90%, about 91%, about 92%, about 93%, about 94%, about 95%, about 96%, about 97%, about 98, about 99%, about 99.5% or more by weight (on a molar basis) of all macromolecular species in a particular composition.

In a related sense, the invention provides methods of enriching compositions for one or more molecules of the invention, such as one or more polypeptides of the invention (e.g., one or more variant proteases of the invention) or one or more nucleic acids of the invention (e.g., one or more nucleic acids encoding one or more variant proteases of the invention). A composition is enriched for a molecule when there is a substantial increase in the concentration of the molecule after application of a purification or enrichment technique. A substantially pure polypeptide or polynucleotide will typically comprise at least about 55%, about 60%, about 70%, about 80%, about 85%, about 90%, about 91%, about 92%, about 93%, about 94%, about 95%, about 96%, about 97%, about 98, about 99%, about 99.5% or more by weight (on a molar basis) of all macromolecular species in a particular composition.

As used herein, the term "combinatorial mutagenesis" or "combinatorial" refers to methods in which libraries of nucleic acid variants of a reference nucleic acid sequence are generated. In these libraries, the variants contain one or several mutations chosen from a predefined set of mutations. The methods also provide means to introduce random mutations which were not members of the predefined set of mutations. Some such methods include those set forth in U.S. Pat. No. 6,582,914, hereby incorporated by reference. Some such combinatorial mutagenesis methods include and/or encompass methods embodied in commercially available kits (e.g., QUIKCHANGE® Multi Site-Directed Mutagenesis Kit (Stratagene), PCR fusion/extension PCR).

As used herein, "having improved properties" used in connection with a variant protease refers to a variant protease with improved or enhanced wash or cleaning performance, and/or improved or enhanced stability optionally with retained wash or cleaning performance, relative to the corresponding reference protease (e.g., wild-type or naturally-occurring protease). The improved properties of a variant protease may comprise improved wash or cleaning performance and/or improved stability. In some embodiments, the invention provides variant proteases of the invention that exhibit one of more of the following properties: improved hand wash performance, improved hand or manual dishwashing performance, improved automatic dishwashing performance, improved laundry performance, and/or improved stability relative to a reference protease (e.g., wild-type protease, such as a wild-type subtilisin).

As used herein, the term "functional assay" refers to an assay that provides an indication of a protein's activity. In some embodiments, the term refers to assay systems in which a protein is analyzed for its ability to function in its usual capacity. For example, in the case of enzymes, a functional assay involves determining the effectiveness of the enzyme in catalyzing a reaction.

As used herein, the term "target property" refers to the property of the starting gene that is to be altered. It is not intended that the present invention be limited to any particular target property. However, in some embodiments, the target property is the stability of a gene product (e.g., resistance to denaturation, proteolysis or other degradative factors), while in other embodiments, the level of production in a production host is altered.

The term "property" or grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, enhancer function), a property affecting RNA processing (e.g., RNA splicing, RNA stability, RNA conformation, and post-transcriptional modification), a property affecting translation (e.g., level, regulation, binding of mRNA to ribosomal proteins, post-translational modification). For example, a binding site for a transcription factor, polymerase, regulatory factor, etc., of a nucleic acid may be altered to produce desired characteristics or to identify undesirable characteristics.

The term "property" or grammatical equivalents thereof in the context of a polypeptide (including proteins), as used herein, refer to any characteristic or attribute of a polypeptide that can be selected or detected. These properties include, but are not limited to oxidative stability, substrate specificity, catalytic activity, enzymatic activity, thermal stability, alkaline stability, pH activity profile, resistance to proteolytic degradation, $K_M$, $k_{cat}$, $k_{cat}/K_M$ ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and/or ability to treat disease, etc.

As used herein, the term "screening" has its usual meaning in the art. In one exemplary screening process, a mutant nucleic acid or variant polypeptide encoded therefrom is provided and a property of the mutant nucleic acid or variant polypeptide, respectively, is assessed or determined. The determined property of the mutant nucleic acid or variant polypeptide may be compared to a property of the corresponding precursor (parent) nucleic acid or to the property of the corresponding parent polypeptide, respectively.

It will be apparent to the skilled artisan that the screening procedure for obtaining a nucleic acid or protein with an altered property depends upon the property of the starting material the modification of which the generation of the mutant nucleic acid is intended to facilitate. The skilled artisan will therefore appreciate that the invention is not limited to any specific property to be screened for and that the following description of properties lists illustrative examples only. Methods for screening for any particular property are generally described in the art. For example, one can measure binding, pH, specificity, etc., before and after mutation, wherein a change indicates an alteration. Preferably, the screens are performed in a high-throughput manner, including multiple samples being screened simultaneously, including, but not limited to assays utilizing chips, phage display, and multiple substrates and/or indicators.

As used herein, in some embodiments, a screening process encompasses one or more selection steps in which variants of interest are enriched from a population of variants. Examples of these embodiments include the selection of variants that confer a growth advantage to the host organism, as well as phage display or any other method of display, where variants can be captured from a population of variants based on their binding or catalytic properties. In some embodiments, a library of variants is exposed to stress (e.g., heat, denaturation, etc.) and subsequently variants that are still intact are identified in a screen or enriched by selection. It is intended that the term encompass any suitable means for selection. Indeed, it is not intended that the present invention be limited to any particular method of screening.

The terms "modified nucleic acid sequence" and "modified gene" are used interchangeably herein to refer to a nucleic acid sequence that includes a deletion, insertion or interruption of naturally occurring (i.e., wild-type) nucleic acid sequence. In some embodiments, the expression product of the modified nucleic acid sequence is a truncated protein (e.g., if the modification is a deletion or interruption of the sequence). In some embodiments, the truncated protein retains biological activity. In alternative embodiments, the expression product of the modified nucleic acid sequence is an elongated protein (e.g., modifications comprising an insertion into the nucleic acid sequence). In some embodiments, a nucleotide insertion in the nucleic acid sequence leads to a truncated protein (e.g., when the insertion results in the formation of a stop codon). Thus, an insertion may result in either a truncated protein or an elongated protein as an expression product.

A "mutant" nucleic acid sequence typically refers to a nucleic acid sequence that has an alteration in at least one codon occurring in a host cell's wild-type sequence such that the expression product of the mutant nucleic acid sequence is a protein with an altered amino acid sequence relative to the wild-type protein. The expression product may have an altered functional capacity (e.g., enhanced enzymatic activity).

As used herein, the phrase "alteration in substrate specificity" refers to changes in the substrate specificity of an enzyme. In some embodiments, a change in substrate specificity is defined as a change in $k_{cat}$ and/or $K_m$ for a particular substrate, resulting from mutations of the enzyme or alteration of reaction conditions. The substrate specificity of an enzyme is determined by comparing the catalytic efficiencies it exhibits with different substrates. These determinations find particular use in assessing the efficiency of mutant enzymes, as it is generally desired to produce variant enzymes that exhibit greater ratios of $k_{cat}/K_m$ for substrates of interest. However, it is not intended that the present invention be limited to any particular substrate composition or substrate specificity.

As used herein, "surface property" is used in reference to electrostatic charge, as well as properties such as the hydrophobicity and hydrophilicity exhibited by the surface of a protein.

As used herein, the term "net charge" is defined as the sum of all charges present in a molecule. "Net charge changes" are made to a parent protein molecule to provide a variant that has a net charge that differs from that of the parent molecule (i.e., the variant has a net charge that is not the same as that of the parent molecule). For example, substitution of a neutral amino acid with a negatively charged amino acid or a positively charged amino acid with a neutral amino acid results in net charge of −1 with respect to the parent molecule. Substitution of a positively charged amino acid with a negatively charged amino acid results in a net charge of −2 with respect to the parent. Substitution of a neutral amino acid with a positively charged amino acid or a negatively charged amino acid with a neutral amino acid results in net charge of +1 with respect to the parent. Substitution of a negatively charged amino acid with a positively charged amino acid results in a net charge of +2 with respect to the parent. The net charge of a parent protein can also be altered by deletion and/or insertion of charged amino acids The terms "thermally stable" and "thermostable" and "thermostability" refer to proteases that retain a specified amount of enzymatic activity after exposure to identified temperatures over a given period of time under conditions prevailing during the proteolytic, hydrolyzing, cleaning or other process of the invention, while being exposed to altered temperatures. "Altered temperatures" encompass increased or decreased temperatures. In some embodiments, the proteases retain at least about 50%, about 60%, about 70%, about 75%, about 80%, about 85%, about 90%, about 92%, about 95%, about 96%, about 97%, about 98%, or about 99% proteolytic activity after exposure to altered temperatures over a given time period, for example, at least about 60 minutes, about 120 minutes, about 180 minutes, about 240 minutes, about 300 minutes, etc.

The term "enhanced stability" in the context of an oxidation, chelator, thermal and/or pH stable protease refers to a higher retained proteolytic activity over time as compared to other proteases (e.g., subtilisin proteases) and/or wild-type enzymes.

The term "diminished stability" in the context of an oxidation, chelator, thermal and/or pH stable protease refers to a lower retained proteolytic activity over time as compared to other proteases (e.g., subtilisin proteases) and/or wild-type enzymes.

The term "cleaning activity" refers to a cleaning performance achieved by a variant protease or reference protease under conditions prevailing during the proteolytic, hydrolyzing, cleaning, or other process of the invention. In some embodiments, cleaning performance of a variant protease or reference protease may be determined by using various assays for cleaning one or more various enzyme sensitive stains on an item or surface (e.g., a stain resulting from food, grass, blood, ink, milk, oil, and/or egg protein). Cleaning performance of a variant or reference protease can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO 99/34011 and U.S. Pat. No. 6,605,458, both of which are herein incorporated by reference, as well as those cleaning assays and methods included in the Examples provided below.

The term "cleaning effective amount" of a variant protease or reference protease refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "cleaning adjunct material" refers to any liquid, solid, or gaseous material included in cleaning composition other than a variant protease of the invention. In some embodiments, the cleaning compositions of the present invention include one of more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

The term "enhanced performance" in the context of cleaning activity refers to an increased or greater cleaning activity by an enzyme on certain enzyme sensitive stains such as egg, milk, grass, ink, oil, and/or blood, as determined by usual evaluation after a standard wash cycle and/or multiple wash cycles.

The term "diminished performance" in the context of cleaning activity refers to a decreased or lesser cleaning activity by an enzyme on certain enzyme sensitive stains such as egg, milk, grass or blood, as determined by usual evaluation after a standard wash cycle.

The term "comparative performance" in the context of cleaning activity of a variant protease of the invention refers to at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.5% of the cleaning activity of a comparative or reference protease (e.g., commercially available proteases), including, but not limited to for example, OPTIMASE™ protease (Genencor), PURAFECT™ protease products (Genencor), SAVINASE™ protease (Novozymes), BPN'-variants (See e.g., U.S. Pat. No. Re 34,606), RELEASE™, DURAZYME™, EVERLASE™, KANNASE™ protease (Novozymes), MAXACAL™, MAXAPEM™, PROPERASE™ proteases (Genencor; See also, U.S. Pat. No. Re 34,606, and U.S. Pat. Nos. 5,700,676; 5,955,340; 6,312,936; and 6,482,628), and *B. lentus* variant protease products (e.g., those described in WO 92/21760, WO 95/23221 and/or WO 97/07770). Cleaning performance can be determined by comparing the variant proteases of the present invention with reference subtilisin proteases in various cleaning assays concerning enzyme sensitive stains such as grass, blood, ink, oil, and/or milk as determined by usual spectrophotometric or analytical methodologies after standard wash cycle conditions.

As used herein, the term "consumer product" means fabric and home care product. As used herein, the term "fabric and home care product" or "fabric and household care product" includes products generally intended to be used or consumed in the form in which they are sold and that are for treating fabrics, hard surfaces and any other surfaces, and cleaning systems all for the care and cleaning of inanimate surfaces, as well as fabric conditioner products and other products designed specifically for the care and maintenance of fabrics, and air care products, including: air care including air fresheners and scent delivery systems, car care, pet care, livestock care, personal care, jewelry care, dishwashing, fabric conditioning (including softening and/or freshening), laundry detergency, laundry and rinse additive and/or care, pre-treatment cleaning compositions, hard surface cleaning and/or treatment including floor and toilet bowl cleaners, glass cleaners and/or treatments, tile cleaners and/or treatments, ceramic cleaners and/or treatments, and other cleaning for consumer or institutional use. In some embodiments, the fabric and home care products are suitable for use on wounds and/or skin. "Fabric and home care product" includes consumer and institutional products.

As used herein, the term "non-fabric and home care products" refers to compositions that are added to other compositions to produce an end product that may be a fabric and home care product.

As used herein, the term "institutional cleaning composition" refers to products suitable for use in institutions including but not limited to schools, hospitals, factories, stores, corporations, buildings, restaurants, office complexes and buildings, processing and/or manufacturing plants, veterinary hospitals, factory farms, factory ranches, etc.

As used herein, the term "cleaning and/or treatment composition" is a subset of fabric and home care products that includes, unless otherwise indicated, compositions suitable for cleaning and/or treating items. Such products include, but are not limited to, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use: car or carpet shampoos, bathroom cleaners including toilet bowl cleaners; as well as cleaning auxiliaries such as bleach additives and "stain-stick" or pre-treat types, substrate-laden products such as dryer added sheets.

Indeed, as used herein, "cleaning composition" or "cleaning formulation" of the invention refers to any composition of the invention useful for removing or eliminating a compound (e.g., undesired compound) from an object, item or surface to be cleaned, including, but not limited to for example, a fabric, fabric item, dishware item, tableware item, glassware item, contact lens, other solid substrate, hair (shampoo) (including human or animal hair), skin (soap or and cream), teeth (mouthwashes, toothpastes), surface of an item or object (e.g., hard surfaces, such as the hard surface of a table, table top, wall, furniture item, floor, ceiling, non-dishware item, non-tableware item, etc.), filters, membranes (e.g., filtration membranes, including but not limited to ultrafiltration membranes), etc. The term encompasses any material and/or added compound selected for the particular type of cleaning composition desired and the form of the product (e.g., liquid, gel, granule, spray, or other composition), as long as the composition is compatible with the protease and other enzyme(s) used in the composition. The specific selection of cleaning composition materials are readily made by considering the surface, object, item, or fabric to be cleaned, and the desired form of the composition for the cleaning conditions during use.

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwash compositions (e.g., "hand" or "manual" dishwashing detergents) and automatic dishwashing compositions (e.g., "automatic dishwashing detergents").

Cleaning composition or cleaning formulations, as used herein, include, unless otherwise indicated, granular or powder-form all-purpose or heavy-duty washing agents, especially cleaning detergents; liquid, granular, gel, solid, tablet, or paste-form all-purpose washing agents, especially the so-called heavy-duty liquid (HDL) detergent or heavy-duty powder detergent (HDD) types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to for example, hand or manual or automatic dishwashing detergent compositions, oral cleaning compositions, denture cleaning compositions, and personal cleansing compositions.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, car or carpet shampoos, bathroom cleaners including toilet bowl cleaners; fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets. All of such products which are applicable may be in standard, concentrated or even highly concentrated form even to the extent that such products may in certain aspect be non-aqueous.

As used herein, the term "detergent composition" or "detergent formulation" is used in reference to a composition intended for use in a wash medium for the cleaning of soiled or dirty objects, including particular fabric and/or non-fabric objects or items. Such compositions of the present invention are not limited to any particular detergent composition or formulation. Indeed, in some embodiments, the detergents of the invention comprise at least one variant protease of the invention and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the invention, such as, but not limited to, cleaning compositions or detergent compositions, do not contain any phosphate (e.g., phosphate salt or phosphate builder).

As used herein, the term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc.

As used herein, "wash performance" of a protease (e.g., a variant protease of the invention) refers to the contribution of a variant protease to washing that provides additional cleaning performance to the detergent as compared to the detergent without the addition of the variant protease to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

The term "improved wash performance" is used to indicate that a better end result is obtained in stain removal under relevant washing conditions, or that less variant protease, on weight basis, is needed to obtain the same end result relative to the corresponding wild-type or starting parent protease.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

The position of an amino acid residue in a given amino acid sequence is typically numbered herein using the numbering of the position of the corresponding amino acid residue of the *B. amyloliquefaciens* subtilisin BPN' amino acid sequence shown in SEQ ID NO:1. The *B. amyloliquefaciens* subtilisin BPN' amino acid sequence of SEQ ID NO:1, thus serves as a reference sequence. A given amino acid sequence, such as a variant protease amino acid sequence described herein, can be aligned with the BPN' sequence (SEQ ID NO:1) using an alignment algorithm as described herein, and an amino acid residue in the given amino acid sequence that aligns (preferably optimally aligns) with an amino acid residue in the BPN' sequence can be conveniently numbered by reference to the corresponding amino acid residue in the subtilisin BPN' sequence. Alternatively, if amino acid residue positions of the subtilisin variant protease sequences are numbered using the actual numbering of the amino acid residue positions in the GG36 amino acid sequence (SEQ ID NO:2), and not by reference to corresponding amino acid positions in the BPN' sequence upon alignment, the subtilisin variant protease can be described as a variant protease of the GG36 protease shown in SEQ ID NO:2

Generally, the nomenclature used herein and many of the laboratory procedures in cell culture, molecular genetics, molecular biology, nucleic acid chemistry, and protein chemistry described below are well known and commonly employed by those of ordinary skill in the art. Methods for production and manipulation of recombinant nucleic acid methods, nucleic acid synthesis, cell culture methods, and transgene incorporation (e.g., transfection, electroporation) are known to those skilled in the art and are described in numerous standard texts. Oligonucleotide synthesis and purification steps are typically performed according to specifications. Techniques and procedures are generally performed according to conventional methods well known in the art and various general references that are provided throughout this document. Procedures therein are believed to be well known to those of ordinary skill in the art and are provided for the convenience of the reader.

Polypeptides of the Invention

The present invention provides novel polypeptides, which may be collectively referred to as "polypeptides of the invention." Polypeptides of the invention include isolated, recombinant, substantially pure, or non-naturally occurring variant protease polypeptides, including for example, variant subtilisin polypeptides, having enzymatic activity (e.g., proteolytic activity). In some embodiments, polypeptides of the invention are useful in cleaning applications and may be incorporated into cleaning compositions that are useful in methods of cleaning an item or a surface (e.g., of surface of an item) in need of cleaning.

In some embodiments, a variant protease of the invention comprises a "variant subtilisin." In some embodiments, the invention provides a "*Bacillus* sp. variant protease." In some embodiments, the invention provides a "*Bacillus* sp. variant subtilisin."

In some embodiments, the invention includes an isolated, recombinant, substantially pure, or non-naturally occurring variant protease having proteolytic activity, which polypeptide comprises a polypeptide sequence having at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.5%, or 100% sequence identity to the amino acid sequences encoding the variant proteases provided herein.

As noted above, the variant protease polypeptides of the invention have enzymatic activities (e.g., proteolytic activities) and thus are useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more variant protease polypeptides of the invention are described infra. The enzymatic activity (e.g., protease activity) of a variant protease polypeptide of the invention can be determined readily using procedures well known to those of ordinary skill in the art. The Examples presented infra describe methods for evaluating the enzymatic activity, cleaning performance, and/or washing performance. The performance of variant proteases of the invention in removing stains (e.g., a proteinaceous stain), cleaning hard surfaces, or cleaning laundry, dishware or tableware item(s) can be readily determined using procedures well known in the art and/or by using procedures set forth in the Examples.

A polypeptide of the invention can be subject to various changes, such as one or more amino acid insertions, deletions, and/or substitutions, either conservative or non-conservative, including where such changes do not substantially alter the enzymatic activity of the polypeptide. Similarly, a nucleic acid of the invention can also be subject to various changes, such as one or more substitutions of one or more nucleic acids in one or more codons such that a particular codon encodes the same or a different amino acid, resulting in either a silent variation (e.g., mutation in a nucleotide sequence results in a silent mutation in the amino acid sequence, for example when the encoded amino acid is not altered by the nucleic acid mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded variant protease compared to the variant protease encoded by the original nucleic acid sequence. A nucleic acid of the invention can also be modified to include one or more codons that provide for optimum expression in an expression system (e.g., bacterial expression system), while, if desired, said one or more codons still encode the same amino acid(s).

In some embodiments, the present invention provides a genus of polypeptides comprising variant protease polypeptides having the desired enzymatic activity (e.g., protease activity or cleaning performance activity) which comprise sequences having the amino acid substitutions described herein and also which comprise one or more additional amino acid substitutions, such as conservative and non-conservative substitutions, wherein the polypeptide exhibits, maintains, or approximately maintains the desired enzymatic activity (e.g., protease activity or subtilisin activity, as reflected in the cleaning activity or performance of the variant protease). Amino acid substitutions in accordance with the invention may include, but are not limited to, one or more non-conservative substitutions and/or one or more conservative amino acid substitutions. A conservative amino acid residue substitution typically involves exchanging a member within one functional class of amino acid residues for a residue that belongs to the same functional class (identical amino acid residues are considered functionally homologous or conserved in calculating percent functional homology). A conservative amino acid substitution typically involves the substitution of an amino acid in an amino acid sequence with a functionally similar amino acid. For example, alanine, glycine, senile, and threonine are functionally similar and thus may serve as conservative amino acid substitutions for one another. Aspartic acid and glutamic acid may serve as conservative substitutions for one another. Asparagine and glutamine may serve as conservative substitutions for one another. Arginine, lysine, and histidine may serve as conservative substitutions for one another. Isoleucine, leucine, methionine, and valine may serve as conservative substitutions for one another. Phenylalanine, tyrosine, and tryptophan may serve as conservative substitutions for one another.

Other conservative amino acid substitution groups can be envisioned. For example, amino acids can be grouped by similar function or chemical structure or composition (e.g., acidic, basic, aliphatic, aromatic, sulfur-containing). For instance, an aliphatic grouping may comprise: Glycine (G), Alanine (A), Valine (V), Leucine (L), Isoleucine (I). Other groups containing amino acids that are considered conservative substitutions for one another include: aromatic: Phenylalanine (F), Tyrosine (Y), Tryptophan (W); sulfur-containing: Methionine (M), Cysteine (C); Basic: Arginine (R), Lysine (K), Histidine (H); Acidic: Aspartic acid (D), Glutamic acid (E); non-polar uncharged residues, Cysteine (C), Methionine (M), and Proline (P); hydrophilic uncharged residues: Serine (S), Threonine (T), Asparagine (N), and Glutamine (Q). Additional groupings of amino acids are well-known to those of skill in the art and described in various standard textbooks. Listing of a polypeptide sequence herein, in conjunction with the above substitution groups, provides an express listing of all conservatively substituted polypeptide sequences.

More conservative substitutions exist within the amino acid residue classes described above, which also or alternatively can be suitable. Conservation groups for substitutions that are more conservative include: valine-leucine-isoleucine, phenylalanine-tyrosine, lysine-arginine, alanine-valine, and asparagine-glutamine. Thus, for example, in some embodiments, the invention provides an isolated or recombinant variant protease polypeptide (e.g., variant subtilisin) having proteolytic activity, said variant protease polypeptide comprising an amino acid sequence having at least about 90%, about 95%, about 96%, about 97%, about 98%, about 99%, or about 99.5% sequence identity to the amino acid sequence of SEQ ID NO:2. A conservative substitution of one amino acid for another in a variant protease of the invention is not expected to alter significantly the enzymatic activity or cleaning performance activity of the variant protease. Enzymatic activity or cleaning performance activity of the resultant protease can be readily determined using the standard assays and the assays described herein.

Conservatively substituted variations of a polypeptide sequence of the invention (e.g., variant proteases of the invention) include substitutions of a small percentage, sometimes less than about 25%, about 20%, about 15%, about 14%, about 13%, about 12%, about 11%, about 10%, about 9%, about 8%, about 7%, or about 6% of the amino acids of the polypeptide sequence, or less than about 5%, about 4%, about 3%, about 2%, or about 1%, of the amino acids of the polypeptide sequence, with a conservatively selected amino acid of the same conservative substitution group.

As described elsewhere herein in greater detail and in the Examples provided herein, polypeptides of the invention may have cleaning abilities that may be compared to known proteases, including known subtilisins. Exemplary known subtilisin proteases include, but are not limited to, for example, *B. lentus* subtilisin GG36, *B. amyloliquefaciens* subtilisin BPN', *B. amyloliquefaciens* subtilisin BPN'-

Y217L, and *B. clausii* PB92. The amino acid sequence of the mature *B. lentus* subtilisin GG36 protein is:

(SEQ ID NO: 2)
AQSVPWGISRVQAPAAHNRGLTGSGVKVAVLDTGISTHPDLNIRGGASFV

PGEPSTQDGNGHGTHVAGTIAALNNSIGVLGVAPSAELYAVKVLGASGSG

SVSSIAQGLEWAGNNGMHVANLSLGSPSPSATLEQAVNSATSRGVLVVAA

SGNSGAGSISYPARYANAMAVGATDQNNNRASFSQYGAGLDIVAPGVNVQ

STYPGSTYASLNGTSMATPHVAGAAALVKQKNPSWSNVQIRNHLKNTATS

LGSTNLYGSGLVNAEAATR

The amino acid sequence of mature *B. amyloliquefaciens* subtilisin BPN' protein is:

(SEQ ID NO: 1)
AQSVPYGVSQIKAPALHSQGYTGSNVKVAVIDSGIDSSHPDLKVAGGASM

VPSETNPFQDNNSHGTHVAGTVAALNNSIGVLGVAPSASLYAVKVLGADG

SGQYSWIINGIEWAIANNMDVINMSLGGPSGSAALKAAVDKAVASGVVVV

AAAGNEGTSGSSSTVGYPGKYPSVIAVGAVDSSNQRASFSSVGPELDVMA

PGVSIQSTLPGNKYGAYNGTSMASPHVAGAAALILSKHPNWTNTQVRSSL

ENTTTKLGDSFYYGKGLINVQAAAQ

The present invention provides polypeptides comprising subtilisin variants of *Bacillus* subtilisin, wherein the subtilisin variant is a mature form having proteolytic activity and comprises an amino acid sequence comprising a combination of amino acid substitutions selected from: X1R, X2W, X2M, X2R, X2A, X2S, X3R, X4R, X4C, X4S, X8A, X9F, X9W, X9A, X10S, X10M, X10H, X10A, X12R, X12F, X14K, X14F, X14Q, X15R, X15F, X16S, X17R, X17M, X17F, X18R, X18K, X20F, X20R, X20K, X22Y, X22A, X22R, X22V, X22Q, X22W, X22L, X23F, X23S, X23A, X24W, X24R, X24H, X24F, X24Q, X24L, X25V, X25F, X25R, X26F, X27V, X27F, X27L, X27R, X28N, X28E, X28A, X29T, X30E, X31F, X33D, X33G, X33S, X34P, X35M, X36F, X36R, X36F, X38L, X38F, X38R, X40L, X40W, X40N, X40R, X40T, X40H, X42I, X43D, X43I, X43R, X43M, X43F, X43W, X43S, X43A, X45T, X46R, X48R, X50C, X51H, X51W, X51F, X52F, X52E, X52N, X55Y, X57R, X59R, X59A, X59F, X60A, X60Q, X60P, X62E, X62Q, X63I, X63V, X63T, X63P, X63D, X63M, X63H, X63Q, X63E, X63A, X63S, X64F, X64T, X68C, X68A, X69N, X69P, X69W, X69T, X71G, X72C, X74C, X75F, X75A, X75R, X75E, X76D, X78I, X78R, X78N, X79W, X79Q, X81R, X82V, X82T, X82F, X82M, X82R, X85M, X86L, X86I, X86W, X89P, X89T, X89V, X89G, X89W, X89H, X89F, X89L, X89I, X91N, X91F, X92F, X94N, X99G, X99F, X99M, X99T, X99P, X100I, X100S, X100N, X100Q, X101N, X101A, X101G, X101P, X101F, X101E, X101T, X101D, X102H, X102N, X102E, X102T, X102A, X103G, X103D, X103N, X104D, X104E, X104I, X104L, X105Q, X105E, X105T, X106F, X106V, X106G, X106E, X106T, X106D, X106A, X107F, X107M, X108G, X108I, X109M, X111V, X111I, X112V, X112L, X112Q, X114G, X115K, X115R, X116A, X116K, X116L, X117F, X118I, X118R, X119C, X120F, X120A, X120R, X121E, X121F, X123G, X123E, X124S, X128F, X128H, X128I, X128L, X128Q, X128N, X128M, X128D, X129E, X132E, X132A, X138G, X144R, X147L, X148I, X158E, X158E, X159E, X159C, X160D, X166D, X166E, X167W, X175V, X177C, X181A, X182R, X183F, X183I, X183D, X183R, X183M, X185E, X185I, X185V, X186H, X186K, X188R, X188E, X188D, X192H, X192W, X194V, X194F, X194E, X197F, X198L, X198F, X203E, X203C, X208S, X209N, X209F, X209E, X209S, X209H, X209G, X209T, X209L, X210R, X210V, X210L, X211R, X211Q, X212I, X212M, X212F, X213A, X214F, X215F, X215N, X215D, X215H, X215E, X216F, X216A, X217N, X217E, X217D, X218P, X218D, X218E, X224A, X224G, X227I, X230E, X231I, X231C, X233C, X234F, X235F, X236F, X236N, X238L, X238K, X238R, X239K, X239S, X239T, X239G, X239H, X239R, X239N, X239F, X240R, X241R, X242L, X242R, X243R, X243F, X244R, X246S, X248I, X248V, X248R, X249R, X249T, X250I, X251S, X251R, X252I, X252F, X252H, X252R, X253F, X253I, X253R, X254C, X256N, X258R, X260V, X260I, X262H, X262D, X263F, X265F, X267N, X267V, X267M, X269I, X269R, X270C, X271F, X271V, X271I, X271P, X271H, X271M, X271T, X271L, X271A, X272F, X272R, X272F, X273I, X273F, and X274G, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising subtilisin variants of a *Bacillus* subtilisin, wherein the subtilisin variant is a mature form having proteolytic activity and comprises an amino acid sequence comprising a combination of amino acid substitutions selected from: X16S, X18R, X20R, X22A, X24R, X43R/D, X45T, X76D, X101A, X103G, X104L, X111V, X128N, X148I, X230E, X242R, and X249R, wherein the amino acid positions of the subtilisin variant are numbered by correspondence with the amino acid sequence of *B. amyloliquefaciens* subtilisin BPN' set forth as SEQ ID NO:1.

The present invention also provides polypeptides comprising subtilisin variants of a *Bacillus* subtilisin, wherein the subtilisin variant is a mature form having proteolytic activity and comprises an amino acid sequence comprising a combination of amino acid substitutions selected from: X1R, X230E, X271L, X115R, X20R, X249R, X235F, X27V/F/L, X75E, X82R, X18R, X269R, X43D, X43R, X76D, X45T, X212F, X242R, X24R, X78R, X9A, X22R, X121E, X244R, X28E, X30E, X4R, and X241R, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising subtilisin variants of a *Bacillus* subtilisin, wherein the subtilisin variant is a mature form having proteolytic activity and comprises an amino acid sequence comprising a combination of amino acid substitutions selected from: X062E-X158E, X103G-X158E, X128N-X158E, X016S-X158E, X104L-X158E, X089P-X158E, X111V-X158E, X022A-X158E, X101A-X158E, X148I-X158E, X129E-X158E, X022A-X089P, X016S-X089P, X062E-X089P, X062E-X271F, X158E-X271F, X186H-X271F, X129E-X271F, X111V-X271F, X209E-X271F, X016S-X271F, X188D-X271F, X022A-X271F, X159E-X271F, X104L-X271F, X101A-X271F, X089P-X271F, X128N-X271F, X103G-X271F, X148I-X271F, X249R-X271F, X062E-X159E, X016S-X159E, X128N-X159E, X148I-X159E, X111V-X159E, X089P-X159E, X022A-X159E, X129E-X159E, X103G-X159E, X104L-X159E, X158E-X159E, X101A-X159E, X158E-X249R, X111V-X249R, X129E-X249R, X062E-X249R, X016S-X249R, X186H-X249R, X148I-X249R, X159E-X249R, X101A-X249R, X188D-X249R, X104L-X249R, X209E-X249R, X022A-X249R, X128N-X249R, X103G-X249R, X089P-X249R, X022A-X111V, X101A-X111V, X016S-X111V, X104L-X111V, X062E-X111V, X103G-X111V, X089P-X111V, X016S-X148I, X062E-X148I, X022A-X148I, X129E-X148I, X104L-X148I, X103G-X148I, X128N-X148I, X101A-X148I, X089P-X148I, X111V-X148I, X016S-X062E, X022A-X062E, X062E-X129E, X022A-X129E, X128N-X129E, X016S-X129E, X101A-X129E, X104L-X129E, X089P-X129E, X103G-X129E, X111V-X129E, X062E-X186H, X128N-X186H, X101A-X186H, X022A-X186H, X016S-X186H, X158E-X186H, X089P-X186H, X129E-X186H, X159E-X186H, X103G-X186H, X104L-X186H, X111V-X186H, X148I-X186H, X062E-X101A, X022A-X101A, X016S-X101A, X089P-X101A, X062E-X103G, X022A-X103G, X016S-X103G, X101A-X103G, X089P-X103G, X062E-X128N, X016S-X128N, X022A-X128N, X101A-X128N, X104L-X128N, X089P-X128N, X103G-X128N, X111V-X128N, X111V-X188D, X062E-X188D, X016S-X188D, X148I-X188D, X022A-X188D, X128N-X188D, X101A-X188D, X104L-X188D, X089P-X188D, X129E-X188D, X159E-X188D, X186H-X188D, X103G-X188D, X158E-X188D, X016S-X022A, X016S-X104L, X022A-X104L, X101A-X104L, X062E-X104L, X103G-X104L, X089P-X104L, X159E-X209E, X111V-X209E, X101A-X209E, X016S-X209E, X128N-X209E, X148I-X209E, X129E-X209E, X062E-X209E, X022A-X209E, X103G-X209E, X158E-X209E, X188D-X209E, X104L-X209E, X089P-X209E, and X186H-X209E, wherein the amino acid positions of the subtilisin variant are numbered by correspondence with the amino acid sequence of *B. amyloliquefaciens* subtilisin BPN' set forth as SEQ ID NO:1.

The present invention also provides polypeptides comprising subtilisin variants of a *Bacillus* subtilisin, wherein the subtilisin variant is a mature form having proteolytic activity and comprises an amino acid sequence comprising a combination of amino acid substitutions selected from: X018R-X241R, X020R-X241R, X024R-X241R, X009A-X241R, X020R-X241R, X004R-X241R, X043R-X241R, X078R-X241R, X022R-X241R, X115R-X241R, X001R-X241R, X212F-X241R, X082R-X241R, X018R-X244R, X024R-X244R, X078R-X244R, X020R-X244R, X212F-X244R, X009A-X244R, X082R-X244R, X001R-X244R, X043R-X244R, X022R-X244R, X004R-X244R, X115R-X244R, X241R-X244R, X242R-X244R, X001R-X004R, X009A-X022R, X018R-X022R, X020R-X022R, X004R-X022R, X001R-X022R, X024R-X242R, X018R-X242R, X004R-X242R, X020R-X242R, X212F-X242R, X082R-X242R, X078R-X242R, X001R-X242R, X009A-X242R, X022R-X242R, X115R-X242R, X043R-X242R, X241R-X242R, X018R-X212F, X022R-X212F, X004R-X212F, X024R-X212F, X001R-X212F, X115R-X212F, X020R-X212F, X009A-X212F, X043R-X212F, X078R-X212F, X082R-X212F, X009A-X078R, X020R-X078R, X024R-X078R, X022R-X078R, X018R-X078R, X004R-X078R, X001R-X078R, X043R-X078R, X022R-X024R, X020R-X024R, X018R-X024R, X001R-X024R, X004R-X024R, X009A-X024R, X004R-X009A, X001R-X009A, X242R-X269R, X024R-X269R, X020R-X269R, X022R-X269R, X249R-X269R, X212F-X269R, X043R-X269R, X244R-X269R, X001R-X269R, X018R-X269R, X078R-X269R, X009A-X269R, X115R-X269R, X241R-X269R, X004R-X269R, X082R-X269R, X018R-X043R, X020R-X043R, X004R-X043R, X022R-X043R, X009A-X043R, X001R-X043R, X024R-X043R, X009A-X018R, X004R-X018R, X001R-X018R, X024R-X082R, X009A-X082R, X018R-X082R, X001R-X082R, X078R-X082R, X020R-X082R, X022R-X082R, X004R-X082R, X043R-X082R, X043R-X249R, X020R-X249R, X004R-X249R, X018R-X249R, X009A-X249R, X212F-X249R, X022R-X249R, X024R-X249R, X115R-X249R, X001R-X249R, X082R-X249R, X242R-X249R, X241R-X249R, X244R-X249R, X078R-X249R, X018R-X115R, X020R-X115R, X022R-X115R, X078R-X115R, X009A-X115R, X004R-X115R, X001R-X115R, X082R-X115R, X043R-X115R, X024R-X115R, X009A-X020R, X018R-X020R, X004R-X020R, X001R-X020R, X009A-X271L, X020R-X271L, X024R-X271L, X244R-X271L, X241R-X271L, X043R-X271L, X022R-X271L, X249R-X271L, X212F-X271L, X115R-X271L, X242R-X271L, X078R-X271L, X004R-X271L, X269R-X271L, X001R-X271L, X018R-X271L, and X082R-X271L, wherein the amino acid positions of the subtilisin variant are numbered by correspondence with the amino acid sequence of *B. amyloliquefaciens* subtilisin BPN' set forth as SEQ ID NO:1.

The present invention further provides isolated subtilisin variants, wherein the subtilisin variants are mature forms having proteolytic activity and comprise amino acid sequences comprising a combination of amino acid substitutions selected from: X020R-X-43R, X020K-X062E, X024F-X116L, X020K-X024F, X024R-X174T, X024R-X118R, X024R-X235F, X024R-X086R, X024R-X086W, X078R-X118R, X033S-X118R, X033S-X235F, X209A-X241R, X020R-X076D, X018R-X245R, X024R-X045T, X232V-X245R, X118R-X172V, X118R-X194T, X008T-X024R, X235F-X243F, X018R-X103A, X018R-X104I, X086W-X118R, X086W-X243F, X086W-X209A, X024C-X033S, X024R-X232V, X024R-X243F, X024R-X239Q, X024R-X101G, X024R-X141G, X024R-X033S, X024R-X274I, X024R-X209A, X078R-X086W, X101G-X232V, X033S-X148F, X033S-X086W, X033S-X201S, X033S-X078R, X033S-X241R, X033S-X209A, X230E-X249R, X232V-X249R, X118R-X235F, X076D-X245R, X086W-X235F, X024R-X247H, X024R-X104A, X078R-X235F, X101G-X249R, X103A-X232V, X033S-X048T, X033S-X239T, X033S-X253A, X143A-X209A, X209A-X235F, X018R-X045T, X209A-X243F, X024R-X272P, X024R-X269C, X101G-X104I, X104I-X232V, X076D-X249R, and X024R-X076D wherein the amino acid positions of the subtilisin variant are numbered by correspondence with the amino acid sequence of *B. amyloliquefaciens* subtilisin BPN' set forth as SEQ ID NO:1.

The present invention further provides isolated subtilisin variants, wherein the subtilisin variants are mature forms having proteolytic activity and comprise amino acid sequences comprising a combination of amino acid substitutions selected from: X020R-X076D, X024R-X045T, X230E-X249R, X018R-X045T, X018R-X245R, X101G-X232V, X024R-X232V, X232V-X245R, X024R-X101G, X018R-X104I, X018R-X103A, X101G-X249R, X232V-X249R, X103A-X232V, X076D-X245R, X101G-X104I, X104I-X232V, X076D-X249R, X024R-X076D, X024F-X116L, X020K-X024F, X020K-X062E, X033S-X118R, X024R-X086W, X024R-X118R, X024R-X086R, X209A-X241R, X024R-X241R, X024R-X235F, X118R-X209A, X078R-X118R, X033S-X235F, X024R-X174T, X086W-X209A, X008T-X024R, X086W-X118R, X033S-X241R, X024R-X243F, X024R-X209A, X033S-X086W, X024R-X033S, X086W-X243F, X033S-X201S, X024R-X239Q, X078R-X086W, X235F-X243F, X118R-X172V, X033S-X148F, X033S-X078R, X033S-X243F, X024C-X033S, X118R-X194T, X033S-X209A, X024R-X141G, X024R-X274I, X086W-X235F, X015T-X033S, X209A-X235F, X024R-X247H, X078R-X235F, X024R-X104A, X033S-X048T, X118R-X235F, X033S-X253A, X143A-X209A, X033S-X239T, X209A-X243F, X024R-X272P, and X024R-X269C, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X004R-X009A-X020R-X242R, X020R-X043R-X241R, X020R-X242R-X269R, X004R-X009A-X020R-X043R, X004R-X020R-X249R, X018R-X024R-X244R, X009A-X022R-X212F-X241R, X020R-X043R-X269R, X018R-X024R-X242R, X004R-X009A-X043R-X241R, X020R-X043R-X244R, X020R-X022R-X242R, X004R-X020R-X043R, X004R-X009A-X020R-X043R-X242R, X020R-X043R-X242R, X020R-X043R-X242R-X249R, X020R-X212F-X249R, X004R-X009A-X241R, X001R-X009A-X043R, X020R-X043R-X249R, X009A-X020R-X043R-X241R, X020R-X022R-X043R, X020R-X249R-X269R, X020R-X022R-X241R, X004R-X009A-X024R-X043R-X241R, X009A-X043R-X078R, X004R-X020R-X024R-X244R, X020R-X022R-X078R-X242R, X020R-X024R-X242R-X249R, X004R-X009A-X078R-X241R, X009A-X043R-X078R-X242R, X004R-X020R-X024R, X009A-X043R-X212F, X020R-X043R-X212F, X024R-X078R-X212F, X009A-X020R-X024R-X043R, X009A-X022R-X043R-X078R, X020R-X022R-X212F-X241R, X020R-X043R-X212F-X241R, X009A-X043R-X241R, X020R-X043R-X271L, X020R-X022R-X078R-X241R, X020R-X024R-X043R-X242R, X020R-X022R-X043R-X241R, X009A-X020R-X043R-X212F, X004R-X009A-X020R-X024R-X242R, X020R-X043R-X249R-X271L, X020R-X022R-X024R-X242R, X009A-X022R-X078R-X212F, X020R-X043R-X242R-X271L, X009A-X022R-X078R-X212F-X241R, X004R-X020R-X024R-X249R, X020R-X022R-X271L, X020R-X022R-X043R-X212F, X004R-X020R-X024R-X043R-X242R, X004R-X020R-X024R-X043R, X004R-X009A-X022R-X078R-X212F, X020R-X022R-X078R-X212F-X241R, and X020R-X022R-X269R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X018R-X020R-X043D-X045T-X230E, X018R-X043R-X045T-X242R-X249R, X024R-X043D-X249R, X018R-X020R-X045T, X020R-X024R-X076D-X249R, X024R-X043R-X230E-X242R, X018R-X024R-X043D-X230E, X020R-X076D, X018R-X024R-X043D-X076D-X249R, X024R-X043R-X076D-X249R, X018R-X024R-X045T-X242R, X020R-X043D-X076D-X230E-X249R, X020R-X043R-X045T-X242R, X018R-X024R-X076D-X249R, X018R-X020R-X024R-X043D-X045T-X233I-X242R, X024R-X043R-X230E, X018R-X020R-X043D, X043R-X242R-X249R, X020R-X043R-X045T-X230E, X043R-X076D-X242R-X249R, X020R-X024R-X045T-X230E-X242R, X024R-X045T-X076D-X230E-X242R-X249R, X024R-X045T, X024R-X043R-X045T-X076D-X230E-X249R, X018R-X024R-X043D-X045T-X249R, X018R-X043R-X045T-X249R, X024R-X043R-X242R, X018R-X020R-X043R-X076D-X249R, X020R-X024R-X043D-X249R, X020R-X043R-X230E-X242R, X020R-X043R-X242R, X018R-X043R-X076D-X230E, X020R-X024R-X043D-X242R, X020R-X043R-X230E, X018R-X020R-X043R-X076D-X242R-X249R, X043D-X045T-X076D-X249R, X018R-X043R-X242R-X249R, X018R-X020R-X043R-X045T-X242R, X018R-X020R-X043D-X230E-X242R, X020R-X024R-X043R-X045T-X249R, X024R-X043R-X249R, X020R-X024R-X27E-X043R-X076D-X230E, X024R-X043R-X045T-X242R, X018R-X020R-X024R-X043R-X045T-X076D-X230E, X020R-X043R-X076D-X230E-X249R, X018R-X043R-X045T-X242R, X020R-X242R-X249R, X018R-X043R-X076D-X230E-X242R-X249R, X018R-X024R-X076D, X020R-X024R-X27R-X043D-X242R-X249R, X018R-X020R-X024R-X043D-X076D-X242R, X018R-X043R-X076D-X242R-X249R, X018R-X024R-X043D-X230E-X249R, X018R-X020R-X043D-X249R, X018R-X020R-X043D-X045T-X076D-X242R, X024R-X043R-X076D-X230E-X242R, X020R-X024R-X381-X043R-X045T-X076D-X242R-X249R, X018R-X020R-X043R, X018R-X024R-X045T-X230E-X242R, X018R-X020R-X249R, X024R-X043R-X076D, X018R-X020R-X024R-X043R-X045T-X076D-X249R, X018R-X043D-X045T-X076D-X242R-X249R, X024R-X043D-X242R-X249R, X018R-X020R-X024R-X043D-X045T-X242R, X020R-X024R-X043R-X076D, X018R-X020R-X043D-X045T-X230E-X242R, X020R-X024R-X043R-X045T-X076D-X242R-X249R, X018R-X043R-X045T-X076D-X242R, X018R-X020R-X043R-X076D-X230E-X242R, X018R-X024R-X043D-X249R, X018R-X024R-X043R-X045T-X230E-X249R, X018R-X020R-X043R-X045T-X076D-X249R, X018R-X024R-X242R, X018R-X043R-X045T-X076D-X230E-X242R, X045T-X242R-X249R, X018R-X024R-X043D-X242R, X018R-X020R-X043D-X045T-X240P, X024R-X043R-X045T-X242R-X249R, X018R-X024R-X30S-X31S-X321-X33Q-X34V-X35F, X018R-X020R-X043R-X076D, X020R-X043D-X045T-X076D-X242R-X249R, X018R-X024R-X043D-X230E-X242R, X018R-X024R-X043D-X242R-X249R, X024R-X043D-X045T-X242R-X249R, X043R-X230E-X249R, X024R-X043R-X076D-X230E-X249R, X020R-X024R-X043D-X076D-X249R, X024R-X045T-X242R-X273V, X020R-X024R-X045T-X076D-X242R-X249R, X018R-X024R-X043D-X076D-X242R, X018R-X043R-X076D-X230E-X249R, X018R-X020R-X043R-X045T-X249R, X018R-X043R-X045T-X230E-X242R, X020R-X024R-X043D-X045T-X230E-X242R, X018R-X043D-X230E-X249R, X018R-X043R-X076D-X242R, X018R-X020R-X076D, X018R-X020R-X043D-X076D-X242R-X249R, X020R-X024R-X043D-X076D-X242R-X249R, X043D-X242R-X249R, X018R-X020R-X024R-X043R-X076D, X018R-X020R-X043D-X045T-X076D-X249R, X018R-X020R-X043R-X045T-X076D-X230E-X249R, X018R-X076D-X242R, X020R-X043R-X249R, X018R-X076D-X242R-X249R, X018R-X024R-X045T-X230E-X249R, X230E-X249R, X018R-X045T-X249R, X020R-X043R-X076D, X043R-X045T-X249R, X018R-X043D-X076D-X242R-X249R, X043R-X076D-X249R, X018R-X045T, X020R-X076D-X230E-X242R, X020R-X024R-X043D-X045T, X024R-X043D-X076D-X242R-X249R, X020R-X045T-X249R, X043R-X076D-X153A-X249R, X043R-X076D-X230E-X249R, X018R-X043D-X076D-X249R, and X020R-X043R-X076D-X227I, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X101G-X103A-X104I-X232V-X236H-X245R-X252K, X101G-X103A-X104I-X232V-X245R-X248R, X101G-X103A-X104I-X159R-X232V-X245R-X248D, X101G-X103A-X104I-X159D-X232V-X245R-X248R, X101G-X103A-X104I-X232V-X245R, X101G-X103A-X104I-X159D-X232V-X245R, and X101G-X103A-X104I-X232V-X245R-X248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X101G-X103A-X104I-X129E-X188D-X232V-X238R-X245R-X248D, X024R-X101G-X103A-X104I-X129E-X158E-X188D-X232V-X245R-X248D-X249R, X022A-X101G-X103A-X104I-X129E-X158E-X188D-X232V-X245R-X248D-X249R, X022A-X024R-X101G-X103A-X104I-X129E-X158E-X188D-X232V-X245R-X248D-X249R, X024R-X101G-X103A-X104I-X129E-X188D-X232V-X245R-X248D-X249R, X024R-X101G-X103A-X104I-X129E-X159E-X188D-X232V-X245R-X248D-X249R, X024R-X101G-X103A-X104I-X128N-X129E-X158E-X232V-X245R-X248D-X249R, X024R-X101G-X103A-X104I-X148I-X158E-X188D-X232V-X245R-X248D, X022A-X024R-X101G-X103A-X104I-X129E-X159E-X188D-X232V-X245R-X248D-X249R, X024R-X101G-X103A-X104I-X128N-X129E-X232V-X245R-X248D, X101G-X103A-X104I-X129E-X188D-X232V-X245R-X248D-X249R, X024R-X101G-X103A-X104I-X129E-X158E-X232V-X245R-X248D-X249R, X022A-X024R-X101G-X103A-X104I-X158E-X159E-X188D-X232V-X245R-X248D-X249R, X022A-X024R-X101G-X103A-X104I-X129E-X158E-X159E-X188D-X232V-X238R-X245R-X248D, X024R-X101G-X103A-X104I-X129E-X148I-X158E-X232V-X245R-X248D, X016S-X024R-X101G-X103A-X104I-X158E-X188D-X232V-X245R-X248D-X249R, X101G-X103A-X104I-X158E-X159E-X232V-X245R-X248D-X249R, X022A-X101G-X103A-X104I-X129E-X158E-X159E-X232V-X238R-X245R-X248D, X022A-X024R-X101G-X103A-X104I-X129E-X158E-X159E-X232V-X245R-X248D-X249R, X022A-X024R-X101G-X103A-X104I-X128N-X158E-X188D-X232V-X245R-X248D, X024R-X101G-X103A-X104I-X129E-X188D-X232V-X245R-X248D, X022A-X024R-X101G-X103A-X104I-X129E-X158E-X232V-X245R-X248D, X022A-X024R-X101G-X103A-X104I-X129E-X232V-X245R-X248D, X022A-X024R-X101G-X103A-X104I-X129E-X188D-X232V-X245R-X248D, X024R-X101G-X103A-X104I-X158E-X188D-X232V-X238R-X245R-X248D, X022A-X101G-X103A-X104I-X128N-X129E-X188D-X232V-X238R-X245R-X248D, X024R-X101G-X103A-X104I-X129E-X188D-X232V-X238R-X245R-X248D, X024R-X101G-X103A-X104I-X158E-X159E-X188D-X232V-X245R-X248D, X022A-X024R-X101G-X103A-X104I-X128N-X188D-X232V-X245R-X248D, X024R-X101G-X103A-X104I-X129E-X158E-X188D-X232V-X245R-X248D, X022A-X024R-X101G-X103A-X104I-X128N-X129E-X158E-X232V-X245R-X248D, X024R-X101G-X103A-X104I-X159E-X188D-X232V-X245R-X248D, X022A-X101G-X103A-X104I-X128N-X129E-X232V-X238R-X245R-X248D, X024R-X101G-X103A-X104I-X129E-X159E-X232V-X245R-X248D, X022A-X024R-X101G-X103A-X104I-X129E-X158E-X188D-X232V-X238R-X245R-X248D, X022A-X024R-X101G-X103A-X104I-X158E-X159E-X188D-X232V-X245R-X248D, X024R-X101G-X103A-X104I-X159E-X188D-X232V-X245R-X248D-X249R, X022A-X101G-X103A-X104I-X129E-X158E-X232V-X238R-X245R-X248D, X022A-X024R-X101G-X103A-X104I-X129E-X158E-X232V-X245R-X248D-X249R, X024R-X101G-X103A-X104I-X148I-X158E-X232V-X245R-X248D, X022A-X101G-X103A-X104I-X158E-X159E-X188D-X232V-X245R-X248D-X249R, X022A-X101G-X103A-X104I-X158E-X188D-X232V-X245R-X248D, X022A-X101G-X103A-X104I-X129E-X188D-X232V-X238R-X245R-X248D, X024R-X101G-X103A-X104I-X129E-X158E-X159E-X188D-X232V-X245R-X248D-X249R, X022A-X024R-X101G-X103A-X104I-X158E-X159E-X188D-X232V-X238R-X245R-X248D, X101G-X103A-X104I-X129E-X158E-X188D-X232V-X245R-X248D-X249R, X024R-X101G-X103A-X104I-X128N-X158E-X232V-X245R-X248D, X022A-X024R-X101G-X103A-X104I-X128N-X129E-X188D-X232V-X245R-X248D, X022A-X101G-X103A-X104I-X129E-X159E-X232V-X238R-X245R-X248D, X101G-X103A-X104I-X129E-X159E-X232V-X245R-X248D-X249R, X022A-X101G-X103A-X104I-X129E-X158E-X232V-X245R-X248D-X249R, X024R-X101G-X103A-X104I-X129E-X148I-X158E-X188D-X232V-X245R-X248D, X022A-X101G-X103A-X104I-X129E-X159E-X232V-X245R-X248D-X249R, X024R-X101G-X103A-X104I-X159E-X188D-X232V-X238R-X245R-X248D, X024R-X101G-X103A-X104I-X129E-X158E-X159E-X232V-X245R-X248D-X249R, X024R-X101G-X103A-X104I-X129E-X158E-X159E-X232V-X238R-X245R-X248D, X024R-X101G-X103A-X104I-X128N-X159E-X188D-X232V-X245R-X248D, X022A-X101G-X103A-X104I-X159E-X188D-X232V-X245R-X248D-X249R, X024R-X101G-X103A-X104I-X129E-X159E-X188D-X232V-X238R-X245R-X248D, X101G-X103A-X104I-X158E-X232V-X238R-X245R-X248D, X022A-X101G-X103A-X104I-X129E-X159E-X188D-X232V-X245R-X248D-X249R, X024R-X101G-X103A-X104I-X129E-X148I-X188D-X232V-X245R-X248D, X024R-X101G-X103A-X104I-X158E-X232V-X245R-X248D-X249R, X022A-X101G-X103A-X104I-X158E-X159E-X232V-X238R-X245R-X248D, X024R-X101G-X103A-X104I-X158E-X159E-X232V-X238R-X245R-X248D, X022A-X101G-X103A-X104I-X129E-X158E-X159E-X232V-X245R-X248D-X249R, X101G-X103A-X104I-X129E-X158E-X188D-X232V-X238R-X245R-X248D, X022A-X024R-X101G-X103A-X104I-X129E-X158E-X159E-X232V-X245R-X248D, X101G-X103A-X104I-X188D-X232V-X238R-X245R-X248D, X022A-X024R-X101G-X103A-X104I-X158E-X232V-X245R-X248D-X249R, X022A-X024R-X101G-X103A-X104I-X148I-X158E-X232V-X245R-X248D, X101G-X103A-X104I-X129E-X158E-X159E-X232V-X238R-X245R-X248D, X022A-X101G-X103A-X104I-X159E-X188D-X232V-X238R-X245R-X248D, X022A-X024R-X101G-X103A-X104I-X129E-X158E-X159E-X188D-X232V-X245R-X248D-X249R, X022A-X101G-X103A-X104I-X129E-X232V-X238R-X245R-X248D, X022A-X024R-X101G-X103A-X104I-X188D-X232V-X245R-X248D-X249R, X101G-X103A-X104I-X129E-X158E-X159E-X232V-X245R-X248D-X249R, X022A-X101G-X103A-X104I-X158E-X159E-X232V-X245R-X248D-X249R, X101G-X103A-X104I-X129E-X188D-X232V-X245R-X248D, X024R-X101G-X103A-X104I-X129E-X159E-X232V-X238R-X245R-X248D, X101G-X103A-X104I-X128N-X129E-X232V-X245R-X248D, X101G-X103A-

X104I-X158E-X188D-X232V-X245R-X248D, X022A-X024R-X101G-X103A-X104I-X129E-X232V-X245R-X248D-X249R, X101G-X103A-X104I-X129E-X159E-X232V-X238R-X245R-X248D, X101G-X103A-X104I-X158E-X159E-X188D-X232V-X238R-X245R-X248D, X022A-X024R-X101G-X103A-X104I-X232V-X245R-X248D-X249R, X022A-X024R-X101G-X103A-X104I-X129E-X148I-X232V-X245R-X248D, X022A-X024R-X101G-X103A-X104I-X158E-X232V-X238R-X245R-X248D, X101G-X103A-X104I-X128N-X129E-X232V-X238R-X245R-X248D, X022A-X101G-X103A-X104I-X128N-X159E-X232V-X245R-X248D, X022A-X101G-X103A-X104I-X128N-X129E-X158E-X232V-X238R-X245R-X248D, X101G-X103A-X104I-X128N-X129E-X188D-X232V-X245R-X248D-X249R, X022A-X024R-X101G-X103A-X104I-X128N-X129E-X158E-X188D-X232V-X245R-X248D-X249R, X024R-X101G-X103A-X104I-X128N-X158E-X159E-X188D-X232V-X245R-X248D, X022A-X024K-X101G-X103A-X104I-X128N-X158E-X159E-X232V-X245R-X248D, X101G-X103A-X104I-X129E-X148I-X188D-X232V-X245R-X248D, X024R-X101G-X103A-X104I-X148I-X232V-X245R-X248D, X022A-X101G-X103A-X104I-X148I-X188D-X232V-X245R-X248D, X024R-X101G-X103A-X104I-X128N-X129E-X188D-X232V-X245R-X248D, X101G-X103A-X104I-X128N-X129E-X158E-X232V-X238R-X245R-X248D, X022A-X024R-X101G-X103A-X104I-X129E-X148I-X158E-X188D-X232V-X245R-X248D, X022A-X024R-X101G-X103A-X104I-X148I-X158E-X188D-X232V-X245R-X248D, X101G-X103A-X104I-X148I-X159E-X232V-X245R-X248D, X022A-X024R-X101G-X103A-X104I-X158E-X188D-X232V-X245R-X248D, and X101G-X103A-X104I-X128N-X129E-X158E-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X022A-X024R-X101G-X103A-X104I-X158E-X232V-X245R-X248D-X249R, X022A-X024R-X101G-X103A-X104I-X129E-X232V-X245R-X248D-X249R, X024R-X101G-X103A-X104I-X158E-X159E-X232V-X238R-X245R-X248D, X024R-X101G-X103A-X104I-X232V-X245R-X248D-X249R, X101G-X103A-X104I-X158E-X232V-X245R-X248D-X249R, X101G-X103A-X104I-X188D-X232V-X245R-X248D-X249R, X024R-X101G-X103A-X104I-X159E-X188D-X232V-X245R-X248D-X249R, X022A-X024R-X101G-X103A-X104I-X158E-X232V-X238R-X245R-X248D, X024R-X101G-X103A-X104I-X159E-X188D-X232V-X238R-X245R-X248D, X022A-X024R-X101G-X103A-X104I-X129E-X232V-X245R-X248D, X024R-X101G-X103A-X104I-X148I-X232V-X245R-X248D, X024R-X101G-X103A-X104I-X129E-X158E-X232V-X245R-X248D-X249R, X024R-X101G-X103A-X104I-X148I-X158E-X232V-X245R-X248D, X022A-X024R-X101G-X103A-X104I-X129E-X158E-X232V-X245R-X248D-X249R, X016S-X024R-X101G-X103A-X104I-X158E-X188D-X232V-X245R-X248D-X249R, X024R-X101G-X103A-X104I-X129E-X159E-X232V-X238R-X245R-X248D, X024R-X101G-X103A-X104I-X129E-X188D-X232V-X245R-X248D-X249R, X022A-X101G-X103A-X104I-X129E-X232V-X238R-X245R-X248D, X022A-X024R-X101G-X103A-X104I-X148I-X158E-X232V-X245R-X248D, X024R-X101G-X103A-X104I-X129E-X188D-X232V-X238R-X245R-X248D, X022A-X024R-X101G-X103A-X104I-X158E-X159E-X188D-X232V-X238R-X245R-X248D, X022A-X101G-X103A-X104I-X158E-X159E-X232V-X238R-X245R-X248D, X022A-X024R-X101G-X103A-X104I-X129E-X158E-X232V-X245R-X248D, X101G-X103A-X104I-X158E-X188D-X232V-X245R-X248D-X249R, X022A-X101G-X103A-X104I-X158E-X159E-X232V-X245R-X248D-X249R, and X024R-X101G-X103A-X104I-X158E-X159E-X232V-X245R-X248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X104L-X128N-X158E-X186H-X249R, X128N-X158E-X188D-X249R, X062E-X128N-X158E-X159E-X271F, X062E-X158E-X188D-X249R-X271F, X062E-X158E-X186H-X249R-X271F, X128N-X158E-X188D-X209E-X271F, X062E-X159E-X188D-X249R, X016S-X062E-X158E-X186H-X249R, X062E-X158E-X159E-X249R, X101A-X128N-X158E-X209E-X249R, X128N-X158E-X186H-X271F, X062E-X158E-X188D-X249R, X062E-X158E-X186H-X271F, X062E-X158E-X186H-X249R, X062E-X101A-X186H-X249R, X062E-X101A-X158E-X186H-X271F, X062E-X104L-X158E-X188D-X249R-X271F, X062E-X159E-X186H-X249R, X062E-X159E-X249R, X128N-X158E-X186H-X249R, X128N-X158E-X188D-X271F, X062E-X158E-X249R, X062E-X186H-X188D-X249R-X271F, X128N-X158E-X209E-, X062E-X101A-X158E-X249R, X104L-X128N-X158E-X186H-X271F, X062E-X101A-X158E-X186H-X249R-X271F, X016S-X062E-X158E-X249R, X062E-X101A-X159E-X249R, X128N-X158E-X186H-X188D-X271F, X101A-X128N-X158E-X186H-X271F, X062E-X101A-X188D-X249R, X101A-X104L-X158E-X186H-X188D-X249R, X062E-X159E-X249R-X271F, X128N-X158E-X159E-X271F, X016S-X062E-X104L-X158E-X186H-X271F, X022A-X128N-X158E-X249R, X128N-X158E-X249R, X062E-X101A-X104L-X158E-X186H-X271F, X016S-X062E-X158E-X186H-X271F, X104L-X128N-X158E-X249R, X104L-X128N-X158E-X188D-X249R, X022A-X062E-X158E, X062E-X101A-X188D-X249R-X271F, X062E-X158E-X249R-X271F, X104L-X128N-X158E-X186H-X188D-X271F, X062E-X101A-X186H-X271F, X062E-X104L-X159E-X249R, X062E-X186H-X249R, X062E-X101A-X186H-X249R-X271F, X101A-X158E-X186H-X188D-X249R, X062E-X101A-X186H, X101A-X128N-X129E-X186H-X249R, X101A-X103G-X158E-X186H-X249R, X016S-X062E-X104L-X186H-X188D-X271F, X104L-X158E-X186H-X249R, X101A-X128N-X158E-X188D-X209E-X271F, X062E-X101A-X186H-X188D-X271F, X016S-X062E-X158E-X249R-X271F, X062E-X128N-X158E, X062E-X128N-X159E-X249R, X062E-X101A-X158E-X188D-X249R, X101A-X128N-X158E-X249R, X062E-X158E-X186H-X188D-X249R, X016S-X104L-X158E-X186H-X271F, X062E-X148I-X159E, X062E-X101A-X158E-X186H-X249R, X062E-X101A-X186H-X188D-X249R, X104L-X158E-X186H-X188D-X249R, X062E-X101A-X104L-X186H-X188D-X271F, X022A-X101A-X158E-X186H-X249R, X101A-X128N-X158E-X209E, X158E-X186H-X188D-X249R-X271F, X104L-X158E-X186H-X188D-X249R-X271F, X101A-X104L-X158E-X186H-

X249R, X104L-X158E-X249R, X101A-X104L-X128N-X158E-X186H-X271F, X016S-X104L-X188D-X249R, X101A-X104L-X158E-X186H-X188D-X271F, X104L-X128N-X159E-X271F, X104L-X158E-X186H-X249R-X271F, X158E-X186H-X249R, X101A-X158E-X186H-X249R, X104L-X158E-X188D-X249R-X271F, X016S-X128N-X158E-X186H, X104L-X128N-X186H-X188D-X249R, X016S-X101A-X128N-X186H, X016S-X062E-X128N-X186H-X271F, X016S-X128N-X186H-X271F, X128N-X129E-X186H, X158E-X186H-X249R-X271F, X016S-X158E-X249R, X016S-X158E-X186H-X249R, X016S-X022A-X158E-X186H-X271F, X089P-X101A-X129E-X186H, X022A-X128N-X158E-X186H, X101A-X104L-X128N-X158E-X186H, X022A-X128N-X186H-X188D-, X062E-X104L-X158E-X186H-X188D-X249R, X022A-X158E-X186H-X249R-X271F, X022A-X104L-X158E-X249R, X101A-X111V-X129E, X016S-X158E-X249R-X271F, X016S-X111V-X188D-, X022A-X104L-X186H-X188D-X249R, and X104L-X148I-X188D-X249R, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X001R-X101G-X103A-X104I-X232V-X245R, X004R-X101G-X103A-X104I-X232V-X245R, X043R-X101G-X103A-X104I-X232V-X245R-X271L, X078R-X101G-X103A-X104I-X232V-X245R, X004R-X043R-X101G-X103A-X104I-X232V-X245R, X018R-X043R-X101G-X103A-X104I-X232V-X245R, X020R-X101G-X103A-X104I-X232V-X245R, X101G-X103A-X104I-X232V-X245R-X271L, X020R-X043R-X101G-X103A-X104I-X232V-X245R, X024R-X043R-X101G-X103A-X104I-X232V-X245R, X020R-X025R-X116A-X167W, X018R-X101G-X103A-X104I-X232V-X245R, X022R-X101G-X103A-X104I-X232V-X245R, X078R-X103N-X106G-X167W-X236N, X018R-X043D-X101G-X103A-X104I-X232V-X245R-X269R, X043R-X101G-X103A-X104I-X232V-X245R-X269R, X024R-X101A-X120E-X194F-X249R, X020R-X043D-X101G-X103A-X104I-X232V-X245R-X269R, X101G-X103A-X104I-X212F-X232V-X245R, X020R-X144R-X185I-X233C-X236N, X023A-X078R-X216F-X236N-X249R, X101G-X103A-X104I-X232V-X245R-X269R, X101G-X103A-X104I-X115R-X232V-X245R, X052N-X078R-X103N-X148I-X213A, X018R-X043D-X101G-X103A-X104I-X232V-X245R-X249R, X024R-X043D-X101G-X103A-X104I-X232V-X245R-X249R, X024R-X043D-X101G-X103A-X104I-X232V-X245R-X269R, X025R-X089I-X116A-X239S-X270C, X024R-X101G-X103A-X104I-X232V-X245R, X148I-X213A-X252R, X024R-X025R-X183D-X192W-X239S, X046R-X194F-X212M, X104L-X217E-X224A-X249R-X252R, X023A-X091F-X121F-X192W-X236N, X101G-X103A-X104I-X232V-X244R-X245R, X099F-X144R-X167W-X252R, X101G-X103A-X104I-X232V-X245R-X249R, X043R-X101G-X103A-X104I-X232V-X245R, X022W-X078R-X167W-X212M-X270C, X121F-X252R-X270C, X020R-X103N-X216F-X236N-X252R, X043R-X101G-X103A-X104I-X232V-X245R-X249R, X023A-X052N-X192W-X198L-X252R, X025R-X046R-X121F, X024R-X078R-X104L-X116A-X183D, X046R-X059A-X103N-X211Q-X212M, X020R-X052N-X062Q-X091F-X192W, X023A-X052N-X144R-X192W-X216F, X101G-X103A-X104I-X232V-X242R-X245R, X052N-X103N-X116A-X148I-X192W, X089I-X116A-X117F-X224A-X249R, X144R-X211Q-X238L-X239S-X249R, X043A-X062Q-X194F-X211Q, X020R-X024R-X052N-X059A-X216F, X024R-X167W-X224A-X249R, X057R-X167W-X249R, X025R-X103N-X186K-X194F-X224A, X105T-X128N-X144R-X148I-X212M, X020R-X059A-X144R-X192W-X224A, X024R-X043A-X117F-X194F-X211Q, X117F-X194F-X213A-X270C, X078R-X091F-X121F-X233C-X252R, X057R-X099F-X105T-X198L-X213A, X023A-X091F-X101A-X198L-X252R, X062Q-X103N-X121F-X144R-X249R, X043R-X101G-X103A-X104I-X232V-X242R-X245R, X023A-X024R-X117F-X212M-X216F, X104L-X213A-X216F, X194F-X211Q-X236N, X062Q-X103N-X117F-X194F, X024R-X062Q-X104L-X106G-X249R, X057R-X089I-X198L, X046R-X059A-X106G-X217E-X249R, X117F-X213A-X215F, X101A-X120E-X192W-X215F-X224A, X043A-X057R-X117F-X144R-X183D, X046R-X183D-X238L, X025R-X043A-X089I-X117F, X078R-X104L-X213A-X215F-X224A, X091F-X099F-X101A-X105T-X167W, X106G-X117F-X238L, X046R-X089I-X091F-X101A-X116A, X020R-X062Q-X089I-X186K-X212M, X057R-X099F-X121F-X185I-X192W, X046R-X089I-X192W-X233C-X270C, X089I-X117F-X185I-X215F-X233C, X052N-X104L-X183D-X216F-X249R, X078R-X099F-X116A-X186K-X224A, X025R-X105T-X128N-X144R-X270C, X105T-X211Q-X216F, X024R-X046R-X091F-X121F, X106G-X185I-X216F-X236N, X062Q-X101A-X236N-X252R-X270C, X025R-X043A-X091F-X198L-X270C, X020R-X023A-X104L-X192W-X233C, X024R-X043A-X105T-X106G-X198L, X020R-X089I-X217E, X024R-X091F-X198L-X215F-X239S, X046R-X089I-X099F-X186K-X212M, X104L-X120E-X186K-X216F-X252R, X022W-X194F-X213A-X233C-X238L, X099F-X105T-X106G-X194F-X212M, X089I-X105T-X116A-X215F-X216F, X025R-X116A-X120E-X224A-X270C, X043A-X059A-X101A-X216F-X224A, X057R-X183D-X236N, X025R-X062Q-X128N-X144R-X185I, X103N-X120E-X167W-X198L-X233C, X022W-X089I-X216F, X024R-X106G-X116A-X212M-X224A, X020R-X052N-X101A-X198L-X233C, X089I-X091F-X185I-X211Q-X270C, X111I-X215F-X239S, X024R-X116A-X186K-X233C-X236N, and X023A-X103N-X106G-X212M-X215F, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X020R-X022W-X078R-X101A-X103A-X104I-X116S-X213A-X215F-X232V-X245R, X018R-X078R-X101G-X103A-X104I-X232V-X245R, X024R-X045T-X101G-X103A-X104I-X232V-X245R-X269R, X020R-X022W-X078R-X101G-X103A-X104I-X116A-X232V-X245R, X020R-X22W-X101G-X103A-X104I-X232V-X245R, X018R-X043R-X101G-X103A-X104I-X232V-X245R, X018R-X022W-X024R-X076D-X101A-X116A-X232V-X245R, X018R-X104I-X232V-X249R, X018R-X024R-X076D-X101A-X116A-X211Q-X249R, X018R-X043D-X078R-X101G-X103A-X104I-X217E-X232V-X245R, X018R-X043R-X101G-X103A-X104I-X232V-X245R-X269R, X018R-X045T-X076D-X101G-X103A-X104I-X232V-X245R-X269R, X076D-X078R-X101G-X103A-X104I-X232V-X245R-X269R, X020R-X043D-X078R-X101G-X103A-X104I-X232V-

X245R, X018R-X043D-X076D-X101G-X103A-X104I-X232V-X245R-X269R, X024R-X045T-X076D-X078R-X101G-X103A-X104I-X232V-X245R-X269R, X018R-X103A-X232V-X249R, X018R-X101G-X104I-X232V-X245R, X020R-X024R-X101G-X103A-X104I-X217E-X232V-X245R-X249R, X018R-X22K-X043D-X101G-X103A-X104I-X232V-X245R, X043R-X045T-X101G-X103A-X104I-X232V-X245R-X269R, X020R-X22W-X101G-X103A-X104I-X211Q-X232V-X245R, X024R-X076D-X078R-X101G-X103A-X104I-X232V-X245R-X269R, X020R-X22W-X078R-X101A-X103A-X104I-X116A-X183D-X232V, X018R-X024R-X076D-X116A-X215F-X249R, X018R-X043R-X045T-X101G-X103A-X104I-X232V-X245R, X024R-X043R-X076D-X101G-X103A-X104I-X232V-X245R, X020R-X022W-X101G-X103A-X104I-X232V-X245R, X020R-X022W-X101G-X103A-X104I-X211Q-X232V-X245R, X020R-X022W-X078R-X101G-X103A-X104I-X116A-X213A-X215F-X232V-X245R, X043D-X076D-X078R-X101G-X103A-X104I-X232V-X245R-X269R, X018R-X024R-X076D-X101A-X116A-X213A-X249R, X018R-X024R-X076D-X116A-X211Q-X249R, X043R-X045T-X076D-X078R-X101G-X103A-X104I-X232V-X245R, X018R-X101G-X245R, X020R-X22W-X101A-X103A-X104I-X211Q-X213A-X232V-X245R, X020R-X024R-X043D-X076D-X078R-X101G-X103A-X104I-X232V-X245R, X018R-X045T-X076D-X078R-X101G-X103A-X104I-X232V-X245R, X020R-X078R-X101G-X103A-X104I-X211Q-X213A-X215F-X232V-X245R, X045T-X078R-X101G-X103A-X104I-X232V-X245R-X269R, X024R-X043D-X101G-X103A-X104I-X232V-X245R-X269R, X018R-X101G-X103A-X249R, X018R-X22W-X024R-X076D-X101A-X116A-X232V-X245R, X018R-X101G-X104I-X232V-X249R, X020R-X22W-X101A-X103A-X104I-X215F-X232V-X245R, X018R-X024R-X076D-X211Q-X213A-X249R, X018R-X022W-X024R-X076D-X101A-X198L-X249R, X024R-X101G-X103A-X104I-X232V-X245R, X020R-X076D-X101G-X103A-X104I-X232V-X245R-X269R, X020R-X101G-X103A-X104I-X232V-X245R-X269R, X043D-X078R-X101G-X103A-X104I-X232V-X245R, X020R-X101G-X104I-X213A-X215F-X232V-X245R, X020R-X101G-X103A-X104I-X116A-X215F-X232V-X245R, X024R-X103A-X104I-X249R, X018R-X076D-X078R-X101G-X103A-X104I-X232V-X245R, X045T-X076D-X078R-X101G-X103A-X104I-X232V-X245R-X269R, X024R-X101G-X104I-X245R, X020R-X101G-X103A-X104I-X211Q-X213A-X215F-X232V-X245R, X024R-X103A-X104I-X232V-X249R, X018R-X024R-X076D-X116A-X211Q-X215F-X249R, X018R-X245R, X024R-X103A-X245R, X024R-X103A-X104I-X245R, X020R-X078R-X101G-X232V-X245R, X018R-X024R-X076D-X104I-X249R, X018R-X024R-X104I-X249R, X024R-X101G-X103A-X104I-X232V-X245R, X018R-X024R-X076D-X211Q-X215F-X249R, X019H-X020R-X022W-X078R-X101G-X103A-X104I-X211Q-X232V-X245R, X018R-X024R-X076D-X101A-X198L-X211Q-X213A-X249R, X018R-X024R-X043D-X101G-X103A-X104I-X232V-X245R, X020R-X22W-X103A-X104I-X232V-X245R, X018R-X103A-X104I-X249R, X018R-X022W-X024R-X076D-X101A-X198L-X215F-X249R, X018R-X024R-X101G-X104I-X232V, X078R-X101G-X103A-X104I-X232V-X245R-X269R, X024R-X043R-X076D-X078R-X101G-X103A-X104I-X232V-X245R, X018R-X020R-X043D-X076D-X101G-X103A-X104I-X232V-X245R, X018R-X22W-X024R-X076D-X116A-X213A-X249R, X018R-X024R-X101G-X104I, X020R-X101A-X103A-X104I-X215F-X232V-X245R, X018R-X045T-X078R-X101G-X103A-X104I-X232V-X245R, X018R-X101G-X103A-X245R, X043R-X076D-X078R-X101G-X103A-X104I-X232V-X245R, X020R-X022W-X101A-X103A-X104I-X211Q-X215F-X232V-X245R, X020R-X22W-X078R-X101G-X103A-X104I-X116A-X213A-X215F-X232V-X245R, X020R-X078R-X101G-X103A-X104I-X215F-X232V-X245R, X020R-X022W-X078R-X101G-X103A-X104I-X116A-X183D-X232V-X245R, X076D-X101G-X103A-X104I-X232V-X245R, X076D-X101G-X103A-X104I-X232V-X245R-X269R, X020R-X22W-X101A-X103A-X104I-X232V-X245R, X020R-X101G-X103A-X232V-X245R, X020R-X022W-X078R-X101A-X103A-X104I-X116A-X183D-X232V-X245R, X018R-X020R-X024R-X045T-X076D-X101G-X103A-X104I-X232V-X245R-X269R, X043R-X045T-X078R-X101G-X103A-X104I-X232V-X245R, X018R-X101G-X104I-X249R, X020R-X22W-X078R-X101G-X103A-X104I-X116A-X183D-X232V-X245R, X020R-X022W-X101G-X103A-X104I-X198L-X211Q-X213A-X232V-X245R, X020R-X078R-X101A-X103A-X104I-X116A-X183D-X213A-X232V-X245R, X024R-X076D-X104I-X232V-X245R, X018R-X020R-X076D-X101G-X103A-X104I-X232V-X245R, X018R-X024R-X076D-X101G-X104I-X232V-X249R, X018R-X043D-X078R-X101G-X103A-X104I-X232V-X245R, X001T-X018R-X024R-X076D-X116A-X213A-X249R, X076D-X078R-X101G-X103A-X104I-X232V-X245R, X020R-X078R-X101G-X103A-X104I-X116A-X232V-X245R, X043R-X076D-X101G-X103A-X104I-X232V-X245R, X018R-X045T-X101G-X103A-X104I-X232V-X245R, X018R-X076D-X101G-X104I-X232V-X245R, X020R-X078R-X101G-X103A-X104I-X116A-X183D-X232V-X245R, X018R-X024R-X076D-X101A-X211Q-X213A-X215F-X249R, X045T-X078R-X101G-X103A-X104I-X232V-X245R, X043R-X076D-X101G-X103A-X104I-X232V-X245R-X269R, X020R-X022W-X078R-X101G-X103A-X104I-X116A-X183D-X213A-X232V-X245R, X020R-X022W-X101G-X103A-X104I-X116A-X183D-X213A-X232V-X245R, X020R-X101G-X198L-X215F-X232V-X245R, X018R-X024R-X076D-X213A-X215F-X249R, X020R-X078R-X101G-X103A-X104I-X116A-X211Q-X232V-X245R, X020R-X022W-X078R-X101A-X103A-X104I-X116A-X183D-X215F-X232V-X245R, X020R-X022W-X078R-X101A-X103A-X104I-X116A-X183D-X213A-X232V-X245R, X024R-X232V-X245R, X018R-X024R-X043D-X101G-X103A-X104I-X232V-X245R-X269R, X018R-X024R-X076D-X101A-X215F-X249R, X018R-X022W-X024R-X076D-X116A-X213A-X249R, X101G-X103A-X104I-X232V-X245R, X018R-X024R-X076D-X211Q-X213A-X215F-X249R, X018R-X024R-X076D-X116A-X213A-X215F-X249R, X043D-X076D-X078R-X101G-X103A-X104I-X232V-X245R-X269R, X043D-X078R-X101G-X103A-X104I-X232V-X245R-X249R, X020R-X022W-X078R-X101G-X103A-X104I-X116A-X183D-X211Q-X232V-X245R, X018R-X024R-X076D-X101A-X198L-X211Q-X215V-X249R, X018R-X022W-X024R-X076D-X116A-X211Q-X249R, X020R-X103A-X104I-X232V-X245R, X020R-X22W-X101A-X103A-X104I-X211Q-X215F-X232V-X245R, X024R-X076D-X101G-X103A-X104I-X232V-X245R, X020R-X101G-X103A-X104I-X116A-X232V-X245R, X018R-X22W-X024R-X076D-X198L-X215F-X249R, X020R-X022W-X103A-X104I-X232V-X245R, X020R-X022W-X101A-X103A-X104I-X211Q-X213A-X232V-X245R, X020R-X022W-X101G-X103A-X104I-X211Q-X213A-X215F-X232V-X245R, X018R-X043R-X045T-X076D-X101G-X103A-X104I-X232V-X245R,

X018R-X022W-X024R-X076D-X101A-X198L-X213A-X215F-X249R, X018R-X22W-X024R-X076D-X101A-X215F-X249R, X020R-X045T-X101G-X103A-X104I-X232V-X245R, X020R-X078R-X101A-X103A-X104I-X180A-X232V-X245R, X020R-X022W-X078R-X101G-X103A-X104I-X116A-X183D-X215F-X232V-X245R, X018R-X101G-X103A-X104I, X020R-X22W-X101A-X103A-X104I-X116A-X211Q-X213A-X215F-X232V-X245R, X018R-X024R-X076D-X103A-X232V-X245R, X020R-X078R-X101A-X103A-X104I-X116A-X183D-X232V-X245R, X018R-X024R-X076D-X211Q-X249R, X020R-X101A-X103A-X104I-X213A-X215F-X232V-X245R, X018R-X020R-X043D-X101G-X103A-X104I-X232V-X245R, X020R-X022W-X101A-X103A-X104I-X211Q-X232V-X245R, X020R-X022W-X101A-X103A-X104I-X116A-X211Q-X215F-X232V-X245R, X020R-X022W-X101A-X103A-X104I-X116A-X211Q-X232V-X245R, X018R-X024R-X076D-X232V-X249R, X018R-X024R-X045T-X076D-X101G-X103A-X104I-X232V-X245R-X269R, X018R-X076D-X245R, X024R-X104I-X245R, X101G-X232V, X020R-X22W-X101A-X103A-X104I-X116A-X211Q-X215F-X232V-X245R, X018R-X020R-X022W-X024R-X076D-X116A-X183D-X198L-X213A-X249R, X020R-X022W-X078R-X101A-X103A-X104I-X232V-X245R, X020R-X022W-X078R-X101A-X103A-X104I-X198L-X232V-X245R, X024R-X245R-X249R, X020R-X101G-X103A-X104I-X116A-X211Q-X232V-X245R, X018R-X22W-X024R-X076D-X116A-X211Q-X249R, X024R-X101G-X104I-X249R, X018R-X024R-X076D-X116A-X198L-X211Q-X213A-X215F-X249R, X018R-X024R-X104I, X020R-X022W-X078R-X101A-X103A-X104I-X183D-X198L-X213A-X215F-X232V-X245R, X018R-X020R-X22W-X024R-X076D-X116A-X183D-X198L-X213A-X249R, X020R-X022W-X101A-X103A-X104I-X232V-X245R, X012H-X020R-X078R-X101G-X103A-X104I-X198L-X211Q-X213A-X232V-X245R, X018R-X024R-X076D-X101A-X211Q-X215F-X249R, X018R-X024R-X076D-X213A-X249R, X024R-X104I-X249R, X018R-X022W-X024R-X076D-X211Q-X249R, X018R-X076D-X103A-X104I-X249R, X043R-X076D-X101G-X103A-X104I-X217E-X232V-X245R, X020R-X078R-X101G-X103A-X104I-X183D-X211Q-X213A-X232V-X245R-X271G, X018R-X022W-X024R-X076D-X101A-X116A-X198L-X215F-X249R, X018R-X024R-X043D-X076D-X101G-X103A-X104I-X232V-X245R, X018R-X024R-X076D-X101A-X198L-X215F-X249R, X018R-X022W-X024R-X076D-X116A-X198L-X211Q-X213A-X249R, X018R-X024R-X076D-X101A-X116A-X213A-X215F-X249R, X020R-X043D-X045T-X078R-X101G-X103A-X104I-X232V-X245R, X045T-X078R-X101G-X103A-X104I-X232V-X245R-X249R, X018R-X22W-X024R-X076D-X101A-X116A-X215F-X249R, X043D-X101G-X103A-X104I-X232V-X245R-X269R, X020R-X022W-X078R-X101A-X103A-X104I-X116A-X183D-X213A-X215F-X232V-X245R, X018R-X024R-X076D-X116A-X211Q-X213A-X215F-X249R, X024R-X103A-X175L-X232V-X249R, X018R-X024R-X076D-X116A-X213A-X249R, X020R-X045T-X076D-X101G-X103A-X104I-X232V-X245R, X020R-X078R-X101A-X103A-X104I-X116A-X183D-X211Q-X213A-X215F-X232V-X245R, X024R-X043R-X045T-X076D-X078R-X101G-X103A-X104I-X232V-X245R, X018R-X024R-X076D-X101A-X116A-X198L-X213A-X215F-X249R, X043R-X045T-X101G-X103A-X104I-X232V-X245R, X018R-X022W-X024R-X076D-X101A-X198L-X211Q-X245R, X020R-X024R-X043D-X076D-X078R-X101G-X103A-X104I-X232V-X245R-X269R, X024R-X232V, X020R-X078R-X101A-X103A-X104I-X116A-X183D-X211Q-X232V-X245R, X024R-X076D-X101G-X232V-X245R, X018R-X076D-X101G-X103A-X104I-X249R, X018R-X024R-X076D-X198M-X211Q-X213A-X215F-X249R, X018R-X22W-X024R-X076D-X101A-X198L-X215F-X249R, X018R-X043R-X076D-X101G-X103A-X104I-X232V-X245R-X269R, X020R-X022W-X103A-X211Q-X213A-X215F-X232V-X245R, X020R-X078R-X101A-X103A-X104I-X116A-X183D-X211Q-X213A-X232V-X245R, X045T-X076D-X101G-X103A-X104I-X232V-X245R-X269R, X018R-X22W-X024R-X076D-X101A-X211Q-X213A-X249R, X018R-X024R-X076D-X116A-X198L-X215F-X249R-X268G, X018R-X022W-X024R-X076D-X101A-X211Q-X249R, X018R-X022W-X024R-X076D-X101A-X116A-X198L-X211Q-X249R, X101G-X103A-X104I-X245R, X018R-X076D-X101G-X232V-X245R, X018R-X020R-X045T-X101G-X103A-X104I-X232V-X245R, X018R-X022W-X024R-X076D-X101A-X116A-X198L-X249R, X018R-X022W-X024R-X076D-X116A-X198L-X213A-X249R, X078R-X101G-X103A-X104I-X232V-X245R-X249R, X018R-X078R-X101G-X103A-X104I-X217E-X232V-X245R, X020R-X043R-X076D-X101G-X103A-X104I-X232V-X245R-X269R, X018R-X043D-X076D-X101G-X103A-X104I-X232V-X245R-X249R, X045T-X101G-X103A-X104I-X232V-X245R-X269R, X024R-X103A-X232V, X018R-X024R-X076D-X101A-X211Q-X249R, X043D-X101G-X103A-X104I-X232V-X245R-X249R, X018R-X043R-X045T-X076D-X076T-X101G-X103A-X104I-X232V-X245R-X273T, X018R-X020R-X043D-X078R-X101G-X103A-X104I-X232V-X245R, X020R-X078R-X101A-X103A-X104I-X183D-X215F-X232V-X245R, X018R-X024R-X076D-X101G-X232V, X232V-X245R, X043R-X045T-X076D-X078R-X101G-X103A-X104I-X232V-X234I-X245R, X024R-X076D-X103A-X104I-X245R, X020R-X078R-X101A-X103A-X104I-X211Q-X213A-X232V-X245R, X043D-X078R-X101G-X103A-X104I-X232V-X245R-X269R-X272V, X018R-X020R-X024R-X076D-X116A-X183D-X198L-X211Q-X249R, X018R-X103A-X104I-X232V, X020R-X022W-X101G-X103A-X104I-X116A-X183D-X213A-X215F-X232V-X245R, X024R-X043R-X076D-X101G-X103A-X104I-X232V-X245R-X269R, X018R-X022W-X024R-X076D-X213A-X215F-X249R, X018R-X024R-X076D-X101A-X116A-X198L-X211Q-X213A-X249R, X020R-X22W-X078R-X101A-X103A-X104I-X116A-X183D-X213A-X232V-X245R, X020R-X022W-X078R-X101G-X103A-X104I-X211Q-X213A-X232V-X245R, X020R-X022W-X101A-X103A-X104I-X215F-X232V-X245R, X018R-X020R-X024R-X076D-X116A-X183D-X215F-X249R, X018R-X024R-X076D-X116A-X117I-X183D-X213A-X249R, X018R-X022W-X024R-X076D-X101A-X116A-X198L-X213A-X249R, X018R-X22W-X024R-X076D-X101A-X198L-X213A-X215F-X249R, X018R-X043D-X078R-X101G-X103A-X104I-X232V-X245R-X249R, X018R-X076D-X101G-X103A-X104I-X232V-X245R-X249R, X020R-X022W-X101G-X103A-X104I-X116A-X183D-X198L-X232V-X245R, X018R-X043R-X045T-X076D-X101G-X103A-X104I-X232V-X245R-X269R, X018R-X024R-X076D-X116A-X198L-X209H-X213A-X249R, X020R-X022W-X101A-X103A-X104I-X116A-X183D-X211Q-X213A-X232V-X245R, X024R-X076D-X101G-X175L-X232V-X245R, X018R-X043D-X045T-X101G-X103A-X104I-X232V-X245R, X045T-X076D-X078R-X101G-X103A-X104I-X232V-X245R, X020R-X078R-X101A-X103A-X104I-X116A-X183D-X198L-X215F-X232V-X245R, X043R-X076D-X101G-

X103A-X104I-X232V-X245R-X249R, X018R-X024R-X076D-X198L-X213A-X215F-X249R, X018R-X022W-X024R-X076D-X198L-X215F-X249R, X018R-X024R-X076D-X116A-X213A-X215F-X249R, X018R-X022W-X024R-X076D-X101A-X116A-X198L-X213A-X215F-X249R, X018R-X022W-X024R-X076D-X116A-X211Q-X213A-X249R, X018R-X024R-X245R, X018R-X022W-X024R-X076D-X101A-X116A-X215F-X249R, X024R-X076D-X104I-X245R, X027R-X043R-X101G-X103A-X104I-X232V-X245R-X269R, X018R-X024R-X076D-X116A-X198L-X211Q-X213A-X249R, X018R-X024R-X076D-X116A-X198L-X249R, X018R-X024R-X076D-X183D-X198L-X211Q-X213A-X215F-X249R, X020R-X022W-X101A-X103A-X104I-X116A-X211Q-X213A-X215F-X232V-X245R, X018R-X043D-X045T-X078R-X101G-X103A-X104I-X232V-X245R, X043R-X045T-X076D-X078R-X101G-X103A-X104I-X232V-X245R-X269R, X018R-X22W-X024R-X076D-X116A-X213A-X215F-X249R, X018R-X022W-X024R-X076D-X116A-X211Q-X215F-X249R, X020R-X078R-X101G-X103A-X104I-X116A-X183D-X213A-X232V-X245R, X018R-X076D-X101G-X103A-X104I-X232V-X245R, X018R-X101G-X104I, X020R-X078R-X101G-X103A-X104I-X116A-X183D-X211Q-X213A-X215F-X232V-X245R, X020R-X078R-X101A-X103A-X104I-X232V-X245R, X018R-X024R-X076D-X101A-X198L-X211Q-X249R, X018R-X024R-X076D-X198L-X211Q-X213A-X249R, X018R-X022W-X024R-X076D-X101A-X116A-X198L-X211Q-X213A-X249R, X018R-X076D-X249R, X018R-X020R-X024R-X076D-X101A-X116A-X183D-X198L-X249R, X018R-X024R-X076D-X101A-X116A-X211Q-X213A-X249R, X020R-X022W-X078R-X101A-X103A-X104I-X116A-X183D-X211Q-X213A-X215F-X232V-X245R, X020R-X022W-X101G-X103A-X104I-X114T-X213A-X215F-X232V-X245R, X018R-X22W-X024R-X076D-X116A-X211Q-X213A-X249R, X018R-X020R-X022W-X024R-X076D-X101A-X116A-X183D-X249R, X020R-X101A-X103A-X104I-X116A-X183D-X213A-X232V-X245R, X018R-X022W-X024R-X076D-X101A-X211Q-X213A-X249R, X018R-X022K-X043D-X101G-X103A-X104I-X232V-X245R, X018R-X101G-X103A-X104I-X232V-X245R-X269R, X020R-X078R-X101G-X103A-X104I-X116A-X183D-X211Q-X213A-X215F-X232V, X018R-X024R-X076D-X116A-X249R, X020R-X024R-X076D-X101G-X103A-X104I-X232V-X245R, X043D-X076D-X101G-X103A-X104I-X232V-X245R-X269R, X018R-X024R-X076D-X101A-X116A-X198L-X211Q-X249R, X018R-X022W-X024R-X076D-X198L-X213A-X215F-X249R, X018R-X043D-X076D-X078R-X101G-X103A-X104I-X232V-X245R-X269R, X020R-X22W-X101G-X103A-X104I-X116A-X183D-X213A-X215F-X232V-X245R, X020R-X101G-X103A-X104I-X183D-X211Q-X232V-X245R-, X018R-X024R-X076D-X101A-X198L-X213A-X249R, X018R-X024R-X076D-X101A-X198L-X249R, X018R-X024R-X045T-X076D-X101G-X103A-X104I-X232V-X245R-X249R, X018R-X024R-X076D-X101A-X183D-X213A-X249R, X018R-X043D-X076D-X078R-X101G-X103A-X104I-X232V-X245R, X020R-X078R-X101G-X103A-X104I-X116A-X131V-X183D-X213A-X232V-X245R, X018R-X045T-X076D-X101G-X103A-X104I-X232V-X245R, X018R-X024R-X076D-X101A-X183D-X211Q-X249R, X076D-X101G-X103A-X104I-X232V-X245R-X249R, X024R-X101G-X245R, X024R-X076D-X101G-X245R, X076D-X078R-X101G-X103A-X104I-X232V-X245R-X249R, X018R-X020R-X024R-X076D-X101A-X183D-X211Q-X215F-X249R, X024R-X101G, X018R-X22W-X024R-X076D-X213A-X215F-X249R, X020R-X043D-X101G-X103A-X104I-X232V-X245R, X020R-X022W-X101G-X103A-X104I-X183D-X198L-X213A-X215F-X232V-X245R, X018R-X043D-X045T-X101G-X103A-X104I-X232V-X245R-X269R, X043D-X076D-X078R-X101G-X103A-X104I-X232V-X245R, X024R-X045T-X076D-X101G-X103A-X104I-X232V-X245R-X269R, X020R-X022W-X101A-X103A-X104I-X198L-X211Q-X215F-X232V-X245R, X020R-X022W-X101G-X103A-X104I-X116A-X183D-X215F-X232V-X245R, X018R-X020R-X076D-X101G-X103A-X104I-X232V-X245R-X249R, X018R-X022W-X024R-X076D-X101A-X215F-X249R, X018R-X104I, X018R-X024R-X076D-X116A-X198L-X215F-X249R, X018R-X024R-X076D-X088I-X101A-X116A-X198L-X211Q-X215F-X249R, X018R-X022W-X024R-X076D-X101A-X116A-X211Q-X213A-X249R, X043R-X045T-X076D-X101G-X103A-X104I-X232V-X245R-X269R, X018R-X076D-X101G-X104I-X249R, X018R-X022W-X024R-X076D-X101A-X213A-X215F-X249R, X018R-X22W-X024R-X076D-X101A-X116A-X198L-X215F-X249R, X018R-X020R-X101G-X103A-X104I-X232V-X245R-X249R, X101G-X103A-X104I-X232V-X245R-X249R-X269R, X024R-X076D-X245R, X018R-X020R-X043R-X045T-X076D-X101G-X103A-X104I-X232V-X245R, X018R-X020R-X024R-X076D-X215F-X249R, X018R-X024R-X076D-X101A-X116A-X183D-X198L-X213A-X249R, X018R-X020R-X024R-X076D-X211Q-X215F-X249R, X043D-X101G-X103A-X104I-X232V-X245R, X020R-X22W-X078R-X101A-X103A-X104I-X116A-X183D-X215F-X232V-X245R, X018R-X024R-X076D-X198L-X211Q-X215F-X249R, X043R-X076D-X078R-X101G-X103A-X104I-X232V-X245R-X269R, X043R-X078R-X101G-X103A-X104I-X232V-X245R-X269R, X020R-X043D-X101G-X103A-X104I-X232V-X245R-X249R, X018R-X022W-X024R-X076D-X101A-X213A-X249R, X020R-X022W-X101A-X116A-X198L-X211Q-X213A-X215F-X249R, X043R-X045T-X078R-X101G-X103A-X104I-X218S-X232V-X245R, X018R-X103A, X020R-X22W-X101G-X103A-X104I-X116A-X183D-X215F-X232V-X245R, X018R-X024R-X076D-X101A-X249R, X018R-X022W-X024R-X076D-X211Q-X213A-X249R, X024R-X043R-X045T-X076D-X101G-X103A-X104I-X232V-X245R, X020R-X022W-X101A-X103A-X104I-X116A-X183D-X232V-X245R, X020R-X101A-X103A-X104I-X116A-X183D-X211Q-X213A-X215F-X232V-X245R, X027R-X045T-X076D-X078R-X101G-X103A-X104I-X232V-X245R-X269R, X020R-X045T-X076D-X101G-X103A-X104I-X232V-X245R-X249R, X018R-X020R-X024R-X076D-X116A-X183D-X213A-X215F-X249R, X018R-X024R-X076D-X104I, X101G-X103A-X104I-X232V-X249R, X018R-X024R-X076D-X116A-X183D-X211Q-X249R, X018R-X020R-X024R-X076D-X116A-X215F-X249R, X018R-X024R-X076D-X183D-X213A-X215F-X249R, X018R-X022W-X024R-X076D-X198L-X211Q-X249R, X043D-X078R-X101G-X103A-X104I-X232V-X245R-X269R-X275S, X020R-X022W-X101A-X103A-X104I-X116A-X183D-X211Q-X232V-X245R, X018R-X022W-X024R-X076D-X101A-X198L-X211Q-X213A-X215F-X249R, X018R-X022W-X024R-X076D-X101A-X116A-X198L-X211Q-X213A-X215F-X249R, X018R-X020R-X024R-X076D-X183D-X249R, X018R-X024R-X076D-X116A-X198L-X213A-X249R, X018R-X022W-X024R-X076D-X101A-X116A-X211Q-X249R, X004M-X018R-X024R-X076D-X116A-X198L-X211Q-X213A-X249R, X104I-X232V-X249R, X020R-X022W-X101G-X103A-X104I-X116A-X183D-X211Q-X215F-X232V-

X245R, X020R-X101A-X103A-X104I-X116A-X183D-X211Q-X232V-X245R-X274I, X020R-X101A-X103A-X104I-X213A-X232V-X245R, X020R-X101G-X103A-X104I-X116A-X183D-X211Q-X213A-X232V-X245R, X020R-X024R-X043D-X078R-X101G-X103A-X104I-X232V-X245R, X018R-X024R-X076D-X103A-X249R, X018R-X020R-X024R-X076D-X101A-X116A-X183D-X211Q-X215F-X249R, X018R-X020R-X024R-X076D-X116A-X183D-X198L-X249R, X018R-X022W-X024R-X076D-X116A-X198L-X215F-X249R, X018R-X024R-X076D-X101A-X211Q-X213A-X215F-X249R-X270V, X018R-X043D-X045T-X076D-X078R-X101G-X103A-X104I-X232V-X245R-X269R, X020R-X022W-X101G-X103A-X104I-X183D-X232V-X245R, X018R-X020R-X022W-X024R-X076D-X101A-X116A-X213A-X249R, X018R-X022W-X024R-X076D-X198L-X211Q-X215F-X249R, X018R-X022W-X024R-X076D-X198L-X213A-X249R, X020R-X022W-X101G-X103A-X104I-X116A-X183D-X232V-X245R, X018R-X22W-X024R-X076D-X116A-X198L-X213A-X249R, X043R-X045T-X078R-X101G-X103A-X104I-X232V-X245R-X269R, X018R-X024R-X076D-X101G-X103A-X104I-X232V, X101G-X249R, X024R-X076D-X101G-X103A-X104I-X175L-X249R, X020R-X022W-X101A-X103A-X104I-X116A-X183D-X232V-X245R-X269S, X018R-X024R-X076D-X101A-X116A-X198L-X249R, X018R-X022W-X024R-X076D-X116A-X249R, X018R-X020R-X024R-X076D-X101A-X183D-X198L-X215F-X249R, X018R-X024R-X076D-X213A-X215F-X249R-X260K, X018R-X024R-X076D-X116A-X211Q-X213A-X249R, X018R-X020R-X022W-X024R-X076D-X116A-X198L-X249R, X024R-X076D-X101G-X103A-X104I-X245R, X024R-X076D-X103A-X249R, X018R-X101G-X103A-X104I-X232V-X245R-X249R, X018R-X024R-X076D-X198L-X211Q-X249R, X018R-X022W-X024R-X076D-X101A-X198L-X211Q-X213A-X249R, X020R-X024R-X045T-X101G-X103A-X104I-X232V-X245R, X018R-X020R-X024R-X076D-X183D-X211Q-X213A-X249R, X018R-X043D-X045T-X078R-X101G-X103A-X104I-X232V-X245R-X272D, X018R-X024R-X076D-X116A-X198L-X213A-X215F-X249R, X018R-X22W-X024R-X076D-X101A-X198L-X249R, X018R-X022W-X024R-X076D-X116A-X198L-X249R, X024R-X076D-X101G-X103A-X232V, X024R-X103A-X104I, X018R-X024R-X076D-X101A-X116A-X183D-X211Q-X215F-X249R, X024R-X045T-X076D-X101G-X103A-X104I-X232V-X245R-X249R, X020R-X101G-X103A-X104I-X116A-X183D-X232V-X245R, X024R-X043D-X076D-X101G-X103A-X104I-X232V-X245R-X269R, X020R-X022W-X101A-X103A-X104I-X183D-X211Q-X213A-X215F-X232V-X245R, X020R-X045T-X076D-X078R-X101G-X103A-X104I-X232V-X245R-X269R, X018R-X024R-X076D-X101A-X116A-X198L-X211Q-X215F-X249R, X020R-X101A-X103A-X104I-X116A-X183D-X215F-X232V-X245R, X018R-X043R-X101G-X103A-X104I-X232V-X245R-X249R, X018R-X024R-X076D-X198L-X213A-X249R, X018R-X024R-X076D-X116A-X183D-X213A-X249R, X020R-X043D-X101G-X103A-X104I-X232V-X245R-X269R, X024R-X076D-X103A-X245R, X018R-X022W-X024R-X076D-X101A-X116A-X211Q-X213A-X215F-X249R, X103A-X104I-X245R, X018R-X022W-X024R-X076D-X211Q-X215F-X249R, X018R-X022W-X024R-X076D-X116A-X183D-X198L-X249R, X018R-X022W-X024R-X076D-X198L-X211Q-X213A-X249R, X018R-X024R-X076D-X116A-X183D-X211Q-X213A-X215F-X249R, X018R-X020R-X043D-X045T-X076D-X101G-X103A-X104I-X232V-X245R-X269R, X018R-X020R-X022W-X024R-X076D-X101A-X211Q-X213A-X215F-X249R, X016T-X043R-X045T-X076D-X101G-X103A-X104I-X232V-X245R-X269R, X018R-X022W-X024R-X076D-X116A-X215F-X249R, X043R-X076D-X101G-X103T-X104I-X232V-X245R-X249R-X269R, X020R-X078R-X101A-X103A-X104I-X115E-X116A-X183D-X211Q-X213A-X232V-X245R, X018R-X024R-X076D-X198L-X249R, X018R-X024R-X076D-X101A-X116A-X183D-X249R, X020R-X101G-X103A-X104I-X116A-X183D-X211Q-X232V-X245R, X018R-X024R-X076D-X101G, X076D-X101G-X232V-X245R, X018R-X076D-X101G-X103A-X104I-X245R, X018R-X045T-X101G-X103A-X104I-X232V-X245R-X249R, X018R-X024R-X076D-X215F-X249R, X018R-X104I-X232V, X043D-X045T-X076D-X078R-X101G-X103A-X104I-X232V-X245R, X024R-X076D-X101G-X232V-X249R, X103A-X232V-X245R, X020R-X101G-X103A-X104I-X116A-X183D-X211Q-X213A-X215F-X232V-X245R, X018R-X020R-X024R-X076D-X116A-X183D-X198L-X211Q-X215F-X249R, X018R-X022W-X024R-X076D-X101A-X198L-X211Q-X215F-X249R, X024R-X076D-X103A-X104I-X249R, X024R-X101G-X103A-X104I, X020R-X101G-X103A-X104I-X116A-X183D-X211Q-X215F-X232V-X245R, X018R-X022W-X024R-X076D-X101A-X116A-X183D-X215F-X249R, X020R-X022W-X101G-X103A-X104I-X116A-X183D-X211Q-X213A-X215F-X232V-X245R, X020R-X024R-X045T-X076D-X101G-X103A-X104I-X232V-X245R, X018R-X022W-X024R-X076D-X116A-X183D-X213A-X249R, X018R-X020R-X024R-X076D-X131T-X215F-X249R, X018R-X024R-X076D-X101A-X116A-X183D-X211Q-X213A-X215F-X249R, X018R-X024R-X076D-X101A-X116A-X211Q-X213A-X215F-X249R, X018R-X024R-X076D-X198L-X215F-X249R, X018R-X022W-X024R-X076D-X183D-X211Q-X249R, X018R-X022W-X024R-X076D-X101A-X116A-X213A-X215F-X249R, X018R-X020R-X024R-X045T-X076D-X101G-X103A-X104I-X232V-X245R, X043R-X101G-X103A-X104I-X245R-X249R, X018R-X076D-X232V-X249R, X018K-X076D-X078R-X101G-X103A-X104I-X217E-X232V-X245R-X269R, X018R-X020R-X024R-X043D-X076D-X078R-X101G-X103A-X104I-X232V-X245R, X018R-X022W-X024R-X076D-X101A-X116A-X213A-X215F-X249R-X267I, X232V-X249R, X018R-X020R-X024R-X076D-X116A-X211Q-X213A-X215F-X249R, X076D-X104I-X245R, X018R-X020R-X024R-X076D-X183D-X198L-X211Q-X215F-X249R, X018R-X024R-X076D-X101A-X211Q-X213A-X249R, X024R-X101G-X103A-X232V, X018R-X020R-X022W-X024R-X076D-X116A-X183D-X198L-X213A-X215F-X249R, X018R-X020R-X024R-X076D-X116A-X183D-X198L-X211Q-X213A-X249R, X018R-X020R-X022W-X024R-X076D-X101A-X215F-X249R, X020R-X022W-X101A-X103A-X104I-X116A-X183D-X211Q-X215F-X232V-X245R, X018R-X024R-X076D-X116A-X198L-X211Q-X249R, X103A-X232V-X249R, X018R-X020R-X024R-X076D-X116A-X183D-X198L-X215F-X249R, X018R-X024R-X076D-X116A-X183D-X198L-X213A-X249R, X018R-X022W-X024R-X076D-X183D-X213A-X249R, X018R-X024R-X076D-X101A-X213A-X215F-X249R, X018R-X022W-X024R-X076D-X101A-X116A-X183D-X211Q-X249R, X018R-X045T-X101G-X103A-X104I-X232V-X245R-X269R, X018R-X020R-X045T-X076D-X078R-X101G-X103A-X104I-X232V-X245R, X018R-X022W-X024R-X076D-X116A-X198L-X213A-X215F-X249R, X020R-X022W-X101G-X103A-X104I-X116A-X183D-X211Q-X213A-X232V-X245R, X018R-X020R-X024R-X076D-X198L-X249R, X018R-

X020R-X022W-X024R-X076D-X101A-X116A-X211Q-X249R, X020R-X022W-X101A-X103A-X104I-X116A-X183D-X232V-X245R-X274I, X024R-X103A-X245R-X249R, X018R-X022W-X024R-X076D-X101A-X116A-X183D-X198L-X249R, X018R-X024R-X076D-X101A-X198L-X211Q-X215F-X249R, X018R-X022W-X024R-X076D-X116A-X198L-X211Q-X215F-X249R, X018R-X020R-X022W-X024R-X076D-X116A-X183D-X213A-X249R, X018R-X043D-X045T-X076D-X101G-X103A-X104I-X232V-X245R-X269R, X018R-X022W-X024R-X076D-X116A-X211Q-X213A-X215F-X249R, X018R-X024R-X076D-X101A-X183D-X198L-X213A-X249R, X043D-X076D-X101G-X103A-X104I-X232V-X245R-X249R, X018R-X024R-X076D-X198L-X211Q-X213A-X215F-X249R, X018R-X020R-X024R-X076D-X116A-X183D-X213A-X249R, X103A-X232V, X018R-X022W-X024R-X076D-X116A-X183D-X215F-X249R, X018R-X024R-X076D-X101A-X116A-X249R, X018R-X043R-X078R-X101G-X103A-X104I-X232V-X245R, X018R-X020R-X022W-X024R-X076D-X101A-X183D-X211Q-X215F-X249R, X043R-X076D-X078R-X101G-X103A-X104I-X232V-X245R-X249R, X018R-X020R-X024R-X076D-X101A-X116A-X183D-X198L-X213A-X249R, X018R-X024R-X076D-X183D-X198L-X213A-X249R, X018R-X022W-X024R-X076D-X101A-X183D-X211Q-X249R, X018R-X020R-X024R-X076D-X198L-X213A-X215F-X249R, X018R-X020R-X022W-X024R-X076D-X183D-X211Q-X213A-X249R, X018R-X022W-X024R-X076D-X198L-X249R, X018R-X024R-X076D-X183D-X198L-X211Q-X249R, X020R-X022W-X101A-X103A-X104I-X116A-X183D-X213A-X232V-X245R, X018R-X020R-X024R-X076D-X116A-X183D-X211Q-X213A-X249R, X018R-X024R-X076D-X116A-X183D-X198L-X211Q-X213A-X215F-X249R, X020R-X022W-X101A-X103A-X104I-X116A-X183D-X215F-X232V-X245R, X018R-X024R-X076D-X101A-X183D-X249R, X018R-X024R-X076D-X232V, X018R-X022W-X024R-X076D-X101A-X116A-X249R, X020R-X101A-X103A-X104I-X116A-X183D-X198L-X211Q-X213A-X215F-X232V-X245R, X020R-X022W-X101G-X103A-X104I-X116A-X183D-X211Q-X232V-X245R-X263S, X024R-X076D-X101G-X104I-X232V-X249R, X043R-X078R-X101G-X103A-X104I-X232V-X245R, X024R-X076D-X078R-X101G-X103A-X104I-X232V-X245R-X249R, X018R-X024R-X076D-X101A-X183D-X198L-X213A-X215F-X249R, X018R-X020R-X024R-X076D-X198L-X215F-X249R, X018R-X020R-X024R-X076D-X101A-X116A-X213A-X249R, X018R-X024R-X076D-X101A-X197A-X213A-X215F-X249R, X024R-X101G-X103A, X018R-X024R-X076D-X101A-X116A-X211Q-X215F-X249R, X043R-X076D-X078R-X101G-X103A-X104I-X217E-X232V-X245R, X024R-X104I-X232V, X018R-X024R-X076D-X183D-X211Q-X249R, X020R-X043R-X045T-X078R-X101G-X103A-X104I-X232V-X245R, X018R-X020R-X022W-X024R-X076D-X101A-X116A-X183D-X213A-X249R, X018R-X024R-X076D-X116A-X150T-X213A-X249R, X018R-X024R-X076D-X183D-X213A-X249R, X018R-X020R-X024R-X076D-X116A-X183D-X211Q-X215F-X249R, X018R-X020R-X024R-X076D-X211Q-X249R, X018R-X024R-X076D-X101A-X116A-X183D-X198L-X249R, X024R-X076D-X232V-X249R, X018R-X020R-X022W-X024R-X076D-X101A-X116A-X183D-X198L-X211Q-X213A-X249R, X018R-X022W-X024R-X076D-X101A-X116T-X198L-X215F-X249R, X018R-X024R-X076D-X183D-X198L-X211Q-X215F-X249R, X018R-X022R-X024R-X076D-X101A-X116A-X183D-X211Q-X249R, X045T-X101G-X103A-X104I-X232V-X245R, X018R-X020R-X024R-X076D-X101A-X183D-X211Q-X249R, X020R-X101G-X103A-X104I-X116A-X183D-X213A-X232V-X245R, X076D-X101G-X103A-X245R, X020R-X043D-X078R-X101G-X103A-X104I-X232V-X245R-X249R, X018R-X024R-X076D-X116A-X183D-X249R, X018R-X024R-X076D-X101A-X183D-X211Q-X213A-X215F-X249R, X018R-X020R-X022W-X024R-X076D-X101A-X116A-X198L-X249R, X018R-X22W-X024R-X076D-X211Q-X213A-X249R, X018R-X020R-X024R-X076D-X183D-X211Q-X249R, X018R-X020R-X024R-X076D-X101A-X116A-X183D-X213A-X249R, X043R-X078R-X101G-X103A-X104I-X217E-X232V-X245R, X018R-X022W-X024R-X076D-X101A-X215F-X249R, X018R-X020R-X024R-X076D-X101A-X183D-X198L-X211Q-X213A-X249R, X076D-X101G-X104I-X249R, X018R-X022W-X024R-X076D-X101A-X116A-X183D-X213A-X249R, X018R-X024R-X076D-X183D-X249R, X018R-X024R-X076D-X101A-X183D-X198L-X215F-X249R, X018R-X022W-X024R-X076D-X183D-X198L-X215F-X249R, X018R-X022W-X024R-X076D-X101A-X198L-X211Q-X249R, X020R-X101A-X103A-X104I-X116A-X183D-X232V-X245R, X018R-X024R-X076D-X116A-X183D-X198L-X211Q-X249R, X018R-X020R-X024R-X101G-X103A-X104I-X232V-X245R, X018R-X076D-X078R-X101G-X103A-X104I-X217E-X232V-X245R, X020R-X101A-X103A-X104I-X116A-X183D-X211Q-X232V-X245R, X018R-X022W-X024R-X076D-X101A-X183D-X198L-X209H-X249R, X018R-X024R-X076D-X183D-X198L-X213A-X215F-X249R, X018R-X024R-X076D-X101A-X116A-X183D-X211Q-X213A-X249R, X018R-X022W-X024R-X076D-X101A-X116A-X183D-X211Q-X213A-X249R, X018R-X024R-X076D-X183D-X198L-X249R, X018R-X024R-X076D-X183D-X215F-X249R, X018R-X020R-X024R-X076D-X211Q-X213A-X215F-X249R, X076D-X245R, X076D-X101G-X104I-X245R, X018R-X022W-X024R-X076D-X101A-X211Q-X215F-X249R, X018R-X022W-X024R-X076D-X101A-X116A-X183D-X211Q-X215F-X249R, X018R-X020R-X022W-X024R-X076D-X101A-X211Q-X213A-X249R, X020R-X024R-X043R-X101G-X103A-X104I-X232V-X245R, X018R-X024R-X076D-X116A-X183D-X211Q-X215F-X249R, X020R-X101A-X103A-X104I-X116A-X183D-X213A-X215F-X232V-X245R, X101G-X103A-X104I, X018R-X020R-X024R-X076D-X101A-X116A-X183D-X211Q-X213A-X249R, X018R-X020R-X024R-X076D-X204D-X213A-X249R, X018R-X022W-X024R-X076D-X183D-X198L-X249R, X018R-X024R-X076D-X101A-X116A-X183D-X215F-X249R, X018R-X022W-X024R-X076D-X116A-X183D-X198L-X211Q-X213A-X209V-X249R, X018R-X022W-X024R-X076D-X101A-X116A-X183D-X211Q-X213A-X215F-X249R, X018R-X024R-X076D-X101A-X116A-X198L-X213A-X249R, X018R-X020R-X024R-X076D-X101A-X116A-X211Q-X213A-X249R, X018R-X020R-X022W-X024R-X076D-X101A-X116A-X183D-X211Q-X213A-X215F-X249R, X018R-X024R-X076D-X101A-X116A-X183D-X213A-X215F-X249R, X018R-X024R-X076D-X101A-X183D-X198L-X211Q-X213A-X215F-X249R, X018R-X024R-X076D-X101A-X183D-X198L-X211Q-X213A-X249R, X018R-X043R-X045T-X078R-X101G-X103A-X104I-X217E-X232V-X245R, X018R-X024R-X076D-X183D-X211Q-X213A-X215F-X249R, X018R-X022W-X024R-X076D-X116A-X183D-X198L-X215F-X249R, X018R-X020R-X024R-X076D-X116A-X249R, X018R-X020R-X022W-X024R-X076D-X101A-X211Q-X215F-X249R, X018R-X020R-X024R-X076D-X183D-X211Q-X213A-X215F-X249R, X018R-

X020R-X022W-X024R-X076D-X198L-X213A-X249R, X018R-X020R-X024R-X076D-X101A-X211Q-X215F-X249R-X269D, X018R-X020R-X043D-X101G-X103A-X104I-X232V-X245R-X269R, X018R-X022W-X024R-X076D-X101A-X183D-X198L-X213A-X249R, X020R-X022W-X101G-X103A-X104I-X183D-X215F-X232V-X245R, X018R-X022W-X024R-X076D-X116A-X183D-X198L-X209H-X211Q-X249R, X018R-X020R-X022W-X024R-X076D-X101A-X116A-X183D-X211Q-X249R, X076D-X232V-X245R, X043D-X045T-X078R-X101G-X103A-X104I-X232V-X245R, X018R-X020R-X024R-X076D-X116A-X198L-X211Q-X215F-X245R, X018R-X020R-X022W-X024R-X076D-X213A-X249R, X020R-X024R-X043D-X078R-X101G-X103A-X104I-X232V-X245R-X249R, X018R-X020R-X022W-X024R-X076D-X101A-X198L-X215F-X249R, X020R-X090S-X101G-X103A-X104I-X116A-X183D-X213A-X215F-X232V-X245R, X018R-X020R-X022W-X024R-X076D-X101A-X198L-X211Q-X213A-X215F-X249R, X018R-X020R-X024R-X076D-X101A-X183D-X213A-X215F-X249R, X018R-X024R-X076D-X116A-X183D-X198L-X211Q-X213A-X249R, X043D-X045T-X078R-X101G-X103A-X104I-X232V-X245R-X269R, X018R-X024R-X076D-X101A-X183D-X215F-X249R, X018R-X020R-X024R-X076D-X101A-X183D-X198L-X213A-X249R, X020R-X022W-X101A-X103A-X104I-X116A-X183D-X198L-X211Q-X213A-X215F-X232V-X245R, X018R-X020R-X024R-X043D-X076D-X101G-X103A-X104I-X232V-X245R-X269R, X018R-X024R-X076D-X101A-X183D-X213A-X215F-X249R, X018R-X020R-X022W-X024R-X076D-X101A-X116A-X198L-X211Q-X213A-X215F-X249R, X018R-X020R-X043D-X101G-X103A-X104I-X217E-X232V-X245R, X076D-X103A-X104I-X232V-X245R, X045T-X076D-X078R-X101G-X103A-X104I-X232V-X245R-X249R, X018R-X022W-X024R-X076D-X101A-X183D-X211Q-X215F-X249R, X018R-X022W-X024R-X076D-X101A-X116A-X183D-X249R, X018R-X024R-X076D-X116A-X183D-X198L-X211Q-X215F-X249R, X018R-X020R-X043D-X076D-X078R-X101G-X103A-X104I-X217E-X232V-X245R, X076D-X103A-X104I-X245R, X018R-X020R-X024R-X076D-X101A-X116A-X211Q-X213A-X215F-X249R, X018R-X024R-X076D-X101A-X183D-X198L-X249R, X018R-X022W-X024R-X076D-X116A-X183D-X198L-X211Q-X215F-X249R, X018R-X024R-X076D-X116A-X183D-X213A-X215F-X249R, X018R-X022W-X024R-X076D-X116A-X183D-X198L-X211Q-X249R, X018R-X024R-X076D-X101G-X245R, X018R-X024R-X076D-X101A-X116A-X183D-X198L-X213A-X215F-X249R, X043R-X045T-X076D-X101G-X103A-X104I-X232V-X245R, X018R-X020R-X022W-X024R-X076D-X116A-X198L-X213A-X215F-X249R, X076D-X104I-X232V-X245R, X027R-X043R-X045T-X076D-X101G-X103A-X104I-X232V-X245R, X018R-X022W-X024R-X076D-X101A-X183D-X213A-X215F-X249R, X018R-X024R-X076D-X103A-X104I-X135I-X232V, X018R-X020R-X022W-X024R-X076D-X183D-X198L-X211Q-X249R, X018R-X020R-X022W-X024R-X076D-X101A-X116A-X183D-X198L-X215F-X249R, X018R-X024R-X076D-X101A-X116A-X183D-X211Q-X249R, X018R-X022W-X024R-X076D-X183D-X211Q-X213A-X215F-X249R, X076D-X101G-X103A-X104I-X232V-X249R, X005S-X018R-X022W-X024R-X076D-X101A-X213A-X215F-X249R, X018R-X024R-X076D-X116A-X183D-X215F-X249R, X018R-X024R-X076D-X183D-X198L-X215F-X249R, X018R-X020R-X024R-X076D-X101A-X116A-X183D-X249R, X018R-X022W-X024R-X076D-X116A-X183D-X211Q-X249R, X018R-X020R-X022W-X024R-X076D-X101A-X116A-X249R, X018R-X022W-X024R-X076D-X101A-X116A-X183D-X198L-X213A-X249R, X018R-X022W-X024R-X076D-X101A-X183D-X211Q-X213A-X249R, X018R-X020R-X024R-X076D-X116A-X198L-X249R, X018R-X024R-X076D-X183D-X211Q-X213A-X249R, X018R-X024R-X076D-X101A-X116A-X183D-X213A-X249R, X018R-X024R-X076D-X116A-X183D-X198L-X215F-X249R, X018R-X022W-X024R-X076D-X183D-X198L-X211Q-X215F-X249R, X018R-X022W-X024R-X076D-X183D-X249R, X018R-X022W-X024R-X076D-X101A-X183D-X198L-X215F-X249R, X018R-X020R-X043D-X045T-X076D-X101G-X103A-X104I-X232V-X245R, X020R-X022W-X101A-X103A-X104I-X183D-X198L-X215F-X232V-X245R, X076D-X101G-X103A-X104I-X249R, X018R-X020R-X024R-X076D-X183D-X198L-X215F-X249R, X018R-X020R-X022W-X024R-X076D-X101A-X183D-X215F-X249R, X018R-X020R-X024R-X076D-X211Q-X213A-X249R, X018R-X024R-X076D-X116A-X183D-X211Q-X213A-X249R, X018R-X024R-X076D-X116A-X183D-X198L-X249R, X018R-X020R-X024R-X076D-X211Q-X243D-X249R, X018R-X020R-X045T-X076D-X101G-X103A-X104I-X232V-X245R-X249R, X018R-X022W-X024R-X076D-X183D-X198L-X211Q-X213A-X249R, X018R-X024R-X076D-X101A-X116A-X183D-X198L-X211Q-X213A-X249R, X018R-X022W-X024R-X076D-X116A-X198L-X211Q-X213A-X215F-X249R, X024R-X076D-X101G, X018R-X020R-X024R-X076D-X101A-X198L-X213A-X215F-X249R, X018R-X022W-X024R-X076D-X116A-X183D-X211Q-X213A-X249R, X018R-X020R-X024R-X076D-X183D-X215F-X249R, X018R-X043D-X076D-X078R-X101G-X103A-X104I-X232V-X245R-X249R, X018R-X022W-X024R-X076D-X116A-X183D-X211Q-X213A-X245R, X020R-X024R-X076D-X078R-X101G-X103A-X104I-X232V-X245R-X249R, X018R-X020R-X045T-X101G-X103A-X104I-X232V-X245R-X249R, X018R-X024R-X076D-X101A-X183D-X198L-X211Q-X249R, X018R-X022W-X024R-X076D-X183D-X211Q-X213A-X249R, X018R-X020R-X024R-X076D-X116A-X198L-X211Q-X215F-X249R-X269S, X018R-X020R-X022W-X024R-X076D-X101A-X116A-X183D-X198L-X211Q-X215F-X249R, X020R-X022W-X101A-X103A-X104I-X183D-X213A-X215F-X232V-X245R, X018R-X024R-X076D-X086V-X101A-X183D-X198L-X211Q-X249R, X018R-X076D-X101G-X198T-X232V, X018R-X020R-X024R-X076D-X101A-X116A-X183D-X198L-X211Q-X215F-X249R, X018R-X022W-X024R-X076D-X101A-X116A-X183D-X213A-X215F-X249R, X018R-X022W-X024R-X076D-X101A-X183D-X211Q-X213A-X215F-X249R, X018R-X024R-X076D-X183D-X249R-X248T, X018R-X076D-X104I-X245R-X249R, X018R-X022W-X024R-X076D-X101A-X116A-X183D-X198L-X215F-X249R, X018R-X022W-X024R-X076D-X116A-X183D-X213A-X215F-X249R, X018R-X020R-X022W-X024R-X076D-X116A-X183D-X211Q-X213A-X215F-X249R, X018R-X020R-X024R-X076D-X101A-X249R, X018R-X020R-X024R-X076D-X101A-X116A-X213A-X215F-X249R, X018R-X022W-X024R-X076D-X116A-X183D-X211Q-X215F-X249R, X018R-X022W-X024R-X076D-X116A-X183D-X198L-X211Q-X213A-X249R, X043R-X045T-X078R-X101G-X103A-X104I-X217E-X232V-X245R, X043R-X045T-X101G-X103A-X104I-X232V-X245R-X249R, X018R-X076D-X101G-X104I, X020R-X045T-X076D-X078R-X101G-X103A-X104I-X232V-X245R-X249R, X043D-X076D-X101G-X103A-X104I-X232V-X245R, X018R-X020R-X022W-X024R-X076D-

X101A-X116A-X183D-X198L-X249R, X018R-X076D-X104I, X018R-X020R-X043D-X101G-X103A-X104I-X232V-X245R-X249R, X018R-X020R-X022W-X024R-X076D-X183D-X211Q-X249R, X018R-X024R-X076D-X101A-X183D-X198L-X211Q-X215F-X249R, X101G-X104I, X018R-X022W-X024R-X076D-X116A-X183D-X198L-X211Q-X213A-X215F-X249R, X018R-X020R-X024R-X076D-X101A-X183D-X211Q-X213A-X215F-X249R, X018R-X020R-X024R-X076D-X116A-X183D-X215F-X249R-X263D, X018R-X022W-X024R-X076D-X101A-X183D-X249R, X018R-X024R-X076D-X101A-X116A-X183D-X198L-X215F-X249R, X018R-X022W-X024R-X076D-X116A-X198L-X215F-X249R-X269H, X018R-X043D-X045T-X076D-X078R-X101G-X103A-X104I-X232V-X245R, X018R-X024R-X045T-X076D-X078R-X101G-X103A-X104I-X232V-X245R-X269R, X078R-X101G-X103A-X104I-X217E-X232V-X245R, X018R-X020R-X022W-X024R-X076D-X101A-X183D-X198L-X213A-X215F-X249R, X018R-X020R-X024R-X076D-X183D-X198L-X213A-X249R, X018R-X020R-X022W-X024R-X076D-X116A-X198L-X211Q-X215F-X249R, X018R-X020R-X022W-X024R-X076D-X116A-X183D-X211Q-X249R, X018R-X020R-X022W-X024R-X076D-X101A-X198L-X211Q-X213A-X249R, X018R-X020R-X022W-X024R-X076D-X249R, X020R-X022W-X101G-X103A-X104I-X116A-X183D-X198L-X211Q-X213A-X215F-X232V-X245R, X104I-X232V, X018R-X020R-X022W-X024R-X076D-X101A-X116A-X183D-X211Q-X215F-X249R, X018R-X020R-X022W-X024R-X076D-X101A-X116A-X183D-X198L-X211Q-X213A-X215F-X249R, X018R-X020R-X022W-X024R-X076D-X101A-X183D-X213A-X215F-X249R, X018R-X022W-X024R-X076D-X101A-X183D-X198L-X211Q-X213A-X249R, X018R-X022W-X024R-X076D-X101A-X183D-X198L-X249R, X043D-X045T-X101G-X103A-X104I-X232V-X245R-X269R, X018R-X020R-X024R-X076D-X101A-X183D-X198L-X211Q-X249R, X018R-X020R-X043R-X101G-X103A-X104I-X217E-X232V-X245R, X024R-X043R-X076D-X078R-X101G-X103A-X104I-X232V-X245R-X269R, X043R-X045T-X076D-X078R-X101G-X103A-X104I-X166F-X176P-X179V-X184T-X187P-X194P, X018R-X022W-X024R-X041E-X076D-X101A-X160T-X183D-X211Q-X213A-X249R, X018R-X020R-X022W-X024R-X076D-X116A-X183D-X198L-X211Q-X215F-X249R, X018R-X020R-X022W-X024R-X076D-X101A-X116A-X198L-X213A-X249R, X018R-X022W-X024R-X076D-X101A-X116A-X183D-X198L-X211Q-X213A-X249R, X018R-X020R-X024R-X076D-X198L-X213A-X249R, X018R-X020R-X022W-X024R-X076D-X116A-X183D-X198L-X211Q-X249R, X018R-X020R-X024R-X076D-X183D-X211Q-X215F-X249R, X024R-X076D-X104I, X018R-X076D-X101G-X232V, X018R-X024R-X076D-X101A-X116A-X183D-X198L-X211Q-X213A-X215F-X249R, X018R-X020R-X022W-X024R-X076D-X116A-X183D-X215F-X249R, X018R-X024R-X031F-X076D-X116A-X183D-X211Q-X213A-X215F-X249R, X018R-X024R-X076D-X101A-X116A-X183D-X198L-X213A-X249R-X269S, X018R-X020R-X024R-X076D-X101A-X116A-X198L-X215F-X249R, X018R-X043R-X076D-X078R-X101G-X103A-X104I-X232V-X245R-X269R, X018R-X020R-X024R-X076D-X101A-X114T-X198L-X211Q-X215F-X249R, X024R-X043R-X078R-X101G-X103A-X104I-X217E-X232V-X245R, X024R-X076D-X103A-X104I-X232V, X018R-X020R-X022W-X024R-X076D-X101A-X198L-X211Q-X215F-X249R, X101G-X104I-X232V, X018R-X022W-X024R-X076D-X183D-X198L-X213A-X215F-X249R, X018R-X022W-X024R-X076D-X183D-X198L-X211Q-X249R, X018R-X020R-X024R-X076D-X183D-X213A-X249R, X018R-X024R-X076D-X101A-X183D-X211Q-X215F-X249R, X018R-X020R-X022W-X024R-X076D-X116A-X211Q-X213A-X249R, X018R-X078R-X101G-X103A-X104I-X232V-X245R-X269R, X018R-X022W-X024R-X076D-X101A-X116A-X183D-X211Q-X215F-X249R-X260A, X076D-X249R, X018R-X022W-X024R-X076D-X183D-X211Q-X215F-X249R, X018R-X020R-X024R-X076D-X116A-X211Q-X215F-X249R, X018R-X020R-X024R-X076D-X213A-X249R, X018R-X020R-X022W-X024R-X076D-X116A-X183D-X198L-X249R, X018R-X020R-X022W-X024R-X076D-X101A-X183D-X249R, X076D-X104I-X249R, X020R-X022W-X101A-X103A-X104I-X116A-X183D-X211Q-X213A-X215F-X232V-X245R, X024R-X043R-X045T-X078R-X101G-X103A-X104I-X217E-X232V-X245R, X018R-X020R-X022W-X024R-X076D-X183D-X198L-X215F-X249R, X018R-X076D-X101G-X103A, X020R-X024R-X101G-X103A-X104I-X232V-X245R-X269R, X018R-X020R-X024R-X076D-X101A-X116A-X183D-X211Q-X249R, X101G-X103A-X232V, X024R-X076D-X101G-X232V, X018R-X022W-X024R-X076D-X101A-X183D-X198L-X211Q-X249R, X018R-X020R-X024R-X076D-X101A-X183D-X198L-X211Q-X215F-X249R, X018R-X020R-X024R-X076D-X183D-X198L-X249R, X018R-X022W-X024R-X076D-X101A-X116A-X183D-X198L-X211Q-X249R, X018R-X020R-X024R-X076D-X116A-X156V-X183D-X211Q-X215F-X249R-X269S, X045T-X076D-X101G-X103A-X104I-X232V-X245R-X249R, X018R-X020R-X024R-X076D-X101A-X183D-X198L-X249R, X018R-X020R-X022W-X024R-X076D-X198L-X211Q-X215F-X249R, X018R-X020R-X022W-X024R-X076D-X101A-X116A-X198L-X211Q-X215F-X249R, X018R-X020R-X022W-X024R-X076D-X116A-X249R, X018R-X076D-X101G, X018R-X024R-X076D-X116A-X183D-X198L-X213A-X215F-X249R, X018R-X020R-X022W-X024R-X076D-X101A-X116A-X198L-X213A-X215F-X249R, X018R-X024R-X076D-X101A-X116A-X183D-X198L-X211Q-X249R, X018R-X076D-X232V, X018R-X020R-X024R-X076D-X101A-X232V-X245R, X018R-X043D-X045T-X076D-X101G-X103A-X104I-X232V-X245R, X018R-X022W-X024R-X076D-X183D-X213A-X215F-X249R, X018R-X024R-X076D-X101A-X116A-X211Q-X213A-X237D-X249R, X018R-X020R-X024R-X076D-X101A-X116A-X183D-X211Q-X249R-X275S, X018R-X022W-X024R-X076D-X101A-X116A-X183D-X198L-X211Q-X213A-X215F-X249R, X024R-X076D, X018R-X024R-X076D-X183D-X211Q-X215F-X249R, X018R-X022W-X024R-X076D-X116A-X183D-X198L-X213A-X215F-X249R, X076D-X104I-X232V-X249R, X018R-X076D-X103A-X232V, X018R-X020R-X024R-X076D-X101A-X116A-X183D-X198L-X211Q-X213A-X249R, X018R-X020R-X024R-X076D-X101A-X183D-X213A-X249R, X018R-X020R-X024R-X076D-X101A-X175E-X183D-X211Q-X215F-X249R, X018R-X020R-X043D-X078R-X101G-X103A-X104I-X217E-X232V-X245R-X273E, X020R-X024R-X043D-X045T-X076D-X101G-X103A-X104I-X232V-X245R, X005S-X101G-X103A-X104I-X232V-X245R-X249R, X103A-X104I-X232V, X018R-X020R-X024R-X068A-X076D-X101A-X116A-X213A-X215F-X249R, X018R-X022W-X024R-X076D-X101A-X198L-X215F-X249R-X275 S, X018R-X024R-X076D-X183D-X198L-X211Q-X213A-X249R, and X043D-X045T-X101G-X103A-X104I-X232V-X245R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X018R-X024R-X043R-X076D-X249R-X269R, X018R-X022R-X024R-X043R-X076D-X249R, X018R-X043D-X101G-X103A-X104I-X232V-X245R, X020R-X043D-X101G-X103A-X104I-X232V-X245R, X043D-X101G-X103A-X104I-X232V-X245R-X269R, X043D-X078R-X101G-X103A-X104I-X232V-X245R, X043R-X076D-X101G-X103A-X104I-X232V-X245R, X022R-X043R-X101G-X103A-X104I-X232V-X245R, X043R-X078R-X101G-X103A-X104I-X232V-X245R, X020R-X076D-X101G-X103A-X104I-X232V-X245R, X043R-X076D-X101G-X103A-X104I-X232V-X245R, X022R-X076D-X101G-X103A-X104I-X232V-X245R, X076D-X078R-X101G-X103A-X104I-X232V-X245R, X018R-X024R-X043R-X076D-X249R, X018R-X024R-X076D-X242R-X249R, X018R-X024R-X076D-X249R-X269R, X018R-X022R-X024R-X076D-X249R, X018R-X024R-X076D-X078R-X249R, X018R-X024R-X043D-X076D-X249R-X269R, X018R-X022R-X024R-X043D-X076D-X249R, X018R-X024R-X043D-X076D-X078R-X249R, X020R-X101G-X103G-X104I-X232V-X245R, X020R-X101G-X103A-X104L-X232V-X245R, X020R-X101G-X103A-X104V-X232V-X245R, X020R-X101G-X103S-X104I-X232V-X245R, X020R-X101G-X103S-X104L-X232V-X245R, X020R-X101S-X103S-X104I-X232V-X245R, X020R-X101S-X103S-X104L-X232V-X245R, X020R-X101A-X103A-X104L-X232V-X245R, X020R-X101S-X103 S-X104V-X232V-X245R, X020R-X101S-X103A-X104I-X232V-X245R, X020R-X101S-X103A-X104V-X232V-X245R, X020R-X101S-X103G-X104I-X232V-X245R, X020R-X101S-X103G-X104V-X232V-X245R, X020R-X101A-X103A-X104V-X232V-X245R, X020R-X101A-X103S-X104I-X232V-X245R, X020R-X101A-X103 S-X104V-X232V-X245R, X018R-X024R-X043R-X076D-X078R-X249R, X024R-X043D-X101G-X103A-X104I-X232V-X245R, X043D-X101G-X103A-X104I-X232V-X245R-X249R, X024R-X076D-X101G-X103A-X104I-X232V-X245R, X076D-X101G-X103A-X104I-X232V-X242R-X245R, X018R-X020R-X024R-X076D-X217E-X249R, X018R-X024R-X043R-X076D-X217E-X249R, X018R-X024R-X043D-X076D-X242R-X249R, X018R-X020R-X024R-X043R-X076D-X249R, X020R-X101A-X103G-X104V-X232V-X245R, X043D-X101G-X103A-X104I-X232V-X245R, X018R-X024R-X076D-X217E-X249R-X269R, and X018R-X024R-X076D-X217E-X242R-X249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X020R-X101A-X103A-X104I-X118R-X232V-X245R, X020R-X024R-X116A-X213A, X043R-X101A-X116A-X215F-X269R, X024R-X043R-X101A-X116A, X024R-X043R-X101A-X116A-X215F-X269R, X020R-X101G-X103A-X104I-X215F-X232V-X245R, X043R-X101A-X269R, X024R-X043R-X116A-X213A-X269R, X020R-X024R-X043R-X045T-X101A-X213A, X024R-X043R-X116A-X215F-X269R, X020R-X024R-X213A-X215F, X020R-X116A-X269R, X024R-X116A-X213A-X269R, X043R-X101A-X116A-X269R, X101G-X103A-X104I-X116A-X213A-X232V-X245R-X269R, X024R-X043R-X045T-X101A-X116A-X215F-X269R, X020R-X043R-X101A-X269R, X101A-X103A-X104I-X213A-X232V-X245R-X269R, X024R-X215F-X269R, X043R-X101A-X116A-X213A-X215F-X269R, X043R-X101A-X213A-X269R, X020R-X024R-X043R-X045T-X116A-X213A, X101G-X103A-X104I-X232V-X245R-X269R, X024R-X043R-X045T-X101A-X116A-X213A-X269R, X024R-X043R-X045T-X269R, X020R-X043R-X045T-X101A-X269R, X024R-X043R-X116A-X269R, X020R-X024R-X043R-X045T, X043R-X116A-X269R, X024R-X043R-X101A-X215F-X269R, X024R-X043R-X045T-X213A-X215F-X269R, X020R-X024R-X045T-X269R, X020R-X043R-X101A-X116A-X213A-X215F, X020R-X101G-X103A-X104I-X213A-X215F-X232V-X245R, X020R-X024R-X045T-X116A-X269R, X020R-X101A-X116A-X269R, X024R-X043R-X215F, X020R-X024R-X213A, X024R-X043R-X101A-X215F, X020R-X024R-X043R-X045T-X116A, X020R-X024R-X043R-X045T-X101A-X269R, X020R-X024R-X101A-X215F, X020R-X024R-X116A-X213A-X215F, X020R-X024R-X116A, X020R-X024R-X101A-X116A, X043R-X213A-X215F-X269R, X024R-X101A-X269R, X024R-X043R-X116A-X215F, X020R-X038A-X043R-X101A, X020R-X024R-X116A-X215F, X024R-X043R-X101A-X213A, X014L-X020R-X024R-X043R-X045T-X101A-X215F, X020R-X024R-X215F, X020R-X116A-X215F-X269R, X020R-X045T-X116A-X269R, X020R-X024R-X043R-X045T-X215F, and X020R-X024R-X043R-X045T-X116A-X213A-X215F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X043R-X076D-X101A-X103A-X104I-X158E-X188D-X232V-X245R-X248D-X249R-X271F, X024R-X043R-X076D-X101A-X103A-X104I-X158E-X188D-X217E-X232V-X245R-X248D-X249R, X101A-X103A-X104I-X158E-X188D-X232V-X245R-X248D-X249R-X271F-X271F, X101A-X103A-X104I-X158E-X188D-X217E-X232V-X245R-X248D-X249R-X271F, X076D-X101G-X103A-X104I-X114V-X158E-X188D-X232V-X245R-X248D-X249R-X271F, X024R-X076D-X101G-X103A-X104I-X158E-X188D-X232V-X245R-X248D-X249R-X271F, X024R-X043R-X101A-X103A-X104I-X158E-X188D-X217E-X232V-X245R-X248D-X249R, X024R-X043R-X101A-X103A-X104I-X158E-X188D-X232V-X245R-X248D-X249R, X024R-X101A-X103A-X104I-X158E-X166D-X188D-X217E-X232V-X245R-X248D-X249R, X076D-X101G-X103A-X104I-X128L-X158E-X188D-X232V-X245R-X248D-X249R-X271F, and X043R-X076D-X101G-X103A-X104I-X158E-X166D-X188D-X232V-X245R-X248D-X249R-X271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X022A-X101G-X103A-X104I-

X159D-X217E-X232V-X245R-X248D-X271F, X022A-X043R-X101G-X103A-X104I-X159D-X188D-X217E-X232V-X245R-X248D-X271F, X022A-X101G-X103A-X104I-X159D-X188D-X232V-X245R-X248D-X271F, X043R-X101A-X103A-X104I-X158E-X188D-X217E-X232V-X245R-X248D-X249R, X043R-X076D-X101A-X103A-X104I-X158E-X188D-X217E-X232V-X245R-X248D-X249R-X271F, X024R-X101G-X103A-X104I-X158E-X188D-X217E-X232V-X245R-X248D-X249R, X024R-X101G-X103A-X104I-X158E-X188D-X232V-X245R-X248D-X249R, X101G-X103A-X104I-X158E-X188D-X232V-X245R-X248D-X249R, X024R-X101G-X103A-X104I-X158E-X183D-X188D-X232V-X245R-X248D-X249R, X022A-X076D-X101G-X103A-X104I-X159D-X188D-X232V-X245R-X248D-X271F, X022A-X043R-X076D-X101G-X103A-X104I-X159D-X188D-X232V-X245R-X248D-X271F, X022A-X076D-X101G-X103A-X104I-X159D-X232V-X245R-X248D-X271F, X022A-X101G-X103A-X104I-X159D-X232V-X245R-X248D-X271F, X076D-X101A-X103A-X104I-X158E-X188D-X232V-X245R-X248D-X249R-X271F, X043R-X101A-X103A-X104I-X158E-X166D-X188D-X232V-X245R-X248D-X249R, X024R-X076D-X101A-X103A-X104I-X158E-X166D-X188D-X232V-X245R-X248D-X249R-X271F, X076D-X101A-X103A-X104I-X158E-X188D-X232V-X245R-X248D-X249R, X101A-X103A-X104I-X158E-X166D-X188D-X232V-X245R-X248D-X249R-X271F, X043R-X076D-X101A-X103A-X104I-X158E-X166D-X188D-X232V-X245R-X248D-X249R-X271F, X101G-X103A-X104I-X158E-X166D-X188D-X232V-X245R-X248D-X249R-X271F, X101A-X103A-X104I-X158E-X188D-X232V-X245R-X248D-X249R-X271F, X101A-X103A-X104I-X158E-X188D-X217E-X232V-X245R-X248D-X249R, X076D-X101A-X103A-X104I-X158E-X166D-X188D-X232V-X245R-X248D-X249R-X271F, X101G-X103A-X104I-X158E-X183D-X188D-X232V-X245R-X248D-X249R, X024R-X101G-X103A-X104I-X128L-X158E-X188D-X232V-X245R-X248D-X249R, X076D-X101G-X103A-X104I-X158E-X166D-X188D-X232V-X245R-X248D-X249R-X271F, X043R-X076D-X101A-X103A-X104I-X158E-X166D-X188D-X232V-X245R-X248D-X249R, and X076D-X101A-X103A-X104I-X158E-X188D-X217E-X232V-X245R-X248D-X249R-X271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X017R-X022A-X076D-X101G-X103A-X104I-X159D-X188D-X232V-X245R-X248D-X271F, X022A-X043R-X101G-X103A-X104I-X159D-X232V-X245R-X248D-X271F, X022A-X101G-X103A-X104I-X159D-X188D-X232V-X245R-X248D-X249R-X271F, X017R-X022A-X076D-X101G-X103A-X104I-X159D-X232V-X245R-X248D-X271F, X022A-X076D-X101G-X103A-X104I-X159D-X232V-X245R-X248D-X249R-X271F, X022A-X101G-X102A-X103A-X104I-X159D-X188D-X232V-X245R-X248D-X271F, and X022A-X043R-X076D-X101G-X103A-X104I-X159D-X232V-X245R-X248D-X249R-X271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X101S-X103A-X104I-X158E-X188D-X232V-X245R-X248D-X249R, X101 S-X103G-X104V-X158E-X188D-X232V-X245R-X248D-X249R, X101G-X103S-X104I-X158E-X188D-X232V-X245R-X248D-X249R, X101A-X103A-X104I-X158E-X188D-X232V-X245R-X248D-X249R, X101A-X103A-X104L-X158E-X188D-X232V-X245R-X248D-X249R, X101G-X103G-X104I-X158E-X188D-X232V-X245R-X248D-X249R, X101S-X103G-X104I-X158E-X188D-X232V-X245R-X248D-X249R, X101S-X103S-X104I-X158E-X188D-X232V-X245R-X248D-X249R, X101S-X103S-X104V-X158E-X188D-X232V-X245R-X248D-X249R, X101A-X103 S-X104I-X158E-X188D-X232V-X245R-X248D-X249R, X101A-X103S-X104I-X159E-X232V-X245R-X248D-X249R, X101S-X103A-X104I-X159E-X232V-X245R-X248D-X249R, X101G-X103A-X104L-X158E-X188D-X232V-X245R-X248D-X249R, X101A-X103A-X104L-X159E-X232V-X245R-X248D-X249R, X101A-X103S-X104L-X159E-X232V-X245R-X248D-X249R, X101G-X103S-X104L-X159E-X232V-X245R-X248D-X249R, X101 S-X103A-X104L-X159E-X232V-X245R-X248D-X249R, X101A-X103G-X104V-X159E-X232V-X245R-X248D-X249R, and X101S-X103A-X104V-X159E-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X026F-X051W-X104L-X106E, X026F-X031F-X078N-X102A-X160D, X020K-X100S-X116L-X158E-X166D-X243F, X033S-X043W-X218D-X239G-X243F, X022L-X038F-X048R-X062E-X100S-X186K, X101D-X103N-X116L-X144R-X215D, X104L-X105T-X213A-X217E-X256N, X043W-X101D-X212M-X243F, X026F-X048R-X105T-X213A-X218D-X224A, X024F-X101D-X118R-X215D-X250I-X272F, X121F-X185E-X224A-X239G, X022L-X031F-X102A-X128D-X224A-X243F, X062E-X078N-X102A-X116L-X144R-X250I, X022L-X038F-X121F-X160D-X272F, X026F-X078N-X159C-X186K-X243F, X024F-X048R-X118R-X166D-X217E, X023A-X038F-X078N-X100S-X212M-X215D, X100S-X116L-X158E-X213A, X078N-X104L-X118R-X128D, X102A-X103N-X105T-X194E, X022L-X078N-X128D-X213A, X027R-X100S-X118R-X160D-X188D-X243F, X024F-X102A-X186K-X213A-X217E-X243F, X033 S-X105T-X188D-X216F, X023A-X100S-X194E-X212M, X048R-X128D-X185E-X239G, X020K-X024F-X033 S-X129E-X194E, X020K-X027R-X129E-X166D-X239G, X022L-X023A-X027R-X101D-X104L-X216F, X033S-X118R-X129E-X194E-X239G, X022L-X078N-X116L-X129E-X256N, X027R-X101D-X103N-X105T-X272F, X048R-X078N-X116L-X185E-X217E-X239G, X023A-X024F-X027R-X062E, X024F-X103N-X104L-X118R-X188D, X026F-X104L-X256N-X272F, X024F-X043W-X104L-X121F-X129E, X062E-X078N-X116L-X224A, X023A-X024F-X051W-X158E, X027R-X038F-X102A-X116L, X062E-X078N-X144R-X212M, X031F-X116L-X256N-X272F, X022L-X033S-X104L-X116L-X160D-X186K, X024F-X118R-X129E-X186K-X213A, X043W-X105T-X213A-X215D-X216F, X031F-

X105T-X186K-X188D, X026F-X194E-X213A-X256N, and X103N-X160D-X250I-X256N, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X022A-X024R-X101D-X103A-X104I-X118R-X159D-X188D-X232V-X248D-X271F, X022A-X024R-X103A-X104I-X129E-X159D-X188D-X232V-X248D-X271F, X022A-X024R-X103A-X104I-X118R-X159D-X188D-X217D-X232V-X248D, X022A-X024R-X101D-X103A-X104I-X118R-X129E-X159D-X188D-X232V-X245R-X248D, X022A-X024R-X101D-X103A-X104I-X159D-X188D-X232V-X245R-X248D, X022A-X043R-X103A-X104I-X118R-X129E-X159D-X188D-X232V-X245R-X248D, X022A-X043R-X103A-X104I-X118R-X128I-X129E-X159D-X188D-X232V-X248D, X022A-X043R-X101D-X103A-X104I-X118R-X129E-X159D-X188D-X232V-X248D-X271F, X022A-X024R-X043R-X101D-X103A-X104I-X159D-X188D-X232V-X245R-X248D, X022A-X103A-X104I-X159D-X188D-X232V-X248D, X022A-X024R-X103A-X104I-X118R-X129E-X159D-X188D-X232V-X248D-X271F, X022A-X024R-X103A-X104I-X159D-X188D-X217D-X232V-X245R-X248D-X271F, X022A-X043R-X062E-X103A-X104I-X159D-X188D-X232V-X245R-X248D-X271F, X022A-X043R-X103A-X104I-X129E-X159D-X188D-X232V-X245R-X248D, X022A-X024R-X103A-X104I-X159D-X188D-X217D-X232V-X248D-X271F, X022A-X103A-X104I-X118R-X159D-X188D-X217D-X232V-X245R-X248D, X022A-X024R-X101D-X103A-X104I-X118R-X128I-X159D-X188D-X232V-X245R-X248D, X022A-X024R-X043R-X103A-X104I-X159D-X188D-X217D-X232V-X248D-X271F, X022A-X043R-X103A-X104I-X118R-X159D-X188D-X217D-X232V-X248D-X271F, X022A-X043R-X103A-X104I-X118R-X159D-X188D-X232V-X248D-X271F, X022A-X103A-X104I-X128I-X129E-X159D-X188D-X232V-X248D-X271F, X022A-X103A-X104I-X159D-X188D-X217D-X232V-X245R-X248D-X271F, X022A-X043R-X103A-X104I-X128I-X159D-X188D-X232V-X245R-X248D, X022A-X101D-X103A-X104I-X118R-X159D-X188D-X217D-X232V-X245R-X248D-X271F, X022A-X103A-X104I-X118R-X129E-X159D-X188D-X232V-X245R-X248D-X271F, X022A-X024R-X043R-X103A-X104I-X118R-X159D-X188D-X217D-X232V-X248D, X022A-X062E-X103A-X104I-X118R-X159D-X188D-X232V-X245R-X248D, X022A-X043R-X101D-X103A-X104I-X118R-X129E-X159D-X188D-X217D-X232V, X022A-X024R-X103A-X104I-X159D-X188D-X217D-X232V-X248D, X022A-X024R-X043R-X103A-X104I-X118R-X128I-X129E-X159D-X188D-X217D-X232V-X248D-X271F, and X022A-X103A-X104I-X118R-X159D-X188D-X217D-X232V-X245R-X248D-X271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X020K-X024F-X062E-X188D-X239G, X024F-X062E-X116L-X239G, X020K-X023A-X062E-X188D, X020K-X023A-X024F-X062E-X118R-X188D-X213A, X020K-X043W-X062E-X116L-X188D-X213A-X239G, X023A-X062E-X116L-X118R, X023A-X024F-X062E-X116L-X118R, X024F-X116L, X024F-X062E-X188D-X213A, X023A-X062E-X116L-X118R-X188D-X239G, X020K-X024F-X062E, X020K-X043W-X062E-X116L-X239G, X024F-X062E-X116L-X213A-X239G, X020K-X024F-X043W-X062E-X116L-X213A, X020K-X023A-X024F-X062E-X116L-X188D-X213A, X024F-X062E-X188D-X239G, X023A-X043W-X062E-X116L-X118R-X213A, X062E-X188D-X239G, X020K-X024F-X062E-X239G, X024F-X116L-X118R-X188D-X239G, X020K-X023A-X062E-X116L-X118R-X213A, X020K-X023A-X024F-X062E-X188D-X213A-X239G, X024F-X043W-X118R-X188D, X023A-X024F-X116L-X118R-X188D-X213A, X020K-X023A-X043W-X116L-X188D-X213A-X239G, X023A-X024F-X116L-X188D-X239G, X023A-X043W-X116L-X118R-X188D, X023A-X024F-X118R-X188D-X239G, X023A-X024F-X043W-X062E-X116L-X118R, X020K-X043W-X188D-X213A, X024F-X062E-X118R-X239G, X023A-X043W-X188D-X213A, X020K-X024F-X043W-X062E-X116L-X118R-X188D-X239G, X020K-X116L-X188D-X239G, X020K-X043W-X062E-X118R, X020K-X043W-X116L-X188D-X213A, X020K-X024F, X023A-X043W-X116L-X239G, X023A-X024F-X043W-X116L-X118R-X188D-X239G, X020K-X023A-X043W-X213A, and X023A-X024F-X062E-X118R-X213A-X239G, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X020K-X023A-X043W-X118R-X128I-X129E-X159D-X188D, X024F-X118R-X128I-X129E-X159D, X020K-X024F-X062E-X116L-X118R-X188D, X020K-X062E-X116L-X188D, X062E-X116L-X118R-X213A, X020K-X023A-X062E-X116L-X188D, X062E-X116L-X118R-X188D, X020K-X062E-X116L-X213A, X020K-X023A-X062E-X116L, X020K-X062E-X188D-X213A, X020K-X062E, X020K-X024F-X062E-X116L-X188D, X020K-X043W-X062E-X116L-X188D, X020K-X024F-X062E-X188D-X213A, X062E-X116L-X188D-X213A, X020K-X062E-X116L, X020K-X023A-X062E-X116L-X188D-X213A, X023A-X024F-X062E-X116L-X213A, X022A-X043R-X103A-X104I-X128I-X129E-X159D-X188D-X232V-X245R-X248D, X022A-X043R-X103A-X104I-X118R-X128I-X129E-X159D-X188D-X232V-X248D-X271F, X024F-X062E-X116L-X188D, X022A-X024R-X103A-X104I-X118R-X128I-X129E-X159D-X188D-X232V-X248D, X023A-X062E-X116L-X188D, X043W-X062E-X116L, X020K-X023A-X116L-X188D, X043W-X062E-X116L-X188D, X024F-X062E-X116L, X062E-X116L-X188D, and X022A-X024R-X103A-X104I-X128I-X159D-X188D-X232V-X248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X087R-X101G-X103A-X104I-X109R-X212P-X232V-X245R-X271V, X101G-X103A-X104I-X109R-X232V-X245R, X101G-X103A-X104I-

X109R-X212P-X232V-X245R-X271V, X101G-X103A-X104I-X109R-X212P-X232V-X245R, X076D-587R-X103A-X104I-X212P-X271V, X076D-X103A-X104I-X109R, X076D-X103A-X104I-X212P-X271V, X076D-X103A-X104I-X109R-X245R, and X076D-X103A-X104I-X212P-X245L-X271V, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X024R-X086W-X118R, X024R-X078R-X086W-X243F, X024R-X033S-X086S-X087N-X209A, X033S-X118R, X024R-X078R-X086W-X118R-X270T, X024R-X033S-X086W-X118R, X078R-X086W-X243F, X033S-X078R-X086W-X118R-X209A, X033S-X078R-X209A, X086W-X118R-X243F, X024R-X086W, X078R-X086W-X235F, X024R-X118R, X024R-X086R, X101G-X103A-X104I-X232V, X024R-X033S-X078R-X086W-X118R, X024R-X118R-X209A, X209A-X241R, X033S-X086W-X243F, X033S-X172V-X209A, X118R-X209A-X243F, X024R-X086S-X141G, X024R-X118R-X209A-X243F, X024R-X033S-X086S-X085N-X235F, X024R-X033S-X133V, X024R-X033S-X078R-X086W, X024R-X086W-X209A, X024R-X241R, X033S-X118R-X243F, X024R-X235F, X024R-X078R-X086W, X024R-X118R-X209A-X235F, X024R-X209A-X241R, X033S-X118R-X241R, X086W-X118R-X209A, X033S-X118R-X159D-X209A, X033S-X078R-X086W, X024R-X086W-X243F, X118R-X209A, X024R-X086W-X118R-X203I, X078R-X209A-X235F, X024R-X033S-X241R, X078R-X118R, X033S-X118R-X209A-X243F, X021M-X024R-X033S, X024R-X033S-X086W, X033S-X235F, X078R-X086W-X209A, X024R-X033S-X209A-X235F, X033S-X086W-X118R, X024R-X033S-X078R-X209A, X033S-X086W-X118R-X209A-X243F, X086W-X209A-X243F, X005S-X078R-X118R-X241R, X024R-X174T, X033S-X209A-X243F, X086W-X118R-X133V, X024R-X033S-X118R, X024R-X086W-X209A-X235F, X086W-X209A, X008T-X024R, X086W-X118R, X033S-X241R, X005S-X024R-X033S-X243F, X024R-X209A-X242P, X024R-X033S-X078R-X118R, X024R-X033S-X194T, X024R-X243F, X024R-X209A, X024R-X033S-X118R-X209A, X033S-X086W, X024R-X033S, X024R-X033S-X078R-X243F, X086W-X243F, X033S-X118D-X138V-X209A, X033S-X209A-X235F, X024R-X086R-X118R, X033S-X201S, X024R-X239Q, X033S-X118R-X209A-, X078R-X086W, X235F-X243F, X024R-X209A-X235F, X118R-X172V, X017Y-X024R-X033S-X086W, X033S-X148F, X024R-X118R-X235F, X033S-X078R, X033S-X243F, X024C-X033S, X118R-X194T, X033S-X209A, X118R-X209A-X235F, X024R-X033S-X209A-X243F, X024R-X033S-X235F, X024R-X033S-X118R-X235F, X024R-X141G, X024R-X274I, X024R-X033S-X209A, X086W-X235F, X024R-X209A-X243F, X004E-X033S-X078R, X086W-X209A-X235F, X015T-X033S, X033S-X086W-X156L-X209A, X024R-X118R-X243F-X269H, X209A-X235F, X024R-X247H, X024R-X033S-X228T, X078R-X235F, X024R-X033S-X174V-X235F, X024R-X235F-X243F, X024R-X033S-X235F-X241R, X024R-X033S-X151V, X024R-X104A, X033S-X048T, X012H-X104A-X118R, X118R-X235F, X033S-X253A, X143A-X209A, X024R-X033S-X243F, X033S-X239T, X209A-X243F, X024R-X033S-X129H-X184D-X253M, X024R-X085V-X086W-X118R-X235F, X024R-X272P, and X024R-X269C, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: X020R-X087D-X101G-X103A-X104I-X232V-X245R, X020R-X101G-X103A-X104I-X150L-X232V-X245R, X018R-X020R-X024R-X076D-X087D-X249R, X018R-X020R-X024R-X076D-X150L-X249R, X018R-X024R-X043R-X076D-X087D-X249R, X018R-X024R-X043R-X076D-X150L-X249R, X018R-X024R-X076D-X078R-X087D-X249R, X018R-X024R-X076D-X078R-X150L-X249R, X018R-X024R-X076D-X087D-X249R-X269R, X018R-X024R-X076D-X087D-X242R-X249R, X018R-X024R-X076D-X087D-X150L-X249R, X018R-X024R-X076D-X150L-X249R, X018R-X087D-X101G-X103A-X104I-X232V-X245R, X018R-X101G-X103A-X104I-X150L-X232V-X245R, X018R-X022R-X024R-X076D-X087D-X249R, X018R-X022R-X024R-X076D-X150L-X249R, X043R-X087D-X101G-X103A-X104I-X232V-X245R-X269R, X043R-X101G-X103A-X104I-X150L-X232V-X245R, X024R-X087D-X101G-X103A-X104I-X232V-X245R, X024R-X101G-X103A-X104I-X150L-X232V-X245R, X078R-X087D-X101G-X103A-X104I-X232V-X245R, X078R-X101G-X103A-X104I-X150L-X232V-X245R, X087D-X101G-X103A-X104I-X232V-X245R-X269R, X101G-X103A-X104I-X150L-X232V-X245R-X249R, X101G-X103A-X104I-X150L-X232V-X245R-X269R, X022R-X087D-X101G-X103A-X104I-X232V-X245R, X018R-X024R-X043D-X076D-X150L-X249R, X043R-X087D-X101G-X103A-X104I-X232V-X245R, X022R-X101G-X103A-X104I-X150L-X232V-X245R, X018R-X024R-X043D-X076D-X087D-X249R, X018R-X024R-X076D-X087D-X249R, X018R-X024R-X076D-X150L-X242R-X249R, X043R-X101G-X103A-X104I-X150L-X232V-X245R-X269R, X076D-X101G-X103A-X104I-X150L-X232V-X245R, X087D-X101G-X103A-X104I-X232V-X242R-X245R, X101G-X103A-X104I-X150L-X232V-X245R, X076D-X087D-X101G-X103A-X104I-X232V-X245R, X087D-X101G-X103A-X104I-X232V-X245R, and X101G-X103A-X104I-X150L-X232V-X242R-X245R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X024R-X101G-X103A-X104I-X129Q-X158E-X188D-X217E-X232V-X245R-X248D-X249R, X024R-X101G-X103A-X104I-X130A-X158E-X183D-X188D-X232V-X245R-X248D-X249R, X024R-X101G-X103A-X104I-X129Q-X158E-X183D-X188D-X232V-X245R-X248D-X249R, X101G-X103A-X104I-X130A-X158E-X188D-X232V-X245R-X248D-X249R, X024R-X101G-X103A-X104I-X129Q-X158E-X188D-X232V-X245R-X248D-X249R, X024R-X101G-X103A-X104I-X130A-X158E-X188D-X232V-X245R-X248D-X249R, X024R-X101G-X103A-X104I-X129Q-X130A-X158E-X183D-X188D-X232V-X245R-X248D-X249R, X024R-X101G-X103A-X104I-X128L-X129Q-X158E-X188D-X232V-X245R-X248D-X249R, X024R-X101G-

X103A-X104I-X129Q-X130A-X158E-X188D-X232V-X245R-X248D-X249R, X101G-X103A-X104I-X129Q-X158E-X188D-X232V-X245R-X248D-X249R, X101G-X103A-X104I-X129Q-X130A-X158E-X188D-X232V-X245R-X248D-X249R, X024R-X101G-X103A-X104I-X128L-X129Q-X130A-X158E-X188D-X232V-X245R-X248D-X249R, X101G-X103A-X104I-X128L-X129Q-X158E-X188D-X232V-X245R-X248D-X249R, and X024R-X027R-X101G-X103A-X104I-X128L-X129Q-X130A-X158E-X188D-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X101G-X103A-X104I-X232V-X222Q-X245R, X101G-X103A-X104I-X158E-X188D-X222S-X232V-X245R-X248D-X249R, X101G-X103A-X104I-X158E-X188D-X222Q-X232V-X245R-X248D-X249R, X076D-X101G-X103A-X104I-X232V-X222Q-X245R, X101G-X103A-X104I-X232V-X222S-X245R, X076D-X101G-X103A-X104I-X232V-X222S-X245R, and X076D-X101G-X103A-X104I-X158E-X188D-X222S-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: X024R-X101G-X103A-X104I-X128L-X129Q-X158E-X188D-X232V-X245R-X248D-X249R, X101G-X103A-X104I-X130A-X158E-X188D-X232V-X245R-X248D-X249R, X024R-X101G-X103A-X104I-X158E-X188D-X232V-X245R-X248D-X249R, X101G-X103A-X104I-X128L-X129Q-X158E-X188D-X232V-X245R-X248D-X249R, X101G-X103A-X104I-X129Q-X130A-X158E-X188D-X232V-X245R-X248D-X249R, X101G-X103A-X104I-X130A-X158E-X183D-X188D-X217E-X232V-X245R-X248D-X249R, X024R-X101G-X103A-X104I-X128L-X129Q-X130A-X158E-X188D-X232V-X245R-X248D-X249R, X024R-X101G-X103A-X104I-X129Q-X158E-X188D-X217E-X232V-X245R-X248D-X249R, X101G-X103A-X104I-X128L-X130A-X158E-X188D-X217E-X232V-X245R-X248D-X249R, X024R-X101G-X103A-X104I-X128L-X129Q-X158E-X183D-X188D-X232V-X245R-X248D-X249R, X024R-X101G-X103A-X104I-X128L-X129Q-X130A-X158E-X183D-X188D-X232V-X245R-X248D-X249R, X024R-X101G-X103A-X104I-X128L-X129Q-X158E-X188D-X232V-X245R-X248D-X249R-X271G, X101G-X103A-X104I-X129Q-X158E-X183D-X188D-X232V-X245R-X248D-X249R, X024R-X101G-X103A-X104I-X130A-X158E-X188D-X217E-X232V-X245R-X248D-X249R, X024R-X101G-X103A-X104I-X128L-X158E-X183D-X188D-X232V-X245R-X248D-X249R, X101G-X103A-X104I-X129Q-X158E-X188D-X217E-X232V-X245R-X248D-X249R, and X024R-X101G-X103A-X104I-X128L-X130A-X158E-X188D-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising subtilisin variants of a *Bacillus* subtilisin, wherein the subtilisin variant is a mature form having proteolytic activity and comprises an amino acid sequence comprising a combination of amino acid substitutions selected from: X101G-X103A-X104I, X22A-X101A-X209E, S103G-L111V-G159E, X22A-X103G-X159E, X22A-X111V-X159E, X22A-X128N-X271F-X209E, X22A-X103G-X111V, X62E-X111V-X128N, X22A-X111V-X128N, X22A-X62E-X111V, X101A-X103G-X104L-X188D, X101G-X103A-X104I-X159D, X101A-X103G-X104L-X128N, X22A-X101A-X159E, X101A-X103G-X104L, X101A-X103G-X104L-X159E, X22A-X101A-X103G-X104L, X101A-X103G-X104L-X209E, X22A-X209E-X271F, X22A-X101A-X271F, and X101A-X209E-X271F, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising subtilisin variants of a *Bacillus* subtilisin, wherein the subtilisin variant is a mature form having proteolytic activity and comprises an amino acid sequence comprising a combination of amino acid substitutions selected from: X103A-X104I-X159D-X232V-X236H-X245R-X248D-X252K, X101G-X104I-X159D-X232V-X236H-X245R-X248D-X252K, X101G-X103A-X159D-X232V-X236H-X245R-X248D-X252K, X101G-X103A-X104L-X232V-X236H-X245R-X248D-X252K, X101G-X103A-X104L-X159D-X236H-X245R-X248D-X252K, X101G-X103A-X104L-X159D-X232V-X245R-X248D-X252K, X101G-X103A-X104L-X159D-X232V-X236H-X248D-X252K, X101G-X103A-X104L-X159D-X232V-X236H-X245R-X252K, and X101G-X103A-X104L-X159D-X232V-X236H-X245R-X248D, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising subtilisin variants of a *Bacillus* subtilisin, wherein the subtilisin variant is a mature form having proteolytic activity and comprises an amino acid sequence comprising a combination of amino acid substitutions selected from: X101G-X103A-X104I-X159D-X232V-X245R-X248D, X101G-X103A-X104I-X159D-X232V-X245R-X248D-X271F, X101G-X103A-X104I-X159D-X232V-X245R-X248D-X238R, X101G-X103A-X104I-X159D-X232V-X245R-X248D-X248R, X101G-X103A-X104I-X159D-X232V-X245R-X248D-X253R, X101G-X103A-X104I-X159D-X232V-X245R-X248D-X24R, X101G-X103A-X104I-X159D-X232V-X245R-X248D-X76D, X101G-X103A-X104I-X159E-X232V-X245R-X248D-X249R, X101G-X103A-X104I-X159E-X232V-X245R-X248D-X271F, X101G-X103A-X104I-X158E-X232V-X245R-X248D-X249R, X101G-X103A-X104I-X158E-X232V-X245R-X248D-X271F, X22A-X101G-X103A-X104I-X159D-X232V-X245R-X248D-X249R, X22A-X101G-X103A-X104I-X159D-X232V-X245R-X248D-X271F, X62E-X101G-X103A-X104I-X159D-X232V-X245R-X248D-X249R, and X62E-X101G-X103A-X104I-X159D-X232V-X245R-X248D-X271F, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising subtilisin variants of a *Bacillus* subtilisin, wherein the subtilisin variant is a mature form having proteolytic activity and comprises an amino acid sequence comprising a combination of amino acid substitutions selected from: X20R-X43R-X249R, X20R-X22R-X43R, X20R-X43R-X242R, X20R-X43R-X271L, X20R-X43R-X244R, X20R-X24R-X43R-X242R, X9A-X22R-X78R-X212F-X241R, X9A-X20R-X43R-X212F, X9A-X43R-X212F, X20R-X43R-X212F, X20R-X22R-X43R-X212F, X24R-X78R-X212F, X9A-X43R-X78R, X9A-X43R-X78R-X242R, X9A-X20R-X43R-X78R, X20R-X24R-X43R-X78R-X242R, X22R-X24R-X78R-X212F, X9A-X20R-X43R-X78R-X242R, X20R-X43R-X78R-X249R, X20R-X43R-X78R, X9A-X78R-X212F, X9A-X22R-X43R-X78R, X9A-X20R-X24R-X43R, X9A-X22R-X78R-X212F, X4R-X9A-X22R-X78R-X212F, X20R-X24R-X43R, X1R-X9A-X43R, X20R-X24R-X43R-X115R, X9A-X24R-X43R, X20R-X22R-X24R-X43R, X1R-X24R-X43R, X9A-X20R-X24R-X43R-X242R, X9A-X20R-X22R-X78R-X212F, X9A-X24R-X43R-X244R, X9A-X24R-X43R-X242R, X4R-X9A-X22R-X24R-X212F, and X22R-X24R-X43R, wherein the amino acid positions of the subtilisin variant are numbered by correspondence with the amino acid sequence of B. amyloliquefaciens subtilisin BPN' set forth as SEQ ID NO:1.

The present invention further provides polypeptides comprising subtilisin variants of a Bacillus subtilisin, wherein the subtilisin variant is a mature form having proteolytic activity and comprises an amino acid sequence comprising a combination of amino acid substitutions selected from: X101G-X103A-X104I-X232V-X245R-X248D, X101G-X103A-X104I-X159D-X232V-X245R, X101G-X103A-X104I-X159R-X232V-X245R-X248D, X101G-X103A-X104I-X159D-X232V-X245R-X248R, X101G-X103A-X104I-X232V-X245R, X101G-X103A-X104I-X232V-X245R-X248R, X101G-X103A-X104I-X159R-X232V-X245R-X248R, and X101G, X103A, X104I, X232V, X236H, X245R, and X252K, wherein the amino acid positions of the subtilisin variant are numbered by correspondence with the amino acid sequence of B. amyloliquefaciens subtilisin BPN' set forth as SEQ ID NO:1.

The present invention further provides polypeptides comprising subtilisin variants of a Bacillus subtilisin, wherein the subtilisin variant is a mature form having proteolytic activity and comprises an amino acid sequence comprising a combination of amino acid substitutions selected from: X16S, X22A, X24R, X62E, X76D, X89P, X101A/G, X103G/A, X104L/I, X111V, X128N, X129E, X232V, X148I, X158E, X159D/E, X166D, X186H, X188D, X209E, X236H, X238R, X245R, X248D/R, X249R, X252K/R, X253R, and X271F, wherein the amino acid positions of the subtilisin variant are numbered by correspondence with the amino acid sequence of B. amyloliquefaciens subtilisin BPN' set forth as SEQ ID NO:1.

The present invention further provides polypeptides comprising subtilisin variants of a Bacillus subtilisin, wherein the subtilisin variant is a mature form having proteolytic activity and comprises an amino acid sequence comprising a combination of amino acid substitutions selected from: N062E-A158E, S103G-A158E, S128N-A158E, A016S-A158E, V104L-A158E, E089P-A158E, L111V-A158E, T022A-A158E, S101A-A158E, L148I-A158E, P129E-A158E, T022A-E089P, A016S-E089P, N062E-E089P, N062E-E271F, A158E-E271F, R186H-E271F, P129E-E271F, L111V-E271F, Y209E-E271F, A016S-E271F, S188D-E271F, T022A-E271F, G159E-E271F, V104L-E271F, S101A-E271F, E089P-E271F, S128N-E271F, S103G-E271F, L148I-E271F, H249R-E271F, N062E-G159E, A016S-G159E, S128N-G159E, L148I-G159E, L111V-G159E, E089P-G159E, T022A-G159E, P129E-G159E, S103G-G159E, V104L-G159E, A158E-G159E, S101A-G159E, A158E-H249R, L111V-H249R, P129E-H249R, N062E-H249R, A016S-H249R, R186H-H249R, L148I-H249R, G159E-H249R, S101A-H249R, S188D-H249R, V104L-H249R, Y209E-H249R, T022A-H249R, S128N-H249R, S103G-H249R, E089P-H249R, T022A-L111V, S101A-L111V, A016S-L111V, V104L-L111V, N062E-L111V, S103G-L111V, E089P-L111V, A016S-L148I, N062E-L148I, T022A-L148I, P129E-L148I, V104L-L148I, S103G-L148I, S128N-L148I, S101A-L148I, E089P-L148I, L111V-L148I, A016S-N062E, T022A-N062E, N062E-P129E, T022A-P129E, S128N-P129E, A016S-P129E, S101A-P129E, V104L-P129E, E089P-P129E, S103G-P129E, L111V-P129E, N062E-R186H, S128N-R186H, S101A-R186H, T022A-R186H, A016S-R186H, A158E-R186H, E089P-R186H, P129E-R186H, G159E-R186H, S103G-R186H, V104L-R186H, L111V-R186H, L148I-R186H, N062E-S101A, T022A-S101A, A016S-S101A, E089P-S101A, N062E-S103G, T022A-S103G, A016S-S103G, S101A-S103G, E089P-S103G, N062E-S128N, A016S-S128N, T022A-S128N, S101A-S128N, V104L-S128N, E089P-S128N, S103G-S128N, L111V-S128N, L111V-S188D, N062E-S188D, A016S-S188D, L148I-S188D, T022A-S188D, S128N-S188D, S101A-S188D, V104L-S188D, E089P-S188D, P129E-S188D, G159E-S188D, R186H-S188D, S103G-S188D, A158E-S188D, A016S-T022A, A016S-V104L, T022A-V104L, S101A-V104L, N062E-V104L, S103G-V104L, E089P-V104L, G159E-Y209E, L111V-Y209E, S101A-Y209E, A016S-Y209E, S128N-Y209E, L148I-Y209E, P129E-Y209E, N062E-Y209E, T022A-Y209E, S103G-Y209E, A158E-Y209E, S188D-Y209E, V104L-Y209E, E089P-Y209E, and R186H-Y209E, wherein the amino acid positions of the subtilisin variant are numbered by correspondence with the amino acid sequence of B. amyloliquefaciens subtilisin BPN' set forth as SEQ ID NO: 1.

The present invention further provides polypeptides comprising subtilisin variants having proteolytic activity comprising an amino acid sequence comprising a combination of amino acid substitutions selected from: N018R-W241R, G020R-W241R, S024R-W241R, S009A-W241R, G020R-W241R, V004R-W241R, N043R-W241R, S078R-W241R, T022R-W241R, G115R-W241R, A001R-W241R, S212F-W241R, L082R-W241R, N018R-V244R, S024R-V244R, S078R-V244R, G020R-V244R, S212F-V244R, S009A-V244R, L082R-V244R, A001R-V244R, N043R-V244R, T022R-V244R, V004R-V244R, G115R-V244R, W241R-V244R, S242R-V244R, A001R-V004R, S009A-T022R, N018R-T022R, G020R-T022R, V004R-T022R, A001R-T022R, S024R-S242R, N018R-S242R, V004R-S242R, G020R-S242R, S212F-S242R, L082R-S242R, S078R-S242R, A001R-S242R, S009A-S242R, T022R-S242R, G115R-S242R, N043R-S242R, W241R-S242R, N018R-S212F, T022R-S212F, V004R-S212F, S024R-S212F, A001R-S212F, G115R-S212F, G020R-S212F, S009A-S212F, N043R-S212F, S078R-S212F, L082R-S212F, S009A-S078R, G020R-S078R, S024R-S078R, T022R-S078R, N018R-S078R, V004R-S078R, A001R-S078R, N043R-S078R, T022R-S024R, G020R-S024R, N018R-S024R, A001R-S024R, V004R-S024R, S009A-S024R, V004R-S009A, A001R-S009A, S242R-N269R, S024R-N269R, G020R-N269R, T022R-N269R, H249R-N269R, S212F-N269R, N043R-N269R, V244R-N269R, A001R-N269R, N018R-N269R, S078R-N269R, S009A-N269R, G115R-N269R, W241R-N269R, V004R-N269R, L082R-N269R, N018R-N043R, G020R-N043R, V004R-N043R, T022R-N043R, S009A-N043R, A001R-N043R, S024R-N043R, S009A-N018R, V004R-N018R, A001R-N018R, S024R-L082R, S009A-L082R, N018R-L082R, A001R-L082R, S078R-L082R, G020R-L082R, T022R-L082R, V004R-L082R, N043R-L082R, N043R-H249R, G020R-H249R, V004R-H249R, N018R-H249R, S009A-H249R, S212F-H249R, T022R-H249R, S024R-H249R, G115R-H249R, A001R-H249R, L082R-H249R, S242R-H249R, W241R-H249R, V244R-H249R, S078R-H249R, N018R-G115R, G020R-G115R, T022R-G115R, S078R-G115R, S009A-G115R, V004R-G115R, A001R-G115R, L082R-G115R, N043R-G115R, S024R-G115R, S009A-G020R, N018R-G020R, V004R-G020R, A001R-G020R, S009A-E271L, G020R-E271L, S024R-E271L, V244R-E271L, W241R-E271L, N043R-E271L, T022R-E271L, H249R-E271L, S212F-E271L, G115R-E271L, S242R-E271L, S078R-E271L, V004R-E271L, N269R-E271L, A001R-E271L, N018R-E271L, and L082R-E271L, wherein the amino acid positions of the subtilisin variant are numbered by correspondence with the amino acid sequence of *B. amyloliquefaciens* subtilisin BPN' set forth as SEQ ID NO: 1.

The present invention further provides isolated subtilisin variants, wherein said subtilisin variant is a mature form having proteolytic activity and comprises an amino acid sequence comprising a combination of amino acid substitutions selected from: G020R-N043R, N062E-A158E, S103G-A158E, S128N-A158E, A016S-A158E, V104L-A158E, E089P-A158E, L111V-A158E, T022A-A158E, S101A-A158E, L148I-A158E, P129E-A158E, T022A-E089P, A016S-E089P, N062E-E089P, N062E-E271F, A158E-E271F, R186H-E271F, P129E-E271F, L111V-E271F, Y209E-E271F, A016S-E271F, S188D-E271F, T022A-E271F, G159E-E271F, V104L-E271F, S101A-E271F, E089P-E271F, S128N-E271F, S103G-E271F, L148I-E271F, H249R-E271F, N062E-G159E, A016S-G159E, S128N-G159E, L148I-G159E, L111V-G159E, E089P-G159E, T022A-G159E, P129E-G159E, S103G-G159E, V104L-G159E, A158E-G159E, S101A-G159E, A158E-H249R, L111V-H249R, P129E-H249R, N062E-H249R, A016S-H249R, R186H-H249R, L148I-H249R, G159E-H249R, S101A-H249R, S188D-H249R, V104L-H249R, Y209E-H249R, T022A-H249R, S128N-H249R, S103G-H249R, E089P-H249R, T022A-L111V, S101A-L111V, A016S-L111V, V104L-L111V, N062E-L111V, S103G-L111V, E089P-L111V, A016S-L148I, N062E-L148I, T022A-L148I, P129E-L148I, V104L-L148I, S103G-L148I, S128N-L148I, S101A-L148I, E089P-L148I, L111V-L148I, A016S-N062E, T022A-N062E, N062E-P129E, T022A-P129E, S128N-P129E, A016S-P129E, S101A-P129E, V104L-P129E, E089P-P129E, S103G-P129E, L111V-P129E, N062E-R186H, S128N-R186H, S101A-R186H, T022A-R186H, A016S-R186H, A158E-R186H, E089P-R186H, P129E-R186H, G159E-R186H, S103G-R186H, V104L-R186H, L111V-R186H, L148I-R186H, N062E-S101A, T022A-S101A, A016S-S101A, E089P-S101A, N062E-S103G, T022A-S103G, A016S-S103G, S101A-S103G, E089P-S103G, N062E-S128N, A016S-S128N, T022A-S128N, S101A-S128N, V104L-S128N, E089P-S128N, S103G-S128N, L111V-S128N, L111V-S188D, N062E-S188D, A016S-S188D, L148I-S188D, T022A-S188D, S128N-S188D, S101A-S188D, V104L-S188D, E089P-S188D, P129E-S188D, G159E-S188D, R186H-S188D, S103G-S188D, A158E-S188D, A016S-T022A, A016S-V104L, T022A-V104L, S101A-V104L, N062E-V104L, S103G-V104L, E089P-V104L, G159E-Y209E, L111V-Y209E, S101A-Y209E, A016S-Y209E, S128N-Y209E, L148I-Y209E, P129E-Y209E, N062E-Y209E, T022A-Y209E, S103G-Y209E, A158E-Y209E, S188D-Y209E, V104L-Y209E, E089P-Y209E, R186H-Y209E, N018R-W241R, G020R-W241R, S024R-W241R, S009A-W241R, G020R-W241R, V004R-W241R, N043R-W241R, S078R-W241R, T022R-W241R, G115R-W241R, A001R-W241R, S212F-W241R, L082R-W241R, N018R-V244R, S024R-V244R, S078R-V244R, G020R-V244R, S212F-V244R, S009A-V244R, L082R-V244R, A001R-V244R, N043R-V244R, T022R-V244R, V004R-V244R, G115R-V244R, W241R-V244R, S242R-V244R, A001R-V004R, S009A-T022R, N018R-T022R, G020R-T022R, V004R-T022R, A001R-T022R, S024R-S242R, N018R-S242R, V004R-S242R, G020R-S242R, S212F-S242R, L082R-S242R, S078R-S242R, A001R-S242R, S009A-S242R, T022R-S242R, G115R-S242R, N043R-S242R, W241R-S242R, N018R-S212F, T022R-S212F, V004R-S212F, S024R-S212F, A001R-S212F, G115R-S212F, G020R-S212F, S009A-S212F, N043R-S212F, S078R-S212F, L082R-S212F, S009A-S078R, G020R-S078R, S024R-S078R, T022R-S078R, N018R-S078R, V004R-S078R, A001R-S078R, N043R-S078R, T022R-S024R, G020R-S024R, N018R-S024R, A001R-S024R, V004R-S024R, S009A-S024R, V004R-S009A, A001R-S009A, S242R-N269R, S024R-N269R, G020R-N269R, T022R-N269R, H249R-N269R, S212F-N269R, N043R-N269R, V244R-N269R, A001R-N269R, N018R-N269R, S078R-N269R, S009A-N269R, G115R-N269R, W241R-N269R, V004R-N269R, L082R-N269R, N018R-N043R, G020R-N043R, V004R-N043R, T022R-N043R, S009A-N043R, A001R-N043R, S024R-N043R, S009A-N018R, V004R-N018R, A001R-N018R, S024R-L082R, S009A-L082R, N018R-L082R, A001R-L082R, S078R-L082R, G020R-L082R, T022R-L082R, V004R-L082R, N043R-L082R, N043R-H249R, G020R-H249R, V004R-H249R, N018R-H249R, S009A-H249R, S212F-H249R, T022R-H249R, S024R-H249R, G115R-H249R, A001R-H249R, L082R-H249R, S242R-H249R, W241R-H249R, V244R-H249R, S078R-H249R, N018R-G115R, G020R-G115R, T022R-G115R, S078R-G115R, S009A-G115R, V004R-G115R, A001R-G115R, L082R-G115R, N043R-G115R, S024R-G115R, S009A-G020R, N018R-G020R, V004R-G020R, A001R-G020R, S009A-E271L, G020R-E271L, S024R-E271L, V244R-E271L, W241R-E271L, N043R-E271L, T022R-E271L, H249R-E271L, S212F-E271L, G115R-E271L, S242R-E271L, S078R-E271L, V004R-E271L, N269R-E271L, A001R-E271L, N018R-E271L, and L082R-E271L, and wherein the total net charge of the variant is 0, +1, +2, +3, +4, +5, −1, −2, −3, −4, or −5 relative to the total net charge of the *Bacillus lentus* subtilisin GG36 protease, and wherein the total net charge is obtained by one or more substitutions selected from: N43D, R45T, N62E, N76D, S101D, P129E, A158E, G159D, G159E, S166D, S188D, A230E, N18R, G20K, G20R, T22R, S24R, N43R, G118R, Q245R, H249R, N269R, E271F, and E271L, and wherein amino acid positions of the protease variant are numbered according to the numbering of corresponding amino acid positions in the amino acid sequence of *Bacillus amyloliquefaciens* subtilisin BPN' shown in SEQ ID NO:1.

The present invention further provides isolated subtilisin variants, wherein the subtilisin variants are mature forms having proteolytic activity and comprise amino acid sequences comprising a combination of amino acid substitutions selected from: G020R-N043R, G020K-N062E, S024F-N116L, G020K-S024F, S024R-A174T, S024R-G118R, S024R-K235F, S024R-P086R, S024R-P086W, S078R-G118R, T033S-G118R, T033S-K235F, Y209A-

W241R, G020R-N076D, N018R-Q245R, S024R-R045T, A232V-Q245R, G118R-A172V, G118R-A194T, I008T-S024R, K235F-N243F, N018R-S103A, N018R-V104I, P086W-G118R, P086W-N243F, P086W-Y209A, S024C-T033S, S024R-A232V, S024R-N243F, S024R-P239Q, S024R-S101G, S024R-S141G, S024R-T033S, S024R-T274I, S024R-Y209A, S078R-P086W, S101G-A232V, T033S-L148F, T033S-P086W, T033S-P201S, T033S-S078R, T033S-W241R, T033S-Y209A, A230E-H249R, A232V-H249R, G118R-K235F, N076D-Q245R, P086W-K235F, S024R-R247H, S024R-V104A, S078R-K235F, S101G-H249R, S103A-A232V, T033S-A048T, T033S-P239T, T033S-T253A, T143A-Y209A, Y209A-K235F, N018R-R045T, Y209A-N243F, S024R-A272P, S024R-R269C, S101G-V104I, V104I-A232V, N076D-H249R, and S024R-N076D wherein the amino acid positions of the subtilisin variant are numbered by correspondence with the amino acid sequence of *B. amyloliquefaciens* subtilisin BPN' set forth as SEQ ID NO:1.

The present invention further provides isolated subtilisin variants, wherein the subtilisin variants are mature forms having proteolytic activity and comprise amino acid sequences comprising a combination of amino acid substitutions selected from: G020R-N076D, S024R-R045T, A230E-H249R, N018R-R045T, N018R-Q245R, S101G-A232V, S024R-A232V, A232V-Q245R, S024R-S101G, N018R-V104I, N018R-S103A, S101G-H249R, A232V-H249R, S103A-A232V, N076D-Q245R, S101G-V104I, V104I-A232V, N076D-H249R, S024R-N076D, S024F-N116L, G020K-S024F, G020K-N062E, T033S-G118R, S024R-P086W, S024R-G118R, S024R-P086R, Y209A-W241R, S024R-W241R, S024R-K235F, G118R-Y209A, S078R-G118R, T033S-K235F, S024R-A174T, P086W-Y209A, I008T-S024R, P086W-G118R, T033S-W241R, S024R-N243F, S024R-Y209A, T033S-P086W, S024R-T033S, P086W-N243F, T033S-P201S, S024R-P239Q, S078R-P086W, K235F-N243F, G118R-A172V, T033S-L148F, T033S-S078R, T033S-N243F, S024C-T033S, G118R-A194T, T033S-Y209A, S024R-S141G, S024R-T274I, P086W-K235F, A015T-T033S, Y209A-K235F, S024R-R247H, S078R-K235F, S024R-V104A, T033S-A048T, G118R-K235F, T033S-T253A, T143A-Y209A, T033S-P239T, Y209A-N243F, S024R-A272P, and S024R-R269C, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: V004R-S009A-G020R-S242R, G020R-N043R-W241R, G020R-S242R-N269R, V004R-S009A-G020R-N043R, V004R-G020R-H249R, N018R-S024R-V244R, S009A-T022R-S212F-W241R, G020R-N043R-N269R, N018R-S024R-S242R, V004R-S009A-N043R-W241R, G020R-N043R-V244R, G020R-T022R-S242R, V004R-G020R-N043R, V004R-S009A-G020R-N043R-S242R, G020R-N043R-S242R, G020R-N043R-S242R-H249R, G020R-S212F-H249R, V004R-S009A-W241R, A001R-S009A-N043R, G020R-N043R-H249R, S009A-G020R-N043R-W241R, G020R-T022R-N043R, G020R-H249R-N269R, G020R-T022R-W241R, V004R-S009A-S024R-N043R-W241R, S009A-N043R-S078R, V004R-G020R-S024R-V244R, G020R-T022R-S078R-S242R, G020R-S024R-S242R-H249R, V004R-S009A-S078R-W241R, S009A-N043R-S078R-S242R, V004R-G020R-S024R, S009A-N043R-S212F, G020R-N043R-S212F, S024R-S078R-S212F, S009A-G020R-S024R-N043R, S009A-T022R-N043R-S078R, G020R-T022R-S212F-W241R, G020R-N043R-S212F-W241R, S009A-N043R-W241R, G020R-N043R-E271L, G020R-T022R-S078R-W241R, G020R-S024R-N043R-S242R, G020R-T022R-N043R-W241R, S009A-G020R-N043R-S212F, V004R-S009A-G020R-S024R-S242R, G020R-N043R-H249R-E271L, G020R-T022R-S024R-S242R, S009A-T022R-S078R-S212F, G020R-N043R-S242R-E271L, S009A-T022R-S078R-S212F-W241R, V004R-G020R-S024R-H249R, G020R-T022R-E271L, G020R-T022R-N043R-S212F, V004R-G020R-S024R-N043R-S242R, V004R-G020R-S024R-N043R, V004R-S009A-T022R-S078R-S212F, G020R-T022R-S078R-S212F-W241R, and G020R-T022R-N269R, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: N018R-G020R-N043R-R045T-A230E, N018R-N043R-R045T-S242R-H249R, S024R-N043D-H249R, N018R-G020R-R045T, G020R-S024R-N076D-H249R, S024R-N043R-A230E-S242R, N018R-S024R-N043D-A230E, G020R-N076D, N018R-S024R-N043D-N076D-H249R, S024R-N043R-N076D-H249R, N018R-S024R-R045T-S242R, G020R-N043D-N076D-A230E-H249R, G020R-N043R-R045T-S242R, N018R-S024R-N076D-H249R, N018R-G020R-S024R-N043D-R045T-L233I-S242R, S024R-N043R-A230E, N018R-G020R-N043D, N043R-S242R-H249R, G020R-N043R-R045T-A230E, N043R-N076D-S242R-H249R, G020R-S024R-R045T-A230E-S242R, S024R-R045T-N076D-A230E-S242R-H249R, S024R-R045T, S024R-N043R-R045T-N076D-A230E-H249R, N018R-S024R-N043D-R045T-H249R, N018R-N043R-R045T-H249R, S024R-N043R-S242R, N018R-G020R-N043R-N076D-H249R, G020R-S024R-N043D-H249R, G020R-N043R-A230E-S242R, G020R-N043R-S242R, N018R-N043R-N076D-A230E, G020R-S024R-N043D-S242R, G020R-N043R-A230E, N018R-G020R-N043R-N076D-S242R-H249R, N043D-R045T-N076D-H249R, N018R-N043R-S242R-H249R, N018R-G020R-N043R-R045T-S242R, N018R-G020R-N043D-A230E-S242R, G020R-S024R-N043R-R045T-H249R, S024R-N043R-H249R, G020R-S024R-K27E-N043R-N076D-A230E, S024R-N043R-R045T-S242R, N018R-G020R-S024R-N043R-R045T-N076D-A230E, G020R-N043R-N076D-A230E-H249R, N018R-N043R-R045T-S242R, G020R-S242R-H249R, N018R-N043R-N076D-A230E-S242R-H249R, N018R-S024R-N076D, G020R-S024R-K27R-N043D-S242R-H249R, N018R-G020R-S024R-N043D-N076D-S242R, N018R-N043R-N076D-S242R-H249R, N018R-S024R-N043D-A230E-H249R, N018R-G020R-N043D-H249R, N018R-G020R-N043D-R045T-N076D-S242R, S024R-N043R-N076D-A230E-S242R, G020R-S024R-T381-N043R-R045T-N076D-S242R-H249R, N018R-G020R-N043R, N018R-S024R-R045T-A230E-S242R, N018R-G020R-H249R, S024R-N043R-N076D, N018R-G020R-S024R-N043R-R045T-N076D-H249R, N018R-N043R-R045T-N076D-S242R-H249R, S024R-N043D-S242R-H249R, N018R-G020R-S024R-N043D-R045T-S242R, G020R-S024R-N043R-N076D, N018R-G020R-N043D-R045T-A230E-S242R, G020R-S024R-N043R-R045T-N076D-

S242R-H249R, N018R-N043R-R045T-N076D-S242R, N018R-G020R-N043R-N076D-A230E-S242R, N018R-S024R-N043D-H249R, N018R-S024R-N043R-R045T-A230E-H249R, N018R-G020R-N043R-R045T-N076D-H249R, N018R-S024R-S242R, N018R-N043R-R045T-N076D-A230E-S242R, R045T-S242R-H249R, N018R-S024R-N043D-S242R, N018R-G020R-N043D-R045T-S240P, S024R-N043R-R045T-S242R-H249R, N018R-S024R-V30S-L31S-D321-T33Q-G34V-135F, N018R-G020R-N043R-N076D, G020R-N043D-R045T-N076D-S242R-H249R, N018R-S024R-N043D-A230E-S242R, N018R-S024R-N043D-S242R-H249R, S024R-N043D-R045T-S242R-H249R, N043R-A230E-H249R, S024R-N043R-N076D-A230E-H249R, G020R-S024R-N043D-N076D-H249R, S024R-R045T-S242R-A273V, G020R-S024R-R045T-N076D-S242R-H249R, N018R-S024R-N043D-N076D-S242R, N018R-N043R-N076D-A230E-H249R, N018R-G020R-N043R-R045T-H249R, N018R-N043R-R045T-A230E-S242R, G020R-S024R-N043D-R045T-A230E-S242R, N018R-N043D-A230E-H249R, N018R-N043R-N076D-S242R, N018R-G020R-N076D, N018R-G020R-N043D-N076D-S242R-H249R, G020R-S024R-N043D-N076D-S242R-H249R, N043D-S242R-H249R, N018R-G020R-S024R-N043R-N076D, N018R-G020R-N043D-R045T-N076D-H249R, N018R-G020R-N043R-R045T-N076D-A230E-H249R, N018R-N076D-S242R, G020R-N043R-H249R, N018R-N076D-S242R-H249R, N018R-S024R-R045T-A230E-H249R, A230E-H249R, N018R-R045T-H249R, G020R-N043R-N076D, N043R-R045T-H249R, N018R-N043D-N076D-S242R-H249R, N043R-N076D-H249R, N018R-R045T, G020R-N076D-A230E-S242R, G020R-S024R-N043D-R045T, S024R-N043D-N076D-S242R-H249R, G020R-R045T-H249R, N043R-N076D-S153A-H249R, N043R-N076D-A230E-H249R, N018R-N043D-N076D-H249R, and G020R-N043R-N076D-V227I, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101G-S103A-V104I-A232V-Q236H-Q245R-N252K, S101G-S103A-V104I-A232V-Q245R-N248R, S101G-S103A-V104I-G159R-A232V-Q245R-N248D, S101G-S103A-V104I-G159D-A232V-Q245R-N248R, S101G-S103A-V104I-A232V-Q245R, S101G-S103A-V104I-G159D-A232V-Q245R, and S101G-S103A-V104I-A232V-Q245R-N248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101G-S103A-V104I-P129E-S188D-A232V-N238R-Q245R-N248D, S024R-S101G-S103A-V104I-P129E-A158E-S188D-A232V-Q245R-N248D-H249R, T022A-S101G-S103A-V104I-P129E-A158E-S188D-A232V-Q245R-N248D-H249R, T022A-S024R-S101G-S103A-V104I-P129E-A158E-S188D-A232V-Q245R-N248D-H249R, S024R-S101G-S103A-V104I-P129E-S188D-A232V-Q245R-N248D-H249R, S024R-S101G-S103A-V104I-P129E-G159E-S188D-A232V-Q245R-N248D-H249R, S024R-S101G-S103A-V104I-S128N-P129E-A158E-A232V-Q245R-N248D-H249R, S024R-S101G-S103A-V104I-L148I-A158E-S188D-A232V-Q245R-N248D, T022A-S024R-S101G-S103A-V104I-P129E-G159E-S188D-A232V-Q245R-N248D-H249R, S024R-S101G-S103A-V104I-S128N-P129E-A232V-Q245R-N248D, S101G-S103A-V104I-P129E-S188D-A232V-Q245R-N248D-H249R, S024R-S101G-S103A-V104I-P129E-A158E-A232V-Q245R-N248D-H249R, T022A-S024R-S101G-S103A-V104I-A158E-G159E-S188D-A232V-Q245R-N248D-H249R, T022A-S024R-S101G-S103A-V104I-P129E-A158E-G159E-S188D-A232V-N238R-Q245R-N248D, S024R-S101G-S103A-V104I-P129E-L148I-A158E-A232V-Q245R-N248D, A016S-S024R-S101G-S103A-V104I-A158E-S188D-A232V-Q245R-N248D-H249R, S101G-S103A-V104I-A158E-G159E-A232V-Q245R-N248D-H249R, T022A-S101G-S103A-V104I-P129E-A158E-G159E-A232V-N238R-Q245R-N248D, T022A-S024R-S101G-S103A-V104I-P129E-A158E-G159E-A232V-Q245R-N248D-H249R, T022A-S024R-S101G-S103A-V104I-S128N-A158E-S188D-A232V-Q245R-N248D, S024R-S101G-S103A-V104I-P129E-S188D-A232V-Q245R-N248D, T022A-S024R-S101G-S103A-V104I-P129E-A158E-A232V-Q245R-N248D, T022A-S024R-S101G-S103A-V104I-P129E-A232V-Q245R-N248D, T022A-S024R-S101G-S103A-V104I-P129E-S188D-A232V-Q245R-N248D, S024R-S101G-S103A-V104I-A158E-S188D-A232V-N238R-Q245R-N248D, T022A-S101G-S103A-V104I-S128N-P129E-S188D-A232V-N238R-Q245R-N248D, S024R-S101G-S103A-V104I-P129E-S188D-A232V-N238R-Q245R-N248D, S024R-S101G-S103A-V104I-A158E-G159E-S188D-A232V-Q245R-N248D, T022A-S024R-S101G-S103A-V104I-S128N-S188D-A232V-Q245R-N248D, S024R-S101G-S103A-V104I-P129E-A158E-S188D-A232V-Q245R-N248D, T022A-S024R-S101G-S103A-V104I-S128N-P129E-A158E-A232V-Q245R-N248D, S024R-S101G-S103A-V104I-G159E-S188D-A232V-Q245R-N248D, T022A-S101G-S103A-V104I-S128N-P129E-A232V-N238R-Q245R-N248D, S024R-S101G-S103A-V104I-P129E-G159E-A232V-Q245R-N248D, T022A-S024R-S101G-S103A-V104I-P129E-A158E-S188D-A232V-N238R-Q245R-N248D, T022A-S024R-S101G-S103A-V104I-A158E-G159E-S188D-A232V-Q245R-N248D, S024R-S101G-S103A-V104I-G159E-S188D-A232V-Q245R-N248D-H249R, T022A-S101G-S103A-V104I-P129E-A158E-A232V-N238R-Q245R-N248D, T022A-S024R-S101G-S103A-V104I-P129E-A158E-A232V-Q245R-N248D-H249R, S024R-S101G-S103A-V104I-L148I-A158E-A232V-Q245R-N248D, T022A-S101G-S103A-V104I-A158E-G159E-S188D-A232V-Q245R-N248D-H249R, T022A-S101G-S103A-V104I-A158E-S188D-A232V-Q245R-N248D, T022A-S101G-S103A-V104I-P129E-S188D-A232V-N238R-Q245R-N248D, S024R-S101G-S103A-V104I-P129E-A158E-G159E-S188D-A232V-Q245R-N248D-H249R, T022A-S024R-S101G-S103A-V104I-A158E-G159E-S188D-A232V-N238R-Q245R-N248D, S101G-S103A-V104I-P129E-A158E-S188D-A232V-Q245R-N248D-H249R, S024R-S101G-S103A-V104I-S128N-A158E-A232V-Q245R-N248D, T022A-S024R-S101G-S103A-V104I-S128N-P129E-S188D-A232V-Q245R-N248D, T022A-S101G-S103A-V104I-P129E-G159E-A232V-N238R-Q245R-N248D, S101G-S103A-V104I-P129E-G159E-A232V-Q245R-N248D-H249R, T022A-S101G-S103A-V104I-P129E-A158E-A232V-Q245R-N248D-H249R, S024R-S101G-S103A-V104I-P129E-L148I-A158E-S188D-A232V-

Q245R-N248D, T022A-S101G-S103A-V104I-P129E-G159E-A232V-Q245R-N248D-H249R, S024R-S101G-S103A-V104I-G159E-S188D-A232V-N238R-Q245R-N248D, S024R-S101G-S103A-V104I-P129E-A158E-G159E-A232V-Q245R-N248D-H249R, S024R-S101G-S103A-V104I-P129E-A158E-G159E-A232V-N238R-Q245R-N248D, S024R-S101G-S103A-V104I-S128N-G159E-S188D-A232V-Q245R-N248D, T022A-S101G-S103A-V104I-G159E-S188D-A232V-Q245R-N248D-H249R, S024R-S101G-S103A-V104I-P129E-G159E-S188D-A232V-N238R-Q245R-N248D, S101G-S103A-V104I-A158E-A232V-N238R-Q245R-N248D, T022A-S101G-S103A-V104I-P129E-G159E-S188D-A232V-Q245R-N248D-H249R, S024R-S101G-S103A-V104I-P129E-L148I-S188D-A232V-Q245R-N248D, S024R-S101G-S103A-V104I-A158E-A232V-Q245R-N248D-H249R, T022A-S101G-S103A-V104I-A158E-G159E-A232V-N238R-Q245R-N248D, S024R-S101G-S103A-V104I-A158E-G159E-A232V-N238R-Q245R-N248D, T022A-S101G-S103A-V104I-P129E-A158E-G159E-A232V-Q245R-N248D-H249R, S101G-S103A-V104I-P129E-A158E-S188D-A232V-N238R-Q245R-N248D, T022A-S024R-S101G-S103A-V104I-P129E-A158E-G159E-A232V-Q245R-N248D, S101G-S103A-V104I-S188D-A232V-N238R-Q245R-N248D, T022A-S024R-S101G-S103A-V104I-A158E-A232V-Q245R-N248D-H249R, T022A-S024R-S101G-S103A-V104I-L148I-A158E-A232V-Q245R-N248D, S101G-S103A-V104I-P129E-A158E-G159E-A232V-N238R-Q245R-N248D, T022A-S101G-S103A-V104I-G159E-S188D-A232V-N238R-Q245R-N248D, T022A-S024R-S101G-S103A-V104I-P129E-A158E-G159E-S188D-A232V-Q245R-N248D-H249R, T022A-S101G-S103A-V104I-P129E-A232V-N238R-Q245R-N248D, T022A-S024R-S101G-S103A-V104I-S188D-A232V-Q245R-N248D-H249R, S101G-S103A-V104I-P129E-A158E-G159E-A232V-Q245R-N248D-H249R, T022A-S101G-S103A-V104I-A158E-G159E-A232V-Q245R-N248D-H249R, S101G-S103A-V104I-P129E-S188D-A232V-Q245R-N248D, S024R-S101G-S103A-V104I-P129E-G159E-A232V-N238R-Q245R-N248D, S101G-S103A-V104I-S128N-P129E-A232V-Q245R-N248D, S101G-S103A-V104I-A158E-S188D-A232V-Q245R-N248D, T022A-S024R-S101G-S103A-V104I-P129E-A232V-Q245R-N248D-H249R, S101G-S103A-V104I-P129E-G159E-A232V-N238R-Q245R-N248D, S101G-S103A-V104I-A158E-G159E-S188D-A232V-N238R-Q245R-N248D, S024R-S101G-S103A-V104I-A232V-Q245R-N248D-H249R, T022A-S024R-S101G-S103A-V104I-P129E-L148I-A232V-Q245R-N248D, T022A-S024R-S101G-S103A-V104I-A158E-A232V-N238R-Q245R-N248D, S101G-S103A-V104I-S128N-P129E-A232V-N238R-Q245R-N248D, T022A-S101G-S103A-V104I-S128N-G159E-A232V-Q245R-N248D, T022A-S101G-S103A-V104I-S128N-P129E-A158E-A232V-N238R-Q245R-N248D, S101G-S103A-V104I-S128N-P129E-S188D-A232V-Q245R-N248D-H249R, T022A-S024R-S101G-S103A-V104I-S128N-P129E-A158E-S188D-A232V-Q245R-N248D-H249R, S024R-S101G-S103A-V104I-S128N-A158E-G159E-S188D-A232V-Q245R-N248D, T022A-S024K-S101G-S103A-V104I-S128N-A158E-G159E-A232V-Q245R-N248D, S101G-S103A-V104I-P129E-L148I-S188D-A232V-Q245R-N248D, S024R-S101G-S103A-V104I-L148I-A232V-Q245R-N248D, T022A-S101G-S103A-V104I-L148I-S188D-A232V-Q245R-N248D, S024R-S101G-S103A-V104I-S128N-P129E-S188D-A232V-Q245R-N248D, S101G-S103A-V104I-S128N-P129E-A158E-A232V-N238R-Q245R-N248D, T022A-S024R-S101G-S103A-V104I-P129E-L148I-A158E-S188D-A232V-Q245R-N248D, T022A-S024R-S101G-S103A-V104I-L148I-A158E-S188D-A232V-Q245R-N248D, S101G-S103A-V104I-L148I-G159E-A232V-Q245R-N248D, T022A-S024R-S101G-S103A-V104I-A158E-S188D-A232V-Q245R-N248D, and S101G-S103A-V104I-S128N-P129E-A158E-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: T022A-S024R-S101G-S103A-V104I-A158E-A232V-Q245R-N248D-H249R, T022A-S024R-S101G-S103A-V104I-P129E-A232V-Q245R-N248D-H249R, S024R-S101G-S103A-V104I-A158E-G159E-A232V-N238R-Q245R-N248D, S024R-S101G-S103A-V104I-A232V-Q245R-N248D-H249R, S101G-S103A-V104I-A158E-A232V-Q245R-N248D-H249R, S101G-S103A-V104I-S188D-A232V-Q245R-N248D-H249R, S024R-S101G-S103A-V104I-G159E-S188D-A232V-Q245R-N248D-H249R, T022A-S024R-S101G-S103A-V104I-A158E-A232V-N238R-Q245R-N248D, S024R-S101G-S103A-V104I-G159E-S188D-A232V-N238R-Q245R-N248D, T022A-S024R-S101G-S103A-V104I-P129E-A232V-Q245R-N248D, S024R-S101G-S103A-V104I-L148I-A232V-Q245R-N248D, S024R-S101G-S103A-V104I-P129E-A158E-A232V-Q245R-N248D-H249R, S024R-S101G-S103A-V104I-L148I-A158E-A232V-Q245R-N248D, T022A-S024R-S101G-S103A-V104I-P129E-A158E-A232V-Q245R-N248D-H249R, A016S-S024R-S101G-S103A-V104I-A158E-S188D-A232V-Q245R-N248D-H249R, S024R-S101G-S103A-V104I-P129E-G159E-A232V-N238R-Q245R-N248D, S024R-S101G-S103A-V104I-P129E-S188D-A232V-Q245R-N248D-H249R, T022A-S101G-S103A-V104I-P129E-A232V-N238R-Q245R-N248D, T022A-S024R-S101G-S103A-V104I-L148I-A158E-A232V-Q245R-N248D, S024R-S101G-S103A-V104I-P129E-S188D-A232V-N238R-Q245R-N248D, T022A-S024R-S101G-S103A-V104I-A158E-G159E-S188D-A232V-N238R-Q245R-N248D, T022A-S101G-S103A-V104I-A158E-G159E-A232V-N238R-Q245R-N248D, T022A-S024R-S101G-S103A-V104I-P129E-A158E-A232V-Q245R-N248D, S101G-S103A-V104I-A158E-S188D-A232V-Q245R-N248D-H249R, T022A-S101G-S103A-V104I-A158E-G159E-A232V-Q245R-N248D-H249R, and S024R-S101G-S103A-V104I-A158E-G159E-A232V-Q245R-N248D, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: V104L-S128N-A158E-R186H-H249R, S128N-A158E-S188D-H249R, N062E-S128N-A158E-G159E-E271F, N062E-A158E-S188D-H249R-E271F, N062E-A158E-R186H-H249R-E271F, S128N-A158E-S188D-Y209E-E271F, N062E-G159E-S188D-H249R, A016S-N062E-A158E-R186H-H249R, N062E-A158E-G159E-H249R, S101A-S128N-A158E-Y209E-

H249R, S128N-A158E-R186H-E271F, N062E-A158E-S188D-H249R, N062E-A158E-R186H-E271F, N062E-A158E-R186H-H249R, N062E-S101A-R186H-H249R, N062E-S101A-A158E-R186H-E271F, N062E-V104L-A158E-S188D-H249R-E271F, N062E-G159E-R186H-H249R, N062E-G159E-H249R, S128N-A158E-R186H-H249R, S128N-A158E-S188D-E271F, N062E-A158E-H249R, N062E-R186H-S188D-H249R-E271F, S128N-A158E-Y209E-, N062E-S101A-A158E-H249R, V104L-S128N-A158E-R186H-E271F, N062E-S101A-A158E-R186H-H249R-E271F, A016S-N062E-A158E-H249R, N062E-S101A-G159E-H249R, S128N-A158E-R186H-S188D-E271F, S101A-S128N-A158E-R186H-E271F, N062E-S101A-S188D-H249R, S101A-V104L-A158E-R186H-S188D-H249R, N062E-G159E-H249R-E271F, S128N-A158E-G159E-E271F, A016S-N062E-V104L-A158E-R186H-E271F, T022A-S128N-A158E-H249R, S128N-A158E-H249R, N062E-S101A-V104L-A158E-R186H-E271F, A016S-N062E-A158E-R186H-E271F, V104L-S128N-A158E-H249R, V104L-S128N-A158E-S188D-H249R, T022A-N062E-A158E, N062E-S101A-S188D-H249R-E271F, N062E-A158E-H249R-E271F, V104L-S128N-A158E-R186H-S188D-E271F, N062E-S101A-R186H-E271F, N062E-V104L-G159E-H249R, N062E-R186H-H249R, N062E-S101A-R186H-H249R-E271F, S101A-A158E-R186H-S188D-H249R, N062E-S101A-R186H, S101A-S128N-P129E-R186H-H249R, S101A-S103G-A158E-R186H-H249R, A016S-N062E-V104L-R186H-S188D-E271F, V104L-A158E-R186H-H249R, S101A-S128N-A158E-S188D-Y209E-E271F, N062E-S101A-R186H-S188D-E271F, A016S-N062E-A158E-H249R-E271F, N062E-S128N-A158E, N062E-S128N-G159E-H249R, N062E-S101A-A158E-S188D-H249R, S101A-S128N-A158E-H249R, N062E-A158E-R186H-S188D-H249R, A016S-V104L-A158E-R186H-E271F, N062E-L148I-G159E, N062E-S101A-A158E-R186H-H249R, N062E-S101A-R186H-S188D-H249R, V104L-A158E-R186H-S188D-H249R, N062E-S101A-V104L-R186H-S188D-E271F, T022A-S101A-A158E-R186H-H249R, S101A-S128N-A158E-Y209E, A158E-R186H-S188D-H249R-E271F, V104L-A158E-R186H-S188D-H249R-E271F, S101A-V104L-A158E-R186H-H249R, V104L-A158E-H249R, S101A-V104L-S128N-A158E-R186H-E271F, A016S-V104L-S188D-H249R, S101A-V104L-A158E-R186H-S188D-E271F, V104L-S128N-G159E-E271F, V104L-A158E-R186H-H249R-E271F, A158E-R186H-H249R, S101A-A158E-R186H-H249R, V104L-A158E-S188D-H249R-E271F, A016S-S128N-A158E-R186H, V104L-S128N-R186H-S188D-H249R, A016S-S101A-S128N-R186H, A016S-N062E-S128N-R186H-E271F, A016S-S128N-R186H-E271F, S128N-P129E-R186H, A158E-R186H-H249R-E271F, A016S-A158E-H249R, A016S-A158E-R186H-H249R, A016S-T022A-A158E-R186H-E271F, E089P-S101A-P129E-R186H, T022A-S128N-A158E-R186H, S101A-V104L-S128N-A158E-R186H, T022A-S128N-R186H-S188D-, N062E-V104L-A158E-R186H-S188D-H249R, T022A-A158E-R186H-H249R-E271F, T022A-V104L-A158E-H249R, S101A-L111V-P129E, A016S-A158E-H249R-E271F, A016S-L111V-S188D-, T022A-V104L-R186H-S188D-H249R, and V104L-L148I-S188D-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: A001R-S101G-S103A-V104I-A232V-Q245R, V004R-S101G-S103A-V104I-A232V-Q245R, N043R-S101G-S103A-V104I-A232V-Q245R-E271L, S078R-S101G-S103A-V104I-A232V-Q245R, V004R-N043R-S101G-S103A-V104I-A232V-Q245R, N018R-N043R-S101G-S103A-V104I-A232V-Q245R, G020R-S101G-S103A-V104I-A232V-Q245R, S101G-S103A-V104I-A232V-Q245R-E271L, G020R-N043R-S101G-S103A-V104I-A232V-Q245R, S024R-N043R-S101G-S103A-V104I-A232V-Q245R, G020R-G025R-N116A-Y167W, N018R-S101G-S103A-V104I-A232V-Q245R, T022R-S101G-S103A-V104I-A232V-Q245R, S078R-S103N-S106G-Y167W-Q236N, N018R-N043D-S101G-S103A-V104I-A232V-Q245R-N269R, N043R-S101G-S103A-V104I-A232V-Q245R-N269R, S024R-S101A-H120E-A194F-H249R, G020R-N043D-S101G-S103A-V104I-A232V-Q245R-N269R, S101G-S103A-V104I-S212F-A232V-Q245R, G020R-S144R-N185I-L233C-Q236N, G023A-S078R-S216F-Q236N-H249R, S101G-S103A-V104I-A232V-Q245R-N269R, S101G-S103A-V104I-G115R-A232V-Q245R, P052N-S078R-S103N-L148I-T213A, N018R-N043D-S101G-S103A-V104I-A232V-Q245R-H249R, S024R-N043D-S101G-S103A-V104I-A232V-Q245R-H249R, S024R-N043D-S101G-S103A-V104I-A232V-Q245R-N269R, G025R-E089I-N116A-P239S-A270C, S024R-S101G-S103A-V104I-A232V-Q245R, L148I-T213A-N252R, S024R-G025R-N183D-Y192W-P239S, G046R-A194F-S212M, V104L-L217E-T224A-H249R-N252R, G023A-Y091F-V121F-Y192W-Q236N, S101G-S103A-V104I-A232V-V244R-Q245R, S099F-S144R-Y167W-N252R, S101G-S103A-V104I-A232V-Q245R-H249R, N043R-S101G-S103A-V104I-A232V-Q245R, T022W-S078R-Y167W-S212M-A270C, V121F-N252R-A270C, G020R-S103N-S216F-Q236N-N252R, N043R-S101G-S103A-V104I-A232V-Q245R-H249R, G023A-P052N-Y192W-I198L-N252R, G025R-G046R-V121F, S024R-S078R-V104L-N116A-N183D, G046R-Q059A-S103N-G211Q-S212M, G020R-P052N-N062Q-Y091F-Y192W, G023A-P052N-S144R-Y192W-S216F, S101G-S103A-V104I-A232V-S242R-Q245R, P052N-S103N-N116A-L148I-Y192W, E089I-N116A-N117F-T224A-H249R, S144R-G211Q-N238L-P239S-H249R, N043A-N062Q-A194F-G211Q, G020R-S024R-P052N-Q059A-S216F, S024R-Y167W-T224A-H249R, T057R-Y167W-H249R, G025R-S103N-R186K-A194F-T224A, S105T-S128N-S144R-L148I-S212M, G020R-Q059A-S144R-Y192W-T224A, S024R-N043A-N117F-A194F-G211Q, N117F-A 194F-T213A-A270C, S078R-Y091F-V121F-L233C-N252R, T057R-S099F-S105T-I198L-T213A, G023A-Y091F-S101A-I198L-N252R, N062Q-S103N-V121F-S144R-H249R, N043R-S101G-S103A-V104I-A232V-S242R-Q245R, G023A-S024R-N117F-S212M-S216F, V104L-T213A-S216F, A194F-G211Q-Q236N, N062Q-S103N-N117F-A194F, S024R-N062Q-V104L-S106G-H249R, T057R-E089I-I198L, G046R-Q059A-S106G-L217E-H249R, N117F-T213A-A215F, S101A-H120E-Y192W-A215F-T224A, N043A-T057R-N117F-S144R-N183D, G046R-N183D-N238L, G025R-N043A-E089I-N117F, S078R-V104L-T213A-A215F-T224A, Y091F-S099F-S101A-S105T-Y167W, S106G-N117F-N238L, G046R-E089I-Y091F-S101A-N116A, G020R-N062Q-E089I-R186K-S212M, T057R-S099F-V121F-N185I-Y192W, G046R-E089I-Y192W-L233C-A270C, E089I-N117F-N185I-A215F-L233C, P052N-V104L-N183D-S216F-H249R, S078R-S099F-N116A-R186K-T224A, G025R-S105T-S128N-S144R-A270C, S105T-G211Q-S216F, S024R-G046R-Y091F-V121F, S106G-N185I-S216F-Q236N, N062Q-S101A-Q236N-N252R-A270C, G025R-N043A-Y091F-I198L-A270C, G020R-G023A-V104L-Y192W-L233C, S024R-N043A-S105T-S106G-I198L, G020R-E089I-L217E, S024R-Y091F-I198L-A215F-P239S, G046R-E089I-S099F-R186K-S212M, V104L-H120E-R186K-S216F-N252R, T022W-A194F-T213A-L233C-N238L, S099F-S105T-S106G-A194F-S212M, E089I-S105T-N116A-A215F-S216F, G025R-N116A-H120E-T224A-A270C, N043A-Q059A-S101A-S216F-T224A, T057R-N183D-Q236N, G025R-N062Q-S128N-S144R-N185I, S103N-H120E-Y167W-I198L-L233C, T022W-E089I-S216F, S024R-S106G-N116A-S212M-T224A, G020R-P052N-S101A-I198L-L233C, E089I-Y091F-N185I-G211Q-A270C, L111I-A215F-P239S, S024R-N116A-R186K-L233C-Q236N, and G023A-S103N-S106G-S212M-A215F, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: G020R-T022W-S078R-S101A-S103A-V104I-N116S-T213A-A215F-A232V-Q245R, N018R-S078R-S101G-S103A-V104I-A232V-Q245R, S024R-R045T-S101G-S103A-V104I-A232V-Q245R-N269R, G020R-T022W-S078R-S101G-S103A-V104I-N116A-A232V-Q245R, G020R-T22W-S101G-S103A-V104I-A232V-Q245R, N018R-N043R-S101G-S103A-V104I-A232V-Q245R, N018R-T022W-S024R-N076D-S101A-N116A-A232V-Q245R, N018R-V104I-A232V-H249R, N018R-S024R-N076D-S101A-N116A-G211Q-H249R, N018R-N043D-S078R-S101G-S103A-V104I-L217E-A232V-Q245R, N018R-N043R-S101G-S103A-V104I-A232V-Q245R-N269R, N018R-R045T-N076D-S101G-S103A-V104I-A232V-Q245R-N269R, N076D-S078R-S101G-S103A-V104I-A232V-Q245R-N269R, G020R-N043D-S078R-S101G-S103A-V104I-A232V-Q245R, N018R-N043D-N076D-S101G-S103A-V104I-A232V-Q245R-N269R, S024R-R045T-N076D-S078R-S101G-S103A-V104I-A232V-Q245R-N269R, N018R-S103A-A232V-H249R, N018R-S101G-V104I-A232V-Q245R, G020R-S024R-S101G-S103A-V104I-L217E-A232V-Q245R-H249R, N018R-T22K-N043D-S101G-S103A-V104I-A232V-Q245R, N043R-R045T-S101G-S103A-V104I-A232V-Q245R-N269R, G020R-T22W-S101G-S103A-V104I-G211Q-A232V-Q245R, S024R-N076D-S078R-S101G-S103A-V104I-A232V-Q245R-N269R, G020R-T22W-S078R-S101A-S103A-V104I-N116A-N183D-A232V, N018R-S024R-N076D-N116A-A215F-H249R, N018R-N043R-R045T-S101G-S103A-V104I-A232V-Q245R, S024R-N043R-N076D-S101G-S103A-V104I-A232V-Q245R, G020R-T022W-S101G-S103A-V104I-A232V-Q245R, G020R-T022W-S101G-S103A-V104I-G211Q-A232V-Q245R, G020R-T022W-S078R-S101G-S103A-V104I-N116A-T213A-A215F-A232V-Q245R, N043D-N076D-S078R-S101G-S103A-V104I-A232V-Q245R-N269R, N018R-S024R-N076D-S101A-N116A-T213A-H249R, N018R-S024R-N076D-N116A-G211Q-H249R, N043R-R045T-N076D-S078R-S101G-S103A-V104I-A232V-Q245R, N018R-S101G-Q245R, G020R-T22W-S101A-S103A-V104I-G211Q-T213A-A232V-Q245R, G020R-S024R-N043D-N076D-S078R-S101G-S103A-V104I-A232V-Q245R, N018R-R045T-N076D-S078R-S101G-S103A-V104I-A232V-Q245R, G020R-S078R-S101G-S103A-V104I-G211Q-T213A-A215F-A232V-Q245R, R045T-S078R-S101G-S103A-V104I-A232V-Q245R-N269R, S024R-N043D-S101G-S103A-V104I-A232V-Q245R-N269R, N018R-S101G-S103A-H249R, N018R-T22W-S024R-N076D-S101A-N116A-A232V-Q245R, N018R-S101G-V104I-A232V-H249R, G020R-T22W-S101A-S103A-V104I-A215F-A232V-Q245R, N018R-S024R-N076D-G211Q-T213A-H249R, N018R-T022W-S024R-N076D-S101A-I198L-H249R, S024R-S101G-S103A-V104I-A232V-Q245R, G020R-N076D-S101G-S103A-V104I-A232V-Q245R-N269R, G020R-S101G-S103A-V104I-A232V-Q245R-N269R, N043D-S078R-S101G-S103A-V104I-A232V-Q245R, G020R-S101G-V104I-T213A-A215F-A232V-Q245R, G020R-S101G-S103A-V104I-N116A-A215F-A232V-Q245R, S024R-S103A-V104I-H249R, N018R-N076D-S078R-S101G-S103A-V104I-A232V-Q245R, R045T-N076D-S078R-S101G-S103A-V104I-A232V-Q245R-N269R, S024R-S101G-V104I-Q245R, G020R-S101G-S103A-V104I-G211Q-T213A-A215F-A232V-Q245R, S024R-S103A-V104I-A232V-H249R, N018R-S024R-N076D-N116A-G211Q-A215F-H249R, N018R-Q245R, S024R-S103A-Q245R, S024R-S103A-V104I-Q245R, G020R-S078R-S101G-A232V-Q245R, N018R-S024R-N076D-V104I-H249R, N018R-S024R-V104I-H249R, S024R-S101G-S103A-V104I-A232V-Q245R, N018R-S024R-N076D-G211Q-A215F-H249R, R019H-G020R-T022W-S078R-S101G-S103A-V104I-G211Q-A232V-Q245R, N018R-S024R-N076D-S101A-I198L-G211Q-T213A-H249R, N018R-S024R-N043D-S101G-S103A-V104I-A232V-Q245R, G020R-T22W-S103A-V104I-A232V-Q245R, N018R-S103A-V104I-H249R, N018R-T022W-S024R-N076D-S101A-I198L-A215F-H249R, N018R-S024R-S101G-V104I-A232V, S078R-S101G-S103A-V104I-A232V-Q245R-N269R, S024R-N043R-N076D-S078R-S101G-S103A-V104I-A232V-Q245R, N018R-G020R-N043D-N076D-S101G-S103A-V104I-A232V-Q245R, N018R-T22W-S024R-N076D-N116A-T213A-H249R, N018R-S024R-S101G-V104I, G020R-S101A-S103A-V104I-A215F-A232V-Q245R, N018R-R045T-S078R-S101G-S103A-V104I-A232V-Q245R, N018R-S101G-S103A-Q245R, N043R-N076D-S078R-S101G-S103A-V104I-A232V-Q245R, G020R-T022W-S101A-S103A-V104I-G211Q-A215F-A232V-Q245R, G020R-T22W-S078R-S101G-S103A-V104I-N116A-T213A-A215F-A232V-Q245R, G020R-S078R-S101G-S103A-V104I-A215F-A232V-Q245R, G020R-T022W-S078R-S101G-S103A-V104I-N116A-N183D-A232V-Q245R, N076D-S101G-S103A-V104I-A232V-Q245R, N076D-S101G-S103A-V104I-A232V-Q245R-N269R, G020R-T22W-S101A-S103A-V104I-A232V-Q245R, G020R-S101G-S103A-A232V-Q245R, G020R-T022W-S078R-S101A-S103A-V104I-N116A-N183D-A232V-Q245R, N018R-G020R-S024R-R045T-N076D-S101G-S103A-V104I-A232V-Q245R-N269R, N043R-R045T-S078R-S101G-S103A-V104I-A232V-Q245R, N018R-S101G-V104I-H249R, G020R-T22W-S078R-S101G-S103A-V104I-N116A-N183D-A232V-Q245R, G020R-T022W-S101G-S103A-V104I-I198L-G211Q-T213A-A232V-Q245R, G020R-S078R-S101A-S103A-V104I-N116A-N183D-T213A-A232V-Q245R, S024R-N076D-V104I-A232V-Q245R, N018R-G020R-N076D-S101G-S103A-V104I-A232V-Q245R, N018R-S024R-N076D-S101G-V104I-A232V-H249R, N018R-N043D-S078R-S101G-S103A-V104I-A232V-Q245R, A001T-N018R-S024R-N076D-N116A-T213A-H249R, N076D-S078R-S101G-S103A-V104I-A232V-Q245R, G020R-S078R-S101G-S103A-V104I-N116A-A232V-Q245R, N043R-N076D-S101G-S103A-V104I-A232V-Q245R, N018R-R045T-S101G-S103A-V104I-A232V-Q245R, N018R-N076D-S101G-V104I-A232V-Q245R, G020R-S078R-S101G-S103A-V104I-N116A-N183D-A232V-Q245R, N018R-S024R-N076D-S101A-G211Q-T213A-A215F-H249R, R045T-S078R-S101G-S103A-V104I-A232V-Q245R, N043R-N076D-S101G-S103A-V104I-A232V-Q245R-N269R, G020R-T022W-S078R-S101G-S103A-V104I-N116A-N183D-T213A-A232V-Q245R, G020R-T022W-S101G-S103A-V104I-N116A-N183D-T213A-A232V-Q245R, G020R-S101G-I198L-A215F-A232V-Q245R, N018R-S024R-N076D-T213A-A215F-H249R, G020R-S078R-S101G-S103A-V104I-N116A-G211Q-A232V-Q245R, G020R-T022W-S078R-S101A-S103A-V104I-N116A-N183D-A215F-A232V-Q245R, G020R-T022W-S078R-S101A-S103A-V104I-N116A-N183D-T213A-A232V-Q245R, S024R-A232V-Q245R, N018R-S024R-N043D-S101G-S103A-V104I-A232V-Q245R-N269R, N018R-S024R-N076D-S101A-A215F-H249R, N018R-T022W-S024R-N076D-N116A-T213A-H249R, S101G-S103A-V104I-A232V-Q245R, N018R-S024R-N076D-G211Q-T213A-A215F-H249R, N018R-S024R-N076D-N116A-T213A-A215F-H249R, N043D-N076D-S078R-S101G-S103A-V104I-A232V-Q245R-N269R, N043D-S078R-S101G-S103A-V104I-A232V-Q245R-H249R, G020R-T022W-S078R-S101G-S103A-V104I-N116A-N183D-G211Q-A232V-Q245R, N018R-S024R-N076D-S101A-I198L-G211Q-A215V-H249R, N018R-T022W-S024R-N076D-N116A-G211Q-H249R, G020R-S103A-V104I-A232V-Q245R, G020R-T22W-S101A-S103A-V104I-G211Q-A215F-A232V-Q245R, S024R-N076D-S101G-S103A-V104I-A232V-Q245R, G020R-S101G-S103A-V104I-N116A-A232V-Q245R, N018R-T22W-S024R-N076D-I198L-A215F-H249R, G020R-T022W-S103A-V104I-A232V-Q245R, G020R-T022W-S101A-S103A-V104I-G211Q-T213A-A232V-Q245R, G020R-T022W-S101G-S103A-V104I-G211Q-T213A-A215F-A232V-Q245R, N018R-N043R-R045T-N076D-S101G-S103A-V104I-A232V-Q245R, N018R-T022W-S024R-N076D-S101A-I198L-T213A-A215F-H249R, N018R-T22W-S024R-N076D-S101A-A215F-H249R, G020R-R045T-S101G-S103A-V104I-A232V-Q245R, G020R-S078R-S101G-S103A-V104I-T180A-A232V-Q245R, G020R-T022W-S078R-S101G-S103A-V104I-N116A-N183D-A215F-A232V-Q245R, N018R-S101G-S103A-V104I, G020R-T22W-S101A-S103A-V104I-N116A-G211Q-T213A-A215F-A232V-Q245R, N018R-S024R-N076D-S103A-A232V-Q245R, G020R-S078R-S101A-S103A-V104I-N116A-N183D-A232V-Q245R, N018R-S024R-N076D-G211Q-H249R, G020R-S101A-S103A-V104I-T213A-A215F-A232V-Q245R, N018R-G020R-N043D-S101G-S103A-V104I-A232V-Q245R, G020R-T022W-S101A-S103A-V104I-G211Q-A232V-Q245R, G020R-T022W-S101A-S103A-V104I-N116A-G211Q-A215F-A232V-Q245R, G020R-T022W-S101A-S103A-V104I-N116A-G211Q-A232V-Q245R, N018R-S024R-N076D-A232V-H249R, N018R-S024R-R045T-N076D-S101G-S103A-V104I-A232V-Q245R-N269R, N018R-N076D-Q245R, S024R-V104I-Q245R, S101G-A232V, G020R-T22W-S101A-S103A-V104I-N116A-G211Q-A215F-A232V-Q245R, N018R-G020R-T022W-S024R-N076D-N116A-N183D-I198L-T213A-H249R, G020R-T022W-S078R-S101A-S103A-V104I-A232V-Q245R, G020R-T022W-S078R-S101A-S103A-V104I-I198L-A232V-Q245R, S024R-Q245R-H249R, G020R-S101G-S103A-V104I-N116A-G211Q-A232V-Q245R, N018R-T22W-S024R-N076D-N116A-G211Q-H249R, S024R-S101G-V104I-H249R, N018R-S024R-N076D-N116A-I198L-G211Q-T213A-A215F-H249R, N018R-S024R-V104I, G020R-T022W-S078R-S101A-S103A-V104I-N183D-I198L-T213A-A215F-A232V-Q245R, N018R-G020R-T22W-S024R-N076D-N116A-N183D-I198L-T213A-H249R, G020R-T022W-S101A-S103A-V104I-A232V-Q245R, Q012H-G020R-S078R-S101G-S103A-V104I-I198L-G211Q-T213A-A232V-Q245R, N018R-S024R-N076D-S101A-G211Q-A215F-H249R, N018R-S024R-N076D-T213A-H249R, S024R-V104I-H249R, N018R-T022W-S024R-N076D-G211Q-H249R, N018R-N076D-S103A-V104I-H249R, N043R-N076D-S101G-S103A-V104I-L217E-A232V-Q245R, G020R-S078R-S101G-S103A-V104I-N183D-G211Q-T213A-A232V-Q245R-E271G, N018R-T022W-S024R-N076D-S101A-N116A-I198L-A215F-H249R, N018R-S024R-N043D-N076D-S101G-S103A-V104I-A232V-Q245R, N018R-S024R-N076D-S101A-I198L-A215F-H249R, N018R-T022W-S024R-N076D-N116A-I198L-G211Q-T213A-H249R, N018R-S024R-N076D-S101A-N116A-T213A-A215F-H249R, G020R-N043D-R045T-S078R-S101G-S103A-V104I-A232V-Q245R, R045T-S078R-S101G-S103A-V104I-A232V-Q245R-H249R, N018R-T22W-S024R-N076D-S101A-N116A-A215F-H249R, N043D-S101G-S103A-V104I-A232V-Q245R-N269R, G020R-T022W-S078R-S101A-S103A-V104I-N116A-N183D-T213A-A215F-A232V-Q245R, N018R-S024R-N076D-N116A-G211Q-T213A-A215F-H249R, S024R-S103A-M175L-A232V-H249R, N018R-S024R-N076D-N116A-T213A-H249R, G020R-R045T-N076D-S101G-S103A-V104I-A232V-Q245R, G020R-S078R-S101A-S103A-V104I-N116A-N183D-G211Q-T213A-A215F-A232V-Q245R, S024R-N043R-R045T-N076D-S078R-S101G-S103A-V104I-A232V-Q245R, N018R-S024R-N076D-S101A-N116A-I198L-T213A-A215F-H249R, N043R-R045T-S101G-S103A-V104I-A232V-Q245R, N018R-T022W-S024R-N076D-S101A-I198L-G211Q-Q245R, G020R-S024R-N043D-N076D-S078R-S101G-S103A-V104I-A232V-Q245R-N269R, S024R-A232V, G020R-S078R-S101A-S103A-V104I-N116A-N183D-G211Q-A232V-Q245R, S024R-N076D-S101G-A232V-Q245R, N018R-N076D-S101G-S103A-V104I-H249R, N018R-S024R-N076D-I198M-G211Q-T213A-A215F-H249R, N018R-T22W-S024R-N076D-S101A-I198L-A215F-H249R, N018R-N043R-N076D-S101G-S103A-V104I-A232V-Q245R-N269R, G020R-T022W-S103A-G211Q-T213A-A215F-A232V-Q245R, G020R-S078R-S101A-S103A-V104I-N116A-N183D-G211Q-T213A-A232V-Q245R, R045T-N076D-S101G-S103A-V104I-A232V-Q245R-N269R, N018R-T22W-S024R-N076D-S101A-G211Q-T213A-H249R, N018R-S024R-N076D-N116A-I198L-A215F-H249R-V268G, N018R-T022W-S024R-N076D-S101A-G211Q-H249R, N018R-T022W-S024R-N076D-S101A-N116A-I198L-G211Q-H249R, S101G-S103A-V104I-Q245R, N018R-N076D-S101G-A232V-Q245R, N018R-G020R-R045T-S101G-S103A-V104I-A232V-Q245R, N018R-T022W-S024R-N076D-S101A-N116A-I198L-H249R, N018R-T022W-S024R-N076D-N116A-I198L-T213A-H249R, S078R-S101G-S103A-V104I-A232V-Q245R-H249R, N018R-S078R-S101G-S103A-V104I-L217E-A232V-Q245R, G020R-N043R-N076D-S101G-S103A-V104I-A232V-Q245R-N269R, N018R-N043D-N076D-S101G-S103A-V104I-A232V-Q245R-H249R, R045T-S101G-

S103A-V104I-A232V-Q245R-N269R, S024R-S103A-A232V, N018R-S024R-N076D-S101A-G211Q-H249R, N043D-S101G-S103A-V104I-A232V-Q245R-H249R, N018R-N043R-R045T-N076D-S076T-S101G-S103A-V104I-A232V-Q245R-A273T, N018R-G020R-N043D-S078R-S101G-S103A-V104I-A232V-Q245R, G020R-S078R-S101A-S103A-V104I-N183D-A215F-A232V-Q245R, N018R-S024R-N076D-S101G-A232V, A232V-Q245R, N043R-R045T-N076D-S078R-S101G-S103A-V104I-A232V-V234I-Q245R, S024R-N076D-S103A-V104I-Q245R, G020R-S078R-S101A-S103A-V104I-G211Q-T213A-A232V-Q245R, N043D-S078R-S101G-S103A-V104I-A232V-Q245R-N269R-A272V, N018R-G020R-S024R-N076D-N116A-N183D-I198L-G211Q-H249R, N018R-S103A-V104I-A232V, G020R-T022W-S101G-S103A-V104I-N116A-N183D-T213A-A215F-A232V-Q245R, S024R-N043R-N076D-S101G-S103A-V104I-A232V-Q245R-N269R, N018R-T022W-S024R-N076D-T213A-A215F-H249R, N018R-S024R-N076D-S101A-N116A-I198L-G211Q-T213A-H249R, G020R-T22W-S078R-S101A-S103A-V104I-N116A-N183D-T213A-A232V-Q245R, G020R-T022W-S078R-S101G-S103A-V104I-G211Q-T213A-A232V-Q245R, G020R-T022W-S101A-S103A-V104I-A215F-A232V-Q245R, N018R-G020R-S024R-N076D-N116A-N183D-A215F-H249R, N018R-S024R-N076D-N116A-M117I-N183D-T213A-H249R, N018R-T022W-S024R-N076D-S101A-N116A-I198L-T213A-H249R, N018R-T22W-S024R-N076D-S101A-I198L-T213A-A215F-H249R, N018R-N043D-S078R-S101G-S103A-V104I-A232V-Q245R-H249R, N018R-N076D-S101G-S103A-V104I-A232V-Q245R-H249R, G020R-T022W-S101G-S103A-V104I-N116A-N183D-I198L-A232V-Q245R, N018R-N043R-R045T-N076D-S101G-S103A-V104I-A232V-Q245R-N269R, N018R-S024R-N076D-N116A-I198L-Y209H-T213A-H249R, G020R-T022W-S101A-S103A-V104I-N116A-N183D-G211Q-T213A-A232V-Q245R, S024R-N076D-S101G-M175L-A232V-Q245R, N018R-N043D-R045T-S101G-S103A-V104I-A232V-Q245R, R045T-N076D-S078R-S101G-S103A-V104I-A232V-Q245R, G020R-S078R-S101A-S103A-V104I-N116A-N183D-I198L-A215F-A232V-Q245R, N043R-N076D-S101G-S103A-V104I-A232V-Q245R-H249R, N018R-S024R-N076D-I198L-T213A-A215F-H249R, N018R-T022W-S024R-N076D-I198L-A215F-H249R, N018R-T022W-S024R-N076D-N116A-T213A-A215F-H249R, N018R-T022W-S024R-N076D-S101A-N116A-I198L-T213A-A215F-H249R, N018R-T022W-S024R-N076D-N116A-G211Q-T213A-H249R, N018R-S024R-Q245R, N018R-T022W-S024R-N076D-S101A-N116A-A215F-H249R, S024R-N076D-V104I-Q245R, K027R-N043R-S101G-S103A-V104I-A232V-Q245R-N269R, N018R-S024R-N076D-N116A-I198L-G211Q-T213A-H249R, N018R-S024R-N076D-N116A-I198L-H249R, N018R-S024R-N076D-N183D-I198L-G211Q-T213A-A215F-H249R, G020R-T022W-S101A-S103A-V104I-N116A-G211Q-T213A-A215F-A232V-Q245R, N018R-N043D-R045T-S078R-S101G-S103A-V104I-A232V-Q245R, N043R-R045T-N076D-S078R-S101G-S103A-V104I-A232V-Q245R-N269R, N018R-T22W-S024R-N076D-N116A-T213A-A215F-H249R, N018R-T022W-S024R-N076D-N116A-G211Q-A215F-H249R, G020R-S078R-S101G-S103A-V104I-N116A-N183D-T213A-A232V-Q245R, N018R-N076D-S101G-S103A-V104I-A232V-Q245R, N018R-S101G-V104I, G020R-S078R-S101G-S103A-V104I-N116A-N183D-G211Q-T213A-A215F-A232V-Q245R, G020R-S078R-S101A-S103A-V104I-A232V-Q245R, N018R-S024R-N076D-S101A-I198L-G211Q-H249R, N018R-S024R-N076D-I198L-G211Q-T213A-H249R, N018R-T022W-S024R-N076D-S101A-N116A-I198L-G211Q-T213A-H249R, N018R-N076D-H249R, N018R-G020R-S024R-N076D-S101A-N116A-N183D-I198L-H249R, N018R-S024R-N076D-S101A-N116A-G211Q-T213A-H249R, G020R-T022W-S078R-S101A-S103A-V104I-N116A-N183D-G211Q-T213A-A215F-A232V-Q245R, G020R-T022W-S101G-S103A-V104I-A114T-T213A-A215F-A232V-Q245R, N018R-T22W-S024R-N076D-N116A-G211Q-T213A-H249R, N018R-G020R-T022W-S024R-N076D-S101A-N116A-N183D-H249R, G020R-S101A-S103A-V104I-N116A-N183D-T213A-A232V-Q245R, N018R-T022W-S024R-N076D-S101A-G211Q-T213A-H249R, N018R-T022K-N043D-S101G-S103A-V104I-A232V-Q245R, N018R-S101G-S103A-V104I-A232V-Q245R-N269R, G020R-S078R-S101G-S103A-V104I-N116A-N183D-G211Q-T213A-A215F-A232V, N018R-S024R-N076D-N116A-H249R, G020R-S024R-N076D-S101G-S103A-V104I-A232V-Q245R, N043D-N076D-S101G-S103A-V104I-A232V-Q245R-N269R, N018R-S024R-N076D-S101A-N116A-I198L-G211Q-H249R, N018R-T022W-S024R-N076D-I198L-T213A-A215F-H249R, N018R-N043D-N076D-S078R-S101G-S103A-V104I-A232V-Q245R-N269R, G020R-T22W-S101G-S103A-V104I-N116A-N183D-T213A-A215F-A232V-Q245R, G020R-S101G-S103A-V104I-N183D-G211Q-A232V-Q245R-, N018R-S024R-N076D-S101A-I198L-T213A-H249R, N018R-S024R-N076D-S101A-I198L-H249R, N018R-S024R-R045T-N076D-S101G-S103A-V104I-A232V-Q245R-H249R, N018R-S024R-N076D-S101A-N183D-T213A-H249R, N018R-N043D-N076D-S078R-S101G-S103A-V104I-A232V-Q245R, G020R-S078R-S101G-S103A-V104I-N116A-A131V-N183D-T213A-A232V-Q245R, N018R-R045T-N076D-S101G-S103A-V104I-A232V-Q245R, N018R-S024R-N076D-S101A-N183D-G211Q-H249R, N076D-S101G-S103A-V104I-A232V-Q245R-H249R, S024R-S101G-Q245R, S024R-N076D-S101G-Q245R, N076D-S078R-S101G-S103A-V104I-A232V-Q245R-H249R, N018R-G020R-S024R-N076D-S101A-N183D-G211Q-A215F-H249R, S024R-S101G, N018R-T22W-S024R-N076D-T213A-A215F-H249R, G020R-N043D-S101G-S103A-V104I-A232V-Q245R, G020R-T022W-S101G-S103A-V104I-N183D-I198L-T213A-A215F-A232V-Q245R, N018R-N043D-R045T-S101G-S103A-V104I-A232V-Q245R-N269R, N043D-N076D-S078R-S101G-S103A-V104I-A232V-Q245R, S024R-R045T-N076D-S101G-S103A-V104I-A232V-Q245R-N269R, G020R-T022W-S101A-S103A-V104I-I198L-G211Q-A215F-A232V-Q245R, G020R-T022W-S101G-S103A-V104I-N116A-N183D-A215F-A232V-Q245R, N018R-G020R-N076D-S101G-S103A-V104I-A232V-Q245R-H249R, N018R-T022W-S024R-N076D-S101A-A215F-H249R, N018R-V104I, N018R-S024R-N076D-N116A-I198L-A215F-H249R, N018R-S024R-N076D-L088I-S101A-N116A-I198L-G211Q-A215F-H249R, N018R-T022W-S024R-N076D-S101A-N116A-G211Q-T213A-H249R, N043R-R045T-N076D-S101G-S103A-V104I-A232V-Q245R-N269R, N018R-N076D-S101G-V104I-H249R, N018R-T022W-S024R-N076D-S101A-T213A-A215F-H249R, N018R-T22W-S024R-N076D-S101A-N116A-I198L-A215F-H249R, N018R-G020R-S101G-S103A-V104I-A232V-Q245R-H249R, S101G-S103A-V104I-A232V-Q245R-H249R-N269R, S024R-N076D-Q245R, N018R-G020R-N043R-R045T-N076D-S101G-S103A-V104I-A232V-Q245R, N018R-G020R-S024R-

N076D-A215F-H249R, N018R-S024R-N076D-S101A-N116A-N183D-I198L-T213A-H249R, N018R-G020R-S024R-N076D-G211Q-A215F-H249R, N043D-S101G-S103A-V104I-A232V-Q245R, G020R-T22W-S078R-S101A-S103A-V104I-N116A-N183D-A215F-A232V-Q245R, N018R-S024R-N076D-I198L-G211Q-A215F-H249R, N043R-N076D-S078R-S101G-S103A-V104I-A232V-Q245R-N269R, N043R-S078R-S101G-S103A-V104I-A232V-Q245R-N269R, G020R-N043D-S101G-S103A-V104I-A232V-Q245R-H249R, N018R-T022W-S024R-N076D-S101A-T213A-H249R, G020R-T022W-S101A-N116A-I198L-G211Q-T213A-A215F-H249R, N043R-R045T-S078R-S101G-S103A-V104I-N218S-A232V-Q245R, N018R-S103A, G020R-T22W-S101G-S103A-V104I-N116A-N183D-A215F-A232V-Q245R, N018R-S024R-N076D-S101A-H249R, N018R-T022W-S024R-N076D-G211Q-T213A-H249R, S024R-N043R-R045T-N076D-S101G-S103A-V104I-A232V-Q245R, G020R-T022W-S101A-S103A-V104I-N116A-N183D-A232V-Q245R, G020R-S101A-S103A-V104I-N116A-N183D-G211Q-T213A-A215F-A232V-Q245R, K027R-R045T-N076D-S078R-S101G-S103A-V104I-A232V-Q245R-N269R, G020R-R045T-N076D-S101G-S103A-V104I-A232V-Q245R-H249R, N018R-G020R-S024R-N076D-N116A-N183D-T213A-A215F-H249R, N018R-S024R-N076D-V104I, S101G-S103A-V104I-A232V-H249R, N018R-S024R-N076D-N116A-N183D-G211Q-H249R, N018R-G020R-S024R-N076D-N116A-A215F-H249R, N018R-S024R-N076D-N183D-T213A-A215F-H249R, N018R-T022W-S024R-N076D-I198L-G211Q-H249R, N043D-S078R-S101G-S103A-V104I-A232V-Q245R-N269R-R275S, G020R-T022W-S101A-S103A-V104I-N116A-N183D-G211Q-A232V-Q245R, N018R-T022W-S024R-N076D-S101A-I198L-G211Q-T213A-A215F-H249R, N018R-T022W-S024R-N076D-S101A-N116A-I198L-G211Q-T213A-A215F-H249R, N018R-G020R-S024R-N076D-N183D-H249R, N018R-S024R-N076D-N116A-I198L-T213A-H249R, N018R-T022W-S024R-N076D-S101A-N116A-G211Q-H249R, V004M-N018R-S024R-N076D-N116A-I198L-G211Q-T213A-H249R, V104I-A232V-H249R, G020R-T022W-S101G-S103A-V104I-N116A-N183D-G211Q-A215F-A232V-Q245R, G020R-S101A-S103A-V104I-N116A-N183D-G211Q-A232V-Q245R-T274I, G020R-S101A-S103A-V104I-T213A-A232V-Q245R, G020R-S101G-S103A-V104I-N116A-N183D-G211Q-T213A-A232V-Q245R, G020R-S024R-N043D-S078R-S101G-S103A-V104I-A232V-Q245R, N018R-S024R-N076D-S103A-H249R, N018R-G020R-S024R-N076D-S101A-N116A-N183D-G211Q-A215F-H249R, N018R-G020R-S024R-N076D-N116A-N183D-I198L-H249R, N018R-T022W-S024R-N076D-N116A-I198L-A215F-H249R, N018R-S024R-N076D-S101A-G211Q-T213A-A215F-H249R-A270V, N018R-N043D-R045T-N076D-S078R-S101G-S103A-V104I-A232V-Q245R-N269R, G020R-T022W-S101G-S103A-V104I-N183D-A232V-Q245R, N018R-G020R-T022W-S024R-N076D-S101A-N116A-T213A-H249R, N018R-T022W-S024R-N076D-I198L-G211Q-A215F-H249R, N018R-T022W-S024R-N076D-I198L-T213A-H249R, G020R-T022W-S101G-S103A-V104I-N116A-N183D-A232V-Q245R, N018R-T22W-S024R-N076D-N116A-I198L-T213A-H249R, N043R-R045T-S078R-S101G-S103A-V104I-A232V-Q245R-N269R, N018R-S024R-N076D-S101G-S103A-V104I-A232V, S101G-H249R, S024R-N076D-S101G-S103A-V104I-M175L-H249R, G020R-T022W-S101A-S103A-V104I-N116A-N183D-A232V-Q245R-N269S, N018R-S024R-N076D-S101A-N116A-I198L-H249R, N018R-T022W-S024R-N076D-N116A-H249R, N018R-G020R-S024R-N076D-S101A-N183D-I198L-A215F-H249R, N018R-S024R-N076D-T213A-A215F-H249R-T260K, N018R-S024R-N076D-N116A-G211Q-T213A-H249R, N018R-G020R-T022W-S024R-N076D-N116A-I198L-H249R, S024R-N076D-S101G-S103A-V104I-Q245R, S024R-N076D-S103A-H249R, N018R-S101G-S103A-V104I-A232V-Q245R-H249R, N018R-S024R-N076D-I198L-G211Q-H249R, N018R-T022W-S024R-N076D-S101A-I198L-G211Q-T213A-H249R, G020R-S024R-R045T-S101G-S103A-V104I-A232V-Q245R, N018R-G020R-S024R-N076D-N183D-G211Q-T213A-H249R, N018R-N043D-R045T-S078R-S101G-S103A-V104I-A232V-Q245R-A272D, N018R-S024R-N076D-N116A-I198L-T213A-A215F-H249R, N018R-T22W-S024R-N076D-S101A-I198L-H249R, N018R-T022W-S024R-N076D-N116A-I198L-H249R, S024R-N076D-S101G-S103A-A232V, S024R-S103A-V104I, N018R-S024R-N076D-S101A-N116A-N183D-G211Q-A215F-H249R, S024R-R045T-N076D-S101G-S103A-V104I-A232V-Q245R-H249R, G020R-S101G-S103A-V104I-N116A-N183D-A232V-Q245R, S024R-N043D-N076D-S101G-S103A-V104I-A232V-Q245R-N269R, G020R-T022W-S101A-S103A-V104I-N183D-G211Q-T213A-A215F-A232V-Q245R, G020R-R045T-N076D-S078R-S101G-S103A-V104I-A232V-Q245R-N269R, N018R-S024R-N076D-S101A-N116A-I198L-G211Q-A215F-H249R, G020R-S101A-S103A-V104I-N116A-N183D-A215F-A232V-Q245R, N018R-N043R-S101G-S103A-V104I-A232V-Q245R-H249R, N018R-S024R-N076D-I198L-T213A-H249R, N018R-S024R-N076D-N116A-N183D-T213A-H249R, G020R-N043D-S101G-S103A-V104I-A232V-Q245R-N269R, S024R-N076D-S103A-Q245R, N018R-T022W-S024R-N076D-S101A-N116A-G211Q-T213A-A215F-H249R, S103A-V104I-Q245R, N018R-T022W-S024R-N076D-G211Q-A215F-H249R, N018R-T022W-S024R-N076D-N116A-N183D-I198L-H249R, N018R-T022W-S024R-N076D-I198L-G211Q-T213A-H249R, N018R-S024R-N076D-N116A-N183D-G211Q-T213A-A215F-H249R, N018R-G020R-N043D-R045T-N076D-S101G-S103A-V104I-A232V-Q245R-N269R, N018R-G020R-T022W-S024R-N076D-S101A-G211Q-T213A-A215F-H249R, A016T-N043R-R045T-N076D-S101G-S103A-V104I-A232V-Q245R-N269R, N018R-T022W-S024R-N076D-N116A-A215F-H249R, N043R-N076D-S101G-S103T-V104I-A232V-Q245R-H249R-N269R, G020R-S078R-S101A-S103A-V104I-G115E-N116A-N183D-G211Q-T213A-A232V-Q245R, N018R-S024R-N076D-I198L-H249R, N018R-S024R-N076D-S101A-N116A-N183D-H249R, G020R-S101G-S103A-V104I-N116A-N183D-G211Q-A232V-Q245R, N018R-S024R-N076D-S101G, N076D-S101G-A232V-Q245R, N018R-N076D-S101G-S103A-V104I-Q245R, N018R-R045T-S101G-S103A-V104I-A232V-Q245R-H249R, N018R-S024R-N076D-A215F-H249R, N018R-V104I-A232V, N043D-R045T-N076D-S078R-S101G-S103A-V104I-A232V-Q245R, S024R-N076D-S101G-A232V-H249R, S103A-A232V-Q245R, G020R-S101G-S103A-V104I-N116A-N183D-G211Q-T213A-A215F-A232V-Q245R, N018R-G020R-S024R-N076D-N116A-N183D-I198L-G211Q-A215F-H249R, N018R-T022W-S024R-N076D-S101A-I198L-G211Q-A215F-H249R, S024R-N076D-S103A-V104I-H249R, S024R-S101G-S103A-V104I, G020R-S101G-S103A-V104I-N116A-N183D-G211Q-A215F-A232V-Q245R, N018R-T022W-S024R-N076D-S101A-N116A-N183D-A215F-H249R, G020R-T022W-S101G-

S103A-V104I-N116A-N183D-G211Q-T213A-A215F-A232V-Q245R, G020R-S024R-R045T-N076D-S101G-S103A-V104I-A232V-Q245R, N018R-T022W-S024R-N076D-N183D-T213A-H249R, N018R-G020R-S024R-N076D-A131T-A215F-H249R, N018R-G020R-S024R-N076D-S101A-N116A-N183D-G211Q-T213A-A215F-H249R, N018R-S024R-N076D-S101A-N116A-G211Q-T213A-A215F-H249R, N018R-S024R-N076D-I198L-A215F-H249R, N018R-T022W-S024R-N076D-N183D-G211Q-H249R, N018R-T022W-S024R-N076D-S101A-N116A-T213A-A215F-H249R, N018R-G020R-S024R-R045T-N076D-S101G-S103A-V104I-A232V-Q245R, N043R-S101G-S103A-V104I-Q245R-H249R, N018R-N076D-A232V-H249R, NO 18K-N076D-S078R-S101G-S103A-V104I-L217E-A232V-Q245R-N269R, N018R-G020R-S024R-N043D-N076D-S078R-S101G-S103A-V104I-A232V-Q245R, N018R-T022W-S024R-N076D-S101A-N116A-T213A-A215F-H249R-L267I, A232V-H249R, N018R-G020R-S024R-N076D-N116A-G211Q-T213A-A215F-H249R, N076D-V104I-Q245R, N018R-G020R-S024R-N076D-N183D-I198L-G211Q-A215F-H249R, N018R-S024R-N076D-S101A-G211Q-T213A-H249R, S024R-S101G-S103A-A232V, N018R-G020R-T022W-S024R-N076D-N116A-N183D-I198L-T213A-A215F-H249R, N018R-G020R-S024R-N076D-N116A-N183D-I198L-G211Q-T213A-H249R, N018R-G020R-T022W-S024R-N076D-S101A-A215F-H249R, G020R-T022W-S101A-S103A-V104I-N116A-N183D-G211Q-A215F-A232V-Q245R, N018R-S024R-N076D-N116A-I198L-G211Q-H249R, S103A-A232V-H249R, N018R-G020R-S024R-N076D-N116A-N183D-I198L-A215F-H249R, N018R-S024R-N076D-N116A-N183D-I198L-T213A-H249R, N018R-T022W-S024R-N076D-N183D-T213A-H249R, N018R-S024R-N076D-S101A-T213A-A215F-H249R, N018R-T022W-S024R-N076D-S101A-N116A-N183D-G211Q-H249R, N018R-R045T-S101G-S103A-V104I-A232V-Q245R-N269R, N018R-G020R-R045T-N076D-S078R-S101G-S103A-V104I-A232V-Q245R, N018R-T022W-S024R-N076D-N116A-I198L-T213A-A215F-H249R, G020R-T022W-S101G-S103A-V104I-N116A-N183D-G211Q-T213A-A232V-Q245R, N018R-G020R-S024R-N076D-I198L-H249R, N018R-G020R-T022W-S024R-N076D-S101A-N116A-G211Q-H249R, G020R-T022W-S101A-S103A-V104I-N116A-N183D-A232V-Q245R-T274I, S024R-S103A-Q245R-H249R, N018R-T022W-S024R-N076D-S101A-N116A-N183D-I198L-H249R, N018R-S024R-N076D-S101A-I198L-G211Q-A215F-H249R, N018R-T022W-S024R-N076D-N116A-I198L-G211Q-A215F-H249R, N018R-G020R-T022W-S024R-N076D-N116A-N183D-T213A-H249R, N018R-N043D-R045T-N076D-S101G-S103A-V104I-A232V-Q245R-N269R, N018R-T022W-S024R-N076D-N116A-G211Q-T213A-A215F-H249R, N018R-S024R-N076D-S101A-N183D-I198L-T213A-H249R, N043D-N076D-S101G-S103A-V104I-A232V-Q245R-H249R, N018R-S024R-N076D-I198L-G211Q-T213A-A215F-H249R, N018R-G020R-S024R-N076D-N116A-N183D-T213A-H249R, S103A-A232V, N018R-T022W-S024R-N076D-N116A-N183D-A215F-H249R, N018R-S024R-N076D-S101A-N116A-H249R, N018R-N043R-S078R-S101G-S103A-V104I-A232V-Q245R, N018R-G020R-T022W-S024R-N076D-S101A-N183D-G211Q-A215F-H249R, N043R-N076D-S078R-S101G-S103A-V104I-A232V-Q245R-H249R, N018R-G020R-S024R-N076D-S101A-N116A-N183D-I198L-T213A-H249R, N018R-S024R-N076D-N183D-I198L-T213A-H249R, N018R-T022W-S024R-N076D-S101A-N183D-G211Q-H249R, N018R-G020R-S024R-N076D-I198L-T213A-A215F-H249R, N018R-G020R-T022W-S024R-N076D-N183D-G211Q-T213A-H249R, N018R-T022W-S024R-N076D-I198L-H249R, N018R-S024R-N076D-N183D-I198L-G211Q-H249R, G020R-T022W-S101A-S103A-V104I-N116A-N183D-T213A-A232V-Q245R, N018R-G020R-S024R-N076D-N116A-N183D-G211Q-T213A-H249R, N018R-S024R-N076D-N116A-N183D-I198L-G211Q-T213A-A215F-H249R, G020R-T022W-S101A-S103A-V104I-N116A-N183D-A215F-A232V-Q245R, N018R-S024R-N076D-S101A-N183D-H249R, N018R-S024R-N076D-A232V, N018R-T022W-S024R-N076D-S101A-N116A-H249R, G020R-S101A-S103A-V104I-N116A-N183D-I198L-G211Q-T213A-A215F-A232V-Q245R, G020R-T022W-S101G-S103A-V104I-N116A-N183D-G211Q-A232V-Q245R-N263S, S024R-N076D-S101G-V104I-A232V-H249R, N043R-S078R-S101G-S103A-V104I-A232V-Q245R, S024R-N076D-S078R-S101G-S103A-V104I-A232V-Q245R-H249R, N018R-S024R-N076D-S101A-N183D-I198L-T213A-A215F-H249R, N018R-G020R-S024R-N076D-I198L-A215F-H249R, N018R-G020R-S024R-N076D-S101A-N116A-T213A-H249R, N018R-S024R-N076D-S101A-V197A-T213A-A215F-H249R, S024R-S101G-S103A, N018R-S024R-N076D-S101A-N116A-G211Q-A215F-H249R, N043R-N076D-S078R-S101G-S103A-V104I-L217E-A232V-Q245R, S024R-V104I-A232V, N018R-S024R-N076D-N183D-G211Q-H249R, G020R-N043R-R045T-S078R-S101G-S103A-V104I-A232V-Q245R, N018R-G020R-T022W-S024R-N076D-S101A-N116A-N183D-T213A-H249R, N018R-S024R-N076D-N116A-A150T-T213A-H249R, N018R-S024R-N076D-N183D-T213A-H249R, N018R-G020R-S024R-N076D-N116A-N183D-G211Q-A215F-H249R, N018R-G020R-S024R-N076D-G211Q-H249R, N018R-S024R-N076D-S101A-N116A-N183D-I198L-H249R, S024R-N076D-A232V-H249R, N018R-G020R-T022W-S024R-N076D-S101A-N116A-N183D-I198L-G211Q-T213A-H249R, N018R-T022W-S024R-N076D-S101A-N116T-I198L-A215F-H249R, N018R-S024R-N076D-N183D-I198L-G211Q-A215F-H249R, N018R-T022R-S024R-N076D-S101A-N116A-N183D-G211Q-H249R, R045T-S101G-S103A-V104I-A232V-Q245R, N018R-G020R-S024R-N076D-S101A-N183D-G211Q-H249R, G020R-S101G-S103A-V104I-N116A-N183D-T213A-A232V-Q245R, N076D-S101G-S103A-Q245R, G020R-N043D-S078R-S101G-S103A-V104I-A232V-Q245R-H249R, N018R-S024R-N076D-N116A-N183D-H249R, N018R-S024R-N076D-S101A-N183D-G211Q-T213A-A215F-H249R, N018R-G020R-T022W-S024R-N076D-S101A-N116A-I198L-H249R, N018R-T22W-S024R-N076D-G211Q-T213A-H249R, N018R-G020R-S024R-N076D-N183D-G211Q-H249R, N018R-G020R-S024R-N076D-S101A-N116A-N183D-T213A-H249R, N043R-S078R-S101G-S103A-V104I-L217E-A232V-Q245R, N018R-T022W-S024R-N076D-S101A-A215F-H249R, N018R-G020R-S024R-N076D-S101A-N183D-I198L-G211Q-T213A-H249R, N076D-S101G-V104I-H249R, N018R-T022W-S024R-N076D-S101A-N116A-N183D-T213A-H249R, N018R-S024R-N076D-N183D-H249R, N018R-S024R-N076D-S101A-N183D-I198L-A215F-H249R, N018R-T022W-S024R-N076D-N183D-I198L-A215F-H249R, N018R-T022W-S024R-N076D-S101A-I198L-G211Q-H249R, G020R-S101A-S103A-V104I-N116A-N183D-A232V-Q245R, N018R-S024R-N076D-N116A-N183D-I198L-G211Q-H249R, N018R-G020R-S024R-S101G-S103A-V104I-A232V-Q245R, N018R-N076D-S078R-S101G-S103A-

V104I-L217E-A232V-Q245R, G020R-S101A-S103A-V104I-N116A-N183D-G211Q-A232V-Q245R, N018R-T022W-S024R-N076D-S101A-N183D-I198L-Y209H-H249R, N018R-S024R-N076D-N183D-I198L-T213A-A215F-H249R, N018R-S024R-N076D-S101A-N116A-N183D-G211Q-T213A-H249R, N018R-T022W-S024R-N076D-S101A-N116A-N183D-G211Q-T213A-H249R, N018R-S024R-N076D-N183D-I198L-H249R, N018R-S024R-N076D-N183D-A215F-H249R, N018R-G020R-S024R-N076D-G211Q-T213A-A215F-H249R, N076D-Q245R, N076D-S101G-V104I-Q245R, N018R-T022W-S024R-N076D-S101A-G211Q-A215F-H249R, N018R-T022W-S024R-N076D-S101A-N116A-N183D-G211Q-A215F-H249R, N018R-G020R-T022W-S024R-N076D-S101A-G211Q-T213A-H249R, G020R-S024R-N043R-S101G-S103A-V104I-A232V-Q245R, N018R-S024R-N076D-N116A-N183D-G211Q-A215F-H249R, G020R-S101A-S103A-V104I-N116A-N183D-T213A-A215F-A232V-Q245R, S101G-S103A-V104I, N018R-G020R-S024R-N076D-S101A-N116A-N183D-G211Q-T213A-H249R, N018R-G020R-S024R-N076D-N204D-T213A-H249R, N018R-T022W-S024R-N076D-N183D-I198L-H249R, N018R-S024R-N076D-S101A-N116A-N183D-A215F-H249R, N018R-T022W-S024R-N076D-N116A-N183D-I198L-G211Q-T213A-A209V-H249R, N018R-T022W-S024R-N076D-S101A-N116A-N183D-G211Q-T213A-A215F-H249R, N018R-S024R-N076D-S101A-N116A-I198L-T213A-H249R, N018R-G020R-S024R-N076D-S101A-N116A-G211Q-T213A-H249R, N018R-G020R-T022W-S024R-N076D-S101A-N116A-N183D-G211Q-T213A-A215F-H249R, N018R-S024R-N076D-S101A-N116A-N183D-T213A-A215F-H249R, N018R-S024R-N076D-S101A-N183D-I198L-G211Q-T213A-A215F-H249R, N018R-S024R-N076D-S101A-N183D-I198L-G211Q-T213A-H249R, N018R-N043R-R045T-S078R-S101G-S103A-V104I-L217E-A232V-Q245R, N018R-S024R-N076D-N183D-G211Q-T213A-A215F-H249R, N018R-T022W-S024R-N076D-N116A-N183D-I198L-A215F-H249R, N018R-G020R-S024R-N076D-N116A-H249R, N018R-G020R-T022W-S024R-N076D-S101A-G211Q-A215F-H249R, N018R-G020R-S024R-N076D-N183D-G211Q-T213A-A215F-H249R, N018R-G020R-T022W-S024R-N076D-I198L-T213A-H249R, N018R-G020R-S024R-N076D-S101A-G211Q-A215F-H249R-N269D, N018R-G020R-N043D-S101G-S103A-V104I-A232V-Q245R-N269R, N018R-T022W-S024R-N076D-S101A-N183D-I198L-T213A-H249R, G020R-T022W-S101G-S103A-V104I-N183D-A215F-A232V-Q245R, N018R-T022W-S024R-N076D-N116A-N183D-I198L-Y209H-G211Q-H249R, N018R-G020R-T022W-S024R-N076D-S101A-N116A-N183D-G211Q-H249R, N076D-A232V-Q245R, N043D-R045T-S078R-S101G-S103A-V104I-A232V-Q245R, N018R-G020R-S024R-N076D-N116A-I198L-G211Q-A215F-Q245R, N018R-G020R-T022W-S024R-N076D-T213A-H249R, G020R-S024R-N043D-S078R-S101G-S103A-V104I-A232V-Q245R-H249R, N018R-G020R-T022W-S024R-N076D-S101A-I198L-A215F-H249R, G020R-A090S-S101G-S103A-V104I-N116A-N183D-T213A-A215F-A232V-Q245R, N018R-G020R-T022W-S024R-N076D-S101A-I198L-G211Q-T213A-A215F-H249R, N018R-G020R-S024R-N076D-S101A-N183D-T213A-A215F-H249R, N018R-S024R-N076D-N116A-N183D-I198L-G211Q-T213A-H249R, N043D-R045T-S078R-S101G-S103A-V104I-A232V-Q245R-N269R, N018R-S024R-N076D-S101A-N183D-A215F-H249R, N018R-G020R-S024R-N076D-S101A-N183D-I198L-T213A-H249R, G020R-T022W-S101A-S103A-V104I-N116A-N183D-I198L-G211Q-T213A-A215F-A232V-Q245R, N018R-G020R-S024R-N043D-N076D-S101G-S103A-V104I-A232V-Q245R-N269R, N018R-S024R-N076D-S101A-N183D-T213A-A215F-H249R, N018R-G020R-T022W-S024R-N076D-S101A-N116A-I198L-G211Q-T213A-A215F-H249R, N018R-G020R-N043D-S101G-S103A-V104I-L217E-A232V-Q245R, N076D-S103A-V104I-A232V-Q245R, R045T-N076D-S078R-S101G-S103A-V104I-A232V-Q245R-H249R, N018R-T022W-S024R-N076D-S101A-N183D-G211Q-A215F-H249R, N018R-T022W-S024R-N076D-S101A-N116A-N183D-H249R, N018R-S024R-N076D-N116A-N183D-I198L-G211Q-A215F-H249R, N018R-G020R-N043D-N076D-S078R-S101G-S103A-V104I-L217E-A232V-Q245R, N076D-S103A-V104I-Q245R, N018R-G020R-S024R-N076D-S101A-N116A-G211Q-T213A-A215F-H249R, N018R-S024R-N076D-S101A-N183D-I198L-H249R, N018R-T022W-S024R-N076D-N116A-N183D-I198L-G211Q-A215F-H249R, N018R-S024R-N076D-N116A-N183D-T213A-A215F-H249R, N018R-T022W-S024R-N076D-N116A-N183D-I198L-G211Q-H249R, N018R-S024R-N076D-S101G-Q245R, N018R-S024R-N076D-S101A-N116A-N183D-I198L-T213A-A215F-H249R, N043R-R045T-N076D-S101G-S103A-V104I-A232V-Q245R, N018R-G020R-T022W-S024R-N076D-N116A-I198L-T213A-A215F-H249R, N076D-V104I-A232V-Q245R, K027R-N043R-R045T-N076D-S101G-S103A-V104I-A232V-Q245R, N018R-T022W-S024R-N076D-S101A-N183D-T213A-A215F-H249R, N018R-S024R-N076D-S103A-V104I-L135I-A232V, N018R-G020R-T022W-S024R-N076D-N183D-I198L-G211Q-H249R, N018R-G020R-T022W-S024R-N076D-S101A-N116A-N183D-I198L-A215F-H249R, N018R-S024R-N076D-S101A-N116A-N183D-G211Q-H249R, N018R-T022W-S024R-N076D-N183D-G211Q-T213A-A215F-H249R, N076D-S101G-S103A-V104I-A232V-H249R, P005S-N018R-T022W-S024R-N076D-S101A-T213A-A215F-H249R, N018R-S024R-N076D-N116A-N183D-A215F-H249R, N018R-S024R-N076D-N183D-I198L-A215F-H249R, N018R-G020R-S024R-N076D-S101A-N116A-N183D-H249R, N018R-T022W-S024R-N076D-N116A-N183D-G211Q-H249R, N018R-G020R-T022W-S024R-N076D-S101A-N116A-H249R, N018R-T022W-S024R-N076D-S101A-N116A-N183D-I198L-T213A-H249R, N018R-T022W-S024R-N076D-S101A-N183D-G211Q-T213A-H249R, N018R-G020R-S024R-N076D-N116A-I198L-H249R, N018R-S024R-N076D-N183D-G211Q-T213A-H249R, N018R-S024R-N076D-S101A-N116A-N183D-T213A-H249R, N018R-S024R-N076D-N116A-N183D-I198L-A215F-H249R, N018R-T022W-S024R-N076D-N183D-I198L-G211Q-A215F-H249R, N018R-T022W-S024R-N076D-N183D-H249R, N018R-T022W-S024R-N076D-S101A-N183D-I198L-A215F-H249R, N018R-G020R-N043D-R045T-N076D-S101G-S103A-V104I-A232V-Q245R, G020R-T022W-S101A-S103A-V104I-N183D-I198L-A215F-A232V-Q245R, N076D-S101G-S103A-V104I-H249R, N018R-G020R-S024R-N076D-N183D-I198L-A215F-H249R, N018R-G020R-T022W-S024R-N076D-S101A-N183D-A215F-H249R, N018R-G020R-S024R-N076D-G211Q-T213A-H249R, N018R-S024R-N076D-N116A-N183D-G211Q-T213A-H249R, N018R-S024R-N076D-N116A-N183D-I198L-H249R, N018R-G020R-S024R-N076D-G211Q-N243D-H249R, N018R-G020R-R045T-N076D-S101G-S103A-V104I-A232V-Q245R-H249R, N018R-T022W-S024R-N076D-N183D-I198L-G211Q-T213A-H249R, N018R-S024R-N076D-

S101A-N116A-N183D-I198L-G211Q-T213A-H249R, N018R-T022W-S024R-N076D-N116A-I198L-G211Q-T213A-A215F-H249R, S024R-N076D-S101G, N018R-G020R-S024R-N076D-S101A-I198L-T213A-A215F-H249R, N018R-T022W-S024R-N076D-N116A-N183D-G211Q-T213A-H249R, N018R-G020R-S024R-N076D-N183D-A215F-H249R, N018R-N043D-N076D-S078R-S101G-S103A-V104I-A232V-Q245R-H249R, N018R-T022W-S024R-N076D-N116A-N183D-G211Q-T213A-Q245R, G020R-S024R-N076D-S078R-S101G-S103A-V104I-A232V-Q245R-H249R, N018R-G020R-R045T-S101G-S103A-V104I-A232V-Q245R-H249R, N018R-S024R-N076D-S101A-N183D-I198L-G211Q-H249R, N018R-T022W-S024R-N076D-N183D-G211Q-T213A-H249R, N018R-G020R-S024R-N076D-N116A-I198L-G211Q-A215F-H249R-N269S, N018R-G020R-T022W-S024R-N076D-S101A-N116A-N183D-I198L-G211Q-A215F-H249R, G020R-T022W-S101A-S103A-V104I-N183D-T213A-A215F-A232V-Q245R, N018R-S024R-N076D-A086V-S101A-N183D-I198L-G211Q-H249R, N018R-N076D-S101G-I198T-A232V, N018R-G020R-S024R-N076D-S101A-N116A-N183D-I198L-G211Q-A215F-H249R, N018R-T022W-S024R-N076D-S101A-N116A-N183D-T213A-A215F-H249R, N018R-T022W-S024R-N076D-S101A-N183D-G211Q-T213A-A215F-H249R, N018R-S024R-N076D-N183D-H249R-A248T, N018R-N076D-V104I-Q245R-H249R, N018R-T022W-S024R-N076D-S101A-N116A-N183D-I198L-A215F-H249R, N018R-T022W-S024R-N076D-N116A-N183D-T213A-A215F-H249R, N018R-G020R-T022W-S024R-N076D-N116A-N183D-G211Q-T213A-A215F-H249R, N018R-G020R-S024R-N076D-S101A-H249R, N018R-G020R-S024R-N076D-S101A-N116A-T213A-A215F-H249R, N018R-T022W-S024R-N076D-N116A-N183D-G211Q-A215F-H249R, N018R-T022W-S024R-N076D-N116A-N183D-I198L-G211Q-T213A-H249R, N043R-R045T-S078R-S101G-S103A-V104I-L217E-A232V-Q245R, N043R-R045T-S101G-S103A-V104I-A232V-Q245R-H249R, N018R-N076D-S101G-V104I, G020R-R045T-N076D-S078R-S101G-S103A-V104I-A232V-Q245R-H249R, N043D-N076D-S101G-S103A-V104I-A232V-Q245R, N018R-G020R-T022W-S024R-N076D-S101A-N116A-N183D-I198L-H249R, N018R-N076D-V104I, N018R-G020R-N043D-S101G-S103A-V104I-A232V-Q245R-H249R, N018R-G020R-T022W-S024R-N076D-N183D-G211Q-H249R, N018R-S024R-N076D-S101A-N183D-I198L-G211Q-A215F-H249R, S101G-V104I, N018R-T022W-S024R-N076D-N116A-N183D-I198L-G211Q-T213A-A215F-H249R, N018R-G020R-S024R-N076D-S101A-N183D-G211Q-T213A-A215F-H249R, N018R-G020R-S024R-N076D-N116A-N183D-A215F-H249R-N263D, N018R-T022W-S024R-N076D-S101A-N183D-H249R, N018R-S024R-N076D-S101A-N116A-N183D-I198L-A215F-H249R, N018R-T022W-S024R-N076D-N116A-I198L-A215F-H249R-R269H, N018R-N043D-R045T-N076D-S078R-S101G-S103A-V104I-A232V-Q245R, N018R-S024R-R045T-N076D-S078R-S101G-S103A-V104I-A232V-Q245R-N269R, S078R-S101G-S103A-V104I-L217E-A232V-Q245R, N018R-G020R-T022W-S024R-N076D-S101A-N183D-I198L-T213A-A215F-H249R, N018R-G020R-S024R-N076D-N183D-I198L-T213A-H249R, N018R-G020R-T022W-S024R-N076D-N116A-I198L-G211Q-A215F-H249R, N018R-G020R-T022W-S024R-N076D-N116A-N183D-G211Q-H249R, N018R-G020R-T022W-S024R-N076D-S101A-I198L-G211Q-T213A-H249R, N018R-G020R-T022W-S024R-N076D-H249R, G020R-T022W-S101G-S103A-V104I-N116A-N183D-I198L-G211Q-T213A-A215F-A232V-Q245R, V104I-A232V, N018R-G020R-T022W-S024R-N076D-S101A-N116A-N183D-G211Q-A215F-H249R, N018R-G020R-T022W-S024R-N076D-S101A-N116A-N183D-I198L-G211Q-T213A-A215F-H249R, N018R-G020R-T022W-S024R-N076D-S101A-N183D-T213A-A215F-H249R, N018R-T022W-S024R-N076D-S101A-N183D-I198L-G211Q-T213A-H249R, N018R-T022W-S024R-N076D-S101A-N183D-I198L-H249R, N043D-R045T-S101G-S103A-V104I-A232V-Q245R-N269R, N018R-G020R-S024R-N076D-S101A-N183D-I198L-G211Q-H249R, N018R-G020R-N043R-S101G-S103A-V104I-L217E-A232V-Q245R, S024R-N043R-N076D-S078R-S101G-S103A-V104I-A232V-Q245R-N269R, N043R-R045T-N076D-S078R-S101G-S103A-V104I-Y166F-A176P-A179V-N184T-A187P-A194P, N018R-T022W-S024R-D041E-N076D-S101A-S160T-N183D-G211Q-T213A-H249R, N018R-G020R-T022W-S024R-N076D-N116A-N183D-I198L-G211Q-A215F-H249R, N018R-G020R-T022W-S024R-N076D-S101A-N116A-I198L-T213A-H249R, N018R-T022W-S024R-N076D-S101A-N116A-N183D-I198L-G211Q-T213A-H249R, N018R-G020R-S024R-N076D-I198L-T213A-H249R, N018R-G020R-T022W-S024R-N076D-N116A-N183D-I198L-G211Q-H249R, N018R-G020R-S024R-N076D-N183D-G211Q-A215F-H249R, S024R-N076D-V104I, N018R-N076D-S101G-A232V, N018R-S024R-N076D-S101A-N116A-N183D-I198L-G211Q-T213A-A215F-H249R, N018R-G020R-T022W-S024R-N076D-N116A-N183D-A215F-H249R, N018R-S024R-L031F-N076D-N116A-N183D-G211Q-T213A-A215F-H249R, N018R-S024R-N076D-S101A-N116A-N183D-I198L-T213A-H249R-N269S, N018R-G020R-S024R-N076D-S101A-N116A-I198L-A215F-H249R, N018R-N043R-N076D-S078R-S101G-S103A-V104I-A232V-Q245R-N269R, N018R-G020R-S024R-N076D-S101A-N114T-I198L-G211Q-A215F-H249R, S024R-N043R-S078R-S101G-S103A-V104I-L217E-A232V-Q245R, S024R-N076D-S103A-V104I-A232V, N018R-G020R-T022W-S024R-N076D-S101A-I198L-G211Q-A215F-H249R, S101G-V104I-A232V, N018R-T022W-S024R-N076D-N183D-I198L-T213A-A215F-H249R, N018R-T022W-S024R-N076D-N183D-I198L-G211Q-H249R, N018R-G020R-S024R-N076D-N183D-T213A-H249R, N018R-S024R-N076D-S101A-N183D-G211Q-A215F-H249R, N018R-G020R-T022W-S024R-N076D-N116A-G211Q-T213A-H249R, N018R-S078R-S101G-S103A-V104I-A232V-Q245R-N269R, N018R-T022W-S024R-N076D-S101A-N116A-N183D-G211Q-A215F-H249R-T260A, N076D-H249R, N018R-T022W-S024R-N076D-N183D-G211Q-A215F-H249R, N018R-G020R-S024R-N076D-N116A-G211Q-A215F-H249R, N018R-G020R-S024R-N076D-T213A-H249R, N018R-G020R-T022W-S024R-N076D-N116A-N183D-I198L-H249R, N018R-G020R-T022W-S024R-N076D-S101A-N183D-H249R, N076D-V104I-H249R, G020R-T022W-S101A-S103A-V104I-N116A-N183D-G211Q-T213A-A215F-A232V-Q245R, S024R-N043R-R045T-S078R-S101G-S103A-V104I-L217E-A232V-Q245R, N018R-G020R-T022W-S024R-N076D-N183D-I198L-A215F-H249R, N018R-N076D-S101G-S103A, G020R-S024R-S101G-S103A-V104I-A232V-Q245R-N269R, N018R-G020R-S024R-N076D-S101A-N116A-N183D-G211Q-H249R, S101G-S103A-A232V, S024R-N076D-S101G-A232V, N018R-T022W-S024R-N076D-S101A-N183D-I198L-G211Q-H249R, N018R-G020R-S024R-N076D-S101A-N183D-I198L-G211Q-A215F-H249R, N018R-G020R-

S024R-N076D-N183D-I198L-H249R, N018R-T022W-S024R-N076D-S101A-N116A-N183D-I198L-G211Q-H249R, N018R-G020R-S024R-N076D-N116A-A156V-N183D-G211Q-A215F-H249R-N269S, R045T-N076D-S101G-S103A-V104I-A232V-Q245R-H249R, N018R-G020R-S024R-N076D-S101A-N183D-I198L-H249R, N018R-G020R-T022W-S024R-N076D-I198L-G211Q-A215F-H249R, N018R-G020R-T022W-S024R-N076D-S101A-N116A-I198L-G211Q-A215F-H249R, N018R-G020R-T022W-S024R-N076D-N116A-H249R, N018R-N076D-S101G, N018R-S024R-N076D-N116A-N183D-I198L-T213A-A215F-H249R, N018R-G020R-T022W-S024R-N076D-S101A-N116A-I198L-T213A-A215F-H249R, N018R-S024R-N076D-S101A-N116A-N183D-I198L-G211Q-H249R, N018R-N076D-A232V, N018R-G020R-S024R-N076D-S101A-A232V-Q245R, N018R-N043D-R045T-N076D-S101G-S103A-V104I-A232V-Q245R, N018R-T022W-S024R-N076D-N183D-T213A-A215F-H249R, N018R-S024R-N076D-S101A-N116A-G211Q-T213A-N237D-H249R, N018R-G020R-S024R-N076D-S101A-N116A-N183D-G211Q-H249R-R275S, N018R-T022W-S024R-N076D-S101A-N116A-N183D-I198L-G211Q-T213A-A215F-H249R, S024R-N076D, N018R-S024R-N076D-N183D-G211Q-A215F-H249R, N018R-T022W-S024R-N076D-N116A-N183D-I198L-T213A-A215F-H249R, N076D-V104I-A232V-H249R, N018R-N076D-S103A-A232V, N018R-G020R-S024R-N076D-S101A-N116A-N183D-I198L-G211Q-T213A-H249R, N018R-G020R-S024R-N076D-S101A-N183D-T213A-H249R, N018R-G020R-S024R-N076D-S101A-D175E-N183D-G211Q-A215F-H249R, N018R-G020R-N043D-S078R-S101G-S103A-V104I-L217E-A232V-Q245R-A273E, G020R-S024R-N043D-R045T-N076D-S101G-S103A-V104I-A232V-Q245R, P005S-S101G-S103A-V104I-A232V-Q245R-H249R, S103A-V104I-A232V, N018R-G020R-S024R-V068A-N076D-S101A-N116A-T213A-A215F-H249R, N018R-T022W-S024R-N076D-S101A-I198L-A215F-H249R-R275S, N018R-S024R-N076D-N183D-I198L-G211Q-T213A-H249R, and N043D-R045T-S101G-S103A-V104I-A232V-Q245R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: N018R-S024R-N043R-N076D-H249R-N269R, N018R-T022R-S024R-N043R-N076D-H249R, N018R-N043D-S101G-S103A-V104I-A232V-Q245R, G020R-N043D-S101G-S103A-V104I-A232V-Q245R, N043D-S101G-S103A-V104I-A232V-Q245R-N269R, N043D-S078R-S101G-S103A-V104I-A232V-Q245R, N043R-N076D-S101G-S103A-V104I-A232V-Q245R, T022R-N043R-S101G-S103A-V104I-A232V-Q245R, N043R-S078R-S101G-S103A-V104I-A232V-Q245R, G020R-N076D-S101G-S103A-V104I-A232V-Q245R, N043R-N076D-S101G-S103A-V104I-A232V-Q245R, T022R-N076D-S101G-S103A-V104I-A232V-Q245R, N076D-S078R-S101G-S103A-V104I-A232V-Q245R, N018R-S024R-N043R-N076D-H249R, N018R-S024R-N076D-S242R-H249R, N018R-S024R-N076D-H249R-N269R, N018R-T022R-S024R-N076D-H249R, N018R-S024R-N076D-S078R-H249R, N018R-S024R-N043D-N076D-H249R-N269R, N018R-T022R-S024R-N043D-N076D-H249R, N018R-S024R-N043D-N076D-S078R-H249R, G020R-S101G-S103G-V104I-A232V-Q245R, G020R-S101G-S103A-V104L-A232V-Q245R, G020R-S101G-S103A-V104V-A232V-Q245R, G020R-S101G-S103S-V104I-A232V-Q245R, G020R-S101G-S103S-V104L-A232V-Q245R, G020R-S101S-S103S-V104I-A232V-Q245R, G020R-S101S-S103S-V104L-A232V-Q245R, G020R-S101A-S103A-V104L-A232V-Q245R, G020R-S101S-S103S-V104V-A232V-Q245R, G020R-S101S-S103A-V104I-A232V-Q245R, G020R-S101S-S103A-V104V-A232V-Q245R, G020R-S101S-S103G-V104I-A232V-Q245R, G020R-S101S-S103G-V104V-A232V-Q245R, G020R-S101A-S103A-V104V-A232V-Q245R, G020R-S101A-S103S-V104I-A232V-Q245R, G020R-S101A-S103S-V104V-A232V-Q245R, N018R-S024R-N043R-N076D-S078R-H249R, S024R-N043D-S101G-S103A-V104I-A232V-Q245R, N043D-S101G-S103A-V104I-A232V-Q245R-H249R, S024R-N076D-S101G-S103A-V104I-A232V-Q245R, N076D-S101G-S103A-V104I-A232V-S242R-Q245R, N018R-G020R-S024R-N076D-L217E-H249R, N018R-S024R-N043R-N076D-L217E-H249R, N018R-S024R-N043D-N076D-S242R-H249R, N018R-G020R-S024R-N043R-N076D-H249R, G020R-S101A-S103G-V104V-A232V-Q245R, N043D-S101G-S103A-V104I-A232V-Q245R, N018R-S024R-N076D-L217E-H249R-N269R, and N018R-S024R-N076D-L217E-S242R-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: G020R-S101A-S103A-V104I-G118R-A232V-Q245R, G020R-S024R-N116A-T213A, N043R-S101A-N116A-A215F-N269R, S024R-N043R-S101A-N116A, S024R-N043R-S101A-N116A-A215F-N269R, G020R-S101G-S103A-V104I-A215F-A232V-Q245R, N043R-S101A-N269R, S024R-N043R-N116A-T213A-N269R, G020R-S024R-N043R-R045T-S101A-T213A, S024R-N043R-N116A-A215F-N269R, G020R-S024R-T213A-A215F, G020R-N116A-N269R, S024R-N116A-T213A-N269R, N043R-S101A-N116A-N269R, S101G-S103A-V104I-N116A-T213A-A232V-Q245R-N269R, S024R-N043R-R045T-S101A-N116A-A215F-N269R, G020R-N043R-S101A-N269R, S101A-S103A-V104I-T213A-A232V-Q245R-N269R, S024R-A215F-N269R, N043R-S101A-N116A-T213A-A215F-N269R, N043R-S101A-T213A-N269R, G020R-S024R-N043R-R045T-N116A-T213A, S101G-S103A-V104I-A232V-Q245R-N269R, S024R-N043R-R045T-S101A-N116A-T213A-N269R, S024R-N043R-R045T-N269R, G020R-N043R-R045T-S101A-N269R, S024R-N043R-N116A-N269R, G020R-S024R-N043R-R045T, N043R-N116A-N269R, S024R-N043R-S101A-A215F-N269R, S024R-N043R-R045T-T213A-A215F-N269R, G020R-S024R-R045T-N269R, G020R-N043R-S101A-N116A-T213A-A215F, G020R-S101G-S103A-V104I-T213A-A215F-A232V-Q245R, G020R-S024R-R045T-N116A-N269R, G020R-S101A-N116A-N269R, S024R-N043R-A215F, G020R-S024R-T213A, S024R-N043R-S101A-A215F, G020R-S024R-N043R-R045T-N116A, G020R-S024R-N043R-R045T-S101A-N269R, G020R-S024R-S101A-A215F, G020R-S024R-N116A-T213A-A215F, G020R-S024R-N116A, G020R-S024R-S101A-N116A, N043R-T213A-A215F-N269R, S024R-S101A-N269R, S024R-N043R-N116A-A215F, G020R-T038A-N043R-S101A, G020R-S024R-N116A-A215F, S024R-N043R-S101A-T213A, P014L-G020R-S024R-N043R-R045T-S101A-A215F, G020R-S024R-A215F, G020R-N116A-A215F-N269R, G020R-R045T-N116A-N269R, G020R-S024R-N043R-R045T-A215F, and G020R-S024R-N043R-R045T-N116A-T213A-A215F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: N043R-N076D-S101A-S103A-V104I-A158E-S188D-A232V-Q245R-N248D-H249R-E271F, S024R-N043R-N076D-S101A-S103A-V104I-A158E-S188D-L217E-A232V-Q245R-N248D-H249R, S101A-S103A-V104I-A158E-S188D-A232V-Q245R-N248D-H249R-E271F-E271F, S101A-S103A-V104I-A158E-S188D-L217E-A232V-Q245R-N248D-H249R-E271F, N076D-S101G-S103A-V104I-A114V-A158E-S188D-A232V-Q245R-N248D-H249R-E271F, S024R-N076D-S101G-S103A-V104I-A158E-S188D-A232V-Q245R-N248D-H249R-E271F, S024R-N043R-S101A-S103A-V104I-A158E-S188D-L217E-A232V-Q245R-N248D-H249R, S024R-N043R-S101A-S103A-V104I-A158E-S188D-A232V-Q245R-N248D-H249R, S024R-S101A-S103A-V104I-A158E-S166D-S188D-L217E-A232V-Q245R-N248D-H249R, N076D-S101G-S103A-V104I-S128L-A158E-S188D-A232V-Q245R-N248D-H249R-E271F, and N043R-N076D-S101G-S103A-V104I-A158E-S166D-S188D-A232V-Q245R-N248D-H249R-E271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: T022A-S101G-S103A-V104I-G159D-L217E-A232V-Q245R-N248D-E271F, T022A-N043R-S101G-S103A-V104I-G159D-S188D-L217E-A232V-Q245R-N248D-E271F, T022A-S101G-S103A-V104I-G159D-S188D-A232V-Q245R-N248D-E271F, N043R-S101A-S103A-V104I-A158E-S188D-L217E-A232V-Q245R-N248D-H249R, N043R-N076D-S101A-S103A-V104I-A158E-S188D-L217E-A232V-Q245R-N248D-H249R-E271F, S024R-S101G-S103A-V104I-A158E-S188D-L217E-A232V-Q245R-N248D-H249R, S024R-S101G-S103A-V104I-A158E-S188D-A232V-Q245R-N248D-H249R, S101G-S103A-V104I-A158E-S188D-A232V-Q245R-N248D-H249R, S024R-S101G-S103A-V104I-A158E-N183D-S188D-A232V-Q245R-N248D-H249R, T022A-N076D-S101G-S103A-V104I-G159D-S188D-A232V-Q245R-N248D-E271F, T022A-N043R-N076D-S101G-S103A-V104I-G159D-S188D-A232V-Q245R-N248D-E271F, T022A-N076D-S101G-S103A-V104I-G159D-A232V-Q245R-N248D-E271F, T022A-S101G-S103A-V104I-G159D-A232V-Q245R-N248D-E271F, N076D-S101A-S103A-V104I-A158E-S188D-A232V-Q245R-N248D-H249R-E271F, N043R-S101A-S103A-V104I-A158E-S166D-S188D-A232V-Q245R-N248D-H249R, S024R-N076D-S101A-S103A-V104I-A158E-S166D-S188D-A232V-Q245R-N248D-H249R-E271F, N076D-S101A-S103A-V104I-A158E-S188D-A232V-Q245R-N248D-H249R, S101A-S103A-V104I-A158E-S166D-S188D-A232V-Q245R-N248D-H249R-E271F, N043R-N076D-S101A-S103A-V104I-A158E-S166D-S188D-A232V-Q245R-N248D-H249R-E271F, S101G-S103A-V104I-A158E-S166D-S188D-A232V-Q245R-N248D-H249R-E271F, S101A-S103A-V104I-A158E-S188D-A232V-Q245R-N248D-H249R-E271F, S101A-S103A-V104I-A158E-S188D-L217E-A232V-Q245R-N248D-H249R, N076D-S101A-S103A-V104I-A158E-S166D-S188D-A232V-Q245R-N248D-H249R-E271F, S101G-S103A-V104I-A158E-N183D-S188D-A232V-Q245R-N248D-H249R, S024R-S101G-S103A-V104I-S128L-A158E-S188D-A232V-Q245R-N248D-H249R, N076D-S101G-S103A-V104I-A158E-S166D-S188D-A232V-Q245R-N248D-H249R-E271F, N043R-N076D-S101A-S103A-V104I-A158E-S166D-S188D-A232V-Q245R-N248D-H249R, and N076D-S101A-S103A-V104I-A158E-S188D-L217E-A232V-Q245R-N248D-H249R-E271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: H017R-T022A-N076D-S101G-S103A-V104I-G159D-S188D-A232V-Q245R-N248D-E271F, T022A-N043R-S101G-S103A-V104I-G159D-A232V-Q245R-N248D-E271F, T022A-S101G-S103A-V104I-G159D-S188D-A232V-Q245R-N248D-H249R-E271F, H017R-T022A-N076D-S101G-S103A-V104I-G159D-A232V-Q245R-N248D-E271F, T022A-N076D-S101G-S103A-V104I-G159D-A232V-Q245R-N248D-H249R-E271F, T022A-S101G-G102A-S103A-V104I-G159D-S188D-A232V-Q245R-N248D-E271F, and T022A-N043R-N076D-S101G-S103A-V104I-G159D-A232V-Q245R-N248D-H249R-E271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101 S-S103A-V104I-A158E-S188D-A232V-Q245R-N248D-H249R, S101S-S103G-V104V-A158E-S188D-A232V-Q245R-N248D-H249R, S101G-S103S-V104I-A158E-S188D-A232V-Q245R-N248D-H249R, S101A-S103A-V104I-A158E-S188D-A232V-Q245R-N248D-H249R, S101A-S103A-V104L-A158E-S188D-A232V-Q245R-N248D-H249R, S101G-S103G-V104I-A158E-S188D-A232V-Q245R-N248D-H249R, S101S-S103G-V104I-A158E-S188D-A232V-Q245R-N248D-H249R, S101S-S103 S-V104I-A158E-S188D-A232V-Q245R-N248D-H249R, S101S-S103S-V104V-A158E-S188D-A232V-Q245R-N248D-H249R, S101A-S103S-V104I-A158E-S188D-A232V-Q245R-N248D-H249R, S101A-S103 S-V104I-G159E-A232V-Q245R-N248D-H249R, S101S-S103A-V104I-G159E-A232V-Q245R-N248D-H249R, S101G-S103A-V104L-A158E-S188D-A232V-Q245R-N248D-H249R, S101A-S103A-V104L-G159E-A232V-Q245R-N248D-H249R, S101A-S103S-V104L-G159E-A232V-Q245R-N248D-H249R, S101G-S103S-V104L-G159E-A232V-Q245R-N248D-H249R, S101S-S103A-V104L-G159E-A232V-Q245R-N248D-H249R, S101A-S103G-V104V-G159E-A232V-Q245R-N248D-H249R, and S101S-S103A-V104V-

G159E-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: V026F-V051W-V104L-S106E, V026F-L031F-S078N-G102A-S160D, G020K-G100S-N116L-A158E-S166D-N243F, T033S-N043W-N218D-P239G-N243F, T022L-T038F-A048R-N062E-G100S-R186K, S101D-S103N-N116L-S144R-A215D, V104L-S105T-T213A-L217E-S256N, N043W-S101D-S212M-N243F, V026F-A048R-S105T-T213A-N218D-T224A, S024F-S101D-G118R-A215D-L250I-A272F, V121F-N185E-T224A-P239G, T022L-L031F-G102A-S128D-T224A-N243F, N062E-S078N-G102A-N116L-S144R-L250I, T022L-T038F-V121F-S160D-A272F, V026F-S078N-G159C-R186K-N243F, S024F-A048R-G118R-S166D-L217E, G023A-T038F-S078N-G100S-S212M-A215D, G100S-N116L-A158E-T213A, S078N-V104L-G118R-S128D, G102A-S103N-S105T-A194E, T022L-S078N-S128D-T213A, K027R-G100S-G118R-S160D-S188D-N243F, S024F-G102A-R186K-T213A-L217E-N243F, T033S-S105T-S188D-S216F, G023A-G100S-A194E-S212M, A048R-S128D-N185E-P239G, G020K-S024F-T033S-P129E-A194E, G020K-K027R-P129E-S166D-P239G, T022L-G023A-K027R-S101D-V104L-S216F, T033S-G118R-P129E-A194E-P239G, T022L-S078N-N116L-P129E-S256N, K027R-S101D-S103N-S105T-A272F, A048R-S078N-N116L-N185E-L217E-P239G, G023A-S024F-K027R-N062E, S024F-S103N-V104L-G118R-S188D, V026F-V104L-S256N-A272F, S024F-N043W-V104L-V121F-P129E, N062E-S078N-N116L-T224A, G023A-S024F-V051W-A158E, K027R-T038F-G102A-N116L, N062E-S078N-S144R-S212M, L031F-N116L-S256N-A272F, T022L-T033S-V104L-N116L-S160D-R186K, S024F-G118R-P129E-R186K-T213A, N043W-S105T-T213A-A215D-S216F, L031F-S105T-R186K-S188D, V026F-A194E-T213A-S256N, and S103N-S160D-L250I-S256N, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: T022A-S024R-S101D-S103A-V104I-G118R-G159D-S188D-A232V-N248D-E271F, T022A-S024R-S103A-V104I-P129E-G159D-S188D-A232V-N248D-E271F, T022A-S024R-S103A-V104I-G118R-G159D-S188D-L217D-A232V-N248D, T022A-S024R-S101D-S103A-V104I-G118R-P129E-G159D-S188D-A232V-Q245R-N248D, T022A-S024R-S101D-S103A-V104I-G159D-S188D-A232V-Q245R-N248D, T022A-N043R-S103A-V104I-G118R-P129E-G159D-S188D-A232V-Q245R-N248D, T022A-N043R-S103A-V104I-G118R-S128I-P129E-G159D-S188D-A232V-N248D, T022A-N043R-S101D-S103A-V104I-G118R-P129E-G159D-S188D-A232V-N248D-E271F, T022A-S024R-N043R-S101D-S103A-V104I-G159D-S188D-A232V-Q245R-N248D, T022A-S103A-V104I-G159D-S188D-A232V-N248D, T022A-S024R-S103A-V104I-G118R-P129E-G159D-S188D-A232V-N248D-E271F, T022A-S024R-S103A-V104I-G159D-S188D-L217D-A232V-Q245R-N248D-E271F, T022A-N043R-N062E-S103A-V104I-G159D-S188D-A232V-Q245R-N248D-E271F, T022A-N043R-S103A-V104I-P129E-G159D-S188D-A232V-Q245R-N248D, T022A-S024R-S103A-V104I-G159D-S188D-L217D-A232V-N248D-E271F, T022A-S103A-V104I-G118R-G159D-S188D-L217D-A232V-Q245R-N248D, T022A-S024R-S101D-S103A-V104I-G118R-S128I-G159D-S188D-A232V-Q245R-N248D, T022A-S024R-N043R-S103A-V104I-G159D-S188D-L217D-A232V-N248D-E271F, T022A-N043R-S103A-V104I-G118R-G159D-S188D-L217D-A232V-N248D-E271F, T022A-N043R-S103A-V104I-G118R-G159D-S188D-A232V-N248D-E271F, T022A-S103A-V104I-S128I-P129E-G159D-S188D-A232V-N248D-E271F, T022A-S103A-V104I-G159D-S188D-L217D-A232V-Q245R-N248D-E271F, T022A-N043R-S103A-V104I-S128I-G159D-S188D-A232V-Q245R-N248D, T022A-S101D-S103A-V104I-G118R-G159D-S188D-L217D-A232V-Q245R-N248D-E271F, T022A-S103A-V104I-G118R-P129E-G159D-S188D-A232V-Q245R-N248D-E271F, T022A-S024R-N043R-S103A-V104I-G118R-G159D-S188D-L217D-A232V-N248D, T022A-N062E-S103A-V104I-G118R-G159D-S188D-A232V-Q245R-N248D, T022A-N043R-S101D-S103A-V104I-G118R-P129E-G159D-S188D-L217D-A232V, T022A-S024R-S103A-V104I-G159D-S188D-L217D-A232V-N248D, T022A-S024R-N043R-S103A-V104I-G118R-S128I-P129E-G159D-S188D-L217D-A232V-N248D-E271F, and T022A-S103A-V104I-G118R-G159D-S188D-L217D-A232V-Q245R-N248D-E271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: G020K-S024F-N062E-S188D-P239G, S024F-N062E-N116L-P239G, G020K-G023A-N062E-S188D, G020K-G023A-S024F-N062E-G118R-S188D-T213A, G020K-N043W-N062E-N116L-S188D-T213A-P239G, G023A-N062E-N116L-G118R, G023A-S024F-N062E-N116L-G118R, S024F-N116L, S024F-N062E-S188D-T213A, G023A-N062E-N116L-G118R-S188D-P239G, G020K-S024F-N062E, G020K-N043W-N062E-N116L-P239G, S024F-N062E-N116L-T213A-P239G, G020K-S024F-N043W-N062E-N116L-T213A, G020K-G023A-S024F-N062E-N116L-S188D-T213A, S024F-N062E-S188D-P239G, G023A-N043W-N062E-N116L-G118R-T213A, N062E-S188D-P239G, G020K-S024F-N062E-P239G, S024F-N116L-G118R-S188D-P239G, G020K-G023A-N062E-N116L-G118R-T213A, G020K-G023A-S024F-N062E-S188D-T213A-P239G, S024F-N043W-G118R-S188D, G023A-S024F-N116L-G118R-S188D-T213A, G020K-G023A-N043W-N116L-S188D-T213A-P239G, G023A-S024F-N116L-S188D-P239G, G023A-N043W-N116L-G118R-S188D, G023A-S024F-G118R-S188D-P239G, G023A-S024F-N043W-N062E-N116L-G118R, G020K-N043W-S188D-T213A, S024F-N062E-G118R-P239G, G023A-N043W-S188D-T213A, G020K-S024F-N043W-N062E-N116L-G118R-S188D-P239G, G020K-N116L-S188D-P239G, G020K-N043W-N062E-G118R, G020K-N043W-N116L-S188D-T213A, G020K-S024F, G023A-N043W-N116L-P239G, G023A-S024F-N043W-N116L-G118R-S188D-P239G, G020K-G023A-N043W-T213A, and G023A-S024F-

N062E-G118R-T213A-P239G, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: G020K-G023A-N043W-G118R-S128I-P129E-G159D-S188D, S024F-G118R-S128I-P129E-G159D, G020K-S024F-N062E-N116L-G118R-S188D, G020K-N062E-N116L-S188D, N062E-N116L-G118R-T213A, G020K-G023A-N062E-N116L-S188D, N062E-N116L-G118R-S188D, G020K-N062E-N116L-T213A, G020K-G023A-N062E-N116L, G020K-N062E-S188D-T213A, G020K-N062E, G020K-S024F-N062E-N116L-S188D, G020K-N043W-N062E-N116L-S188D, G020K-S024F-N062E-S188D-T213A, N062E-N116L-S188D-T213A, G020K-N062E-N116L, G020K-G023A-N062E-N116L-S188D-T213A, G023A-S024F-N062E-N116L-T213A, T022A-N043R-S103A-V104I-S128I-P129E-G159D-S188D-A232V-Q245R-N248D, T022A-N043R-S103A-V104I-G118R-S128I-P129E-G159D-S188D-A232V-N248D-E271F, S024F-N062E-N116L-S188D, T022A-S024R-S103A-V104I-G118R-S128I-P129E-G159D-S188D-A232V-N248D, G023A-N062E-N116L-S188D, N043W-N062E-N116L, G020K-G023A-N116L-S188D, N043W-N062E-N116L-S188D, S024F-N062E-N116L, N062E-N116L-S188D, and T022A-S024R-S103A-V104I-S128I-G159D-S188D-A232V-N248D, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: S087R-S101G-S103A-V104I-Q109R-S212P-A232V-Q245R-E271V, S101G-S103A-V104I-Q109R-A232V-Q245R, S101G-S103A-V104I-Q109R-S212P-A232V-Q245R-E271V, S101G-S103A-V104I-Q109R-S212P-A232V-Q245R, N076D-S87R-S103A-V104I-S212P-E271V, N076D-S103A-V104I-Q109R, N076D-S103A-V104I-S212P-E271V, N076D-S103A-V104I-Q109R-Q245R, and N076D-S103A-V104I-S212P-Q245L-E271V, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: S024R-P086W-G118R, S024R-S078R-P086W-N243F, S024R-T033S-P086S-S087N-Y209A, T033S-G118R, S024R-S078R-P086W-G118R-A270T, S024R-T033S-P086W-G118R, S078R-P086W-N243F, T033S-S078R-P086W-G118R-Y209A, T033S-S078R-Y209A, P086W-G118R-N243F, S024R-P086W, S078R-P086W-K235F, S024R-G118R, S024R-P086R, S101G-S103A-V104I-A232V, S024R-T033S-S078R-P086W-G118R, S024R-G118R-Y209A, Y209A-W241R, T033S-P086W-N243F, T033S-A172V-Y209A, G118R-Y209A-N243F, S024R-P086S-S141G, S024R-G118R-Y209A-N243F, S024R-T033S-P086S-S085N-K235F, S024R-T033S-A133V, S024R-T033S-S078R-P086W, S024R-P086W-Y209A, S024R-W241R, T033S-G118R-N243F, S024R-K235F, S024R-S078R-P086W, S024R-G118R-Y209A-K235F, S024R-Y209A-W241R, T033S-G118R-W241R, P086W-G118R-Y209A, T033S-G118R-G159D-Y209A, T033S-S078R-P086W, S024R-P086W-N243F, G118R-Y209A, S024R-P086W-G118R-V203I, S078R-Y209A-K235F, S024R-T033S-W241R, S078R-G118R, T033S-G118R-Y209A-N243F, L021M-S024R-T033S, S024R-T033S-P086W, T033S-K235F, S078R-P086W-Y209A, S024R-T033S-Y209A-K235F, T033S-P086W-G118R, S024R-T033S-S078R-Y209A, T033S-P086W-G118R-Y209A-N243F, P086W-Y209A-N243F, M5S-S078R-G118R-W241R, S024R-A174T, T033S-Y209A-N243F, P086W-G118R-A133V, S024R-T033S-G118R, S024R-P086W-Y209A-K235F, P086W-Y209A, I008T-S024R, P086W-G118R, T033S-W241R, P005S-S024R-T033S-N243F, S024R-Y209A-S242P, S024R-T033S-S078R-G118R, S024R-T033S-A194T, S024R-N243F, S024R-Y209A, S024R-T033S-G118R-Y209A, T033S-P086W, S024R-T033S, S024R-T033S-S078R-N243F, P086W-N243F, T033S-G118D-A138V-Y209A, T033S-Y209A-K235F, S024R-P086R-G118R, T033S-P201S, S024R-P239Q, T033S-G118R-Y209A-, S078R-P086W, K235F-N243F, S024R-Y209A-K235F, G118R-A172V, H017Y-S024R-T033S-P086W, T033S-L148F, S024R-G118R-K235F, T033S-S078R, T033S-N243F, S024C-T033S, G118R-A194T, T033S-Y209A, G118R-Y209A-K235F, S024R-T033S-Y209A-N243F, S024R-T033S-K235F, S024R-T033S-G118R-K235F, S024R-S141G, S024R-T274I, S024R-T033S-Y209A, P086W-K235F, S024R-Y209A-N243F, V004E-T033S-S078R, P086W-Y209A-K235F, A015T-T033S, T033S-P086W-S156L-Y209A, S024R-G118R-N243F-R269H, Y209A-K235F, S024R-R247H, S024R-T033S-A228T, S078R-K235F, S024R-T033S-A174V-K235F, S024R-K235F-N243F, S024R-T033S-K235F-W241R, S024R-T033S-A151V, S024R-V104A, T033S-A048T, Q012H-V104A-G118R, G118R-K235F, T033S-T253A, T143A-Y209A, S024R-T033S-N243F, T033S-P239T, Y209A-N243F, S024R-T033S-P129H-N184D-T253M, S024R-A085V-P086W-G118R-K235F, S024R-A272P, and S024R-R269C, wherein the amino acid positions of the subtilisin variant are numbered by correspondence with the amino acid sequence of *B. amyloliquefaciens* subtilisin BPN' set forth as SEQ ID NO:1.

The present invention also provides isolated protease variants wherein said protease variant comprises one or more, preferably two or more or preferably three or more of the following mutations X1R, X2S, X4R, X4S, X9A, X10S, X14K, X16S, X17R, X18R, X20R, X22A, X22R, X24R, X24W, X25R, X25V, X26F, X42I, X43R, X43A, X46R, X52F, X52E, X52N, X57R, X59A, X62E, X62Q, X68A, X68C, X71G, X72C, X74C. X75A, X75F, X75R, X76D, X78R, X82R, X86W, X89P, X89T, X89G, X89H, X89I, X89V, X89W, X91N, X94N, X100S, X101A, X101N, X101G, X101D, X103G, X103N, X104L, X104I, X106V, X106G, X108I, X111V, X112V, X115K, X115R, X117F, X118I, X121F, X128D, X128F, X128L, X128N, X129E, X144R, X148I, X158E, X159E, X160D, X166D, X185E, X185I, X186H, X188E, X188D, X197F, X203E, X209S, X209N, X209F, X209T, X209E, X209H, X209G, X210R, X212I, X212F, X214F, X215N, X215D, X215E, X217E, X217N, X224A, X230E, X231I, X236F, X238R, X238K, X239K, X239G, X239R, X239S, X241R, X242R, X242L, X243R, X244R, X248I, X248V, X249R, X250I, X252R, X253R, X262D, X263F, X265F, X267V, X267N, X269I, X269R, X271F, X271I, X271H, X271P, X271T, X271V, X271L and X272F, and optionally one or more of the following mutations: X103A, X159D, X236H, X245R, X248D and X252K.

The present invention also provides isolated protease variants, wherein said protease variant comprises one or more of the following set of mutations:

a) G020K-G023A-N043W-G118R-S128I-P129E-G159D-S188D, G020K-G023A-N062E-N116L, G020K-G023A-N062E-N116L-S188D, G020K-G023A-N062E-N116L-S188D-T213A, G020K-G100S-N116L-A158E-S166D-N243F, G020K-N043W-N062E-N116L-S188D, G020K-N062E, G020K-N062E-N116L, G020K-N062E-N116L-S188D, G020K-N062E-N116L-T213A, G020K-N062E-S188D-T213A, G020K-S024F-N062E-N116L-G118R-S188D, G020K-S024F-N062E-N116L-S188D, G020K-S024F-N062E-S188D-T213A, G023A-N062E-N116L-S188D, G023A-S024F-N062E-N116L-T213A, N043R-N076D-S101A-S103A-V104I-A158E-S188D-L217E-A232V-Q245R-N248D-H249R-E271F, N043R-S101A-S103A-V104I-A158E-S188D-L217E-A232V-Q245R-N248D-H249R, N043W-N062E-N116L, N043W-S101D-S212M-N243F, N062E-N116L-G118R-S188D, N062E-N116L-G118R-T213A, N062E-N116L-S188D-T213A, S024F-G118R-S128I-P129E-G159D, S024F-N062E-N116L-S188D, S024R-S101G-S103A-V104I-A158E-N183D-S188D-A232V-Q245R-N248D-H249R, S024R-S101G-S103A-V104I-A158E-S188D-A232V-Q245R-N248D-H249R, S024R-S101G-S103A-V104I-A158E-S188D-L217E-A232V-Q245R-N248D-H249R, S024R-S101G-S103A-V104I-P129Q-A158E-N183D-S188D-A232V-Q245R-N248D-H249R, S024R-S101G-S103A-V104I-P129Q-A158E-S188D-A232V-Q245R-N248D-H249R, S024R-S101G-S103A-V104I-P129Q-A158E-S188D-L217E-A232V-Q245R-N248D-H249R, S024R-S101G-S103A-V104I-P129Q-S130A-A158E-N183D-S188D-A232V-Q245R-N248D-H249R, S024R-S101G-S103A-V104I-S128L-P129Q-A158E-S188D-A232V-Q245R-N248D-H249R, S024R-S101G-S103A-V104I-S130A-A158E-N183D-S188D-A232V-Q245R-N248D-H249R, S024R-S101G-S103A-V104I-S130A-A158E-S188D-A232V-Q245R-N248D-H249R, S101D-S103N-N116L-S144R-A215D, S101G-S103A-V104I-A158E-S188D-A232V-Q245R-N248D-H249R, S101G-S103A-V104I-S130A-A158E-S188D-A232V-Q245R-N248D-H249R, T022A-N043R-S101G-S103A-V104I-G159D-S188D-L217E-A232V-Q245R-N248D-E271F, T022A-N043R-S103A-V104I-G118R-S128I-P129E-G159D-S188D-A232V-N248D-E271F, T022A-N043R-S103A-V104I-S128I-P129E-G159D-S188D-A232V-Q245R-N248D, T022A-S024R-S103A-V104I-G118R-S128I-P129E-G159D-S188D-A232V-N248D, T022A-S101G-S103A-V104I-G159D-L217E-A232V-Q245R-N248D-E271F, T022A-S101G-S103A-V104I-G159D-S188D-A232V-Q245R-N248D-E271F, T022L-T038F-A048R-N062E-G100S-R186K, T033S-N043W-N218D-P239G-N243F, V026F-A048R-S105T-T213A-N218D-T224A, V026F-L031F-S078N-G102A-S160D, V026F-V051W-V104L-S106E, V104L-S105T-T213A-L217E-S256N, A016S-N062E-A158E-H249R, A016S-N062E-A158E-R186H-E271F, A016S-N062E-A158E-R186H-H249R, A016S-N062E-V104L-A158E-R186H-E271F, A016S-S024R-S101G-S103A-V104I-A158E-S188D-A232V-Q245R-N248D-H249R, G020K-G023A-N062E-S188D, G020K-G023A-S024F-N062E-G118R-S188D-T213A, G020K-N043W-N062E-N116L-S188D-T213A-P239G, G020K-S024F-N062E-S188D-P239G, G023A-N062E-N116L-G118R, G023A-N062E-N116L-G118R-S188D-P239G, G023A-S024F-N062E-N116L-G118R, H017R-T022A-N076D-S101G-S103A-V104I-G159D-S188D-A232V-Q245R-N248D-E271F, N043R-N076D-S101A-S103A-V104I-A158E-S188D-A232V-Q245R-N248D-H249R-E271F, N062E-A158E-G159E-H249R, N062E-A158E-H249R, N062E-A158E-R186H-E271F, N062E-A158E-R186H-H249R, N062E-A158E-R186H-H249R-E271F, N062E-A158E-S188D-H249R, N062E-A158E-S188D-H249R-E271F, N062E-G159E-H249R, N062E-G159E-H249R-E271F, N062E-G159E-R186H-H249R, N062E-G159E-S188D-H249R, N062E-R186H-S188D-H249R-E271F, N062E-S101A-A158E-H249R, N062E-S101A-A158E-R186H-E271F, N062E-S101A-A158E-R186H-H249R-E271F, N062E-S101A-G159E-H249R, N062E-S101A-R186H-H249R, N062E-S101A-S188D-H249R, N062E-S101A-S188D-H249R-E271F, N062E-S101A-V104L-A158E-R186H-E271F, N062E-S128N-A158E-G159E-E271F, N062E-V104L-A158E-S188D-H249R-E271F, N076D-S101G-S103A-V104I-A232V-M222Q-Q245R, S024F-N062E-N116L-P239G, S024F-N062E-S188D-T213A, S024F-N116L, S024R-N043R-N076D-S101A-S103A-V104I-A158E-S188D-L217E-A232V-Q245R-N248D-H249R, S024R-S101G-S103A-V104I-A158E-G159E-A232V-N238R-Q245R-N248D, S024R-S101G-S103A-V104I-A158E-G159E-S188D-A232V-Q245R-N248D, S024R-S101G-S103A-V104I-A158E-S188D-A232V-N238R-Q245R-N248D, S024R-S101G-S103A-V104I-A232V-Q245R-N248D-H249R, S024R-S101G-S103A-V104I-G159E-S188D-A232V-N238R-Q245R-N248D, S024R-S101G-S103A-V104I-G159E-S188D-A232V-Q245R-N248D, S024R-S101G-S103A-V104I-G159E-S188D-A232V-Q245R-N248D-H249R, S024R-S101G-S103A-V104I-L148I-A158E-A232V-Q245R-N248D, S024R-S101G-S103A-V104I-L148I-A158E-S188D-A232V-Q245R-N248D, S024R-S101G-S103A-V104I-L148I-A232V-Q245R-N248D, S024R-S101G-S103A-V104I-P129E-A158E-A232V-Q245R-N248D-H249R, S024R-S101G-S103A-V104I-P129E-A158E-G159E-S188D-A232V-Q245R-N248D-H249R, S024R-S101G-S103A-V104I-P129E-A158E-S188D-A232V-Q245R-N248D, S024R-S101G-S103A-V104I-P129E-A158E-S188D-A232V-Q245R-N248D-H249R, S024R-S101G-S103A-V104I-P129E-G159E-A232V-Q245R-N248D, S024R-S101G-S103A-V104I-P129E-G159E-S188D-A232V-Q245R-N248D-H249R, S024R-S101G-S103A-V104I-P129E-L148I-A158E-A232V-Q245R-N248D, S024R-S101G-S103A-V104I-P129E-S188D-A232V-N238R-Q245R-N248D, S024R-S101G-S103A-V104I-P129E-S188D-A232V-Q245R-N248D, S024R-S101G-S103A-V104I-P129E-S188D-A232V-Q245R-N248D-H249R, S024R-S101G-S103A-V104I-S128N-A158E-A232V-Q245R-N248D, S024R-S101G-S103A-V104I-S128N-P129E-A158E-A232V-Q245R-N248D-H249R, S024R-S101G-S103A-V104I-S128N-P129E-A232V-Q245R-N248D, S101A-S103A-V104I-A158E-S188D-A232V-Q245R-N248D-H249R, S101A-S103A-V104I-A158E-S188D-A232V-Q245R-N248D-H249R-E271F-E271F, S101A-S103A-V104L-A158E-S188D-A232V-Q245R-N248D-H249R, S101A-S128N-A158E-R186H-E271F, S101A-S128N-A158E-Y209E-H249R, S101A-V104L-A158E-R186H-S188D-H249R, S101G-S103A-V104I-A158E-A232V-Q245R-N248D-H249R, S101G-S103A-V104I-A158E-G159E-A232V-Q245R-N248D-H249R, S101G-S103A-V104I-A158E-S188D-M222Q-A232V-Q245R-N248D-H249R, S101G-S103A-V104I-A158E-S188D-M222S-A232V-Q245R-N248D-H249R, S101G-S103A-V104I-A232V-

M222Q-Q245R, S101G-S103A-V104I-P129E-A158E-S188D-A232V-Q245R-N248D-H249R, S101G-S103A-V104I-P129E-G159E-A232V-Q245R-N248D-H249R, S101G-S103A-V104I-P129E-S188D-A232V-N238R-Q245R-N248D, S101G-S103A-V104I-P129E-S188D-A232V-Q245R-N248D-H249R, S101G-S103A-V104I-S188D-A232V-Q245R-N248D-H249R, S101G-S103G-V104I-A158E-S188D-A232V-Q245R-N248D-H249R, S101G-S103S-V104I-A158E-S188D-A232V-Q245R-N248D-H249R, S101S-S103A-V104I-A158E-S188D-A232V-Q245R-N248D-H249R, S101S-S103G-V104I-A158E-S188D-A232V-Q245R-N248D-H249R, S101S-S103G-V104V-A158E-S188D-A232V-Q245R-N248D-H249R, S128N-A158E-G159E-E271F, S128N-A158E-H249R, S128N-A158E-R186H-E271F, S128N-A158E-R186H-H249R, S128N-A158E-R186H-S188D-E271F, S128N-A158E-S188D-E271F, S128N-A158E-S188D-H249R, S128N-A158E-S188D-Y209E-E271F, S128N-A158E-Y209E-, T022A-N043R-S103A-V104I-G118R-P129E-G159D-S188D-A232V-Q245R-N248D, T022A-N062E-A158E, T022A-S024R-S101D-S103A-V104I-G118R-G159D-S188D-A232V-N248D-E271F, T022A-S024R-S101D-S103A-V104I-G118R-P129E-G159D-S188D-A232V-Q245R-N248D, T022A-S024R-S101D-S103A-V104I-G159D-S188D-A232V-Q245R-N248D, T022A-S024R-S101G-S103A-V104I-A158E-A232V-N238R-Q245R-N248D, T022A-S024R-S101G-S103A-V104I-A158E-A232V-Q245R-N248D-H249R, T022A-S024R-S101G-S103A-V104I-A158E-G159E-S188D-A232V-N238R-Q245R-N248D, T022A-S024R-S101G-S103A-V104I-A158E-G159E-S188D-A232V-Q245R-N248D, T022A-S024R-S101G-S103A-V104I-A158E-G159E-S188D-A232V-Q245R-N248D-H249R, T022A-S024R-S101G-S103A-V104I-P129E-A158E-A232V-Q245R-N248D, T022A-S024R-S101G-S103A-V104I-P129E-A158E-A232V-Q245R-N248D-H249R, T022A-S024R-S101G-S103A-V104I-P129E-A158E-G159E-A232V-Q245R-N248D-H249R, T022A-S024R-S101G-S103A-V104I-P129E-A158E-G159E-S188D-A232V-N238R-Q245R-N248D, T022A-S024R-S101G-S103A-V104I-P129E-A158E-S188D-A232V-N238R-Q245R-N248D, T022A-S024R-S101G-S103A-V104I-P129E-A158E-S188D-A232V-Q245R-N248D-H249R, T022A-S024R-S101G-S103A-V104I-P129E-A232V-Q245R-N248D, T022A-S024R-S101G-S103A-V104I-P129E-A232V-Q245R-N248D-H249R, T022A-S024R-S101G-S103A-V104I-P129E-G159E-S188D-A232V-Q245R-N248D-H249R, T022A-S024R-S101G-S103A-V104I-P129E-S188D-A232V-Q245R-N248D, T022A-S024R-S101G-S103A-V104I-S128N-A158E-S188D-A232V-Q245R-N248D, T022A-S024R-S101G-S103A-V104I-S128N-P129E-A158E-A232V-Q245R-N248D, T022A-S024R-S101G-S103A-V104I-S128N-P129E-S188D-A232V-Q245R-N248D, T022A-S024R-S101G-S103A-V104I-S128N-S188D-A232V-Q245R-N248D, T022A-S024R-S103A-V104I-G118R-G159D-S188D-L217D-A232V-N248D, T022A-S024R-S103A-V104I-P129E-G159D-S188D-A232V-N248D-E271F, T022A-S101G-S103A-V104I-A158E-G159E-S188D-A232V-Q245R-N248D-H249R, T022A-S101G-S103A-V104I-A158E-S188D-A232V-Q245R-N248D, T022A-S101G-S103A-V104I-P129E-A158E-A232V-N238R-Q245R-N248D, T022A-S101G-S103A-V104I-P129E-A158E-G159E-A232V-N238R-Q245R-N248D, T022A-S101G-S103A-V104I-P129E-A158E-S188D-A232V-Q245R-N248D-H249R, T022A-S101G-S103A-V104I-P129E-G159E-A232V-N238R-Q245R-N248D, T022A-S101G-S103A-V104I-P129E-S188D-A232V-N238R-Q245R-N248D-H249R, T022A-S101G-S103A-V104I-S128N-P129E-A232V-N238R-Q245R-N248D, T022A-S101G-S103A-V104I-S128N-P129E-A232V-N238R-Q245R-N248D, T022A-S128N-A158E-H249R, V104L-S128N-A158E-H249R, V104L-S128N-A158E-R186H-E271F, V104L-S128N-A158E-R186H-H249R, and/or V104L-S128N-A158E-S188D-H249R;

b) A016S-N062E-A158E-H249R-E271F, A016S-N062E-S128N-R186H-E271F, A016S-N062E-V104L-R186H-S188D-E271F, A016S-S101A-S128N-R186H, A016S-S128N-A158E-R186H, A016S-V104L-A158E-R186H-E271F, A016S-V104L-S188D-H249R, A158E-R186H-H249R, A158E-R186H-S188D-H249R-E271F, G020K-G023A-N116L-S188D, G020K-G023A-S024F-N062E-N116L-S188D-T213A, G020K-N043W-N062E-N116L-P239G, G020K-S024F-N043W-N062E-N116L-T213A, G020K-S024F-N062E, G023A-N043W-N062E-N116L-G118R-T213A, G023A-T038F-S078N-G100S-S212M-A215D, G100S-N116L-A158E-T213A, G102A-S103N-S105T-A194E, H017R-T022A-N076D-S101G-S103A-V104I-G159D-A232V-Q245R-N248D-E271F, N043R-N076D-S101A-S103A-V104I-A158E-S166D-S188D-A232V-Q245R-N248D-H249R-E271F, N043R-S101A-S103A-V104I-A158E-S166D-S188D-A232V-Q245R-N248D-H249R, N043W-N062E-N116L-S188D, N062E-A158E-H249R-E271F, N062E-A158E-R186H-S188D-H249R, N062E-L148I-G159E, N062E-N116L-S188D, N062E-R186H-H249R, N062E-S078N-G102A-N116L-S144R-L250I, N062E-S101A-A158E-R186H-H249R, N062E-S101A-A158E-S188D-H249R, N062E-S101A-R186H, N062E-S101A-R186H-E271F, N062E-S101A-R186H-H249R-E271F, N062E-S101A-R186H-S188D-E271F, N062E-S101A-R186H-S188D-H249R, N062E-S101A-V104L-R186H-S188D-E271F, N062E-S128N-A158E, N062E-S128N-G159E-H249R, N062E-S188D-P239G, N062E-V104L-G159E-H249R, N076D-S101A-S103A-V104I-A158E-S166D-S188D-A232V-Q245R-N248D-H249R-E271F, N076D-S101A-S103A-V104I-A158E-S188D-A232V-Q245R-N248D-H249R, N076D-S101A-S103A-V104I-A158E-S188D-A232V-Q245R-N248D-H249R-E271F, N076D-S101G-S103A-V104I-A114V-A158E-S188D-A232V-Q245R-N248D-H249R-E271F, N076D-S101G-S103A-V104I-A232V-M222S-Q245R, S024F-A048R-G118R-S166D-L217E, S024F-N062E-N116L, S024F-N062E-N116L-T213A-P239G, S024F-N062E-S188D-P239G, S024F-S101D-G118R-A215D-L250I-A272F, S024R-K027R-S101G-S103A-V104I-S128L-P129Q-S130A-A158E-S188D-A232V-Q245R-N248D-H249R, S024R-N076D-S101A-S103A-V104I-A158E-S166D-S188D-A232V-Q245R-N248D-H249R-E271F, S024R-S101G-S103A-V104I-A158E-A232V-Q245R-N248D-H249R, S024R-S101G-S103A-V104I-P129E-A158E-G159E-A232V-N238R-Q245R-N248D, S024R-S101G-S103A-V104I-P129E-A158E-G159E-A232V-Q245R-N248D-H249R, S024R-S101G-S103A-V104I-P129E-G159E-A232V-N238R-Q245R-N248D, S024R-S101G-S103A-V104I-P129E-G159E-S188D-A232V-N238R-Q245R-N248D, S024R-S101G-S103A-V104I-P129E-L148I-A158E-S188D-A232V-Q245R-N248D, S024R-S101G-S103A-V104I-P129E-L148I-S188D-A232V-Q245R-N248D, S024R-S101G-S103A-V104I-P129Q-S130A-A158E-S188D-A232V-Q245R-N248D-H249R, S024R-S101G-S103A-V104I-S128L-A158E-S188D-A232V-Q245R-N248D-H249R, S024R-S101G-S103A-V104I-S128L-P129Q-S130A-A158E-S188D-A232V-Q245R-N248D-H249R, S024R-

S101G-S103A-V104I-S128N-G159E-S188D-A232V-Q245R-N248D, S078N-V104L-G118R-S128D, S101A-A158E-R186H-H249R, S101A-A158E-R186H-S188D-H249R, S101A-S103A-V104I-A158E-S166D-S188D-A232V-Q245R-N248D-H249R-E271F, S101A-S103A-V104I-A158E-S188D-A232V-Q245R-N248D-H249R-E271F, S101A-S103A-V104I-A158E-S188D-L217E-A232V-Q245R-N248D-H249R, S101A-S103A-V104I-A158E-S188D-L217E-A232V-Q245R-N248D-H249R-E271F, S101A-S103G-A158E-R186H-H249R, S101A-S103S-V104I-A158E-S188D-A232V-Q245R-N248D-H249R, S101A-S103S-V104I-G159E-A232V-Q245R-N248D-H249R, S101A-S128N-A158E-H249R, S101A-S128N-A158E-S188D-Y209E-E271F, S101A-S128N-A158E-Y209E, S101A-S128N-P129E-R186H-H249R, S101A-V104L-A158E-R186H-H249R, S101A-V104L-A158E-R186H-S188D-E271F, S101A-V104L-S128N-A158E-R186H-E271F, S101G-S103A-V104I-A158E-A232V-N238R-Q245R-N248D, S101G-S103A-V104I-A158E-G159E-S188D-A232V-N238R-Q245R-N248D, S101G-S103A-V104I-A158E-N183D-S188D-A232V-Q245R-N248D-H249R, S101G-S103A-V104I-A158E-S166D-S188D-A232V-Q245R-N248D-H249R-E271F, S101G-S103A-V104I-A158E-S188D-A232V-Q245R-N248D, S101G-S103A-V104I-A232V-M222S-Q245R, S101G-S103A-V104I-P129E-A158E-G159E-A232V-N238R-Q245R-N248D, S101G-S103A-V104I-P129E-A158E-G159E-A232V-Q245R-N248D-H249R, S101G-S103A-V104I-P129E-A158E-S188D-A232V-N238R-Q245R-N248D, S101G-S103A-V104I-P129E-G159E-A232V-N238R-Q245R-N248D, S101G-S103A-V104I-P129E-S188D-A232V-Q245R-N248D, S101G-S103A-V104I-P129Q-A158E-S188D-A232V-Q245R-N248D-H249R, S101G-S103A-V104I-P129Q-S130A-A158E-S188D-A232V-Q245R-N248D-H249R, S101G-S103A-V104I-S128L-P129Q-A158E-S188D-A232V-Q245R-N248D-H249R, S101G-S103A-V104I-S128L-S130A-A158E-S188D-L217E-A232V-Q245R-N248D-H249R, S101G-S103A-V104I-S128N-P129E-A232V-N238R-Q245R-N248D, S101G-S103A-V104I-S128N-P129E-A232V-Q245R-N248D, S101G-S103A-V104I-S130A-A158E-N183D-S188D-L217E-A232V-Q245R-N248D-H249R, S101G-S103A-V104I-S188D-A232V-N238R-Q245R-N248D, S101G-S103A-V104L-A158E-S188D-A232V-Q245R-N248D-H249R, S101S-S103A-V104I-G159E-A232V-Q245R-N248D-H249R, S101S-S103S-V104I-A158E-S188D-A232V-Q245R-N248D-H249R, S101S-S103S-V104V-A158E-S188D-A232V-Q245R-N248D-H249R, T022A-N043R-N062E-S103A-V104I-G159D-S188D-A232V-Q245R-N248D-E271F, T022A-N043R-N076D-S101G-S103A-V104I-G159D-S188D-A232V-Q245R-N248D-E271F, T022A-N043R-S101D-S103A-V104I-G118R-P129E-G159D-S188D-A232V-N248D-E271F, T022A-N043R-S101G-S103A-V104I-G159D-A232V-Q245R-N248D-E271F, T022A-N043R-S103A-V104I-G118R-G159D-S188D-A232V-N248D-E271F, T022A-N043R-S103A-V104I-G118R-G159D-S188D-L217D-A232V-N248D-E271F, T022A-N043R-S103A-V104I-G118R-S128I-P129E-G159D-S188D-A232V-N248D, T022A-N043R-S103A-V104I-P129E-G159D-S188D-A232V-Q245R-N248D, T022A-N076D-S101G-S103A-V104I-G159D-A232V-Q245R-N248D-E271F, T022A-N076D-S101G-S103A-V104I-G159D-S188D-A232V-Q245R-N248D-E271F, T022A-S024R-N043R-S101D-S103A-V104I-G159D-S188D-A232V-Q245R-N248D, T022A-S024R-N043R-S103A-V104I-G159D-S188D-L217D-A232V-N248D-E271F, T022A-S024R-S101D-S103A-V104I-G118R-S128I-G159D-S188D-A232V-Q245R-N248D, T022A-S024R-S101G-S103A-V104I-L148I-A158E-A232V-Q245R-N248D, T022A-S024R-S101G-S103A-V104I-P129E-A158E-G159E-A232V-Q245R-N248D, T022A-S024R-S101G-S103A-V104I-P129E-A158E-G159E-S188D-A232V-Q245R-N248D-H249R, T022A-S024R-S101G-S103A-V104I-P129E-L148I-A232V-Q245R-N248D, T022A-S024R-S101G-S103A-V104I-S188D-A232V-Q245R-N248D-H249R, T022A-S024R-S103A-V104I-G118R-P129E-G159D-S188D-A232V-N248D-E271F, T022A-S024R-S103A-V104I-G159D-S188D-L217D-A232V-N248D-E271F, T022A-S024R-S103A-V104I-G159D-S188D-L217D-A232V-Q245R-N248D-E271F, T022A-S101A-A158E-R186H-H249R, T022A-S101G-S103A-V104I-A158E-G159E-A232V-N238R-Q245R-N248D, T022A-S101G-S103A-V104I-A158E-G159E-A232V-Q245R-N248D-H249R, T022A-S101G-S103A-V104I-G159D-A232V-Q245R-N248D-E271F, T022A-S101G-S103A-V104I-G159D-S188D-A232V-Q245R-N248D-H249R-E271F, T022A-S101G-S103A-V104I-G159E-S188D-A232V-N238R-Q245R-N248D, T022A-S101G-S103A-V104I-G159E-S188D-A232V-Q245R-N248D-H249R, T022A-S101G-S103A-V104I-P129E-A158E-A232V-Q245R-N248D-H249R, T022A-S101G-S103A-V104I-P129E-A158E-G159E-A232V-Q245R-N248D-H249R, T022A-S101G-S103A-V104I-P129E-A232V-N238R-Q245R-N248D, T022A-S101G-S103A-V104I-P129E-G159E-A232V-Q245R-N248D-H249R, T022A-S101G-S103A-V104I-P129E-G159E-S188D-A232V-Q245R-N248D-H249R, T022A-S103A-V104I-G118R-G159D-S188D-L217D-A232V-Q245R-N248D, T022A-S103A-V104I-G159D-S188D-A232V-N248D, T022L-L031F-G102A-S128D-T224A-N243F, T022L-T038F-V121F-S160D-A272F, V026F-S078N-G159C-R186K-N243F, V104L-A158E-H249R, V104L-A158E-R186H-H249R, V104L-A158E-R186H-H249R-E271F, V104L-A158E-R186H-S188D-H249R, V104L-A158E-R186H-S188D-H249R-E271F, V104L-A158E-S188D-H249R-E271F, V104L-S128N-A158E-R186H-S188D-E271F, V104L-S128N-G159E-E271F, V104L-S128N-R186H-S188D-H249R, and/or V121F-N185E-T224A-P239G;

c) A016S-S128N-R186H-E271F, N076D-S101G-S103A-V104I-A158E-S188D-M222S-A232V-Q245R-N248D-H249R, S024R-S101G-S103A-V104I-S128L-P129Q-A158E-N183D-S188D-A232V-Q245R-N248D-H249R, S024R-S101G-S103A-V104I-S128L-P129Q-A158E-S188D-A232V-Q245R-N248D-H249R-E271G, S024R-S101G-S103A-V104I-S128L-P129Q-S130A-A158E-N183D-S188D-A232V-Q245R-N248D-H249R, S101G-S103A-V104I-P129Q-A158E-N183D-S188D-A232V-Q245R-N248D-H249R, T022A-N076D-S101G-S103A-V104I-G159D-A232V-Q245R-N248D-H249R-E271F, T022A-S101G-G102A-S103A-V104I-G159D-S188D-A232V-Q245R-N248D-E271F, A016S-A158E-H249R, A016S-A158E-H249R-E271F, A016S-A158E-R186H-H249R, A016S-L111V-S188D-, A016S-T022A-A158E-R186H-E271F, A048R-S078N-N116L-N185E-L217E-P239G, A048R-S128D-N185E-P239G, A158E-R186H-H249R-E271F, E089P-S101A-P129E-R186H, G020K-G023A-N043W-N116L-S188D-T213A-P239G, G020K-G023A-N062E-N116L-G118R-T213A, G020K-G023A-S024F-N062E-S188D-T213A-P239G, G020K-K027R-P129E-S166D-P239G, G020K-S024F-N062E-P239G, G020K-S024F-T033S-P129E-A194E, G023A-G100S-A194E-S212M, G023A-N043W-N116L-G118R-S188D, G023A-S024F-G118R-S188D-P239G, G023A-S024F-

K027R-N062E, G023A-S024F-N043W-N062E-N116L-G118R, G023A-S024F-N116L-G118R-S188D-T213A, G023A-S024F-N116L-S188D-P239G, K027R-G100S-G118R-S160D-S188D-N243F, K027R-S101D-S188D-S105T-A272F, N043R-N076D-S101A-S103A-V104I-A158E-S166D-S188D-A232V-Q245R-N248D-H249R, N062E-S078N-N116L-T224A, N062E-V104L-A158E-R186H-S188D-H249R, N076D-S101A-S103A-V104I-A158E-S188D-L217E-A232V-Q245R-N248D-H249R-E271F, N076D-S101G-S103A-V104I-A158E-S166D-S188D-A232V-Q245R-N248D-H249R-E271F, S024F-G102A-R186K-T213A-L217E-N243F, S024F-N043W-G118R-S188D, S024F-N043W-V104L-V121F-P129E, S024F-N116L-G118R-S188D-P239G, S024F-S103N-V104L-G118R-S188D, S024R-N043R-S101A-S103A-V104I-A158E-S188D-A232V-Q245R-N248D-H249R, S024R-N043R-S101A-S103A-V104I-A158E-S188D-L217E-A232V-Q245R-N248D-H249R, S024R-N076D-S101G-S103A-V104I-A158E-S188D-A232V-Q245R-N248D-H249R-E271F, S024R-S101G-S103A-V104I-A158E-G159E-A232V-Q245R-N248D, S024R-S101G-S103A-V104I-S128N-A158E-G159E-S188D-A232V-Q245R-N248D, S024R-S101G-S103A-V104I-S128N-P129E-S188D-A232V-Q245R-N248D, S101A-L111V-P129E, S101A-S103A-V104L-G159E-A232V-Q245R-N248D-H249R, S101A-S103S-V104L-G159E-A232V-Q245R-N248D-H249R, S101A-V104L-S128N-A158E-R186H, S101G-S103A-V104I-P129E-L148I-S188D-A232V-Q245R-N248D, S101G-S103A-V104I-S128N-P129E-A158E-A232V-N238R-Q245R-N248D, S101G-S103A-V104I-S128N-P129E-S188D-A232V-Q245R-N248D-H249R, S101G-S103S-V104L-G159E-A232V-Q245R-N248D-H249R, S101S-S103A-V104L-G159E-A232V-Q245R-N248D-H249R, S128N-P129E-R186H, T022A-A158E-R186H-H249R-E271F, T022A-S024K-S101G-S103A-V104I-S128N-A158E-G159E-A232V-Q245R-N248D, T022A-S024R-S101G-S103A-V104I-S128N-P129E-A158E-S188D-A232V-Q245R-N248D-H249R, T022A-S024R-S103A-V104I-S128I-G159D-S188D-A232V-N248D, T022A-S101G-S103A-V104I-L148I-S188D-A232V-Q245R-N248D, T022A-S101G-S103A-V104I-S128N-G159E-A232V-Q245R-N248D, T022A-S101G-S103A-V104I-S128N-P129E-A158E-A232V-N238R-Q245R-N248D, T022A-S128N-A158E-R186H, T022A-S128N-R186H-S188D-, T022A-V104L-A158E-H249R, T022A-V104L-R186H-S188D-H249R, T022L-G023A-K027R-S101D-V104L-S216F, T022L-S078N-N116L-P129E-S256N, T022L-S078N-S128D-T213A, T033S-G118R-P129E-A194E-P239G, T033S-S105T-S188D-S216F, V026F-V104L-S256N-A272F, T022A-N043R-S103A-V104I-S128I-G159D-S188D-A232V-Q245R-N248D, T022A-S024R-N043R-S103A-V104I-G118R-G159D-S188D-L217D-A232V-N248D, T022A-S101D-S103A-V104I-G118R-G159D-S188D-L217D-A232V-Q245R-N248D-E271F, T022A-S103A-V104I-G118R-P129E-G159D-S188D-A232V-Q245R-N248D-E271F, T022A-S103A-V104I-G159D-S188D-L217D-A232V-Q245R-N248D-E271F, and/or T022A-S103A-V104I-S128I-P129E-G159D-S188D-A232V-N248D-E271F;

d) G118R-Y209A, G118R-Y209A-N243F, L021M-S024R-T033S, P005S-S078R-G118R-W241R, P086W-G118R-A133V, P086W-G118R-N243F, P086W-G118R-Y209A, P086W-Y209A-N243F, S024R-A174T, S024R-G118R, S024R-G118R-Y209A, S024R-G118R-Y209A-K235F, S024R-G118R-Y209A-N243F, S024R-K235F, S024R-P086R, S024R-P086S-S141G, S024R-P086W, S024R-P086W-G118R, S024R-P086W-G118R-V203I, S024R-P086W-N243F, S024R-P086W-Y209A, S024R-S078R-P086W, S024R-S078R-P086W-G118R-A270T, S024R-S078R-P086W-N243F, S024R-T033S-A133V, S024R-T033S-G118R, S024R-T033S-P086S-S085N-K235F, S024R-T033S-P086S-S087N-Y209A, S024R-T033S-P086W, S024R-T033S-P086W-G118R, S024R-T033S-S078R-P086W, S024R-T033S-S078R-P086W-G118R, S024R-T033S-S078R-Y209A, S024R-T033S-W241R, S024R-T033S-Y209A-K235F, S024R-Y209A-W241R, S078R-G118R, S078R-P086W-K235F, S078R-P086W-N243F, S078R-P086W-Y209A, S078R-Y209A-K235F, T033S-A172V-Y209A, T033S-G118R, T033S-G118R-G159D-Y209A, T033S-G118R-N243F, T033S-G118R-W241R, T033S-G118R-Y209A-N243F, T033S-K235F, T033S-P086W-G118R, T033S-P086W-G118R-Y209A-N243F, T033S-P086W-N243F, T033S-S078R-P086W, T033S-S078R-P086W-G118R-Y209A, T033S-S078R-Y209A, T033S-Y209A-N243F, Y209A-W241R, A001R-S009A-N043R, A001R-S101G-S103A-V104I-A232V-Q245R, A001T-N018R-S024R-N076D-N116A-T213A-H249R, A194F-G211Q-Q236N, E089I-N116A-N117F-T224A-H249R, G020R-G025R-N116A-Y167W, G020R-H249R-N269R, G020R-N043D-N076D-A230E-H249R, G020R-N043D-S078R-S101G-S103A-V104I-A232V-Q245R, G020R-N043D-S101G-S103A-V104I-A232V-Q245R, G020R-N043D-S101G-S103A-V104I-A232V-Q245R-N269R, G020R-N043R-A230E, G020R-N043R-A230E-S242R, G020R-N043R-E271L, G020R-N043R-H249R, G020R-N043R-H249R-E271L, G020R-N043R-N269R, G020R-N043R-R045T-A230E, G020R-N043R-R045T-S101A-N269R, G020R-N043R-R045T-S242R, G020R-N043R-S101A-N116A-T213A-A215F, G020R-N043R-S101A-N269R, G020R-N043R-S101G-S103A-V104I-A232V-Q245R, G020R-N043R-S212F, G020R-N043R-S212F-W241R, G020R-N043R-S242R, G020R-N043R-S242R-E271L, G020R-N043R-S242R-H249R, G020R-N043R-V244R, G020R-N043R-W241R, G020R-N062Q-E089I-R186K-S212M, G020R-N076D, G020R-N076D-S101G-S103A-V104I-A232V-Q245R, G020R-N076D-S101G-S103A-V104I-A232V-Q245R-N269R, G020R-N116A-N269R, G020R-P052N-N062Q-Y091F-Y192W, G020R-Q059A-S144R-Y192W-T224A, G020R-S024R-K27E-N043R-N076D-A230E, G020R-S024R-N043D-H249R, G020R-S024R-N043D-N076D-S078R-S101G-S103A-V104I-A232V-Q245R, G020R-S024R-N043D-S242R, G020R-S024R-N043R-R045T, G020R-S024R-N043R-R045T-H249R, G020R-S024R-N043R-R045T-N116A, G020R-S024R-N043R-R045T-N116A-T213A, G020R-S024R-N043R-R045T-S101A-N269R, G020R-S024R-N043R-R045T-S101A-T213A, G020R-S024R-N043R-S242R, G020R-S024R-N076D-H249R, G020R-S024R-N116A, G020R-S024R-N116A-A215F, G020R-S024R-N116A-T213A, G020R-S024R-N116A-T213A-A215F, G020R-S024R-P052N-Q059A-S216F, G020R-S024R-R045T-A230E-S242R, G020R-S024R-R045T-N116A-N269R, G020R-S024R-R045T-N269R, G020R-S024R-S101A-A215F, G020R-S024R-S101A-N116A, G020R-S024R-S101G-S103A-V104I-L217E-A232V-Q245R-H249R, G020R-S024R-S242R-H249R, G020R-S024R-T213A, G020R-S024R-T213A-A215F, G020R-S078R-S101A-S103A-V104I-N116A-N183D-T213A-A232V-Q245R, G020R-S078R-S101G-A232V-Q245R, G020R-S078R-S101G-S103A-V104I-A215F-A232V-Q245R, G020R-S078R-S101G-S103A-V104I-G211Q-T213A-A215F-A232V-Q245R, G020R-S078R-S101G-S103A-V104I-N116A-A232V-Q245R, G020R-

S078R-S101G-S103A-V104I-N116A-G211Q-A232V-Q245R, G020R-S078R-S101G-S103A-V104I-N116A-N183D-A232V-Q245R, G020R-S087D-S101G-S103A-V104I-A232V-Q245R, G020R-S101A-N116A-N269R, G020R-S101A-S103A-V104I-A215F-A232V-Q245R, G020R-S101A-S103A-V104I-G118R-A232V-Q245R, G020R-S101A-S103A-V104L-A232V-Q245R, G020R-S101A-S103A-V104V-A232V-Q245R, G020R-S101A-S103 S-V104I-A232V-Q245R, G020R-S101A-S103S-V104V-A232V-Q245R, G020R-S101G-I198L-A215F-A232V-Q245R, G020R-S101G-S103A-A232V-Q245R, G020R-S101G-S103A-V104I-A215F-A232V-Q245R, G020R-S101G-S103A-V104I-A232V-Q245R, G020R-S101G-S103A-V104I-A232V-Q245R-N269R, G020R-S101G-S103A-V104I-G211Q-T213A-A215F-A232V-Q245R, G020R-S101G-S103A-V104I-N116A-A215F-A232V-Q245R, G020R-S101G-S103A-V104I-T213A-A215F-A232V-Q245R, G020R-S101G-S103A-V104I-V150L-A232V-Q245R, G020R-S101G-S103A-V104L-A232V-Q245R, G020R-S101G-S103A-V104V-A232V-Q245R, G020R-S101G-S103G-V104I-A232V-Q245R, G020R-S101G-S103S-V104I-A232V-Q245R, G020R-S101G-S103S-V104L-A232V-Q245R, G020R-S101G-V104I-T213A-A215F-A232V-Q245R, G020R-S101S-S103A-V104I-A232V-Q245R, G020R-S101S-S103A-V104V-A232V-Q245R, G020R-S101S-S103G-V104I-A232V-Q245R, G020R-S101S-S103G-V104V-A232V-Q245R, G020R-S101S-S103S-V104I-A232V-Q245R, G020R-S101S-S103S-V104L-A232V-Q245R, G020R-S101S-S103S-V104V-A232V-Q245R, G020R-S103N-S216F-Q236N-N252R, G020R-S144R-N185I-L233C-Q236N, G020R-S212F-H249R, G020R-S242R-N269R, G020R-T022R-E271L, G020R-T022R-N043R, G020R-T022R-N043R-S212F, G020R-T022R-N043R-W241R, G020R-T022R-S024R-S242R, G020R-T022R-S078R-S242R, G020R-T022R-S078R-W241R, G020R-T022R-S212F-W241R, G020R-T022R-S242R, G020R-T022R-W241R, G020R-T022W-S078R-S101A-S103A-V104I-N116A-N183D-A215F-A232V-Q245R, G020R-T022W-S078R-S101A-S103A-V104I-N116A-N183D-A232V-Q245R, G020R-T022W-S078R-S101A-S103A-V104I-N116A-N183D-T213A-A232V-Q245R, G020R-T022W-S078R-S101A-S103A-V104I-N116S-T213A-A215F-A232V-Q245R, G020R-T022W-S078R-S101G-S103A-V104I-N116A-A232V-Q245R, G020R-T022W-S078R-S101G-S103A-V104I-N116A-N183D-A232V-Q245R, G020R-T022W-S078R-S101G-S103A-V104I-N116A-N183D-G211Q-A232V-Q245R, G020R-T022W-S078R-S101G-S103A-V104I-N116A-N183D-T213A-A232V-Q245R, G020R-T022W-S078R-S101G-S103A-V104I-N116A-T213A-A215F-A232V-Q245R, G020R-T022W-S101A-S103A-V104I-G211Q-A215F-A232V-Q245R, G020R-T022W-S101G-S103A-V104I-A232V-Q245R, G020R-T022W-S101G-S103A-V104I-G211Q-A232V-Q245R, G020R-T022W-S101G-S103A-V104I-I198L-G211Q-T213A-A232V-Q245R, G020R-T022W-S101G-S103A-V104I-N116A-N183D-T213A-A232V-Q245R, G020R-T038A-N043R-S101A, G020R-T22W-S078R-S101A-S103A-V104I-N116A-N183D-A232V, G020R-T22W-S078R-S101G-S103A-V104I-N116A-N183D-A232V-Q245R, G020R-T22W-S078R-S101G-S103A-V104I-N116A-T213A-A215F-A232V-Q245R, G020R-T22W-S101A-S103A-V104I-A215F-A232V-Q245R, G020R-T22W-S101A-S103A-V104I-A232V-Q245R, G020R-T22W-S101A-S103A-V104I-G211Q-T213A-A232V-Q245R, G020R-T22W-S101G-S103A-V104I-A232V-Q245R, G020R-T22W-S101G-S103A-V104I-G211Q-A232V-Q245R, G020R-T22W-S103A-V104I-A232V-Q245R, G023A-P052N-S144R-Y192W-S216F, G023A-P052N-Y192W-I198L-N252R, G023A-S024R-N117F-S212M-S216F, G023A-S078R-S216F-Q236N-H249R, G023A-Y091F-S101A-I198L-N252R, G023A-Y091F-V121F-Y192W-Q236N, G025R-E089I-N116A-P239S-A270C, G025R-G046R-V121F, G025R-N043A-E089I-N117F, G025R-S103N-R186K-A194F-T224A, G046R-A194F-S212M, G046R-E089I-Y091F-S101A-N116A, G046R-E089I-Y192W-L233C-A270C, G046R-N183D-N238L, G046R-Q059A-S103N-G211Q-S212M, G046R-Q059A-S106G-L217E-H249R, L148I-T213A-N252R, N018R-G020R-N043D, N018R-G020R-N043D-A230E-S242R, N018R-G020R-N043D-N076D-S101G-S103A-V104I-A232V-Q245R, N018R-G020R-N043D-R045T-A230E, N018R-G020R-N043R-N076D-H249R, N018R-G020R-N043R-N076D-S242R-H249R, N018R-G020R-N043R-R045T-S242R, N018R-G020R-N076D-S101G-S103A-V104I-A232V-Q245R, N018R-G020R-R045T, N018R-G020R-S024R-N043D-R045T-L233I-S242R, N018R-G020R-S024R-N043R-R045T-N076D-A230E, N018R-G020R-S024R-N076D-S087D-H249R, N018R-G020R-S024R-N076D-V150L-H249R, N018R-G020R-S024R-R045T-N076D-S101G-S103A-V104I-A232V-Q245R-N269R, N018R-N043D-N076D-S101G-S103A-V104I-A232V-Q245R-N269R, N018R-N043D-S078R-S101G-S103A-V104I-A232V-Q245R, N018R-N043D-S078R-S101G-S103A-V104I-L217E-A232V-Q245R, N018R-N043D-S101G-S103A-V104I-A232V-Q245R, N018R-N043D-S101G-S103A-V104I-A232V-Q245R-H249R, N018R-N043D-S101G-S103A-V104I-A232V-Q245R-N269R, N018R-N043R-N076D-A230E, N018R-N043R-R045T-H249R, N018R-N043R-R045T-S101G-S103A-V104I-A232V-Q245R, N018R-N043R-R045T-S242R-H249R, N018R-N043R-S101G-S103A-V104I-A232V-Q245R, N018R-N043R-S101G-S103A-V104I-A232V-Q245R-N269R, N018R-N043R-S242R-H249R, N018R-N076D-S078R-S101G-S103A-V104I-A232V-Q245R, N018R-N076D-S101G-V104I-A232V-Q245R, N018R-Q245R, N018R-R045T-N076D-S078R-S101G-S103A-V104I-A232V-Q245R, N018R-R045T-N076D-S101G-S103A-V104I-A232V-Q245R-N269R, N018R-R045T-S078R-S101G-S103A-V104I-A232V-Q245R, N018R-R045T-S101G-S103A-V104I-A232V-Q245R, N018R-S024R-N043D-A230E, N018R-S024R-N043D-N076D-H249R, N018R-S024R-N043D-N076D-H249R-N269R, N018R-S024R-N043D-N076D-S078R-H249R, N018R-S024R-N043D-R045T-H249R, N018R-S024R-N043D-S101G-S103A-V104I-A232V-Q245R, N018R-S024R-N043D-S101G-S103A-V104I-A232V-Q245R-N269R, N018R-S024R-N043R-N076D-H249R, N018R-S024R-N043R-N076D-H249R-N269R, N018R-S024R-N043R-N076D-S087D-H249R, N018R-S024R-N043R-N076D-V150L-H249R, N018R-S024R-N076D-G211Q-A215F-H249R, N018R-S024R-N076D-G211Q-T213A-A215F-H249R, N018R-S024R-N076D-G211Q-T213A-H249R, N018R-S024R-N076D-H249R, N018R-S024R-N076D-H249R-N269R, N018R-S024R-N076D-N116A-A215F-H249R, N018R-S024R-N076D-N116A-G211Q-A215F-H249R, N018R-S024R-N076D-N116A-G211Q-H249R, N018R-S024R-N076D-N116A-T213A-A215F-H249R, N018R-S024R-N076D-S078R-H249R, N018R-S024R-N076D-S078R-S087D-H249R, N018R-S024R-N076D-S078R-V150L-H249R, N018R-S024R-N076D-S087D-H249R-N269R, N018R-S024R-N076D-S087D-S242R-H249R, N018R-S024R-N076D-S087D-V150L-H249R, N018R-S024R-N076D-S101A-A215F-

H249R, N018R-S024R-N076D-S101A-G211Q-T213A-A215F-H249R, N018R-S024R-N076D-S101A-I198L-G211Q-A215V-H249R, N018R-S024R-N076D-S101A-I198L-G211Q-T213A-H249R, N018R-S024R-N076D-S101A-N116A-G211Q-H249R, N018R-S024R-N076D-S101A-N116A-T213A-H249R, N018R-S024R-N076D-S101G-V104I-A232V-H249R, N018R-S024R-N076D-S242R-H249R, N018R-S024R-N076D-T213A-A215F-H249R, N018R-S024R-N076D-V104I-H249R, N018R-S024R-N076D-V150L-H249R, N018R-S024R-R045T-S242R, N018R-S024R-S101G-V104I, N018R-S024R-S101G-V104I-A232V, N018R-S024R-S242R, N018R-S024R-V104I-H249R, N018R-S024R-V244R, N018R-S078R-S101G-S103A-V104I-A232V-Q245R, N018R-S087D-S101G-S103A-V104I-A232V-Q245R, N018R-S101G-Q245R, N018R-S101G-S103A-H249R, N018R-S101G-S103A-Q245R, N018R-S101G-S103A-V104I-A232V-Q245R, N018R-S101G-S103A-V104I-V150L-A232V-Q245R, N018R-S101G-V104I-A232V-H249R, N018R-S101G-V104I-A232V-Q245R, N018R-S101G-V104I-H249R, N018R-S103A-A232V-H249R, N018R-S103A-V104I-H249R, N018R-T022R-S024R-N043D-N076D-H249R, N018R-T022R-S024R-N043R-N076D-H249R, N018R-T022R-S024R-N076D-H249R, N018R-T022R-S024R-N076D-S087D-H249R, N018R-T022R-S024R-N076D-V150L-H249R, N018R-T022W-S024R-N076D-N116A-G211Q-H249R, N018R-T022W-S024R-N076D-N116A-T213A-H249R, N018R-T022W-S024R-N076D-S101A-I198L-A215F-H249R, N018R-T022W-S024R-N076D-S101A-I198L-H249R, N018R-T022W-S024R-N076D-S101A-N116A-A232V-Q245R, N018R-T22K-N043D-S101G-S103A-V104I-A232V-Q245R, N018R-T22W-S024R-N076D-N116A-T213A-H249R, N018R-T22W-S024R-N076D-S101A-N116A-A232V-Q245R, N018R-V104I-A232V-H249R, N043A-N062Q-A194F-G211Q, N043A-T057R-N117F-S144R-N183D, N043D-N076D-S078R-S101G-S103A-V104I-A232V-Q245R-N269R, N043D-R045T-N076D-H249R, N043D-S078R-S101G-S103A-V104I-A232V-Q245R, N043D-S078R-S101G-S103A-V104I-A232V-Q245R-H249R, N043D-S101G-S103A-V104I-A232V-Q245R-N269R, N043R-N076D-S078R-S101G-S103A-V104I-A232V-Q245R, N043R-N076D-S101G-S103A-V104I-A232V-Q245R, N043R-N076D-S101G-S103A-V104I-A232V-Q245R-N269R, N043R-N076D-S242R-H249R, N043R-N116A-N269R, N043R-R045T-N076D-S078R-S101G-S103A-V104I-A232V-Q245R, N043R-R045T-S078R-S101G-S103A-V104I-A232V-Q245R, N043R-R045T-S101G-S103A-V104I-A232V-Q245R-N269R, N043R-S078R-S101G-S103A-V104I-A232V-Q245R, N043R-S087D-S101G-S103A-V104I-A232V-Q245R-N269R, N043R-S101A-N116A-A215F-N269R, N043R-S101A-N116A-N269R, N043R-S101A-N116A-T213A-A215F-N269R, N043R-S101A-N269R, N043R-S101A-T213A-N269R, N043R-S101G-S103A-V104I-A232V-Q245R, N043R-S101G-S103A-V104I-A232V-Q245R-E271L, N043R-S101G-S103A-V104I-A232V-Q245R-H249R, N043R-S101G-S103A-V104I-A232V-Q245R-N269R, N043R-S101G-S103A-V104I-A232V-S242R-Q245R, N043R-S101G-S103A-V104I-V150L-A232V-Q245R, N043R-S242R-H249R, N043R-T213A-A215F-N269R, N062Q-S103N-N117F-A194F, N062Q-S103N-V121F-S144R-H249R, N076D-S078R-S101G-S103A-V104I-A232V-Q245R, N076D-S078R-S101G-S103A-V104I-A232V-Q245R-N269R, N076D-S101G-S103A-V104I-A232V-Q245R, N076D-S101G-S103A-V104I-A232V-Q245R-N269R, N076D-S103A-V104I-Q109R, N076D-S103A-V104I-Q109R-Q245R, N076D-S103A-V104I-S212P-E271V, N076D-S103A-V104I-S212P-Q245L-E271V, N076D-S87R-S103A-V104I-S212P-E271V, N117F-A194F-T213A-A270C, N117F-T213A-A215F, P052N-S078R-S103N-L148I-T213A, P052N-S103N-N116A-L148I-Y192W, R019H-G020R-T022W-S078R-S101G-S103A-V104I-G211Q-A232V-Q245R, R045T-N076D-S078R-S101G-S103A-V104I-A232V-Q245R-N269R, R045T-S078R-S101G-S103A-V104I-A232V-Q245R, R045T-S078R-S101G-S103A-V104I-A232V-Q245R-N269R, S009A-G020R-N043R-S212F, S009A-G020R-N043R-W241R, S009A-G020R-S024R-N043R, S009A-N043R-S078R, S009A-N043R-S078R-S242R, S009A-N043R-S212F, S009A-N043R-W241R, S009A-T022R-N043R-S078R, S009A-T022R-S078R-S212F, S009A-T022R-S078R-S212F-W241R, S009A-T022R-S212F-W241R, S024R-A215F-N269R, S024R-A232V-Q245R, S024R-G025R-N183D-Y192W-P239S, S024R-N043A-N117F-A194F-G211Q, S024R-N043D-H249R, S024R-N043D-S101G-S103A-V104I-A232V-Q245R-H249R, S024R-N043D-S101G-S103A-V104I-A232V-Q245R-N269R, S024R-N043R-A215F, S024R-N043R-A230E, S024R-N043R-A230E-S242R, S024R-N043R-N076D-H249R, S024R-N043R-N076D-S078R-S101G-S103A-V104I-A232V-Q245R, S024R-N043R-N076D-S101G-S103A-V104I-A232V-Q245R, S024R-N043R-N116A-A215F, S024R-N043R-N116A-A215F-N269R, S024R-N043R-N116A-N269R, S024R-N043R-N116A-T213A-N269R, S024R-N043R-R045T-N076D-A230E-H249R, S024R-N043R-R045T-N269R, S024R-N043R-R045T-S101A-N116A-A215F-N269R, S024R-N043R-R045T-S101A-N116A-T213A-N269R, S024R-N043R-R045T-S242R, S024R-N043R-R045T-T213A-A215F-N269R, S024R-N043R-S101A-A215F, S024R-N043R-S101A-A215F-N269R, S024R-N043R-S101A-N116A, S024R-N043R-S101A-N116A-A215F-N269R, S024R-N043R-S101G-S103A-V104I-A232V-Q245R, S024R-N043R-S242R, S024R-N062Q-V104L-S106G-H249R, S024R-N076D-S078R-S101G-S103A-V104I-A232V-Q245R-N269R, S024R-N076D-V104I-A232V-Q245R, S024R-N116A-T213A-N269R, S024R-R045T, S024R-R045T-N076D-A230E-S242R-H249R, S024R-R045T-N076D-S078R-S101G-S103A-V104I-A232V-Q245R-N269R, S024R-R045T-S101G-S103A-V104I-A232V-Q245R-N269R, S024R-S078R-S212F, S024R-S078R-V104L-N116A-N183D, S024R-S087D-S101G-S103A-V104I-A232V-Q245R, S024R-S101A-H120E-A194F-H249R, S024R-S101A-N269R, S024R-S101G-S103A-V104I-A232V-Q245R, S024R-S101G-S103A-V104I-V150L-A232V-Q245R, S024R-S101G-V104I-Q245R, S024R-S103A-Q245R, S024R-S103A-V104I-A232V-H249R, S024R-S103A-V104I-H249R, S024R-S103A-V104I-Q245R, S024R-Y167W-T224A-H249R, S078R-S087D-S101G-S103A-V104I-A232V-Q245R, S078R-S101G-S103A-V104I-A232V-Q245R, S078R-S101G-S103A-V104I-A232V-Q245R-N269R, S078R-S101G-S103A-V104I-V150L-A232V-Q245R, S078R-S103N-S106G-Y167W-Q236N, S078R-V104L-T213A-A215F-T224A, S078R-Y091F-V121F-L233C-N252R, S087D-S101G-S103A-V104I-A232V-Q245R-N269R, S087R-S101G-S103A-V104I-Q109R-S212P-A232V-Q245R-E271V, S099F-S144R-Y167W-N252R, S101A-H120E-Y192W-A215F-T224A, S101A-S103A-V104I-T213A-A232V-Q245R-N269R, S101G-S103A-V104I-A232V-Q245R, S101G-S103A-V104I-A232V-Q245R-E271L, S101G-S103A-V104I-A232V-Q245R-H249R, S101G-S103A-V104I-A232V-Q245R-

N269R, S101G-S103A-V104I-A232V-Q245R-N269R, S101G-S103A-V104I-A232V-S242R-Q245R, S101G-S103A-V104I-A232V-V244R-Q245R, S101G-S103A-V104I-G115R-A232V-Q245R, S101G-S103A-V104I-N116A-T213A-A232V-Q245R-N269R, S101G-S103A-V104I-Q109R-A232V-Q245R, S101G-S103A-V104I-Q109R-S212P-A232V-Q245R, S101G-S103A-V104I-Q109R-S212P-A232V-Q245R-E271V, S101G-S103A-V104I-S212F-A232V-Q245R, S101G-S103A-V104I-V150L-A232V-Q245R-H249R, S101G-S103A-V104I-V150L-A232V-Q245R-N269R, S105T-S128N-S144R-L148I-S212M, S106G-N117F-N238L, S144R-G211Q-N238L-P239S-H249R, T022R-N043R-S101G-S103A-V104I-A232V-Q245R, T022R-N076D-S101G-S103A-V104I-A232V-Q245R, T022R-S087D-S101G-S103A-V104I-A232V-Q245R, T022R-S101G-S103A-V104I-A232V-Q245R, T022W-S078R-Y167W-S212M-A270C, T057R-E089I-I198L, T057R-S099F-S105T-I198L-T213A, T057R-S099F-V121F-N185I-Y192W, T057R-Y167W-H249R, V004R-G020R-H249R, V004R-G020R-N043R, V004R-G020R-S024R, V004R-G020R-S024R-H249R, V004R-G020R-S024R-N043R, V004R-G020R-S024R-N043R-S242R, V004R-G020R-S024R-V244R, V004R-N043R-S101G-S103A-V104I-A232V-Q245R, V004R-S009A-G020R-N043R, V004R-S009A-G020R-N043R-S242R, V004R-S009A-G020R-S024R-S242R, V004R-S009A-G020R-S242R, V004R-S009A-N043R-W241R, V004R-S009A-S024R-N043R-W241R, V004R-S009A-S078R-W241R, V004R-S009A-W241R, V004R-S101G-S103A-V104I-A232V-Q245R, V104L-L217E-T224A-H249R-N252R, V104L-T213A-S216F, V121F-N252R-A270C, and/or Y091F-S099F-S101A-S105T-Y167W;

e) S101G-S103A-V104I-A232V-Q236H-Q245R-N252K, S101G-S103A-V104I-A232V-Q245R-N248R, S101G-S103A-V104I-G159R-A232V-Q245R-N248D, A232V-Q245R, E089I-N117F-N185I-A215F-L233C, G020R-E089I-L217E, G020R-G023A-V104L-Y192W-L233C, G020R-N043D-R045T-N076D-S242R-H249R, G020R-N043D-R045T-S078R-S101G-S103A-V104I-A232V-Q245R, G020R-N043D-S101G-S103A-V104I-A232V-Q245R-H249R, G020R-N043R-N076D-A230E-H249R, G020R-N043R-N076D-S101G-S103A-V104I-A232V-Q245R-N269R, G020R-N116A-A215F-N269R, G020R-R045T-N076D-S101G-S103A-V104I-A232V-Q245R, G020R-R045T-N076D-S101G-S103A-V104I-A232V-Q245R-H249R, G020R-R045T-N116A-N269R, G020R-R045T-S101G-S103A-V104I-A232V-Q245R, G020R-S024R-A215F, G020R-S024R-K27R-N043D-S242R-H249R, G020R-S024R-N043D-N076D-S078R-S101G-S103A-V104I-A232V-Q245R-N269R, G020R-S024R-N043R-N076D, G020R-S024R-N043R-R045T-A215F, G020R-S024R-N043R-R045T-N076D-S242R-H249R, G020R-S024R-N043R-R045T-N116A-T213A-A215F, G020R-S024R-N076D-S101G-S103A-V104I-A232V-Q245R, G020R-S024R-T381-N043R-R045T-N076D-S242R-H249R, G020R-S078R-S101A-S103A-V104I-A232V-Q245R, G020R-S078R-S101A-S103A-V104I-G211Q-T213A-A232V-Q245R, G020R-S078R-S101A-S103A-V104I-N116A-N183D-A232V-Q245R, G020R-S078R-S101A-S103A-V104I-N116A-N183D-G211Q-A232V-Q245R, G020R-S078R-S101A-S103A-V104I-N116A-N183D-G211Q-T213A-A215F-A232V-Q245R, G020R-S078R-S101A-S103A-V104I-N116A-N183D-G211Q-T213A-A232V-Q245R, G020R-S078R-S101A-S103A-V104I-N116A-N183D-I198L-A215F-A232V-Q245R, G020R-S078R-S101A-S103A-V104I-N183D-A215F-A232V-Q245R, G020R-S078R-S101G-S103A-V104I-N116A-A131V-N183D-T213A-A232V-Q245R, G020R-S078R-S101G-S103A-V104I-N116A-N183D-G211Q-T213A-A215F-A232V, G020R-S078R-S101G-S103A-V104I-N116A-N183D-G211Q-T213A-A215F-A232V-Q245R, G020R-S078R-S101G-S103A-V104I-N116A-N183D-T213A-A232V-Q245R, G020R-S078R-S101G-S103A-V104I-N183D-G211Q-T213A-A232V-Q245R-E271G, G020R-S078R-S101G-S103A-V104I-T180A-A232V-Q245R, G020R-S101A-S103A-V104I-N116A-N183D-G211Q-T213A-A215F-A232V-Q245R, G020R-S101A-S103A-V104I-N116A-N183D-T213A-A232V-Q245R, G020R-S101A-S103A-V104I-T213A-A215F-A232V-Q245R, G020R-S101A-S103G-V104V-A232V-Q245R, G020R-S101G-S103A-V104I-N116A-A232V-Q245R, G020R-S101G-S103A-V104I-N116A-G211Q-A232V-Q245R, G020R-S101G-S103A-V104I-N183D-G211Q-A232V-Q245R-, G020R-S103A-V104I-A232V-Q245R, G020R-S242R-H249R, G020R-T022W-S078R-S101A-S103A-V104I-A232V-Q245R, G020R-T022W-S078R-S101A-S103A-V104I-I198L-A232V-Q245R, G020R-T022W-S078R-S101A-S103A-V104I-N116A-N183D-G211Q-T213A-A215F-A232V-Q245R, G020R-T022W-S078R-S101A-S103A-V104I-N116A-N183D-T213A-A215F-A232V-Q245R, G020R-T022W-S078R-S101A-S103A-V104I-N183D-I198L-T213A-A215F-A232V-Q245R, G020R-T022W-S078R-S101G-S103A-V104I-G211Q-T213A-A232V-Q245R, G020R-T022W-S078R-S101G-S103A-V104I-N116A-N183D-A215F-A232V-Q245R, G020R-T022W-S101A-N116A-I198L-G211Q-T213A-A215F-H249R, G020R-T022W-S101A-S103A-V104I-A215F-A232V-Q245R, G020R-T022W-S101A-S103A-V104I-A232V-Q245R, G020R-T022W-S101A-S103A-V104I-G211Q-A232V-Q245R, G020R-T022W-S101A-S103A-V104I-G211Q-T213A-A232V-Q245R, G020R-T022W-S101A-S103A-V104I-I198L-G211Q-A215F-A232V-Q245R, G020R-T022W-S101A-S103A-V104I-N116A-G211Q-A215F-A232V-Q245R, G020R-T022W-S101A-S103A-V104I-N116A-G211Q-A232V-Q245R, G020R-T022W-S101A-S103A-V104I-N116A-G211Q-T213A-A215F-A232V-Q245R, G020R-T022W-S101A-S103A-V104I-N116A-N183D-A232V-Q245R, G020R-T022W-S101A-S103A-V104I-N116A-N183D-G211Q-A232V-Q245R, G020R-T022W-S101A-S103A-V104I-N116A-N183D-G211Q-T213A-A232V-Q245R, G020R-T022W-S101G-S103A-V104I-A114T-T213A-A215F-A232V-Q245R, G020R-T022W-S101G-S103A-V104I-G211Q-T213A-A215F-A232V-Q245R, G020R-T022W-S101G-S103A-V104I-N116A-N183D-A215F-A232V-Q245R, G020R-T022W-S101G-S103A-V104I-N116A-N183D-G211Q-A215F-A232V-Q245R, G020R-T022W-S101G-S103A-V104I-N116A-N183D-I198L-A232V-Q245R, G020R-T022W-S101G-S103A-V104I-N116A-N183D-T213A-A215F-A232V-Q245R, G020R-T022W-S101G-S103A-V104I-N183D-I198L-T213A-A215F-A232V-Q245R, G020R-T022W-S103A-G211Q-T213A-A215F-A232V-Q245R, G020R-T022W-S103A-V104I-A232V-Q245R, G020R-T22W-S078R-S101A-S103A-V104I-N116A-N183D-A215F-A232V-Q245R, G020R-T22W-S078R-S101A-S103A-V104I-N116A-N183D-T213A-A232V-Q245R, G020R-T22W-S101A-S103A-V104I-G211Q-A215F-A232V-Q245R, G020R-T22W-S101A-S103A-V104I-N116A-G211Q-A215F-A232V-Q245R, G020R-T22W-S101A-S103A-V104I-N116A-G211Q-T213A-A215F-A232V-Q245R, G020R-T22W-S101G-S103A-V104I-N116A-N183D-A215F-A232V-Q245R, G020R-T22W-S101G-S103A-V104I-N116A-N183D-T213A-A215F-A232V-

Q245R, G025R-N043A-Y091F-I198L-A270C, G025R-S105T-S128N-S144R-A270C, G046R-E089I-S099F-R186K-S212M, G118R-A172V, G118R-A194T, G118R-Y209A-K235F, H017Y-S024R-T033S-P086W, I008T-S024R, K027R-N043R-S101G-S103A-V104I-A232V-Q245R-N269R, K027R-R045T-N076D-S078R-S101G-S103A-V104I-A232V-Q245R-N269R, K235F-N243F, N018R-G020R-H249R, N018R-G020R-N043D-H249R, N018R-G020R-N043D-R045T-A230E-S242R, N018R-G020R-N043D-R045T-N076D-S242R, N018R-G020R-N043D-R045T-S240P, N018R-G020R-N043D-S078R-S101G-S103A-V104I-A232V-Q245R, N018R-G020R-N043D-S101G-S103A-V104I-A232V-Q245R, N018R-G020R-N043R, N018R-G020R-N043R-N076D, N018R-G020R-N043R-N076D-A230E-S242R, N018R-G020R-N043R-R045T-N076D-H249R, N018R-G020R-N043R-R045T-N076D-S101G-S103A-V104I-A232V-Q245R, N018R-G020R-N076D-S101G-S103A-V104I-A232V-Q245R-H249R, N018R-G020R-R045T-S101G-S103A-V104I-A232V-Q245R, N018R-G020R-S024R-N043D-N076D-S242R, N018R-G020R-S024R-N043D-R045T-S242R, N018R-G020R-S024R-N043R-N076D-H249R, N018R-G020R-S024R-N043R-R045T-N076D-H249R, N018R-G020R-S024R-N076D-A215F-H249R, N018R-G020R-S024R-N076D-G211Q-A215F-H249R, N018R-G020R-S024R-N076D-L217E-H249R, N018R-G020R-S024R-N076D-N116A-A215F-H249R, N018R-G020R-S024R-N076D-N116A-N183D-A215F-H249R, N018R-G020R-S024R-N076D-N116A-N183D-I198L-G211Q-H249R, N018R-G020R-S024R-N076D-N116A-N183D-T213A-A215F-H249R, N018R-G020R-S024R-N076D-N183D-H249R, N018R-G020R-S024R-N076D-S101A-N116A-N183D-I198L-H249R, N018R-G020R-S024R-N076D-S101A-N183D-G211Q-A215F-H249R, N018R-G020R-S101G-S103A-V104I-A232V-Q245R-H249R, N018R-G020R-T022W-S024R-N076D-N116A-N183D-I198L-T213A-H249R, N018R-G020R-T022W-S024R-N076D-S101A-N116A-N183D-H249R, N018R-G020R-T22W-S024R-N076D-N116A-N183D-I198L-T213A-H249R, N018R-N043D-N076D-S078R-S101G-S103A-V104I-A232V-Q245R, N018R-N043D-N076D-S078R-S101G-S103A-V104I-A232V-Q245R-N269R, N018R-N043D-N076D-S101G-S103A-V104I-A232V-Q245R-H249R, N018R-N043D-R045T-N076D-S242R-H249R, N018R-N043D-R045T-S078R-S101G-S103A-V104I-A232V-Q245R, N018R-N043D-R045T-S101G-S103A-V104I-A232V-Q245R, N018R-N043D-R045T-S101G-S103A-V104I-A232V-Q245R-N269R, N018R-N043D-S078R-S101G-S103A-V104I-A232V-Q245R-H249R, N018R-N043R-N076D-A230E-S242R-H249R, N018R-N043R-N076D-S101G-S103A-V104I-A232V-Q245R-N269R, N018R-N043R-N076D-S242R-H249R, N018R-N043R-R045T-N076D-A230E-S242R, N018R-N043R-R045T-N076D-S076T-S101G-S103A-V104I-A232V-Q245R-A273T, N018R-N043R-R045T-N076D-S101G-S103A-V104I-A232V-Q245R, N018R-N043R-R045T-N076D-S101G-S103A-V104I-A232V-Q245R-N269R, N018R-N043R-R045T-N076D-S242R, N018R-N043R-R045T-S242R, N018R-N076D-H249R, N018R-N076D-Q245R, N018R-N076D-S101G-A232V-Q245R, N018R-N076D-S101G-S103A-V104I-A232V-Q245R, N018R-N076D-S101G-S103A-V104I-A232V-Q245R-H249R, N018R-N076D-S101G-S103A-V104I-H249R, N018R-N076D-S101G-V104I-H249R, N018R-N076D-S103A-V104I-H249R, N018R-R045T-N076D-S101G-S103A-V104I-A232V-Q245R, N018R-S024R-N043D-A230E-H249R, N018R-S024R-N043D-A230E-S242R, N018R-S024R-N043D-H249R, N018R-S024R-N043D-N076D-S101G-S103A-V104I-A232V-Q245R, N018R-S024R-N043D-N076D-S242R-H249R, N018R-S024R-N043D-N076D-V150L-H249R, N018R-S024R-N043D-S242R, N018R-S024R-N043D-S242R-H249R, N018R-S024R-N043R-N076D-L217E-H249R, N018R-S024R-N043R-N076D-S078R-H249R, N018R-S024R-N043R-R045T-A230E-H249R, N018R-S024R-N076D, N018R-S024R-N076D-A232V-H249R, N018R-S024R-N076D-G211Q-H249R, N018R-S024R-N076D-I198L-G211Q-A215F-H249R, N018R-S024R-N076D-I198L-G211Q-T213A-H249R, N018R-S024R-N076D-I198L-T213A-A215F-H249R, N018R-S024R-N076D-I198M-G211Q-T213A-A215F-H249R, N018R-S024R-N076D-L088I-S101A-N116A-I198L-G211Q-A215F-H249R, N018R-S024R-N076D-N116A-G211Q-T213A-A215F-H249R, N018R-S024R-N076D-N116A-H249R, N018R-S024R-N076D-N116A-I198L-A215F-H249R, N018R-S024R-N076D-N116A-I198L-A215F-H249R-V268G, N018R-S024R-N076D-N116A-I198L-G211Q-T213A-A215F-H249R, N018R-S024R-N076D-N116A-I198L-G211Q-T213A-H249R, N018R-S024R-N076D-N116A-I198L-H249R, N018R-S024R-N076D-N116A-I198L-T213A-H249R, N018R-S024R-N076D-N116A-I198L-Y209H-T213A-H249R, N018R-S024R-N076D-N116A-M117I-N183D-T213A-H249R, N018R-S024R-N076D-N116A-N183D-G211Q-H249R, N018R-S024R-N076D-N116A-T213A-H249R, N018R-S024R-N076D-N183D-I198L-G211Q-T213A-A215F-H249R, N018R-S024R-N076D-N183D-T213A-A215F-H249R, N018R-S024R-N076D-S101A-G211Q-A215F-H249R, N018R-S024R-N076D-S101A-G211Q-H249R, N018R-S024R-N076D-S101A-H249R, N018R-S024R-N076D-S101A-I198L-A215F-H249R, N018R-S024R-N076D-S101A-I198L-G211Q-H249R, N018R-S024R-N076D-S101A-I198L-H249R, N018R-S024R-N076D-S101A-I198L-T213A-H249R, N018R-S024R-N076D-S101A-N116A-G211Q-T213A-H249R, N018R-S024R-N076D-S101A-N116A-I198L-G211Q-H249R, N018R-S024R-N076D-S101A-N116A-I198L-G211Q-T213A-H249R, N018R-S024R-N076D-S101A-N116A-I198L-T213A-A215F-H249R, N018R-S024R-N076D-S101A-N116A-N183D-I198L-T213A-H249R, N018R-S024R-N076D-S101A-N116A-T213A-A215F-H249R, N018R-S024R-N076D-S101A-N183D-G211Q-H249R, N018R-S024R-N076D-S101A-N183D-T213A-H249R, N018R-S024R-N076D-S101G-A232V, N018R-S024R-N076D-S103A-A232V-Q245R, N018R-S024R-N076D-T213A-H249R, N018R-S024R-N076D-V104I, N018R-S024R-Q245R, N018R-S024R-R045T-A230E-S242R, N018R-S024R-R045T-N076D-S101G-S103A-V104I-A232V-Q245R-H249R, N018R-S024R-R045T-N076D-S101G-S103A-V104I-A232V-Q245R-N269R, N018R-S024R-S242R, N018R-S024R-V104I, N018R-S024R-V30S-L31S-D321-T33Q-G34V-135F, N018R-S078R-S101G-S103A-V104I-L217E-A232V-Q245R, N018R-S101G-S103A-V104I, N018R-S101G-S103A-V104I-A232V-Q245R-N269R, N018R-S101G-V104I, N018R-S103A, N018R-S103A-V104I-A232V, N018R-T022K-N043D-S101G-S103A-V104I-A232V-Q245R, N018R-T022W-S024R-N076D-G211Q-H249R, N018R-T022W-S024R-N076D-G211Q-T213A-H249R, N018R-T022W-S024R-N076D-I198L-A215F-H249R, N018R-T022W-S024R-N076D-I198L-G211Q-H249R, N018R-T022W-S024R-N076D-I198L-T213A-A215F-H249R, N018R-T022W-S024R-N076D-N116A-G211Q-A215F-H249R, N018R-T022W-S024R-N076D-N116A-G211Q-T213A-H249R, N018R-T022W-S024R-N076D-N116A-

I198L-G211Q-T213A-H249R, N018R-T022W-S024R-N076D-N116A-I198L-T213A-H249R, N018R-T022W-S024R-N076D-N116A-T213A-A215F-H249R, N018R-T022W-S024R-N076D-S101A-A215F-H249R, N018R-T022W-S024R-N076D-S101A-G211Q-H249R, N018R-T022W-S024R-N076D-S101A-G211Q-T213A-H249R, N018R-T022W-S024R-N076D-S101A-I198L-G211Q-Q245R, N018R-T022W-S024R-N076D-S101A-I198L-G211Q-T213A-A215F-H249R, N018R-T022W-S024R-N076D-S101A-I198L-T213A-A215F-H249R, N018R-T022W-S024R-N076D-S101A-N116A-A215F-H249R, N018R-T022W-S024R-N076D-S101A-N116A-G211Q-H249R, N018R-T022W-S024R-N076D-S101A-N116A-G211Q-T213A-H249R, N018R-T022W-S024R-N076D-S101A-N116A-I198L-A215F-H249R, N018R-T022W-S024R-N076D-S101A-N116A-I198L-G211Q-H249R, N018R-T022W-S024R-N076D-S101A-N116A-I198L-G211Q-T213A-A215F-H249R, N018R-T022W-S024R-N076D-S101A-N116A-I198L-G211Q-T213A-H249R, N018R-T022W-S024R-N076D-S101A-N116A-I198L-H249R, N018R-T022W-S024R-N076D-S101A-N116A-I198L-T213A-A215F-H249R, N018R-T022W-S024R-N076D-S101A-N116A-I198L-T213A-H249R, N018R-T022W-S024R-N076D-S101A-T213A-A215F-H249R, N018R-T022W-S024R-N076D-S101A-T213A-H249R, N018R-T022W-S024R-N076D-T213A-A215F-H249R, N018R-T22W-S024R-N076D-I198L-A215F-H249R, N018R-T22W-S024R-N076D-N116A-G211Q-H249R, N018R-T22W-S024R-N076D-N116A-G211Q-T213A-H249R, N018R-T22W-S024R-N076D-N116A-T213A-A215F-H249R, N018R-T22W-S024R-N076D-S101A-A215F-H249R, N018R-T22W-S024R-N076D-S101A-G211Q-T213A-H249R, N018R-T22W-S024R-N076D-S101A-I198L-A215F-H249R, N018R-T22W-S024R-N076D-S101A-I198L-T213A-A215F-H249R, N018R-T22W-S024R-N076D-S101A-N116A-A215F-H249R, N018R-T22W-S024R-N076D-S101A-N116A-I198L-A215F-H249R, N018R-T22W-S024R-N076D-T213A-A215F-H249R, N018R-V104I, N043D-N076D-S078R-S101G-S103A-V104I-A232V-Q245R, N043D-N076D-S101G-S103A-V104I-A232V-Q245R-N269R, N043D-S078R-S101G-S103A-V104I-A232V-Q245R-N269R-A272V, N043D-S078R-S101G-S103A-V104I-A232V-Q245R-N269R-R275S, N043D-S101G-S103A-V104I-A232V-Q245R, N043D-S101G-S103A-V104I-A232V-Q245R-H249R, N043R-N076D-S078R-S101G-S103A-V104I-A232V-Q245R-N269R, N043R-N076D-S101G-S103A-V104I-A232V-Q245R-H249R, N043R-N076D-S101G-S103A-V104I-L217E-A232V-Q245R, N043R-R045T-N076D-S078R-S101G-S103A-V104I-A232V-Q245R-N269R, N043R-R045T-N076D-S078R-S101G-S103A-V104I-A232V-V234I-Q245R, N043R-R045T-N076D-S101G-S103A-V104I-A232V-Q245R-N269R, N043R-R045T-S078R-S101G-S103A-V104I-N218S-A232V-Q245R, N043R-R045T-S101G-S103A-V104I-A232V-Q245R, N043R-S078R-S101G-S103A-V104I-A232V-Q245R-N269R, N043R-S087D-S101G-S103A-V104I-A232V-Q245R, N062Q-S101A-Q236N-N252R-A270C, N076D-S078R-S101G-S103A-V104I-A232V-Q245R-H249R, N076D-S101G-S103A-V104I-A232V-Q245R-H249R, N076D-S101G-S103A-V104I-A232V-S242R-Q245R, P005S-S024R-T033S-N243F, P014L-G020R-S024R-N043R-R045T-S101A-A215F, P052N-V104L-N183D-S216F-H249R, P086W-G118R, P086W-N243F, P086W-Y209A, Q012H-G020R-S078R-S101G-S103A-V104I-I198L-G211Q-T213A-A232V-Q245R, R045T-N076D-S078R-S101G-S103A-V104I-A232V-Q245R, R045T-N076D-S101G-S103A-V104I-A232V-Q245R-N269R, R045T-S078R-S101G-S103A-V104I-A232V-Q245R-H249R, R045T-S101G-S103A-V104I-A232V-Q245R-N269R, R045T-S242R-H249R, S024C-T033S, S024R-A232V, S024R-G046R-Y091F-V121F, S024R-G118R-K235F, S024R-N043A-S105T-S106G-I198L, S024R-N043D-R045T-S242R-H249R, S024R-N043D-S101G-S103A-V104I-A232V-Q245R, S024R-N043D-S242R-H249R, S024R-N043R-N076D, S024R-N043R-N076D-A230E-S242R, S024R-N043R-N076D-S101G-S103A-V104I-A232V-Q245R-N269R, S024R-N043R-R045T-N076D-S078R-S101G-S103A-V104I-A232V-Q245R, S024R-N043R-R045T-N076D-S101G-S103A-V104I-A232V-Q245R, S024R-N043R-R045T-S242R-H249R, S024R-N043R-S101A-T213A, S024R-N076D-Q245R, S024R-N076D-S101G-A232V-Q245R, S024R-N076D-S101G-M175L-A232V-Q245R, S024R-N076D-S101G-Q245R, S024R-N076D-S101G-S103A-V104I-A232V-Q245R, S024R-N076D-S103A-V104I-Q245R, S024R-N076D-V104I-Q245R, S024R-N243F, S024R-P086R-G118R, S024R-P086W-Y209A-K235F, S024R-P239Q, S024R-Q245R-H249R, S024R-R045T-N076D-S101G-S103A-V104I-A232V-Q245R-N269R, S024R-S101G, S024R-S101G-Q245R, S024R-S101G-V104I-H249R, S024R-S103A-A232V, S024R-S103A-M175L-A232V-H249R, S024R-S141G, S024R-T033S, S024R-T033S-A194T, S024R-T033S-G118R-K235F, S024R-T033S-G118R-Y209A, S024R-T033S-K235F, S024R-T033S-S078R-G118R, S024R-T033S-S078R-N243F, S024R-T033S-Y209A, S024R-T033S-Y209A-N243F, S024R-T274I, S024R-V104I-H249R, S024R-V104I-Q245R, S024R-Y091F-I198L-A215F-P239S, S024R-Y209A, S024R-Y209A-K235F, S024R-Y209A-S242P, S078R-P086W, S078R-S099F-N116A-R186K-T224A, S078R-S101G-S103A-V104I-A232V-Q245R-H249R, S101G-A232V, S101G-S103A-V104I-A232V-H249R, S101G-S103A-V104I-A232V-Q245R-H249R-N269R, S101G-S103A-V104I-Q245R, S105T-G211Q-S216F, S106G-N185I-S216F-Q236N, T022R-S101G-S103A-V104I-V150L-A232V-Q245R, T033S-G118D-A138V-Y209A, T033S-G118R-Y209A-, T033S-L148F, T033S-N243F, T033S-P086W, T033S-P201S, T033S-S078R, T033S-W241R, T033S-Y209A, T033S-Y209A-K235F, V004M-N018R-S024R-N076D-N116A-I198L-G211Q-T213A-H249R, V104I-A232V-H249R, and/or V104L-H120E-R186K-S216F-N252R;

f) A015T-T033S, A016T-N043R-R045T-N076D-S101G-S103A-V104I-A232V-Q245R-N269R, A230E-H249R, A232V-H249R, E089I-S105T-N116A-A215F-S216F, E089I-Y091F-N185I-G211Q-A270C, G020R-A090S-S101G-S103A-V104I-N116A-N183D-T213A-A215F-A232V-Q245R, G020R-N043D-S078R-S101G-S103A-V104I-A232V-Q245R-H249R, G020R-N043R-N076D, G020R-N043R-R045T-S078R-S101G-S103A-V104I-A232V-Q245R, G020R-P052N-S101A-I198L-L233C, G020R-R045T-N076D-S078R-S101G-S103A-V104I-A232V-Q245R-N269R, G020R-S024R-N043D-N076D-H249R, G020R-S024R-N043D-N076D-S242R-H249R, G020R-S024R-N043D-R045T-A230E-S242R, G020R-S024R-N043D-S078R-S101G-S103A-V104I-A232V-Q245R, G020R-S024R-N043D-S078R-S101G-S103A-V104I-A232V-Q245R-H249R, G020R-S024R-N043R-S101G-S103A-V104I-A232V-Q245R, G020R-S024R-N076D-S078R-S101G-S103A-V104I-A232V-Q245R-H249R, G020R-S024R-R045T-N076D-S101G-S103A-V104I-A232V-Q245R, G020R-S024R-R045T-N076D-S242R-H249R, G020R-S024R-R045T-S101G-S103A-

V104I-A232V-Q245R, V104I-G115E-N116A-N183D-G211Q-T213A-A232V-Q245R, G020R-S101A-S103A-V104I-N116A-N183D-A215F-A232V-Q245R, G020R-S101A-S103A-V104I-N116A-N183D-A232V-Q245R, G020R-S101A-S103A-V104I-N116A-N183D-G211Q-A232V-Q245R, G020R-S101A-S103A-V104I-N116A-N183D-G211Q-A232V-Q245R-T274I, G020R-S101A-S103A-V104I-N116A-N183D-I198L-G211Q-T213A-A215F-A232V-Q245R, G020R-S101A-S103A-V104I-N116A-N183D-T213A-A215F-A232V-Q245R, G020R-S101A-S103A-V104I-T213A-A232V-Q245R, G020R-S101G-S103A-V104I-N116A-N183D-A232V-Q245R, G020R-S101G-S103A-V104I-N116A-N183D-G211Q-A215F-A232V-Q245R, G020R-S101G-S103A-V104I-N116A-N183D-G211Q-A232V-Q245R, G020R-S101G-S103A-V104I-N116A-N183D-G211Q-T213A-A215F-A232V-Q245R, G020R-S101G-S103A-V104I-N116A-N183D-G211Q-T213A-A232V-Q245R, G020R-S101G-S103A-V104I-N116A-N183D-T213A-A232V-Q245R, G020R-T022R-N269R, G020R-T022R-S078R-S212F-W241R, G020R-T022W-S101A-S103A-V104I-N116A-N183D-A215F-A232V-Q245R, G020R-T022W-S101A-S103A-V104I-N116A-N183D-A232V-Q245R-N269S, G020R-T022W-S101A-S103A-V104I-N116A-N183D-A232V-Q245R-T274I, G020R-T022W-S101A-S103A-V104I-N116A-N183D-G211Q-A215F-A232V-Q245R, G020R-T022W-S101A-S103A-V104I-N116A-N183D-I198L-G211Q-T213A-A215F-A232V-Q245R, G020R-T022W-S101A-S103A-V104I-N116A-N183D-T213A-A232V-Q245R, G020R-T022W-S101A-S103A-V104I-N183D-G211Q-T213A-A215F-A232V-Q245R, G020R-T022W-S101A-S103A-V104I-N183D-I198L-A215F-A232V-Q245R, G020R-T022W-S101A-S103A-V104I-N183D-T213A-A215F-A232V-Q245R, G020R-T022W-S101G-S103A-V104I-N116A-N183D-A232V-Q245R, G020R-T022W-S101G-S103A-V104I-N116A-N183D-G211Q-A232V-Q245R-N263S, G020R-T022W-S101G-S103A-V104I-N116A-N183D-G211Q-T213A-A215F-A232V-Q245R, G020R-T022W-S101G-S103A-V104I-N116A-N183D-G211Q-T213A-A232V-Q245R, G020R-T022W-S101G-S103A-V104I-N183D-A215F-A232V-Q245R, G020R-T022W-S101G-S103A-V104I-N183D-A232V-Q245R, G025R-N062Q-S128N-S144R-N185I, G025R-N116A-H120E-T224A-A270C, G118R-K235F, K027R-N043R-R045T-N076D-S101G-S103A-V104I-A232V-Q245R, N018K-N076D-S078R-S101G-S103A-V104I-L217E-A232V-Q245R-N269R, N018R-G020R-N043D-N076D-S078R-S101G-S103A-V104I-L217E-A232V-Q245R, N018R-G020R-N043D-N076D-S242R-H249R, N018R-G020R-N043D-R045T-N076D-H249R, N018R-G020R-N043D-R045T-N076D-S101G-S103A-V104I-A232V-Q245R, N018R-G020R-N043D-R045T-N076D-S101G-S103A-V104I-A232V-Q245R-N269R, N018R-G020R-N043D-S101G-S103A-V104I-A232V-Q245R-N269R, N018R-G020R-N043D-S101G-S103A-V104I-L217E-A232V-Q245R, N018R-G020R-N043R-R045T-H249R, N018R-G020R-N043R-R045T-N076D-A230E-H249R, N018R-G020R-N076D, N018R-G020R-R045T-N076D-S078R-S101G-S103A-V104I-A232V-Q245R, N018R-G020R-R045T-N076D-S101G-S103A-V104I-A232V-Q245R-H249R, N018R-G020R-R045T-S101G-S103A-V104I-A232V-Q245R-H249R, N018R-G020R-S024R-N043D-N076D-S078R-S101G-S103A-V104I-A232V-Q245R, N018R-G020R-S024R-N043D-N076D-S101G-S103A-V104I-A232V-Q245R-N269R, N018R-G020R-S024R-N043R-N076D, N018R-G020R-S024R-N076D-A131T-A215F-H249R, N018R-G020R-S024R-N076D-G211Q-H249R, N018R-G020R-S024R-N076D-G211Q-N243D-H249R, N018R-G020R-S024R-N076D-G211Q-T213A-A215F-H249R, N018R-G020R-S024R-N076D-G211Q-T213A-H249R, N018R-G020R-S024R-N076D-I198L-A215F-H249R, N018R-G020R-S024R-N076D-I198L-H249R, N018R-G020R-S024R-N076D-I198L-T213A-A215F-H249R, N018R-G020R-S024R-N076D-N116A-G211Q-T213A-A215F-H249R, N018R-G020R-S024R-N076D-N116A-H249R, N018R-G020R-S024R-N076D-N116A-I198L-G211Q-A215F-H249R-N269S, N018R-G020R-S024R-N076D-N116A-I198L-G211Q-A215F-Q245R, N018R-G020R-S024R-N076D-N116A-I198L-H249R, N018R-G020R-S024R-N076D-N116A-N183D-G211Q-A215F-H249R, N018R-G020R-S024R-N076D-N116A-N183D-G211Q-T213A-H249R, N018R-G020R-S024R-N076D-N116A-N183D-I198L-A215F-H249R, N018R-G020R-S024R-N076D-N116A-N183D-I198L-G211Q-A215F-H249R, N018R-G020R-S024R-N076D-N116A-N183D-I198L-G211Q-T213A-H249R, N018R-G020R-S024R-N076D-N116A-N183D-I198L-H249R, N018R-G020R-S024R-N076D-N116A-N183D-T213A-H249R, N018R-G020R-S024R-N076D-N183D-A215F-H249R, N018R-G020R-S024R-N076D-N183D-G211Q-H249R, N018R-G020R-S024R-N076D-N183D-G211Q-T213A-A215F-H249R, N018R-G020R-S024R-N076D-N183D-G211Q-T213A-H249R, N018R-G020R-S024R-N076D-N183D-I198L-A215F-H249R, N018R-G020R-S024R-N076D-N183D-I198L-G211Q-A215F-H249R, N018R-G020R-S024R-N076D-N204D-T213A-H249R, N018R-G020R-S024R-N076D-S101A-G211Q-A215F-H249R-N269D, N018R-G020R-S024R-N076D-S101A-H249R, N018R-G020R-S024R-N076D-S101A-I198L-T213A-A215F-H249R, N018R-G020R-S024R-N076D-S101A-N116A-G211Q-T213A-A215F-H249R, N018R-G020R-S024R-N076D-S101A-N116A-G211Q-T213A-H249R, N018R-G020R-S024R-N076D-S101A-N116A-N183D-G211Q-A215F-H249R, N018R-G020R-S024R-N076D-S101A-N116A-N183D-G211Q-T213A-H249R, N018R-G020R-S024R-N076D-S101A-N116A-N183D-H249R, N018R-G020R-S024R-N076D-S101A-N116A-N183D-I198L-G211Q-A215F-H249R, N018R-G020R-S024R-N076D-S101A-N116A-N183D-I198L-T213A-H249R, N018R-G020R-S024R-N076D-S101A-N116A-N183D-T213A-H249R, N018R-G020R-S024R-N076D-S101A-N116A-T213A-A215F-H249R, N018R-G020R-S024R-N076D-S101A-N116A-T213A-H249R, N018R-G020R-S024R-N076D-S101A-N183D-G211Q-H249R, N018R-G020R-S024R-N076D-S101A-N183D-I198L-A215F-H249R, N018R-G020R-S024R-N076D-S101A-N183D-I198L-G211Q-T213A-H249R, N018R-G020R-S024R-N076D-S101A-N183D-I198L-T213A-H249R, N018R-G020R-S024R-N076D-S101A-N183D-T213A-A215F-H249R, N018R-G020R-S024R-R045T-N076D-S101G-S103A-V104I-A232V-Q245R, N018R-G020R-S024R-S101G-S103A-V104I-A232V-Q245R, N018R-G020R-T022W-S024R-N076D-I198L-T213A-H249R, N018R-G020R-T022W-S024R-N076D-N116A-I198L-H249R, N018R-G020R-T022W-S024R-N076D-N116A-I198L-T213A-A215F-H249R, N018R-G020R-T022W-S024R-N076D-N116A-N183D-G211Q-T213A-A215F-H249R, N018R-G020R-T022W-S024R-N076D-N116A-N183D-I198L-T213A-A215F-H249R, N018R-G020R-T022W-S024R-N076D-N116A-N183D-T213A-H249R, N018R-G020R-T022W-S024R-N076D-N183D-G211Q-T213A-H249R, N018R-G020R-T022W-S024R-N076D-N183D-I198L-G211Q-H249R, N018R-G020R-T022W-

S024R-N076D-S101A-A215F-H249R, N018R-T022W-S024R-N076D-S101A-G211Q-A215F-H249R, N018R-G020R-S024R-N076D-S101A-G211Q-H249R, N018R-G020R-T022W-S024R-N076D-S101A-G211Q-T213A-A215F-H249R, N018R-G020R-T022W-S024R-N076D-S101A-G211Q-T213A-H249R, N018R-G020R-T022W-S024R-N076D-S101A-I198L-A215F-H249R, N018R-G020R-T022W-S024R-N076D-S101A-I198L-G211Q-T213A-A215F-H249R, N018R-G020R-T022W-S024R-N076D-S101A-N116A-G211Q-H249R, N018R-G020R-T022W-S024R-N076D-S101A-N116A-H249R, N018R-G020R-T022W-S024R-N076D-S101A-N116A-I198L-G211Q-T213A-A215F-H249R, N018R-G020R-T022W-S024R-N076D-S101A-N116A-I198L-H249R, N018R-G020R-T022W-S024R-N076D-S101A-N116A-N183D-G211Q-H249R, N018R-G020R-T022W-S024R-N076D-S101A-N116A-N183D-G211Q-T213A-A215F-H249R, N018R-G020R-T022W-S024R-N076D-S101A-N116A-N183D-I198L-A215F-H249R, N018R-G020R-T022W-S024R-N076D-S101A-N116A-N183D-I198L-G211Q-A215F-H249R, N018R-G020R-T022W-S024R-N076D-S101A-N116A-N183D-I198L-G211Q-T213A-H249R, N018R-G020R-T022W-S024R-N076D-S101A-N116A-N183D-T213A-H249R, N018R-G020R-T022W-S024R-N076D-S101A-N116A-T213A-H249R, N018R-G020R-T022W-S024R-N076D-S101A-N183D-A215F-H249R, N018R-G020R-T022W-S024R-N076D-S101A-N183D-G211Q-A215F-H249R, N018R-G020R-T022W-S024R-N076D-T213A-H249R, N018R-N043D-A230E-H249R, N018R-N043D-N076D-S078R-S101G-S103A-V104I-A232V-Q245R-H249R, N018R-N043D-N076D-S242R-H249R, N018R-N043D-R045T-N076D-S078R-S101G-S103A-V104I-A232V-Q245R-N269R, N018R-N043D-R045T-N076D-S101G-S103A-V104I-A232V-Q245R-N269R, N018R-N043D-R045T-S078R-S101G-S103A-V104I-A232V-Q245R-A272D, N018R-N043R-N076D-A230E-H249R, N018R-N043R-N076D-S242R, N018R-N043R-R045T-A230E-S242R, N018R-N043R-R045T-S078R-S101G-S103A-V104I-L217E-A232V-Q245R, N018R-N043R-S078R-S101G-S103A-V104I-A232V-Q245R, N018R-N043R-S101G-S103A-V104I-A232V-Q245R-H249R, N018R-N076D-A232V-H249R, N018R-N076D-S078R-S101G-S103A-V104I-L217E-A232V-Q245R, N018R-N076D-S101G-I198T-A232V, N018R-N076D-S101G-S103A-V104I-Q245R, N018R-N076D-S101G-V104I, N018R-N076D-S242R, N018R-N076D-S242R-H249R, N018R-N076D-V104I-Q245R-H249R, N018R-R045T-H249R, N018R-R045T-S101G-S103A-V104I-A232V-Q245R-H249R, N018R-R045T-S101G-S103A-V104I-A232V-Q245R-N269R, N018R-S024R-N043D-N076D-S087D-H249R, N018R-S024R-N043D-N076D-S242R, N018R-S024R-N076D-A086V-S101A-N183D-I198L-G211Q-H249R, N018R-S024R-N076D-A215F-H249R, N018R-S024R-N076D-A232V, N018R-S024R-N076D-I198L-A215F-H249R, N018R-S024R-N076D-I198L-G211Q-H249R, N018R-S024R-N076D-I198L-G211Q-T213A-A215F-H249R, N018R-S024R-N076D-I198L-H249R, N018R-S024R-N076D-I198L-T213A-H249R, N018R-S024R-N076D-L217E-H249R-N269R, N018R-S024R-N076D-N116A-A150T-T213A-H249R, N018R-S024R-N076D-N116A-G211Q-T213A-H249R, N018R-S024R-N076D-N116A-I198L-G211Q-H249R, N018R-S024R-N076D-N116A-I198L-T213A-A215F-H249R, N018R-S024R-N076D-N116A-N183D-A215F-H249R, N018R-S024R-N076D-N116A-N183D-G211Q-A215F-H249R, N018R-S024R-N076D-N116A-N183D-G211Q-T213A-A215F-H249R, N018R-S024R-N076D-N116A-N183D-G211Q-T213A-H249R, N018R-S024R-N076D-N116A-N183D-H249R, N018R-S024R-N076D-N116A-N183D-I198L-A215F-H249R, N018R-S024R-N076D-N116A-N183D-I198L-G211Q-A215F-H249R, N018R-S024R-N076D-N116A-N183D-I198L-G211Q-H249R, N018R-S024R-N076D-N116A-N183D-I198L-G211Q-T213A-A215F-H249R, N018R-S024R-N076D-N116A-N183D-I198L-G211Q-T213A-H249R, N018R-S024R-N076D-N116A-N183D-I198L-H249R, N018R-S024R-N076D-N116A-N183D-I198L-T213A-H249R, N018R-S024R-N076D-N116A-N183D-T213A-A215F-H249R, N018R-S024R-N076D-N116A-N183D-T213A-H249R, N018R-S024R-N076D-N183D-A215F-H249R, N018R-S024R-N076D-N183D-G211Q-H249R, N018R-S024R-N076D-N183D-G211Q-T213A-A215F-H249R, N018R-S024R-N076D-N183D-G211Q-T213A-H249R, N018R-S024R-N076D-N183D-H249R, N018R-S024R-N076D-N183D-H249R-A248T, N018R-S024R-N076D-N183D-I198L-A215F-H249R, N018R-S024R-N076D-N183D-I198L-G211Q-A215F-H249R, N018R-S024R-N076D-N183D-I198L-G211Q-H249R, N018R-S024R-N076D-N183D-I198L-H249R, N018R-S024R-N076D-N183D-I198L-T213A-A215F-H249R, N018R-S024R-N076D-N183D-I198L-T213A-H249R, N018R-S024R-N076D-N183D-T213A-H249R, N018R-S024R-N076D-S087D-H249R, N018R-S024R-N076D-S101A-G211Q-T213A-A215F-H249R-A270V, N018R-S024R-N076D-S101A-G211Q-T213A-H249R, N018R-S024R-N076D-S101A-I198L-G211Q-A215F-H249R, N018R-S024R-N076D-S101A-N116A-G211Q-A215F-H249R, N018R-S024R-N076D-S101A-N116A-G211Q-T213A-A215F-H249R, N018R-S024R-N076D-S101A-N116A-H249R, N018R-S024R-N076D-S101A-N116A-I198L-G211Q-A215F-H249R, N018R-S024R-N076D-S101A-N116A-I198L-H249R, N018R-S024R-N076D-S101A-N116A-I198L-T213A-H249R, N018R-S024R-N076D-S101A-N116A-N183D-A215F-H249R, N018R-S024R-N076D-S101A-N116A-N183D-G211Q-A215F-H249R, N018R-S024R-N076D-S101A-N116A-N183D-G211Q-H249R, N018R-S024R-N076D-S101A-N116A-N183D-G211Q-T213A-A215F-H249R, N018R-S024R-N076D-S101A-N116A-N183D-G211Q-T213A-H249R, N018R-S024R-N076D-S101A-N116A-N183D-H249R, N018R-S024R-N076D-S101A-N116A-N183D-I198L-G211Q-T213A-H249R, N018R-S024R-N076D-S101A-N116A-N183D-I198L-H249R, N018R-S024R-N076D-S101A-N116A-N183D-I198L-T213A-A215F-H249R, N018R-S024R-N076D-S101A-N116A-N183D-T213A-A215F-H249R, N018R-S024R-N076D-S101A-N116A-N183D-T213A-H249R, N018R-S024R-N076D-S101A-N183D-A215F-H249R, N018R-S024R-N076D-S101A-N183D-G211Q-T213A-A215F-H249R, N018R-S024R-N076D-S101A-N183D-H249R, N018R-S024R-N076D-S101A-N183D-I198L-A215F-H249R, N018R-S024R-N076D-S101A-N183D-I198L-G211Q-H249R, N018R-S024R-N076D-S101A-N183D-I198L-G211Q-T213A-A215F-H249R, N018R-S024R-N076D-S101A-N183D-I198L-G211Q-T213A-H249R, N018R-S024R-N076D-S101A-N183D-I198L-H249R, N018R-S024R-N076D-S101A-N183D-I198L-T213A-A215F-H249R, N018R-S024R-N076D-S101A-N183D-I198L-T213A-H249R, N018R-S024R-N076D-S101A-N183D-T213A-A215F-H249R, N018R-S024R-N076D-S101A-T213A-A215F-H249R, N018R-S024R-N076D-S101A-V197A-T213A-A215F-H249R, N018R-S024R-N076D-S101G, N018R-S024R-N076D-S101G-Q245R, N018R-S024R-N076D-S101G-S103A-V104I-A232V, N018R-S024R-N076D-S103A-H249R, N018R-S024R-N076D-S103A-V104I-

L135I-A232V, N018R-S024R-N076D-T213A-A215F-H249R-T260K, N018R-S024R-N076D-V150L-S242R-H249R, N018R-S024R-R045T-A230E-H249R, N018R-S101G-S103A-V104I-A232V-Q245R-H249R, N018R-T022R-S024R-N076D-S101A-N116A-N183D-G211Q-H249R, N018R-T022W-S024R-N076D-G211Q-A215F-H249R, N018R-T022W-S024R-N076D-I198L-G211Q-A215F-H249R, N018R-T022W-S024R-N076D-I198L-G211Q-T213A-H249R, N018R-T022W-S024R-N076D-I198L-H249R, N018R-T022W-S024R-N076D-I198L-T213A-H249R, N018R-T022W-S024R-N076D-N116A-A215F-H249R, N018R-T022W-S024R-N076D-N116A-G211Q-T213A-A215F-H249R, N018R-T022W-S024R-N076D-N116A-H249R, N018R-T022W-S024R-N076D-N116A-I198L-A215F-H249R, N018R-T022W-S024R-N076D-N116A-I198L-G211Q-A215F-H249R, N018R-T022W-S024R-N076D-N116A-I198L-G211Q-T213A-A215F-H249R, N018R-T022W-S024R-N076D-N116A-I198L-H249R, N018R-T022W-S024R-N076D-N116A-I198L-T213A-A215F-H249R, N018R-T022W-S024R-N076D-N116A-N183D-A215F-H249R, N018R-T022W-S024R-N076D-N116A-N183D-G211Q-A215F-H249R, N018R-T022W-S024R-N076D-N116A-N183D-G211Q-H249R, N018R-T022W-S024R-N076D-N116A-N183D-G211Q-T213A-H249R, N018R-T022W-S024R-N076D-N116A-N183D-G211Q-T213A-Q245R, N018R-T022W-S024R-N076D-N116A-N183D-I198L-A215F-H249R, N018R-T022W-S024R-N076D-N116A-N183D-I198L-G211Q-A215F-H249R, N018R-T022W-S024R-N076D-N116A-N183D-I198L-G211Q-H249R, N018R-T022W-S024R-N076D-N116A-N183D-I198L-G211Q-T213A-A209V-H249R, N018R-T022W-S024R-N076D-N116A-N183D-I198L-G211Q-T213A-H249R, N018R-T022W-S024R-N076D-N116A-N183D-I198L-H249R, N018R-T022W-S024R-N076D-N116A-N183D-I198L-Y209H-G211Q-H249R, N018R-T022W-S024R-N076D-N116A-N183D-T213A-A215F-H249R, N018R-T022W-S024R-N076D-N116A-N183D-T213A-H249R, N018R-T022W-S024R-N076D-N183D-G211Q-H249R, N018R-T022W-S024R-N076D-N183D-G211Q-T213A-A215F-H249R, N018R-T022W-S024R-N076D-N183D-G211Q-T213A-H249R, N018R-T022W-S024R-N076D-N183D-H249R, N018R-T022W-S024R-N076D-N183D-I198L-A215F-H249R, N018R-T022W-S024R-N076D-N183D-I198L-G211Q-A215F-H249R, N018R-T022W-S024R-N076D-N183D-I198L-G211Q-T213A-H249R, N018R-T022W-S024R-N076D-N183D-I198L-H249R, N018R-T022W-S024R-N076D-N183D-T213A-H249R, N018R-T022W-S024R-N076D-S101A-G211Q-A215F-H249R, N018R-T022W-S024R-N076D-S101A-I198L-G211Q-A215F-H249R, N018R-T022W-S024R-N076D-S101A-I198L-G211Q-H249R, N018R-T022W-S024R-N076D-S101A-I198L-G211Q-T213A-H249R, N018R-T022W-S024R-N076D-S101A-N116A-G211Q-T213A-A215F-H249R, N018R-T022W-S024R-N076D-S101A-N116A-H249R, N018R-T022W-S024R-N076D-S101A-N116A-N183D-A215F-H249R, N018R-T022W-S024R-N076D-S101A-N116A-N183D-G211Q-A215F-H249R, N018R-T022W-S024R-N076D-S101A-N116A-N183D-G211Q-H249R, N018R-T022W-S024R-N076D-S101A-N116A-N183D-G211Q-T213A-A215F-H249R, N018R-T022W-S024R-N076D-S101A-N116A-N183D-G211Q-T213A-H249R, N018R-T022W-S024R-N076D-S101A-N116A-N183D-H249R, N018R-T022W-S024R-N076D-S101A-N116A-N183D-I198L-A215F-H249R, N018R-T022W-S024R-N076D-S101A-N116A-N183D-I198L-H249R, N018R-T022W-S024R-N076D-S101A-N116A-N183D-I198L-T213A-H249R, N018R-T022W-S024R-N076D-S101A-N116A-N183D-T213A-A215F-H249R, N018R-T022W-S024R-N076D-S101A-N116A-N183D-T213A-H249R, N018R-T022W-S024R-N076D-S101A-N116A-T213A-A215F-H249R, N018R-T022W-S024R-N076D-S101A-N116A-T213A-A215F-H249R-L267I, N018R-T022W-S024R-N076D-S101A-N116T-I198L-A215F-H249R, N018R-T022W-S024R-N076D-S101A-N183D-G211Q-A215F-H249R, N018R-T022W-S024R-N076D-S101A-N183D-G211Q-H249R, N018R-T022W-S024R-N076D-S101A-N183D-G211Q-T213A-A215F-H249R, N018R-T022W-S024R-N076D-S101A-N183D-G211Q-T213A-H249R, N018R-T022W-S024R-N076D-S101A-N183D-I198L-A215F-H249R, N018R-T022W-S024R-N076D-S101A-N183D-I198L-T213A-H249R, N018R-T022W-S024R-N076D-S101A-N183D-I198L-Y209H-H249R, N018R-T022W-S024R-N076D-S101A-N183D-T213A-A215F-H249R, N018R-T22W-S024R-N076D-G211Q-T213A-H249R, N018R-T22W-S024R-N076D-N116A-I198L-T213A-H249R, N018R-T22W-S024R-N076D-S101A-I198L-H249R, N018R-V104I-A232V, N043A-Q059A-S101A-S216F-T224A, N043D-N076D-S101G-S103A-V104I-A232V-Q245R-H249R, N043D-R045T-N076D-S078R-S101G-S103A-V104I-A232V-Q245R, N043D-R045T-S078R-S101G-S103A-V104I-A232V-Q245R, N043D-R045T-S078R-S101G-S103A-V104I-A232V-Q245R-N269R, N043D-S242R-H249R, N043R-A230E-H249R, N043R-N076D-S078R-S101G-S103A-V104I-A232V-Q245R-H249R, N043R-N076D-S078R-S101G-S103A-V104I-L217E-A232V-Q245R, N043R-N076D-S101G-S103T-V104I-A232V-Q245R-H249R-N269R, N043R-R045T-H249R, N043R-R045T-N076D-S101G-S103A-V104I-A232V-Q245R, N043R-R045T-S078R-S101G-S103A-V104I-A232V-Q245R-N269R, N043R-R045T-S078R-S101G-S103A-V104I-L217E-A232V-Q245R, N043R-R045T-S101G-S103A-V104I-A232V-Q245R-H249R, N043R-S078R-S101G-S103A-V104I-L217E-A232V-Q245R, N043R-S101G-S103A-V104I-Q245R-H249R, N043R-S101G-S103A-V104I-V150L-A232V-Q245R-N269R, N076D-A232V-Q245R, N076D-Q245R, N076D-S101G-A232V-Q245R, N076D-S101G-S103A-Q245R, N076D-S101G-S103A-V104I-A232V-H249R, N076D-S101G-S103A-V104I-H249R, N076D-S101G-S103A-V104I-V150L-A232V-Q245R, N076D-S101G-V104I-H249R, N076D-S101G-V104I-Q245R, N076D-S103A-V104I-A232V-Q245R, N076D-S103A-V104I-Q245R, N076D-V104I-A232V-Q245R, N076D-V104I-Q245R, P005S-N018R-T022W-S024R-N076D-S101A-T213A-A215F-H249R, P086W-K235F, P086W-Y209A-K235F, Q012H-V104A-G118R, R045T-N076D-S078R-S101G-S103A-V104I-A232V-Q245R-H249R, R045T-S101G-S103A-V104I-A232V-Q245R, S024R-G118R-N243F-R269H, S024R-K235F-N243F, S024R-N043D-N076D-S101G-S103A-V104I-A232V-Q245R-N269R, S024R-N043R-N076D-A230E-H249R, S024R-N076D-A232V-H249R, S024R-N076D-S078R-S101G-S103A-V104I-A232V-Q245R-H249R, S024R-N076D-S101G, S024R-N076D-S101G-A232V-H249R, S024R-N076D-S101G-S103A-A232V, S024R-N076D-S101G-S103A-V104I-M175L-H249R, S024R-N076D-S101G-S103A-V104I-Q245R, S024R-N076D-S101G-V104I-A232V-H249R, S024R-N076D-S103A-H249R, S024R-N076D-S103A-Q245R, S024R-N076D-S103A-V104I-H249R, S024R-R045T-N076D-S101G-S103A-V104I-A232V-Q245R-H249R, S024R-R045T-S242R-A273V, S024R-R247H, S024R-S101G-S103A, S024R-S101G-S103A-A232V, S024R-S101G-S103A-V104I,

S024R-S103A-Q245R-H249R, S024R-S103A-V104I, S024R-S106G-N116A-S212M-T224A, S024R-T033S-A151V, S024R-T033S-A174V-K235F, S024R-T033S-A228T, S024R-T033S-K235F-W241R, S024R-T033S-N243F, S024R-V104A, S024R-V104I-A232V, S024R-Y209A-N243F, S078R-K235F, S087D-S101G-S103A-V104I-A232V-S242R-Q245R, S099F-S105T-S106G-A194F-S212M, S101G-H249R, S101G-S103A-V104I, S101G-S103A-V104I-A232V-Q245R-N248D, S101G-S103A-V104I-G159D-A232V-Q245R, S101G-S103A-V104I-G159D-A232V-Q245R-N248R, S101G-S103A-V104I-V150L-A232V-Q245R, S103A-A232V, S103A-A232V-H249R, S103A-A232V-Q245R, S103A-V104I-Q245R, S103N-H120E-Y167W-I198L-L233C, T022W-A194F-T213A-L233C-N238L, T022W-E089I-S216F, T033S-A048T, T033S-P086W-S156L-Y209A, T033S-P239T, T033S-T253A, T057R-N183D-Q236N, T143A-Y209A, V004E-T033S-S078R, V004R-S009A-T022R-S078R-S212F, and/or Y209A-K235F; and optionally one or more of the following mutations: S103A, G159D, Q236H, Q245R, N248D and N252K.

The present invention also provides isolated protease variants, wherein said protease variant has at least one, or even two or more charged mutations selected from the group consisting of N062E, S101D, P129E, A158E, G159D/E, S166D, and/or S188D, preferably having a charge of 0, −1, −2, −3, −4 or −5, preferably 0, −1, −2 or −3, most preferably −1 or −2 relative to the enzyme of SEQ ID NO:1. Said protease variants can also include any of the variants listed in the application.

The present invention also provides isolated protease variants, wherein said protease variant has one or two or more charged mutations selected from the group consisting of N018R, G020K/R, T022R, S024R, N043R, Q245R, H249R and/or N269R, preferably having a charge of 0, +1, +2, +3, +4 or +5, preferably +1, +2 or +3, most preferably +2 relative to the enzyme of SEQ ID NO:1. Said protease variants can also include any of the variants listed in the application.

The present invention also provides isolated subtilisin variants, wherein the subtilisin variants are mature forms having proteolytic activity and comprise amino acid sequences comprising a combination of amino acid substitutions selected from: G020R-S087D-S101G-S103A-V104I-A232V-Q245R, G020R-S101G-S103A-V104I-V150L-A232V-Q245R, N018R-G020R-S024R-N076D-S087D-H249R, N018R-G020R-S024R-N076D-V150L-H249R, N018R-S024R-N043R-N076D-S087D-H249R, N018R-S024R-N043R-N076D-V150L-H249R, N018R-S024R-N076D-S078R-S087D-H249R, N018R-S024R-N076D-S078R-V150L-H249R, N018R-S024R-N076D-S087D-H249R-N269R, N018R-S024R-N076D-S087D-S242R-H249R, N018R-S024R-N076D-S087D-V150L-H249R, N018R-S024R-N076D-V150L-H249R, N018R-S087D-S101G-S103A-V104I-A232V-Q245R, N018R-S101G-S103A-V104I-V150L-A232V-Q245R, N018R-T022R-S024R-N076D-S087D-H249R, N018R-T022R-S024R-N076D-V150L-H249R, N043R-S087D-S101G-S103A-V104I-A232V-Q245R-N269R, N043R-S101G-S103A-V104I-V150L-A232V-Q245R, S024R-S087D-S101G-S103A-V104I-A232V-Q245R, S024R-S101G-S103A-V104I-V150L-A232V-Q245R, S078R-S087D-S101G-S103A-V104I-A232V-Q245R, S078R-S101G-S103A-V104I-V150L-A232V-Q245R, S087D-S101G-S103A-V104I-A232V-Q245R-N269R, S101G-S103A-V104I-V150L-A232V-Q245R-H249R, S101G-S103A-V104I-V150L-A232V-Q245R-N269R, T022R-S087D-S101G-S103A-V104I-A232V-Q245R, N018R-S024R-N043D-N076D-V150L-H249R, N043R-S087D-S101G-S103A-V104I-A232V-Q245R, T022R-S101G-S103A-V104I-V150L-A232V-Q245R, N018R-S024R-N043D-N076D-S087D-H249R, N018R-S024R-N076D-S087D-H249R, N018R-S024R-N076D-V150L-S242R-H249R, N043R-S101G-S103A-V104I-V150L-A232V-Q245R-N269R, N076D-S101G-S103A-V104I-V150L-A232V-Q245R, S087D-S101G-S103A-V104I-A232V-S242R-Q245R, S101G-S103A-V104I-V150L-A232V-Q245R, N076D-S087D-S101G-S103A-V104I-A232V-Q245R, S087D-S101G-S103A-V104I-A232V-Q245R, and S101G-S103A-V104I-V150L-A232V-S242R-Q245R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S024R-S101G-S103A-V104I-P129Q-A158E-S188D-L217E-A232V-Q245R-N248D-H249R, S024R-S101G-S103A-V104I-S130A-A158E-N183D-S188D-A232V-Q245R-N248D-H249R, S024R-S101G-S103A-V104I-P129Q-A158E-N183D-S188D-A232V-Q245R-N248D-H249R, S101G-S103A-V104I-S130A-A158E-S188D-A232V-Q245R-N248D-H249R, S024R-S101G-S103A-V104I-P129Q-A158E-S188D-A232V-Q245R-N248D-H249R, S024R-S101G-S103A-V104I-S130A-A158E-S188D-A232V-Q245R-N248D-H249R, S024R-S101G-S103A-V104I-P129Q-S130A-A158E-N183D-S188D-A232V-Q245R-N248D-H249R, S024R-S101G-S103A-V104I-S128L-P129Q-A158E-S188D-A232V-Q245R-N248D-H249R, S024R-S101G-S103A-V104I-P129Q-S130A-A158E-S188D-A232V-Q245R-N248D-H249R, S101G-S103A-V104I-P129Q-A158E-S188D-A232V-Q245R-N248D-H249R, S101G-S103A-V104I-P129Q-S130A-A158E-S188D-A232V-Q245R-N248D-H249R, S024R-S101G-S103A-V104I-S128L-P129Q-S130A-A158E-S188D-A232V-Q245R-N248D-H249R, S101G-S103A-V104I-S128L-P129Q-A158E-S188D-A232V-Q245R-N248D-H249R, and S024R-K027R-S101G-S103A-V104I-S128L-P129Q-S130A-A158E-S188D-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101G-S103A-V104I-A232V-M222Q-Q245R, S101G-S103A-V104I-A158E-S188D-M222 S-A232V-Q245R-N248D-H249R, S101G-S103A-V104I-A158E-S188D-M222Q-A232V-Q245R-N248D-H249R, N076D-S101G-S103A-V104I-A232V-M222Q-Q245R, S101G-S103A-V104I-A232V-M222S-Q245R, N076D-S101G-S103A-V104I-A232V-M222S-Q245R, and N076D-S101G-S103A-V104I-A158E-S188D-M222S-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S024R-S101G-S103A-V104I-S128L-P129Q-A158E-S188D-A232V-Q245R-N248D-H249R, S101G-S103A-V104I-S130A-A158E-S188D-A232V-Q245R-N248D-H249R, S024R-S101G-S103A-V104I-A158E-S188D-A232V-Q245R-N248D-H249R, S101G-S103A-V104I-S128L-P129Q-A158E-S188D-A232V-Q245R-N248D-H249R, S101G-S103A-V104I-P129Q-S130A-A158E-S188D-A232V-Q245R-N248D-H249R, S101G-S103A-V104I-S130A-A158E-N183D-S188D-L217E-A232V-Q245R-N248D-H249R, S024R-S101G-S103A-V104I-S128L-P129Q-S130A-A158E-S188D-A232V-Q245R-N248D-H249R, S024R-S101G-S103A-V104I-P129Q-A158E-S188D-L217E-A232V-Q245R-N248D-H249R, S101G-S103A-V104I-S128L-S130A-A158E-S188D-L217E-A232V-Q245R-N248D-H249R, S024R-S101G-S103A-V104I-S128L-P129Q-A158E-N183D-S188D-A232V-Q245R-N248D-H249R, S024R-S101G-S103A-V104I-S128L-P129Q-S130A-A158E-N183D-S188D-A232V-Q245R-N248D-H249R, S024R-S101G-S103A-V104I-S128L-P129Q-A158E-S188D-A232V-Q245R-N248D-H249R-E271G, S101G-S103A-V104I-P129Q-A158E-N183D-S188D-A232V-Q245R-N248D-H249R, S024R-S101G-S103A-V104I-S130A-A158E-S188D-L217E-A232V-Q245R-N248D-H249R, S024R-S101G-S103A-V104I-S128L-A158E-N183D-S188D-A232V-Q245R-N248D-H249R, S101G-S103A-V104I-P129Q-A158E-S188D-L217E-A232V-Q245R-N248D-H249R, and S024R-S101G-S103A-V104I-S128L-S130A-A158E-S188D-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising subtilisin variants having proteolytic activity comprising an amino acid sequence comprising a combination of amino acid substitutions selected from: S101G-S103A-V104I, T22A-S101A-Y209E, S103G-L111V-G159E, T22A-S103G-G159E, T22A-L111V-G159E, T22A-S128N-E271F-Y209E, T22A-S103G-L111V, N62E-L111V-S128N, T22A-L111V-S128N, T22A-N62E-L111V, S101A-S103G-V104L-S188D, S101G-S103A-V104I-G159D, S101A-S103G-V104L-S128N, T22A-S101A-G159E, S101A-S103G-V104L, S101A-S103G-V104L-G159E, T22A-S101A-S103G-V104L, S101A-S103G-V104L-Y209E, T22A-Y209E-E271F, T22A-S101A-E271F, and S101A-Y209E-E271F, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising subtilisin variants having proteolytic activity comprising an amino acid sequence comprising a combination of amino acid substitutions selected from: S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, and S101G-S103A-V104L-G159D-A232V-Q236H-Q245R-N248D, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising subtilisin variants having proteolytic activity comprising an amino acid sequence comprising a combination of amino acid substitutions selected from: S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N238R, S101G-S103A-V104I-G159D-A232V-Q245R-N248D-N248R, S101G-S103A-V104I-G159D-A232V-Q245R-N248D-T253R, S101G-S103A-V104I-G159D-A232V-Q245R-N248D-524R, S101G-S103A-V104I-G159D-A232V-Q245R-N248D-N76D, S101G-S103A-V104I-G159E-A232V-Q245R-N248D-H249R, S101G-S103A-V104I-G159E-A232V-Q245R-N248D-E271F, S101G-S103A-V104I-A158E-A232V-Q245R-N248D-H249R, S101G-S103A-V104I-A158E-A232V-Q245R-N248D-E271F, T22A-S101G-S103A-V104I-G159D-A232V-Q245R-N248D-H249R, T22A-S101G-S103A-V104I-G159D-A232V-Q245R-N248D-E271F, N62E-S101G-S103A-V104I-G159D-A232V-Q245R-N248D-H249R, and N62E-S101G-S103A-V104I-G159D-A232V-Q245R-N248D-E271F, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising subtilisin variants having proteolytic activity comprising an amino acid sequence comprising a combination of amino acid substitutions selected from: A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, W241R, G20R-N43R-H249R, G20R-T22R-N43R, G20R-N43R-S242R, G20R-N43R-E271L, G20R-N43R-V244R, G20R-S24R-N43R-S242R, S9A-T22R-S78R-S212F-W241R, S9A-G20R-N43R-S212F, S9A-N43R-S212F, G20R-N43R-S212F, G20R-T22R-N43R-S212F, S24R-S78R-S212F, S9A-N43R-578R, S9A-N43R-578R-S242R, S9A-G20R-N43R-S78R, G20R-S24R-N43R-S78R-S242R, T22R-S24R-S78R-S212F, S9A-G20R-N43R-S78R-S242R, G20R-N43R-S78R-H249R, G20R-N43R-S78R, S9A-S78R-S212F, S9A-T22R-N43R-578R, S9A-G20R-S24R-N43R, S9A-T22R-S78R-S212F, V4R-S9A-T22R-S78R-S212F, G20R-S24R-N43R, A1R-S9A-N43R, G20R-S24R-N43R-G115R, S9A-524R-N43R, G20R-T22R-S24R-N43R, A1R-S24R-N43R, S9A-G20R-S24R-N43R-S242R, S9A-G20R-T22R-S78R-S212F, S9A-524R-N43R-V244R, S9A-524R-N43R-S242R, V4R-S9A-T22R-S24R-S212F, and T22R-524R-N43R, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising subtilisin variants having proteolytic activity and comprising an amino acid sequence comprising a combination of amino acid substitutions selected from: S101G-S103A-V104I-A232V-Q245R-N248D, S101G-S103A-V104I-G159D-A232V-Q245R, S101G-S103A-V104I-G159R-A232V-Q245R-N248D, S101G-S103A-V104I-G159D-A232V-Q245R-N248R, S101G-S103A-V104I-A232V-Q245R, S101G-S103A-V104I-A232V-Q245R-N248R, S101G-S103A-V104I-G159R-A232V-Q245R-N248R, S101G, S103A, V104I, A232V, Q236H, and Q245R, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising subtilisin variants having proteolytic activity and comprising an amino acid sequence comprising a combination of amino acid substitutions selected from: A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, and E271F wherein amino acid positions of the subtilisin variant are numbered by correspondence with the amino acid sequence of *B. amyloliquefaciens* subtilisin BPN' set forth as SEQ ID NO:1.

The present invention also provides protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of G20K, G20R, G23A, S24F, S24R, N43R, N43W, R45T, N62E, N76D, S101A, N116A, N116L, G118R, S128I, P129E, S188D, T213A, A215F, L217E, P239G, and N269R, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention further provides polypeptides comprising subtilisin variants having proteolytic activity and comprising an amino acid sequence comprising a combination of amino acid substitutions selected from: A1R, Q2S, Q2M, Q2A, Q2R, Q2W, S3R, V4R, V4S, V4C, I8A, S9A, S9F, S9W, R10S, R10A, R10H, R10M, Q12F, Q12R, P14K, P14F, P14Q, A15R, A15F, A16S, H17R, H17M, H17F, N18R, N18K, G20F, G20K, G20R, T22A, T22R, T22Y, T22V, T22Q, T22L, T22W, G23A, G23S, G23F, S24R, S24F, S24W, S24Q, S24H, S24L, G25V, G25F, G25R, V26F, K27L, K27F, K27R, K27V, V28A, V28N, V28E, A29T, V30E, L31F, T33S, T33G, T33D, G34P, I35M, S36T, S36F, S36R, T38L, T38F, T38R, P40N, P40L, P40T, P40W, P40H, P40R, L42I, N43A, N43F, N43I, N43S, N43R, N43M, N43W, N43D, R45T, G46R, A48R, F50C, V51W, V51F, V51H, P52F, P52E, P52N, P55Y, T57R, Q59A, Q59F, Q59R, D60P, D60Q, D60A, N62E, N62Q, G63V, G63M, G63T, G63I, G63A, G63S, G63H, G63Q, G63D, G63E, G63P, H64F, H64T, V68A, V68C, A69N, A69T, A69P, A69W, T71G, T71G, I72C, A74C, L75A, L75F, L75E, L75R, N76D, S78A, S78N, S78I, S78R, I79W, I79Q, V81R, L82F, L82T, L82V, L82R, L82M, A85M, P86W, P86L, P86I, E89P, E89T, E89G, E89H, E89W, E89L, E89V, E89W, E89F, E89I, Y91N, Y91R, A92F, K94N, S99F, S99T, S99P, S99G, S99M, G100S, G100N, G100Q, G100I, S101A, S101N, S101G, S101D, S101T, S101D, S101E, S101P, S101F, G102A, G102T, G102N, G102H, G102E, S103G, S103N, S103D, S103A, V104L, V104I, V104E, V104D, S105T, S105E, S105Q, S106G, S106T, S106E, S106D, S106A, S106V, S106F, I107M, I107F, A108I, A108G, Q109M, L111V, L111I, E112V, E112L, E112Q, A114G, G115K, G115R, N116K, N116A, N116L, N117F, G118R, G118I, M119C, H120A, H120F, H120R, V121F, V121F, V121E, N123G, N123E, L124S, S128D, S128F, S128L, S128N, S128H, S128M, S128I, S128Q, P129E, S132A, S132E, A138G, S144R, V147L, L148I, A158E, G159D, G159E, G159C, S160D, S166D, S166E, Y167W, M175V, V177C, D181A, Q182R, N183I, N183D, N183M, N183R, N183F, N183R, N185E, N185V, N185I, R186H, R186K, S188E, S188D, S188R, Y192H, Y192W, A194E, A194V, A194F, D197F, D197F, I198L, I198F, V203E, V203C, T208S, Y209S, Y209N, Y209F, Y209T, Y209E, Y209H, Y209G, Y209L, P210R, P210V, P210L, G211Q, G211R, S212I, S212M, S212F, T213A, Y214F, A215N, A215D, A215E, A215H, A215F, S216F, S216A, L217E, L217N, L217D, N218D, N218P, N218E, T224A, T224G, V227I, A230E, A231I, A231C, A232V, L233C, V234F, K235F, Q236F, Q236N, Q236H, N238R, N238K, N238L, P239K, P239G, P239R, P239R, P239H, P239T, P239N, P239S, P239F, S240R, W241R, S242L, S242R, N243F, N243R, V244R, Q245R, I246S, N248D, N248V, N248I, N248R, H249R, H249T, L250I, K251R, K251S, N252I, N252F, N252R, N252K, N252H, T253I, T253R, T253F, A254C, S256N, G258R, T260V, T260I, L262D, L262H, Y263F, S265F, L267V, L267N, L267M, N269I, N269R, A270C, E271I, E271H, E271V, E271H, E271M, E271L, E271P, E271A, E271F, E271T, A272F, A272F, A272R, A273F, A273I, and T274G, wherein the amino acid positions of the subtilisin variant are numbered by correspondence with the amino acid sequence of *B. amyloliquefaciens* subtilisin BPN' set forth as SEQ ID NO:1.

The present invention further provides polypeptides comprising protease variant of *Bacillus lentus* subtilisin GG36 protease, wherein the *Bacillus lentus* subtilisin GG36 protease comprises the amino acid sequence shown in SEQ ID NO:2, and wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, 25, 30, 35, 40, 45, or 50 mutations at amino acid positions selected from amino acid 1, 2, 3, 4, 8, 9, 10, 12, 14, 15, 16, 17, 18, 20, 22, 23, 24, 25, 26, 27, 28, 29, 30, 31, 33, 34, 35, 36, 38, 40, 42, 43, 45, 46, 48, 50, 51, 52, 55, 57, 59, 60, 62, 63, 64, 68, 69, 71, 72, 74, 75, 76, 78, 79, 81, 82, 85, 86, 89, 91, 92, 94, 99, 100, 101, 102, 103, 104, 105, 106, 107, 108, 109, 111, 112, 114, 115, 116, 117, 118, 119, 120, 121, 123, 124, 128, 129, 132, 138, 144, 147, 148, 158, 159, 160, 166, 167, 175, 177, 181, 182, 183, 185, 186, 188, 192, 194, 197, 198, 203, 208, 209, 210, 211, 212, 213, 214, 215, 216, 217, 218, 224, 227, 230, 231, 233, 234, 235, 236, 236, 238, 238, 239, 240, 241, 242, 243, 244, 246, 248, 249, 250, 251, 252, 253, 254, 256, 258, 260, 262, 263, 265, 267, 269, 270, 271, 272, 273, and 274, wherein the amino acid positions of the subtilisin variant are numbered by correspondence with the amino acid sequence of *B. amyloliquefaciens* subtilisin BPN' set forth as SEQ ID NO:1

The present invention further provides polypeptides comprising protease variants of *Bacillus lentus* subtilisin GG36 protease, wherein the *Bacillus lentus* subtilisin GG36 protease comprises the amino acid sequence shown in SEQ ID NO:2, and wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, 25, 30, 35, 40, 45, or 50 mutations selected from the group of A1R, Q2S, Q2M, Q2A, Q2R, Q2W, S3R, V4R, V4S, V4C, I8A, S9A, S9F, S9W, R10S, R10A, R10H, R10M, Q12F, Q12R, P14K, P14F, P14Q, A15R, A15F, A16S, H17R, H17M, H17F, N18R, N18K, G20F, G20K, G20R, T22A, T22R, T22Y, T22V, T22Q, T22L, T22W, G23A, G23S, G23F, S24R, S24F, S24W, S24Q, S24H, S24L, G25V, G25F, G25R, V26F, K27L, K27F, K27R, K27V, V28A, V28N, V28E, A29T, V30E, L31F, T33S, T33G, T33D, G34P, I35M, S36T, S36F, S36R, T38L, T38F, T38R, P40N, P40L, P40T, P40W, P40H, P40R, L42I, N43A, N43F, N43I, N43S, N43R, N43M, N43W, N43D, R45T, G46R, A48R, F50C, V51W, V51F, V51H, P52F, P52E, P52N, P55Y, T57R, Q59A, Q59F, Q59R, D60P, D60Q, D60A, N62E, N62Q, G63V, G63M, G63T, G63I, G63A, G63S, G63H, G63Q, G63D, G63E, G63P, H64F, H64T, V68A, V68C, A69N, A69T, A69P, A69W, T71G, T71G, I72C, A74C, L75A, L75F, L75E, L75R, N76D, S78R, S78N, S78I, S78R, I79W, I79Q, V81R, L82F, L82T, L82V, L82R, L82M, A85M, P86W, P86L, P86I, E89P, E89T, E89G, E89H, E89W, E89L, E89V, E89W, E89F, E89I, Y91N, Y91F, A92F, K94N, S99F, S99T, S99P, S99G, S99M, G100S, G100N, G100Q, G100I, S101A, S101N, S101G, S101D, S101T, S101D, S101E, S101P, S101F, G102A, G102T, G102N, G102H, G102E, S103G, S103N, S103D, S103A, V104L, V104I, V104E, V104D, S105T, S105E, S105Q, S106G, S106T, S106E, S106D, S106A, S106V, S106F, I107M, I107F, A108I, A108G, Q109M, L111V, L111I, E112V, E112L, E112Q, A114G, G115K, G115R, N116K, N116A, N116L, N117F, G118R, G118I, M119C, H120A, H120F, H120R, V121F, V121F, V121E, N123G, N123E, L124S, S128D, S128F, S128L, S128N, S128H, S128M, S128I, S128Q, P129E, S132A, S132E, A138G, S144R, V147L, L148I, A158E, G159D, G159E, G159C, S160D, S166D, S166E, Y167W, M175V, V177C, D181A, Q182R, N183I, N183D, N183M, N183R, N183F, N183R, N185E, N185V, N185I, R186H, R186K, S188E, S188D, S188R, Y192H, Y192W, A194E, A194V, A194F, D197F, D197F, I198L, I198F, V203E, V203C, T208S, Y209S, Y209N, Y209F, Y209T, Y209E, Y209H, Y209G, Y209L, P210R, P210V, P210L, G211Q, G211R, S212I, S212M, S212F, T213A, Y214F, A215N, A215D, A215E, A215H, A215F, S216F, S216A, L217E, L217N, L217D, N218D, N218P, N218E, T224A, T224G, V227I, A230E, A231I, A231C, A232V, L233C, V234F, K235F, Q236F, Q236N, Q236H, N238R, N238K, N238L, P239K, P239G, P239R, P239R, P239H, P239T, P239N, P239S, P239F, S240R, W241R, S242L, S242R, N243F, N243R, V244R, Q245R, I246S, N248D, N248V, N248I, N248R, H249R, H249T, L250I, K251R, K251S, N252I, N252F, N252R, N252K, N252H, T253I, T253R, T253F, A254C, S256N, G258R, T260V, T260I, L262D, L262H, Y263F, S265F, L267V, L267N, L267M, N269I, N269R, A270C, E271I, E271H, E271V, E271H, E271M, E271L, E271P, E271A, E271F, E271T, A272F, A272F, A272R, A273F, A273I, and T274G, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention further provides polypeptides comprising protease variants of *Bacillus lentus* subtilisin GG36 protease, wherein the *Bacillus lentus* subtilisin GG36 protease comprises the amino acid sequence shown in SEQ ID NO:2, and wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, 25, 30, 35, 40, 45, or 50 mutations selected from the group of A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E, G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N. N269I, N269R, E271F, E271I, E271H, E271P, E271T, E271V, E271L and A272F, and optionally comprises at least one mutation selected from the group of S103A, G159D, Q236H, Q245R, N248D and N252K, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention further provides polypeptides comprising protease variants of *Bacillus lentus* subtilisin GG36 protease, wherein the *Bacillus lentus* subtilisin GG36 protease comprises the amino acid sequence shown in SEQ ID NO:2, and wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, 25, 30, 35, 40, 45, or 50 mutations selected from the group of A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E. G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N. N269I, N269R, E271F, E271I, E271H, E271P, E271T, E271V, E271L and A272F, and optionally comprises at least one mutation selected from the group of S103A, G159D, Q236H, Q245R, N248D and N252K, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention further provides polypeptides comprising protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, 25, 30, 35, 40, 45, or 50 mutations selected from the group of A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, E271F, A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, and W241R, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of G20K, G20R, G23A, S24F, S24R, N43R, N43W, R45T, N62E, N76D, S101A, N116A, N116L, G118R, S128I, P129E, S188D, T213A, A215F, L217E, P239G, and N269R, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention further provides polypeptides comprising protease variants of *Bacillus lentus* subtilisin GG36 protease, wherein the *Bacillus lentus* subtilisin GG36 protease comprises the amino acid sequence shown in SEQ ID NO:2, and wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, 25, 30, 35, 40, 45 or 50 mutations selected from the group of A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, E271F, A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, and W241R, wherein the amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention further provides polypeptides comprising protease variants comprising an amino acid sequence which differs from the amino acid sequence of SEQ ID NO:2, and wherein the total net charge of the protease variant is 0, +1, +2, +3, +4, +5, −1, −2, −3, −4, or −5 relative to the total net charge of the *Bacillus lentus* subtilisin GG36 protease, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants comprising amino acid sequence which differs from the amino acid sequence of SEQ ID NO:2, and wherein the total net charge of the protease variant is 0 relative to the total net charge of the *Bacillus lentus* subtilisin GG36 protease, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants comprising amino acid sequence which differs from the amino acid sequence of SEQ ID NO:2 wherein the protease variants are mature forms having proteolytic activity and comprise amino acid sequences comprising a combination of amino acid substitutions selected from: G020R-N043R, G020K-N062E, S024F-N116L, G020K-S024F, S024R-A174T, S024R-G118R, S024R-K235F, S024R-P086R, S024R-P086W, S078R-G118R, T033S-G118R, T033S-K235F, Y209A-W241R, G020R-N076D, N018R-Q245R, S024R-R045T, A232V-Q245R, G118R-A172V, G118R-A194T, I008T-S024R, K235F-N243F, N018R-S103A, N018R-V104I, P086W-G118R, P086W-N243F, P086W-Y209A, S024C-T033S, S024R-A232V, S024R-N243F, S024R-P239Q, S024R-S101G, S024R-S141G, S024R-T033S, S024R-T274I, S024R-Y209A, S078R-P086W, S101G-A232V, T033S-L148F, T033S-P086W, T033S-P201S, T033S-S078R, T033S-W241R, T033S-Y209A, A230E-H249R, A232V-H249R, G118R-K235F, N076D-Q245R, P086W-K235F, S024R-R247H, S024R-V104A, S078R-K235F, S101G-H249R, S103A-A232V, T033S-A048T, T033S-P239T, T033S-T253A, T143A-Y209A, Y209A-K235F, N018R-R045T, Y209A-N243F, S024R-A272P, S024R-R269C, S101G-V104I, V104I-A232V, N076D-H249R, and S024R-N076D, and wherein the total net charge of the protease variant is 0, +1, +2, +3, +4, +5, −1, −2, −3, −4, or −5 relative to the total net charge of the *Bacillus lentus* subtilisin GG36 protease, and wherein the total net charge is obtained by one or more substitutions selected from: N43D, R45T, N62E, N76D, S101D, P129E, A158E, G159D, G159E, S166D, S188D, A230E, N18R, G20K, G20R, T22R, S24R, N43R, G118R, Q245R, H249R, N269R, E271F, and E271L, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants comprising amino acid sequence which differs from the amino acid sequence of SEQ ID NO:2 wherein the protease variants are mature forms having proteolytic activity and comprise amino acid sequences comprising a combination of amino acid substitutions selected from: G020R-N076D, S024R-R045T, A230E-H249R, N018R-R045T, N018R-

Q245R, S101G-A232V, S024R-A232V, A232V-Q245R, S024R-S101G, N018R-V104I, N018R-S103A, S101G-H249R, A232V-H249R, S103A-A232V, N076D-Q245R, S101G-V104I, V104I-A232V, N076D-H249R, S024R-N076D, S024F-N116L, G020K-S024F, G020K-N062E, T033S-G118R, S024R-P086W, S024R-G118R, S024R-P086R, Y209A-W241R, S024R-W241R, S024R-K235F, G118R-Y209A, S078R-G118R, T033S-K235F, S024R-A174T, P086W-Y209A, I008T-S024R, P086W-G118R, T033S-W241R, S024R-N243F, S024R-Y209A, T033S-P086W, S024R-T033S, P086W-N243F, T033S-P201S, S024R-P239Q, S078R-P086W, K235F-N243F, G118R-A172V, T033S-L148F, T033S-S078R, T033S-N243F, S024C-T033S, G118R-A194T, T033S-Y209A, S024R-S141G, S024R-T274I, P086W-K235F, A015T-T033S, Y209A-K235F, S024R-R247H, S078R-K235F, S024R-V104A, T033S-A048T, G118R-K235F, T033S-T253A, T143A-Y209A, T033S-P239T, Y209A-N243F, S024R-A272P, and S024R-R269C, and wherein the total net charge of the protease variant is 0, +1, +2, +3, +4, +5, −1, −2, −3, −4, or −5 relative to the total net charge of the *Bacillus lentus* subtilisin GG36 protease, and wherein the total net charge is obtained by one or more substitutions selected from: N43D, R45T, N62E, N76D, S101D, P129E, A158E, G159D, G159E, S166D, S188D, A230E, N18R, G20K, G20R, T22R, S24R, N43R, G118R, Q245R, H249R, N269R, E271F, and E271L, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants comprising amino acid sequence which differs from the amino acid sequence of SEQ ID NO:2 wherein the protease variants are mature forms having proteolytic activity and comprise amino acid sequences comprising a combination of amino acid substitutions selected from: G020K-G023A-N043W-G118R-S128I-P129E-G159D-S188D, G020K-G023A-N062E-N116L, G020K-G023A-N062E-N116L-S188D, G020K-G023A-N062E-N116L-S188D-T213A, G020K-G100S-N116L-A158E-S166D-N243F, G020K-N043W-N062E-N116L-S188D, G020K-N062E, G020K-N062E-N116L, G020K-N062E-N116L-S188D, G020K-N062E-N116L-T213A, G020K-N062E-S188D-T213A, G020K-S024F-N062E-N116L-G118R-S188D, G020K-S024F-N062E-N116L-S188D, G020K-S024F-N062E-S188D-T213A, G023A-N062E-N116L-S188D, G023A-S024F-N062E-N116L-T213A, N043R-N076D-S101A-S103A-V104I-A158E-S188D-L217E-A232V-Q245R-N248D-H249R-E271F, N043R-S101A-S103A-V104I-A158E-S188D-L217E-A232V-Q245R-N248D-H249R, N043W-N062E-N116L, N043W-S101D-S212M-N243F, N062E-N116L-G118R-S188D, N062E-N116L-G118R-T213A, N062E-N116L-S188D-T213A, S024F-G118R-S128I-P129E-G159D, S024F-N062E-N116L-S188D, S024R-S101G-S103A-V104I-A158E-N183D-S188D-A232V-Q245R-N248D-H249R, S024R-S101G-S103A-V104I-A158E-S188D-A232V-Q245R-N248D-H249R, S024R-S101G-S103A-V104I-A158E-S188D-L217E-A232V-Q245R-N248D-H249R, S024R-S101G-S103A-V104I-P129Q-A158E-N183D-S188D-A232V-Q245R-N248D-H249R, S024R-S101G-S103A-V104I-P129Q-A158E-S188D-A232V-Q245R-N248D-H249R, S024R-S101G-S103A-V104I-P129Q-A158E-S188D-L217E-A232V-Q245R-N248D-H249R, S024R-S101G-S103A-V104I-P129Q-S130A-A158E-N183D-S188D-A232V-Q245R-N248D-H249R, S024R-S101G-S103A-V104I-S128L-P129Q-A158E-S188D-A232V-Q245R-N248D-H249R, S024R-S101G-S103A-V104I-S130A-A158E-N183D-S188D-A232V-Q245R-N248D-H249R, S024R-S101G-S103A-V104I-S130A-A158E-S188D-A232V-Q245R-N248D-H249R, S101D-S103N-N116L-S144R-A215D, S101G-S103A-V104I-A158E-S188D-A232V-Q245R-N248D-H249R, S101G-S103A-V104I-S130A-A158E-S188D-A232V-Q245R-N248D-H249R, T022A-N043R-S101G-S103A-V104I-G159D-S188D-L217E-A232V-Q245R-N248D-E271F, T022A-N043R-S103A-V104I-G118R-S128I-P129E-G159D-S188D-A232V-N248D-E271F, T022A-N043R-S103A-V104I-S128I-P129E-G159D-S188D-A232V-Q245R-N248D, T022A-S024R-S103A-V104I-G118R-S128I-P129E-G159D-S188D-A232V-N248D, T022A-S101G-S103A-V104I-G159D-L217E-A232V-Q245R-N248D-E271F, T022A-S101G-S103A-V104I-G159D-S188D-A232V-Q245R-N248D-E271F, T022L-T038F-A048R-N062E-G100S-R186K, T033S-N043W-N218D-P239G-N243F, V026F-A048R-S105T-T213A-N218D-T224A, V026F-L031F-S078N-G102A-S160D, V026F-V051W-V104L-S106E, V104L-S105T-T213A-L217E-S256N, A016S-N062E-A158E-H249R, A016S-N062E-A158E-R186H-E271F, A016S-N062E-A158E-R186H-H249R, A016S-N062E-V104L-A158E-R186H-E271F, A016S-S024R-S101G-S103A-V104I-A158E-S188D-A232V-Q245R-N248D-H249R, G020K-G023A-N062E-S188D, G020K-G023A-S024F-N062E-G118R-S188D-T213A, G020K-N043W-N062E-N116L-S188D-T213A-P239G, G020K-S024F-N062E-S188D-P239G, G023A-N062E-N116L-G118R, G023A-N062E-N116L-G118R-S188D-P239G, G023A-S024F-N062E-N116L-G118R, H017R-T022A-N076D-S101G-S103A-V104I-G159D-S188D-A232V-Q245R-N248D-E271F, N043R-N076D-S101A-S103A-V104I-A158E-S188D-A232V-Q245R-N248D-H249R-E271F, N062E-A158E-G159E-H249R, N062E-A158E-H249R, N062E-A158E-R186H-E271F, N062E-A158E-R186H-H249R, N062E-A158E-R186H-H249R-E271F, N062E-A158E-S188D-H249R, N062E-A158E-S188D-H249R-E271F, N062E-G159E-H249R, N062E-G159E-H249R-E271F, N062E-G159E-R186H-H249R, N062E-G159E-S188D-H249R, N062E-R186H-S188D-H249R-E271F, N062E-S101A-A158E-H249R, N062E-S101A-A158E-R186H-E271F, N062E-S101A-A158E-R186H-H249R-E271F, N062E-S101A-G159E-H249R, N062E-S101A-R186H-H249R, N062E-S101A-S188D-H249R, N062E-S101A-S188D-H249R-E271F, N062E-S101A-V104L-A158E-R186H-E271F, N062E-S128N-A158E-G159E-E271F, N062E-V104L-A158E-S188D-H249R-E271F, N076D-S101G-S103A-V104I-A232V-M222Q-Q245R, S024F-N062E-N116L-P239G, S024F-N062E-S188D-T213A, S024F-N116L, S024R-N043R-N076D-S101A-S103A-V104I-A158E-S188D-L217E-A232V-Q245R-N248D-H249R, S024R-S101G-S103A-V104I-A158E-G159E-A232V-N238R-Q245R-N248D, S024R-S101G-S103A-V104I-A158E-G159E-S188D-A232V-Q245R-N248D, S024R-S101G-S103A-V104I-A158E-S188D-A232V-N238R-Q245R-N248D, S024R-S101G-S103A-V104I-A232V-Q245R-N248D-H249R, S024R-S101G-S103A-V104I-G159E-S188D-A232V-N238R-Q245R-N248D, S024R-S101G-S103A-V104I-G159E-S188D-A232V-Q245R-N248D, S024R-S101G-S103A-V104I-G159E-S188D-A232V-Q245R-N248D-H249R, S024R-S101G-S103A-V104I-L148I-A158E-A232V-Q245R-N248D, S024R-S101G-S103A-V104I-L148I-A158E-

S188D-A232V-Q245R-N248D, S024R-S101G-S103A-V104I-L148I-A232V-Q245R-N248D, S024R-S101G-S103A-V104I-P129E-A158E-A232V-Q245R-N248D-H249R, S024R-S101G-S103A-V104I-P129E-A158E-G159E-S188D-A232V-Q245R-N248D-H249R, S024R-S101G-S103A-V104I-P129E-A158E-S188D-A232V-Q245R-N248D, S024R-S101G-S103A-V104I-P129E-A158E-S188D-A232V-Q245R-N248D-H249R, S024R-S101G-S103A-V104I-P129E-G159E-A232V-Q245R-N248D, S024R-S101G-S103A-V104I-P129E-G159E-S188D-A232V-Q245R-N248D-H249R, S024R-S101G-S103A-V104I-P129E-L148I-A158E-A232V-Q245R-N248D, S024R-S101G-S103A-V104I-P129E-S188D-A232V-N238R-Q245R-N248D, S024R-S101G-S103A-V104I-P129E-S188D-A232V-Q245R-N248D, S024R-S101G-S103A-V104I-P129E-S188D-A232V-Q245R-N248D-H249R, S024R-S101G-S103A-V104I-S128N-A158E-A232V-Q245R-N248D, S024R-S101G-S103A-V104I-S128N-P129E-A158E-A232V-Q245R-N248D-H249R, S024R-S101G-S103A-V104I-S128N-P129E-A232V-Q245R-N248D, S101A-S103A-V104I-A158E-S188D-A232V-Q245R-N248D-H249R, S101A-S103A-V104I-A158E-S188D-A232V-Q245R-N248D-H249R-E271F-E271F, S101A-S103A-V104L-A158E-S188D-A232V-Q245R-N248D-H249R, S101A-S128N-A158E-R186H-E271F, S101A-S128N-A158E-Y209E-H249R, S101A-V104L-A158E-R186H-S188D-H249R, S101G-S103A-V104I-A158E-A232V-Q245R-N248D-H249R, S101G-S103A-V104I-A158E-G159E-A232V-Q245R-N248D-H249R, S101G-S103A-V104I-A158E-S188D-M222Q-A232V-Q245R-N248D-H249R, S101G-S103A-V104I-A158E-S188D-M222S-A232V-Q245R-N248D-H249R, S101G-S103A-V104I-A232V-M222Q-Q245R, S101G-S103A-V104I-P129E-A158E-S188D-A232V-Q245R-N248D-H249R, S101G-S103A-V104I-P129E-G159E-A232V-Q245R-N248D-H249R, S101G-S103A-V104I-P129E-S188D-A232V-N238R-Q245R-N248D, S101G-S103A-V104I-P129E-S188D-A232V-Q245R-N248D-H249R, S101G-S103A-V104I-S188D-A232V-Q245R-N248D-H249R, S101G-S103G-V104I-A158E-S188D-A232V-Q245R-N248D-H249R, S101G-S103S-V104I-A158E-S188D-A232V-Q245R-N248D-H249R, S101S-S103A-V104I-A158E-S188D-A232V-Q245R-N248D-H249R, S101S-S103G-V104I-A158E-S188D-A232V-Q245R-N248D-H249R, S101S-S103G-V104V-A158E-S188D-A232V-Q245R-N248D-H249R, S128N-A158E-G159E-E271F, S128N-A158E-H249R, S128N-A158E-R186H-E271F, S128N-A158E-R186H-H249R, S128N-A158E-R186H-S188D-E271F, S128N-A158E-S188D-E271F, S128N-A158E-S188D-H249R, S128N-A158E-S188D-Y209E-E271F, S128N-A158E-Y209E-, T022A-N043R-S103A-V104I-G118R-P129E-G159D-S188D-A232V-Q245R-N248D, T022A-N062E-A158E, T022A-S024R-S101D-S103A-V104I-G118R-G159D-S188D-A232V-N248D-E271F, T022A-S024R-S101D-S103A-V104I-G118R-P129E-G159D-S188D-A232V-Q245R-N248D, T022A-S024R-S101D-S103A-V104I-G159D-S188D-A232V-Q245R-N248D, T022A-S024R-S101G-S103A-V104I-A158E-A232V-N238R-Q245R-N248D, T022A-S024R-S101G-S103A-V104I-A158E-A232V-Q245R-N248D-H249R, T022A-S024R-S101G-S103A-V104I-A158E-G159E-S188D-A232V-N238R-Q245R-N248D, T022A-S024R-S101G-S103A-V104I-A158E-G159E-S188D-A232V-Q245R-N248D, T022A-S024R-S101G-S103A-V104I-A158E-G159E-S188D-A232V-Q245R-N248D-H249R, T022A-S024R-S101G-S103A-V104I-P129E-A158E-A232V-Q245R-N248D, T022A-S024R-S101G-S103A-V104I-P129E-A158E-A232V-Q245R-N248D-H249R, T022A-S024R-S101G-S103A-V104I-P129E-A158E-G159E-A232V-Q245R-N248D-H249R, T022A-S024R-S101G-S103A-V104I-P129E-A158E-G159E-S188D-A232V-N238R-Q245R-N248D, T022A-S024R-S101G-S103A-V104I-P129E-A158E-S188D-A232V-N238R-Q245R-N248D, T022A-S024R-S101G-S103A-V104I-P129E-A158E-S188D-A232V-Q245R-N248D-H249R, T022A-S024R-S101G-S103A-V104I-P129E-A232V-Q245R-N248D, T022A-S024R-S101G-S103A-V104I-P129E-A232V-Q245R-N248D-H249R, T022A-S024R-S101G-S103A-V104I-P129E-G159E-S188D-A232V-Q245R-N248D-H249R, T022A-S024R-S101G-S103A-V104I-P129E-S188D-A232V-Q245R-N248D, T022A-S024R-S101G-S103A-V104I-S128N-A158E-S188D-A232V-Q245R-N248D, T022A-S024R-S101G-S103A-V104I-S128N-P129E-A158E-A232V-Q245R-N248D, T022A-S024R-S101G-S103A-V104I-S128N-P129E-S188D-A232V-Q245R-N248D, T022A-S024R-S101G-S103A-V104I-S128N-S188D-A232V-Q245R-N248D, T022A-S024R-S103A-V104I-G118R-G159D-S188D-L217D-A232V-N248D, T022A-S024R-S103A-V104I-P129E-G159D-S188D-A232V-N248D-E271F, T022A-S101G-S103A-V104I-A158E-G159E-S188D-A232V-Q245R-N248D-H249R, T022A-S101G-S103A-V104I-A158E-S188D-A232V-Q245R-N248D, T022A-S101G-S103A-V104I-P129E-A158E-A232V-N238R-Q245R-N248D, T022A-S101G-S103A-V104I-P129E-A158E-G159E-A232V-N238R-Q245R-N248D, T022A-S101G-S103A-V104I-P129E-A158E-S188D-A232V-Q245R-N248D-H249R, T022A-S101G-S103A-V104I-P129E-G159E-A232V-N238R-Q245R-N248D, T022A-S101G-S103A-V104I-P129E-S188D-A232V-N238R-Q245R-N248D, T022A-S101G-S103A-V104I-S128N-P129E-A232V-N238R-Q245R-N248D, T022A-S101G-S103A-V104I-S128N-P129E-S188D-A232V-N238R-Q245R-N248D, T022A-S128N-A158E-H249R, V104L-S128N-A158E-H249R, V104L-S128N-A158E-R186H-E271F, V104L-S128N-A158E-R186H-H249R, and V104L-S128N-A158E-S188D-H249R, and wherein the total net charge of the protease variant is 0, +1, +2, +3, +4, +5, −1, −2, −3, −4, or −5 relative to the total net charge of the *Bacillus lentus* subtilisin GG36 protease, and wherein the total net charge is obtained by one or more substitutions selected from: N43D, R45T, N62E, N76D, S101D, P129E, A158E, G159D, G159E, S166D, S188D, A230E, N18R, G20K, G20R, T22R, S24R, N43R, G118R, Q245R, H249R, N269R, E271F, and E271L, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants comprising amino acid sequence which differs from the amino acid sequence of SEQ ID NO:2 wherein the protease variants are mature forms having proteolytic activity and comprise amino acid sequences comprising a combination of amino acid substitutions selected from: A016S-N062E-A158E-H249R-E271F, A016S-N062E-S128N-R186H-E271F, A016S-N062E-V104L-R186H-S188D-E271F, A016S-S101A-S128N-R186H, A016S-S128N-A158E-R186H, A016S-V104L-A158E-R186H-E271F, A016S-V104L-S188D-H249R, A158E-R186H-H249R, A158E-R186H-S188D-H249R-E271F, G020K-G023A-N116L-

S188D, G020K-G023A-S024F-N062E-N116L-S188D-T213A, G020K-N043W-N062E-N116L-P239G, G020K-S024F-N043W-N062E-N116L-T213A, G020K-S024F-N062E, G023A-N043W-N062E-N116L-G118R-T213A, G023A-T038F-S078N-G100S-S212M-A215D, G100S-N116L-A158E-T213A, G102A-S103N-S105T-A194E, H017R-T022A-N076D-S101G-S103A-V104I-G159D-A232V-Q245R-N248D-E271F, N043R-N076D-S101A-S103A-V104I-A158E-S166D-S188D-A232V-Q245R-N248D-H249R-E271F, N043R-S101A-S103A-V104I-A158E-S166D-S188D-A232V-Q245R-N248D-H249R, N043W-N062E-N116L-S188D, N062E-A158E-H249R-E271F, N062E-A158E-R186H-S188D-H249R, N062E-L148I-G159E, N062E-N116L-S188D, N062E-R186H-H249R, N062E-S078N-G102A-N116L-S144R-L250I, N062E-S101A-A158E-R186H-H249R, N062E-S101A-A158E-S188D-H249R, N062E-S101A-R186H, N062E-S101A-R186H-E271F, N062E-S101A-R186H-H249R-E271F, N062E-S101A-R186H-S188D-E271F, N062E-S101A-R186H-S188D-H249R, N062E-S101A-V104L-R186H-S188D-E271F, N062E-S128N-A158E, N062E-S128N-G159E-H249R, N062E-S188D-P239G, N062E-V104L-G159E-H249R, N076D-S101A-S103A-V104I-A158E-S166D-S188D-A232V-Q245R-N248D-H249R-E271F, N076D-S101A-S103A-V104I-A158E-S188D-A232V-Q245R-N248D-H249R, N076D-S101A-S103A-V104I-A158E-S188D-A232V-Q245R-N248D-H249R-E271F, N076D-S101G-S103A-V104I-A114V-A158E-S188D-A232V-Q245R-N248D-H249R-E271F, N076D-S101G-S103A-V104I-A232V-M222S-Q245R, S024F-A048R-G118R-S166D-L217E, S024F-N062E-N116L, S024F-N062E-N116L-T213A-P239G, S024F-N062E-S188D-P239G, S024F-S101D-G118R-A215D-L250I-A272F, S024R-K027R-S101G-S103A-V104I-S128L-P129Q-S130A-A158E-S188D-A232V-Q245R-N248D-H249R, S024R-N076D-S101A-S103A-V104I-A158E-S166D-S188D-A232V-Q245R-N248D-H249R-E271F, S024R-S101G-S103A-V104I-A158E-A232V-Q245R-N248D-H249R, S024R-S101G-S103A-V104I-P129E-A158E-G159E-A232V-N238R-Q245R-N248D, S024R-S101G-S103A-V104I-P129E-A158E-G159E-A232V-Q245R-N248D-H249R, S024R-S101G-S103A-V104I-P129E-G159E-A232V-N238R-Q245R-N248D, S024R-S101G-S103A-V104I-P129E-G159E-S188D-A232V-N238R-Q245R-N248D, S024R-S101G-S103A-V104I-P129E-L148I-A158E-S188D-A232V-Q245R-N248D, S024R-S101G-S103A-V104I-P129E-L148I-S188D-A232V-Q245R-N248D, S024R-S101G-S103A-V104I-P129Q-S130A-A158E-S188D-A232V-Q245R-N248D-H249R, S024R-S101G-S103A-V104I-S128L-A158E-S188D-A232V-Q245R-N248D-H249R, S024R-S101G-S103A-V104I-S128L-P129Q-S130A-A158E-S188D-A232V-Q245R-N248D-H249R, S024R-S101G-S103A-V104I-S128N-G159E-S188D-A232V-Q245R-N248D, S078N-V104L-G118R-S128D, S101A-A158E-R186H-H249R, S101A-A158E-R186H-S188D-H249R, S101A-S103A-V104I-A158E-S166D-S188D-A232V-Q245R-N248D-H249R-E271F, S101A-S103A-V104I-A158E-S188D-A232V-Q245R-N248D-H249R-E271F, S101A-S103A-V104I-A158E-S188D-L217E-A232V-Q245R-N248D-H249R, S101A-S103A-V104I-A158E-S188D-L217E-A232V-Q245R-N248D-H249R-E271F, S101A-S103G-A158E-R186H-H249R, S101A-S103S-V104I-A158E-S188D-A232V-Q245R-N248D-H249R, S101A-S103S-V104I-G159E-A232V-Q245R-N248D-H249R, S101A-S128N-A158E-H249R, S101A-S128N-A158E-S188D-Y209E-E271F, S101A-S128N-A158E-Y209E, S101A-S128N-P129E-R186H-H249R, S101A-V104L-A158E-R186H-H249R, S101A-V104L-A158E-R186H-S188D-E271F, S101A-V104L-S128N-A158E-R186H-E271F, S101G-S103A-V104I-A158E-A232V-N238R-Q245R-N248D, S101G-S103A-V104I-A158E-G159E-S188D-A232V-N238R-Q245R-N248D, S101G-S103A-V104I-A158E-N183D-S188D-A232V-Q245R-N248D-H249R, S101G-S103A-V104I-A158E-S166D-S188D-A232V-Q245R-N248D-H249R-E271F, S101G-S103A-V104I-A158E-S188D-A232V-Q245R-N248D, S101G-S103A-V104I-A232V-M222S-Q245R, S101G-S103A-V104I-P129E-A158E-G159E-A232V-N238R-Q245R-N248D, S101G-S103A-V104I-P129E-A158E-G159E-A232V-Q245R-N248D-H249R, S101G-S103A-V104I-P129E-A158E-S188D-A232V-N238R-Q245R-N248D, S101G-S103A-V104I-P129E-G159E-A232V-N238R-Q245R-N248D, S101G-S103A-V104I-P129E-S188D-A232V-Q245R-N248D, S101G-S103A-V104I-P129Q-A158E-S188D-A232V-Q245R-N248D-H249R, S101G-S103A-V104I-P129Q-S130A-A158E-S188D-A232V-Q245R-N248D-H249R, S101G-S103A-V104I-S128L-P129Q-A158E-S188D-A232V-Q245R-N248D-H249R, S101G-S103A-V104I-S128L-S130A-A158E-S188D-L217E-A232V-Q245R-N248D-H249R, S101G-S103A-V104I-S128N-P129E-A232V-N238R-Q245R-N248D, S101G-S103A-V104I-S128N-P129E-A232V-Q245R-N248D, S101G-S103A-V104I-S130A-A158E-N183D-S188D-L217E-A232V-Q245R-N248D-H249R, S101G-S103A-V104I-S188D-A232V-N238R-Q245R-N248D, S101G-S103A-V104L-A158E-S188D-A232V-Q245R-N248D-H249R, S101S-S103A-V104I-G159E-A232V-Q245R-N248D-H249R, S101S-S103S-V104I-A158E-S188D-A232V-Q245R-N248D-H249R, S101S-S103S-V104V-A158E-S188D-A232V-Q245R-N248D-H249R, T022A-N043R-N062E-S103A-V104I-G159D-S188D-A232V-Q245R-N248D-E271F, T022A-N043R-N076D-S101G-S103A-V104I-G159D-S188D-A232V-Q245R-N248D-E271F, T022A-N043R-S101D-S103A-V104I-G118R-P129E-G159D-S188D-A232V-N248D-E271F, T022A-N043R-S101G-S103A-V104I-G159D-A232V-Q245R-N248D-E271F, T022A-N043R-S103A-V104I-G118R-G159D-S188D-A232V-N248D-E271F, T022A-N043R-S103A-V104I-G118R-G159D-S188D-L217D-A232V-N248D-E271F, T022A-N043R-S103A-V104I-G118R-S128I-P129E-G159D-S188D-A232V-N248D, T022A-N043R-S103A-V104I-P129E-G159D-S188D-A232V-Q245R-N248D, T022A-N076D-S101G-S103A-V104I-G159D-A232V-Q245R-N248D-E271F, T022A-N076D-S101G-S103A-V104I-G159D-S188D-A232V-Q245R-N248D-E271F, T022A-S024R-N043R-S101D-S103A-V104I-G159D-S188D-A232V-Q245R-N248D, T022A-S024R-N043R-S103A-V104I-G159D-S188D-L217D-A232V-N248D-E271F, T022A-S024R-S101D-S103A-V104I-G118R-S128I-G159D-S188D-A232V-Q245R-N248D, T022A-S024R-S101G-S103A-V104I-L148I-A158E-A232V-Q245R-N248D, T022A-S024R-S101G-S103A-V104I-P129E-A158E-G159E-A232V-Q245R-N248D, T022A-S024R-S101G-S103A-V104I-P129E-A158E-G159E-S188D-A232V-Q245R-N248D-H249R, T022A-S024R-S101G-S103A-V104I-P129E-L148I-A232V-Q245R-N248D, T022A-S024R-S101G-S103A-V104I-S188D-A232V-Q245R-N248D-H249R, T022A-S024R-S103A-V104I-G118R-P129E-G159D-S188D-A232V-N248D-E271F, T022A-S024R-S103A-V104I-G159D-S188D-L217D-A232V-N248D-E271F, T022A-S024R-S103A-V104I-G159D-S188D-L217D-A232V-Q245R-N248D-E271F, T022A-S101A-A158E-

R186H-H249R, T022A-S101G-S103A-V104I-A158E-G159E-A232V-N238R-Q245R-N248D, T022A-S101G-S103A-V104I-A158E-G159E-A232V-Q245R-N248D-H249R, T022A-S101G-S103A-V104I-G159D-A232V-Q245R-N248D-E271F, T022A-S101G-S103A-V104I-G159D-S188D-A232V-Q245R-N248D-H249R-E271F, T022A-S101G-S103A-V104I-G159E-S188D-A232V-N238R-Q245R-N248D, T022A-S101G-S103A-V104I-G159E-S188D-A232V-Q245R-N248D-H249R, T022A-S101G-S103A-V104I-P129E-A158E-A232V-Q245R-N248D-H249R, T022A-S101G-S103A-V104I-P129E-A158E-G159E-A232V-Q245R-N248D-H249R, T022A-S101G-S103A-V104I-P129E-A232V-N238R-Q245R-N248D, T022A-S101G-S103A-V104I-P129E-G159E-A232V-Q245R-N248D-H249R, T022A-S101G-S103A-V104I-P129E-G159E-S188D-A232V-Q245R-N248D-H249R, T022A-S103A-V104I-G118R-G159D-S188D-L217D-A232V-Q245R-N248D, T022A-S103A-V104I-G159D-S188D-A232V-N248D, T022L-L031F-G102A-S128D-T224A-N243F, T022L-T038F-V121F-S160D-A272F, V026F-S078N-G159C-R186K-N243F, V104L-A158E-H249R, V104L-A158E-R186H-H249R, V104L-A158E-R186H-H249R-E271F, V104L-A158E-R186H-S188D-H249R, V104L-A158E-R186H-S188D-H249R-E271F, V104L-A158E-S188D-H249R-E271F, V104L-S128N-A158E-R186H-S188D-E271F, V104L-S128N-G159E-E271F, V104L-S128N-R186H-S188D-H249R, and V121F-N185E-T224A-P239G, and wherein the total net charge of the protease variant is 0, +1, +2, +3, +4, +5, −1, −2, −3, −4, or −5 relative to the total net charge of the *Bacillus lentus* subtilisin GG36 protease, and wherein the total net charge is obtained by one or more substitutions selected from: N43D, R45T, N62E, N76D, S101D, P129E, A158E, G159D, G159E, S166D, S188D, A230E, N18R, G20K, G20R, T22R, S24R, N43R, G118R, Q245R, H249R, N269R, E271F, and E271L, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants comprising amino acid sequence which differs from the amino acid sequence of SEQ ID NO:2 wherein the protease variants are mature forms having proteolytic activity and comprise amino acid sequences comprising a combination of amino acid substitutions selected from: A016S-S128N-R186H-E271F, N076D-S101G-S103A-V104I-A158E-S188D-M222S-A232V-Q245R-N248D-H249R, S024R-S101G-S103A-V104I-S128L-P129Q-A158E-N183D-S188D-A232V-Q245R-N248D-H249R, S024R-S101G-S103A-V104I-S128L-P129Q-A158E-S188D-A232V-Q245R-N248D-H249R-E271G, S024R-S101G-S103A-V104I-S128L-P129Q-S130A-A158E-N183D-S188D-A232V-Q245R-N248D-H249R, S101G-S103A-V104I-P129Q-A158E-N183D-S188D-A232V-Q245R-N248D-H249R, T022A-N076D-S101G-S103A-V104I-G159D-A232V-Q245R-N248D-H249R-E271F, T022A-S101G-G102A-S103A-V104I-G159D-S188D-A232V-Q245R-N248D-E271F, A016S-A158E-H249R, A016S-A158E-H249R-E271F, A016S-A158E-R186H-H249R, A016S-L111V-S188D-, A016S-T022A-A158E-R186H-E271F, A048R-S078N-N116L-N185E-L217E-P239G, A048R-S128D-N185E-P239G, A158E-R186H-H249R-E271F, E089P-S101A-P129E-R186H, G020K-G023A-N043W-N116L-S188D-T213A-P239G, G020K-G023A-N062E-N116L-G118R-T213A, G020K-G023A-S024F-N062E-S188D-T213A-P239G, G020K-K027R-P129E-S166D-P239G, G020K-S024F-N062E-P239G, G020K-S024F-T033S-P129E-A194E, G023A-G100S-A194E-S212M, G023A-N043W-N116L-G118R-S188D, G023A-S024F-G118R-S188D-P239G, G023A-S024F-K027R-N062E, G023A-S024F-N043W-N062E-N116L-G118R, G023A-S024F-N116L-G118R-S188D-T213A, G023A-S024F-N116L-S188D-P239G, K027R-G100S-G118R-S160D-S188D-N243F, K027R-S101D-S103N-S105T-A272F, N043R-N076D-S101A-S103A-V104I-A158E-S166D-S188D-A232V-Q245R-N248D-H249R, N062E-S078N-N116L-T224A, N062E-V104L-A158E-R186H-S188D-H249R, N076D-S101A-S103A-V104I-A158E-S188D-L217E-A232V-Q245R-N248D-H249R-E271F, N076D-S101G-S103A-V104I-A158E-S166D-S188D-A232V-Q245R-N248D-H249R-E271F, S024F-G102A-R186K-T213A-L217E-N243F, S024F-N043W-G118R-S188D, S024F-N043W-V104L-V121F-P129E, S024F-N116L-G118R-S188D-P239G, S024F-S103N-V104L-G118R-S188D, S024R-N043R-S101A-S103A-V104I-A158E-S188D-A232V-Q245R-N248D-H249R, S024R-N043R-S101A-S103A-V104I-A158E-S188D-L217E-A232V-Q245R-N248D-H249R, S024R-N076D-S101G-S103A-V104I-A158E-S188D-A232V-Q245R-N248D-H249R-E271F, S024R-S101G-S103A-V104I-A158E-G159E-A232V-Q245R-N248D, S024R-S101G-S103A-V104I-S128N-A158E-G159E-S188D-A232V-Q245R-N248D, S024R-S101G-S103A-V104I-S128N-P129E-S188D-A232V-Q245R-N248D, S101A-L111V-P129E, S101A-S103A-V104L-G159E-A232V-Q245R-N248D-H249R, S101A-S103 S-V104L-G159E-A232V-Q245R-N248D-H249R, S101A-V104L-S128N-A158E-R186H, S101G-S103A-V104I-P129E-L148I-S188D-A232V-Q245R-N248D, S101G-S103A-V104I-S128N-P129E-A158E-A232V-N238R-Q245R-N248D, S101G-S103A-V104I-S128N-P129E-S188D-A232V-Q245R-N248D-H249R, S101G-S103S-V104L-G159E-A232V-Q245R-N248D-H249R, S101S-S103A-V104L-G159E-A232V-Q245R-N248D-H249R, S128N-P129E-R186H, T022A-A158E-R186H-H249R-E271F, T022A-S024K-S101G-S103A-V104I-S128N-A158E-G159E-A232V-Q245R-N248D, T022A-S024R-S101G-S103A-V104I-S128N-P129E-A158E-S188D-A232V-Q245R-N248D-H249R, T022A-S024R-S103A-V104I-S128I-G159D-S188D-A232V-N248D, T022A-S101G-S103A-V104I-L148I-S188D-A232V-Q245R-N248D, T022A-S101G-S103A-V104I-S128N-G159E-A232V-Q245R-N248D, T022A-S101G-S103A-V104I-S128N-P129E-A158E-A232V-N238R-Q245R-N248D, T022A-S128N-A158E-R186H, T022A-S128N-R186H-S188D-, T022A-V104L-A158E-H249R, T022A-V104L-R186H-S188D-H249R, T022L-G023A-K027R-S101D-V104L-S216F, T022L-S078N-N116L-P129E-S256N, T022L-S078N-S128D-T213A, T033S-G118R-P129E-A194E-P239G, T033S-S105T-S188D-S216F, V026F-V104L-S256N-A272F, T022A-N043R-S103A-V104I-S128I-G159D-S188D-A232V-Q245R-N248D, T022A-S024R-N043R-S103A-V104I-G118R-G159D-S188D-L217D-A232V-N248D, T022A-S101D-S103A-V104I-G118R-G159D-S188D-L217D-A232V-Q245R-N248D-E271F, T022A-S103A-V104I-G118R-P129E-G159D-S188D-A232V-Q245R-N248D-E271F, T022A-S103A-V104I-G159D-S188D-L217D-A232V-Q245R-N248D-E271F, T022A-S103A-V104I-S128I-P129E-G159D-S188D-A232V-N248D-E271F, T022A-S024R-S101G-S103A-V104I-P129E-L148I-A158E-

S188D-A232V-Q245R-N248D, T022A-S024R-S101G-S103A-V104I-L148I-A158E-S188D-A232V-Q245R-N248D, S101G-S103A-V104I-L148I-G159E-A232V-Q245R-N248D, T022A-S024R-S101G-S103A-V104I-A158E-S188D-A232V-Q245R-N248D, S101G-S103A-V104I-S128N-P129E-A158E-A232V-Q245R-N248D-H249R, V104L-L148I-S188D-H249R, S024R-S101A-S103A-V104I-A158E-S166D-S188D-L217E-A232V-Q245R-N248D-H249R, N076D-S101G-S103A-V104I-S128L-A158E-S188D-A232V-Q245R-N248D-H249R-E271F, N043R-N076D-S101G-S103A-V104I-A158E-S166D-S188D-A232V-Q245R-N248D-H249R-E271F, T022A-N043R-N076D-S101G-S103A-V104I-G159D-A232V-Q245R-N248D-H249R-E271F, S101A-S103G-V104V-G159E-A232V-Q245R-N248D-H249R, S101S-S103A-V104V-G159E-A232V-Q245R-N248D-H249R, G023A-S024F-V051W-A158E, K027R-T038F-G102A-N116L, N062E-S078N-S144R-S212M, L031F-N116L-S256N-A272F, T022L-T033S-V104L-N116L-S160D-R186K, S024F-G118R-P129E-R186K-T213A, N043W-S105T-T213A-A215D-S216F, L031F-S105T-R186K-S188D, V026F-A 194E-T213A-S256N, S103N-S160D-L250I-S256N, S024R-S101G-S103A-V104I-S130A-A158E-S188D-L217E-A232V-Q245R-N248D-H249R, S024R-S101G-S103A-V104I-S128L-A158E-N183D-S188D-A232V-Q245R-N248D-H249R, S101G-S103A-V104I-P129Q-A158E-S188D-L217E-A232V-Q245R-N248D-H249R, S024R-S101G-S103A-V104I-S128L-S130A-A158E-S188D-A232V-Q245R-N248D-H249R, T022A-N062E-S103A-V104I-G118R-G159D-S188D-A232V-Q245R-N248D, T022A-N043R-S101D-S103A-V104I-G118R-P129E-G159D-S188D-L217D-A232V, T022A-S024R-S103A-V104I-G159D-S188D-L217D-A232V-N248D, T022A-S024R-N043R-S103A-V104I-G118R-S128I-P129E-G159D-S188D-L217D-A232V-N248D-E271F, T022A-S103A-V104I-G118R-G159D-S188D-L217D-A232V-Q245R-N248D-E271F, G020K-N043W-S188D-T213A, S024F-N062E-G118R-P239G, G023A-N043W-S188D-T213A, G020K-S024F-N043W-N062E-N116L-G118R-S188D-P239G, G020K-N116L-S188D-P239G, G020K-N043W-N062E-G118R, G020K-N043W-N116L-S188D-T213A, G020K-S024F, G023A-N043W-N116L-P239G, G023A-S024F-N043W-N116L-G118R-S188D-P239G, G020K-G023A-N043W-T213A, and G023A-S024F-N062E-G118R-T213A-P239G, and wherein the total net charge of the protease variant is 0, +1, +2, +3, +4, +5, −1, −2, −3, −4, or −5 relative to the total net charge of the *Bacillus lentus* subtilisin GG36 protease, and wherein the total net charge is obtained by one or more substitutions selected from: N43D, R45T, N62E, N76D, S101D, P129E, A158E, G159D, G159E, S166D, S188D, A230E, N18R, G20K, G20R, T22R, S24R, N43R, G118R, Q245R, H249R, N269R, E271F, and E271L, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants comprising amino acid sequence which differs from the amino acid sequence of SEQ ID NO:2 wherein the protease variants are mature forms having proteolytic activity and comprise amino acid sequences comprising a combination of amino acid substitutions selected from: G118R-Y209A, G118R-Y209A-N243F, L021M-S024R-T033S, P005S-S078R-G118R-W241R, P086W-G118R-A133V, P086W-G118R-N243F, P086W-G118R-Y209A, P086W-Y209A-N243F, S024R-A174T, S024R-G118R, S024R-G118R-Y209A, S024R-G118R-Y209A-K235F, S024R-G118R-Y209A-N243F, S024R-K235F, S024R-P086R, S024R-P086S-S141G, S024R-P086W, S024R-P086W-G118R, S024R-P086W-G118R-V203I, S024R-P086W-N243F, S024R-P086W-Y209A, S024R-S078R-P086W, S024R-S078R-P086W-G118R-A270T, S024R-S078R-P086W-N243F, S024R-T033S-A133V, S024R-T033S-G118R, S024R-T033S-P086S-S085N-K235F, S024R-T033S-P086S-S087N-Y209A, S024R-T033S-P086W, S024R-T033S-P086W-G118R, S024R-T033S-S078R-P086W, S024R-T033S-S078R-P086W-G118R, S024R-T033S-S078R-Y209A, S024R-T033S-W241R, S024R-T033S-Y209A-K235F, S024R-Y209A-W241R, S078R-G118R, S078R-P086W-K235F, S078R-P086W-N243F, S078R-P086W-Y209A, S078R-Y209A-K235F, T033S-A172V-Y209A, T033S-G118R, T033S-G118R-G159D-Y209A, T033S-G118R-N243F, T033S-G118R-W241R, T033S-G118R-Y209A-N243F, T033S-K235F, T033S-P086W-G118R, T033S-P086W-G118R-Y209A-N243F, T033S-P086W-N243F, T033S-S078R-P086W, T033S-S078R-P086W-G118R-Y209A, T033S-S078R-Y209A, T033S-Y209A-N243F, Y209A-W241R, A001R-S009A-N043R, A001R-S101G-S103A-V104I-A232V-Q245R, A001T-N018R-S024R-N076D-N116A-T213A-H249R, A194F-G211Q-Q236N, E089I-N116A-N117F-T224A-H249R, G020R-G025R-N116A-Y167W, G020R-H249R-N269R, G020R-N043D-N076D-A230E-H249R, G020R-N043D-S078R-S101G-S103A-V104I-A232V-Q245R, G020R-N043D-S101G-S103A-V104I-A232V-Q245R, G020R-N043D-S101G-S103A-V104I-A232V-Q245R-N269R, G020R-N043R-A230E, G020R-N043R-A230E-S242R, G020R-N043R-E271L, G020R-N043R-H249R, G020R-N043R-H249R-E271L, G020R-N043R-N269R, G020R-N043R-R045T-A230E, G020R-N043R-R045T-S101A-N269R, G020R-N043R-R045T-S242R, G020R-N043R-S101A-N116A-T213A-A215F, G020R-N043R-S101A-N269R, G020R-N043R-S101G-S103A-V104I-A232V-Q245R, G020R-N043R-S212F, G020R-N043R-S212F-W241R, G020R-N043R-S242R, G020R-N043R-S242R-E271L, G020R-N043R-S242R-H249R, G020R-N043R-V244R, G020R-N043R-W241R, G020R-N062Q-E089I-R186K-S212M, G020R-N076D, G020R-N076D-S101G-S103A-V104I-A232V-Q245R, G020R-N076D-S101G-S103A-V104I-A232V-Q245R-N269R, G020R-N116A-N269R, G020R-P052N-N062Q-Y091F-Y192W, G020R-Q059A-S144R-Y192W-T224A, G020R-S024R-K27E-N043R-N076D-A230E, G020R-S024R-N043D-H249R, G020R-S024R-N043D-N076D-S078R-S101G-S103A-V104I-A232V-Q245R, G020R-S024R-N043D-S242R, G020R-S024R-N043R-R045T, G020R-S024R-N043R-R045T-H249R, G020R-S024R-N043R-R045T-N116A, G020R-S024R-N043R-R045T-N116A-T213A, G020R-S024R-N043R-R045T-S101A-N269R, G020R-S024R-N043R-R045T-S101A-T213A, G020R-S024R-N043R-S242R, G020R-S024R-N076D-H249R, G020R-S024R-N116A, G020R-S024R-N116A-A215F, G020R-S024R-N116A-T213A, G020R-S024R-N116A-T213A-A215F, G020R-S024R-P052N-Q059A-S216F, G020R-S024R-R045T-A230E-S242R, G020R-S024R-R045T-N116A-N269R, G020R-S024R-R045T-N269R, G020R-S024R-S101A-A215F, G020R-S024R-S101A-N116A, G020R-S024R-S101G-S103A-V104I-L217E-A232V-Q245R-H249R, G020R-S024R-S242R-H249R, G020R-S024R-T213A, G020R-S024R-T213A-A215F, G020R-S078R-

S101A-S103A-V104I-N116A-N183D-T213A-A232V-Q245R, G020R-S078R-S101G-A232V-Q245R, G020R-S078R-S101G-S103A-V104I-A215F-A232V-Q245R, G020R-S078R-S101G-S103A-V104I-G211Q-T213A-A215F-A232V-Q245R, G020R-S078R-S101G-S103A-V104I-N116A-A232V-Q245R, G020R-S078R-S101G-S103A-V104I-N116A-G211Q-A232V-Q245R, G020R-S078R-S101G-S103A-V104I-N116A-N183D-A232V-Q245R, G020R-S087D-S101G-S103A-V104I-A232V-Q245R, G020R-S101A-N116A-N269R, G020R-S101A-S103A-V104I-A215F-A232V-Q245R, G020R-S101A-S103A-V104I-G118R-A232V-Q245R, G020R-S101A-S103A-V104L-A232V-Q245R, G020R-S101A-S103A-V104V-A232V-Q245R, G020R-S101A-S103S-V104I-A232V-Q245R, G020R-S101A-S103S-V104V-A232V-Q245R, G020R-S101G-I198L-A215F-A232V-Q245R, G020R-S101G-S103A-A232V-Q245R, G020R-S101G-S103A-V104I-A215F-A232V-Q245R, G020R-S101G-S103A-V104I-A232V-Q245R, G020R-S101G-S103A-V104I-A232V-Q245R-N269R, G020R-S101G-S103A-V104I-G211Q-T213A-A215F-A232V-Q245R, G020R-S101G-S103A-V104I-N116A-A215F-A232V-Q245R, G020R-S101G-S103A-V104I-T213A-A215F-A232V-Q245R, G020R-S101G-S103A-V104I-V150L-A232V-Q245R, G020R-S101G-S103A-V104L-A232V-Q245R, G020R-S101G-S103A-V104V-A232V-Q245R, G020R-S101G-S103G-V104I-A232V-Q245R, G020R-S101G-S103S-V104I-A232V-Q245R, G020R-S101G-S103S-V104L-A232V-Q245R, G020R-S101G-V104I-T213A-A215F-A232V-Q245R, G020R-S101S-S103A-V104I-A232V-Q245R, G020R-S101S-S103A-V104V-A232V-Q245R, G020R-S101S-S103G-V104I-A232V-Q245R, G020R-S101S-S103G-V104V-A232V-Q245R, G020R-S101S-S103S-V104I-A232V-Q245R, G020R-S101S-S103S-V104L-A232V-Q245R, G020R-S101S-S103S-V104V-A232V-Q245R, G020R-S103N-S216F-Q236N-N252R, G020R-S144R-N185I-L233C-Q236N, G020R-S212F-H249R, G020R-S242R-N269R, G020R-T022R-E271L, G020R-T022R-N043R, G020R-T022R-N043R-S212F, G020R-T022R-N043R-W241R, G020R-T022R-S024R-S242R, G020R-T022R-S078R-S242R, G020R-T022R-S078R-W241R, G020R-T022R-S212F-W241R, G020R-T022R-S242R, G020R-T022R-W241R, G020R-T022W-S078R-S101A-S103A-V104I-N116A-N183D-A215F-A232V-Q245R, G020R-T022W-S078R-S101A-S103A-V104I-N116A-N183D-A232V-Q245R, G020R-T022W-S078R-S101A-S103A-V104I-N116A-N183D-T213A-A232V-Q245R, G020R-T022W-S078R-S101A-S103A-V104I-N116S-T213A-A215F-A232V-Q245R, G020R-T022W-S078R-S101G-S103A-V104I-N116A-A232V-Q245R, G020R-T022W-S078R-S101G-S103A-V104I-N116A-N183D-A232V-Q245R, G020R-T022W-S078R-S101G-S103A-V104I-N116A-N183D-G211Q-A232V-Q245R, G020R-T022W-S078R-S101G-S103A-V104I-N116A-N183D-T213A-A232V-Q245R, G020R-T022W-S078R-S101G-S103A-V104I-N116A-T213A-A215F-A232V-Q245R, G020R-T022W-S101A-S103A-V104I-G211Q-A215F-A232V-Q245R, G020R-T022W-S101G-S103A-V104I-A232V-Q245R, G020R-T022W-S101G-S103A-V104I-G211Q-A232V-Q245R, G020R-T022W-S101G-S103A-V104I-I198L-G211Q-T213A-A232V-Q245R, G020R-T022W-S101G-S103A-V104I-N116A-N183D-T213A-A232V-Q245R, G020R-T038A-N043R-S101A, G020R-T22W-S078R-S101A-S103A-V104I-N116A-N183D-A232V, G020R-T22W-S078R-S101G-S103A-V104I-N116A-N183D-A232V-Q245R, G020R-T22W-S078R-S101G-S103A-V104I-N116A-T213A-A215F-A232V-Q245R, G020R-T22W-S101A-S103A-V104I-A215F-A232V-Q245R, G020R-T22W-S101A-S103A-V104I-A232V-Q245R, G020R-T22W-S101A-S103A-V104I-G211Q-T213A-A232V-Q245R, G020R-T22W-S101G-S103A-V104I-A232V-Q245R, G020R-T22W-S101G-S103A-V104I-G211Q-A232V-Q245R, G020R-T22W-S103A-V104I-A232V-Q245R, G023A-P052N-S144R-Y192W-S216F, G023A-P052N-Y192W-I198L-N252R, G023A-S024R-N117F-S212M-S216F, G023A-S078R-S216F-Q236N-H249R, G023A-Y091F-S101A-I198L-N252R, G023A-Y091F-V121F-Y192W-Q236N, G025R-E089I-N116A-P239S-A270C, G025R-G046R-V121F, G025R-N043A-E089I-N117F, G025R-S103N-R186K-A194F-T224A, G046R-A194F-S212M, G046R-E089I-Y091F-S101A-N116A, G046R-E089I-Y192W-L233C-A270C, G046R-N183D-N238L, G046R-Q059A-S103N-G211Q-S212M, G046R-Q059A-S106G-L217E-H249R, L148I-T213A-N252R, N018R-G020R-N043D, N018R-G020R-N043D-A230E-S242R, N018R-G020R-N043D-N076D-S101G-S103A-V104I-A232V-Q245R, N018R-G020R-N043D-R045T-A230E, N018R-G020R-N043R-N076D-H249R, N018R-G020R-N043R-N076D-S242R-H249R, N018R-G020R-N043R-R045T-S242R, N018R-G020R-N076D-S101G-S103A-V104I-A232V-Q245R, N018R-G020R-R045T, N018R-G020R-S024R-N043D-R045T-L233I-S242R, N018R-G020R-S024R-N043R-R045T-N076D-A230E, N018R-G020R-S024R-N076D-S087D-H249R, N018R-G020R-S024R-N076D-V150L-H249R, N018R-G020R-S024R-R045T-N076D-S101G-S103A-V104I-A232V-Q245R-N269R, N018R-N043D-N076D-S101G-S103A-V104I-A232V-Q245R-N269R, N018R-N043D-S078R-S101G-S103A-V104I-A232V-Q245R, N018R-N043D-S078R-S101G-S103A-V104I-L217E-A232V-Q245R, N018R-N043D-S101G-S103A-V104I-A232V-Q245R, N018R-N043D-S101G-S103A-V104I-A232V-Q245R-H249R, N018R-N043D-S101G-S103A-V104I-A232V-Q245R-N269R, N018R-N043R-N076D-A230E, N018R-N043R-R045T-H249R, N018R-N043R-R045T-S101G-S103A-V104I-A232V-Q245R, N018R-N043R-R045T-S242R-H249R, N018R-N043R-S101G-S103A-V104I-A232V-Q245R, N018R-N043R-S101G-S103A-V104I-A232V-Q245R-N269R, N018R-N043R-S242R-H249R, N018R-N076D-S078R-S101G-S103A-V104I-A232V-Q245R, N018R-N076D-S101G-V104I-A232V-Q245R, N018R-Q245R, N018R-R045T-N076D-S078R-S101G-S103A-V104I-A232V-Q245R, N018R-R045T-N076D-S101G-S103A-V104I-A232V-Q245R-N269R, N018R-R045T-S078R-S101G-S103A-V104I-A232V-Q245R, N018R-R045T-S101G-S103A-V104I-A232V-Q245R, N018R-S024R-N043D-A230E, N018R-S024R-N043D-N076D-H249R, N018R-S024R-N043D-N076D-H249R-N269R, N018R-S024R-N043D-N076D-S078R-H249R, N018R-S024R-N043D-R045T-H249R, N018R-S024R-N043D-S101G-S103A-V104I-A232V-Q245R, N018R-S024R-N043D-S101G-S103A-V104I-A232V-Q245R-N269R, N018R-S024R-N043R-N076D-H249R, N018R-S024R-N043R-N076D-H249R-N269R, N018R-S024R-N043R-N076D-S087D-H249R, N018R-S024R-N043R-N076D-V150L-H249R, N018R-S024R-N076D-G211Q-A215F-H249R, N018R-S024R-N076D-G211Q-T213A-A215F-H249R, N018R-S024R-N076D-G211Q-T213A-H249R, N018R-S024R-N076D-H249R, N018R-S024R-N076D-H249R-N269R, N018R-S024R-N076D-N116A-A215F-H249R, N018R-S024R-N076D-N116A-G211Q-A215F-H249R, N018R-S024R-N076D-N116A-G211Q-H249R, N018R-S024R-N076D-N116A-T213A-A215F-H249R,

N018R-S024R-N076D-S078R-H249R, N018R-S024R-N076D-S078R-S087D-H249R, N018R-S024R-N076D-S078R-V150L-H249R, N018R-S024R-N076D-S087D-H249R-N269R, N018R-S024R-N076D-S087D-S242R-H249R, N018R-S024R-N076D-S087D-V150L-H249R, N018R-S024R-N076D-S101A-A215F-H249R, N018R-S024R-N076D-S101A-G211Q-T213A-A215F-H249R, N018R-S024R-N076D-S101A-I198L-G211Q-A215V-H249R, N018R-S024R-N076D-S101A-I198L-G211Q-T213A-H249R, N018R-S024R-N076D-S101A-N116A-G211Q-H249R, N018R-S024R-N076D-S101A-N116A-T213A-H249R, N018R-S024R-N076D-S101G-V104I-A232V-H249R, N018R-S024R-N076D-S242R-H249R, N018R-S024R-N076D-T213A-A215F-H249R, N018R-S024R-N076D-V104I-H249R, N018R-S024R-N076D-V150L-H249R, N018R-S024R-R045T-S242R, N018R-S024R-S101G-V104I, N018R-S024R-S101G-V104I-A232V, N018R-S024R-S242R, N018R-S024R-V104I-H249R, N018R-S024R-V244R, N018R-S078R-S101G-S103A-V104I-A232V-Q245R, N018R-S087D-S101G-S103A-V104I-A232V-Q245R, N018R-S101G-Q245R, N018R-S101G-S103A-H249R, N018R-S101G-S103A-Q245R, N018R-S101G-S103A-V104I-A232V-Q245R, N018R-S101G-S103A-V104I-V150L-A232V-Q245R, N018R-S101G-V104I-A232V-H249R, N018R-S101G-V104I-A232V-Q245R, N018R-S101G-V104I-H249R, N018R-S103A-A232V-H249R, N018R-S103A-V104I-H249R, N018R-T022R-S024R-N043D-N076D-H249R, N018R-T022R-S024R-N043R-N076D-H249R, N018R-T022R-S024R-N076D-H249R, N018R-T022R-S024R-N076D-S087D-H249R, N018R-T022R-S024R-N076D-V150L-H249R, N018R-T022W-S024R-N076D-N116A-G211Q-H249R, N018R-T022W-S024R-N076D-N116A-T213A-H249R, N018R-T022W-S024R-N076D-S101A-I198L-A215F-H249R, N018R-T022W-S024R-N076D-S101A-I198L-H249R, N018R-T022W-S024R-N076D-S101A-N116A-A232V-Q245R, N018R-T22K-N043D-S101G-S103A-V104I-A232V-Q245R, N018R-T22W-S024R-N076D-N116A-T213A-H249R, N018R-T22W-S024R-N076D-S101A-N116A-A232V-Q245R, N018R-V104I-A232V-H249R, N043A-N062Q-A194F-G211Q, N043A-T057R-N117F-S144R-N183D, N043D-N076D-S078R-S101G-S103A-V104I-A232V-Q245R-N269R, N043D-R045T-N076D-H249R, N043D-S078R-S101G-S103A-V104I-A232V-Q245R, N043D-S078R-S101G-S103A-V104I-A232V-Q245R-H249R, N043D-S101G-S103A-V104I-A232V-Q245R-N269R, N043R-N076D-S078R-S101G-S103A-V104I-A232V-Q245R, N043R-N076D-S101G-S103A-V104I-A232V-Q245R, N043R-N076D-S101G-S103A-V104I-A232V-Q245R-N269R, N043R-N076D-S242R-H249R, N043R-N116A-N269R, N043R-R045T-N076D-S078R-S101G-S103A-V104I-A232V-Q245R, N043R-R045T-S078R-S101G-S103A-V104I-A232V-Q245R, N043R-R045T-S101G-S103A-V104I-A232V-Q245R-N269R, N043R-S078R-S101G-S103A-V104I-A232V-Q245R, N043R-S087D-S101G-S103A-V104I-A232V-Q245R-N269R, N043R-S101A-N116A-A215F-N269R, N043R-S101A-N116A-N269R, N043R-S101A-N116A-T213A-A215F-N269R, N043R-S101A-N269R, N043R-S101A-T213A-N269R, N043R-S101G-S103A-V104I-A232V-Q245R, N043R-S101G-S103A-V104I-A232V-Q245R-E271L, N043R-S101G-S103A-V104I-A232V-Q245R-H249R, N043R-S101G-S103A-V104I-A232V-Q245R-N269R, N043R-S101G-S103A-V104I-A232V-S242R-Q245R, N043R-S101G-S103A-V104I-V150L-A232V-Q245R, N043R-S242R-H249R, N043R-T213A-A215F-N269R, N062Q-S103N-N117F-A194F, N062Q-S103N-V121F-S144R-H249R, N076D-S078R-S101G-S103A-V104I-A232V-Q245R, N076D-S078R-S101G-S103A-V104I-A232V-Q245R-N269R, N076D-S101G-S103A-V104I-A232V-Q245R, N076D-S101G-S103A-V104I-A232V-Q245R-N269R, N076D-S103A-V104I-Q109R, N076D-S103A-V104I-Q109R-Q245R, N076D-S103A-V104I-S212P-E271V, N076D-S103A-V104I-S212P-Q245L-E271V, N076D-S87R-S103A-V104I-S212P-E271V, N117F-A194F-T213A-A270C, N117F-T213A-A215F, P052N-S078R-S103N-L148I-T213A, P052N-S103N-N116A-L148I-Y192W, R019H-G020R-T022W-S078R-S101G-S103A-V104I-G211Q-A232V-Q245R, R045T-N076D-S078R-S101G-S103A-V104I-A232V-Q245R-N269R, R045T-S078R-S101G-S103A-V104I-A232V-Q245R, R045T-S078R-S101G-S103A-V104I-A232V-Q245R-N269R, S009A-G020R-N043R-S212F, S009A-G020R-N043R-W241R, S009A-G020R-S024R-N043R, S009A-N043R-S078R, S009A-N043R-S078R-S242R, S009A-N043R-S212F, S009A-N043R-W241R, S009A-T022R-N043R-S078R, S009A-T022R-S078R-S212F, S009A-T022R-S078R-S212F-W241R, S009A-T022-S212F-W241R, S024R-A215F-N269R, S024R-A232V-Q245R, S024R-G025R-N183D-Y192W-P239S, S024R-N043R-N117F-A194F-G211Q, S024R-N043D-H249R, S024R-N043D-S101G-S103A-V104I-A232V-Q245R-H249R, S024R-N043D-S101G-S103A-V104I-A232V-Q245R-N269R, S024R-N043R-A215F, S024R-N043R-A230E, S024R-N043R-A230E-S242R, S024R-N043R-H249R, S024R-N043R-N076D-H249R, S024R-N043R-N076D-S078R-S101G-S103A-V104I-A232V-Q245R, S024R-N043R-N076D-S101G-S103A-V104I-A232V-Q245R, S024R-N043R-N116A-A215F, S024R-N043R-N116A-A215F-N269R, S024R-N043R-N116A-N269R, S024R-N043R-N116A-T213A-N269R, S024R-N043R-R045T-N076D-A230E-H249R, S024R-N043R-R045T-N269R, S024R-N043R-R045T-S101A-N116A-A215F-N269R, S024R-N043R-R045T-S101A-N116A-T213A-N269R, S024R-N043R-R045T-S242R, S024R-N043R-R045T-T213A-A215F-N269R, S024R-N043R-S101A-A215F, S024R-N043R-S101A-A215F-N269R, S024R-N043R-S101A-N116A, S024R-N043R-S101A-N116A-A215F-N269R, S024R-N043R-S101G-S103A-V104I-A232V-Q245R, S024R-N043R-S242R, S024R-N062Q-V104L-S106G-H249R, S024R-N076D-S078R-S101G-S103A-V104I-A232V-Q245R-N269R, S024R-N076D-V104I-A232V-Q245R, S024R-N116A-T213A-N269R, S024R-R045T, S024R-R045T-N076D-A230E-S242R-H249R, S024R-R045T-N076D-S078R-S101G-S103A-V104I-A232V-Q245R-N269R, S024R-R045T-S101G-S103A-V104I-A232V-Q245R-N269R, S024R-S078R-S212F, S024R-S078R-V104L-N116A-N183D, S024R-S087D-S101G-S103A-V104I-A232V-Q245R, S024R-S101A-H120E-A194F-H249R, S024R-S101A-N269R, S024R-S101G-S103A-V104I-A232V-Q245R, S024R-S101G-S103A-V104I-V150L-A232V-Q245R, S024R-S101G-V104I-Q245R, S024R-S103A-Q245R, S024R-S103A-V104I-A232V-H249R, S024R-S103A-V104I-H249R, S024R-S103A-V104I-Q245R, S024R-Y167W-T224A-H249R, S078R-S087D-S101G-S103A-V104I-A232V-Q245R, S078R-S101G-S103A-V104I-A232V-Q245R, S078R-S101G-S103A-V104I-A232V-Q245R-N269R, S078R-S101G-S103A-V104I-V150L-A232V-Q245R, S078R-S103N-S106G-Y167W-Q236N, S078R-V104L-T213A-A215F-T224A, S078R-Y091F-V121F-L233C-N252R, S087D-S101G-S103A-V104I-A232V-Q245R-N269R, S087R-S101G-S103A-V104I-Q109R-S212P-A232V-

Q245R-E271V, S099F-S144R-Y167W-N252R, S101A-H120E-Y192W-A215F-T224A, S101A-S103A-V104I-T213A-A232V-Q245R-N269R, S101G-S103A-V104I-A232V-Q245R, S101G-S103A-V104I-A232V-Q245R-E271L, S101G-S103A-V104I-A232V-Q245R-H249R, S101G-S103A-V104I-A232V-Q245R-N269R, S101G-S103A-V104I-A232V-Q245R-N269R, S101G-S103A-V104I-A232V-S242R-Q245R, S101G-S103A-V104I-A232V-V244R-Q245R, S101G-S103A-V104I-G115R-A232V-Q245R, S101G-S103A-V104I-N116A-T213A-A232V-Q245R-N269R, S101G-S103A-V104I-Q109R-A232V-Q245R, S101G-S103A-V104I-Q109R-S212P-A232V-Q245R, S101G-S103A-V104I-Q109R-S212P-A232V-Q245R-E271V, S101G-S103A-V104I-S212F-A232V-Q245R, S101G-S103A-V104I-V150L-A232V-Q245R-H249R, S101G-S103A-V104I-V150L-A232V-Q245R-N269R, S105T-S128N-S144R-L148I-S212M, S106G-N117F-N238L, S144R-G211Q-N238L-P239S-H249R, T022R-N043R-S101G-S103A-V104I-A232V-Q245R, T022R-N076D-S101G-S103A-V104I-A232V-Q245R, T022R-S087D-S101G-S103A-V104I-A232V-Q245R, T022R-S101G-S103A-V104I-A232V-Q245R, T022W-S078R-Y167W-S212M-A270C, T057R-E089I-I198L, T057R-S099F-S105T-I198L-T213A, T057R-S099F-V121F-N185I-Y192W, T057R-Y167W-H249R, V004R-G020R-H249R, V004R-G020R-N043R, V004R-G020R-S024R, V004R-G020R-S024R-H249R, V004R-G020R-S024R-N043R, V004R-G020R-S024R-N043R-S242R, V004R-G020R-S024R-V244R, V004R-N043R-S101G-S103A-V104I-A232V-Q245R, V004R-S009A-G020R-N043R, V004R-S009A-G020R-N043R-S242R, V004R-S009A-G020R-S024R-S242R, V004R-S009A-G020R-S242R, V004R-S009A-N043R-W241R, V004R-S009A-S024R-N043R-W241R, V004R-S009A-S078R-W241R, V004R-S009A-W241R, V004R-S101G-S103A-V104I-A232V-Q245R, V104L-L217E-T224A-H249R-N252R, V104L-T213A-S216F, V121F-N252R-A270C, and Y091F-S099F-S101A-S105T-Y167W, and wherein the total net charge of the protease variant is 0, +1, +2, +3, +4, +5, −1, −2, −3, −4, or −5 relative to the total net charge of the *Bacillus lentus* subtilisin GG36 protease, and wherein the total net charge is obtained by one or more substitutions selected from: N43D, R45T, N62E, N76D, S101D, P129E, A158E, G159D, G159E, S166D, S188D, A230E, N18R, G20K, G20R, T22R, S24R, N43R, G118R, Q245R, H249R, N269R, E271F, and E271L, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants comprising amino acid sequence which differs from the amino acid sequence of SEQ ID NO:2 wherein the protease variants are mature forms having proteolytic activity and comprise amino acid sequences comprising a combination of amino acid substitutions selected from: S101G-S103A-V104I-A232V-Q236H-Q245R-N252K, S101G-S103A-V104I-A232V-Q245R-N248R, S101G-S103A-V104I-G159R-A232V-Q245R-N248D, A232V-Q245R, E089I-N117F-N185I-A215F-L233C, G020R-E089I-L217E, G020R-G023A-V104L-Y192W-L233C, G020R-N043D-R045T-N076D-S242R-H249R, G020R-N043D-R045T-S078R-S101G-S103A-V104I-A232V-Q245R, G020R-N043D-S101G-S103A-V104I-A232V-Q245R-H249R, G020R-N043R-N076D-A230E-H249R, G020R-N043R-N076D-S101G-S103A-V104I-A232V-Q245R-N269R, G020R-N116A-A215F-N269R, G020R-R045T-N076D-S101G-S103A-V104I-A232V-Q245R, G020R-R045T-N076D-S101G-S103A-V104I-A232V-Q245R-H249R, G020R-R045T-N116A-N269R, G020R-R045T-S101G-S103A-V104I-A232V-Q245R, G020R-S024R-A215F, G020R-S024R-K27R-N043D-S242R-H249R, G020R-S024R-N043D-N076D-S078R-S101G-S103A-V104I-A232V-Q245R-N269R, G020R-S024R-N043R-N076D, G020R-S024R-N043R-R045T-A215F, G020R-S024R-N043R-R045T-N076D-S242R-H249R, G020R-S024R-N043R-R045T-N116A-T213A-A215F, G020R-S024R-N076D-S101G-S103A-V104I-A232V-Q245R, G020R-S024R-T381-N043R-R045T-N076D-S242R-H249R, G020R-S078R-S101A-S103A-V104I-A232V-Q245R, G020R-S078R-S101A-S103A-V104I-G211Q-T213A-A232V-Q245R, G020R-S078R-S101A-S103A-V104I-N116A-N183D-A232V-Q245R, G020R-S078R-S101A-S103A-V104I-N116A-N183D-G211Q-A232V-Q245R, G020R-S078R-S101A-S103A-V104I-N116A-N183D-G211Q-T213A-A215F-A232V-Q245R, G020R-S078R-S101A-S103A-V104I-N116A-N183D-G211Q-T213A-A232V-Q245R, G020R-S078R-S101A-S103A-V104I-N116A-N183D-I198L-A215F-A232V-Q245R, G020R-S078R-S101A-S103A-V104I-N183D-A215F-A232V-Q245R, G020R-S078R-S101G-S103A-V104I-N116A-A131V-N183D-T213A-A232V-Q245R, G020R-S078R-S101G-S103A-V104I-N116A-N183D-G211Q-T213A-A215F-A232V, G020R-S078R-S101G-S103A-V104I-N116A-N183D-G211Q-T213A-A215F-A232V-Q245R, G020R-S078R-S101G-S103A-V104I-N116A-N183D-T213A-A232V-Q245R, G020R-S078R-S101G-S103A-V104I-N183D-G211Q-T213A-A232V-Q245R-E271G, G020R-S078R-S101G-S103A-V104I-T180A-A232V-Q245R, G020R-S101A-S103A-V104I-N116A-N183D-G211Q-T213A-A215F-A232V-Q245R, G020R-S101A-S103A-V104I-N116A-N183D-T213A-A232V-Q245R, G020R-S101A-S103A-V104I-T213A-A215F-A232V-Q245R, G020R-S101A-S103G-V104V-A232V-Q245R, G020R-S101G-S103A-V104I-N116A-A232V-Q245R, G020R-S101G-S103A-V104I-N116A-G211Q-A232V-Q245R, G020R-S101G-S103A-V104I-N183D-G211Q-A232V-Q245R-, G020R-S103A-V104I-A232V-Q245R, G020R-S242R-H249R, G020R-T022W-S078R-S101A-S103A-V104I-A232V-Q245R, G020R-T022W-S078R-S101A-S103A-V104I-I198L-A232V-Q245R, G020R-T022W-S078R-S101A-S103A-V104I-N116A-N183D-G211Q-T213A-A215F-A232V-Q245R, G020R-T022W-S078R-S101A-S103A-V104I-N116A-N183D-T213A-A215F-A232V-Q245R, G020R-T022W-S078R-S101A-S103A-V104I-N183D-I198L-T213A-A215F-A232V-Q245R, G020R-T022W-S078R-S101G-S103A-V104I-G211Q-T213A-A232V-Q245R, G020R-T022W-S078R-S101G-S103A-V104I-N116A-N183D-A215F-A232V-Q245R, G020R-T022W-S101A-N116A-I198L-G211Q-T213A-A215F-H249R, G020R-T022W-S101A-S103A-V104I-A215F-A232V-Q245R, G020R-T022W-S101A-S103A-V104I-A232V-Q245R, G020R-T022W-S101A-S103A-V104I-G211Q-A232V-Q245R, G020R-T022W-S101A-S103A-V104I-G211Q-T213A-A232V-Q245R, G020R-T022W-S101A-S103A-V104I-I198L-G211Q-A215F-A232V-Q245R, G020R-T022W-S101A-S103A-V104I-N116A-G211Q-A215F-A232V-Q245R, G020R-T022W-S101A-S103A-V104I-N116A-G211Q-A232V-Q245R, G020R-T022W-S101A-S103A-V104I-N116A-G211Q-T213A-A215F-A232V-Q245R, G020R-T022W-

S101A-S103A-V104I-N116A-N183D-A232V-Q245R, G020R-T022W-S101A-S103A-V104I-N116A-N183D-G211Q-A232V-Q245R, G020R-T022W-S101A-S103A-V104I-N116A-N183D-G211Q-T213A-A232V-Q245R, G020R-T022W-S101G-S103A-V104I-A114T-T213A-A215F-A232V-Q245R, G020R-T022W-S101G-S103A-V104I-G211Q-T213A-A215F-A232V-Q245R, G020R-T022W-S101G-S103A-V104I-N116A-N183D-A215F-A232V-Q245R, G020R-T022W-S101G-S103A-V104I-N116A-N183D-G211Q-A215F-A232V-Q245R, G020R-T022W-S101G-S103A-V104I-N116A-N183D-I198L-A232V-Q245R, G020R-T022W-S101G-S103A-V104I-N116A-N183D-T213A-A215F-A232V-Q245R, G020R-T022W-S101G-S103A-V104I-N183D-I198L-T213A-A215F-A232V-Q245R, G020R-T022W-S103A-G211Q-T213A-A215F-A232V-Q245R, G020R-T022W-S103A-V104I-A232V-Q245R, G020R-T22W-S078R-S101A-S103A-V104I-N116A-N183D-A215F-A232V-Q245R, G020R-T22W-S078R-S101A-S103A-V104I-N116A-N183D-T213A-A232V-Q245R, G020R-T22W-S101A-S103A-V104I-G211Q-A215F-A232V-Q245R, G020R-T22W-S101A-S103A-V104I-N116A-G211Q-A215F-A232V-Q245R, G020R-T22W-S101A-S103A-V104I-N116A-G211Q-T213A-A215F-A232V-Q245R, G020R-T22W-S101G-S103A-V104I-N116A-N183D-A215F-A232V-Q245R, G020R-T22W-S101G-S103A-V104I-N116A-N183D-T213A-A215F-A232V-Q245R, G025R-N043A-Y091F-I198L-A270C, G025R-S105T-S128N-S144R-A270C, G046R-E089I-S099F-R186K-S212M, G118R-A172V, G118R-A194T, G118R-Y209A-K235F, H017Y-S024R-T033S-P086W, I008T-S024R, K027R-N043R-S101G-S103A-V104I-A232V-Q245R-N269R, K027R-R045T-N076D-S078R-S101G-S103A-V104I-A232V-Q245R-N269R, K235F-N243F, N018R-G020R-H249R, N018R-G020R-N043D-H249R, N018R-G020R-N043D-R045T-A230E-S242R, N018R-G020R-N043D-R045T-N076D-S242R, N018R-G020R-N043D-R045T-S240P, N018R-G020R-N043D-S078R-S101G-S103A-V104I-A232V-Q245R, N018R-G020R-N043D-S101G-S103A-V104I-A232V-Q245R, N018R-G020R-N043R, N018R-G020R-N043R-N076D, N018R-G020R-N043R-N076D-A230E-S242R, N018R-G020R-N043R-R045T-N076D-H249R, N018R-G020R-N043R-R045T-N076D-S101G-S103A-V104I-A232V-Q245R, N018R-G020R-N076D-S101G-S103A-V104I-A232V-Q245R-H249R, N018R-G020R-R045T-S101G-S103A-V104I-A232V-Q245R, N018R-G020R-S024R-N043D-N076D-S242R, N018R-G020R-S024R-N043D-R045T-S242R, N018R-G020R-S024R-N043R-N076D-H249R, N018R-G020R-S024R-N043R-R045T-N076D-H249R, N018R-G020R-S024R-N076D-A215F-H249R, N018R-G020R-S024R-N076D-G211Q-A215F-H249R, N018R-G020R-S024R-N076D-L217E-H249R, N018R-G020R-S024R-N076D-N116A-A215F-H249R, N018R-G020R-S024R-N076D-N116A-N183D-A215F-H249R, N018R-G020R-S024R-N076D-N116A-N183D-I198L-G211Q-H249R, N018R-G020R-S024R-N076D-N116A-N183D-T213A-A215F-H249R, N018R-G020R-S024R-N076D-N183D-H249R, N018R-G020R-S024R-N076D-S101A-N116A-N183D-I198L-H249R, N018R-G020R-S024R-N076D-S101A-N183D-G211Q-A215F-H249R, N018R-G020R-S101G-S103A-V104I-A232V-Q245R-H249R, N018R-G020R-T022W-S024R-N076D-N116A-N183D-I198L-T213A-H249R, N018R-G020R-T022W-S024R-N076D-S101A-N116A-N183D-H249R, N018R-G020R-T22W-S024R-N076D-N116A-N183D-I198L-T213A-H249R, N018R-N043D-N076D-S078R-S101G-S103A-V104I-A232V-Q245R, N018R-N043D-N076D-S078R-S101G-S103A-V104I-A232V-Q245R-N269R, N018R-N043D-N076D-S101G-S103A-V104I-A232V-Q245R-H249R, N018R-N043D-R045T-N076D-S242R-H249R, N018R-N043D-R045T-S078R-S101G-S103A-V104I-A232V-Q245R, N018R-N043D-R045T-S101G-S103A-V104I-A232V-Q245R, N018R-N043D-R045T-S101G-S103A-V104I-A232V-Q245R-N269R, N018R-N043D-S078R-S101G-S103A-V104I-A232V-Q245R-H249R, N018R-N043R-N076D-A230E-S242R-H249R, N018R-N043R-N076D-S101G-S103A-V104I-A232V-Q245R-N269R, N018R-N043R-N076D-S242R-H249R, N018R-N043R-R045T-N076D-A230E-S242R, N018R-N043R-R045T-N076D-S076T-S101G-S103A-V104I-A232V-Q245R-A273T, N018R-N043R-R045T-N076D-S101G-S103A-V104I-A232V-Q245R, N018R-N043R-R045T-N076D-S101G-S103A-V104I-A232V-Q245R-N269R, N018R-N043R-R045T-N076D-S242R, N018R-N043R-R045T-S242R, N018R-N076D-H249R, N018R-N076D-Q245R, N018R-N076D-S101G-A232V-Q245R, N018R-N076D-S101G-S103A-V104I-A232V-Q245R, N018R-N076D-S101G-S103A-V104I-A232V-Q245R-H249R, N018R-N076D-S101G-S103A-V104I-H249R, N018R-N076D-S101G-V104I-H249R, N018R-N076D-S103A-V104I-H249R, N018R-R045T-N076D-S101G-S103A-V104I-A232V-Q245R, N018R-S024R-N043D-A230E-H249R, N018R-S024R-N043D-A230E-S242R, N018R-S024R-N043D-H249R, N018R-S024R-N043D-N076D-S101G-S103A-V104I-A232V-Q245R, N018R-S024R-N043D-N076D-S242R-H249R, N018R-S024R-N043D-N076D-V150L-H249R, N018R-S024R-N043D-S242R, N018R-S024R-N043D-S242R-H249R, N018R-S024R-N043R-N076D-L217E-H249R, N018R-S024R-N043R-N076D-S078R-H249R, N018R-S024R-N043R-R045T-A230E-H249R, N018R-S024R-N076D, N018R-S024R-N076D-A232V-H249R, N018R-S024R-N076D-G211Q-H249R, N018R-S024R-N076D-I198L-G211Q-A215F-H249R, N018R-S024R-N076D-I198L-G211Q-T213A-H249R, N018R-S024R-N076D-I198L-T213A-A215F-H249R, N018R-S024R-N076D-I198M-G211Q-T213A-A215F-H249R, N018R-S024R-N076D-L088I-S101A-N116A-I198L-G211Q-A215F-H249R, N018R-S024R-N076D-N116A-G211Q-T213A-A215F-H249R, N018R-S024R-N076D-N116A-H249R, N018R-S024R-N076D-N116A-I198L-A215F-H249R, N018R-S024R-N076D-N116A-I198L-A215F-H249R-V268G, N018R-S024R-N076D-N116A-I198L-G211Q-T213A-A215F-H249R, N018R-S024R-N076D-N116A-I198L-G211Q-T213A-H249R, N018R-S024R-N076D-N116A-I198L-H249R, N018R-S024R-N076D-N116A-I198L-T213A-H249R, N018R-S024R-N076D-N116A-I198L-Y209H-T213A-H249R, N018R-S024R-N076D-N116A-M117I-N183D-T213A-H249R, N018R-S024R-N076D-N116A-N183D-G211Q-H249R, N018R-S024R-N076D-N116A-T213A-H249R, N018R-S024R-N076D-N183D-I198L-G211Q-T213A-A215F-H249R, N018R-S024R-N076D-N183D-T213A-A215F-H249R, N018R-S024R-N076D-S101A-G211Q-A215F-H249R, N018R-S024R-N076D-S101A-G211Q-H249R, N018R-S024R-N076D-S101A-H249R, N018R-S024R-N076D-S101A-I198L-A215F-H249R, N018R-S024R-N076D-S101A-I198L-G211Q-H249R, N018R-S024R-N076D-S101A-I198L-H249R, N018R-S024R-N076D-S101A-I198L-T213A-H249R, N018R-S024R-N076D-S101A-N116A-G211Q-T213A-H249R, N018R-S024R-N076D-S101A-N116A-I198L-G211Q-H249R, N018R-S024R-N076D-S101A-N116A-I198L-G211Q-T213A-H249R, N018R-S024R-N076D-S101A-N116A-I198L-

T213A-A215F-H249R, N018R-S024R-N076D-S101A-N116A-N183D-I198L-T213A-H249R, N018R-S024R-N076D-S101A-N116A-T213A-A215F-H249R, N018R-S024R-N076D-S101A-N183D-G211Q-H249R, N018R-S024R-N076D-S101A-N183D-T213A-H249R, N018R-S024R-N076D-S101G-A232V, N018R-S024R-N076D-S103A-A232V-Q245R, N018R-S024R-N076D-T213A-H249R, N018R-S024R-N076D-V104I, N018R-S024R-Q245R, N018R-S024R-R045T-A230E-S242R, N018R-S024R-R045T-N076D-S101G-S103A-V104I-A232V-Q245R-H249R, N018R-S024R-R045T-N076D-S101G-S103A-V104I-A232V-Q245R-N269R, N018R-S024R-S242R, N018R-S024R-V104I, N018R-S024R-V30S-L31S-D321-T33Q-G34V-135F, N018R-S078R-S101G-S103A-V104I-L217E-A232V-Q245R, N018R-S101G-S103A-V104I, N018R-S101G-S103A-V104I-A232V-Q245R-N269R, N018R-S101G-V104I, N018R-S103A, N018R-S103A-V104I-A232V, N018R-T022K-N043D-S101G-S103A-V104I-A232V-Q245R, N018R-T022W-S024R-N076D-G211Q-H249R, N018R-T022W-S024R-N076D-G211Q-T213A-H249R, N018R-T022W-S024R-N076D-I198L-A215F-H249R, N018R-T022W-S024R-N076D-I198L-G211Q-H249R, N018R-T022W-S024R-N076D-I198L-T213A-A215F-H249R, N018R-T022W-S024R-N076D-N116A-G211Q-A215F-H249R, N018R-T022W-S024R-N076D-N116A-G211Q-T213A-H249R, N018R-T022W-S024R-N076D-N116A-I198L-G211Q-T213A-H249R, N018R-T022W-S024R-N076D-N116A-I198L-T213A-H249R, N018R-T022W-S024R-N076D-N116A-T213A-A215F-H249R, N018R-T022W-S024R-N076D-S101A-A215F-H249R, N018R-T022W-S024R-N076D-S101A-G211Q-H249R, N018R-T022W-S024R-N076D-S101A-G211Q-T213A-H249R, N018R-T022W-S024R-N076D-S101A-I198L-G211Q-Q245R, N018R-T022W-S024R-N076D-S101A-I198L-G211Q-T213A-A215F-H249R, N018R-T022W-S024R-N076D-S101A-I198L-T213A-A215F-H249R, N018R-T022W-S024R-N076D-S101A-N116A-A215F-H249R, N018R-T022W-S024R-N076D-S101A-N116A-G211Q-H249R, N018R-T022W-S024R-N076D-S101A-N116A-G211Q-T213A-H249R, N018R-T022W-S024R-N076D-S101A-N116A-I198L-A215F-H249R, N018R-T022W-S024R-N076D-S101A-N116A-I198L-G211Q-H249R, N018R-T022W-S024R-N076D-S101A-N116A-I198L-G211Q-T213A-A215F-H249R, N018R-T022W-S024R-N076D-S101A-N116A-I198L-G211Q-T213A-H249R, N018R-T022W-S024R-N076D-S101A-N116A-I198L-H249R, N018R-T022W-S024R-N076D-S101A-N116A-I198L-T213A-A215F-H249R, N018R-T022W-S024R-N076D-S101A-N116A-I198L-T213A-H249R, N018R-T022W-S024R-N076D-S101A-T213A-A215F-H249R, N018R-T022W-S024R-N076D-S101A-T213A-H249R, N018R-T022W-S024R-N076D-T213A-A215F-H249R, N018R-T22W-S024R-N076D-I198L-A215F-H249R, N018R-T22W-S024R-N076D-N116A-G211Q-H249R, N018R-T22W-S024R-N076D-N116A-G211Q-T213A-H249R, N018R-T22W-S024R-N076D-N116A-T213A-A215F-H249R, N018R-T22W-S024R-N076D-S101A-A215F-H249R, N018R-T22W-S024R-N076D-S101A-G211Q-T213A-H249R, N018R-T22W-S024R-N076D-S101A-I198L-A215F-H249R, N018R-T22W-S024R-N076D-S101A-I198L-T213A-A215F-H249R, N018R-T22W-S024R-N076D-S101A-N116A-A215F-H249R, N018R-T22W-S024R-N076D-S101A-N116A-I198L-A215F-H249R, N018R-T22W-S024R-N076D-T213A-A215F-H249R, N018R-V104I, N043D-N076D-S078R-S101G-S103A-V104I-A232V-Q245R, N043D-N076D-S101G-S103A-V104I-A232V-Q245R-N269R, N043D-S078R-S101G-S103A-V104I-A232V-Q245R-N269R-A272V, N043D-S078R-S101G-S103A-V104I-A232V-Q245R-N269R-R275S, N043D-S101G-S103A-V104I-A232V-Q245R, N043D-S101G-S103A-V104I-A232V-Q245R-H249R, N043R-N076D-S078R-S101G-S103A-V104I-A232V-Q245R-N269R, N043R-N076D-S101G-S103A-V104I-A232V-Q245R-H249R, N043R-N076D-S101G-S103A-V104I-L217E-A232V-Q245R, N043R-R045T-N076D-S078R-S101G-S103A-V104I-A232V-Q245R-N269R, N043R-R045T-N076D-S078R-S101G-S103A-V104I-A232V-V234I-Q245R, N043R-R045T-N076D-S101G-S103A-V104I-A232V-Q245R-N269R, N043R-R045T-S078R-S101G-S103A-V104I-N218S-A232V-Q245R, N043R-R045T-S101G-S103A-V104I-A232V-Q245R, N043R-S078R-S101G-S103A-V104I-A232V-Q245R-N269R, N043R-S087D-S101G-S103A-V104I-A232V-Q245R, N062Q-S101A-Q236N-N252R-A270C, N076D-S078R-S101G-S103A-V104I-A232V-Q245R-H249R, N076D-S101G-S103A-V104I-A232V-Q245R-H249R, N076D-S101G-S103A-V104I-A232V-S242R-Q245R, P005S-S024R-T033S-N243F, P014L-G020R-S024R-N043R-R045T-S101A-A215F, P052N-V104L-N183D-S216F-H249R, P086W-G118R, P086W-N243F, P086W-Y209A, Q012H-G020R-S078R-S101G-S103A-V104I-I198L-G211Q-T213A-A232V-Q245R, R045T-N076D-S078R-S101G-S103A-V104I-A232V-Q245R, R045T-N076D-S101G-S103A-V104I-A232V-Q245R-N269R, R045T-S078R-S101G-S103A-V104I-A232V-Q245R-H249R, R045T-S101G-S103A-V104I-A232V-Q245R-N269R, R045T-S242R-H249R, S024C-T033S, S024R-A232V, S024R-G046R-Y091F-V121F, S024R-G118R-K235F, S024R-N043A-S105T-S106G-I198L, S024R-N043D-R045T-S242R-H249R, S024R-N043D-S101G-S103A-V104I-A232V-Q245R, S024R-N043D-S242R-H249R, S024R-N043R-N076D, S024R-N043R-N076D-A230E-S242R, S024R-N043R-N076D-S101G-S103A-V104I-A232V-Q245R-N269R, S024R-N043R-R045T-N076D-S078R-S101G-S103A-V104I-A232V-Q245R, S024R-N043R-R045T-N076D-S101G-S103A-V104I-A232V-Q245R, S024R-N043R-R045T-S242R-H249R, S024R-N043R-S101A-T213A, S024R-N076D-Q245R, S024R-N076D-S101G-A232V-Q245R, S024R-N076D-S101G-M175L-A232V-Q245R, S024R-N076D-S101G-Q245R, S024R-N076D-S101G-S103A-V104I-A232V-Q245R, S024R-N076D-S103A-V104I-Q245R, S024R-N076D-V104I-Q245R, S024R-N243F, S024R-P086R-G118R, S024R-P086W-Y209A-K235F, S024R-P239Q, S024R-Q245R-H249R, S024R-R045T-N076D-S101G-S103A-V104I-A232V-Q245R-N269R, S024R-S101G, S024R-S101G-Q245R, S024R-S101G-V104I-H249R, S024R-S103A-A232V, S024R-S103A-M175L-A232V-H249R, S024R-S141G, S024R-T033S, S024R-T033S-A194T, S024R-T033S-G118R-K235F, S024R-T033S-G118R-Y209A, S024R-T033S-K235F, S024R-T033S-S078R-G118R, S024R-T033S-S078R-N243F, S024R-T033S-Y209A, S024R-T033S-Y209A-N243F, S024R-T274I, S024R-V104I-H249R, S024R-V104I-Q245R, S024R-Y091F-I198L-A215F-P239S, S024R-Y209A, S024R-Y209A-K235F, S024R-Y209A-S242P, S078R-P086W, S078R-S099F-N116A-R186K-T224A, S078R-S101G-S103A-V104I-A232V-Q245R-H249R, S101G-A232V, S101G-S103A-V104I-A232V-H249R, S101G-S103A-V104I-A232V-Q245R-H249R-N269R, S101G-S103A-V104I-Q245R, S105T-G211Q-S216F, S106G-N185I-S216F-Q236N, T022R-S101G-S103A-V104I-V150L-A232V-Q245R, T033S-G118D-A138V-Y209A, T033S-

G118R-Y209A-, T033S-L148F, T033S-N243F, T033S-P086W, T033S-P201S, T033S-S078R, T033S-W241R, T033S-Y209A, T033S-Y209A-K235F, V004M-N018R-S024R-N076D-N116A-I198L-G211Q-T213A-H249R, V104I-A232V-H249R, and V104L-H120E-R186K-S216F-N252R, and wherein the total net charge of the protease variant is 0, +1, +2, +3, +4, +5, −1, −2, −3, −4, or −5 relative to the total net charge of the *Bacillus lentus* subtilisin GG36 protease, and wherein the total net charge is obtained by one or more substitutions selected from: N43D, R45T, N62E, N76D, S101D, P129E, A158E, G159D, G159E, S166D, S188D, A230E, N18R, G20K, G20R, T22R, S24R, N43R, G118R, Q245R, H249R, N269R, E271F, and E271L, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants comprising amino acid sequence which differs from the amino acid sequence of SEQ ID NO:2 wherein the protease variants are mature forms having proteolytic activity and comprise amino acid sequences comprising a combination of amino acid substitutions selected from: A015T-T033S, A016T-N043R-R045T-N076D-S101G-S103A-V104I-A232V-Q245R-N269R, A230E-H249R, A232V-H249R, E089I-S105T-N116A-A215F-S216F, E089I-Y091F-N185I-G211Q-A270C, G020R-A090S-S101G-S103A-V104I-N116A-N183D-T213A-A215F-A232V-Q245R, G020R-N043D-S078R-S101G-S103A-V104I-A232V-Q245R-H249R, G020R-N043R-N076D, G020R-N043R-R045T-S078R-S101G-S103A-V104I-A232V-Q245R, G020R-P052N-S101A-I198L-L233C, G020R-R045T-N076D-S078R-S101G-S103A-V104I-A232V-Q245R-N269R, G020R-S024R-N043D-N076D-H249R, G020R-S024R-N043D-N076D-S242R-H249R, G020R-S024R-N043D-R045T-A230E-S242R, G020R-S024R-N043D-S078R-S101G-S103A-V104I-A232V-Q245R, G020R-S024R-N043D-S078R-S101G-S103A-V104I-A232V-Q245R-H249R, G020R-S024R-N043R-S101G-S103A-V104I-A232V-Q245R, G020R-S024R-N076D-S078R-S101G-S103A-V104I-A232V-Q245R-H249R, G020R-S024R-R045T-N076D-S101G-S103A-V104I-A232V-Q245R, G020R-S024R-R045T-N076D-S242R-H249R, G020R-S024R-R045T-S101G-S103A-V104I-A232V-Q245R, G020R-S078R-S101A-S103A-V104I-G115E-N116A-N183D-G211Q-T213A-A232V-Q245R, G020R-S101A-S103A-V104I-N116A-N183D-A215F-A232V-Q245R, G020R-S101A-S103A-V104I-N116A-N183D-A232V-Q245R, G020R-S101A-S103A-V104I-N116A-N183D-G211Q-A232V-Q245R, G020R-S101A-S103A-V104I-N116A-N183D-G211Q-A232V-Q245R-T274I, G020R-S101A-S103A-V104I-N116A-N183D-I198L-G211Q-T213A-A215F-A232V-Q245R, G020R-S101A-S103A-V104I-N116A-N183D-T213A-A215F-A232V-Q245R, G020R-S101A-S103A-V104I-T213A-A232V-Q245R, G020R-S101G-S103A-V104I-N116A-N183D-A232V-Q245R, G020R-S101G-S103A-V104I-N116A-N183D-G211Q-A215F-A232V-Q245R, G020R-S101G-S103A-V104I-N116A-N183D-G211Q-A232V-Q245R, G020R-S101G-S103A-V104I-N116A-N183D-G211Q-T213A-A215F-A232V-Q245R, G020R-S101G-S103A-V104I-N116A-N183D-G211Q-T213A-A232V-Q245R, G020R-S101G-S103A-V104I-N116A-N183D-T213A-A232V-Q245R, G020R-T022R-N269R, G020R-T022R-S078R-S212F-W241R, G020R-T022W-S101A-S103A-V104I-N116A-N183D-A215F-A232V-Q245R, G020R-T022W-S101A-S103A-V104I-N116A-N183D-A232V-Q245R-N269S, G020R-T022W-S101A-S103A-V104I-N116A-N183D-A232V-Q245R-T274I, G020R-T022W-S101A-S103A-V104I-N116A-N183D-G211Q-A215F-A232V-Q245R, G020R-T022W-S101A-S103A-V104I-N116A-N183D-I198L-G211Q-T213A-A215F-A232V-Q245R, G020R-T022W-S101A-S103A-V104I-N116A-N183D-T213A-A232V-Q245R, G020R-T022W-S101A-S103A-V104I-N183D-G211Q-T213A-A215F-A232V-Q245R, G020R-T022W-S101A-S103A-V104I-N183D-I198L-A215F-A232V-Q245R, G020R-T022W-S101A-S103A-V104I-N183D-T213A-A215F-A232V-Q245R, G020R-T022W-S101G-S103A-V104I-N116A-N183D-A232V-Q245R, G020R-T022W-S101G-S103A-V104I-N116A-N183D-G211Q-A232V-Q245R-N263S, G020R-T022W-S101G-S103A-V104I-N116A-N183D-G211Q-T213A-A215F-A232V-Q245R, G020R-T022W-S101G-S103A-V104I-N116A-N183D-G211Q-T213A-A232V-Q245R, G020R-T022W-S101G-S103A-V104I-N183D-A215F-A232V-Q245R, G020R-T022W-S101G-S103A-V104I-N183D-A232V-Q245R, G025R-N062Q-S128N-S144R-N185I, G025R-N116A-H120E-T224A-A270C, G118R-K235F, K027R-N043R-R045T-N076D-S101G-S103A-V104I-A232V-Q245R, N018K-N076D-S078R-S101G-S103A-V104I-L217E-A232V-Q245R-N269R, N018R-G020R-N043D-N076D-S078R-S101G-S103A-V104I-L217E-A232V-Q245R, N018R-G020R-N043D-N076D-S242R-H249R, N018R-G020R-N043D-R045T-N076D-H249R, N018R-G020R-N043D-R045T-N076D-S101G-S103A-V104I-A232V-Q245R, N018R-G020R-N043D-R045T-N076D-S101G-S103A-V104I-A232V-Q245R-N269R, N018R-G020R-N043D-S101G-S103A-V104I-A232V-Q245R-N269R, N018R-G020R-N043D-S101G-S103A-V104I-L217E-A232V-Q245R, N018R-G020R-N043R-R045T-H249R, N018R-G020R-N043R-R045T-N076D-A230E-H249R, N018R-G020R-N076D, N018R-G020R-R045T-N076D-S078R-S101G-S103A-V104I-A232V-Q245R, N018R-G020R-R045T-N076D-S101G-S103A-V104I-A232V-Q245R-H249R, N018R-G020R-R045T-S101G-S103A-V104I-A232V-Q245R-H249R, N018R-G020R-S024R-N043D-N076D-S078R-S101G-S103A-V104I-A232V-Q245R, N018R-G020R-S024R-N043D-N076D-S101G-S103A-V104I-A232V-Q245R-N269R, N018R-G020R-S024R-N043R-N076D, N018R-G020R-S024R-N076D-A131T-A215F-H249R, N018R-G020R-S024R-N076D-G211Q-H249R, N018R-G020R-S024R-N076D-G211Q-N243D-H249R, N018R-G020R-S024R-N076D-G211Q-T213A-A215F-H249R, N018R-G020R-S024R-N076D-G211Q-T213A-H249R, N018R-G020R-S024R-N076D-I198L-A215F-H249R, N018R-G020R-S024R-N076D-I198L-H249R, N018R-G020R-S024R-N076D-I198L-T213A-A215F-H249R, N018R-G020R-S024R-N076D-N116A-G211Q-T213A-A215F-H249R, N018R-G020R-S024R-N076D-N116A-H249R, N018R-G020R-S024R-N076D-N116A-I198L-G211Q-A215F-H249R-N269S, N018R-G020R-S024R-N076D-N116A-I198L-G211Q-A215F-Q245R, N018R-G020R-S024R-N076D-N116A-I198L-H249R, N018R-G020R-S024R-N076D-N116A-N183D-G211Q-A215F-H249R, N018R-G020R-S024R-N076D-N116A-N183D-G211Q-T213A-H249R, N018R-G020R-S024R-N076D-N116A-N183D-I198L-A215F-H249R, N018R-G020R-S024R-N076D-N116A-N183D-I198L-G211Q-A215F-H249R, N018R-G020R-S024R-N076D-N116A-N183D-I198L-G211Q-T213A-H249R, N018R-G020R-S024R-N076D-

N116A-N183D-I198L-H249R, N018R-G020R-S024R-N076D-N116A-N183D-T213A-H249R, N018R-G020R-S024R-N076D-N183D-A215F-H249R, N018R-G020R-S024R-N076D-N183D-G211Q-H249R, N018R-G020R-S024R-N076D-N183D-G211Q-T213A-A215F-H249R, N018R-G020R-S024R-N076D-N183D-G211Q-T213A-H249R, N018R-G020R-S024R-N076D-N183D-I198L-A215F-H249R, N018R-G020R-S024R-N076D-N183D-I198L-G211Q-A215F-H249R, N018R-G020R-S024R-N076D-N204D-T213A-H249R, N018R-G020R-S024R-N076D-S101A-G211Q-A215F-H249R-N269D, N018R-G020R-S024R-N076D-S101A-H249R, N018R-G020R-S024R-N076D-S101A-I198L-T213A-A215F-H249R, N018R-G020R-S024R-N076D-S101A-N116A-G211Q-T213A-A215F-H249R, N018R-G020R-S024R-N076D-S101A-N116A-G211Q-T213A-H249R, N018R-G020R-S024R-N076D-S101A-N116A-N183D-G211Q-A215F-H249R, N018R-G020R-S024R-N076D-S101A-N116A-N183D-G211Q-T213A-H249R, N018R-G020R-S024R-N076D-S101A-N116A-N183D-H249R, N018R-G020R-S024R-N076D-S101A-N116A-N183D-I198L-G211Q-A215F-H249R, N018R-G020R-S024R-N076D-S101A-N116A-N183D-I198L-T213A-H249R, N018R-G020R-S024R-N076D-S101A-N116A-N183D-T213A-H249R, N018R-G020R-S024R-N076D-S101A-N116A-T213A-A215F-H249R, N018R-G020R-S024R-N076D-S101A-N116A-T213A-H249R, N018R-G020R-S024R-N076D-S101A-N183D-G211Q-H249R, N018R-G020R-S024R-N076D-S101A-N183D-I198L-A215F-H249R, N018R-G020R-S024R-N076D-S101A-N183D-I198L-G211Q-T213A-H249R, N018R-G020R-S024R-N076D-S101A-N183D-I198L-T213A-H249R, N018R-G020R-S024R-N076D-S101A-N183D-T213A-A215F-H249R, N018R-G020R-S024R-R045T-N076D-S101G-S103A-V104I-A232V-Q245R, N018R-G020R-S024R-S101G-S103A-V104I-A232V-Q245R, N018R-G020R-T022W-S024R-N076D-I198L-T213A-H249R, N018R-G020R-T022W-S024R-N076D-N116A-I198L-H249R, N018R-G020R-T022W-S024R-N076D-N116A-I198L-T213A-A215F-H249R, N018R-G020R-T022W-S024R-N076D-N116A-N183D-G211Q-T213A-A215F-H249R, N018R-G020R-T022W-S024R-N076D-N116A-N183D-I198L-T213A-A215F-H249R, N018R-G020R-T022W-S024R-N076D-N116A-N183D-T213A-H249R, N018R-G020R-T022W-S024R-N076D-N183D-G211Q-T213A-H249R, N018R-G020R-T022W-S024R-N076D-N183D-I198L-G211Q-H249R, N018R-G020R-T022W-S024R-N076D-S101A-A215F-H249R, N018R-G020R-T022W-S024R-N076D-S101A-G211Q-A215F-H249R, N018R-G020R-T022W-S024R-N076D-S101A-G211Q-T213A-A215F-H249R, N018R-G020R-T022W-S024R-N076D-S101A-G211Q-T213A-H249R, N018R-G020R-T022W-S024R-N076D-S101A-I198L-A215F-H249R, N018R-G020R-T022W-S024R-N076D-S101A-I198L-G211Q-T213A-A215F-H249R, N018R-G020R-T022W-S024R-N076D-S101A-N116A-G211Q-H249R, N018R-G020R-T022W-S024R-N076D-S101A-N116A-H249R, N018R-G020R-T022W-S024R-N076D-S101A-N116A-I198L-G211Q-T213A-A215F-H249R, N018R-G020R-T022W-S024R-N076D-S101A-N116A-I198L-H249R, N018R-G020R-T022W-S024R-N076D-S101A-N116A-N183D-G211Q-H249R, N018R-G020R-T022W-S024R-N076D-S101A-N116A-N183D-G211Q-T213A-A215F-H249R, N018R-G020R-T022W-S024R-N076D-S101A-N116A-N183D-I198L-A215F-H249R, N018R-G020R-T022W-S024R-N076D-S101A-N116A-N183D-I198L-G211Q-A215F-H249R, N018R-G020R-T022W-S024R-N076D-S101A-N116A-N183D-I198L-G211Q-T213A-H249R, N018R-G020R-T022W-S024R-N076D-S101A-N116A-N183D-T213A-H249R, N018R-G020R-T022W-S024R-N076D-S101A-N116A-T213A-H249R, N018R-G020R-T022W-S024R-N076D-S101A-N183D-A215F-H249R, N018R-G020R-T022W-S024R-N076D-S101A-N183D-G211Q-A215F-H249R, N018R-G020R-T022W-S024R-N076D-T213A-H249R, N018R-N043D-A230E-H249R, N018R-N043D-N076D-S078R-S101G-S103A-V104I-A232V-Q245R-H249R, N018R-N043D-N076D-S242R-H249R, N018R-N043D-R045T-N076D-S078R-S101G-S103A-V104I-A232V-Q245R-N269R, N018R-N043D-R045T-N076D-S101G-S103A-V104I-A232V-Q245R-N269R, N018R-N043D-R045T-S078R-S101G-S103A-V104I-A232V-Q245R-A272D, N018R-N043R-N076D-A230E-H249R, N018R-N043R-N076D-S242R, N018R-N043R-R045T-A230E-S242R, N018R-N043R-R045T-S078R-S101G-S103A-V104I-L217E-A232V-Q245R, N018R-N043R-S078R-S101G-S103A-V104I-A232V-Q245R, N018R-N043R-S101G-S103A-V104I-A232V-Q245R-H249R, N018R-N076D-A232V-H249R, N018R-N076D-S078R-S101G-S103A-V104I-L217E-A232V-Q245R, N018R-N076D-S101G-I198T-A232V, N018R-N076D-S101G-S103A-V104I-Q245R, N018R-N076D-S101G-V104I, N018R-N076D-S242R, N018R-N076D-S242R-H249R, N018R-N076D-V104I-Q245R-H249R, N018R-R045T-H249R, N018R-R045T-S101G-S103A-V104I-A232V-Q245R-H249R, N018R-R045T-S101G-S103A-V104I-A232V-Q245R-N269R, N018R-S024R-N043D-N076D-S087D-H249R, N018R-S024R-N043D-N076D-S242R, N018R-S024R-N076D-A086V-S101A-N183D-I198L-G211Q-H249R, N018R-S024R-N076D-A215F-H249R, N018R-S024R-N076D-A232V, N018R-S024R-N076D-I198L-A215F-H249R, N018R-S024R-N076D-I198L-G211Q-H249R, N018R-S024R-N076D-I198L-G211Q-T213A-A215F-H249R, N018R-S024R-N076D-I198L-H249R, N018R-S024R-N076D-I198L-T213A-H249R, N018R-S024R-N076D-L217E-H249R-N269R, N018R-S024R-N076D-N116A-A150T-T213A-H249R, N018R-S024R-N076D-N116A-G211Q-T213A-H249R, N018R-S024R-N076D-N116A-I198L-G211Q-H249R, N018R-S024R-N076D-N116A-I198L-T213A-A215F-H249R, N018R-S024R-N076D-N116A-N183D-A215F-H249R, N018R-S024R-N076D-N116A-N183D-G211Q-A215F-H249R, N018R-S024R-N076D-N116A-N183D-G211Q-T213A-A215F-H249R, N018R-S024R-N076D-N116A-N183D-G211Q-T213A-H249R, N018R-S024R-N076D-N116A-N183D-H249R, N018R-S024R-N076D-N116A-N183D-I198L-A215F-H249R, N018R-S024R-N076D-N116A-N183D-I198L-G211Q-A215F-H249R, N018R-S024R-N076D-N116A-N183D-I198L-G211Q-H249R, N018R-S024R-N076D-N116A-N183D-I198L-G211Q-T213A-A215F-H249R, N018R-S024R-N076D-N116A-N183D-I198L-G211Q-T213A-H249R, N018R-S024R-N076D-N116A-N183D-I198L-H249R, N018R-S024R-N076D-N116A-N183D-I198L-T213A-H249R, N018R-S024R-N076D-N116A-N183D-T213A-A215F-H249R, N018R-S024R-N076D-N116A-N183D-T213A-H249R, N018R-S024R-N076D-N183D-A215F-H249R, N018R-S024R-N076D-N183D-G211Q-H249R, N018R-S024R-N076D-N183D-G211Q-T213A-A215F-H249R, N018R-S024R-N076D-N183D-G211Q-T213A-H249R, N018R-S024R-N076D-N183D-H249R, N018R-S024R-N076D-N183D-H249R-A248T, N018R-S024R-N076D-N183D-I198L-A215F-H249R, N018R-S024R-N076D-N183D-I198L-G211Q-A215F-H249R, N018R-S024R-N076D-N183D-I198L-G211Q-H249R, N018R-S024R-N076D-

N183D-I198L-H249R, N018R-S024R-N076D-N183D-I198L-T213A-A215F-H249R, N018R-S024R-N076D-N183D-I198L-T213A-H249R, N018R-S024R-N076D-N183D-T213A-H249R, N018R-S024R-N076D-S087D-H249R, N018R-S024R-N076D-S101A-G211Q-T213A-A215F-H249R-A270V, N018R-S024R-N076D-S101A-G211Q-T213A-H249R, N018R-S024R-N076D-S101A-I198L-G211Q-A215F-H249R, N018R-S024R-N076D-S101A-N116A-G211Q-A215F-H249R, N018R-S024R-N076D-S101A-N116A-G211Q-T213A-A215F-H249R, N018R-S024R-N076D-S101A-N116A-H249R, N018R-S024R-N076D-S101A-N116A-I198L-G211Q-A215F-H249R, N018R-S024R-N076D-S101A-N116A-I198L-H249R, N018R-S024R-N076D-S101A-N116A-I198L-T213A-H249R, N018R-S024R-N076D-S101A-N116A-N183D-A215F-H249R, N018R-S024R-N076D-S101A-N116A-N183D-G211Q-A215F-H249R, N018R-S024R-N076D-S101A-N116A-N183D-G211Q-H249R, N018R-S024R-N076D-S101A-N116A-N183D-G211Q-T213A-A215F-H249R, N018R-S024R-N076D-S101A-N116A-N183D-G211Q-T213A-H249R, N018R-S024R-N076D-S101A-N116A-N183D-H249R, N018R-S024R-N076D-S101A-N116A-N183D-I198L-G211Q-T213A-H249R, N018R-S024R-N076D-S101A-N116A-N183D-I198L-H249R, N018R-S024R-N076D-S101A-N116A-N183D-I198L-T213A-A215F-H249R, N018R-S024R-N076D-S101A-N116A-N183D-T213A-A215F-H249R, N018R-S024R-N076D-S101A-N116A-N183D-T213A-H249R, N018R-S024R-N076D-S101A-N183D-A215F-H249R, N018R-S024R-N076D-S101A-N183D-G211Q-T213A-A215F-H249R, N018R-S024R-N076D-S101A-N183D-H249R, N018R-S024R-N076D-S101A-N183D-I198L-A215F-H249R, N018R-S024R-N076D-S101A-N183D-I198L-G211Q-H249R, N018R-S024R-N076D-S101A-N183D-I198L-G211Q-T213A-A215F-H249R, N018R-S024R-N076D-S101A-N183D-I198L-G211Q-T213A-H249R, N018R-S024R-N076D-S101A-N183D-I198L-H249R, N018R-S024R-N076D-S101A-N183D-I198L-T213A-A215F-H249R, N018R-S024R-N076D-S101A-N183D-I198L-T213A-H249R, N018R-S024R-N076D-S101A-N183D-T213A-A215F-H249R, N018R-S024R-N076D-S101A-T213A-A215F-H249R, N018R-S024R-N076D-S101A-V197A-T213A-A215F-H249R, N018R-S024R-N076D-S101G, N018R-S024R-N076D-S101G-Q245R, N018R-S024R-N076D-S101G-S103A-V104I-A232V, N018R-S024R-N076D-S103A-H249R, N018R-S024R-N076D-S103A-V104I-L135I-A232V, N018R-S024R-N076D-T213A-A215F-H249R-T260K, N018R-S024R-N076D-V150L-S242R-H249R, N018R-S024R-R045T-A230E-H249R, N018R-S101G-S103A-V104I-A232V-Q245R-H249R, N018R-T022R-S024R-N076D-S101A-N116A-N183D-G211Q-H249R, N018R-T022W-S024R-N076D-G211Q-A215F-H249R, N018R-T022W-S024R-N076D-I198L-G211Q-A215F-H249R, N018R-T022W-S024R-N076D-I198L-G211Q-T213A-H249R, N018R-T022W-S024R-N076D-I198L-H249R, N018R-T022W-S024R-N076D-I198L-T213A-H249R, N018R-T022W-S024R-N076D-N116A-A215F-H249R, N018R-T022W-S024R-N076D-N116A-G211Q-T213A-A215F-H249R, N018R-T022W-S024R-N076D-N116A-H249R, N018R-T022W-S024R-N076D-N116A-I198L-A215F-H249R, N018R-T022W-S024R-N076D-N116A-I198L-G211Q-A215F-H249R, N018R-T022W-S024R-N076D-N116A-I198L-G211Q-T213A-A215F-H249R, N018R-T022W-S024R-N076D-N116A-I198L-H249R, N018R-T022W-S024R-N076D-N116A-I198L-T213A-A215F-H249R, N018R-T022W-S024R-N076D-N116A-N183D-A215F-H249R, N018R-T022W-S024R-N076D-N116A-N183D-G211Q-A215F-H249R, N018R-T022W-S024R-N076D-N116A-N183D-G211Q-H249R, N018R-T022W-S024R-N076D-N116A-N183D-G211Q-T213A-H249R, N018R-T022W-S024R-N076D-N116A-N183D-G211Q-T213A-Q245R, N018R-T022W-S024R-N076D-N116A-N183D-I198L-A215F-H249R, N018R-T022W-S024R-N076D-N116A-N183D-I198L-G211Q-A215F-H249R, N018R-T022W-S024R-N076D-N116A-N183D-I198L-G211Q-H249R, N018R-T022W-S024R-N076D-N116A-N183D-I198L-G211Q-T213A-A209V-H249R, N018R-T022W-S024R-N076D-N116A-N183D-I198L-G211Q-T213A-H249R, N018R-T022W-S024R-N076D-N116A-N183D-I198L-H249R, N018R-T022W-S024R-N076D-N116A-N183D-I198L-Y209H-G211Q-H249R, N018R-T022W-S024R-N076D-N116A-N183D-T213A-A215F-H249R, N018R-T022W-S024R-N076D-N116A-N183D-T213A-H249R, N018R-T022W-S024R-N076D-N183D-G211Q-H249R, N018R-T022W-S024R-N076D-N183D-G211Q-T213A-A215F-H249R, N018R-T022W-S024R-N076D-N183D-G211Q-T213A-H249R, N018R-T022W-S024R-N076D-N183D-H249R, N018R-T022W-S024R-N076D-N183D-I198L-A215F-H249R, N018R-T022W-S024R-N076D-N183D-I198L-G211Q-A215F-H249R, N018R-T022W-S024R-N076D-N183D-I198L-G211Q-T213A-H249R, N018R-T022W-S024R-N076D-N183D-I198L-H249R, N018R-T022W-S024R-N076D-N183D-T213A-H249R, N018R-T022W-S024R-N076D-S101A-G211Q-A215F-H249R, N018R-T022W-S024R-N076D-S101A-I198L-G211Q-A215F-H249R, N018R-T022W-S024R-N076D-S101A-I198L-G211Q-H249R, N018R-T022W-S024R-N076D-S101A-I198L-G211Q-T213A-H249R, N018R-T022W-S024R-N076D-S101A-N116A-G211Q-T213A-A215F-H249R, N018R-T022W-S024R-N076D-S101A-N116A-H249R, N018R-T022W-S024R-N076D-S101A-N116A-N183D-A215F-H249R, N018R-T022W-S024R-N076D-S101A-N116A-N183D-G211Q-A215F-H249R, N018R-T022W-S024R-N076D-S101A-N116A-N183D-G211Q-H249R, N018R-T022W-S024R-N076D-S101A-N116A-N183D-G211Q-T213A-A215F-H249R, N018R-T022W-S024R-N076D-S101A-N116A-N183D-G211Q-T213A-H249R, N018R-T022W-S024R-N076D-S101A-N116A-N183D-H249R, N018R-T022W-S024R-N076D-S101A-N116A-N183D-I198L-A215F-H249R, N018R-T022W-S024R-N076D-S101A-N116A-N183D-I198L-H249R, N018R-T022W-S024R-N076D-S101A-N116A-N183D-I198L-T213A-H249R, N018R-T022W-S024R-N076D-S101A-N116A-N183D-T213A-A215F-H249R, N018R-T022W-S024R-N076D-S101A-N116A-N183D-T213A-H249R, N018R-T022W-S024R-N076D-S101A-N116A-T213A-A215F-H249R, N018R-T022W-S024R-N076D-S101A-N116A-T213A-A215F-H249R-L267I, N018R-T022W-S024R-N076D-S101A-N116T-I198L-A215F-H249R, N018R-T022W-S024R-N076D-S101A-N183D-G211Q-A215F-H249R, N018R-T022W-S024R-N076D-S101A-N183D-G211Q-H249R, N018R-T022W-S024R-N076D-S101A-N183D-G211Q-T213A-A215F-H249R, N018R-T022W-S024R-N076D-S101A-N183D-G211Q-T213A-H249R, N018R-T022W-S024R-N076D-S101A-N183D-I198L-A215F-H249R, N018R-T022W-S024R-N076D-S101A-N183D-I198L-T213A-H249R, N018R-T022W-S024R-N076D-S101A-N183D-I198L-Y209H-H249R, N018R-T022W-S024R-N076D-S101A-N183D-T213A-A215F-H249R, N018R-T22W-S024R-N076D-G211Q-T213A-H249R, N018R-T22W-S024R-N076D-N116A-I198L-T213A-H249R, N018R-T22W-S024R-N076D-S101A-I198L-H249R,

N018R-V104I-A232V, N043A-Q059A-S101A-S216F-T224A, N043D-N076D-S101G-S103A-V104I-A232V-Q245R-H249R, N043D-R045T-N076D-S078R-S101G-S103A-V104I-A232V-Q245R, N043D-R045T-S078R-S101G-S103A-V104I-A232V-Q245R, N043D-R045T-S078R-S101G-S103A-V104I-A232V-Q245R-N269R, N043D-S242R-H249R, N043R-A230E-H249R, N043R-N076D-S078R-S101G-S103A-V104I-A232V-Q245R-H249R, N043R-N076D-S078R-S101G-S103A-V104I-L217E-A232V-Q245R, N043R-N076D-S101G-S103T-V104I-A232V-Q245R-H249R-N269R, N043R-R045T-H249R, N043R-R045T-N076D-S101G-S103A-V104I-A232V-Q245R, N043R-R045T-S078R-S101G-S103A-V104I-A232V-Q245R-N269R, N043R-R045T-S078R-S101G-S103A-V104I-L217E-A232V-Q245R, N043R-R045T-S101G-S103A-V104I-A232V-Q245R-H249R, N043R-S078R-S101G-S103A-V104I-L217E-A232V-Q245R, N043R-S101G-S103A-V104I-Q245R-H249R, N043R-S101G-S103A-V104I-V150L-A232V-Q245R-N269R, N076D-A232V-Q245R, N076D-Q245R, N076D-S101G-A232V-Q245R, N076D-S101G-S103A-Q245R, N076D-S101G-S103A-V104I-A232V-H249R, N076D-S101G-S103A-V104I-H249R, N076D-S101G-S103A-V104I-V150L-A232V-Q245R, N076D-S101G-V104I-H249R, N076D-S101G-V104I-Q245R, N076D-S103A-V104I-A232V-Q245R, N076D-S103A-V104I-Q245R, N076D-V104I-A232V-Q245R, N076D-V104I-Q245R, P005S-N018R-T022W-S024R-N076D-S101A-T213A-A215F-H249R, P086W-K235F, P086W-Y209A-K235F, Q012H-V104A-G118R, R045T-N076D-S078R-S101G-S103A-V104I-A232V-Q245R-H249R, R045T-S101G-S103A-V104I-A232V-Q245R, S024R-G118R-N243F-R269H, S024R-K235F-N243F, S024R-N043D-N076D-S101G-S103A-V104I-A232V-Q245R-N269R, S024R-N043R-N076D-A230E-H249R, S024R-N076D-A232V-H249R, S024R-N076D-S078R-S101G-S103A-V104I-A232V-Q245R-H249R, S024R-N076D-S101G, S024R-N076D-S101G-A232V-H249R, S024R-N076D-S101G-S103A-A232V, S024R-N076D-S101G-S103A-V104I-M175L-H249R, S024R-N076D-S101G-S103A-V104I-Q245R, S024R-N076D-S101G-V104I-A232V-H249R, S024R-N076D-S103A-H249R, S024R-N076D-S103A-Q245R, S024R-N076D-S103A-V104I-H249R, S024R-R045T-N076D-S101G-S103A-V104I-A232V-Q245R-H249R, S024R-R045T-S242R-A273V, S024R-R247H, S024R-S101G-S103A, S024R-S101G-S103A-A232V, S024R-S101G-S103A-V104I, S024R-S103A-Q245R-H249R, S024R-S103A-V104I, S024R-S106G-N116A-S212M-T224A, S024R-T033S-A151V, S024R-T033S-A174V-K235F, S024R-T033S-A228T, S024R-T033S-K235F-W241R, S024R-T033S-N243F, S024R-V104A, S024R-V104I-A232V, S024R-Y209A-N243F, S078R-K235F, S087D-S101G-S103A-V104I-A232V-S242R-Q245R, S099F-S105T-S106G-A194F-S212M, S101G-H249R, S101G-S103A-V104I, S101G-S103A-V104I-A232V-Q245R-N248D, S101G-S103A-V104I-G159D-A232V-Q245R, S101G-S103A-V104I-G159D-A232V-Q245R-N248R, S101G-S103A-V104I-V150L-A232V-Q245R, S103A-A232V, S103A-A232V-H249R, S103A-A232V-Q245R, S103A-V104I-Q245R, S103N-H120E-Y167W-I198L-L233C, T022W-A194F-T213A-L233C-N238L, T022W-E089I-S216F, T033S-A048T, T033S-P086W-S156L-Y209A, T033S-P239T, T033S-T253A, T057R-N183D-Q236N, T143A-Y209A, V004E-T033S-S078R, V004R-S009A-T022R-S078R-S212F, Y209A-K235F, N043R-N076D-H249R, N018R-R045T, G020R-N076D-A230E-S242R, G020R-S024R-N043D-R045T, S024R-N043D-N076D-S242R-H249R, G020R-R045T-H249R, N043R-N076D-S153A-H249R, N043R-N076D-A230E-H249R, N018R-N043D-N076D-H249R, G020R-N043R-N076D-V227I, L111I-A215F-P239S, S024R-N116A-R186K-L233C-Q236N, G023A-S103N-S106G-S212M-A215F, Y209A-N243F, S024R-T033S-P129H-N184D-T253M, S024R-A085V-P086W-G118R-K235F, S024R-A272P, S024R-R269C, G020R-R045T-N076D-S078R-S101G-S103A-V104I-A232V-Q245R-H249R, N043D-N076D-S101G-S103A-V104I-A232V-Q245R, N018R-G020R-T022W-S024R-N076D-S101A-N116A-N183D-I198L-H249R, N018R-N076D-V104I, N018R-G020R-N043D-S101G-S103A-V104I-A232V-Q245R-H249R, N018R-G020R-T022W-S024R-N076D-N183D-G211Q-H249R, N018R-S024R-N076D-S101A-N183D-I198L-G211Q-A215F-H249R, S101G-V104I, N018R-T022W-S024R-N076D-N116A-N183D-I198L-G211Q-T213A-A215F-H249R, N018R-G020R-S024R-N076D-S101A-N183D-G211Q-T213A-A215F-H249R, N018R-G020R-S024R-N076D-N116A-N183D-A215F-H249R-N263D, N018R-T022W-S024R-N076D-S101A-N183D-H249R, N018R-S024R-N076D-S101A-N116A-N183D-I198L-A215F-H249R, N018R-T022W-S024R-N076D-N116A-I198L-A215F-H249R-R269H, N018R-N043D-R045T-N076D-S078R-S101G-S103A-V104I-A232V-Q245R, N018R-S024R-R045T-N076D-S078R-S101G-S103A-V104I-A232V-Q245R-N269R, S078R-S101G-S103A-V104I-L217E-A232V-Q245R, N018R-G020R-T022W-S024R-N076D-S101A-N183D-I198L-T213A-A215F-H249R, N018R-G020R-S024R-N076D-N183D-I198L-T213A-H249R, N018R-G020R-T022W-S024R-N076D-N116A-I198L-G211Q-A215F-H249R, N018R-G020R-T022W-S024R-N076D-N116A-N183D-G211Q-H249R, N018R-G020R-T022W-S024R-N076D-S101A-I198L-G211Q-T213A-H249R, N018R-G020R-T022W-S024R-N076D-H249R, G020R-T022W-S101G-S103A-V104I-N116A-N183D-I198L-G211Q-T213A-A215F-A232V-Q245R, V104I-A232V, N018R-G020R-T022W-S024R-N076D-S101A-N116A-N183D-G211Q-A215F-H249R, N018R-G020R-T022W-S024R-N076D-S101A-N116A-N183D-I198L-G211Q-T213A-A215F-H249R, N018R-G020R-T022W-S024R-N076D-S101A-N183D-T213A-A215F-H249R, N018R-T022W-S024R-N076D-S101A-N183D-I198L-G211Q-T213A-H249R, N018R-T022W-S024R-N076D-S101A-N183D-I198L-H249R, N043D-R045T-S101G-S103A-V104I-A232V-Q245R-N269R, N018R-G020R-S024R-N076D-S101A-N183D-I198L-G211Q-H249R, N018R-G020R-N043R-S101G-S103A-V104I-L217E-A232V-Q245R, S024R-N043R-N076D-S078R-S101G-S103A-V104I-A232V-Q245R-N269R, N043R-R045T-N076D-S078R-S101G-S103A-V104I-Y166F-A176P-A179V-N184T-A187P-A194P, N018R-T022W-S024R-D041E-N076D-S101A-S160T-N183D-G211Q-T213A-H249R, N018R-G020R-T022W-S024R-N076D-N116A-N183D-I198L-G211Q-A215F-H249R, N018R-G020R-T022W-S024R-N076D-S101A-N116A-I198L-T213A-H249R, N018R-T022W-S024R-N076D-S101A-N116A-N183D-I198L-G211Q-T213A-H249R, N018R-G020R-S024R-N076D-I198L-T213A-H249R, N018R-G020R-T022W-S024R-N076D-N116A-N183D-I198L-G211Q-H249R, N018R-G020R-S024R-N076D-N183D-G211Q-A215F-H249R, S024R-N076D-V104I, N018R-N076D-S101G-A232V, N018R-S024R-N076D-S101A-N116A-N183D-I198L-G211Q-T213A-A215F-H249R, N018R-G020R-T022W-S024R-N076D-N116A-N183D-A215F-H249R, N018R-S024R-L031F-N076D-N116A-N183D-G211Q-T213A-A215F-H249R,

N018R-S024R-N076D-S101A-N116A-N183D-I198L-T213A-H249R-N269S, N018R-G020R-S024R-N076D-S101A-N116A-I198L-A215F-H249R, N018R-N043R-N076D-S078R-S101G-S103A-V104I-A232V-Q245R-N269R, N018R-G020R-S024R-N076D-S101A-N114T-I198L-G211Q-A215F-H249R, S024R-N043R-S078R-S101G-S103A-V104I-L217E-A232V-Q245R, S024R-N076D-S103A-V104I-A232V, N018R-G020R-T022W-S024R-N076D-S101A-I198L-G211Q-A215F-H249R, S101G-V104I-A232V, N018R-T022W-S024R-N076D-N183D-I198L-T213A-A215F-H249R, N018R-T022W-S024R-N076D-N183D-I198L-G211Q-H249R, N018R-G020R-S024R-N076D-N183D-T213A-H249R, N018R-S024R-N076D-S101A-N183D-G211Q-A215F-H249R, N018R-G020R-T022W-S024R-N076D-N116A-G211Q-T213A-H249R, N018R-S078R-S101G-S103A-V104I-A232V-Q245R-N269R, N018R-T022W-S024R-N076D-S101A-N116A-N183D-G211Q-A215F-H249R-T260A, N076D-H249R, N018R-T022W-S024R-N076D-N183D-G211Q-A215F-H249R, N018R-G020R-S024R-N076D-N116A-G211Q-A215F-H249R, N018R-G020R-S024R-N076D-T213A-H249R, N018R-G020R-T022W-S024R-N076D-N116A-N183D-I198L-H249R, N018R-G020R-T022W-S024R-N076D-S101A-N183D-H249R, N076D-V104I-H249R, G020R-T022W-S101A-S103A-V104I-N116A-N183D-G211Q-T213A-A215F-A232V-Q245R, S024R-N043R-R045T-S078R-S101G-S103A-V104I-L217E-A232V-Q245R, N018R-G020R-T022W-S024R-N076D-N183D-I198L-A215F-H249R, N018R-N076D-S101G-S103A, G020R-S024R-S101G-S103A-V104I-A232V-Q245R-N269R, N018R-G020R-S024R-N076D-S101A-N116A-N183D-G211Q-H249R, S101G-S103A-A232V, S024R-N076D-S101G-A232V, N018R-T022W-S024R-N076D-S101A-N183D-I198L-G211Q-H249R, N018R-G020R-S024R-N076D-S101A-N183D-I198L-G211Q-A215F-H249R, N018R-G020R-S024R-N076D-N183D-I198L-H249R, N018R-T022W-S024R-N076D-S101A-N116A-N183D-I198L-G211Q-H249R, N018R-G020R-S024R-N076D-N116A-A156V-N183D-G211Q-A215F-H249R-N269S, R045T-N076D-S101G-S103A-V104I-A232V-Q245R-H249R, N018R-G020R-S024R-N076D-S101A-N183D-I198L-H249R, N018R-G020R-T022W-S024R-N076D-I198L-G211Q-A215F-H249R, N018R-G020R-T022W-S024R-N076D-S101A-N116A-I198L-G211Q-A215F-H249R, N018R-G020R-T022W-S024R-N076D-N116A-H249R, N018R-N076D-S101G, N018R-S024R-N076D-N116A-N183D-I198L-T213A-A215F-H249R, N018R-G020R-T022W-S024R-N076D-S101A-N116A-I198L-T213A-A215F-H249R, N018R-S024R-N076D-S101A-N116A-N183D-I198L-G211Q-H249R, N018R-N076D-A232V, N018R-G020R-S024R-N076D-S101A-A232V-Q245R, N018R-N043D-R045T-N076D-S101G-S103A-V104I-A232V-Q245R, N018R-T022W-S024R-N076D-N183D-T213A-A215F-H249R, N018R-S024R-N076D-S101A-N116A-G211Q-T213A-N237D-H249R, N018R-G020R-S024R-N076D-S101A-N116A-N183D-G211Q-H249R-R275S, N018R-T022W-S024R-N076D-S101A-N116A-N183D-I198L-G211Q-T213A-A215F-H249R, S024R-N076D, N018R-S024R-N076D-N183D-G211Q-A215F-H249R, N018R-T022W-S024R-N076D-N116A-N183D-I198L-T213A-A215F-H249R, N076D-V104I-A232V-H249R, N018R-N076D-S103A-A232V, N018R-G020R-S024R-N076D-S101A-N116A-N183D-I198L-G211Q-T213A-H249R, N018R-G020R-S024R-N076D-S101A-N183D-T213A-H249R, N018R-G020R-S024R-N076D-S101A-D175E-N183D-G211Q-A215F-H249R, N018R-G020R-N043D-S078R-S101G-S103A-V104I-L217E-A232V-Q245R-A273E, G020R-S024R-N043D-R045T-N076D-S101G-S103A-V104I-A232V-Q245R, P005S-S101G-S103A-V104I-A232V-Q245R-H249R, S103A-V104I-A232V, N018R-G020R-S024R-V068A-N076D-S101A-N116A-T213A-A215F-H249R, N018R-T022W-S024R-N076D-S101A-I198L-A215F-H249R-R275S, N018R-S024R-N076D-N183D-I198L-G211Q-T213A-H249R, N043D-R045T-S101G-S103A-V104I-A232V-Q245R, N018R-S024R-N076D-L217E-S242R-H249R, N076D-S087D-S101G-S103A-V104I-A232V-Q245R, S087D-S101G-S103A-V104I-A232V-Q245R, and S101G-S103A-V104I-V150L-A232V-S242R-Q245R, and wherein the total net charge of the protease variant is 0, +1, +2, +3, +4, +5, −1, −2, −3, −4, or −5 relative to the total net charge of the *Bacillus lentus* subtilisin GG36 protease, and wherein the total net charge is obtained by one or more substitutions selected from: N43D, R45T, N62E, N76D, S101D, P129E, A158E, G159D, G159E, S166D, S188D, A230E, N18R, G20K, G20R, T22R, S24R, N43R, G118R, Q245R, H249R, N269R, E271F, and E271L, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

In another aspect the inventors have found that preferred proteases comprise at least one, or even two or more charged mutations selected from the group consisting of N062E, S101D, P129E, A158E, G159D/E, S166D, and/or S188D. Such proteases are particularly preferred for incorporation into detergent compositions suitable for addition to water to make a wash liquor preferably having low ionic strength or low detergent concentration. Thus in a preferred aspect of the invention, these proteases will form part of a detergent composition that is added to water, either for a handwashing or machine washing process, typically within a washing machine, to form a wash liquor, whose conductivity is from about 0.1 mS/cm to about 3 mS/cm, from about 0.3 mS/cm to about 2.5 mS/cm, or even from about 0.5 mS/cm to about 2 mS/cm.

In a further aspect such proteases that comprise at least one, or even two or more charged mutations selected from the group consisting of N062E, S101D, P129E, A158E, G159D/E, S166D, and/or S188D have a charge of 0, −1, −2, −3, −4 or −5, preferably 0, −1, −2 or −3, most preferably −1 or −2 relative to the enzyme of SEQ ID NO:1.

In accordance with the present invention, particularly preferred proteases for use in the invention:

(a) comprise one or more charged mutations selected from the group consisting of N062E, S101D, P129E, A158E, G159D/E, S166D, and/or S188D;

(b) have a charge of 0, −1, −2, −3, −4 or −5, preferably 0, −1, −2 or −3, most preferably −1 or −2 relative to the enzyme of SEQ ID NO:1; and (c) comprise one, two, three or more mutations to arrive at a desired net charge selected from the group comprising G20K, S024R, G118R, Q245R, H249R and/or E271F/L.

By "mutations to arrive at a desired net charge" it is intended to mean that when the enzyme variant is compared to the *Bacillus lentus* subtilisin GG36 protease, the total net charge of the variant relative to *Bacillus lentus* subtilisin GG36 can be adjusted to be within the preferred range by selecting one or more further mutations preferably selected from the mutations identified, for example listed in (c) above.

Preferably these preferred proteases form part of a detergent composition that is added to water, either in a hand or machine washing process, typically within a washing machine, to form a wash liquor, whose conductivity is from about 0.1 mS/cm to about 3 mS/cm, from about 0.3 mS/cm to about 2.5 mS/cm, or even from about 0.5 mS/cm to about 2 mS/cm.

Without wishing to be bound by theory it is believed that these mutations to arrive at a desired net charge provide enhanced overall protease performance by ensuring optimal charge of the molecule for low ionic strength conditions, or wash liquors comprising low detergent concentration—it is only through careful combination of certain mutations, of which these are preferred, that such preferred proteases can be obtained.

In another aspect the inventors have found that preferred proteases comprise at least one or two or more charged mutations selected from the group consisting of N018R, G020K/R, T022R, S024R, N043R, Q245R, H249R and/or N269R. Such proteases are particularly preferred for incorporation into detergent compositions which will be added to water to make a wash liquor preferably having high ionic strength or high detergent concentration. For example these preferred proteases may form part of a detergent composition that is added to water, either for hand washing or machine washing, typically within a washing machine, to form a wash liquor, whose conductivity is from above about 3 mS/cm to about 30 mS/cm, from about 3.5 mS/cm to about 20 mS/cm, or even from about 4 mS/cm to about 10 mS/cm.

In a further aspect such proteases comprise at least one, or two or even more charged mutations selected from the group consisting of N018R, G020K/R, T022R, S024R, N043R, Q245R, H249R and/or N269R have a charge of 0, +1, +2, +3, +4 or +5, preferably +1, +2 or +3, most preferably +2 relative to the enzyme of SEQ ID NO:1.

Particularly preferred proteases:
(a) comprise one or two or more charged mutations selected from the group consisting of N018R, G020K/R, T022R, S024R, N043R, Q245R, H249R and/or N269R;
(b) have a charge of 0, +1, +2, +3, +4 or +5, preferably +1, +2 or +3, most preferably +2 relative to the enzyme of SEQ ID NO:1; and
(c) comprise mutations to arrive at a desired net charge selected from the group consisting of N043D, R045T, N076D and/or A230E.

Preferably these proteases form part of a detergent composition that is added to water either in a hand or machine washing process, typically within a washing machine, to form a wash liquor, whose conductivity is from above about 3 mS/cm to about 30 mS/cm, from about 3.5 mS/cm to about 20 mS/cm, or even from about 4 mS/cm to about 10 mS/cm.

Without wishing to be bound by theory it is believed that these mutations to arrive at a desired net charge provide enhanced overall protease performance in high ionic strength or high detergent concentration conditions—it is only through careful combination of certain mutations, of which these are preferred, that such preferred proteases can be obtained.

The present invention further provides polypeptides comprising protease variants having one or more of the following characteristics: a) a Test Method 2 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; b) a Test Method 3 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; c) a Test Method 4 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or d) a Test Method 6 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5. Test Method 2, Test Method 3, Test Method 4, and Test Method 6 are explicitly described infra in the section of Example 1 entitled "Test_Methods".

Nucleic Acids of the Invention

The invention provides isolated, non-naturally occurring, or recombinant nucleic acids (also referred to herein as "polynucleotides"), which may be collectively referred to as "nucleic acids of the invention" or "polynucleotides of the invention", which encode polypeptides of the invention. Nucleic acids of the invention, including all described below, are useful in recombinant production (e.g., expression) of polypeptides of the invention, typically through expression of a plasmid expression vector comprising a sequence encoding the polypeptide of interest or fragment thereof. As discussed above, polypeptides include variant protease polypeptides, including variant subtilisin polypeptides having enzymatic activity (e.g., proteolytic activity) which are useful in cleaning applications and cleaning compositions for cleaning an item or a surface (e.g., surface of an item) in need of cleaning.

In some embodiments, the invention provides an isolated, recombinant, substantially pure, or non-naturally occurring nucleic acid comprising a nucleotide sequence encoding any polypeptide (including any fusion protein, etc.) of the invention described above in the section entitled "Polypeptides of the Invention" and elsewhere herein. The invention also provides an isolated, recombinant, substantially pure, or non-naturally-occurring nucleic acid comprising a nucleotide sequence encoding a combination of two or more of any polypeptides of the invention described above and elsewhere herein.

Also provided is an isolated, recombinant, substantially pure, or non-naturally occurring nucleic acid comprising a polynucleotide sequence which encodes a variant protease having proteolytic activity, said variant protease (e.g., variant subtilisin) comprising an amino acid sequence which differs from the amino acid sequence of SEQ ID NO:2 by no more than 50, no more than 40, no more than 30, no more than 35, no more than 25, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, no more than 2, or no more than 1 amino acid residue(s), wherein amino acid positions of the variant subtilisin are numbered according to the numbering of corresponding amino acid positions in the amino acid sequence of *Bacillus amyloliquefaciens* subtilisin BPN' shown in SEQ ID NO:1 as determined by alignment of the variant protease amino acid sequence with the *Bacillus amyloliquefaciens* subtilisin BPN' amino acid sequence.

The present invention provides nucleic acids encoding a subtilisin variant of *Bacillus* subtilisin, wherein the subtilisin variant is a mature form having proteolytic activity and comprises an amino acid sequence comprising a combination of amino acid substitutions selected from: X1R, X2W, X2M, X2R, X2A, X2S, X3R, X4R, X4C, X4S, X8A, X9F, X9W, X9A, X10S, X10M, X10H, X10A, X12R, X12F, X14K, X14F, X14Q, X15R, X15F, X16S, X17R, X17M, X17F, X18R, X18K, X20F, X20R, X20K, X22Y, X22A, X22R, X22V, X22Q, X22W, X22L, X23F, X23S, X23A, X24W, X24R, X24H, X24F, X24Q, X24L, X25V, X25F, X25R, X26F, X27V, X27F, X27L, X27R, X28N, X28E, X28A, X29T, X30E, X31F, X33D, X33G, X33S, X34P, X35M, X36F, X36R, X36T, X38L, X38F, X38R, X40L, X40W, X40N, X40R, X40T, X40H, X42I, X43D, X43I, X43R, X43M, X43F, X43W, X43S, X43A, X45T, X46R, X48R, X50C, X51H, X51W, X51F, X52F, X52E, X52N, X55Y, X57R, X59R, X59A, X59F, X60A, X60Q, X60P, X62E, X62Q, X63I, X63V, X63T, X63P, X63D, X63M, X63H, X63Q, X63E, X63A, X63S, X64F, X64T, X68C, X68A, X69N, X69P, X69W, X69T, X71G, X72C, X74C, X75F, X75A, X75R, X75E, X76D, X78I, X78R, X78N, X79W, X79Q, X81R, X82V, X82T, X82F, X82M, X82R, X85M, X86L, X86I, X86W, X89P, X89T, X89V, X89G, X89W, X89H, X89F, X89L, X89I, X91N, X91F, X92F, X94N, X99G, X99F, X99M, X99T, X99P, X100I, X100S, X100N, X100Q, X101N, X101A, X101G, X101P, X101F, X101E, X101T, X101D, X102H, X102N, X102E, X102T, X102A, X103G, X103D, X103N, X104D, X104E, X104I, X104L, X105Q, X105E, X105T, X106F, X106V, X106G, X106E, X106T, X106D, X106A, X107F, X107M, X108G, X108I, X109M, X111V, X111I, X112V, X112L, X112Q, X114G, X115K, X115R, X116A, X116K, X116L, X117F, X118I, X118R, X119C, X120F, X120A, X120R, X121E, X121F, X123G, X123E, X124S, X128F, X128H, X128I, X128L, X128Q, X128N, X128M, X128D, X129E, X132E, X132A, X138G, X144R, X147L, X148I, X158E, X158E, X159E, X159C, X160D, X166D, X166E, X167W, X175V, X177C, X181A, X182R, X183F, X183I, X183D, X183R, X183M, X185E, X185I, X185V, X186H, X186K, X188R, X188E, X188D, X192H, X192W, X194V, X194F, X194E, X197F, X198L, X198F, X203E, X203C, X208S, X209N, X209F, X209E, X209S, X209H, X209G, X209T, X209L, X210R, X210V, X210L, X211R, X211Q, X212I, X212M, X212F, X213A, X214F, X215F, X215N, X215D, X215H, X215E, X216F, X216A, X217N, X217E, X217D, X218P, X218D, X218E, X224A, X224G, X227I, X230E, X231I, X231C, X233C, X234F, X235F, X236F, X236N, X238L, X238K, X238R, X239K, X239S, X239T, X239G, X239H, X239R, X239N, X239F, X240R, X241R, X242L, X242R, X243R, X243F, X244R, X246S, X248I, X248V, X248R, X249R, X249T, X250I, X251S, X251R, X252I, X252F, X252H, X252R, X253F, X253I, X253R, X254C, X256N, X258R, X260V, X260I, X262H, X262D, X263F, X265F, X267N, X267V, X267M, X269I, X269R, X270C, X271F, X271V, X271I, X271P, X271H, X271M, X271T, X271L, X271A, X272F, X272R, X272F, X273I, X273F, and X274G, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin, wherein the subtilisin variant is a mature form having proteolytic activity and comprises an amino acid sequence comprising a combination of amino acid substitutions selected from: X16S, X18R, X20R, X22A, X24R, X43R/D, X45T, X76D, X101A, X103G, X104L, X111V, X128N, X148I, X230E, X242R, and X249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin, wherein the subtilisin variant is a mature form having proteolytic activity and comprises an amino acid sequence comprising a combination of amino acid substitutions selected from: X1R, X230E, X271L, X115R, X20R, X249R, X235F, X27V/F/L, X75E, X82R, X18R, X269R, X43D, X43R, X76D, X45T, X212F, X242R, X24R, X78R, X9A, X22R, X121E, X244R, X28E, X30E, X4R, and X241R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin wherein the subtilisin variant is a mature form having proteolytic activity and comprises an amino acid sequence comprising a combination of amino acid substitutions selected from: X062E-X158E, X103G-X158E, X128N-X158E, X016S-X158E, X104L-X158E, X089P-X158E, X111V-X158E, X022A-X158E, X101A-X158E, X148I-X158E, X129E-X158E, X022A-X089P, X016S-X089P, X062E-X089P, X062E-X271F, X158E-X271F, X186H-X271F, X129E-X271F, X111V-X271F, X209E-X271F, X016S-X271F, X188D-X271F, X022A-X271F, X159E-X271F, X104L-X271F, X101A-X271F, X089P-X271F, X128N-X271F, X103G-X271F, X148I-X271F, X249R-X271F, X062E-X159E, X016S-X159E, X128N-X159E, X148I-X159E, X111V-X159E, X089P-X159E, X022A-X159E, X129E-X159E, X103G-X159E, X104L-X159E, X158E-X159E, X101A-X159E, X158E-X249R, X111V-X249R, X129E-X249R, X062E-X249R, X016S-X249R, X186H-X249R, X148I-X249R, X159E-X249R, X101A-X249R, X188D-X249R, X104L-X249R, X209E-X249R, X022A-X249R, X128N-X249R, X103G-X249R, X089P-X249R, X022A-X111V, X101A-X111V, X016S-X111V, X104L-X111V, X062E-X111V, X103G-X111V, X089P-X111V, X016S-X148I, X062E-X148I, X022A-X148I, X129E-X148I, X104L-X148I, X103G-X148I, X128N-X148I, X101A-X148I, X089P-X148I, X111V-X148I, X016S-X062E, X022A-X062E, X062E-X129E, X022A-X129E, X128N-X129E, X016S-X129E, X101A-X129E, X104L-X129E, X089P-X129E, X103G-X129E, X111V-X129E, X062E-X186H, X128N-X186H, X101A-X186H, X022A-X186H, X016S-X186H, X158E-X186H, X089P-X186H, X129E-X186H, X159E-X186H, X103G-X186H, X104L-X186H, X111V-X186H, X148I-X186H, X062E-X101A, X022A-X101A, X016S-X101A, X089P-X101A, X062E-X103G, X022A-X103G, X016S-X103G, X101A-X103G, X089P-X103G, X062E-X128N, X016S-X128N, X022A-X128N, X101A-X128N, X104L-X128N, X089P-X128N, X103G-X128N, X111V-X128N, X111V-X188D, X062E-X188D, X016S-X188D, X148I-X188D, X022A-X188D, X128N-X188D, X101A-X188D, X104L-X188D, X089P-X188D, X129E-X188D, X159E-X188D, X186H-X188D, X103G-X188D, X158E-X188D, X016S-X022A, X016S-X104L, X022A-X104L, X101A-X104L, X062E-X104L, X103G-X104L, X089P-X104L, X159E-X209E, X111V-X209E, X101A-X209E, X016S-X209E, X128N-X209E, X148I-X209E, X129E-X209E, X062E-X209E, X022A-X209E, X103G-X209E, X158E-X209E, X188D-X209E, X104L-X209E, X089P-X209E, and X186H-X209E, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant wherein the subtilisin variant is a mature form having proteolytic activity and comprises an amino acid sequence comprising a combination of amino acid substitutions selected from: X018R-X241R, X020R-

X241R, X024R-X241R, X009A-X241R, X020R-X241R, X004R-X241R, X043R-X241R, X078R-X241R, X022R-X241R, X115R-X241R, X001R-X241R, X212F-X241R, X082R-X241R, X018R-X244R, X024R-X244R, X078R-X244R, X020R-X244R, X212F-X244R, X009A-X244R, X082R-X244R, X001R-X244R, X043R-X244R, X022R-X244R, X004R-X244R, X115R-X244R, X241R-X244R, X242R-X244R, X001R-X004R, X009A-X022R, X018R-X022R, X020R-X022R, X004R-X022R, X001R-X022R, X024R-X242R, X018R-X242R, X004R-X242R, X020R-X242R, X212F-X242R, X082R-X242R, X078R-X242R, X001R-X242R, X009A-X242R, X022R-X242R, X115R-X242R, X043R-X242R, X241R-X242R, X018R-X212F, X022R-X212F, X004R-X212F, X024R-X212F, X001R-X212F, X115R-X212F, X020R-X212F, X009A-X212F, X043R-X212F, X078R-X212F, X082R-X212F, X009A-X078R, X020R-X078R, X024R-X078R, X022R-X078R, X018R-X078R, X004R-X078R, X001R-X078R, X043R-X078R, X022R-X024R, X020R-X024R, X018R-X024R, X001R-X024R, X004R-X024R, X009A-X024R, X004R-X009A, X001R-X009A, X242R-X269R, X024R-X269R, X020R-X269R, X022R-X269R, X249R-X269R, X212F-X269R, X043R-X269R, X244R-X269R, X001R-X269R, X018R-X269R, X078R-X269R, X009A-X269R, X115R-X269R, X241R-X269R, X004R-X269R, X082R-X269R, X018R-X043R, X020R-X043R, X004R-X043R, X022R-X043R, X009A-X043R, X001R-X043R, X024R-X043R, X009A-X018R, X004R-X018R, X001R-X018R, X024R-X082R, X009A-X082R, X018R-X082R, X001R-X082R, X078R-X082R, X020R-X082R, X022R-X082R, X004R-X082R, X043R-X082R, X043R-X249R, X020R-X249R, X004R-X249R, X018R-X249R, X009A-X249R, X212F-X249R, X022R-X249R, X024R-X249R, X115R-X249R, X001R-X249R, X082R-X249R, X242R-X249R, X241R-X249R, X244R-X249R, X078R-X249R, X018R-X115R, X020R-X115R, X022R-X115R, X078R-X115R, X009A-X115R, X004R-X115R, X001R-X115R, X082R-X115R, X043R-X115R, X024R-X115R, X009A-X020R, X018R-X020R, X004R-X020R, X001R-X020R, X009A-X271L, X020R-X271L, X024R-X271L, X244R-X271L, X241R-X271L, X043R-X271L, X022R-X271L, X249R-X271L, X212F-X271L, X115R-X271L, X242R-X271L, X078R-X271L, X004R-X271L, X269R-X271L, X001R-X271L, X018R-X271L, and X082R-X271L, wherein the amino acid positions of the subtilisin variant are numbered by correspondence with the amino acid sequence of *B. amyloliquefaciens* subtilisin BPN' set forth as SEQ ID NO: 1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X020R-X-43R, X020K-X062E, X024F-X116L, X020K-X024F, X024R-X174T, X024R-X118R, X024R-X235F, X024R-X086R, X024R-X086W, X078R-X118R, X033S-X118R, X033S-X235F, X209A-X241R, X020R-X076D, X018R-X245R, X024R-X045T, X232V-X245R, X118R-X172V, X118R-X194T, X008T-X024R, X235F-X243F, X018R-X103A, X018R-X104I, X086W-X118R, X086W-X243F, X086W-X209A, X024C-X033S, X024R-X232V, X024R-X243F, X024R-X239Q, X024R-X101G, X024R-X141G, X024R-X033S, X024R-X274I, X024R-X209A, X078R-X086W, X101G-X232V, X033S-X148F, X033S-X086W, X033S-X201S, X033S-X078R, X033S-X241R, X033S-X209A, X230E-X249R, X232V-X249R, X118R-X235F, X076D-X245R, X086W-X235F, X024R-X247H, X024R-X104A, X078R-X235F, X101G-X249R, X103A-X232V, X033S-X048T, X033S-X239T, X033S-X253A, X143A-X209A, X209A-X235F, X018R-X045T, X209A-X243F, X024R-X272P, X024R-X269C, X101G-X104I, X104I-X232V, X076D-X249R, and X024R-X076D wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X020R-X076D, X024R-X045T, X230E-X249R, X018R-X045T, X018R-X245R, X101G-X232V, X024R-X232V, X232V-X245R, X024R-X101G, X018R-X104I, X018R-X103A, X101G-X249R, X232V-X249R, X103A-X232V, X076D-X245R, X101G-X104I, X104I-X232V, X076D-X249R, X024R-X076D, X024F-X116L, X020K-X024F, X020K-X062E, X033S-X118R, X024R-X086W, X024R-X118R, X024R-X086R, X209A-X241R, X024R-X241R, X024R-X235F, X118R-X209A, X078R-X118R, X033S-X235F, X024R-X174T, X086W-X209A, X008T-X024R, X086W-X118R, X033S-X241R, X024R-X243F, X024R-X209A, X033S-X086W, X024R-X033S, X086W-X243F, X033S-X201S, X024R-X239Q, X078R-X086W, X235F-X243F, X118R-X172V, X033S-X148F, X033S-X078R, X033S-X243F, X024C-X033S, X118R-X194T, X033S-X209A, X024R-X141G, X024R-X274I, X086W-X235F, X015T-X033S, X209A-X235F, X024R-X247H, X078R-X235F, X024R-X104A, X033S-X048T, X118R-X235F, X033S-X253A, X143A-X209A, X033S-X239T, X209A-X243F, X024R-X272P, and X024R-X269C, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X004R-X009A-X020R-X242R, X020R-X043R-X241R, X020R-X242R-X269R, X004R-X009A-X020R-X043R, X004R-X020R-X249R, X018R-X024R-X244R, X009A-X022R-X212F-X241R, X020R-X043R-X269R, X018R-X024R-X242R, X004R-X009A-X043R-X241R, X020R-X043R-X244R, X020R-X022R-X242R, X004R-X020R-X043R, X004R-X009A-X020R-X043R-X242R, X020R-X043R-X242R, X020R-X043R-X242R-X249R, X020R-X212F-X249R, X004R-X009A-X241R, X001R-X009A-X043R, X020R-X043R-X249R, X009A-X020R-X043R-X241R, X020R-X022R-X043R, X020R-X249R-X269R, X020R-X022R-X241R, X004R-X009A-X024R-X043R-X241R, X009A-X043R-X078R, X004R-X020R-X024R-X244R, X020R-X022R-X078R-X242R, X020R-X024R-X242R-X249R, X004R-X009A-X078R-X241R, X009A-X043R-X078R-X242R, X004R-X020R-X024R, X009A-X043R-X212F, X020R-X043R-X212F, X024R-X078R-X212F, X009A-X020R-X024R-X043R, X009A-X022R-X043R-X078R, X020R-X022R-X212F-X241R, X020R-X043R-X212F-X241R, X009A-X043R-X241R, X020R-X043R-X271L, X020R-X022R-X078R-X241R, X020R-X024R-X043R-X242R, X020R-X022R-X043R-X241R, X009A-X020R-X043R-X212F, X004R-X009A-X020R-X024R-X242R, X020R-X043R-X249R-X271L, X020R-X022R-X024R-X242R, X009A-X022R-X078R-X212F, X020R-X043R-X242R-X271L, X009A-X022R-X078R-X212F-X241R, X004R-X020R-X024R-X249R, X020R-X022R-X271L, X020R-

X022R-X043R-X212F, X004R-X020R-X024R-X043R-X242R, X004R-X020R-X024R-X043R, X004R-X009A-X022R-X078R-X212F, X020R-X022R-X078R-X212F-X241R, and X020R-X022R-X269R, wherein the amino acid positions of the subtilisin variant are numbered by correspondence with the amino acid sequence of *B. amyloliquefaciens* subtilisin BPN' set forth as SEQ ID NO: 1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X018R-X020R-X043D-X045T-X230E, X018R-X043R-X045T-X242R-X249R, X024R-X043D-X249R, X018R-X020R-X045T, X020R-X024R-X076D-X249R, X024R-X043R-X230E-X242R, X018R-X024R-X043D-X230E, X020R-X076D, X018R-X024R-X043D-X076D-X249R, X024R-X043R-X076D-X249R, X018R-X024R-X045T-X242R, X020R-X043D-X076D-X230E-X249R, X020R-X043R-X045T-X242R, X018R-X024R-X076D-X249R, X018R-X020R-X024R-X043D-X045T-X233I-X242R, X024R-X043R-X230E, X018R-X020R-X043D, X043R-X242R-X249R, X020R-X043R-X045T-X230E, X043R-X076D-X242R-X249R, X020R-X043R-X045T-X230E-X242R, X024R-X045T-X076D-X230E-X242R-X249R, X024R-X045T, X024R-X043R-X045T-X076D-X230E-X249R, X018R-X024R-X043D-X045T-X249R, X018R-X043R-X045T-X249R, X024R-X043R-X242R, X018R-X020R-X043R-X076D-X249R, X020R-X024R-X043D-X249R, X020R-X043R-X230E-X242R, X020R-X043R-X242R, X018R-X043R-X076D-X230E, X020R-X024R-X043D-X242R, X020R-X043R-X230E, X018R-X020R-X043R-X076D-X242R-X249R, X043D-X045T-X076D-X249R, X018R-X043R-X242R-X249R, X018R-X020R-X043R-X045T-X242R, X018R-X020R-X043D-X230E-X242R, X020R-X024R-X043R-X045T-X249R, X024R-X043R-X249R, X020R-X024R-X27E-X043R-X076D-X230E, X024R-X043R-X045T-X242R, X018R-X020R-X024R-X043R-X045T-X076D-X230E, X020R-X043R-X076D-X230E-X249R, X018R-X043R-X045T-X242R, X020R-X242R-X249R, X018R-X043R-X076D-X230E-X242R-X249R, X018R-X024R-X076D, X020R-X024R-X27R-X043D-X242R-X249R, X018R-X020R-X024R-X043D-X076D-X242R, X018R-X043R-X076D-X242R-X249R, X018R-X024R-X043D-X230E-X249R, X018R-X020R-X043D-X249R, X018R-X020R-X043D-X045T-X076D-X242R, X024R-X043R-X076D-X230E-X242R, X020R-X024R-X381-X043R-X045T-X076D-X242R-X249R, X018R-X020R-X043R, X018R-X024R-X045T-X230E-X242R, X018R-X020R-X249R, X024R-X043R-X076D, X018R-X020R-X024R-X043R-X045T-X076D-X249R, X018R-X043D-X045T-X076D-X242R-X249R, X024R-X043D-X242R-X249R, X018R-X020R-X024R-X043D-X045T-X242R, X020R-X024R-X043R-X076D, X018R-X020R-X043D-X045T-X230E-X242R, X020R-X024R-X043R-X045T-X076D-X242R-X249R, X018R-X043R-X045T-X076D-X242R, X018R-X020R-X043R-X076D-X230E-X242R, X018R-X024R-X043D-X249R, X018R-X024R-X043R-X045T-X230E-X249R, X018R-X020R-X043R-X045T-X076D-X249R, X018R-X024R-X242R, X018R-X043R-X045T-X076D-X230E-X242R, X045T-X242R-X249R, X018R-X024R-X043D-X242R, X018R-X020R-X043D-X045T-X240P, X024R-X043R-X045T-X242R-X249R, X018R-X024R-X30S-X31S-X321-X33Q-X34V-X35F, X018R-X020R-X043R-X076D, X020R-X043D-X045T-X076D-X242R-X249R, X018R-X024R-X043D-X230E-X242R, X018R-X024R-X043D-X242R-X249R, X024R-X043D-X045T-X242R-X249R, X024R-X043R-X076D-X230E-X249R, X020R-X024R-X043R-X076D-X230E-X249R, X020R-X024R-X043D-X076D-X230E-X249R, X043D-X076D-X249R, X024R-X045T-X242R-X273V, X020R-X024R-X045T-X076D-X242R-X249R, X018R-X024R-X043D-X076D-X242R, X018R-X043R-X076D-X230E-X249R, X018R-X020R-X043R-X045T-X249R, X018R-X043R-X045T-X230E-X242R, X020R-X024R-X043D-X045T-X230E-X242R, X018R-X043D-X230E-X249R, X018R-X043R-X076D-X242R, X018R-X020R-X076D, X018R-X020R-X043D-X076D-X242R-X249R, X020R-X024R-X043D-X076D-X242R-X249R, X043D-X242R-X249R, X018R-X020R-X024R-X043R-X076D, X018R-X020R-X043D-X045T-X076D-X249R, X018R-X020R-X043R-X045T-X076D-X230E-X249R, X018R-X076D-X242R, X020R-X043R-X249R, X018R-X076D-X242R-X249R, X018R-X024R-X045T-X230E-X249R, X230E-X249R, X018R-X045T-X249R, X020R-X043R-X076D, X043R-X045T-X249R, X018R-X043D-X076D-X242R-X249R, X043R-X076D-X249R, X018R-X045T, X020R-X076D-X230E-X242R, X020R-X024R-X043D-X045T, X024R-X043D-X076D-X242R-X249R, X020R-X045T-X249R, X043R-X076D-X153A-X249R, X043R-X076D-X230E-X249R, X018R-X043D-X076D-X249R, and X020R-X043R-X076D-X227I, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X101G-X103A-X104I-X232V-X236H-X245R-X252K, X101G-X103A-X104I-X232V-X245R-X248R, X101G-X103A-X104I-X159R-X232V-X245R-X248D, X101G-X103A-X104I-X159D-X232V-X245R-X248R, X101G-X103A-X104I-X232V-X245R, X101G-X103A-X104I-X159D-X232V-X245R, and X101G-X103A-X104I-X232V-X245R-X248D, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X101G-X103A-X104I-X129E-X188D-X232V-X238R-X245R-X248D, X024R-X101G-X103A-X104I-X129E-X158E-X188D-X232V-X245R-X248D-X249R, X022A-X101G-X103A-X104I-X129E-X158E-X188D-X232V-X245R-X248D-X249R, X022A-X024R-X101G-X103A-X104I-X129E-X158E-X188D-X232V-X245R-X248D-X249R, X024R-X101G-X103A-X104I-X129E-X188D-X232V-X245R-X248D-X249R, X024R-X101G-X103A-X104I-X129E-X159E-X188D-X232V-X245R-X248D-X249R, X024R-X101G-X103A-X104I-X128N-X129E-X158E-X232V-X245R-X248D-X249R, X024R-X101G-X103A-X104I-X148I-X158E-X188D-X232V-X245R-X248D, X022A-X024R-X101G-X103A-X104I-X129E-X159E-X188D-X232V-X245R-X248D-X249R, X024R-X101G-X103A-X104I-X128N-X129E-X232V-X245R-X248D, X101G-X103A-X104I-X129E-X188D-X232V-X245R-X248D-X249R, X024R-X101G-X103A-X104I-X129E-X158E-X232V-X245R-X248D-X249R, X022A-X024R-X101G-X103A-X104I-X158E-X159E-X188D-X232V-X245R-X248D-X249R, X022A-X024R-X101G-X103A-X104I-X129E-

X158E-X159E-X188D-X232V-X238R-X245R-X248D, X024R-X101G-X103A-X104I-X129E-X148I-X158E-X232V-X245R-X248D, X016S-X024R-X101G-X103A-X104I-X158E-X188D-X232V-X245R-X248D-X249R, X101G-X103A-X104I-X158E-X159E-X232V-X245R-X248D-X249R, X022A-X101G-X103A-X104I-X129E-X158E-X159E-X232V-X238R-X245R-X248D, X022A-X024R-X101G-X103A-X104I-X129E-X158E-X159E-X232V-X245R-X248D-X249R, X022A-X024R-X101G-X103A-X104I-X128N-X158E-X188D-X232V-X245R-X248D, X024R-X101G-X103A-X104I-X129E-X188D-X232V-X245R-X248D, X022A-X024R-X101G-X103A-X104I-X129E-X158E-X232V-X245R-X248D, X022A-X024R-X101G-X103A-X104I-X129E-X232V-X245R-X248D, X022A-X024R-X101G-X103A-X104I-X129E-X188D-X232V-X245R-X248D, X024R-X101G-X103A-X104I-X158E-X188D-X232V-X238R-X245R-X248D, X022A-X101G-X103A-X104I-X128N-X129E-X188D-X232V-X238R-X245R-X248D, X024R-X101G-X103A-X104I-X129E-X188D-X232V-X238R-X245R-X248D, X024R-X101G-X103A-X104I-X158E-X159E-X188D-X232V-X245R-X248D, X022A-X024R-X101G-X103A-X104I-X128N-X188D-X232V-X245R-X248D, X024R-X101G-X103A-X104I-X129E-X158E-X188D-X232V-X245R-X248D, X022A-X024R-X101G-X103A-X104I-X128N-X129E-X158E-X232V-X245R-X248D, X024R-X101G-X103A-X104I-X159E-X188D-X232V-X245R-X248D, X022A-X101G-X103A-X104I-X128N-X129E-X232V-X238R-X245R-X248D, X024R-X101G-X103A-X104I-X129E-X159E-X232V-X245R-X248D, X022A-X024R-X101G-X103A-X104I-X129E-X158E-X188D-X232V-X238R-X245R-X248D, X022A-X024R-X101G-X103A-X104I-X158E-X159E-X188D-X232V-X245R-X248D, X024R-X101G-X103A-X104I-X159E-X188D-X232V-X245R-X248D-X249R, X022A-X101G-X103A-X104I-X129E-X158E-X232V-X238R-X245R-X248D, X022A-X024R-X101G-X103A-X104I-X129E-X158E-X232V-X245R-X248D-X249R, X024R-X101G-X103A-X104I-X148I-X158E-X232V-X245R-X248D, X022A-X101G-X103A-X104I-X158E-X159E-X188D-X232V-X245R-X248D-X249R, X022A-X101G-X103A-X104I-X158E-X188D-X232V-X245R-X248D, X022A-X101G-X103A-X104I-X129E-X188D-X232V-X238R-X245R-X248D, X024R-X101G-X103A-X104I-X129E-X158E-X159E-X188D-X232V-X245R-X248D-X249R, X022A-X024R-X101G-X103A-X104I-X158E-X159E-X188D-X232V-X238R-X245R-X248D, X101G-X103A-X104I-X129E-X158E-X188D-X232V-X245R-X248D-X249R, X024R-X101G-X103A-X104I-X128N-X158E-X232V-X245R-X248D, X022A-X024R-X101G-X103A-X104I-X128N-X129E-X188D-X232V-X245R-X248D, X022A-X101G-X103A-X104I-X129E-X159E-X232V-X238R-X245R-X248D, X101G-X103A-X104I-X129E-X159E-X232V-X245R-X248D-X249R, X022A-X101G-X103A-X104I-X129E-X158E-X232V-X245R-X248D-X249R, X024R-X101G-X103A-X104I-X129E-X148I-X158E-X188D-X232V-X245R-X248D, X022A-X101G-X103A-X104I-X129E-X159E-X232V-X245R-X248D-X249R, X024R-X101G-X103A-X104I-X159E-X188D-X232V-X238R-X245R-X248D, X024R-X101G-X103A-X104I-X129E-X158E-X159E-X232V-X245R-X248D-X249R, X024R-X101G-X103A-X104I-X129E-X158E-X159E-X232V-X238R-X245R-X248D, X024R-X101G-X103A-X104I-X128N-X159E-X188D-X232V-X245R-X248D, X022A-X101G-X103A-X104I-X159E-X188D-X232V-X245R-X248D-X249R, X024R-X101G-X103A-X104I-X129E-X159E-X188D-X232V-X238R-X245R-X248D, X101G-X103A-X104I-X158E-X232V-X238R-X245R-X248D, X022A-X101G-X103A-X104I-X129E-X159E-X188D-X232V-X245R-X248D-X249R, X024R-X101G-X103A-X104I-X129E-X148I-X188D-X232V-X245R-X248D, X024R-X101G-X103A-X104I-X158E-X232V-X245R-X248D-X249R, X022A-X101G-X103A-X104I-X158E-X159E-X232V-X238R-X245R-X248D, X024R-X101G-X103A-X104I-X158E-X159E-X232V-X238R-X245R-X248D, X022A-X101G-X103A-X104I-X129E-X158E-X159E-X232V-X245R-X248D-X249R, X101G-X103A-X104I-X129E-X158E-X188D-X232V-X238R-X245R-X248D, X022A-X024R-X101G-X103A-X104I-X129E-X158E-X159E-X232V-X245R-X248D, X101G-X103A-X104I-X188D-X232V-X238R-X245R-X248D, X022A-X024R-X101G-X103A-X104I-X158E-X232V-X245R-X248D-X249R, X022A-X024R-X101G-X103A-X104I-X148I-X158E-X232V-X245R-X248D, X101G-X103A-X104I-X129E-X158E-X159E-X232V-X238R-X245R-X248D, X022A-X101G-X103A-X104I-X159E-X188D-X232V-X238R-X245R-X248D, X022A-X024R-X101G-X103A-X104I-X129E-X158E-X159E-X188D-X232V-X245R-X248D-X249R, X022A-X101G-X103A-X104I-X129E-X232V-X238R-X245R-X248D, X022A-X024R-X101G-X103A-X104I-X188D-X232V-X245R-X248D-X249R, X101G-X103A-X104I-X129E-X158E-X159E-X232V-X245R-X248D-X249R, X022A-X101G-X103A-X104I-X158E-X159E-X232V-X245R-X248D-X249R, X101G-X103A-X104I-X129E-X188D-X232V-X245R-X248D, X024R-X101G-X103A-X104I-X129E-X159E-X232V-X238R-X245R-X248D, X101G-X103A-X104I-X128N-X129E-X232V-X245R-X248D, X101G-X103A-X104I-X158E-X188D-X232V-X245R-X248D, X022A-X024R-X101G-X103A-X104I-X129E-X232V-X245R-X248D-X249R, X101G-X103A-X104I-X129E-X159E-X232V-X238R-X245R-X248D, X101G-X103A-X104I-X158E-X159E-X188D-X232V-X238R-X245R-X248D, X024R-X101G-X103A-X104I-X232V-X245R-X248D-X249R, X022A-X024R-X101G-X103A-X104I-X129E-X148I-X232V-X245R-X248D, X022A-X024R-X101G-X103A-X104I-X158E-X232V-X238R-X245R-X248D, X101G-X103A-X104I-X128N-X129E-X232V-X238R-X245R-X248D, X022A-X101G-X103A-X104I-X128N-X159E-X232V-X245R-X248D, X022A-X101G-X103A-X104I-X128N-X129E-X158E-X232V-X238R-X245R-X248D, X101G-X103A-X104I-X128N-X129E-X188D-X232V-X245R-X248D-X249R, X022A-X024R-X101G-X103A-X104I-X128N-X129E-X158E-X188D-X232V-X245R-X248D-X249R, X024R-X101G-X103A-X104I-X128N-X158E-X159E-X188D-X232V-X245R-X248D, X022A-X024K-X101G-X103A-X104I-X128N-X158E-X159E-X232V-X245R-X248D, X101G-X103A-X104I-X129E-X148I-X188D-X232V-X245R-X248D, X024R-X101G-X103A-X104I-X148I-X232V-X245R-X248D, X022A-X101G-X103A-X104I-X148I-X188D-X232V-X245R-X248D, X024R-X101G-X103A-X104I-X128N-X129E-X188D-X232V-X245R-X248D, X101G-X103A-X104I-X128N-X129E-X158E-X232V-X238R-X245R-X248D, X022A-X024R-X101G-X103A-X104I-X129E-X148I-X158E-X188D-X232V-X245R-X248D, X022A-X024R-X101G-X103A-X104I-X148I-X158E-X188D-X232V-X245R-X248D, X101G-X103A-X104I-X148I-X159E-X232V-X245R-X248D, X022A-X024R-X101G-X103A-X104I-X158E-X188D-X232V-X245R-X248D, and X101G-X103A-X104I-X128N-X129E-X158E-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X022A-X024R-X101G-X103A-X104I-X158E-X232V-X245R-X248D-X249R, X022A-X024R-X101G-X103A-X104I-X129E-X232V-X245R-X248D-X249R, X024R-X101G-X103A-X104I-X158E-X159E-X232V-X238R-X245R-X248D, X024R-X101G-X103A-X104I-X232V-X245R-X248D-X249R, X101G-X103A-X104I-X158E-X232V-X245R-X248D-X249R, X101G-X103A-X104I-X188D-X232V-X245R-X248D-X249R, X024R-X101G-X103A-X104I-X159E-X188D-X232V-X245R-X248D-X249R, X022A-X024R-X101G-X103A-X104I-X158E-X232V-X238R-X245R-X248D, X024R-X101G-X103A-X104I-X159E-X188D-X232V-X238R-X245R-X248D, X022A-X024R-X101G-X103A-X104I-X129E-X232V-X245R-X248D, X024R-X101G-X103A-X104I-X148I-X232V-X245R-X248D, X024R-X101G-X103A-X104I-X129E-X158E-X232V-X245R-X248D-X249R, X024R-X101G-X103A-X104I-X148I-X158E-X232V-X245R-X248D, X022A-X024R-X101G-X103A-X104I-X129E-X158E-X232V-X245R-X248D-X249R, X016S-X024R-X101G-X103A-X104I-X158E-X188D-X232V-X245R-X248D-X249R, X024R-X101G-X103A-X104I-X129E-X159E-X232V-X238R-X245R-X248D, X024R-X101G-X103A-X104I-X129E-X188D-X232V-X245R-X248D-X249R, X022A-X101G-X103A-X104I-X129E-X232V-X238R-X245R-X248D, X022A-X024R-X101G-X103A-X104I-X148I-X158E-X232V-X245R-X248D, X024R-X101G-X103A-X104I-X129E-X188D-X232V-X238R-X245R-X248D, X022A-X024R-X101G-X103A-X104I-X158E-X159E-X188D-X232V-X238R-X245R-X248D, X022A-X101G-X103A-X104I-X158E-X159E-X232V-X238R-X245R-X248D, X022A-X024R-X101G-X103A-X104I-X129E-X158E-X232V-X245R-X248D, X101G-X103A-X104I-X158E-X188D-X232V-X245R-X248D-X249R, X022A-X101G-X103A-X104I-X158E-X159E-X232V-X245R-X248D-X249R, and X024R-X101G-X103A-X104I-X158E-X159E-X232V-X245R-X248D, wherein the amino acid positions of the subtilisin variant are numbered by correspondence with the amino acid sequence of *B. amyloliquefaciens* subtilisin BPN' set forth as SEQ ID NO: 1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X104L-X128N-X158E-X186H-X249R, X128N-X158E-X188D-X249R, X062E-X128N-X158E-X159E-X271F, X062E-X158E-X188D-X249R-X271F, X062E-X158E-X186H-X249R-X271F, X128N-X158E-X188D-X209E-X271F, X062E-X159E-X188D-X249R, X016S-X062E-X158E-X186H-X249R, X062E-X158E-X159E-X249R, X101A-X128N-X158E-X209E-X249R, X128N-X158E-X186H-X271F, X062E-X158E-X188D-X249R, X062E-X158E-X186H-X271F, X062E-X158E-X186H-X249R, X062E-X101A-X186H-X249R, X062E-X101A-X158E-X186H-X271F, X062E-X104L-X158E-X188D-X249R-X271F, X062E-X159E-X186H-X249R, X062E-X159E-X186H-X249R, X128N-X158E-X186H-X188D-X271F, X062E-X158E-X249R, X062E-X186H-X188D-X249R-X271F, X128N-X158E-X209E-, X062E-X101A-X158E-X249R, X104L-X128N-X158E-X186H-X271F, X062E-X101A-X158E-X186H-X249R-X271F, X016S-X062E-X158E-X249R, X062E-X101A-X159E-X249R, X128N-X158E-X186H-X188D-X271F, X101A-X128N-X158E-X186H-X271F, X062E-X101A-X188D-X249R, X101A-X104L-X158E-X186H-X188D-X249R, X062E-X159E-X249R-X271F, X128N-X158E-X159E-X271F, X016S-X062E-X104L-X158E-X186H-X271F, X022A-X128N-X158E-X249R, X128N-X158E-X249R, X062E-X101A-X104L-X158E-X186H-X271F, X016S-X062E-X158E-X186H-X271F, X104L-X128N-X158E-X249R, X104L-X128N-X158E-X188D-X249R, X022A-X062E-X158E, X062E-X101A-X188D-X249R-X271F, X062E-X158E-X249R-X271F, X104L-X128N-X158E-X186H-X188D-X271F, X062E-X101A-X186H-X271F, X062E-X104L-X159E-X249R, X062E-X186H-X249R, X062E-X101A-X186H-X249R-X271F, X101A-X158E-X186H-X188D-X249R, X062E-X101A-X186H, X101A-X128N-X129E-X186H-X249R, X101A-X103G-X158E-X186H-X249R, X016S-X062E-X104L-X186H-X188D-X271F, X104L-X158E-X186H-X249R, X101A-X128N-X158E-X188D-X209E-X271F, X062E-X101A-X186H-X188D-X271F, X016S-X062E-X158E-X249R-X271F, X062E-X128N-X158E, X062E-X128N-X159E-X249R, X062E-X101A-X158E-X188D-X249R, X101A-X128N-X158E-X249R, X062E-X158E-X186H-X188D-X249R, X016S-X104L-X158E-X186H-X271F, X062E-X148I-X159E, X062E-X101A-X158E-X186H-X249R, X062E-X101A-X186H-X188D-X249R, X104L-X158E-X186H-X188D-X249R, X062E-X101A-X104L-X186H-X188D-X271F, X022A-X101A-X158E-X186H-X249R, X101A-X128N-X158E-X209E, X158E-X186H-X188D-X249R-X271F, X104L-X158E-X186H-X188D-X249R-X271F, X101A-X104L-X158E-X186H-X249R, X104L-X158E-X249R, X101A-X104L-X128N-X158E-X186H-X271F, X016S-X104L-X188D-X249R, X101A-X104L-X158E-X186H-X188D-X271F, X104L-X128N-X159E-X271F, X104L-X158E-X186H-X249R-X271F, X158E-X186H-X249R, X101A-X158E-X186H-X249R, X104L-X158E-X188D-X249R-X271F, X016S-X128N-X158E-X186H, X104L-X128N-X186H-X188D-X249R, X016S-X101A-X128N-X186H, X016S-X062E-X128N-X186H-X271F, X016S-X128N-X186H-X271F, X128N-X129E-X186H, X158E-X186H-X249R-X271F, X016S-X158E-X249R, X016S-X158E-X186H-X249R, X016S-X022A-X158E-X186H-X271F, X089P-X101A-X129E-X186H, X022A-X128N-X158E-X186H, X101A-X104L-X128N-X158E-X186H, X022A-X128N-X186H-X188D-, X062E-X104L-X158E-X186H-X188D-X249R, X022A-X158E-X186H-X249R-X271F, X022A-X104L-X158E-X249R, X101A-X111V-X129E, X016S-X158E-X249R-X271F, X016S-X111V-X188D-, X022A-X104L-X186H-X188D-X249R, and X104L-X148I-X188D-X249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X001R-X101G-X103A-X104I-X232V-X245R, X004R-X101G-X103A-X104I-X232V-X245R, X043R-X101G-X103A-X104I-X232V-X245R-X271L, X078R-X101G-X103A-X104I-X232V-X245R, X004R-X043R-X101G-X103A-X104I-X232V-X245R, X018R-X043R-X101G-X103A-X104I-X232V-X245R, X020R-X101G-X103A-X104I-X232V-X245R, X101G-X103A-X104I-X232V-X245R-X271L, X020R-

X043R-X101G-X103A-X104I-X232V-X245R, X024R-X043R-X101G-X103A-X104I-X232V-X245R, X020R-X025R-X116A-X167W, X018R-X101G-X103A-X104I-X232V-X245R, X022R-X101G-X103A-X104I-X232V-X245R, X078R-X103N-X106G-X167W-X236N, X018R-X043D-X101G-X103A-X104I-X232V-X245R-X269R, X043R-X101G-X103A-X104I-X232V-X245R-X269R, X024R-X101A-X120E-X194F-X249R, X020R-X043D-X101G-X103A-X104I-X232V-X245R-X269R, X101G-X103A-X104I-X212F-X232V-X245R, X020R-X144R-X185I-X233C-X236N, X023A-X078R-X216F-X236N-X249R, X101G-X103A-X104I-X232V-X245R-X269R, X101G-X103A-X104I-X115R-X232V-X245R, X052N-X078R-X103N-X148I-X213A, X018R-X043D-X101G-X103A-X104I-X232V-X245R-X249R, X024R-X043D-X101G-X103A-X104I-X232V-X245R-X249R, X024R-X043D-X101G-X103A-X104I-X232V-X245R-X269R, X025R-X089I-X116A-X239S-X270C, X024R-X101G-X103A-X104I-X232V-X245R, X148I-X213A-X252R, X024R-X025R-X183D-X192W-X239S, X046R-X194F-X212M, X104L-X217E-X224A-X249R-X252R, X023A-X091F-X121F-X192W-X236N, X101G-X103A-X104I-X232V-X244R-X245R, X099F-X144R-X167W-X252R, X101G-X103A-X104I-X232V-X245R-X249R, X043R-X101G-X103A-X104I-X232V-X245R, X022W-X078R-X167W-X212M-X270C, X121F-X252R-X270C, X020R-X103N-X216F-X236N-X252R, X043R-X101G-X103A-X104I-X232V-X245R-X249R, X023A-X052N-X192W-X198L-X252R, X025R-X046R-X121F, X024R-X078R-X104L-X116A-X183D, X046R-X059A-X103N-X211Q-X212M, X020R-X052N-X062Q-X091F-X192W, X023A-X052N-X144R-X192W-X216F, X101G-X103A-X104I-X232V-X242R-X245R, X052N-X103N-X116A-X148I-X192W, X089I-X116A-X117F-X224A-X249R, X144R-X211Q-X238L-X239S-X249R, X043A-X062Q-X194F-X211Q, X020R-X024R-X052N-X059A-X216F, X024R-X167W-X224A-X249R, X057R-X167W-X249R, X025R-X103N-X186K-X194F-X224A, X105T-X128N-X144R-X148I-X212M, X020R-X059A-X144R-X192W-X224A, X024R-X043A-X117F-X194F-X211Q, X117F-X194F-X213A-X270C, X078R-X091F-X121F-X233C-X252R, X057R-X099F-X105T-X198L-X213A, X023A-X091F-X101A-X198L-X252R, X062Q-X103N-X121F-X144R-X249R, X043R-X101G-X103A-X104I-X232V-X242R-X245R, X023A-X024R-X117F-X212M-X216F, X104L-X213A-X216F, X194F-X211Q-X236N, X062Q-X103N-X117F-X194F, X024R-X062Q-X104L-X106G-X249R, X057R-X089I-X198L, X046R-X059A-X106G-X217E-X249R, X117F-X213A-X215F, X101A-X120E-X192W-X215F-X224A, X043A-X057R-X117F-X144R-X183D, X046R-X183D-X238L, X025R-X043A-X089I-X117F, X078R-X104L-X213A-X215F-X224A, X091F-X099F-X101A-X105T-X167W, X106G-X117F-X238L, X046R-X089I-X091F-X101A-X116A, X020R-X062Q-X089I-X186K-X212M, X057R-X099F-X121F-X185I-X192W, X046R-X089I-X192W-X233C-X270C, X089I-X117F-X185I-X215F-X233C, X052N-X104L-X183D-X216F-X249R, X078R-X099F-X116A-X186K-X224A, X025R-X105T-X128N-X144R-X270C, X105T-X211Q-X216F, X024R-X046R-X091F-X121F, X106G-X185I-X216F-X236N, X062Q-X101A-X236N-X252R-X270C, X025R-X043A-X091F-X198L-X270C, X020R-X023A-X104L-X192W-X233C, X024R-X043A-X105T-X106G-X198L, X020R-X089I-X217E, X024R-X091F-X198L-X215F-X239S, X046R-X089I-X099F-X186K-X212M, X104L-X120E-X186K-X216F-X252R, X022W-X194F-X213A-X233C-X238L, X099F-X105T-X106G-X194F-X212M, X089I-X105T-X116A-X215F-X216F, X025R-X116A-X120E-X224A-X270C, X043A-X059A-X101A-X216F-X224A, X057R-X183D-X236N, X025R-X062Q-X128N-X144R-X185I, X103N-X120E-X167W-X198L-X233C, X022W-X089I-X216F, X024R-X106G-X116A-X212M-X224A, X020R-X052N-X101A-X198L-X233C, X089I-X091F-X185I-X211Q-X270C, X111I-X215F-X239S, X024R-X116A-X186K-X233C-X236N, and X023A-X103N-X106G-X212M-X215F, wherein the amino acid positions of the subtilisin variant are numbered by correspondence with the amino acid sequence of *B. amyloliquefaciens* subtilisin BPN' set forth as SEQ ID NO: 1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X020R-X022W-X078R-X101A-X103A-X104I-X116S-X213A-X215F-X232V-X245R, X018R-X078R-X101G-X103A-X104I-X232V-X245R, X024R-X045T-X101G-X103A-X104I-X232V-X245R-X269R, X020R-X022W-X078R-X101G-X103A-X104I-X116A-X232V-X245R, X020R-X22W-X101G-X103A-X104I-X232V-X245R, X018R-X043R-X101G-X103A-X104I-X232V-X245R, X018R-X022W-X024R-X076D-X101A-X116A-X232V-X245R, X018R-X104I-X232V-X249R, X018R-X024R-X076D-X101A-X116A-X211Q-X249R, X018R-X043D-X078R-X101G-X103A-X104I-X217E-X232V-X245R, X018R-X043R-X101G-X103A-X104I-X232V-X245R-X269R, X018R-X045T-X076D-X101G-X103A-X104I-X232V-X245R-X269R, X076D-X078R-X101G-X103A-X104I-X232V-X245R-X269R, X020R-X043D-X078R-X101G-X103A-X104I-X232V-X245R, X018R-X043D-X076D-X101G-X103A-X104I-X232V-X245R-X269R, X024R-X045T-X076D-X078R-X101G-X103A-X104I-X232V-X245R-X269R, X018R-X103A-X232V-X249R, X018R-X101G-X104I-X232V-X245R, X020R-X024R-X101G-X103A-X104I-X217E-X232V-X245R-X249R, X018R-X22K-X043D-X101G-X103A-X104I-X232V-X245R, X043R-X045T-X101G-X103A-X104I-X232V-X245R-X269R, X020R-X22W-X101G-X103A-X104I-X211Q-X232V-X245R, X024R-X076D-X078R-X101G-X103A-X104I-X232V-X245R-X269R, X020R-X22W-X078R-X101A-X103A-X104I-X116A-X183D-X232V, X018R-X024R-X076D-X116A-X215F-X249R, X018R-X043R-X045T-X101G-X103A-X104I-X232V-X245R, X024R-X043R-X076D-X101G-X103A-X104I-X232V-X245R, X020R-X022W-X101G-X103A-X104I-X232V-X245R, X020R-X022W-X101G-X103A-X104I-X211Q-X232V-X245R, X020R-X022W-X078R-X101G-X103A-X104I-X116A-X213A-X215F-X232V-X245R, X043D-X076D-X078R-X101G-X103A-X104I-X232V-X245R-X269R, X018R-X024R-X076D-X101A-X116A-X213A-X249R, X018R-X024R-X076D-X116A-X211Q-X249R, X043R-X045T-X076D-X078R-X101G-X103A-X104I-X232V-X245R, X018R-X101G-X245R, X020R-X22W-X101A-X103A-X104I-X211Q-X213A-X232V-X245R, X020R-X024R-X043D-X076D-X078R-X101G-X103A-X104I-X232V-X245R, X018R-X045T-X076D-X078R-X101G-X103A-X104I-X232V-X245R, X020R-X078R-X101G-X103A-X104I-X211Q-X213A-X215F-X232V-X245R, X045T-X078R-X101G-X103A-X104I-X232V-X245R-X269R, X024R-X043D-X101G-X103A-X104I-X232V-X245R-X269R, X018R-X101G-X103A-X249R, X018R-X22W-X024R-X076D-X101A-X116A-X232V-X245R, X018R-X101G-X104I-X232V-X249R, X020R-X22W-X101A-X103A-X104I-X215F-X232V-X245R, X018R-X024R-X076D-

X211Q-X213A-X249R, X018R-X022W-X024R-X076D-X101A-X198L-X249R, X024R-X101G-X103A-X104I-X232V-X245R, X020R-X076D-X101G-X103A-X104I-X232V-X245R-X269R, X020R-X101G-X103A-X104I-X232V-X245R-X269R, X043D-X078R-X101G-X103A-X104I-X232V-X245R, X020R-X101G-X104I-X213A-X215F-X232V-X245R, X020R-X101G-X103A-X104I-X116A-X215F-X232V-X245R, X024R-X103A-X104I-X249R, X018R-X076D-X078R-X101G-X103A-X104I-X249R, X045T-X076D-X078R-X101G-X103A-X104I-X232V-X245R-X269R, X024R-X101G-X104I-X245R, X020R-X101G-X103A-X104I-X211Q-X213A-X215F-X232V-X245R, X024R-X103A-X104I-X232V-X249R, X018R-X024R-X076D-X116A-X211Q-X215F-X249R, X018R-X245R, X024R-X103A-X245R, X024R-X103A-X104I-X245R, X020R-X078R-X101G-X232V-X245R, X018R-X024R-X076D-X104I-X249R, X018R-X024R-X104I-X249R, X024R-X101G-X103A-X104I-X232V-X245R, X018R-X024R-X076D-X211Q-X215F-X249R, X019H-X020R-X022W-X078R-X101G-X103A-X104I-X211Q-X232V-X245R, X018R-X024R-X076D-X101A-X198L-X211Q-X213A-X249R, X018R-X024R-X043D-X101G-X103A-X104I-X232V-X245R, X020R-X22W-X103A-X104I-X232V-X245R, X018R-X103A-X104I-X249R, X018R-X022W-X024R-X076D-X101A-X198L-X215F-X249R, X018R-X024R-X101G-X104I-X232V, X078R-X101G-X103A-X104I-X232V-X245R-X269R, X024R-X043R-X076D-X078R-X101G-X103A-X104I-X232V-X245R, X018R-X020R-X043D-X076D-X101G-X103A-X104I-X232V-X245R, X018R-X22W-X024R-X076D-X116A-X213A-X249R, X018R-X024R-X101G-X104I, X020R-X101A-X103A-X104I-X215F-X232V-X245R, X018R-X045T-X078R-X101G-X103A-X104I-X232V-X245R, X018R-X101G-X103A-X245R, X043R-X076D-X078R-X101G-X103A-X104I-X232V-X245R, X020R-X022W-X101A-X103A-X104I-X211Q-X215F-X232V-X245R, X020R-X22W-X078R-X101G-X103A-X104I-X116A-X213A-X215F-X232V-X245R, X020R-X078R-X101G-X103A-X104I-X215F-X232V-X245R, X020R-X022W-X078R-X101G-X103A-X104I-X116A-X183D-X232V-X245R, X076D-X101G-X103A-X104I-X232V-X245R, X076D-X101G-X103A-X104I-X232V-X245R-X269R, X020R-X22W-X101A-X103A-X104I-X232V-X245R, X020R-X101G-X103A-X232V-X245R, X020R-X022W-X078R-X101A-X103A-X104I-X116A-X183D-X232V-X245R, X018R-X020R-X024R-X045T-X076D-X101G-X103A-X104I-X232V-X245R-X269R, X043R-X045T-X078R-X101G-X103A-X104I-X232V-X245R, X018R-X101G-X104I-X249R, X020R-X22W-X078R-X101G-X103A-X104I-X116A-X183D-X232V-X245R, X020R-X022W-X101G-X103A-X104I-X198L-X211Q-X213A-X232V-X245R, X020R-X078R-X101A-X103A-X104I-X116A-X183D-X213A-X232V-X245R, X024R-X076D-X104I-X232V-X245R, X018R-X020R-X076D-X101G-X103A-X104I-X232V-X245R, X018R-X024R-X076D-X101G-X104I-X232V-X249R, X018R-X043D-X078R-X101G-X103A-X104I-X232V-X245R, X001T-X018R-X024R-X076D-X116A-X213A-X249R, X076D-X078R-X101G-X103A-X104I-X232V-X245R, X020R-X078R-X101G-X103A-X104I-X116A-X232V-X245R, X043R-X076D-X101G-X103A-X104I-X232V-X245R, X018R-X045T-X101G-X103A-X104I-X232V-X245R, X018R-X076D-X101G-X104I-X232V-X245R, X020R-X078R-X101G-X103A-X104I-X116A-X183D-X232V-X245R, X018R-X024R-X076D-X101A-X211Q-X213A-X215F-X249R, X045T-X078R-X101G-X103A-X104I-X232V-X245R, X043R-X076D-X101G-X103A-X104I-X232V-X245R-X269R, X020R-X022W-X078R-X101G-X103A-X104I-X116A-X183D-X213A-X232V-X245R, X020R-X022W-X101G-X103A-X104I-X116A-X183D-X213A-X232V-X245R, X020R-X101G-X198L-X215F-X232V-X245R, X018R-X024R-X076D-X213A-X215F-X249R, X020R-X078R-X101G-X103A-X104I-X116A-X211Q-X232V-X245R, X020R-X022W-X078R-X101A-X103A-X104I-X116A-X183D-X215F-X232V-X245R, X020R-X022W-X078R-X101A-X103A-X104I-X116A-X183D-X213A-X232V-X245R, X024R-X232V-X245R, X018R-X024R-X043D-X101G-X103A-X104I-X232V-X245R-X269R, X018R-X024R-X076D-X101A-X215F-X249R, X018R-X022W-X024R-X076D-X116A-X213A-X249R, X101G-X103A-X104I-X232V-X245R, X018R-X024R-X076D-X211Q-X213A-X215F-X249R, X018R-X024R-X076D-X116A-X213A-X215F-X249R, X043D-X076D-X078R-X101G-X103A-X104I-X232V-X245R-X269R, X043D-X078R-X101G-X103A-X104I-X232V-X245R-X249R, X020R-X022W-X078R-X101G-X103A-X104I-X116A-X183D-X211Q-X232V-X245R, X018R-X024R-X076D-X101A-X198L-X211Q-X215V-X249R, X018R-X022W-X024R-X076D-X116A-X211Q-X249R, X020R-X103A-X104I-X232V-X245R, X020R-X22W-X101A-X103A-X104I-X211Q-X215F-X232V-X245R, X024R-X076D-X101G-X103A-X104I-X232V-X245R, X020R-X101G-X103A-X104I-X116A-X232V-X245R, X018R-X22W-X024R-X076D-X198L-X215F-X249R, X020R-X022W-X103A-X104I-X232V-X245R, X020R-X022W-X101A-X103A-X104I-X211Q-X213A-X232V-X245R, X020R-X022W-X101G-X103A-X104I-X211Q-X213A-X215F-X232V-X245R, X018R-X043R-X045T-X076D-X101G-X103A-X104I-X232V-X245R, X018R-X022W-X024R-X076D-X101A-X198L-X213A-X215F-X249R, X018R-X22W-X024R-X076D-X101A-X215F-X249R, X020R-X045T-X101G-X103A-X104I-X232V-X245R, X020R-X078R-X101G-X103A-X104I-X180A-X232V-X245R, X020R-X022W-X078R-X101G-X103A-X104I-X116A-X183D-X215F-X232V-X245R, X018R-X101G-X103A-X104I, X020R-X22W-X101A-X103A-X104I-X116A-X211Q-X213A-X215F-X232V-X245R, X018R-X024R-X076D-X103A-X232V-X245R, X020R-X078R-X101A-X103A-X104I-X116A-X183D-X232V-X245R, X018R-X024R-X076D-X211Q-X249R, X020R-X101A-X103A-X104I-X213A-X215F-X232V-X245R, X018R-X020R-X043D-X101G-X103A-X104I-X232V-X245R, X020R-X022W-X101A-X103A-X104I-X211Q-X232V-X245R, X020R-X022W-X101A-X103A-X104I-X116A-X211Q-X215F-X232V-X245R, X020R-X022W-X101A-X103A-X104I-X116A-X211Q-X232V-X245R, X018R-X024R-X076D-X232V-X249R, X018R-X024R-X045T-X076D-X101G-X103A-X104I-X232V-X245R-X269R, X018R-X076D-X245R, X024R-X104I-X245R, X101G-X232V, X020R-X22W-X101A-X103A-X104I-X116A-X211Q-X215F-X232V-X245R, X018R-X020R-X022W-X024R-X076D-X116A-X183D-X198L-X213A-X249R, X020R-X022W-X078R-X101A-X103A-X104I-X232V-X245R, X020R-X022W-X078R-X101A-X103A-X104I-X198L-X232V-X245R, X024R-X245R-X249R, X020R-X101G-X103A-X104I-X116A-X211Q-X232V-X245R, X018R-X22W-X024R-X076D-X116A-X211Q-X249R, X024R-X101G-X104I-X249R, X018R-X024R-X076D-X116A-X198L-X211Q-X213A-X215F-X249R, X018R-X024R-X104I, X020R-X022W-X078R-X101A-X103A-X104I-X183D-X198L-X213A-X215F-X232V-X245R, X018R-X020R-X22W-X024R-X076D-X116A-X183D-X198L-X213A-X249R, X020R-X022W-X101A-X103A-X104I-X232V-X245R, X012H-

X020R-X078R-X101G-X103A-X104I-X198L-X211Q-X213A-X232V-X245R, X018R-X024R-X076D-X101A-X211Q-X215F-X249R, X018R-X024R-X076D-X213A-X249R, X024R-X104I-X249R, X018R-X022W-X024R-X076D-X211Q-X249R, X018R-X076D-X103A-X104I-X249R, X043R-X076D-X101G-X103A-X104I-X217E-X232V-X245R, X020R-X078R-X101G-X103A-X104I-X183D-X211Q-X213A-X232V-X245R-X271G, X018R-X022W-X024R-X076D-X101A-X116A-X198L-X215F-X249R, X018R-X024R-X043D-X076D-X101G-X103A-X104I-X232V-X245R, X018R-X024R-X076D-X101A-X198L-X215F-X249R, X018R-X022W-X024R-X076D-X116A-X198L-X211Q-X213A-X249R, X018R-X024R-X076D-X101A-X116A-X213A-X215F-X249R, X020R-X043D-X045T-X078R-X101G-X103A-X104I-X232V-X245R, X045T-X078R-X101G-X103A-X104I-X232V-X245R-X249R, X018R-X22W-X024R-X076D-X101A-X116A-X215F-X249R, X043D-X101G-X103A-X104I-X232V-X245R-X269R, X020R-X022W-X078R-X101A-X103A-X104I-X116A-X183D-X213A-X215F-X232V-X245R, X018R-X024R-X076D-X116A-X211Q-X213A-X215F-X249R, X024R-X103A-X175L-X232V-X249R, X018R-X024R-X076D-X116A-X213A-X249R, X020R-X045T-X076D-X101G-X103A-X104I-X232V-X245R, X020R-X078R-X101A-X103A-X104I-X116A-X183D-X211Q-X213A-X215F-X232V-X245R, X024R-X043R-X045T-X076D-X078R-X101G-X103A-X104I-X232V-X245R, X018R-X024R-X076D-X101A-X116A-X198L-X213A-X215F-X249R, X043R-X045T-X101G-X103A-X104I-X232V-X245R, X018R-X022W-X024R-X076D-X101A-X198L-X211Q-X245R, X020R-X024R-X043D-X076D-X078R-X101G-X103A-X104I-X232V-X245R-X269R, X024R-X232V, X020R-X078R-X101A-X103A-X104I-X116A-X183D-X211Q-X232V-X245R, X024R-X076D-X101G-X232V-X245R, X018R-X076D-X101G-X103A-X104I-X249R, X018R-X024R-X076D-X198M-X211Q-X213A-X215F-X249R, X018R-X22W-X024R-X076D-X101A-X198L-X215F-X249R, X018R-X043R-X076D-X101G-X103A-X104I-X232V-X245R-X269R, X020R-X022W-X103A-X211Q-X213A-X215F-X232V-X245R, X020R-X078R-X101A-X103A-X104I-X116A-X183D-X211Q-X213A-X232V-X245R, X045T-X076D-X101G-X103A-X104I-X232V-X245R-X269R, X018R-X22W-X024R-X076D-X101A-X211Q-X213A-X249R, X018R-X024R-X076D-X116A-X198L-X215F-X249R-X268G, X018R-X022W-X024R-X076D-X101A-X211Q-X249R, X018R-X022W-X024R-X076D-X101A-X116A-X198L-X211Q-X249R, X101G-X103A-X104I-X245R, X018R-X076D-X101G-X232V-X245R, X018R-X020R-X045T-X101G-X103A-X104I-X232V-X245R, X018R-X022W-X024R-X076D-X101A-X116A-X198L-X249R, X018R-X022W-X024R-X076D-X116A-X198L-X213A-X249R, X078R-X101G-X103A-X104I-X232V-X245R-X249R, X018R-X078R-X101G-X103A-X104I-X217E-X232V-X245R, X020R-X043R-X076D-X101G-X103A-X104I-X232V-X245R-X269R, X018R-X043D-X076D-X101G-X103A-X104I-X232V-X245R-X249R, X045T-X101G-X103A-X104I-X232V-X245R-X269R, X024R-X103A-X232V, X018R-X024R-X076D-X101A-X211Q-X249R, X043D-X101G-X103A-X104I-X232V-X245R-X249R, X018R-X043R-X045T-X076D-X076T-X101G-X103A-X104I-X232V-X245R-X273T, X018R-X020R-X043D-X078R-X101G-X103A-X104I-X232V-X245R, X020R-X078R-X101A-X103A-X104I-X183D-X215F-X232V-X245R, X018R-X024R-X076D-X101G-X232V, X232V-X245R, X043R-X045T-X076D-X078R-X101G-X103A-X104I-X232V-X234I-X245R, X024R-X076D-X103A-X104I-X245R, X020R-X078R-X101A-X103A-X104I-X211Q-X213A-X232V-X245R, X043D-X078R-X101G-X103A-X104I-X232V-X245R-X269R-X272V, X018R-X020R-X024R-X076D-X116A-X183D-X198L-X211Q-X249R, X018R-X103A-X104I-X232V, X020R-X022W-X101G-X103A-X104I-X116A-X183D-X213A-X215F-X232V-X245R, X024R-X043R-X076D-X101G-X103A-X104I-X232V-X245R-X269R, X018R-X022W-X024R-X076D-X213A-X215F-X249R, X018R-X024R-X076D-X101A-X116A-X198L-X211Q-X213A-X249R, X020R-X22W-X078R-X101A-X103A-X104I-X116A-X183D-X213A-X232V-X245R, X020R-X022W-X078R-X101G-X103A-X104I-X211Q-X213A-X232V-X245R, X020R-X022W-X101A-X103A-X104I-X215F-X232V-X245R, X018R-X020R-X024R-X076D-X116A-X183D-X215F-X249R, X018R-X024R-X076D-X116A-X117I-X183D-X213A-X249R, X018R-X022W-X024R-X076D-X101A-X116A-X198L-X213A-X249R, X018R-X22W-X024R-X076D-X101A-X198L-X213A-X215F-X249R, X018R-X043D-X078R-X101G-X103A-X104I-X232V-X245R-X249R, X018R-X076D-X101G-X103A-X104I-X232V-X245R-X249R, X020R-X022W-X101G-X103A-X104I-X116A-X183D-X198L-X232V-X245R, X018R-X043R-X045T-X076D-X101G-X103A-X104I-X232V-X245R-X269R, X018R-X024R-X076D-X116A-X198L-X209H-X213A-X249R, X020R-X022W-X101A-X103A-X104I-X116A-X183D-X211Q-X213A-X232V-X245R, X024R-X076D-X101G-X175L-X232V-X245R, X018R-X043D-X045T-X101G-X103A-X104I-X232V-X245R, X045T-X076D-X078R-X101G-X103A-X104I-X232V-X245R, X020R-X078R-X101A-X103A-X104I-X116A-X183D-X198L-X215F-X232V-X245R, X043R-X076D-X101G-X103A-X104I-X232V-X245R-X249R, X018R-X024R-X076D-X198L-X213A-X215F-X249R, X018R-X022W-X024R-X076D-X198L-X215F-X249R, X018R-X022W-X024R-X076D-X116A-X213A-X215F-X249R, X018R-X022W-X024R-X076D-X101A-X116A-X198L-X213A-X215F-X249R, X018R-X022W-X024R-X076D-X116A-X211Q-X213A-X249R, X018R-X024R-X245R, X018R-X022W-X024R-X076D-X101A-X116A-X215F-X249R, X024R-X076D-X104I-X245R, X027R-X043R-X101G-X103A-X104I-X232V-X245R-X269R, X018R-X024R-X076D-X116A-X198L-X211Q-X213A-X249R, X018R-X024R-X076D-X116A-X198L-X249R, X018R-X024R-X076D-X183D-X198L-X211Q-X213A-X215F-X249R, X020R-X022W-X101A-X103A-X104I-X116A-X211Q-X213A-X215F-X232V-X245R, X018R-X043D-X045T-X078R-X101G-X103A-X104I-X232V-X245R, X043R-X045T-X076D-X078R-X101G-X103A-X104I-X232V-X245R-X269R, X018R-X22W-X024R-X076D-X116A-X213A-X215F-X249R, X018R-X022W-X024R-X076D-X116A-X211Q-X215F-X249R, X020R-X078R-X101G-X103A-X104I-X116A-X183D-X213A-X232V-X245R, X018R-X076D-X101G-X103A-X104I-X232V-X245R, X018R-X101G-X104I, X020R-X078R-X101G-X103A-X104I-X116A-X183D-X211Q-X213A-X215F-X232V-X245R, X020R-X078R-X101A-X103A-X104I-X232V-X245R, X018R-X024R-X076D-X101A-X198L-X211Q-X249R, X018R-X024R-X076D-X198L-X211Q-X213A-X249R, X018R-X022W-X024R-X076D-X101A-X116A-X198L-X211Q-X213A-X249R, X018R-X076D-X249R, X018R-X020R-X024R-X076D-X101A-X116A-X183D-X198L-X249R, X018R-X024R-X076D-X101A-X116A-X211Q-X213A-X249R, X020R-X022W-X078R-X101A-X103A-X104I-X116A-X183D-X211Q-X213A-X215F-X232V-X245R, X020R-X022W-X101G-X103A-X104I-X114T-X213A-X215F-X232V-X245R, X018R-

X22W-X024R-X076D-X116A-X211Q-X213A-X249R, X018R-X020R-X022W-X024R-X076D-X101A-X116A-X183D-X249R, X020R-X101A-X103A-X104I-X116A-X183D-X213A-X232V-X245R, X018R-X022W-X024R-X076D-X101A-X211Q-X213A-X249R, X018R-X022K-X043D-X101G-X103A-X104I-X232V-X245R, X018R-X101G-X103A-X104I-X232V-X245R-X269R, X020R-X078R-X101G-X103A-X104I-X116A-X183D-X211Q-X213A-X215F-X232V, X018R-X024R-X076D-X116A-X249R, X020R-X024R-X076D-X101G-X103A-X104I-X232V-X245R, X043D-X076D-X101G-X103A-X104I-X232V-X245R-X269R, X018R-X024R-X076D-X101A-X116A-X198L-X211Q-X249R, X018R-X022W-X024R-X076D-X198L-X213A-X215F-X249R, X018R-X043D-X076D-X078R-X101G-X103A-X104I-X232V-X245R-X269R, X020R-X22W-X101G-X103A-X104I-X116A-X183D-X213A-X215F-X232V-X245R, X020R-X101G-X103A-X104I-X183D-X211Q-X232V-X245R-, X018R-X024R-X076D-X101A-X198L-X213A-X249R, X018R-X024R-X076D-X101A-X198L-X249R, X018R-X024R-X045T-X076D-X101G-X103A-X104I-X232V-X245R-X249R, X018R-X024R-X076D-X101A-X183D-X213A-X249R, X018R-X043D-X076D-X078R-X101G-X103A-X104I-X232V-X245R, X020R-X078R-X101G-X103A-X104I-X116A-X131V-X183D-X213A-X232V-X245R, X018R-X045T-X076D-X101G-X103A-X104I-X232V-X245R, X018R-X024R-X076D-X101A-X183D-X211Q-X249R, X076D-X101G-X103A-X104I-X232V-X245R-X249R, X024R-X101G-X245R, X024R-X076D-X101G-X245R, X076D-X078R-X101G-X103A-X104I-X232V-X245R-X249R, X018R-X020R-X024R-X076D-X101A-X183D-X211Q-X215F-X249R, X024R-X101G, X018R-X22W-X024R-X076D-X213A-X215F-X249R, X020R-X043D-X101G-X103A-X104I-X232V-X245R, X020R-X022W-X101G-X103A-X104I-X183D-X198L-X213A-X215F-X232V-X245R, X018R-X043D-X045T-X101G-X103A-X104I-X232V-X245R-X269R, X043D-X076D-X078R-X101G-X103A-X104I-X232V-X245R, X024R-X045T-X076D-X101G-X103A-X104I-X232V-X245R-X269R, X020R-X022W-X101A-X103A-X104I-X198L-X211Q-X215F-X232V-X245R, X020R-X022W-X101G-X103A-X104I-X116A-X183D-X215F-X232V-X245R, X018R-X020R-X076D-X101G-X103A-X104I-X232V-X245R-X249R, X018R-X022W-X024R-X076D-X101A-X215F-X249R, X018R-X104I, X018R-X024R-X076D-X116A-X198L-X215F-X249R, X018R-X024R-X076D-X088I-X101A-X116A-X198L-X211Q-X215F-X249R, X018R-X022W-X024R-X076D-X101A-X116A-X211Q-X213A-X249R, X043R-X045T-X076D-X101G-X103A-X104I-X232V-X245R-X269R, X018R-X076D-X101G-X104I-X249R, X018R-X022W-X024R-X076D-X101A-X213A-X215F-X249R, X018R-X22W-X024R-X076D-X101A-X116A-X198L-X215F-X249R, X018R-X020R-X101G-X103A-X104I-X232V-X245R-X249R, X101G-X103A-X104I-X232V-X245R-X249R-X269R, X024R-X076D-X245R, X018R-X020R-X043R-X045T-X076D-X101G-X103A-X104I-X232V-X245R, X018R-X020R-X024R-X076D-X215F-X249R, X018R-X024R-X076D-X101A-X116A-X183D-X198L-X213A-X249R, X018R-X020R-X024R-X076D-X211Q-X215F-X249R, X043D-X101G-X103A-X104I-X232V-X245R, X020R-X22W-X078R-X101A-X103A-X104I-X116A-X183D-X215F-X232V-X245R, X018R-X024R-X076D-X198L-X211Q-X215F-X249R, X043R-X076D-X078R-X101G-X103A-X104I-X232V-X245R-X269R, X043R-X078R-X101G-X103A-X104I-X232V-X245R-X269R, X020R-X043D-X101G-X103A-X104I-X232V-X245R-X249R, X018R-X022W-X024R-X076D-X101A-X213A-X249R, X020R-X022W-X101A-X116A-X198L-X211Q-X213A-X215F-X249R, X043R-X045T-X078R-X101G-X103A-X104I-X218S-X232V-X245R, X018R-X103A, X020R-X22W-X101G-X103A-X104I-X116A-X183D-X215F-X232V-X245R, X018R-X024R-X076D-X101A-X249R, X018R-X022W-X024R-X076D-X211Q-X213A-X249R, X024R-X043R-X045T-X076D-X101G-X103A-X104I-X232V-X245R, X020R-X022W-X101A-X103A-X104I-X116A-X183D-X232V-X245R, X020R-X101A-X103A-X104I-X116A-X183D-X211Q-X213A-X215F-X232V-X245R, X027R-X045T-X076D-X078R-X101G-X103A-X104I-X232V-X245R-X269R, X020R-X045T-X076D-X101G-X103A-X104I-X232V-X245R-X249R, X018R-X020R-X024R-X076D-X116A-X183D-X213A-X215F-X249R, X018R-X024R-X076D-X104I, X101G-X103A-X104I-X232V-X249R, X018R-X024R-X076D-X116A-X183D-X211Q-X249R, X018R-X020R-X024R-X076D-X116A-X215F-X249R, X018R-X024R-X076D-X183D-X213A-X215F-X249R, X018R-X022W-X024R-X076D-X198L-X211Q-X249R, X043D-X078R-X101G-X103A-X104I-X232V-X245R-X269R-X275S, X020R-X022W-X101A-X103A-X104I-X116A-X183D-X211Q-X232V-X245R, X018R-X022W-X024R-X076D-X101A-X198L-X211Q-X213A-X215F-X249R, X018R-X022W-X024R-X076D-X101A-X116A-X198L-X211Q-X213A-X215F-X249R, X018R-X020R-X024R-X076D-X183D-X249R, X018R-X024R-X076D-X116A-X198L-X213A-X249R, X018R-X022W-X024R-X076D-X101A-X116A-X211Q-X249R, X004M-X018R-X024R-X076D-X116A-X198L-X211Q-X213A-X249R, X104I-X232V-X249R, X020R-X022W-X101G-X103A-X104I-X116A-X183D-X211Q-X215F-X232V-X245R, X020R-X101A-X103A-X104I-X116A-X183D-X211Q-X232V-X245R-X274I, X020R-X101A-X103A-X104I-X213A-X232V-X245R, X020R-X101G-X103A-X104I-X116A-X183D-X211Q-X213A-X232V-X245R, X020R-X024R-X043D-X078R-X101G-X103A-X104I-X232V-X245R, X018R-X024R-X076D-X103A-X249R, X018R-X020R-X024R-X076D-X101A-X116A-X183D-X211Q-X215F-X249R, X018R-X020R-X024R-X076D-X116A-X183D-X198L-X249R, X018R-X022W-X024R-X076D-X116A-X198L-X215F-X249R, X018R-X024R-X076D-X101A-X211Q-X213A-X215F-X249R-X270V, X018R-X043D-X045T-X076D-X078R-X101G-X103A-X104I-X232V-X245R-X269R, X020R-X022W-X101G-X103A-X104I-X183D-X232V-X245R, X018R-X020R-X022W-X024R-X076D-X101A-X116A-X213A-X249R, X018R-X022W-X024R-X076D-X198L-X211Q-X215F-X249R, X018R-X022W-X024R-X076D-X198L-X213A-X249R, X020R-X022W-X101G-X103A-X104I-X116A-X183D-X232V-X245R, X018R-X22W-X024R-X076D-X116A-X198L-X213A-X249R, X043R-X045T-X078R-X101G-X103A-X104I-X232V-X245R-X269R, X018R-X024R-X076D-X101G-X103A-X104I-X232V, X101G-X249R, X024R-X076D-X101G-X103A-X104I-X175L-X249R, X020R-X022W-X101A-X103A-X104I-X116A-X183D-X232V-X245R-X269S, X018R-X024R-X076D-X101A-X116A-X198L-X249R, X018R-X022W-X024R-X076D-X116A-X249R, X018R-X020R-X024R-X076D-X101A-X183D-X198L-X215F-X249R, X018R-X024R-X076D-X213A-X215F-X249R-X260K, X018R-X024R-X076D-X116A-X211Q-X213A-X249R, X018R-X020R-X022W-X024R-X076D-X116A-X198L-X249R, X024R-X076D-X101G-X103A-X104I-X245R, X024R-X076D-X103A-X249R, X018R-X101G-X103A-X104I-X232V-X245R-X249R, X018R-X024R-X076D-X198L-X211Q-X249R, X018R-X022W-X024R-X076D-X101A-

X198L-X211Q-X213A-X249R, X020R-X024R-X045T-X101G-X103A-X104I-X232V-X245R, X018R-X020R-X024R-X076D-X183D-X211Q-X213A-X249R, X018R-X043D-X045T-X076D-X101G-X103A-X104I-X232V-X245R-X272D, X018R-X024R-X076D-X116A-X198L-X213A-X215F-X249R, X018R-X22W-X024R-X076D-X101A-X198L-X249R, X018R-X022W-X024R-X076D-X116A-X198L-X249R, X024R-X076D-X101G-X103A-X232V, X024R-X103A-X104I, X018R-X024R-X076D-X101A-X116A-X183D-X211Q-X215F-X249R, X024R-X045T-X076D-X101G-X103A-X104I-X232V-X245R-X249R, X020R-X101G-X103A-X104I-X116A-X183D-X232V-X245R, X024R-X043D-X076D-X101G-X103A-X104I-X232V-X245R-X269R, X020R-X022W-X101A-X103A-X104I-X183D-X211Q-X213A-X215F-X232V-X245R, X020R-X045T-X076D-X078R-X101G-X103A-X104I-X232V-X245R-X269R, X018R-X024R-X076D-X101A-X116A-X198L-X211Q-X215F-X249R, X020R-X101A-X103A-X104I-X116A-X183D-X215F-X232V-X245R, X018R-X043R-X101G-X103A-X104I-X232V-X245R-X249R, X018R-X024R-X076D-X198L-X213A-X249R, X018R-X024R-X076D-X116A-X183D-X213A-X249R, X020R-X043D-X101G-X103A-X104I-X232V-X245R-X269R, X024R-X076D-X103A-X245R, X018R-X022W-X024R-X076D-X101A-X116A-X211Q-X213A-X215F-X249R, X103A-X104I-X245R, X018R-X022W-X024R-X076D-X211Q-X215F-X249R, X018R-X022W-X024R-X076D-X116A-X183D-X198L-X249R, X018R-X022W-X024R-X076D-X198L-X211Q-X213A-X249R, X018R-X024R-X076D-X116A-X183D-X211Q-X213A-X215F-X249R, X018R-X020R-X043D-X045T-X076D-X101G-X103A-X104I-X232V-X245R-X269R, X018R-X020R-X022W-X024R-X076D-X101A-X211Q-X213A-X215F-X249R, X016T-X043R-X045T-X076D-X101G-X103A-X104I-X232V-X245R-X269R, X018R-X022W-X024R-X076D-X116A-X215F-X249R, X043R-X076D-X101G-X103T-X104I-X232V-X245R-X249R-X269R, X020R-X078R-X101A-X103A-X104I-X115E-X116A-X183D-X211Q-X213A-X232V-X245R, X018R-X024R-X076D-X198L-X249R, X018R-X024R-X076D-X101A-X116A-X183D-X249R, X020R-X101G-X103A-X104I-X116A-X183D-X211Q-X232V-X245R, X018R-X024R-X076D-X101G, X076D-X101G-X232V-X245R, X018R-X076D-X101G-X103A-X104I-X245R, X018R-X045T-X101G-X103A-X104I-X232V-X245R-X249R, X018R-X024R-X076D-X215F-X249R, X018R-X104I-X232V, X043D-X045T-X076D-X078R-X101G-X103A-X104I-X232V-X245R, X024R-X076D-X101G-X232V-X249R, X103A-X232V-X245R, X020R-X101G-X103A-X104I-X116A-X183D-X211Q-X213A-X215F-X232V-X245R, X018R-X020R-X024R-X076D-X116A-X183D-X198L-X211Q-X215F-X249R, X018R-X022W-X024R-X076D-X101A-X198L-X211Q-X215F-X249R, X024R-X076D-X103A-X104I-X249R, X024R-X101G-X103A-X104I, X020R-X101G-X103A-X104I-X116A-X183D-X211Q-X215F-X232V-X245R, X018R-X022W-X024R-X076D-X101A-X116A-X183D-X215F-X249R, X020R-X022W-X101G-X103A-X104I-X116A-X183D-X211Q-X213A-X215F-X232V-X245R, X020R-X024R-X045T-X076D-X101G-X103A-X104I-X232V-X245R, X018R-X022W-X024R-X076D-X116A-X183D-X213A-X249R, X018R-X020R-X024R-X076D-X131T-X215F-X249R, X018R-X024R-X076D-X101A-X116A-X183D-X211Q-X213A-X215F-X249R, X018R-X024R-X076D-X101A-X116A-X211Q-X213A-X215F-X249R, X018R-X024R-X076D-X198L-X215F-X249R, X018R-X022W-X024R-X076D-X183D-X211Q-X249R, X018R-X022W-X024R-X076D-X101A-X116A-X213A-X215F-X249R, X018R-X020R-X024R-X045T-X076D-X101G-X103A-X104I-X232V-X245R, X043R-X101G-X103A-X104I-X245R-X249R, X018R-X076D-X232V-X249R, X018K-X076D-X078R-X101G-X103A-X104I-X217E-X232V-X245R-X269R, X018R-X020R-X024R-X043D-X076D-X078R-X101G-X103A-X104I-X232V-X245R, X018R-X022W-X024R-X076D-X101A-X116A-X213A-X215F-X249R-X267I, X232V-X249R, X018R-X020R-X024R-X076D-X116A-X211Q-X213A-X215F-X249R, X076D-X104I-X245R, X018R-X020R-X024R-X076D-X183D-X198L-X211Q-X215F-X249R, X018R-X024R-X076D-X101A-X211Q-X213A-X249R, X024R-X101G-X103A-X232V, X018R-X020R-X022W-X024R-X076D-X116A-X183D-X198L-X213A-X215F-X249R, X018R-X020R-X024R-X076D-X116A-X183D-X198L-X211Q-X213A-X249R, X018R-X020R-X022W-X024R-X076D-X101A-X215F-X249R, X020R-X022W-X101A-X103A-X104I-X116A-X183D-X211Q-X215F-X232V-X245R, X018R-X024R-X076D-X116A-X198L-X211Q-X249R, X103A-X232V-X249R, X018R-X020R-X024R-X076D-X116A-X183D-X198L-X215F-X249R, X018R-X024R-X076D-X116A-X183D-X198L-X213A-X249R, X018R-X022W-X024R-X076D-X183D-X213A-X249R, X018R-X024R-X076D-X101A-X213A-X215F-X249R, X018R-X022W-X024R-X076D-X101A-X116A-X183D-X211Q-X249R, X018R-X045T-X101G-X103A-X104I-X232V-X245R-X269R, X018R-X020R-X045T-X076D-X078R-X101G-X103A-X104I-X232V-X245R, X018R-X022W-X024R-X076D-X116A-X198L-X213A-X215F-X249R, X020R-X022W-X101G-X103A-X104I-X116A-X183D-X211Q-X213A-X232V-X245R, X018R-X020R-X024R-X076D-X198L-X249R, X018R-X020R-X022W-X024R-X076D-X101A-X116A-X211Q-X249R, X020R-X022W-X101A-X103A-X104I-X116A-X183D-X232V-X245R-X274I, X024R-X103A-X245R-X249R, X018R-X022W-X024R-X076D-X101A-X116A-X183D-X198L-X249R, X018R-X024R-X076D-X101A-X198L-X211Q-X215F-X249R, X018R-X022W-X024R-X076D-X116A-X198L-X211Q-X215F-X249R, X018R-X020R-X022W-X024R-X076D-X116A-X183D-X213A-X249R, X018R-X043D-X045T-X076D-X101G-X103A-X104I-X232V-X245R-X269R, X018R-X022W-X024R-X076D-X116A-X211Q-X213A-X215F-X249R, X018R-X024R-X076D-X101A-X183D-X198L-X213A-X249R, X043D-X076D-X101G-X103A-X104I-X232V-X245R-X249R, X018R-X024R-X076D-X198L-X211Q-X213A-X215F-X249R, X018R-X020R-X024R-X076D-X116A-X183D-X213A-X249R, X103A-X232V, X018R-X022W-X024R-X076D-X116A-X183D-X215F-X249R, X018R-X024R-X076D-X101A-X116A-X249R, X018R-X043R-X078R-X101G-X103A-X104I-X232V-X245R, X018R-X020R-X022W-X024R-X076D-X101A-X183D-X211Q-X215F-X249R, X043R-X076D-X078R-X101G-X103A-X104I-X232V-X245R-X249R, X018R-X020R-X024R-X076D-X101A-X116A-X183D-X198L-X213A-X249R, X018R-X024R-X076D-X183D-X198L-X213A-X249R, X018R-X022W-X024R-X076D-X101A-X183D-X211Q-X249R, X018R-X020R-X024R-X076D-X198L-X213A-X215F-X249R, X018R-X020R-X022W-X024R-X076D-X183D-X211Q-X213A-X249R, X018R-X022W-X024R-X076D-X198L-X249R, X018R-X024R-X076D-X183D-X198L-X211Q-X249R, X020R-X022W-X101A-X103A-X104I-X116A-X183D-X213A-X232V-X245R, X018R-X020R-X024R-X076D-X116A-X183D-X211Q-X213A-X249R, X018R-X024R-X076D-X116A-X183D-X198L-X211Q-X213A-X215F-X249R, X020R-X022W-X101A-X103A-X104I-X116A-X183D-X215F-X232V-

X245R, X018R-X024R-X076D-X101A-X183D-X249R, X018R-X024R-X076D-X232V, X018R-X022W-X024R-X076D-X101A-X116A-X249R, X020R-X101A-X103A-X104I-X116A-X183D-X198L-X211Q-X213A-X215F-X232V-X245R, X020R-X022W-X101G-X103A-X104I-X116A-X183D-X211Q-X232V-X245R-X263S, X024R-X076D-X101G-X104I-X232V-X249R, X043R-X078R-X101G-X103A-X104I-X232V-X245R, X024R-X076D-X078R-X101G-X103A-X104I-X232V-X245R-X249R, X018R-X024R-X076D-X101A-X183D-X198L-X213A-X215F-X249R, X018R-X020R-X024R-X076D-X198L-X215F-X249R, X018R-X020R-X024R-X076D-X101A-X116A-X213A-X249R, X018R-X024R-X076D-X101A-X197A-X213A-X215F-X249R, X024R-X101G-X103A, X018R-X024R-X076D-X101A-X116A-X211Q-X215F-X249R, X043R-X076D-X078R-X101G-X103A-X104I-X217E-X232V-X245R, X024R-X104I-X232V, X018R-X024R-X076D-X183D-X211Q-X249R, X020R-X043R-X045T-X078R-X101G-X103A-X104I-X232V-X245R, X018R-X020R-X022W-X024R-X076D-X101A-X116A-X183D-X213A-X249R, X018R-X024R-X076D-X116A-X150T-X213A-X249R, X018R-X024R-X076D-X183D-X213A-X249R, X018R-X020R-X024R-X076D-X116A-X183D-X215F-X249R, X018R-X020R-X024R-X076D-X211Q-X249R, X018R-X024R-X076D-X101A-X116A-X183D-X198L-X249R, X024R-X076D-X232V-X249R, X018R-X020R-X022W-X024R-X076D-X101A-X116A-X183D-X198L-X211Q-X213A-X249R, X018R-X022W-X024R-X076D-X101A-X116T-X198L-X215F-X249R, X018R-X024R-X076D-X183D-X198L-X211Q-X215F-X249R, X018R-X022R-X024R-X076D-X101A-X116A-X183D-X211Q-X249R, X045T-X101G-X103A-X104I-X232V-X245R, X018R-X020R-X024R-X076D-X101A-X183D-X211Q-X249R, X020R-X101G-X103A-X104I-X116A-X183D-X213A-X232V-X245R, X076D-X101G-X103A-X245R, X020R-X043D-X078R-X101G-X103A-X104I-X232V-X245R-X249R, X018R-X024R-X076D-X116A-X183D-X249R, X018R-X024R-X076D-X101A-X183D-X211Q-X213A-X215F-X249R, X018R-X020R-X022W-X024R-X076D-X101A-X116A-X198L-X249R, X018R-X22W-X024R-X076D-X211Q-X213A-X249R, X018R-X020R-X024R-X076D-X183D-X211Q-X249R, X018R-X020R-X024R-X076D-X101A-X116A-X183D-X213A-X249R, X043R-X078R-X101G-X103A-X104I-X217E-X232V-X245R, X018R-X022W-X024R-X076D-X101A-X215F-X249R, X018R-X020R-X024R-X076D-X101A-X183D-X198L-X211Q-X213A-X249R, X076D-X101G-X104I-X249R, X018R-X022W-X024R-X076D-X101A-X116A-X183D-X213A-X249R, X018R-X024R-X076D-X183D-X249R, X018R-X024R-X076D-X101A-X183D-X198L-X215F-X249R, X018R-X022W-X024R-X076D-X183D-X198L-X215F-X249R, X018R-X022W-X024R-X076D-X101A-X198L-X211Q-X249R, X020R-X101A-X103A-X104I-X116A-X183D-X232V-X245R, X018R-X024R-X076D-X116A-X183D-X198L-X211Q-X249R, X018R-X020R-X024R-X101G-X103A-X104I-X232V-X245R, X018R-X076D-X078R-X101G-X103A-X104I-X217E-X232V-X245R, X020R-X101A-X103A-X104I-X116A-X183D-X211Q-X232V-X245R, X018R-X022W-X024R-X076D-X101A-X183D-X198L-X209H-X249R, X018R-X024R-X076D-X183D-X198L-X213A-X215F-X249R, X018R-X024R-X076D-X101A-X116A-X183D-X211Q-X213A-X249R, X018R-X022W-X024R-X076D-X101A-X116A-X183D-X211Q-X213A-X249R, X018R-X024R-X076D-X183D-X198L-X249R, X018R-X024R-X076D-X183D-X215F-X249R, X018R-X020R-X024R-X076D-X211Q-X213A-X215F-X249R, X076D-X245R, X076D-X101G-X104I-X245R, X018R-X022W-X024R-X076D-X101A-X211Q-X215F-X249R, X018R-X022W-X024R-X076D-X101A-X116A-X183D-X211Q-X215F-X249R, X018R-X020R-X022W-X024R-X076D-X101A-X211Q-X213A-X249R, X020R-X024R-X043R-X101G-X103A-X104I-X232V-X245R, X018R-X024R-X076D-X116A-X183D-X211Q-X215F-X249R, X020R-X101A-X103A-X104I-X116A-X183D-X213A-X215F-X232V-X245R, X101G-X103A-X104I, X018R-X020R-X024R-X076D-X101A-X116A-X183D-X211Q-X213A-X249R, X018R-X020R-X024R-X076D-X204D-X213A-X249R, X018R-X022W-X024R-X076D-X183D-X198L-X249R, X018R-X024R-X076D-X101A-X116A-X183D-X215F-X249R, X018R-X022W-X024R-X076D-X116A-X183D-X198L-X211Q-X213A-X209V-X249R, X018R-X022W-X024R-X076D-X101A-X116A-X183D-X211Q-X213A-X215F-X249R, X018R-X024R-X076D-X101A-X116A-X198L-X213A-X249R, X018R-X020R-X024R-X076D-X101A-X116A-X211Q-X213A-X249R, X018R-X020R-X022W-X024R-X076D-X101A-X116A-X183D-X211Q-X213A-X215F-X249R, X018R-X024R-X076D-X101A-X116A-X183D-X213A-X215F-X249R, X018R-X024R-X076D-X101A-X183D-X198L-X211Q-X213A-X215F-X249R, X018R-X024R-X076D-X101A-X183D-X198L-X211Q-X213A-X249R, X018R-X043R-X045T-X078R-X101G-X103A-X104I-X217E-X232V-X245R, X018R-X024R-X076D-X183D-X211Q-X213A-X215F-X249R, X018R-X022W-X024R-X076D-X116A-X183D-X198L-X215F-X249R, X018R-X020R-X024R-X076D-X116A-X249R, X018R-X020R-X022W-X024R-X076D-X101A-X211Q-X215F-X249R, X018R-X020R-X024R-X076D-X183D-X211Q-X213A-X215F-X249R, X018R-X020R-X022W-X024R-X076D-X198L-X213A-X249R, X018R-X020R-X024R-X076D-X101A-X211Q-X215F-X249R-X269D, X018R-X020R-X043D-X101G-X103A-X104I-X232V-X245R-X269R, X018R-X022W-X024R-X076D-X101A-X183D-X198L-X213A-X249R, X020R-X022W-X101G-X103A-X104I-X183D-X215F-X232V-X245R, X018R-X022W-X024R-X076D-X116A-X183D-X198L-X209H-X211Q-X249R, X018R-X020R-X022W-X024R-X076D-X101A-X116A-X183D-X211Q-X249R, X076D-X232V-X245R, X043D-X045T-X078R-X101G-X103A-X104I-X232V-X245R, X018R-X020R-X024R-X076D-X116A-X198L-X211Q-X215F-X245R, X018R-X020R-X022W-X024R-X076D-X213A-X249R, X020R-X024R-X043D-X078R-X101G-X103A-X104I-X232V-X245R-X249R, X018R-X020R-X022W-X024R-X076D-X101A-X198L-X215F-X249R, X020R-X090S-X101G-X103A-X104I-X116A-X183D-X213A-X215F-X232V-X245R, X018R-X020R-X022W-X024R-X076D-X101A-X198L-X211Q-X213A-X215F-X249R, X018R-X020R-X024R-X076D-X101A-X183D-X213A-X215F-X249R, X018R-X024R-X076D-X116A-X183D-X198L-X211Q-X213A-X249R, X043D-X045T-X078R-X101G-X103A-X104I-X232V-X245R-X269R, X018R-X024R-X076D-X101A-X183D-X215F-X249R, X018R-X020R-X024R-X076D-X101A-X183D-X198L-X213A-X249R, X020R-X022W-X101A-X103A-X104I-X116A-X183D-X198L-X211Q-X213A-X215F-X232V-X245R, X018R-X020R-X024R-X043D-X076D-X101G-X103A-X104I-X232V-X245R-X269R, X018R-X024R-X076D-X101A-X183D-X213A-X215F-X249R, X018R-X020R-X022W-X024R-X076D-X101A-X116A-X198L-X211Q-X213A-X215F-X249R, X018R-X020R-X043D-X101G-X103A-X104I-X217E-X232V-X245R, X076D-X103A-X104I-X232V-X245R, X045T-X076D-X078R-X101G-X103A-X104I-X232V-X245R-X249R, X018R-X022W-X024R-

X076D-X101A-X183D-X211Q-X215F-X249R, X018R-X022W-X024R-X076D-X101A-X116A-X183D-X249R, X018R-X024R-X076D-X116A-X183D-X198L-X211Q-X215F-X249R, X018R-X020R-X043D-X076D-X078R-X101G-X103A-X104I-X217E-X232V-X245R, X076D-X103A-X104I-X245R, X018R-X020R-X024R-X076D-X101A-X116A-X211Q-X213A-X215F-X249R, X018R-X024R-X076D-X101A-X183D-X198L-X249R, X018R-X022W-X024R-X076D-X116A-X183D-X198L-X211Q-X215F-X249R, X018R-X024R-X076D-X116A-X183D-X213A-X215F-X249R, X018R-X022W-X024R-X076D-X116A-X183D-X198L-X211Q-X249R, X018R-X024R-X076D-X101G-X245R, X018R-X024R-X076D-X101A-X116A-X183D-X198L-X213A-X215F-X249R, X043R-X045T-X076D-X101G-X103A-X104I-X232V-X245R, X018R-X020R-X022W-X024R-X076D-X116A-X198L-X213A-X215F-X249R, X076D-X104I-X232V-X245R, X027R-X043R-X045T-X076D-X101G-X103A-X104I-X232V-X245R, X018R-X022W-X024R-X076D-X101A-X183D-X213A-X215F-X249R, X018R-X024R-X076D-X103A-X104I-X135I-X232V, X018R-X020R-X022W-X024R-X076D-X183D-X198L-X211Q-X249R, X018R-X020R-X022W-X024R-X076D-X101A-X116A-X183D-X198L-X215F-X249R, X018R-X024R-X076D-X101A-X116A-X183D-X211Q-X249R, X018R-X022W-X024R-X076D-X183D-X211Q-X213A-X215F-X249R, X076D-X101G-X103A-X104I-X232V-X249R, X005S-X018R-X022W-X024R-X076D-X101A-X213A-X215F-X249R, X018R-X024R-X076D-X116A-X183D-X215F-X249R, X018R-X024R-X076D-X183D-X198L-X215F-X249R, X018R-X020R-X024R-X076D-X101A-X116A-X183D-X249R, X018R-X022W-X024R-X076D-X116A-X183D-X211Q-X249R, X018R-X020R-X022W-X024R-X076D-X101A-X116A-X249R, X018R-X022W-X024R-X076D-X101A-X116A-X183D-X198L-X213A-X249R, X018R-X022W-X024R-X076D-X101A-X183D-X211Q-X213A-X249R, X018R-X020R-X024R-X076D-X116A-X198L-X249R, X018R-X024R-X076D-X183D-X211Q-X213A-X249R, X018R-X024R-X076D-X101A-X116A-X183D-X213A-X249R, X018R-X024R-X076D-X116A-X183D-X198L-X215F-X249R, X018R-X022W-X024R-X076D-X183D-X198L-X211Q-X215F-X249R, X018R-X022W-X024R-X076D-X183D-X249R, X018R-X022W-X024R-X076D-X101A-X183D-X198L-X215F-X249R, X018R-X020R-X043D-X045T-X076D-X101G-X103A-X104I-X232V-X245R, X020R-X022W-X101A-X103A-X104I-X183D-X198L-X215F-X232V-X245R, X076D-X101G-X103A-X104I-X249R, X018R-X020R-X024R-X076D-X183D-X198L-X215F-X249R, X018R-X020R-X022W-X024R-X076D-X101A-X183D-X215F-X249R, X018R-X020R-X024R-X076D-X211Q-X213A-X249R, X018R-X024R-X076D-X116A-X183D-X211Q-X213A-X249R, X018R-X024R-X076D-X116A-X183D-X198L-X249R, X018R-X020R-X024R-X076D-X211Q-X243D-X249R, X018R-X020R-X045T-X076D-X101G-X103A-X104I-X232V-X245R-X249R, X018R-X022W-X024R-X076D-X183D-X198L-X211Q-X213A-X249R, X018R-X024R-X076D-X101A-X116A-X183D-X198L-X211Q-X213A-X249R, X018R-X022W-X024R-X076D-X116A-X198L-X211Q-X213A-X215F-X249R, X024R-X076D-X101G, X018R-X020R-X024R-X076D-X101A-X198L-X213A-X215F-X249R, X018R-X022W-X024R-X076D-X116A-X183D-X211Q-X213A-X249R, X018R-X020R-X024R-X076D-X183D-X215F-X249R, X018R-X043D-X076D-X078R-X101G-X103A-X104I-X232V-X245R-X249R, X018R-X022W-X024R-X076D-X116A-X183D-X211Q-X213A-X245R, X020R-X024R-X076D-X078R-X101G-X103A-X104I-X232V-X245R-X249R, X018R-X020R-X045T-X101G-X103A-X104I-X232V-X245R-X249R, X018R-X024R-X076D-X101A-X183D-X198L-X211Q-X249R, X018R-X022W-X024R-X076D-X183D-X211Q-X213A-X249R, X018R-X020R-X024R-X076D-X116A-X198L-X211Q-X215F-X249R-X269S, X018R-X020R-X022W-X024R-X076D-X101A-X116A-X183D-X198L-X211Q-X215F-X249R, X020R-X022W-X101A-X103A-X104I-X183D-X213A-X215F-X232V-X245R, X018R-X024R-X076D-X086V-X101A-X183D-X198L-X211Q-X249R, X018R-X076D-X101G-X198T-X232V, X018R-X020R-X024R-X076D-X101A-X116A-X183D-X198L-X211Q-X215F-X249R, X018R-X022W-X024R-X076D-X101A-X116A-X183D-X213A-X215F-X249R, X018R-X022W-X024R-X076D-X101A-X183D-X211Q-X213A-X215F-X249R, X018R-X024R-X076D-X183D-X249R-X248T, X018R-X076D-X104I-X245R-X249R, X018R-X022W-X024R-X076D-X101A-X116A-X183D-X198L-X215F-X249R, X018R-X022W-X024R-X076D-X116A-X183D-X213A-X215F-X249R, X018R-X020R-X022W-X024R-X076D-X116A-X183D-X211Q-X213A-X215F-X249R, X018R-X020R-X024R-X076D-X101A-X249R, X018R-X020R-X024R-X076D-X101A-X116A-X213A-X215F-X249R, X018R-X022W-X024R-X076D-X116A-X183D-X211Q-X215F-X249R, X018R-X022W-X024R-X076D-X116A-X183D-X198L-X211Q-X213A-X249R, X043R-X045T-X078R-X101G-X103A-X104I-X217E-X232V-X245R, X043R-X045T-X101G-X103A-X104I-X232V-X245R-X249R, X018R-X076D-X101G-X104I, X020R-X045T-X076D-X078R-X101G-X103A-X104I-X232V-X245R-X249R, X043D-X076D-X101G-X103A-X104I-X232V-X245R, X018R-X020R-X022W-X024R-X076D-X101A-X116A-X183D-X198L-X249R, X018R-X076D-X104I, X018R-X020R-X043D-X101G-X103A-X104I-X232V-X245R-X249R, X018R-X020R-X022W-X024R-X076D-X183D-X211Q-X249R, X018R-X024R-X076D-X101A-X183D-X198L-X211Q-X215F-X249R, X101G-X104I, X018R-X022W-X024R-X076D-X116A-X183D-X198L-X211Q-X213A-X215F-X249R, X018R-X020R-X024R-X076D-X101A-X183D-X211Q-X213A-X215F-X249R, X018R-X020R-X024R-X076D-X116A-X183D-X215F-X249R-X263D, X018R-X022W-X024R-X076D-X101A-X183D-X249R, X018R-X024R-X076D-X101A-X116A-X183D-X198L-X215F-X249R, X018R-X022W-X024R-X076D-X116A-X198L-X215F-X249R-X269H, X018R-X043D-X045T-X076D-X078R-X101G-X103A-X104I-X232V-X245R, X018R-X024R-X045T-X076D-X078R-X101G-X103A-X104I-X232V-X245R-X269R, X078R-X101G-X103A-X104I-X217E-X232V-X245R, X018R-X020R-X022W-X024R-X076D-X101A-X183D-X198L-X213A-X215F-X249R, X018R-X020R-X024R-X076D-X183D-X198L-X213A-X249R, X018R-X020R-X022W-X024R-X076D-X116A-X198L-X211Q-X215F-X249R, X018R-X020R-X022W-X024R-X076D-X116A-X183D-X211Q-X249R, X018R-X020R-X022W-X024R-X076D-X101A-X198L-X211Q-X213A-X249R, X018R-X020R-X022W-X024R-X076D-X249R, X020R-X022W-X101G-X103A-X104I-X116A-X183D-X198L-X211Q-X213A-X215F-X232V-X245R, X104I-X232V, X018R-X020R-X022W-X024R-X076D-X101A-X116A-X183D-X211Q-X215F-X249R, X018R-X020R-X022W-X024R-X076D-X101A-X116A-X183D-X198L-X211Q-X213A-X215F-X249R, X018R-X020R-X022W-X024R-X076D-X101A-X183D-X213A-X215F-X249R, X018R-X022W-X024R-X076D-X101A-X183D-X198L-X211Q-X213A-X249R, X018R-X022W-X024R-X076D-X101A-X183D-X198L-X249R, X043D-X045T-X101G-X103A-

X104I-X232V-X245R-X269R, X018R-X020R-X024R-X076D-X101A-X183D-X198L-X211Q-X249R, X018R-X020R-X043R-X101G-X103A-X104I-X217E-X232V-X245R, X024R-X043R-X076D-X078R-X101G-X103A-X104I-X232V-X245R-X269R, X043R-X045T-X076D-X078R-X101G-X103A-X104I-X166F-X176P-X179V-X184T-X187P-X194P, X018R-X022W-X024R-X041E-X076D-X101A-X160T-X183D-X211Q-X213A-X249R, X018R-X020R-X022W-X024R-X076D-X116A-X183D-X198L-X211Q-X215F-X249R, X018R-X020R-X022W-X024R-X076D-X101A-X116A-X198L-X213A-X249R, X018R-X022W-X024R-X076D-X101A-X116A-X183D-X198L-X211Q-X213A-X249R, X018R-X020R-X024R-X076D-X198L-X213A-X249R, X018R-X020R-X022W-X024R-X076D-X116A-X183D-X198L-X211Q-X249R, X018R-X020R-X024R-X076D-X183D-X211Q-X215F-X249R, X024R-X076D-X104I, X018R-X076D-X101G-X232V, X018R-X024R-X076D-X101A-X116A-X183D-X198L-X211Q-X213A-X215F-X249R, X018R-X020R-X022W-X024R-X076D-X116A-X183D-X215F-X249R, X018R-X024R-X031F-X076D-X116A-X183D-X211Q-X213A-X215F-X249R, X018R-X024R-X076D-X101A-X116A-X183D-X198L-X213A-X249R-X269S, X018R-X020R-X024R-X076D-X101A-X116A-X198L-X215F-X249R, X018R-X043R-X076D-X078R-X101G-X103A-X104I-X232V-X245R-X269R, X018R-X020R-X024R-X076D-X101A-X114T-X198L-X211Q-X215F-X249R, X024R-X043R-X078R-X101G-X103A-X104I-X217E-X232V-X245R, X024R-X076D-X103A-X104I-X232V, X018R-X020R-X022W-X024R-X076D-X101A-X198L-X211Q-X215F-X249R, X101G-X104I-X232V, X018R-X022W-X024R-X076D-X183D-X198L-X213A-X215F-X249R, X018R-X022W-X024R-X076D-X183D-X198L-X211Q-X249R, X018R-X020R-X024R-X076D-X183D-X213A-X249R, X018R-X024R-X076D-X101A-X183D-X211Q-X215F-X249R, X018R-X020R-X022W-X024R-X076D-X116A-X211Q-X213A-X249R, X018R-X078R-X101G-X103A-X104I-X232V-X245R-X269R, X018R-X022W-X024R-X076D-X101A-X116A-X183D-X211Q-X215F-X249R-X260A, X076D-X249R, X018R-X022W-X024R-X076D-X183D-X211Q-X215F-X249R, X018R-X020R-X024R-X076D-X116A-X211Q-X215F-X249R, X018R-X020R-X024R-X076D-X213A-X249R, X018R-X020R-X022W-X024R-X076D-X116A-X183D-X198L-X249R, X018R-X020R-X022W-X024R-X076D-X101A-X183D-X249R, X076D-X104I-X249R, X020R-X022W-X101A-X103A-X104I-X116A-X183D-X211Q-X213A-X215F-X232V-X245R, X024R-X043R-X045T-X078R-X101G-X103A-X104I-X217E-X232V-X245R, X018R-X020R-X022W-X024R-X076D-X183D-X198L-X215F-X249R, X018R-X076D-X101G-X103A, X020R-X024R-X101G-X103A-X104I-X232V-X245R-X269R, X018R-X020R-X024R-X076D-X101A-X116A-X183D-X211Q-X249R, X101G-X103A-X232V, X024R-X076D-X101G-X232V, X018R-X022W-X024R-X076D-X101A-X183D-X198L-X211Q-X249R, X018R-X020R-X024R-X076D-X101A-X183D-X198L-X211Q-X215F-X249R, X018R-X020R-X024R-X076D-X183D-X198L-X249R, X018R-X022W-X024R-X076D-X101A-X116A-X183D-X198L-X211Q-X249R, X018R-X020R-X024R-X076D-X116A-X156V-X183D-X211Q-X215F-X249R-X269S, X045T-X076D-X101G-X103A-X104I-X232V-X245R-X249R, X018R-X020R-X024R-X076D-X101A-X183D-X198L-X249R, X018R-X020R-X022W-X024R-X076D-X198L-X211Q-X215F-X249R, X018R-X020R-X022W-X024R-X076D-X101A-X116A-X198L-X211Q-X215F-X249R, X018R-X020R-X022W-X024R-X076D-X116A-X249R, X018R-X076D-X101G, X018R-X024R-X076D-X116A-X183D-X198L-X213A-X215F-X249R, X018R-X020R-X022W-X024R-X076D-X101A-X116A-X198L-X213A-X215F-X249R, X018R-X024R-X076D-X101A-X116A-X183D-X198L-X211Q-X249R, X018R-X076D-X232V, X018R-X020R-X024R-X076D-X101A-X232V-X245R, X018R-X043D-X045T-X076D-X101G-X103A-X104I-X232V-X245R, X018R-X022W-X024R-X076D-X183D-X213A-X215F-X249R, X018R-X024R-X076D-X101A-X116A-X211Q-X213A-X237D-X249R, X018R-X020R-X024R-X076D-X101A-X116A-X183D-X211Q-X249R-X275S, X018R-X022W-X024R-X076D-X101A-X116A-X183D-X198L-X211Q-X213A-X215F-X249R, X024R-X076D, X018R-X024R-X076D-X183D-X211Q-X215F-X249R, X018R-X022W-X024R-X076D-X116A-X183D-X198L-X213A-X215F-X249R, X076D-X104I-X232V-X249R, X018R-X076D-X103A-X232V, X018R-X020R-X024R-X076D-X101A-X116A-X183D-X198L-X211Q-X213A-X249R, X018R-X020R-X024R-X076D-X101A-X183D-X213A-X249R, X018R-X020R-X024R-X076D-X101A-X175E-X183D-X211Q-X215F-X249R, X018R-X020R-X043D-X078R-X101G-X103A-X104I-X217E-X232V-X245R-X273E, X020R-X024R-X043D-X045T-X076D-X101G-X103A-X104I-X232V-X245R, X005S-X101G-X103A-X104I-X232V-X245R-X249R, X103A-X104I-X232V, X018R-X020R-X024R-X068A-X076D-X101A-X116A-X213A-X215F-X249R, X018R-X022W-X024R-X076D-X101A-X198L-X215F-X249R-X275S, X018R-X024R-X076D-X183D-X198L-X211Q-X213A-X249R, and X043D-X045T-X101G-X103A-X104I-X232V-X245R, wherein the amino acid positions of the subtilisin variant are numbered by correspondence with the amino acid sequence of *B. amyloliquefaciens* subtilisin BPN' set forth as SEQ ID NO: 1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X018R-X024R-X043R-X076D-X249R-X269R, X018R-X022R-X024R-X043R-X076D-X249R, X018R-X043D-X101G-X103A-X104I-X232V-X245R, X020R-X043D-X101G-X103A-X104I-X232V-X245R, X043D-X101G-X103A-X104I-X232V-X245R-X269R, X043D-X078R-X101G-X103A-X104I-X232V-X245R, X043R-X076D-X101G-X103A-X104I-X232V-X245R, X022R-X043R-X101G-X103A-X104I-X232V-X245R, X043R-X078R-X101G-X103A-X104I-X232V-X245R, X020R-X076D-X101G-X103A-X104I-X232V-X245R, X043R-X076D-X101G-X103A-X104I-X232V-X245R, X022R-X076D-X101G-X103A-X104I-X232V-X245R, X076D-X078R-X101G-X103A-X104I-X232V-X245R, X018R-X024R-X043R-X076D-X249R, X018R-X024R-X076D-X242R-X249R, X018R-X024R-X076D-X249R-X269R, X018R-X022R-X024R-X076D-X249R, X018R-X024R-X076D-X078R-X249R, X018R-X024R-X043D-X076D-X249R-X269R, X018R-X022R-X024R-X043D-X076D-X249R, X018R-X024R-X043D-X076D-X078R-X249R, X020R-X101G-X103G-X104I-X232V-X245R, X020R-X101G-X103A-X104L-X232V-X245R, X020R-X101G-X103A-X104V-X232V-X245R, X020R-X101G-X103S-X104I-X232V-X245R, X020R-X101S-X103S-X104I-X232V-X245R, X020R-X101S-X103S-X104I-X232V-X245R, X020R-X101A-X103A-X104L-X232V-X245R, X020R-X101 S-X103S-X104V-X232V-X245R, X020R-X101S-X103A-X104I-X232V-X245R, X020R-X101S-X103A-X104V-X232V-X245R, X020R-

X101S-X103G-X104I-X232V-X245R, X020R-X101S-X103G-X104V-X232V-X245R, X020R-X101A-X103A-X104V-X232V-X245R, X020R-X101A-X103S-X104I-X232V-X245R, X020R-X101A-X103S-X104V-X232V-X245R, X018R-X024R-X043R-X076D-X078R-X249R, X024R-X043D-X101G-X103A-X104I-X232V-X245R, X043D-X101G-X103A-X104I-X232V-X245R-X249R, X024R-X076D-X101G-X103A-X104I-X232V-X245R, X076D-X101G-X103A-X104I-X232V-X242R-X245R, X018R-X020R-X024R-X076D-X217E-X249R, X018R-X024R-X043R-X076D-X217E-X249R, X018R-X024R-X043D-X076D-X242R-X249R, X018R-X020R-X024R-X043R-X076D-X249R, X020R-X101A-X103G-X104V-X232V-X245R, X043D-X101G-X103A-X104I-X232V-X245R, X018R-X024R-X076D-X217E-X249R-X269R, and X018R-X024R-X076D-X217E-X242R-X249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X020R-X101A-X103A-X104I-X118R-X232V-X245R, X020R-X024R-X116A-X213A, X043R-X101A-X116A-X215F-X269R, X024R-X043R-X101A-X116A, X024R-X043R-X101A-X116A-X215F-X269R, X020R-X101G-X103A-X104I-X215F-X232V-X245R, X043R-X101A-X269R, X024R-X043R-X116A-X213A-X269R, X020R-X024R-X043R-X045T-X101A-X213A, X024R-X043R-X116A-X215F-X269R, X020R-X024R-X213A-X215F, X020R-X116A-X269R, X024R-X116A-X213A-X269R, X043R-X101A-X116A-X269R, X101G-X103A-X104I-X116A-X213A-X232V-X245R-X269R, X024R-X043R-X045T-X101A-X116A-X215F-X269R, X020R-X043R-X101A-X269R, X101A-X103A-X104I-X213A-X232V-X245R-X269R, X024R-X215F-X269R, X043R-X101A-X116A-X213A-X215F-X269R, X043R-X101A-X213A-X269R, X020R-X024R-X043R-X045T-X116A-X213A, X101G-X103A-X104I-X232V-X245R-X269R, X024R-X043R-X045T-X101A-X116A-X213A-X269R, X024R-X043R-X045T-X116A-X269R, X020R-X043R-X045T-X101A-X269R, X024R-X043R-X116A-X269R, X020R-X024R-X043R-X045T, X043R-X116A-X269R, X024R-X043R-X101A-X215F-X269R, X024R-X043R-X045T-X213A-X215F-X269R, X020R-X024R-X045T-X269R, X020R-X043R-X101A-X116A-X213A-X215F, X020R-X101G-X103A-X104I-X213A-X215F-X232V-X245R, X020R-X024R-X045T-X116A-X269R, X020R-X101A-X116A-X269R, X024R-X043R-X215F, X020R-X024R-X213A, X024R-X043R-X101A-X215F, X020R-X024R-X043R-X045T-X116A, X020R-X024R-X043R-X045T-X101A-X269R, X020R-X024R-X101A-X215F, X020R-X024R-X116A-X213A-X215F, X020R-X024R-X116A, X020R-X024R-X101A-X116A, X043R-X213A-X215F-X269R, X024R-X101A-X269R, X024R-X043R-X116A-X215F, X020R-X038A-X043R-X101A, X020R-X024R-X116A-X215F, X024R-X043R-X101A-X213A, X014L-X020R-X024R-X043R-X045T-X101A-X215F, X020R-X024R-X215F, X020R-X116A-X215F-X269R, X020R-X045T-X116A-X269R, X020R-X024R-X043R-X045T-X215F, and X020R-X024R-X043R-X045T-X116A-X213A-X215F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X043R-X076D-X101A-X103A-X104I-X158E-X188D-X232V-X245R-X248D-X249R-X271F, X024R-X043R-X076D-X101A-X103A-X104I-X158E-X188D-X217E-X232V-X245R-X248D-X249R, X101A-X103A-X104I-X158E-X188D-X232V-X245R-X248D-X249R-X271F-X271F, X101A-X103A-X104I-X158E-X188D-X217E-X232V-X245R-X248D-X249R-X271F, X076D-X101G-X103A-X104I-X114V-X158E-X188D-X232V-X245R-X248D-X249R-X271F, X024R-X076D-X101G-X103A-X104I-X158E-X188D-X232V-X245R-X248D-X249R-X271F, X024R-X043R-X101A-X103A-X104I-X158E-X188D-X217E-X232V-X245R-X248D-X249R, X024R-X043R-X101A-X103A-X104I-X158E-X188D-X232V-X245R-X248D-X249R, X024R-X101A-X103A-X104I-X158E-X166D-X188D-X217E-X232V-X245R-X248D-X249R, X076D-X101G-X103A-X104I-X128L-X158E-X188D-X232V-X245R-X248D-X249R-X271F, and X043R-X076D-X101G-X103A-X104I-X158E-X166D-X188D-X232V-X245R-X248D-X249R-X271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X022A-X101G-X103A-X104I-X159D-X217E-X232V-X245R-X248D-X271F, X022A-X043R-X101G-X103A-X104I-X159D-X188D-X217E-X232V-X245R-X248D-X271F, X022A-X101G-X103A-X104I-X159D-X188D-X232V-X245R-X248D-X271F, X043R-X101A-X103A-X104I-X158E-X188D-X217E-X232V-X245R-X248D-X249R, X043R-X076D-X101A-X103A-X104I-X158E-X188D-X217E-X232V-X245R-X248D-X249R-X271F, X024R-X101G-X103A-X104I-X158E-X188D-X217E-X232V-X245R-X248D-X249R, X024R-X101G-X103A-X104I-X158E-X188D-X232V-X245R-X248D-X249R, X101G-X103A-X104I-X158E-X188D-X232V-X245R-X248D-X249R, X024R-X101G-X103A-X104I-X158E-X183D-X188D-X232V-X245R-X248D-X249R, X022A-X076D-X101G-X103A-X104I-X159D-X188D-X232V-X245R-X248D-X271F, X022A-X043R-X076D-X101G-X103A-X104I-X159D-X188D-X232V-X245R-X248D-X271F, X022A-X076D-X101G-X103A-X104I-X159D-X232V-X245R-X248D-X271F, X022A-X101G-X103A-X104I-X159D-X232V-X245R-X248D-X271F, X076D-X101A-X103A-X104I-X158E-X188D-X232V-X245R-X248D-X249R-X271F, X043R-X101A-X103A-X104I-X158E-X166D-X188D-X232V-X245R-X248D-X249R, X024R-X076D-X101A-X103A-X104I-X158E-X166D-X188D-X232V-X245R-X248D-X249R-X271F, X076D-X101A-X103A-X104I-X158E-X188D-X232V-X245R-X248D-X249R, X101A-X103A-X104I-X158E-X166D-X188D-X232V-X245R-X248D-X249R-X271F, X043R-X076D-X101A-X103A-X104I-X158E-X166D-X188D-X232V-X245R-X248D-X249R-X271F, X101G-X103A-X104I-X158E-X166D-X188D-X232V-X245R-X248D-X249R-X271F, X101A-X103A-X104I-X158E-X188D-X232V-X245R-X248D-X249R-X271F, X101A-X103A-X104I-X158E-X188D-X217E-X232V-X245R-X248D-X249R, X076D-X101A-X103A-X104I-X158E-X166D-X188D-X232V-X245R-

X248D-X249R-X271F, X101G-X103A-X104I-X158E-X183D-X188D-X232V-X245R-X248D-X249R, X024R-X101G-X103A-X104I-X128L-X158E-X188D-X232V-X245R-X248D-X249R, X076D-X101G-X103A-X104I-X158E-X166D-X188D-X232V-X245R-X248D-X249R-X271F, X043R-X076D-X101A-X103A-X104I-X158E-X166D-X188D-X232V-X245R-X248D-X249R, and X076D-X101A-X103A-X104I-X158E-X188D-X217E-X232V-X245R-X248D-X249R-X271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X017R-X022A-X076D-X101G-X103A-X104I-X159D-X188D-X232V-X245R-X248D-X271F, X022A-X043R-X101G-X103A-X104I-X159D-X232V-X245R-X248D-X271F, X022A-X101G-X103A-X104I-X159D-X188D-X232V-X245R-X248D-X249R-X271F, X017R-X022A-X076D-X101G-X103A-X104I-X159D-X232V-X245R-X248D-X271F, X022A-X076D-X101G-X103A-X104I-X159D-X232V-X245R-X248D-X249R-X271F, X022A-X101G-X102A-X103A-X104I-X159D-X188D-X232V-X245R-X248D-X271F, and X022A-X043R-X076D-X101G-X103A-X104I-X159D-X232V-X245R-X248D-X249R-X271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X101S-X103A-X104I-X158E-X188D-X232V-X245R-X248D-X249R, X101S-X103G-X104V-X158E-X188D-X232V-X245R-X248D-X249R, X101G-X103S-X104I-X158E-X188D-X232V-X245R-X248D-X249R, X101A-X103A-X104I-X158E-X188D-X232V-X245R-X248D-X249R, X101A-X103A-X104L-X158E-X188D-X232V-X245R-X248D-X249R, X101G-X103G-X104I-X158E-X188D-X232V-X245R-X248D-X249R, X101 S-X103G-X104I-X158E-X188D-X232V-X245R-X248D-X249R, X101S-X103S-X104I-X158E-X188D-X232V-X245R-X248D-X249R, X101S-X103S-X104V-X158E-X188D-X232V-X245R-X248D-X249R, X101A-X103S-X104I-X158E-X188D-X232V-X245R-X248D-X249R, X101A-X103S-X104I-X159E-X232V-X245R-X248D-X249R, X101S-X103A-X104I-X159E-X232V-X245R-X248D-X249R, X101G-X103A-X104L-X158E-X188D-X232V-X245R-X248D-X249R, X101A-X103A-X104L-X159E-X232V-X245R-X248D-X249R, X101A-X103S-X104L-X159E-X232V-X245R-X248D-X249R, X101G-X103S-X104L-X159E-X232V-X245R-X248D-X249R, X101S-X103A-X104L-X159E-X232V-X245R-X248D-X249R, X101A-X103G-X104V-X159E-X232V-X245R-X248D-X249R, and X101S-X103A-X104V-X159E-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X026F-X051W-X104L-X106E, X026F-X031F-X078N-X102A-X160D, X020K-X100S-X116L-X158E-X166D-X243F, X033S-X043W-X218D-X239G-X243F, X022L-X038F-X048R-X062E-X100S-X186K, X101D-X103N-X116L-X144R-X215D, X104L-X105T-X213A-X217E-X256N, X043W-X101D-X212M-X243F, X026F-X048R-X105T-X213A-X218D-X224A, X024F-X101D-X118R-X215D-X250I-X272F, X121F-X185E-X224A-X239G, X022L-X031F-X102A-X128D-X224A-X243F, X062E-X078N-X102A-X116L-X144R-X250I, X022L-X038F-X121F-X160D-X272F, X026F-X078N-X159C-X186K-X243F, X024F-X048R-X118R-X166D-X217E, X023A-X038F-X078N-X100S-X212M-X215D, X100S-X116L-X158E-X213A, X078N-X104L-X118R-X128D, X102A-X103N-X105T-X194E, X022L-X078N-X128D-X213A, X027R-X100S-X118R-X160D-X188D-X243F, X024F-X102A-X186K-X213A-X217E-X243F, X033S-X105T-X188D-X216F, X023A-X100S-X194E-X212M, X048R-X128D-X185E-X239G, X020K-X024F-X033S-X129E-X194E, X020K-X027R-X129E-X166D-X239G, X022L-X023A-X027R-X101D-X104L-X216F, X033S-X118R-X129E-X194E-X239G, X022L-X078N-X116L-X129E-X256N, X027R-X101D-X103N-X105T-X272F, X048R-X078N-X116L-X185E-X217E-X239G, X023A-X024F-X027R-X062E, X024F-X103N-X104L-X118R-X188D, X026F-X104L-X256N-X272F, X024F-X043W-X104L-X121F-X129E, X062E-X078N-X116L-X224A, X023A-X024F-X051W-X158E, X027R-X038F-X102A-X116L, X062E-X078N-X144R-X212M, X031F-X116L-X256N-X272F, X022L-X033S-X104L-X116L-X160D-X186K, X024F-X118R-X129E-X186K-X213A, X043W-X105T-X213A-X215D-X216F, X031F-X105T-X186K-X188D, X026F-X194E-X213A-X256N, and X103N-X160D-X250I-X256N, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X022A-X024R-X101D-X103A-X104I-X118R-X159D-X188D-X232V-X248D-X271F, X022A-X024R-X103A-X104I-X129E-X159D-X188D-X232V-X248D-X271F, X022A-X024R-X103A-X104I-X118R-X159D-X188D-X217D-X232V-X248D, X022A-X024R-X101D-X103A-X104I-X118R-X129E-X159D-X188D-X232V-X245R-X248D, X022A-X024R-X101D-X103A-X104I-X159D-X188D-X232V-X245R-X248D, X022A-X043R-X103A-X104I-X118R-X129E-X159D-X188D-X232V-X245R-X248D, X022A-X043R-X103A-X104I-X118R-X128I-X129E-X159D-X188D-X232V-X248D, X022A-X043R-X101D-X103A-X104I-X118R-X129E-X159D-X188D-X232V-X248D-X271F, X022A-X024R-X043R-X101D-X103A-X104I-X159D-X188D-X232V-X245R-X248D, X022A-X103A-X104I-X159D-X188D-X232V-X248D, X022A-X024R-X103A-X104I-X118R-X129E-X159D-X188D-X232V-X248D-X271F, X022A-X024R-X103A-X104I-X159D-X188D-X217D-X232V-X245R-X248D-X271F, X022A-X043R-X062E-X103A-X104I-X159D-X188D-X232V-X245R-X248D-X271F, X022A-X043R-X103A-X104I-X129E-X159D-X188D-X232V-X245R-X248D, X022A-X024R-X103A-X104I-X159D-X188D-X217D-X232V-X248D-X271F, X022A-X103A-X104I-X118R-X159D-X188D-X217D-X232V-X245R-X248D, X022A-X024R-X101D-X103A-X104I-X118R-X128I-X159D-X188D-X232V-

X245R-X248D, X022A-X024R-X043R-X103A-X104I-X159D-X188D-X217D-X232V-X248D-X271F, X022A-X043R-X103A-X104I-X118R-X159D-X188D-X217D-X232V-X248D-X271F, X022A-X043R-X103A-X104I-X118R-X159D-X188D-X232V-X248D-X271F, X022A-X103A-X104I-X128I-X129E-X159D-X188D-X232V-X248D-X271F, X022A-X103A-X104I-X159D-X188D-X217D-X232V-X245R-X248D-X271F, X022A-X043R-X103A-X104I-X128I-X159D-X188D-X232V-X245R-X248D, X022A-X101D-X103A-X104I-X118R-X159D-X188D-X217D-X232V-X245R-X248D-X271F, X022A-X103A-X104I-X118R-X129E-X159D-X188D-X232V-X245R-X248D-X271F, X022A-X024R-X043R-X103A-X104I-X118R-X159D-X188D-X217D-X232V-X248D, X022A-X062E-X103A-X104I-X118R-X159D-X188D-X232V-X245R-X248D, X022A-X043R-X101D-X103A-X104I-X118R-X129E-X159D-X188D-X217D-X232V, X022A-X024R-X103A-X104I-X159D-X188D-X217D-X232V-X248D, X022A-X024R-X043R-X103A-X104I-X118R-X128I-X129E-X159D-X188D-X217D-X232V-X248D-X271F, and X022A-X103A-X104I-X118R-X159D-X188D-X217D-X232V-X245R-X248D-X271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X020K-X024F-X062E-X188D-X239G, X024F-X062E-X116L-X239G, X020K-X023A-X062E-X188D, X020K-X023A-X024F-X062E-X118R-X188D-X213A, X020K-X043W-X062E-X116L-X188D-X213A-X239G, X023A-X062E-X116L-X118R, X023A-X024F-X062E-X116L-X118R, X024F-X116L, X024F-X062E-X188D-X213A, X023A-X062E-X116L-X118R-X188D-X239G, X020K-X024F-X062E, X020K-X043W-X062E-X116L-X239G, X024F-X062E-X116L-X213A-X239G, X020K-X024F-X043W-X062E-X116L-X213A, X020K-X023A-X024F-X062E-X116L-X188D-X213A, X024F-X062E-X188D-X239G, X023A-X043W-X062E-X116L-X118R-X213A, X062E-X188D-X239G, X020K-X024F-X062E-X239G, X024F-X116L-X118R-X188D-X239G, X020K-X023A-X062E-X116L-X118R-X213A, X020K-X023A-X024F-X062E-X188D-X213A-X239G, X024F-X043W-X118R-X188D, X023A-X024F-X116L-X118R-X188D-X213A, X020K-X023A-X043W-X116L-X188D-X213A-X239G, X023A-X024F-X116L-X188D-X239G, X023A-X043W-X116L-X118R-X188D, X023A-X024F-X118R-X188D-X239G, X023A-X024F-X043W-X062E-X116L-X118R, X020K-X043W-X188D-X213A, X024F-X062E-X118R-X239G, X023A-X043W-X188D-X213A, X020K-X024F-X043W-X062E-X116L-X118R-X188D-X239G, X020K-X116L-X188D-X239G, X020K-X043W-X062E-X118R, X020K-X043W-X116L-X188D-X213A, X020K-X024F, X023A-X043W-X116L-X239G, X023A-X024F-X043W-X116L-X118R-X188D-X239G, X020K-X023A-X043W-X213A, and X023A-X024F-X062E-X118R-X213A-X239G, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X020K-X023A-X043W-X118R-X128I-X129E-X159D-X188D, X024F-X118R-X128I-X129E-X159D, X020K-X024F-X062E-X116L-X118R-X188D, X020K-X062E-X116L-X188D, X062E-X116L-X118R-X213A, X020K-X023A-X062E-X116L-X188D, X062E-X116L-X118R-X188D, X020K-X062E-X116L-X213A, X020K-X023A-X062E-X116L, X020K-X062E-X188D-X213A, X020K-X062E, X020K-X024F-X062E-X116L-X188D, X020K-X043W-X062E-X116L-X188D, X020K-X024F-X062E-X188D-X213A, X062E-X116L-X188D-X213A, X020K-X062E-X116L, X020K-X023A-X062E-X116L-X188D-X213A, X023A-X024F-X062E-X116L-X213A, X022A-X043R-X103A-X104I-X128I-X129E-X159D-X188D-X232V-X245R-X248D, X022A-X043R-X103A-X104I-X118R-X128I-X129E-X159D-X188D-X232V-X248D-X271F, X024F-X062E-X116L-X188D, X022A-X024R-X103A-X104I-X118R-X128I-X129E-X159D-X188D-X232V-X248D, X023A-X062E-X116L-X188D, X043W-X062E-X116L, X020K-X023A-X116L-X188D, X043W-X062E-X116L-X188D, X024F-X062E-X116L, X062E-X116L-X188D, and X022A-X024R-X103A-X104I-X128I-X159D-X188D-X232V-X248D, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X087R-X101G-X103A-X104I-X109R-X212P-X232V-X245R-X271V, X101G-X103A-X104I-X109R-X232V-X245R, X101G-X103A-X104I-X109R-X212P-X232V-X245R-X271V, X101G-X103A-X104I-X109R-X212P-X232V-X245R, X076D-587R-X103A-X104I-X212P-X271V, X076D-X103A-X104I-X109R, X076D-X103A-X104I-X212P-X271V, X076D-X103A-X104I-X109R-X245R, and X076D-X103A-X104I-X212P-X245L-X271V, wherein the amino acid positions of the subtilisin variant are numbered by correspondence with the amino acid sequence of *B. amyloliquefaciens* subtilisin BPN' set forth as SEQ ID NO: 1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X024R-X086W-X118R, X024R-X078R-X086W-X243F, X024R-X033S-X086S-X087N-X209A, X033S-X118R, X024R-X078R-X086W-X118R-X270T, X024R-X033S-X086W-X118R, X078R-X086W-X243F, X033S-X078R-X086W-X118R-X209A, X033S-X078R-X209A, X086W-X118R-X243F, X024R-X086W, X078R-X086W-X235F, X024R-X118R, X024R-X086R, X101G-X103A-X104I-X232V, X024R-X033S-X078R-X086W-X118R, X024R-X118R-X209A, X209A-X241R, X033S-X086W-X243F, X033S-X172V-X209A, X118R-X209A-X243F, X024R-X086S-X141G, X024R-X118R-X209A-X243F, X024R-X033S-X086S-X085N-X235F, X024R-X033S-X133V, X024R-X033S-X078R-X086W, X024R-X086W-X209A, X024R-X241R, X033S-X118R-X243F, X024R-X235F, X024R-X078R-X086W, X024R-X118R-X209A-X235F, X024R-X209A-X241R, X033S-X118R-X241R, X086W-X118R-X209A, X033S-X118R-X159D-X209A, X033S-X078R-X086W, X024R-X086W-X243F, X118R-X209A, X024R-X086W-X118R-X203I, X078R-X209A-X235F, X024R-X033S-X241R, X078R-X118R, X033S-X118R-X209A-X243F, X021M-

X024R-X033S, X024R-X033S-X086W, X033S-X235F, X078R-X086W-X209A, X024R-X033S-X209A-X235F, X033S-X086W-X118R, X024R-X033S-X078R-X209A, X033S-X086W-X118R-X209A-X243F, X086W-X209A-X243F, X005S-X078R-X118R-X241R, X024R-X174T, X033S-X209A-X243F, X086W-X118R-X133V, X024R-X033S-X118R, X024R-X086W-X209A-X235F, X086W-X209A, X008T-X024R, X086W-X118R, X033S-X241R, X005S-X024R-X033S-X243F, X024R-X209A-X242P, X024R-X033S-X078R-X118R, X024R-X033S-X194T, X024R-X243F, X024R-X209A, X024R-X033S-X118R-X209A, X033S-X086W, X024R-X033S, X024R-X033S-X078R-X243F, X086W-X243F, X033S-X118D-X138V-X209A, X033S-X209A-X235F, X024R-X086R-X118R, X033S-X201S, X024R-X239Q, X033S-X118R-X209A-, X078R-X086W, X235F-X243F, X024R-X209A-X235F, X118R-X172V, X017Y-X024R-X033S-X086W, X033S-X148F, X024R-X118R-X235F, X033S-X078R, X033S-X243F, X024C-X033S, X118R-X194T, X033S-X209A, X118R-X209A-X235F, X024R-X033S-X209A-X243F, X024R-X033S-X235F, X024R-X033S-X118R-X235F, X024R-X141G, X024R-X274I, X024R-X033S-X209A, X086W-X235F, X024R-X209A-X243F, X004E-X033S-X078R, X086W-X209A-X235F, X015T-X033S, X033S-X086W-X156L-X209A, X024R-X118R-X243F-X269H, X209A-X235F, X024R-X247H, X024R-X033S-X228T, X078R-X235F, X024R-X033S-X174V-X235F, X024R-X235F-X243F, X024R-X033S-X235F-X241R, X024R-X033S-X151V, X024R-X104A, X033S-X048T, X012H-X104A-X118R, X118R-X235F, X033S-X253A, X143A-X209A, X024R-X033S-X243F, X033S-X239T, X209A-X243F, X024R-X033S-X129H-X184D-X253M, X024R-X085V-X086W-X118R-X235F, X024R-X272P, and X024R-X269C, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X020R-X087D-X101G-X103A-X104I-X232V-X245R, X020R-X101G-X103A-X104I-X150L-X232V-X245R, X018R-X020R-X024R-X076D-X087D-X249R, X018R-X020R-X024R-X076D-X150L-X249R, X018R-X024R-X043R-X076D-X087D-X249R, X018R-X024R-X043R-X076D-X150L-X249R, X018R-X024R-X076D-X078R-X087D-X249R, X018R-X024R-X076D-X078R-X150L-X249R, X018R-X024R-X076D-X087D-X249R-X269R, X018R-X024R-X076D-X087D-X242R-X249R, X018R-X024R-X076D-X087D-X150L-X249R, X018R-X024R-X076D-X150L-X249R, X018R-X087D-X101G-X103A-X104I-X232V-X245R, X018R-X101G-X103A-X104I-X150L-X232V-X245R, X018R-X022R-X024R-X076D-X087D-X249R, X018R-X022R-X024R-X076D-X150L-X249R, X043R-X087D-X101G-X103A-X104I-X232V-X245R-X269R, X043R-X101G-X103A-X104I-X150L-X232V-X245R, X024R-X087D-X101G-X103A-X104I-X232V-X245R, X024R-X101G-X103A-X104I-X150L-X232V-X245R, X078R-X087D-X101G-X103A-X104I-X232V-X245R, X078R-X101G-X103A-X104I-X150L-X232V-X245R, X087D-X101G-X103A-X104I-X232V-X245R-X269R, X101G-X103A-X104I-X150L-X232V-X245R-X269R, X022R-X087D-X101G-X103A-X104I-X232V-X245R, X018R-X024R-X043D-X076D-X150L-X249R, X043R-X087D-X101G-X103A-X104I-X232V-X245R, X022R-X101G-X103A-X104I-X150L-X232V-X245R, X018R-X024R-X043D-X076D-X087D-X249R, X018R-X024R-X076D-X087D-X249R, X018R-X024R-X076D-X087D-X249R, X018R-X024R-X076D-X150L-X242R-X249R, X043R-X101G-X103A-X104I-X150L-X232V-X245R-X269R, X076D-X101G-X103A-X104I-X150L-X232V-X245R, X087D-X101G-X103A-X104I-X232V-X242R-X245R, X101G-X103A-X104I-X150L-X232V-X245R, X076D-X087D-X101G-X103A-X104I-X232V-X245R, X087D-X101G-X103A-X104I-X232V-X245R, and X101G-X103A-X104I-X150L-X232V-X242R-X245R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X024R-X101G-X103A-X104I-X129Q-X158E-X188D-X217E-X232V-X245R-X248D-X249R, X024R-X101G-X103A-X104I-X130A-X158E-X183D-X188D-X232V-X245R-X248D-X249R, X024R-X101G-X103A-X104I-X129Q-X158E-X183D-X188D-X232V-X245R-X248D-X249R, X101G-X103A-X104I-X130A-X158E-X188D-X232V-X245R-X248D-X249R, X024R-X101G-X103A-X104I-X129Q-X158E-X188D-X232V-X245R-X248D-X249R, X024R-X101G-X103A-X104I-X130A-X158E-X188D-X232V-X245R-X248D-X249R, X024R-X101G-X103A-X104I-X129Q-X130A-X158E-X183D-X188D-X232V-X245R-X248D-X249R, X024R-X101G-X103A-X104I-X128L-X129Q-X158E-X188D-X232V-X245R-X248D-X249R, X024R-X101G-X103A-X104I-X129Q-X130A-X158E-X188D-X232V-X245R-X248D-X249R, X101G-X103A-X104I-X129Q-X158E-X188D-X232V-X245R-X248D-X249R, X101G-X103A-X104I-X129Q-X130A-X158E-X188D-X232V-X245R-X248D-X249R, X024R-X101G-X103A-X104I-X128L-X129Q-X130A-X158E-X188D-X232V-X245R-X248D-X249R, X101G-X103A-X104I-X128L-X129Q-X158E-X188D-X232V-X245R-X248D-X249R, and X024R-X027R-X101G-X103A-X104I-X128L-X129Q-X130A-X158E-X188D-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X101G-X103A-X104I-X232V-X222Q-X245R, X101G-X103A-X104I-X158E-X188D-X222S-X232V-X245R-X248D-X249R, X101G-X103A-X104I-X158E-X188D-X222Q-X232V-X245R-X248D-X249R, X076D-X101G-X103A-X104I-X232V-X222Q-X245R, X101G-X103A-X104I-X232V-X222S-X245R, X076D-X101G-X103A-X104I-X232V-X222S-X245R, and X076D-X101G-X103A-X104I-X158E-X188D-X222S-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X024R-X101G-X103A-X104I-X128L-X129Q-X158E-X188D-X232V-X245R-X248D-X249R, X101G-X103A-X104I-X130A-X158E-X188D-X232V-X245R-X248D-X249R, X024R-X101G-X103A-X104I-X158E-X188D-X232V-X245R-X248D-X249R, X101G-X103A-X104I-X128L-X129Q-X158E-X188D-X232V-X245R-X248D-X249R, X101G-X103A-X104I-X129Q-X130A-X158E-X188D-X232V-X245R-X248D-X249R, X101G-X103A-X104I-X130A-X158E-X183D-X188D-X217E-X232V-X245R-X248D-X249R, X024R-X101G-X103A-X104I-X128L-X129Q-X130A-X158E-X188D-X232V-X245R-X248D-X249R, X024R-X101G-X103A-X104I-X129Q-X158E-X188D-X217E-X232V-X245R-X248D-X249R, X101G-X103A-X104I-X128L-X130A-X158E-X188D-X217E-X232V-X245R-X248D-X249R, X024R-X101G-X103A-X104I-X128L-X129Q-X158E-X183D-X188D-X232V-X245R-X248D-X249R, X024R-X101G-X103A-X104I-X128L-X129Q-X130A-X158E-X183D-X188D-X232V-X245R-X248D-X249R, X024R-X101G-X103A-X104I-X128L-X129Q-X158E-X188D-X232V-X245R-X248D-X249R-X271G, X101G-X103A-X104I-X129Q-X158E-X183D-X188D-X232V-X245R-X248D-X249R, X024R-X101G-X103A-X104I-X130A-X158E-X188D-X217E-X232V-X245R-X248D-X249R, X024R-X101G-X103A-X104I-X128L-X158E-X183D-X188D-X232V-X245R-X248D-X249R, X101G-X103A-X104I-X129Q-X158E-X188D-X217E-X232V-X245R-X248D-X249R, and X024R-X101G-X103A-X104I-X128L-X130A-X158E-X188D-X232V-X245R-X248D-X249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant, wherein the subtilisin variant is a mature form having proteolytic activity and comprises an amino acid sequence comprising a combination of amino acid substitutions selected from: X101G-X103A-X104I, X22A-X101A-X209E, S103G-L111V-G159E, X22A-X103G-X159E, X22A-X111V-X159E, X22A-X128N-X271F-X209E, X22A-X103G-X111V, X62E-X111V-X128N, X22A-X111V-X128N, X22A-X62E-X111V, X101A-X103G-X104L-X188D, X101G-X103A-X104I-X159D, X101A-X103G-X104L-X128N, X22A-X101A-X159E, X101A-X103G-X104L, X101A-X103G-X104L-X159E, X22A-X101A-X103G-X104L, X101A-X103G-X104L-X209E, X22A-X209E-X271F, X22A-X101A-X271F, and X101A-X209E-X271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding *Bacillus* subtilisin variants of a *Bacillus* subtilisin, wherein the subtilisin variant is a mature form having proteolytic activity and comprises an amino acid sequence comprising a combination of amino acid substitutions selected from: X103A-X104I-X159D-X232V-X236H-X245R-X248D-X252K, X101G-X104I-X159D-X232V-X236H-X245R-X248D-X252K, X101G-X103A-X159D-X232V-X236H-X245R-X248D-X252K, X101G-X103A-X104L-X232V-X236H-X245R-X248D-X252K, X101G-X103A-X104L-X159D-X236H-X245R-X248D-X252K, X101G-X103A-X104L-X159D-X232V-X245R-X248D-X252K, X101G-X103A-X104L-X159D-X232V-X236H-X248D-X252K, X101G-X103A-X104L-X159D-X232V-X236H-X245R-X252K, and X101G-X103A-X104L-X159D-X232V-X236H-X245R-X248D, wherein the amino acid positions of the subtilisin variant are numbered by correspondence with the amino acid sequence of *B. amyloliquefaciens* subtilisin BPN' set forth as SEQ ID NO: 1.

The present invention provides nucleic acids encoding *Bacillus* subtilisin variant, wherein the subtilisin variant is a mature form having proteolytic activity and comprises an amino acid sequence comprising a combination of amino acid substitutions selected from: X101G-X103A-X104I-X159D-X232V-X245R-X248D, X101G-X103A-X104I-X159D-X232V-X245R-X248D-X271F, X101G-X103A-X104I-X159D-X232V-X245R-X248D-X238R, X101G-X103A-X104I-X159D-X232V-X245R-X248D-X248R, X101G-X103A-X104I-X159D-X232V-X245R-X248D-X253R, X101G-X103A-X104I-X159D-X232V-X245R-X248D-X24R, X101G-X103A-X104I-X159D-X232V-X245R-X248D-X76D, X101G-X103A-X104I-X159E-X232V-X245R-X248D-X249R, X101G-X103A-X104I-X159E-X232V-X245R-X248D-X271F, X101G-X103A-X104I-X158E-X232V-X245R-X248D-X249R, X101G-X103A-X104I-X158E-X232V-X245R-X248D-X271F, X22A-X101G-X103A-X104I-X159D-X232V-X245R-X248D-X249R, X22A-X101G-X103A-X104I-X159D-X232V-X245R-X248D-X271F, X62E-X101G-X103A-X104I-X159D-X232V-X245R-X248D-X249R, and X62E-X101G-X103A-X104I-X159D-X232V-X245R-X248D-X271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin, wherein the subtilisin variant is a mature form having proteolytic activity and comprises an amino acid sequence comprising a combination of amino acid substitutions selected from: X20R-X43R-X249R, X20R-X22R-X43R, X20R-X43R-X242R, X20R-X43R-X271L, X20R-X43R-X244R, X20R-X24R-X43R-X242R, X9A-X22R-X78R-X212F-X241R, X9A-X20R-X43R-X212F, X9A-X43R-X212F, X20R-X43R-X212F, X20R-X22R-X43R-X212F, X24R-X78R-X212F, X9A-X43R-X78R, X9A-X43R-X78R-X242R, X9A-X20R-X43R-X78R, X20R-X24R-X43R-X78R-X242R, X22R-X24R-X78R-X212F, X9A-X20R-X43R-X78R-X242R, X20R-X43R-X78R-X249R, X20R-X43R-X78R, X9A-X78R-X212F, X9A-X22R-X43R-X78R, X9A-X20R-X24R-X43R, X9A-X22R-X78R-X212F, X4R-X9A-X22R-X78R-X212F, X20R-X24R-X43R, X1R-X9A-X43R, X20R-X24R-X43R-X115R, X9A-X24R-X43R, X20R-X22R-X24R-X43R, X1R-X24R-X43R, X9A-X20R-X24R-X43R-X242R, X9A-X20R-X22R-X78R-X212F, X9A-X24R-X43R-X244R, X9A-X24R-X43R-X242R, X4R-X9A-X22R-X24R-X212F, and X22R-X24R-X43R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant of a *Bacillus* subtilisin, wherein the subtilisin variant is a mature form having proteolytic activity and comprises an amino acid sequence comprising a combination of amino acid substitutions selected from: X101G-X103A-X104I-X232V-X245R-X248D, X101G-X103A-X104I-X159D-X232V-X245R, X101G-X103A-X104I-X159R-X232V-X245R-X248D, X101G-X103A-X104I-X159D-X232V-X245R-X248R, X101G-X103A-X104I-X232V-X245R, X101G-X103A-X104I-X232V-X245R-X248R, X101G-X103A-X104I-X159R-X232V-X245R-X248R, and X101G, X103A, X104I, X232V, X236H, X245R, and X252K, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin, wherein the subtilisin variant is a mature form having proteolytic activity and comprises an amino acid sequence comprising a combination of amino acid substitutions selected from: X16S, X22A, X24R, X62E, X76D, X89P, X101A/G, X103G/A, X104L/I, X111V, X128N, X129E, X232V, X148I, X158E, X159D/E, X166D, X186H, X188D, X209E, X236H, X238R, X245R, X248D/R, X249R, X252K/R, X253R, and X271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding *Bacillus* subtilisin, wherein the subtilisin variant is a mature form having proteolytic activity and comprises an amino acid sequence comprising a combination of amino acid substitutions selected from: N062E-A158E, S103G-A158E, S128N-A158E, A016S-A158E, V104L-A158E, E089P-A158E, L111V-A158E, T022A-A158E, S101A-A158E, L148I-A158E, P129E-A158E, T022A-E089P, A016S-E089P, N062E-E089P, N062E-E271F, A158E-E271F, R186H-E271F, P129E-E271F, L111V-E271F, Y209E-E271F, A016S-E271F, S188D-E271F, T022A-E271F, G159E-E271F, V104L-E271F, S101A-E271F, E089P-E271F, S128N-E271F, S103G-E271F, L148I-E271F, H249R-E271F, N062E-G159E, A016S-G159E, S128N-G159E, L148I-G159E, L111V-G159E, E089P-G159E, T022A-G159E, P129E-G159E, S103G-G159E, V104L-G159E, A158E-G159E, S101A-G159E, A158E-H249R, L111V-H249R, P129E-H249R, N062E-H249R, A016S-H249R, R186H-H249R, L148I-H249R, G159E-H249R, S101A-H249R, S188D-H249R, V104L-H249R, Y209E-H249R, T022A-H249R, S128N-H249R, S103G-H249R, E089P-H249R, T022A-L111V, S101A-L111V, A016S-L111V, V104L-L111V, N062E-L111V, S103G-L111V, E089P-L111V, A016S-L148I, N062E-L148I, T022A-L148I, P129E-L148I, V104L-L148I, S103G-L148I, S128N-L148I, S101A-L148I, E089P-L148I, L111V-L148I, A016S-N062E, T022A-N062E, N062E-P129E, T022A-P129E, S128N-P129E, A016S-P129E, S101A-P129E, V104L-P129E, E089P-P129E, S103G-P129E, L111V-P129E, N062E-R186H, S128N-R186H, S101A-R186H, T022A-R186H, A016S-R186H, A158E-R186H, E089P-R186H, P129E-R186H, G159E-R186H, S103G-R186H, V104L-R186H, L111V-R186H, L148I-R186H, N062E-S101A, T022A-S101A, A016S-S101A, E089P-S101A, N062E-S103G, T022A-S103G, A016S-S103G, S101A-S103G, E089P-S103G, N062E-S128N, A016S-S128N, T022A-S128N, S101A-S128N, V104L-S128N, E089P-S128N, S103G-S128N, L111V-S128N, L111V-S188D, N062E-S188D, A016S-S188D, L148I-S188D, T022A-S188D, S128N-S188D, S101A-S188D, V104L-S188D, E089P-S188D, P129E-S188D, G159E-S188D, R186H-S188D, S103G-S188D, A158E-S188D, A016S-T022A, A016S-V104L, T022A-V104L, S101A-V104L, N062E-V104L, S103G-V104L, E089P-V104L, G159E-Y209E, L111V-Y209E, S101A-Y209E, A016S-Y209E, S128N-Y209E, L148I-Y209E, P129E-Y209E, N062E-Y209E, T022A-Y209E, S103G-Y209E, A158E-Y209E, S188D-Y209E, V104L-Y209E, E089P-Y209E, and R186H-Y209E, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: N018R-W241R, G020R-W241R, S024R-W241R, S009A-W241R, G020R-W241R, V004R-W241R, N043R-W241R, S078R-W241R, T022R-W241R, G115R-W241R, A001R-W241R, S212F-W241R, L082R-W241R, N018R-V244R, S024R-V244R, S078R-V244R, G020R-V244R, S212F-V244R, S009A-V244R, L082R-V244R, A001R-V244R, N043R-V244R, T022R-V244R, V004R-V244R, G115R-V244R, W241R-V244R, S242R-V244R, A001R-V004R, S009A-T022R, N018R-T022R, G020R-T022R, V004R-T022R, A001R-T022R, S024R-S242R, N018R-S242R, V004R-S242R, G020R-S242R, S212F-S242R, L082R-S242R, S078R-S242R, A001R-S242R, S009A-S242R, T022R-S242R, G115R-S242R, N043R-S242R, W241R-S242R, N018R-S212F, T022R-S212F, V004R-S212F, S024R-S212F, A001R-S212F, G115R-S212F, G020R-S212F, S009A-S212F, N043R-S212F, S078R-S212F, L082R-S212F, S009A-S078R, G020R-S078R, S024R-S078R, T022R-S078R, N018R-S078R, V004R-S078R, A001R-S078R, N043R-S078R, T022R-S024R, G020R-S024R, N018R-S024R, A001R-S024R, V004R-S024R, S009A-S024R, V004R-S009A, A001R-S009A, S242R-N269R, S024R-N269R, G020R-N269R, T022R-N269R, H249R-N269R, S212F-N269R, N043R-N269R, V244R-N269R, A001R-N269R, N018R-N269R, S078R-N269R, S009A-N269R, G115R-N269R, W241R-N269R, V004R-N269R, L082R-N269R, N018R-N043R, G020R-N043R, V004R-N043R, T022R-N043R, S009A-N043R, A001R-N043R, S024R-N043R, S009A-N018R, V004R-N018R, A001R-N018R, S024R-L082R, S009A-L082R, N018R-L082R, A001R-L082R, S078R-L082R, G020R-L082R, T022R-L082R, V004R-L082R, N043R-L082R, N043R-H249R, G020R-H249R, V004R-H249R, N018R-H249R, S009A-H249R, S212F-H249R, T022R-H249R, S024R-H249R, G115R-H249R, A001R-H249R, L082R-H249R, S242R-H249R, W241R-H249R, V244R-H249R, S078R-H249R, N018R-G115R, G020R-G115R, T022R-G115R, S078R-G115R, S009A-G115R, V004R-G115R, A001R-G115R, L082R-G115R, N043R-G115R, S024R-G115R, S009A-G020R, N018R-G020R, V004R-G020R, A001R-G020R, S009A-E271L, G020R-E271L, S024R-E271L, V244R-E271L, W241R-E271L, N043R-E271L, T022R-E271L, H249R-E271L, S212F-E271L, G115R-E271L, S242R-E271L, S078R-E271L, V004R-E271L, N269R-E271L, A001R-E271L, N018R-E271L, and L082R-E271L, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: G020R-N043R, G020K-N062E, S024F-N116L, G020K-S024F, S024R-A174T, S024R-G118R, S024R-K235F, S024R-P086R, S024R-P086W, S078R-G118R, T033S-G118R, T033S-K235F, Y209A-W241R, G020R-N076D, N018R-Q245R, S024R-R045T, A232V-Q245R, G118R-A172V, G118R-A194T, I008T-S024R, K235F-N243F, N018R-S103A, N018R-V104I, P086W-G118R, P086W-N243F, P086W-Y209A, S024C-T033S, S024R-A232V, S024R-N243F, S024R-P239Q, S024R-S101G, S024R-S141G, S024R-T033S, S024R-T274I, S024R-Y209A, S078R-P086W, S101G-A232V, T033S-L148F, T033S-P086W, T033S-P201S, T033S-S078R, T033S-W241R, T033S-Y209A, A230E-H249R, A232V-H249R, G118R-K235F, N076D-Q245R, P086W-K235F, S024R-R247H, S024R-V104A, S078R-K235F, S101G-H249R, S103A-A232V, T033S-A048T, T033S-P239T, T033S-T253A, T143A-Y209A, Y209A-K235F, N018R-R045T, Y209A-N243F, S024R-A272P, S024R-R269C, S101G-V104I, V104I-A232V, N076D-H249R, and S024R-N076D wherein the amino acid positions of the subtilisin variant are numbered by correspondence with the amino acid sequence of B. amyloliquefaciens subtilisin BPN' set forth as SEQ ID NO:1.

The present invention provides nucleic acids encoding a Bacillus subtilisin variant having proteolytic activity comprising an amino acid sequence comprising a combination of amino acid substitutions selected from: G020R-N076D, S024R-R045T, A230E-H249R, N018R-R045T, N018R-Q245R, S101G-A232V, S024R-A232V, A232V-Q245R, S024R-S101G, N018R-V104I, N018R-S103A, S101G-H249R, A232V-H249R, S103A-A232V, N076D-Q245R, S101G-V104I, V104I-A232V, N076D-H249R, S024R-N076D, S024F-N116L, G020K-S024F, G020K-N062E, T033S-G118R, S024R-P086W, S024R-G118R, S024R-P086R, Y209A-W241R, S024R-W241R, S024R-K235F, G118R-Y209A, S078R-G118R, T033S-K235F, S024R-A174T, P086W-Y209A, I008T-S024R, P086W-G118R, T033S-W241R, S024R-N243F, S024R-Y209A, T033S-P086W, S024R-T033S, P086W-N243F, T033S-P201S, S024R-P239Q, S078R-P086W, K235F-N243F, G118R-A172V, T033S-L148F, T033S-S078R, T033S-N243F, S024C-T033S, G118R-A194T, T033S-Y209A, S024R-S141G, S024R-T274I, P086W-K235F, A015T-T033S, Y209A-K235F, S024R-R247H, S078R-K235F, S024R-V104A, T033S-A048T, G118R-K235F, T033S-T253A, T143A-Y209A, T033S-P239T, Y209A-N243F, S024R-A272P, and S024R-R269C, wherein the amino acid positions of the subtilisin variant are numbered by correspondence with the amino acid sequence of B. amyloliquefaciens subtilisin BPN' set forth as SEQ ID NO: 1.

The present invention provides nucleic acids encoding a Bacillus subtilisin variant having proteolytic activity comprising an amino acid sequence comprising a combination of amino acid substitutions selected from: V004R-S009A-G020R-S242R, G020R-N043R-W241R, G020R-S242R-N269R, V004R-S009A-G020R-N043R, V004R-G020R-H249R, N018R-S024R-V244R, S009A-T022R-S212F-W241R, G020R-N043R-N269R, N018R-S024R-S242R, V004R-S009A-N043R-W241R, G020R-N043R-V244R, G020R-T022R-S242R, V004R-G020R-N043R, V004R-S009A-G020R-N043R-S242R, G020R-N043R-S242R, G020R-N043R-S242R-H249R, G020R-S212F-H249R, V004R-S009A-W241R, A001R-S009A-N043R, G020R-N043R-H249R, S009A-G020R-N043R-W241R, G020R-T022R-N043R, G020R-H249R-N269R, G020R-T022R-W241R, V004R-S009A-S024R-N043R-W241R, S009A-N043R-S078R, V004R-G020R-S024R-V244R, G020R-T022R-S078R-S242R, G020R-S024R-S242R-H249R, V004R-S009A-S078R-W241R, S009A-N043R-S078R-S242R, V004R-G020R-S024R, S009A-N043R-S212F, G020R-N043R-S212F, S024R-S078R-S212F, S009A-G020R-S024R-N043R, S009A-T022R-N043R-S078R, G020R-T022R-S212F-W241R, G020R-N043R-S212F-W241R, S009A-N043R-W241R, G020R-N043R-E271L, G020R-T022R-S078R-W241R, G020R-S024R-N043R-S242R, G020R-T022R-N043R-W241R, S009A-G020R-N043R-S212F, V004R-S009A-G020R-S242R, G020R-N043R-H249R-E271L, G020R-T022R-S024R-S242R, S009A-T022R-S078R-S212F, G020R-N043R-S242R-E271L, S009A-T022R-S078R-S212F-W241R, V004R-G020R-S024R-H249R, G020R-T022R-E271L, G020R-T022R-N043R-S212F, V004R-G020R-S024R-N043R-S242R, V004R-G020R-S024R-N043R, V004R-S009A-T022R-S078R-S212F, G020R-T022R-S078R-S212F-W241R, and G020R-T022R-N269R, wherein the amino acid positions of the subtilisin variant are numbered by correspondence with the amino acid sequence of B. amyloliquefaciens subtilisin BPN' set forth as SEQ ID NO: 1.

The present invention provides nucleic acids encoding a Bacillus subtilisin variant having proteolytic activity comprising an amino acid sequence comprising a combination of amino acid substitutions selected from: N018R-G020R-N043D-R045T-A230E, N018R-N043R-R045T-S242R-H249R, S024R-N043D-H249R, N018R-G020R-R045T, G020R-S024R-N076D-H249R, S024R-N043R-A230E-S242R, N018R-S024R-N043D-A230E, G020R-N076D, N018R-S024R-N043D-N076D-H249R, S024R-N043R-N076D-H249R, N018R-S024R-R045T-S242R, G020R-N043D-N076D-A230E-H249R, G020R-N043R-R045T-S242R, N018R-S024R-N076D-H249R, N018R-G020R-S024R-N043D-R045T-L233I-S242R, S024R-N043R-A230E, N018R-G020R-N043D, N043R-S242R-H249R, G020R-N043R-R045T-A230E, N043R-N076D-S242R-H249R, G020R-S024R-R045T-A230E-S242R, S024R-R045T-N076D-A230E-S242R-H249R, S024R-R045T, S024R-N043R-R045T-N076D-A230E-H249R, N018R-S024R-N043D-R045T-H249R, N018R-N043R-R045T-H249R, S024R-N043R-S242R, N018R-G020R-N043R-N076D-H249R, G020R-S024R-N043D-H249R, G020R-N043R-A230E-S242R, G020R-N043R-S242R, N018R-N043R-N076D-A230E, G020R-S024R-N043D-S242R, G020R-N043R-A230E, N018R-G020R-N043R-N076D-S242R-H249R, N043D-R045T-N076D-H249R, N018R-N043R-S242R-H249R, N018R-G020R-N043R-R045T-S242R, N018R-G020R-N043D-A230E-S242R, G020R-S024R-N043R-R045T-H249R, S024R-N043R-H249R, G020R-S024R-K27E-N043R-N076D-A230E, S024R-N043R-R045T-S242R, N018R-G020R-S024R-N043R-R045T-N076D-A230E, G020R-N043R-N076D-A230E-H249R, N018R-N043R-R045T-S242R, G020R-S242R-H249R, N018R-N043R-N076D-A230E-S242R-H249R, N018R-S024R-N076D, G020R-S024R-K27E-N043D-S242R-H249R, N018R-G020R-S024R-N043D-N076D-S242R, N018R-N043R-N076D-S242R-H249R, N018R-S024R-N043D-A230E-H249R, N018R-G020R-N043D-H249R, N018R-G020R-N043D-R045T-N076D-S242R, S024R-N043R-N076D-A230E-S242R, G020R-S024R-T381-N043R-R045T-N076D-S242R-H249R, N018R-G020R-N043R, N018R-S024R-R045T-A230E-S242R, N018R-G020R-H249R, S024R-N043R-N076D, N018R-G020R-S024R-N043R-R045T-N076D-H249R, N018R-N043D-R045T-N076D-S242R-H249R, S024R-N043D-S242R-H249R, N018R-G020R-S024R-N043D-R045T-S242R, G020R-S024R-N043R-N076D, N018R-G020R-N043D-R045T-A230E-S242R, G020R-S024R-N043R-R045T-N076D-S242R-H249R, N018R-N043R-R045T-N076D-S242R, N018R-G020R-N043R-N076D-A230E-S242R, N018R-S024R-N043D-H249R, N018R-S024R-N043R-R045T-A230E-H249R, N018R-G020R-N043R-R045T-N076D-H249R, N018R-S024R-S242R, N018R-N043R-R045T-N076D-A230E-S242R, R045T-S242R-H249R, N018R-S024R-N043D-S242R, N018R-G020R-N043D-R045T-S240P, S024R-N043R-R045T-S242R-H249R, N018R-S024R-V30S-L31S-D321-T33Q-G34V-I35F, N018R-G020R-N043R-N076D, G020R-N043D-R045T-N076D-S242R-H249R, N018R-S024R-N043D-

A230E-S242R, N018R-S024R-N043D-S242R-H249R, S024R-N043D-R045T-S242R-H249R, N043R-A230E-H249R, S024R-N043R-N076D-A230E-H249R, G020R-S024R-N043D-N076D-H249R, S024R-R045T-S242R-A273V, G020R-S024R-R045T-N076D-S242R-H249R, N018R-S024R-N043D-N076D-S242R, N018R-N043R-N076D-A230E-H249R, N018R-G020R-N043R-R045T-H249R, N018R-N043R-R045T-A230E-S242R, G020R-S024R-N043D-R045T-A230E-S242R, N018R-N043D-A230E-H249R, N018R-N043R-N076D-S242R, N018R-G020R-N076D, N018R-G020R-N043D-N076D-S242R-H249R, G020R-S024R-N043D-N076D-S242R-H249R, N043D-S242R-H249R, N018R-G020R-S024R-N043R-N076D, N018R-G020R-N043D-R045T-N076D-H249R, N018R-G020R-N043R-R045T-N076D-A230E-H249R, N018R-N076D-S242R, G020R-N043R-H249R, N018R-N076D-S242R-H249R, N018R-S024R-R045T-A230E-H249R, A230E-H249R, N018R-R045T-H249R, G020R-N043R-N076D, N043R-R045T-H249R, N018R-N043D-N076D-S242R-H249R, N043R-N076D-H249R, N018R-R045T, G020R-N076D-A230E-S242R, G020R-S024R-N043D-R045T, S024R-N043D-N076D-S242R-H249R, G020R-R045T-H249R, N043R-N076D-S153A-H249R, N043R-N076D-A230E-H249R, N018R-N043D-N076D-H249R, and G020R-N043R-N076D-V227I, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: S101G-S103A-V104I-A232V-Q236H-Q245R-N252K, S101G-S103A-V104I-A232V-Q245R-N248R, S101G-S103A-V104I-G159R-A232V-Q245R-N248D, S101G-S103A-V104I-G159D-A232V-Q245R-N248R, S101G-S103A-V104I-A232V-Q245R, S101G-S103A-V104I-G159D-A232V-Q245R, and S101G-S103A-V104I-A232V-Q245R-N248D, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: S101G-S103A-V104I-P129E-S188D-A232V-N238R-Q245R-N248D, S024R-S101G-S103A-V104I-P129E-A158E-S188D-A232V-Q245R-N248D-H249R, T022A-S101G-S103A-V104I-P129E-A158E-S188D-A232V-Q245R-N248D-H249R, T022A-S024R-S101G-S103A-V104I-P129E-A158E-S188D-A232V-Q245R-N248D-H249R, S024R-S101G-S103A-V104I-P129E-S188D-A232V-Q245R-N248D-H249R, S024R-S101G-S103A-V104I-P129E-G159E-S188D-A232V-Q245R-N248D-H249R, S024R-S101G-S103A-V104I-S128N-P129E-A158E-A232V-Q245R-N248D-H249R, S024R-S101G-S103A-V104I-L148I-A158E-S188D-A232V-Q245R-N248D, T022A-S024R-S101G-S103A-V104I-P129E-G159E-S188D-A232V-Q245R-N248D-H249R, S024R-S101G-S103A-V104I-S128N-P129E-A232V-Q245R-N248D, S101G-S103A-V104I-P129E-S188D-A232V-Q245R-N248D-H249R, S024R-S101G-S103A-V104I-P129E-A158E-A232V-Q245R-N248D-H249R, T022A-S024R-S101G-S103A-V104I-A158E-G159E-S188D-A232V-Q245R-N248D-H249R, T022A-S024R-S101G-S103A-V104I-P129E-A158E-G159E-S188D-A232V-N238R-Q245R-N248D, S024R-S101G-S103A-V104I-P129E-L148I-A158E-A232V-Q245R-N248D, A016S-S024R-S101G-S103A-V104I-A158E-S188D-A232V-Q245R-N248D-H249R, S101G-S103A-V104I-A158E-G159E-A232V-Q245R-N248D-H249R, T022A-S101G-S103A-V104I-P129E-A158E-G159E-A232V-N238R-Q245R-N248D, T022A-S024R-S101G-S103A-V104I-P129E-A158E-G159E-A232V-Q245R-N248D-H249R, T022A-S024R-S101G-S103A-V104I-S128N-A158E-S188D-A232V-Q245R-N248D, S024R-S101G-S103A-V104I-P129E-S188D-A232V-Q245R-N248D, T022A-S024R-S101G-S103A-V104I-P129E-A158E-A232V-Q245R-N248D, T022A-S024R-S101G-S103A-V104I-P129E-A232V-Q245R-N248D, T022A-S024R-S101G-S103A-V104I-P129E-S188D-A232V-Q245R-N248D, S024R-S101G-S103A-V104I-A158E-S188D-A232V-N238R-Q245R-N248D, T022A-S101G-S103A-V104I-S128N-P129E-S188D-A232V-N238R-Q245R-N248D, S024R-S101G-S103A-V104I-P129E-S188D-A232V-N238R-Q245R-N248D, S024R-S101G-S103A-V104I-A158E-G159E-S188D-A232V-Q245R-N248D, T022A-S024R-S101G-S103A-V104I-S128N-S188D-A232V-Q245R-N248D, S024R-S101G-S103A-V104I-P129E-A158E-S188D-A232V-Q245R-N248D, T022A-S024R-S101G-S103A-V104I-S128N-P129E-A158E-A232V-Q245R-N248D, S024R-S101G-S103A-V104I-G159E-S188D-A232V-Q245R-N248D, T022A-S101G-S103A-V104I-S128N-P129E-A232V-N238R-Q245R-N248D, S024R-S101G-S103A-V104I-P129E-G159E-A232V-Q245R-N248D, T022A-S024R-S101G-S103A-V104I-P129E-A158E-S188D-A232V-N238R-Q245R-N248D, T022A-S024R-S101G-S103A-V104I-A158E-G159E-S188D-A232V-Q245R-N248D, S024R-S101G-S103A-V104I-G159E-S188D-A232V-Q245R-N248D-H249R, T022A-S101G-S103A-V104I-P129E-A158E-A232V-N238R-Q245R-N248D, T022A-S024R-S101G-S103A-V104I-P129E-A158E-A232V-Q245R-N248D-H249R, S024R-S101G-S103A-V104I-L148I-A158E-A232V-Q245R-N248D, T022A-S101G-S103A-V104I-A158E-G159E-S188D-A232V-Q245R-N248D-H249R, T022A-S101G-S103A-V104I-A158E-S188D-A232V-Q245R-N248D, T022A-S101G-S103A-V104I-P129E-S188D-A232V-N238R-Q245R-N248D, S024R-S101G-S103A-V104I-P129E-A158E-G159E-S188D-A232V-Q245R-N248D-H249R, T022A-S024R-S101G-S103A-V104I-A158E-G159E-S188D-A232V-N238R-Q245R-N248D, S101G-S103A-V104I-P129E-A158E-S188D-A232V-Q245R-N248D-H249R, S024R-S101G-S103A-V104I-S128N-A158E-A232V-Q245R-N248D, T022A-S024R-S101G-S103A-V104I-S128N-P129E-S188D-A232V-Q245R-N248D, T022A-S101G-S103A-V104I-P129E-G159E-A232V-N238R-Q245R-N248D, S101G-S103A-V104I-P129E-G159E-A232V-Q245R-N248D-H249R, T022A-S101G-S103A-V104I-P129E-A158E-A232V-Q245R-N248D-H249R, S024R-S101G-S103A-V104I-P129E-L148I-A158E-S188D-A232V-Q245R-N248D, T022A-S101G-S103A-V104I-P129E-G159E-A232V-Q245R-N248D-H249R, S024R-S101G-S103A-V104I-G159E-S188D-A232V-N238R-Q245R-N248D, S024R-S101G-S103A-V104I-P129E-A158E-G159E-A232V-Q245R-N248D-H249R, S024R-S101G-S103A-V104I-P129E-A158E-G159E-A232V-N238R-Q245R-N248D, S024R-S101G-S103A-V104I-S128N-G159E-S188D-A232V-Q245R-N248D, T022A-S101G-S103A-V104I-G159E-S188D-A232V-Q245R-N248D-H249R, S024R-S101G-S103A-V104I-P129E-G159E-S188D-A232V-N238R-Q245R-N248D, S101G-S103A-V104I-A158E-A232V-N238R-

Q245R-N248D, T022A-S101G-S103A-V104I-P129E-G159E-S188D-A232V-Q245R-N248D-H249R, S024R-S101G-S103A-V104I-P129E-L148I-S188D-A232V-Q245R-N248D, S024R-S101G-S103A-V104I-A158E-A232V-Q245R-N248D-H249R, T022A-S101G-S103A-V104I-A158E-G159E-A232V-N238R-Q245R-N248D, S024R-S101G-S103A-V104I-A158E-G159E-A232V-N238R-Q245R-N248D, T022A-S101G-S103A-V104I-P129E-A158E-G159E-A232V-Q245R-N248D-H249R, S101G-S103A-V104I-P129E-A158E-S188D-A232V-N238R-Q245R-N248D, T022A-S024R-S101G-S103A-V104I-P129E-A158E-G159E-A232V-Q245R-N248D, S101G-S103A-V104I-S188D-A232V-N238R-Q245R-N248D, T022A-S024R-S101G-S103A-V104I-A158E-A232V-Q245R-N248D-H249R, T022A-S024R-S101G-S103A-V104I-L148I-A158E-A232V-Q245R-N248D, S101G-S103A-V104I-P129E-A158E-G159E-A232V-N238R-Q245R-N248D, T022A-S101G-S103A-V104I-G159E-S188D-A232V-N238R-Q245R-N248D, T022A-S024R-S101G-S103A-V104I-P129E-A158E-G159E-S188D-A232V-Q245R-N248D-H249R, T022A-S101G-S103A-V104I-P129E-A232V-N238R-Q245R-N248D, T022A-S024R-S101G-S103A-V104I-S188D-A232V-Q245R-N248D-H249R, S101G-S103A-V104I-P129E-A158E-G159E-A232V-Q245R-N248D-H249R, T022A-S101G-S103A-V104I-A158E-G159E-A232V-Q245R-N248D-H249R, S101G-S103A-V104I-P129E-S188D-A232V-Q245R-N248D, S024R-S101G-S103A-V104I-P129E-G159E-A232V-N238R-Q245R-N248D, S101G-S103A-V104I-S128N-P129E-A232V-Q245R-N248D, S101G-S103A-V104I-A158E-S188D-A232V-Q245R-N248D, T022A-S024R-S101G-S103A-V104I-P129E-A232V-Q245R-N248D-H249R, S101G-S103A-V104I-P129E-G159E-A232V-N238R-Q245R-N248D, S101G-S103A-V104I-A158E-G159E-S188D-A232V-N238R-Q245R-N248D, S024R-S101G-S103A-V104I-A232V-Q245R-N248D-H249R, T022A-S024R-S101G-S103A-V104I-P129E-L148I-A232V-Q245R-N248D, T022A-S024R-S101G-S103A-V104I-A158E-A232V-N238R-Q245R-N248D, S101G-S103A-V104I-S128N-P129E-A232V-N238R-Q245R-N248D, T022A-S101G-S103A-V104I-S128N-G159E-A232V-Q245R-N248D, T022A-S101G-S103A-V104I-S128N-P129E-A158E-A232V-N238R-Q245R-N248D, S101G-S103A-V104I-S128N-P129E-S188D-A232V-Q245R-N248D-H249R, T022A-S024R-S101G-S103A-V104I-S128N-P129E-A158E-S188D-A232V-Q245R-N248D-H249R, S024R-S101G-S103A-V104I-S128N-A158E-G159E-S188D-A232V-Q245R-N248D, T022A-S024K-S101G-S103A-V104I-S128N-A158E-G159E-A232V-Q245R-N248D, S101G-S103A-V104I-P129E-L148I-S188D-A232V-Q245R-N248D, S024R-S101G-S103A-V104I-L148I-A232V-Q245R-N248D, T022A-S101G-S103A-V104I-L148I-S188D-A232V-Q245R-N248D, S024R-S101G-S103A-V104I-S128N-P129E-S188D-A232V-Q245R-N248D, S101G-S103A-V104I-S128N-P129E-A158E-A232V-N238R-Q245R-N248D, T022A-S024R-S101G-S103A-V104I-P129E-L148I-A158E-S188D-A232V-Q245R-N248D, T022A-S024R-S101G-S103A-V104I-L148I-A158E-S188D-A232V-Q245R-N248D, S101G-S103A-V104I-L148I-G159E-A232V-Q245R-N248D, T022A-S024R-S101G-S103A-V104I-A158E-S188D-A232V-Q245R-N248D, and S101G-S103A-V104I-S128N-P129E-A158E-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: T022A-S024R-S101G-S103A-V104I-A158E-A232V-Q245R-N248D-H249R, T022A-S024R-S101G-S103A-V104I-P129E-A232V-Q245R-N248D-H249R, S024R-S101G-S103A-V104I-A158E-G159E-A232V-N238R-Q245R-N248D, S024R-S101G-S103A-V104I-A232V-Q245R-N248D-H249R, S101G-S103A-V104I-A158E-A232V-Q245R-N248D-H249R, S101G-S103A-V104I-S188D-A232V-Q245R-N248D-H249R, S024R-S101G-S103A-V104I-G159E-S188D-A232V-Q245R-N248D-H249R, T022A-S024R-S101G-S103A-V104I-A158E-A232V-N238R-Q245R-N248D, S024R-S101G-S103A-V104I-G159E-S188D-A232V-N238R-Q245R-N248D, T022A-S024R-S101G-S103A-V104I-P129E-A232V-Q245R-N248D, S024R-S101G-S103A-V104I-L148I-A232V-Q245R-N248D, S024R-S101G-S103A-V104I-P129E-A158E-A232V-Q245R-N248D-H249R, S024R-S101G-S103A-V104I-L148I-A158E-A232V-Q245R-N248D, T022A-S024R-S101G-S103A-V104I-P129E-A158E-A232V-Q245R-N248D-H249R, A016S-S024R-S101G-S103A-V104I-A158E-S188D-A232V-Q245R-N248D-H249R, S024R-S101G-S103A-V104I-P129E-G159E-A232V-N238R-Q245R-N248D, S024R-S101G-S103A-V104I-P129E-S188D-A232V-Q245R-N248D-H249R, T022A-S101G-S103A-V104I-P129E-A232V-N238R-Q245R-N248D, T022A-S024R-S101G-S103A-V104I-L148I-A158E-A232V-Q245R-N248D, S024R-S101G-S103A-V104I-P129E-S188D-A232V-N238R-Q245R-N248D, T022A-S024R-S101G-S103A-V104I-A158E-G159E-S188D-A232V-N238R-Q245R-N248D, T022A-S101G-S103A-V104I-A158E-G159E-A232V-N238R-Q245R-N248D, T022A-S024R-S101G-S103A-V104I-P129E-A158E-A232V-Q245R-N248D, S101G-S103A-V104I-A158E-S188D-A232V-Q245R-N248D-H249R, T022A-S101G-S103A-V104I-A158E-G159E-A232V-Q245R-N248D-H249R, and S024R-S101G-S103A-V104I-A158E-G159E-A232V-Q245R-N248D, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: V104L-S128N-A158E-R186H-H249R, S128N-A158E-S188D-H249R, N062E-S128N-A158E-G159E-E271F, N062E-A158E-S188D-H249R-E271F, N062E-A158E-R186H-H249R-E271F, S128N-A158E-S188D-Y209E-E271F, N062E-G159E-S188D-H249R, A016S-N062E-A158E-R186H-H249R, N062E-A158E-G159E-H249R, S101A-S128N-A158E-Y209E-H249R, S128N-A158E-R186H-E271F, N062E-A158E-S188D-H249R, N062E-A158E-R186H-E271F, N062E-A158E-R186H-H249R, N062E-S101A-R186H-H249R, N062E-S101A-A158E-R186H-E271F, N062E-V104L-A158E-S188D-H249R-E271F, N062E-G159E-R186H-H249R, N062E-G159E-H249R, S128N-A158E-R186H-H249R, S128N-A158E-S188D-E271F, N062E-A158E-H249R, N062E-R186H-S188D-H249R-E271F, S128N-A158E-Y209E-, N062E-S101A-A158E-H249R, V104L-S128N-A158E-R186H-E271F, N062E-S101A-A158E-R186H-H249R-E271F, A016S-N062E-A158E-H249R, N062E-S101A-G159E-H249R, S128N-A158E-R186H-S188D-E271F, S101A-S128N-A158E-R186H-E271F, N062E-S101A-S188D-H249R, S101A-

V104L-A158E-R186H-S188D-H249R, N062E-G159E-H249R-E271F, S128N-A158E-G159E-E271F, A016S-N062E-V104L-A158E-R186H-E271F, T022A-S128N-A158E-H249R, S128N-A158E-H249R, N062E-S101A-V104L-A158E-R186H-E271F, A016S-N062E-A158E-R186H-E271F, V104L-S128N-A158E-H249R, V104L-S128N-A158E-S188D-H249R, T022A-N062E-A158E, N062E-S101A-S188D-H249R-E271F, N062E-A158E-H249R-E271F, V104L-S128N-A158E-R186H-S188D-E271F, N062E-S101A-R186H-E271F, N062E-V104L-G159E-H249R, N062E-R186H-H249R, N062E-S101A-R186H-H249R-E271F, S101A-A158E-R186H-S188D-H249R, N062E-S101A-R186H, S101A-S128N-P129E-R186H-H249R, S101A-S103G-A158E-R186H-H249R, A016S-N062E-V104L-R186H-S188D-E271F, V104L-A158E-R186H-H249R, S101A-S128N-A158E-S188D-Y209E-E271F, N062E-S101A-R186H-S188D-E271F, A016S-N062E-A158E-H249R-E271F, N062E-S128N-A158E, N062E-S128N-G159E-H249R, N062E-S101A-A158E-S188D-H249R, S101A-S128N-A158E-H249R, N062E-A158E-R186H-S188D-H249R, A016S-V104L-A158E-R186H-E271F, N062E-L148I-G159E, N062E-S101A-A158E-R186H-H249R, N062E-S101A-R186H-S188D-H249R, V104L-A158E-R186H-S188D-H249R, N062E-S101A-V104L-R186H-S188D-E271F, T022A-S101A-A158E-R186H-H249R, S101A-S128N-A158E-Y209E, A158E-R186H-S188D-H249R-E271F, V104L-A158E-R186H-S188D-H249R-E271F, S101A-V104L-A158E-R186H-H249R, V104L-A158E-H249R, S101A-V104L-S128N-A158E-R186H-E271F, A016S-V104L-S188D-H249R, S101A-V104L-A158E-R186H-S188D-E271F, V104L-S128N-G159E-E271F, V104L-A158E-R186H-H249R-E271F, A158E-R186H-H249R, S101A-A158E-R186H-H249R, V104L-A158E-S188D-H249R-E271F, A016S-S128N-A158E-R186H, V104L-S128N-R186H-S188D-H249R, A016S-S101A-S128N-R186H, A016S-N062E-S128N-R186H-E271F, A016S-S128N-R186H-E271F, S128N-P129E-R186H, A158E-R186H-H249R-E271F, A016S-A158E-H249R, A016S-A158E-R186H-H249R, A016S-T022A-A158E-R186H-E271F, E089P-S101A-P129E-R186H, T022A-S128N-A158E-R186H, S101A-V104L-S128N-A158E-R186H, T022A-S128N-R186H-S188D-, N062E-V104L-A158E-R186H-S188D-H249R, T022A-A158E-R186H-H249R-E271F, T022A-V104L-A158E-H249R, S101A-L111V-P129E, A016S-A158E-H249R-E271F, A016S-L111V-S188D-, T022A-V104L-R186H-S188D-H249R, and V104L-L148I-S188D-H249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: A001R-S101G-S103A-V104I-A232V-Q245R, V004R-S101G-S103A-V104I-A232V-Q245R, N043R-S101G-S103A-V104I-A232V-Q245R-E271L, S078R-S101G-S103A-V104I-A232V-Q245R, V004R-N043R-S101G-S103A-V104I-A232V-Q245R, N018R-N043R-S101G-S103A-V104I-A232V-Q245R, G020R-S101G-S103A-V104I-A232V-Q245R, S101G-S103A-V104I-A232V-Q245R-E271L, G020R-N043R-S101G-S103A-V104I-A232V-Q245R, S024R-N043R-S101G-S103A-V104I-A232V-Q245R, G020R-G025R-N116A-Y167W, N018R-S101G-S103A-V104I-A232V-Q245R, T022R-S101G-S103A-V104I-A232V-Q245R, S078R-S103N-S106G-Y167W-Q236N, N018R-N043D-S101G-S103A-V104I-A232V-Q245R-N269R, N043R-S101G-S103A-V104I-A232V-Q245R-N269R, S024R-S101A-H120E-A194F-H249R, G020R-N043D-S101G-S103A-V104I-A232V-Q245R-N269R, S101G-S103A-V104I-S212F-A232V-Q245R, G020R-S144R-N185I-L233C-Q236N, G023A-S078R-S216F-Q236N-H249R, S101G-S103A-V104I-A232V-Q245R-N269R, S101G-S103A-V104I-G115R-A232V-Q245R, P052N-S078R-S103N-L148I-T213A, N018R-N043D-S101G-S103A-V104I-A232V-Q245R-H249R, S024R-N043D-S101G-S103A-V104I-A232V-Q245R-H249R, S024R-N043D-S101G-S103A-V104I-A232V-Q245R-N269R, G025R-E089I-N116A-P239S-A270C, S024R-S101G-S103A-V104I-A232V-Q245R, L148I-T213A-N252R, S024R-G025R-N183D-Y192W-P239S, G046R-A194F-S212M, V104L-L217E-T224A-H249R-N252R, G023A-Y091F-V121F-Y192W-Q236N, S101G-S103A-V104I-A232V-V244R-Q245R, S099F-S144R-Y167W-N252R, S101G-S103A-V104I-A232V-Q245R-H249R, N043R-S101G-S103A-V104I-A232V-Q245R, T022W-S078R-Y167W-S212M-A270C, V121F-N252R-A270C, G020R-S103N-S216F-Q236N-N252R, N043R-S101G-S103A-V104I-A232V-Q245R-H249R, G023A-P052N-Y192W-I198L-N252R, G025R-G046R-V121F, S024R-S078R-V104L-N116A-N183D, G046R-Q059A-S103N-G211Q-S212M, G020R-P052N-N062Q-Y091F-Y192W, G023A-P052N-S144R-Y192W-S216F, S101G-S103A-V104I-A232V-S242R-Q245R, P052N-S103N-N116A-L148I-Y192W, E089I-N116A-N117F-T224A-H249R, S144R-G211Q-N238L-P239S-H249R, N043A-N062Q-A194F-G211Q, G020R-S024R-P052N-Q059A-S216F, S024R-Y167W-T224A-H249R, T057R-Y167W-H249R, G025R-S103N-R186K-A194F-T224A, S105T-S128N-S144R-L148I-S212M, G020R-Q059A-S144R-Y192W-T224A, S024R-N043A-N117F-A194F-G211Q, N117F-A194F-T213A-A270C, S078R-Y091F-V121F-L233C-N252R, T057R-S099F-S105T-I198L-T213A, G023A-Y091F-S101A-I198L-N252R, N062Q-S103N-V121F-S144R-H249R, N043R-S101G-S103A-V104I-A232V-S242R-Q245R, G023A-S024R-N117F-S212M-S216F, V104L-T213A-S216F, A194F-G211Q-Q236N, N062Q-S103N-N117F-A194F, S024R-N062Q-V104L-S106G-H249R, T057R-E089I-I198L, G046R-Q059A-S106G-L217E-H249R, N117F-T213A-A215F, S101A-H120E-Y192W-A215F-T224A, N043A-T057R-N117F-S144R-N183D, G046R-N183D-N238L, G025R-N043A-E089I-N117F, S078R-V104L-T213A-A215F-T224A, Y091F-S099F-S101A-S105T-Y167W, S106G-N117F-N238L, G046R-E089I-Y091F-S101A-N116A, G020R-N062Q-E089I-R186K-S212M, T057R-S099F-V121F-N185I-Y192W, G046R-E089I-Y192W-L233C-A270C, E089I-N117F-N185I-A215F-L233C, P052N-V104L-N183D-S216F-H249R, S078R-S099F-N116A-R186K-T224A, G025R-S105T-S128N-S144R-A270C, S105T-G211Q-S216F, S024R-G046R-Y091F-V121F, S106G-N185I-S216F-Q236N, N062Q-S101A-Q236N-N252R-A270C, G025R-N043A-Y091F-I198L-A270C, G020R-G023A-V104L-Y192W-L233C, S024R-N043A-S105T-S106G-I198L, G020R-E089I-L217E, S024R-Y091F-I198L-A215F-P239S, G046R-E089I-S099F-R186K-S212M, V104L-H120E-R186K-S216F-N252R, T022W-A194F-T213A-L233C-N238L, S099F-S105T-S106G-A194F-S212M, E089I-S105T-N116A-A215F-S216F, G025R-N116A-H120E-T224A-A270C, N043A-Q059A-S101A-S216F-T224A, T057R-N183D-Q236N, G025R-N062Q-S128N-S144R-N185I, S103N-H120E-Y167W-I198L-L233C, T022W-E089I-S216F, S024R-S106G-N116A-

S212M-T224A, G020R-P052N-S101A-I198L-L233C, E089I-Y091F-N185I-G211Q-A270C, L111I-A215F-P239S, S024R-N116A-R186K-L233C-Q236N, and G023A-S103N-S106G-S212M-A215F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: G020R-T022W-S078R-S101A-S103A-V104I-N116S-T213A-A215F-A232V-Q245R, N018R-S078R-S101G-S103A-V104I-A232V-Q245R, S024R-R045T-S101G-S103A-V104I-A232V-Q245R-N269R, G020R-T022W-S078R-S101G-S103A-V104I-N116A-A232V-Q245R, G020R-T22W-S101G-S103A-V104I-A232V-Q245R, N018R-N043R-S101G-S103A-V104I-A232V-Q245R, N018R-T022W-S024R-N076D-S101A-N116A-A232V-Q245R, N018R-V104I-A232V-H249R, N018R-S024R-N076D-S101A-N116A-G211Q-H249R, N018R-N043D-S078R-S101G-S103A-V104I-L217E-A232V-Q245R, N018R-N043R-S101G-S103A-V104I-A232V-Q245R-N269R, N018R-R045T-N076D-S101G-S103A-V104I-A232V-Q245R-N269R, N076D-S078R-S101G-S103A-V104I-A232V-Q245R-N269R, G020R-N043D-S078R-S101G-S103A-V104I-A232V-Q245R, N018R-N043D-N076D-S101G-S103A-V104I-A232V-Q245R-N269R, S024R-R045T-N076D-S078R-S101G-S103A-V104I-A232V-Q245R-N269R, N018R-S103A-A232V-H249R, N018R-S101G-V104I-A232V-Q245R, G020R-S024R-S101G-S103A-V104I-L217E-A232V-Q245R-H249R, N018R-T22K-N043D-S101G-S103A-V104I-A232V-Q245R, N043R-R045T-S101G-S103A-V104I-A232V-Q245R-N269R, G020R-T22W-S101G-S103A-V104I-G211Q-A232V-Q245R, S024R-N076D-S078R-S101G-S103A-V104I-A232V-Q245R-N269R, G020R-T22W-S078R-S101A-S103A-V104I-N116A-N183D-A232V, N018R-S024R-N076D-N116A-A215F-H249R, N018R-N043R-R045T-S101G-S103A-V104I-A232V-Q245R, S024R-N043R-N076D-S101G-S103A-V104I-A232V-Q245R, G020R-T022W-S101G-S103A-V104I-A232V-Q245R, G020R-T022W-S101G-S103A-V104I-G211Q-A232V-Q245R, G020R-T022W-S078R-S101G-S103A-V104I-N116A-T213A-A215F-A232V-Q245R, N043D-N076D-S078R-S101G-S103A-V104I-A232V-Q245R-N269R, N018R-S024R-N076D-S101A-N116A-T213A-H249R, N018R-S024R-N076D-N116A-G211Q-H249R, N043R-R045T-N076D-S078R-S101G-S103A-V104I-A232V-Q245R, N018R-S101G-Q245R, G020R-T22W-S101A-S103A-V104I-G211Q-T213A-A232V-Q245R, G020R-S024R-N043D-N076D-S078R-S101G-S103A-V104I-A232V-Q245R, N018R-R045T-N076D-S078R-S101G-S103A-V104I-A232V-Q245R, G020R-S078R-S101G-S103A-V104I-G211Q-T213A-A215F-A232V-Q245R, R045T-S078R-S101G-S103A-V104I-A232V-Q245R-N269R, S024R-N043D-S101G-S103A-V104I-A232V-Q245R-N269R, N018R-S101G-S103A-H249R, N018R-T22W-S024R-N076D-S101A-N116A-A232V-Q245R, N018R-S101G-V104I-A232V-H249R, G020R-T22W-S101A-S103A-V104I-A215F-A232V-Q245R, N018R-S024R-N076D-G211Q-T213A-H249R, N018R-T022W-S024R-N076D-S101A-I198L-H249R, S024R-S101G-S103A-V104I-A232V-Q245R, G020R-N076D-S101G-S103A-V104I-A232V-Q245R-N269R, G020R-S101G-S103A-V104I-A232V-Q245R-N269R, N043D-S078R-S101G-S103A-V104I-A232V-Q245R, G020R-S101G-V104I-T213A-A215F-A232V-Q245R, G020R-S101G-S103A-V104I-N116A-A215F-A232V-Q245R, S024R-S103A-V104I-H249R, N018R-N076D-S078R-S101G-S103A-V104I-A232V-Q245R, R045T-N076D-S078R-S101G-S103A-V104I-A232V-Q245R-N269R, S024R-S101G-V104I-Q245R, G020R-S101G-S103A-V104I-G211Q-T213A-A215F-A232V-Q245R, S024R-S103A-V104I-A232V-H249R, N018R-S024R-N076D-N116A-G211Q-A215F-H249R, N018R-Q245R, S024R-S103A-Q245R, S024R-S103A-V104I-Q245R, G020R-S078R-S101G-A232V-Q245R, N018R-S024R-N076D-V104I-H249R, N018R-S024R-V104I-H249R, S024R-S101G-S103A-V104I-A232V-Q245R, N018R-S024R-N076D-G211Q-A215F-H249R, R019H-G020R-T022W-S078R-S101G-S103A-V104I-G211Q-A232V-Q245R, N018R-S024R-N076D-S101A-I198L-G211Q-T213A-H249R, N018R-S024R-N043D-S101G-S103A-V104I-A232V-Q245R, G020R-T22W-S103A-V104I-A232V-Q245R, N018R-S103A-V104I-H249R, N018R-T022W-S024R-N076D-S101A-I198L-A215F-H249R, N018R-S024R-S101G-V104I-A232V, S078R-S101G-S103A-V104I-A232V-Q245R-N269R, S024R-N043R-N076D-S078R-S101G-S103A-V104I-A232V-Q245R, N018R-G020R-N043D-N076D-S101G-S103A-V104I-A232V-Q245R, N018R-T22W-S024R-N076D-N116A-T213A-H249R, N018R-S024R-S101G-V104I, G020R-S101A-S103A-V104I-A215F-A232V-Q245R, N018R-R045T-S078R-S101G-S103A-V104I-A232V-Q245R, N018R-S101G-S103A-Q245R, N043R-N076D-S078R-S101G-S103A-V104I-A232V-Q245R, G020R-T022W-S101A-S103A-V104I-G211Q-A215F-A232V-Q245R, G020R-T22W-S078R-S101G-S103A-V104I-N116A-T213A-A215F-A232V-Q245R, G020R-S078R-S101G-S103A-V104I-A215F-A232V-Q245R, G020R-T022W-S078R-S101G-S103A-V104I-N116A-N183D-A232V-Q245R, N076D-S101G-S103A-V104I-A232V-Q245R, N076D-S101G-S103A-V104I-A232V-Q245R-N269R, G020R-T22W-S101A-S103A-V104I-A232V-Q245R, G020R-S101G-S103A-A232V-Q245R, G020R-T022W-S078R-S101A-S103A-V104I-N116A-N183D-A232V-Q245R, N018R-G020R-S024R-R045T-N076D-S101G-S103A-V104I-A232V-Q245R-N269R, N043R-R045T-S078R-S101G-S103A-V104I-A232V-Q245R, N018R-S101G-V104I-H249R, G020R-T22W-S078R-S101G-S103A-V104I-N116A-N183D-A232V-Q245R, G020R-T022W-S101G-S103A-V104I-I198L-G211Q-T213A-A232V-Q245R, G020R-S078R-S101A-S103A-V104I-N116A-N183D-T213A-A232V-Q245R, S024R-N076D-V104I-A232V-Q245R, N018R-G020R-N076D-S101G-S103A-V104I-A232V-Q245R, N018R-S024R-N076D-S101G-V104I-A232V-H249R, N018R-N043D-S078R-S101G-S103A-V104I-A232V-Q245R, A001T-N018R-S024R-N076D-N116A-T213A-H249R, N076D-S078R-S101G-S103A-V104I-A232V-Q245R, G020R-S078R-S101G-S103A-V104I-N116A-A232V-Q245R, N043R-N076D-S101G-S103A-V104I-A232V-Q245R, N018R-R045T-S101G-S103A-V104I-A232V-Q245R, N018R-N076D-S101G-V104I-A232V-Q245R, G020R-S078R-S101G-S103A-V104I-N116A-N183D-A232V-Q245R, N018R-S024R-N076D-S101A-G211Q-T213A-A215F-H249R, R045T-S078R-S101G-S103A-V104I-A232V-Q245R, N043R-N076D-S101G-S103A-V104I-A232V-Q245R-N269R, G020R-T022W-S078R-S101G-S103A-V104I-N116A-N183D-T213A-A232V-Q245R, G020R-T022W-S101G-S103A-V104I-N116A-N183D-T213A-A232V-Q245R, G020R-S101G-I198L-A215F-A232V-Q245R, N018R-S024R-N076D-T213A-A215F-H249R, G020R-S078R-S101G-

S103A-V104I-N116A-G211Q-A232V-Q245R, G020R-T022W-S078R-S101A-S103A-V104I-N116A-N183D-A215F-A232V-Q245R, G020R-T022W-S078R-S101A-S103A-V104I-N116A-N183D-T213A-A232V-Q245R, S024R-A232V-Q245R, N018R-S024R-N043D-S101G-S103A-V104I-A232V-Q245R-N269R, N018R-S024R-N076D-S101A-A215F-H249R, N018R-T022W-S024R-N076D-N116A-T213A-H249R, S101G-S103A-V104I-A232V-Q245R, N018R-S024R-N076D-G211Q-T213A-A215F-H249R, N018R-S024R-N076D-N116A-T213A-A215F-H249R, N043D-N076D-S078R-S101G-S103A-V104I-A232V-Q245R-N269R, N043D-S078R-S101G-S103A-V104I-A232V-Q245R-H249R, G020R-T022W-S078R-S101G-S103A-V104I-N116A-N183D-G211Q-A232V-Q245R, N018R-S024R-N076D-S101A-I198L-G211Q-A215V-H249R, N018R-T022W-S024R-N076D-N116A-G211Q-H249R, G020R-S103A-V104I-A232V-Q245R, G020R-T22W-S101A-S103A-V104I-G211Q-A215F-A232V-Q245R, S024R-N076D-S101G-S103A-V104I-A232V-Q245R, G020R-S101G-S103A-V104I-N116A-A232V-Q245R, N018R-T22W-S024R-N076D-I198L-A215F-H249R, G020R-T022W-S103A-V104I-A232V-Q245R, G020R-T022W-S101A-S103A-V104I-G211Q-T213A-A232V-Q245R, G020R-T022W-S101G-S103A-V104I-G211Q-T213A-A215F-A232V-Q245R, N018R-N043R-R045T-N076D-S101G-S103A-V104I-A232V-Q245R, N018R-T022W-S024R-N076D-S101A-I198L-T213A-A215F-H249R, N018R-T22W-S024R-N076D-S101A-A215F-H249R, G020R-R045T-S101G-S103A-V104I-A232V-Q245R, G020R-S078R-S101G-S103A-V104I-T180A-A232V-Q245R, G020R-T022W-S078R-S101G-S103A-V104I-N116A-N183D-A215F-A232V-Q245R, N018R-S101G-S103A-V104I, G020R-T22W-S101A-S103A-V104I-N116A-G211Q-T213A-A215F-A232V-Q245R, N018R-S024R-N076D-S103A-A232V-Q245R, G020R-S078R-S101A-S103A-V104I-N116A-N183D-A232V-Q245R, N018R-S024R-N076D-G211Q-H249R, G020R-S101A-S103A-V104I-T213A-A215F-A232V-Q245R, N018R-G020R-N043D-S101G-S103A-V104I-A232V-Q245R, G020R-T022W-S101A-S103A-V104I-G211Q-A232V-Q245R, G020R-T022W-S101A-S103A-V104I-N116A-G211Q-A215F-A232V-Q245R, G020R-T022W-S101A-S103A-V104I-N116A-G211Q-A232V-Q245R, N018R-S024R-N076D-A232V-H249R, N018R-S024R-R045T-N076D-S101G-S103A-V104I-A232V-Q245R-N269R, N018R-N076D-Q245R, S024R-V104I-Q245R, S101G-A232V, G020R-T22W-S101A-S103A-V104I-N116A-G211Q-A215F-A232V-Q245R, N018R-G020R-T022W-S024R-N076D-N116A-N183D-I198L-T213A-H249R, G020R-T022W-S078R-S101A-S103A-V104I-A232V-Q245R, G020R-T022W-S078R-S101A-S103A-V104I-I198L-A232V-Q245R, S024R-Q245R-H249R, G020R-S101G-S103A-V104I-N116A-G211Q-A232V-Q245R, N018R-T22W-S024R-N076D-N116A-G211Q-H249R, S024R-S101G-V104I-H249R, N018R-S024R-N076D-N116A-I198L-G211Q-T213A-A215F-H249R, N018R-S024R-V104I, G020R-T022W-S078R-S101A-S103A-V104I-N183D-I198L-T213A-A215F-A232V-Q245R, N018R-G020R-T22W-S024R-N076D-N116A-N183D-I198L-T213A-H249R, G020R-T022W-S101A-S103A-V104I-A232V-Q245R, Q012H-G020R-S078R-S101G-S103A-V104I-I198L-G211Q-T213A-A232V-Q245R, N018R-S024R-N076D-S101A-G211Q-A215F-H249R, N018R-S024R-N076D-T213A-H249R, S024R-V104I-H249R, N018R-T022W-S024R-N076D-G211Q-H249R, N018R-N076D-S103A-V104I-H249R, N043R-N076D-S101G-S103A-V104I-L217E-A232V-Q245R, G020R-S078R-S101G-S103A-V104I-N183D-G211Q-T213A-A232V-Q245R-E271G, N018R-T022W-S024R-N076D-S101A-N116A-I198L-A215F-H249R, N018R-S024R-N043D-N076D-S101G-S103A-V104I-A232V-Q245R, N018R-S024R-N076D-S101A-I198L-A215F-H249R, N018R-T022W-S024R-N076D-N116A-I198L-G211Q-T213A-H249R, N018R-S024R-N076D-S101A-N116A-T213A-A215F-H249R, G020R-N043D-R045T-S078R-S101G-S103A-V104I-A232V-Q245R, R045T-S078R-S101G-S103A-V104I-A232V-Q245R-H249R, N018R-T22W-S024R-N076D-S101A-N116A-A215F-H249R, N043D-S101G-S103A-V104I-A232V-Q245R-N269R, G020R-T022W-S078R-S101A-S103A-V104I-N116A-N183D-T213A-A215F-A232V-Q245R, N018R-S024R-N076D-N116A-G211Q-T213A-A215F-H249R, S024R-S103A-M175L-A232V-H249R, N018R-S024R-N076D-N116A-T213A-H249R, G020R-R045T-N076D-S101G-S103A-V104I-A232V-Q245R, G020R-S078R-S101A-S103A-V104I-N116A-N183D-G211Q-T213A-A215F-A232V-Q245R, S024R-N043R-R045T-N076D-S078R-S101G-S103A-V104I-A232V-Q245R, N018R-S024R-N076D-S101A-N116A-I198L-T213A-A215F-H249R, N043R-R045T-S101G-S103A-V104I-A232V-Q245R, N018R-T022W-S024R-N076D-S101A-I198L-G211Q-Q245R, G020R-S024R-N043D-N076D-S078R-S101G-S103A-V104I-A232V-Q245R-N269R, S024R-A232V, G020R-S078R-S101A-S103A-V104I-N116A-N183D-G211Q-A232V-Q245R, S024R-N076D-S101G-A232V-Q245R, N018R-N076D-S101G-S103A-V104I-H249R, N018R-S024R-N076D-I198M-G211Q-T213A-A215F-H249R, N018R-T22W-S024R-N076D-S101A-I198L-A215F-H249R, N018R-N043R-N076D-S101G-S103A-V104I-A232V-Q245R-N269R, G020R-T022W-S103A-G211Q-T213A-A215F-A232V-Q245R, G020R-S078R-S101A-S103A-V104I-N116A-N183D-G211Q-T213A-A232V-Q245R, R045T-N076D-S101G-S103A-V104I-A232V-Q245R-N269R, N018R-T22W-S024R-N076D-S101A-G211Q-T213A-H249R, N018R-S024R-N076D-N116A-I198L-A215F-H249R-V268G, N018R-T022W-S024R-N076D-S101A-G211Q-H249R, N018R-T022W-S024R-N076D-S101A-N116A-I198L-G211Q-H249R, S101G-S103A-V104I-Q245R, N018R-N076D-S101G-A232V-Q245R, N018R-G020R-R045T-S101G-S103A-V104I-A232V-Q245R, N018R-T022W-S024R-N076D-S101A-N116A-I198L-H249R, N018R-T022W-S024R-N076D-N116A-I198L-T213A-H249R, S078R-S101G-S103A-V104I-A232V-Q245R-H249R, N018R-S078R-S101G-S103A-V104I-L217E-A232V-Q245R, G020R-N043R-N076D-S101G-S103A-V104I-A232V-Q245R-N269R, N018R-N043D-N076D-S101G-S103A-V104I-A232V-Q245R-H249R, R045T-S101G-S103A-V104I-A232V-Q245R-N269R, S024R-S103A-A232V, N018R-S024R-N076D-S101A-G211Q-H249R, N043D-S101G-S103A-V104I-A232V-Q245R-H249R, N018R-N043R-R045T-N076D-S076T-S101G-S103A-V104I-A232V-Q245R-A273T, N018R-G020R-N043D-S078R-S101G-S103A-V104I-A232V-Q245R, G020R-S078R-S101A-S103A-V104I-N183D-A215F-A232V-Q245R, N018R-S024R-N076D-S101G-A232V, A232V-Q245R, N043R-R045T-N076D-S078R-S101G-S103A-V104I-A232V-V234I-Q245R, S024R-N076D-S103A-V104I-Q245R, G020R-S078R-S101A-S103A-V104I-G211Q-T213A-A232V-Q245R, N043D-S078R-S101G-S103A-V104I-A232V-Q245R-N269R-A272V, N018R-G020R-S024R-N076D-N116A-N183D-I198L-G211Q-H249R, N018R-S103A-V104I-A232V, G020R-T022W-S101G-S103A-V104I-N116A-N183D-

T213A-A215F-A232V-Q245R, S024R-N043R-N076D-S101G-S103A-V104I-A232V-Q245R-N269R, N018R-T022W-S024R-N076D-T213A-A215F-H249R, N018R-S024R-N076D-S101A-N116A-I198L-G211Q-T213A-H249R, G020R-T22W-S078R-S101A-S103A-V104I-N116A-N183D-T213A-A232V-Q245R, G020R-T022W-S078R-S101G-S103A-V104I-G211Q-T213A-A232V-Q245R, G020R-T022W-S101A-S103A-V104I-A215F-A232V-Q245R, N018R-G020R-S024R-N076D-N116A-N183D-A215F-H249R, N018R-S024R-N076D-N116A-M117I-N183D-T213A-H249R, N018R-T022W-S024R-N076D-S101A-N116A-I198L-T213A-H249R, N018R-T22W-S024R-N076D-S101A-I198L-T213A-A215F-H249R, N018R-N043D-S078R-S101G-S103A-V104I-A232V-Q245R-H249R, N018R-N076D-S101G-S103A-V104I-A232V-Q245R-H249R, G020R-T022W-S101G-S103A-V104I-N116A-N183D-I198L-A232V-Q245R, N018R-N043R-R045T-N076D-S101G-S103A-V104I-A232V-Q245R-N269R, N018R-S024R-N076D-N116A-I198L-Y209H-T213A-H249R, G020R-T022W-S101A-S103A-V104I-N116A-N183D-G211Q-T213A-A232V-Q245R, S024R-N076D-S101G-M175L-A232V-Q245R, N018R-N043D-R045T-S101G-S103A-V104I-A232V-Q245R, R045T-N076D-S078R-S101G-S103A-V104I-A232V-Q245R, G020R-S078R-S101A-S103A-V104I-N116A-N183D-I198L-A215F-A232V-Q245R, N043R-N076D-S101G-S103A-V104I-A232V-Q245R-H249R, N018R-S024R-N076D-I198L-T213A-A215F-H249R, N018R-T022W-S024R-N076D-I198L-A215F-H249R, N018R-T022W-S024R-N076D-N116A-T213A-A215F-H249R, N018R-T022W-S024R-N076D-S101A-N116A-I198L-T213A-A215F-H249R, N018R-T022W-S024R-N076D-N116A-G211Q-T213A-H249R, N018R-S024R-Q245R, N018R-T022W-S024R-N076D-S101A-N116A-A215F-H249R, S024R-N076D-V104I-Q245R, K027R-N043R-S101G-S103A-V104I-A232V-Q245R-N269R, N018R-S024R-N076D-N116A-I198L-G211Q-T213A-H249R, N018R-S024R-N076D-N116A-I198L-H249R, N018R-S024R-N076D-N183D-I198L-G211Q-T213A-A215F-H249R, G020R-T022W-S101A-S103A-V104I-N116A-G211Q-T213A-A215F-A232V-Q245R, N018R-N043D-R045T-S078R-S101G-S103A-V104I-A232V-Q245R, N043R-R045T-N076D-S078R-S101G-S103A-V104I-A232V-Q245R-N269R, N018R-T22W-S024R-N076D-N116A-T213A-A215F-H249R, N018R-T022W-S024R-N076D-N116A-G211Q-A215F-H249R, G020R-S078R-S101G-S103A-V104I-N116A-N183D-T213A-A232V-Q245R, N018R-N076D-S101G-S103A-V104I-A232V-Q245R, N018R-S101G-V104I, G020R-S078R-S101G-S103A-V104I-N116A-N183D-G211Q-T213A-A215F-A232V-Q245R, G020R-S078R-S101A-S103A-V104I-A232V-Q245R, N018R-S024R-N076D-S101A-I198L-G211Q-H249R, N018R-S024R-N076D-I198L-G211Q-T213A-H249R, N018R-T022W-S024R-N076D-S101A-N116A-I198L-G211Q-T213A-H249R, N018R-N076D-H249R, N018R-G020R-S024R-N076D-S101A-N116A-N183D-I198L-H249R, N018R-S024R-N076D-S101A-N116A-G211Q-T213A-H249R, G020R-T022W-S078R-S101A-S103A-V104I-N116A-N183D-G211Q-T213A-A215F-A232V-Q245R, G020R-T022W-S101G-S103A-V104I-A114T-T213A-A215F-A232V-Q245R, N018R-T22W-S024R-N076D-N116A-G211Q-T213A-H249R, N018R-G020R-T022W-S024R-N076D-S101A-N116A-N183D-H249R, G020R-S101A-S103A-V104I-N116A-N183D-T213A-A232V-Q245R, N018R-T022W-S024R-N076D-S101A-G211Q-T213A-H249R, N018R-T022K-N043D-S101G-S103A-V104I-A232V-Q245R, N018R-S101G-S103A-V104I-A232V-Q245R-N269R, G020R-S078R-S101G-S103A-V104I-N116A-N183D-G211Q-T213A-A215F-A232V, N018R-S024R-N076D-N116A-H249R, G020R-S024R-N076D-S101G-S103A-V104I-A232V-Q245R, N043D-N076D-S101G-S103A-V104I-A232V-Q245R-N269R, N018R-S024R-N076D-S101A-N116A-I198L-G211Q-H249R, N018R-T022W-S024R-N076D-I198L-T213A-A215F-H249R, N018R-N043D-N076D-S078R-S101G-S103A-V104I-A232V-Q245R-N269R, G020R-T22W-S101G-S103A-V104I-N116A-N183D-T213A-A215F-A232V-Q245R, G020R-S101G-S103A-V104I-N183D-G211Q-A232V-Q245R-, N018R-S024R-N076D-S101A-I198L-T213A-H249R, N018R-S024R-N076D-S101A-I198L-H249R, N018R-S024R-R045T-N076D-S101G-S103A-V104I-A232V-Q245R-H249R, N018R-S024R-N076D-S101A-N183D-T213A-H249R, N018R-N043D-N076D-S078R-S101G-S103A-V104I-A232V-Q245R, G020R-S078R-S101G-S103A-V104I-N116A-A131V-N183D-T213A-A232V-Q245R, N018R-R045T-N076D-S101G-S103A-V104I-A232V-Q245R, N018R-S024R-N076D-S101A-N183D-G211Q-H249R, N076D-S101G-S103A-V104I-A232V-Q245R-H249R, S024R-S101G-Q245R, S024R-N076D-S101G-Q245R, N076D-S078R-S101G-S103A-V104I-A232V-Q245R-H249R, N018R-G020R-S024R-N076D-S101A-N183D-G211Q-A215F-H249R, S024R-S101G, N018R-T22W-S024R-N076D-T213A-A215F-H249R, G020R-N043D-S101G-S103A-V104I-A232V-Q245R, G020R-T022W-S101G-S103A-V104I-N183D-I198L-T213A-A215F-A232V-Q245R, N018R-N043D-R045T-S101G-S103A-V104I-A232V-Q245R-N269R, N043D-N076D-S078R-S101G-S103A-V104I-A232V-Q245R, S024R-R045T-N076D-S101G-S103A-V104I-A232V-Q245R-N269R, G020R-T022W-S101A-S103A-V104I-I198L-G211Q-A215F-A232V-Q245R, G020R-T022W-S101G-S103A-V104I-N116A-N183D-A215F-A232V-Q245R, N018R-G020R-N076D-S101G-S103A-V104I-A232V-Q245R-H249R, N018R-T022W-S024R-N076D-S101A-A215F-H249R, N018R-V104I, N018R-S024R-N076D-N116A-I198L-A215F-H249R, N018R-S024R-N076D-L088I-S101A-N116A-I198L-G211Q-A215F-H249R, N018R-T022W-S024R-N076D-S101A-N116A-G211Q-T213A-H249R, N043R-R045T-N076D-S101G-S103A-V104I-A232V-Q245R-N269R, N018R-N076D-S101G-V104I-H249R, N018R-T022W-S024R-N076D-S101A-T213A-A215F-H249R, N018R-T22W-S024R-N076D-S101A-N116A-I198L-A215F-H249R, N018R-G020R-S101G-S103A-V104I-A232V-Q245R-H249R, S101G-S103A-V104I-A232V-Q245R-H249R-N269R, S024R-N076D-Q245R, N018R-G020R-N043R-R045T-N076D-S101G-S103A-V104I-A232V-Q245R, N018R-G020R-S024R-N076D-A215F-H249R, N018R-S024R-N076D-S101A-N116A-N183D-I198L-T213A-H249R, N018R-G020R-S024R-N076D-G211Q-A215F-H249R, N043D-S101G-S103A-V104I-A232V-Q245R, G020R-T22W-S078R-S101A-S103A-V104I-N116A-N183D-A215F-A232V-Q245R, N018R-S024R-N076D-I198L-G211Q-A215F-H249R, N043R-N076D-S078R-S101G-S103A-V104I-A232V-Q245R-N269R, N043R-S078R-S101G-S103A-V104I-A232V-Q245R-N269R, G020R-N043D-S101G-S103A-V104I-A232V-Q245R-H249R, N018R-T022W-S024R-N076D-S101A-T213A-H249R, G020R-T022W-S101A-N116A-I198L-G211Q-T213A-A215F-H249R, N043R-R045T-S078R-S101G-S103A-V104I-N218S-A232V-Q245R, N018R-S103A, G020R-T22W-S101G-S103A-V104I-N116A-N183D-A215F-A232V-Q245R, N018R-S024R-N076D-S101A-H249R,

N018R-T022W-S024R-N076D-G211Q-T213A-H249R, S024R-N043R-R045T-N076D-S101G-S103A-V104I-A232V-Q245R, G020R-T022W-S101A-S103A-V104I-N116A-N183D-A232V-Q245R, G020R-S101A-S103A-V104I-N116A-N183D-G211Q-T213A-A215F-A232V-Q245R, K027R-R045T-N076D-S078R-S101G-S103A-V104I-A232V-Q245R-N269R, G020R-R045T-N076D-S101G-S103A-V104I-A232V-Q245R-H249R, N018R-G020R-S024R-N076D-N116A-N183D-T213A-A215F-H249R, N018R-S024R-N076D-V104I, S101G-S103A-V104I-A232V-H249R, N018R-S024R-N076D-N116A-N183D-G211Q-H249R, N018R-G020R-S024R-N076D-N116A-A215F-H249R, N018R-S024R-N076D-N183D-T213A-A215F-H249R, N018R-T022W-S024R-N076D-I198L-G211Q-H249R, N043D-S078R-S101G-S103A-V104I-A232V-Q245R-N269R-R275S, G020R-T022W-S101A-S103A-V104I-N116A-N183D-G211Q-A232V-Q245R, N018R-T022W-S024R-N076D-S101A-I198L-G211Q-T213A-A215F-H249R, N018R-T022W-S024R-N076D-S101A-N116A-I198L-G211Q-T213A-A215F-H249R, N018R-G020R-S024R-N076D-N183D-H249R, N018R-S024R-N076D-N116A-I198L-T213A-H249R, N018R-T022W-S024R-N076D-S101A-N116A-G211Q-H249R, V004M-N018R-S024R-N076D-N116A-I198L-G211Q-T213A-H249R, V104I-A232V-H249R, G020R-T022W-S101G-S103A-V104I-N116A-N183D-G211Q-A215F-A232V-Q245R, G020R-S101A-S103A-V104I-N116A-N183D-G211Q-A232V-Q245R-T274I, G020R-S101A-S103A-V104I-T213A-A232V-Q245R, G020R-S101G-S103A-V104I-N116A-N183D-G211Q-T213A-A232V-Q245R, G020R-S024R-N043D-S078R-S101G-S103A-V104I-A232V-Q245R, N018R-S024R-N076D-S103A-H249R, N018R-G020R-S024R-N076D-S101A-N116A-N183D-G211Q-A215F-H249R, N018R-G020R-S024R-N076D-N116A-N183D-I198L-H249R, N018R-T022W-S024R-N076D-N116A-I198L-A215F-H249R, N018R-S024R-N076D-S101A-G211Q-T213A-A215F-H249R-A270V, N018R-N043D-R045T-N076D-S078R-S101G-S103A-V104I-A232V-Q245R-N269R, G020R-T022W-S101G-S103A-V104I-N183D-A232V-Q245R, N018R-G020R-T022W-S024R-N076D-S101A-N116A-T213A-H249R, N018R-T022W-S024R-N076D-I198L-G211Q-A215F-H249R, N018R-T022W-S024R-N076D-I198L-T213A-H249R, G020R-T022W-S101G-S103A-V104I-N116A-N183D-A232V-Q245R, N018R-T22W-S024R-N076D-N116A-I198L-T213A-H249R, N043R-R045T-S078R-S101G-S103A-V104I-A232V-Q245R-N269R, N018R-S024R-N076D-S101G-S103A-V104I-A232V, S101G-H249R, S024R-N076D-S101G-S103A-V104I-M175L-H249R, G020R-T022W-S101A-S103A-V104I-N116A-N183D-A232V-Q245R-N269S, N018R-S024R-N076D-S101A-N116A-I198L-H249R, N018R-T022W-S024R-N076D-N116A-H249R, N018R-G020R-S024R-N076D-S101A-N183D-I198L-A215F-H249R, N018R-S024R-N076D-T213A-A215F-H249R-T260K, N018R-S024R-N076D-N116A-G211Q-T213A-H249R, N018R-G020R-T022W-S024R-N076D-N116A-I198L-H249R, S024R-N076D-S101G-S103A-V104I-Q245R, S024R-N076D-S103A-H249R, N018R-S101G-S103A-V104I-A232V-Q245R-H249R, N018R-S024R-N076D-I198L-G211Q-H249R, N018R-T022W-S024R-N076D-S101A-I198L-G211Q-T213A-H249R, G020R-S024R-R045T-S101G-S103A-V104I-A232V-Q245R, N018R-G020R-S024R-N076D-N183D-G211Q-T213A-H249R, N018R-N043D-R045T-S078R-S101G-S103A-V104I-A232V-Q245R-A272D, N018R-S024R-N076D-N116A-I198L-T213A-A215F-H249R, N018R-T22W-S024R-N076D-S101A-I198L-H249R, N018R-T022W-S024R-N076D-N116A-I198L-H249R, S024R-N076D-S101G-S103A-A232V, S024R-S103A-V104I, N018R-S024R-N076D-S101A-N116A-N183D-G211Q-A215F-H249R, S024R-R045T-N076D-S101G-S103A-V104I-A232V-Q245R-H249R, G020R-S101G-S103A-V104I-N116A-N183D-A232V-Q245R, S024R-N043D-N076D-S101G-S103A-V104I-A232V-Q245R-N269R, G020R-T022W-S101A-S103A-V104I-N183D-G211Q-T213A-A215F-A232V-Q245R, G020R-R045T-N076D-S078R-S101G-S103A-V104I-A232V-Q245R-N269R, N018R-S024R-N076D-S101A-N116A-I198L-G211Q-A215F-H249R, G020R-S101A-S103A-V104I-N116A-N183D-A215F-A232V-Q245R, N018R-N043R-S101G-S103A-V104I-A232V-Q245R-H249R, N018R-S024R-N076D-I198L-T213A-H249R, N018R-S024R-N076D-N116A-N183D-T213A-H249R, G020R-N043D-S101G-S103A-V104I-A232V-Q245R-N269R, S024R-N076D-S103A-Q245R, N018R-T022W-S024R-N076D-S101A-N116A-G211Q-T213A-A215F-H249R, S103A-V104I-Q245R, N018R-T022W-S024R-N076D-G211Q-A215F-H249R, N018R-T022W-S024R-N076D-N116A-N183D-I198L-H249R, N018R-T022W-S024R-N076D-I198L-G211Q-T213A-H249R, N018R-S024R-N076D-N116A-N183D-G211Q-T213A-A215F-H249R, N018R-G020R-N043D-R045T-N076D-S101G-S103A-V104I-A232V-Q245R-N269R, N018R-G020R-T022W-S024R-N076D-S101A-G211Q-T213A-A215F-H249R, A016T-N043R-R045T-N076D-S101G-S103A-V104I-A232V-Q245R-N269R, N018R-T022W-S024R-N076D-N116A-A215F-H249R, N043R-N076D-S101G-S103T-V104I-A232V-Q245R-H249R-N269R, G020R-S078R-S101A-S103A-V104I-G115E-N116A-N183D-G211Q-T213A-A232V-Q245R, N018R-S024R-N076D-I198L-H249R, N018R-S024R-N076D-S101A-N116A-N183D-H249R, G020R-S101G-S103A-V104I-N116A-N183D-G211Q-A232V-Q245R, N018R-S024R-N076D-S101G, N076D-S101G-A232V-Q245R, N018R-N076D-S101G-S103A-V104I-Q245R, N018R-R045T-S101G-S103A-V104I-A232V-Q245R-H249R, N018R-S024R-N076D-A215F-H249R, N018R-V104I-A232V, N043D-R045T-N076D-S078R-S101G-S103A-V104I-A232V-Q245R, S024R-N076D-S101G-A232V-H249R, S103A-A232V-Q245R, G020R-S101G-S103A-V104I-N116A-N183D-G211Q-T213A-A215F-A232V-Q245R, N018R-G020R-S024R-N076D-N116A-N183D-I198L-G211Q-A215F-H249R, N018R-T022W-S024R-N076D-S101A-I198L-G211Q-A215F-H249R, S024R-N076D-S103A-V104I-H249R, S024R-S101G-S103A-V104I, G020R-S101G-S103A-V104I-N116A-N183D-G211Q-A215F-A232V-Q245R, N018R-T022W-S024R-N076D-S101A-N116A-N183D-A215F-H249R, G020R-T022W-S101G-S103A-V104I-N116A-N183D-G211Q-T213A-A215F-A232V-Q245R, G020R-S024R-R045T-N076D-S101G-S103A-V104I-A232V-Q245R, N018R-T022W-S024R-N076D-N116A-N183D-T213A-H249R, N018R-G020R-S024R-N076D-A131T-A215F-H249R, N018R-S024R-N076D-S101A-N116A-N183D-G211Q-T213A-A215F-H249R, N018R-S024R-N076D-S101A-N116A-G211Q-T213A-A215F-H249R, N018R-S024R-N076D-I198L-A215F-H249R, N018R-T022W-S024R-N076D-N183D-G211Q-H249R, N018R-T022W-S024R-N076D-S101A-N116A-T213A-A215F-H249R, N018R-G020R-S024R-R045T-N076D-S101G-S103A-V104I-A232V-Q245R, N043R-S101G-S103A-V104I-Q245R-H249R, N018R-N076D-A232V-H249R, N018K-N076D-S078R-S101G-S103A-V104I-L217E-A232V-Q245R-N269R, N018R-G020R-S024R-N043D-N076D-S078R-

S101G-S103A-V104I-A232V-Q245R, N018R-T022W-S024R-N076D-S101A-N116A-T213A-A215F-H249R-L267I, A232V-H249R, N018R-G020R-S024R-N076D-N116A-G211Q-T213A-A215F-H249R, N076D-V104I-Q245R, N018R-G020R-S024R-N076D-N183D-I198L-G211Q-A215F-H249R, N018R-S024R-N076D-S101A-G211Q-T213A-H249R, S024R-S101G-S103A-A232V, N018R-G020R-T022W-S024R-N076D-N116A-N183D-I198L-T213A-A215F-H249R, N018R-G020R-S024R-N076D-N116A-N183D-I198L-G211Q-T213A-H249R, N018R-G020R-T022W-S024R-N076D-S101A-A215F-H249R, G020R-T022W-S101A-S103A-V104I-N116A-N183D-G211Q-A215F-A232V-Q245R, N018R-S024R-N076D-N116A-I198L-G211Q-H249R, S103A-A232V-H249R, N018R-G020R-S024R-N076D-N116A-N183D-I198L-A215F-H249R, N018R-S024R-N076D-N116A-N183D-I198L-T213A-H249R, N018R-T022W-S024R-N076D-N183D-T213A-H249R, N018R-S024R-N076D-S101A-T213A-A215F-H249R, N018R-T022W-S024R-N076D-S101A-N116A-N183D-G211Q-H249R, N018R-R045T-S101G-S103A-V104I-A232V-Q245R-N269R, N018R-G020R-R045T-N076D-S078R-S101G-S103A-V104I-A232V-Q245R, N018R-T022W-S024R-N076D-N116A-I198L-T213A-A215F-H249R, G020R-T022W-S101G-S103A-V104I-N116A-N183D-G211Q-T213A-A232V-Q245R, N018R-G020R-S024R-N076D-I198L-H249R, N018R-G020R-T022W-S024R-N076D-S101A-N116A-G211Q-H249R, G020R-T022W-S101A-S103A-V104I-N116A-N183D-A232V-Q245R-T274I, S024R-S103A-Q245R-H249R, N018R-T022W-S024R-N076D-S101A-N116A-N183D-I198L-H249R, N018R-S024R-N076D-S101A-I198L-G211Q-A215F-H249R, N018R-T022W-S024R-N076D-N116A-I198L-G211Q-A215F-H249R, N018R-G020R-T022W-S024R-N076D-N116A-N183D-T213A-H249R, N018R-N043D-R045T-N076D-S101G-S103A-V104I-A232V-Q245R-N269R, N018R-T022W-S024R-N076D-N116A-G211Q-T213A-A215F-H249R, N018R-S024R-N076D-S101A-N183D-I198L-T213A-H249R, N043D-N076D-S101G-S103A-V104I-A232V-Q245R-H249R, N018R-S024R-N076D-I198L-G211Q-T213A-A215F-H249R, N018R-G020R-S024R-N076D-N116A-N183D-T213A-H249R, S103A-A232V, N018R-T022W-S024R-N076D-N116A-N183D-A215F-H249R, N018R-S024R-N076D-S101A-N116A-H249R, N018R-N043R-S078R-S101G-S103A-V104I-A232V-Q245R, N018R-G020R-T022W-S024R-N076D-S101A-N183D-G211Q-A215F-H249R, N043R-N076D-S078R-S101G-S103A-V104I-A232V-Q245R-H249R, N018R-G020R-S024R-N076D-S101A-N116A-N183D-I198L-T213A-H249R, N018R-S024R-N076D-N183D-I198L-T213A-H249R, N018R-T022W-S024R-N076D-S101A-N183D-G211Q-H249R, N018R-G020R-S024R-N076D-I198L-T213A-A215F-H249R, N018R-G020R-T022W-S024R-N076D-N183D-G211Q-T213A-H249R, N018R-T022W-S024R-N076D-I198L-H249R, N018R-S024R-N076D-N183D-I198L-G211Q-H249R, G020R-T022W-S101A-S103A-V104I-N116A-N183D-T213A-A232V-Q245R, N018R-G020R-S024R-N076D-N116A-N183D-G211Q-T213A-H249R, N018R-S024R-N076D-N116A-N183D-I198L-G211Q-T213A-A215F-H249R, G020R-T022W-S101A-S103A-V104I-N116A-N183D-A215F-A232V-Q245R, N018R-S024R-N076D-S101A-N183D-H249R, N018R-S024R-N076D-A232V, N018R-T022W-S024R-N076D-S101A-N116A-H249R, G020R-S101A-S103A-V104I-N116A-N183D-I198L-G211Q-T213A-A215F-A232V-Q245R, G020R-T022W-S101G-S103A-V104I-N116A-N183D-G211Q-A232V-Q245R-N263S, S024R-N076D-S101G-V104I-A232V-H249R, N043R-S078R-S101G-S103A-V104I-A232V-Q245R, S024R-N076D-S078R-S101G-S103A-V104I-A232V-Q245R-H249R, N018R-S024R-N076D-S101A-N183D-I198L-T213A-A215F-H249R, N018R-G020R-S024R-N076D-I198L-A215F-H249R, N018R-G020R-S024R-N076D-S101A-N116A-T213A-H249R, N018R-S024R-N076D-S101A-V197A-T213A-A215F-H249R, S024R-S101G-S103A, N018R-S024R-N076D-S101A-N116A-G211Q-A215F-H249R, N043R-N076D-S078R-S101G-S103A-V104I-L217E-A232V-Q245R, S024R-V104I-A232V, N018R-S024R-N076D-N183D-G211Q-H249R, G020R-N043R-R045T-S078R-S101G-S103A-V104I-A232V-Q245R, N018R-G020R-T022W-S024R-N076D-S101A-N116A-N183D-T213A-H249R, N018R-S024R-N076D-N116A-A150T-T213A-H249R, N018R-S024R-N076D-N183D-T213A-H249R, N018R-G020R-S024R-N076D-N116A-N183D-G211Q-A215F-H249R, N018R-G020R-S024R-N076D-G211Q-H249R, N018R-S024R-N076D-S101A-N116A-N183D-I198L-H249R, S024R-N076D-A232V-H249R, N018R-G020R-T022W-S024R-N076D-S101A-N116A-N183D-I198L-G211Q-T213A-H249R, N018R-T022W-S024R-N076D-S101A-N116T-I198L-A215F-H249R, N018R-S024R-N076D-N183D-I198L-G211Q-A215F-H249R, N018R-T022R-S024R-N076D-S101A-N116A-N183D-G211Q-H249R, R045T-S101G-S103A-V104I-A232V-Q245R, N018R-G020R-S024R-N076D-S101A-N183D-G211Q-H249R, G020R-S101G-S103A-V104I-N116A-N183D-T213A-A232V-Q245R, N076D-S101G-S103A-Q245R, G020R-N043D-S078R-S101G-S103A-V104I-A232V-Q245R-H249R, N018R-S024R-N076D-N116A-N183D-H249R, N018R-S024R-N076D-S101A-N183D-G211Q-T213A-A215F-H249R, N018R-G020R-T022W-S024R-N076D-S101A-N116A-I198L-H249R, N018R-T22W-S024R-N076D-G211Q-T213A-H249R, N018R-G020R-S024R-N076D-N183D-G211Q-H249R, N018R-G020R-S024R-N076D-S101A-N116A-N183D-T213A-H249R, N043R-S078R-S101G-S103A-V104I-L217E-A232V-Q245R, N018R-T022W-S024R-N076D-S101A-A215F-H249R, N018R-G020R-S024R-N076D-S101A-N183D-I198L-G211Q-T213A-H249R, N076D-S101G-V104I-H249R, N018R-T022W-S024R-N076D-S101A-N116A-N183D-T213A-H249R, N018R-S024R-N076D-N183D-H249R, N018R-S024R-N076D-S101A-N183D-I198L-A215F-H249R, N018R-T022W-S024R-N076D-N183D-I198L-A215F-H249R, N018R-T022W-S024R-N076D-S101A-I198L-G211Q-H249R, G020R-S101A-S103A-V104I-N116A-N183D-A232V-Q245R, N018R-S024R-N076D-N116A-N183D-I198L-G211Q-H249R, N018R-G020R-S024R-S101G-S103A-V104I-A232V-Q245R, N018R-N076D-S078R-S101G-S103A-V104I-L217E-A232V-Q245R, G020R-S101A-S103A-V104I-N116A-N183D-G211Q-A232V-Q245R, N018R-T022W-S024R-N076D-S101A-N183D-I198L-Y209H-H249R, N018R-S024R-N076D-N183D-I198L-T213A-A215F-H249R, N018R-S024R-N076D-S101A-N116A-N183D-G211Q-T213A-H249R, N018R-T022W-S024R-N076D-S101A-N116A-N183D-G211Q-T213A-H249R, N018R-S024R-N076D-N183D-I198L-H249R, N018R-S024R-N076D-N183D-A215F-H249R, N018R-G020R-S024R-N076D-G211Q-T213A-A215F-H249R, N076D-Q245R, N076D-S101G-V104I-Q245R, N018R-T022W-S024R-N076D-S101A-G211Q-A215F-H249R, N018R-T022W-S024R-N076D-S101A-N116A-N183D-G211Q-A215F-H249R, N018R-G020R-T022W-S024R-N076D-S101A-G211Q-T213A-H249R, G020R-S024R-N043R-S101G-S103A-V104I-A232V-Q245R,

N018R-S024R-N076D-N116A-N183D-G211Q-A215F-H249R, G020R-S101A-S103A-V104I-N116A-N183D-T213A-A215F-A232V-Q245R, S101G-S103A-V104I-N018R-G020R-S024R-N076D-S101A-N116A-N183D-G211Q-T213A-H249R, N018R-G020R-S024R-N076D-N204D-T213A-H249R, N018R-T022W-S024R-N076D-N183D-I198L-H249R, N018R-S024R-N076D-S101A-N116A-N183D-A215F-H249R, N018R-T022W-S024R-N076D-N116A-N183D-I198L-G211Q-T213A-A209V-H249R, N018R-T022W-S024R-N076D-S101A-N116A-N183D-G211Q-T213A-A215F-H249R, N018R-S024R-N076D-S101A-N116A-I198L-T213A-H249R, N018R-G020R-S024R-N076D-S101A-N116A-G211Q-T213A-H249R, N018R-G020R-T022W-S024R-N076D-S101A-N116A-N183D-G211Q-T213A-A215F-H249R, N018R-S024R-N076D-S101A-N116A-N183D-T213A-A215F-H249R, N018R-S024R-N076D-S101A-N183D-I198L-G211Q-T213A-A215F-H249R, N018R-S024R-N076D-S101A-N183D-I198L-G211Q-T213A-H249R, N018R-N043R-R045T-S078R-S101G-S103A-V104I-L217E-A232V-Q245R, N018R-S024R-N076D-N183D-G211Q-T213A-A215F-H249R, N018R-T022W-S024R-N076D-N116A-N183D-I198L-A215F-H249R, N018R-G020R-S024R-N076D-N116A-H249R, N018R-G020R-T022W-S024R-N076D-S101A-G211Q-A215F-H249R, N018R-G020R-S024R-N076D-N183D-G211Q-T213A-A215F-H249R, N018R-G020R-T022W-S024R-N076D-I198L-T213A-H249R, N018R-G020R-S024R-N076D-S101A-G211Q-A215F-H249R-N269D, N018R-G020R-N043D-S101G-S103A-V104I-A232V-Q245R-N269R, N018R-T022W-S024R-N076D-S101A-N183D-I198L-T213A-H249R, G020R-T022W-S101G-S103A-V104I-N183D-A215F-A232V-Q245R, N018R-T022W-S024R-N076D-N116A-N183D-I198L-Y209H-G211Q-H249R, N018R-G020R-T022W-S024R-N076D-S101A-N116A-N183D-G211Q-H249R, N076D-A232V-Q245R, N043D-R045T-S078R-S101G-S103A-V104I-A232V-Q245R, N018R-G020R-S024R-N076D-N116A-I198L-G211Q-A215F-Q245R, N018R-G020R-T022W-S024R-N076D-T213A-H249R, G020R-S024R-N043D-S078R-S101G-S103A-V104I-A232V-Q245R-H249R, N018R-G020R-T022W-S024R-N076D-S101A-I198L-A215F-H249R, G020R-A090S-S101G-S103A-V104I-N116A-N183D-T213A-A215F-A232V-Q245R, N018R-G020R-T022W-S024R-N076D-S101A-I198L-G211Q-T213A-A215F-H249R, N018R-G020R-S024R-N076D-S101A-N183D-T213A-A215F-H249R, N018R-S024R-N076D-N116A-N183D-I198L-G211Q-T213A-H249R, N043D-R045T-S078R-S101G-S103A-V104I-A232V-Q245R-N269R, N018R-S024R-N076D-S101A-N183D-A215F-H249R, N018R-G020R-S024R-N076D-S101A-N183D-I198L-T213A-H249R, G020R-T022W-S101A-S103A-V104I-N116A-N183D-I198L-G211Q-T213A-A215F-A232V-Q245R, N018R-G020R-S024R-N043D-N076D-S101G-S103A-V104I-A232V-Q245R-N269R, N018R-S024R-N076D-S101A-N183D-T213A-A215F-H249R, N018R-G020R-T022W-S024R-N076D-S101A-N116A-I198L-G211Q-T213A-A215F-H249R, N018R-G020R-N043D-S101G-S103A-V104I-L217E-A232V-Q245R, N076D-S103A-V104I-A232V-Q245R, R045T-N076D-S078R-S101G-S103A-V104I-A232V-Q245R-H249R, N018R-T022W-S024R-N076D-S101A-N183D-G211Q-A215F-H249R, N018R-T022W-S024R-N076D-S101A-N116A-N183D-H249R, N018R-S024R-N076D-N116A-N183D-I198L-G211Q-A215F-H249R, N018R-G020R-N043D-N076D-S078R-S101G-S103A-V104I-L217E-A232V-Q245R, N076D-S103A-V104I-Q245R, N018R-G020R-S024R-N076D-S101A-N116A-G211Q-T213A-A215F-H249R, N018R-S024R-N076D-S101A-N183D-I198L-H249R, N018R-T022W-S024R-N076D-N116A-N183D-I198L-G211Q-A215F-H249R, N018R-S024R-N076D-N116A-N183D-T213A-A215F-H249R, N018R-T022W-S024R-N076D-N116A-N183D-I198L-G211Q-H249R, N018R-S024R-N076D-S101G-Q245R, N018R-S024R-N076D-S101A-N116A-N183D-I198L-T213A-A215F-H249R, N043R-R045T-N076D-S101G-S103A-V104I-A232V-Q245R, N018R-G020R-T022W-S024R-N076D-N116A-I198L-T213A-A215F-H249R, N076D-V104I-A232V-Q245R, K027R-N043R-R045T-N076D-S101G-S103A-V104I-A232V-Q245R, N018R-T022W-S024R-N076D-S101A-N183D-T213A-A215F-H249R, N018R-S024R-N076D-S103A-V104I-L135I-A232V, N018R-G020R-T022W-S024R-N076D-N183D-I198L-G211Q-H249R, N018R-G020R-T022W-S024R-N076D-S101A-N116A-N183D-I198L-A215F-H249R, N018R-S024R-N076D-S101A-N116A-N183D-G211Q-H249R, N018R-T022W-S024R-N076D-N183D-G211Q-T213A-A215F-H249R, N076D-S101G-S103A-V104I-A232V-H249R, P005S-N018R-T022W-S024R-N076D-S101A-T213A-A215F-H249R, N018R-S024R-N076D-N116A-N183D-A215F-H249R, N018R-S024R-N076D-N183D-I198L-A215F-H249R, N018R-G020R-S024R-N076D-S101A-N116A-N183D-H249R, N018R-T022W-S024R-N076D-N116A-N183D-G211Q-H249R, N018R-G020R-T022W-S024R-N076D-S101A-N116A-H249R, N018R-T022W-S024R-N076D-S101A-N116A-N183D-I198L-T213A-H249R, N018R-T022W-S024R-N076D-S101A-N183D-G211Q-T213A-H249R, N018R-G020R-S024R-N076D-N116A-I198L-H249R, N018R-S024R-N076D-N183D-G211Q-T213A-H249R, N018R-S024R-N076D-S101A-N116A-N183D-T213A-H249R, N018R-S024R-N076D-N116A-N183D-I198L-A215F-H249R, N018R-T022W-S024R-N076D-N183D-I198L-G211Q-A215F-H249R, N018R-T022W-S024R-N076D-N183D-H249R, N018R-T022W-S024R-N076D-S101A-N183D-I198L-A215F-H249R, N018R-G020R-N043D-R045T-N076D-S101G-S103A-V104I-A232V-Q245R, G020R-T022W-S101A-S103A-V104I-N183D-I198L-A215F-A232V-Q245R, N076D-S101G-S103A-V104I-H249R, N018R-G020R-S024R-N076D-N183D-I198L-A215F-H249R, N018R-G020R-T022W-S024R-N076D-S101A-N183D-A215F-H249R, N018R-G020R-S024R-N076D-G211Q-T213A-H249R, N018R-S024R-N076D-N116A-N183D-G211Q-T213A-H249R, N018R-S024R-N076D-N116A-N183D-I198L-H249R, N018R-G020R-S024R-N076D-G211Q-N243D-H249R, N018R-G020R-R045T-N076D-S101G-S103A-V104I-A232V-Q245R-H249R, N018R-T022W-S024R-N076D-N183D-I198L-G211Q-T213A-H249R, N018R-S024R-N076D-S101A-N116A-N183D-I198L-G211Q-T213A-H249R, N018R-T022W-S024R-N076D-N116A-I198L-G211Q-T213A-A215F-H249R, S024R-N076D-S101G, N018R-G020R-S024R-N076D-S101A-I198L-T213A-A215F-H249R, N018R-T022W-S024R-N076D-N116A-N183D-G211Q-T213A-H249R, N018R-G020R-S024R-N076D-N183D-A215F-H249R, N018R-N043D-N076D-S078R-S101G-S103A-V104I-A232V-Q245R-H249R, N018R-T022W-S024R-N076D-N116A-N183D-G211Q-T213A-Q245R, G020R-S024R-N076D-S078R-S101G-S103A-V104I-A232V-Q245R-H249R, N018R-G020R-R045T-S101G-S103A-V104I-A232V-Q245R-H249R, N018R-S024R-N076D-S101A-N183D-I198L-G211Q-H249R, N018R-T022W-S024R-N076D-N183D-G211Q-T213A-H249R, N018R-G020R-S024R-N076D-N116A-I198L-G211Q-A215F-H249R-N269S, N018R-

G020R-T022W-S024R-N076D-S101A-N116A-N183D-I198L-G211Q-A215F-H249R, G020R-T022W-S101A-S103A-V104I-N183D-T213A-A215F-A232V-Q245R, N018R-S024R-N076D-A086V-S101A-N183D-I198L-G211Q-H249R, N018R-N076D-S101G-I198T-A232V, N018R-G020R-S024R-N076D-S101A-N116A-N183D-I198L-G211Q-A215F-H249R, N018R-T022W-S024R-N076D-S101A-N116A-N183D-T213A-A215F-H249R, N018R-T022W-S024R-N076D-S101A-N183D-G211Q-T213A-A215F-H249R, N018R-S024R-N076D-N183D-H249R-A248T, N018R-N076D-V104I-Q245R-H249R, N018R-T022W-S024R-N076D-S101A-N116A-N183D-I198L-A215F-H249R, N018R-T022W-S024R-N076D-N116A-N183D-T213A-A215F-H249R, N018R-G020R-T022W-S024R-N076D-N116A-N183D-G211Q-T213A-A215F-H249R, N018R-G020R-S024R-N076D-S101A-H249R, N018R-G020R-S024R-N076D-S101A-N116A-T213A-A215F-H249R, N018R-T022W-S024R-N076D-N116A-N183D-G211Q-A215F-H249R, N018R-T022W-S024R-N076D-N116A-N183D-I198L-G211Q-T213A-H249R, N043R-R045T-S078R-S101G-S103A-V104I-L217E-A232V-Q245R, N043R-R045T-S101G-S103A-V104I-A232V-Q245R-H249R, N018R-N076D-S101G-V104I, G020R-R045T-N076D-S078R-S101G-S103A-V104I-A232V-Q245R-H249R, N043D-N076D-S101G-S103A-V104I-A232V-Q245R, N018R-G020R-T022W-S024R-N076D-S101A-N116A-N183D-I198L-H249R, N018R-N076D-V104I, N018R-G020R-N043D-S101G-S103A-V104I-A232V-Q245R-H249R, N018R-G020R-T022W-S024R-N076D-N183D-G211Q-H249R, N018R-S024R-N076D-S101A-N183D-I198L-G211Q-A215F-H249R, S101G-V104I, N018R-T022W-S024R-N076D-N116A-N183D-I198L-G211Q-T213A-A215F-H249R, N018R-G020R-S024R-N076D-S101A-N183D-G211Q-T213A-A215F-H249R, N018R-G020R-S024R-N076D-N116A-N183D-A215F-H249R-N263D, N018R-T022W-S024R-N076D-S101A-N183D-H249R, N018R-S024R-N076D-S101A-N116A-N183D-I198L-A215F-H249R, N018R-T022W-S024R-N076D-N116A-I198L-A215F-H249R-R269H, N018R-N043D-R045T-N076D-S078R-S101G-S103A-V104I-A232V-Q245R, N018R-S024R-R045T-N076D-S078R-S101G-S103A-V104I-A232V-Q245R-N269R, S078R-S101G-S103A-V104I-L217E-A232V-Q245R, N018R-G020R-T022W-S024R-N076D-S101A-N183D-I198L-T213A-A215F-H249R, N018R-G020R-S024R-N076D-N183D-I198L-T213A-H249R, N018R-G020R-T022W-S024R-N076D-N116A-I198L-G211Q-A215F-H249R, N018R-G020R-T022W-S024R-N076D-N116A-N183D-G211Q-H249R, N018R-G020R-T022W-S024R-N076D-S101A-I198L-G211Q-T213A-H249R, N018R-G020R-T022W-S024R-N076D-H249R, G020R-T022W-S101G-S103A-V104I-N116A-N183D-I198L-G211Q-T213A-A215F-A232V-Q245R, V104I-A232V, N018R-G020R-T022W-S024R-N076D-S101A-N116A-N183D-G211Q-A215F-H249R, N018R-G020R-T022W-S024R-N076D-S101A-N116A-N183D-I198L-G211Q-T213A-A215F-H249R, N018R-G020R-T022W-S024R-N076D-S101A-N183D-T213A-A215F-H249R, N018R-T022W-S024R-N076D-S101A-N183D-I198L-G211Q-T213A-H249R, N018R-T022W-S024R-N076D-S101A-N183D-I198L-H249R, N043D-R045T-S101G-S103A-V104I-A232V-Q245R-N269R, N018R-G020R-S024R-N076D-S101A-N183D-I198L-G211Q-H249R, N018R-G020R-N043R-S101G-S103A-V104I-L217E-A232V-Q245R, S024R-N043R-N076D-S078R-S101G-S103A-V104I-A232V-Q245R-N269R, N043R-R045T-N076D-S078R-S101G-S103A-V104I-Y166F-A176P-A179V-N184T-A187P-A194P, N018R-T022W-S024R-D041E-N076D-S101A-S160T-N183D-G211Q-T213A-H249R, N018R-G020R-T022W-S024R-N076D-N116A-N183D-I198L-G211Q-A215F-H249R, N018R-G020R-T022W-S024R-N076D-S101A-N116A-I198L-T213A-H249R, N018R-T022W-S024R-N076D-S101A-N116A-N183D-I198L-G211Q-T213A-H249R, N018R-G020R-S024R-N076D-I198L-T213A-H249R, N018R-G020R-T022W-S024R-N076D-N116A-N183D-I198L-G211Q-H249R, N018R-G020R-S024R-N076D-N183D-G211Q-A215F-H249R, S024R-N076D-V104I, N018R-N076D-S101G-A232V, N018R-S024R-N076D-S101A-N116A-N183D-I198L-G211Q-T213A-A215F-H249R, N018R-G020R-T022W-S024R-N076D-N116A-N183D-A215F-H249R, N018R-S024R-L031F-N076D-N116A-N183D-G211Q-T213A-A215F-H249R, N018R-S024R-N076D-S101A-N116A-N183D-I198L-T213A-H249R-N269S, N018R-G020R-S024R-N076D-S101A-N116A-I198L-A215F-H249R, N018R-N043R-N076D-S078R-S101G-S103A-V104I-A232V-Q245R-N269R, N018R-G020R-S024R-N076D-S101A-N114T-I198L-G211Q-A215F-H249R, S024R-N043R-S078R-S101G-S103A-V104I-L217E-A232V-Q245R, S024R-N076D-S103A-V104I-A232V, N018R-G020R-T022W-S024R-N076D-S101A-I198L-G211Q-A215F-H249R, S101G-V104I-A232V, N018R-T022W-S024R-N076D-N183D-I198L-T213A-A215F-H249R, N018R-T022W-S024R-N076D-N183D-I198L-G211Q-H249R, N018R-G020R-S024R-N076D-N183D-T213A-H249R, N018R-S024R-N076D-S101A-N183D-G211Q-A215F-H249R, N018R-G020R-T022W-S024R-N076D-N116A-G211Q-T213A-H249R, N018R-S078R-S101G-S103A-V104I-A232V-Q245R-N269R, N018R-T022W-S024R-N076D-S101A-N116A-N183D-G211Q-A215F-H249R-T260A, N076D-H249R, N018R-T022W-S024R-N076D-N183D-G211Q-A215F-H249R, N018R-G020R-S024R-N076D-N116A-G211Q-A215F-H249R, N018R-G020R-S024R-N076D-T213A-H249R, N018R-G020R-T022W-S024R-N076D-N116A-N183D-I198L-H249R, N018R-G020R-T022W-S024R-N076D-S101A-N183D-H249R, N076D-V104I-H249R, G020R-T022W-S101A-S103A-V104I-N116A-N183D-G211Q-T213A-A215F-A232V-Q245R, S024R-N043R-R045T-S078R-S101G-S103A-V104I-L217E-A232V-Q245R, N018R-G020R-T022W-S024R-N076D-N183D-I198L-A215F-H249R, N018R-N076D-S101G-S103A, G020R-S024R-S101G-S103A-V104I-A232V-Q245R-N269R, N018R-G020R-S024R-N076D-S101A-N116A-N183D-G211Q-H249R, S101G-S103A-A232V, S024R-N076D-S101G-A232V, N018R-T022W-S024R-N076D-S101A-N183D-I198L-G211Q-H249R, N018R-G020R-S024R-N076D-S101A-N183D-I198L-G211Q-A215F-H249R, N018R-G020R-S024R-N076D-N183D-I198L-H249R, N018R-T022W-S024R-N076D-S101A-N116A-N183D-I198L-G211Q-H249R, N018R-G020R-S024R-N076D-N116A-A156V-N183D-G211Q-A215F-H249R-N269S, R045T-N076D-S101G-S103A-V104I-A232V-Q245R-H249R, N018R-G020R-S024R-N076D-S101A-N183D-I198L-H249R, N018R-G020R-T022W-S024R-N076D-I198L-G211Q-A215F-H249R, N018R-G020R-T022W-S024R-N076D-S101A-N116A-I198L-G211Q-A215F-H249R, N018R-G020R-T022W-S024R-N076D-N116A-H249R, N018R-N076D-S101G, N018R-S024R-N076D-N116A-N183D-I198L-T213A-A215F-H249R, N018R-G020R-T022W-S024R-N076D-S101A-N116A-I198L-T213A-A215F-H249R, N018R-S024R-N076D-S101A-N116A-N183D-I198L-G211Q-H249R, N018R-N076D-A232V, N018R-G020R-S024R-N076D-S101A-A232V-

Q245R, N018R-N043D-R045T-N076D-S101G-S103A-V104I-A232V-Q245R, N018R-T022W-S024R-N076D-N183D-T213A-A215F-H249R, N018R-S024R-N076D-S101A-N116A-G211Q-T213A-N237D-H249R, N018R-G020R-S024R-N076D-S101A-N116A-N183D-G211Q-H249R-R275S, N018R-T022W-S024R-N076D-S101A-N116A-N183D-I198L-G211Q-T213A-A215F-H249R, S024R-N076D, N018R-S024R-N076D-N183D-G211Q-A215F-H249R, N018R-T022W-S024R-N076D-N116A-N183D-I198L-T213A-A215F-H249R, N076D-V104I-A232V-H249R, N018R-N076D-S103A-A232V, N018R-G020R-S024R-N076D-S101A-N116A-N183D-I198L-G211Q-T213A-H249R, N018R-G020R-S024R-N076D-S101A-N183D-T213A-H249R, N018R-G020R-S024R-N076D-S101A-D175E-N183D-G211Q-A215F-H249R, N018R-G020R-N043D-S078R-S101G-S103A-V104I-L217E-A232V-Q245R-A273E, G020R-S024R-N043D-R045T-N076D-S101G-S103A-V104I-A232V-Q245R, P005S-S101G-S103A-V104I-A232V-Q245R-H249R, S103A-V104I-A232V, N018R-G020R-S024R-V068A-N076D-S101A-N116A-T213A-A215F-H249R, N018R-T022W-S024R-N076D-S101A-I198L-A215F-H249R-R275S, N018R-S024R-N076D-N183D-I198L-G211Q-T213A-H249R, and N043R-R045T-S101G-S103A-V104I-A232V-Q245R, wherein the amino acid positions of the subtilisin variant are numbered by correspondence with the amino acid sequence of *B. amyloliquefaciens* subtilisin BPN' set forth as SEQ ID NO: 1.

The present invention provides nucleic acids encoding a *Bacillus* subtilisin variant having proteolytic activity comprising an amino acid sequence comprising a combination of amino acid substitutions selected from: N018R-S024R-N043R-N076D-H249R-N269R, N018R-T022R-S024R-N043R-N076D-H249R, N018R-N043D-S101G-S103A-V104I-A232V-Q245R, G020R-N043D-S101G-S103A-V104I-A232V-Q245R, N043D-S101G-S103A-V104I-A232V-Q245R-N269R, N043D-S078R-S101G-S103A-V104I-A232V-Q245R, N043R-N076D-S101G-S103A-V104I-A232V-Q245R, T022R-N043R-S101G-S103A-V104I-A232V-Q245R, N043R-S078R-S101G-S103A-V104I-A232V-Q245R, G020R-N076D-S101G-S103A-V104I-A232V-Q245R, N043R-N076D-S101G-S103A-V104I-A232V-Q245R, T022R-N076D-S101G-S103A-V104I-A232V-Q245R, N076D-S078R-S101G-S103A-V104I-A232V-Q245R, N018R-S024R-N043R-N076D-H249R, N018R-S024R-N076D-S242R-H249R, N018R-S024R-N076D-H249R-N269R, N018R-T022R-S024R-N076D-H249R, N018R-S024R-N076D-S078R-H249R, N018R-S024R-N043D-N076D-H249R-N269R, N018R-T022R-S024R-N043D-N076D-H249R, N018R-S024R-N043D-N076D-S078R-H249R, G020R-S101G-S103G-V104I-A232V-Q245R, G020R-S101G-S103A-V104L-A232V-Q245R, G020R-S101G-S103A-V104V-A232V-Q245R, G020R-S101G-S103S-V104I-A232V-Q245R, G020R-S101G-S103S-V104L-A232V-Q245R, G020R-S101S-S103S-V104I-A232V-Q245R, G020R-S101S-S103S-V104L-A232V-Q245R, G020R-S101A-S103A-V104L-A232V-Q245R, G020R-S101S-S103S-V104V-A232V-Q245R, G020R-S101S-S103A-V104I-A232V-Q245R, G020R-S101S-S103A-V104V-A232V-Q245R, G020R-S101S-S103G-V104I-A232V-Q245R, G020R-S101S-S103G-V104V-A232V-Q245R, G020R-S101A-S103A-V104V-A232V-Q245R, G020R-S101A-S103S-V104I-A232V-Q245R, G020R-S101A-S103S-V104V-A232V-Q245R, N018R-S024R-N043R-N076D-S078R-H249R, S024R-N043D-S101G-S103A-V104I-A232V-Q245R, N043D-S101G-S103A-V104I-A232V-Q245R-H249R, S024R-N076D-S101G-S103A-V104I-A232V-Q245R, N076D-S101G-S103A-V104I-A232V-S242R-Q245R, N018R-G020R-S024R-N076D-L217E-H249R, N018R-S024R-N043R-N076D-L217E-H249R, N018R-S024R-N043D-N076D-S242R-H249R, N018R-G020R-S024R-N043R-N076D-H249R, G020R-S101A-S103G-V104V-A232V-Q245R, N043D-S101G-S103A-V104I-A232V-Q245R, N018R-S024R-N076D-L217E-H249R-N269R, and N018R-S024R-N076D-L217E-S242R-H249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: G020R-S101A-S103A-V104I-G118R-A232V-Q245R, G020R-S024R-N116A-T213A, N043R-S101A-N116A-A215F-N269R, S024R-N043R-S101A-N116A, S024R-N043R-S101A-N116A-A215F-N269R, G020R-S101G-S103A-V104I-A215F-A232V-Q245R, N043R-S101A-N269R, S024R-N043R-N116A-T213A-N269R, G020R-S024R-N043R-R045T-S101A-T213A, S024R-N043R-N116A-A215F-N269R, G020R-S024R-T213A-A215F, G020R-N116A-N269R, S024R-N116A-T213A-N269R, N043R-S101A-N116A-N269R, S101G-S103A-V104I-N116A-T213A-A232V-Q245R-N269R, S024R-N043R-R045T-S101A-N116A-A215F-N269R, G020R-N043R-S101A-N269R, S101A-S103A-V104I-T213A-A232V-Q245R-N269R, S024R-A215F-N269R, N043R-S101A-N116A-T213A-A215F-N269R, N043R-S101A-T213A-N269R, G020R-S024R-N043R-R045T-N116A-T213A, S101G-S103A-V104I-A232V-Q245R-N269R, S024R-N043R-R045T-S101A-N116A-T213A-N269R, S024R-N043R-R045T-N269R, G020R-N043R-R045T-S101A-N269R, S024R-N043R-N116A-N269R, G020R-S024R-N043R-R045T, N043R-N116A-N269R, S024R-N043R-S101A-A215F-N269R, S024R-N043R-R045T-T213A-A215F-N269R, G020R-S024R-R045T-N269R, G020R-N043R-S101A-N116A-T213A-A215F, G020R-S101G-S103A-V104I-T213A-A215F-A232V-Q245R, G020R-S024R-R045T-N116A-N269R, G020R-S101A-N116A-N269R, S024R-N043R-A215F, G020R-S024R-T213A, S024R-N043R-S101A-A215F, G020R-S024R-N043R-R045T-N116A, G020R-S024R-N043R-R045T-S101A-N269R, G020R-S024R-S101A-A215F, G020R-S024R-N116A-T213A-A215F, G020R-S024R-N116A, G020R-S024R-S101A-N116A, N043R-T213A-A215F-N269R, S024R-S101A-N269R, S024R-N043R-N116A-A215F, G020R-T038A-N043R-S101A, G020R-S024R-N116A-A215F, S024R-N043R-S101A-T213A, P014L-G020R-S024R-N043R-R045T-S101A-A215F, G020R-S024R-A215F, G020R-N116A-A215F-N269R, G020R-R045T-N116A-N269R, G020R-S024R-N043R-R045T-A215F, and G020R-S024R-N043R-R045T-N116A-T213A-A215F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: N043R-N076D-S101A-S103A-V104I-A158E-S188D-A232V-Q245R-N248D-H249R-E271F, S024R-N043R-N076D-S101A-S103A-V104I-A158E-S188D-L217E-A232V-Q245R-N248D-H249R, S101A-S103A-V104I-A158E-S188D-

A232V-Q245R-N248D-H249R-E271F-E271F, S101A-S103A-V104I-A158E-S188D-L217E-A232V-Q245R-N248D-H249R-E271F, N076D-S101G-S103A-V104I-A114V-A158E-S188D-A232V-Q245R-N248D-H249R-E271F, S024R-N076D-S101G-S103A-V104I-A158E-S188D-A232V-Q245R-N248D-H249R-E271F, S024R-N043R-S101A-S103A-V104I-A158E-S188D-L217E-A232V-Q245R-N248D-H249R, S024R-N043R-S101A-S103A-V104I-A158E-S188D-A232V-Q245R-N248D-H249R, S024R-S101A-S103A-V104I-A158E-S166D-S188D-L217E-A232V-Q245R-N248D-H249R, N076D-S101G-S103A-V104I-S128L-A158E-S188D-A232V-Q245R-N248D-H249R-E271F, and N043R-N076D-S101G-S103A-V104I-A158E-S166D-S188D-A232V-Q245R-N248D-H249R-E271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: T022A-S101G-S103A-V104I-G159D-L217E-A232V-Q245R-N248D-E271F, T022A-N043R-S101G-S103A-V104I-G159D-S188D-L217E-A232V-Q245R-N248D-E271F, T022A-S101G-S103A-V104I-G159D-S188D-A232V-Q245R-N248D-E271F, N043R-S101A-S103A-V104I-A158E-S188D-L217E-A232V-Q245R-N248D-H249R, N043R-N076D-S101A-S103A-V104I-A158E-S188D-L217E-A232V-Q245R-N248D-H249R-E271F, S024R-S101G-S103A-V104I-A158E-S188D-L217E-A232V-Q245R-N248D-H249R, S024R-S101G-S103A-V104I-A158E-S188D-A232V-Q245R-N248D-H249R, S101G-S103A-V104I-A158E-S188D-A232V-Q245R-N248D-H249R, S024R-S101G-S103A-V104I-A158E-N183D-S188D-A232V-Q245R-N248D-H249R, T022A-N076D-S101G-S103A-V104I-G159D-S188D-A232V-Q245R-N248D-E271F, T022A-N043R-N076D-S101G-S103A-V104I-G159D-S188D-A232V-Q245R-N248D-E271F, T022A-N076D-S101G-S103A-V104I-G159D-A232V-Q245R-N248D-E271F, T022A-S101G-S103A-V104I-G159D-A232V-Q245R-N248D-E271F, N076D-S101A-S103A-V104I-A158E-S188D-A232V-Q245R-N248D-H249R-E271F, N043R-S101A-S103A-V104I-A158E-S166D-S188D-A232V-Q245R-N248D-H249R, S024R-N076D-S101A-S103A-V104I-A158E-S166D-S188D-A232V-Q245R-N248D-H249R-E271F, N076D-S101A-S103A-V104I-A158E-S188D-A232V-Q245R-N248D-H249R, S101A-S103A-V104I-A158E-S166D-S188D-A232V-Q245R-N248D-H249R-E271F, N043R-N076D-S101A-S103A-V104I-A158E-S166D-S188D-A232V-Q245R-N248D-H249R-E271F, S101G-S103A-V104I-A158E-S166D-S188D-A232V-Q245R-N248D-H249R-E271F, S101A-S103A-V104I-A158E-S188D-A232V-Q245R-N248D-H249R-E271F, S101A-S103A-V104I-A158E-S188D-L217E-A232V-Q245R-N248D-H249R, N076D-S101A-S103A-V104I-A158E-S166D-S188D-A232V-Q245R-N248D-H249R-E271F, S101G-S103A-V104I-A158E-N183D-S188D-A232V-Q245R-N248D-H249R, S024R-S101G-S103A-V104I-S128L-A158E-S188D-A232V-Q245R-N248D-H249R, N076D-S101G-S103A-V104I-A158E-S166D-S188D-A232V-Q245R-N248D-H249R-E271F, N043R-N076D-S101A-S103A-V104I-A158E-S166D-S188D-A232V-Q245R-N248D-H249R, and N076D-S101A-S103A-V104I-A158E-S188D-L217E-A232V-Q245R-N248D-H249R-E271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: H017R-T022A-N076D-S101G-S103A-V104I-G159D-S188D-A232V-Q245R-N248D-E271F, T022A-N043R-S101G-S103A-V104I-G159D-A232V-Q245R-N248D-E271F, T022A-S101G-S103A-V104I-G159D-S188D-A232V-Q245R-N248D-H249R-E271F, H017R-T022A-N076D-S101G-S103A-V104I-G159D-A232V-Q245R-N248D-E271F, T022A-N076D-S101G-S103A-V104I-G159D-A232V-Q245R-N248D-H249R-E271F, T022A-S101G-G102A-S103A-V104I-G159D-S188D-A232V-Q245R-N248D-E271F, and T022A-N043R-N076D-S101G-S103A-V104I-G159D-A232V-Q245R-N248D-H249R-E271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: S101 S-S103A-V104I-A158E-S188D-A232V-Q245R-N248D-H249R, S101S-S103G-V104V-A158E-S188D-A232V-Q245R-N248D-H249R, S101G-S103 S-V104I-A158E-S188D-A232V-Q245R-N248D-H249R, S101A-S103A-V104I-A158E-S188D-A232V-Q245R-N248D-H249R, S101A-S103A-V104L-A158E-S188D-A232V-Q245R-N248D-H249R, S101G-S103G-V104I-A158E-S188D-A232V-Q245R-N248D-H249R, S101 S-S103G-V104I-A158E-S188D-A232V-Q245R-N248D-H249R, S101S-S103S-V104I-A158E-S188D-A232V-Q245R-N248D-H249R, S101S-S103S-V104V-A158E-S188D-A232V-Q245R-N248D-H249R, S101A-S103S-V104I-A158E-S188D-A232V-Q245R-N248D-H249R, S101A-S103S-V104I-G159E-A232V-Q245R-N248D-H249R, S101S-S103A-V104I-G159E-A232V-Q245R-N248D-H249R, S101G-S103A-V104L-A158E-S188D-A232V-Q245R-N248D-H249R, S101A-S103A-V104L-G159E-A232V-Q245R-N248D-H249R, S101A-S103S-V104L-G159E-A232V-Q245R-N248D-H249R, S101G-S103 S-V104L-G159E-A232V-Q245R-N248D-H249R, S101S-S103A-V104L-G159E-A232V-Q245R-N248D-H249R, S101A-S103G-V104V-G159E-A232V-Q245R-N248D-H249R, and S101S-S103A-V104V-G159E-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: V026F-V051W-V104L-S106E, V026F-L031F-S078N-G102A-S160D, G020K-G100S-N116L-A158E-S166D-N243F, T033S-N043W-N218D-P239G-N243F, T022L-T038F-A048R-N062E-G100S-R186K, S101D-S103N-N116L-S144R-A215D, V104L-S105T-T213A-L217E-S256N, N043W-S101D-S212M-N243F, V026F-A048R-S105T-T213A-N218D-T224A, S024F-S101D-G118R-A215D-L250I-A272F, V121F-N185E-T224A-P239G, T022L-L031F-G102A-S128D-T224A-N243F, N062E-S078N-G102A-N116L-S144R-L250I, T022L-T038F-V121F-S160D-A272F, V026F-S078N-G159C-R186K-N243F, S024F-A048R-G118R-S166D-L217E, G023A-T038F-S078N-

G100S-S212M-A215D, G100S-N116L-A158E-T213A, S078N-V104L-G118R-S128D, G102A-S103N-S105T-A194E, T022L-S078N-S128D-T213A, K027R-G100S-G118R-S160D-S188D-N243F, S024F-G102A-R186K-T213A-L217E-N243F, T033S-S105T-S188D-S216F, G023A-G100S-A194E-S212M, A048R-S128D-N185E-P239G, G020K-S024F-T033S-P129E-A194E, G020K-K027R-P129E-S166D-P239G, T022L-G023A-K027R-S101D-V104L-S216F, T033S-G118R-P129E-A194E-P239G, T022L-S078N-N116L-P129E-S256N, K027R-S101D-S103N-S105T-A272F, A048R-S078N-N116L-N185E-L217E-P239G, G023A-S024F-K027R-N062E, S024F-S103N-V104L-G118R-S188D, V026F-V104L-S256N-A272F, S024F-N043W-V104L-V121F-P129E, N062E-S078N-N116L-T224A, G023A-S024F-V051W-A158E, K027R-T038F-G102A-N116L, N062E-S078N-S144R-S212M, L031F-N116L-S256N-A272F, T022L-T033S-V104L-N116L-S160D-R186K, S024F-G118R-P129E-R186K-T213A, N043W-S105T-T213A-A215D-S216F, L031F-S105T-R186K-S188D, V026F-A194E-T213A-S256N, and S103N-S160D-L250I-S256N, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: T022A-S024R-S101D-S103A-V104I-G118R-G159D-S188D-A232V-N248D-E271F, T022A-S024R-S103A-V104I-P129E-G159D-S188D-A232V-N248D-E271F, T022A-S024R-S103A-V104I-G118R-G159D-S188D-L217D-A232V-N248D, T022A-S024R-S101D-S103A-V104I-G118R-P129E-G159D-S188D-A232V-Q245R-N248D, T022A-S024R-S101D-S103A-V104I-G159D-S188D-A232V-Q245R-N248D, T022A-N043R-S103A-V104I-G118R-P129E-G159D-S188D-A232V-Q245R-N248D, T022A-N043R-S103A-V104I-G118R-S128I-P129E-G159D-S188D-A232V-N248D, T022A-N043R-S101D-S103A-V104I-G118R-P129E-G159D-S188D-A232V-N248D-E271F, T022A-S024R-N043R-S101D-S103A-V104I-G159D-S188D-A232V-Q245R-N248D, T022A-S103A-V104I-G159D-S188D-A232V-N248D, T022A-S024R-S103A-V104I-G118R-P129E-G159D-S188D-A232V-N248D-E271F, T022A-S024R-S103A-V104I-G159D-S188D-L217D-A232V-Q245R-N248D-E271F, T022A-N043R-N062E-S103A-V104I-G159D-S188D-A232V-Q245R-N248D-E271F, T022A-N043R-S103A-V104I-P129E-G159D-S188D-A232V-Q245R-N248D, T022A-S024R-S103A-V104I-G159D-S188D-L217D-A232V-N248D-E271F, T022A-S103A-V104I-G118R-G159D-S188D-L217D-A232V-Q245R-N248D, T022A-S024R-S101D-S103A-V104I-G118R-S128I-G159D-S188D-A232V-Q245R-N248D, T022A-S024R-N043R-S103A-V104I-G159D-S188D-L217D-A232V-N248D-E271F, T022A-N043R-S103A-V104I-G118R-G159D-S188D-L217D-A232V-N248D-E271F, T022A-N043R-S103A-V104I-G118R-G159D-S188D-A232V-N248D-E271F, T022A-S103A-V104I-S128I-P129E-G159D-S188D-A232V-N248D-E271F, T022A-S103A-V104I-G159D-S188D-L217D-A232V-Q245R-N248D-E271F, T022A-N043R-S103A-V104I-S128I-G159D-S188D-A232V-Q245R-N248D, T022A-S101D-S103A-V104I-G118R-G159D-S188D-L217D-A232V-Q245R-N248D-E271F, T022A-S103A-V104I-G118R-P129E-G159D-S188D-A232V-Q245R-N248D-E271F, T022A-S024R-N043R-S103A-V104I-G118R-G159D-S188D-L217D-A232V-N248D, T022A-N062E-S103A-V104I-G118R-G159D-S188D-A232V-Q245R-N248D, T022A-N043R-S101D-S103A-V104I-G118R-P129E-G159D-S188D-L217D-A232V, T022A-S024R-S103A-V104I-G159D-S188D-L217D-A232V-N248D, T022A-S024R-N043R-S103A-V104I-G118R-S128I-P129E-G159D-S188D-L217D-A232V-N248D, T022A-S103A-V104I-G118R-G159D-S188D-L217D-A232V-N248D-E271F, and T022A-S103A-V104I-G118R-G159D-S188D-L217D-A232V-Q245R-N248D-E271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: G020K-S024F-N062E-S188D-P239G, S024F-N062E-N116L-P239G, G020K-G023A-N062E-S188D, G020K-G023A-S024F-N062E-G118R-S188D-T213A, G020K-N043W-N062E-N116L-S188D-T213A-P239G, G023A-N062E-N116L-G118R, G023A-S024F-N062E-N116L-G118R, S024F-N116L, S024F-N062E-S188D-T213A, G023A-N062E-N116L-G118R-S188D-P239G, G020K-S024F-N062E, G020K-N043W-N062E-N116L-P239G, S024F-N062E-N116L-T213A-P239G, G020K-S024F-N043W-N062E-N116L-T213A, G020K-G023A-S024F-N062E-N116L-S188D-T213A, S024F-N062E-S188D-P239G, G023A-N043W-N062E-N116L-G118R-T213A, N062E-S188D-P239G, G020K-S024F-N062E-P239G, S024F-N116L-G118R-S188D-P239G, G020K-G023A-N062E-N116L-G118R-T213A, G020K-G023A-S024F-N062E-S188D-T213A-P239G, S024F-N043W-G118R-S188D, G023A-S024F-N116L-G118R-S188D-T213A, G020K-G023A-N043W-N116L-S188D-T213A-P239G, G023A-S024F-N116L-S188D-P239G, G023A-N043W-N116L-G118R-S188D, G023A-S024F-G118R-S188D-P239G, G023A-S024F-N043W-N062E-N116L-G118R, G020K-N043W-S188D-T213A, S024F-N062E-G118R-P239G, G023A-N043W-S188D-T213A, G020K-S024F-N043W-N062E-N116L-G118R-S188D-P239G, G020K-N116L-S188D-P239G, G020K-N043W-N062E-G118R, G020K-N043W-N116L-S188D-T213A, G020K-S024F, G023A-N043W-N116L-P239G, G023A-S024F-N043W-N116L-G118R-S188D-P239G, G020K-G023A-N043W-T213A, and G023A-S024F-N062E-G118R-T213A-P239G, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: G020K-G023A-N043W-G118R-S128I-P129E-G159D-S188D, S024F-G118R-S128I-P129E-G159D, G020K-S024F-N062E-N116L-G118R-S188D, G020K-N062E-N116L-S188D, N062E-N116L-G118R-T213A, G020K-G023A-N062E-N116L-S188D, N062E-N116L-G118R-S188D, G020K-N062E-N116L-T213A, G020K-G023A-N062E-N116L, G020K-N062E-S188D-T213A, G020K-N062E, G020K-S024F-N062E-N116L-S188D, G020K-N043W-N062E-N116L-S188D, G020K-S024F-N062E-S188D-T213A, N062E-N116L-S188D-T213A, G020K-N062E-N116L, G020K-G023A-N062E-N116L-S188D-T213A, G023A-S024F-N062E-N116L-T213A, T022A-N043R-S103A-V104I-S128I-P129E-G159D-S188D-A232V-Q245R-N248D, T022A-N043R-S103A-V104I-G118R-S128I-P129E-G159D-S188D-A232V-N248D-E271F, S024F-

N062E-N116L-S188D, T022A-S024R-S103A-V104I-G118R-S128I-P129E-G159D-S188D-A232V-N248D, G023A-N062E-N116L-S188D, N043W-N062E-N116L, G020K-G023A-N116L-S188D, N043W-N062E-N116L-S188D, S024F-N062E-N116L, N062E-N116L-S188D, and T022A-S024R-S103A-V104I-S128I-G159D-S188D-A232V-N248D, wherein the amino acid positions of the subtilisin variant are numbered by correspondence with the amino acid sequence of B. amyloliquefaciens subtilisin BPN' set forth as SEQ ID NO:1.

The present invention provides nucleic acids encoding a Bacillus subtilisin variant having proteolytic activity comprising an amino acid sequence comprising a combination of amino acid substitutions selected from: S087R-S101G-S103A-V104I-Q109R-S212P-A232V-Q245R-E271V, S101G-S103A-V104I-Q109R-A232V-Q245R, S101G-S103A-V104I-Q109R-S212P-A232V-Q245R-E271V, S101G-S103A-V104I-Q109R-S212P-A232V-Q245R, N076D-S87R-S103A-V104I-S212P-E271V, N076D-S103A-V104I-Q109R, N076D-S103A-V104I-S212P-E271V, N076D-S103A-V104I-Q109R-Q245R, and N076D-S103A-V104I-S212P-Q245L-E271V, wherein the amino acid positions of the subtilisin variant are numbered by correspondence with the amino acid sequence of B. amyloliquefaciens subtilisin BPN' set forth as SEQ ID NO:1.

The present invention provides nucleic acids encoding a Bacillus subtilisin variant having proteolytic activity comprising an amino acid sequence comprising a combination of amino acid substitutions selected from: S024R-P086W-G118R, S024R-S078R-P086W-N243F, S024R-T033S-P086S-S087N-Y209A, T033S-G118R, S024R-S078R-P086W-G118R-A270T, S024R-T033S-P086W-G118R, S078R-P086W-N243F, T033S-S078R-P086W-G118R-Y209A, T033S-S078R-Y209A, P086W-G118R-N243F, S024R-P086W, S078R-P086W-K235F, S024R-G118R, S024R-P086R, S101G-S103A-V104I-A232V, S024R-T033S-S078R-P086W-G118R, S024R-G118R-Y209A, Y209A-W241R, T033S-P086W-N243F, T033S-A172V-Y209A, G118R-Y209A-N243F, S024R-P086S-S141G, S024R-G118R-Y209A-N243F, S024R-T033S-P086S-S085N-K235F, S024R-T033S-A133V, S024R-T033S-S078R-P086W, S024R-P086W-Y209A, S024R-W241R, T033S-G118R-N243F, S024R-K235F, S024R-S078R-P086W, S024R-G118R-Y209A-K235F, S024R-Y209A-W241R, T033S-G118R-W241R, P086W-G118R-Y209A, T033S-G118R-G159D-Y209A, T033S-S078R-P086W, S024R-P086W-N243F, G118R-Y209A, S024R-P086W-G118R-V203I, S078R-Y209A-K235F, S024R-T033S-W241R, S078R-G118R, T033S-G118R-Y209A-N243F, L021M-S024R-T033S, S024R-T033S-P086W, T033S-K235F, S078R-P086W-Y209A, S024R-T033S-Y209A-K235F, T033S-P086W-G118R, S024R-T033S-S078R-Y209A, T033S-P086W-G118R-Y209A-N243F, P086W-Y209A-N243F, P005S-S078R-G118R-W241R, S024R-A174T, T033S-Y209A-N243F, P086W-G118R-A133V, S024R-T033S-G118R, S024R-P086W-Y209A-K235F, P086W-Y209A, I008T-S024R, P086W-G118R, T033S-W241R, P005S-S024R-T033S-N243F, S024R-Y209A-S242P, S024R-T033S-S078R-G118R, S024R-T033S-A194T, S024R-N243F, S024R-Y209A, S024R-T033S-G118R-Y209A, T033S-P086W, S024R-T033S, S024R-T033S-S078R-N243F, P086W-N243F, T033S-G118D-A138V-Y209A, T033S-Y209A-K235F, S024R-P086R-G118R, T033S-P201S, S024R-P239Q, T033S-G118R-Y209A-, S078R-P086W, K235F-N243F, S024R-Y209A-K235F, G118R-A172V, H017Y-S024R-T033S-P086W, T033S-L148F, S024R-G118R-K235F, T033S-S078R, T033S-N243F, S024C-T033S, G118R-A194T, T033S-Y209A, G118R-Y209A-K235F, S024R-T033S-Y209A-N243F, S024R-T033S-K235F, S024R-T033S-G118R-K235F, S024R-S141G, S024R-T274I, S024R-T033S-Y209A, P086W-K235F, S024R-Y209A-N243F, V004E-T033S-S078R, P086W-Y209A-K235F, A015T-T033S, T033S-P086W-S156L-Y209A, S024R-G118R-N243F-R269H, Y209A-K235F, S024R-R247H, S024R-T033S-A228T, S078R-K235F, S024R-T033S-A174V-K235F, S024R-K235F-N243F, S024R-T033S-K235F-W241R, S024R-T033S-A151V, S024R-V104A, T033S-A048T, Q012H-V104A-G118R, G118R-K235F, T033S-T253A, T143A-Y209A, S024R-T033S-N243F, T033S-P239T, Y209A-N243F, S024R-T033S-P129H-N184D-T253M, S024R-A085V-P086W-G118R-K235F, S024R-A272P, and S024R-R269C, wherein the amino acid positions of the subtilisin variant are numbered by correspondence with the amino acid sequence of B. amyloliquefaciens subtilisin BPN' set forth as SEQ ID NO:1.

The present invention provides nucleic acids encoding a Bacillus subtilisin variant having proteolytic activity comprising an amino acid sequence comprising a combination of amino acid substitutions selected from: G020R-S087D-S101G-S103A-V104I-A232V-Q245R, G020R-S101G-S103A-V104I-V150L-A232V-Q245R, N018R-G020R-S024R-N076D-S087D-H249R, N018R-G020R-S024R-N076D-V150L-H249R, N018R-S024R-N043R-N076D-S087D-H249R, N018R-S024R-N043R-N076D-V150L-H249R, N018R-S024R-N076D-S078R-S087D-H249R, N018R-S024R-N076D-S078R-V150L-H249R, N018R-S024R-N076D-S087D-H249R-N269R, N018R-S024R-N076D-S087D-S242R-H249R, N018R-S024R-N076D-S087D-V150L-H249R, N018R-S024R-N076D-V150L-H249R, N018R-S087D-S101G-S103A-V104I-A232V-Q245R, N018R-S101G-S103A-V104I-V150L-A232V-Q245R, N018R-T022R-S024R-N076D-S087D-H249R, N018R-T022R-S024R-N076D-V150L-H249R, N043R-S087D-S101G-S103A-V104I-A232V-Q245R-N269R, N043R-S101G-S103A-V104I-V150L-A232V-Q245R, S024R-S087D-S101G-S103A-V104I-A232V-Q245R, S024R-S101G-S103A-V104I-V150L-A232V-Q245R, S078R-S087D-S101G-S103A-V104I-A232V-Q245R, S078R-S101G-S103A-V104I-V150L-A232V-Q245R, S087D-S101G-S103A-V104I-A232V-Q245R-N269R, S101G-S103A-V104I-V150L-A232V-Q245R-H249R, S101G-S103A-V104I-V150L-A232V-Q245R-N269R, T022R-S087D-S101G-S103A-V104I-A232V-Q245R, N018R-S024R-N043D-N076D-V150L-H249R, N043R-S087D-S101G-S103A-V104I-A232V-Q245R, T022R-S101G-S103A-V104I-V150L-A232V-Q245R, N018R-S024R-N043D-N076D-S087D-H249R, N018R-S024R-N076D-S087D-H249R, N018R-S024R-N076D-V150L-S242R-H249R, N043R-S101G-S103A-V104I-V150L-A232V-Q245R-N269R, N076D-S101G-S103A-V104I-V150L-A232V-Q245R, S087D-S101G-S103A-V104I-A232V-S242R-Q245R, S101G-S103A-V104I-V150L-A232V-Q245R, N076D-S087D-S101G-S103A-V104I-A232V-Q245R, S087D-S101G-S103A-V104I-A232V-Q245R, and S101G-S103A-V104I-V150L-A232V-S242R-Q245R, wherein the amino acid positions of the subtilisin variant are numbered by correspondence with the amino acid sequence of B. amyloliquefaciens subtilisin BPN' set forth as SEQ ID NO:1.

The present invention provides nucleic acids encoding a Bacillus subtilisin variant having proteolytic activity comprising an amino acid sequence comprising a combination of amino acid substitutions selected from: S024R-S101G-

S103A-V104I-P129Q-A158E-S188D-L217E-A232V-Q245R-N248D-H249R, S024R-S101G-S103A-V104I-S130A-A158E-N183D-S188D-A232V-Q245R-N248D-H249R, S024R-S101G-S103A-V104I-P129Q-A158E-N183D-S188D-A232V-Q245R-N248D-H249R, S101G-S103A-V104I-S130A-A158E-S188D-A232V-Q245R-N248D-H249R, S024R-S101G-S103A-V104I-P129Q-A158E-S188D-A232V-Q245R-N248D-H249R, S024R-S101G-S103A-V104I-S130A-A158E-S188D-A232V-Q245R-N248D-H249R, S024R-S101G-S103A-V104I-P129Q-S130A-A158E-N183D-S188D-A232V-Q245R-N248D-H249R, S024R-S101G-S103A-V104I-S128L-P129Q-A158E-S188D-A232V-Q245R-N248D-H249R, S024R-S101G-S103A-V104I-P129Q-S130A-A158E-S188D-A232V-Q245R-N248D-H249R, S101G-S103A-V104I-P129Q-A158E-S188D-A232V-Q245R-N248D-H249R, S101G-S103A-V104I-P129Q-S130A-A158E-S188D-A232V-Q245R-N248D-H249R, S024R-S101G-S103A-V104I-S128L-P129Q-S130A-A158E-S188D-A232V-Q245R-N248D-H249R, S101G-S103A-V104I-S128L-P129Q-A158E-S188D-A232V-Q245R-N248D-H249R, and S024R-K027R-S101G-S103A-V104I-S128L-P129Q-S130A-A158E-S188D-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: S101G-S103A-V104I-A232V-M222Q-Q245R, S101G-S103A-V104I-A158E-S188D-M222S-A232V-Q245R-N248D-H249R, S101G-S103A-V104I-A158E-S188D-M222Q-A232V-Q245R-N248D-H249R, N076D-S101G-S103A-V104I-A232V-M222Q-Q245R, S101G-S103A-V104I-A232V-M222S-Q245R, N076D-S101G-S103A-V104I-A232V-M222S-Q245R, and N076D-S101G-S103A-V104I-A158E-S188D-M222S-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: S024R-S101G-S103A-V104I-S128L-P129Q-A158E-S188D-A232V-Q245R-N248D-H249R, S101G-S103A-V104I-S130A-A158E-S188D-A232V-Q245R-N248D-H249R, S024R-S101G-S103A-V104I-A158E-S188D-A232V-Q245R-N248D-H249R, S101G-S103A-V104I-S128L-P129Q-A158E-S188D-A232V-Q245R-N248D-H249R, S101G-S103A-V104I-P129Q-S130A-A158E-S188D-A232V-Q245R-N248D-H249R, S101G-S103A-V104I-S130A-A158E-N183D-S188D-L217E-A232V-Q245R-N248D-H249R, S024R-S101G-S103A-V104I-S128L-P129Q-S130A-A158E-S188D-A232V-Q245R-N248D-H249R, S024R-S101G-S103A-V104I-P129Q-A158E-S188D-L217E-A232V-Q245R-N248D-H249R, S101G-S103A-V104I-S128L-S130A-A158E-S188D-L217E-A232V-Q245R-N248D-H249R, S024R-S101G-S103A-V104I-S128L-P129Q-A158E-N183D-S188D-A232V-Q245R-N248D-H249R, S024R-S101G-S103A-V104I-S128L-P129Q-S130A-A158E-N183D-S188D-A232V-Q245R-N248D-H249R, S024R-S101G-S103A-V104I-S128L-P129Q-A158E-S188D-A232V-Q245R-N248D-H249R-E271G, S101G-S103A-V104I-P129Q-A158E-N183D-S188D-A232V-Q245R-N248D-H249R, S024R-S101G-S103A-V104I-S130A-A158E-S188D-L217E-A232V-Q245R-N248D-H249R, S024R-S101G-S103A-V104I-S128L-A158E-N183D-S188D-A232V-Q245R-N248D-H249R, S101G-S103A-V104I-P129Q-A158E-S188D-L217E-A232V-Q245R-N248D-H249R, and S024R-S101G-S103A-V104I-S128L-S130A-A158E-S188D-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: S101G-S103A-V104I, T22A-S101A-Y209E, S103G-L111V-G159E, T22A-S103G-G159E, T22A-L111V-G159E, T22A-S128N-E271F-Y209E, T22A-S103G-L111V, N62E-L111V-S128N, T22A-L111V-S128N, T22A-N62E-L111V, S101A-S103G-V104L-S188D, S101G-S103A-V104I-G159D, S101A-S103G-V104L-S128N, T22A-S101A-G159E, S101A-S103G-V104L, S101A-S103G-V104L-G159E, T22A-S101A-S103G-V104L, S101A-S103G-V104L-Y209E, T22A-Y209E-E271F, T22A-S101A-E271F, and S101A-Y209E-E271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, and S101G-S103A-V104L-G159D-A232V-Q236H-Q245R-N248D, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N238R, S101G-S103A-V104I-G159D-A232V-Q245R-N248D-N248R, S101G-S103A-V104I-G159D-A232V-Q245R-N248D-T253R, S101G-S103A-V104I-G159D-A232V-Q245R-N248D-524R, S101G-S103A-V104I-G159D-A232V-Q245R-N248D-N76D, S101G-S103A-V104I-G159E-A232V-Q245R-N248D-H249R, S101G-S103A-V104I-G159E-A232V-Q245R-N248D-E271F, S101G-S103A-V104I-A158E-A232V-Q245R-N248D-H249R, S101G-S103A-V104I-A158E-A232V-Q245R-N248D-E271F, T22A-S101G-S103A-V104I-G159D-A232V-Q245R-N248D-H249R, T22A-S101G-S103A-V104I-G159D-A232V-Q245R-N248D-E271F, N62E-S101G-S103A-V104I-G159D-A232V-Q245R-N248D-H249R, and N62E-S101G-S103A-V104I-G159D-A232V-Q245R-

N248D-E271F, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant having proteolytic activity comprising an amino acid sequence comprising a combination of amino acid substitutions selected from: A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, W241R, G20R-N43R-H249R, G20R-T22R-N43R, G20R-N43R-S242R, G20R-N43R-E271L, G20R-N43R-V244R, G20R-S24R-N43R-S242R, S9A-T22R-S78R-S212F-W241R, S9A-G20R-N43R-S212F, S9A-N43R-S212F, G20R-N43R-S212F, G20R-T22R-N43R-S212F, S24R-S78R-S212F, S9A-N43R-S78R, S9A-N43R-S78R-S242R, S9A-G20R-N43R-S78R, G20R-S24R-N43R-S78R-S242R, T22R-S24R-S78R-S212F, S9A-G20R-N43R-S78R-S242R, G20R-N43R-S78R-H249R, G20R-N43R-S78R, S9A-S78R-S212F, S9A-T22R-N43R-S78R, S9A-G20R-S24R-N43R, S9A-T22R-S78R-S212F, V4R-S9A-T22R-S78R-S212F, G20R-S24R-N43R, A1R-S9A-N43R, G20R-S24R-N43R-G115R, S9A-S24R-N43R, G20R-T22R-S24R-N43R, A1R-S24R-N43R, S9A-G20R-S24R-N43R-S242R, S9A-G20R-T22R-S78R-S212F, S9A-S24R-N43R-V244R, S9A-S24R-N43R-S242R, V4R-S9A-T22R-S24R-S212F, and T22R-S24R-N43R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding *Bacillus* subtilisin variant having proteolytic activity and comprising an amino acid sequence comprising a combination of amino acid substitutions selected from: S101G-S103A-V104I-A232V-Q245R-N248D, S101G-S103A-V104I-G159D-A232V-Q245R, S101G-S103A-V104I-G159R-A232V-Q245R-N248D, S101G-S103A-V104I-G159D-A232V-Q245R-N248R, S101G-S103A-V104I-A232V-Q245R, S101G-S103A-V104I-A232V-Q245R-N248R, S101G-S103A-V104I-G159R-A232V-Q245R-N248R, S101G, S103A, V104I, A232V, Q236H, and Q245R, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding *Bacillus* subtilisin variant having proteolytic activity and comprising an amino acid sequence comprising a combination of amino acid substitutions selected from: A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, and E271F wherein amino acid positions of the subtilisin variant are numbered by correspondence with the amino acid sequence of *B. amyloliquefaciens* subtilisin BPN' set forth as SEQ ID NO:1.

The present invention also provides protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of G20K, G20R, G23A, S24F, S24R, N43R, N43W, R45T, N62E, N76D, S101A, N116A, N116L, G118R, S128I, P129E, S188D, T213A, A215F, L217E, P239G, and N269R, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention provides nucleic acids encoding a *Bacillus* subtilisin variant having proteolytic activity and comprising an amino acid sequence comprising a combination of amino acid substitutions selected from: A1R, Q2S, Q2M, Q2A, Q2R, Q2W, S3R, V4R, V4S, V4C, I8A, S9A, S9F, S9W, R10S, R10A, R10H, R10M, Q12F, Q12R, P14K, P14F, P14Q, A15R, A15F, A16S, H17R, H17M, H17F, N18R, N18K, G20F, G20K, G20R, T22A, T22R, T22Y, T22V, T22Q, T22L, T22W, G23A, G23S, G23F, S24R, S24F, S24W, S24Q, S24H, S24L, G25V, G25F, G25R, V26F, K27L, K27F, K27R, K27V, V28A, V28N, V28E, A29T, V30E, L31F, T33S, T33G, T33D, G34P, I35M, S36T, S36F, S36R, T38L, T38F, T38R, P40N, P40L, P40T, P40W, P40H, P40R, L42I, N43A, N43F, N43I, N43S, N43R, N43M, N43W, N43D, R45T, G46R, A48R, F50C, V51W, V51F, V51H, P52F, P52E, P52N, P55Y, T57R, Q59A, Q59F, Q59R, D60P, D60Q, D60A, N62E, N62Q, G63V, G63M, G63T, G63I, G63A, G63S, G63H, G63Q, G63D, G63E, G63P, H64F, H64T, V68A, V68C, A69N, A69T, A69P, A69W, T71G, T71G, I72C, A74C, L75A, L75F, L75E, L75R, N76D, S78R, S78N, S78I, S78R, I79W, I79Q, V81R, L82F, L82T, L82V, L82R, L82M, A85M, P86W, P86L, P86I, E89P, E89T, E89G, E89H, E89W, E89L, E89V, E89W, E89F, E89I, Y91N, Y91F, A92F, K94N, S99F, S99T, S99P, S99G, S99M, G100S, G100N, G100Q, G100I, S101A, S101N, S101G, S101D, S101T, S101D, S101E, S101P, S101F, G102A, G102T, G102N, G102H, G102E, S103G, S103N, S103D, S103A, V104L, V104I, V104E, V104D, S105T, S105E, S105Q, S106G, S106T, S106E, S106D, S106A, S106V, S106F, I107M, I107F, A108I, A108G, Q109M, L111V, L111I, E112V, E112L, E112Q, A114G, G115K, G115R, N116K, N116A, N116L, N117F, G118R, G118I, M119C, H120A, H120F, H120R, V121F, V121F, V121E, N123G, N123E, L124S, S128D, S128F, S128L, S128N, S128H, S128M, S128I, S128Q, P129E, S132A, S132E, A138G, S144R, V147L, L148I, A158E, G159D, G159E, G159C, S160D, S166D, S166E, Y167W, M175V, V177C, D181A, Q182R, N183I, N183D, N183M, N183R, N183F, N183R, N185E, N185V, N185I, R186H, R186K, S188E, S188D, S188R, Y192H, Y192W, A194E, A194V, A194F, D197F, D197F, I198L, I198F, V203E, V203C, T208S, Y209S, Y209N, Y209F, Y209T, Y209E, Y209H, Y209G, Y209L, P210R, P210V, P210L, G211Q, G211R, S212I, S212M, S212F, T213A, Y214F, A215N, A215D, A215E, A215H, A215F, S216F, S216A, L217E, L217N, L217D, N218D, N218P, N218E, T224A, T224G, V227I, A230E, A231I, A231C, A232V, L233C, V234F, K235F, Q236F, Q236N, Q236H, N238R, N238K, N238L, P239K, P239G, P239R, P239R, P239H, P239T, P239N, P239S, P239F, S240R, W241R, S242L, S242R, N243F, N243R, V244R, Q245R, I246S, N248D, N248V, N248I, N248R, H249R, H249T, L250I, K251R, K251S, N252I, N252F, N252R, N252K, N252H, T253I, T253R, T253F, A254C, S256N, G258R, T260V, T260I, L262D, L262H, Y263F, S265F, L267V, L267K, L267M, N269I, N269R, A270C, E271I, E271H, E271V, E271H, E271M, E271L, E271P, E271A, E271F, E271T, A272F, A272F, A272R, A273F, A273I, and T274G, wherein the amino acid positions of the subtilisin variant are numbered by correspondence with the amino acid sequence of *B. amyloliquefaciens* subtilisin BPN' set forth as SEQ ID NO:1.

The present invention provides nucleic acids encoding a *Bacillus* subtilisin variant of *Bacillus lentus* subtilisin GG36 protease, wherein the *Bacillus lentus* subtilisin GG36 protease comprises the amino acid sequence shown in SEQ ID NO:2, and wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations at amino acid positions selected from amino acid 1, 2, 3, 4, 8, 9, 10, 12, 14, 15, 16, 17, 18, 20, 22, 23, 24, 25, 26, 27, 28, 29, 30, 31, 33, 34, 35, 36, 38, 40, 42, 43, 45, 46, 48, 50, 51, 52, 55, 57, 59, 60, 62, 63, 64, 68, 69, 71, 72, 74, 75, 76, 78, 79, 81, 82, 85, 86, 89, 91, 92, 94, 99, 100, 101, 102, 103, 104, 105, 106, 107, 108, 109, 111, 112, 114, 115, 116, 117, 118, 119, 120, 121, 123, 124, 128, 129, 132, 138, 44, 147, 148, 158, 159, 160, 166, 167, 175, 177, 181, 182, 183, 185, 186, 188, 192, 194, 197, 198, 203, 208, 209, 210, 211, 212, 213, 214, 215, 216, 217, 218, 224, 227, 230, 231, 233, 234, 235, 236, 236, 238, 238, 239, 240, 241, 242, 243, 244, 246, 248, 249, 250, 251, 252, 253, 254, 256, 258, 260, 262, 263, 265, 267, 269, 270, 271, 272, 273, and 274, wherein the amino acid positions of the subtilisin variant are numbered by correspondence with the amino acid sequence of *B. amyloliquefaciens* subtilisin BPN' set forth as SEQ ID NO:1, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the variant protease amino acid sequence with the *Bacillus amyloliquefaciens* subtilisin BPN' amino acid sequence.

The present invention provides nucleic acids encoding a *Bacillus* subtilisin variant of *Bacillus lentus* subtilisin GG36 protease, wherein the *Bacillus lentus* subtilisin GG36 protease comprises the amino acid sequence shown in SEQ ID NO:2, and wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, 25, 30, 35, 40, 45, or 50 mutations selected from the group of A1R, Q2S, Q2M, Q2A, Q2R, Q2W, S3R, V4R, V4S, V4C, I8A, S9A, S9F, S9W, R10S, R10A, R10H, R10M, Q12F, Q12R, P14K, P14F, P14Q, A15R, A15F, A16S, H17R, H17M, H17F, N18R, N18K, G20F, G20K, G20R, T22A, T22R, T22Y, T22V, T22Q, T22L, T22W, G23A, G23S, G23F, S24R, S24F, S24W, S24Q, S24H, S24L, G25V, G25F, G25R, V26F, K27L, K27F, K27R, K27V, V28A, V28N, V28E, A29T, V30E, L31F, T33S, T33G, T33D, G34P, I35M, S36T, S36F, S36R, T38L, T38F, T38P, P40N, P40L, P40T, P40W, P40H, P40R, L42I, N43A, N43F, N43I, N43S, N43R, N43M, N43W, N43D, R45T, G46R, A48R, F50C, V51W, V51F, V51H, P52F, P52E, P52N, P55Y, T57R, Q59A, Q59F, Q59R, D60P, D60Q, D60A, N62E, N62Q, G63V, G63M, G63T, G63I, G63A, G63S, G63H, G63Q, G63D, G63E, G63P, H64F, H64T, V68A, V68C, A69N, A69T, A69P, A69W, T71G, T71G, I72C, A74C, L75A, L75F, L75E, L75R, N76D, S78R, S78N, S78I, S78R, I79W, I79Q, V81R, L82F, L82T, L82V, L82R, L82M, A85M, P86W, P86L, P86I, E89P, E89T, E89G, E89H, E89W, E89L, E89V, E89W, E89F, E89I, Y91N, Y91F, A92F, K94N, N99F, N99S, N99P, S99G, S99M, G100S, G100N, G100Q, G100I, S101A, S101N, S101G, S101D, S101T, S101D, S101E, S101P, S101F, G102A, G102T, G102N, G102H, G102E, S103G, S103N, S103D, S103A, V104L, V104I, V104E, V104D, S105T, S105E, S105Q, S106G, S106T, S106E, S106D, S106A, S106V, S106F, I107M, I107F, A108I, A108G, Q109M, L111V, L111I, E112V, E112L, E112Q, A114G, G115K, G115R, N116K, N116A, N116L, N117F, G118R, G118I, M119C, H120A, H120F, H120R, V121F, V121F, V121E, N123G, N123E, L124S, S128D, S128F, S128L, S128N, S128H, S128M, S128I, S128Q, P129E, S132A, S132E, A138G, S144R, V147L, L148I, A158E, G159D, G159E, G159C, S160D, S166D, S166E, Y167W, M175V, V177C, D181A, Q182R, N183I, N183D, N183M, N183R, N183F, N183R, N185E, N185V, N185I, R186H, R186K, S188E, S188D, S188R, Y192H, Y192W, A194E, A194V, A194F, D197F, D197F, I198L, I198F, V203E, V203C, T208S, Y209S, Y209N, Y209F, Y209T, Y209E, Y209H, Y209G, Y209L, P210R, P210V, P210L, G211Q, G211R, S212I, S212M, S212F, T213A, Y214F, A215N, A215D, A215E, A215H, A215F, S216F, S216A, L217E, L217N, L217D, N218D, N218P, N218E, T224A, T224G, V227I, A230E, A231I, A231C, A232V, L233C, V234F, K235F, Q236F, Q236N, Q236H, N238R, N238K, N238L, P239K, P239G, P239R, P239R, P239H, P239T, P239N, P239S, P239F, S240R, W241R, S242L, S242R, N243F, N243R, V244R, Q245R, I246S, N248D, N248V, N248I, N248R, H249R, H249T, L250I, K251R, K251S, N252I, N252F, N252R, N252K, N252H, T253I, T253R, T253F, A254C, S256N, G258R, T260V, T260I, L262D, L262H, Y263F, S265F, L267V, L267N, L267M, N269I, N269R, A270C, E271I, E271H, E271V, E271H, E271M, E271L, E271P, E271A, E271F, E271T, A272F, A272F, A272R, A273F, A273I, and T274G, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention provides nucleic acids encoding a *Bacillus* subtilisin variant of *Bacillus lentus* subtilisin GG36 protease, wherein the *Bacillus lentus* subtilisin GG36 protease comprises the amino acid sequence shown in SEQ ID NO:2, and wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, 25, 30, 35, 40, 45, or 50 mutations selected from the group of A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E, G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N, N269I, N269R, E271F, E271I, E271H, E271P, E271T, E271V, E271L and A272F, and optionally comprises at least one mutation selected from the group of S103A, G159D, Q236H, Q245R, N248D and N252K, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention provides nucleic acids encoding a *Bacillus* subtilisin variant of *Bacillus lentus* subtilisin GG36 protease, wherein the *Bacillus lentus* subtilisin GG36 protease comprises the amino acid sequence shown in SEQ ID NO:2, and wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, 25, 30, 35, 40, 45, or 50 mutations selected from the group of A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106D, A108I, L111V, E112V, G115K, G115R, N117F, G118I, V121F, S128D, S128F, S128L, S128N, P129E, S144R, L148I, A158E. G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N. N269I, N269R, E271F, E271I, E271H, E271P, E271T, E271V, E271L and A272F, and optionally comprises at least one mutation selected from the group of S103A, G159D, Q236H, Q245R, N248D and N252K, The present invention provides nucleic acids encoding a *Bacillus* subtilisin variant of *Bacillus lentus* subtilisin GG36 protease, wherein the *Bacillus lentus* subtilisin GG36 protease comprises the amino acid sequence shown in SEQ ID NO:2, and wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, 25, 30, 35, 40, 45, or 50 mutations selected from the group of A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, E271F, A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, and W241R, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, and E271F, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention provides nucleic acids encoding *Bacillus* subtilisin variant of *Bacillus lentus* subtilisin GG36 protease, wherein the *Bacillus lentus* subtilisin GG36 protease comprises the amino acid sequence shown in SEQ ID NO:2, and wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, 25, 30, 35, 40, 45, or 50 mutations selected from the group of A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, E271F, A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, and W241R, wherein the amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants of *Bacillus lentus* subtilisin GG36 protease, wherein the *Bacillus lentus* subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of G20K, G20R, G23A, S24F, S24R, N43R, N43W, R45T, N62E, N76D, S101A, N116A, N116L, G118R, S128I, P129E, S188D, T213A, A215F, L217E, P239G, and N269R, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention provides nucleic acids encoding a *Bacillus* subtilisin variant comprising an amino acid sequence which differs from the amino acid sequence of SEQ ID NO:2, and wherein the total net charge of the protease variant is +1, +2, +3, +4, +5, 0, −1, −2, −3, −4, or −5 relative to the total net charge of the *Bacillus lentus* subtilisin GG36 protease, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention also provides protease variants comprising amino acid sequence which differs from the amino acid sequence of SEQ ID NO:2, and wherein the total net charge of the protease variant is 0 relative to the total net charge of the *Bacillus lentus* subtilisin GG36 protease, and wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

The present invention provides nucleic acids encoding a *Bacillus* subtilisin variant having one or more of the following characteristics: a) a Test Method 2 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; b) a Test Method 3 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; c) a Test Method 4 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or d) a Test Method 6 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5. Test Method 2, Test Method 3, Test Method 4, and Test Method 6 are explicitly described infra in the section of Example 1 entitled "Test Methods".

As indicated herein, suitable cold water protease variants are variants of a parent protease, said parent protease's sequence being at least 97%, at least 99% or 100% identical to the amino acid sequence of SEQ ID NO:1, said protease variant having one or more of the following characteristics: a) Test Method 2 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; b) a Test Method 3 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; c) a Test Method 4 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or d) a Test Method 6 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5. Test Method 2, Test Method 3, Test Method 4, and Test Method 6 are explicitly described infra in the section of Example 1 entitled "Test_Methods". All mutations referenced herein utilize the BPN' numbering scheme as shown in FIG. 1. In some embodiments, the variants referenced herein refer to variants having amino acid sequences compared to the amino acid sequence of SEQ ID NO:2, using the BPN' numbering scheme.

In some embodiments, the variants provided herein refer to variants of a parent protease, wherein the parent protease's sequence being at least 97%, at least 99% or 100% identical to the amino acid sequence of SEQ ID NO:1.

Suitable cold water proteases can be derived from subtilisins, particularly those derived from subtilisin *Bacillus lentus* GG36 of SEQ ID NO:2 and in some embodiments, comprise one or more of the following mutations: A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E. G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N. N269I, N269R, E271F, E271I, E271H, E271P, E271T, E271V, E271L and/or A272F.

In some embodiments, suitable cold water protease variants include subtilisins, particularly those derived from *Bacillus lentus* GG36 of SEQ ID NO:2, comprising one or more of the following sets of mutations: T022R-S024R, S009A-E271L, N018R-W241R, N018R-G115R, N043R-H249R, G020R-H249R, V004R-H249R, G020R-S024R, N018R-H249R, S009A-G020R, G020R-W241R, S009A-S078R, G020R-G115R, N018R-S024R, S024R-S242R, T022R-G115R, N018R-N043R, G020R-N043R, N018R-S242R, S242R-N269R, N018R-V244R, S024R-N269R, G020R-E271L, S024R-E271L, V004R-S009A, G020R-N269R, A001R-S024R, V244R-E271L, S009A-N018R, W241R-E271L, V004R-S024R, S009A-H249R, S009A-T022R, N062E-P129E, N062E-G159E, A016S-L148I, A158E-H249R, A016S-N062E, L111V-S188D, T022A-N062E, N062E-L148I, T022A-P129E, N062E-E271F, N062E-A158E, A016S-G159E, N062E-R186H, S128N-G159E, N062E-S188D, N062E-S128N, L148I-G159E, S103G-A158E, L111V-G159E, A158E-E271F, A016S-S188D, T022A-L111V, S128N-A158E, A016S-A158E, V104L-A158E, S128N-R186H, G159E-Y209E, N062E-S101A, L111V-Y209E, L148I-S188D, S101A-Y209E, T022A-S188D, A016S-T022A, S128N-P129E, A016S-Y209E, A016S-S128N, T022A-E089P, S128N-Y209E, E089P-A158E, N062E-S103G, R186H-E271F, A016S-P129E, E089P-G159E, L111V-H249R, S101A-P129E, L148I-Y209E, T022A-G159E, P129E-H249R, P129E-Y209E, V104L-P129E, S128N-S188D, L111V-A158E, T022A-A158E, N062E-Y209E, N062E-H249R, S101A-R186H, E089P-P129E, P129E-E271, T22A-L111V-G159E, S101A-S103G-V104L-Y209E, S101A-S103G-V104L-G159E, S101A-S103G-V104L-S188D, S101G-S103A-V104I-G159D, T22A-S103G-G159E, T22A-S128N-E271F-Y209E, T22A-Y209E-E271F, T22A-S101A-Y209E, S101A-Y209E-E271F, T22A-L111V-S128N, T22A-S101A-G159E, S101A-S103G-V104L, T22A-S101A-S103G-V104L, S101A-S103G-V104L, S101G-S103A-V104I, S101A-S103G-V104L-S128N, S103A-V104I-G159D-A232V-Q236H-Q245R-N248D-N252K, S101G-V104I-G159D-A232V-Q236H-Q245R-N248D-N252K, S101G-

S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, S101G-S103A-V104L-G159D-A232V-Q236H-Q245R-N248D, N62E-S101G-S103A-V104I-G159D-A232V-Q245R-N248D-E271F, N62E-S101G-S103A-V104I-G159D-A232V-Q245R-N248D-H249R, T22A-S101G-S103A-V104I-G159D-A232V-Q245R-N248D-H249R, S101G-S103A-V104I-G159D-A232V-Q245R-N248D-S24R, S101G-S103A-V104I-G159D-A232V-Q245R-N248D-T253R, S101G-S103A-V104I-A158E-A232V-Q245R-N248D-H249R, T22A-S101G-S103A-V104I-G159D-A232V-Q245R-N248D-E271F, S101G-S103A-V104I-G159E-A232V-Q245R-N248D-H249R, S101G-S103A-V104I-G159D-A232V-Q245R-N248D-N238R, S101G-S103A-V104I-A158E-A232V-Q245R-N248D-E271F, S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N76D, and/or S101G-S103A-V104I-G159E-A232V-Q245R-N248D-E271F.

The present invention further provides isolated subtilisin variants, wherein the subtilisin variants are mature forms having proteolytic activity and comprise amino acid sequences comprising a combination of amino acid substitutions selected from: G020R-N043R, G020K-N062E, S024F-N116L, G020K-S024F, S024R-A174T, S024R-G118R, S024R-K235F, S024R-P086R, S024R-P086W, S078R-G118R, T033S-G118R, T033S-K235F, Y209A-W241R, G020R-N076D, N018R-Q245R, S024R-R045T, A232V-Q245R, G118R-A172V, G118R-A194T, I008T-S024R, K235F-N243F, N018R-S103A, N018R-V104I, P086W-G118R, P086W-N243F, P086W-Y209A, S024C-T033S, S024R-A232V, S024R-N243F, S024R-P239Q, S024R-S101G, S024R-S141G, S024R-T033S, S024R-T274I, S024R-Y209A, S078R-P086W, S101G-A232V, T033S-L148F, T033S-P086W, T033S-P201S, T033S-S078R, T033S-W241R, T033S-Y209A, A230E-H249R, A232V-H249R, G118R-K235F, N076D-Q245R, P086W-K235F, S024R-R247H, S024R-V104A, S078R-K235F, S101G-H249R, S103A-A232V, T033S-A048T, T033S-P239T, T033S-T253A, T143A-Y209A, Y209A-K235F, N018R-R045T, Y209A-N243F, S024R-A272P, S024R-R269C, S101G-V104I, V104I-A232V, N076D-H249R, and S024R-N076D wherein the amino acid positions of the subtilisin variant are numbered by correspondence with the amino acid sequence of *B. amyloliquefaciens* subtilisin BPN' set forth as SEQ ID NO:1.

The present invention further provides isolated subtilisin variants, wherein the subtilisin variants are mature forms having proteolytic activity and comprise amino acid sequences comprising a combination of amino acid substitutions selected from: G020R-N076D, S024R-R045T, A230E-H249R, N018R-R045T, N018R-Q245R, S101G-A232V, S024R-A232V, A232V-Q245R, S024R-S101G, N018R-V104I, N018R-S103A, S101G-H249R, A232V-H249R, S103A-A232V, N076D-Q245R, S101G-V104I, V104I-A232V, N076D-H249R, S024R-N076D, S024F-N116L, G020K-S024F, G020K-N062E, T033S-G118R, S024R-P086W, S024R-G118R, S024R-P086R, Y209A-W241R, S024R-W241R, S024R-K235F, G118R-Y209A, S078R-G118R, T033S-K235F, S024R-A174T, P086W-Y209A, I008T-S024R, P086W-G118R, T033S-W241R, S024R-N243F, S024R-Y209A, T033S-P086W, S024R-T033S, P086W-N243F, T033S-P201S, S024R-P239Q, S078R-P086W, K235F-N243F, G118R-A172V, T033S-L148F, T033S-S078R, T033S-N243F, S024C-T033S, G118R-A194T, T033S-Y209A, S024R-S141G, S024R-T274I, P086W-K235F, A015T-T033S, Y209A-K235F, S024R-R247H, S078R-K235F, S024R-V104A, T033S-A048T, G118R-K235F, T033S-T253A, T143A-Y209A, T033S-P239T, Y209A-N243F, S024R-A272P, and S024R-R269C, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: V004R-S009A-G020R-S242R, G020R-N043R-W241R, G020R-S242R-N269R, V004R-S009A-G020R-N043R, V004R-G020R-H249R, N018R-S024R-V244R, S009A-T022R-S212F-W241R, G020R-N043R-N269R, N018R-S024R-S242R, V004R-S009A-N043R-W241R, G020R-N043R-V244R, G020R-T022R-S242R, V004R-G020R-N043R, V004R-S009A-G020R-N043R-S242R, G020R-N043R-S242R, G020R-N043R-S242R-H249R, G020R-S212F-H249R, V004R-S009A-W241R, A001R-S009A-N043R, G020R-N043R-H249R, S009A-G020R-N043R-W241R, G020R-T022R-N043R, G020R-H249R-N269R, G020R-T022R-W241R, V004R-S009A-S024R-N043R-W241R, S009A-N043R-S078R, V004R-G020R-S024R-V244R, G020R-T022R-S078R-S242R, G020R-S024R-S242R-H249R, V004R-S009A-S078R-W241R, S009A-N043R-S078R-S242R, V004R-G020R-S024R, S009A-N043R-S212F, G020R-N043R-S212F, S024R-S078R-S212F, S009A-G020R-S024R-N043R, S009A-T022R-N043R-S078R, G020R-T022R-S212F-W241R, G020R-N043R-S212F-W241R, S009A-N043R-W241R, G020R-N043R-E271L, G020R-T022R-S078R-W241R, G020R-S024R-N043R-S242R, G020R-T022R-N043R-W241R, S009A-G020R-N043R-S212F, V004R-S009A-G020R-S024R-S242R, G020R-N043R-H249R-E271L, G020R-T022R-S024R-S242R, S009A-T022R-S078R-S212F, G020R-N043R-S242R-E271L, S009A-T022R-S078R-S212F-W241R, V004R-G020R-S024R-H249R, G020R-T022R-E271L, G020R-T022R-N043R-S212F, V004R-G020R-S024R-N043R-S242R, V004R-G020R-S024R-N043R, V004R-S009A-T022R-S078R-S212F, G020R-T022R-S078R-S212F-W241R, and G020R-T022R-N269R, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: N018R-G020R-N043D-R045T-A230E, N018R-N043R-R045T-S242R-H249R, S024R-N043D-H249R, N018R-G020R-R045T, G020R-S024R-N076D-H249R, S024R-N043R-A230E-S242R, N018R-S024R-N043D-A230E, G020R-N076D, N018R-S024R-N043D-N076D-H249R, S024R-N043R-N076D-H249R, N018R-S024R-R045T-S242R, G020R-N043D-N076D-A230E-H249R, G020R-N043R-R045T-S242R, N018R-S024R-N076D-H249R, N018R-G020R-S024R-N043D-R045T-L233I-S242R, S024R-N043R-A230E, N018R-G020R-N043D, N043R-S242R-H249R, G020R-N043R-

R045T-A230E, N043R-N076D-S242R-H249R, G020R-S024R-R045T-A230E-S242R, S024R-R045T-N076D-A230E-S242R-H249R, S024R-R045T, S024R-N043R-R045T-N076D-A230E-H249R, N018R-S024R-N043D-R045T-H249R, N018R-N043R-R045T-H249R, S024R-N043R-S242R, N018R-G020R-N043R-N076D-H249R, G020R-S024R-N043D-H249R, G020R-N043R-A230E-S242R, G020R-N043R-S242R, N018R-N043R-N076D-A230E, G020R-S024R-N043D-S242R, G020R-N043R-A230E, N018R-G020R-N043R-N076D-S242R-H249R, N043D-R045T-N076D-H249R, N018R-N043R-S242R-H249R, N018R-G020R-N043R-R045T-S242R, N018R-G020R-N043D-A230E-S242R, G020R-S024R-N043R-R045T-H249R, S024R-N043R-H249R, G020R-S024R-K27E-N043R-N076D-A230E, S024R-N043R-R045T-S242R, N018R-G020R-S024R-N043R-R045T-N076D-A230E, G020R-N043R-N076D-A230E-H249R, N018R-N043R-R045T-S242R, G020R-S242R-H249R, N018R-N043R-N076D-A230E-S242R-H249R, N018R-S024R-N076D, G020R-S024R-K27R-N043D-S242R-H249R, N018R-G020R-S024R-N043D-N076D-S242R, N018R-N043R-N076D-S242R-H249R, N018R-S024R-N043D-A230E-H249R, N018R-G020R-N043D-H249R, N018R-G020R-N043D-R045T-N076D-S242R, S024R-N043R-N076D-A230E-S242R, G020R-S024R-T381-N043R-R045T-N076D-S242R-H249R, N018R-G020R-N043R, N018R-S024R-R045T-A230E-S242R, N018R-G020R-H249R, S024R-N043R-N076D, N018R-G020R-S024R-N043R-R045T-N076D-H249R, N018R-N043D-R045T-N076D-S242R-H249R, S024R-N043D-S242R-H249R, N018R-G020R-S024R-N043D-R045T-S242R, G020R-S024R-N043R-N076D, N018R-G020R-N043D-R045T-A230E-S242R, G020R-S024R-N043R-R045T-N076D-S242R-H249R, N018R-N043R-R045T-N076D-S242R, N018R-G020R-N043R-N076D-A230E-S242R, N018R-S024R-N043D-H249R, N018R-S024R-N043R-R045T-A230E-H249R, N018R-G020R-N043R-R045T-N076D-H249R, N018R-S024R-S242R, N018R-N043R-R045T-N076D-A230E-S242R, R045T-S242R-H249R, N018R-S024R-N043D-S242R, N018R-G020R-N043D-R045T-S240P, S024R-N043R-R045T-S242R-H249R, N018R-S024R-V30S-L31S-D321-T33Q-G34V-I35F, N018R-G020R-N043R-N076D, G020R-N043D-R045T-N076D-S242R-H249R, N018R-S024R-N043D-A230E-S242R, N018R-S024R-N043D-S242R-H249R, S024R-N043D-R045T-S242R-H249R, N043R-A230E-H249R, S024R-N043R-N076D-A230E-H249R, G020R-S024R-N043D-N076D-H249R, S024R-R045T-S242R-A273V, G020R-S024R-R045T-N076D-S242R-H249R, N018R-S024R-N043D-N076D-S242R, N018R-N043R-N076D-A230E-H249R, N018R-G020R-N043R-R045T-H249R, N018R-N043R-R045T-A230E-S242R, G020R-S024R-N043D-R045T-A230E-S242R, N018R-N043D-A230E-H249R, N018R-N043R-N076D-S242R, N018R-G020R-N076D, N018R-G020R-N043D-N076D-S242R-H249R, G020R-S024R-N043D-N076D-S242R-H249R, N043D-S242R-H249R, N018R-G020R-S024R-N043R-N076D, N018R-G020R-N043D-R045T-N076D-H249R, N018R-G020R-N043R-R045T-N076D-A230E-H249R, N018R-N076D-S242R, G020R-N043R-H249R, N018R-N076D-S242R-H249R, N018R-S024R-R045T-A230E-H249R, A230E-H249R, N018R-R045T-H249R, G020R-N043R-N076D, N043R-R045T-H249R, N018R-N043D-N076D-S242R-H249R, N043R-N076D-H249R, N018R-R045T, G020R-N076D-A230E-S242R, G020R-S024R-N043D-R045T, S024R-N043D-N076D-S242R-H249R, G020R-R045T-H249R, N043R-N076D-S153A-H249R, N043R-N076D-A230E-H249R, N018R-N043D-N076D-H249R, and G020R-N043R-N076D-V227I, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101G-S103A-V104I-A232V-Q236H-Q245R-N252K, S101G-S103A-V104I-A232V-Q245R-N248R, S101G-S103A-V104I-G159R-A232V-Q245R-N248D, S101G-S103A-V104I-G159D-A232V-Q245R-N248R, S101G-S103A-V104I-A232V-Q245R, S101G-S103A-V104I-G159D-A232V-Q245R, and S101G-S103A-V104I-A232V-Q245R-N248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101G-S103A-V104I-P129E-S188D-A232V-N238R-Q245R-N248D, S024R-S101G-S103A-V104I-P129E-A158E-S188D-A232V-Q245R-N248D-H249R, T022A-S101G-S103A-V104I-P129E-A158E-S188D-A232V-Q245R-N248D-H249R, T022A-S024R-S101G-S103A-V104I-P129E-A158E-S188D-A232V-Q245R-N248D-H249R, S024R-S101G-S103A-V104I-P129E-S188D-A232V-Q245R-N248D-H249R, S024R-S101G-S103A-V104I-P129E-G159E-S188D-A232V-Q245R-N248D-H249R, S024R-S101G-S103A-V104I-S128N-P129E-A158E-A232V-Q245R-N248D-H249R, S024R-S101G-S103A-V104I-L148I-A158E-S188D-A232V-Q245R-N248D, T022A-S024R-S101G-S103A-V104I-P129E-G159E-S188D-A232V-Q245R-N248D-H249R, S024R-S101G-S103A-V104I-S128N-P129E-A232V-Q245R-N248D, S101G-S103A-V104I-P129E-S188D-A232V-Q245R-N248D-H249R, S024R-S101G-S103A-V104I-P129E-A158E-A232V-Q245R-N248D-H249R, T022A-S024R-S101G-S103A-V104I-A158E-G159E-S188D-A232V-Q245R-N248D-H249R, T022A-S024R-S101G-S103A-V104I-P129E-A158E-G159E-S188D-A232V-N238R-Q245R-N248D, S024R-S101G-S103A-V104I-P129E-L148I-A158E-A232V-Q245R-N248D, A016S-S024R-S101G-S103A-V104I-A158E-S188D-A232V-Q245R-N248D-H249R, S101G-S103A-V104I-A158E-G159E-A232V-Q245R-N248D-H249R, T022A-S101G-S103A-V104I-P129E-A158E-G159E-A232V-N238R-Q245R-N248D, T022A-S024R-S101G-S103A-V104I-P129E-A158E-G159E-A232V-Q245R-N248D-H249R, T022A-S024R-S101G-S103A-V104I-S128N-A158E-S188D-A232V-Q245R-N248D, S024R-S101G-S103A-V104I-P129E-S188D-A232V-Q245R-N248D, T022A-S024R-S101G-S103A-V104I-P129E-A158E-A232V-Q245R-N248D, T022A-S024R-S101G-S103A-V104I-P129E-A232V-Q245R-N248D, T022A-S024R-S101G-S103A-V104I-P129E-S188D-A232V-Q245R-N248D, S024R-S101G-S103A-V104I-A158E-S188D-A232V-N238R-Q245R-N248D, T022A-S101G-S103A-V104I-S128N-P129E-S188D-A232V-N238R-Q245R-N248D, S024R-S101G-S103A-V104I-P129E-S188D-A232V-N238R-Q245R-N248D, S024R-S101G-S103A-V104I-A158E-G159E-S188D-A232V-Q245R-N248D, T022A-S024R-S101G-S103A-V104I-S128N-S188D-A232V-Q245R-N248D, S024R-S101G-S103A-

V104I-P129E-A158E-S188D-A232V-Q245R-N248D, T022A-S024R-S101G-S103A-V104I-S128N-P129E-A158E-A232V-Q245R-N248D, S024R-S101G-S103A-V104I-G159E-S188D-A232V-Q245R-N248D, T022A-S101G-S103A-V104I-S128N-P129E-A232V-N238R-Q245R-N248D, S024R-S101G-S103A-V104I-P129E-G159E-A232V-Q245R-N248D, T022A-S024R-S101G-S103A-V104I-P129E-A158E-S188D-A232V-N238R-Q245R-N248D, T022A-S024R-S101G-S103A-V104I-A158E-G159E-S188D-A232V-Q245R-N248D, S024R-S101G-S103A-V104I-G159E-S188D-A232V-Q245R-N248D-H249R, T022A-S101G-S103A-V104I-P129E-A158E-A232V-N238R-Q245R-N248D, T022A-S024R-S101G-S103A-V104I-P129E-A158E-A232V-Q245R-N248D-H249R, S024R-S101G-S103A-V104I-L148I-A158E-A232V-Q245R-N248D, T022A-S101G-S103A-V104I-A158E-G159E-S188D-A232V-Q245R-N248D-H249R, T022A-S101G-S103A-V104I-A158E-S188D-A232V-Q245R-N248D, T022A-S101G-S103A-V104I-P129E-S188D-A232V-N238R-Q245R-N248D, S024R-S101G-S103A-V104I-P129E-A158E-G159E-S188D-A232V-Q245R-N248D-H249R, T022A-S024R-S101G-S103A-V104I-A158E-G159E-S188D-A232V-N238R-Q245R-N248D, S101G-S103A-V104I-P129E-A158E-S188D-A232V-Q245R-N248D-H249R, S024R-S101G-S103A-V104I-S128N-A158E-A232V-Q245R-N248D, T022A-S024R-S101G-S103A-V104I-S128N-P129E-S188D-A232V-Q245R-N248D, T022A-S101G-S103A-V104I-P129E-G159E-A232V-N238R-Q245R-N248D, S101G-S103A-V104I-P129E-G159E-A232V-Q245R-N248D-H249R, T022A-S101G-S103A-V104I-P129E-A158E-A232V-Q245R-N248D-H249R, S024R-S101G-S103A-V104I-P129E-L148I-A158E-S188D-A232V-Q245R-N248D, T022A-S101G-S103A-V104I-P129E-G159E-A232V-Q245R-N248D-H249R, S024R-S101G-S103A-V104I-G159E-S188D-A232V-N238R-Q245R-N248D, S024R-S101G-S103A-V104I-P129E-A158E-G159E-A232V-Q245R-N248D-H249R, S024R-S101G-S103A-V104I-P129E-A158E-G159E-A232V-N238R-Q245R-N248D, S024R-S101G-S103A-V104I-S128N-G159E-S188D-A232V-Q245R-N248D, T022A-S101G-S103A-V104I-G159E-S188D-A232V-Q245R-N248D-H249R, S024R-S101G-S103A-V104I-P129E-G159E-S188D-A232V-N238R-Q245R-N248D, S101G-S103A-V104I-A158E-A232V-N238R-Q245R-N248D, T022A-S101G-S103A-V104I-P129E-G159E-S188D-A232V-Q245R-N248D-H249R, S024R-S101G-S103A-V104I-P129E-L148I-S188D-A232V-Q245R-N248D, S024R-S101G-S103A-V104I-A158E-A232V-Q245R-N248D-H249R, T022A-S101G-S103A-V104I-A158E-G159E-A232V-N238R-Q245R-N248D, S024R-S101G-S103A-V104I-A158E-G159E-A232V-N238R-Q245R-N248D, T022A-S101G-S103A-V104I-P129E-A158E-G159E-A232V-Q245R-N248D-H249R, S101G-S103A-V104I-P129E-A158E-S188D-A232V-N238R-Q245R-N248D, T022A-S024R-S101G-S103A-V104I-P129E-A158E-G159E-A232V-Q245R-N248D, S101G-S103A-V104I-S188D-A232V-N238R-Q245R-N248D, T022A-S024R-S101G-S103A-V104I-A158E-A232V-Q245R-N248D-H249R, T022A-S024R-S101G-S103A-V104I-L148I-A158E-A232V-Q245R-N248D, S101G-S103A-V104I-P129E-A158E-G159E-A232V-N238R-Q245R-N248D, T022A-S101G-S103A-V104I-G159E-S188D-A232V-N238R-Q245R-N248D, T022A-S024R-S101G-S103A-V104I-P129E-A158E-G159E-S188D-A232V-Q245R-N248D-H249R, T022A-S101G-S103A-V104I-P129E-A232V-N238R-Q245R-N248D, T022A-S024R-S101G-S103A-V104I-S188D-A232V-Q245R-N248D-H249R, S101G-S103A-V104I-P129E-A158E-G159E-A232V-Q245R-N248D-H249R, T022A-S101G-S103A-V104I-A158E-G159E-A232V-Q245R-N248D-H249R, S101G-S103A-V104I-P129E-S188D-A232V-Q245R-N248D, S024R-S101G-S103A-V104I-P129E-G159E-A232V-N238R-Q245R-N248D, S101G-S103A-V104I-S128N-P129E-A232V-Q245R-N248D, S101G-S103A-V104I-A158E-S188D-A232V-Q245R-N248D, T022A-S024R-S101G-S103A-V104I-P129E-A232V-Q245R-N248D-H249R, S101G-S103A-V104I-P129E-G159E-A232V-N238R-Q245R-N248D, S101G-S103A-V104I-A158E-G159E-S188D-A232V-N238R-Q245R-N248D, S024R-S101G-S103A-V104I-A232V-Q245R-N248D-H249R, T022A-S024R-S101G-S103A-V104I-P129E-L148I-A232V-Q245R-N248D, T022A-S024R-S101G-S103A-V104I-A158E-A232V-N238R-Q245R-N248D, S101G-S103A-V104I-S128N-P129E-A232V-N238R-Q245R-N248D, T022A-S101G-S103A-V104I-S128N-G159E-A232V-Q245R-N248D, T022A-S101G-S103A-V104I-S128N-P129E-A158E-A232V-N238R-Q245R-N248D, S101G-S103A-V104I-S128N-P129E-S188D-A232V-Q245R-N248D-H249R, T022A-S024R-S101G-S103A-V104I-S128N-P129E-A158E-S188D-A232V-Q245R-N248D-H249R, S024R-S101G-S103A-V104I-S128N-A158E-G159E-S188D-A232V-Q245R-N248D, T022A-S024K-S101G-S103A-V104I-S128N-A158E-G159E-A232V-Q245R-N248D, S101G-S103A-V104I-P129E-L148I-S188D-A232V-Q245R-N248D, S024R-S101G-S103A-V104I-L148I-A232V-Q245R-N248D, T022A-S101G-S103A-V104I-L148I-S188D-A232V-Q245R-N248D, S024R-S101G-S103A-V104I-S128N-P129E-S188D-A232V-Q245R-N248D, S101G-S103A-V104I-S128N-P129E-A158E-A232V-N238R-Q245R-N248D, T022A-S024R-S101G-S103A-V104I-P129E-L148I-A158E-S188D-A232V-Q245R-N248D, T022A-S024R-S101G-S103A-V104I-L148I-A158E-S188D-A232V-Q245R-N248D, S101G-S103A-V104I-L148I-G159E-A232V-Q245R-N248D, T022A-S024R-S101G-S103A-V104I-A158E-S188D-A232V-Q245R-N248D, and S101G-S103A-V104I-S128N-P129E-A158E-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: T022A-S024R-S101G-S103A-V104I-A158E-A232V-Q245R-N248D-H249R, T022A-S024R-S101G-S103A-V104I-P129E-A232V-Q245R-N248D-H249R, S024R-S101G-S103A-V104I-A158E-G159E-A232V-N238R-Q245R-N248D, S024R-S101G-S103A-V104I-A232V-Q245R-N248D-H249R, S101G-S103A-V104I-A158E-A232V-Q245R-N248D-H249R, S101G-S103A-V104I-S188D-A232V-Q245R-N248D-H249R, S024R-S101G-S103A-V104I-G159E-S188D-A232V-Q245R-N248D-H249R, T022A-S024R-S101G-S103A-V104I-A158E-A232V-N238R-Q245R-N248D, S024R-S101G-S103A-V104I-G159E-S188D-A232V-N238R-Q245R-N248D, T022A-S024R-S101G-S103A-V104I-P129E-A232V-Q245R-N248D, S024R-S101G-S103A-V104I-L148I-A232V-Q245R-N248D, S024R-S101G-S103A-V104I-P129E-A158E-A232V-Q245R-N248D-H249R, S024R-S101G-S103A-V104I-L148I-A158E-A232V-Q245R-N248D, T022A-S024R-S101G-

S103A-V104I-P129E-A158E-A232V-Q245R-N248D-H249R, A016S-S024R-S101G-S103A-V104I-A158E-S188D-A232V-Q245R-N248D-H249R, S024R-S101G-S103A-V104I-P129E-G159E-A232V-N238R-Q245R-N248D, S024R-S101G-S103A-V104I-P129E-S188D-A232V-Q245R-N248D-H249R, T022A-S101G-S103A-V104I-P129E-A232V-N238R-Q245R-N248D, T022A-S024R-S101G-S103A-V104I-L148I-A158E-A232V-Q245R-N248D, S024R-S101G-S103A-V104I-P129E-S188D-A232V-N238R-Q245R-N248D, T022A-S024R-S101G-S103A-V104I-A158E-G159E-S188D-A232V-N238R-Q245R-N248D, T022A-S101G-S103A-V104I-A158E-G159E-A232V-N238R-Q245R-N248D, T022A-S024R-S101G-S103A-V104I-P129E-A158E-A232V-Q245R-N248D, S101G-S103A-V104I-A158E-S188D-A232V-Q245R-N248D-H249R, T022A-S101G-S103A-V104I-A158E-G159E-A232V-Q245R-N248D-H249R, and S024R-S101G-S103A-V104I-A158E-G159E-A232V-Q245R-N248D, wherein the amino acid positions of the subtilisin variant are numbered by correspondence with the amino acid sequence of *B. amyloliquefaciens* subtilisin BPN' set forth as SEQ ID NO: 1.

The present invention also provides isolated subtilisin variants, wherein the subtilisin variants are mature forms having proteolytic activity and comprise amino acid sequences comprising a combination of amino acid substitutions selected from: V104L-S128N-A158E-R186H-H249R, S128N-A158E-S188D-H249R, N062E-S128N-A158E-G159E-E271F, N062E-A158E-S188D-H249R-E271F, N062E-A158E-R186H-H249R-E271F, S128N-A158E-S188D-Y209E-E271F, N062E-G159E-S188D-H249R, A016S-N062E-A158E-R186H-H249R, N062E-A158E-G159E-H249R, S101A-S128N-A158E-Y209E-H249R, S128N-A158E-R186H-E271F, N062E-A158E-S188D-H249R, N062E-A158E-R186H-E271F, N062E-A158E-R186H-H249R, N062E-S101A-R186H-H249R, N062E-S101A-A158E-R186H-E271F, N062E-V104L-A158E-S188D-H249R-E271F, N062E-G159E-R186H-H249R, N062E-G159E-H249R, S128N-A158E-R186H-H249R, S128N-A158E-S188D-E271F, N062E-A158E-H249R, N062E-R186H-S188D-H249R-E271F, S128N-A158E-Y209E-, N062E-S101A-A158E-H249R, V104L-S128N-A158E-R186H-E271F, N062E-S101A-A158E-R186H-H249R-E271F, A016S-N062E-A158E-H249R, N062E-S101A-G159E-H249R, S128N-A158E-R186H-S188D-E271F, S101A-S128N-A158E-R186H-E271F, N062E-S101A-S188D-H249R, S101A-V104L-A158E-R186H-S188D-H249R, N062E-G159E-H249R-E271F, S128N-A158E-G159E-E271F, A016S-N062E-V104L-A158E-R186H-E271F, T022A-S128N-A158E-H249R, S128N-A158E-H249R, N062E-S101A-V104L-A158E-R186H-E271F, A016S-N062E-A158E-R186H-E271F, V104L-S128N-A158E-H249R, V104L-S128N-A158E-S188D-H249R, T022A-N062E-A158E, N062E-S101A-S188D-H249R-E271F, N062E-A158E-H249R-E271F, V104L-S128N-A158E-R186H-S188D-E271F, N062E-S101A-R186H-E271F, N062E-V104L-G159E-H249R, N062E-R186H-H249R, N062E-S101A-R186H-H249R-E271F, S101A-A158E-R186H-S188D-H249R, N062E-S101A-R186H, S101A-S128N-P129E-R186H-H249R, S101A-S103G-A158E-R186H-H249R, A016S-N062E-V104L-R186H-S188D-E271F, V104L-A158E-R186H-H249R, S101A-S128N-A158E-S188D-Y209E-E271F, N062E-S101A-R186H-S188D-E271F, A016S-N062E-A158E-H249R-E271F, N062E-S128N-A158E, N062E-S128N-G159E-H249R, N062E-S101A-A158E-S188D-H249R, S101A-S128N-A158E-H249R, N062E-A158E-R186H-S188D-H249R, A016S-V104L-A158E-R186H-E271F, N062E-L148I-G159E, N062E-S101A-A158E-R186H-H249R, N062E-S101A-R186H-S188D-H249R, V104L-A158E-R186H-S188D-H249R, N062E-S101A-V104L-R186H-S188D-E271F, T022A-S101A-A158E-R186H-H249R, S101A-S128N-A158E-Y209E, A158E-R186H-S188D-H249R-E271F, V104L-A158E-R186H-S188D-H249R-E271F, S101A-V104L-A158E-R186H-H249R, V104L-A158E-H249R, S101A-V104L-S128N-A158E-R186H-E271F, A016S-V104L-S188D-H249R, S101A-V104L-A158E-R186H-S188D-E271F, V104L-S128N-G159E-E271F, V104L-A158E-R186H-H249R-E271F, A158E-R186H-H249R, S101A-A158E-R186H-H249R, V104L-A158E-S188D-H249R-E271F, A016S-S128N-A158E-R186H, V104L-S128N-R186H-S188D-H249R, A016S-S101A-S128N-R186H, A016S-N062E-S128N-R186H-E271F, A016S-S128N-R186H-E271F, S128N-P129E-R186H, A158E-R186H-H249R-E271F, A016S-A158E-H249R, A016S-A158E-R186H-H249R, A016S-T022A-A158E-R186H-E271F, E089P-S101A-P129E-R186H, T022A-S128N-A158E-R186H, S101A-V104L-S128N-A158E-R186H, T022A-S128N-R186H-S188D-, N062E-V104L-A158E-R186H-S188D-H249R, T022A-A158E-R186H-H249R-E271F, T022A-V104L-A158E-H249R, S101A-L111V-P129E, A016S-A158E-H249R-E271F, A016S-L111V-S188D-, T022A-V104L-R186H-S188D-H249R, and V104L-L148I-S188D-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: A001R-S101G-S103A-V104I-A232V-Q245R, V004R-S101G-S103A-V104I-A232V-Q245R, N043R-S101G-S103A-V104I-A232V-Q245R-E271L, S078R-S101G-S103A-V104I-A232V-Q245R, V004R-N043R-S101G-S103A-V104I-A232V-Q245R, N018R-N043R-S101G-S103A-V104I-A232V-Q245R, G020R-S101G-S103A-V104I-A232V-Q245R, S101G-S103A-V104I-A232V-Q245R-E271L, G020R-N043R-S101G-S103A-V104I-A232V-Q245R, S024R-N043R-S101G-S103A-V104I-A232V-Q245R, G020R-G025R-N116A-Y167W, N018R-S101G-S103A-V104I-A232V-Q245R, T022R-S101G-S103A-V104I-A232V-Q245R, S078R-S103N-S106G-Y167W-Q236N, N018R-N043D-S101G-S103A-V104I-A232V-Q245R-N269R, N043R-S101G-S103A-V104I-A232V-Q245R-N269R, S024R-S101A-H120E-A194F-H249R, G020R-N043D-S101G-S103A-V104I-A232V-Q245R-N269R, S101G-S103A-V104I-S212F-A232V-Q245R, G020R-S144R-N185I-L233C-Q236N, G023A-S078R-S216F-Q236N-H249R, S101G-S103A-V104I-A232V-Q245R-N269R, S101G-S103A-V104I-G115R-A232V-Q245R, P052N-S078R-S103N-L148I-T213A, N018R-N043D-S101G-S103A-V104I-A232V-Q245R-H249R, S024R-N043D-S101G-S103A-V104I-A232V-Q245R-H249R, S024R-N043D-S101G-S103A-V104I-A232V-Q245R-N269R, G025R-E089I-N116A-P239S-A270C, S024R-S101G-S103A-V104I-A232V-Q245R, L148I-T213A-N252R, S024R-G025R-N183D-Y192W-P239S, G046R-A194F-S212M, V104L-L217E-T224A-H249R-N252R, G023A-Y091F-V121F-Y192W-Q236N, S101G-S103A-V104I-A232V-V244R-Q245R, S099F-S144R-Y167W-N252R, S101G-S103A-V104I-A232V-Q245R-H249R, N043R-S101G-

S103A-V104I-A232V-Q245R, T022W-S078R-Y167W-S212M-A270C, V121F-N252R-A270C, G020R-S103N-S216F-Q236N-N252R, N043R-S101G-S103A-V104I-A232V-Q245R-H249R, G023A-P052N-Y192W-I198L-N252R, G025R-G046R-V121F, S024R-S078R-V104L-N116A-N183D, G046R-Q059A-S103N-G211Q-S212M, G020R-P052N-N062Q-Y091F-Y192W, G023A-P052N-S144R-Y192W-S216F, S101G-S103A-V104I-A232V-S242R-Q245R, P052N-S103N-N116A-L148I-Y192W, E089I-N116A-N117F-T224A-H249R, S144R-G211Q-N238L-P239S-H249R, N043A-N062Q-A194F-G211Q, G020R-S024R-P052N-Q059A-S216F, S024R-Y167W-T224A-H249R, T057R-Y167W-H249R, G025R-S103N-R186K-A194F-T224A, S105T-S128N-S144R-L148I-S212M, G020R-Q059A-S144R-Y192W-T224A, S024R-N043A-N117F-A194F-G211Q, N117F-A 194F-T213A-A270C, S078R-Y091F-V121F-L233C-N252R, T057R-S099F-S105T-I198L-T213A, G023A-Y091F-S101A-I198L-N252R, N062Q-S103N-V121F-S144R-H249R, N043R-S101G-S103A-V104I-A232V-S242R-Q245R, G023A-S024R-N117F-S212M-S216F, V104L-T213A-S216F, A194F-G211Q-Q236N, N062Q-S103N-N117F-A194F, S024R-N062Q-V104L-S106G-H249R, T057R-E089I-I198L, G046R-Q059A-S106G-L217E-H249R, N117F-T213A-A215F, S101A-H120E-Y192W-A215F-T224A, N043A-T057R-N117F-S144R-N183D, G046R-N183D-N238L, G025R-N043A-E089I-N117F, S078R-V104L-T213A-A215F-T224A, Y091F-S099F-S101A-S105T-Y167W, S106G-N117F-N238L, G046R-E089I-Y091F-S101A-N116A, G020R-N062Q-E089I-R186K-S212M, T057R-S099F-V121F-N185I-Y192W, G046R-E089I-Y192W-L233C-A270C, E089I-N117F-N185I-A215F-L233C, P052N-V104L-N183D-S216F-H249R, S078R-S099F-N116A-R186K-T224A, G025R-S105T-S128N-S144R-A270C, S105T-G211Q-S216F, S024R-G046R-Y091F-V121F, S106G-N185I-S216F-Q236N, N062Q-S101A-Q236N-N252R-A270C, G025R-N043A-Y091F-I198L-A270C, G020R-G023A-V104L-Y192W-L233C, S024R-N043A-S105T-S106G-I198L, G020R-E089I-L217E, S024R-Y091F-I198L-A215F-P239S, G046R-E089I-S099F-R186K-S212M, V104L-H120E-R186K-S216F-N252R, T022W-A194F-T213A-L233C-N238L, S099F-S105T-S106G-A194F-S212M, E089I-S105T-N116A-A215F-S216F, G025R-N116A-H120E-T224A-A270C, N043A-Q059A-S101A-S216F-T224A, T057R-N183D-Q236N, G025R-N062Q-S128N-S144R-N185I, S103N-H120E-Y167W-I198L-L233C, T022W-E089I-S216F, S024R-S106G-N116A-S212M-T224A, G020R-P052N-S101A-I198L-L233C, E089I-Y091F-N185I-G211Q-A270C, L111I-A215F-P239S, S024R-N116A-R186K-L233C-Q236N, and G023A-S103N-S106G-S212M-A215F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: G020R-T022W-S078R-S101A-S103A-V104I-N116S-T213A-A215F-A232V-Q245R, N018R-S078R-S101G-S103A-V104I-A232V-Q245R, S024R-R045T-S101G-S103A-V104I-A232V-Q245R-N269R, G020R-T022W-S078R-S101G-S103A-V104I-N116A-A232V-Q245R, G020R-T22W-S101G-S103A-V104I-A232V-Q245R, N018R-N043R-S101G-S103A-V104I-A232V-Q245R, N018R-T022W-S024R-N076D-S101A-N116A-A232V-Q245R, N018R-V104I-A232V-H249R, N018R-S024R-N076D-S101A-N116A-G211Q-H249R, N018R-N043D-S078R-S101G-S103A-V104I-L217E-A232V-Q245R, N018R-N043R-S101G-S103A-V104I-A232V-Q245R-N269R, N018R-R045T-N076D-S101G-S103A-V104I-A232V-Q245R-N269R, N076D-S078R-S101G-S103A-V104I-A232V-Q245R-N269R, G020R-N043D-S078R-S101G-S103A-V104I-A232V-Q245R, N018R-N043D-N076D-S101G-S103A-V104I-A232V-Q245R-N269R, S024R-R045T-N076D-S078R-S101G-S103A-V104I-A232V-Q245R-N269R, N018R-S103A-A232V-H249R, N018R-S101G-V104I-A232V-Q245R, G020R-S024R-S101G-S103A-V104I-L217E-A232V-Q245R-H249R, N018R-T22K-N043D-S101G-S103A-V104I-A232V-Q245R, N043R-R045T-S101G-S103A-V104I-A232V-Q245R-N269R, G020R-T22W-S101G-S103A-V104I-G211Q-A232V-Q245R, S024R-N076D-S078R-S101G-S103A-V104I-A232V-Q245R-N269R, G020R-T22W-S078R-S101A-S103A-V104I-N116A-N183D-A232V, N018R-S024R-N076D-N116A-A215F-H249R, N018R-N043R-R045T-S101G-S103A-V104I-A232V-Q245R, S024R-N043R-N076D-S101G-S103A-V104I-A232V-Q245R, G020R-T022W-S101G-S103A-V104I-A232V-Q245R, G020R-T022W-S101G-S103A-V104I-G211Q-A232V-Q245R, G020R-T022W-S078R-S101G-S103A-V104I-N116A-T213A-A215F-A232V-Q245R, N043D-N076D-S078R-S101G-S103A-V104I-A232V-Q245R-N269R, N018R-S024R-N076D-S101A-N116A-T213A-H249R, N018R-S024R-N076D-N116A-G211Q-H249R, N043R-R045T-N076D-S078R-S101G-S103A-V104I-A232V-Q245R, N018R-S101G-Q245R, G020R-T22W-S101A-S103A-V104I-G211Q-T213A-A232V-Q245R, G020R-S024R-N043D-N076D-S078R-S101G-S103A-V104I-A232V-Q245R, N018R-R045T-N076D-S078R-S101G-S103A-V104I-A232V-Q245R, G020R-S078R-S101G-S103A-V104I-G211Q-T213A-A215F-A232V-Q245R, R045T-S078R-S101G-S103A-V104I-A232V-Q245R-N269R, S024R-N043D-S101G-S103A-V104I-A232V-Q245R-N269R, N018R-S101G-S103A-H249R, N018R-T22W-S024R-N076D-S101A-N116A-A232V-Q245R, N018R-S101G-V104I-A232V-H249R, G020R-T22W-S101A-S103A-V104I-A215F-A232V-Q245R, N018R-S024R-N076D-G211Q-T213A-H249R, N018R-T022W-S024R-N076D-S101A-I198L-H249R, S024R-S101G-S103A-V104I-A232V-Q245R, G020R-N076D-S101G-S103A-V104I-A232V-Q245R-N269R, G020R-S101G-S103A-V104I-A232V-Q245R-N269R, N043D-S078R-S101G-S103A-V104I-A232V-Q245R, G020R-S101G-V104I-T213A-A215F-A232V-Q245R, G020R-S101G-S103A-V104I-N116A-A215F-A232V-Q245R, S024R-S103A-V104I-H249R, N018R-N076D-S078R-S101G-S103A-V104I-A232V-Q245R, R045T-N076D-S078R-S101G-S103A-V104I-A232V-Q245R-N269R, S024R-S101G-V104I-Q245R, G020R-S101G-S103A-V104I-G211Q-T213A-A215F-A232V-Q245R, S024R-S103A-V104I-A232V-H249R, N018R-S024R-N076D-N116A-G211Q-A215F-H249R, N018R-Q245R, S024R-S103A-Q245R, S024R-S103A-V104I-Q245R, G020R-S078R-S101G-A232V-Q245R, N018R-S024R-N076D-V104I-H249R, N018R-S024R-V104I-H249R, S024R-S101G-S103A-V104I-A232V-Q245R, N018R-S024R-N076D-G211Q-A215F-H249R, R019H-G020R-T022W-S078R-S101G-S103A-V104I-G211Q-A232V-Q245R, N018R-S024R-N076D-S101A-I198L-G211Q-T213A-H249R, N018R-S024R-N043D-S101G-S103A-V104I-A232V-Q245R, G020R-T22W-S103A-V104I-A232V-Q245R, N018R-S103A-V104I-

H249R, N018R-T022W-S024R-N076D-S101A-I198L-A215F-H249R, N018R-S024R-S101G-V104I-A232V, S078R-S101G-S103A-V104I-A232V-Q245R-N269R, S024R-N043R-N076D-S078R-S101G-S103A-V104I-A232V-Q245R, N018R-G020R-N043D-N076D-S101G-S103A-V104I-A232V-Q245R, N018R-T22W-S024R-N076D-N116A-T213A-H249R, N018R-S024R-S101G-V104I, G020R-S101A-S103A-V104I-A215F-A232V-Q245R, N018R-R045T-S078R-S101G-S103A-V104I-A232V-Q245R, N018R-S101G-S103A-Q245R, N043R-N076D-S078R-S101G-S103A-V104I-A232V-Q245R, G020R-T022W-S101A-S103A-V104I-G211Q-A215F-A232V-Q245R, G020R-T22W-S078R-S101G-S103A-V104I-N116A-T213A-A215F-A232V-Q245R, G020R-S078R-S101G-S103A-V104I-A215F-A232V-Q245R, G020R-T022W-S078R-S101G-S103A-V104I-N116A-N183D-A232V-Q245R, N076D-S101G-S103A-V104I-A232V-Q245R, N076D-S101G-S103A-V104I-A232V-Q245R-N269R, G020R-T22W-S101A-S103A-V104I-A232V-Q245R, G020R-S101G-S103A-A232V-Q245R, G020R-T022W-S078R-S101A-S103A-V104I-N116A-N183D-A232V-Q245R, N018R-G020R-S024R-R045T-N076D-S101G-S103A-V104I-A232V-Q245R-N269R, N043R-R045T-S078R-S101G-S103A-V104I-A232V-Q245R, N018R-S101G-V104I-H249R, G020R-T22W-S078R-S101G-S103A-V104I-N116A-N183D-A232V-Q245R, G020R-T022W-S101G-S103A-V104I-I198L-G211Q-T213A-A232V-Q245R, G020R-S078R-S101A-S103A-V104I-N116A-N183D-T213A-A232V-Q245R, S024R-N076D-V104I-A232V-Q245R, N018R-G020R-N076D-S101G-S103A-V104I-A232V-Q245R, N018R-S024R-N076D-S101G-V104I-A232V-H249R, N018R-N043D-S078R-S101G-S103A-V104I-A232V-Q245R, A001T-N018R-S024R-N076D-N116A-T213A-H249R, N076D-S078R-S101G-S103A-V104I-A232V-Q245R, G020R-S078R-S101G-S103A-V104I-N116A-A232V-Q245R, N043R-N076D-S101G-S103A-V104I-A232V-Q245R, N018R-R045T-S101G-S103A-V104I-A232V-Q245R, N018R-N076D-S101G-V104I-A232V-Q245R, G020R-S078R-S101G-S103A-V104I-N116A-N183D-A232V-Q245R, N018R-S024R-N076D-S101A-G211Q-T213A-A215F-H249R, R045T-S078R-S101G-S103A-V104I-A232V-Q245R, N043R-N076D-S101G-S103A-V104I-A232V-Q245R-N269R, G020R-T022W-S078R-S101G-S103A-V104I-N116A-N183D-T213A-A232V-Q245R, G020R-T022W-S101G-S103A-V104I-N116A-N183D-T213A-A232V-Q245R, G020R-S101G-I198L-A215F-A232V-Q245R, N018R-S024R-N076D-T213A-A215F-H249R, G020R-S078R-S101G-S103A-V104I-N116A-G211Q-A232V-Q245R, G020R-T022W-S078R-S101A-S103A-V104I-N116A-N183D-A215F-A232V-Q245R, G020R-T022W-S078R-S101A-S103A-V104I-N116A-N183D-T213A-A232V-Q245R, S024R-A232V-Q245R, N018R-S024R-N043D-S101G-S103A-V104I-A232V-Q245R-N269R, N018R-S024R-N076D-S101A-A215F-H249R, N018R-T022W-S024R-N076D-N116A-T213A-H249R, S101G-S103A-V104I-A232V-Q245R, N018R-S024R-N076D-G211Q-T213A-A215F-H249R, N018R-S024R-N076D-N116A-T213A-A215F-H249R, N043D-N076D-S078R-S101G-S103A-V104I-A232V-Q245R-N269R, N043D-S078R-S101G-S103A-V104I-A232V-Q245R-H249R, G020R-T022W-S078R-S101G-S103A-V104I-N116A-N183D-G211Q-A232V-Q245R, N018R-S024R-N076D-S101A-I198L-G211Q-A215V-H249R, N018R-T022W-S024R-N076D-N116A-G211Q-H249R, G020R-S103A-V104I-A232V-Q245R, G020R-T22W-S101A-S103A-V104I-G211Q-A215F-A232V-Q245R, S024R-N076D-S101G-S103A-V104I-A232V-Q245R, G020R-S101G-S103A-V104I-N116A-A232V-Q245R, N018R-T22W-S024R-N076D-I198L-A215F-H249R, G020R-T022W-S103A-V104I-A232V-Q245R, G020R-T022W-S101A-S103A-V104I-G211Q-T213A-A232V-Q245R, G020R-T022W-S101G-S103A-V104I-G211Q-T213A-A215F-A232V-Q245R, N018R-N043R-R045T-N076D-S101G-S103A-V104I-A232V-Q245R, N018R-T022W-S024R-N076D-S101A-I198L-T213A-A215F-H249R, N018R-T22W-S024R-N076D-S101A-A215F-H249R, G020R-R045T-S101G-S103A-V104I-A232V-Q245R, G020R-S078R-S101G-S103A-V104I-T180A-A232V-Q245R, G020R-T022W-S078R-S101G-S103A-V104I-N116A-N183D-A215F-A232V-Q245R, N018R-S101G-S103A-V104I, G020R-T22W-S101A-S103A-V104I-N116A-G211Q-T213A-A215F-A232V-Q245R, N018R-S024R-N076D-S103A-A232V-Q245R, G020R-S078R-S101A-S103A-V104I-N116A-N183D-A232V-Q245R, N018R-S024R-N076D-G211Q-H249R, G020R-S101A-S103A-V104I-T213A-A215F-A232V-Q245R, N018R-G020R-N043D-S101G-S103A-V104I-A232V-Q245R, G020R-T022W-S101A-S103A-V104I-G211Q-A232V-Q245R, G020R-T022W-S101A-S103A-V104I-N116A-G211Q-A215F-A232V-Q245R, G020R-T022W-S101A-S103A-V104I-N116A-G211Q-A232V-Q245R, N018R-S024R-N076D-A232V-H249R, N018R-S024R-R045T-N076D-S101G-S103A-V104I-A232V-Q245R-N269R, N018R-N076D-Q245R, S024R-V104I-Q245R, S101G-A232V, G020R-T22W-S101A-S103A-V104I-N116A-G211Q-A215F-A232V-Q245R, N018R-G020R-T022W-S024R-N076D-N116A-N183D-I198L-T213A-H249R, G020R-T022W-S078R-S101A-S103A-V104I-A232V-Q245R, G020R-T022W-S078R-S101A-S103A-V104I-I198L-A232V-Q245R, S024R-Q245R-H249R, G020R-S101G-S103A-V104I-N116A-G211Q-A232V-Q245R, N018R-T22W-S024R-N076D-N116A-G211Q-H249R, S024R-S101G-V104I-H249R, N018R-S024R-N076D-N116A-I198L-G211Q-T213A-A215F-H249R, N018R-S024R-V104I, G020R-T022W-S078R-S101A-S103A-V104I-N183D-I198L-T213A-A215F-A232V-Q245R, N018R-G020R-T22W-S024R-N076D-N116A-N183D-I198L-T213A-H249R, G020R-T022W-S101A-S103A-V104I-A232V-Q245R, Q012H-G020R-S078R-S101G-S103A-V104I-I198L-G211Q-T213A-A232V-Q245R, N018R-S024R-N076D-S101A-G211Q-A215F-H249R, N018R-S024R-N076D-T213A-H249R, S024R-V104I-H249R, N018R-T022W-S024R-N076D-G211Q-H249R, N018R-N076D-S103A-V104I-H249R, N043R-N076D-S101G-S103A-V104I-L217E-A232V-Q245R, G020R-S078R-S101G-S103A-V104I-N183D-G211Q-T213A-A232V-Q245R-E271G, N018R-T022W-S024R-N076D-S101A-N116A-I198L-A215F-H249R, N018R-S024R-N043D-N076D-S101G-S103A-V104I-A232V-Q245R, N018R-S024R-N076D-S101A-I198L-A215F-H249R, N018R-T022W-S024R-N076D-N116A-I198L-G211Q-T213A-H249R, N018R-S024R-N076D-S101A-N116A-T213A-A215F-H249R, G020R-N043D-R045T-S078R-S101G-S103A-V104I-A232V-Q245R, R045T-S078R-S101G-S103A-V104I-A232V-Q245R-H249R, N018R-T22W-S024R-N076D-S101A-N116A-A215F-H249R, N043D-S101G-S103A-V104I-A232V-Q245R-N269R, G020R-T022W-S078R-S101A-S103A-V104I-N116A-N183D-T213A-A215F-A232V-Q245R, N018R-S024R-N076D-N116A-G211Q-T213A-A215F-H249R, S024R-S103A-M175L-A232V-H249R, N018R-S024R-N076D-N116A-T213A-H249R, G020R-R045T-N076D-S101G-S103A-V104I-A232V-Q245R, G020R-

S078R-S101A-S103A-V104I-N116A-N183D-G211Q-T213A-A215F-A232V-Q245R, S024R-N043R-R045T-N076D-S078R-S101G-S103A-V104I-A232V-Q245R, N018R-S024R-N076D-S101A-N116A-I198L-T213A-A215F-H249R, N043R-R045T-S101G-S103A-V104I-A232V-Q245R, N018R-T022W-S024R-N076D-S101A-I198L-G211Q-Q245R, G020R-S024R-N043D-N076D-S078R-S101G-S103A-V104I-A232V-Q245R-N269R, S024R-A232V, G020R-S078R-S101A-S103A-V104I-N116A-N183D-G211Q-A232V-Q245R, S024R-N076D-S101G-A232V-Q245R, N018R-N076D-S101G-S103A-V104I-H249R, N018R-S024R-N076D-I198M-G211Q-T213A-A215F-H249R, N018R-T22W-S024R-N076D-S101A-I198L-A215F-H249R, N018R-N043R-N076D-S101G-S103A-V104I-A232V-Q245R-N269R, G020R-T022W-S103A-G211Q-T213A-A215F-A232V-Q245R, G020R-S078R-S101A-S103A-V104I-N116A-N183D-G211Q-T213A-A232V-Q245R, R045T-N076D-S101G-S103A-V104I-A232V-Q245R-N269R, N018R-T22W-S024R-N076D-S101A-G211Q-T213A-H249R, N018R-S024R-N076D-N116A-I198L-A215F-H249R-V268G, N018R-T022W-S024R-N076D-S101A-G211Q-H249R, N018R-T022W-S024R-N076D-S101A-N116A-I198L-G211Q-H249R, S101G-S103A-V104I-Q245R, N018R-N076D-S101G-A232V-Q245R, N018R-G020R-R045T-S101G-S103A-V104I-A232V-Q245R, N018R-T022W-S024R-N076D-S101A-N116A-I198L-H249R, N018R-T022W-S024R-N076D-N116A-I198L-T213A-H249R, S078R-S101G-S103A-V104I-A232V-Q245R-H249R, N018R-S078R-S101G-S103A-V104I-L217E-A232V-Q245R, G020R-N043R-N076D-S101G-S103A-V104I-A232V-Q245R-N269R, N018R-N043D-N076D-S101G-S103A-V104I-A232V-Q245R-H249R, R045T-S101G-S103A-V104I-A232V-Q245R-N269R, S024R-S103A-A232V, N018R-S024R-N076D-S101A-G211Q-H249R, N043D-S101G-S103A-V104I-A232V-Q245R-H249R, N018R-N043R-R045T-N076D-S076T-S101G-S103A-V104I-A232V-Q245R-A273T, N018R-G020R-N043D-S078R-S101G-S103A-V104I-A232V-Q245R, G020R-S078R-S101A-S103A-V104I-N183D-A215F-A232V-Q245R, N018R-S024R-N076D-S101G-A232V, A232V-Q245R, N043R-R045T-N076D-S078R-S101G-S103A-V104I-A232V-V234I-Q245R, S024R-N076D-S103A-V104I-Q245R, G020R-S078R-S101A-S103A-V104I-G211Q-T213A-A232V-Q245R, N043D-S078R-S101G-S103A-V104I-A232V-Q245R-N269R-A272V, N018R-G020R-S024R-N076D-N116A-N183D-I198L-G211Q-H249R, N018R-S103A-V104I-A232V, G020R-T022W-S101G-S103A-V104I-N116A-N183D-T213A-A215F-A232V-Q245R, S024R-N043R-N076D-S101G-S103A-V104I-A232V-Q245R-N269R, N018R-T022W-S024R-N076D-T213A-A215F-H249R, N018R-S024R-N076D-S101A-N116A-I198L-G211Q-T213A-H249R, G020R-T22W-S078R-S101A-S103A-V104I-N116A-N183D-T213A-A232V-Q245R, G020R-T022W-S078R-S101G-S103A-V104I-G211Q-T213A-A232V-Q245R, G020R-T022W-S101A-S103A-V104I-A215F-A232V-Q245R, N018R-G020R-S024R-N076D-N116A-N183D-A215F-H249R, N018R-S024R-N076D-N116A-M117I-N183D-T213A-H249R, N018R-T022W-S024R-N076D-S101A-N116A-I198L-T213A-H249R, N018R-T22W-S024R-N076D-S101A-I198L-T213A-A215F-H249R, N018R-N043D-S078R-S101G-S103A-V104I-A232V-Q245R-H249R, N018R-N076D-S101G-S103A-V104I-A232V-Q245R-H249R, G020R-T022W-S101G-S103A-V104I-N116A-N183D-I198L-A232V-Q245R, N018R-N043R-R045T-N076D-S101G-S103A-V104I-A232V-Q245R-N269R, N018R-S024R-N076D-N116A-I198L-Y209H-T213A-H249R, G020R-T022W-S101A-S103A-V104I-N116A-N183D-G211Q-T213A-A232V-Q245R, S024R-N076D-S101G-M175L-A232V-Q245R, N018R-N043D-R045T-S101G-S103A-V104I-A232V-Q245R, R045T-N076D-S078R-S101G-S103A-V104I-A232V-Q245R, G020R-S078R-S101A-S103A-V104I-N116A-N183D-I198L-A215F-A232V-Q245R, N043R-N076D-S101G-S103A-V104I-A232V-Q245R-H249R, N018R-S024R-N076D-I198L-T213A-A215F-H249R, N018R-T022W-S024R-N076D-I198L-A215F-H249R, N018R-T022W-S024R-N076D-N116A-T213A-A215F-H249R, N018R-T022W-S024R-N076D-S101A-N116A-I198L-T213A-A215F-H249R, N018R-T022W-S024R-N076D-N116A-G211Q-T213A-H249R, N018R-S024R-Q245R, N018R-T022W-S024R-N076D-S101A-N116A-A215F-H249R, S024R-N076D-V104I-Q245R, K027R-N043R-S101G-S103A-V104I-A232V-Q245R-N269R, N018R-S024R-N076D-N116A-I198L-G211Q-T213A-H249R, N018R-S024R-N076D-N116A-I198L-H249R, N018R-S024R-N076D-N183D-I198L-G211Q-T213A-A215F-H249R, G020R-T022W-S101A-S103A-V104I-N116A-G211Q-T213A-A215F-A232V-Q245R, N018R-N043D-R045T-S078R-S101G-S103A-V104I-A232V-Q245R, N043R-R045T-N076D-S078R-S101G-S103A-V104I-A232V-Q245R-N269R, N018R-T22W-S024R-N076D-N116A-T213A-A215F-H249R, N018R-T022W-S024R-N076D-N116A-G211Q-A215F-H249R, G020R-S078R-S101G-S103A-V104I-N116A-N183D-T213A-A232V-Q245R, N018R-N076D-S101G-S103A-V104I-A232V-Q245R, N018R-S101G-V104I, G020R-S078R-S101G-S103A-V104I-N116A-N183D-G211Q-T213A-A215F-A232V-Q245R, G020R-S078R-S101A-S103A-V104I-A232V-Q245R, N018R-S024R-N076D-S101A-I198L-G211Q-H249R, N018R-S024R-N076D-I198L-G211Q-T213A-H249R, N018R-T022W-S024R-N076D-S101A-N116A-I198L-G211Q-T213A-H249R, N018R-N076D-H249R, N018R-G020R-S024R-N076D-S101A-N116A-N183D-I198L-H249R, N018R-S024R-N076D-S101A-N116A-G211Q-T213A-H249R, G020R-T022W-S078R-S101A-S103A-V104I-N116A-N183D-G211Q-T213A-A215F-A232V-Q245R, G020R-T022W-S101G-S103A-V104I-A114T-T213A-A215F-A232V-Q245R, N018R-T22W-S024R-N076D-N116A-G211Q-T213A-H249R, N018R-G020R-T022W-S024R-N076D-S101A-N116A-N183D-H249R, G020R-S101A-S103A-V104I-N116A-N183D-T213A-A232V-Q245R, N018R-T022W-S024R-N076D-S101A-G211Q-T213A-H249R, N018R-T022K-N043D-S101G-S103A-V104I-A232V-Q245R, N018R-S101G-S103A-V104I-A232V-Q245R-N269R, G020R-S078R-S101G-S103A-V104I-N116A-N183D-G211Q-T213A-A215F-A232V, N018R-S024R-N076D-N116A-H249R, G020R-S024R-N076D-S101G-S103A-V104I-A232V-Q245R, N043D-N076D-S101G-S103A-V104I-A232V-Q245R-N269R, N018R-S024R-N076D-S101A-N116A-I198L-G211Q-H249R, N018R-T022W-S024R-N076D-I198L-T213A-A215F-H249R, N018R-N043D-N076D-S078R-S101G-S103A-V104I-A232V-Q245R-N269R, G020R-T22W-S101G-S103A-V104I-N116A-N183D-T213A-A215F-A232V-Q245R, G020R-S101G-S103A-V104I-N183D-G211Q-A232V-Q245R-, N018R-S024R-N076D-S101A-I198L-T213A-H249R, N018R-S024R-N076D-S101A-I198L-H249R, N018R-S024R-R045T-N076D-S101G-S103A-V104I-A232V-Q245R-H249R, N018R-S024R-N076D-S101A-N183D-T213A-H249R, N018R-N043D-N076D-S078R-S101G-S103A-V104I-A232V-Q245R, G020R-S078R-S101G-S103A-V104I-

N116A-A131V-N183D-T213A-A232V-Q245R, N018R-R045T-N076D-S101G-S103A-V104I-A232V-Q245R, N018R-S024R-N076D-S101A-N183D-G211Q-H249R, N076D-S101G-S103A-V104I-A232V-Q245R-H249R, S024R-S101G-Q245R, S024R-N076D-S101G-Q245R, N076D-S078R-S101G-S103A-V104I-A232V-Q245R-H249R, N018R-G020R-S024R-N076D-S101A-N183D-G211Q-A215F-H249R, S024R-S101G, N018R-T22W-S024R-N076D-T213A-A215F-H249R, G020R-N043D-S101G-S103A-V104I-A232V-Q245R, G020R-T022W-S101G-S103A-V104I-N183D-I198L-T213A-A215F-A232V-Q245R, N018R-N043D-R045T-S101G-S103A-V104I-A232V-Q245R-N269R, N043D-N076D-S078R-S101G-S103A-V104I-A232V-Q245R, S024R-R045 T-N076D-S101G-S103A-V104I-A232V-Q245R-N269R, G020R-T022W-S101A-S103A-V104I-I198L-G211Q-A215F-A232V-Q245R, G020R-T022W-S101G-S103A-V104I-N116A-N183D-A215F-A232V-Q245R, N018R-G020R-N076D-S101G-S103A-V104I-A232V-Q245R-H249R, N018R-T022W-S024R-N076D-S101A-A215F-H249R, N018R-V104I, N018R-S024R-N076D-N116A-I198L-A215F-H249R, N018R-S024R-N076D-L088I-S101A-N116A-I198L-G211Q-A215F-H249R, N018R-T022W-S024R-N076D-S101A-N116A-G211Q-T213A-H249R, N043R-R045T-N076D-S101G-S103A-V104I-A232V-Q245R-N269R, N018R-N076D-S101G-V104I-H249R, N018R-T022W-S024R-N076D-S101A-T213A-A215F-H249R, N018R-T22W-S024R-N076D-S101A-N116A-I198L-A215F-H249R, N018R-G020R-S101G-S103A-V104I-A232V-Q245R-H249R, S101G-S103A-V104I-A232V-Q245R-H249R-N269R, S024R-N076D-Q245R, N018R-G020R-N043R-R045T-N076D-S101G-S103A-V104I-A232V-Q245R, N018R-G020R-S024R-N076D-A215F-H249R, N018R-S024R-N076D-S101A-N116A-N183D-I198L-T213A-H249R, N018R-G020R-S024R-N076D-G211Q-A215F-H249R, N043D-S101G-S103A-V104I-A232V-Q245R, G020R-T22W-S078R-S101A-S103A-V104I-N116A-N183D-A215F-A232V-Q245R, N018R-S024R-N076D-I198L-G211Q-A215F-H249R, N043R-N076D-S078R-S101G-S103A-V104I-A232V-Q245R-N269R, N043R-S078R-S101G-S103A-V104I-A232V-Q245R-N269R, G020R-N043D-S101G-S103A-V104I-A232V-Q245R-H249R, N018R-T022W-S024R-N076D-S101A-T213A-H249R, G020R-T022W-S101A-N116A-I198L-G211Q-T213A-A215F-H249R, N043R-R045T-S078R-S101G-S103A-V104I-N218S-A232V-Q245R, N018R-S103A, G020R-T22W-S101G-S103A-V104I-N116A-N183D-A215F-A232V-Q245R, N018R-S024R-N076D-S101A-H249R, N018R-T022W-S024R-N076D-G211Q-T213A-H249R, S024R-N043R-R045T-N076D-S101G-S103A-V104I-A232V-Q245R, G020R-T022W-S101A-S103A-V104I-N116A-N183D-A232V-Q245R, G020R-S101A-S103A-V104I-N116A-N183D-G211Q-T213A-A215F-A232V-Q245R, K027R-R045T-N076D-S078R-S101G-S103A-V104I-A232V-Q245R-N269R, G020R-R045T-N076D-S101G-S103A-V104I-A232V-Q245R-H249R, N018R-G020R-S024R-N076D-N116A-N183D-T213A-A215F-H249R, N018R-S024R-N076D-V104I, S101G-S103A-V104I-A232V-H249R, N018R-S024R-N076D-N116A-N183D-G211Q-H249R, N018R-G020R-S024R-N076D-N116A-A215F-H249R, N018R-S024R-N076D-N183D-T213A-A215F-H249R, N018R-T022W-S024R-N076D-I198L-G211Q-H249R, N043D-S078R-S101G-S103A-V104I-A232V-Q245R-N269R-R275S, G020R-T022W-S101A-S103A-V104I-N116A-N183D-G211Q-A232V-Q245R, N018R-T022W-S024R-N076D-S101A-I198L-G211Q-T213A-A215F-H249R, N018R-T022W-S024R-N076D-S101A-N116A-I198L-G211Q-T213A-A215F-H249R, N018R-G020R-S024R-N076D-N183D-H249R, N018R-S024R-N076D-N116A-I198L-T213A-H249R, N018R-T022W-S024R-N076D-S101A-N116A-G211Q-H249R, V004M-N018R-S024R-N076D-N116A-I198L-G211Q-T213A-H249R, V104I-A232V-H249R, G020R-T022W-S101G-S103A-V104I-N116A-N183D-G211Q-A215F-A232V-Q245R, G020R-S101A-S103A-V104I-N116A-N183D-G211Q-A232V-Q245R-T274I, G020R-S101A-S103A-V104I-T213A-A232V-Q245R, G020R-S101G-S103A-V104I-N116A-N183D-G211Q-T213A-A232V-Q245R, G020R-S024R-N043D-S078R-S101G-S103A-V104I-A232V-Q245R, N018R-S024R-N076D-S103A-H249R, N018R-G020R-S024R-N076D-S101A-N116A-N183D-G211Q-A215F-H249R, N018R-G020R-S024R-N076D-N116A-N183D-I198L-H249R, N018R-T022W-S024R-N076D-N116A-I198L-A215F-H249R, N018R-S024R-N076D-S101A-G211Q-T213A-A215F-H249R-A270V, N018R-N043D-R045T-N076D-S078R-S101G-S103A-V104I-A232V-Q245R-N269R, G020R-T022W-S101G-S103A-V104I-N183D-A232V-Q245R, N018R-G020R-T022W-S024R-N076D-S101A-N116A-T213A-H249R, N018R-T022W-S024R-N076D-I198L-G211Q-A215F-H249R, N018R-T022W-S024R-N076D-I198L-T213A-H249R, G020R-T022W-S101G-S103A-V104I-N116A-N183D-A232V-Q245R, N018R-T22W-S024R-N076D-N116A-I198L-T213A-H249R, N043R-R045T-S078R-S101G-S103A-V104I-A232V-Q245R-N269R, N018R-S024R-N076D-S101G-S103A-V104I-A232V, S101G-H249R, S024R-N076D-S101G-S103A-V104I-M175L-H249R, G020R-T022W-S101A-S103A-V104I-N116A-N183D-A232V-Q245R-N269S, N018R-S024R-N076D-S101A-N116A-I198L-H249R, N018R-T022W-S024R-N076D-N116A-H249R, N018R-G020R-S024R-N076D-S101A-N183D-I198L-A215F-H249R, N018R-S024R-N076D-T213A-A215F-H249R-T260K, N018R-S024R-N076D-N116A-G211Q-T213A-H249R, N018R-G020R-T022W-S024R-N076D-N116A-I198L-H249R, S024R-N076D-S101G-S103A-V104I-Q245R, S024R-N076D-S103A-H249R, N018R-S101G-S103A-V104I-A232V-Q245R-H249R, N018R-S024R-N076D-I198L-G211Q-H249R, N018R-T022W-S024R-N076D-S101A-I198L-G211Q-T213A-H249R, G020R-S024R-R045T-S101G-S103A-V104I-A232V-Q245R, N018R-G020R-S024R-N076D-N183D-G211Q-T213A-H249R, N018R-N043D-R045T-S078R-S101G-S103A-V104I-A232V-Q245R-A272D, N018R-S024R-N076D-N116A-I198L-T213A-A215F-H249R, N018R-T22W-S024R-N076D-S101A-I198L-H249R, N018R-T022W-S024R-N076D-N116A-I198L-H249R, S024R-N076D-S101G-S103A-A232V, S024R-S103A-V104I, N018R-S024R-N076D-S101A-N116A-N183D-G211Q-A215F-H249R, S024R-R045T-N076D-S101G-S103A-V104I-A232V-Q245R-H249R, G020R-S101G-S103A-V104I-N116A-N183D-A232V-Q245R, S024R-N043D-N076D-S101G-S103A-V104I-A232V-Q245R-N269R, G020R-T022W-S101A-S103A-V104I-N183D-G211Q-T213A-A215F-A232V-Q245R, G020R-R045T-N076D-S078R-S101G-S103A-V104I-A232V-Q245R-N269R, N018R-S024R-N076D-S101A-N116A-I198L-G211Q-A215F-H249R, G020R-S101A-S103A-V104I-N116A-N183D-A215F-A232V-Q245R, N018R-N043R-S101G-S103A-V104I-A232V-Q245R-H249R, N018R-S024R-N076D-I198L-T213A-H249R, N018R-S024R-N076D-N116A-N183D-T213A-H249R, G020R-N043D-S101G-S103A-V104I-A232V-Q245R-N269R, S024R-N076D-S103A-Q245R, N018R-T022W-

S024R-N076D-S101A-N116A-G211Q-T213A-A215F-H249R, S103A-V104I-Q245R, N018R-T022W-S024R-N076D-G211Q-A215F-H249R, N018R-T022W-S024R-N076D-N116A-N183D-I198L-H249R, N018R-T022W-S024R-N076D-I198L-G211Q-T213A-H249R, N018R-S024R-N076D-N116A-N183D-G211Q-T213A-A215F-H249R, N018R-G020R-N043D-R045T-N076D-S101G-S103A-V104I-A232V-Q245R-N269R, N018R-G020R-T022W-S024R-N076D-S101A-G211Q-T213A-A215F-H249R, A016T-N043R-R045T-N076D-S101G-S103A-V104I-A232V-Q245R-N269R, N018R-T022W-S024R-N076D-N116A-A215F-H249R, N043R-N076D-S101G-S103T-V104I-A232V-Q245R-H249R-N269R, G020R-S078R-S101A-S103A-V104I-G115E-N116A-N183D-G211Q-T213A-A232V-Q245R, N018R-S024R-N076D-I198L-H249R, N018R-S024R-N076D-S101A-N116A-N183D-H249R, G020R-S101G-S103A-V104I-N116A-N183D-G211Q-A232V-Q245R, N018R-S024R-N076D-S101G, N076D-S101G-A232V-Q245R, N018R-N076D-S101G-S103A-V104I-Q245R, N018R-R045T-S101G-S103A-V104I-A232V-Q245R-H249R, N018R-S024R-N076D-A215F-H249R, N018R-V104I-A232V, N043D-R045T-N076D-S078R-S101G-S103A-V104I-A232V-Q245R, S024R-N076D-S101G-A232V-H249R, S103A-A232V-Q245R, G020R-S101G-S103A-V104I-N116A-N183D-G211Q-T213A-A215F-A232V-Q245R, N018R-G020R-S024R-N076D-N116A-N183D-I198L-G211Q-A215F-H249R, N018R-T022W-S024R-N076D-S101A-I198L-G211Q-A215F-H249R, S024R-N076D-S103A-V104I-H249R, S024R-S101G-S103A-V104I, G020R-S101G-S103A-V104I-N116A-N183D-G211Q-A215F-A232V-Q245R, N018R-T022W-S024R-N076D-S101A-N116A-N183D-A215F-H249R, G020R-T022W-S101G-S103A-V104I-N116A-N183D-G211Q-T213A-A215F-A232V-Q245R, G020R-S024R-R045T-N076D-S101G-S103A-V104I-A232V-Q245R, N018R-T022W-S024R-N076D-N116A-N183D-T213A-H249R, N018R-G020R-S024R-N076D-A131T-A215F-H249R, N018R-S024R-N076D-S101A-N116A-N183D-G211Q-T213A-A215F-H249R, N018R-S024R-N076D-S101A-N116A-G211Q-T213A-A215F-H249R, N018R-S024R-N076D-I198L-A215F-H249R, N018R-T022W-S024R-N076D-N183D-G211Q-H249R, N018R-T022W-S024R-N076D-S101A-N116A-T213A-A215F-H249R, N018R-G020R-S024R-R045T-N076D-S101G-S103A-V104I-A232V-Q245R, N043R-S101G-S103A-V104I-Q245R-H249R, N018R-N076D-A232V-H249R, NO 18K-N076D-S078R-S101G-S103A-V104I-L217E-A232V-Q245R-N269R, N018R-G020R-S024R-N043D-N076D-S078R-S101G-S103A-V104I-A232V-Q245R, N018R-T022W-S024R-N076D-S101A-N116A-T213A-A215F-H249R-L267I, A232V-H249R, N018R-G020R-S024R-N076D-N116A-G211Q-T213A-A215F-H249R, N076D-V104I-Q245R, N018R-G020R-S024R-N076D-N183D-I198L-G211Q-A215F-H249R, N018R-S024R-N076D-S101A-G211Q-T213A-H249R, S024R-S101G-S103A-A232V, N018R-G020R-T022W-S024R-N076D-N116A-N183D-I198L-T213A-A215F-H249R, N018R-G020R-S024R-N076D-N116A-N183D-I198L-G211Q-T213A-H249R, N018R-G020R-T022W-S024R-N076D-S101A-A215F-H249R, G020R-T022W-S101A-S103A-V104I-N116A-N183D-G211Q-A215F-A232V-Q245R, N018R-S024R-N076D-N116A-I198L-G211Q-H249R, S103A-A232V-H249R, N018R-G020R-S024R-N076D-N116A-N183D-I198L-A215F-H249R, N018R-S024R-N076D-N116A-N183D-I198L-T213A-H249R, N018R-T022W-S024R-N076D-N183D-T213A-H249R, N018R-S024R-N076D-S101A-T213A-A215F-H249R, N018R-T022W-S024R-N076D-S101A-N116A-N183D-G211Q-H249R, N018R-R045T-S101G-S103A-V104I-A232V-Q245R-N269R, N018R-G020R-R045T-N076D-S078R-S101G-S103A-V104I-A232V-Q245R, N018R-T022W-S024R-N076D-N116A-I198L-T213A-A215F-H249R, G020R-T022W-S101G-S103A-V104I-N116A-N183D-G211Q-T213A-A232V-Q245R, N018R-G020R-S024R-N076D-I198L-H249R, N018R-G020R-T022W-S024R-N076D-S101A-N116A-G211Q-H249R, G020R-T022W-S101A-S103A-V104I-N116A-N183D-A232V-Q245R-T274I, S024R-S103A-Q245R-H249R, N018R-T022W-S024R-N076D-S101A-N116A-N183D-I198L-H249R, N018R-S024R-N076D-S101A-I198L-G211Q-A215F-H249R, N018R-T022W-S024R-N076D-N116A-I198L-G211Q-A215F-H249R, N018R-G020R-T022W-S024R-N076D-N116A-N183D-T213A-H249R, N018R-N043D-R045T-N076D-S101G-S103A-V104I-A232V-Q245R-N269R, N018R-T022W-S024R-N076D-N116A-G211Q-T213A-A215F-H249R, N018R-S024R-N076D-S101A-N183D-I198L-T213A-H249R, N043D-N076D-S101G-S103A-V104I-A232V-Q245R-H249R, N018R-S024R-N076D-I198L-G211Q-T213A-A215F-H249R, N018R-G020R-S024R-N076D-N116A-N183D-T213A-H249R, S103A-A232V, N018R-T022W-S024R-N076D-N116A-N183D-A215F-H249R, N018R-S024R-N076D-S101A-N116A-H249R, N018R-N043R-S078R-S101G-S103A-V104I-A232V-Q245R, N018R-G020R-T022W-S024R-N076D-S101A-N183D-G211Q-A215F-H249R, N043R-N076D-S078R-S101G-S103A-V104I-A232V-Q245R-H249R, N018R-G020R-S024R-N076D-S101A-N116A-N183D-I198L-T213A-H249R, N018R-S024R-N076D-N183D-I198L-T213A-H249R, N018R-T022W-S024R-N076D-S101A-N183D-G211Q-H249R, N018R-G020R-S024R-N076D-I198L-T213A-A215F-H249R, N018R-G020R-T022W-S024R-N076D-N183D-G211Q-T213A-H249R, N018R-T022W-S024R-N076D-I198L-H249R, N018R-S024R-N076D-N183D-I198L-G211Q-H249R, G020R-T022W-S101A-S103A-V104I-N116A-N183D-T213A-A232V-Q245R, N018R-G020R-S024R-N076D-N116A-N183D-G211Q-T213A-H249R, N018R-S024R-N076D-N116A-N183D-I198L-G211Q-T213A-A215F-H249R, G020R-T022W-S101A-S103A-V104I-N116A-N183D-A215F-A232V-Q245R, N018R-S024R-N076D-S101A-N183D-H249R, N018R-S024R-N076D-A232V, N018R-T022W-S024R-N076D-S101A-N116A-H249R, G020R-S101A-S103A-V104I-N116A-N183D-I198L-G211Q-T213A-A215F-A232V-Q245R, G020R-T022W-S101G-S103A-V104I-N116A-N183D-G211Q-A232V-Q245R-N263S, S024R-N076D-S101G-V104I-A232V-H249R, N043R-S078R-S101G-S103A-V104I-A232V-Q245R, S024R-N076D-S078R-S101G-S103A-V104I-A232V-Q245R-H249R, N018R-S024R-N076D-S101A-N183D-I198L-T213A-A215F-H249R, N018R-G020R-S024R-N076D-I198L-A215F-H249R, N018R-G020R-S024R-N076D-S101A-N116A-T213A-H249R, N018R-S024R-N076D-S101A-V197A-T213A-A215F-H249R, S024R-S101G-S103A, N018R-S024R-N076D-S101A-N116A-G211Q-A215F-H249R, N043R-N076D-S078R-S101G-S103A-V104I-L217E-A232V-Q245R, S024R-V104I-A232V, N018R-S024R-N076D-N183D-G211Q-H249R, G020R-N043R-R045T-S078R-S101G-S103A-V104I-A232V-Q245R, N018R-G020R-T022W-S024R-N076D-S101A-N116A-N183D-T213A-H249R, N018R-S024R-N076D-N116A-A150T-T213A-H249R, N018R-S024R-N076D-N183D-T213A-H249R, N018R-G020R-S024R-N076D-N116A-N183D-G211Q-A215F-H249R, N018R-G020R-S024R-N076D-

G211Q-H249R, N018R-S024R-N076D-S101A-N116A-N183D-I198L-H249R, S024R-N076D-A232V-H249R, N018R-G020R-T022W-S024R-N076D-S101A-N116A-N183D-G198L-T213A-H249R, N018R-T022W-S024R-N076D-S101A-N116T-I198L-A215F-H249R, N018R-S024R-N076D-N183D-I198L-G211Q-A215F-H249R, N018R-T022R-S024R-N076D-S101A-N116A-N183D-G211Q-H249R, R045T-S101G-S103A-V104I-A232V-Q245R, N018R-G020R-S024R-N076D-S101A-N183D-G211Q-H249R, G020R-S101G-S103A-V104I-N116A-N183D-T213A-A232V-Q245R, N076D-S101G-S103A-Q245R, G020R-N043D-S078R-S101G-S103A-V104I-A232V-Q245R-H249R, N018R-S024R-N076D-N116A-N183D-H249R, N018R-S024R-N076D-S101A-N183D-G211Q-T213A-A215F-H249R, N018R-G020R-T022W-S024R-N076D-S101A-N116A-I198L-H249R, N018R-T22W-S024R-N076D-G211Q-T213A-H249R, N018R-G020R-S024R-N076D-N183D-G211Q-H249R, N018R-G020R-S024R-N076D-S101A-N116A-N183D-T213A-H249R, N043R-S078R-S101G-S103A-V104I-L217E-A232V-Q245R, N018R-T022W-S024R-N076D-S101A-A215F-H249R, N018R-G020R-S024R-N076D-S101A-N183D-I198L-G211Q-T213A-H249R, N076D-S101G-V104I-H249R, N018R-T022W-S024R-N076D-S101A-N116A-N183D-T213A-H249R, N018R-S024R-N076D-N183D-H249R, N018R-S024R-N076D-S101A-N183D-I198L-A215F-H249R, N018R-T022W-S024R-N076D-N183D-I198L-A215F-H249R, N018R-T022W-S024R-N076D-S101A-I198L-G211Q-H249R, G020R-S101A-S103A-V104I-N116A-N183D-A232V-Q245R, N018R-S024R-N076D-N116A-N183D-I198L-G211Q-H249R, N018R-G020R-S024R-S101G-S103A-V104I-A232V-Q245R, N018R-N076D-S078R-S101G-S103A-V104I-L217E-A232V-Q245R, G020R-S101A-S103A-V104I-N116A-N183D-G211Q-A232V-Q245R, N018R-T022W-S024R-N076D-S101A-N183D-I198L-Y209H-H249R, N018R-S024R-N076D-N183D-I198L-T213A-A215F-H249R, N018R-S024R-N076D-S101A-N116A-N183D-G211Q-T213A-H249R, N018R-T022W-S024R-N076D-S101A-N116A-N183D-G211Q-T213A-H249R, N018R-S024R-N076D-N183D-I198L-H249R, N018R-S024R-N076D-N183D-A215F-H249R, N018R-G020R-S024R-N076D-G211Q-T213A-A215F-H249R, N076D-Q245R, N076D-S101G-V104I-Q245R, N018R-T022W-S024R-N076D-S101A-G211Q-A215F-H249R, N018R-T022W-S024R-N076D-S101A-N116A-N183D-G211Q-A215F-H249R, N018R-G020R-T022W-S024R-N076D-S101A-G211Q-T213A-H249R, G020R-S024R-N043R-S101G-S103A-V104I-A232V-Q245R, N018R-S024R-N076D-N116A-N183D-G211Q-A215F-H249R, G020R-S101A-S103A-V104I-N116A-N183D-T213A-A215F-A232V-Q245R, S101G-S103A-V104I, N018R-G020R-S024R-N076D-S101A-N116A-N183D-G211Q-T213A-H249R, N018R-G020R-S024R-N076D-N204D-T213A-H249R, N018R-T022W-S024R-N076D-N183D-I198L-H249R, N018R-S024R-N076D-S101A-N116A-N183D-A215F-H249R, N018R-T022W-S024R-N076D-N116A-N183D-I198L-G211Q-T213A-A209V-H249R, N018R-T022W-S024R-N076D-S101A-N116A-N183D-G211Q-T213A-A215F-H249R, N018R-S024R-N076D-S101A-N116A-I198L-T213A-H249R, N018R-G020R-S024R-N076D-S101A-N116A-G211Q-T213A-H249R, N018R-G020R-T022W-S024R-N076D-S101A-N116A-N183D-G211Q-T213A-A215F-H249R, N018R-S024R-N076D-S101A-N116A-N183D-T213A-A215F-H249R, N018R-S024R-N076D-S101A-N183D-I198L-G211Q-T213A-A215F-H249R, N018R-S024R-N076D-S101A-N183D-I198L-G211Q-T213A-H249R, N018R-N043R-R045T-S078R-S101G-S103A-V104I-L217E-A232V-Q245R, N018R-S024R-N076D-N183D-G211Q-T213A-A215F-H249R, N018R-T022W-S024R-N076D-N116A-N183D-I198L-A215F-H249R, N018R-G020R-S024R-N076D-N116A-H249R, N018R-G020R-T022W-S024R-N076D-S101A-G211Q-A215F-H249R, N018R-G020R-S024R-N076D-N183D-G211Q-T213A-A215F-H249R, N018R-G020R-T022W-S024R-N076D-I198L-T213A-H249R, N018R-G020R-S024R-N076D-S101A-G211Q-A215F-H249R-N269D, N018R-G020R-N043D-S101G-S103A-V104I-A232V-Q245R-N269R, N018R-T022W-S024R-N076D-S101A-N183D-I198L-T213A-H249R, G020R-T022W-S101G-S103A-V104I-N183D-A215F-A232V-Q245R, N018R-T022W-S024R-N076D-N116A-N183D-I198L-Y209H-G211Q-H249R, N018R-G020R-T022W-S024R-N076D-S101A-N116A-N183D-G211Q-H249R, N076D-A232V-Q245R, N043D-R045T-S078R-S101G-S103A-V104I-A232V-Q245R, N018R-G020R-S024R-N076D-N116A-I198L-G211Q-A215F-Q245R, N018R-G020R-T022W-S024R-N076D-T213A-H249R, G020R-S024R-N043D-S078R-S101G-S103A-V104I-A232V-Q245R-H249R, N018R-G020R-T022W-S024R-N076D-S101A-I198L-A215F-H249R, G020R-A090S-S101G-S103A-V104I-N116A-N183D-T213A-A215F-A232V-Q245R, N018R-G020R-T022W-S024R-N076D-S101A-I198L-G211Q-T213A-A215F-H249R, N018R-G020R-S024R-N076D-S101A-N183D-T213A-A215F-H249R, N018R-S024R-N076D-N116A-N183D-I198L-G211Q-T213A-H249R, N043D-R045T-S078R-S101G-S103A-V104I-A232V-Q245R-N269R, N018R-S024R-N076D-S101A-N183D-A215F-H249R, N018R-G020R-S024R-N076D-S101A-N183D-I198L-T213A-H249R, G020R-T022W-S101A-S103A-V104I-N116A-N183D-I198L-G211Q-T213A-A215F-A232V-Q245R, N018R-G020R-S024R-N043D-N076D-S101G-S103A-V104I-A232V-Q245R-N269R, N018R-S024R-N076D-S101A-N183D-T213A-A215F-H249R, N018R-G020R-T022W-S024R-N076D-S101A-N116A-I198L-G211Q-T213A-A215F-H249R, N018R-G020R-N043D-S101G-S103A-V104I-L217E-A232V-Q245R, N076D-S103A-V104I-A232V-Q245R, R045T-N076D-S078R-S101G-S103A-V104I-A232V-Q245R-H249R, N018R-T022W-S024R-N076D-S101A-N183D-G211Q-A215F-H249R, N018R-T022W-S024R-N076D-S101A-N116A-N183D-H249R, N018R-S024R-N076D-N116A-N183D-I198L-G211Q-A215F-H249R, N018R-G020R-N043D-N076D-S078R-S101G-S103A-V104I-L217E-A232V-Q245R, N076D-S103A-V104I-Q245R, N018R-G020R-S024R-N076D-S101A-N116A-G211Q-T213A-A215F-H249R, N018R-S024R-N076D-S101A-N183D-I198L-H249R, N018R-T022W-S024R-N076D-N116A-N183D-I198L-G211Q-A215F-H249R, N018R-S024R-N076D-N116A-N183D-T213A-A215F-H249R, N018R-T022W-S024R-N076D-N116A-N183D-I198L-G211Q-H249R, N018R-S024R-N076D-S101G-Q245R, N018R-S024R-N076D-S101A-N116A-N183D-I198L-T213A-A215F-H249R, N043R-R045T-N076D-S101G-S103A-V104I-A232V-Q245R, N018R-G020R-T022W-S024R-N076D-N116A-I198L-T213A-A215F-H249R, N076D-V104I-A232V-Q245R, K027R-N043R-R045T-N076D-S101G-S103A-V104I-A232V-Q245R, N018R-T022W-S024R-N076D-S101A-N183D-T213A-A215F-H249R, N018R-S024R-N076D-S103A-V104I-L135I-A232V, N018R-G020R-T022W-S024R-N076D-N183D-I198L-G211Q-H249R, N018R-G020R-T022W-S024R-N076D-S101A-N116A-N183D-I198L-A215F-H249R, N018R-S024R-N076D-S101A-N116A-

N183D-G211Q-H249R, N018R-T022W-S024R-N076D-N183D-G211Q-T213A-A215F-H249R, N076D-S101G-S103A-V104I-A232V-H249R, P005S-N018R-T022W-S024R-N076D-S101A-T213A-A215F-H249R, N018R-S024R-N076D-N116A-N183D-A215F-H249R, N018R-S024R-N076D-N183D-I198L-A215F-H249R, N018R-G020R-S024R-N076D-S101A-N116A-N183D-H249R, N018R-T022W-S024R-N076D-N116A-N183D-G211Q-H249R, N018R-G020R-T022W-S024R-N076D-S101A-N116A-H249R, N018R-T022W-S024R-N076D-S101A-N116A-N183D-I198L-T213A-H249R, N018R-T022W-S024R-N076D-S101A-N183D-G211Q-T213A-H249R, N018R-G020R-S024R-N076D-N116A-I198L-H249R, N018R-S024R-N076D-N183D-G211Q-T213A-H249R, N018R-S024R-N076D-S101A-N116A-N183D-T213A-H249R, N018R-S024R-N076D-N116A-N183D-I198L-A215F-H249R, N018R-T022W-S024R-N076D-N183D-I198L-G211Q-A215F-H249R, N018R-T022W-S024R-N076D-N183D-H249R, N018R-T022W-S024R-N076D-S101A-N183D-I198L-A215F-H249R, N018R-G020R-N043D-R045T-N076D-S101G-S103A-V104I-A232V-Q245R, G020R-T022W-S101A-S103A-V104I-N183D-I198L-A215F-A232V-Q245R, N076D-S101G-S103A-V104I-H249R, N018R-G020R-S024R-N076D-N183D-I198L-A215F-H249R, N018R-G020R-T022W-S024R-N076D-S101A-N183D-A215F-H249R, N018R-G020R-S024R-N076D-G211Q-T213A-H249R, N018R-S024R-N076D-N116A-N183D-G211Q-T213A-H249R, N018R-S024R-N076D-N116A-N183D-I198L-H249R, N018R-G020R-S024R-N076D-G211Q-N243D-H249R, N018R-G020R-R045T-N076D-S101G-S103A-V104I-A232V-Q245R-H249R, N018R-T022W-S024R-N076D-N183D-I198L-G211Q-T213A-H249R, N018R-S024R-N076D-S101A-N116A-N183D-I198L-G211Q-T213A-H249R, N018R-T022W-S024R-N076D-N116A-I198L-G211Q-T213A-A215F-H249R, S024R-N076D-S101G, N018R-G020R-S024R-N076D-S101A-I198L-T213A-A215F-H249R, N018R-T022W-S024R-N076D-N116A-N183D-G211Q-T213A-H249R, N018R-G020R-S024R-N076D-N183D-A215F-H249R, N018R-N043D-N076D-S078R-S101G-S103A-V104I-A232V-Q245R-H249R, N018R-T022W-S024R-N076D-N116A-N183D-G211Q-T213A-Q245R, G020R-S024R-N076D-S078R-S101G-S103A-V104I-A232V-Q245R-H249R, N018R-G020R-R045T-S101G-S103A-V104I-A232V-Q245R-H249R, N018R-S024R-N076D-S101A-N183D-I198L-G211Q-H249R, N018R-T022W-S024R-N076D-N183D-G211Q-T213A-H249R, N018R-G020R-S024R-N076D-N116A-I198L-G211Q-A215F-H249R-N269S, N018R-G020R-T022W-S024R-N076D-S101A-N116A-N183D-I198L-G211Q-A215F-H249R, G020R-T022W-S101A-S103A-V104I-N183D-T213A-A215F-A232V-Q245R, N018R-S024R-N076D-A086V-S101A-N183D-I198L-G211Q-H249R, N018R-N076D-S101G-I198T-A232V, N018R-G020R-S024R-N076D-S101A-N116A-N183D-I198L-G211Q-A215F-H249R, N018R-T022W-S024R-N076D-S101A-N116A-N183D-T213A-A215F-H249R, N018R-T022W-S024R-N076D-S101A-N183D-G211Q-T213A-A215F-H249R, N018R-S024R-N076D-N183D-H249R-A248T, N018R-N076D-V104I-Q245R-H249R, N018R-T022W-S024R-N076D-S101A-N116A-N183D-I198L-A215F-H249R, N018R-T022W-S024R-N076D-N116A-N183D-T213A-A215F-H249R, N018R-G020R-T022W-S024R-N076D-N116A-N183D-G211Q-T213A-A215F-H249R, N018R-G020R-S024R-N076D-S101A-H249R, N018R-G020R-S024R-N076D-S101A-N116A-T213A-A215F-H249R, N018R-T022W-S024R-N076D-N116A-N183D-G211Q-A215F-H249R, N018R-T022W-S024R-N076D-N116A-N183D-I198L-G211Q-T213A-H249R, N043R-R045T-S078R-S101G-S103A-V104I-L217E-A232V-Q245R, N043R-R045T-S101G-S103A-V104I-A232V-Q245R-H249R, N018R-N076D-S101G-V104I, G020R-R045T-N076D-S078R-S101G-S103A-V104I-A232V-Q245R-H249R, N043D-N076D-S101G-S103A-V104I-A232V-Q245R, N018R-G020R-T022W-S024R-N076D-S101A-N116A-N183D-I198L-H249R, N018R-N076D-V104I, N018R-G020R-N043D-S101G-S103A-V104I-A232V-Q245R-H249R, N018R-G020R-T022W-S024R-N076D-N183D-G211Q-H249R, N018R-S024R-N076D-S101A-N183D-I198L-G211Q-A215F-H249R, S101G-V104I, N018R-T022W-S024R-N076D-N116A-N183D-I198L-G211Q-T213A-A215F-H249R, N018R-G020R-S024R-N076D-S101A-N183D-G211Q-T213A-A215F-H249R, N018R-G020R-S024R-N076D-N116A-N183D-A215F-H249R-N263D, N018R-T022W-S024R-N076D-S101A-N183D-H249R, N018R-S024R-N076D-S101A-N116A-N183D-I198L-A215F-H249R, N018R-T022W-S024R-N076D-N116A-I198L-A215F-H249R-R269H, N018R-N043D-R045T-N076D-S078R-S101G-S103A-V104I-A232V-Q245R, N018R-S024R-R045T-N076D-S078R-S101G-S103A-V104I-A232V-Q245R-N269R, S078R-S101G-S103A-V104I-L217E-A232V-Q245R, N018R-G020R-T022W-S024R-N076D-S101A-N183D-I198L-T213A-A215F-H249R, N018R-G020R-S024R-N076D-N183D-I198L-T213A-H249R, N018R-G020R-T022W-S024R-N076D-N116A-I198L-G211Q-A215F-H249R, N018R-G020R-T022W-S024R-N076D-N116A-N183D-G211Q-H249R, N018R-G020R-T022W-S024R-N076D-S101A-I198L-G211Q-T213A-H249R, N018R-G020R-T022W-S024R-N076D-H249R, G020R-T022W-S101G-S103A-V104I-N116A-N183D-I198L-G211Q-T213A-A215F-A232V-Q245R, V104I-A232V, N018R-G020R-T022W-S024R-N076D-S101A-N116A-N183D-G211Q-A215F-H249R, N018R-G020R-T022W-S024R-N076D-S101A-N116A-N183D-I198L-G211Q-T213A-A215F-H249R, N018R-G020R-T022W-S024R-N076D-S101A-N183D-T213A-A215F-H249R, N018R-T022W-S024R-N076D-S101A-N183D-I198L-G211Q-T213A-H249R, N018R-T022W-S024R-N076D-S101A-N183D-I198L-H249R, N043D-R045T-S101G-S103A-V104I-A232V-Q245R-N269R, N018R-G020R-S024R-N076D-S101A-N183D-I198L-G211Q-H249R, N018R-G020R-N043R-S101G-S103A-V104I-L217E-A232V-Q245R, S024R-N043R-N076D-S078R-S101G-S103A-V104I-A232V-Q245R-N269R, N043R-R045T-N076D-S078R-S101G-S103A-V104I-Y166F-A176P-A179V-N184T-A187P-A194P, N018R-T022W-S024R-D041E-N076D-S101A-S160T-N183D-G211Q-T213A-H249R, N018R-G020R-T022W-S024R-N076D-N116A-N183D-I198L-G211Q-A215F-H249R, N018R-G020R-T022W-S024R-N076D-S101A-N116A-I198L-T213A-H249R, N018R-T022W-S024R-N076D-S101A-N116A-N183D-I198L-G211Q-T213A-H249R, N018R-G020R-S024R-N076D-I198L-T213A-H249R, N018R-G020R-T022W-S024R-N076D-N116A-N183D-I198L-G211Q-H249R, N018R-G020R-S024R-N076D-N183D-G211Q-A215F-H249R, S024R-N076D-V104I, N018R-N076D-S101G-A232V, N018R-S024R-N076D-S101A-N116A-N183D-I198L-G211Q-T213A-A215F-H249R, N018R-G020R-T022W-S024R-N076D-N116A-N183D-A215F-H249R, N018R-S024R-L031F-N076D-N116A-N183D-G211Q-T213A-A215F-H249R, N018R-S024R-N076D-S101A-N116A-N183D-I198L-T213A-H249R-N269S, N018R-G020R-S024R-N076D-S101A-N116A-I198L-A215F-H249R,

N018R-N043R-N076D-S078R-S101G-S103A-V104I-A232V-Q245R-N269R, N018R-G020R-S024R-N076D-S101A-N114T-I198L-G211Q-A215F-H249R, S024R-N043R-S078R-S101G-S103A-V104I-L217E-A232V-Q245R, S024R-N076D-S103A-V104I-A232V, N018R-G020R-T022W-S024R-N076D-S101A-I198L-G211Q-A215F-H249R, S101G-V104I-A232V, N018R-T022W-S024R-N076D-N183D-I198L-T213A-A215F-H249R, N018R-T022W-S024R-N076D-N183D-I198L-G211Q-H249R, N018R-G020R-S024R-N076D-N183D-T213A-H249R, N018R-S024R-N076D-S101A-N183D-G211Q-A215F-H249R, N018R-G020R-T022W-S024R-N076D-N116A-G211Q-T213A-H249R, N018R-S078R-S101G-S103A-V104I-A232V-Q245R-N269R, N018R-T022W-S024R-N076D-S101A-N116A-N183D-G211Q-A215F-H249R-T260A, N076D-H249R, N018R-T022W-S024R-N076D-N183D-G211Q-A215F-H249R, N018R-G020R-S024R-N076D-N116A-G211Q-A215F-H249R, N018R-G020R-S024R-N076D-T213A-H249R, N018R-G020R-T022W-S024R-N076D-N116A-N183D-I198L-H249R, N018R-G020R-T022W-S024R-N076D-S101A-N183D-H249R, N076D-V104I-H249R, G020R-T022W-S101A-S103A-V104I-N116A-N183D-G211Q-T213A-A215F-A232V-Q245R, S024R-N043R-R045T-S078R-S101G-S103A-V104I-L217E-A232V-Q245R, N018R-G020R-T022W-S024R-N076D-N183D-I198L-A215F-H249R, N018R-N076D-S101G-S103A, G020R-S024R-S101G-S103A-V104I-A232V-Q245R-N269R, N018R-G020R-S024R-N076D-S101A-N116A-N183D-G211Q-H249R, S101G-S103A-A232V, S024R-N076D-S101G-A232V, N018R-T022W-S024R-N076D-S101A-N183D-I198L-G211Q-H249R, N018R-G020R-S024R-N076D-S101A-N183D-I198L-G211Q-A215F-H249R, N018R-G020R-S024R-N076D-N183D-I198L-H249R, N018R-T022W-S024R-N076D-S101A-N116A-N183D-I198L-G211Q-H249R, N018R-G020R-S024R-N076D-N116A-A156V-N183D-G211Q-A215F-H249R-N269S, R045T-N076D-S101G-S103A-V104I-A232V-Q245R-H249R, N018R-G020R-S024R-N076D-S101A-N183D-I198L-H249R, N018R-G020R-T022W-S024R-N076D-I198L-G211Q-A215F-H249R, N018R-G020R-T022W-S024R-N076D-S101A-N116A-I198L-G211Q-A215F-H249R, N018R-G020R-T022W-S024R-N076D-N116A-H249R, N018R-N076D-S101G, N018R-S024R-N076D-N116A-N183D-I198L-T213A-A215F-H249R, N018R-G020R-T022W-S024R-N076D-S101A-N116A-I198L-T213A-A215F-H249R, N018R-S024R-N076D-S101A-N116A-N183D-I198L-G211Q-H249R, N018R-N076D-A232V, N018R-G020R-S024R-N076D-S101A-A232V-Q245R, N018R-N043D-R045T-N076D-S101G-S103A-V104I-A232V-Q245R, N018R-T022W-S024R-N076D-N183D-T213A-A215F-H249R, N018R-S024R-N076D-S101A-N116A-G211Q-T213A-N237D-H249R, N018R-G020R-S024R-N076D-S101A-N116A-N183D-G211Q-H249R-R275S, N018R-T022W-S024R-N076D-S101A-N116A-N183D-I198L-G211Q-T213A-A215F-H249R, S024R-N076D, N018R-S024R-N076D-N183D-G211Q-A215F-H249R, N018R-T022W-S024R-N076D-N116A-N183D-I198L-T213A-A215F-H249R, N076D-V104I-A232V-H249R, N018R-N076D-S103A-A232V, N018R-G020R-S024R-N076D-S101A-N116A-N183D-I198L-G211Q-T213A-H249R, N018R-G020R-S024R-N076D-S101A-N183D-T213A-H249R, N018R-G020R-S024R-N076D-S101A-D175E-N183D-G211Q-A215F-H249R, N018R-G020R-N043D-S078R-S101G-S103A-V104I-L217E-A232V-Q245R-A273E, G020R-S024R-N043D-R045T-N076D-S101G-S103A-V104I-A232V-Q245R, P005S-S101G-S103A-V104I-A232V-Q245R-H249R, S103A-V104I-A232V, N018R-G020R-S024R-V068A-N076D-S101A-N116A-T213A-A215F-H249R, N018R-T022W-S024R-N076D-S101A-I198L-A215F-H249R-R275S, N018R-S024R-N076D-N183D-I198L-G211Q-T213A-H249R, and N043D-R045T-S101G-S103A-V104I-A232V-Q245R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: N018R-S024R-N043R-N076D-H249R-N269R, N018R-T022R-S024R-N043R-N076D-H249R, N018R-N043D-S101G-S103A-V104I-A232V-Q245R, G020R-N043D-S101G-S103A-V104I-A232V-Q245R, N043D-S101G-S103A-V104I-A232V-Q245R-N269R, N043D-S078R-S101G-S103A-V104I-A232V-Q245R, N043R-N076D-S101G-S103A-V104I-A232V-Q245R, T022R-N043R-S101G-S103A-V104I-A232V-Q245R, N043R-S078R-S101G-S103A-V104I-A232V-Q245R, G020R-N076D-S101G-S103A-V104I-A232V-Q245R, N043R-N076D-S101G-S103A-V104I-A232V-Q245R, T022R-N076D-S101G-S103A-V104I-A232V-Q245R, N076D-S078R-S101G-S103A-V104I-A232V-Q245R, N018R-S024R-N043R-N076D-H249R, N018R-S024R-N076D-S242R-H249R, N018R-S024R-N076D-H249R-N269R, N018R-T022R-S024R-N076D-H249R, N018R-S024R-N076D-S078R-H249R, N018R-S024R-N043D-N076D-H249R-N269R, N018R-T022R-S024R-N043D-N076D-H249R, N018R-S024R-N043D-N076D-S078R-H249R, G020R-S101G-S103G-V104I-A232V-Q245R, G020R-S101G-S103A-V104L-A232V-Q245R, G020R-S101G-S103A-V104V-A232V-Q245R, G020R-S101G-S103S-V104I-A232V-Q245R, G020R-S101G-S103S-V104L-A232V-Q245R, G020R-S101S-S103S-V104I-A232V-Q245R, G020R-S101S-S103S-V104L-A232V-Q245R, G020R-S101A-S103A-V104L-A232V-Q245R, G020R-S101S-S103S-V104V-A232V-Q245R, G020R-S101S-S103A-V104I-A232V-Q245R, G020R-S101S-S103A-V104V-A232V-Q245R, G020R-S101S-S103G-V104I-A232V-Q245R, G020R-S101S-S103G-V104V-A232V-Q245R, G020R-S101A-S103A-V104V-A232V-Q245R, G020R-S101A-S103S-V104I-A232V-Q245R, G020R-S101A-S103S-V104V-A232V-Q245R, N018R-S024R-N043R-N076D-S078R-H249R, S024R-N043D-S101G-S103A-V104I-A232V-Q245R, N043D-S101G-S103A-V104I-A232V-Q245R-H249R, S024R-N076D-S101G-S103A-V104I-A232V-Q245R, N076D-S101G-S103A-V104I-A232V-S242R-Q245R, N018R-G020R-S024R-N076D-L217E-H249R, N018R-S024R-N043R-N076D-L217E-H249R, N018R-S024R-N043D-N076D-S242R-H249R, N018R-G020R-S024R-N043R-N076D-H249R, G020R-S101A-S103G-V104V-A232V-Q245R, N043D-S101G-S103A-V104I-A232V-Q245R, N018R-S024R-N076D-L217E-H249R-N269R, and N018R-S024R-N076D-L217E-S242R-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: G020R-S101A-S103A-V104I-

G118R-A232V-Q245R, G020R-S024R-N116A-T213A, N043R-S101A-N116A-A215F-N269R, S024R-N043R-S101A-N116A, S024R-N043R-S101A-N116A-A215F-N269R, G020R-S101G-S103A-V104I-A215F-A232V-Q245R, N043R-S101A-N269R, S024R-N043R-N116A-T213A-N269R, G020R-S024R-N043R-R045T-S101A-T213A, S024R-N043R-N116A-A215F-N269R, G020R-S024R-T213A-A215F, G020R-N116A-N269R, S024R-N116A-T213A-N269R, N043R-S101A-N116A-N269R, S101G-S103A-V104I-N116A-T213A-A232V-Q245R-N269R, S024R-N043R-R045T-S101A-N116A-A215F-N269R, G020R-N043R-S101A-N269R, S101A-S103A-V104I-T213A-A232V-Q245R-N269R, S024R-A215F-N269R, N043R-S101A-N116A-T213A-A215F-N269R, N043R-S101A-T213A-N269R, G020R-S024R-N043R-R045T-N116A-T213A, S101G-S103A-V104I-A232V-Q245R-N269R, S024R-N043R-R045T-S101A-N116A-T213A-N269R, S024R-N043R-R045T-N269R, G020R-N043R-R045T-S101A-N269R, S024R-N043R-N116A-N269R, G020R-S024R-N043R-R045T, N043R-N116A-N269R, S024R-N043R-S101A-A215F-N269R, S024R-N043R-R045T-T213A-A215F-N269R, G020R-S024R-R045T-N269R, G020R-N043R-S101A-N116A-T213A-A215F, G020R-S101G-S103A-V104I-T213A-A215F-A232V-Q245R, G020R-S024R-R045T-N116A-N269R, G020R-S101A-N116A-N269R, S024R-N043R-A215F, G020R-S024R-T213A, S024R-N043R-S101A-A215F, G020R-S024R-N043R-R045T-N116A, G020R-S024R-N043R-R045T-S101A-N269R, G020R-S024R-S101A-A215F, G020R-S024R-N116A-T213A-A215F, G020R-S024R-N116A, G020R-S024R-S101A-N116A, N043R-T213A-A215F-N269R, S024R-S101A-N269R, S024R-N043R-N116A-A215F, G020R-T038A-N043R-S101A, G020R-S024R-N116A-A215F, S024R-N043R-S101A-T213A, P014L-G020R-S024R-N043R-R045T-S101A-A215F, G020R-S024R-A215F, G020R-N116A-A215F-N269R, G020R-R045T-N116A-N269R, G020R-S024R-N043R-R045T-A215F, and G020R-S024R-N043R-R045T-N116A-T213A-A215F, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: N043R-N076D-S101A-S103A-V104I-A158E-S188D-A232V-Q245R-N248D-H249R-E271F, S024R-N043R-N076D-S101A-S103A-V104I-A158E-S188D-L217E-A232V-Q245R-N248D-H249R, S101A-S103A-V104I-A158E-S188D-A232V-Q245R-N248D-H249R-E271F-E271F, S101A-S103A-V104I-A158E-S188D-L217E-A232V-Q245R-N248D-H249R-E271F, N076D-S101G-S103A-V104I-A114V-A158E-S188D-A232V-Q245R-N248D-H249R-E271F, S024R-N076D-S101G-S103A-V104I-A158E-S188D-A232V-Q245R-N248D-H249R-E271F, S024R-N043R-S101A-S103A-V104I-A158E-S188D-L217E-A232V-Q245R-N248D-H249R, S024R-N043R-S101A-S103A-V104I-A158E-S188D-A232V-Q245R-N248D-H249R, S024R-S101A-S103A-V104I-A158E-S166D-S188D-L217E-A232V-Q245R-N248D-H249R, N076D-S101G-S103A-V104I-S128L-A158E-S188D-A232V-Q245R-N248D-H249R-E271F, and N043R-N076D-S101G-S103A-V104I-A158E-S166D-S188D-A232V-Q245R-N248D-H249R-E271F, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: T022A-S101G-S103A-V104I-G159D-L217E-A232V-Q245R-N248D-E271F, T022A-N043R-S101G-S103A-V104I-G159D-S188D-L217E-A232V-Q245R-N248D-E271F, T022A-S101G-S103A-V104I-G159D-S188D-A232V-Q245R-N248D-E271F, N043R-S101A-S103A-V104I-A158E-S188D-L217E-A232V-Q245R-N248D-H249R, N043R-N076D-S101A-S103A-V104I-A158E-S188D-L217E-A232V-Q245R-N248D-H249R-E271F, S024R-S101G-S103A-V104I-A158E-S188D-L217E-A232V-Q245R-N248D-H249R, S024R-S101G-S103A-V104I-A158E-S188D-A232V-Q245R-N248D-H249R, S101G-S103A-V104I-A158E-S188D-A232V-Q245R-N248D-H249R, S024R-S101G-S103A-V104I-A158E-N183D-S188D-A232V-Q245R-N248D-H249R, T022A-N076D-S101G-S103A-V104I-G159D-S188D-A232V-Q245R-N248D-E271F, T022A-N043R-N076D-S101G-S103A-V104I-G159D-S188D-A232V-Q245R-N248D-E271F, T022A-N076D-S101G-S103A-V104I-G159D-A232V-Q245R-N248D-E271F, T022A-S101G-S103A-V104I-G159D-A232V-Q245R-N248D-E271F, N076D-S101A-S103A-V104I-A158E-S188D-A232V-Q245R-N248D-H249R-E271F, N043R-S101A-S103A-V104I-A158E-S166D-S188D-A232V-Q245R-N248D-H249R, S024R-N076D-S101A-S103A-V104I-A158E-S166D-S188D-A232V-Q245R-N248D-H249R-E271F, N076D-S101A-S103A-V104I-A158E-S188D-A232V-Q245R-N248D-H249R, S101A-S103A-V104I-A158E-S166D-S188D-A232V-Q245R-N248D-H249R-E271F, N043R-N076D-S101A-S103A-V104I-A158E-S166D-S188D-A232V-Q245R-N248D-H249R-E271F, S101G-S103A-V104I-A158E-S166D-S188D-A232V-Q245R-N248D-H249R-E271F, S101A-S103A-V104I-A158E-S188D-A232V-Q245R-N248D-H249R-E271F, S101A-S103A-V104I-A158E-S188D-L217E-A232V-Q245R-N248D-H249R, N076D-S101A-S103A-V104I-A158E-S166D-S188D-A232V-Q245R-N248D-H249R-E271F, S101G-S103A-V104I-A158E-N183D-S188D-A232V-Q245R-N248D-H249R, S024R-S101G-S103A-V104I-S128L-A158E-S188D-A232V-Q245R-N248D-H249R, N076D-S101G-S103A-V104I-A158E-S166D-S188D-A232V-Q245R-N248D-H249R-E271F, N043R-N076D-S101A-S103A-V104I-A158E-S166D-S188D-A232V-Q245R-N248D-H249R, and N076D-S101A-S103A-V104I-A158E-S188D-L217E-A232V-Q245R-N248D-H249R-E271F, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: H017R-T022A-N076D-S101G-S103A-V104I-G159D-S188D-A232V-Q245R-N248D-E271F, T022A-N043R-S101G-S103A-V104I-G159D-A232V-Q245R-N248D-E271F, T022A-S101G-S103A-V104I-G159D-S188D-A232V-Q245R-N248D-H249R-E271F, H017R-T022A-N076D-S101G-S103A-V104I-G159D-A232V-Q245R-N248D-E271F, T022A-N076D-S101G-S103A-V104I-G159D-A232V-Q245R-N248D-

H249R-E271F, T022A-S101G-G102A-S103A-V104I-G159D-S188D-A232V-Q245R-N248D-E271F, and T022A-N043R-N076D-S101G-S103A-V104I-G159D-A232V-Q245R-N248D-H249R-E271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101S-S103A-V104I-A158E-S188D-A232V-Q245R-N248D-H249R, S101S-S103G-V104V-A158E-S188D-A232V-Q245R-N248D-H249R, S101G-S103S-V104I-A158E-S188D-A232V-Q245R-N248D-H249R, S101A-S103A-V104I-A158E-S188D-A232V-Q245R-N248D-H249R, S101A-S103A-V104L-A158E-S188D-A232V-Q245R-N248D-H249R, S101G-S103G-V104I-A158E-S188D-A232V-Q245R-N248D-H249R, S101S-S103G-V104I-A158E-S188D-A232V-Q245R-N248D-H249R, S101S-S103S-V104I-A158E-S188D-A232V-Q245R-N248D-H249R, S101S-S103S-V104V-A158E-S188D-A232V-Q245R-N248D-H249R, S101A-S103S-V104I-A158E-S188D-A232V-Q245R-N248D-H249R, S101A-S103S-V104I-G159E-A232V-Q245R-N248D-H249R, S101S-S103A-V104I-G159E-A232V-Q245R-N248D-H249R, S101G-S103A-V104L-A158E-S188D-A232V-Q245R-N248D-H249R, S101A-S103A-V104L-G159E-A232V-Q245R-N248D-H249R, S101A-S103S-V104L-G159E-A232V-Q245R-N248D-H249R, S101G-S103S-V104L-G159E-A232V-Q245R-N248D-H249R, S101S-S103A-V104L-G159E-A232V-Q245R-N248D-H249R, S101A-S103G-V104V-G159E-A232V-Q245R-N248D-H249R, and S101S-S103A-V104V-G159E-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: V026F-V051W-V104L-S106E, V026F-L031F-S078N-G102A-S160D, G020K-G100S-N116L-A158E-S166D-N243F, T033S-N043W-N218D-P239G-N243F, T022L-T038F-A048R-N062E-G100S-R186K, S101D-S103N-N116L-S144R-A215D, V104L-S105T-T213A-L217E-S256N, N043W-S101D-S212M-N243F, V026F-A048R-S105T-T213A-N218D-T224A, S024F-S101D-G118R-A215D-L250I-A272F, V121F-N185E-T224A-P239G, T022L-L031F-G102A-S128D-T224A-N243F, N062E-S078N-G102A-N116L-S144R-L250I, T022L-T038F-V121F-S160D-A272F, V026F-S078N-G159C-R186K-N243F, S024F-A048R-G118R-S166D-L217E, G023A-T038F-S078N-G100S-S212M-A215D, G100S-N116L-A158E-T213A, S078N-V104L-G118R-S128D, G102A-S103N-S105T-A194E, T022L-S078N-S128D-T213A, K027R-G100S-G118R-S160D-S188D-N243F, S024F-G102A-R186K-T213A-L217E-N243F, T033S-S105T-S188D-S216F, G023A-G100S-A194E-S212M, A048R-S128D-N185E-P239G, G020K-S024F-T033S-P129E-A194E, G020K-K027R-P129E-S166D-P239G, T022L-G023A-K027R-S101D-V104L-S216F, T033S-G118R-P129E-A194E-P239G, T022L-S078N-N116L-P129E-S256N, K027R-S101D-S103N-S105T-A272F, A048R-S078N-N116L-N185E-L217E-P239G, G023A-S024F-K027R-N062E, S024F-S103N-V104L-G118R-S188D, V026F-V104L-S256N-A272F, S024F-N043W-V104L-V121F-P129E, N062E-S078N-N116L-T224A, G023A-S024F-V051W-A158E, K027R-T038F-G102A-N116L, N062E-S078N-S144R-S212M, L031F-N116L-S256N-A272F, T022L-T033S-V104L-N116L-S160D-R186K, S024F-G118R-P129E-R186K-T213A, N043W-S105T-T213A-A215D-S216F, L031F-S105T-R186K-S188D, V026F-A194E-T213A-S256N, and S103N-S160D-L250I-S256N, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: T022A-S024R-S101D-S103A-V104I-G118R-G159D-S188D-A232V-N248D-E271F, T022A-S024R-S103A-V104I-P129E-G159D-S188D-A232V-N248D-E271F, T022A-S024R-S103A-V104I-G118R-G159D-S188D-L217D-A232V-N248D, T022A-S024R-S101D-S103A-V104I-G118R-P129E-G159D-S188D-A232V-Q245R-N248D, T022A-S024R-S101D-S103A-V104I-G159D-S188D-A232V-Q245R-N248D, T022A-N043R-S103A-V104I-G118R-P129E-G159D-S188D-A232V-Q245R-N248D, T022A-N043R-S103A-V104I-G118R-S128I-P129E-G159D-S188D-A232V-N248D, T022A-N043R-S101D-S103A-V104I-G118R-P129E-G159D-S188D-A232V-N248D-E271F, T022A-S024R-N043R-S101D-S103A-V104I-G159D-S188D-A232V-Q245R-N248D, T022A-S103A-V104I-G159D-S188D-A232V-N248D, T022A-S024R-S103A-V104I-G118R-P129E-G159D-S188D-A232V-N248D-E271F, T022A-S024R-S103A-V104I-G159D-S188D-L217D-A232V-Q245R-N248D-E271F, T022A-N043R-N062E-S103A-V104I-G159D-S188D-A232V-Q245R-N248D-E271F, T022A-N043R-S103A-V104I-P129E-G159D-S188D-A232V-Q245R-N248D, T022A-S024R-S103A-V104I-G159D-S188D-L217D-A232V-N248D-E271F, T022A-S103A-V104I-G118R-G159D-S188D-L217D-A232V-Q245R-N248D, T022A-S024R-S101D-S103A-V104I-G118R-S128I-G159D-S188D-A232V-Q245R-N248D, T022A-S024R-N043R-S103A-V104I-G159D-S188D-L217D-A232V-N248D-E271F, T022A-N043R-S103A-V104I-G118R-G159D-S188D-L217D-A232V-N248D-E271F, T022A-N043R-S103A-V104I-G118R-G159D-S188D-A232V-N248D-E271F, T022A-S103A-V104I-S128I-P129E-G159D-S188D-A232V-N248D-E271F, T022A-S103A-V104I-G159D-S188D-L217D-A232V-Q245R-N248D-E271F, T022A-N043R-S103A-V104I-S128I-G159D-S188D-A232V-Q245R-N248D, T022A-S101D-S103A-V104I-G118R-G159D-S188D-L217D-A232V-Q245R-N248D-E271F, T022A-S103A-V104I-G118R-P129E-G159D-S188D-A232V-Q245R-N248D-E271F, T022A-S024R-N043R-S103A-V104I-G118R-G159D-S188D-L217D-A232V-N248D, T022A-N062E-S103A-V104I-G118R-G159D-S188D-A232V-Q245R-N248D, T022A-N043R-S101D-S103A-V104I-G118R-P129E-G159D-S188D-L217D-A232V, T022A-S024R-S103A-V104I-G159D-S188D-L217D-A232V-N248D, T022A-S024R-N043R-S103A-V104I-G118R-S128I-P129E-G159D-S188D-L217D-A232V-N248D-E271F, and T022A-S103A-V104I-G118R-G159D-S188D-L217D-A232V-Q245R-N248D-E271F, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: G020K-S024F-N062E-S188D-P239G, S024F-N062E-N116L-P239G, G020K-G023A-N062E-S188D, G020K-G023A-S024F-N062E-G118R-S188D-T213A, G020K-N043W-N062E-N116L-S188D-T213A-P239G, G023A-N062E-N116L-G118R, G023A-S024F-N062E-N116L-G118R, S024F-N116L, S024F-N062E-S188D-T213A, G023A-N062E-N116L-G118R-S188D-P239G, G020K-S024F-N062E, G020K-N043W-N062E-N116L-P239G, S024F-N062E-N116L-T213A-P239G, G020K-S024F-N043W-N062E-N116L-T213A, G020K-G023A-S024F-N062E-N116L-S188D-T213A, S024F-N062E-S188D-P239G, G023A-N043W-N062E-N116L-G118R-T213A, N062E-S188D-P239G, G020K-S024F-N062E-P239G, S024F-N116L-G118R-S188D-P239G, G020K-G023A-N062E-N116L-G118R-T213A, G020K-G023A-S024F-N062E-S188D-T213A-P239G, S024F-N043W-G118R-S188D, G023A-S024F-N116L-G118R-S188D-T213A, G020K-G023A-N043W-N116L-S188D-T213A-P239G, G023A-S024F-N116L-S188D-P239G, G023A-N043W-N116L-G118R-S188D, G023A-S024F-G118R-S188D-P239G, G023A-S024F-N043W-N062E-N116L-G118R, G020K-N043W-S188D-T213A, S024F-N062E-G118R-P239G, G023A-N043W-S188D-T213A, G020K-S024F-N043W-N062E-N116L-G118R-S188D-P239G, G020K-N116L-S188D-P239G, G020K-N043W-N062E-G118R, G020K-N043W-N116L-S188D-T213A, G020K-S024F, G023A-N043W-N116L-P239G, G023A-S024F-N043W-N116L-G118R-S188D-P239G, G020K-G023A-N043W-T213A, and G023A-S024F-N062E-G118R-T213A-P239G, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: G020K-G023A-N043W-G118R-S128I-P129E-G159D-S188D, S024F-G118R-S128I-P129E-G159D, G020K-S024F-N062E-N116L-G118R-S188D, G020K-N062E-N116L-S188D, N062E-N116L-G118R-T213A, G020K-G023A-N062E-N116L-S188D, N062E-N116L-G118R-S188D, G020K-N062E-N116L-T213A, G020K-G023A-N062E-N116L, G020K-N062E-S188D-T213A, G020K-N062E, G020K-S024F-N062E-N116L-S188D, G020K-N043W-N062E-N116L-S188D, G020K-S024F-N062E-S188D-T213A, N062E-N116L-S188D-T213A, G020K-N062E-N116L, G020K-G023A-N062E-N116L-S188D-T213A, G023A-S024F-N062E-N116L-T213A, T022A-N043R-S103A-V104I-S128I-P129E-G159D-S188D-A232V-Q245R-N248D, T022A-N043R-S103A-V104I-G118R-S128I-P129E-G159D-S188D-A232V-N248D-E271F, S024F-N062E-N116L-S188D, T022A-S024R-S103A-V104I-G118R-S128I-P129E-G159D-S188D-A232V-N248D, G023A-N062E-N116L-S188D, N043W-N062E-N116L, G020K-G023A-N116L-S188D, N043W-N062E-N116L-S188D, S024F-N062E-N116L, N062E-N116L-S188D, and T022A-S024R-S103A-V104I-S128I-G159D-S188D-A232V-N248D, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S087R-S101G-S103A-V104I-Q109R-S212P-A232V-Q245R-E271V, S101G-S103A-V104I-Q109R-A232V-Q245R, S101G-S103A-V104I-Q109R-S212P-A232V-Q245R-E271V, S101G-S103A-V104I-Q109R-S212P-A232V-Q245R, N076D-587R-S103A-V104I-S212P-E271V, N076D-S103A-V104I-Q109R, N076D-S103A-V104I-S212P-E271V, N076D-S103A-V104I-Q109R-Q245R, and N076D-S103A-V104I-S212P-Q245L-E271V, wherein the amino acid positions of the subtilisin variant are numbered by correspondence with the amino acid sequence of *B. amyloliquefaciens* subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S024R-P086W-G118R, S024R-S078R-P086W-N243F, S024R-T033S-P086S-S087N-Y209A, T033S-G118R, S024R-S078R-P086W-G118R-A270T, S024R-T033S-P086W-G118R, S078R-P086W-N243F, T033S-S078R-P086W-G118R-Y209A, T033S-S078R-Y209A, P086W-G118R-N243F, S024R-P086W, S078R-P086W-K235F, S024R-G118R, S024R-P086R, S101G-S103A-V104I-A232V, S024R-T033S-S078R-P086W-G118R, S024R-G118R-Y209A, Y209A-W241R, T033S-P086W-N243F, T033S-A172V-Y209A, G118R-Y209A-N243F, S024R-P086S-S141G, S024R-G118R-Y209A-N243F, S024R-T033S-P086S-S085N-K235F, S024R-T033S-A133V, S024R-T033S-S078R-P086W, S024R-P086W-Y209A, S024R-W241R, T033S-G118R-N243F, S024R-K235F, S024R-S078R-P086W, S024R-G118R-Y209A-K235F, S024R-Y209A-W241R, T033S-G118R-W241R, P086W-G118R-Y209A, T033S-G118R-G159D-Y209A, T033S-S078R-P086W, S024R-P086W-N243F, G118R-Y209A, S024R-P086W-G118R-V203I, S078R-Y209A-K235F, S024R-T033S-W241R, S078R-G118R, T033S-G118R-Y209A-N243F, L021M-S024R-T033S, S024R-T033S-P086W, T033S-K235F, S078R-P086W-Y209A, S024R-T033S-Y209A-K235F, T033S-P086W-G118R, S024R-T033S-S078R-Y209A, T033S-P086W-G118R-Y209A-N243F, P086W-Y209A-N243F, P005S-S078R-G118R-W241R, S024R-A174T, T033S-Y209A-N243F, P086W-G118R-A133V, S024R-T033S-G118R, S024R-P086W-Y209A-K235F, P086W-Y209A, I008T-S024R, P086W-G118R, T033S-W241R, P005S-S024R-T033S-N243F, S024R-Y209A-S242P, S024R-T033S-S078R-G118R, S024R-T033S-A194T, S024R-N243F, S024R-Y209A, S024R-T033S-G118R-Y209A, T033S-P086W, S024R-T033S, S024R-T033S-S078R-N243F, P086W-N243F, T033S-G118D-A138V-Y209A, T033S-Y209A-K235F, S024R-P086R-G118R, T033S-P201S, S024R-P239Q, T033S-G118R-Y209A-, S078R-P086W, K235F-N243F, S024R-Y209A-K235F, G118R-A172V, H017Y-S024R-T033S-P086W, T033S-L148F, S024R-G118R-K235F, T033S-S078R, T033S-N243F, S024C-T033S, G118R-A194T, T033S-Y209A, G118R-Y209A-K235F, S024R-T033S-Y209A-N243F, S024R-T033S-K235F, S024R-T033S-G118R-K235F, S024R-S141G, S024R-T274I, S024R-T033S-Y209A, P086W-K235F, S024R-Y209A-N243F, V004E-T033S-S078R, P086W-Y209A-K235F, A015T-T033S, T033S-P086W-S156L-Y209A, S024R-G118R-N243F-R269H, Y209A-K235F, S024R-R247H, S024R-T033S-A228T, S078R-

K235F, S024R-T033S-A174V-K235F, S024R-K235F-N243F, S024R-T033S-K235F-W241R, S024R-T033S-A151V, S024R-V104A, T033S-A048T, Q012H-V104A-G118R, G118R-K235F, T033S-T253A, T143A-Y209A, S024R-T033S-N243F, T033S-P239T, Y209A-N243F, S024R-T033S-P129H-N184D-T253M, S024R-A085V-P086W-G118R-K235F, S024R-A272P, and S024R-R269C, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: G020R-S087D-S101G-S103A-V104I-A232V-Q245R, G020R-S101G-S103A-V104I-V150L-A232V-Q245R, N018R-G020R-S024R-N076D-S087D-H249R, N018R-G020R-S024R-N076D-V150L-H249R, N018R-S024R-N043R-N076D-S087D-H249R, N018R-S024R-N043R-N076D-V150L-H249R, N018R-S024R-N076D-S078D-S087D-H249R, N018R-S024R-N076D-S078D-V150L-H249R, N018R-S024R-N076D-S087D-H249R-N269R, N018R-S024R-N076D-S087D-S242R-H249R, N018R-S024R-N076D-S087D-V150L-H249R, N018R-S024R-N076D-V150L-H249R, N018R-S087D-S101G-S103A-V104I-A232V-Q245R, N018R-S101G-S103A-V104I-V150L-A232V-Q245R, N018R-T022R-S024R-N076D-S087D-H249R, N018R-T022R-S024R-N076D-V150L-H249R, N043R-S087D-S101G-S103A-V104I-A232V-Q245R-N269R, N043R-S101G-S103A-V104I-V150L-A232V-Q245R, S024R-S087D-S101G-S103A-V104I-A232V-Q245R, S024R-S101G-S103A-V104I-V150L-A232V-Q245R, S078R-S087D-S101G-S103A-V104I-A232V-Q245R, S078R-S101G-S103A-V104I-V150L-A232V-Q245R, S087D-S101G-S103A-V104I-A232V-Q245R-N269R, S101G-S103A-V104I-V150L-A232V-Q245R-H249R, S101G-S103A-V104I-V150L-A232V-Q245R-N269R, T022R-S087D-S101G-S103A-V104I-A232V-Q245R, N018R-S024R-N043D-N076D-V150L-H249R, N043R-S087D-S101G-S103A-V104I-A232V-Q245R, T022R-S101G-S103A-V104I-V150L-A232V-Q245R, N018R-S024R-N043R-N076D-S087D-H249R, N018R-S024R-N076D-S087D-H249R, N018R-S024R-N076D-V150L-S242R-H249R, N043R-S101G-S103A-V104I-V150L-A232V-Q245R-N269R, N076D-S101G-S103A-V104I-V150L-A232V-Q245R, S087D-S101G-S103A-V104I-A232V-S242R-Q245R, S101G-S103A-V104I-V150L-A232V-Q245R, N076D-S087D-S101G-S103A-V104I-A232V-Q245R, S087D-S101G-S103A-V104I-A232V-Q245R, and S101G-S103A-V104I-V150L-A232V-S242R-Q245R, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S024R-S101G-S103A-V104I-P129Q-A158E-S188D-L217E-A232V-Q245R-N248D-H249R, S024R-S101G-S103A-V104I-S130A-A158E-N183D-S188D-A232V-Q245R-N248D-H249R, S024R-S101G-S103A-V104I-P129Q-A158E-N183D-S188D-A232V-Q245R-N248D-H249R, S101G-S103A-V104I-S130A-A158E-S188D-A232V-Q245R-N248D-H249R, S024R-S101G-S103A-V104I-P129Q-A158E-S188D-A232V-Q245R-N248D-H249R, S024R-S101G-S103A-V104I-S130A-A158E-S188D-A232V-Q245R-N248D-H249R, S024R-S101G-S103A-V104I-P129Q-S130A-A158E-S188D-A232V-Q245R-N248D-H249R, S024R-S101G-S103A-V104I-S128L-P129Q-A158E-S188D-A232V-Q245R-N248D-H249R, S024R-S101G-S103A-V104I-P129Q-A158E-S188D-A232V-Q245R-N248D-H249R, S101G-S103A-V104I-P129Q-A158E-S188D-A232V-Q245R-N248D-H249R, S101G-S103A-V104I-P129Q-S130A-A158E-S188D-A232V-Q245R-N248D-H249R, S024R-S101G-S103A-V104I-S128L-P129Q-S130A-A158E-S188D-A232V-Q245R-N248D-H249R, S101G-S103A-V104I-S128L-P129Q-A158E-S188D-A232V-Q245R-N248D-H249R, and S024R-K027R-S101G-S103A-V104I-S128L-P129Q-S130A-A158E-S188D-A232V-Q245R-N248D-H249R, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S101G-S103A-V104I-A232V-M222Q-Q245R, S101G-S103A-V104I-A158E-S188D-M222S-A232V-Q245R-N248D-H249R, S101G-S103A-V104I-A158E-S188D-M222Q-A232V-Q245R-N248D-H249R, N076D-S101G-S103A-V104I-A232V-M222Q-Q245R, S101G-S103A-V104I-A232V-M222S-Q245R, N076D-S101G-S103A-V104I-A232V-M222S-Q245R, and N076D-S101G-S103A-V104I-A158E-S188D-M222S-A232V-Q245R-N248D-H249R, wherein the amino acid positions of the subtilisin variant are numbered by correspondence with the amino acid sequence of B. amyloliquefaciens subtilisin BPN' set forth as SEQ ID NO:1.

The present invention also provides isolated subtilisin variants, wherein the subtilisin variants are mature forms having proteolytic activity and comprise amino acid sequences comprising a combination of amino acid substitutions selected from: S024R-S101G-S103A-V104I-S128L-P129Q-A158E-S188D-A232V-Q245R-N248D-H249R, S101G-S103A-V104I-S130A-A158E-S188D-A232V-Q245R-N248D-H249R, S024R-S101G-S103A-V104I-A158E-S188D-A232V-Q245R-N248D-H249R, S101G-S103A-V104I-S128L-P129Q-A158E-S188D-A232V-Q245R-N248D-H249R, S101G-S103A-V104I-P129Q-S130A-A158E-S188D-A232V-Q245R-N248D-H249R, S101G-S103A-V104I-S130A-A158E-N183D-S188D-L217E-A232V-Q245R-N248D-H249R, S024R-S101G-S103A-V104I-S128L-P129Q-S130A-A158E-S188D-A232V-Q245R-N248D-H249R, S024R-S101G-S103A-V104I-P129Q-A158E-S188D-L217E-A232V-Q245R-N248D-H249R, S101G-S103A-V104I-S128L-S130A-A158E-S188D-L217E-A232V-Q245R-N248D-H249R, S024R-S101G-S103A-V104I-S128L-P129Q-A158E-N183D-S188D-A232V-Q245R-N248D-H249R, S024R-S101G-S103A-V104I-S128L-P129Q-S130A-A158E-N183D-S188D-A232V-Q245R-N248D-H249R, S024R-S101G-S103A-V104I-S128L-P129Q-A158E-S188D-A232V-Q245R-N248D-H249R-E271G, S101G-S103A-V104I-P129Q-A158E-N183D-S188D-A232V-Q245R-N248D-H249R, S024R-S101G-S103A-V104I-S130A-A158E-S188D-L217E-A232V-Q245R-N248D-H249R, S024R-S101G-S103A-V104I-S128L-A158E-N183D-S188D-A232V-Q245R-N248D-H249R, S101G-S103A-V104I-P129Q-A158E-S188D-L217E-A232V-Q245R-N248D-H249R, and S024R-S101G-S103A-V104I-S128L-

S130A-A158E-S188D-A232V-Q245R-N248D-H249R, wherein the amino acid positions of the subtilisin variant are numbered by correspondence with the amino acid sequence of *B. amyloliquefaciens* subtilisin BPN' set forth as SEQ ID NO:1.

In some embodiments, suitable cold water protease variants include variants of subtilisins, particularly those derived from *Bacillus lentus* GG36 of SEQ ID NO:2, wherein the variants comprise three, four, five, six, seven, eight, nine, 10, 11, 12, 13, 14 15, 16, 17, 18, 19, 20, 21, 22, 23, 24, or even 25 mutations within the group of positions comprising positions 1, 2, 4, 9, 10, 14, 16, 17, 18, 20, 22, 24, 25, 26, 42, 43, 46, 52, 57, 59, 62, 68, 71, 72, 74, 75, 76, 78, 82, 86, 89, 91, 94, 100, 101, 103, 104, 106, 108, 111, 112, 115, 117, 118, 121, 128, 129, 144, 148, 158, 159, 160, 166, 185, 186, 188, 197, 203, 209, 210, 212, 214, 215, 217, 224, 230, 231, 236, 238, 239, 241, 242, 243, 244, 248, 249, 250, 252, 253, 262, 263, 265, 267, 269, 271 and 272.

In some embodiments, suitable cold water protease variants include variants of subtilisins, particularly those derived from *Bacillus lentus* GG36 of SEQ ID NO:2, wherein the variants comprise a total of three, four, five, six, seven, eight, nine, 10, 11, 12, 13, 14, 15, 16, 17, 18, 19, 20, 21, 22, 23, 24, or even 25 mutations selected from: A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E. G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N, N269I, N269R, E271F, E271I, E271H, E271P, E271T, E271V, E271L and A272F; and optionally one or more of the following mutations: S103A, G159D, Q236H, Q245R, N248D and N252K.

In some embodiments, the cold water protease variant comprises one or more mutations, and having a total net charge of −5, −4, −3, −2, −1 or 0 relative to *B. lentus* subtilisin GG36 wild-type (SEQ ID NO:2)

In some embodiments, the cold water protease variants are low ionic strength cold water protease variants. Such low ionic strength cold water protease variants comprising one or more mutations, and having a total net charge of −5, −4, −3, −2, −1 or 0 relative to *B. lentus* subtilisin GG36 protease wild-type (SEQ ID NO:2). In some embodiments, these mutations are selected from: two or more of the following mutations: A1R, Q2S, V4R, V4S, S9A, R10S, P14K, A16S, T22A, T22R, S24R, G25V, V26F, L42I, P52F, P52E, P52N, N62E, N62Q, V68A, V68C, T71G, I72C, A74C. L75A, L75F, 578R, E89P, E89T, E89G, E89H, E89W, Y91N, K94N, G100S, S101A, S101N, S101G, S101D, S103G, S103N, V104L, V104I, A108I, L111V, E112V, G115K, N117F, V121F, S128D, S128F, S128L, S128N, P129E, L148I, A158E. G159E, S160D, S166D, N185E, R186H, S188E, S188D, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, N248V, H249R, L250I, L262D, Y263F, S265F, L267V, L267N. N269I, N269R, E271F, E271I, E271H and A272F; and/or one or more of the following sets of mutations: N062E-P129E, N062E-G159E, A016S-L148I, A158E-H249R, A016S-N062E, L111V-S188D, T022A-N062E, N062E-L148I, T022A-P129E, N062E-E271F, N062E-A158E, A016S-G159E, N062E-R186H, S128N-G159E, N062E-S188D, N062E-S128N, L148I-G159E, S103G-A158E, L111V-G159E, A158E-E271F, A016S-S188D, T022A-L111V, S128N-A158E, A016S-A158E, V104L-A158E, S128N-R186H, G159E-Y209E, N062E-S101A, L111V-Y209E, L148I-S188D, S101A-Y209E, T022A-S188D, A016S-T022A, S128N-P129E, A016S-Y209E, A016S-S128N, T022A-E089P, S128N-Y209E, E089P-A158E, N062E-S103G, R186H-E271F, A016S-P129E, E089P-G159E, L111V-H249R, S101A-P129E, L148I-Y209E, T022A-G159E, P129E-H249R, P129E-Y209E, V104L-P129E, S128N-S188D, L111V-A158E, T022A-A158E, N062E-Y209E, N062E-H249R, S101A-R186H, E089P-P129E, P129E-E271F, T22A-L111V-G159E, S101A-S103G-V104L-Y209E, S101A-S103G-V104L-G159E, S101A-S103G-V104L-S188D, S101G-S103A-V104I-G159D, T22A-S103G-G159E, T22A-S128N-E271F-Y209E, T22A-Y209E-E271F, T22A-S101A-Y209E, S101A-Y209E-E271F, T22A-L111V-S128N, T22A-S101A-G159E, S101A-S103G-V104L, T22A-S101A-S103G-V104L, S101A-S103G-V104L, S101G-S103A-V104I, S101A-S103G-V104L-S128N, S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, S101G-S103A-V104L-G159D-A232V-Q236H-Q245R-N248D, N62E-S101G-S103A-V104I-G159D-A232V-Q245R-N248D-E271F, N62E-S101G-S103A-V104I-G159D-A232V-Q245R-N248D-H249R, T22A-S101G-S103A-V104I-G159D-A232V-Q245R-N248D-H249R, S101G-S103A-V104I-G159D-A232V-Q245R-N248D-524R, S101G-S103A-V104I-G159D-A232V-Q245R-N248D-T253R, S101G-S103A-V104I-A158E-A232V-Q245R-N248D-H249R, T22A-S101G-S103A-V104I-G159D-A232V-Q245R-N248D-E271F, S101G-S103A-V104I-G159E-A232V-Q245R-N248D-H249R, S101G-S103A-V104I-G159D-A232V-Q245R-N248D-N238R, S101G-S103A-V104I-A158E-A232V-Q245R-N248D-E271F, S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N76D and S101G-S103A-V104I-G159E-A232V-Q245R-N248D-E271F.

In some embodiments, the above low ionic strength cold water protease variants form part of a detergent composition that is diluted in water, typically within a laundry washing machine, to form a laundry detergent wash liquor, whose conductivity is from about 0.1 mS/cm to about 3 mS/cm, from about 0.3 mS/cm to about 2.5 mS/cm, or even from about 0.5 mS/cm to about 2 mS/cm In some embodiments, the cold water protease variants are high ionic strength cold water protease variants. Such high ionic strength cold water protease variants comprise two or more mutations, and have a total net charge of +5, +4, +3, +2, +1 or 0 relative to *B. lentus* subtilisin GG36 protease wild-type (SEQ ID NO:2). In some embodiments, these mutations are selected from: two or more of the following mutations V4R, H17R, N18R, G20R, T22R, S24R, S24W, G25R, N43R, N43A, G46R, P52F, P52N, T57R, Q59A, N62Q, T71G, L75R, N76D, S78R, L82R, P86W, E89P, E89W, E89T, E89I, E89H, E89V, V104L, S106V, S106G, G115R, G118I, V121F, S144R, N185I, D197F, Y209N, Y209S, L217E, A231I, P239R, P239S, W241R, S242R, S242L, N243R, V244R, N248I, H249R, N252R, T253R, E271T, E271V, E271L, E271H, E271F, E271P, A1R, S9A, S212F and N269R; and/or one or more of the following sets of mutations T022R-S024R, S009A-E271L, N018R-W241R, N018R-G115R, N043R-H249R, G020R-H249R, V004R-H249R, G020R-S024R, N018R-H249R, S009A-G020R, G020R-W241R, S009A-S078R, G020R-G115R, N018R-S024R, S024R-S242R, T022R-G115R, N018R-N043R, G020R-N043R, N018R-S242R, S242R-N269R, N018R-V244R, S024R-N269R, G020R-E271L, S024R-E271L, V004R-S009A, G020R-N269R, A001R-S024R, V244R-E271L, S009A-N018R, W241R-E271L, V004R-S024R, S009A-H249R, S009A-T022R, S101G-S103A-V104I-G159D-A232V-Q245R-N248D-E271F, S101G-S103A-V104I-A158E-A232V-Q245R-N248D-E271F, S101G-S103A-V104I-A158E-A232V-Q245R-N248D-H249R, S101G-S103A-V104I-G159D-A232V-Q245R-N248D-S24R, S101G-S103A-V104L-G159D-A232V-Q236H-Q245R-N252K, S101G-S103A-V104L-A232V-Q236H-Q245R-N248D-N252K In some embodiments, the above high ionic strength cold water protease variants form part of a detergent composition that is diluted in water, typically within a laundry washing machine, to form a laundry detergent wash liquor, whose conductivity is from about 3 mS/cm to about 30 mS/cm, from about 3.5 mS/cm to about 20 mS/cm, or even from about 4 mS/cm to about 10 mS/cm.

The charge of the cold water protease variants is expressed relative to *B. lentus* subtilisin GG36 protease wild-type having the amino acid sequence of SEQ ID NO:2. The amino acids that impart a single negative charge are D and E and those that impart a single positive charge are R, H and K. Any amino acid change versus SEQ ID NO:2 that changes a charge is used to calculate the charge of the cold water protease variant. For example, introducing a negative charge mutation from a wild-type neutral position will add a net charge of −1 to the cold water protease variant, whereas introducing a negative charge mutation (D or E) from a wild-type positive amino acid residue (R, H or K) will add a net charge of −2. Summing the charge changes from all the amino acid residues that are different for the cold water protease variant versus *B. lentus* subtilisin GG36 protease wild-type having the amino acid sequence of SEQ ID NO:2 gives the charge change of the cold water protease variant. Without wishing to be bound by theory, it is believed that: the preferred charge range for cold water proteases to be used in low conductivity laundry detergent solutions is −5, −4, −3, −2, −1, 0, particularly −2, −1; the preferred charge range for cold water proteases to be used in high conductivity laundry detergent solutions is +5, +4, +3, +2, +1, 0, particularly +2, +1. By correctly selecting the charge unexpectedly improved levels of cold water cleaning performance can be obtained. "Low conductivity laundry detergent solutions" are defined as having a conductivity of from about 0.1 mS/cm to about 3 mS/cm, from about 0.3 mS/cm to about 2.5 mS/cm, or even from about 0.5 mS/cm to about 2 mS/cm. "High conductivity laundry detergent solutions" are defined as having a conductivity of from about 3 mS/cm to about 30 mS/cm, from about 3.5 mS/cm to about 20 mS/cm, or even from about 4 mS/cm to about 10 mS/cm. It is intended that the above examples be non-limiting. Once mutations are combined to optimize cold water performance, the enzyme charge can also be balanced by mutations in further positions.

In some embodiments, the invention provides provides an isolated, recombinant, substantially pure, or non-naturally occurring variant protease (e.g., variant subtilisin) having proteolytic activity, said variant protease comprising an amino acid sequence which differs from the amino acid sequence shown in SEQ ID NO:2 by no more than 50, no more than 45, no more than 40, no more than 35, no more than 30, no more than 25, no more than 20, no more than 19, no more than 18, no more than 17, no more than 16, no more than 15, no more than 14, no more than 13, no more than 12, no more than 11, no more than 10, no more than 9, or no more than 8 amino acid residues, wherein amino acid positions are numbered according to the numbering of corresponding amino acid positions in the amino acid sequence of *Bacillus amyloliquefaciens* subtilisin BPN' shown in SEQ ID NO:1, as determined by alignment of the variant protease amino acid sequence with the *Bacillus amyloliquefaciens* subtilisin BPN' amino acid sequence, wherein the variant subtilisin includes the substitutions 101G/103A/104I/159D/232V/236H/245R/248D/252K.

In some embodiments, the invention provides an isolated, recombinant, substantially pure, or non-naturally occurring variant protease (e.g., variant subtilisin) having proteolytic activity, said variant protease comprising an amino acid sequence which differs from the amino acid sequence shown in SEQ ID NO:2 by no more than 50, no more than 45, no more than 40, no more than 35, no more than 30, no more than 25, no more than 20, no more than 19, no more than 18, no more than 17, no more than 16, no more than 15, no more than 14, no more than 13, no more than 12, no more than 11, no more than 10, no more than 9, no more than 6, no more than 5, no more than 4, no more than 3, no more than 2 amino acid residues, wherein amino acid positions are numbered according to the numbering of corresponding amino acid positions in the amino acid sequence of *Bacillus amyloliquefaciens* subtilisin BPN' shown in SEQ ID NO:1, as determined by alignment of the variant protease amino acid sequence with the *Bacillus amyloliquefaciens* subtilisin BPN' amino acid sequence, wherein the variant subtilisin includes the substitution 87N.

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods, or polymerase mediated recombination methods) to form essentially any desired continuous nucleic acid sequence. The synthesis of the nucleic acids of the invention can be also facilitated (or alternatively accomplished) by any suitable method known in the art, including but not limited to chemical synthesis using the classical phosphoramidite method (See e.g., Beaucage et al. Tetrahedron Letters 22:1859-69 [1981]); or the method described by Matthes et al. (See, Matthes et al., EMBO J. 3:801-805 [1984], as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann. Rev. Biochem. 53:323 [1984]; and Itakura et al., Science 198:1056 [1984]).

As indicated above, recombinant DNA techniques useful in modification of nucleic acids are well known in the art. For example, techniques such as restriction endonuclease digestion, ligation, reverse transcription and cDNA production, and polymerase chain reaction (e.g., PCR) are known and readily employed by those of skill in the art. Nucleotides of the invention may also be obtained by screening cDNA libraries (e.g., cDNA libraries generated using mutagenesis techniques commonly used in the art, including those described herein) using one or more oligonucleotide probes that can hybridize to or PCR-amplify polynucleotides which encode a variant protease polypeptide(s) of the invention. Procedures for screening and isolating cDNA clones and PCR amplification procedures are well known to those of skill in the art and described in standard references known to those skilled in the art. Some nucleic acids of the invention can be obtained by altering a naturally occurring polynucleotide backbone (e.g., that encodes an enzyme or parent protease) by, for example, a known mutagenesis procedure (e.g., site-directed mutagenesis, site saturation mutagenesis, and in vitro recombination).

Methods for Making Modified Variant Proteases of the Invention

A variety of methods are known in the art that are suitable for generating modified polynucleotides of the invention that encode variant proteases of the invention, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches. Methods for making modified polynucleotides and proteins (e.g., variant proteases) include DNA shuffling methodologies, methods based on non-homologous recombination of genes, such as ITCHY (See, Ostermeier et al., 7:2139-44 [1999]), SCRACHY (See, Lutz et al. 98:11248-53 [2001]), SHIPREC (See, Sieber et al., 19:456-60 [2001]), and NRR (See, Bittker et al., 20:1024-9 [2001]; Bittker et al., 101:7011-6 [2004]), and methods that rely on the use of oligonucleotides to insert random and targeted mutations, deletions and/or insertions (See, Ness et al., 20:1251-5 [2002]; Coco et al., 20:1246-50 [2002]; Zha et al., 4:34-9 [2003]; Glaser et al., 149:3903-13 [1992]).

Vectors, Cells, and Methods for Producing Variant Proteases of the Invention

The present invention provides isolated or recombinant vectors comprising at least one polynucleotide of the invention described herein (e.g., a polynucleotide encoding a variant protease of the invention described herein), isolated or recombinant expression vectors or expression cassettes comprising at least one nucleic acid or polynucleotide of the invention, isolated, substantially pure, or recombinant DNA constructs comprising at least one nucleic acid or polynucleotide of the invention, isolated or recombinant cells comprising at least one polynucleotide of the invention, cell cultures comprising cells comprising at least one polynucleotide of the invention, cell cultures comprising at least one nucleic acid or polynucleotide of the invention, and compositions comprising one or more such vectors, nucleic acids, expression vectors, expression cassettes, DNA constructs, cells, cell cultures, or any combination or mixtures thereof.

In some embodiments, the invention provides recombinant cells comprising at least one vector (e.g., expression vector or DNA construct) of the invention which comprises at least one nucleic acid or polynucleotide of the invention. Some such recombinant cells are transformed or transfected with such at least one vector. Such cells are typically referred to as host cells. Some such cells comprise bacterial cells, including, but are not limited to Bacillus sp. cells, such as B. subtilis cells. The invention also provides recombinant cells (e.g., recombinant host cells) comprising at least one variant protease of the invention.

In some embodiments, the invention provides a vector comprising a nucleic acid or polynucleotide of the invention. In some embodiments, the vector is an expression vector or expression cassette in which a polynucleotide sequence of the invention which encodes a variant protease of the invention is operably linked to one or additional nucleic acid segments required for efficient gene expression (e.g., a promoter operably linked to the polynucleotide of the invention which encodes a variant protease of the invention). A vector may include a transcription terminator and/or a selection gene, such as an antibiotic resistance gene that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pXX, pC194, pJH101, pE194, pHP13 (See, Harwood and Cutting [eds.], Chapter 3, *Molecular Biological Methods for Bacillus*, John Wiley & Sons [1990]; suitable replicating plasmids for *B. subtilis* include those listed on p. 92; See also, Perego, Integrational Vectors for Genetic Manipulations in *Bacillus subtilis*, in Sonenshein et al., [eds.] *Bacillus subtilis and Other Gram-Positive Bacteria: Biochemistry, Physiology and Molecular Genetics*, American Society for Microbiology, Washington, D.C. [1993], pp. 615-624).

For expression and production of a protein of interest (e.g., variant protease) in a cell, at least one expression vector comprising at least one copy of a polynucleotide encoding the modified protease, and preferably comprising multiple copies, is transformed into the cell under conditions suitable for expression of the protease. In some embodiments of the present invention, a polynucleotide sequence encoding the variant protease (as well as other sequences included in the vector) is integrated into the genome of the host cell, while in other embodiments, a plasmid vector comprising a polynucleotide sequence encoding the variant protease remains as autonomous extra-chromosomal element within the cell. The invention provides both extrachromosomal nucleic acid elements as well as incoming nucleotide sequences that are integrated into the host cell genome. The vectors described herein are useful for production of the variant proteases of the invention. In some embodiments, a polynucleotide construct encoding the variant protease is present on an integrating vector that enables the integration and optionally the amplification of the polynucleotide encoding the variant protease into the bacterial chromosome. Examples of sites for integration are well known to those skilled in the art. In some embodiments, transcription of a polynucleotide encoding a variant protease of the invention is effectuated by a promoter that is the wild-type promoter for the selected precursor protease. In some other embodiments, the promoter is heterologous to the precursor protease, but is functional in the host cell. Specifically, examples of suitable promoters for use in bacterial host cells include, but are not limited to, for example, the amyE, amyQ, amyL, pstS, sacB, pSPAC, pAprE, pVeg, pHpaII promoters, the promoter of the *B. stearothermophilus* maltogenic amylase gene, the *B. amyloliquefaciens* (BAN) amylase gene, the *B. subtilis* alkaline protease gene, the *B. clausii* alkaline protease gene the *B. pumilis* xylosidase gene, the *B. thuringiensis* cryIIIA, and the *B. licheniformis* alpha-amylase gene. Additional promoters include, but are not limited to the A4 promoter, as well as phage Lambda $P_R$ or $P_L$ promoters, and the *E. coli* lac, trp or tac promoters.

Variant proteases of the present invention can be produced in host cells of any suitable Gram-positive microorganism, including bacteria and fungi. For example, in some embodiments, the variant protease is produced in host cells of fungal and/or bacterial origin. In some embodiments, the host cells are *Bacillus* sp., *Streptomyces* sp., *Escherichia* sp. or *Aspergillus* sp. In some embodiments, the variant proteases are produced by *Bacillus* sp. host cells. Examples of *Bacillus* sp. host cells that find use in the production of the variant proteases of the invention include, but are not limited to *B. licheniformis, B. lentus, B. subtilis, B. amyloliquefaciens, B. lentus, B. brevis, B. stearothermophilus, B. alkalophilus, B. coagulans, B. circulars, B. pumilis, B. thuringiensis, B. clausii,* and *B. megaterium*, as well as other organisms within the genus *Bacillus*. In some embodiments, *B. subtilis* host cells are used for production of variant proteases. U.S. Pat. Nos. 5,264,366 and 4,760,025 (RE 34,606) describe various *Bacillus* host strains that can be used for producing variant proteases of the invention, although other suitable strains can be used.

Several industrial bacterial strains that can be used to produce variant proteases of the invention include non-recombinant (i.e., wild-type) *Bacillus* sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *Bacillus subtilis* host strain. Numerous *B. subtilis* strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211strain (See e.g., Hoch et al., Genetics 73:215-228 [1973]; See also, U.S. Pat. Nos. 4,450,235 and 4,302,544, and EP 0134048, each of which is incorporated by reference in its entirety). The use of *B. subtilis* as an expression host cells is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the *Bacillus* host cell is a *Bacillus* sp. that includes a mutation or deletion in at least one of the following genes, degU, degS, degR and degQ. Preferably the mutation is in a degU gene, and more preferably the mutation is degU(Hy)32 (See e.g., Msadek et al., J. Bacteriol. 172:824-834 [1990]; and Olmos et al., Mol. Gen. Genet. 253:562-567 [1997]). One suitable host strain is a *Bacillus subtilis* carrying a degU32(Hy) mutation. In some embodiments, the *Bacillus* host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered *Bacillus* strain of the invention. In some embodiments, these mutations occur alone, while in other embodiments, combinations of mutations are present. In some embodiments, an altered *Bacillus* host cell strain that can be used to produce a variant protease of the invention is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments, the *Bacillus* sp. host cell comprises a deletion of 9 protease genes (See e.g., U.S. Pat. Appln. Pub. No. 2005/0202535, incorporated herein by reference).

Host cells are transformed with at least one nucleic acid encoding at least one variant protease of the invention using any suitable method known in the art. Whether the nucleic acid is incorporated into a vector or is used without the presence of plasmid DNA, it is typically introduced into a microorganism, in some embodiments, preferably an *E. coli* cell or a competent *Bacillus* cell. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Those of skill in the art are well aware of suitable methods for introducing nucleic acid or polynucleotide sequences of the invention into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and congression, transduction, and protoplast fusion are well known and suited for use in the present invention. Methods of transformation are used to introduce a DNA construct or vector comprising a nucleic acid encoding a variant protease of the present invention into a host cell. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J. Bacteriol. 154: 1077-1087 [1983]; and Weinrauch et al., J. Bacteriol. 169: 1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding a variant protease of the invention (i.e., an intermediate cell is not used to amplify, or otherwise process, the DNA construct or vector prior to introduction into the host cell). Introduction of the DNA construct or vector of the invention into the host cell includes those physical and chemical methods known in the art to introduce a nucleic acid sequence (e.g., DNA sequence) into a host cell without insertion into a plasmid or vector. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells of the present invention are cultured in conventional nutrient media. The suitable specific culture conditions, such as temperature, pH and the like are known to those skilled in the art and are well described in the scientific literature. In some embodiments, the invention provides a culture (e.g., cell culture) comprising at least one variant protease or at least one nucleic acid of the invention. Also provided are compositions comprising at least one nucleic acid, vector, or DNA construct of the invention.

In some embodiments, host cells transformed with at least one polynucleotide sequence encoding at least one variant protease of the invention are cultured in a suitable nutrient medium under conditions permitting the expression of the present protease, after which the resulting protease is recovered from the culture. The medium used to culture the cells comprises any conventional medium suitable for growing the host cells, such as minimal or complex media containing appropriate supplements. Suitable media are available from commercial suppliers or may be prepared according to published recipes (See e.g., the catalogues of the American Type Culture Collection). In some embodiments, the protease produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Any method suitable for recovering or purifying a variant protease finds use in the present invention.

In some embodiments, a variant protease produced by a recombinant host cell is secreted into the culture medium. A nucleic acid sequence that encodes a purification facilitating domain may be used to facilitate purification of soluble proteins. A vector or DNA construct comprising a polynucleotide sequence encoding a variant protease may further comprise a nucleic acid sequence encoding a purification facilitating domain to facilitate purification of the variant protease (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system (e.g., protein A domains available from Immunex Corp., Seattle, Wash.). The inclusion of a cleavable linker sequence such as Factor XA or enterokinase (e.g., sequences available from Invitrogen, San Diego, Calif.) between the purification domain and the heterologous protein also find use to facilitate purification.

Assays for detecting and measuring the enzymatic activity of an enzyme, such as a variant protease of the invention, are well known. Various assays for detecting and measuring activity of proteases (e.g., variant proteases of the invention), are also known to those of ordinary skill in the art. In particular, assays are available for measuring protease activity that are based on the release of acid-soluble peptides from casein or hemoglobin, measured as absorbance at 280 nm or colorimetrically using the Folin method, well known to those skilled in the art. Other exemplary assays involve the solubilization of chromogenic substrates (See e.g., Ward, "Proteinases," in Fogarty (ed.)., *Microbial Enzymes and Biotechnology*, Applied Science, London, [1983], pp. 251-317). Other exemplary assays include, but are not limited to succinyl-Ala-Ala-Pro-Phe-para nitroanilide assay (suc-AAPF-pNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

A variety of methods can be used to determine the level of production of a mature protease (e.g., mature variant proteases of the present invention) in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med. 158:1211 [1983]).

In some other embodiments, the invention provides methods for making or producing a mature variant protease of the invention. A mature variant protease does not include a signal peptide or a propeptide sequence. Some methods comprise making or producing a variant protease of the invention in a recombinant bacterial host cell, such as for example, a *Bacillus* sp. cell (e.g., a *B. subtilis* cell). In some embodiments, the invention provides a method of producing a variant protease of the invention, the method comprising cultivating a recombinant host cell comprising a recombinant expression vector comprising a nucleic acid encoding a variant protease of the invention under conditions conducive to the production of the variant protease. Some such methods further comprise recovering the variant protease from the culture.

In some embodiments the invention provides methods of producing a variant protease of the invention, the methods comprising: (a) introducing a recombinant expression vector comprising a nucleic acid encoding a variant protease of the invention into a population of cells (e.g., bacterial cells, such as *B. subtilis* cells); and (b) culturing the cells in a culture medium under conditions conducive to produce the variant protease encoded by the expression vector. Some such methods further comprise: (c) isolating the variant protease from the cells or from the culture medium.

Fabric and Home Care Products

In some embodiments, the protease variants of the present invention can be used in compositions comprising an adjunct material and a protease variant, wherein the composition is a fabric and home care product.

In some embodiments, the fabric and home care product compositions comprise at least one protease variant comprising one or more, preferably two or more of the following mutations X1R, X2S, X4R, X4S, X9A, X10S, X14K, X161S, X17R, X18R, X20R, X22A, X22R, X24R, X24W, X25R, X25V, X26F, X42I, X43R, X43A, X46R, X52F, X52E, X52N, X57R, X59A, X62E, X62Q, X68A, X68C, X71G, X72C, X74C. X75A, X75F, X75R, X76D, X78H, X82R, X86W, X89P, X89T, X89G, X89H, X89I, X89V, X89W, X91N, X94N, X100S, X101A, X101N, X101G, X101D, X103G, X103N, X104L, X104I, X106V, X106G, X108I, X111V, X112V, X115K, X115R, X117F, X118I, X121F, X128D, X128F, X128L, X128N, X129E, X144R, X148I, X158E, X159E, X160D, X166D, X185E, X185I, X186H, X188E, X188D, X197F, X203E, X209S, X209N, X209F, X209T, X209E, X209H, X209G, X210R, X212I, X212F, X214F, X215N, X215D, X215E, X217E, X217N, X224A, X230E, X231I, X236F, X238R, X238K, X239K, X239G, X239R, X239S, X241R, X242R, X242L, X243R, X244R, X248I, X248V, X249R, X250I, X252R, X253R, X262D, X263F, X265F, X267V, X267N, X269I, X269R, X271F, X271I, X271H, X271P, X271T, X271V, X271L and X272F.

In some embodiments, the fabric and home care product compositions comprise at least one protease variant comprising one or more of the following of sets of mutations X022R-X024R, X009A-X271L, X018R-X241R, X018R-X115R, X043R-X249R, X020R-X249R, X004R-X249R, X020R-X024R, X018R-X249R, X009A-X020R, X020R-X241R, X009A-X078R, X020R-X115R, X018R-X024R, X024R-X242R, X022R-X115R, X018R-X043R, X020R-X043R, X018R-X242R, X242R-X269R, X018R-X244R, X024R-X269R, X020R-X271L, X024R-X271L, X004R-X009A, X020R-X269R, X001R-X024R, X244R-X271L, X009A-X018R, X241R-X271L, X004R-X024R, X009A-X249R, X009A-X022R, X062E-X129E, X062E-X159E, X016S-X148I, X158E-X249R, X016S-X062E, X111V-X188D, X022A-X062E, X062E-X148I, X022A-X129E, X062E-X271F, X062E-X158E, X016S-X159E, X062E-X186H, X128N-X159E, X062E-X188D, X062E-X128N, X148I-X159E, X103G-X158E, X111V-X159E, X158E-X271F, X016S-X188D, X022A-X111V, X128N-X158E, X016S-X158E, X104L-X158E, X128N-X186H, X159E-X209E, X062E-X101A, X111V-X209E, X148I-X188D, X101A-X209E, X022A-X188D, X016S-X022A, X128N-X129E, X016S-X209E, X016S-X128N, X022A-X089P, X128N-X209E, X089P-X158E, X062E-X103G, X186H-X271F, X016S-X129E, X089P-X159E, X111V-X249R, X101A-X129E, X148I-X209E, X022A-X159E, X129E-X249R, X129E-X209E, X104L-X129E, X128N-X188D, X111V-X158E, X022A-X158E, X062E-X209E, X062E-X249R, X101A-X186H, X089P-X129E, X129E-X271, X22A-X111V-X159E, X101A-X103G-X104L-X209E, X101A-X103G-X104L-X159E, X101A-X103G-X104L-X188D, X101G-X103A-X104I-X159D, X22A-X103G-X159E, X22A-X128N-X271F-X209E, X22A-X209E-X271F, X22A-X101A-X209E, X101A-X209E-X271F, X22A-X111V-X128N, X22A-X101A-X159E, X101A-X103G-X104L, X22A-X101A-X103G-X104L, X101A-X103G-X104L, X101G-X103A-X104I, X101A-X103G-X104L-X128N, X103A-X104I-X159D-X232V-X236H-X245R-X248D-X252K, X101G-X104I-X159D-X232V-X236H-X245R-X248D-X252K, X101G-X103A-X159D-X232V-X236H-X245R-X248D-X252K, X101G-X103A-X104L-X232V-X236H-X245R-X248D-X252K, X101G-X103A-X104L-X159D-X236H-X245R-X248D-X252K, X101G-X103A-X104L-X159D-X232V-X245R-X248D-X252K, X101G-X103A-X104L-X159D-X232V-X236H-X248D-X252K, X101G-X103A-X104L-X159D-X232V-X236H-X245R-X252K, X101G-X103A-X104L-X159D-X232V-X236H-X245R-X248D, X62E-X101G-X103A-X104I-X159D-X232V-X245R-X248D-X271F, X62E-X101G-X103A-X104I-X159D-X232V-X245R-X248D-X249R, X22A-X101G-X103A-X104I-X159D-X232V-X245R-X248D-X249R, X101G-X103A-X104I-X159D-X232V-X245R-X248D-X24R, X101G-X103A-X104I-X159D-X232V-X245R-X248D-X253R, X101G-X103A-X104I-X158E-X232V-X245R-X248D-X249R, X22A-X101G-X103A-X104I-X159D-X232V-X245R-X248D-X271F, X101G-X103A-X104I-X159E-X232V-X245R-X248D-X249R, X101G-X103A-X104I-X159D-X232V-X245R-X248D-X238R, X101G-X103A-X104I-X158E-X232V-X245R-X248D-X271F, X101G-X103A-X104I-X159D-X232V-X245R-X248D, X101G-X103A-X104I-X159D-X232V-X245R-X248D-X271F, X101G-X103A-X104I-X159D-X232V-X245R-X248D-X76D and X101G-X103A-X104I-X159E-X232V-X245R-X248D-X271F.

In some embodiments, the fabric and home care product compositions comprise at least one protease variant comprising one or more of the following of sets of mutations X022R-X024R, X009A-X271L, X018R-X241R, X018R-X115R, X043R-X249R, X020R-X249R, X004R-X249R, X020R-X024R, X018R-X249R, X009A-X020R, X020R-X241R, X009A-X078R, X020R-X115R, X018R-X024R, X024R-X242R, X022R-X115R, X018R-X043R, X020R-X043R, X018R-X242R, X242R-X269R, X018R-X244R, X024R-X269R, X020R-X271L, X024R-X271L, X004R-X009A, X020R-X269R, X001R-X024R, X244R-X271L, X009A-X018R, X241R-X271L, X004R-X024R, X009A-X249R, X009A-X022R, X062E-X129E, X062E-X159E, X016S-X148I, X158E-X249R, X016S-X062E, X111V-X188D, X022A-X062E, X062E-X148I, X022A-X129E, X062E-X271F, X062E-X158E, X016S-X159E, X062E-X186H, X128N-X159E, X062E-X188D, X062E-X128N, X148I-X159E, X103G-X158E, X111V-X159E, X158E-X271F, X016S-X188D, X022A-X111V, X128N-X158E, X016S-X158E, X104L-X158E, X128N-X186H, X159E-X209E, X062E-X101A, X111V-X209E, X148I-X188D, X101A-X209E, X022A-X188D, X016S-X022A, X128N-X129E, X016S-X209E, X016S-X128N, X022A-X089P, X128N-X209E, X089P-X158E, X062E-X103G, X186H-X271F, X016S-X129E, X089P-X159E, X111V-X249R, X101A-X129E, X148I-X209E, X022A-X159E, X129E-X249R, X129E-X209E, X104L-X129E, X128N-X188D, X111V-X158E, X022A-X158E, X062E-X209E, X062E-X249R, X101A-X186H, X089P-X129E, X129E-X271, X22A-X111V-X159E, X101A-X103G-X104L-X209E, X101A-X103G-X104L-X159E, X101A-X103G-X104L-X188D, X101G-X103A-X104I-X159D, X22A-X103G-X159E, X22A-X128N-X271F-X209E, X22A-X209E-X271F, X22A-X101A-X209E, X101A-X209E-X271F, X22A-X111V-X128N, X22A-X101A-X159E, X101A-X103G-X104L, X22A-X101A-X103G-X104L, X101A-X103G-X104L, X101G-X103A-X104I, X101A-X103G-X104L-X128N, X103A-X104I-X159D-X232V-X236H-X245R-X248D-X252K, X101G-X104I-X159D-X232V-X236H-X245R-X248D-X252K, X101G-X103A-X159D-X232V-X236H-X245R-X248D-X252K, X101G-X103A-X104L-X232V-X236H-X245R-X248D-X252K, X101G-X103A-X104L-X159D-X236H-X245R-X248D-X252K, X101G-X103A-X104L-X159D-X232V-X245R-X248D-X252K, X101G-X103A-X104L-X159D-X232V-X236H-X248D-X252K, X101G-X103A-X104L-X159D-X232V-X236H-X245R-X252K, X101G-X103A-X104L-X159D-X232V-X236H-X245R-X248D, X62E-X101G-X103A-X104I-X159D-X232V-X245R-X248D-X271F, X62E-X101G-X103A-X104I-X159D-X232V-X245R-X248D-X249R, X22A-X101G-X103A-X104I-X159D-X232V-X245R-X248D-X249R, X101G-X103A-X104I-X159D-

X232V-X245R-X248D-X24R, X101G-X103A-X104I-X159D-X232V-X245R-X248D-X253R, X101G-X103A-X104I-X158E-X232V-X245R-X248D-X249R, X22A-X101G-X103A-X104I-X159D-X232V-X245R-X248D-X271F, X101G-X103A-X104I-X159E-X232V-X245R-X248D-X249R, X101G-X103A-X104I-X159D-X232V-X245R-X248D-X238R, X101G-X103A-X104I-X158E-X232V-X245R-X248D-X271F, X101G-X103A-X104I-X159D-X232V-X245R-X248D, X101G-X103A-X104I-X159D-X232V-X245R-X248D-X271F, X101G-X103A-X104I-X159D-X232V-X245R-X248D-X76D and X101G-X103A-X104I-X159E-X232V-X245R-X248D-X271F.

In some embodiments, the fabric and home care product compositions comprise at least one protease variant comprising a total of three, four, five, six, seven, eight, nine, 10, 11, 12, 13, 14, 15, 16, 17, 18, 19, 20, 21, 22, 23, 24, or even 25 mutations selected from: X1R, X2S, V4R, V4S, X9A, X10S, X14K, X16S, H17R, X18R, X20R, X22A, X22R, X24R, X24W, X25R, X25V, X26F, X42I, X43R, X43A, G46R, X52F, X52E, X52N, T57R, Q59A, X62E, X62Q, X68A, X68C, X71G, X72C, X74C, X75A, X75F, X75R, X76D, X78R, L82R, P86W, X89P, X89T, X89G, X89H, X89I, X89V, X89W, X91N, X94N, X100S, X101A, X101N, X101G, X101D, X103G, X103N, X104L, X104I, X106V, X106G, X108I, X111V, X112V, X115K, X115R, X117F, X118I, X121F, X128D, X128F, X128L, X128N, X129E, X144R, X148I, X158E, X159E, X160D, X166D, X185E, X185I, X186H, X188E, X188D, D197F, X203E, X209S, X209N, X209F, X209T, X209E, X209H, X209G, X210R, X212I, X212F, X214F, X215N, X215D, X215E, X217E, X217N, X224A, X230E, X231I, X236F, X238R, X238K, X239K, X239G, X239R, X239S, X241R, X242R, X242L, X243R, X244R, X248I, X248V, X249R, X250I, X252R, X253R, X262D, X263F, X265F, X267V, X267N, X269I, X269R, X271F, X271I, X271H, X271P, X271T, X271V, X271L and X272F; and optionally one or more of the following mutations: X103A, X159D, X236H, X245R, X248D and X252K.

In some embodiments, the fabric and home care product compositions comprise at least one protease variant comprising: two or more of the following mutations: X1R, X2S, V4R, V4S, X9A, X10S, X14K, X16S, X22A, X22R, X24R, X25V, X26F, X42I, X52F, X52E, X52N, X62E, X62Q, X68A, X68C, X71G, X72C, X74C, X75A, X75F, X78R, X89P, X89T, X89G, X89H, X89W, X91N, X94N, X100S, X101A, X101N, X101G, X101D, X103G, X103N, X104L, X104I, X108I, X111V, X112V, X115K, X117F, X121F, X128D, X128F, X128L, X128N, X129E, X148I, X158E, X159E, X160D, X166D, X185E, X186H, X188E, X188D, X203E, X209S, X209N, X209F, X209T, X209E, X209H, X209G, X210R, X212I, X212F, X214F, X215N, X215D, X215E, X217E, X217N, X224A, X230E, X231I, X236F, X238R, X238K, X239K, X239G, X248V, X249R, X250I, X262D, X263F, X265F, X267V, X267N, X269I, X269R, X271F, X271I, X271H and X272F; and/or one or more of the following sets of mutations: X062E-X129E, X062E-X159E, X016S-X148I, X158E-X249R, X016S-X062E, X111V-X188D, X022A-X062E, X062E-X148I, X022A-X129E, X062E-X271F, X062E-X158E, X016S-X159E, X062E-X186H, X128N-X159E, X062E-X188D, X062E-X128N, X148I-X159E, X103G-X158E, X111V-X159E, X158E-X271F, X016S-X188D, X022A-X111V, X128N-X158E, X016S-X158E, X104L-X158E, X128N-X186H, X159E-X209E, X062E-X101A, X111V-X209E, X148I-X188D, X101A-X209E, X022A-X188D, X016S-X022A, X128N-X129E, X016S-X209E, X016S-X128N, X022A-X089P, X128N-X209E, X089P-X158E, X062E-X103G, X186H-X271F, X016S-X129E, X089P-X159E, X111V-X249R, X101A-X129E, X148I-X209E, X022A-X159E, X129E-X249R, X129E-X209E, X104L-X129E, X128N-X188D, X111V-X158E, X022A-X158E, X062E-X209E, X062E-X249R, X101A-X186H, X089P-X129E, X129E-X271F, X22A-X111V-X159E, X101A-X103G-X104L-X209E, X101A-X103G-X104L-X159E, X101A-X103G-X104L-X188D, X101G-X103A-X104I-X159D, X22A-X103G-X159E, X22A-X128N-X271F-X209E, X22A-X209E-X271F, X22A-X101A-X209E, X101A-X209E-X271F, X22A-X111V-X128N, X22A-X101A-X159E, X101A-X103G-X104L, X22A-X101A-X103G-X104L, X101A-X103G-X104L, X101G-X103A-X104I, X101A-X103G-X104L-X128N, X103A-X104I-X159D-X232V-X236H-X245R-X248D-X252K, X101G-X104I-X159D-X232V-X236H-X245R-X248D-X252K, X101G-X103A-X159D-X232V-X236H-X245R-X248D-X252K, X101G-X103A-X104L-X232V-X236H-X245R-X248D-X252K, X101G-X103A-X104L-X159D-X236H-X245R-X248D-X252K, X101G-X103A-X104L-X159D-X232V-X245R-X248D-X252K, X101G-X103A-X104L-X159D-X232V-X236H-X248D-X252K, X101G-X103A-X104L-X159D-X232V-X236H-X245R-X252K, X101G-X103A-X104L-X159D-X232V-X236H-X245R-X248D, X62E-X101G-X103A-X104I-X159D-X232V-X245R-X248D-X271F, X62E-X101G-X103A-X104I-X159D-X232V-X245R-X248D-X249R, X22A-X101G-X103A-X104I-X159D-X232V-X245R-X248D-X249R, X101G-X103A-X104I-X159D-X232V-X245R-X248D-X24R, X101G-X103A-X104I-X159D-X232V-X245R-X248D-X253R, X101G-X103A-X104I-X158E-X232V-X245R-X248D-X249R, X22A-X101G-X103A-X104I-X159D-X232V-X245R-X248D-X271F, X101G-X103A-X104I-X159E-X232V-X245R-X248D-X249R, X101G-X103A-X104I-X159D-X232V-X245R-X248D-X238R, X101G-X103A-X104I-X158E-X232V-X245R-X248D-X271F, X101G-X103A-X104I-X159D-X232V-X245R-X248D, X101G-X103A-X104I-X159D-X232V-X245R-X248D-X271F, X101G-X103A-X104I-X159D-X232V-X245R-X248D-X76D and X101G-X103A-X104I-X159E-X232V-X245R-X248D-X271F; wherein the at least one protease variant has a total net charge of 0, −1, −2, −3, −4 or −5 relative to the *B. lentus* subtilisin GG36 protease having the amino acid sequence of SEQ ID NO:2.

In some embodiments, the fabric and home care product compositions comprise at least one protease variant comprising: two or more of the following mutations X4R, X17R, X18R, X20R, X22R, X24R, X24W, X25R, X43R, X43A, X46R, X52F, X52N, X57R, X59A, X62Q, X71G, X75R, X76D, X78R, X82R, X86W, X89P, X89W, X89T, X89I, X89H, X89V, X104L, X106V, X106G, X115R, X118I, X121F, X144R, X185I, X197F, X209N, X209S, X217E, X231I, X239R, X239S, X241R, X242R, X242L, X243R, X244R, X248I, X249R, X252R, X253R, X271T, X271V, X271L, X271H, X271F, X271P, X1R, X9A, X212F and X269R; and/or one or more of the following sets of mutations X022R-X024R, X009A-X271L, X018R-X241R, X018R-X115R, X043R-X249R, X020R-X249R, X004R-X249R, X020R-X024R, X018R-X249R, X009A-X020R, X020R-X241R, X009A-X078R, X020R-X115R, X018R-X024R, X024R-X242R, X022R-X115R, X018R-X043R, X020R-X043R, X018R-X242R, X242R-X269R, X018R-X244R, X024R-X269R, X020R-X271L, X024R-X271L, X004R-X009A, X020R-X269R, X001R-X024R, X244R-X271L, X009A-X018R, X241R-X271L, X004R-X024R, X009A-X249R, X009A-X022R, X101G-X103A-X104I-X159D-X232V-X245R-X248D-X271F, X101G-X103A-

X104I-X158E-X232V-X245R-X248D-X271F, X101G-X103A-X104I-X158E-X232V-X245R-X248D-X249R, X101G-X103A-X104I-X159D-X232V-X245R-X248D-X24R, X101G-X103A-X104L-X159D-X232V-X236H-X245R-X252K, X101G-X103A-X104L-X232V-X236H-X245R-X248D-X252K; wherein the at least one protease variant has a total net charge of 0, +1, +2, +3, +4 or +5 relative to the *B. lentus* subtilisin GG36 protease having the amino acid sequence of SEQ ID NO:2.

In some embodiments, the protease variant(s) of the fabric and home care product compositions are derived from a parent protease that is commercially available (e.g., SAVINASE®, POLARZYME®, KANNASE®, LIQUINASE®, LIQUINASE ULTRA®, SAVINASE ULTRA®, or OVOZYME® by Novozymes A/S); MAXACAL®, PROPERASE®, PURAFECT®, FN3®, FN4® and PURAFECT OXP®, PURAFAST™, PURAFECT® PRIME, or PURAMAX® by Genencor International) and those available from Henkel/Kemira, namely BLAP (sequence shown in FIG. 29 of U.S. Pat. No. 5,352,604 with the following mutations S99D+S101 R+S103A+V104I+G159S, hereinafter referred to as BLAP) and BLAP X (BLAP with S3T+V4I+V205I).

In some embodiments, the fabric and home care product compositions comprise at least one protease variant whose parent has proteolytic activity, wherein the variant protease comprises an amino acid sequence which differs from the amino acid sequence shown in SEQ ID NO:2 by no more than 50, no more than 40, no more than 35, no more than 30, no more than 25, no more than 20, no more than 19, no more than 18, no more than 17, no more than 16, no more than 15, no more than 14, no more than 13, no more than 12, no more than 11, no more than 10, no more than 9, or no more than 8 amino acid residues, wherein amino acid positions are numbered according to the numbering of corresponding amino acid positions in the amino acid sequence of *Bacillus amyloliquefaciens* subtilisin BPN' shown in SEQ ID NO:1, as determined by alignment of the variant protease amino acid sequence with the *Bacillus amyloliquefaciens* subtilisin BPN' amino acid sequence, wherein the variant subtilisin includes one of the following sets of substitutions: X101G-X103A-X104I-X159D-X232V-X236H-X245R-X248D-X252K; or X87N; or X87N-S101G-V104N; or X76D, X103A-X104I; or Y167A-R170S-A194P; or X87N-G118V-X129Q-X130A In some embodiments, the fabric and home care product compositions comprise one or more, or even two or more of the following mutations A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E, G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239P, P239S, W241R, S242R, S242L, N243R, V244R, N248I, N248V, H249R, L250I, N252R, T253R, L262D, Y263F, S265F, L267V, L267N, N269I, N269R, E271F, E271I, E271H, E271P, E271T, E271V, E271L and A272F In some embodiments, the fabric and home care product compositions comprise at least one protease variant comprising one or more of the following of sets of mutations T022R-S024R, S009A-E271L, N018R-W241R, N018R-G115R, N043R-H249R, G020R-H249R, V004R-H249R, G020R-S024R, N018R-H249R, S009A-G020R, G020R-W241R, S009A-S078R, G020R-G115R, N018R-S024R, S024R-S242R, T022R-G115R, N018R-N043R, G020R-N043R, N018R-S242R, S242R-N269R, N018R-V244R, S024R-N269R, G020R-E271L, S024R-E271L, V004R-S009A, G020R-N269R, A001R-S024R, V244R-E271L, S009A-N018R, W241R-E271L, V004R-S024R, S009A-H249R, S009A-T022R, N062E-P129E, N062E-G159E, A016S-L148I, A158E-H249R, A016S-N062E, L111V-S188D, T022A-N062E, N062E-L148I, T022A-P129E, N062E-E271F, N062E-A158E, A016S-G159E, N062E-R186H, S128N-G159E, N062E-S188D, N062E-S128N, L148I-G159E, S103G-A158E, L111V-G159E, A158E-E271F, A016S-S188D, T022A-L111V, S128N-A158E, A016S-A158E, V104L-A158E, S128N-R186H, G159E-Y209E, N062E-S101A, L111V-Y209E, L148I-S188D, S101A-Y209E, T022A-S188D, A016S-T022A, S128N-P129E, A016S-Y209E, A016S-S128N, T022A-E089P, S128N-Y209E, E089P-A158E, N062E-S103G, R186H-E271F, A016S-P129E, E089P-G159E, L111V-H249R, S101A-P129E, L148I-Y209E, T022A-G159E, P129E-H249R, P129E-Y209E, V104L-P129E, S128N-S188D, L111V-A158E, T022A-A158E, N062E-Y209E, N062E-H249R, S101A-R186H, E089P-P129E, P129E-E271, T22A-L111V-G159E, S101A-S103G-V104L-Y209E, S101A-S103G-V104L-G159E, S101A-S103G-V104L-S188D, S101G-S103A-V104I-G159D, T22A-S103G-G159E, T22A-S128N-E271F-Y209E, T22A-Y209E-E271F, T22A-S101A-Y209E, S101A-Y209E-E271F, T22A-L111V-S128N, T22A-S101A-G159E, S101A-S103G-V104L, T22A-S101A-S103G-V104L, S101A-S103G-V104L, S101G-S103A-V104I, S101A-S103G-V104L-S128N, S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, S101G-S103A-V104L-G159D-A232V-Q236H-Q245R-N248D, N62E-S101G-S103A-V104I-G159D-A232V-Q245R-N248D-E271F, N62E-S101G-S103A-V104I-G159D-A232V-Q245R-N248D-H249R, T22A-S101G-S103A-V104I-G159D-A232V-Q245R-N248D-H249R, S101G-S103A-V104I-G159D-A232V-Q245R-N248D-524R, S101G-S103A-V104I-G159D-A232V-Q245R-N248D-T253R, S101G-S103A-V104I-A158E-A232V-Q245R-N248D-H249R, T22A-S101G-S103A-V104I-G159D-A232V-Q245R-N248D-E271F, S101G-S103A-V104I-G159E-A232V-Q245R-N248D-H249R, S101G-S103A-V104I-G159D-A232V-Q245R-N248D-N238R, S101G-S103A-V104I-A158E-A232V-Q245R-N248D-E271F, S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N76D and S101G-S103A-V104I-G159E-A232V-Q245R-N248D-E271F.

In some embodiments, the fabric and home care product compositions comprise at least one protease variant comprising one or more of the following of sets of mutations T022R-S024R, S009A-E271L, N018R-W241R, N018R-G115R, N043R-H249R, G020R-H249R, V004R-H249R, G020R-S024R, N018R-H249R, S009A-G020R, G020R-W241R, S009A-S078R, G020R-G115R, N018R-S024R, S024R-S242R, T022R-G115R, N018R-N043R, G020R-N043R, N018R-S242R, S242R-N269R, N018R-V244R, S024R-N269R, G020R-E271L, S024R-E271L, V004R-S009A, G020R-N269R, A001R-S024R, V244R-E271L, S009A-N018R, W241R-E271L, V004R-S024R, S009A-H249R, S009A-T022R, N062E-P129E, N062E-G159E, A016S-L148I, A158E-H249R, A016S-N062E, L111V-S188D, T022A-N062E, N062E-L148I, T022A-P129E, N062E-E271F, N062E-A158E, A016S-G159E, N062E-R186H, S128N-G159E, N062E-S188D, N062E-S128N, L148I-G159E, S103G-A158E, L111V-G159E, A158E-E271F, A016S-S188D, T022A-L111V, S128N-A158E, A016S-A158E, V104L-A158E, S128N-R186H, G159E-Y209E, N062E-S101A, L111V-Y209E, L148I-S188D, S101A-Y209E, T022A-S188D, A016S-T022A, S128N-P129E, A016S-Y209E, A016S-S128N, T022A-E089P, S128N-Y209E, E089P-A158E, N062E-S103G, R186H-E271F, A016S-P129E, E089P-G159E, L111V-H249R, S101A-P129E, L148I-Y209E, T022A-G159E, P129E-H249R, P129E-Y209E, V104L-P129E, S128N-S188D, L111V-A158E, T022A-A158E, N062E-Y209E, N062E-H249R, S101A-R186H, E089P-P129E, P129E-E271, T22A-L111V-G159E, S101A-S103G-V104L-Y209E, S101A-S103G-V104L-G159E, S101A-S103G-V104L-S188D, S101G-S103A-V104I-G159D, T22A-S103G-G159E, T22A-S128N-E271F-Y209E, T22A-Y209E-E271F, T22A-S101A-Y209E, S101A-Y209E-E271F, T22A-L111V-S128N, T22A-S101A-G159E, S101A-S103G-V104L, 122A-S101A-S103G-V104L, S101A-S103G-V104L, S101G-S103A-V104I, S101A-S103G-V104L-S128N, S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, S101G-S103A-V104L-G159D-A232V-Q236H-Q245R-N248D, N62E-S101G-S103A-V104I-G159D-A232V-Q245R-N248D-E271F, N62E-S101G-S103A-V104I-G159D-A232V-Q245R-N248D-H249R, T22A-S101G-S103A-V104I-G159D-A232V-Q245R-N248D-H249R, S101G-S103A-V104I-G159D-A232V-Q245R-N248D-524R, S101G-S103A-V104I-G159D-A232V-Q245R-N248D-T253R, S101G-S103A-V104I-A158E-A232V-Q245R-N248D-H249R, T22A-S101G-S103A-V104I-G159D-A232V-Q245R-N248D-E271F, S101G-S103A-V104I-G159E-A232V-Q245R-N248D-H249R, S101G-S103A-V104I-G159D-A232V-Q245R-N248D-N238R, S101G-S103A-V104I-A158E-A232V-Q245R-N248D-E271F, S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N76D and S101G-S103A-V104I-G159E-A232V-Q245R-N248D-E271F In some embodiments, the fabric and home care product compositions comprise at least one protease variant comprising three, four, five, six, seven, eight, nine, 10, 11, 12, 13, 14, 15, 16, 17, 18, 19, 20, 21, 22, 23, 24 or even 25 mutations within the group of positions comprising positions 1, 2, 4, 9, 10, 14, 16, 17, 18, 20, 22, 24, 25, 26, 42, 43, 46, 52, 57, 59, 62, 68, 71, 72, 74, 75, 76, 78, 82, 86, 89, 91, 94, 100, 101, 103, 104, 106, 108, 111, 112, 115, 117, 118, 121, 128, 129, 144, 148, 158, 159, 160, 166, 185, 186, 188, 197, 203, 209, 210, 212, 214, 215, 217, 224, 230, 231, 236, 238, 239, 241, 242, 243, 244, 248, 249, 250, 252, 253, 262, 263, 265, 267, 269, 271 and 272.

In some embodiments, the fabric and home care product compositions comprise at least one protease variant comprising a total of three, four, five, six, seven, eight, nine, 10, 11, 12, 13, 14, 15, 16, 17, 18, 19, 20, 21, 22, 23, 24, or even 25 mutations selected from: A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C, L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E, G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N. N269I, N269R, E271F, E271I, E271H, E271P, E271T, E271V, E271L and A272F; and optionally one or more of the following mutations: S103A, G159D, Q236H, Q245R, N248D and N252K.

In some embodiments, the fabric and home care product compositions, comprise at least one protease variant comprising: two or more of the following mutations: A1R, Q2S, V4R, V4S, S9A, R10S, P14K, A16S, T22A, T22R, S24R, G25V, V26F, L42I, P52F, P52E, P52N, N62E, N62Q, V68A, V68C, T71G, I72C, A74C. L75A, L75F, S78R, E89P, E89T, E89G, E89H, E89W, Y91N, K94N, G100S, S101A, S101N, S101G, S101D, S103G, S103N, V104L, V104I, A108I, L111V, E112V, G115K, N117F, V121F, S128D, S128F, S128L, S128N, P129E, L148I, A158E, G159E, S160D, S166D, N185E, R186H, S188E, S188D, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, N248V, H249R, L250I, L262D, Y263F, S265F, L267V, L267N, N269I, N269R, E271F, E271I, E271H and A272F; and/or one or more of the following sets of mutations: N062E-P129E, N062E-G159E, A016S-L148I, A158E-H249R, A016S-N062E, L111V-S188D, T022A-N062E, N062E-L148I, T022A-P129E, N062E-E271F, N062E-A158E, A016S-G159E, N062E-R186H, S128N-G159E, N062E-S188D, N062E-S128N, L148I-G159E, S103G-A158E, L111V-G159E, A158E-E271F, A016S-S188D, T022A-L111V, S128N-A158E, A016S-A158E, V104L-A158E, S128N-R186H, G159E-Y209E, N062E-S101A, L111V-Y209E, L148I-S188D, S101A-Y209E, T022A-S188D, A016S-T022A, S128N-P129E, A016S-Y209E, A016S-S128N, T022A-E089P, S128N-Y209E, E089P-A158E, N062E-S103G, R186H-E271F, A016S-P129E, E089P-G159E, L111V-H249R, S101A-P129E, L148I-Y209E, T022A-G159E, P129E-H249R, P129E-Y209E, V104L-P129E, S128N-S188D, L111V-A158E, T022A-A158E, N062E-Y209E, N062E-H249R, S101A-R186H, E089P-P129E, P129E-E271F, T22A-L111V-G159E, S101A-S103G-V104L-Y209E, S101A-S103G-V104L-G159E, S101A-S103G-V104L-S188D, S101G-S103A-V104I-G159D, T22A-S103G-G159E, T22A-S128N-E271F-Y209E, T22A-Y209E-E271F, T22A-S101A-Y209E, S101A-Y209E-E271F, T22A-L111V-S128N, T22A-S101A-G159E, S101A-S103G-V104L, T22A-S101A-S103G-V104L, S101A-S103G-V104L, S101G-S103A-V104I, S101A-S103G-V104L-S128N, S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, S101G-S103A-V104L-G159D-A232V-Q236H-Q245R-N248D, N62E-S101G-S103A-V104I-G159D-A232V-Q245R-N248D-E271F, N62E-S101G-S103A-V104I-G159D-A232V-Q245R-N248D-H249R, T22A-S101G-S103A-V104I-G159D-A232V-Q245R-N248D-H249R, S101G-S103A-V104I-G159D-A232V-Q245R-N248D-524R, S101G-S103A-V104I-G159D-A232V-Q245R-N248D-T253R, S101G-S103A-V104I-A158E-A232V-Q245R-N248D-H249R, T22A-S101G-S103A-V104I-G159D-A232V-Q245R-N248D-E271F, S101G-S103A-V104I-G159E-A232V-Q245R-N248D-H249R, S101G-S103A-V104I-G159D-A232V-Q245R-N248D-N238R, S101G-S103A-V104I-A158E-A232V-Q245R-N248D-E271F, S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N76D and S101G-S103A-V104I-G159E-A232V-Q245R-N248D-E271F; wherein the at least one protease variant has a total net charge of 0, +1, +2, +3, +4 or +5 relative to *B. lentus* subtilisin GG36 protease having the amino acid sequence of SEQ ID NO:2.

In some embodiments, the fabric and home care product compositions comprise at least one protease variant, wherein at least one protease variant is a mature form having proteolytic activity and which comprises amino acid sequences comprising a combination of amino acid substitutions selected from: X1R, X230E, X271L, X115R, X20R, X249R, X235F, X27V/F/L, X75E, X82R, X18R, X269R, X43D, X43R, X76D, X45T, X212F, X242R, X24R, X78R, X9A, X22R, X121E, X244R, X28E, X30E, X4R, and X241R, wherein the amino acid positions of the subtilisin variant are numbered by correspondence with the amino acid sequence of *B. amyloliquefaciens* subtilisin BPN' set forth as SEQ ID NO:1.

In some embodiments, the fabric and home care product compositions comprise at least one protease variant, wherein at least one protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, and W241R, wherein amino acid positions of the protease variant are numbered according to the numbering of corresponding amino acid positions in the amino acid sequence of *Bacillus amyloliquefaciens* subtilisin BPN' shown in SEQ ID NO:1, as determined by alignment of the protease variant amino acid sequence with the *Bacillus amyloliquefaciens* subtilisin BPN' amino acid sequence.

In some embodiments, the fabric and home care product compositions comprise at least one protease variant, wherein at least one protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, and W241R, and optionally comprises at least one mutation selected from the group of S103A, G159D, Q236H, Q245R, N248D and N252K, wherein amino acid positions of the protease variant are numbered according to the numbering of corresponding amino acid positions in the amino acid sequence of *Bacillus amyloliquefaciens* subtilisin BPN' shown in SEQ ID NO:1, as determined by alignment of the protease variant amino acid sequence with the *Bacillus amyloliquefaciens* subtilisin BPN' amino acid sequence.

In some embodiments, the fabric and home care product compositions comprise at least one protease variant, wherein at least one protease variant is a mature form having proteolytic activity and which comprises amino acid sequences comprising a combination of amino acid substitutions selected from: X16S, X18R, X20R, X22A, X24R, X43R/D, X45T, X76D, X101A, X103G, X104L, X111V, X128N, X148I, X230E, X242R, and X249R, wherein the amino acid positions of the subtilisin variant are numbered by correspondence with the amino acid sequence of *B. amyloliquefaciens* subtilisin BPN' set forth as SEQ ID NO:1.

In some embodiments, the fabric and home care product compositions comprise at least one protease variant, wherein at least one protease variant is a mature form having proteolytic activity and which comprises amino acid sequences comprising a combination of amino acid substitutions selected from: A16S, N18R, G20R, T22A, S24R, N43R, N43D, R45T, N76D, S101A, S103G, V104L, L111V, S128N, L148I, A230E, S242R, and H249R, wherein the amino acid positions of the subtilisin variant are numbered by correspondence with the amino acid sequence of *B. amyloliquefaciens* subtilisin BPN' set forth as SEQ ID NO:1.

In some embodiments, the fabric and home care product compositions comprise at least one protease variant, wherein at least one protease variant is a mature form having proteolytic activity and comprises an amino acid sequence comprising a combination of amino acid substitutions selected from: X20R-X43R-X249R, X20R-X22R-X43R, X20R-X43R-X242R, X20R-X43R-X271L, X20R-X43R-X244R, X20R-X24R-X43R-X242R, X9A-X22R-X78R-X212F-X241R, X9A-X20R-X43R-X212F, X9A-X43R-X212F, X20R-X43R-X212F, X20R-X22R-X43R-X212F, X24R-X78R-X212F, X9A-X43R-X78R, X9A-X43R-X78R-X242R, X9A-X20R-X43R-X78R, X20R-X24R-X43R-X78R-X242R, X22R-X24R-X78R-X212F, X9A-X20R-X43R-X78R-X242R, X20R-X43R-X78R-X249R, X20R-X43R-X78R, X9A-X78R-X212F, X9A-X22R-X43R-X78R, X9A-X20R-X24R-X43R, X9A-X22R-X78R-X212F, X4R-X9A-X22R-X78R-X212F, X20R-X24R-X43R, X1R-X9A-X43R, X20R-X24R-X43R-X115R, X9A-X24R-X43R, X20R-X22R-X24R-X43R, X1R-X24R-X43R, X9A-X20R-X24R-X43R-X242R, X9A-X20R-X22R-X78R-X212F, X9A-X24R-X43R-X244R, X9A-X24R-X43R-X242R, X4R-X9A-X22R-X24R-X212F, and X22R-X24R-X43R, wherein the amino acid positions of the subtilisin variant are numbered by correspondence with the amino acid sequence of B. amyloliquefaciens subtilisin BPN' set forth as SEQ ID NO:1.

In some embodiments, the fabric and home care product compositions comprise at least one protease variant, wherein at least one protease variant is a mature form having proteolytic activity and comprises an amino acid sequence comprising a combination of amino acid substitutions selected from: A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, W241R, G20R-N43R-H249R, G20R-T22R-N43R, G20R-N43R-S242R, G20R-N43R-E271L, G20R-N43R-V244R, G20R-S24R-N43R-S242R, S9A-T22R-S78R-S212F-W241R, S9A-G20R-N43R-S212F, S9A-N43R-S212F, G20R-N43R-S212F, G20R-T22R-N43R-S212F, S24R-S78R-S212F, S9A-N43R-578R, S9A-N43R-578R-S242R, S9A-G20R-N43R-S78R, G20R-S24R-N43R-S78R-S242R, T22R-524R-578R-S212F, S9A-G20R-N43R-S78R-S242R, G20R-N43R-S78R-H249R, G20R-N43R-S78R, S9A-S78R-S212F, S9A-T22R-N43R-578R, S9A-G20R-S24R-N43R, S9A-T22R-S78R-S212F, V4R-S9A-T22R-578R-S212F, G20R-S24R-N43R, A1R-S9A-N43R, G20R-S24R-N43R-G115R, S9A-524R-N43R, G20R-T22R-S24R-N43R, A1R-S24R-N43R, S9A-G20R-S24R-N43R-S242R, S9A-G20R-T22R-S78R-S212F, S9A-524R-N43R-V244R, S9A-524R-N43R-S242R, V4R-S9A-T22R-S24R-S212F, and T22R-524R-N43R, wherein the amino acid positions of the subtilisin variant are numbered by correspondence with the amino acid sequence of B. amyloliquefaciens subtilisin BPN' set forth as SEQ ID NO:1.

In some embodiments, the fabric and home care product compositions comprise at least one protease variant, wherein at least one protease variant is a mature form having proteolytic activity and comprises an amino acid sequence comprising a combination of amino acid substitutions selected from: X101G-X103A-X104I-X232V-X245R-X248D, X101G-X103A-X104I-X159D-X232V-X245R, X101G-X103A-X104I-X159R-X232V-X245R-X248D, X101G-X103A-X104I-X159D-X232V-X245R-X248R, X101G-X103A-X104I-X232V-X245R, X101G-X103A-X104I-X232V-X245R-X248D, X101G-X103A-X104I-X159R-X232V-X245R-X248R, and X101G, X103A, X104I, X232V, X236H, X245R, and X252K, wherein the amino acid positions of the subtilisin variant are numbered by correspondence with the amino acid sequence of B. amyloliquefaciens subtilisin BPN' set forth as SEQ ID NO:1.

In some embodiments, the fabric and home care product compositions comprise at least one protease variant, wherein at least one protease variant is a mature form having proteolytic activity and which comprises amino acid sequences comprising a combination of amino acid substitutions selected from: S101G-S103A-V104I-A232V-Q245R-N248D, S101G-S103A-V104I-G159D-A232V-Q245R, S101G-S103A-V104I-G159R-A232V-Q245R-N248D, S101G-S103A-V104I-G159D-A232V-Q245R-N248R, S101G-S103A-V104I-A232V-Q245R, S101G-S103A-V104I-A232V-Q245R-N248R, S101G-S103A-V104I-G159R-A232V-Q245R-N248R, S101G, S103A, V104I, A232V, Q236H, and Q245R, wherein the amino acid positions of the subtilisin variant are numbered by correspondence with the amino acid sequence of B. amyloliquefaciens subtilisin BPN' set forth as SEQ ID NO:1.

In one aspect, of said composition, said composition comprises a cold water protease variant, wherein said cold water protease variant is a mature form having proteolytic activity and comprises amino acid sequences comprising a combination of amino acid substitutions selected from: X16S, X22A, X24R, X62E, X76D, X89P, X101A/G, X103G/A, X104L/I, X111V, X128N, X129E, X232V, X148I, X158E, X159D/E, X166D, X186H, X188D, X209E, X236H, X238R, X245R, X248D/R, X249R, X252K/R, X253R, and X271F, wherein the amino acid positions of the subtilisin variant are numbered by correspondence with the amino acid sequence of B. amyloliquefaciens subtilisin BPN' set forth as SEQ ID NO:1.

In some embodiments, the fabric and home care product compositions comprise at least one protease variant, wherein at least one protease variant is a mature form having proteolytic activity and comprises an amino acid sequence comprising a combination of amino acid substitutions selected from: A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, and E271F wherein amino acid positions of the subtilisin variant are numbered by correspondence with the amino acid sequence of B. amyloliquefaciens subtilisin BPN' set forth as SEQ ID NO:1.

The present invention also provides protease variants of Bacillus lentus subtilisin GG36 protease, wherein the Bacillus lentus subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, and E271F, wherein amino acid positions of the protease variant are numbered according to the numbering of corresponding amino acid positions in the amino acid sequence of Bacillus amyloliquefaciens subtilisin BPN' shown in SEQ ID NO:1 as determined by alignment of the protease variant amino acid sequence with the Bacillus amyloliquefaciens subtilisin BPN' amino acid sequence.

In some embodiments, the fabric and home care product compositions comprise at least one protease variant that comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, and E271F, wherein amino acid positions of the protease variant are numbered according to the numbering of corresponding amino acid positions in the amino acid sequence of Bacillus amyloliquefaciens subtilisin BPN' shown in SEQ ID NO:1, as determined by alignment of the protease variant amino acid sequence with the Bacillus amyloliquefaciens subtilisin BPN' amino acid sequence.

The present invention also provides protease variants of Bacillus lentus subtilisin GG36 protease, wherein the Bacillus lentus subtilisin GG36 protease comprises the amino acid sequence shown in SEQ ID NO:2, wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A16S, T22A, S24R, N62E, N76D, E89P, S101A/G, S103G/A, V104L/I, S128N, P129E, A232V, L148I, A158E, G159D/E, R186H, S188D, Y209E, Q236H, Q245R, N248D/R, H249R, N252K/R, T253R, and E271F, wherein amino acid positions of the protease variant are numbered according to the numbering of corresponding amino acid positions in the amino acid sequence of *Bacillus amyloliquefaciens* subtilisin BPN' shown in SEQ ID NO:1 as determined by alignment of the protease variant amino acid sequence with the *Bacillus amyloliquefaciens* subtilisin BPN' amino acid sequence.

In some embodiments, the fabric and home care product compositions comprise at least one protease variant comprising an amino acid sequence which differs from the amino acid sequence of SEQ ID NO:2 and wherein the total net charge of the protease variant is 0, +1, +2, +3, +4, +5, −1, −2, −3, −4, or −5 relative to the total net charge of the *Bacillus lentus* subtilisin GG36 protease, and wherein amino acid positions of the protease variant are numbered according to the numbering of corresponding amino acid positions in the amino acid sequence of *Bacillus amyloliquefaciens* subtilisin BPN' shown in SEQ ID NO:1, as determined by alignment of the protease variant amino acid sequence with the *Bacillus amyloliquefaciens* subtilisin BPN' amino acid sequence.

In some embodiments, the fabric and home care product compositions comprise at least one protease variant comprising an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E, G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N. N269I, N269R, E271F, E271I, E271H, E271P, E271T, E271V, E271L and A272F, and optionally comprises at least one mutation selected from the group of S103A, G159D, Q236H, Q245R, N248D and N252K, wherein amino acid positions of the protease variant are numbered according to the numbering of corresponding amino acid positions in the amino acid sequence of *Bacillus amyloliquefaciens* subtilisin BPN' shown in SEQ ID NO:1, as determined by alignment of the protease variant amino acid sequence with the *Bacillus amyloliquefaciens* subtilisin BPN' amino acid sequence.

In some embodiments, the fabric and home care product compositions comprise at least one protease variant comprising an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A16S, T22A, S24R, N62E, N76D, E89P, S101A/G, S103G/A, V104L/I, L111V, S128N, P129E, A232V, L148I, A158E, G159D/E, R186H, S188D, Y209E, Q236H, Q245R, N248D/R, H249R, N252K/R, T253R, and E271F, wherein amino acid positions of the protease variant are numbered according to the numbering of corresponding amino acid positions in the amino acid sequence of *Bacillus amyloliquefaciens* subtilisin BPN' shown in SEQ ID NO:1, as determined by alignment of the protease variant amino acid sequence with the *Bacillus amyloliquefaciens* subtilisin BPN' amino acid sequence.

In some embodiments, the fabric and home care product compositions comprise at least one protease variant comprising an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, and W241R, wherein amino acid positions of the protease variant are numbered according to the numbering of corresponding amino acid positions in the amino acid sequence of *Bacillus amyloliquefaciens* subtilisin BPN' shown in SEQ ID NO:1, as determined by alignment of the protease variant amino acid sequence with the *Bacillus amyloliquefaciens* subtilisin BPN' amino acid sequence.

In some embodiments, the fabric and home care product compositions comprise at least one protease variant comprising an amino acid sequence which differs from the amino acid sequence of SEQ ID NO:2, wherein said protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations selected from the group of A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, and W241R, and optionally comprises at least one mutation selected from the group of S103A, G159D, Q236H, Q245R, N248D and N252K, wherein amino acid positions of the protease variant are numbered according to the numbering of corresponding amino acid positions in the amino acid sequence of *Bacillus amyloliquefaciens* subtilisin BPN' shown in SEQ ID NO:1, as determined by alignment of the protease variant amino acid sequence with the *Bacillus amyloliquefaciens* subtilisin BPN' amino acid sequence.

In some embodiments, the fabric and home care product compositions comprise at least one protease variant comprising two or more of the following mutations V4R, H17R, N18R, G20R, T22R, S24R, S24W, G25R, N43R, N43A, G46R, P52F, P52N, T57R, Q59A, N62Q, T71G, L75R, N76D, S78R, L82R, P86W, E89P, E89W, E89T, E89I, E89H, E89V, V104L, S106V, S106G, G115R, G118I, V121F, S144R, N185I, D197F, Y209N, Y209S, L217E, A231I, P239R, P239S, W241R, S242R, S242L, N243R, V244R, N248I, H249R, N252R, T253R, E271T, E271V, E271L, E271H, E271F, E271P, S9A, S212F and N269R; and/or one or more of the following sets of mutations T022R-S024R, S009A-E271L, N018R-W241R, N018R-G115R, N043R-H249R, G020R-H249R, V004R-H249R, G020R-S024R, N018R-H249R, S009A-G020R, G020R-W241R, S009A-S078R, G020R-G115R, N018R-S024R, S024R-S242R, T022R-G115R, N018R-N043R, G020R-N043R, N018R-S242R, S242R-N269R, N018R-V244R, S024R-N269R, G020R-E271L, S024R-E271L, V004R-

S009A, G020R-N269R, A001R-S024R, V244R-E271L, S009A-N018R, W241R-E271L, V004R-S024R, S009A-H249R, S009A-T022R, S101G-S103A-V104I-G159D-A232V-Q245R-N248D-E271F, S101G-S103A-V104I-A158E-A232V-Q245R-N248D-E271F, S101G-S103A-V104I-A158E-A232V-Q245R-N248D-H249R, S101G-S103A-V104I-G159D-A232V-Q245R-N248D-524R, S101G-S103A-V104L-G159D-A232V-Q236H-Q245R-N252K and S101G-S103A-V104L-A232V-Q236H-Q245R-N248D-N252K; wherein at least one protease variant has a total net charge of 0, −1, −2, −3, −4 or −5 relative to B. lentus subtilisin GG36 protease having the amino acid sequence of SEQ ID NO:2.

In some embodiments, the fabric and home care product compositions comprising at least one protease variant comprise at least one adjunct material selected from an encapsulate comprising a perfume, a hueing agent, surfactants, builders, chelating agents, dye transfer inhibiting agents, dispersants, additional enzymes, enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents, pigments and mixtures thereof.

In some embodiments, the fabric and home care product compositions comprise at least one adjunct material selected from perfume encapsulates, fabric hueing agents, cold-water soluble brighteners, a bleach catalyst that may comprise a material selected from iminium cations, iminium polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof; first wash lipases; bacterial cleaning cellulases; Guerbet nonionic surfactants; and mixtures thereof.

In some embodiments, the fabric and home care product compositions comprising at least one protease variant further comprise at least one additional non-immunoequivalent protease selected from subtilisins (EC 3.4.21.62); trypsin-like or chymotrypsin-like proteases; metalloproteases; and mixtures thereof.

In some embodiments, the fabric and home care product compositions comprising at least one protease variant further comprise at least one additional non-immunoequivalent protease selected from: subtilisins (EC 3.4.21.62) derived from B. subtilis, B. amyloliquefaciens, B. pumilus and B. gibsonii; trypsin proteases and/or chymotrypsin proteases derived from Cellulomonas; metalloproteases derived from Bacillus amyloliquefaciens; and mixtures thereof.

In some embodiments, the fabric and home care product compositions comprising at least one protease variant further comprise at least one additional enzyme selected from hemicellulases, peroxidases, proteases, cellulases, cellobiose dehydrogenases, xyloglucanases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, lichenases glucanases, arabinosidases, hyaluronidases, chondroitinases, laccases, amylases, and mixtures thereof.

In some embodiments, the fabric and home care product compositions comprising at least one protease variant further comprise at least one additional enzyme selected from first-wash lipases; alpha-amylases; bacterial cleaning cellulases; and mixtures thereof.

In some embodiments, the fabric and home care product compositions comprising at least one protease variant further comprise at least one of the following: an encapsulate comprising a perfume comprises a perfume micro capsule; a hueing agent comprising a material selected from basic, acid, hydrophobic, direct and polymeric dyes, and dye-conjugates having a peak absorption wavelength of from 550 nm to 650 nm and mixtures thereof; a detersive surfactant comprising a material selected from anionic detersive surfactants, non-ionic detersive surfactant, cationic detersive surfactants, zwitterionic detersive surfactants and amphoteric detersive surfactants and mixtures thereof; a builder comprising a material selected from zeolites, phosphates and mixtures thereof; a silicate salt comprising a material selected from sodium silicate, potassium silicate and mixtures thereof; a brightener comprising a material selected from cold-water soluble brighteners and mixtures thereof; a carboxylate polymer comprising a material selected from maleate/acrylate random copolymer or polyacrylate homopolymer and mixtures thereof, a soil release polymer comprising a material selected from terephthalate co-polymers and mixtures thereof; a cellulosic polymer comprising a material selected from alkyl cellulose, alkyl alkoxyalkyl cellulose, carboxyalkyl cellulose, alkyl carboxyalkyl cellulose and mixtures thereof; a bleach catalyst comprising a material selected from iminium cations, iminium polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof; a bleach activator comprising a material selected from dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED), nonanoyloxybenzene sulphonate (NOBS) and mixtures thereof; a source of hydrogen peroxide comprising a material selected from inorganic perhydrate salts, including alkali metal salts such as sodium salts of perborate (usually mono- or tetra-hydrate), percarbonate, persulphate, perphosphate, persilicate salts and mixtures thereof; a chelant comprising a material selected from DTPA (diethylene triamine pentaacetic acid), HEDP (hydroxyethane diphosphonic acid), DTPMP (diethylene triamine penta(methylene phosphonic acid)), ethylenediaminedisuccinic acid (EDDS), 1,2-dihydroxybenzene-3,5-disulfonic acid disodium salt hydrate, derivatives of said chelants; and mixtures thereof.

In some embodiments, the fabric and home care product compositions comprising at least one protease variant comprise a fabric hueing agent selected from the group consisting of dyes; dye-clay conjugates comprising at least one cationic-basic dye and a smectite clay; and mixtures thereof.

In some embodiments, the fabric and home care product compositions comprising at least one protease variant comprise at least one fabric hueing agent selected from small molecule dyes; polymeric dyes and mixtures thereof; dye-clay conjugates comprising at least one cationic-basic dye and a smectite clay; and mixtures thereof.

In some embodiments, the fabric and home care product compositions comprising at least one protease variant are provided in single or multiple-compartment unit doses. In some embodiments, the composition is a multi-compartment unit dose, wherein the protease variant is in a different compartment than any source of hydrogen peroxide and/or chelant and/or additional enzyme.

In some embodiments, the fabric and home care product compositions comprising at least one protease variant comprises a wash liquor, wherein at least one protease variant comprises: two or more of the following mutations: A1R, Q2S, V4R, V4S, S9A, R10S, P14K, A16S, T22A, T22R, S24R, G25V, V26F, L42I, P52F, P52E, P52N, N62E, N62Q, V68A, V68C, T71G, I72C, A74C. L75A, L75F, S78R, E89P, E89T, E89G, E89H, E89W, Y91N, K94N, G100S, S101A, S101N, S101G, S101D, S103G, S103N, V104L, V104I, A108I, L111V, E112V, G115K, N117F, V121F, S128D, S128F, S128L, S128N, P129E, L148I, A158E. G159E, S160D, S166D, N185E, R186H, S188E, S188D, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, N248V, H249R, L250I, L262D, Y263F, S265F, L267V, L267N, N269I, N269R, E271F, E271I, E271H and A272F; and/or one or more of the following sets of mutations: N062E-P129E, N062E-G159E, A016S-L148I, A158E-H249R, A016S-N062E, L111V-S188D, T022A-N062E, N062E-L148I, T022A-P129E, N062E-E271F, N062E-A158E, A016S-G159E, N062E-R186H, S128N-G159E, N062E-S188D, N062E-S128N, L148I-G159E, S103G-A158E, L111V-G159E, A158E-E271F, A016S-S188D, T022A-L111V, S128N-A158E, A016S-A158E, V104L-A158E, S128N-R186H, G159E-Y209E, N062E-S101A, L111V-Y209E, L148I-S188D, S101A-Y209E, T022A-S188D, A016S-T022A, S128N-P129E, A016S-Y209E, A016S-S128N, T022A-E089P, S128N-Y209E, E089P-A158E, N062E-S103G, R186H-E271F, A016S-P129E, E089P-G159E, L111V-H249R, S101A-P129E, L148I-Y209E, T022A-G159E, P129E-H249R, P129E-Y209E, V104L-P129E, S128N-S188D, L111V-A158E, T022A-A158E, N062E-Y209E, N062E-H249R, S101A-R186H, E089P-P129E, P129E-E271F, T22A-L111V-G159E, S101A-S103G-V104L-Y209E, S101A-S103G-V104L-G159E, S101A-S103G-V104L-S188D, S101G-S103A-V104I-G159D, T22A-S103G-G159E, T22A-S128N-E271F-Y209E, T22A-Y209E-E271F, T22A-S101A-Y209E, S101A-Y209E-E271F, T22A-L111V-S128N, T22A-S101A-G159E, S101A-S103G-V104L, T22A-S101A-S103G-V104L, S101A-S103G-V104L, S101G-S103A-V104I, S101A-S103G-V104L-S128N, S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, S101G-S103A-V104L-G159D-A232V-Q236H-Q245R-N248D, N62E-S101G-S103A-V104I-G159D-A232V-Q245R-N248D-E271F, N62E-S101G-S103A-V104I-G159D-A232V-Q245R-N248D-H249R, T22A-S101G-S103A-V104I-G159D-A232V-Q245R-N248D-H249R, S101G-S103A-V104I-G159D-A232V-Q245R-N248D-524R, S101G-S103A-V104I-G159D-A232V-Q245R-N248D-T253R, S101G-S103A-V104I-A158E-A232V-Q245R-N248D-H249R, T22A-S101G-S103A-V104I-G159D-A232V-Q245R-N248D-E271F, S101G-S103A-V104I-G159E-A232V-Q245R-N248D-H249R, S101G-S103A-V104I-G159D-A232V-Q245R-N248D-N238R, S101G-S103A-V104I-A158E-A232V-Q245R-N248D-E271F, S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N76D and S101G-S103A-V104I-G159E-A232V-Q245R-N248D-E271F; said cold water protease variant having a total net charge of +1, 0, −1, −2, −3, −4 or −5 relative to *B. lentus* subtilisin GG36 protease having the amino acid sequence of SEQ ID NO:1 and; wherein the wash liquor has a conductivity of from about 0.1 mS/cm to about 3 mS/cm, from about 0.3 mS/cm to about 2.5 mS/cm, or even from about 0.5 mS/cm to about 2 mS/cm.

In some embodiments, the fabric and home care product compositions comprising at least one protease variant comprises a wash liquor comprising an adjunct material, wherein at least one protease variant comprises: two or more of the following mutations V4R, H17R, N18R, G20R, T22R, S24R, S24W, G25R, N43R, N43A, G46R, P52F, P52N, T57R, Q59A, N62Q, T71G, L75R, N76D, S78R, L82R, P86W, E89P, E89W, E89T, E89I, E89H, E89V, V104L, S106V, S106G, G115R, G118I, V121F, S144R, N185I, D197F, Y209N, Y209S, L217E, A231I, P239R, P239S, W241R, S242R, S242L, N243R, V244R, N248I, H249R, N252R, T253R, E271T, E271V, E271L, E271H, E271F, E271P, A1R, S9A, S212F and N269R; and/or one or more of the following sets of mutations T022R-S024R, S009A-E271L, N018R-W241R, N018R-G115R, N043R-H249R, G020R-H249R, V004R-H249R, G020R-S024R, N018R-H249R, S009A-G020R, G020R-W241R, S009A-S078R, G020R-G115R, N018R-S024R, S024R-S242R, T022R-G115R, N018R-N043R, G020R-N043R, N018R-S242R, S242R-N269R, N018R-V244R, S024R-N269R, G020R-E271L, S024R-E271L, V004R-S009A, G020R-N269R, A001R-S024R, V244R-E271L, S009A-N018R, W241R-E271L, V004R-S024R, S009A-H249R, S009A-T022R, S101G-S103A-V104I-G159D-A232V-Q245R-N248D-E271F, S101G-S103A-V104I-A158E-A232V-Q245R-N248D-E271F, S101G-S103A-V104I-A158E-A232V-Q245R-N248D-H249R, S101G-S103A-V104I-G159D-A232V-Q245R-N248D-524R, S101G-S103A-V104L-G159D-A232V-Q236H-Q245R-N252K and S101G-S103A-V104L-A232V-Q236H-Q245R-N248D-N252K, said cold water protease variant having a total net charge of 0, +1, +2, +3, +4 or +5 relative to *B. lentus* subtilisin GG36 protease having the amino acid sequence of SEQ ID NO:2; and said laundry detergent wash liquor having conductivity of from about 3 mS/cm to about 30 mS/cm, from about 3.5 mS/cm to about 20 mS/cm, or even from about 4 mS/cm to about 10 mS/cm.

In some embodiments, the fabric and home care product compositions comprising at least one protease variant comprise one or more of the following ingredients (based on total composition weight): from about 0.0005 wt % to about 0.1 wt %, from about 0.001 wt % to about 0.05 wt %, or even from about 0.002 wt % to about 0.03 wt % of said cold water protease variant; and one or more of the following: from about 0.00003 wt % to about 0.1 wt % fabric hueing agent; from about 0.001 wt % to about 5 wt %, perfume capsules; from about 0.001 wt % to about 1 wt %, cold-water soluble brighteners; from about 0.00003 wt % to about 0.1 wt % bleach catalysts; from about 0.00003 wt % to about 0.1 wt % first wash lipases; from about 0.00003 wt % to about 0.1 wt % bacterial cleaning cellulases; and/or from about 0.05 wt % to about 20 wt % Guerbet nonionic surfactants.

In some embodiments, the fabric and home care product composition is a granular or powder laundry detergent that does not comprise a cold water protease.

In some embodiments, the fabric and home care product composition is a liquid laundry detergent, a dish washing detergent.

It is intended that the fabric and home care product is provided in any suitable form, including a fluid or solid. The fabric and home care product may be in the form of a unit dose pouch, especially when in the form of a liquid, and typically the fabric and home care product is at least partially, or even completely, enclosed by a water-soluble pouch. In addition, in some embodiments of the fabric and home care products comprising at least one protease variant, the fabric and home care product may have any combination of parameters and/or characteristics detailed above.

Cleaning Compositions

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. In the exemplified detergent compositions, the enzymes levels are expressed by pure enzyme by weight of the total composition and unless otherwise specified, the detergent ingredients are expressed by weight of the total compositions.

As indicated herein, in some embodiments, the cleaning compositions of the present invention further comprise adjunct materials including, but not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the variant proteases of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.).

The cleaning compositions of the present invention are advantageously employed for example, in laundry applications, hard surface cleaning, dishwashing applications, as well as cosmetic applications such as dentures, teeth, hair and skin. In addition, due to the unique advantages of increased effectiveness in lower temperature solutions, the enzymes of the present invention are ideally suited for laundry applications. Furthermore, the enzymes of the present invention find use in granular and liquid compositions.

The variant proteases of the present invention also find use in cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more proteases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the protease variants provided herein, alone or in combination with other proteases and/or additional enzymes. The required level of enzyme is achieved by the addition of one or more protease variants of the present invention. Typically the present cleaning compositions comprise at least about 0.0001 weight percent, from about 0.0001 to about 10, from about 0.001 to about 1, or even from about 0.01 to about 0.1 weight percent of at least one of the variant proteases of the present invention.

The cleaning compositions herein are typically formulated such that, during use in aqueous cleaning operations, the wash water will have a pH of from about 5.0 to about 11.5 or even from about 7.5 to about 10.5. Liquid product formulations are typically formulated to have a neat pH from about 3.0 to about 9.0 or even from about 3 to about 5. Granular laundry products are typically formulated to have a pH from about 9 to about 11. Techniques for controlling pH at recommended usage levels include the use of buffers, alkalis, acids, etc., and are well known to those skilled in the art.

Suitable "low pH cleaning compositions" typically have a neat pH of from about 3 to about 5, and are typically free of surfactants that hydrolyze in such a pH environment. Such surfactants include sodium alkyl sulfate surfactants that comprise at least one ethylene oxide moiety or even from about 1 to about 16 moles of ethylene oxide. Such cleaning compositions typically comprise a sufficient amount of a pH modifier, such as sodium hydroxide, monoethanolamine or hydrochloric acid, to provide such cleaning composition with a neat pH of from about 3 to about 5. Such compositions typically comprise at least one acid stable enzyme. In some embodiments, the compositions are liquids, while in other embodiments, they are solids. The pH of such liquid compositions is typically measured as a neat pH. The pH of such solid compositions is measured as a 10% solids solution of said composition wherein the solvent is distilled water. In these embodiments, all pH measurements are taken at 20° C., unless otherwise indicated.

In some embodiments, when the variant protease(s) is/are employed in a granular composition or liquid, it is desirable for the variant protease to be in the form of an encapsulated particle to protect the variant protease from other components of the granular composition during storage. In addition, encapsulation is also a means of controlling the availability of the variant protease during the cleaning process. In some embodiments, encapsulation enhances the performance of the variant protease(s) and/or additional enzymes. In this regard, the variant proteases of the present invention are encapsulated with any suitable encapsulating material known in the art. In some embodiments, the encapsulating material typically encapsulates at least part of the catalyst for the variant protease(s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP 0 922 499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

As described herein, the variant proteases of the present invention find particular use in the cleaning industry, including, but not limited to laundry and dish detergents. These applications place enzymes under various environmental stresses. The variant proteases of the present invention provide advantages over many currently used enzymes, due to their stability under various conditions.

Indeed, there are a variety of wash conditions including varying detergent formulations, wash water volumes, wash water temperatures, and lengths of wash time, to which proteases involved in washing are exposed. In addition, detergent formulations used in different geographical areas have different concentrations of their relevant components present in the wash water. For example, European detergents typically have about 4500-5000 ppm of detergent components in the wash water, while Japanese detergents typically have approximately 667 ppm of detergent components in the wash water. In North America, particularly the United States, detergents typically have about 975 ppm of detergent components present in the wash water.

A low detergent concentration system includes detergents where less than about 800 ppm of the detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of the detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of the detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between about 10 and about 30° C. (e.g., about 20° C.), whereas the temperature of wash water in Europe is typically between about 30 and about 60° C. (e.g., about 40° C.). However, in the interest of saving energy, many consumers are switching to using cold water washing. In addition, in some further regions, cold water is typically used for laundry, as well as dish washing applications. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

Accordingly, in some embodiments, the present invention provides variant proteases that show surprising wash performance in at least one set of wash conditions (e.g., water temperature, water hardness, and/or detergent concentration). In some embodiments, the variant proteases of the present invention are comparable in wash performance to other subtilisin proteases. In some embodiments, the variant proteases of the present invention exhibit enhanced wash performance as compared to subtilisin proteases currently commercially available. Thus, in some embodiments of the present invention, the variant proteases provided herein exhibit enhanced oxidative stability, enhanced thermal stability, enhanced cleaning capabilities under various conditions, and/or enhanced chelator stability. In addition, the variant proteases of the present invention find use in cleaning compositions that do not include detergents, again either alone or in combination with builders and stabilizers.

In some embodiments of the present invention, the cleaning compositions comprise at least one variant protease of the present invention at a level from about 0.00001% to about 10% by weight of the composition and the balance (e.g., about 99.999% to about 90.0%) comprising cleaning adjunct materials by weight of composition. In some other embodiments of the present invention, the cleaning compositions of the present invention comprises at least one variant protease at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In some embodiments, the cleaning compositions of the present invention comprise one or more additional detergent enzymes, which provide cleaning performance and/or fabric care and/or dishwashing benefits. Examples of suitable enzymes include, but are not limited to, hemicellulases, cellulases, peroxidases, proteases, xylanases, lipases, phospholipases, esterases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidases, chondroitinases, laccases, and amylases, or any combinations or mixtures thereof. In some embodiments, a combination of enzymes is used (i.e., a "cocktail") comprising conventional applicable enzymes like protease, lipase, cutinase and/or cellulase in conjunction with amylase is used.

In addition to the protease variants provided herein, any other suitable protease finds use in the compositions of the present invention. Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from Bacillus (e.g., subtilisin, lentus, amyloliquefaciens, subtilisin Carlsberg, subtilisin 309, subtilisin 147 and subtilisin 168). Additional examples include those mutant proteases described in U.S. Pat. Nos. RE 34,606, 5,955,340, 5,700,676, 6,312,936, and 6,482,628, all of which are incorporated herein by reference. Additional protease examples include, but are not limited to trypsin (e.g., of porcine or bovine origin), and the Fusarium protease described in WO 89/06270. In some embodiments, commercially available protease enzymes that find use in the present invention include, but are not limited to MAXATASE®, MAXACAL™, MAXAPEM™, OPTICLEAN®, OPTIMASE®, PROPERASE®, PURAFECT®, PURAFECT® OXP, PURAMAX™, EXCELLASE™, and PURAFAST™ (Genencor); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); BLAP™ and BLAP™ variants (Henkel Kommanditgesellschaft auf Aktien, Duesseldorf, Germany), and KAP (B. alkalophilus subtilisin; Kao Corp., Tokyo, Japan). Various proteases are described in WO95/23221, WO 92/21760, U.S. Pat. Publ. No. 2008/0090747, and U.S. Pat. Nos. 5,801,039, 5,340,735, 5,500,364, 5,855,625, U.S. RE 34,606, 5,955,340, 5,700,676, 6,312,936, and 6,482,628, and various other patents. In some further embodiments, metalloproteases find use in the present invention, including but not limited to the neutral metalloprotease described in WO 07/044993.

In addition, any suitable lipase finds use in the present invention. Suitable lipases include, but are not limited to those of bacterial or fungal origin. Chemically or genetically modified mutants are encompassed by the present invention. Examples of useful lipases include Humicola lanuginosa lipase (See e.g., EP 258 068, and EP 305 216), Rhizomucor miehei lipase (See e.g., EP 238 023), Candida lipase, such as C. antarctica lipase (e.g., the C. antarctica lipase A or B; See e.g., EP 214 761), Pseudomonas lipases such as P. alcaligenes lipase and P. pseudoalcaligenes lipase (See e.g., EP 218 272), P. cepacia lipase (See e.g., EP 331 376), P. stutzeri lipase (See e.g., GB 1,372,034), P. fluorescens lipase, Bacillus lipase (e.g., B. subtilis lipase [Dartois et al., Biochem. Biophys. Acta 1131:253-260 [1993]); B. stearothermophilus lipase [See e.g., JP 64/744992]; and B. pumilus lipase [See e.g., WO 91/16422]).

Furthermore, a number of cloned lipases find use in some embodiments of the present invention, including but not limited to Penicillium camembertii lipase (See, Yamaguchi et al., Gene 103:61-67 [1991]), Geotricum candidum lipase (See, Schimada et al., J. Biochem., 106:383-388 [1989]), and various Rhizopus lipases such as R. delemar lipase (See, Hass et al., Gene 109:117-113 [1991]), a R. niveus lipase (Kugimiya et al., Biosci. Biotech. Biochem. 56:716-719 [1992]) and R. oryzae lipase.

Other types of lipolytic enzymes such as cutinases also find use in some embodiments of the present invention, including but not limited to the cutinase derived from

*Pseudomonas mendocina* (See, WO 88/09367), and the cutinase derived from *Fusarium solani pisi* (See, WO 90/09446).

Additional suitable lipases include commercially available lipases such as M1 LIPASE™ LUMA FAST™, and LIPOMAX™ (Genencor); LIPEX®, LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from about 0.00001% to about 10% of additional lipase by weight of the composition and the balance of cleaning adjunct materials by weight of composition. In some other embodiments of the present invention, the cleaning compositions of the present invention also comprise lipases at a level of about 0.0001% to about 10%, about 0.001% to about 5%, about 0.001% to about 2%, about 0.005% to about 0.5% lipase by weight of the composition.

In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296, 839). Commercially available amylases that find use in the present invention include, but are not limited to DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P (Genencor).

In some embodiments of the present invention, the cleaning compositions of the present invention further comprise amylases at a level from about 0.00001% to about 10% of additional amylase by weight of the composition and the balance of cleaning adjunct materials by weight of composition. In some other embodiments of the present invention, the cleaning compositions of the present invention also comprise amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257). Commercially available cellulases that find use in the present include, but are not limited to CELLUZYME®, CAREZYME® (Novozymes), and KAC-500(B)™ (Kao Corporation). In some embodiments, cellulases are incorporated as portions or fragments of mature wild-type or variant cellulases, wherein a portion of the N-terminus is deleted (See e.g., U.S. Pat. No. 5,874, 276). In some embodiments, the cleaning compositions of the present invention further comprise cellulases at a level from about 0.00001% to about 10% of additional cellulase by weight of the composition and the balance of cleaning adjunct materials by weight of composition. In some other embodiments of the present invention, the cleaning compositions of the present invention also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114, 6,602,842, and 6,440,991, all of which are incorporated herein by reference). In some embodiments, the cleaning compositions of the present invention further comprise mannanases at a level from about 0.00001% to about 10% of additional mannanase by weight of the composition and the balance of cleaning adjunct materials by weight of composition. In some embodiments of the present invention, the cleaning compositions of the present invention also comprise mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001% to about 10% of additional peroxidase and/or oxidase by weight of the composition and the balance of cleaning adjunct materials by weight of composition. In some other embodiments of the present invention, the cleaning compositions of the present invention also comprise, peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See e.g., WO 05/056782). In addition, in some embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the variant protease(s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dye transfer inhibiting agents, catalytic materials, hydrogen peroxide, sources of hydrogen peroxide, preformed peracids, polymeric dispersing agents, clay soil removal agents, structure elasticizing agents, dispersants, suds suppressors, dyes, perfumes, colorants, filler salts, hydrotropes, photoactivators, fluorescers, fabric conditioners, fabric softeners, carriers, hydrotropes, processing aids, solvents, pigments, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the variant proteases of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.).

In some embodiments, an effective amount of one or more variant protease(s) provided herein is included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the variant proteases of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with the variant proteases of the present invention. Thus, in some embodiments, the compositions comprising at least one variant protease of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one variant protease of the present invention are fabric cleaning compositions such as those described in U.S. Pat. Nos. 6,610,642 and 6,376,450. In addition, the variant proteases of the present invention find use in granular laundry detergent compositions of particular utility under European or Japanese washing conditions (See e.g., U.S. Pat. No. 6,610,642).

In some alternative embodiments, the present invention provides hard surface cleaning compositions comprising at least one variant protease provided herein. Thus, in some embodiments, the compositions comprising at least one variant protease of the present invention is a hard surface cleaning composition such as those described in U.S. Pat. Nos. 6,610,642, 6,376,450, and 6,376,450.

In yet further embodiments, the present invention provides dishwashing compositions comprising at least one variant protease provided herein. Thus, in some embodiments, the compositions comprising at least one variant protease of the present invention is a hard surface cleaning composition such as those in U.S. Pat. Nos. 6,610,642 and 6,376,450. In some still further embodiments, the present invention provides dishwashing compositions comprising at least one variant protease provided herein. In some further embodiments, the compositions comprising at least one variant protease of the present invention comprise oral care compositions such as those in U.S. Pat. Nos. 6,376,450, and 6,376,450. The formulations and descriptions of the compounds and cleaning adjunct materials contained in the aforementioned U.S. Pat. Nos. 6,376,450, 6,605,458, 6,605,458, and 6,610,642, find use with the variant proteases provided herein.

The cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,565,422, 5,516,448, 5,489,392, and 5,486,303, all of which are incorporated herein by reference. When a low pH cleaning composition is desired, the pH of such composition is adjusted via the addition of a material such as monoethanolamine or an acidic material such as HCl.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the variant proteases of the present invention. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/ or pigments. In addition to the disclosure below, suitable examples of such other adjuncts and levels of use are found in U.S. Pat. Nos. 5,576,282, 6,306,812, and 6,326,348, incorporated by reference. The aforementioned adjunct ingredients may constitute the balance of the cleaning compositions of the present invention.

In some embodiments, the cleaning compositions according to the present invention comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some low pH cleaning composition embodiments (e.g., compositions having a neat pH of from about 3 to about 5), the composition typically does not contain alkyl ethoxylated sulfate, as it is believed that such surfactant may be hydrolyzed by such compositions the acidic contents. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP 2 100 949).

In some embodiments, the cleaning compositions of the present invention contain at least one chelating agent. Suitable chelating agents include, but are not limited to, copper, iron and/or manganese chelating agents and mixtures thereof. In embodiments in which at least one chelating agent is used, the cleaning compositions of the present invention comprise from about 0.1% to about 15% or even from about 3.0% to about 10% chelating agent by weight of the subject cleaning composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in some embodiments, anti-redeposition agents find use in some embodiments of the present invention. In some embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some embodiments, the anti-redeposition agent is a non-ionic surfactant as known in the art (See e.g., EP 2 100 949).

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1% to about 20%. In some embodiments, silicates are present at a level of from about 5% to about 15% by weight of the composition.

In some still additional embodiments, the cleaning compositions of the present invention also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized by any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO 07/145964). In some embodiments, reversible protease inhibitors also find use, such as boron-containing compounds (e.g., borate, 4-formyl phenyl boronic acid) and/or a tripeptide aldehyde find use to further improve stability, as desired.

In some embodiments, bleaches, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP 2 100 949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP 2 100 949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612, 5,227,084, 4,810,410, WO 99/06521, and EP 2 100 949).

In some embodiments, the cleaning compositions of the present invention contain one or more catalytic metal complexes. In some embodiments, a metal-containing bleach catalyst finds use. In some embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In some additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some embodiments, provide from about 0.005 ppm to about 25 ppm, more preferably from about 0.05 ppm to about 10 ppm, and most preferably from about 0.1 ppm to about 5 ppm, of the MRL in the wash liquor.

In some embodiments, transition-metals in the instant transition-metal bleach catalyst include, but are not limited to manganese, iron and chromium. MRLs also include, but are not limited to special ultra-rigid ligands that are cross-bridged (e.g., 5,12-diethyl-1,5,8,12-tetraazabicyclo[6.6.2] hexadecane). Suitable transition metal MRLs are readily prepared by known procedures (See e.g., WO 2000/32601, and U.S. Pat. No. 6,225,464).

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 9426860 and WO 94/26859). In some embodiments, the metal care agent is a zinc salt. In some further embodiments, the cleaning compositions of the present invention comprise from about 0.1% to about 5% by weight of one or more metal care agent.

As indicated above, the cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,516,448, 5,489,392, and 5,486,303, all of which are incorporated herein by reference. In some embodiments in which a low pH cleaning composition is desired, the pH of such composition is adjusted via the addition of an acidic material such as HCl.

The cleaning compositions disclosed herein of find use in cleaning a situs (e.g., a surface, item, dishware, or fabric). Typically, at least a portion of the situs is contacted with an embodiment of the present cleaning composition, in neat form or diluted in a wash liquor, and then the situs is optionally washed and/or rinsed. For purposes of the present invention, "washing" includes but is not limited to, scrubbing, and mechanical agitation. In some embodiments, the cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

Processes of Making and Using Cleaning Compositions

The cleaning compositions of the present invention are formulated into any suitable form and prepared by any suitable process chosen by the formulator, (See e.g., U.S. Pat. Nos. 5,879,584, 5,691,297, 5,574,005, 5,569,645, 5,565,422, 5,516,448, 5,489,392, 5,486,303, 4,515,705, 4,537,706, 4,515,707, 4,550,862, 4,561,998, 4,597,898, 4,968,451, 5,565,145, 5,929,022, 6,294,514 and 6,376,445).

In some embodiments, the cleaning compositions of the present invention are provided in unit dose form, including tablets, capsules, sachets, pouches, and multi-compartment pouches. In some embodiments, the unit dose format is designed to provide controlled release of the ingredients within a multi-compartment pouch (or other unit dose format). Suitable unit dose and controlled release formats are known in the art (See e.g., EP 2 100 949, WO 02/102955, U.S. Pat. Nos. 4,765,916 and 4,972,017, and WO 04/111178 for materials suitable for use in unit dose and controlled release formats). In some embodiments, the unit dose form is provided by tablets wrapped with a water-soluble film or water-soluble pouches. Various formats for unit doses are provided in EP 2 100 947, and are known in the art.

Methods of Use

In some embodiments, the cleaning compositions of the present invention find use in cleaning surfaces (e.g., dishware), laundry, hard surfaces, contact lenses, etc. In some embodiments, at least a portion of the surface is contacted with at least one embodiment of the cleaning compositions of the present invention, in neat form or diluted in a wash liquor, and then the surface is optionally washed and/or rinsed. For purposes of the present invention, "washing" includes, but is not limited to, scrubbing, and mechanical washing. In some embodiments, the cleaning compositions of the present invention are used at concentrations of from about 500 ppm to about 15,000 ppm in solution. In some embodiments in which the wash solvent is water, the water temperature typically ranges from about 5° C. to about 90° C.

The present invention provides methods for cleaning or washing an item or surface (e.g., hard surface) in need of cleaning, including, but not limited to methods for cleaning or washing a dishware item, a tableware item, a fabric item, a laundry item, personal care item, etc., or the like, and methods for cleaning or washing a hard or soft surface (e.g., a hard surface of an item).

In some embodiments, the present invention provides a method for cleaning an item, object, or surface in need of cleaning, the method comprising contacting the item or surface (or a portion of the item or surface desired to be cleaned) with at least one variant subtilisin protease of the present invention or a composition of the present invention for a sufficient time and/or under conditions suitable and/or effective to clean the item, object, or surface to a desired degree. Some such methods further comprise rinsing the item, object, or surface with water. For some such methods, the cleaning composition is a dishwashing detergent composition and the item or object to be cleaned is a dishware item or tableware item. As used herein, a "dishware item" is an item generally used in serving or eating food. A dishware item can be, but is not limited to for example, a dish, plate, cup, bowl, etc., and the like. As used herein, "tableware" is a broader term that includes, but is not limited to for example, dishes, cutlery, knives, forks, spoons, chopsticks, glassware, pitchers, sauce boats, drinking vessels, serving items, etc. It is intended that "tableware item" includes any of these or similar items for serving or eating food. For some such methods, the cleaning composition is an automatic dishwashing detergent composition or a hand dishwashing detergent composition and the item or object to be cleaned is a dishware or tableware item. For some such methods, the cleaning composition is a laundry detergent composition (e.g., a power laundry detergent composition or a liquid laundry detergent composition), and the item to be cleaned is a fabric item. In some other embodiments, the cleaning composition is a laundry pre-treatment composition.

In some embodiments, the present invention provides methods for cleaning or washing a fabric item optionally in need of cleaning or washing, respectively. In some embodiments, the methods comprise providing a composition comprising the variant protease, including but not limited to fabric or laundry cleaning composition, and a fabric item or laundry item in need of cleaning, and contacting the fabric item or laundry item (or a portion of the item desired to be cleaned) with the composition under conditions sufficient or effective to clean or wash the fabric or laundry item to a desired degree.

In some embodiments, the present invention provides a method for cleaning or washing an item or surface (e.g., hard surface) optionally in need of cleaning, the method comprising providing an item or surface to be cleaned or washed and contacting the item or surface (or a portion of the item or surface desired to be cleaned or washed) with at least one subtilisin variant of the invention or a composition of the invention comprising at least one such subtilisin variant for a sufficient time and/or under conditions sufficient or effective to clean or wash the item or surface to a desired degree. Such compositions include, but are not limited to for example, a cleaning composition or detergent composition of the invention (e.g., a hand dishwashing detergent composition, hand dishwashing cleaning composition, laundry detergent or fabric detergent or laundry or fabric cleaning composition, liquid laundry detergent, liquid laundry cleaning composition, powder laundry detergent composition, powder laundry cleaning composition, automatic dishwashing detergent composition, laundry booster cleaning or detergent composition, laundry cleaning additive, and laundry pre-spotter composition, etc.). In some embodiments, the method is repeated one or more times, particularly if additional cleaning or washing is desired. For example, in some instance, the method optionally further comprises allowing the item or surface to remain in contact with the at least one variant protease or composition for a period of time sufficient or effective to clean or wash the item or surface to the desired degree. In some embodiments, the methods further comprise rinsing the item or surface with water and/or another liquid. In some embodiments, the methods further comprise contacting the item or surface with at least one variant protease of the invention or a composition of the invention again and allowing the item or surface to remain in contact with the at least one variant protease or composition for a period of time sufficient to clean or wash the item or surface to the desired degree. In some embodiments, the cleaning composition is a dishwashing detergent composition and the item to be cleaned is a dishware or tableware item. In some embodiments of the present methods, the cleaning composition is an automatic dishwashing detergent composition or a hand dishwashing detergent composition and the item to be cleaned is a dishware or tableware item. In some embodiments of the methods, the cleaning composition is a laundry detergent composition and the item to be cleaned is a fabric item.

The present invention also provides methods of cleaning a tableware or dishware item in an automatic dishwashing machine, the method comprising providing an automatic dishwashing machine, placing an amount of an automatic dishwashing composition comprising at least one subtilisin variant of the present invention or a composition of the invention sufficient to clean the tableware or dishware item in the machine (e.g., by placing the composition in an appropriate or provided detergent compartment or dispenser in the machine), putting a dishware or tableware item in the machine, and operating the machine so as to clean the tableware or dishware item (e.g., as per the manufacturer's instructions). In some embodiments, the methods include any automatic dishwashing composition described herein, which comprises, but is not limited to at least one subtilisin variant provided herein. The amount of automatic dishwashing composition to be used can be readily determined according to the manufacturer's instructions or suggestions and any form of automatic dishwashing composition comprising at least one variant protease of the invention (e.g., liquid, powder, solid, gel, tablet, etc.), including any described herein, may be employed.

The present invention also provides methods for cleaning a surface, item or object optionally in need of cleaning, the method comprises contacting the item or surface (or a portion of the item or surface desired to be cleaned) with at least one variant subtilisin of the present invention or a cleaning composition of the invention in neat form or diluted in a wash liquor for a sufficient time and/or under conditions sufficient or effective to clean or wash the item or surface to a desired degree. The surface, item, or object may then be (optionally) washed and/or rinsed if desired. For purposes of the present invention, "washing" includes, but is not limited to for example, scrubbing and mechanical agitation. In some embodiments, the cleaning compositions are employed at concentrations of from about 500 ppm to about 15,000 ppm in solution (e.g., aqueous solution). When the wash solvent is water, the water temperature typically ranges from about 5° C. to about 90° C. and when the surface, item or object comprises a fabric, the water to fabric mass ratio is typically from about 1:1 to about 30:1.

The present invention also provides methods of cleaning a laundry or fabric item in an washing machine, the method comprising providing an washing machine, placing an amount of a laundry detergent composition comprising at least one variant subtilisin of the invention sufficient to clean the laundry or fabric item in the machine (e.g., by placing the composition in an appropriate or provided detergent compartment or dispenser in the machine), placing the laundry or fabric item in the machine, and operating the machine so as to clean the laundry or fabric item (e.g., as per the manufacturer's instructions). The methods of the present invention include any laundry washing detergent composition described herein, comprising but not limited to at least one of any variant subtilisin provided herein. The amount of laundry detergent composition to be used can be readily determined according to manufacturer's instructions or suggestions and any form of laundry detergent composition comprising at least one variant protease of the invention (e.g., solid, powder, liquid, tablet, gel, etc.), including any described herein, may be employed.

EXPERIMENTAL

The present invention is described in further detail in the following examples which are not in any way intended to limit the scope of the invention as claimed.

In the experimental disclosure which follows, the following abbreviations apply: PI (Performance Index), ppm (parts per million); M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml and mL (milliliters); µl and µL (microliters); cm (centimeters); mm (millimeters); µm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); rpm (revolutions per minute); GH (degrees German hardness); $H_2O$ (water); $dH_2O$ (deionized water); HCl (hydrochloric acid); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); w/w (weight to weight); g (gravity); OD (optical density); ppm (parts per million); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto-Tryptone, 24 g/l glycerol, 2.31 g/l $KH_2PO_4$, and 12.54 g/l $K_2HPO_4$); OD280 (optical density at 280 nm); $OD_{600}$ (optical density at 600 nm); $A_{405}$ (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN®-20); PEG (polyethylene glycol); PCR (polymerase chain reaction); RT-PCR (reverse transcription PCR); SDS (sodium dodecyl sulfate); Tris (tris (hydroxymethyl)aminomethane); HEPES (N-[2-Hydroxyethyl]piperazine-N-[2-ethanesulfonic acid]); HBS (HEPES buffered saline); Tris-HCl (tris[Hydroxymethyl]aminomethane-hydrochloride); Tricine (N-[tris-(hydroxymethyl)-methyl]-glycine); CHES (2-(N-cyclo-hexylamino) ethanesulfonic acid); TAPS (3-{[tris-(hydroxymethyl)-methyl]-amino}-propanesulfonic acid); CAPS (3-(cyclohexylamino)-propane-sulfonic acid; DMSO (dimethyl sulfoxide); DTT (1,4-dithio-DL-threitol); SA (sinapinic acid (s,5-dimethoxy-4-hydroxy cinnamic acid); TCA (trichloroacetic acid); Glut and GSH (reduced glutathione); GSSG (oxidized glutathione); TCEP (Tris[2-carboxyethyl] phosphine); Ci (Curies); mCi (milliCuries); µCi (microCuries); HPLC (high pressure liquid chromatography); RP-HPLC (reverse phase high pressure liquid chromatography); TLC (thin layer chromatography); MALDI-TOF (matrix-assisted laser desorption/ionization—time of flight); Ts (tosyl); Bn (benzyl); Ph (phenyl); Ms (mesyl); Et (ethyl), Me (methyl); Taq (*Thermus aquaticus* DNA polymerase); Klenow (DNA polymerase I large (Klenow) fragment); EGTA (ethylene glycol-bis(β-aminoethyl ether) N, N, N', N'-tetraacetic acid); EDTA (ethylenediaminetetracetic acid); bla (β-lactamase or ampicillin-resistance gene); HDL (high density liquid); HDD (heavy duty powder detergent); HSG (high suds granular detergent); CEE (Central and Eastern Europe); WE (Western Europe); NA, when used in reference to detergents (North America); Japan and JPN, when used in reference to detergents (Japan); MJ Research (MJ Research, Reno, Nev.); Baseclear (Baseclear BV, Inc., Leiden, the Netherlands); PerSeptive (PerSeptive Biosystems, Framingham, Mass.); ThermoFinnigan (ThermoFinnigan, San Jose, Calif.); Argo (Argo BioAnalytica, Morris Plains, N.J.); Seitz EKS (SeitzSchenk Filtersystems GmbH, Bad Kreuznach, Germany); Pall (Pall Corp., East Hills, N.Y. and Bad Kreuznach, Germany); Spectrum (Spectrum Laboratories, Dominguez Rancho, Calif.); Molecular Structure (Molecular Structure Corp., Woodlands, Tex.); Accelrys (Accelrys, Inc., San Diego, Calif.); Chemical Computing (Chemical Computing Corp., Montreal, Canada); New Brunswick (New Brunswick Scientific, Co., Edison, N.J.); CFT (Center for Test Materials, Vlaardingen, the Netherlands); P&G and Procter & Gamble (Procter & Gamble, Inc., Cincinnati, Ohio); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Finnzymes (Finnzymes Oy, Espoo, Finland); Kelco (CP Kelco, Wilmington, Del.); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); NCBI (National Center for Biotechnology Information); Applied Biosystems (Applied Biosystems, Foster City, Calif.); BD Biosciences and/or Clontech (BD Biosciences CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc., King of Prussia, Pa.); Difco (Difco Laboratories, Detroit, Mich.); Mediatech (Mediatech, Herndon, Va.; Santa Cruz (Santa Cruz Biotechnology, Inc., Santa Cruz, Calif.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Sorvall (Sorvall brand, from Kendro Laboratory Products, Asheville, N.C.); Molecular Devices (Molecular Devices, Corp., Sunnyvale, Calif.); R&D Systems (R&D Systems, Minneapolis, Minn.); Siegfried Handel (Siegfried Handel AG, Zofingen, Switzerland); Stratagene (Stratagene Cloning Systems, La Jolla, Calif.); Marsh (Marsh Biosciences, Rochester, N.Y.); Geneart (Geneart GmbH, Regensburg, Germany); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); New Objective (New Objective brand; Scientific Instrument Services, Inc., Ringoes, N.J.); Waters (Waters, Inc., Milford, Mass.); Matrix Science (Matrix Science, Boston, Mass.); Dionex (Dionex, Corp., Sunnyvale, Calif.); Monsanto (Monsanto Co., St. Louis, Mo.); Wintershall (Wintershall AG, Kassel, Germany); BASF (BASF Co., Florham Park, N.J.); Huntsman (Huntsman Petrochemical Corp., Salt Lake City, Utah); Shell Chemicals (Shell Chemicals, Inc., London, UK); Stepan (Stepan, Northfield, Ill.); Clariant (Clariant, Sulzbach, Germany); Industrial Zeolite (Industrial Zeolite Ltd., Grays, Essex, UK); Jungbunzlauer (Jungbunzlauer, Basel, Switzerland); Solvay (Solvay, Brussels, Belgium); 3V Sigma (3V Sigma, Bergamo, Italy); Innospec (Innospec, Ellesmere Port, UK); Thermphos (Thermphos, Vlissiggen-Ost, the Netherlands); Ciba Specialty (Ciba Specialty Chemicals, Basel, Switzerland); Dow Corning (Dow Corning, Barry, UK); Enichem (Enichem Iberica, Barcelona, Spain); Fluka Chemie AG (Fluka Chemie AG, Buchs, Switzerland); Gist-Brocades (Gist-Brocades, NV, Delft, the Netherlands); Dow Corning (Dow Corning Corp., Midland, Mich.); Mettler-Toledo (Mettler-Toledo Inc, Columbus, Ohio); RB (Reckitt-Benckiser, Slough, UK); and Microsoft (Microsoft, Inc., Redmond, Wash.).

As used herein, in some lists, a leading "0" is indicated, in order to provide a three number designation for each site (e.g., "001" is the same as "1," so "A001C" is the same as "A1C"). In some lists, the leading "0" is not included. In addition, as used herein, "X" refers to any amino acid.

In the exemplified detergent compositions provided herein, the enzymes levels are expressed by pure enzyme by weight of the total composition and unless otherwise specified, the detergent ingredients are expressed by weight of the total compositions. The abbreviated component identifications therein have the following meanings:

| Abbreviation | Ingredient |
|---|---|
| LAS | Sodium linear $C_{11-13}$ alkyl benzene sulfonate. |
| NaC16-17HSAS | Sodium $C_{16-17}$ highly soluble alkyl sulfate |
| TAS | Sodium tallow alkyl sulphate. |
| CxyAS | Sodium $C_{1x}$-$C_{1y}$ alkyl sulfate. |
| CxyEz | $C_{1x}$-$C_{1y}$ predominantly linear primary alcohol condensed with an average of z moles of ethylene oxide. |
| CxyAEzS | $C_{1x}$-$C_{1y}$ sodium alkyl sulfate condensed with an average of z moles of ethylene oxide. Added molecule name in the examples. |
| Nonionic | Mixed ethoxylated/propoxylated fatty alcohol e.g. Plurafac LF404 being an alcohol with an average degree of ethoxylation of 3.8 and an average degree of propoxylation of 4.5. |
| QAS | $R_2 \bullet N+(CH_3)_2(C_2H_4OH)$ with $R_2 = C_{12}$-$C_{14}$. |
| Silicate | Amorphous Sodium Silicate ($SiO_2:Na_2O$ ratio = 1.6-3.2:1). |
| Metasilicate | Sodium metasilicate ($SiO_2:Na_2O$ ratio = 1.0). |
| Zeolite A | Hydrated aluminosilicate of formula $Na_{12}(AlO_2SiO_2)_{12} \bullet 27H_2O$ |
| SKS-6 | Crystalline layered silicate of formula $\delta$-$Na_2Si_2O_5$. |
| Sulfate | Anhydrous sodium sulphate. |
| STPP | Sodium Tripolyphosphate. |
| MA/AA | Random copolymer of 4:1 acrylate/maleate, average molecular weight about 70,000-80,000. |
| AA | Sodium polyacrylate polymer of average molecular weight 4,500. |
| Polycarboxylate | Copolymer comprising mixture of carboxylated monomers such as acrylate, maleate and methyacrylate with a MW ranging between 2,000-80,000 such as Sokolan commercially available from BASF, being a copolymer of acrylic acid, MW 4,500. |
| BB1 | 3-(3,4-Dihydroisoquinolinium)propane sulfonate |
| BB2 | 1-(3,4-dihydroisoquinolinium)-decane-2-sulfate |
| PB1 | Sodium perborate monohydrate. |
| PB4 | Sodium perborate tetrahydrate of nominal formula $NaBO_3 \bullet 4H_2O$. |
| Percarbonate | Sodium percarbonate of nominal formula $2Na_2CO_3 \bullet 3H_2O_2$. |
| TAED | Tetraacetyl ethylene diamine. |
| NOBS | Nonanoyloxybenzene sulfonate in the form of the sodium salt. |

-continued

| Abbreviation | Ingredient |
|---|---|
| DTPA | Diethylene triamine pentaacetic acid. |
| HEDP | 1,1-hydroxyethane diphosphonic acid. |
| DETPMP | Diethyltriamine penta (methylene) phosphonate, marketed by Monsanto under the Trade name Dequest 2060. |
| EDDS | Ethylenediamine-N,N'-disuccinic acid, (S,S) isomer in the form of its sodium salt |
| Diamine | Dimethyl aminopropyl amine; 1,6-hezane diamine; 1,3-propane diamine; 2-methyl-1,5-pentane diamine; 1,3-pentanediamine; 1-methyl-diaminopropane. |
| DETBCHD | 5,12-diethyl-1,5,8,12-tetraazabicyclo [6,6,2] hexadecane, dichloride, Mn(II) SALT |
| PAAC | Pentaamine acetate cobalt(III) salt. |
| Paraffin | Paraffin oil sold under the tradename Winog 70 by Wintershall. |
| Paraffin Sulfonate | A Paraffin oil or wax in which some of the hydrogen atoms have been replaced by sulfonate groups. |
| Aldose oxidase | Oxidase enzyme sold under the tradename Aldose Oxidase by Novozymes A/S |
| Galactose oxidase | Galactose oxidase from Sigma |
| nprE | The recombinant form of neutral metalloprotease expressed in Bacillus subtilis (See e.g., WO 07/044993) |
| PMN | Purified neutral metalloprotease from Bacillus amyloliquefacients. |
| Amylase | A suitable amylolytic enzyme, such as those sold under the tradenames PURAFECT ® Ox described in WO 94/18314, WO96/05295 sold by Genencor; NATALASE ®, TERMAMYL ®, FUNGAMYl ® and DURAMYL ™, all available from Novozymes A/S. |
| Lipase | A suitable lipolytic enzyme such as those sold under the tradenames LIPEX ®, LIPOLASE ®, LIPOLASE ® Ultra by Novozymes A/S and Lipomax ™ by Gist-Brocades. |
| Cellulase | A suitable cellulytic enzyme such as those sold under the tradenames CAREZYME ®, CELLUZYME ®, and/or ENDOLASE ® by Novozymes A/S. |
| Pectin Lyase | A suitable pectin lyase, such as those sold under the tradenames PECTAWAY ® and PECTAWASH ® available from Novozymes A/S. |
| PVP | Polyvinylpyrrolidone with an average molecular weight of 60,000 |
| PVNO | Polyvinylpyridine-N-Oxide, with an average molecular weight of 50,000. |
| PVPVI | Copolymer of vinylimidazole and vinylpyrrolidone, with an average molecular weight of 20,000. |
| Brightener 1 | Disodium 4,4'-bis(2-sulphostyryl)biphenyl. |
| Silicone antifoam | Polydimethylsiloxane foam controller with siloxane-oxyalkylene copolymer as dispersing agent with a ratio of said foam controller to said dispersing agent of 10:1 to 100:1. |
| Suds Suppressor | 12% Silicone/silica, 18% stearyl alcohol, 70% starch in granular form. |
| SRP 1 | Anionically end capped poly esters. |
| PEG X | Polyethylene glycol, of a molecular weight of x. |
| PVP K60 ® | Vinylpyrrolidone homopolymer (average MW 160,000) |
| Jeffamine ® ED-2001 | Capped polyethylene glycol from Huntsman |
| Isachem ® AS | A branched alcohol alkyl sulphate from Enichem |
| MME PEG (2000) | Monomethyl ether polyethylene glycol (MW 2000) from Fluka Chemie AG. |
| DC3225C | Silicone suds suppresser, mixture of Silicone oil and Silica from Dow Corning. |
| TEPAE | Tetreaethylenepentaamine ethoxylate. |
| BTA | Benzotriazole. |
| Betaine | $(CH_3)_3N^+CH_2COO^-$ |
| Sugar | Industry grade D-glucose or food grade sugar |
| CFAA | $C_{12}$-$C_{14}$ alkyl N-methyl glucamide |
| TPKFA | $C_{12}$-$C_{14}$ topped whole cut fatty acids. |
| Clay | A hydrated aluminumu silicate in a general formula $Al_2O_3SiO_2 \cdot xH_2O$. Types: Kaolinite, montmorillonite, atapulgite, illite, bentonite, halloysite. |
| pH | Measured as a 1% solution in distilled water at 20° C. |

For North American (NA) and Western European (WE) heavy duty liquid laundry (HDL) detergents, heat inactivation of the enzymes present in commercially-available detergents is performed by placing pre-weighed liquid detergent (in a glass bottle) in a water bath at 95° C. for 2 hours. The incubation time for heat inactivation of NA and WE auto dish washing (ADW) detergents is 8 hours. Both un-heated and heated detergents are assayed within 5 minutes of dissolving the detergent to accurately determine percentage deactivated. Enzyme activity is tested by the AAPF assay.

For testing of enzyme activity in heat-inactivated detergents, working solutions of detergents are made from the heat inactivated stocks. Appropriate amounts of water hardness (e.g., 6 gpg or 12 gpg) and buffer are added to the detergent solutions to match the desired conditions. The solutions are mixed by vortexing or inverting the bottles.

The following Table provides information regarding some of the commercially-available detergents and test conditions used herein. In some experiments, additional and/or other commercially available detergents find use in the following Examples.

TABLE A

| Laundry and Dish Washing Conditions | | | | | | | |
|---|---|---|---|---|---|---|---|
| Region | Form | Dose | Detergent* | Buffer | Gpg | pH | T (°C.) |
| Laundry (Heavy Duty Liquid and Granular) | | | | | | | |
| NA | HDL | 0.78 g/l | P&G TIDE ® 2X | 5 mM HEPES | 6 | 8.0 | 20 |
| WE | HDL | 5.0 g/L | Henkel PERSIL ™ | 5 mM HEPES | 12 | 8.2 | 40 |
| WE | HDG | 8.0 g/L | P&G ARIEL ® | 2 mM Na$_2$CO$_3$ | 12 | 10.5 | 40 |
| JPN | HDG | 0.7 g/L | P&G TIDE ® | 2 mM Na$_2$CO$_3$ | 6 | 10.0 | 20 |
| NA | HDG | 1.0 g/L | P&G TIDE ® | 2 mM Na$_2$CO$_3$ | 6 | 10.0 | 20 |
| Automatic Dish Washing | | | | | | | |
| WE | ADW | 3.0 g/L | RB CALGONIT ™ | 2 mM Na$_2$CO$_3$ | 21 | 10.0 | 40 |

TABLE A-continued

| Laundry and Dish Washing Conditions | | | | | | | |
|---|---|---|---|---|---|---|---|
| Region | Form | Dose | Detergent* | Buffer | Gpg | pH | T (°C.) |
| NA | ADW | 3.0 g/L | P&G CASCADE ® | 2 mM Na$_2$CO$_3$ | 9 | 10.0 | 40 |

In some additional Examples, the following solutions find use:

TABLE B

| Working Detergent Solutions | | | | | |
|---|---|---|---|---|---|
| Detergent | Temp (C.) | Detergent g/L | pH | Buffer | Gpg |
| TIDE ® 2X Cold | 16 | 0.98 | 8 | 5 mM HEPES | 6 |
| TIDE ® 2X Cold | 32 | 0.98 | 8 | 5 mM HEPES | 6 |
| TIDE ® 2X Cold | 16 | 0.98 | 7 | 5 mM MOPS | 6 |

Table C provides granular laundry detergent compositions produced in accordance with the invention suitable for laundering fabrics.

TABLE C

| Granular Laundry Detergent Compositions and Their Components | | | | | | |
|---|---|---|---|---|---|---|
| | Detergent Compositions | | | | | |
| Component | 1 | 2 | 3 | 4 | 5 | 6 |
| Linear alkylbenzenesulfonate with aliphatic carbon chain length $C_{11}$-$C_{12}$ | 15 | 12 | 20 | 10 | 12 | 13 |
| Other surfactants | 1.6 | 1.2 | 1.9 | 3.2 | 0.5 | 1.2 |
| Phosphate builder(s) | 2 | 3 | 4 | | | |
| Zeolite | | 1 | | 1 | 4 | 1 |
| Silicate | 4 | 5 | 2 | 3 | 3 | 5 |
| Sodium Carbonate | 2 | 5 | 5 | 4 | 0 | 3 |
| Polyacrylate (MW 4500) | 1 | 0.6 | 1 | 1 | 1.5 | 1 |
| Carboxymethyl cellulose (Finnfix BDA ex CPKelco) | 1 | — | 0.3 | — | 1.1 | — |
| Celluclean ® (15.6 mg/g) | 0.23 | 0.17 | 0.5 | 0.2 | 0.2 | 0.6 |
| Cold Water Protease* | 0.23 | 0.17 | 0.05 | 0.2 | 0.03 | 0.1 |
| Stainzyme Plus ® (14 mg/g) | 0.23 | 0.17 | 0.5 | 0.2 | 0.2 | 0.6 |
| Mannaway 4.0T (4 mg/g) | 0.1 | | | 0.1 | | 0.1 |
| Lipex 100T (18.6 mg/g) | 0.2 | | 0.1 | | 0.3 | |
| Fluorescent Brightener(s) | 0.16 | 0.06 | 0.16 | 0.18 | 0.16 | 0.16 |
| Diethylenetriamine pentaacetic acid or Ethylene diamine tetraacetic acid | 0.6 | | 0.6 | 0.25 | 0.6 | 0.6 |
| MgSO$_4$ | 1 | 1 | 1 | 0.5 | 1 | 1 |
| Bleach(es) and Bleach activator(s) | 6.88 | | 6.12 | 2.09 | 1.17 | 4.66 |
| Ethoxylated thiophene Hueing Dye[5] | 0.002 | 0.001 | 0.003 | 0.003 | — | — |
| Direct Violet 9 ex Ciba Specialty Chemicals | | | | 0.0006 | 0.0004 | 0.0006 |

TABLE C-continued

Granular Laundry Detergent Compositions and Their Components

| Component | Detergent Compositions | | | | | |
|---|---|---|---|---|---|---|
| | 1 | 2 | 3 | 4 | 5 | 6 |
| Sulfate/Citric Acid/Sodium Bicarbonate/ Moisture/perfume | | | Balance to 100% | | | |

[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2] Polyethylenimine (MW = 600) with 20 ethoxylate groups per —NH.
[3] Amphiphilic alkoxylated grease cleaning polymer is a polyethylenimine (MW = 600) with 24 ethoxylate groups per —NH and 16 propoxylate groups per —NH
[4] Reversible protease inhibitor of structure:

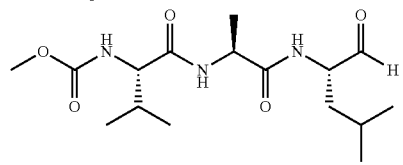

[5] Ethoxylated thiophene Hueing Dye is as described in U.S. Pat. No. 7,208,459 B2.

In Table C, all enzyme levels expressed as % enzyme raw material, except for cold water protease (of this invention) which is expressed as % of active protein added to the product.

Table D provides granular laundry detergent compositions suitable for top-loading automatic washing machines (detergent compositions 7-9) and front loading washing machines (detergent compositions 10-11). The GG36 protease variant tested and/or cold water protease of the present invention is added separately to these formulations.

TABLE D

Granular Laundry Detergent Compositions and Their Components

| Component | Detergent Composition | | | | |
|---|---|---|---|---|---|
| Surfactants | 7 | 8 | 9 | 10 | 11 |
| $C_{16-17}$ Branched alkyl sulfate | 3.55 | 15.8 | | | |
| $C_{12-14}$ alkyl sulphate | | | 1.5 | | |
| Sodium linear alkylbenzenesulfonate with aliphatic chain length $C_{11}$-$C_{12}$ | 9.6 | | 10.6 | 7.5 | 9 |
| Sodium $C_{14/15}$ alcohol ethoxy - 3 - sulfate | 1.15 | | | 2.88 | |
| Sodium $C_{14/15}$ alkyl sulphate | 2.37 | | | | |
| $C_{14/15}$ alcohol ethoxylate with average 7 moles of ethoxylation | | | | 1.17 | 1 |
| mono-$C_{8-10}$ alkyl mono-hydroxyethyl di-methyl quaternary ammonium chloride | | | | | 0.45 |
| Di methyl hydroxyl ethyl lauryl ammonium chloride | | | 0.18 | | |
| Zeolite A | 13.9 | 4.7 | 0.01 | 2.9 | 1.8 |
| Sodium Silicate 1.6.ratio | 4 | 0.2 | | 4 | 4 |
| Sodium Silicate 2.35.ratio | | | 8 | | |
| Citric Acid | | | | 2.5 | 1.4 |
| Sodium tripolyphosphate | | | 5 | | |
| Sodium Carbonate | 24.1 | 30 | 16.9 | 24.4 | 21 |
| Nonanoyloxybenzenesuplhonate | 5.78 | 2.81 | 0.96 | | |
| Oxaziridinium-based bleach booster | | | | 0.03 | 0.017 |
| Tetrasodium S,S,-ethylenediaminedisuccinate | | | | 0.2 | |
| Diethylenetriamine penta (methylene phosphonic acid), heptasodium salt | 0.61 | | | | 0.33 |
| Hydroxyethane dimethylene phosphonic acid | | | | 0.29 | 0.45 |
| Ethylene diamine tetraacetate | | | 0.27 | | |
| MgSO4 | | | 0.47 | 0.5994 | 0.782 |
| Sodium Percarbonate | | 7 | 4.4 | 15.9 | 19.1 |
| Tetra Acetyl Ethylene Diamine | | | | 3.3 | 4.6 |
| Sodium Perborate Monohydrate | | | 1.2 | | |

TABLE D-continued

Granular Laundry Detergent Compositions and Their Components

| Component | Detergent Composition | | | | |
|---|---|---|---|---|---|
| Surfactants | 7 | 8 | 9 | 10 | 11 |
| Carboxymethyl cellulose (e.g. Finnfix BDA ex CPKelco) | 0.1 | | 0.17 | 1.69 | 0.23 |
| Sodium Acrylic acid/maleic acid co-polymer (70/30) | 0.0236 | 3.8 | | 2 | 2.5 |
| Sodium polyacrylate (Sokalan PA30 CL) | 4 | | 0.84 | | |
| Terephthalate polymer | | | | 0.23 | |
| Polyethylene glycol/vinyl acetate random graft co polymer | | | 0.89 | 0.89 | 0.91 |
| Photobleach- zinc phthalocyanine tetrasulfonate | | | 0.005 | 0.001 | 0.002 |
| C.I.Fluorescent Brightener 260 | 0.11 | 0.15 | 0.04 | 0.23 | 0.15 |
| C.I.Fluorescent Brightener 351 (Tinopal ® CBS) | | | 0.1 | | |
| Suds suppressor granule | | 0.25 | | 0.07 | 0.04 |
| Hydrophobically modified carboxy methyl cellulose (Finnifix ® SH-1) | | | 0.019 | 0.028 | |
| Bentonite | | | 8.35 | | |
| Miscellaneous (Dyes, perfumes, process aids, moisture and sodium sulphate) | Balance | Balance | Balance | Balance | Balance |

In Table D, surfactant ingredients can be obtained from any suitable supplier, including but not limited to BASF (e.g., LUTENSOL®), Shell Chemicals, Stepan, Huntsman, and Clariant (e.g., PRAEPAGEN®). Zeolite can be obtained from sources such as Industrial Zeolite. Citric acid and sodium citrate can be obtained from sources such as Jungbunzlauer. Sodium percarbonate, sodium carbonate, sodium bicarbonate and sodium sesquicarbonate can be obtained from sources such as Solvay. Acrylate/maleate copolymers can be obtained from sources such as BASF. Carboxymethylcellulose and hydrophobically modified carboxymethyl cellulose can be obtained from sources such as CPKelco. C.I. Fluorescent Brightener 260 can be obtained from 3V Sigma (e.g., OPTIBLANC®, OPTIBLANC® 2M/G, OPTIBLANC® 2MG/LT Extra, or OPTIBLANC® Ecobright. Tetrasodium S,S-ethylenediamine disuccinate can be obtained from sources such as Innospec. Terephthalate co-polymer can be obtained from Clariant (e.g., REPELOTEX SF 2). In addition, 1-Hydroxyethane-1,1-diphosphonic acid can be obtained from Thermphos. Oxaziridinium-based bleach booster has the following structure, where R1=2-butyloctyl, and was produced according to US 2006/0089284A1.

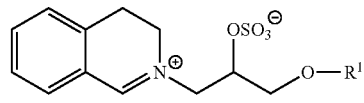

The enzymes NATALASE®, TERMAMYL®, STAINZYME PLUS®, CELLUCLEAN® and MANNAWAY®, can be obtained from Novozymes. Zinc phthalocyanine tetrasulfonate can be obtained from Ciba Specialty Chemicals (e.g., TINOLUX® BMC). Suds suppressor granule can be obtained from Dow Corning. In these detergent compositions, random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

Tables E-G provide additional granular detergent compositions suitable for washing machines (detergents 36a-n). The GG36 protease variant tested or cold water protease of the present invention is added separately to these formulations.

TABLE E

Additional Granular Laundry Detergent Compositions and Their Components

| Component | Detergent Composition | | | | |
|---|---|---|---|---|---|
| Surfactants | 36a | 36b | 36c | 36d | 36e |
| $C_{10}$ Nonionic | | | | 0.1843 | |
| $C_{16-17}$ Branched alkyl sulfate | 3.53 | 3.53 | 3.53 | | |
| $C_{12-14}$ alkyl sulphate | | | | | |
| Sodium linear alkylbenzenesulfonate with aliphatic chain length $C_{11}$-$C_{12}$ | 8.98 | 8.98 | 8.98 | 13.58 | 14.75 |
| Sodium $C_{14/15}$ alcohol ethoxy - 3 - sulfate | 1.28 | 1.28 | 1.28 | | |
| Sodium $C_{14/15}$ alkyl sulphate | 2.36 | 2.36 | 2.36 | | |
| $C_{14/15}$ alcohol ethoxylate with average 7 moles of ethoxylation | | | | | |
| mono-$C_{8-10}$ alkyl mono-hydroxyethyl dimethyl quaternary ammonium chloride | | | | | |

TABLE E-continued

Additional Granular Laundry Detergent Compositions and Their Components

| Component Surfactants | Detergent Composition | | | | |
|---|---|---|---|---|---|
| | 36a | 36b | 36c | 36d | 36e |
| Di methyl hydroxyl ethyl lauryl ammonium chloride | | | | 0.1803 | |
| Zeolite A | 15.31 | 15.31 | 15.31 | | 4.47 |
| Bentonite | | | | 8.35 | |
| Sodium Silicate 1.6.ratio | | | | | 0.16 |
| Sodium Silicate 2.0.ratio | 3.72 | 3.72 | 3.72 | 8.41 | |
| Sodium Silicate 2.35.ratio | | | | | |
| Citric Acid | | | | 0.0066 | |
| Sodium tripolyphosphate | | | | 5.06 | |
| Sodium Carbonate | 26.1 | 26.18 | 26.1 | 15.9 | 29.0 |
| Nonanoyloxybenzenesuplhonate | 5.78 | 5.78 | 5.78 | 1.17 | 1.86 |
| Oxaziridinium-based bleach booster | 0.037 | 0.037 | 0.037 | | |
| Tetrasodium S,S,-ethylenediaminedisuccinate | | | | | |
| Diethylenetriamine penta (methylene phosphonic acid), heptasodium salt | 0.62 | 0.62 | 0.62 | | |
| Hydroxyethane dimethylene phosphonic acid | | | | | |
| Ethylene diamine tetraacetate | | | | 0.2701 | |
| MgSO4 | 0.056 | 0.056 | 0.056 | 0.47 | |
| Sodium Percarbonate | | 7.06 | 7.06 | | 3.64 |
| Tetra Acetyl Ethylene Diamine | | | | | |
| Sodium Perborate Monohydrate | | | | 1.47 | |
| Carboxymethyl cellulose (e.g. Finnfix BDA ex CPKelco) | 0.38 | 0.38 | 0.38 | 0.173 | |
| Sodium Acrylic acid/maleic acid co-polymer (70/30) | 3.79 | 3.78 | 3.79 | | 3.64 |
| Sodium polyacrylate (Sokalan PA30 CL) | 3.78 | 3.78 | 3.78 | 0.842 | |
| Terephthalate polymer | | | | | |
| Polyethylene glycol/vinyl acetate random graft co polymer | | | | 0.89 | |
| Photobleach- zinc phthalocyanine tetrasulfonate | | | | | |
| C.I.Fluorescent Brightener 260 | 0.1125 | 0.1125 | 0.1125 | 0.043 | 0.15 |
| C.I.Fluorescent Brightener 351 (Tinopal ® CBS) | | | | 0.0952 | |
| Suds suppressor granule | 0.015 | 0.015 | 0.015 | | 0.031 |
| Hyrdophobically modified carboxy methyl cellulose (Finnifix ® SH-1) | | | | | |
| Bentonite | | | | | |
| Miscellaneous (Dyes, perfumes, process aids, moisture and sodium sulphate) | Balance | Balance | Balance | Balance | Balance |

TABLE F

Additional Granular Laundry Detergent Compositions and Their Components

| Component Surfactants | Detergent Composition | | | | |
|---|---|---|---|---|---|
| | 36f | 36g | 36h | 36i | 36j |
| $C_{10}$ Nonionic | 0.1142 | 0.2894 | 0.1885 | 0.1846 | 0.1885 |
| $C_{16-17}$ Branched alkyl sulfate | | | | | |
| $C_{12-14}$ alkyl sulphate | | | | | |
| Sodium linear alkylbenzenesulfonate with aliphatic chain length $C_{11}$-$C_{12}$ | 12.94 | 15.69 | 9.01 | 8.42 | 9.51 |
| Sodium $C_{14/15}$ alcohol ethoxy—3-sulfate | | | | | |
| Sodium $C_{14/15}$ alkyl sulphate | | | | | |
| $C_{12/14}$ alcohol ethoxylate with average 7 moles of ethoxylation | 2.9 | | | | |
| $C_{12/14}$ alcohol ethoxylate with average 3 moles of ethoxylation | | | | 2.44 | |
| $C_{14/15}$ alcohol ethoxylate with average 7 moles of ethoxylation | | | 0.97 | 1.17 | 0.97 |
| mono-$C_{8-10}$ alkyl mono-hydroxyethyl di-methyl quaternary ammonium chloride | | | 0.45 | | |
| Di methyl hydroxyl ethyl lauryl ammonium chloride | | 0.195 | | | 0.45 |
| Zeolite A | 2.01 | 0.39 | 1.83 | 2.58 | 0.59 |
| Sodium Silicate 1.6.ratio | | | 4.53 | 5.62 | 4.53 |
| Sodium Silicate 2.0.ratio | | 10.1 | | | |

TABLE F-continued

Additional Granular Laundry Detergent Compositions and Their Components

| Component Surfactants | Detergent Composition | | | | |
|---|---|---|---|---|---|
| | 36f | 36g | 36h | 36i | 36j |
| Sodium Silicate 2.35.ratio | 7.05 | | | | |
| Citric Acid | | | 1.4 | 1.84 | 1.0 |
| Sodium tripolyphosphate | | 5.73 | | | |
| Sodium Carbonate | 12.65 | 15.93 | 21.0 | 27.31 | 20.2 |
| Nonanoyloxybenzenesuplhonate | | 1.73 | | | |
| Oxaziridinium-based bleach booster | | | 0.0168 | 0.0333 | 0.024 |
| Tetrasodium S,S,-ethylenediaminedisuccinate | | | | | |
| Diethylenetriamine penta (methylene phosphonic acid), heptasodium salt | | | 0.327 | | 0.3272 |
| Hydroxyethane dimethylene phosphonic acid | | | 0.45 | 0.2911 | 0.45 |
| Ethylene diamine tetraacetate | | 0.28 | | 0.1957 | |
| $MgSO_4$ | | 0.54 | 0.79 | 0.6494 | 0.793 |
| Sodium Percarbonate | | | 19.1 | 15.85 | 22.5 |
| Tetra Acetyl Ethylene Diamine | | | 4.554 | 3.71 | 5.24 |
| Sodium Perborate Monohydrate | | 5.55 | | | |
| Carboxymethyl cellulose (e.g. Finnfix BDA ex CPKelco) | 0.62 | 0.21 | 0.23 | 1.07 | 0.2622 |
| Sodium Acrylic acid/maleic acid co-polymer (70/30) | 0.40 | 2.61 | 2.5 | 2.00 | 1.75 |
| Sodium polyacrylate (Sokalan PA30 CL) | | | 0.0055 | 0.011 | 0.008 |
| Terephthalate polymer | | | | 0.231 | |
| Polyethylene glycol/vinyl acetate random graft co polymer | 0.55 | 1.40 | 0.911 | 0.8924 | 0.911 |
| Photobleach- zinc phthalocyanine tetrasulfonate | | | | | |
| C.I.Fluorescent Brightener 260 | 0.1174 | 0.048 | 0.1455 | 0.2252 | 0.1455 |
| C.I.Fluorescent Brightener 351 (Tinopal ® CBS) | | 0.1049 | | | |
| Suds suppressor granule | | | 0.04 | 0.0658 | 0.04 |
| Hyrdophobically modified carboxy methyl cellulose (Finnifix ® SH-1) | | | | | |
| Bentonite | | | | | |
| Miscellaneous (Dyes, perfumes, process aids, moisture and sodium sulphate) | Balance | Balance | Balance | Balance | Balance |

TABLE G

Additional Granular Laundry Detergent Compositions and Their Components

| Component Surfactants | Detergent Composition | | | |
|---|---|---|---|---|
| | 36k | 36l | 36m | 36n |
| $C_{10}$ Nonionic | 0.1979 | 0.1979 | 0.1979 | 0.1979 |
| $C_{16-17}$ Branched alkyl sulfate | | | | |
| $C_{12-14}$ alkyl sulphate | | | | |
| Sodium linear alkylbenzenesulfonate with aliphatic chain length $C_{11}$-$C_{12}$ | 8.92 | 8.92 | 11.5 | 11.5 |
| Sodium $C_{14/15}$ alcohol ethoxy—3-sulfate | 1.62 | 1.62 | 1.125 | 1.125 |
| Sodium $C_{14/15}$ alkyl sulphate | | | | |
| $C_{14/15}$ alcohol ethoxylate with average 7 moles of ethoxylation | 1.0 | 1.0 | 1.5 | 1.5 |
| mono-$C_{8-10}$ alkyl mono-hydroxyethyl di-methyl quaternary ammonium chloride | | | | |
| Di methyl hydroxyl ethyl lauryl ammonium chloride | | | | |
| Zeolite A | 1.63 | 1.63 | 2.0 | 2.0 |
| Sodium Silicate 1.6.ratio | 4.75 | 4.75 | 4.75 | 4.75 |
| Sodium Silicate 2.0.ratio | | | 0.06 | 0.06 |
| Sodium Silicate 2.35.ratio | | | | |
| Citric Acid | 1.10 | 1.10 | 1.1 | 1.1 |
| Sodium tripolyphosphate | | | | |
| Sodium Carbonate | 23.3 | 23.3 | 23.3 | 23.3 |
| Nonanoyloxybenzenesuplhonate | | | | |
| Oxaziridinium-based bleach booster | 0.021 | 0.021 | 0.015 | 0.015 |
| Tetrasodium S,S,-ethylenediaminedisuccinate | 0.26 | 0.26 | 0.26 | 0.26 |
| Diethylenetriamine penta (methylene phosphonic acid), heptasodium salt | | | | |

TABLE G-continued

Additional Granular Laundry Detergent Compositions and Their Components

| Component<br>Surfactants | Detergent Composition | | | |
|---|---|---|---|---|
| | 36k | 36l | 36m | 36n |
| Hydroxyethane dimethylene phosphonic acid | 0.47 | 0.47 | 0.47 | 0.47 |
| Ethylene diamine tetraacetate | | | | |
| MgSO4 | 0.83 | 0.83 | 0.82 | 0.82 |
| Sodium Percarbonate | 19.35 | 19.35 | 19.35 | 19.35 |
| Tetra Acetyl Ethylene Diamine | 4.51 | 4.51 | 4.51 | 4.51 |
| Sodium Perborate Monohydrate | | | | |
| Carboxymethyl cellulose (e.g. Finnfix BDA ex CPKelco) | 1.01 | 1.01 | 1.01 | 1.01 |
| Sodium Acrylic acid/maleic acid co-polymer (70/30) | 1.84 | 1.84 | 1.84 | 1.84 |
| Sodium polyacrylate (Sokalan PA30 CL) | 0.007 | 0.007 | 0.005 | 0.005 |
| Terephthalate polymer | 0.179 | 0.179 | 0.179 | 0.179 |
| Polyethylene glycol/vinyl acetate random graft co polymer | 0.96 | 0.96 | 0.96 | 0.96 |
| Photobleach—zinc phthalocyanine tetrasulfonate | | | | |
| C.I.Fluorescent Brightener 260 | 0.153 | 0.153 | 0.171 | 0.171 |
| C.I.Fluorescent Brightener 351 (Tinopal ® CBS) | | | | |
| Suds suppressor granule | 0.042 | 0.042 | 0.042 | 0.042 |
| Hyrdophobically modified carboxy methyl cellulose (Finnifix ® SH-1) | | | | |
| Bentonite | | | | |
| Miscellaneous (Dyes, perfumes, process aids, moisture and sodium sulphate) | Balance | Balance | Balance | Balance | Balance |

Notes for detergent compositions 36 a-n in Tables E, F, G:
Surfactant ingredients can be obtained from BASF, Ludwigshafen, Germany (Lutensol®); Shell Chemicals, London, UK; Stepan, Northfield, Ill., USA; Huntsman, Huntsman, Salt Lake City, Utah, USA; Clariant, Sulzbach, Germany (Praepagen®).
Zeolite can be obtained from Industrial Zeolite (UK) Ltd, Grays, Essex, UK.
Citric acid and sodium citrate can be obtained from Jungbunzlauer, Basel, Switzerland.
Sodium percarbonate, sodium carbonate, sodium bicarbonate and sodium sesquicarbonate can be obtained from Solvay, Brussels, Belgium.
Acrylate/maleate copolymers can be obtained from BASF, Ludwigshafen, Germany.
Carboxymethylcellulose and hydrophobically modified carboxymethyl cellulose can be obtained from CPKelco, Arnhem, The Netherlands.
C.I. Fluorescent Brightener 260 can be obtained from 3V Sigma, Bergamo, Italy as Optiblanc® Optiblanc® 2M/G, Optiblanc® 2MG/LT Extra, or Optiblanc® Ecobright.
Tetrasodium S,S-ethylenediamine disuccinate can be obtained from Innospec, Ellesmere Port, UK.
Terephthalate co-polymer can be obtained from Clariant under the tradename Repelotex SF 2.
1-Hydroxyethane-1,1-diphosphonic acid can be obtained from Thermphos, Vlissingen-Oost, The Netherlands.
Oxaziridinium-based bleach booster has the following structure, where R1=2-butyloctyl, and was produced according to US 2006/0089284A1.

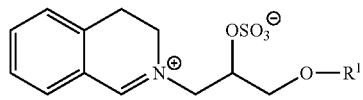

Enzymes Natalase®, Termamyl®, Stainzyme Plus®, Celluclean® and Mannaway®, can be obtained from Novozymes, Bagsvaerd, Denmark.
Zinc phthalocyanine tetrasulfonate can be obtained from Ciba Specialty Chemicals, Basel, Switzerland, as Tinolux® BMC.
Suds suppressor granule can be obtained from Dow Corning, Barry, UK.
Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

Example 1

Assays and Test Methods

This Example describes the various Test Methods and assays used in the development of the present invention. Any deviations from the protocols provided are indicated in the pertinent Examples.
The assays were performed using a Biomek FX Robot (Beckman Coulter) or a multichannel pipettor (e.g., Rainin PipetLite, Mettler-Toledo) and a SpectraMAX MTP Reader (type 340; Molecular Devices).
A. Test Methods
Test Method 1
A protocol to define whether a dye or pigment material is a fabric hueing agent for the purpose of the invention is provided below:
1) Fill two tergotometer pots with 800 ml of Newcastle upon Tyne, UK, City Water (~12 grains per US gallon total hardness, supplied by Northumbrian Water, Pity Me., Durham, Co. Durham, UK).

2) Insert pots into tergotometer, with water temperature controlled at 30° C. and agitation set at 40 rpm for the duration of the experiment.
3) Add 4.8 g of IEC-B detergent (IEC 60456 Washing Machine Reference Base Detergent Type B), supplied by wfk, Brüggen-Bracht, Germany, to each pot.
4) After two minutes, add 2.0 mg active colorant to the first pot.
5) After one minute, add 50 g of flat cotton vest (supplied by Warwick Equest, Consett, County Durham, UK), cut into 5 cm×5 cm swatches, to each pot.
6) After 10 minutes, drain the pots and re-fill with cold Water (16° C.) having a water hardness of 14.4 English Clark Degrees Hardness with a 3:1 Calcium to Magnesium molar ratio.
7) After 2 minutes rinsing, remove fabrics.
8) Repeat steps 3-7 for a further three cycles using the same treatments.
9) Collect and line dry the fabrics indoors for 12 hours.
10) Analyse the swatches using a Hunter Miniscan spectrometer fitted with D65 illuminant and UVA cutting filter, to obtain Hunter a (red-green axis) and Hunter b (yellow-blue axis) values.
11) Average the Hunter a and Hunter b values for each set of fabrics. If the fabrics treated with colorant under assessment show an average difference in hue of greater than 0.2 units on either the a axis or b axis, it is deemed to be a fabric hueing agent for the purpose of the invention.

Test Method 2

For Test Method 2, the BMI microswatch assay provided below is run using the granular detergent composition 10 (See Table D, above). The laundry detergent is dissolved in water that has a hardness of 12 gpg and adjusted to a temperature of 16° C., and the protease variant enzyme of interest is added. Performance of the protease variant enzymes is then determined as per the BMI microswatch assay described. The performance index is determined by comparing the performance of the protease variant enzyme with that of the *B. lentus* GG36 subtilisin enzyme having the amino acid sequence of SEQ ID NO:2, with in all cases the enzyme dosage range being 0.1-5 ppm. Protease variant enzymes having a performance index of 1.1 or greater are viewed to be cold water proteases.

Test Method 3

For Test Method 3, the BMI microswatch assay provided below is run using the granular laundry detergent composition 7 (See Table D, above). The laundry detergent is dissolved in water that has a hardness of 6 gpg and adjusted to a temperature of 16° C., the GG36 protease variant enzyme of interest is added. Performance of the GG36 protease variant enzymes is then determined as per the BMI microswatch assay described. The performance index is determined by comparing the performance of the GG36 protease variant enzyme with that of the *B. lentus* GG36 subtilisin enzyme having the amino acid sequence of SEQ ID NO:2, with in all cases the enzyme dosage range being 0.1-5 ppm. GG36 protease variant enzymes having a performance index of 1.1 or greater are viewed to be cold water proteases.

Test Method 4

For Test Method 4, the BMI microswatch assay is run using the granular laundry detergent composition 7 (See Table D, above). The laundry detergent is dissolved in water that has a hardness of 6 gpg and adjusted to a temperature of 16° C., and the GG36 protease variant enzyme of interest is added. Performance of the GG36 protease variant enzymes is then determined as per the BMI microswatch assay described. The performance index is determined by comparing the performance of the GG36 protease variant enzyme with that of a reference enzyme GG36-A158E, said GG36-A158E reference enzyme consisting of the *B. lentus* subtilisin GG36 protease amino acid sequence of SEQ ID NO:2 with a single substitution of glutamic acid for alanine at position 158 (i.e., the A158E mutation), with in all cases the enzyme dosage range being 0.1-5 ppm. GG36 protease variant enzymes having a performance index of 1.0 or greater are viewed to be cold water proteases.

Test Method 6

For Test Method 6, the BMI microswatch assay is run using one of the detergents 36a 36n in Table 1-2. The detergent is dissolved in water that has a hardness as specified in Table 1-2 and adjusted to a temperature of 16° C. Performance of the variant enzymes is then determined as per the BMI microswatch assay described. The performance index is determined by comparing the performance of the variant with that of the enzyme of SEQ ID NO:2, with the enzyme dosage range being 0.1-5 ppm in all cases. Enzymes having a performance index of 1.1 or greater are viewed to be cold water proteases.

B. Assays

TCA Assay for Protein Content Determination in 96-Well Microtiter Plates

*B. subtilis* cultures were grown 2-3 days at 37° C., shaking at 250-300 rpm with humidified aeration. The cells were removed from the enzyme-containing culture supernatant, by centrifugation and/or filtration. The protease/protein/enzyme concentration was determined using a TCA precipitation assay. An aliquot (20-25 ul) of culture supernatant was transferred to a 96-well flat bottom microtiter plate (MTP; Costar 9017 medium binding clear polystyrene plate) containing 100 µL/well of 0.25 N HCl. The "baseline" read was determined by light scattering/absorbance reading at 405 nm following 5 seconds of mixing. 100 µL/well of 30% (w/v) trichloroacetic acid (TCA) was added to the HCl-containing plate and incubated for 10 minutes at room temperature to facilitate protein precipitation. The light scattering/absorbance at 405 nm of this "test" plate was determined after 5 seconds of mixing. The turbidity/light scattering increase in the samples correlates to the total amount of precipitable protein in the culture supernatant. The calculations were performed by subtracting the "baseline" reading (obtained after addition of HCl) from the "test" reading (obtained after addition of TCA) to provide a relative measure of total protein present. If desired, a standard curve can be created by calibrating the TCA readings with AAPF protease assays (see below) of clones with known specific activity. However, the TCA results are linear with respect to protein concentration from 50 to 500 parts per million (ppm) of protein (where 1 ppm corresponds to 1 mg/L) and can thus be plotted directly against enzyme performance for the purpose of choosing variants with desired performance.

AAPF Protease Assay in 96-Well Microtiter Plates

In order to determine the protease activity of the serine protease variants, the hydrolysis of N-succinyl-L-alanyl-L-alanyl-L-prolyl-L-phenyl-p-nitroanilide (suc-AAPF-pNA) was measured. The reagent solutions used were: 100 mM Tris/HCl, pH 8.6, containing 0.005% TWEEN®-80 (Tris dilution buffer); 100 mM Tris buffer, pH 8.6, containing 1 mM CaCl$_2$) and 0.005% TWEEN®-80 (Tris/Ca buffer); and 160 mM suc-AAPF-pNA in DMSO (suc-AAPF-pNA stock solution) (Sigma: S-7388). To prepare a suc-AAPF-pNA working solution, 1 ml suc-AAPF-pNA stock solution was added to 100 ml Tris/Ca buffer and mixed well for at least 10 seconds. The assay was performed by adding 10 µl of diluted protease solution to each well of a 96-well MTP, immediately followed by the addition of 190 µl of 1 mg/ml suc-AAPF-pNA working solution. The solutions were mixed for 5 sec, and the absorbance change in kinetic mode (25 readings in 5 minutes) was read at 405 nm in an MTP reader, at 25° C. The protease activity was expressed as AU (activity=$\Delta$OD·min$^{-1}$ ml$^{-1}$).

Eglin C Inhibition Assay

As described herein, serine protease concentration and specific activity was determined by titration with an inhibitor called eglin c. Eglin c from the leech *Hirudo medicinalis* is a tight-binding protein inhibitor of subtilisins and ASP protease (Heinz et al., Biochemistry, 31: 8755-66 [1992]), and can therefore be used to measure protease enzyme concentration, which in turn permits specific activity to be calculated. The gene for eglin c was synthesized and expressed in *E. coli* by standard methods. Its properties and inhibitory potency were the same as eglin c purchased from Sigma.

(i) Concentration Determination of an Eglin C Stock Solution

A sample of *Bacillus lentus* subtilisin of known specific activity was diluted in 100 mM Tris buffer, pH 8.6, containing 1 mM CaCl$_2$) and 0.005% TWEEN®-80 (Tris/Ca buffer), to a concentration appropriate for AAPF protease assay described above. Several dilutions of the eglin c stock solution were also made in the Tris/Ca buffer. An aliquot of each diluted eglin c solution was mixed with an equal volume of the diluted *Bacillus lentus* subtilisin solution. An aliquot of the Tris/Ca buffer only, without eglin c, was also mixed with an equal volume of the diluted *Bacillus lentus* subtilisin solution, in order to measure uninhibited subtilisin activity in the absence of eglin c. The mixed solutions were incubated at room temperature for 15-30 minutes and the protease activity of each sample was then measured by AAPF assay described above. Using the known specific activity of *Bacillus lentus* subtilisin, the concentration of active protease in each sample was determined. The concentration of eglin c in each sample was then calculated based on the decrease of the observed protease activity as compared to the uninhibited subtilisin sample that was mixed with Tris/Ca buffer only (without eglin c). Thus, using the known dilutions and volumes of the eglin c solutions, the concentration of eglin c in the stock solution was determined.

(ii) Concentration and Specific Activity Determination of Subtilisin Variants

Samples of subtilisin variants were diluted in 100 mM Tris buffer, pH 8.6, containing 1 mM CaCl$_2$) and 0.005% TWEEN®-80 (Tris/Ca buffer). Several dilutions of the eglin c stock solution of known concentration were also made in the Tris/Ca buffer. An aliquot of each diluted eglin c solution was mixed with an equal volume of a subtilisin variant solution. The mixed solutions were incubated at room temperature for 15-30 minutes and the protease activity of each sample was then measured by AAPF assay. Using the observed decrease of the protease activity upon addition of each eglin c sample and the known concentration of the eglin c, the concentration of the eglin c necessary for the complete inhibition of each subtilisin enzyme variant was calculated. This concentration is equivalent to the enzyme concentration in the sample. An aliquot of the Tris/Ca buffer only, without eglin c, was also mixed with each subtilisin variant sample and the protease activity in the absence of eglin c was measured by AAPF assay. The specific activity of the subtilisin variants was then calculated using the enzyme concentrations as determined above.

BMI Microswatch Assay (BMI Assay)

Pre-rinsed and punched blood, milk and ink (BMI) stained microswatches (EMPA116) of 5.5 millimeter circular diameter in 96 well microtiter plates (MTP; Corning 3641) were obtained from Center for Testmaterials BV (Vlaardingen, The Netherlands).

Detergents 7-11 and 36a-n (Tables D-G) were prepared by mixing for at least 30 minutes in 2 mM sodium carbonate, buffered to pH 10.3 with the appropriate level of water hardness (3:1 Ca:Mg.—CaCl$_2$: MgCl$_2$.6H$_2$O) in Milli-Q water as described in Table 1-1 and Table 1-2. The detergents were aliquoted into 50 ml conical tubes (Falcon), centrifuged to remove precipitate, and chilled on ice for 30 minutes prior to use.

Enzyme concentrations were equalized to a desired fixed concentration ranging from 20-50 ppm relative to a standard of purified GG36. The specific activity of GG36 using AAPF as a substrate was used to convert baseline subtracted TCA values into enzyme concentration in ppm. Once enzyme concentration was determined in ppm, a simple formula was used to calculate the volume of each variant required to add to a fixed volume of buffer (300-600 µL) in order to achieve the desired stock enzyme concentration:

$$x=(\text{target ppm})(v_b)/(y-\text{target ppm})$$

Where x=volume enzyme, y=enzyme concentration, $v_b$=buffer volume

A Perkin-Elmer Janus robot with a Versispan 8 channel arm was used to dispense variable volumes of enzyme from the source plate (Axygen half deep well plate with pooled harvested variants used in the TCA enzyme concentration assay) into the buffer-filled destination plate using conductive tips. Samples were mixed three times by pipetting up and down. The accuracy of the enzyme dilutions was validated by measuring the AAPF activity of the equalized plate and comparing it to that of the source plate, to verify that the correct dilutions had been made.

After equalization, 5-15 µL of enzyme solution was added to a detergent-filled BMI microswatch plate to reach a final volume of ~200 µL. In some instances, the enzyme samples were not equalized, and were instead all diluted equally from the stock plate to give a working range of 0.1-5 ppm. Optimal target concentrations for each assay were determined from a dose response curve measuring cleaning activity over this range for a given detergent.

The MTP was sealed with foil (Bio-Rad) and incubated in iEMS incubator/shaker (Thermo/Labsystems) pre-set to 16° C. in a cold room set to 4° C. or at 32° C. on the benchtop for 30 minutes at 1400 rpm. Following incubation, 120 µL of supernatant was transferred to a fresh MTP (Corning 9017) and read at 600 nm using the SpectraMax reader. True absorbance readings were obtained by subtracting a blank control (no enzyme) from each value.

A performance index (PI) was calculated for each variant. The performance index is the ratio of the absorbance of the supernatant produced by variant enzyme cleaning to the absorbance produced by GG36 cleaning at a fixed enzyme concentration. For the equalized plates, PI values were calculated by dividing the absorbance of a variant by that of the control on a given plate. For non-equalized plates, a standard curve (e.g. Langmuir or four parameter logistic nonlinear regression model fit) is generated from the activity and enzyme concentration of the controls. Using this standard curve, the performance of the variants can be directly compared to the control at any enzyme concentration. The PI is determined by dividing the absorbance of the variants by the calculated absorbance for the control at the same enzyme concentration.

A performance index (PI) that is greater than 1 (PI>1) indicates superior cleaning by a variant as compared to the standard (e.g., GG36), while a PI of 1 (PI=1) identifies a variant that performs the same as the standard, and a PI that is less than 1 (PI<1) identifies a variant that performs worse than the standard.

TABLE 1-1

Final Detergent, Water Hardness, and Buffer Concentrations Used for BMI Microswatch Assays

| Detergent Composition | Final Detergent Concentration (g/L) | Final Water Hardness* (gpg) | Final Sodium Carbonate Buffer Concentration (mM) |
|---|---|---|---|
| 7 | 0.808 | 6 | 2 |
| 8 | 1 | 3 | 2 |
| 9 | 2.3 | 12 | 2 |
| 10 | 5.9 | 12 | 2 |
| 11 | 8.3 | 12 | 2 |

*(3:1 Ca:Mg) Concentration as detailed in text.

TABLE 1-2

Final Detergent, Water Hardness, and Buffer Concentrations Used for BMI Microswatch Assays

| Detergent Composition | Final Detergent Concentration (g/L) | Final Water Hardness* (gpg) | Final Sodium Carbonate Buffer Concentration (mM) |
|---|---|---|---|
| 36a | 0.75 | 6 | 2 |
| 36b | 0.808 | 6 | 2 |
| 36c | 0.808 | 6 | 2 |
| 36d | 2.25 | 12 | 2 |
| 36e | 1 | 3 | 2 |
| 36f | 1.2 | 12 | 2 |
| 36g | 3.96 | 12 | 2 |
| 36h | 7.69 | 20 | 2 |
| 36i | 5 | 10 | 2 |
| 36j | 7.69 | 20 | 2 |
| 36k | 7.69 | 20 | 2 |
| 36l | 6.15 | 10 | 2 |
| 36m | 7.69 | 20 | 2 |
| 36n | 6.15 | 20 | 2 |

*(3:1 Ca:Mg) Concentration as detailed in text.

LAS/EDTA Stability Assay

The stability of protease variants in the presence of a representative anionic surfactant (LAS=linear alkylbene sulfonate, sodium dodecylbenzenesulfonate—DOBS) and di-sodium EDTA is measured after incubation under defined conditions and the residual activity is determined using the AAPF assay described above. The reagents used were dodecyllbenzene sulfonate, sodium salt (DOBS; Sigma No. D-2525), TWEEN®-80 (Sigma No. P-8074), di-sodium EDTA (Siegfried Handel No. 164599-02), HEPES (Sigma No. H-7523), unstressed buffer: 50 mM HEPES (11.9 g/l)+ 0.005% TWEEN®-80, pH 8.0, Stress buffer: 50 mM HEPES (11.9 g/l), 0.1% (w/v) DOBS (1 g/l), 10 mM EDTA (3.36 g/l), pH 8.0, reference protease and protease variant culture supernatants, containing 200-400 µg/ml protein. The equipment used is V- or U-bottom MTP as dilution plates (Greiner 651101 and 650161 respectively), F-bottom MTP (Corning 9017) for unstress and LAS/EDTA buffer as well as for suc-AAPF-pNA plates, Biomek FX (Beckman Coulter), Spectramax Plus 384 MTP Reader (Molecular Devices), and iEMS Incubator/Shaker (Thermo/Labsystems).

The iEMS incubator/shaker (Thermo/Labsystems) is set at 29° C. Culture supernatants were diluted into plates containing unstress buffer to a concentration of ~25 ppm (master dilution plate). For the assay, 20 µl of sample from the master dilution plate is added to plates containing 180 µl unstress buffer to give a final incubation concentration of 2.5 ppm. The contents were mixed and kept at room temperature and the AAPF assay is performed on this plate. In addition, 20 µl of sample from the master dilution plate is also added to plates containing 180 µl stress buffer (50 mM HEPES (11.9 g/l), 0.1% (w/v) DOBS (1 g/l), 10 mM EDTA (3.36 g/l), pH 8.0). The solutions were mixed and immediately placed in 29° C. iEMS shaker for 30 min at 400 rpm. Following 30 minutes of incubation, the AAPF assay is performed on the stress plate. The stability of the samples is determined by calculating the ratio of the residual and initial AAPF activity as follows: Residual Activity (%)= [mOD·min-1 stressed]*100/[mOD·min-1 unstressed].

The final detergent, water hardness and buffer concentrations are determined based on the assay system to be used (e.g., North American, Japanese, Western European, or Central European conditions). In some embodiments, the stain removal performance of the protease variants is determined in commercially available detergents. Heat inactivation of commercial detergent formulas serves to destroy the enzymatic activity of any protein components while retaining the properties of non-enzymatic components. Thus, this method is suitable for preparing commercially purchased detergents for use in testing the enzyme variants of the present invention.

Baked Egg Microtiter Assay

For this assay, 96-well baked egg yolk substrate plates are prepared from chicken egg yolks. Chicken egg yolks are separated from the whites, released from the membrane sac, and diluted 20% (vol/weight) with Milli-Q water. The diluted yolk is stirred for 15 min at room temperature using a magnetic stirrer. Five µL are carefully pipetted into the center of each well of a 96-well V-bottom plate (Costar #3894) using an 8-channel pipette. The plates are baked at 90° C. for 1 hour and cooled at room temperature. The baked egg yolk substrate plates are stored at room temperature and used within one week of preparation. Automatic dish detergents are prepared as described herein and pre-heated to 50° C. A 190 µL aliquot of detergent is added to each well of the 96-well plate using an 8-channel pipette. Ten µL of diluted enzyme is added to each well using a 96-channel pipetting device. The plate is carefully sealed with an adhesive foil sealer and incubated at 50° C. with shaking for 30 min. 120 µL of the reaction mixture is transferred to a new 96-well flat-bottom plate, and the absorbance/light scattering is determined at 405 nm. The absorbance/light scattering at 405 nm is proportional to egg yolk removal.

Egg Yolk Microswatch Assay ("CS-38 Microswatch Assay"; or "EGG" or "Dish")

Automatic dish detergents are prepared as described herein. The equipment used included a New Brunswick Innova 4230 shaker/incubator and a SpectraMAX (type 340) MTP reader. The MTPs are obtained from Costar (type 9017). Aged egg yolk with pigment swatches (CS-38) are obtained from Center for Test Materials (Vlaardingen, Netherlands). Before cutting 0.25-inch circular microswatches, the fabric is washed with water. One microswatch is placed in each well of a 96-well microtiter plate. The test detergent is equilibrated at 50° C. 190 µl of detergent solution is added to each well of the MTP, containing microswatches. To this mixture, 10 µl of the diluted enzyme solution is added. The MTP is sealed with adhesive foil and placed in the incubator for 30 minutes, with agitation. Following incubation, 100 µl of the solution from each well is transferred into a fresh MTP. This MTP is read at 405 nm using a SpectraMax MTP reader. Blank controls, as well as controls containing microswatches and detergent but no enzyme are also included.

In some embodiments, pre-washed microswatches find use. This type of microswatch is pre-washed in deionised water for 20 minutes at ambient temperature. After the pre-washing step, the swatches are put on top of paper towels to dry. The air-dried swatches are then punched using a ¼" circular die on an expulsion press. Finally two microswatches are put into each well of a 96-well MTP vertically to expose the whole surface area (i.e. not flat on the bottom of the well).

Samples of protease variants to be tested are obtained from filtered culture broth of cultures grown in MTP plates. The equipment used is a Biomek FX Robot (Beckman Coulter), a SpectraMAX MTP Reader (type 340; Molecular Devices), an iEMS incubator/shaker (Thermo/Labsystems); F-bottom MTPs (Costar type 9017 used for reading reaction plates after incubation); and V-bottom MTPs (Greiner 651101 used for pre-dilution of supernatant). In this assay, the proteases hydrolyze the substrate and liberate pigment and insoluble particles from the substrate. Thus the rate of turbidity is a measure of enzyme activity.

The stain removal performance of reference serine proteases and variants therefrom on microswatches is determined on a MTP scale in commercially available detergent (Calgonit 5 in 1). CS-38 microswatches (egg-yolk with pigment, aged by heating), obtained from CFT Vlaardingen are used as substrate. Two swatches are used per well. ADW tablets from Calgonit 5 in 1 are used to prepare the detergent solution. To inactivate the protease activity present in the tablets, a 21 g tablet is dissolved in Milli-Q water heated in a water bath to a temperature of 60° C. The solution is cooled to room temperature and the volume of water adjusted to 700 mL. The solution is further diluted with water to achieve a final concentration of 3 g/l. Water hardness is adjusted to 21° GH by adding 1.46 ml of the Ca/Mg-mixture (Ca/Mg mixture [(3:1), 1.92 M $CaCl_2$=282.3 g/L $CaCl_2.2H_2O$; 0.64 M $MgCl_2$=130.1 g/L $MgCl_2.6H_2O$), 15000 gpg]. The enzyme samples are prediluted in 10 mM NaCl, 0.1 mM $CaCl_2$), 0.005% TWEEN®-80 solution and tested at appropriate concentrations.

The incubator is set at the desired temperature of 50° C. 72 µl of dilution buffer is added to the empty V-bottom plate (i.e., a "dilution plate") followed by 8 µl supernatant. 9 µl from the dilution plate is added to plates containing the microswatches incubated in 171 µl detergent solution. 9 µl from the dilution plate is added to plates containing the microswatches to give a total dilution of supernatant of 200×. The microswatch plate (with detergent and enzyme) is covered with tape and placed in the incubator/shaker for 30 minutes at 1400 rpm. Following incubation, 75 µl of the reaction mixture is transferred to an empty F-bottom plate and the absorbance is read in a MTP Reader at 405 nm after de-bubbling with a hair dryer. Blank controls, containing one or two microswatches and detergent without the addition of reference protease containing samples are also included in the test.

The absorbance value obtained is corrected for the blank value (substrate without enzyme), providing a measure of hydrolytic activity. For each sample (variant) the performance index is calculated. The performance index compares the performance of the variant (actual value) and the standard enzyme (theoretical value) at the same protein concentration. In addition, the theoretical values can be calculated, using the parameters of the Langmuir equation of the standard enzyme.

Egg Yolk Stains on Stainless Steel

The stainless steel sheets (10×15 cm; brushed on one side) used in these experiments are thoroughly washed at 95° C. in a laboratory dishwasher with a high-alkalinity commercial detergent (e.g., ECOLAB® detergent; Henkel) to provide sheets that are clean and grease-free. These sheets are deburred prior to their first use. The sheets are dried for 30 minutes at 80° C. in a thermal cabinet before being soiled with egg yolk. The surfaces to be brushed are not touched prior to soiling. Also, no water stains or fluff on the surfaces are permitted. The cooled sheets are weighed before soiling.

The egg yolks are prepared by separating the yolks of approximately 10-11 eggs (200 g of egg yolk) from the whites. The yolks are stirred with a fork in a glass beaker to homogenize the yolk suspension. The yolks are then strained (approx. 0.5 mm mesh) to remove coarse particles and any egg shell fragments.

A flat brush (2.5") is used to apply 1.0±0.1 g egg yolk suspension as uniformly as possible over an area of 140 $cm^2$ on the brushed sides of each of the stainless steel sheets, leaving an approx. 1 cm wide unsoiled rim (adhesive tape is used if needed). The soiled sheets are dried horizontally (to prevent formation of droplets on the edges of the sheets), at room temperature for 4 hours (max. 24 h).

For denaturation, the sheets are immersed for 30 seconds in boiling, demineralized water (using a holding device if necessary). Then, the sheets are dried again for 30 min at 80° C. After drying and cooling, the sheets are weighed. After weighing, the sheets are left for at least 24 hours (20° C., 40-60% relatively humidity) before submitting them to the wash test. In order to meet the testing requirements, only sheets with 500±100 mg/140 $cm^2$ (egg yolk after denaturation), are used in the testing After the wash tests are conducted, the sheets are dried for 30 min at 80° C., in the thermal cabinet, and weighed again after cooling. The percent cleaning performance is determined by dividing the (mg of egg yolk released by washing×100) by the (mg of denatured egg yolk applied).

Minced Meat on Porcelain Plates

For these experiments, dessert plates (Arzberg, white, glazed porcelain) conforming to EN 50242, form 1495, No. 0219, diameter 19 cm are used. A total of 225 g lean pork and beef (half and half) is finely chopped and cooled, after removing visible fat. The mixture is twice run through a mincer. Temperatures above 35° C. are avoided. Then, 225 g of the minced meat is mixed with 75 g of egg (white and yolk mixed together). The preparation is then frozen up to three months at −18° C., prior to use. If pork is not available, beef is used.

The minced meat and egg mixture (300 g) is brought up to room temperature and mixed with 80 ml synthetic water. The mixture is then homogenized using a kitchen hand blender for 2 min. Then, a fork is used to spread 3 g of the minced meat/egg/water mixture on each white porcelain plate, leaving an approx. 2 cm wide unsoiled margin around the rim. The amount applied is 11.8±0.5 mg/$cm^2$. The plates are dried for 2 hours at 120° C. in a preheated thermal cabinet. As soon as the plates are cooled, they are ready for use. The plates are stacked with paper towels between each of the plates.

After washing, the plates are sprayed with ninhydrin solution (1% ethanol) for better identification of the minced meat residues. To promote the color reaction, the plates are heated for 10 min at 80° C. in the thermal cabinet. Evaluation of the washing performance is done by visually inspecting the color reactions of the minced meat residues with reference to the IKW photographic catalogue (IKW).
Egg/Milk Stains on Stainless Steel The stainless steel sheets (10×15 cm; brushed on one side) used in these experiments are thoroughly washed at 95° C. in a laboratory dishwasher with a high-alkalinity commercial detergent to remove grease and clean the sheets. The sheets are polished dry with a cellulose cloth. The surfaces to be brushed are not touched prior to soiling. Also, no water stains or fluff on the surfaces are permitted. Before soiling, the sheets are placed in a thermal cabinet at 80° C., for 30 min. The cooled sheets are weighed before soiling.

The egg yolks and whites of whole raw eggs (3-4 eggs; 160 g/egg) are placed in a bowl and beaten with an egg whisk. Then, 50 ml semi-skimmed UHT (1.5% fat, ultra-high temperature, homogenized) milk are added to the mixture. The milk and egg are mixed without generating froth. A flat brush is used to uniformly distribute 1.0±0.1 g of the egg/milk mixture on the brushed side of the stainless steel sheets, using a balance to check the distribution. A margin of approximately 1.0 cm is left around the short sides of the sheets. The soiled sheets are dried horizontally (to prevent formation of droplets on the edges of the sheets), at room temperature for 4 hours (max. 24 h).

The sheets are then immersed for 30 seconds in boiling, demineralized water (using a holding device if necessary). Then, the sheets are dried again for 30 min at 80° C. After drying and cooling, the sheets are weighed. After weighing, the sheets are left for at least 24 hours (20° C., 40-60% relatively humidity) before submitting them to the wash test. In order to meet the testing requirements, only sheets with 190±10 mg egg yolk are used.

After the wash tests are conducted, the sheets are dried for 30 min at 80° C., in the thermal cabinet, and weighed again after cooling. The percentage cleaning performance is determined by dividing the (mg of egg/milk released by washing×100) by the (mg of egg/milk applied).

Preparation of the Spaghetti Mix Stain on Porcelain Plates

Pasta sauce (390 g) is mixed with 150 g of boiled spaghetti pasta, 25 g of minced meat (improved IKW composition—a combination of 225 gram fat free minced meat and 75 gram egg yolk) and 50 g of Grozette Formaggio cheese. A spoon is used to spread 3 g of this mixture on each white porcelain plate (Arzberg, 19 cm diameter, white, glazed porcelain, conforming to EN 50242, form 1495, No. 0219) leaving an approximately 2 cm wide unsoiled margin around the rim. The plates are dried by baking them for 2 hours at 120° C. in an oven. As soon as the plates are cooled, they are ready for use. The plates are stacked with paper towels between each of the plates for storage. After washing, the plates are sprayed with iodine solution (0.05N) for better identification of the carbohydrate residues. Evaluation of the washing performance is done by visually inspecting the color reactions of the carbohydrate residues with reference to the IKW photographic catalogue (IKW) and rated on a scale of 0-10 (10 being clean).

Performance Index

The performance index compares the performance of the variant (measured value) and the standard enzyme (theoretical value) at the same protein concentration. In addition, the theoretical values can be calculated, using the parameters of a performance dose response curve of the standard protease Example 2

Generation of GG36 Single Mutants Using Site Evaluation Libraries (SELs)

Figure 4:
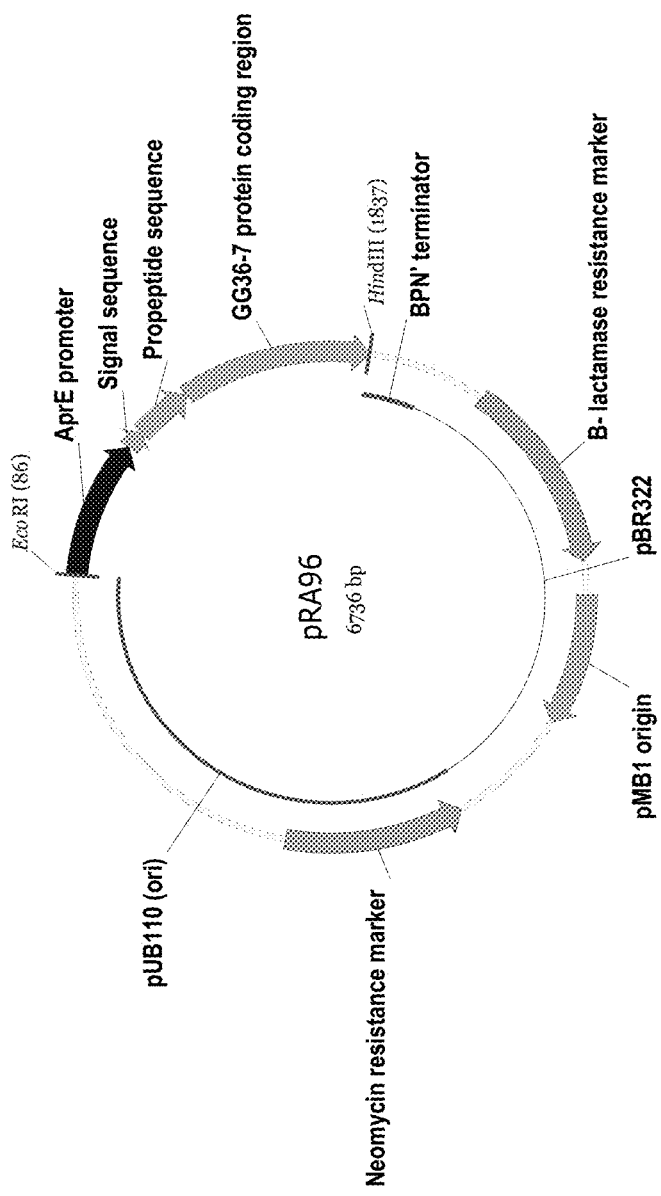
FIG. 4 provides a map of pRA96.

The construction of GG36 SELs described in this example was performed by GENEART using their proprietary methods and technology platform for gene optimization, gene synthesis, library generation and analysis (WO 2004/059556A3, European Patent Nos. 0 200 362 and 0 201 184; and U.S. Pat. Nos. 4,683,195, 4,683,202 and 6,472,184). The GG36 SELs were produced at positions pre-selected by the inventors using the pHPLT-GG36 *B. subtilis* expression plasmid (See, FIG. 2). This *B. subtilis* expression plasmid contains the GG36 expression cassette shown below, the *B. licheniformis* LAT promoter (Plat), and additional elements from pUB110 (McKenzie et al., Plasmid, 15:93-103, 1986) including a replicase gene (reppUB), a neomycin/kanamycin resistance gene (neo) and a bleomycin resistance marker (bleo) (FIG. 4 in U.S. Pat. No. 6,566,112). The pHPLT-GG36 plasmid map is provided at FIG. 2. The GG36 expression cassette sequence is provided below.

The DNA sequence of GG36 (the signal sequence is shown in lower case letters, propeptide in lower case, underlined text, and GG36 mature sequence in uppercase letters) is provided below:

(SEQ ID NO: 3)
Gtgagaagcaaaaaattgtggatcgtcgcgtcgaccgcactactcatttc tgttgctttcagttcatcgatcgcatcggct<u>gctgaagaagcaaaagaaa aatatttaattggctttaatgagcaggaagctgtcagtgagtttgtagaa caagtagaggcaaatgacgaggtcgccattctctctgaggaagaggaagt cgaaattgaattgcttcatgaatttgaaacgattcctgttttatccgttg agttaagcccagaagatgtggacgcgcttgagctcgatccagcgatttct tatattgaagaggatgcagaagtaacgacaatg</u>GCGCAATCAGTGCCATG

GGGAATTAGCCGTGTGCAAGCCCCAGCTGCCCATAACCGTGGATTGACAG

GTTCTGGTGTAAAAGTTGCTGTCCTCGATACAGGTATTTCCACTCATCCA

GACTTAAATATTCGTGGTGGCGCTAGCTTTGTACCAGGGGAACCATCCAC

TCAAGATGGGAATGGGCATGGCACGCATGTGGCCGGGACGATTGCTGCTT

TAAACAATTCGATTGGCGTTCTTGGCGTAGCGCCGAGCGCGGAACTATAC

GCTGTTAAAGTATTAGGGGCGAGCGGTTCAGGTTCGGTCAGCTCGATTGC

CCAAGGATTGGAATGGGCAGGGAACAATGGCATGCACGTTGCTAATTTGA

GTTTAGGAAGCCCTTCGCCAAGTGCCACACTTGAGCAAGCTGTTAATAGC

GCGACTTCTAGAGGCGTTCTTGTTGTAGCGGCATCTGGAAATTCAGGTGC

AGGCTCAATCAGCTATCCGGCCCGTTATGCGAACGCAATGGCAGTCGGAG

CTACTGACCAAAACAACAACCGCGCCAGCTTTTCACAGTATGGCGCAGGG

CTTGACATTGTCGCACCAGGTGTAAACGTGCAGAGCACATACCCAGGTTC

AACGTATGCCAGCTTAAACGGTACATCGATGGCTACTCCTCATGTTGCAG

GTGCAGCAGCCCTTGTTAAACAAAAGAACCCATCTTGGTCCAATGTACAA

ATCCGCAATCATCTAAAGAATACGGCAACGAGCTTAGGAAGCACGAACTT

GTATGGAAGCGGACTTGTCAATGCAGAAGCTGCAACTCGTTAA

The protein sequence of GG36 (the signal sequence is shown in lower case letters, propeptide in lower case, underlined text, and GG36 mature protease sequence in uppercase letters) is provided below:

(SEQ ID NO: 4)
vrskklwivastallisvafsssiasa<u>aeeeakekyligfneqeaysefve</u>
<u>qveandevailseeeeveiellhefetipvlsvelspedvdaleldpais</u>
<u>yieedaevttm</u>AQSVPWGISRVQAPAAHNRGLTGSGVKVAVLDTGISTHP
DLNIRGGASFVPGEPSTQDGNGHGTHVAGTIAALNNSIGVLGVAPSAELY
AVKVLGASGSGSVSSIAQGLEWAGNNGMHVANLSLGSPSPSATLEQAVNS
ATSRGVLVVAASGNSGAGSISYPARYANAMAVGATDQNNNRASFSQYGAG
LDIVAPGVNVQSTYPGSTYASLNGTSMATPHVAGAAALVKQKNPSWSNVQ
IRNHLKNTATSLGSTNLYGSGLVNAEAATR.

The method of mutagenesis was based on the codon-specific mutation approach in which all possible amino acid substitutions are simultaneously created at a specific codon of interest using forward and reverse mutagenesis primers that contain a degenerate codon, NNS ((A, C, T or G), (A, C, T or G), (C or G)) at the site of interest. To construct each of the GG36 SELs, three PCR reactions were performed: two mutagenesis reactions (primary PCR1 and PCR2) to introduce the mutated codon of interest in the mature GG36 DNA sequence using the NNS forward and reverse mutagenesis primers (25-45 nucleotides long), and a third reaction to fuse the two mutagenesis PCR products together to construct the pHPLT-GG36 expression vector having the desired mutated codons in the mature GG36 sequence.

The primer sequences used in this Example are provided below:

TABLE 2-1

Primers

| Sequence | Primer Name |
|---|---|
| CGCGCTTGAGCTCGATCCAGCGATTTC (SEQ ID NO: 9) | SacI-Fw |
| GTCTCCAAGCTTTAACGAGTTGCAG (SEQ ID NO: 10) | HindIII-Rv |
| GCAATTCAGATCTTCCTTCAGGTTATGACC (SEQ ID NO: 11) | pHPLT-BglII-Fw |
| GCATCGAAGATCTGATTGCTTAACTGCTTC (SEQ ID NO: 12) | pHPLT-BglII-Rv |

The Phusion High-Fidelity DNA Polymerase (Finnzymes catalog no. F-530L) was used for all PCRs, and the reactions were executed according to manufacturer's protocols that were supplied with the polymerase. In particular, for primary PCR 1, 1 μL (10 μM) of each of the pHPLT-BglII-Fw primer and a NNS reverse mutagenesis primer were used, and for primary PCR 2, 1 μL (10 μM) of the pHPLT-BglII-Rv primer and a NNS forward mutagenesis primer were used. Each reaction also included 1 μL of the pHPLT-GG36 plasmid template DNA (0.1-1 ng/μL). An MJ Research PTC-200 Peltier thermal cycler was used for the PCRs. The reactions yielded two fragments of approximately 2 to 3 kb having approximately 30 nucleotide overlap surrounding the GG36 codon of interest. The fragments obtained were fused in a third PCR similar to the ones described above using 1 μL of primary PCR 1 reaction mix, 1 μL of primary PCR 2 reaction mix and 1 μL (10 μM) of each of the forward and reverse SacI-Fw and HindIII-Rv primers. The amplified linear 859 bp fragment encoding the GG36 variant gene was purified (using QIAGEN® Qiaquick PCR purification kit) and digested with the SacI and HindIIII restriction enzymes to create cohesive ends on both sides of the fusion fragment. About 50 ng of plasmid pHPLT-GG36 was also purified after digestion with SacI and HindIIII, resulting in a 3.9 kb vector backbone fragment. The digested vector fragment was ligated with 50 ng of the digested 859 bp fragment encoding the variant enzyme using the T4 DNA ligase (Invitrogen) following the manufacturer's protocol for cloning of cohesive ends. Subsequently, the ligation mixture was used to transform B. subtilis cells (ΔaprE, ΔnprE, oppA, ΔspoIIE, degUHy32, ΔamyE::[xylR,pxylA-comK]) as described (WO 2002/014490).

To express the variant proteins for further biochemical analyses, the B. subtilis strains carrying the GG36 variant plasmids were inoculated into microtiter plates containing 150 μl Luria broth medium supplemented with 10 μg/ml neomycin. Plates were grown overnight at 37° C. with 300 rpm shaking and 80% humidity using Enzyscreen lids for microtiter plates (Enzyscreen). Ten microliters from the overnight culture plate were used to inoculate a new microtiter plate containing 190 μl of MBD medium (a MOPS based defined medium) with 10 ug/ml neomycin. MBD medium was prepared essentially as known in the art (See, Neidhardt et al., J. Bacteriol., 119: 736-747 [1974]), except that $NH_4Cl_2$, $FeSO_4$, and $CaCl_2$ were omitted from the base medium, 3 mM $K_2HPO_4$ was used, and the base medium was supplemented with 60 mM urea, and 100 ml of a solution made of 210 g/L glucose, and 350 g/L maltodextrin. The micronutrients were made up as a 100× stock solution containing in one liter, 400 mg $FeSO_4$ $7H_2O$, 100 mg $MnSO_4.H_2O$, 100 mg $ZnSO_4$ $7H_2O$, 50 mg $CuCl_2$ $2H_2O$, 100 mg $CoCl_2$ $6H_2O$, 100 mg $NaMoO_4$ $2H_2O$, 100 mg $Na_2B_4O_7$ $10H_2O$, 10 ml of 1M $CaCl_2$, and 10 ml of 0.5 M sodium citrate. The MBD medium containing microtiter plates were grown for 68 hours at 37° C., 300 rpm, and 80% humidity using Enzyscreen lids (Enzyscreen) for determining protein expression. The next day, cultures were filtered through a micro-filter plate (0.22 μm; Millipore) and the resulting filtrate was used for biochemical analysis. The TCA and BMI microswatch assays for the detergent compositions 7-11 were carried out as described in Example 1. Performance indices were also calculated as described under the BMI assay description in Example 1, and they are shown in Table 2-2 relative to GG36. In the following Tables, the detergent compositions ("Det.") correspond to those shown in Table D, above. Also, as indicated, the amino acid position is listed according to BPN' numbering.

TABLE 2-2

Single Variants of GG36 with
Performance Indices of at Least 0.2
Relative to GG36 in Either TCA or
BMI Microswatch Cleaning at 16° C.
in Detergents 7-11.

| GG36 Amino Acid Position (BPN' Numbering) | WT Residue | Mutant Residue |
|---|---|---|
| 1 | A | R |
| 2 | Q | A |
| 2 | Q | R |

TABLE 2-2-continued

Single Variants of GG36 with Performance Indices of at Least 0.2 Relative to GG36 in Either TCA or BMI Microswatch Cleaning at 16° C. in Detergents 7-11.

| GG36 Amino Acid Position (BPN' Numbering) | WT Residue | Mutant Residue |
|---|---|---|
| 2 | Q | S |
| 2 | Q | M |
| 2 | Q | W |
| 3 | S | R |
| 4 | V | R |
| 4 | V | S |
| 4 | V | C |
| 8 | I | A |
| 9 | S | W |
| 9 | S | F |
| 9 | S | A |
| 10 | R | A |
| 10 | R | M |
| 10 | R | S |
| 10 | R | H |
| 12 | Q | F |
| 12 | Q | R |
| 14 | P | F |
| 14 | P | K |
| 14 | P | Q |
| 15 | A | R |
| 15 | A | F |
| 16 | A | S |
| 17 | H | R |
| 17 | H | F |
| 17 | H | M |
| 18 | N | R |
| 18 | N | K |
| 20 | G | R |
| 20 | G | K |
| 20 | G | F |
| 22 | T | R |
| 22 | T | Q |
| 22 | T | L |
| 22 | T | V |
| 22 | T | W |
| 22 | T | Y |
| 22 | T | A |
| 23 | G | A |
| 23 | G | S |
| 23 | G | F |
| 24 | S | R |
| 24 | S | W |
| 24 | S | H |
| 24 | S | L |
| 24 | S | Q |
| 24 | S | F |
| 25 | G | R |
| 25 | G | F |
| 25 | G | V |
| 26 | V | F |
| 27 | K | R |
| 27 | K | L |
| 27 | K | V |
| 27 | K | F |
| 28 | V | A |
| 28 | V | E |
| 28 | V | N |
| 29 | A | T |
| 30 | V | E |
| 31 | L | F |
| 33 | T | S |
| 33 | T | G |
| 33 | T | D |
| 34 | G | P |
| 35 | I | M |
| 36 | S | T |
| 36 | S | F |
| 36 | S | R |
| 38 | T | R |
| 38 | T | F |
| 38 | T | L |
| 40 | P | H |
| 40 | P | W |
| 40 | P | R |
| 40 | P | N |
| 40 | P | T |
| 40 | P | L |
| 42 | L | I |
| 43 | N | R |
| 43 | N | A |
| 43 | N | S |
| 43 | N | W |
| 43 | N | F |
| 43 | N | I |
| 43 | N | D |
| 43 | N | M |
| 45 | R | T |
| 46 | G | R |
| 48 | A | R |
| 50 | F | C |
| 51 | V | W |
| 51 | V | F |
| 51 | V | H |
| 52 | P | F |
| 52 | P | N |
| 52 | P | E |
| 55 | P | Y |
| 57 | T | R |
| 59 | Q | A |
| 59 | Q | F |
| 59 | Q | R |
| 60 | D | P |
| 60 | D | A |
| 60 | D | Q |
| 62 | N | Q |
| 62 | N | E |
| 63 | G | S |
| 63 | G | A |
| 63 | G | M |
| 63 | G | V |
| 63 | G | T |
| 63 | G | H |
| 63 | G | Q |
| 63 | G | I |
| 63 | G | D |
| 63 | G | E |
| 63 | G | P |
| 64 | H | F |
| 64 | H | T |
| 68 | V | A |
| 68 | V | C |
| 69 | A | N |
| 69 | A | T |
| 69 | A | W |
| 69 | A | P |
| 71 | T | G |
| 72 | I | C |
| 74 | A | C |
| 75 | L | R |
| 75 | L | A |
| 75 | L | E |
| 75 | L | F |
| 78 | S | R |
| 78 | S | I |
| 78 | S | N |
| 79 | I | Q |
| 79 | I | W |

TABLE 2-2-continued

Single Variants of GG36 with Performance Indices of at Least 0.2 Relative to GG36 in Either TCA or BMI Microswatch Cleaning at 16° C. in Detergents 7-11.

| GG36 Amino Acid Position (BPN' Numbering) | WT Residue | Mutant Residue |
|---|---|---|
| 81 | V | R |
| 82 | L | R |
| 82 | L | T |
| 82 | L | M |
| 82 | L | F |
| 82 | L | V |
| 85 | A | M |
| 86 | P | W |
| 86 | P | I |
| 86 | P | L |
| 89 | E | P |
| 89 | E | W |
| 89 | E | T |
| 89 | E | I |
| 89 | E | H |
| 89 | E | V |
| 89 | E | F |
| 89 | E | L |
| 89 | E | W |
| 89 | E | G |
| 91 | Y | F |
| 91 | Y | N |
| 92 | A | F |
| 94 | K | N |
| 99 | S | F |
| 99 | S | T |
| 99 | S | M |
| 99 | S | G |
| 99 | S | P |
| 100 | G | I |
| 100 | G | S |
| 100 | G | N |
| 100 | G | Q |
| 101 | S | N |
| 101 | S | G |
| 101 | S | T |
| 101 | S | A |
| 101 | S | D |
| 101 | S | F |
| 101 | S | D |
| 101 | S | E |
| 101 | S | P |
| 102 | G | A |
| 102 | G | N |
| 102 | G | T |
| 102 | G | E |
| 102 | G | H |
| 103 | S | N |
| 103 | S | G |
| 103 | S | D |
| 104 | V | L |
| 104 | V | I |
| 104 | V | E |
| 104 | V | D |
| 105 | S | T |
| 105 | S | Q |
| 105 | S | E |
| 106 | S | V |
| 106 | S | G |
| 106 | S | T |
| 106 | S | A |
| 106 | S | E |
| 106 | S | D |
| 106 | S | F |
| 107 | I | F |
| 107 | I | M |
| 108 | A | I |
| 108 | A | G |
| 109 | Q | M |

TABLE 2-2-continued

Single Variants of GG36 with Performance Indices of at Least 0.2 Relative to GG36 in Either TCA or BMI Microswatch Cleaning at 16° C. in Detergents 7-11.

| GG36 Amino Acid Position (BPN' Numbering) | WT Residue | Mutant Residue |
|---|---|---|
| 111 | L | V |
| 111 | L | I |
| 112 | E | V |
| 112 | E | L |
| 112 | E | Q |
| 114 | A | G |
| 115 | G | R |
| 115 | G | K |
| 116 | N | L |
| 116 | N | A |
| 116 | N | K |
| 117 | N | F |
| 118 | G | I |
| 118 | G | R |
| 119 | M | C |
| 120 | H | A |
| 120 | H | F |
| 120 | H | R |
| 121 | V | E |
| 121 | V | F |
| 123 | N | G |
| 123 | N | E |
| 124 | L | S |
| 128 | S | N |
| 128 | S | M |
| 128 | S | H |
| 128 | S | Q |
| 128 | S | I |
| 128 | S | F |
| 128 | S | L |
| 128 | S | D |
| 129 | P | E |
| 132 | S | A |
| 132 | S | E |
| 138 | A | G |
| 144 | S | R |
| 147 | V | L |
| 148 | L | I |
| 158 | A | E |
| 159 | G | C |
| 159 | G | E |
| 160 | S | D |
| 166 | S | E |
| 166 | S | D |
| 167 | Y | W |
| 175 | M | V |
| 177 | V | C |
| 181 | D | A |
| 182 | Q | R |
| 183 | N | D |
| 183 | N | R |
| 183 | N | I |
| 183 | N | F |
| 183 | N | M |
| 185 | N | I |
| 185 | N | E |
| 185 | N | V |
| 186 | R | H |
| 186 | R | K |
| 188 | S | R |
| 188 | S | E |
| 188 | S | D |
| 192 | Y | W |
| 192 | Y | H |
| 194 | A | V |
| 194 | A | F |
| 194 | A | E |
| 197 | D | F |
| 198 | I | L |

TABLE 2-2-continued

Single Variants of GG36 with Performance Indices of at Least 0.2 Relative to GG36 in Either TCA or BMI Microswatch Cleaning at 16° C. in Detergents 7-11.

| GG36 Amino Acid Position (BPN' Numbering) | WT Residue | Mutant Residue |
|---|---|---|
| 198 | I | F |
| 203 | V | E |
| 203 | V | C |
| 208 | T | S |
| 209 | Y | N |
| 209 | Y | S |
| 209 | Y | F |
| 209 | Y | T |
| 209 | Y | H |
| 209 | Y | L |
| 209 | Y | G |
| 209 | Y | E |
| 210 | P | V |
| 210 | P | R |
| 210 | P | L |
| 211 | G | R |
| 211 | G | Q |
| 212 | S | I |
| 212 | S | F |
| 212 | S | M |
| 213 | T | A |
| 214 | Y | F |
| 215 | A | F |
| 215 | A | N |
| 215 | A | H |
| 215 | A | E |
| 215 | A | D |
| 216 | S | F |
| 216 | S | A |
| 217 | L | E |
| 217 | L | N |
| 217 | L | D |
| 218 | N | P |
| 218 | N | E |
| 218 | N | D |
| 224 | T | A |
| 224 | T | G |
| 227 | V | I |
| 230 | A | E |
| 231 | A | I |
| 231 | A | C |
| 233 | L | C |
| 234 | V | F |
| 235 | K | F |
| 236 | Q | N |
| 236 | Q | F |
| 238 | N | R |
| 238 | N | K |
| 238 | N | L |
| 239 | P | R |
| 239 | P | S |
| 239 | P | R |
| 239 | P | H |
| 239 | P | N |
| 239 | P | K |
| 239 | P | T |
| 239 | P | F |
| 239 | P | G |
| 240 | S | R |
| 241 | W | R |
| 242 | S | R |
| 243 | N | R |
| 243 | N | F |
| 244 | V | R |
| 246 | I | S |
| 248 | N | I |
| 248 | N | V |
| 248 | N | R |
| 249 | H | R |
| 249 | H | T |
| 250 | L | I |
| 251 | K | R |
| 251 | K | S |
| 252 | N | R |
| 252 | N | F |
| 252 | N | H |
| 252 | N | I |
| 253 | T | R |
| 253 | T | F |
| 253 | T | I |
| 254 | A | C |
| 256 | S | N |
| 258 | G | R |
| 260 | T | V |
| 260 | T | I |
| 262 | L | H |
| 262 | L | D |
| 263 | Y | F |
| 265 | S | F |
| 267 | L | N |
| 267 | L | M |
| 267 | L | V |
| 269 | N | R |
| 269 | N | I |
| 270 | A | C |
| 271 | E | T |
| 271 | E | V |
| 271 | E | L |
| 271 | E | H |
| 271 | E | F |
| 271 | E | P |
| 271 | E | A |
| 271 | E | M |
| 271 | E | I |
| 272 | A | F |
| 272 | A | R |
| 273 | A | I |
| 273 | A | F |
| 274 | T | G |

TABLE 2-3

GG36 Single Variants with Performance Indices of at Least 1.5 Relative to GG36 BMI Microswatch Cleaning at 32° C. in Detergent 7.

GG36 Variant

N62E
A158E
G159E

TABLE 2-4

GG36 Single Variants with Performance Indicees of at least 1.2 Relative to GG36 BMI Microswatch Cleaning at 32° C. in Detergent 10.

GG36 Variant

A1R
S78R
V244R

TABLE 2-4-continued

GG36 Single Variants with
Performance Indicees of at least 1.2
Relative to GG36 BMI Microswatch
Cleaning at 32° C. in Detergent 10.
GG36 Variant

N269R
E271L

Example 3

Construction and Cleaning Performance of the NHJ1 and WCE1 Sets of GG36 Variants The NHJ1 and WCE1 set of GG36 variants described herein were constructed at DNA 2.0, Inc., using the pHPLT-GG36 *B. subtilis* expression plasmid described above (FIG. 2). The variants were expressed in *B. subtilis* cells (genotype: ΔaprE, ΔnprE, amyE::xylRPxylAcomK-phleo) as described in Example 2, and were further characterized using the TCA assay for protein content determination, LAS/EDTA stability assay, and BMI microswatch cleaning assay as described in Example 1. These results are shown in Tables 3-1 and 3-2. In the following Tables, the detergent compositions ("Det.") correspond to those shown in Table D, above. Also, as indicated, the amino acid position is listed according to BPN' numbering.

TABLE 3-1

NHJ1 Variants with
Performance Indices of at least 0.25
Relative to GG36 in Any One of TCA,
LAS/EDTA Stability, or BMI
Microswatch Cleaning at 16° C. in
Detergents 7, 8 or 9.
GG36 Variant
(BPN' Numbering)

N062E-A158E
S103G-A158E
S128N-A158E
A016S-A158E
V104L-A158E
E089P-A158E
L111V-A158E
T022A-A158E
S101A-A158E
L148I-A158E
P129E-A158E
T022A-E089P
A016S-E089P
N062E-E089P
N062E-E271F
A158E-E271F
R186H-E271F
P129E-E271F
L111V-E271F
Y209E-E271F
A016S-E271F
S188D-E271F
T022A-E271F
G159E-E271F
V104L-E271F
S101A-E271F
E089P-E271F
S128N-E271F
S103G-E271F
L148I-E271F
H249R-E271F
N062E-G159E
A016S-G159E
S128N-G159E

TABLE 3-1-continued

NHJ1 Variants with
Performance Indices of at least 0.25
Relative to GG36 in Any One of TCA,
LAS/EDTA Stability, or BMI
Microswatch Cleaning at 16° C. in
Detergents 7, 8 or 9.
GG36 Variant
(BPN' Numbering)

L148I-G159E
L111V-G159E
E089P-G159E
T022A-G159E
P129E-G159E
S103G-G159E
V104L-G159E
A158E-G159E
S101A-G159E
A158E-H249R
L111V-H249R
P129E-H249R
N062E-H249R
A016S-H249R
R186H-H249R
L148I-H249R
G159E-H249R
S101A-H249R
S188D-H249R
V104L-H249R
Y209E-H249R
T022A-H249R
S128N-H249R
S103G-H249R
E089P-H249R
T022A-L111V
S101A-L111V
A016S-L111V
V104L-L111V
N062E-L111V
S103G-L111V
E089P-L111V
A016S-L148I
N062E-L148I
T022A-L148I
P129E-L148I
V104L-L148I
S103G-L148I
S128N-L148I
S101A-L148I
E089P-L148I
L111V-L148I
A016S-N062E
T022A-N062E
N062E-P129E
T022A-P129E
S128N-P129E
A016S-P129E
S101A-P129E
V104L-P129E
E089P-P129E
S103G-P129E
L111V-P129E
N062E-R186H
S128N-R186H
S101A-R186H
T022A-R186H
A016S-R186H
A158E-R186H
E089P-R186H
P129E-R186H
G159E-R186H
S103G-R186H
V104L-R186H
L111V-R186H
L148I-R186H
N062E-S101A
T022A-S101A
A016S-S101A
E089P-S101A
N062E-S103G

TABLE 3-1-continued

NHJ1 Variants with Performance Indices of at least 0.25 Relative to GG36 in Any One of TCA, LAS/EDTA Stability, or BMI Microswatch Cleaning at 16° C. in Detergents 7, 8 or 9. GG36 Variant (BPN' Numbering)

T022A-S103G
A016S-S103G
S101A-S103G
E089P-S103G
N062E-S128N
A016S-S128N
T022A-S128N
S101A-S128N
V104L-S128N
E089P-S128N
S103G-S128N
L111V-S128N
L111V-S188D
N062E-S188D
A016S-S188D
L148I-S188D
T022A-S188D
S128N-S188D
S101A-S188D
V104L-S188D
E089P-S188D
P129E-S188D
G159E-S188D
R186H-S188D
S103G-S188D
A158E-S188D
A016S-T022A
A016S-V104L
T022A-V104L
S101A-V104L
N062E-V104L
S103G-V104L
E089P-V104L
G159E-Y209E
L111V-Y209E
S101A-Y209E
A016S-Y209E
S128N-Y209E
L148I-Y209E
P129E-Y209E
N062E-Y209E
T022A-Y209E
S103G-Y209E
A158E-Y209E
S188D-Y209E
V104L-Y209E
E089P-Y209E
R186H-Y209E
GG36

TABLE 3-2

WCE1 Variants with Performance Indices of at least 0.2 Relative to GG36 in Any One of TCA, LAS/EDTA Stability, or BMI Microswatch Cleaning at 16° C. in Detergents 10 or 11. GG36 Variant (BPN' Numbering)

N018R-W241R
G020R-W241R
S024R-W241R
S009A-W241R
G020R-W241R
V004R-W241R
N043R-W241R
S078R-W241R

TABLE 3-2-continued

WCE1 Variants with Performance Indices of at least 0.2 Relative to GG36 in Any One of TCA, LAS/EDTA Stability, or BMI Microswatch Cleaning at 16° C. in Detergents 10 or 11. GG36 Variant (BPN' Numbering)

T022R-W241R
G115R-W241R
A001R-W241R
S212F-W241R
L082R-W241R
N018R-V244R
S024R-V244R
S078R-V244R
G020R-V244R
S212F-V244R
S009A-V244R
L082R-V244R
A001R-V244R
N043R-V244R
T022R-V244R
V004R-V244R
G115R-V244R
W241R-V244R
S242R-V244R
A001R-V004R
S009A-T022R
N018R-T022R
G020R-T022R
V004R-T022R
A001R-T022R
S024R-S242R
N018R-S242R
V004R-S242R
G020R-S242R
S212F-S242R
L082R-S242R
S078R-S242R
A001R-S242R
S009A-S242R
T022R-S242R
G115R-S242R
N043R-S242R
W241R-S242R
N018R-S212F
T022R-S212F
V004R-S212F
S024R-S212F
A001R-S212F
G115R-S212F
G020R-S212F
S009A-S212F
N043R-S212F
S078R-S212F
L082R-S212F
S009A-S078R
G020R-S078R
S024R-S078R
T022R-S078R
N018R-S078R
V004R-S078R
A001R-S078R
N043R-S078R
T022R-S024R
G020R-S024R
N018R-S024R
A001R-S024R
V004R-S024R
S009A-S024R
V004R-S009A
A001R-S009A
S242R-N269R
S024R-N269R
G020R-N269R
T022R-N269R
H249R-N269R
S212F-N269R
N043R-N269R

TABLE 3-2-continued

WCE1 Variants with
Performance Indices of at least 0.2
Relative to GG36 in Any One of
TCA, LAS/EDTA Stability, or
BMI Microswatch Cleaning at
16° C. in Detergents 10 or 11.
GG36 Variant (BPN' Numbering)

V244R-N269R
A001R-N269R
N018R-N269R
S078R-N269R
S009A-N269R
G115R-N269R
W241R-N269R
V004R-N269R
L082R-N269R
N018R-N043R
G020R-N043R
V004R-N043R
T022R-N043R
S009A-N043R
A001R-N043R
S024R-N043R
S009A-N018R
V004R-N018R
A001R-N018R
S024R-L082R
S009A-L082R
N018R-L082R
A001R-L082R
S078R-L082R
G020R-L082R
T022R-L082R
V004R-L082R
N043R-L082R
N043R-H249R
G020R-H249R
V004R-H249R
N018R-H249R
S009A-H249R
S212F-H249R
T022R-H249R
S024R-H249R
G115R-H249R
A001R-H249R
L082R-H249R
S242R-H249R
W241R-H249R
V244R-H249R
S078R-H249R
N018R-G115R
G020R-G115R
T022R-G115R
S078R-G115R
S009A-G115R
V004R-G115R
A001R-G115R
L082R-G115R
N043R-G115R
S024R-G115R
S009A-G020R
N018R-G020R
V004R-G020R
A001R-G020R
S009A-E271L
G020R-E271L
S024R-E271L
V244R-E271L
W241R-E271L
N043R-E271L
T022R-E271L
H249R-E271L
S212F-E271L
G115R-E271L
S242R-E271L
S078R-E271L
V004R-E271L
N269R-E271L
A001R-E271L
N018R-E271L
L082R-E271L
GG36

Example 4

Construction and Cleaning Performance of NHJ4 Set of GG36 Variants

The NHJ4 set of GG36 variants described in Table 4-4 below were constructed using the pHPLT-GG36 *B. subtilis* expression plasmid (FIG. 2) using PCR fusion or the QUIKCHANGE® Multi Site-directed mutagenesis kit ("QCMS kit"; Stratagene) as described below.

a) Construction of NHJ4 Variants by QUIKCHANGE® Multi Site-Directed Mutagenesis

Variants created using the QUIKCHANGE® Multi Site-Directed Mutagenesis are shown in Table 4-4. The parent plasmid pHPLT-GG36 (template DNA) was methylated using two micrograms of DNA and Dam methylase (NEB), according to the manufacturer's instructions. Site-directed mutants were made by a QuikChange® Multi Site-Directed Mutagenesis Kit ("QCMS kit"; Stratagene) following the manufacturer's protocol (See, Table 4-1 for primer sequences). For efficient transformation of *B. subtilis*, DNA from the QCMS reaction mixtures was amplified by rolling circle amplification (RCA) using the Illustra Templiphi kit (GE Healthcare) and the reaction was performed according to the manufacturer's protocol. One microliter of ten-fold diluted amplified DNA was used to transform 50 μL of competent *B. subtilis* cells (genotype: ΔaprE, ΔnprE, amyE::xylRPxylAcomK-phleo). The transformation mixture was shaken at 37° C. for 1 hour. Ten microliter aliquots of the transformation mixture were plated on skim milk (1.6%) Luria agar plates supplemented with 10 μg/ml of neomycin (Teknova). Subsequently, the colonies producing a clearing area (halo) on skim milk plates were inoculated in 120 μl of LB media containing 10 μg/mL neomycin for plasmid DNA extraction (QIAprep Spin Miniprep kit, Qiagen). The extracted plasmids were sequenced to confirm the presence of the desired mutations.

TABLE 4-1

Primer Sequences Used in Construction of NHJ4 Variants

| Mutations Introduced (BPN' Numbering) | Primer Name | Primer Sequence (5'-phosphorylated) |
|---|---|---|
| S101A S103G V104L | P5939 | AAAGTATTAGGGGCGAGCGGTGCAGGTGGACTTAGCTCGATTGCCCAAGGATTG (SEQ ID NO: 13) |
| G159E | P5940 | CATCTGGAAATTCAGGTGCAGAATCAATCAGCTATCCGGCCCGTTA (SEQ ID NO: 14) |
| T22A | P5941 | CTGCCCATAACCGTGGATTGGCAGGTTCTGGTGTAAAAGTTGCTG (SEQ ID NO: 15) |
| Y209E | P5942 | AGGTGTAAACGTGCAGAGCACAGAACCAGGTTCAACGTATGCCAG (SEQ ID NO: 16) |
| E271F | P5943 | GAAGCGGACTTGTCAATGCATTCGCTGCAACTCGTTAAAGCTTG (SEQ ID NO: 17) |
| S101A | P5944 | AAAGTATTAGGGGCGAGCGGTGCAGGTTCGGTCAGCTCGATTGCCCAA (SEQ ID NO: 18) |
| S103G | P5945 | TATTAGGGGCGAGCGGTTCAGGTGGAGTCAGCTCGATTGCCCAAGGA (SEQ ID NO: 19) |
| L111V | P5946 | GTCAGCTCGATTGCCCAAGGAGTAGAATGGGCAGGGAACAATGGCA (SEQ ID NO: 20) |
| S128N | P5947 | CGTTGCTAATTTGAGTTTAGGAAACCCTTCGCCAAGTGCCACACTTGA (SEQ ID NO: 21) |
| N62E | P5948 | GAACCATCCACTCAAGATGGGGAAGGGCATGGCACGCATGTG (SEQ ID NO: 22) |
| S188D | P5949 | ACCAAAACAACAACCGCGCCGACTTTTCACAGTATGGCGCAGGGCTT (SEQ ID NO: 23) | b) Construction of NHJ4 Variants by Extension PCR

Ten combinatorial mutants of GG36 were created by extension PCR. The list of mutations introduced in the pHPLT-GG36 plasmid and primers used for this purpose are shown in Table 4-2. To create each mutant, several fragments (Table 4-3) were amplified by primers shown in Table 4-2. Each PCR amplification reaction contained 30 pmol of each primer and 100 ng of the DNA template, pHPLT-GG36 plasmid. Amplifications were carried out using Vent DNA polymerase (NEB). The PCR reaction (20 µL) was initially heated at 95° C. for 2.5 min followed by 30 cycles of denaturation at 94° C. for 15 sec., annealing at 55° C. for 15 sec. and extension at 72° C. for 1 min. Following amplification, 2 to 4 PCR fragments (Table 4-3) for each variant were gel-purified, using a QIAGEN® gel-band purification kit and mixed (50 ng of each fragment). These mixtures served as DNA templates for the extension PCR by primers P5954 and P5955 to generate the full-length gene fragment. The PCR conditions were same as described above, except the extension phase, which was carried out at 72° C. for 2 min. The full-length DNA fragment was gel-purified using a QIAGEN® gel-band purification kit, digested with the BamHI and HindIII restriction enzymes and ligated with the pHPLT-GG36, which was digested with the same restriction enzymes. One microliter of the ligation mixtures was amplified using rolling circle amplification by Illustra Templiphi kit according to the manufacturer's instructions (GE Healthcare) to generate multimeric DNA for transformation into *Bacillus subtilis*. Products of the rolling circle amplification were diluted 100-times and used to transform *B. subtilis* cells (genotype: ΔaprE, ΔnprE, amyE::xylRPxylAcomK-phleo). An aliquot of the transformation mix was plated on LB plates containing 1.6% skim milk and 10 µg/mL neomycin and incubated overnight at 37° C. Subsequently, the colonies with halos were inoculated in 120 µl of Luria broth medium containing 10 µg/mL neomycin for plasmid DNA extraction (QIAprep Spin Miniprep kit, Qiagen). The extracted plasmids were sequenced to confirm the presence of the desired mutations. Variants created by the extension PCR are shown in Table 4-4.

TABLE 4-2

List of Primers Used for Construction of NHJ4 Variants with Extension PCR

| Mutation (BPN' numbering) | Primer name | Forward or Reverse | Primer Sequence |
|---|---|---|---|
| | P5950 flanking | Forward | CATATGAGTTATGCAGTTTGTAG (SEQ ID NO: 24) |
| | P5951 flanking | Reverse | TGTTTTTCTTGGAATTGTGCTGT (SEQ ID NO: 25) |

TABLE 4-2-continued

List of Primers Used for Construction of NHJ4 Variants with Extension PCR

| Mutation (BPN' numbering) | Primer name | Forward or Reverse | Primer Sequence |
|---|---|---|---|
|  | P5954 flanking | Forward | CAGTTTGTAGAATGCAAAAAGTG (SEQ ID NO: 26) |
|  | P5955 flanking | Reverse | GACAAGGTAAAGGATAAAACAGC (SEQ ID NO: 27) |
| T22A | P5956 | Forward | CATAACCGTGGATTGGCAGGTTCT GGTGTAAAAGTTGCTG (SEQ ID NO: 28) |
| T22A | P5957 | Reverse | ACTTTTACACCAGAACCTGCCAAT CCACGGTTATGGGCAG (SEQ ID NO: 29) |
| N62E | P5958 | Forward | CACTCAAGATGGGGAAGGGCATG GCACGCATGTGG (SEQ ID NO: 30) |
| N62E | P5959 | Reverse | ATGCGTGCCATGCCCTTCCCCATC TTGAGTGGATGGTTC (SEQ ID NO: 31) |
| S103G | P5960 | Forward | GCGAGCGGTTCAGGTGGAGTCAG CTCGATTGCCCAAGGA (SEQ ID NO: 32) |
| S103G | P5961 | Reverse | TGGGCAATCGAGCTGACTCCACCT GAACCGCTCGCCCCTA (SEQ ID NO: 33) |
| S103G L111V | P5962 | Forward | GTGGAGTCAGCTCGATTGCCCAAG GAGTAGAATGGGCAGGGAACAATGGCAT (SEQ ID NO: 34) |
| S103G L111V | P5963 | Reverse | CATTCTACTCCTTGGGCAATCGAG CTGACTCCACCTGAACCGCTCGCCCCTA (SEQ ID NO: 35) |
| S101G S103A V104I | P5964 | Forward | GCGAGCGGTGGAGGTGCGATCAGCTC GATTGCCCAAGGATTG (SEQ ID NO: 36) |
| S101G S103A V104I | P5965 | Reverse | CTTGGGCAATCGAGCTGATCGCACCT CCACCGCTCGCCCCTAATACTTTA (SEQ ID NO: 37) |
| S101A S103G V104L | P5966 | Forward | GCGAGCGGTGCAGGTGGACTTAGCTC GATTGCCCAAGGATTG (SEQ ID NO: 38) |
| S101A S103G V104L | P5967 | Reverse | CTTGGGCAATCGAGCTAAGTCCACCT GCACCGCTCGCCCCTAATACTTTA (SEQ ID NO: 39) |
| S101A | P5968 | Forward | TATTAGGGGCGAGCGGTGCAGGTTCGG TCAGCTCGATTGC (SEQ ID NO: 40) |
| S101A | P5969 | Reverse | ATCGAGCTGACCGAACCTGCACCGCTC GCCCCTAATACTTTA (SEQ ID NO: 41) |
| S128N | P5970 | Forward | CTAATTTGAGTTTAGGAAACCCTTCGC CAAGTGCCACACTT (SEQ ID NO: 42) |
| S128N | P5971 | Reverse | GCACTTGGCGAAGGGTTTCCTAAACTC AAATTAGCAACGTG (SEQ ID NO: 43) |
| G159D | P5972 | Forward | GAAATTCAGGTGCAGACTCAATCAGCT ATCCGGCCCGTT (SEQ ID NO: 44) |
| G159D | P5973 | Reverse | GGATAGCTGATTGAGTCTGCACCTGAA TTTCCAGATGC (SEQ ID NO: 45) |
| G159E | P5974 | forward | GAAATTCAGGTGCAGAATCAATCAGCT ATCCGGCCCGTT (SEQ ID NO: 46) |
| G159E | P5975 | Reverse | GGATAGCTGATTGATTCTGCACCTGAAT TTCCAGATGC (SEQ ID NO: 47) |
| Y209E | P5976 | forward | AACGTGCAGAGCACAGAACCAGGTTCA ACGTATGCCAGCTT (SEQ ID NO: 48) |
| Y209E | P5977 | Reverse | CATACGTTGAACCTGGTTCTGTGCTCTG CACGTTTACACC (SEQ ID NO: 49) |
| L111V | P5978 | forward | TCGATTGCCCAAGGAGTAGAATGGGCA GGGAACAATGGCAT (SEQ ID NO: 50) |

TABLE 4-2-continued

List of Primers Used for Construction of NHJ4 Variants with Extension PCR

| Mutation (BPN' numbering) | Primer name | Forward or Reverse | Primer Sequence |
|---|---|---|---|
| L111V | P5979 | Reverse | CATTGTTCCCTGCCCATTCTACTCCTTGG GCAATCGAGCTGAC (SEQ ID NO: 51) |

TABLE 4-3

Combinatorial Variants Created by Extension PCR

| Variant # | Variants (BPN Numbering) | Fragment | PCR Fragments |
|---|---|---|---|
| NHJ4-1 | S101G S103A V104I | 1 | P5950 + P5965 |
|  |  | 2 | P5964 + P5951 |
| NHJ4-2 | S101G S103A V104I G159D | 3 | P5950 + P5965 |
|  |  | 4 | P5964 + P5973 |
|  |  | 5 | P5972 + P5951 |
| NHJ4-3 | S101A S103G V104L | 6 | P5950 + P5967 |
|  |  | 7 | P5966 + P5951 |
| NHJ4-4 | S101A S103G V104L G159E | 8 | P5950 + P5967 |
|  |  | 9 | P5966 + P5975 |
|  |  | 10 | P5974 + P5951 |
| NHJ4-5 | S101A S103G V104L T22A | 11 | P5950 + P5957 |
|  |  | 12 | P5956 + P5967 |
|  |  | 13 | P5966 + P5951 |
| NHJ4-10 | T22A S101A Y209E | 14 | P5950 + P5957 |
|  |  | 15 | P5956 + P5969 |
|  |  | 16 | P5968 + P5977 |
|  |  | 17 | P5976 + P5951 |
| NHJ4-11 | S103G L111V G159E | 18 | P5950 + P5963 |
|  |  | 19 | P5962 + P5975 |
|  |  | 20 | P5974 + P5951 |
| NHJ4-12 | T22A S103G G159E | 21 | P5950 + P5957 |
|  |  | 22 | P5956 + P5961 |
|  |  | 23 | P5960 + P5975 |
|  |  | 24 | P5974 + P5951 |
| NHJ4-18 | T22A N62E L111V | 25 | P5950 + P5957 |
|  |  | 26 | P5956 + P5959 |
|  |  | 27 | P5958 + P5979 |
|  |  | 28 | P5978 + P5951 |
| NHJ4-20 | S101A S103G V104L S128N | 29 | P5950 + P5967 |
|  |  | 30 | P5966 + P5971 |
|  |  | 31 | P5970 + P5951 |

To express the NHJ4 set of variant proteins for further biochemical analyses, the *B. subtilis* strains carrying the variant plasmids were inoculated into microtiter plates containing 150 μl Luria broth medium supplemented with 10 μg/ml neomycin. The cultures were grown up for protein expression as described in Example 2, and they were filtered through a micro-filter plate (0.22 μm; Millipore) also as described in Example 2. The resulting filtrate was used for biochemical analysis. The eglin c inhibition assay for protein content determination and BMI microswatch assays tested in various detergents were carried out as described in Example 1. Performance indices are also calculated as described under the BMI assay description in Example 1. Table 4-4 provides information regarding these multiple mutation variants and the results obtained for them. The PI values are relative to GG36. In the following Tables, the detergent compositions ("Det.") correspond to those shown in Table D, above. Also, as indicated, the amino acid position is listed according to BPN' numbering.

TABLE 4-4

NHJ4 Multiple Mutation Variants with BMI Cleaning Performance Indices of at Least 0.2 Relative to GG36 in Detergents 7, 8 or 9, at 16° C.

| Variant Name | Created by | Mutations (BPN' Numbering) GG36 |
|---|---|---|
| NHJ4-1 | Extension PCR | S101G S103A V104I |
| NHJ4-10 | Extension PCR | T22A S101A Y209E |
| NHJ4-11 | Extension PCR | S103G L111V G159E |
| NHJ4-12 | Extension PCR | T22A S103G G159E |
| NHJ4-13 | QCMS | T22A L111V G159E |
| NHJ4-14 | QCMS | T22A S128N E271F Y209E |
| NHJ4-15 | QCMS | T22A S103G L111V |
| NHJ4-16 | QCMS | N62E L111V S128N |
| NHJ4-17 | QCMS | T22A L111V S128N |
| NHJ4-18 | Extension PCR | T22A N62E L111V |
| NHJ4-19 | QCMS | S101A S103G V104L S188D |
| NHJ4-2 | Extension PCR | S101G S103A V104I G159D |
| NHJ4-20 | Extension PCR | S101A S103G V104L S128N |
| NHJ4-24 | QCMS | T22A S101A G159E |
| NHJ4-3 | Extension PCR | S101A S103G V104L |
| NHJ4-4 | Extension PCR | S101A S103G V104L G159E |
| NHJ4-5 | Extension PCR | T22A S101A S103G V104L |
| NHJ4-6 | QCMS | S101A S103G V104L Y209E |
| NHJ4-7 | QCMS | T22A Y209E E271F |
| NHJ4-8 | QCMS | T22A S101A E271F |
| NHJ4-9 | QCMS | S101A Y209E E271F |

Example 5

Construction and Cleaning Performance of NHJ3 Set of GG36 Variants

Figure 3:
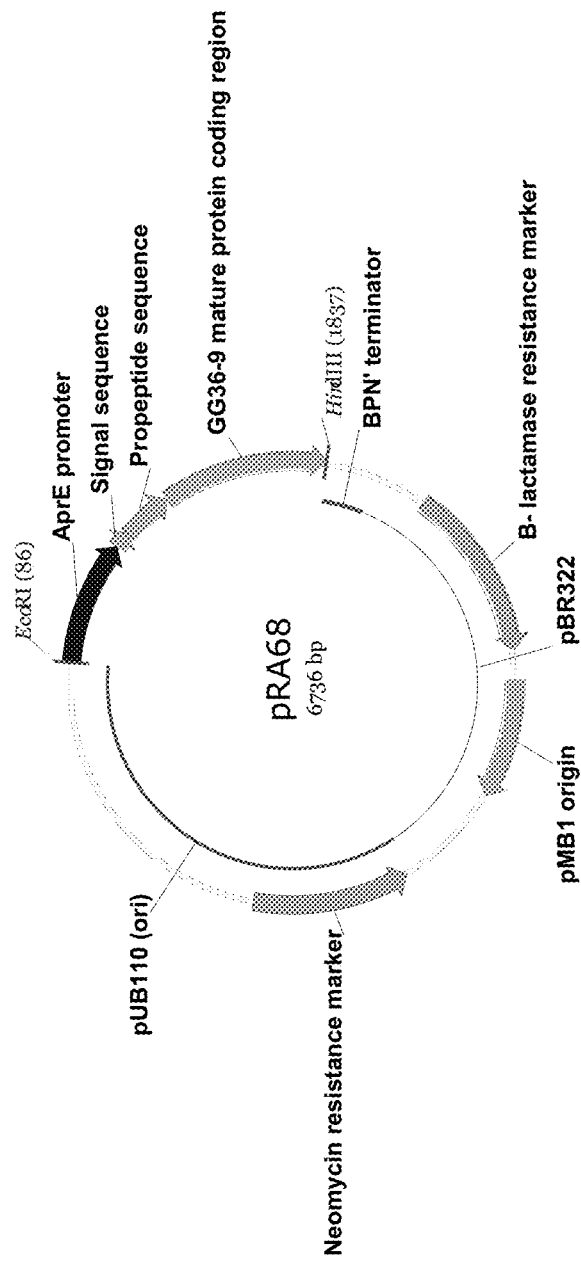
FIG. 3 provides a map of pRA68.

The NHJ3 set of variants described herein are based on a variant of GG36 (referred to as GG36-9) containing the following mutations: S101G, S103A, V104I, G159D, A232V, Q236H, Q245R, N248D, and N252K (BPN' numbering). These variants were created using the QUIKCHANGE® Lightning Site-Directed Mutagenesis Kit (QCLDS kit; Stratagene), with the pRA68 plasmid (See, FIG. 3) as the DNA template. Plasmid pRA68 was derived from the pBN3 vector (See, Babé et al., Biotech. Appl. Biochem. 27:117-124 [1998]).

The DNA sequence of GG36-9 variant (the signal sequence is shown in lower case letters, propeptide in lower case, underlined text, and GG36-9 mature sequence in uppercase letters) is provided below:

(SEQ ID NO: 5)
Gtgagaagcaaaaaattgtggatcgtcgcgtcgaccgcactactcatttc tgttgcttttagttcatcgatcgcatcggctgctgaagaagcaaaagaaa aatatttaattggctttaatgagcaggaagctgtcagtgagtttgtagaa -continued

```
caagtagaggcaaatgacgaggtcgccattctctctgaggaagaggaagt cgaaattgaattgcttcatgaatttgaaacgattcctgttttatccgttg agttaagcccagaagatgtggacgcgcttgaactcgatccagcgatttct tatattgaagaggatgcagaagtaacgacaatgGCGCAATCAGTGCCATG

GGGAATTAGCCGTGTGCAAGCCCCGGCTGCCCATAACCGTGGATTGACAG

GTTCTGGTGTAAAAGTTGCTGTCCTCGATACAGGTATTTCCACTCATCCA

GACTTAAATATTCGTGGTGGCGCTAGCTTTGTACCAGGGGAACCATCCAC

TCAAGATGGGAATGGGCATGGCACGCATGTGGCCGGGACGATTGCTGCTC

TAAACAATTCGATTGGCGTACTTGGCGTAGCGCCGAGCGCGGAACTATAC

GCTGTTAAAGTATTAGGGGCGAGCGGTGGGGGCGCCATCAGCTCGATTGC

CCAAGGATTGGAATGGGCAGGGAACAATGGCATGCACGTTGCTAATTTGA

GTTTAGGAAGCCCTTCGCCAAGTGCCACACTTGAGCAAGCTGTTAATAGC

GCGACTTCTAGGGGCGTTCTTGTTGTAGCGGCATCTGGAAATTCGGGTGC

AGACTCAATCAGCTATCCGGCCCGTTATGCGAACGCAATGGCAGTCGGAG

CTACTGACCAAAACAACAACCGCGCCAGCTTTTCACAGTATGGCGCAGGG

CTTGACATCGTCGCACCAGGTGTAAACGTGCAGAGCACATACCCAGGTTC

AACGTATGCCAGCTTAAACGGTACATCGATGGCTACTCCTCATGTTGCAG

GTGCAGCAGTCCTTGTTAAACATAAGAACCCATCTTGGTCCAATGTACGA

ATCCGCGATCATCTAAAGAAAACGGCAACGAGCTTAGGAAGCACGAACTT

GTATGGAAGCGGACTTGTCAATGCCGAAGCTGCAACTCGTTAA
```

The protein sequence of the GG36-9 variant (the signal sequence is shown in lower case letters, propeptide in lower case, underlined text, and GG36-9 mature protease sequence in uppercase letters) is provided below:

(SEQ ID NO: 6)
vrskklwivastallisvafsssiasa<u>aeeakekyligfneqeavsefve</u>

<u>qveandevailseeeeveiellhefetipvlsvelspedvdaleldpais</u> yieedaevttm AQSVPWGISRVQAPAAHNRGLTGSGVKVAVLDTGISTHP

DLNIRGGASFVPGEPSTQDGNGHGTHVAGTIAALNNSIGVLGVAPSAELY

AVKVLGASGGGAISSIAQGLEWAGNNGMHVANLSLGSPSPSATLEQAVNS

ATSRGVLVVAASGNSGADSISYPARYANAMAVGATDQNNNRASFSQYGAG

LDIVAPGVNVQSTYPGSTYASLNGTSMATPHVAGAAVLVKHKNPSWSNVR

IRDHLKKTATSLGSTNLYGSGLVNAEAATR

To create the NHJ3 variants using the QCLSD kit, mutagenic primers were designed as shown in Table 5-1 for each of the variants. The mutagenesis reaction for each variant consisted of 0.5 ul of 10× Buffer, 0.5 uL of pRA68 plasmid DNA (168 ng/µL), 0.5 µl forward "f" mutagenic primer (25 uM), 0.5 ul reverse "r" mutagenesis primer (25 uM), 1 ul dNTPs (supplied in the QCLSD kit), 1.5 ul Quik solution (supplied in the QCLMS kit), 1 µl Enzyme blend (supplied in the QCLSD kit), and 40 ul of distilled, deionized water to make up a 50 µL reaction volume as per the manufacturer's instructions. The cycling program was 1 cycle at 95° C. for 2 minutes, 18 cycles of 95° C. for 20 seconds, 60° C. for 10 seconds and 68° C. for 3 minutes, 22 seconds, and a final cycle of 68° C. for 5 minutes. Next, 1 µL of DpnI restriction enzyme supplied in the kit was used to digest the plasmid DNA in the reaction, and then 2 µL of the reaction was used to transform TOP 10 E. coli competent cells (Invitrogen). The E. coli transformants were selected on Luria broth medium plates containing 50 ug/mL(ppm) carbenicillin after overnight growth at 37° C. Plasmid DNA was extracted from 4-8 E. coli colonies grown in LA medium containing 50 ug/mL(ppm) carbenicillin using the QIAprep spin miniprep kit (Qiagen). The plasmids were sequenced to confirm the presence of the desired mutations. The variant plasmids were then transformed into B. subtilis cells as described in Example 2. The B. subtilis variant strains were grown up as described in Example 2 for further biochemical analysis, such as protein content determination using the eglin c inhibition assay (Example 1) and the BMI microswatch cleaning assay (Example 1). The results are provided below in Tables 5-2 and 5-3. The PIs are relative to GG36. In the following Tables, the detergent compositions ("Det.") correspond to those shown in Table D, above. Also, as indicated, the amino acid position is listed according to BPN' numbering.

TABLE 5-1

List of Mutagenic Primers Used to Create the NHJ3 Set of Variants
("f" Refers to Forward Primers and "r" Refers to Reverse Primers)

| Variant | Mutation Incorporated (BPN' numbering) | Mutagenic Primer Name | Mutagenic Primer Sequence 5' to 3' |
| --- | --- | --- | --- |
| NHJ3-1 | G101S | p158_G101S_f | GTTAAAGTATTAGGGGCGAGCGGTAGCGGCGCCATCAGCTCGATTGCC (SEQ ID NO: 53) |
| | | p159_G101S_r | GGCAATCGAGCTGATGGCGCCGCTACCGCTCGCCCCTAATACTTTAAC (SEQ ID NO: 54) |
| NHJ3-2 | A103S | p160_A103S_f | GTATTAGGGGCGAGCGGTGGGGGCAGCATCAGCTCGATTGCCCAAGGATTG (SEQ ID NO: 55) |
| | | p161_A103S_r | CAATCCTTGGGCAATCGAGCTGATGCTGCCCCCACCGCTCGCCCCTAATAC (SEQ ID NO: 56) |
| NHJ3-3 | I104V | p142_I104V_f | GGGCGAGCGGTGGGGGCGCCGTTAGCTCGATTGC CCAAGGATTG (SEQ ID NO: 57) |

TABLE 5-1-continued

List of Mutagenic Primers Used to Create the NHJ3 Set of Variants
("f" Refers to Forward Primers and "r" Refers to Reverse Primers)

| Variant | Mutation Incorporated (BPN' numbering) | Mutagenic Primer Name | Mutagenic Primer Sequence 5' to 3' |
|---|---|---|---|
|  |  | p143_I104V_r | CAATCCTTGGGCAATCGAGCTAACGGCGCCCCA CCGCTCGCCC (SEQ ID NO: 58) |
| NHJ3-4 | D159G | p144_D159G_f | GCATCTGGAAATTCGGGTGCAGGCTCAATCAGCT ATCCGGCCCGT (SEQ ID NO: 59) |
|  |  | p145_D159G_r | ACGGGCCGGATAGCTGATTGAGCCTGCACCCGAA TTTCCAGATGC (SEQ ID NO: 60) |
| NHJ3-5 | V232A | p146_V232A_f | CTCATGTTGCAGGTGCAGCAGCACTTGTTAAACAT AAGAACCC (SEQ ID NO: 61) |
|  |  | p147_V232A_r | GGGTTCTTATGTTTAACAAGTGCTGCTGCACCTGC AACATGAG (SEQ ID NO: 62) |
| NHJ3-6 | H236Q | p148_H236Q_f | GTGCAGCAGTCCTTGTTAAACAAAAGAACCCATC TTGGTCCAAT (SEQ ID NO: 63) |
|  |  | p149_H236Q_r | ATTGGACCAAGATGGGTTCTTTTGTTTAACAAGG ACTGCTGCAC (SEQ ID NO: 64) |
| NHJ3-7 | R245Q | p150_R245Q_f | CCATCTTGGTCCAATGTACAAATCCGCGATCATC TAAAGAAAAC (SEQ ID NO: 65) |
|  |  | p151_R245Q_r | GTTTTCTTTAGATGATCGCGGATTTGTACATTGG ACCAAGATGG (SEQ ID NO: 66) |
| NHJ3-8 | D248N | P152_D248N_f | GGTCCAATGTACGAATCCGCAATCATCTAAAGA AAACGGCAAC (SEQ ID NO: 67) |
|  |  | P153_D248N_r | GTTGCCGTTTTCTTTAGATGATTGCGGATTCGTA CATTGGACC (SEQ ID NO: 68) |
| NHJ3-9 | K252N | P154_K252N_f | GAATCCGCGATCATCTAAAGAATACGGCAACGA GCTTAGGAAG (SEQ ID NO: 69) |
|  |  | P155_K252N_r | CTTCCTAAGCTCGTTGCCGTATTCTTTAGATGATC GCGGATTC (SEQ ID NO: 70) |

TABLE 5-2

NHJ3 Multiple Mutation Variants with BMI Cleaning Performance Indices of at Least 1.1 Relative to GG36 in Detergents 7, 8 or 9, at 16° C.

| Variant | Variant Sequence Relative to GG36 (BPN' Numbering) GG36 |
|---|---|
| NHJ3-1 | S103A-V104I-G159D-A232V-Q236H-Q245R-N248D-N252K |
| NHJ3-2 | S101G-V104I-G159D-A232V-Q236H-Q245R-N248D-N252K |
| NHJ3-3 | S101G-S103A-G159D-A232V-Q236H-Q245R-N248D-N252K |
| NHJ3-4 | S101G-S103A-V104L-A232V-Q236H-Q245R-N248D-N252K |
| NHJ3-5 | S101G-S103A-V104L-G159D-Q236H-Q245R-N248D-N252K |
| NHJ3-6 | S101G-S103A-V104L-G159D-A232V-Q245R-N248D-N252K |
| NHJ3-7 | S101G-S103A-V104L-G159D-A232V-Q236H-N248D-N252K |
| NHJ3-8 | S101G-S103A-V104L-G159D-A232V-Q236H-Q245R-N252K |
| NHJ3-9 | S101G-S103A-V104L-G159D-A232V-Q236H-Q245R-N248D |

TABLE 5-3

NHJ3 Multiple Mutation Variants with BMI Cleaning Performance Indices of at Least 0.3 Relative to GG36 in Detergents 10 or 11, at 16° C.

| Variant | Variant Sequence Relative to GG36 (BPN' Numbering) GG36 |
|---|---|
| NHJ3-1 | S103A-V104I-G159D-A232V-Q236H-Q245R-N248D-N252K |
| NHJ3-2 | S101G-V104I-G159D-A232V-Q236H-Q245R-N248D-N252K |
| NHJ3-3 | S101G-S103A-G159D-A232V-Q236H-Q245R-N248D-N252K |
| NHJ3-4 | S101G-S103A-V104L-A232V-Q236H-Q245R-N248D-N252K |
| NHJ3-5 | S101G-S103A-V104L-G159D-Q236H-Q245R-N248D-N252K |
| NHJ3-6 | S101G-S103A-V104L-G159D-A232V-Q245R-N248D-N252K |
| NHJ3-7 | S101G-S103A-V104L-G159D-A232V-Q236H-N248D-N252K |
| NHJ3-8 | S101G-S103A-V104L-G159D-A232V-Q236H-Q245R-N252K |
| NHJ3-9 | S101G-S103A-V104L-G159D-A232V-Q236H-Q245R-N248D |

Example 6

Construction and Cleaning Performance of NHJ5 Set of GG36 Variants

The NHJ5 set of variants described herein are based on a variant of GG36 (referred to as GG36-7) containing the following mutations: S101G, S103A, V104I, G159D, A232V, Q245R, N248D, and (BPN' numbering). These variants were created using the QUIKCHANGE® Lightning Multi Site-Directed Mutagenesis Kit ("QCLMS kit") with the pRA96 plasmid as the DNA template (See, FIG. 4). The mutations incorporated and the sequences of the primers used for introducing the mutations in GG36-7 are shown in Table 6-1. The variants were generated using the methods described in Example 4. The *B. subtilis* variant strains were grown up as described in Example 2 for further biochemical analysis, such as protein content determination using the eglin c inhibition assay (Example 1) and the BMI microswatch cleaning assay (Example 1). The results are provided below in Table 6-2. The PI values are relative to GG36. In the following Tables, the detergent compositions ("Det.") correspond to those shown in Table D, above. Also, as indicated, the amino acid position is listed according to BPN' numbering.

The DNA sequence of GG36-7 variant (the signal sequence is shown in lower case letters, propeptide in lower case, underlined text, and GG36-7 mature protease sequence in uppercase letters) is provided below:

```
                                        (SEQ ID NO: 7)
Gtgagaagcaaaaaattgtggatcgtcgcgtcgaccgcactactcatttc tgttgcttttagttcatcgatcgcatcggctgctgaagaagcaaaagaaa aatatttaattggctttaatgagcaggaagctgtcagtgagtttgtagaa caagtagaggcaaatgacgaggtcgccattctctctgaggaagaggaagt cgaaattgaattgcttcatgaatttgaaacgattcctgttttatccgttg agttaagcccagaagatgtggacgcgcttgaactcgatccagcgatttct tatattgaagaggatgcagaagtaacgacaatgGCGCAATCAGTGCCATG

GGGAATTAGCCGTGTGCAAGCCCCGGCTGCCCATAACCGTGGATTGACAG
```

```
GTTCTGGTGTAAAAGTTGCTGTCCTCGATACAGGTATTTCCACTCATCCA

GACTTAAATATTCGTGGTGGCGCTAGCTTTGTACCAGGGGAACCATCCAC

TCAAGATGGGAATGGGCATGGCACGCATGTGGCCGGGACGATTGCTGCTC

TAAACAATTCGATTGGCGTACTTGGCGTAGCGCCGAGCGCGGAACTATAC

GCTGTTAAAGTATTAGGGGCGAGCGGTGGGGGCGCCATCAGCTCGATTGC

CCAAGGATTGGAATGGGCAGGGAACAATGGCATGCACGTTGCTAATTTGA

GTTTAGGAAGCCCTTCGCCAAGTGCCACACTTGAGCAAGCTGTTAATAGC

GCGACTTCTAGGGGCGTTCTTGTTGTAGCGGCATCTGGAAATTCGGGTGC

AGACTCAATCAGCTATCCGGCCCGTTATGCGAACGCAATGGCAGTCGGAG

CTACTGACCAAAACAACAACCGCGCCAGCTTTTCACAGTATGGCGCAGGG

CTTGACATCGTCGCACCAGGTGTAAACGTGCAGAGCACATACCCAGGTTC

AACGTATGCCAGCTTAAACGGTACATCGATGGCTACTCCTCATGTTGCAG

GTGCAGCAGTCCTTGTTAAACAAAAGAACCCATCTTGGTCCAATGTACGA

ATCCGCGATCATCTAAAGAATACGGCAACGAGCTTAGGAAGCACGAACTT

GTATGGAAGCGGACTTGTCAATGCCGAAGCTGCAACTCGT
```

The protein sequence of GG36-7 variant (signal sequence is shown in lower case letters, propeptide in lower case, underlined text, and GG36-7 mature protease sequence in uppercase letters) is provided below:

```
                                        (SEQ ID NO: 8)
vrskklwivastallisvafsssiasaaeeeakekyliqfneqeavsefve qveandevailseeeeveiellhefetipvlsvelspedvdaleldpais yieedaevttmAQSVPWGISRVQAPAAHNRGLTGSGVKVAVLDTGISTHP

DLNIRGGASFVPGEPSTQDGNGHGTHVAGTIAALNNSIGVLGVAPSAELY

AVKVLGASGGGAISSIAQGLEWAGNNGMHVANLSLGSPSPSATLEQAVNS

ATSRGVLVVAASGNSGADSISYPARYANAMAVGATDQNNNRASFSQYGAG

LDIVAPGVNVQSTYPGSTYASLNGTSMATPHVAGAAVLVKQKNPSWSNVR

IRDHLKNTATSLGSTNLYGSGLVNAEAATR
```

TABLE 6-1

List of Primers Used to Create the NHJ5 Set of Variants

| Primer # | Mutations Used GG36 Numbering (BPN' Numbering Shown in Parentheses) | Primer Sequence |
|---|---|---|
| 168 | H243R (H249R) | GTACGAATCCGCGATAGACTAAAGAATACGGCAACGAG (SEQ ID NO: 71) |
| 170 | E265F (E271F) | GCGGACTTGTCAATGCCTTTGCTGCAACTCGTTAAAGCTTACAT (SEQ ID NO: 72) |
| 172 | D157E (D159E) | GGAAATTCGGGTGCAGAATCAATCAGCTATCCGGCCCGTTA (SEQ ID NO: 73) |
| 174 | A156E (A158E) | CTGGAAATTCGGGTGAAGACTCAATCAGCTATCCGGCC (SEQ ID NO: 74) |
| 176 | A156E-D157G (A158E-D159E) | CGGCATCTGGAAATTCGGGTGAAGGCTCAATCAGCTATCCGGCCCGTTATG (SEQ ID NO: 75) |
| 178 | T22A | CATAACCGTGGATTGGCAGGTTCTGGTGTAAAAGTTGCTGTC (SEQ ID NO: 76) |

TABLE 6-1-continued

List of Primers Used to Create the NHJ5 Set of Variants

| Primer # | Mutations Used GG36 Numbering (BPN' Numbering Shown in Parentheses) | Primer Sequence |
|---|---|---|
| 180 | N60E (N62E) | TCCACTCAAGATGGGGAAGGGCATGGCACGCATGTGGC (SEQ ID NO: 77) |
| 182 | N232R (N238R) | CTTGTTAAACAAAAGAGACCATCTTGGTCCAATGTACGAATC (SEQ ID NO: 78) |
| 184 | D242R (D248R) | AATGTACGAATCCGCAGACATCTAAAGAATACGGCAACGAGC (SEQ ID NO: 79) |
| 186 | T247R (T253R) | CGATCATCTAAAGAATAGAGCAACGAGCTTAGGAAGCACGAAC (SEQ ID NO: 80) |
| 188 | S24R | GTGGATTGACAGGTAGAGGTGTAAAAGTTGCTGTCCTCGATA (SEQ ID NO: 81) |
| 190 | N74D (N76D) | ACGATTGCTGCTCTAGATAATTCGATTGGCGTACTTGGCGTAG (SEQ ID NO: 82) |

TABLE 6-2

NHJ5 Multiple Mutation Variants with BMI Cleaning Performance Indices of at Least 0.6 Relative to GG36 in Detergents 7-11, at 16° C.

| Variant | Variant Sequence Relative to GG36 (BPN' Numbering) GG36 |
|---|---|
| GG36-7 | S101G-S103A-V104I-G159D-A232V-Q245R-N248D |
| NHJ5-1 | S101G-S103A-V104I-G159D-A232V-Q245R-N248D-E271F |
| NHJ5-2 | S101G-S103A-V104I-G159D-A232V-Q245R-N248D-N238R |
| NHJ5-3 | S101G-S103A-V104I-G159D-A232V-Q245R-N248D-N248R |
| NHJ5-4 | S101G-S103A-V104I-G159D-A232V-Q245R-N248D-T253R |
| NHJ5-5 | S101G-S103A-V104I-G159D-A232V-Q245R-N248D-S24R |
| NHJ5-6 | S101G-S103A-V104I-G159D-A232V-Q245R-N248D-N76D |
| NHJ5-7 | S101G-S103A-V104I-G159E-A232V-Q245R-N248D-H249R |
| NHJ5-8 | S101G-S103A-V104I-G159E-A232V-Q245R-N248D-E271F |
| NHJ5-9 | S101G-S103A-V104I-A158E-A232V-Q245R-N248D-H249R |
| NHJ5-10 | S101G-S103A-V104I-A158E-A232V-Q245R-N248D-E271F |
| NHJ5-11 | T22A-S101G-S103A-V104I-G159D-A232V-Q245R-N248D-H249R |
| NHJ5-12 | T22A-S101G-S103A-V104I-G159D-A232V-Q245R-N248D-E271F |
| NHJ5-13 | N62E-S101G-S103A-V104I-G159D-A232V-Q245R-N248D-H249R |
| NHJ5-14 | N62E-S101G-S103A-V104I-G159D-A232V-Q245R-N248D-E271F |

Example 7

Construction of NHJ2 Combinatorial Library

This Example describes the construction of a GG36 combinatorial library involving one or more of the following mutations: A16S, T22A, S101A, S103G, V104L, L111V, S128N, and L148I (BPN' numbering). The pHPLT-GG36 B. subtilis expression plasmid was provided to DNA 2.0 Inc., for the generation of NHJ2 combinatorial library. A ligation reaction of the constructed NHJ library was provided by DNA 2.0, Inc. for transformation in the B. subtilis strain (genotype: ΔaprE, ΔnprE, amyE::xylRPxylAcomK-phleo). The variants generated containing one or several of the mutations described herein can be tested for cold water cleaning applications using methods and detergent compositions described herein.

Example 8

Construction of Additional Libraries and GG36 Variants

Additional libraries and variants are constructed using the following set of mutations: A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, W241R (BPN' numbering). The pHPLT-GG36 B. subtilis expression plasmid was used to construct the libraries and variants at DNA2.0, Inc. A ligation reaction of the library or variant was transformed in the B. subtilis strain (genotype: ΔaprE, ΔnprE, amyE::xylRPxylAcomK-phleo). The variants generated containing one or more of these mutations were tested for cold water cleaning in the BMI microswatch cleaning assay (Example 1) using methods and detergent compositions described herein. The results are provided below in Table 8-1. In the following Tables, the detergent compositions ("Det.") correspond to those shown in Table 1-2, above. Also, as indicated, the amino acid position is listed according to BPN' numbering.

Additional sets of GG36 variants are constructed and tested for cold water cleaning applications using methods and detergent compositions described herein include: G20R-N43R-H249R, G20R-T22R-N43R, G20R-N43R-S242R, G20R-N43R-E271L, G20R-N43R-V244R, G20R-S24R-N43R-S242R, S9A-T22R-S78R-S212F-W241R, S9A-G20R-N43R-S212F, S9A-N43R-S212F, G20R-N43R-S212F, G20R-T22R-N43R-S212F, S24R-S78R-S212F, S9A-N43R-S78R, S9A-N43R-S78R-S242R, S9A-G20R-N43R-S78R, G20R-S24R-N43R-S78R-S242R, T22R-S24R-S78R-S212F, S9A-G20R-N43R-S78R-S242R, G20R-N43R-S78R-H249R, G20R-N43R-S78R, S9A-S78R-S212F, S9A-T22R-N43R-S78R, S9A-G20R-S24R-N43R, S9A-T22R-S78R-S212F, V4R-S9A-T22R-S78R-S212F, G20R-S24R-N43R, A1R-S9A-N43R, G20R-S24R-N43R-G115R, S9A-S24R-N43R, G20R-T22R-S24R-N43R, A1R-S24R-N43R, S9A-G20R-S24R-N43R-S242R, S9A-G20R-T22R-S78R-S212F, S9A-S24R-N43R-V244R, S9A-S24R-N43R-S242R, V4R-S9A-T22R-S24R-S212F, and T22R-S24R-N43R (BPN' numbering).

TABLE 8-1

BMI cleaning performance of WCE4 variants.

| Sequence of GG36 variants (BPN' numbering) | PI Relative to GG36; Detergent 36k or l, BMI assay, 16° C. |
|---|---|
| V004R-S009A-G020R-S242R | +++ |
| G020R-N043R-W241R | +++ |
| G020R-S242R-N269R | +++ |
| V004R-S009A-G020R-N043R- | +++ |
| V004R-G020R-H249R- | +++ |
| N018R-S024R-V244R | +++ |
| S009A-T022R-S212F-W241R | +++ |
| G020R-N043R-N269R- | +++ |
| N018R-S024R-S242R | +++ |
| V004R-S009A-N043R-W241R- | +++ |
| G020R-N043R-V244R- | +++ |
| G020R-T022R-S242R- | +++ |
| V004R-G020R-N043R- | +++ |
| V004R-S009A-G020R-N043R-S242R- | +++ |
| G020R-N043R-S242R- | +++ |
| G020R-N043R-S242R-H249R- | +++ |
| G020R-S212F-H249R- | +++ |
| V004R-S009A-W241R- | +++ |
| A001R-S009A-N043R- | +++ |
| G020R-N043R-H249R- | +++ |
| S009A-G020R-N043R-W241R | +++ |
| G020R-T022R-N043R- | +++ |
| G020R-H249R-N269R- | +++ |
| G020R-T022R-W241R- | +++ |
| V004R-S009A-S024R-N043R-W241R- | +++ |
| S009A-N043R-S078R | +++ |
| V004R-G020R-S024R-V244R- | +++ |
| G020R-T022R-S078R-S242R- | +++ |
| G020R-S024R-S242R-H249R- | +++ |
| V004R-S009A-S078R-W241R- | +++ |
| S009A-N043R-S078R-S242R | +++ |
| V004R-G020R-S024R- | +++ |
| S009A-N043R-S212F | +++ |
| G020R-N043R-S212F- | +++ |
| S024R-S078R-S212F- | +++ |
| S009A-G020R-S024R-N043R | +++ |
| S009A-T022R-N043R-S078R | +++ |
| G020R-T022R-S212F-W241R- | +++ |
| G020R-N043R-S212F-W241R- | +++ |
| S009A-N043R-W241R | +++ |
| G020R-N043R-E271L | +++ |
| G020R-T022R-S078R-W241R- | +++ |
| G020R-S024R-N043R-S242R- | +++ |
| G020R-T022R-N043R-W241R- | +++ |
| S009A-G020R-N043R-S212F | +++ |
| V004R-S009A-G020R-S024R-S242R- | +++ |
| G020R-N043R-H249R-E271L | +++ |
| G020R-T022R-S024R-S242R- | +++ |
| S009A-T022R-S078R-S212F | +++ |
| G020R-N043R-S242R-E271L | +++ |
| S009A-T022R-S078R-S212F-W241R | +++ |
| V004R-G020R-S024R-H249R- | +++ |
| G020R-T022R-E271L | +++ |
| G020R-T022R-N043R-S212F- | +++ |
| V004R-G020R-S024R-N043R-S242R- | +++ |
| V004R-G020R-S024R-N043R- | +++ |
| V004R-S009A-T022R-S078R-S212F- | + |
| G020R-T022R-S078R-S212F-W241R- | + |
| G020R-T022R-N269R- | + |

PI = Performance Index Relative to GG36
PI > or = 1.5 is + + +;
PI between 1.49 and 1.3 = + +;
PI between 1.29 and 1.0 = + in detergent 36k or l

Example 9

Construction and Cleaning Performance of the GG36 Library WCE2

The WCE2 combinatorial library was generated by DNA 2.0, Inc., using the pHPLT-GG36 *B. subtilis* expression plasmid. A ligation reaction of the constructed WCE2 library transformed in the *B. subtilis* strain (genotype: ΔaprE, ΔnprE, amyE::xylRPxylAcomK-phleo). The set of mutations used to generate the WCE2 library are A230E, G20R, H249R, N18R, N43R/D, N76D, R45T, S242R, and S24R (BPN' numbering). The variants generated containing one or more of these mutations are tested for cold water cleaning in the BMI microswatch cleaning assay (Example 1) using methods and detergent compositions described herein. The results are provided below in Table 9-1. In the following Table, the detergent compositions ("Det.") correspond to those shown in Table 1-2 above. Also, as indicated, the amino acid position is listed according to BPN' numbering.

TABLE 9-1

BMI cleaning performance of WCE2 library variants of GG36.

| Sequence of GG36 variants (BPN' numbering) | PI Relative to GG36; BMI assay, Detergent 36h or 36i, 16° C. |
|---|---|
| N018R-G020R-N043R-R045T-A230E | +++ |
| N018R-N043R-R045T-S242R-H249R | +++ |
| S024R-N043D-H249R | +++ |
| N018R-G020R-R045T | +++ |
| G020R-S024R-N076D-H249R | +++ |
| S024R-N043R-A230E-S242R | +++ |
| N018R-S024R-N043D-A230E | ++ |
| G020R-N076D | ++ |
| N018R-S024R-N043D-N076D-H249R | ++ |
| S024R-N043R-N076D-H249R | +++ |
| N018R-S024R-R045T-S242R | ++ |
| G020R-N043D-N076D-A230E-H249R | ++ |
| G020R-N043R-R045T-S242R | +++ |
| N018R-S024R-N076D-H249R | ++ |
| N018R-G020R-S024R-N043D-R045T-L233I-S242R | +++ |
| S024R-N043R-A230E | +++ |
| N018R-G020R-N043D | +++ |
| N043R-S242R-H249R | +++ |
| G020R-N043R-R045T-A230E | +++ |
| N043R-N076D-S242R-H249R | +++ |
| G020R-S024R-R045T-A230E-S242R | +++ |
| S024R-R045T-N076D-A230E-S242R-H249R | +++ |
| S024R-R045T | +++ |
| S024R-N043R-R045T-N076D-A230E-H249R | ++ |
| N018R-S024R-N043D-R045T-H249R | ++ |
| N018R-R045T-H249R | +++ |
| S024R-N043R-S242R | +++ |
| N018R-G020R-N043R-N076D-H249R | +++ |
| G020R-S024R-N043D-H249R | +++ |
| G020R-N043R-A230E-S242R | +++ |
| G020R-N043R-S242R | +++ |
| N018R-N043R-N076D-A230E | ++ |
| G020R-S024R-N043D-S242R | +++ |
| G020R-N043R-A230E | +++ |
| N018R-G020R-N043R-N076D-S242R-H249R | +++ |
| N043D-R045T-N076D-H249R | + |
| N018R-N043R-S242R-H249R | +++ |
| N018R-G020R-N043R-R045T-S242R | +++ |
| N018R-G020R-N043D-A230E-S242R | +++ |
| G020R-S024R-N043R-R045T-H249R | +++ |
| S024R-N043R-H249R | +++ |
| G020R-S024R-K027E-N043R-N076D-A230E | +++ |
| S024R-N043R-R045T-S242R | +++ |
| N018R-G020R-S024R-N043R-R045T-N076D-A230E | +++ |
| G020R-N043R-N076D-A230E-H249R | +++ |
| N018R-R045T-S242R | +++ |
| G020R-S242R-H249R | +++ |
| N018R-N043R-N076D-A230E-S242R-H249R | ++ |
| N018R-S024R-N076D | ++ |
| G020R-S024R-K27R-N043R-S242R-H249R | +++ |
| N018R-G020R-S024R-N043R-N076D-S242R | ++ |
| N018R-N043R-N076D-S242R-H249R | +++ |
| N018R-S024R-N043D-A230E-H249R | +++ |
| N018R-G020R-N043D-H249R | ++ |
| N018R-G020R-N043D-R045T-N076D-S242R | +++ |

TABLE 9-1-continued

BMI cleaning performance of WCE2 library variants of GG36.

| Sequence of GG36 variants (BPN' numbering) | PI Relative to GG36; BMI assay, Detergent 36h or 36i, 16° C. |
|---|---|
| S024R-N043R-N076D-A230E-S242R | +++ |
| G020R-S024R-T38I-N043R-R045T-N076D-S242R-H249R | +++ |
| N018R-G020R-N043R | +++ |
| N018R-S024R-R045T-A230E-S242R | ++ |
| N018R-G020R-H249R | +++ |
| S024R-N043R-N076D | +++ |
| N018R-G020R-S024R-N043R-R045T-N076D-H249R | ++ |
| N018R-N043D-R045T-N076D-S242R-H249R | +++ |
| S024R-N043D-S242R-H249R | +++ |
| N018R-G020R-S024R-N043D-R045T-S242R | ++ |
| G020R-S024R-N043R-N076D | ++ |
| N018R-G020R-N043D-R045T-A230E-S242R | ++ |
| G020R-S024R-N043R-R045T-N076D-S242R-H249R | ++ |
| N018R-N043R-R045T-N076D-S242R | ++ |
| N018R-G020R-N043R-N076D-A230E-S242R | ++ |
| N018R-S024R-N043D-H249R | ++ |
| N018R-S024R-N043R-R045T-A230E-H249R | ++ |
| N018R-G020R-N043R-R045T-N076D-H249R | +++ |
| N018R-S024R-S242R | ++ |
| N018R-N043R-R045T-N076D-A230E-S242R | ++ |
| R045T-S242R-H249R | +++ |
| N018R-S024R-N043R-S242R | +++ |
| N018R-G020R-N043D-R045T-S240P | ++ |
| S024R-N043R-R045T-S242R-H249R | ++ |
| N018R-S024R-V30S-L31S-D32I-T33Q-G34V-I35F | ++ |
| N018R-G020R-N043R-N076D | +++ |
| G020R-N043D-R045T-N076D-S242R-H249R | ++ |
| N018R-S024R-N043D-A230E-S242R | ++ |
| N018R-S024R-N043D-S242R-H249R | +++ |
| S024R-N043R-R045T-S242R-H249R | ++ |
| N043R-A230E-H249R | + |
| N043R-A230E-H249R | + |
| G020R-S024R-N043D-N076D-H249R | ++ |
| S024R-R045T-S242R-A273V | + |
| G020R-S024R-R045T-N076D-S242R-H249R | + |
| N018R-S024R-N043R-N076D-S242R | + |
| N018R-N043R-N076D-A230E-H249R | + |
| N018R-G020R-N043R-R045T-H249R | + |
| N018R-N043R-R045T-A230E-S242R | + |
| G020R-S024R-N043R-R045T-A230E-S242R | + |
| N018R-N043D-A230E-H249R | + |
| N018R-N043R-N076D-S242R | +++ |
| N018R-G020R-N076D | + |
| N018R-G020R-N043D-N076D-S242R-H249R | + |
| G020R-S024R-N043D-N076D-S242R-H249R | +++ |
| N043D-S242R-H249R | +++ |
| N018R-G020R-S024R-N043R-N076D | + |
| N018R-G020R-N043D-R045T-N076D-H249R | + |
| N018R-G020R-N043R-R045T-N076D-A230E-H249R | + |
| N018R-N076D-S242R | + |
| G020R-N043R-H249R | + |
| N018R-N076D-S242R-H249R | + |
| N018R-S024R-R045T-A230E-H249R | + |
| A230E-H249R | +++ |
| N018R-R045T-H249R | + |
| G020R-N043R-N076D | +++ |
| N043R-R045T-H249R | +++ |
| N018R-N043D-N076D-S242R-H249R | + |
| N043R-N076D-H249R | +++ |
| N018R-R045T | + |
| G020R-N076D-A230E-S242R | + |
| G020R-S024R-N043R-R045T | +++ |
| S024R-N043R-N076D-S242R-H249R | +++ |
| G020R-R045T-H249R | + |
| N043R-N076D-S153A-H249R | + |
| N043R-N076D-A230E-H249R | +++ |
| N018R-N043D-N076D-H249R | + |
| G020R-N043R-N076D-V227I | + |

PI = Performance Index Relative to GG36

PI > or = 1.5 is +++; PI between 1.49 and 1.3 = ++; PI between 1.29 and 1.0 = + in detergent 36h or 36i

Example 10

Construction and Cleaning Performance of the WCE3 Set of GG36 Variants

This Example describes the WCE3 set of mutants based on the GG36 variants, GG36-7 (Example 5) and GG36-9 (Example 4). These variants are: S101G-S103A-V104I-A232V-Q245R-N248D, S101G-S103A-V104I-G159D-A232V-Q245R, S101G-S103A-V104I-G159R-A232V-Q245R-N248D, S101G-S103A-V104I-G159D-A232V-Q245R-N248R, S101G-S103A-V104I-A232V-Q245R, S101G-S103A-V104I-A232V-Q245R-N248R, S101G-S103A-V104I-G159R-A232V-Q245R-N248R, and S101G, S103A, V104I, A232V, Q236H, Q245R, and N252K. They were created using the QuikChange® Lightning Multi Site-Directed Mutagenesis Kit (QCLMS kit; Stratagene) with the pRA96 plasmid as the DNA template described in Example 5. The variants generated were tested for cold water cleaning in the BMI microswatch assay (Example 1) using detergents described in Table 1-2.

TABLE 10-1

BMI cleaning performance of WCE3 variants.

| Sequence of GG36 variants (BPN' numbering) | PI Relative to GG36; BMI assay, Detergent 36h or 36i, 16° C. |
|---|---|
| S101G-S103A-V104I-A232V-Q236H-Q245R-N252K | ++ |
| S101G-S103A-V104I-A232V-Q245R-N248R | ++ |
| S101G-S103A-V104I-G159R-A232V-Q245R-N248D | ++ |
| S101G-S103A-V104I-G159D-A232V-Q245R-N248R | + |
| S101G-S103A-V104I-A232V-Q245R | + |
| S101G-S103A-V104I-G159D-A232V-Q245R | + |
| S101G-S103A-V104I-A232V-Q245R-N248D | + |

PI = Performance Index Relative to GG36

PI > or = 1.5 is +++; PI between 1.49 and 1.3 = ++; PI between 1.29 and 1.0 = + in detergent 36h or 36i

Example 11

Construction of Additional Libraries and Variants of GG36

This Example describes the construction of GG36 variants and libraries using one or more of the following mutations: A16S, T22A, S24R, N62E, N76D, E89P, S101A/G, S103G/A, V104L/I, L111V, S128N, P129E, A232V, L148I, A158E, G159D/E, S166D, R186H, S188D, Y209E, Q236H, N238R, Q245R, N248D/R, H249R, N252K/R, T253R, E271F (BPN' numbering) using a *B. subtilis* expression plasmid (e.g., pHPLT-GG36; FIG. 2). The combinatorial variants were constructed by DNA2.0, Inc., using a *B.* subtilis expression plasmid (e.g., pHPLT-GG36; FIG. 2) and the *B. subtilis* strain (genotype: ΔaprE, ΔnprE, amyE::xylRPxylAcomK-phleo). In the case of DNA libraries, a ligation reaction of each of the constructed libraries using a *B. subtilis* expression plasmid (e.g., pHPLT-GG36; FIG. 2) was transformed in the *B. subtilis* strain (genotype: ΔaprE, ΔnprE, amyE::xylRPxylAcomK-phleo). The variants generated containing one or more of the mutations listed above were tested for cold water cleaning in the BMI microswatch assay (Example 1) using detergent compositions described in Table 1-2.

TABLE 11-1

BMI cleaning performance of NHJ6 library variants.

| Sequence of GG36 Variants (BPN' numbering) | PI Relative to GG36; BMI assay; Detergent 36b, 36d or 36e, 16° C. |
|---|---|
| S101G-S103A-V104I-P129E-S188D-A232V-N238R-Q245R-N248D | +++ |
| S024R-S101G-S103A-V104I-P129E-A158E-S188D-A232V-Q245R-N248D-H249R | +++ |
| T022A-S101G-S103A-V104I-P129E-S188D-A232V-Q245R-N248D-H249R | +++ |
| T022A-S024R-S101G-S103A-V104I-P129E-A158E-S188D-A232V-Q245R-N248D-H249R | +++ |
| S024R-S101G-S103A-V104I-P129E-S188D-A232V-Q245R-N248D-H249R | +++ |
| S024R-S101G-S103A-V104I-P129E-G159E-S188D-A232V-Q245R-N248D-H249R | +++ |
| S024R-S101G-S103A-V104I-S128N-P129E-A158E-A232V-Q245R-N248D-H249R | +++ |
| S024R-S101G-S103A-V104I-L148I-A158E-S188D-A232V-Q245R-N248D | +++ |
| T022A-S024R-S101G-S103A-V104I-P129E-G159E-S188D-A232V-Q245R-N248D-H249R | +++ |
| S024R-S101G-S103A-V104I-S128N-P129E-A232V-Q245R-N248D | +++ |
| S101G-S103A-V104I-P129E-S188D-A232V-Q245R-N248D-H249R | +++ |
| S024R-S101G-S103A-V104I-P129E-A158E-A232V-Q245R-N248D-H249R | +++ |
| T022A-S024R-S101G-S103A-V104I-A158E-G159E-S188D-A232V-Q245R-N248D-H249R | +++ |
| T022A-S024R-S101G-S103A-V104I-P129E-A158E-G159E-S188D-A232V-N238R-Q245R-N248D | +++ |
| S024R-S101G-S103A-V104I-P129E-L148I-A158E-A232V-Q245R-N248D | +++ |
| A016S-S024R-S101G-S103A-V104I-A158E-S188D-A232V-Q245R-N248D-H249R | +++ |
| S101G-S103A-V104I-A158E-G159E-A232V-Q245R-N248D-H249R | +++ |
| T022A-S101G-S103A-V104I-P129E-A158E-G159E-A232V-N238R-Q245R-N248D | +++ |
| T022A-S024R-S101G-S103A-V104I-P129E-A158E-G159E-A232V-Q245R-N248D-H249R | +++ |
| T022A-S024R-S101G-S103A-V104I-S128N-A158E-S188D-A232V-Q245R-N248D | +++ |
| S024R-S101G-S103A-V104I-P129E-S188D-A232V-Q245R-N248D | +++ |
| T022A-S024R-S101G-S103A-V104I-P129E-A158E-A232V-Q245R-N248D | +++ |
| T022A-S024R-S101G-S103A-V104I-P129E-A232V-Q245R-N248D | +++ |
| T022A-S024R-S101G-S103A-V104I-P129E-S188D-A232V-Q245R-N248D | +++ |
| S024R-S101G-S103A-V104I-A158E-S188D-A232V-N238R-Q245R-N248D | +++ |
| T022A-S101G-S103A-V104I-S128N-P129E-S188D-A232V-N238R-Q245R-N248D | +++ |
| S024R-S101G-S103A-V104I-P129E-S188D-A232V-N238R-Q245R-N248D | +++ |
| S024R-S101G-S103A-V104I-A158E-G159E-S188D-A232V-Q245R-N248D | +++ |

TABLE 11-1-continued

BMI cleaning performance of NHJ6 library variants.

| Sequence of GG36 Variants (BPN' numbering) | PI Relative to GG36; BMI assay; Detergent 36b, 36d or 36e, 16° C. |
|---|---|
| T022A-S024R-S101G-S103A-V104I-S128N-S188D-A232V-Q245R-N248D | +++ |
| S024R-S101G-S103A-V104I-P129E-A158E-S188D-A232V-Q245R-N248D | +++ |
| T022A-S024R-S101G-S103A-V104I-S128N-P129E-A158E-A232V-Q245R-N248D | +++ |
| S024R-S101G-S103A-V104I-G159E-S188D-A232V-Q245R-N248D | +++ |
| T022A-S101G-S103A-V104I-S128N-P129E-A232V-N238R-Q245R-N248D | +++ |
| S024R-S101G-S103A-V104I-P129E-G159E-A232V-Q245R-N248D | +++ |
| T022A-S024R-S101G-S103A-V104I-P129E-A158E-S188D-A232V-N238R-Q245R-N248D | +++ |
| T022A-S024R-S101G-S103A-V104I-A158E-G159E-S188D-A232V-Q245R-N248D | +++ |
| S024R-S101G-S103A-V104I-G159E-S188D-A232V-Q245R-N248D-H249R | +++ |
| T022A-S101G-S103A-V104I-P129E-A158E-A232V-N238R-Q245R-N248D | +++ |
| T022A-S024R-S101G-S103A-V104I-P129E-A158E-A232V-Q245R-N248D-H249R | +++ |
| S024R-S101G-S103A-V104I-L148I-A158E-A232V-Q245R-N248D | +++ |
| T022A-S101G-S103A-V104I-A158E-G159E-S188D-A232V-Q245R-N248D-H249R | +++ |
| T022A-S101G-S103A-V104I-A158E-S188D-A232V-Q245R-N248D | +++ |
| T022A-S101G-S103A-V104I-P129E-S188D-A232V-N238R-Q245R-N248D | +++ |
| S024R-S101G-S103A-V104I-P129E-A158E-G159E-S188D-A232V-Q245R-N248D-H249R | +++ |
| T022A-S024R-S101G-S103A-V104I-A158E-G159E-S188D-A232V-N238R-Q245R-N248D | +++ |
| S101G-S103A-V104I-P129E-A158E-S188D-A232V-Q245R-N248D-H249R | +++ |
| S024R-S101G-S103A-V104I-S128N-A158E-A232V-Q245R-N248D | +++ |
| T022A-S024R-S101G-S103A-V104I-S128N-P129E-S188D-A232V-Q245R-N248D | +++ |
| T022A-S101G-S103A-V104I-P129E-G159E-A232V-N238R-Q245R-N248D | +++ |
| S101G-S103A-V104I-P129E-G159E-A232V-Q245R-N248D-H249R | +++ |
| T022A-S101G-S103A-V104I-P129E-A158E-A232V-Q245R-N248D-H249R | ++ |
| S024R-S101G-S103A-V104I-P129E-L148I-A158E-S188D-A232V-Q245R-N248D | ++ |
| T022A-S101G-S103A-V104I-P129E-G159E-A232V-Q245R-N248D-H249R | ++ |
| S024R-S101G-S103A-V104I-G159E-S188D-A232V-N238R-Q245R-N248D | ++ |
| S024R-S101G-S103A-V104I-P129E-A158E-G159E-A232V-Q245R-N248D-H249R | ++ |
| S024R-S101G-S103A-V104I-P129E-A158E-G159E-A232V-N238R-Q245R-N248D | ++ |
| S024R-S101G-S103A-V104I-S128N-G159E-S188D-A232V-Q245R-N248D | ++ |
| T022A-S101G-S103A-V104I-G159E-S188D-A232V-Q245R-N248D-H249R | ++ |
| S024R-S101G-S103A-V104I-P129E-G159E-S188D-A232V-N238R-Q245R-N248D | ++ |
| S101G-S103A-V104I-A158E-A232V-N238R-Q245R-N248D | ++ |
| T022A-S101G-S103A-V104I-P129E-G159E-S188D-A232V-Q245R-N248D-H249R | ++ |
| S024R-S101G-S103A-V104I-P129E-L148I-S188D-A232V-Q245R-N248D | ++ |
| S024R-S101G-S103A-V104I-A158E-A232V-Q245R-N248D-H249R | ++ |

TABLE 11-1-continued

BMI cleaning performance of NHJ6 library variants.

| Sequence of GG36 Variants (BPN' numbering) | PI Relative to GG36; BMI assay; Detergent 36b, 36d or 36e, 16° C. |
|---|---|
| T022A-S101G-S103A-V104I-A158E-G159E-A232V-N238R-Q245R-N248D | ++ |
| S024R-S101G-S103A-V104I-A158E-G159E-A232V-N238R-Q245R-N248D | ++ |
| T022A-S101G-S103A-V104I-P129E-A158E-G159E-A232V-Q245R-N248D-H249R | ++ |
| S101G-S103A-V104I-P129E-A158E-S188D-A232V-N238R-Q245R-N248D | ++ |
| T022A-S024R-S101G-S103A-V104I-P129E-A158E-G159E-A232V-Q245R-N248D | ++ |
| S101G-S103A-V104I-S188D-A232V-N238R-Q245R-N248D | ++ |
| T022A-S024R-S101G-S103A-V104I-A158E-A232V-Q245R-N248D-H249R | ++ |
| T022A-S024R-S101G-S103A-V104I-L148I-A158E-A232V-Q245R-N248D | ++ |
| S101G-S103A-V104I-P129E-A158E-G159E-A232V-N238R-Q245R-N248D | ++ |
| T022A-S101G-S103A-V104I-G159E-S188D-A232V-N238R-Q245R-N248D | ++ |
| T022A-S024R-S101G-S103A-V104I-P129E-A158E-G159E-S188D-A232V-Q245R-N248D-H249R | ++ |
| T022A-S101G-S103A-V104I-P129E-A232V-N238R-Q245R-N248D | ++ |
| T022A-S024R-S101G-S103A-V104I-S188D-A232V-Q245R-N248D-H249R | ++ |
| S101G-S103A-V104I-P129E-A158E-G159E-A232V-Q245R-N248D-H249R | ++ |
| T022A-S101G-S103A-V104I-A158E-G159E-A232V-Q245R-N248D-H249R | ++ |
| S101G-S103A-V104I-P129E-S188D-A232V-Q245R-N248D | ++ |
| S024R-S101G-S103A-V104I-P129E-G159E-A232V-N238R-Q245R-N248D | ++ |
| S101G-S103A-V104I-S128N-P129E-A232V-Q245R-N248D | ++ |
| S101G-S103A-V104I-A158E-S188D-A232V-Q245R-N248D | ++ |
| T022A-S024R-S101G-S103A-V104I-P129E-A232V-Q245R-N248D-H249R | ++ |
| S101G-S103A-V104I-P129E-G159E-A232V-N238R-Q245R-N248D | ++ |
| S101G-S103A-V104I-A158E-G159E-S188D-A232V-N238R-Q245R-N248D | ++ |
| S024R-S101G-S103A-V104I-A232V-Q245R-N248D-H249R | ++ |
| T022A-S024R-S101G-S103A-V104I-P129E-L148I-A232V-Q245R-N248D | ++ |
| T022A-S024R-S101G-S103A-V104I-A158E-A232V-N238R-Q245R-N248D | ++ |
| S101G-S103A-V104I-S128N-P129E-A232V-N238R-Q245R-N248D | ++ |
| T022A-S101G-S103A-V104I-S128N-G159E-A232V-Q245R-N248D | + |
| T022A-S101G-S103A-V104I-S128N-P129E-A158E-A232V-N238R-Q245R-N248D | + |
| S101G-S103A-V104I-S128N-P129E-S188D-A232V-Q245R-N248D-H249R | + |
| T022A-S024R-S101G-S103A-V104I-S128N-P129E-A158E-S188D-A232V-Q245R-N248D-H249R | + |
| S024R-S101G-S103A-V104I-S128N-A158E-G159E-S188D-A232V-Q245R-N248D | + |
| T022A-S024K-S101G-S103A-V104I-S128N-A158E-G159E-A232V-Q245R-N248D | + |
| S101G-S103A-V104I-P129E-L148I-S188D-A232V-Q245R-N248D | + |
| S024R-S101G-S103A-V104I-L148I-A232V-Q245R-N248D | + |
| T022A-S101G-S103A-V104I-L148I-S188D-A232V-Q245R-N248D | + |
| S024R-S101G-S103A-V104I-S128N-P129E-S188D-A232V-Q245R-N248D | + |
| S101G-S103A-V104I-S128N-P129E-A158E-A232V-N238R-Q245R-N248D | + |
| T022A-S024R-S101G-S103A-V104I-P129E-L148I-A158E-S188D-A232V-Q245R-N248D | + |
| T022A-S024R-S101G-S103A-V104I-L148I-A158E-S188D-A232V-Q245R-N248D | + |
| S101G-S103A-V104I-L148I-G159E-A232V-Q245R-N248D | + |
| T022A-S024R-S101G-S103A-V104I-A158E-S188D-A232V-Q245R-N248D | + |
| S101G-S103A-V104I-S128N-P129E-A158E-A232V-Q245R-N248D-H249R | + |

PI = Performance Index
PI > or = 1.5 is +++; PI between 1.49 and 1.3 = ++; PI between 1.29 and 1.0 = + in detergent 36b, 36d or 36e

TABLE 11-2

BMI cleaning performance of NHJ6 library variants.

| Sequence of GG36 Variants (BPN' numbering) | PI Relative to GG36; BMI assay, Detergent 36g, 16° C. |
|---|---|
| T022A-S024R-S101G-S103A-V104I-A158E-A232V-Q245R-N248D-H249R | +++ |
| T022A-S024R-S101G-S103A-V104I-P129E-A232V-Q245R-N248D-H249R | +++ |
| S024R-S101G-S103A-V104I-A158E-G159E-A232V-N238R-Q245R-N248D | +++ |
| S024R-S101G-S103A-V104I-A232V-Q245R-N248D-H249R | +++ |
| S101G-S103A-V104I-A158E-A232V-Q245R-N248D-H249R | +++ |
| S101G-S103A-V104I-S188D-A232V-Q245R-N248D-H249R | +++ |
| S024R-S101G-S103A-V104I-G159E-S188D-A232V-Q245R-N248D-H249R | +++ |
| T022A-S024R-S101G-S103A-V104I-A158E-A232V-N238R-Q245R-N248D | +++ |
| S024R-S101G-S103A-V104I-G159E-S188D-A232V-N238R-Q245R-N248D | +++ |
| T022A-S024R-S101G-S103A-V104I-P129E-A232V-Q245R-N248D | +++ |
| S024R-S101G-S103A-V104I-L148I-A232V-Q245R-N248D | +++ |
| S024R-S101G-S103A-V104I-P129E-A158E-A232V-Q245R-N248D-H249R | ++ |
| S024R-S101G-S103A-V104I-L148I-A158E-A232V-Q245R-N248D | ++ |
| T022A-S024R-S101G-S103A-V104I-P129E-A158E-A232V-Q245R-N248D-H249R | ++ |
| A016S-S024R-S101G-S103A-V104I-A158E-S188D-A232V-Q245R-N248D-H249R | ++ |
| S024R-S101G-S103A-V104I-P129E-G159E-A232V-N238R-Q245R-N248D | ++ |
| S024R-S101G-S103A-V104I-P129E-S188D-A232V-Q245R-N248D-H249R | ++ |
| T022A-S101G-S103A-V104I-P129E-A232V-N238R-Q245R-N248D | ++ |
| T022A-S024R-S101G-S103A-V104I-L148I-A158E-A232V-Q245R-N248D | + |
| S024R-S101G-S103A-V104I-P129E-S188D-A232V-N238R-Q245R-N248D | + |

TABLE 11-2-continued

BMI cleaning performance of NHJ6 library variants.

| Sequence of GG36 Variants (BPN' numbering) | PI Relative to GG36; BMI assay, Detergent 36g, 16° C. |
|---|---|
| T022A-S024R-S101G-S103A-V104I-A158E-G159E-S188D-A232V-N238R-Q245R-N248D | + |
| T022A-S101G-S103A-V104I-A158E-G159E-A232V-N238R-Q245R-N248D | + |
| T022A-S024R-S101G-S103A-V104I-P129E-A158E-A232V-Q245R-N248D | + |
| S101G-S103A-V104I-A158E-S188D-A232V-Q245R-N248D-H249R | + |
| T022A-S101G-S103A-V104I-A158E-G159E-A232V-Q245R-N248D-H249R | + |
| S024R-S101G-S103A-V104I-A158E-G159E-A232V-Q245R-N248D | + |

PI = Performance Index
PI > or = 1.5 is +++; PI between 1.49 and 1.3 = ++; PI between 1.29 and 1.0 = +

TABLE 11-3

BMI cleaning performance of NHJ7 combinatorial variants.

| Sequence of GG36 Variants (BPN' numbering) | PI Relative to GG36; BMI assay, Detergent 36b, 36d or 36e, 16° C. |
|---|---|
| V104L-S128N-A158E-R186H-H249R | +++ |
| S128N-A158E-S188D-H249R | +++ |
| N062E-S128N-A158E-G159E-E271F | +++ |
| N062E-A158E-S188D-H249R-E271F | +++ |
| N062E-A158E-R186H-H249R-E271F | +++ |
| S128N-A158E-S188D-Y209E-E271F | +++ |
| N062E-G159E-S188D-H249R | +++ |
| A016S-N062E-A158E-R186H-H249R | +++ |
| N062E-A158E-G159E-H249R | +++ |
| S101A-S128N-A158E-Y209E-H249R | +++ |
| S128N-A158E-R186H-E271F | +++ |
| N062E-A158E-S188D-H249R | +++ |
| N062E-A158E-R186H-E271F | +++ |
| N062E-A158E-R186H-H249R | +++ |
| N062E-S101A-R186H-H249R | +++ |
| N062E-S101A-A158E-R186H-E271F | +++ |
| N062E-V104L-A158E-S188D-H249R-E271F | +++ |
| N062E-G159E-R186H-H249R | +++ |
| N062E-G159E-H249R | +++ |
| S128N-A158E-R186H-H249R | +++ |
| S128N-A158E-S188D-E271F | +++ |
| N062E-A158E-H249R | +++ |
| N062E-R186H-S188D-H249R-E271F | +++ |
| S128N-A158E-Y209E- | +++ |
| N062E-S101A-A158E-H249R | +++ |
| V104L-S128N-A158E-R186H-E271F | +++ |
| N062E-S101A-A158E-R186H-H249R-E271F | +++ |
| A016S-N062E-A158E-H249R | +++ |
| N062E-S101A-G159E-H249R | +++ |
| S128N-A158E-R186H-S188D-E271F | +++ |
| S101A-S128N-A158E-R186H-E271F | +++ |
| N062E-S101A-S188D-H249R | +++ |
| S101A-V104L-A158E-R186H-S188D-H249R | +++ |
| N062E-G159E-H249R-E271F | +++ |
| S128N-A158E-G159E-E271F | +++ |
| A016S-N062E-V104L-A158E-R186H-E271F | +++ |
| T022A-S128N-A158E-H249R | +++ |
| S128N-A158E-H249R | +++ |
| N062E-S101A-V104L-A158E-R186H-E271F | +++ |
| A016S-N062E-A158E-R186H-E271F | +++ |
| V104L-S128N-A158E-H249R | +++ |
| V104L-S128N-A158E-S188D-H249R | +++ |
| T022A-N062E-A158E | +++ |
| N062E-S101A-S188D-H249R-E271F | +++ |
| N062E-A158E-H249R-E271F | ++ |
| V104L-S128N-A158E-R186H-S188D-E271F | ++ |
| N062E-S101A-R186H-E271F | ++ |
| N062E-V104L-G159E-H249R | ++ |
| N062E-R186H-H249R | ++ |
| N062E-S101A-R186H-H249R-E271F | ++ |
| S101A-A158E-R186H-S188D-H249R | ++ |
| N062E-S101A-R186H | ++ |
| S101A-S128N-P129E-R186H-H249R | ++ |
| S101A-S103G-A158E-R186H-H249R | ++ |
| A016S-N062E-V104L-R186H-S188D-E271F | ++ |
| V104L-A158E-R186H-H249R | ++ |
| S101A-S128N-A158E-S188D-Y209E-E271F | ++ |
| N062E-S101A-R186H-S188D-E271F | ++ |
| A016S-N062E-A158E-H249R-E271F | ++ |
| N062E-S128N-A158E | ++ |
| N062E-S128N-G159E-H249R | ++ |
| N062E-S101A-A158E-S188D-H249R | ++ |
| S101A-S128N-A158E-H249R | ++ |
| N062E-A158E-R186H-S188D-H249R | ++ |
| A016S-V104L-A158E-R186H-E271F | ++ |
| N062E-L148I-G159E | ++ |
| N062E-S101A-A158E-R186H-H249R | ++ |
| N062E-S101A-R186H-S188D-H249R | ++ |
| V104L-A158E-R186H-S188D-H249R | ++ |
| N062E-S101A-V104L-R186H-S188D-E271F | ++ |
| T022A-S101A-A158E-R186H-H249R | ++ |
| S101A-S128N-A158E-Y209E | ++ |
| A158E-R186H-S188D-H249R-E271F | ++ |
| V104L-A158E-R186H-S188D-H249R-E271F | ++ |
| S101A-V104L-A158E-R186H-H249R | ++ |
| V104L-A158E-H249R | ++ |
| S101A-V104L-S128N-A158E-R186H-E271F | ++ |
| A016S-V104L-S188D-H249R | ++ |
| S101A-V104L-A158E-R186H-S188D-E271F | ++ |
| V104L-S128N-G159E-E271F | ++ |
| V104L-A158E-R186H-H249R-E271F | ++ |
| A158E-R186H-H249R | ++ |
| S101A-A158E-R186H-H249R | ++ |
| V104L-A158E-S188D-H249R-E271F | ++ |
| A016S-S128N-A158E-R186H | ++ |
| V104L-S128N-R186H-S188D-H249R | ++ |
| A016S-S101A-S128N-R186H | ++ |
| A016S-N062E-S128N-R186H-E271F | ++ |
| A016S-S128N-R186H-E271F | + |
| S128N-P129E-R186H | + |
| A158E-R186H-H249R-E271F | + |
| A016S-A158E-H249R | + |
| A016S-A158E-R186H-H249R | + |
| A016S-T022A-A158E-R186H-E271F | + |
| E089P-S101A-P129E-R186H | + |
| T022A-S128N-A158E-R186H | + |
| S101A-V104L-S128N-A158E-R186H | + |
| T022A-S128N-R186H-S188D- | + |
| N062E-V104L-A158E-R186H-S188D-H249R | + |
| T022A-A158E-R186H-H249R-E271F | + |
| T022A-V104L-A158E-H249R | + |
| S101A-L111V-P129E | + |
| A016S-A158E-H249R-E271F | + |
| A016S-L111V-S188D- | + |
| T022A-V104L-R186H-S188D-H249R | + |
| V104L-L148I-S188D-H249R | + |

PI = Performance Index
PI > or = 1.5 is +++; PI between 1.49 and 1.3 = ++; PI between 1.29 and 1.0 = + in detergent 36b, 36d, 36e

Example 12

Construction of Additional Libraries and Variants of GG36

This Example describes the construction of GG36 variants and libraries in *B. subtilis* using one or more of the following mutations (BPN' numbering): A1R, Q2S, Q2M, Q2A, Q2R, Q2W, S3R, V4R, V4S, V4C, I8A, S9A, S9F, S9W, R10S, R10A, R10H, R10M, Q12F, Q12R, P14K, P14F, P14Q, A15R, A15F, A16S, H17R, H17M, H17F, N18R, N18K, G20F, G20K, G20R, T22A, T22R, T22Y, T22V, T22Q, T22L, T22W, G23A, G23S, G23F, S24R, S24F, S24W, S24Q, S24H, S24L, G25V, G25F, G25R, V26F, K27L, K27F, K27R, K27V, V28A, V28N, V28E, A29T, V30E, L31F, T33S, T33G, T33D, G34P, I35M, S36T, S36F, S36R, T38L, T38F, T38R, P40N, P40L, P40T, P40W, P40H, P40R, L42I, N43A, N43F, N43I, N43S, N43R, N43M, N43W, N43D, R45T, G46R, A48R, F50C, V51W, V51F, V51H, P52F, P52E, P52N, P55Y, T57R, Q59A, Q59F, Q59R, D60P, D60Q, D60A, N62E, N62Q, G63V, G63M, G63T, G63I, G63A, G63S, G63H, G63Q, G63D, G63E, G63P, H64F, V68A, V68C, A69N, A69T, A69P, A69W, T71G, I72C, A74C, L75A, L75F, L75E, L75R, N76D, S78R, S78N, S78I, I79W, I79Q, V81R, L82F, L82T, L82V, L82R, L82M, A85M, P86W, P86L, P86I, E89P, E89T, E89G, E89H, E89L, E89V, E89W, E89F, E89I, Y91N, Y91F, A92F, K94N, S99F, S99T, S99P, S99G, S99M, G100S, G100N, G100Q, G100I, S101A, S101N, S101G, S101T, S101D, S101E, S101P, S101F, G102A, G102T, G102N, G102H, G102E, S103G, S103N, S103D, S103A, V104L, V104I, V104E, V104D, S105T, S105E, S105Q, S106G, S106T, S106E, S106D, S106A, S106V, S106F, I107M, I107F, A108I, A108G, Q109M, L111V, L111I, E112V, E112L, E112Q, A114G, G115K, G115R, N116K, N116A, N116L, N117F, G118R, G118I, M119C, H120A, H120F, H120R, V121F, V121E, N123G, N123E, L124S, S128D, S128F, S128L, S128N, S128H, S128M, S128I, S128Q, P129E, S132A, S132E, A138G, S144R, V147L, L148I, A158E, G159D, G159E, G159C, S160D, S166D, S166E, Y167W, M175V, V177C, D181A, Q182R, N183I, N183D, N183M, N183F, N183R, N185E, N185V, N185I, R186H, R186K, S188E, S188D, S188R, Y192H, Y192W, A194E, A194V, A194F, D197F, I198L, I198F, V203E, V203C, T208S, Y209S, Y209N, Y209F, Y209T, Y209E, Y209H, Y209G, Y209L, P210R, P210V, P210L, G211Q, G211R, S212I, S212M, S212F, T213A, Y214F, A215N, A215D, A215E, A215H, A215F, S216F, S216A, L217E, L217N, L217D, N218D, N218P, N218E, T224A, T224G, V227I, A230E, A231I, A231C, A232V, L233C, V234F, K235F, Q236F, Q236N, Q236H, N238R, N238K, N238L, P239K, P239G, P239R, P239H, P239T, P239N, P239S, P239F, S240R, W241R, S242L, S242R, N243F, N243R, V244R, Q245R, I246S, N248D, N248V, N248I, N248R, H249R, H249T, L250I, K251R, K251S, N252I, N252F, N252R, N252K, N252H, T253I, T253R, T253F, A254C, S256N, G258R, T260V, T260I, L262D, L262H, Y263F, S265F, L267V, L267N, L267M, N269I, N269R, A270C, E271I, E271V, E271H, E271M, E271L, E271P, E271A, E271F, E271T, A272F, A272R, A273F, A273I, and T274G. The variants and libraries were constructed by DNA2.0, Inc., as described in Example 11. The variants generated containing one or more of these mutations were tested for cold water cleaning in the BMI microswatch assay (Example 1) and detergent compositions described in Table 1-2.

TABLE 12-1

BMI cleaning performance of WCE6 and WCE8 variants.

| Sequence of GG36 Variants (BPN' numbering) | PI Relative to GG36; BMI assay, Detergent 36k or 36l, 16° C. |
|---|---|
| A001R-S101G-S103A-V104I-A232V-Q245R | +++ |
| V004R-S101G-S103A-V104I-A232V-Q245R | +++ |
| N043R-S101G-S103A-V104I-A232V-Q245R-E271L | +++ |
| S078R-S101G-S103A-V104I-A232V-Q245R | +++ |
| V004R-N043R-S101G-S103A-V104I-A232V-Q245R | +++ |
| N018R-N043R-S101G-S103A-V104I-A232V-Q245R | +++ |
| G020R-S101G-S103A-V104I-A232V-Q245R | +++ |
| S101G-S103A-V104I-A232V-Q245R-E271L | +++ |
| G020R-N043R-S101G-S103A-V104I-A232V-Q245R | +++ |
| S024R-N043R-S101G-S103A-V104I-A232V-Q245R | +++ |
| G020R-G025R-N116A-Y167W | +++ |
| N018R-S101G-S103A-V104I-A232V-Q245R | +++ |
| T022R-S101G-S103A-V104I-A232V-Q245R | +++ |
| S078R-S103N-S106G-Y167W-Q236N | +++ |
| N018R-N043D-S101G-S103A-V104I-A232V-Q245R-N269R | +++ |
| N043R-S101G-S103A-V104I-A232V-Q245R-N269R | +++ |
| S024R-S101A-H120F-A194F-H249R | +++ |
| G020R-N043D-S101G-S103A-V104I-A232V-Q245R-N269R | +++ |
| S101G-S103A-V104I-S212F-A232V-Q245R | +++ |
| G020R-S144R-N185I-L233C-Q236N | +++ |
| G023A-S078R-S216F-Q236N-H249R | +++ |
| S101G-S103A-V104I-A232V-Q245R-N269R | +++ |
| S101G-S103A-V104I-G115R-A232V-Q245R | +++ |
| P052N-S078R-S103N-L148I-T213A | +++ |
| N018R-N043D-S101G-S103A-V104I-A232V-Q245R-H249R | +++ |
| S024R-N043D-S101G-S103A-V104I-A232V-Q245R-H249R | +++ |
| S024R-N043D-S101G-S103A-V104I-A232V-Q245R-N269R | +++ |
| G025R-E089I-N116A-P239S-A270C | +++ |
| S024R-S101G-S103A-V104I-A232V-Q245R | +++ |
| L148I-T213A-N252R | +++ |
| S024R-G025R-N183D-Y192W-P239S | +++ |
| G046R-A194F-S212M | +++ |
| V104L-L217E-T224A-H249R-N252R | +++ |
| G023A-Y091F-V121F-Y192W-Q236N | +++ |
| S101G-S103A-V104I-A232V-V244R-Q245R | +++ |
| S099F-S144R-Y167W-N252R | +++ |
| S101G-S103A-V104I-A232V-Q245R-H249R | +++ |
| N043R-S101G-S103A-V104I-A232V-Q245R | +++ |
| T022W-S078R-Y167W-S212M-A270C | +++ |
| V121F-N252R-A270C | +++ |
| G020R-S103N-S216F-Q236N-N252R | +++ |
| N043R-S101G-S103A-V104I-A232V-Q245R-H249R | +++ |
| G023A-P052N-Y192W-I198L-N252R | +++ |
| G025R-G046R-V121F | +++ |
| S024R-S078R-V104L-N116A-N183D | +++ |
| G046R-Q059A-S103N-G211Q-S212M | +++ |
| G020R-P052N-N062Q-Y091F-Y192W | +++ |
| G023A-P052N-S144R-Y192W-S216F | +++ |
| S101G-S103A-V104I-A232V-S242R-Q245R | +++ |
| P052N-S103N-N116A-L148I-Y192W | +++ |
| E089I-N116A-N117F-T224A-H249R | +++ |
| S144R-G211Q-N238L-P239S-H249R | +++ |
| N043A-N062Q-A194F-G211Q | +++ |
| G020R-S024R-P052N-Q059A-S216F | +++ |
| S024R-Y167W-T224A-H249R | +++ |
| T057R-Y167W-H249R | +++ |
| G025R-S103N-R186K-A194F-T224A | +++ |
| S105T-S128N-S144R-L148I-S212M | +++ |
| G020R-Q059A-S144R-Y192W-T224A | +++ |
| S024R-N043A-N117F-A194F-G211Q | +++ |
| N117F-A194F-T213A-A270C | +++ |
| S078R-Y091F-V121F-L233C-N252R | +++ |
| T057R-S099F-S105T-I198L-T213A | +++ |
| G023A-Y091F-S101A-I198L-N252R | +++ |
| N062Q-S103N-V121F-S144R-H249R | +++ |
| N043R-S101G-S103A-V104I-A232V-S242R-Q245R | +++ |
| G023A-S024R-N117F-S212M-S216F | +++ |

TABLE 12-1-continued

BMI cleaning performance of WCE6 and WCE8 variants.

| Sequence of GG36 Variants (BPN' numbering) | PI Relative to GG36; BMI assay, Detergent 36k or 36l, 16° C. |
|---|---|
| V104L-T213A-S216F | +++ |
| A194F-G211Q-Q236N | +++ |
| N062Q-S103N-N117F-A194F | +++ |
| S024R-N062Q-V104L-S106G-H249R | +++ |
| T057R-E089I-I198L | +++ |
| G046R-Q059A-S106G-L217E-H249R | +++ |
| N117F-T213A-A215F | +++ |
| S101A-H120F-Y192W-A215F-T224A | +++ |
| N043A-T057R-N117F-S144R-N183D | +++ |
| G046R-N183D-N238L | +++ |
| G025R-N043A-E089I-N117F | +++ |
| S078R-V104L-T213A-A215F-T224A | +++ |
| Y091F-S099F-S101A-S105T-Y167W | +++ |
| S106G-N117F-N238L | +++ |
| G046R-E089I-Y091F-S101A-N116A | +++ |
| G020R-N062Q-E089I-R186K-S212M | +++ |
| T057R-S099F-V121F-N185I-Y192W | +++ |
| G046R-E089I-Y192W-L233C-A270C | +++ |
| E089I-N117F-N185I-A215F-L233C | ++ |
| P052N-V104L-N183D-S216F-H249R | ++ |
| S078R-S099F-N116A-R186K-T224A | ++ |
| G025R-S105T-S128N-S144R-A270C | ++ |
| S105T-G211Q-S216F | ++ |
| S024R-G046R-Y091F-V121F | ++ |
| S106G-N185I-S216F-Q236N | ++ |
| N062Q-S101A-Q236N-N252R-A270C | ++ |
| G025R-N043A-Y091F-I198L-A270C | ++ |
| G020R-G023A-V104L-Y192W-L233C | ++ |
| S024R-N043A-S105T-S106G-I198L | ++ |
| G020R-E089I-L217E | ++ |
| S024R-Y091F-I198L-A215F-P239S | ++ |
| G046R-E089I-S099F-R186K-S212M | ++ |
| V104L-H120F-R186K-S216F-N252R | ++ |
| T022W-A194F-T213A-L233C-N238L | + |
| S099F-S105T-S106G-A194F-S212M | + |
| E089I-S105T-N116A-A215F-S216F | + |
| G025R-N116A-H120F-T224A-A270C | + |
| N043A-Q059A-S101A-S216F-T224A | + |
| T057R-N183D-Q236N | + |
| G025R-N062Q-S128N-S144R-N185I | + |
| S103N-H120F-Y167W-I198L-L233C | + |
| T022W-E089I-S216F | + |
| S024R-S106G-N116A-S212M-T224A | + |
| G020R-P052N-S101A-I198L-L233C | + |
| E089I-Y091F-N185I-G211Q-A270C | + |
| L111I-A215F-P239S | + |
| S024R-N116A-R186K-L233C-Q236N | + |
| G023A-S103N-S106G-S212M-A215F | + |

PI = Performance Index

PI > or = 1.5 is +++; PI between 1.49 and 1.3 = ++; PI between 1.29 and 1.0 = + in detergent 36k or 36l

TABLE 12-2

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| G020R-T022W-S078R-S101A-S103A-V104I-N116S-T213A-A215F-A232V-Q245R | +++ |
| N018R-S078R-S101G-S103A-V104I-A232V-Q245R | +++ |
| S024R-R045T-S101G-S103A-V104I-A232V-Q245R-N269R | +++ |
| G020R-T022W-S078R-S101G-S103A-V104I-N116A-A232V-Q245R | +++ |
| G020R-T22W-S101G-S103A-V104I-A232V-Q245R | +++ |
| N018R-N043R-S101G-S103A-V104I-A232V-Q245R | +++ |
| N018R-T022W-S024R-N076D-S101A-N116A-A232V-Q245R | +++ |
| N018R-V104I-A232V-H249R | +++ |
| N018R-S024R-N076D-S101A-N116A-G211Q-H249R | +++ |
| N018R-N043D-S078R-S101G-S103A-V104I-L217E-A232V-Q245R | +++ |
| N018R-N043R-S101G-S103A-V104I-A232V-Q245R-N269R | +++ |
| N018R-R045T-N076D-S101G-S103A-V104I-A232V-Q245R-N269R | +++ |
| N076D-S078R-S101G-S103A-V104I-A232V-Q245R-N269R | +++ |
| G020R-N043D-S078R-S101G-S103A-V104I-A232V-Q245R | +++ |
| N018R-N043D-N076D-S101G-S103A-V104I-A232V-Q245R-N269R | +++ |
| S024R-R045T-N076D-S078R-S101G-S103A-V104I-A232V-Q245R-N269R | +++ |
| N018R-S103A-A232V-H249R | +++ |
| N018R-S101G-V104I-A232V-Q245R | +++ |
| G020R-S024R-S101G-S103A-V104I-L217E-A232V-Q245R-H249R | +++ |
| N018R-T22K-N043D-S101G-S103A-V104I-A232V-Q245R | +++ |
| N043R-R045T-S101G-S103A-V104I-A232V-Q245R-N269R | +++ |
| G020R-T22W-S101G-S103A-V104I-G211Q-A232V-Q245R | +++ |
| S024R-N076D-S078R-S101G-S103A-V104I-A232V-Q245R-N269R | +++ |
| G020R-T22W-S078R-S101A-S103A-V104I-N116A-N183D-A232V | +++ |
| N018R-S024R-N076D-N116A-A215F-H249R | +++ |
| N018R-N043R-R045T-S101G-S103A-V104I-A232V-Q245R | +++ |
| S024R-N043R-N076D-S101G-S103A-V104I-A232V-Q245R | +++ |
| G020R-T022W-S101G-S103A-V104I-A232V-Q245R | +++ |
| G020R-T022W-S101G-S103A-V104I-G211Q-A232V-Q245R | +++ |
| G020R-T022W-S078R-S101G-S103A-V104I-N116A-T213A-A215F-A232V-Q245R | +++ |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| N043D-N076D-S078R-S101G-S103A-V104I-A232V-Q245R-N269R | +++ |
| N018R-S024R-N076D-S101A-N116A-T213A-H249R | +++ |
| N018R-S024R-N076D-N116A-G211Q-H249R | +++ |
| N043R-R045T-N076D-S078R-S101G-S103A-V104I-A232V-Q245R | +++ |
| N018R-S101G-Q245R | +++ |
| G020R-T22W-S101A-S103A-V104I-G211Q-T213A-A232V-Q245R | +++ |
| G020R-S024R-N043D-N076D-S078R-S101G-S103A-V104I-A232V-Q245R | +++ |
| N018R-R045T-N076D-S078R-S101G-S103A-V104I-A232V-Q245R | +++ |
| G020R-S078R-S101G-S103A-V104I-G211Q-T213A-A215F-A232V-Q245R | +++ |
| R045T-S078R-S101G-S103A-V104I-A232V-Q245R-N269R | +++ |
| S024R-N043D-S101G-S103A-V104I-A232V-Q245R-N269R | +++ |
| N018R-S101G-S103A-H249R | +++ |
| N018R-T22W-S024R-N076D-S101A-N116A-A232V-Q245R | +++ |
| N018R-S101G-V104I-A232V-H249R | +++ |
| G020R-T22W-S101A-S103A-V104I-A215F-A232V-Q245R | +++ |
| N018R-S024R-N076D-G211Q-T213A-H249R | +++ |
| N018R-T022W-S024R-N076D-S101A-I198L-H249R | +++ |
| S024R-S101G-S103A-V104I-A232V-Q245R | +++ |
| G020R-N076D-S101G-S103A-V104I-A232V-Q245R-N269R | +++ |
| G020R-S101G-S103A-V104I-A232V-Q245R-N269R | +++ |
| N043D-S078R-S101G-S103A-V104I-A232V-Q245R | +++ |
| G020R-S101G-V104I-T213A-A215F-A232V-Q245R | +++ |
| G020R-S101G-S103A-V104I-N116A-A215F-A232V-Q245R | +++ |
| S024R-S103A-V104I-H249R | +++ |
| N018R-N076D-S078R-S101G-S103A-V104I-A232V-Q245R | +++ |
| R045T-N076D-S078R-S101G-S103A-V104I-A232V-Q245R-N269R | +++ |
| S024R-S101G-V104I-Q245R | +++ |
| G020R-S101G-S103A-V104I-G211Q-T213A-A215F-A232V-Q245R | +++ |
| S024R-S103A-V104I-A232V-H249R | +++ |
| N018R-S024R-N076D-N116A-G211Q-A215F-H249R | +++ |
| N018R-Q245R | +++ |
| S024R-S103A-Q245R | +++ |
| S024R-S103A-V104I-Q245R | +++ |
| G020R-S078R-S101G-A232V-Q245R | +++ |
| N018R-S024R-N076D-V104I-H249R | +++ |
| N018R-S024R-V104I-H249R | +++ |
| S024R-S101G-S103A-V104I-A232V-Q245R | +++ |
| N018R-S024R-N076D-G211Q-A215F-H249R | +++ |
| R019H-G020R-T022W-S078R-S101G-S103A-V104I-G211Q-A232V-Q245R | +++ |
| N018R-S024R-N076D-S101A-I198L-G211Q-T213A-H249R | +++ |
| N018R-S024R-N043D-S101G-S103A-V104I-A232V-Q245R | +++ |
| G020R-T22W-S103A-V104I-A232V-Q245R | +++ |
| N018R-S103A-V104I-H249R | +++ |
| N018R-T022W-S024R-N076D-S101A-I198L-A215F-H249R | +++ |
| N018R-S024R-S101G-V104I-A232V | +++ |
| S078R-S101G-S103A-V104I-A232V-Q245R-N269R | +++ |
| S024R-N043R-N076D-S078R-S101G-S103A-V104I-A232V-Q245R | +++ |
| N018R-G020R-N043D-N076D-S101G-S103A-V104I-A232V-Q245R | +++ |
| N018R-T22W-S024R-N076D-N116A-T213A-H249R | +++ |
| N018R-S024R-S101G-V104I | +++ |
| G020R-S101A-S103A-V104I-A215F-A232V-Q245R | +++ |
| N018R-R045T-S078R-S101G-S103A-V104I-A232V-Q245R | +++ |
| N018R-S101G-S103A-Q245R | +++ |
| N043R-N076D-S078R-S101G-S103A-V104I-A232V-Q245R | +++ |
| G020R-T022W-S101A-S103A-V104I-G211Q-A215F-A232V-Q245R | +++ |
| G020R-T22W-S078R-S101G-S103A-V104I-N116A-T213A-A215F-A232V-Q245R | +++ |
| G020R-S078R-S101G-S103A-V104I-A215F-A232V-Q245R | +++ |
| G020R-T022W-S078R-S101G-S103A-V104I-N116A-N183D-A232V-Q245R | +++ |
| N076D-S101G-S103A-V104I-A232V-Q245R | +++ |
| N076D-S101G-S103A-V104I-A232V-Q245R-N269R | +++ |
| G020R-T22W-S101A-S103A-V104I-A232V-Q245R | +++ |
| G020R-S101G-S103A-A232V-Q245R | +++ |
| G020R-T022W-S078R-S101A-S103A-V104I-N116A-N183D-A232V-Q245R | +++ |
| N018R-G020R-S024R-R045T-N076D-S101G-S103A-V104I-A232V-Q245R-N269R | +++ |
| N043R-R045T-S078R-S101G-S103A-V104I-A232V-Q245R | +++ |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| N018R-S101G-V104I-H249R | +++ |
| G020R-T22W-S078R-S101G-S103A-V104I-N116A-N183D-A232V-Q245R | +++ |
| G020R-T022W-S101G-S103A-V104I-I198L-G211Q-T213A-A232V-Q245R | +++ |
| G020R-S078R-S101A-S103A-V104I-N116A-N183D-T213A-A232V-Q245R | +++ |
| S024R-N076D-V104I-A232V-Q245R | +++ |
| N018R-G020R-N076D-S101G-S103A-V104I-A232V-Q245R | +++ |
| N018R-S024R-N076D-S101G-V104I-A232V-H249R | +++ |
| N018R-N043D-S078R-S101G-S103A-V104I-A232V-Q245R | +++ |
| A001T-N018R-S024R-N076D-N116A-T213A-H249R | +++ |
| N076D-S078R-S101G-S103A-V104I-A232V-Q245R | +++ |
| G020R-S078R-S101G-S103A-V104I-N116A-A232V-Q245R | +++ |
| N043R-N076D-S101G-S103A-V104I-A232V-Q245R | +++ |
| N018R-R045T-S101G-S103A-V104I-A232V-Q245R | +++ |
| N018R-N076D-S101G-V104I-A232V-Q245R | +++ |
| G020R-S078R-S101G-S103A-V104I-N116A-N183D-A232V-Q245R | +++ |
| N018R-S024R-N076D-S101A-G211Q-T213A-A215F-H249R | +++ |
| R045T-S078R-S101G-S103A-V104I-A232V-Q245R | +++ |
| N043R-N076D-S101G-S103A-V104I-A232V-Q245R-N269R | +++ |
| G020R-T022W-S078R-S101G-S103A-V104I-N116A-N183D-T213A-A232V-Q245R | +++ |
| G020R-T022W-S101G-S103A-V104I-N116A-N183D-T213A-A232V-Q245R | +++ |
| G020R-S101G-I198L-A215F-A232V-Q245R | +++ |
| N018R-S024R-N076D-T213A-A215F-H249R | +++ |
| G020R-S078R-S101G-S103A-V104I-N116A-G211Q-A232V-Q245R | +++ |
| G020R-T022W-S078R-S101A-S103A-V104I-N116A-N183D-A215F-A232V-Q245R | +++ |
| G020R-T022W-S078R-S101A-S103A-V104I-N116A-N183D-T213A-A232V-Q245R | +++ |
| S024R-A232V-Q245R | +++ |
| N018R-S024R-N043D-S101G-S103A-V104I-A232V-Q245R-N269R | +++ |
| N018R-S024R-N076D-S101A-A215F-H249R | +++ |
| N018R-T022W-S024R-N076D-N116A-T213A-H249R | +++ |
| S101G-S103A-V104I-A232V-Q245R | +++ |
| N018R-S024R-N076D-G211Q-T213A-A215F-H249R | +++ |
| N018R-S024R-N076D-N116A-T213A-A215F-H249R | +++ |
| N043D-N076D-S078R-S101G-S103A-V104I-A232V-Q245R-N269R | +++ |
| N043D-S078R-S101G-S103A-V104I-A232V-Q245R-H249R | +++ |
| G020R-T022W-S078R-S101G-S103A-V104I-N116A-N183D-G211Q-A232V-Q245R | +++ |
| N018R-S024R-N076D-S101A-I198L-G211Q-A215V-H249R | +++ |
| N018R-T022W-S024R-N076D-N116A-G211Q-H249R | +++ |
| G020R-S103A-V104I-A232V-Q245R | ++ |
| G020R-T22W-S101A-S103A-V104I-G211Q-A215F-A232V-Q245R | ++ |
| S024R-N076D-S101G-S103A-V104I-A232V-Q245R | ++ |
| G020R-S101G-S103A-V104I-N116A-A232V-Q245R | ++ |
| N018R-T22W-S024R-N076D-I198L-A215F-H249R | ++ |
| G020R-T022W-S103A-V104I-A232V-Q245R | ++ |
| G020R-T022W-S101A-S103A-V104I-G211Q-T213A-A232V-Q245R | ++ |
| G020R-T022W-S101G-S103A-V104I-G211Q-T213A-A215F-A232V-Q245R | ++ |
| N018R-N043R-R045T-N076D-S101G-S103A-V104I-A232V-Q245R | ++ |
| N018R-T022W-S024R-N076D-S101A-I198L-T213A-A215F-H249R | ++ |
| N018R-T22W-S024R-N076D-S101A-A215F-H249R | ++ |
| G020R-R045T-S101G-S103A-V104I-A232V-Q245R | ++ |
| G020R-S078R-S101G-S103A-V104I-T180A-A232V-Q245R | ++ |
| G020R-T022W-S078R-S101G-S103A-V104I-N116A-N183D-A215F-A232V-Q245R | ++ |
| N018R-S101G-S103A-V104I | ++ |
| G020R-T22W-S101A-S103A-V104I-N116A-G211Q-T213A-A215F-A232V-Q245R | ++ |
| N018R-S024R-N076D-S103A-A232V-Q245R | ++ |
| G020R-S078R-S101A-S103A-V104I-N116A-N183D-A232V-Q245R | ++ |
| N018R-S024R-N076D-G211Q-H249R | ++ |
| G020R-S101A-S103A-V104I-T213A-A215F-A232V-Q245R | ++ |
| N018R-G020R-N043D-S101G-S103A-V104I-A232V-Q245R | ++ |
| G020R-T022W-S101A-S103A-V104I-G211Q-A232V-Q245R | ++ |
| G020R-T022W-S101A-S103A-V104I-N116A-G211Q-A215F-A232V-Q245R | ++ |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| G020R-T022W-S101A-S103A-V104I-N116A-G211Q-A232V-Q245R | ++ |
| N018R-S024R-N076D-A232V-H249R | ++ |
| N018R-S024R-R045T-N076D-S101G-S103A-V104I-A232V-Q245R-N269R | ++ |
| N018R-N076D-Q245R | ++ |
| S024R-V104I-Q245R | ++ |
| S101G-A232V | ++ |
| G020R-T22W-S101A-S103A-V104I-N116A-G211Q-A215F-A232V-Q245R | ++ |
| N018R-G020R-T022W-S024R-N076D-N116A-N183D-I198L-T213A-H249R | ++ |
| G020R-T022W-S078R-S101A-S103A-V104I-A232V-Q245R | ++ |
| G020R-T022W-S078R-S101A-S103A-V104I-I198L-A232V-Q245R | ++ |
| S024R-Q245R-H249R | ++ |
| G020R-S101G-S103A-V104I-N116A-G211Q-A232V-Q245R | ++ |
| N018R-T22W-S024R-N076D-N116A-G211Q-H249R | ++ |
| S024R-S101G-V104I-H249R | ++ |
| N018R-S024R-N076D-N116A-I198L-G211Q-T213A-A215F-H249R | ++ |
| N018R-S024R-V104I | ++ |
| G020R-T022W-S078R-S101A-S103A-V104I-N183D-I198L-T213A-A215F-A232V-Q245R | ++ |
| N018R-G020R-T22W-S024R-N076D-N116A-N183D-I198L-T213A-H249R | ++ |
| G020R-T022W-S101A-S103A-V104I-A232V-Q245R | ++ |
| Q012H-G020R-S078R-S101G-S103A-V104I-I198L-G211Q-T213A-A232V-Q245R | ++ |
| N018R-S024R-N076D-S101A-G211Q-A215F-H249R | ++ |
| N018R-S024R-N076D-T213A-H249R | ++ |
| S024R-V104I-H249R | ++ |
| N018R-T022W-S024R-N076D-G211Q-H249R | ++ |
| N018R-N076D-S103A-V104I-H249R | ++ |
| N043R-N076D-S101G-S103A-V104I-L217E-A232V-Q245R | ++ |
| G020R-S078R-S101G-S103A-V104I-N183D-G211Q-T213A-A232V-Q245R-E271G | ++ |
| N018R-T022W-S024R-N076D-S101A-N116A-I198L-A215F-H249R | ++ |
| N018R-S024R-N043D-N076D-S101G-S103A-V104I-A232V-Q245R | ++ |
| N018R-S024R-N076D-S101A-I198L-A215F-H249R | ++ |
| N018R-T022W-S024R-N076D-N116A-I198L-G211Q-T213A-H249R | ++ |
| N018R-S024R-N076D-S101A-N116A-T213A-A215F-H249R | ++ |
| G020R-N043D-R045T-S078R-S101G-S103A-V104I-A232V-Q245R | ++ |
| R045T-S078R-S101G-S103A-V104I-A232V-Q245R-H249R | ++ |
| N018R-T22W-S024R-N076D-S101A-N116A-A215F-H249R | ++ |
| N043D-S101G-S103A-V104I-A232V-Q245R-N269R | ++ |
| G020R-T022W-S078R-S101A-S103A-V104I-N116A-N183D-T213A-A215F-A232V-Q245R | ++ |
| N018R-S024R-N076D-N116A-G211Q-T213A-A215F-H249R | ++ |
| S024R-S103A-M175L-A232V-H249R | ++ |
| N018R-S024R-N076D-N116A-T213A-H249R | ++ |
| G020R-R045T-N076D-S101G-S103A-V104I-A232V-Q245R | ++ |
| G020R-S078R-S101A-S103A-V104I-N116A-N183D-G211Q-T213A-A215F-A232V-Q245R | ++ |
| S024R-N043R-R045T-N076D-S078R-S101G-S103A-V104I-A232V-Q245R | ++ |
| N018R-S024R-N076D-S101A-N116A-I198L-T213A-A215F-H249R | ++ |
| N043R-R045T-S101G-S103A-V104I-A232V-Q245R | ++ |
| N018R-T022W-S024R-N076D-S101A-I198L-G211Q-Q245R | ++ |
| G020R-S024R-N043D-N076D-S078R-S101G-S103A-V104I-A232V-Q245R-N269R | ++ |
| S024R-A232V | ++ |
| G020R-S078R-S101A-S103A-V104I-N116A-N183D-G211Q-A232V-Q245R | ++ |
| S024R-N076D-S101G-A232V-Q245R | ++ |
| N018R-N076D-S101G-S103A-V104I-H249R | ++ |
| N018R-S024R-N076D-I198M-G211Q-T213A-A215F-H249R | ++ |
| N018R-T22W-S024R-N076D-S101A-I198L-A215F-H249R | ++ |
| N018R-N043R-N076D-S101G-S103A-V104I-A232V-Q245R-N269R | ++ |
| G020R-T022W-S103A-G211Q-T213A-A215F-A232V-Q245R | ++ |
| G020R-S078R-S101A-S103A-V104I-N116A-N183D-G211Q-T213A-A232V-Q245R | ++ |
| R045T-N076D-S101G-S103A-V104I-A232V-Q245R-N269R | ++ |
| N018R-T22W-S024R-N076D-S101A-G211Q-T213A-H249R | ++ |
| N018R-S024R-N076D-N116A-I198L-A215F-H249R-V268G | ++ |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| N018R-T022W-S024R-N076D-S101A-G211Q-H249R | ++ |
| N018R-T022W-S024R-N076D-S101A-N116A-I198L-G211Q-H249R | ++ |
| S101G-S103A-V104I-Q245R | ++ |
| N018R-N076D-S101G-A232V-Q245R | ++ |
| N018R-G020R-R045T-S101G-S103A-V104I-A232V-Q245R | ++ |
| N018R-T022W-S024R-N076D-S101A-N116A-I198L-H249R | ++ |
| N018R-T022W-S024R-N076D-N116A-I198L-T213A-H249R | ++ |
| S078R-S101G-S103A-V104I-A232V-Q245R-H249R | ++ |
| N018R-S078R-S101G-S103A-V104I-L217E-A232V-Q245R | ++ |
| G020R-N043R-N076D-S101G-S103A-V104I-A232V-Q245R-N269R | ++ |
| N018R-N043D-N076D-S101G-S103A-V104I-A232V-Q245R-H249R | ++ |
| R045T-S101G-S103A-V104I-A232V-Q245R-N269R | ++ |
| S024R-S103A-A232V | ++ |
| N018R-S024R-N076D-S101A-G211Q-H249R | ++ |
| N043D-S101G-S103A-V104I-A232V-Q245R-H249R | ++ |
| N018R-N043R-R045T-N076D-S076T-S101G-S103A-V104I-A232V-Q245R-A273T | ++ |
| N018R-G020R-N043D-S078R-S101G-S103A-V104I-A232V-Q245R | ++ |
| G020R-S078R-S101A-S103A-V104I-N183D-A215F-A232V-Q245R | ++ |
| N018R-S024R-N076D-S101G-A232V | ++ |
| A232V-Q245R | ++ |
| N043R-R045T-N076D-S078R-S101G-S103A-V104I-A232V-V234I-Q245R | ++ |
| S024R-N076D-S103A-V104I-Q245R | ++ |
| G020R-S078R-S101A-S103A-V104I-G211Q-T213A-A232V-Q245R | ++ |
| N043D-S078R-S101G-S103A-V104I-A232V-Q245R-N269R-A272V | ++ |
| N018R-G020R-S024R-N076D-N116A-N183D-I198L-G211Q-H249R | ++ |
| N018R-S103A-V104I-A232V | ++ |
| G020R-T022W-S101G-S103A-V104I-N116A-N183D-T213A-A215F-A232V-Q245R | ++ |
| S024R-N043R-N076D-S101G-S103A-V104I-A232V-Q245R-N269R | ++ |
| N018R-T022W-S024R-N076D-T213A-A215F-H249R | ++ |
| N018R-S024R-N076D-S101A-N116A-I198L-G211Q-T213A-H249R | ++ |
| G020R-T22W-S078R-S101A-S103A-V104I-N116A-N183D-T213A-A232V-Q245R | ++ |
| G020R-T022W-S078R-S101G-S103A-V104I-G211Q-T213A-A232V-Q245R | ++ |
| G020R-T022W-S101A-S103A-V104I-A215F-A232V-Q245R | ++ |
| N018R-G020R-S024R-N076D-N116A-N183D-A215F-H249R | ++ |
| N018R-S024R-N076D-N116A-M117I-N183D-T213A-H249R | ++ |
| N018R-T022W-S024R-N076D-S101A-N116A-I198L-T213A-H249R | ++ |
| N018R-T22W-S024R-N076D-S101A-I198L-T213A-A215F-H249R | ++ |
| N018R-N043D-S078R-S101G-S103A-V104I-A232V-Q245R-H249R | ++ |
| N018R-N076D-S101G-S103A-V104I-A232V-Q245R-H249R | ++ |
| G020R-T022W-S101G-S103A-V104I-N116A-N183D-I198L-A232V-Q245R | ++ |
| N018R-N043R-R045T-N076D-S101G-S103A-V104I-A232V-Q245R-N269R | ++ |
| N018R-S024R-N076D-N116A-I198L-Y209H-T213A-H249R | ++ |
| G020R-T022W-S101A-S103A-V104I-N116A-N183D-G211Q-T213A-A232V-Q245R | ++ |
| S024R-N076D-S101G-M175L-A232V-Q245R | ++ |
| N018R-N043D-R045T-S101G-S103A-V104I-A232V-Q245R | ++ |
| R045T-N076D-S078R-S101G-S103A-V104I-A232V-Q245R | ++ |
| G020R-S078R-S101A-S103A-V104I-N116A-N183D-I198L-A215F-A232V-Q245R | ++ |
| N043R-N076D-S101G-S103A-V104I-A232V-Q245R-H249R | ++ |
| N018R-S024R-N076D-I198L-T213A-A215F-H249R | ++ |
| N018R-T022W-S024R-N076D-I198L-A215F-H249R | ++ |
| N018R-T022W-S024R-N076D-N116A-T213A-A215F-H249R | ++ |
| N018R-T022W-S024R-N076D-S101A-N116A-I198L-T213A-A215F-H249R | ++ |
| N018R-T022W-S024R-N076D-N116A-G211Q-T213A-H249R | ++ |
| N018R-S024R-Q245R | ++ |
| N018R-T022W-S024R-N076D-S101A-N116A-A215F-H249R | ++ |
| S024R-N076D-V104I-Q245R | ++ |
| K027R-N043R-S101G-S103A-V104I-A232V-Q245R-N269R | ++ |
| N018R-S024R-N076D-N116A-I198L-G211Q-T213A-H249R | ++ |
| N018R-S024R-N076D-N116A-I198L-H249R | ++ |
| N018R-S024R-N076D-N183D-I198L-G211Q-T213A-A215F-H249R | ++ |
| G020R-T022W-S101A-S103A-V104I-N116A-G211Q-T213A-A215F-A232V-Q245R | ++ |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| N018R-N043D-R045T-S078R-S101G-S103A-V104I-A232V-Q245R | ++ |
| N043D-R045T-N076D-S078R-S101G-S103A-V104I-A232V-Q245R-N269R | ++ |
| N018R-T22W-S024R-N076D-N116A-T213A-A215F-H249R | ++ |
| N018R-T022W-S024R-N076D-N116A-G211Q-A215F-H249R | ++ |
| G020R-S078R-S101G-S103A-V104I-N116A-N183D-T213A-A232V-Q245R | ++ |
| N018R-N076D-S101G-S103A-V104I-A232V-Q245R | ++ |
| N018R-S101G-V104I | ++ |
| G020R-S078R-S101G-S103A-V104I-N116A-N183D-G211Q-T213A-A215F-A232V-Q245R | ++ |
| G020R-S078R-S101A-S103A-V104I-A232V-Q245R | ++ |
| N018R-S024R-N076D-S101A-I198L-G211Q-H249R | ++ |
| N018R-S024R-N076D-I198L-G211Q-T213A-H249R | ++ |
| N018R-T022W-S024R-N076D-S101A-N116A-I198L-G211Q-T213A-H249R | ++ |
| N018R-N076D-H249R | ++ |
| N018R-G020R-S024R-N076D-S101A-N116A-N183D-I198L-H249R | ++ |
| N018R-S024R-N076D-S101A-N116A-G211Q-T213A-H249R | ++ |
| G020R-T022W-S078R-S101A-S103A-V104I-N116A-N183D-G211Q-T213A-A215F-A232V-Q245R | ++ |
| G020R-T022W-S101G-S103A-V104I-A114T-T213A-A215F-A232V-Q245R | ++ |
| N018R-T22W-S024R-N076D-N116A-G211Q-T213A-H249R | ++ |
| N018R-G020R-T022W-S024R-N076D-S101A-N116A-N183D-H249R | ++ |
| G020R-S101A-S103A-V104I-N116A-N183D-T213A-A232V-Q245R | ++ |
| N018R-T022W-S024R-N076D-S101A-G211Q-T213A-H249R | ++ |
| N018R-T022K-N043D-S101G-S103A-V104I-A232V-Q245R | ++ |
| N018R-S101G-S103A-V104I-A232V-Q245R-N269R | ++ |
| G020R-S078R-S101G-S103A-V104I-N116A-N183D-G211Q-T213A-A215F-A232V | ++ |
| N018R-S024R-N076D-N116A-H249R | ++ |
| G020R-S024R-N076D-S101G-S103A-V104I-A232V-Q245R | ++ |
| N043D-N076D-S101G-S103A-V104I-A232V-Q245R-N269R | ++ |
| N018R-S024R-N076D-S101A-N116A-I198L-G211Q-H249R | ++ |
| N018R-T022W-S024R-N076D-I198L-T213A-A215F-H249R | ++ |
| N018R-N043D-N076D-S078R-S101G-S103A-V104I-A232V-Q245R-N269R | ++ |
| G020R-T22W-S101G-S103A-V104I-N116A-N183D-T213A-A215F-A232V-Q245R | ++ |
| G020R-S101G-S103A-V104I-N183D-G211Q-A232V-Q245R- | ++ |
| N018R-S024R-N076D-S101A-I198L-T213A-H249R | ++ |
| N018R-S024R-N076D-S101A-I198L-H249R | ++ |
| N018R-S024R-R045T-N076D-S101G-S103A-V104I-A232V-Q245R-H249R | ++ |
| N018R-S024R-N076D-S101A-N183D-T213A-H249R | ++ |
| N018R-N043D-N076D-S078R-S101G-S103A-V104I-A232V-Q245R | ++ |
| G020R-S078R-S101G-S103A-V104I-N116A-A131V-N183D-T213A-A232V-Q245R | ++ |
| N018R-R045T-N076D-S101G-S103A-V104I-A232V-Q245R | ++ |
| N018R-S024R-N076D-S101A-N183D-G211Q-H249R | ++ |
| N076D-S101G-S103A-V104I-A232V-Q245R-H249R | ++ |
| S024R-S101G-Q245R | ++ |
| S024R-N076D-S101G-Q245R | ++ |
| N076D-S078R-S101G-S103A-V104I-A232V-Q245R-H249R | ++ |
| N018R-G020R-S024R-N076D-S101A-N183D-G211Q-A215F-H249R | ++ |
| S024R-S101G | ++ |
| N018R-T22W-S024R-N076D-T213A-A215F-H249R | ++ |
| G020R-N043D-S101G-S103A-V104I-A232V-Q245R | ++ |
| G020R-T022W-S101G-S103A-V104I-N183D-I198L-T213A-A215F-A232V-Q245R | ++ |
| N018R-N043D-R045T-S101G-S103A-V104I-A232V-Q245R-N269R | ++ |
| N043D-N076D-S078R-S101G-S103A-V104I-A232V-Q245R | ++ |
| S024R-R045T-N076D-S101G-S103A-V104I-A232V-Q245R-N269R | ++ |
| G020R-T022W-S101A-S103A-V104I-I198L-G211Q-A215F-A232V-Q245R | ++ |
| G020R-T022W-S101G-S103A-V104I-N116A-N183D-A215F-A232V-Q245R | ++ |
| N018R-G020R-N076D-S101G-S103A-V104I-A232V-Q245R-H249R | ++ |
| N018R-T022W-S024R-N076D-S101A-A215F-H249R | ++ |
| N018R-V104I | ++ |
| N018R-S024R-N076D-N116A-I198L-A215F-H249R | ++ |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| N018R-S024R-N076D-L088I-S101A-N116A-I198L-G211Q-A215F-H249R | ++ |
| N018R-T022W-S024R-N076D-S101A-N116A-G211Q-T213A-H249R | ++ |
| N043R-R045T-N076D-S101G-S103A-V104I-A232V-Q245R-N269R | ++ |
| N018R-N076D-S101G-V104I-H249R | ++ |
| N018R-T022W-S024R-N076D-S101A-T213A-A215F-H249R | ++ |
| N018R-T22W-S024R-N076D-S101A-N116A-I198L-A215F-H249R | ++ |
| N018R-G020R-S101G-S103A-V104I-A232V-Q245R-H249R | ++ |
| S101G-S103A-V104I-A232V-Q245R-H249R-N269R | ++ |
| S024R-N076D-Q245R | ++ |
| N018R-G020R-N043R-R045T-N076D-S101G-S103A-V104I-A232V-Q245R | ++ |
| N018R-G020R-S024R-N076D-A215F-H249R | ++ |
| N018R-S024R-N076D-S101A-N116A-N183D-I198L-T213A-H249R | ++ |
| N018R-G020R-S024R-N076D-G211Q-A215F-H249R | ++ |
| N043D-S101G-S103A-V104I-A232V-Q245R | ++ |
| G020R-T22W-S078R-S101A-S103A-V104I-N116A-N183D-A215F-A232V-Q245R | ++ |
| N018R-S024R-N076D-I198L-G211Q-A215F-H249R | ++ |
| N043R-N076D-S078R-S101G-S103A-V104I-A232V-Q245R-N269R | ++ |
| N043R-S078R-S101G-S103A-V104I-A232V-Q245R-N269R | ++ |
| G020R-N043D-S101G-S103A-V104I-A232V-Q245R-H249R | ++ |
| N018R-T022W-S024R-N076D-S101A-T213A-H249R | ++ |
| G020R-T022W-S101A-N116A-I198L-G211Q-T213A-A215F-H249R | ++ |
| N043R-R045T-S078R-S101G-S103A-V104I-N218S-A232V-Q245R | ++ |
| N018R-S103A | ++ |
| G020R-T22W-S101G-S103A-V104I-N116A-N183D-A215F-A232V-Q245R | ++ |
| N018R-S024R-N076D-S101A-H249R | ++ |
| N018R-T022W-S024R-N076D-G211Q-T213A-H249R | ++ |
| S024R-N043R-R045T-N076D-S101G-S103A-V104I-A232V-Q245R | ++ |
| G020R-T022W-S101A-S103A-V104I-N116A-N183D-A232V-Q245R | ++ |
| G020R-S101A-S103A-V104I-N116A-N183D-G211Q-T213A-A215F-A232V-Q245R | ++ |
| K027R-R045T-N076D-S078R-S101G-S103A-V104I-A232V-Q245R-N269R | ++ |
| G020R-R045T-N076D-S101G-S103A-V104I-A232V-Q245R-H249R | ++ |
| N018R-G020R-S024R-N076D-N116A-N183D-T213A-A215F-H249R | ++ |
| N018R-S024R-N076D-V104I | ++ |
| S101G-S103A-V104I-A232V-H249R | ++ |
| N018R-S024R-N076D-N116A-N183D-G211Q-H249R | ++ |
| N018R-G020R-S024R-N076D-N116A-A215F-H249R | ++ |
| N018R-S024R-N076D-N183D-T213A-A215F-H249R | ++ |
| N018R-T022W-S024R-N076D-I198L-G211Q-H249R | ++ |
| N043D-S078R-S101G-S103A-V104I-A232V-Q245R-N269R-R275S | ++ |
| G020R-T022W-S101A-S103A-V104I-N116A-N183D-G211Q-A232V-Q245R | ++ |
| N018R-T022W-S024R-N076D-S101A-I198L-G211Q-T213A-A215F-H249R | ++ |
| N018R-T022W-S024R-N076D-S101A-N116A-I198L-G211Q-T213A-A215F-H249R | ++ |
| N018R-G020R-S024R-N076D-N183D-H249R | ++ |
| N018R-S024R-N076D-N116A-I198L-T213A-H249R | ++ |
| N018R-T022W-S024R-N076D-S101A-N116A-G211Q-H249R | ++ |
| V004M-N018R-S024R-N076D-N116A-I198L-G211Q-T213A-H249R | ++ |
| V104I-A232V-H249R | ++ |
| G020R-T022W-S101G-S103A-V104I-N116A-N183D-G211Q-A215F-A232V-Q245R | ++ |
| G020R-S101A-S103A-V104I-N116A-N183D-G211Q-A232V-Q245R-T274I | + |
| G020R-S101A-S103A-V104I-T213A-A232V-Q245R | + |
| G020R-S101G-S103A-V104I-N116A-N183D-G211Q-T213A-A232V-Q245R | + |
| G020R-S024R-N043D-S078R-S101G-S103A-V104I-A232V-Q245R | + |
| N018R-S024R-N076D-S103A-H249R | + |
| N018R-G020R-S024R-N076D-S101A-N116A-N183D-G211Q-A215F-H249R | + |
| N018R-G020R-S024R-N076D-N116A-N183D-I198L-H249R | + |
| N018R-T022W-S024R-N076D-N116A-I198L-A215F-H249R | + |
| N018R-S024R-N076D-S101A-G211Q-T213A-A215F-H249R-A270V | + |
| N018R-N043D-R045T-N076D-S078R-S101G-S103A-V104I-A232V-Q245R-N269R | + |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| G020R-T022W-S101G-S103A-V104I-N183D-A232V-Q245R | + |
| N018R-G020R-T022W-S024R-N076D-S101A-N116A-T213A-H249R | + |
| N018R-T022W-S024R-N076D-I198L-G211Q-A215F-H249R | + |
| N018R-T022W-S024R-N076D-I198L-T213A-H249R | + |
| G020R-T022W-S101G-S103A-V104I-N116A-N183D-A232V-Q245R | + |
| N018R-T22W-S024R-N076D-N116A-I198L-T213A-H249R | + |
| N043R-R045T-S078R-S101G-S103A-V104I-A232V-Q245R-N269R | + |
| N018R-S024R-N076D-S101G-S103A-V104I-A232V | + |
| S101G-H249R | + |
| S024R-N076D-S101G-S103A-V104I-M175L-H249R | + |
| G020R-T022W-S101A-S103A-V104I-N116A-N183D-A232V-Q245R-N269S | + |
| N018R-S024R-N076D-S101A-N116A-I198L-H249R | + |
| N018R-T022W-S024R-N076D-N116A-H249R | + |
| N018R-G020R-S024R-N076D-S101A-N183D-I198L-A215F-H249R | + |
| N018R-S024R-N076D-T213A-A215F-H249R-T260K | + |
| N018R-S024R-N076D-N116A-G211Q-T213A-H249R | + |
| N018R-G020R-T022W-S024R-N076D-N116A-I198L-H249R | + |
| S024R-N076D-S101G-S103A-V104I-Q245R | + |
| S024R-N076D-S103A-H249R | + |
| N018R-S101G-S103A-V104I-A232V-Q245R-H249R | + |
| N018R-S024R-N076D-I198L-G211Q-H249R | + |
| N018R-T022W-S024R-N076D-S101A-I198L-G211Q-T213A-H249R | + |
| G020R-S024R-R045T-S101G-S103A-V104I-A232V-Q245R | + |
| N018R-G020R-S024R-N076D-N183D-G211Q-T213A-H249R | + |
| N018R-N043D-R045T-S078R-S101G-S103A-V104I-A232V-Q245R-A272D | + |
| N018R-S024R-N076D-N116A-I198L-T213A-A215F-H249R | + |
| N018R-T22W-S024R-N076D-S101A-I198L-H249R | + |
| N018R-T022W-S024R-N076D-N116A-I198L-H249R | + |
| S024R-N076D-S101G-S103A-A232V | + |
| S024R-S103A-V104I | + |
| N018R-S024R-N076D-S101A-N116A-N183D-G211Q-A215F-H249R | + |
| S024R-R045T-N076D-S101G-S103A-V104I-A232V-Q245R-H249R | + |
| G020R-S101G-S103A-V104I-N116A-N183D-A232V-Q245R | + |
| S024R-N043D-N076D-S101G-S103A-V104I-A232V-Q245R-N269R | + |
| G020R-T022W-S101A-S103A-V104I-N183D-G211Q-T213A-A215F-A232V-Q245R | + |
| G020R-R045T-N076D-S078R-S101G-S103A-V104I-A232V-Q245R-N269R | + |
| N018R-S024R-N076D-S101A-N116A-I198L-G211Q-A215F-H249R | + |
| G020R-S101A-S103A-V104I-N116A-N183D-A215F-A232V-Q245R | + |
| N018R-N043R-S101G-S103A-V104I-A232V-Q245R-H249R | + |
| N018R-S024R-N076D-I198L-T213A-H249R | + |
| N018R-S024R-N076D-N116A-N183D-T213A-H249R | + |
| G020R-N043D-S101G-S103A-V104I-A232V-Q245R-N269R | + |
| S024R-N076D-S103A-Q245R | + |
| N018R-T022W-S024R-N076D-S101A-N116A-G211Q-T213A-A215F-H249R | + |
| S103A-V104I-Q245R | + |
| N018R-T022W-S024R-N076D-G211Q-A215F-H249R | + |
| N018R-T022W-S024R-N076D-N116A-N183D-I198L-H249R | + |
| N018R-T022W-S024R-N076D-I198L-G211Q-T213A-H249R | + |
| N018R-S024R-N076D-N116A-N183D-G211Q-T213A-A215F-H249R | + |
| N018R-G020R-N043D-R045T-N076D-S101G-S103A-V104I-A232V-Q245R-N269R | + |
| N018R-G020R-T022W-S024R-N076D-S101A-G211Q-T213A-A215F-H249R | + |
| A016T-N043R-R045T-N076D-S101G-S103A-V104I-A232V-Q245R-N269R | + |
| N018R-T022W-S024R-N076D-N116A-A215F-H249R | + |
| N043R-N076D-S101G-S103T-V104I-A232V-Q245R-H249R-N269R | + |
| G020R-S078R-S101A-S103A-V104I-G115E-N116A-N183D-G211Q-T213A-A232V-Q245R | + |
| N018R-S024R-N076D-I198L-H249R | + |
| N018R-S024R-N076D-S101A-N116A-N183D-H249R | + |
| G020R-S101G-S103A-V104I-N116A-N183D-G211Q-A232V-Q245R | + |
| N018R-S024R-N076D-S101G | + |
| N076D-S101G-A232V-Q245R | + |
| N018R-N076D-S101G-S103A-V104I-Q245R | + |
| N018R-R045T-S101G-S103A-V104I-A232V-Q245R-H249R | + |
| N018R-S024R-N076D-A215F-H249R | + |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| N018R-V104I-A232V | + |
| N043D-R045T-N076D-S078R-S101G-S103A-V104I-A232V-Q245R | + |
| S024R-N076D-S101G-A232V-H249R | + |
| S103A-A232V-Q245R | + |
| G020R-S101G-S103A-V104I-N116A-N183D-G211Q-T213A-A215F-A232V-Q245R | + |
| N018R-G020R-S024R-N076D-N116A-N183D-I198L-G211Q-A215F-H249R | + |
| N018R-T022W-S024R-N076D-S101A-I198L-G211Q-A215F-H249R | + |
| S024R-N076D-S103A-V104I-H249R | + |
| S024R-S101G-S103A-V104I | + |
| G020R-S101G-S103A-V104I-N116A-N183D-G211Q-A215F-A232V-Q245R | + |
| N018R-T022W-S024R-N076D-S101A-N116A-N183D-A215F-H249R | + |
| G020R-T022W-S101G-S103A-V104I-N116A-N183D-G211Q-T213A-A215F-A232V-Q245R | + |
| G020R-S024R-R045T-N076D-S101G-S103A-V104I-A232V-Q245R | + |
| N018R-T022W-S024R-N076D-N116A-N183D-T213A-H249R | + |
| N018R-G020R-S024R-N076D-A131T-A215F-H249R | + |
| N018R-S024R-N076D-S101A-N116A-N183D-G211Q-T213A-A215F-H249R | + |
| N018R-S024R-N076D-S101A-N116A-G211Q-T213A-A215F-H249R | + |
| N018R-S024R-N076D-I198L-A215F-H249R | + |
| N018R-T022W-S024R-N076D-N183D-G211Q-H249R | + |
| N018R-T022W-S024R-N076D-S101A-N116A-T213A-A215F-H249R | + |
| N018R-G020R-S024R-R045T-N076D-S101G-S103A-V104I-A232V-Q245R | + |
| N043R-S101G-S103A-V104I-Q245R-H249R | + |
| N018R-N076D-A232V-H249R | + |
| N018K-N076D-S078R-S101G-S103A-V104I-L217E-A232V-Q245R-N269R | + |
| N018R-G020R-S024R-N043D-N076D-S078R-S101G-S103A-V104I-A232V-Q245R | + |
| N018R-T022W-S024R-N076D-S101A-N116A-T213A-A215F-H249R-L267I | + |
| A232V-H249R | + |
| N018R-G020R-S024R-N076D-N116A-G211Q-T213A-A215F-H249R | + |
| N076D-V104I-Q245R | + |
| N018R-G020R-S024R-N076D-N183D-I198L-G211Q-A215F-H249R | + |
| N018R-S024R-N076D-S101A-G211Q-T213A-H249R | + |
| S024R-S101G-S103A-A232V | + |
| N018R-G020R-T022W-S024R-N076D-N116A-N183D-I198L-T213A-A215F-H249R | + |
| N018R-G020R-S024R-N076D-N116A-N183D-I198L-G211Q-T213A-H249R | + |
| N018R-G020R-T022W-S024R-N076D-S101A-A215F-H249R | + |
| G020R-T022W-S101A-S103A-V104I-N116A-N183D-G211Q-A215F-A232V-Q245R | + |
| N018R-S024R-N076D-N116A-I198L-G211Q-H249R | + |
| S103A-A232V-H249R | + |
| N018R-G020R-S024R-N076D-N116A-N183D-I198L-A215F-H249R | + |
| N018R-S024R-N076D-N116A-N183D-I198L-T213A-H249R | + |
| N018R-T022W-S024R-N076D-N183D-T213A-H249R | + |
| N018R-S024R-N076D-S101A-T213A-A215F-H249R | + |
| N018R-T022W-S024R-N076D-S101A-N116A-N183D-G211Q-H249R | + |
| N018R-R045T-S101G-S103A-V104I-A232V-Q245R-N269R | + |
| N018R-G020R-R045T-N076D-S078R-S101G-S103A-V104I-A232V-Q245R | + |
| N018R-T022W-S024R-N076D-N116A-I198L-T213A-A215F-H249R | + |
| G020R-T022W-S101G-S103A-V104I-N116A-N183D-G211Q-T213A-A232V-Q245R | + |
| N018R-G020R-S024R-N076D-I198L-H249R | + |
| N018R-G020R-T022W-S024R-N076D-S101A-N116A-G211Q-H249R | + |
| G020R-T022W-S101A-S103A-V104I-N116A-N183D-A232V-Q245R-T274I | + |
| S024R-S103A-Q245R-H249R | + |
| N018R-T022W-S024R-N076D-S101A-N116A-N183D-I198L-H249R | + |
| N018R-S024R-N076D-S101A-I198L-G211Q-A215F-H249R | + |
| N018R-T022W-S024R-N076D-N116A-I198L-G211Q-A215F-H249R | + |
| N018R-G020R-T022W-S024R-N076D-N116A-N183D-T213A-H249R | + |
| N018R-N043D-R045T-N076D-S101G-S103A-V104I-A232V-Q245R-N269R | + |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| N018R-T022W-S024R-N076D-N116A-G211Q-T213A-A215F-H249R | + |
| N018R-S024R-N076D-S101A-N183D-I198L-T213A-H249R | + |
| N043D-N076D-S101G-S103A-V104I-A232V-Q245R-H249R | + |
| N018R-S024R-N076D-I198L-G211Q-T213A-A215F-H249R | + |
| N018R-G020R-S024R-N076D-N116A-N183D-T213A-H249R | + |
| S103A-A232V | + |
| N018R-T022W-S024R-N076D-N116A-N183D-A215F-H249R | + |
| N018R-S024R-N076D-S101A-N116A-H249R | + |
| N018R-N043R-S078R-S101G-S103A-V104I-A232V-Q245R | + |
| N018R-G020R-T022W-S024R-N076D-S101A-N183D-G211Q-A215F-H249R | + |
| N043R-N076D-S078R-S101G-S103A-V104I-A232V-Q245R-H249R | + |
| N018R-G020R-S024R-N076D-S101A-N116A-N183D-I198L-T213A-H249R | + |
| N018R-S024R-N076D-N183D-I198L-T213A-H249R | + |
| N018R-T022W-S024R-N076D-S101A-N183D-G211Q-H249R | + |
| N018R-G020R-S024R-N076D-I198L-T213A-A215F-H249R | + |
| N018R-G020R-T022W-S024R-N076D-N183D-G211Q-T213A-H249R | + |
| N018R-T022W-S024R-N076D-I198L-H249R | + |
| N018R-S024R-N076D-N183D-I198L-G211Q-H249R | + |
| G020R-T022W-S101A-S103A-V104I-N116A-N183D-T213A-A232V-Q245R | + |
| N018R-G020R-S024R-N076D-N116A-N183D-G211Q-T213A-H249R | + |
| N018R-S024R-N076D-N116A-N183D-I198L-G211Q-T213A-A215F-H249R | + |
| G020R-T022W-S101A-S103A-V104I-N116A-N183D-A215F-A232V-Q245R | + |
| N018R-S024R-N076D-S101A-N183D-H249R | + |
| N018R-S024R-N076D-A232V | + |
| N018R-T022W-S024R-N076D-S101A-N116A-H249R | + |
| G020R-S101A-S103A-V104I-N116A-N183D-I198L-G211Q-T213A-A215F-A232V-Q245R | + |
| G020R-T022W-S101G-S103A-V104I-N116A-N183D-G211Q-A232V-Q245R-N263S | + |
| S024R-N076D-S101G-V104I-A232V-H249R | + |
| N043R-S078R-S101G-S103A-V104I-A232V-Q245R | + |
| S024R-N076D-S078R-S101G-S103A-V104I-A232V-Q245R-H249R | + |
| N018R-S024R-N076D-S101A-N183D-I198L-T213A-A215F-H249R | + |
| N018R-G020R-S024R-N076D-I198L-A215F-H249R | + |
| N018R-G020R-S024R-N076D-S101A-N116A-T213A-H249R | + |
| N018R-S024R-N076D-S101A-V197A-T213A-A215F-H249R | + |
| S024R-S101G-S103A | + |
| N018R-S024R-N076D-S101A-N116A-G211Q-A215F-H249R | + |
| N043R-N076D-S078R-S101G-S103A-V104I-L217E-A232V-Q245R | + |
| S024R-V104I-A232V | + |
| N018R-S024R-N076D-N183D-G211Q-H249R | + |
| G020R-N043R-R045T-S078R-S101G-S103A-V104I-A232V-Q245R | + |
| N018R-G020R-T022W-S024R-N076D-S101A-N116A-N183D-T213A-H249R | + |
| N018R-S024R-N076D-N116A-A150T-T213A-H249R | + |
| N018R-S024R-N076D-N183D-T213A-H249R | + |
| N018R-G020R-S024R-N076D-N116A-N183D-G211Q-A215F-H249R | + |
| N018R-G020R-S024R-N076D-G211Q-H249R | + |
| N018R-S024R-N076D-S101A-N116A-N183D-I198L-H249R | + |
| S024R-N076D-A232V-H249R | + |
| N018R-G020R-T022W-S024R-N076D-S101A-N116A-N183D-I198L-G211Q-T213A-H249R | + |
| N018R-T022W-S024R-N076D-S101A-N116T-I198L-A215F-H249R | + |
| N018R-S024R-N076D-N183D-I198L-G211Q-A215F-H249R | + |
| N018R-T022R-S024R-N076D-S101A-N116A-N183D-G211Q-H249R | + |
| R045T-S101G-S103A-V104I-A232V-Q245R | + |
| N018R-G020R-S024R-N076D-S101A-N183D-G211Q-H249R | + |
| G020R-S101G-S103A-V104I-N116A-N183D-T213A-A232V-Q245R | + |
| N076D-S101G-S103A-Q245R | + |
| G020R-N043D-S078R-S101G-S103A-V104I-A232V-Q245R-H249R | + |
| N018R-S024R-N076D-N116A-N183D-H249R | + |
| N018R-S024R-N076D-S101A-N183D-G211Q-T213A-A215F-H249R | + |
| N018R-G020R-T022W-S024R-N076D-S101A-N116A-I198L-H249R | + |
| N018R-T22W-S024R-N076D-G211Q-T213A-H249R | + |
| N018R-G020R-S024R-N076D-N183D-G211Q-H249R | + |
| N018R-G020R-S024R-N076D-S101A-N116A-N183D-T213A-H249R | + |
| N043R-S078R-S101G-S103A-V104I-L217E-A232V-Q245R | + |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| N018R-T022W-S024R-N076D-S101A-A215F-H249R | + |
| N018R-G020R-S024R-N076D-S101A-N183D-I198L-G211Q-T213A-H249R | + |
| N076D-S101G-V104I-H249R | + |
| N018R-T022W-S024R-N076D-S101A-N116A-N183D-T213A-H249R | + |
| N018R-S024R-N076D-N183D-H249R | + |
| N018R-S024R-N076D-S101A-N183D-I198L-A215F-H249R | + |
| N018R-T022W-S024R-N076D-N183D-I198L-A215F-H249R | + |
| N018R-T022W-S024R-N076D-S101A-I198L-G211Q-H249R | + |
| G020R-S101A-S103A-V104I-N116A-N183D-A232V-Q245R | + |
| N018R-S024R-N076D-N116A-N183D-I198L-G211Q-H249R | + |
| N018R-G020R-S024R-S101G-S103A-V104I-A232V-Q245R | + |
| N018R-N076D-S078R-S101G-S103A-V104I-L217E-A232V-Q245R | + |
| G020R-S101A-S103A-V104I-N116A-N183D-G211Q-A232V-Q245R | + |
| N018R-T022W-S024R-N076D-S101A-N183D-I198L-Y209H-H249R | + |
| N018R-S024R-N076D-N183D-I198L-T213A-A215F-H249R | + |
| N018R-S024R-N076D-S101A-N116A-N183D-G211Q-T213A-H249R | + |
| N018R-T022W-S024R-N076D-S101A-N116A-N183D-G211Q-T213A-H249R | + |
| N018R-S024R-N076D-N183D-I198L-H249R | + |
| N018R-S024R-N076D-N183D-A215F-H249R | + |
| N018R-G020R-S024R-N076D-G211Q-T213A-A215F-H249R | + |
| N076D-Q245R | + |
| N076D-S101G-V104I-Q245R | + |
| N018R-T022W-S024R-N076D-S101A-G211Q-A215F-H249R | + |
| N018R-T022W-S024R-N076D-S101A-N116A-N183D-G211Q-A215F-H249R | + |
| N018R-G020R-T022W-S024R-N076D-S101A-G211Q-T213A-H249R | + |
| G020R-S024R-N043R-S101G-S103A-V104I-A232V-Q245R | + |
| N018R-S024R-N076D-N116A-N183D-G211Q-A215F-H249R | + |
| G020R-S101A-S103A-V104I-N116A-N183D-T213A-A215F-A232V-Q245R | + |
| S101G-S103A-V104I | + |
| N018R-G020R-S024R-N076D-S101A-N116A-N183D-G211Q-T213A-H249R | + |
| N018R-G020R-S024R-N076D-N204D-T213A-H249R | + |
| N018R-T022W-S024R-N076D-N183D-I198L-H249R | + |
| N018R-S024R-N076D-S101A-N116A-N183D-A215F-H249R | + |
| N018R-T022W-S024R-N076D-N116A-N183D-I198L-G211Q-T213A-A209V-H249R | + |
| N018R-T022W-S024R-N076D-S101A-N116A-N183D-G211Q-T213A-A215F-H249R | + |
| N018R-S024R-N076D-S101A-N116A-I198L-T213A-H249R | + |
| N018R-G020R-S024R-N076D-S101A-N116A-G211Q-T213A-H249R | + |
| N018R-G020R-T022W-S024R-N076D-S101A-N116A-N183D-G211Q-T213A-A215F-H249R | + |
| N018R-S024R-N076D-S101A-N116A-N183D-T213A-A215F-H249R | + |
| N018R-S024R-N076D-S101A-N183D-I198L-G211Q-T213A-A215F-H249R | + |
| N018R-S024R-N076D-S101A-N183D-I198L-G211Q-T213A-H249R | + |
| N018R-N043R-R045T-S078R-S101G-S103A-V104I-L217E-A232V-Q245R | + |
| N018R-S024R-N076D-N183D-G211Q-T213A-A215F-H249R | + |
| N018R-T022W-S024R-N076D-N116A-N183D-I198L-A215F-H249R | + |
| N018R-G020R-S024R-N076D-N116A-H249R | + |
| N018R-G020R-T022W-S024R-N076D-S101A-G211Q-A215F-H249R | + |
| N018R-G020R-S024R-N076D-N183D-G211Q-T213A-A215F-H249R | + |
| N018R-G020R-T022W-S024R-N076D-I198L-T213A-H249R | + |
| N018R-G020R-S024R-N076D-S101A-G211Q-A215F-H249R-N269D | + |
| N018R-G020R-N043D-S101G-S103A-V104I-A232V-Q245R-N269R | + |
| N018R-T022W-S024R-N076D-S101A-N183D-I198L-T213A-H249R | + |
| G020R-T022W-S101G-S103A-V104I-N183D-A215F-A232V-Q245R | + |
| N018R-T022W-S024R-N076D-N116A-N183D-I198L-Y209H-G211Q-H249R | + |
| N018R-G020R-T022W-S024R-N076D-S101A-N116A-N183D-G211Q-H249R | + |
| N076D-A232V-Q245R | + |
| N043D-R045T-S078R-S101G-S103A-V104I-A232V-Q245R | + |
| N018R-G020R-S024R-N076D-N116A-I198L-G211Q-A215F-Q245R | + |
| N018R-G020R-T022W-S024R-N076D-T213A-H249R | + |
| G020R-S024R-N043D-S078R-S101G-S103A-V104I-A232V-Q245R-H249R | + |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| N018R-G020R-T022W-S024R-N076D-S101A-I198L-A215F-H249R | + |
| G020R-A090S-S101G-S103A-V104I-N116A-N183D-T213A-A215F-A232V-Q245R | + |
| N018R-G020R-T022W-S024R-N076D-S101A-I198L-G211Q-T213A-A215F-H249R | + |
| N018R-G020R-S024R-N076D-S101A-N183D-T213A-A215F-H249R | + |
| N018R-S024R-N076D-N116A-N183D-I198L-G211Q-T213A-H249R | + |
| N043D-R045T-S078R-S101G-S103A-V104I-A232V-Q245R-N269R | + |
| N018R-S024R-N076D-S101A-N183D-A215F-H249R | + |
| N018R-G020R-S024R-N076D-S101A-N183D-I198L-T213A-H249R | + |
| G020R-T022W-S101A-S103A-V104I-N116A-N183D-I198L-G211Q-T213A-A215F-A232V-Q245R | + |
| N018R-G020R-S024R-N043D-N076D-S101G-S103A-V104I-A232V-Q245R-N269R | + |
| N018R-S024R-N076D-S101A-N183D-T213A-A215F-H249R | + |
| N018R-G020R-T022W-S024R-N076D-S101A-N116A-I198L-G211Q-T213A-A215F-H249R | + |
| N018R-G020R-N043D-S101G-S103A-V104I-L217E-A232V-Q245R | + |
| N076D-S103A-V104I-A232V-Q245R | + |
| R045T-N076D-S078R-S101G-S103A-V104I-A232V-Q245R-H249R | + |
| N018R-T022W-S024R-N076D-S101A-N183D-G211Q-A215F-H249R | + |
| N018R-T022W-S024R-N076D-S101A-N116A-N183D-H249R | + |
| N018R-S024R-N076D-N116A-N183D-I198L-G211Q-A215F-H249R | + |
| N018R-G020R-N043D-N076D-S078R-S101G-S103A-V104I-L217E-A232V-Q245R | + |
| N076D-S103A-V104I-Q245R | + |
| N018R-G020R-S024R-N076D-S101A-N116A-G211Q-T213A-A215F-H249R | + |
| N018R-S024R-N076D-S101A-N183D-I198L-H249R | + |
| N018R-T022W-S024R-N076D-N116A-N183D-I198L-G211Q-A215F-H249R | + |
| N018R-S024R-N076D-N116A-N183D-T213A-A215F-H249R | + |
| N018R-T022W-S024R-N076D-N116A-N183D-I198L-G211Q-H249R | + |
| N018R-S024R-N076D-S101G-Q245R | + |
| N018R-S024R-N076D-S101A-N116A-N183D-I198L-T213A-A215F-H249R | + |
| N043R-R045T-N076D-S101G-S103A-V104I-A232V-Q245R | + |
| N018R-G020R-T022W-S024R-N076D-N116A-I198L-T213A-A215F-H249R | + |
| N076D-V104I-A232V-Q245R | + |
| K027R-N043R-R045T-N076D-S101G-S103A-V104I-A232V-Q245R | + |
| N018R-T022W-S024R-N076D-S101A-N183D-T213A-A215F-H249R | + |
| N018R-S024R-N076D-S103A-V104I-L135I-A232V | + |
| N018R-G020R-T022W-S024R-N076D-N183D-I198L-G211Q-H249R | + |
| N018R-G020R-T022W-S024R-N076D-S101A-N116A-N183D-I198L-A215F-H249R | + |
| N018R-S024R-N076D-S101A-N116A-N183D-G211Q-H249R | + |
| N018R-T022W-S024R-N076D-N183D-G211Q-T213A-A215F-H249R | + |
| N076D-S101G-S103A-V104I-A232V-H249R | + |
| P005S-N018R-T022W-S024R-N076D-S101A-T213A-A215F-H249R | + |
| N018R-S024R-N076D-N116A-N183D-A215F-H249R | + |
| N018R-S024R-N076D-N183D-I198L-A215F-H249R | + |
| N018R-G020R-S024R-N076D-S101A-N116A-N183D-H249R | + |
| N018R-T022W-S024R-N076D-N116A-N183D-G211Q-H249R | + |
| N018R-G020R-T022W-S024R-N076D-S101A-N116A-H249R | + |
| N018R-T022W-S024R-N076D-S101A-N116A-N183D-I198L-T213A-H249R | + |
| N018R-T022W-S024R-N076D-S101A-N183D-G211Q-T213A-H249R | + |
| N018R-G020R-S024R-N076D-N116A-I198L-H249R | + |
| N018R-S024R-N076D-N183D-G211Q-T213A-H249R | + |
| N018R-S024R-N076D-S101A-N116A-N183D-T213A-H249R | + |
| N018R-S024R-N076D-N116A-N183D-I198L-A215F-H249R | + |
| N018R-T022W-S024R-N076D-N183D-I198L-G211Q-A215F-H249R | + |
| N018R-T022W-S024R-N076D-N183D-H249R | + |
| N018R-T022W-S024R-N076D-S101A-N183D-I198L-A215F-H249R | + |
| N018R-G020R-N043D-R045T-N076D-S101G-S103A-V104I-A232V-Q245R | + |
| G020R-T022W-S101A-S103A-V104I-N183D-I198L-A215F-A232V-Q245R | + |
| N076D-S101G-S103A-V104I-H249R | + |
| N018R-G020R-S024R-N076D-N183D-I198L-A215F-H249R | + |
| N018R-G020R-T022W-S024R-N076D-S101A-N183D-A215F-H249R | + |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| N018R-G020R-S024R-N076D-G211Q-T213A-H249R | + |
| N018R-S024R-N076D-N116A-N183D-G211Q-T213A-H249R | + |
| N018R-S024R-N076D-N116A-N183D-I198L-H249R | + |
| N018R-G020R-S024R-N076D-G211Q-N243D-H249R | + |
| N018R-G020R-R045T-N076D-S101G-S103A-V104I-A232V-Q245R-H249R | + |
| N018R-T022W-S024R-N076D-N183D-I198L-G211Q-T213A-H249R | + |
| N018R-S024R-N076D-S101A-N116A-N183D-I198L-G211Q-T213A-H249R | + |
| N018R-T022W-S024R-N076D-N116A-I198L-G211Q-T213A-A215F-H249R | + |
| S024R-N076D-S101G | + |
| N018R-G020R-S024R-N076D-S101A-I198L-T213A-A215F-H249R | + |
| N018R-T022W-S024R-N076D-N116A-N183D-G211Q-T213A-H249R | + |
| N018R-G020R-S024R-N076D-N183D-A215F-H249R | + |
| N018R-N043D-N076D-S078R-S101G-S103A-V104I-A232V-Q245R-H249R | + |
| N018R-T022W-S024R-N076D-N116A-N183D-G211Q-T213A-Q245R | + |
| G020R-S024R-N076D-S078R-S101G-S103A-V104I-A232V-Q245R-H249R | + |
| N018R-G020R-R045T-S101G-S103A-V104I-A232V-Q245R-H249R | + |
| N018R-S024R-N076D-S101A-N183D-I198L-G211Q-H249R | + |
| N018R-T022W-S024R-N076D-N183D-G211Q-T213A-H249R | + |
| N018R-G020R-S024R-N076D-N116A-I198L-G211Q-A215F-H249R-N269S | + |
| N018R-G020R-T022W-S024R-N076D-S101A-N116A-N183D-I198L-G211Q-A215F-H249R | + |
| G020R-T022W-S101A-S103A-V104I-N183D-T213A-A215F-A232V-Q245R | + |
| N018R-S024R-N076D-A086V-S101A-N183D-I198L-G211Q-H249R | + |
| N018R-N076D-S101G-I198T-A232V | + |
| N018R-G020R-S024R-N076D-S101A-N116A-N183D-I198L-G211Q-A215F-H249R | + |
| N018R-T022W-S024R-N076D-S101A-N116A-N183D-T213A-A215F-H249R | + |
| N018R-T022W-S024R-N076D-S101A-N183D-G211Q-T213A-A215F-H249R | + |
| N018R-S024R-N076D-N183D-H249R-A248T | + |
| N018R-N076D-V104I-Q245R-H249R | + |
| N018R-T022W-S024R-N076D-S101A-N116A-N183D-I198L-A215F-H249R | + |
| N018R-T022W-S024R-N076D-N116A-N183D-T213A-A215F-H249R | + |
| N018R-G020R-T022W-S024R-N076D-N116A-N183D-G211Q-T213A-A215F-H249R | + |
| N018R-G020R-S024R-N076D-S101A-H249R | + |
| N018R-G020R-S024R-N076D-S101A-N116A-T213A-A215F-H249R | + |
| N018R-T022W-S024R-N076D-N116A-N183D-G211Q-A215F-H249R | + |
| N018R-T022W-S024R-N076D-N116A-N183D-I198L-G211Q-T213A-H249R | + |
| N018R-R045T-S078R-S101G-S103A-V104I-L217E-A232V-Q245R | + |
| N043R-R045T-S101G-S103A-V104I-A232V-Q245R-H249R | + |
| N018R-N076D-S101G-V104I | + |
| G020R-R045T-N076D-S078R-S101G-S103A-V104I-A232V-Q245R-H249R | + |
| N043D-N076D-S101G-S103A-V104I-A232V-Q245R | + |
| N018R-G020R-T022W-S024R-N076D-S101A-N116A-N183D-I198L-H249R | + |
| N018R-N076D-V104I | + |
| N018R-G020R-N043D-S101G-S103A-V104I-A232V-Q245R-H249R | + |
| N018R-G020R-T022W-S024R-N076D-N183D-G211Q-H249R | + |
| N018R-S024R-N076D-S101A-N183D-I198L-G211Q-A215F-H249R | + |
| S101G-V104I | + |
| N018R-T022W-S024R-N076D-N116A-N183D-I198L-G211Q-T213A-A215F-H249R | + |
| N018R-G020R-S024R-N076D-S101A-N183D-G211Q-T213A-A215F-H249R | + |
| N018R-G020R-S024R-N076D-N116A-N183D-A215F-H249R-N263D | + |
| N018R-T022W-S024R-N076D-S101A-N183D-H249R | + |
| N018R-S024R-N076D-S101A-N116A-N183D-I198L-A215F-H249R | + |
| N018R-T022W-S024R-N076D-N116A-I198L-A215F-H249R-R269H | + |
| N018R-N043D-R045T-N076D-S078R-S101G-S103A-V104I-A232V-Q245R | + |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| N018R-S024R-R045T-N076D-S078R-S101G-S103A-V104I-A232V-Q245R-N269R | + |
| S078R-S101G-S103A-V104I-L217E-A232V-Q245R | + |
| N018R-G020R-T022W-S024R-N076D-S101A-N183D-I198L-T213A-A215F-H249R | + |
| N018R-G020R-S024R-N076D-N183D-I198L-T213A-H249R | + |
| N018R-G020R-T022W-S024R-N076D-N116A-I198L-G211Q-A215F-H249R | + |
| N018R-G020R-T022W-S024R-N076D-N116A-N183D-G211Q-H249R | + |
| N018R-G020R-T022W-S024R-N076D-S101A-I198L-G211Q-T213A-H249R | + |
| N018R-G020R-T022W-S024R-N076D-H249R | + |
| G020R-T022W-S101G-S103A-V104I-N116A-N183D-I198L-G211Q-T213A-A215F-A232V-Q245R | + |
| V104I-A232V | + |
| N018R-G020R-T022W-S024R-N076D-S101A-N116A-N183D-G211Q-A215F-H249R | + |
| N018R-G020R-T022W-S024R-N076D-S101A-N116A-N183D-I198L-G211Q-T213A-A215F-H249R | + |
| N018R-G020R-T022W-S024R-N076D-S101A-N183D-T213A-A215F-H249R | + |
| N018R-T022W-S024R-N076D-S101A-N183D-I198L-G211Q-T213A-H249R | + |
| N018R-T022W-S024R-N076D-S101A-N183D-I198L-H249R | + |
| N043D-R045T-S101G-S103A-V104I-A232V-Q245R-N269R | + |
| N018R-G020R-S024R-N076D-S101A-N183D-I198L-G211Q-H249R | + |
| N018R-G020R-N043R-S101G-S103A-V104I-L217E-A232V-Q245R | + |
| S024R-N043R-N076D-S078R-S101G-S103A-V104I-A232V-Q245R-N269R | + |
| N043R-R045T-N076D-S078R-S101G-S103A-V104I-Y166F-A176P-A179V-N184T-A187P-A194P | + |
| N018R-T022W-S024R-D041E-N076D-S101A-S160T-N183D-G211Q-T213A-H249R | + |
| N018R-G020R-T022W-S024R-N076D-N116A-N183D-I198L-G211Q-A215F-H249R | + |
| N018R-G020R-T022W-S024R-N076D-S101A-N116A-I198L-T213A-H249R | + |
| N018R-T022W-S024R-N076D-S101A-N116A-N183D-I198L-G211Q-T213A-H249R | + |
| N018R-G020R-S024R-N076D-I198L-T213A-H249R | + |
| N018R-G020R-T022W-S024R-N076D-N116A-N183D-I198L-G211Q-H249R | + |
| N018R-G020R-S024R-N076D-N183D-G211Q-A215F-H249R | + |
| S024R-N076D-V104I | + |
| N018R-N076D-S101G-A232V | + |
| N018R-S024R-N076D-S101A-N116A-N183D-I198L-G211Q-T213A-A215F-H249R | + |
| N018R-G020R-T022W-S024R-N076D-N116A-N183D-A215F-H249R | + |
| N018R-S024R-L031F-N076D-N116A-N183D-G211Q-T213A-A215F-H249R | + |
| N018R-S024R-N076D-S101A-N116A-N183D-I198L-T213A-H249R-N269S | + |
| N018R-G020R-S024R-N076D-S101A-N116A-I198L-A215F-H249R | + |
| N018R-N043R-N076D-S078R-S101G-S103A-V104I-A232V-Q245R-N269R | + |
| N018R-G020R-S024R-N076D-S101A-N114T-I198L-G211Q-A215F-H249R | + |
| S024R-N043R-S078R-S101G-S103A-V104I-L217E-A232V-Q245R | + |
| S024R-N076D-S103A-V104I-A232V | + |
| N018R-G020R-T022W-S024R-N076D-S101A-I198L-G211Q-A215F-H249R | + |
| S101G-V104I-A232V | + |
| N018R-T022W-S024R-N076D-N183D-I198L-T213A-A215F-H249R | + |
| N018R-T022W-S024R-N076D-N183D-I198L-G211Q-H249R | + |
| N018R-G020R-S024R-N076D-N183D-T213A-H249R | + |
| N018R-S024R-N076D-S101A-N183D-G211Q-A215F-H249R | + |
| N018R-G020R-T022W-S024R-N076D-N116A-G211Q-T213A-H249R | + |
| N018R-S078R-S101G-S103A-V104I-A232V-Q245R-N269R | + |
| N018R-T022W-S024R-N076D-S101A-N116A-N183D-G211Q-A215F-H249R-T260A | + |
| N076D-H249R | + |
| N018R-T022W-S024R-N076D-N183D-G211Q-A215F-H249R | + |

TABLE 12-2-continued

BMI cleaning performance of WCE10 to WCE14 library variants.

| Sequence of GG36 Variants (BPN' numbering) | PI Relative to GG36; BMI assay, Detergent 36k or 36l, 16° C. |
|---|---|
| N018R-G020R-S024R-N076D-N116A-G211Q-A215F-H249R | + |
| N018R-G020R-S024R-N076D-T213A-H249R | + |
| N018R-G020R-T022W-S024R-N076D-N116A-N183D-I198L-H249R | + |
| N018R-G020R-T022W-S024R-N076D-S101A-N183D-H249R | + |
| N076D-V104I-H249R | + |
| G020R-T022W-S101A-S103A-V104I-N116A-N183D-G211Q-T213A-A215F-A232V-Q245R | + |
| S024R-N043R-R045T-S078R-S101G-S103A-V104I-L217E-A232V-Q245R | + |
| N018R-G020R-T022W-S024R-N076D-N183D-I198L-A215F-H249R | + |
| N018R-N076D-S101G-S103A | + |
| G020R-S024R-S101G-S103A-V104I-A232V-Q245R-N269R | + |
| N018R-G020R-S024R-N076D-S101A-N116A-N183D-G211Q-H249R | + |
| S101G-S103A-A232V | + |
| S024R-N076D-S101G-A232V | + |
| N018R-T022W-S024R-N076D-S101A-N183D-I198L-G211Q-H249R | + |
| N018R-G020R-S024R-N076D-S101A-N183D-I198L-G211Q-A215F-H249R | + |
| N018R-G020R-S024R-N076D-N183D-I198L-H249R | + |
| N018R-T022W-S024R-N076D-S101A-N116A-N183D-I198L-G211Q-H249R | + |
| N018R-G020R-S024R-N076D-N116A-A156V-N183D-G211Q-A215F-H249R-N269S | + |
| R045T-N076D-S101G-S103A-V104I-A232V-Q245R-H249R | + |
| N018R-G020R-S024R-N076D-S101A-N183D-I198L-H249R | + |
| N018R-G020R-T022W-S024R-N076D-I198L-G211Q-A215F-H249R | + |
| N018R-G020R-T022W-S024R-N076D-S101A-N116A-I198L-G211Q-A215F-H249R | + |
| N018R-G020R-T022W-S024R-N076D-N116A-H249R | + |
| N018R-N076D-S101G | + |
| N018R-S024R-N076D-N116A-N183D-I198L-T213A-A215F-H249R | + |
| N018R-G020R-T022W-S024R-N076D-S101A-N116A-I198L-T213A-A215F-H249R | + |
| N018R-S024R-N076D-S101A-N116A-N183D-I198L-G211Q-H249R | + |
| N018R-N076D-A232V | + |
| N018R-G020R-S024R-N076D-S101A-A232V-Q245R | + |
| N018R-N043D-R045T-N076D-S101G-S103A-V104I-A232V-Q245R | + |
| N018R-T022W-S024R-N076D-N183D-T213A-A215F-H249R | + |
| N018R-S024R-N076D-S101A-N116A-G211Q-T213A-N237D-H249R | + |
| N018R-G020R-S024R-N076D-S101A-N116A-N183D-G211Q-H249R-R275S | + |
| N018R-T022W-S024R-N076D-S101A-N116A-N183D-I198L-G211Q-T213A-A215F-H249R | + |
| S024R-N076D | + |
| N018R-S024R-N076D-N183D-G211Q-A215F-H249R | + |
| N018R-T022W-S024R-N076D-N116A-N183D-I198L-T213A-A215F-H249R | + |
| N076D-V104I-A232V-H249R | + |
| N018R-N076D-S103A-A232V | + |
| N018R-G020R-S024R-N076D-S101A-N116A-N183D-I198L-G211Q-T213A-H249R | + |
| N018R-G020R-S024R-N076D-S101A-N183D-T213A-H249R | + |
| N018R-G020R-S024R-N076D-S101A-D175E-N183D-G211Q-A215F-H249R | + |
| N018R-G020R-N043D-S078R-S101G-S103A-V104I-L217E-A232V-Q245R-A273E | + |
| G020R-S024R-N043D-R045T-N076D-S101G-S103A-V104I-A232V-Q245R | + |
| P005S-S101G-S103A-V104I-A232V-Q245R-H249R | + |
| S103A-V104I-A232V | + |
| N018R-G020R-S024R-V068A-N076D-S101A-N116A-T213A-A215F-H249R | + |
| N018R-T022W-S024R-N076D-S101A-I198L-A215F-H249R-R275S | + |
| N018R-S024R-N076D-N183D-I198L-G211Q-T213A-H249R | + |
| N043D-R045T-S101G-S103A-V104I-A232V-Q245R | + |

PI = Performance Index
PI > or = 1.5 is +++; PI between 1.49 and 1.3 = ++; PI between 1.29 and 1.0 = + in detergent 36k or 36l

TABLE 12-3

BMI cleaning performance of WCE15 and WCE16 variants.

| Sequence of GG36 Variants (BPN' numbering) | PI Relative to GG36; Detergent 36m, BMI, 16° C. |
|---|---|
| N018R-S024R-N043R-N076D-H249R-N269R | +++ |
| N018R-T022R-S024R-N043R-N076D-H249R | +++ |
| N018R-N043D-S101G-S103A-V104I-A232V-Q245R | +++ |
| G020R-N043D-S101G-S103A-V104I-A232V-Q245R | +++ |
| N043D-S101G-S103A-V104I-A232V-Q245R-N269R | +++ |
| N043D-S078R-S101G-S103A-V104I-A232V-Q245R | +++ |
| N043R-N076D-S101G-S103A-V104I-A232V-Q245R | +++ |
| T022R-N043R-S101G-S103A-V104I-A232V-Q245R | +++ |
| N043R-S078R-S101G-S103A-V104I-A232V-Q245R | +++ |
| G020R-N076D-S101G-S103A-V104I-A232V-Q245R | +++ |
| N043R-N076D-S101G-S103A-V104I-A232V-Q245R | +++ |
| T022R-N076D-S101G-S103A-V104I-A232V-Q245R | +++ |
| N076D-S078R-S101G-S103A-V104I-A232V-Q245R | +++ |
| N018R-S024R-N043R-N076D-H249R | +++ |
| N018R-S024R-N076D-S242R-H249R | +++ |
| N018R-S024R-N076D-H249R-N269R | +++ |
| N018R-T022R-S024R-N076D-H249R | +++ |
| N018R-S024R-N076D-S078R-H249R | +++ |
| N018R-S024R-N043D-N076D-H249R-N269R | +++ |
| N018R-T022R-S024R-N043D-N076D-H249R | +++ |
| N018R-S024R-N043D-N076D-S078R-H249R | +++ |
| G020R-S101G-S103G-V104I-A232V-Q245R | +++ |
| G020R-S101G-S103A-V104L-A232V-Q245R | +++ |
| G020R-S101G-S103A-V104V-A232V-Q245R | +++ |
| G020R-S101G-S103S-V104I-A232V-Q245R | +++ |
| G020R-S101G-S103S-V104L-A232V-Q245R | +++ |
| G020R-S101S-S103S-V104I-A232V-Q245R | +++ |
| G020R-S101S-S103S-V104L-A232V-Q245R | +++ |
| G020R-S101A-S103A-V104L-A232V-Q245R | +++ |
| G020R-S101S-S103S-V104V-A232V-Q245R | +++ |
| G020R-S101S-S103A-V104I-A232V-Q245R | +++ |
| G020R-S101S-S103A-V104V-A232V-Q245R | +++ |
| G020R-S101S-S103G-V104I-A232V-Q245R | +++ |
| G020R-S101S-S103G-V104V-A232V-Q245R | +++ |
| G020R-S101A-S103A-V104V-A232V-Q245R | +++ |
| G020R-S101A-S103S-V104I-A232V-Q245R | +++ |
| G020R-S101A-S103S-V104V-A232V-Q245R | +++ |
| N018R-S024R-N043R-N076D-S078R-H249R | ++ |
| S024R-N043D-S101G-S103A-V104I-A232V-Q245R | ++ |
| N043D-S101G-S103A-V104I-A232V-Q245R-H249R | ++ |
| S024R-N076D-S101G-S103A-V104I-A232V-Q245R | ++ |
| N076D-S101G-S103A-V104I-A232V-S242R-Q245R | ++ |
| N018R-G020R-S024R-N076D-L217E-H249R | ++ |
| N018R-S024R-N043R-N076D-L217E-H249R | ++ |
| N018R-S024R-N043D-N076D-S242R-H249R | ++ |
| N018R-G020R-S024R-N043R-N076D-H249R | ++ |
| G020R-S101A-S103G-V104V-A232V-Q245R | ++ |
| N043D-S101G-S103A-V104I-A232V-Q245R | + |
| N018R-S024R-N076D-L217E-H249R-N269R | + |
| N018R-S024R-N076D-L217E-S242R-H249R | + |

PI = Performance Index
PI > or = 1.5 is +++; PI between 1.49 and 1.3 = ++; PI between 1.29 and 1.0 = + in detergent 36m

TABLE 12-4

BMI cleaning performance of WCE20 and WCE21 library variants.

| Sequence of GG36 Variants (BPN' numbering) | PI Relative to GG36; BMI assay, Detergent 36m or 36n, 16° C. |
|---|---|
| G020R-S101A-S103A-V104I-G118R-A232V-Q245R | +++ |
| G020R-S024R-N116A-T213A | +++ |
| N043R-S101A-N116A-A215F-N269R | +++ |
| S024R-N043R-S101A-N116A | +++ |
| S024R-N043R-S101A-N116A-A215F-N269R | +++ |
| G020R-S101G-S103A-V104I-A215F-A232V-Q245R | +++ |
| N043R-S101A-N269R | +++ |
| S024R-N043R-N116A-T213A-N269R | +++ |
| G020R-S024R-N043R-R045T-S101A-T213A | +++ |
| S024R-N043R-N116A-A215F-N269R | +++ |
| G020R-S024R-T213A-A215F | +++ |
| G020R-N116A-N269R | +++ |
| S024R-N116A-T213A-N269R | +++ |
| N043R-S101A-N116A-N269R | +++ |
| S101G-S103A-V104I-N116A-T213A-A232V-Q245R-N269R | +++ |
| S024R-N043R-R045T-S101A-N116A-A215F-N269R | +++ |
| G020R-N043R-S101A-N269R | +++ |
| S101A-S103A-V104I-T213A-A232V-Q245R-N269R | +++ |
| S024R-A215F-N269R | +++ |
| N043R-S101A-N116A-T213A-A215F-N269R | +++ |
| N043R-S101A-T213A-N269R | +++ |
| G020R-S024R-N043R-R045T-N116A-T213A | +++ |
| S101G-S103A-V104I-A232V-Q245R-N269R | +++ |
| S024R-N043R-R045T-S101A-N116A-T213A-N269R | +++ |
| S024R-N043R-R045T-N269R | +++ |
| G020R-N043R-R045T-S101A-N269R | +++ |
| S024R-N043R-N116A-N269R | +++ |
| G020R-S024R-N043R-R045T | +++ |
| N043R-N116A-N269R | +++ |
| S024R-N043R-S101A-A215F-N269R | +++ |
| S024R-N043R-R045T-T213A-A215F-N269R | +++ |
| G020R-S024R-R045T-N269R | +++ |
| G020R-N043R-S101A-N116A-T213A-A215F | +++ |
| G020R-S101G-S103A-V104I-T213A-A215F-A232V-Q245R | +++ |
| G020R-S024R-R045T-N116A-N269R | +++ |
| G020R-S101A-N116A-N269R | +++ |
| S024R-N043R-A215F | +++ |
| G020R-S024R-T213A | +++ |
| S024R-N043R-S101A-A215F | +++ |
| G020R-S024R-N043R-R045T-N116A | +++ |
| G020R-S024R-N043R-R045T-S101A-N269R | +++ |
| G020R-S024R-S101A-A215F | +++ |
| G020R-S024R-N116A-T213A-A215F | +++ |
| G020R-S024R-N116A | +++ |
| G020R-S024R-S101A-N116A | +++ |
| N043R-T213A-A215F-N269R | +++ |
| S024R-S101A-N269R | +++ |
| S024R-N043R-N116A-A215F | +++ |
| G020R-T038A-N043R-S101A | +++ |
| G020R-S024R-N116A-A215F | +++ |
| S024R-N043R-S101A-T213A | ++ |
| P014L-G020R-S024R-N043R-R045T-S101A-A215F | ++ |
| G020R-S024R-A215F | ++ |
| G020R-N116A-A215F-N269R | ++ |
| G020R-R045T-N116A-N269R | ++ |
| G020R-S024R-N043R-R045T-A215F | ++ |
| G020R-S024R-N043R-R045T-N116A-T213A-A215F | ++ |

PI = Performance Index
PI > or = 1.5 is +++; PI between 1.49 and 1.3 = ++; PI between 1.29 and 1.0 = + in detergent 36m or 36n

TABLE 12-5

BMI cleaning performance of NHJ8 library variants.

| Sequence of GG36 Variants (BPN' numbering) | PI Relative to GG36; BMI assay, Detergent 36f, 16° C. |
|---|---|
| N043R-N076D-S101A-S103A-V104I-A158E-S188D-A232V-Q245R-N248D-H249R-E271F | +++ |
| S024R-N043R-N076D-S101A-S103A-V104I-A158E-S188D-L217E-A232V-Q245R-N248D-H249R | +++ |
| S101A-S103A-V104I-A158E-S188D-A232V-Q245R-N248D-H249R-E271F-E271F | +++ |
| S101A-S103A-V104I-A158E-S188D-L217E-A232V-Q245R-N248D-H249R-E271F | ++ |
| N076D-S101G-S103A-V104I-A114V-A158E-S188D-A232V-Q245R-N248D-H249R-E271F | ++ |
| S024R-N076D-S101G-S103A-V104I-A158E-S188D-A232V-Q245R-N248D-H249R-E271F | + |
| S024R-N043R-S101A-S103A-V104I-A158E-S188D-L217E-A232V-Q245R-N248D-H249R | + |
| S024R-N043R-S101A-S103A-V104I-A158E-S188D-A232V-Q245R-N248D-H249R | + |
| S024R-S101A-S103A-V104I-A158E-S166D-S188D-L217E-A232V-Q245R-N248D-H249R | + |
| N076D-S101G-S103A-V104I-S128L-A158E-S188D-A232V-Q245R-N248D-H249R-E271F | + |
| N043R-N076D-S101G-S103A-V104I-A158E-S166D-S188D-A232V-Q245R-N248D-H249R-E271F | + |

PI = Performance Index
PI > or = 1.3 is +++; PI between 1.29 and 1.2 = ++; PI between 1.19 and 1.0 = + in detergent 36f

TABLE 12-6

BMI cleaning performance of NHJ8, NHJ9, NHJ14 library variants.

| Sequence of GG36 Variants (BPN' numbering) | PI Relative to GG36; BMI assay, Detergent 36c, 16° C. |
|---|---|
| T022A-S101G-S103A-V104I-G159D-L217E-A232V-Q245R-N248D-E271F | +++ |
| T022A-N043R-S101G-S103A-V104I-G159D-S188D-L217E-A232V-Q245R-N248D-E271F | +++ |
| T022A-S101G-S103A-V104I-G159D-S188D-A232V-Q245R-N248D-E271F | +++ |
| N043R-S101A-S103A-V104I-A158E-S188D-L217E-A232V-Q245R-N248D-H249R | +++ |
| N043R-N076D-S101A-S103A-V104I-A158E-S188D-L217E-A232V-Q245R-N248D-H249R-E271F | +++ |
| S024R-S101G-S103A-V104I-A158E-S188D-L217E-A232V-Q245R-N248D-H249R | +++ |
| S024R-S101G-S103A-V104I-A158E-S188D-A232V-Q245R-N248D-H249R | +++ |
| S101G-S103A-V104I-A158E-S188D-A232V-Q245R-N248D-H249R | +++ |
| S024R-S101G-S103A-V104I-A158E-N183D-S188D-A232V-Q245R-N248D-H249R | +++ |
| T022A-N076D-S101G-S103A-V104I-G159D-S188D-A232V-Q245R-N248D-E271F | ++ |
| T022A-N043R-N076D-S101G-S103A-V104I-G159D-S188D-A232V-Q245R-N248D-E271F | ++ |
| T022A-N076D-S101G-S103A-V104I-G159D-A232V-Q245R-N248D-E271F | ++ |
| T022A-S101G-S103A-V104I-G159D-A232V-Q245R-N248D-E271F | ++ |
| N076D-S101A-S103A-V104I-A158E-S188D-A232V-Q245R-N248D-H249R-E271F | ++ |
| N043R-S101A-S103A-V104I-A158E-S166D-S188D-A232V-Q245R-N248D-H249R | ++ |
| S024R-N076D-S101A-S103A-V104I-A158E-S166D-S188D-A232V-Q245R-N248D-H249R-E271F | ++ |
| N076D-S101A-S103A-V104I-A158E-S188D-A232V-Q245R-N248D-H249R | ++ |
| S101A-S103A-V104I-A158E-S166D-S188D-A232V-Q245R-N248D-H249R-E271F | ++ |
| N043R-N076D-S101A-S103A-V104I-A158E-S166D-S188D-A232V-Q245R-N248D-H249R-E271F | ++ |
| S101G-S103A-V104I-A158E-S166D-S188D-A232V-Q245R-N248D-H249R-E271F | ++ |
| S101A-S103A-V104I-A158E-S188D-A232V-Q245R-N248D-H249R-E271F | ++ |
| S101A-S103A-V104I-A158E-S188D-L217E-A232V-Q245R-N248D-H249R | ++ |
| N076D-S101A-S103A-V104I-A158E-S166D-S188D-A232V-Q245R-N248D-H249R-E271F | ++ |
| S101G-S103A-V104I-A158E-N183D-S188D-A232V-Q245R-N248D-H249R | ++ |
| S024R-S101G-S103A-V104I-S128L-A158E-S188D-A232V-Q245R-N248D-H249R | ++ |
| N076D-S101G-S103A-V104I-A158E-S166D-S188D-A232V-Q245R-N248D-H249R-E271F | + |
| N043R-N076D-S101A-S103A-V104I-A158E-S166D-S188D-A232V-Q245R-N248D-H249R | + |
| N076D-S101A-S103A-V104I-A158E-S188D-L217E-A232V-Q245R-N248D-H249R-E271F | + |

PI = Performance Index
PI > or = 1.5 is +++; PI between 1.49 and 1.3 = ++; PI between 1.29 and 1.0 = + in detergent 36c

TABLE 12-7

BMI cleaning performance of NHJ9 library variants.

| Sequence of GG36 Variants (BPN' numbering) | PI Relative to GG36; BMI assay; Detergent 36f, 16° C. |
|---|---|
| H017R-T022A-N076D-S101G-S103A-V104I-G159D-S188D-A232V-Q245R-N248D-E271F | +++ |
| T022A-N043R-S101G-S103A-V104I-G159D-A232V-Q245R-N248D-E271F | ++ |
| T022A-S101G-S103A-V104I-G159D-S188D-A232V-Q245R-N248D-H249R-E271F | ++ |
| H017R-T022A-N076D-S101G-S103A-V104I-G159D-A232V-Q245R-N248D-E271F | ++ |
| T022A-N076D-S101G-S103A-V104I-G159D-A232V-Q245R-N248D-H249R-E271F | + |
| T022A-S101G-G102A-S103A-V104I-G159D-S188D-A232V-Q245R-N248D-E271F | + |
| T022A-N043R-N076D-S101G-S103A-V104I-G159D-A232V-Q245R-N248D-H249R-E271F | + |

PI = Performance Index
PI > or = 1.3 is +++; PI between 1.29 and 1.2 = ++; PI between 1.19 and 1.0 = + for detergent 36f

TABLE 12-8

BMI cleaning performance of NHJ11 variants.

| Sequence of GG36 Variants (BPN' numbering) | PI Relative to GG36; BMI assay, Detergent 36a or 36c1 nil Bleach 16° C. |
|---|---|
| S101S-S103A-V104I-A158E-S188D-A232V-Q245R-N248D-H249R | +++ |
| S101S-S103G-V104V-A158E-S188D-A232V-Q245R-N248D-H249R | +++ |
| S101G-S103S-V104I-A158E-S188D-A232V-Q245R-N248D-H249R | +++ |
| S101A-S103A-V104I-A158E-S188D-A232V-Q245R-N248D-H249R | +++ |
| S101A-S103A-V104L-A158E-S188D-A232V-Q245R-N248D-H249R | +++ |
| S101G-S103G-V104I-A158E-S188D-A232V-Q245R-N248D-H249R | +++ |
| S101S-S103G-V104I-A158E-S188D-A232V-Q245R-N248D-H249R | +++ |
| S101S-S103S-V104I-A158E-S188D-A232V-Q245R-N248D-H249R | ++ |
| S101S-S103S-V104V-A158E-S188D-A232V-Q245R-N248D-H249R | ++ |
| S101A-S103S-V104I-A158E-S188D-A232V-Q245R-N248D-H249R | ++ |
| S101A-S103S-V104I-G159E-A232V-Q245R-N248D-H249R | ++ |
| S101S-S103A-V104I-G159E-A232V-Q245R-N248D-H249R | ++ |
| S101G-S103A-V104L-A158E-S188D-A232V-Q245R-N248D-H249R | ++ |
| S101A-S103A-V104I-G159E-A232V-Q245R-N248D-H249R | + |
| S101A-S103S-V104L-G159E-A232V-Q245R-N248D-H249R | + |
| S101G-S103S-V104L-G159E-A232V-Q245R-N248D-H249R | + |
| S101S-S103A-V104L-G159E-A232V-Q245R-N248D-H249R | + |
| S101A-S103G-V104V-G159E-A232V-Q245R-N248D-H249R | + |
| S101S-S103A-V104V-G159E-A232V-Q245R-N248D-H249R | + |

PI = Performance Index
PI > or = 1.5 is +++; PI between 1.49 and 1.3 = ++; PI between 1.29 and 1.0 = + in detergent 36a or 36c

TABLE 12-9

BMI cleaning performance of NHJ12 variants.

| Sequence of GG36 Variants (BPN' numbering) | PI Relative to GG36; BMI assay, Detergent 36a, 16° C. |
|---|---|
| V026F-V051W-V104L-S106E | +++ |
| V026F-L031F-S078N-G102A-S160D | +++ |
| G020K-G100S-N116L-A158E-S166D-N243F | +++ |
| T033S-N043W-N218D-P239G-N243F | +++ |
| T022L-T038F-A048R-N062E-G100S-R186K | +++ |
| S101D-S103N-N116L-S144R-A215D | +++ |
| V104L-S105T-T213A-L217E-S256N | +++ |
| N043W-S101D-S212M-N243F | +++ |
| V026F-A048R-S105T-T213A-N218D-T224A | +++ |
| S024F-S101D-G118R-A215D-L250I-A272F | ++ |
| V121F-N185E-T224A-P239G | ++ |
| T022L-L031F-G102A-S128D-T224A-N243F | ++ |
| N062E-S078N-G102A-N116L-S144R-L250I | ++ |
| T022L-T038F-V121F-S160D-A272F | ++ |
| V026F-S078N-G159C-R186K-N243F | ++ |
| S024F-A048R-G118R-S166D-L217E | ++ |
| G023A-T038F-S078N-G100S-S212M-A215D | ++ |
| G100S-N116L-A158E-T213A | ++ |
| S078N-V104L-G118R-S128D | ++ |
| G102A-S103N-S105T-A194E | ++ |
| T022L-S078N-S128D-T213A | + |
| K027R-G100S-G118R-S160D-S188D-N243F | + |
| S024F-G102A-R186K-T213A-L217E-N243F | + |
| T033S-S105T-S188D-S216F | + |
| G023A-G100S-A194E-S212M | + |
| A048R-S128D-N185E-P239G | + |
| G020K-S024F-T033S-P129E-A194E | + |
| G020K-K027R-P129E-S166D-P239G | + |
| T022L-G023A-K027R-S101D-V104L-S216F | + |
| T033S-G118R-P129E-A194E-P239G | + |
| T022L-S078N-N116L-P129E-S256N | + |
| K027R-S101D-S103N-S105T-A272F | + |
| A048R-S078N-N116L-N185E-L217E-P239G | + |
| G023A-S024F-K027R-N062E | + |
| S024F-S103N-V104L-G118R-S188D | + |
| V026F-V104L-S256N-A272F | + |
| S024F-N043W-V104L-V121F-P129E | + |
| N062E-S078N-N116L-T224A | + |
| G023A-S024F-V051W-A158E | + |
| K027R-T038F-G102A-N116L | + |
| N062E-S078N-S144R-S212M | + |
| L031F-N116L-S256N-A272F | + |
| T022L-T033S-V104L-N116L-S160D-R186K | + |
| S024F-G118R-P129E-R186K-T213A | + |
| N043W-S105T-T213A-A215D-S216F | + |
| L031F-S105T-R186K-S188D | + |
| V026F-A194E-T213A-S256N | + |
| S103N-S160D-L250I-S256N | + |

PI = Performance Index
PI > or = 1.3 is +++; PI between 1.29 and 1.2 = ++; PI between 1.19 and 1.0 = + in detergent 36a

TABLE 12-10

BMI cleaning performance of NHJ15 library variants.

| Sequence of GG36 Variants (BPN' numbering) | PI Relative to GG36; BMI assay, Detergent 36a, 16° C. |
|---|---|
| T022A-S024R-S101D-S103A-V104I-G118R-G159D-S188D-A232V-N248D-E271F | +++ |
| T022A-S024R-S103A-V104I-P129E-G159D-S188D-A232V-N248D-E271F | +++ |
| T022A-S024R-S103A-V104I-G118R-G159D-S188D-L217D-A232V-N248D | +++ |
| T022A-S024R-S101D-S103A-V104I-G118R-P129E-G159D-S188D-A232V-Q245R-N248D | +++ |
| T022A-S024R-S101D-S103A-V104I-G159D-S188D-A232V-Q245R-N248D | +++ |
| T022A-N043R-S103A-V104I-G118R-P129E-G159D-S188D-A232V-Q245R-N248D | +++ |
| T022A-N043R-S103A-V104I-G118R-S128I-P129E-G159D-S188D-A232V-N248D | ++ |
| T022A-N043R-S101D-S103A-V104I-G118R-P129E-G159D-S188D-A232V-N248D-E271F | ++ |
| T022A-S024R-N043R-S101D-S103A-V104I-G159D-S188D-A232V-Q245R-N248D | ++ |
| T022A-S103A-V104I-G159D-S188D-A232V-N248D | ++ |
| T022A-S024R-S103A-V104I-G118R-P129E-G159D-S188D-A232V-N248D-E271F | ++ |
| T022A-S024R-S103A-V104I-G159D-S188D-L217D-A232V-Q245R-N248D-E271F | ++ |
| T022A-N043R-N062E-S103A-V104I-G159D-S188D-A232V-Q245R-N248D-E271F | ++ |
| T022A-N043R-S103A-V104I-P129E-G159D-S188D-A232V-Q245R-N248D | ++ |
| T022A-S024R-S103A-V104I-G159D-S188D-L217D-A232V-N248D-E271F | ++ |

TABLE 12-10-continued

BMI cleaning performance of NHJ15 library variants.

| Sequence of GG36 Variants (BPN' numbering) | PI Relative to GG36; BMI assay, Detergent 36a, 16° C. |
|---|---|
| T022A-S103A-V104I-G118R-G159D-S188D-L217D-A232V-Q245R-N248D | ++ |
| T022A-S024R-S101D-S103A-V104I-G118R-S128I-G159D-S188D-A232V-Q245R-N248D | ++ |
| T022A-S024R-N043R-S103A-V104I-G159D-S188D-L217D-A232V-N248D-E271F | ++ |
| T022A-N043R-S103A-V104I-G118R-G159D-S188D-L217D-A232V-N248D-E271F | ++ |
| T022A-N043R-S103A-V104I-G118R-G159D-S188D-A232V-N248D-E271F | ++ |
| T022A-S103A-V104I-S128I-P129E-G159D-S188D-A232V-N248D-E271F | + |
| T022A-S103A-V104I-G159D-S188D-L217D-A232V-Q245R-N248D-E271F | + |
| T022A-N043R-S103A-V104I-S128I-G159D-S188D-A232V-Q245R-N248D | + |
| T022A-S101D-S103A-V104I-G118R-G159D-S188D-L217D-A232V-Q245R-N248D-E271F | + |
| T022A-S103A-V104I-G118R-P129E-G159D-S188D-A232V-Q245R-N248D-E271F | + |
| T022A-S024R-N043R-S103A-V104I-G118R-G159D-S188D-L217D-A232V-N248D | + |
| T022A-N062E-S103A-V104I-G118R-G159D-S188D-A232V-Q245R-N248D | + |
| T022A-N043R-S101D-S103A-V104I-G118R-P129E-G159D-S188D-L217D-A232V | + |
| T022A-S024R-S103A-V104I-G159D-S188D-L217D-A232V-N248D | + |
| T022A-S024R-N043R-S103A-V104I-G118R-S128I-P129E-G159D-S188D-L217D-A232V-N248D-E271F | + |
| T022A-S103A-V104I-G118R-G159D-S188D-L217D-A232V-Q245R-N248D-E271F | + |

PI = Performance Index
PI > or = 1.3 is +++; PI between 1.29 and 1.2 = ++; PI between 1.19 and 1.0 = + in detergent 36a

TABLE 12-11

BMI cleaning performance of NHJ16 library variants.

| Sequence of GG36 Variants (BPN' numbering) | PI Relative to GG36; Detergent 36a, 16° C. |
|---|---|
| G020K-S024F-N062E-S188D-P239G | +++ |
| S024F-N062E-N116L-P239G | +++ |
| G020K-G023A-N062E-S188D | +++ |
| G020K-G023A-S024F-N062E-G118R-S188D-T213A | +++ |
| G020K-N043W-N062E-N116L-S188D-T213A-P239G | +++ |
| G023A-N062E-N116L-G118R | +++ |
| G023A-S024F-N062E-N116L-G118R | +++ |
| S024F-N116L | +++ |
| S024F-N062E-S188D-T213A | +++ |
| G023A-N062E-N116L-G118R-S188D-P239G | +++ |
| G020K-S024F-N062E | ++ |
| G020K-N043W-N062E-N116L-P239G | ++ |
| S024F-N062E-N116L-T213A-P239G | ++ |
| G020K-S024F-N043W-N062E-N116L-T213A | ++ |
| G020K-G023A-S024F-N062E-N116L-S188D-T213A | ++ |
| S024F-N062E-S188D-P239G | ++ |
| G023A-N043W-N062E-N116L-G118R-T213A | ++ |
| N062E-S188D-P239G | ++ |
| G020K-S024F-N062E-P239G | + |
| S024F-N116L-G118R-S188D-P239G | + |
| G020K-G023A-N062E-N116L-G118R-T213A | + |
| G020K-G023A-S024F-N062E-S188D-T213A-P239G | + |
| S024F-N043W-G118R-S188D | + |
| G023A-S024F-N116L-G118R-S188D-T213A | + |
| G020K-G023A-N043W-N116L-S188D-T213A-P239G | + |
| G023A-S024F-N116L-S188D-P239G | + |

TABLE 12-11-continued

BMI cleaning performance of NHJ16 library variants.

| Sequence of GG36 Variants (BPN' numbering) | PI Relative to GG36; Detergent 36a, 16° C. |
|---|---|
| G023A-N043W-N116L-G118R-S188D | + |
| G023A-S024F-G118R-S188D-P239G | + |
| G023A-S024F-N043W-N062E-N116L-G118R | + |
| G020K-N043W-S188D-T213A | + |
| S024F-N062E-G118R-P239G | + |
| G023A-N043W-S188D-T213A | + |
| G020K-S024F-N043W-N062E-N116L-G118R-S188D-P239G | + |
| G020K-N116L-S188D-P239G | + |
| G020K-N043W-N062E-G118R | + |
| G020K-N043W-N116L-S188D-T213A | + |
| G020K-S024F | + |
| G023A-N043W-N116L-P239G | + |
| G023A-S024F-N043W-N116L-G118R-S188D-P239G | + |
| G020K-G023A-N043W-T213A | + |
| G023A-S024F-N062E-G118R-T213A-P239G | + |

PI = Performance Index
PI > or = 1.3 is +++; PI between 1.29 and 1.2 = ++; PI between 1.19 and 1.0 = + in detergent 36a

TABLE 12-12

BMI cleaning performance of NHJ15 and NHJ16 library variants.

| Sequence of GG36 Variants (BPN' numbering) | PI Relative to GG36; BMI Detergent 36a, 36d or 36f; 16° C. |
|---|---|
| G020K-G023A-N043W-G118R-S128I-P129E-G159D-S188D | +++ |
| S024F-G118R-S128I-P129E-G159D | +++ |
| G020K-S024F-N062E-N116L-G118R-S188D | +++ |
| G020K-N062E-N116L-S188D | +++ |
| N062E-N116L-G118R-T213A | +++ |
| G020K-G023A-N062E-N116L-S188D | +++ |
| N062E-N116L-G118R-S188D | +++ |
| G020K-N062E-N116L-T213A | +++ |
| G020K-G023A-N062E-N116L | +++ |
| G020K-N062E-S188D-T213A | +++ |
| G020K-N062E | +++ |
| G020K-S024F-N062E-N116L-S188D | +++ |
| G020K-N043W-N062E-N116L-S188D | +++ |
| G020K-S024F-N062E-S188D-T213A | +++ |
| N062E-N116L-S188D-T213A | +++ |
| G020K-N062E-N116L | +++ |
| G020K-G023A-N062E-N116L-S188D-T213A | +++ |
| G023A-S024F-N062E-N116L-T213A | +++ |
| T022A-N043R-S103A-V104I-S128I-P129E-G159D-S188D-A232V-Q245R-N248D | +++ |
| T022A-N043R-S103A-V104I-G118R-S128I-P129E-G159D-S188D-A232V-N248D-E271F | +++ |
| S024F-N062E-N116L-S188D | +++ |
| T022A-S024R-S103A-V104I-G118R-S128I-P129E-G159D-S188D-A232V-N248D | +++ |
| G023A-N062E-N116L-S188D | +++ |
| N043W-N062E-N116L | +++ |
| G020K-G023A-N116L-S188D | ++ |
| N043W-N062E-N116L-S188D | ++ |
| S024F-N062E-N116L | ++ |
| N062E-N116L-S188D | ++ |
| T022A-S024R-S103A-V104I-S128I-G159D-S188D-A232V-N248D | + |

PI = Performance Index
PI > or = 1.3 is +++; PI between 1.29 and 1.2 = ++; PI between 1.19 and 1.0 = + in detergent 36a, 36d or 36f

Example 13

Construction of Additional Libraries and Variants of GG36

This Example describes the cold water cleaning of additional GG36 variants and libraries constructed in *B. subtilis* Most DNA libraries were synthesized at DNA2.0, Inc., using the pHPLT-GG36 *B. subtilis* expression plasmid. Ligation reactions of the constructed libraries were transformed in the *B. subtilis* strain (genotype: ΔaprE, ΔnprE, amyE::xylRPxy-lAcomK-phleo after amplification of the DNA using rolling circle amplification as described in Example 4. The WCE9 and NHJ10 library and variants were created by extension PCR or QuickChange mutagenesis (see Example 4 for description of methods). WCE9 and NHJ10 library and variants were also created using the pHPLT-GG36 *B. subtilis* expression plasmid. The variants were expressed in *B. subtilis* cells (genotype: ΔaprE, ΔnprE, amyE::xylRPxy-lAcomK-phleo) as described in Example 1, and were further characterized using the BMI microswatch cleaning assay as described in Example 1. In the following tables, the detergent compositions ("Det.") correspond to those shown in Table 1-2 above. Also, as indicated, the amino acid position is listed according to BPN' numbering.

TABLE 13-1

BMI cleaning performance of WCE5 variants.

| Sequence of GG36 Variants (BPN' numbering) | PI Relative to GG36; BMI assay, Detergent 36k or 36l, 16° C. |
|---|---|
| S087R-S101G-S103A-V104I-Q109R-S212P-A232V-Q245R-E271V | +++ |
| S101G-S103A-V104I-Q109R-A232V-Q245R | +++ |
| S101G-S103A-V104I-Q109R-S212P-A232V-Q245R-E271V | +++ |
| S101G-S103A-V104I-Q109R-S212P-A232V-Q245R | +++ |
| N076D-S87R-S103A-V104I-S212P-E271V | +++ |
| N076D-S103A-V104I-Q109R | +++ |
| N076D-S103A-V104I-S212P-E271V | +++ |
| N076D-S103A-V104I-Q109R-Q245R | +++ |
| N076D-S103A-V104I-S212P-Q245L-E271V | +++ |

PI = Performance Index
PI > or = 1.5 is +++; PI between 1.49 and 1.3 = ++; PI between 1.29 and 1.0 = + in detergent 36k or 36l

TABLE 13-2

BMI cleaning performance of WCE9 variants.

| Sequence relative to GG36 (BPN' numbering) | PI Relative to GG36; BMI assay, Detergent 36j, 36d, or 36e, 16° C. |
|---|---|
| S024R-P086W-G118R | +++ |
| S024R-S078R-P086W-N243F | +++ |
| S024R-T033S-P086S-S087N-Y209A | +++ |
| T033S-G118R | +++ |
| S024R-S078R-P086W-G118R-A270T | +++ |
| S024R-T033S-P086W-G118R | +++ |
| S078R-P086W-N243F | +++ |
| T033S-S078R-P086W-G118R-Y209A | +++ |
| T033S-S078R-Y209A | +++ |
| P086W-G118R-N243F | +++ |
| S024R-P086W | +++ |
| S078R-P086W-K235F | +++ |
| S024R-G118R | +++ |
| S024R-P086R | +++ |
| S101G-S103A-V104I-A232V | +++ |
| S024R-T033S-S078R-P086W-G118R | +++ |
| S024R-G118R-Y209A | +++ |
| Y209A-W241R | +++ |
| T033S-P086W-N243F | +++ |
| T033S-A172V-Y209A | +++ |
| G118R-Y209A-N243F | +++ |
| S024R-P086S-S141G | +++ |
| S024R-G118R-Y209A-N243F | +++ |
| S024R-T033S-P086S-S085N-K235F | +++ |
| S024R-T033S-A133V | +++ |
| S024R-T033S-S078R-P086W | +++ |
| S024R-P086W-Y209A | +++ |
| S024R-W241R | +++ |
| T033S-G118R-N243F | +++ |
| S024R-K235F | +++ |
| S024R-S078R-P086W | +++ |
| S024R-G118R-Y209A-K235F | +++ |
| S024R-Y209A-W241R | +++ |
| T033S-G118R-W241R | +++ |
| P086W-G118R-Y209A | +++ |
| T033S-G118R-G159D-Y209A | +++ |
| T033S-S078R-P086W | +++ |
| S024R-P086W-N243F | +++ |
| G118R-Y209A | +++ |
| S024R-P086W-G118R-V203I | +++ |
| S078R-Y209A-K235F | +++ |
| S024R-T033S-W241R | +++ |
| S078R-G118R | +++ |
| T033S-G118R-Y209A-N243F | +++ |
| L021M-S024R-T033S | +++ |
| S024R-T033S-P086W | +++ |
| T033S-K235F | +++ |
| S078R-P086W-Y209A | +++ |
| S024R-T033S-Y209A-K235F | +++ |
| T033S-P086W-G118R | +++ |
| S024R-T033S-S078R-Y209A | +++ |
| T033S-P086W-G118R-Y209A-N243F | +++ |
| P086W-Y209A-N243F | +++ |
| P005S-S078R-G118R-W241R | +++ |
| S024R-A174T | +++ |
| T033S-Y209A-N243F | +++ |
| P086W-G118R-A133V | +++ |
| S024R-T033S-G118R | +++ |
| S024R-P086W-Y209A-K235F | ++ |
| P086W-Y209A | ++ |
| I008T-S024R | ++ |
| P086W-G118R | ++ |
| T033S-W241R | ++ |
| P005S-S024R-T033S-N243F | ++ |
| S024R-Y209A-S242P | ++ |
| S024R-T033S-S078R-G118R | ++ |
| S024R-T033S-A194T | ++ |
| S024R-N243F | ++ |
| S024R-Y209A | ++ |
| S024R-T033S-G118R-Y209A | ++ |
| T033S-P086W | ++ |
| S024R-T033S | ++ |
| S024R-T033S-S078R-N243F | ++ |
| P086W-N243F | ++ |
| T033S-G118D-A138V-Y209A | ++ |
| T033S-Y209A-K235F | ++ |
| S024R-P086R-G118R | ++ |
| T033S-P201S | ++ |
| S024R-P239Q | ++ |
| T033S-G118R-Y209A- | ++ |
| S078R-P086W | ++ |
| K235F-N243F | ++ |
| S024R-Y209A-K235F | ++ |
| G118R-A172V | ++ |
| H017Y-S024R-T033S-P086W | ++ |

TABLE 13-2-continued

BMI cleaning performance of WCE9 variants.

| Sequence relative to GG36 (BPN' numbering) | PI Relative to GG36; BMI assay, Detergent 36j, 36d, or 36e, 16° C. |
|---|---|
| T033S-L148F | ++ |
| S024R-G118R-K235F | ++ |
| T033S-S078R | ++ |
| T033S-N243F | ++ |
| S024C-T033S | ++ |
| G118R-A194T | ++ |
| T033S-Y209A | ++ |
| G118R-Y209A-K235F | ++ |
| S024R-T033S-Y209A-N243F | ++ |
| S024R-T033S-K235F | ++ |
| S024R-T033S-G118R-K235F | ++ |
| S024R-S141G | ++ |
| S024R-T274I | ++ |
| S024R-T033S-Y209A | ++ |
| P086W-K235F | + |
| S024R-Y209A-N243F | + |
| V004E-T033S-S078R | + |
| P086W-Y209A-K235F | + |
| A015T-T033S | + |
| T033S-P086W-S156L-Y209A | + |
| S024R-G118R-N243F-R269H | + |
| Y209A-K235F | + |
| S024R-R247H | + |
| S024R-T033S-A228T | + |
| S078R-K235F | + |
| S024R-T033S-A174V-K235F | + |
| S024R-K235F-N243F | + |
| S024R-T033S-K235F-W241R | + |
| S024R-T033S-A151V | + |
| S024R-V104A | + |
| T033S-A048T | + |
| Q012H-V104A-G118R | + |
| G118R-K235F | + |
| T033S-T253A | + |
| T143A-Y209A | + |
| S024R-T033S-N243F | + |
| T033S-P239T | + |
| Y209A-N243F | + |
| S024R-T033S-P129H-N184D-T253M | + |
| S024R-A085V-P086W-G118R-K235F | + |
| S024R-A272P | + |
| S024R-R269C | + |

PI = Performance Index
PI > or = 1.5 is +++; PI between 1.49 and 1.3 = ++; PI between 1.29 and 1.0 = + in detergent 36j, 36d, or 36e

TABLE 13-3

BMI cleaning performance of WCE15 variants.

| Sequence of GG36 Variants (BPN' numbering) | PI Relative to GG36; BMI assay, Detergent 36m, 16° C. |
|---|---|
| G020R-S087D-S101G-S103A-V104I-A232V-Q245R | +++ |
| G020R-S101G-S103A-V104I-V150L-A232V-Q245R | +++ |
| N018R-G020R-S024R-N076D-S087D-H249R | +++ |
| N018R-G020R-S024R-N076D-V150L-H249R | +++ |
| N018R-S024R-N043R-N076D-S087D-H249R | +++ |
| N018R-S024R-N043R-N076D-V150L-H249R | +++ |
| N018R-S024R-N076D-S078R-S087D-H249R | +++ |
| N018R-S024R-N076D-S078R-V150L-H249R | +++ |
| N018R-S024R-N076D-S087D-H249R-N269R | +++ |
| N018R-S024R-N076D-S087D-S242R-H249R | +++ |
| N018R-S024R-N076D-S087D-V150L-H249R | +++ |
| N018R-S024R-N076D-V150L-H249R | +++ |
| N018R-S087D-S101G-S103A-V104I-A232V-Q245R | +++ |
| N018R-S101G-S103A-V104I-V150L-A232V-Q245R | +++ |
| N018R-T022R-S024R-N076D-S087D-H249R | +++ |
| N018R-T022R-S024R-N076D-V150L-H249R | +++ |
| N043R-S087D-S101G-S103A-V104I-A232V-Q245R-N269R | +++ |
| N043R-S101G-S103A-V104I-V150L-A232V-Q245R | +++ |
| S024R-S087D-S101G-S103A-V104I-A232V-Q245R | +++ |
| S024R-S101G-S103A-V104I-V150L-A232V-Q245R | +++ |
| S078R-S087D-S101G-S103A-V104I-A232V-Q245R | +++ |
| S078R-S101G-S103A-V104I-V150L-A232V-Q245R | +++ |
| S087D-S101G-S103A-V104I-A232V-Q245R-N269R | +++ |
| S101G-S103A-V104I-V150L-A232V-Q245R-H249R | +++ |
| S101G-S103A-V104I-V150L-A232V-Q245R-N269R | +++ |
| T022R-S087D-S101G-S103A-V104I-A232V-Q245R | +++ |
| N018R-S024R-N043D-N076D-V150L-H249R | ++ |
| N043R-S087D-S101G-S103A-V104I-A232V-Q245R | ++ |
| T022R-S101G-S103A-V104I-V150L-A232V-Q245R | ++ |
| N018R-S024R-N043D-N076D-S087D-H249R | + |
| N018R-S024R-N076D-S087D-H249R | + |
| N018R-S024R-N076D-V150L-S242R-H249R | + |
| N043R-S101G-S103A-V104I-V150L-A232V-Q245R-N269R | + |
| N076D-S101G-S103A-V104I-V150L-A232V-Q245R | + |
| S087D-S101G-S103A-V104I-A232V-S242R-Q245R | + |
| S101G-S103A-V104I-V150L-A232V-Q245R | + |
| N076D-S087D-S101G-S103A-V104I-A232V-Q245R | + |
| S087D-S101G-S103A-V104I-A232V-Q245R | + |
| S101G-S103A-V104I-V150L-A232V-S242R-Q245R | + |

PI = Performance Index
PI > or = 1.5 is +++; PI between 1.49 and 1.3 = ++; PI between 1.29 and 1.0 = + in detergent 36m

TABLE 13-4

BMI cleaning performance of NHJ14 library variants.

| Sequence of GG36 Variants (BPN' numbering) | PI Relative to GG36; BMI assay, Detergent 36c, 16° C. |
|---|---|
| S024R-S101G-S103A-V104I-P129Q-A158E-S188D-L217E-A232V-Q245R-N248D-H249R | +++ |
| S024R-S101G-S103A-V104I-S130A-A158E-N183D-S188D-A232V-Q245R-N248D-H249R | +++ |
| S024R-S101G-S103A-V104I-P129Q-A158E-N183D-S188D-A232V-Q245R-N248D-H249R | +++ |
| S101G-S103A-V104I-S130A-A158E-S188D-A232V-Q245R-N248D-H249R | +++ |
| S024R-S101G-S103A-V104I-P129Q-A158E-S188D-A232V-Q245R-N248D-H249R | +++ |
| S024R-S101G-S103A-V104I-S130A-A158E-S188D-A232V-Q245R-N248D-H249R | +++ |
| S024R-S101G-S103A-V104I-P129Q-S130A-A158E-N183D-S188D-A232V-Q245R-N248D-H249R | +++ |
| S024R-S101G-S103A-V104I-S128L-P129Q-A158E-S188D-A232V-Q245R-N248D-H249R | +++ |
| S024R-S101G-S103A-V104I-P129Q-S130A-A158E-S188D-A232V-Q245R-N248D-H249R | ++ |
| S101G-S103A-V104I-P129Q-A158E-S188D-A232V-Q245R-N248D-H249R | ++ |
| S101G-S103A-V104I-P129Q-S130A-A158E-S188D-A232V-Q245R-N248D-H249R | ++ |
| S024R-S101G-S103A-V104I-S128L-P129Q-S130A-A158E-S188D-A232V-Q245R-N248D-H249R | ++ |
| S101G-S103A-V104I-S128L-P129Q-A158E-S188D-A232V-Q245R-N248D-H249R | ++ |
| S024R-K027R-S101G-S103A-V104I-S128L-P129Q-S130A-A158E-S188D-A232V-Q245R-N248D-H249R | ++ |

PI = Performance Index
PI > or = 1.5 is +++; PI between 1.49 and 1.3 = ++; PI between 1.29 and 1.0 = + in detergent of Example 36c

TABLE 13-5

BMI cleaning performance of NHJ10 variants.

| Sequence of GG36 Variants (BPN' numbering) | PI Relative to GG36; BMI assay, Detergent 36a, 16° C. |
|---|---|
| S101G-S103A-V104I-A232V-M222Q-Q245R | +++ |
| S101G-S103A-V104I-A158E-S188D-M222S-A232V-Q245R-N248D-H249R | +++ |
| S101G-S103A-V104I-A158E-S188D-M222Q-A232V-Q245R-N248D-H249R | +++ |
| N076D-S101G-S103A-V104I-A232V-M222Q-Q245R | +++ |
| S101G-S103A-V104I-A232V-M222S-Q245R | ++ |
| N076D-S101G-S103A-V104I-A232V-M222S-Q245R | ++ |
| N076D-S101G-S103A-V104I-A158E-S188D-M222S-A232V-Q245R-N248D-H249R | + |

PI = Performance Index
PI > or = 1.3 is +++; PI between 1.29 and 1.2 = ++; PI between 1.19 and 1.0 = + in detergent 36a

TABLE 13-6

BMI cleaning performance of NHJ14 library variants.

| Sequence of GG36 Variants (BPN' numbering) | PI Relative to GG36; BMI assay, Detergent 36f, 16° C. |
|---|---|
| S024R-S101G-S103A-V104I-S128L-P129Q-A158E-S188D-A232V-Q245R-N248D-H249R | +++ |
| S101G-S103A-V104I-S130A-A158E-S188D-A232V-Q245R-N248D-H249R | +++ |
| S024R-S101G-S103A-V104I-A158E-S188D-A232V-Q245R-N248D-H249R | ++ |
| S101G-S103A-V104I-S128L-P129Q-A158E-S188D-A232V-Q245R-N248D-H249R | ++ |
| S101G-S103A-V104I-P129Q-S130A-A158E-S188D-A232V-Q245R-N248D-H249R | ++ |
| S101G-S103A-V104I-S130A-A158E-N183D-S188D-L217E-A232V-Q245R-N248D-H249R | ++ |
| S024R-S101G-S103A-V104I-S128L-P129Q-S130A-A158E-S188D-A232V-Q245R-N248D-H249R | ++ |
| S024R-S101G-S103A-V104I-P129Q-A158E-S188D-L217E-A232V-Q245R-N248D-H249R | ++ |
| S101G-S103A-V104I-S128L-S130A-A158E-S188D-L217E-A232V-Q245R-N248D-H249R | ++ |
| S024R-S101G-S103A-V104I-S128L-P129Q-A158E-N183D-S188D-A232V-Q245R-N248D-H249R | + |
| S024R-S101G-S103A-V104I-S128L-P129Q-S130A-A158E-N183D-S188D-A232V-Q245R-N248D-H249R | + |
| S024R-S101G-S103A-V104I-S128L-P129Q-A158E-S188D-A232V-Q245R-N248D-H249R-E271G | + |
| S101G-S103A-V104I-P129Q-A158E-N183D-S188D-A232V-Q245R-N248D-H249R | + |
| S024R-S101G-S103A-V104I-S130A-A158E-S188D-L217E-A232V-Q245R-N248D-H249R | + |
| S024R-S101G-S103A-V104I-S128L-A158E-N183D-S188D-A232V-Q245R-N248D-H249R | + |
| S101G-S103A-V104I-P129Q-A158E-S188D-L217E-A232V-Q245R-N248D-H249R | + |
| S024R-S101G-S103A-V104I-S128L-S130A-A158E-S188D-A232V-Q245R-N248D-H249R | + |

PI = Performance Index
PI > or = 1.3 is +++; PI between 1.29 and 1.2 = ++; PI between 1.19 and 1.0 = + in detergent 36f

Example 14

Granular and/or Tablet Laundry Compositions

This Example provides various formulations for granular and/or tablet laundry detergents. The following laundry compositions of present invention, which may be in the form of granules or tablet, are provided below. In each of these formulations, at least one protease variant provided herein is included at a concentration of from about 0.0001 to about 10 weight percent. In some alternative embodiments, other concentrations will find use, as determined by the formulator, based on their needs.

TABLE 14-1

Granular and/or Tablet Laundry Compositions

| Compound Base Product | I | II | III | IV | V |
|---|---|---|---|---|---|
| $C_{14}$-$C_{15}$AS or TAS | 8.0 | 5.0 | 3.0 | 3.0 | 3.0 |
| LAS | 8.0 | — | 8.0 | — | 7.0 |
| $C_{12}$-$C_{15}$AE$_3$S | 0.5 | 2.0 | 1.0 | — | — |
| $C_{12}$-$C_{15}$E$_5$ or E$_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |
| MA/AA | 2.0 | 2.0 | 2.0 | — | — |
| AA | — | — | — | — | 4.0 |
| 3Na Citrate 2H$_2$O | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |
| Percarbonate | — | — | 3.8 | 5.2 | — |
| NOBS | 1.9 | — | — | — | — |
| NACA OBS | — | — | 2.0 | — | — |
| TAED | 0.5 | 2.0 | 2.0 | 5.0 | 1.00 |
| BB1 | 0.06 | — | 0.34 | — | 0.14 |
| BB2 | — | 0.14 | — | 0.20 | — |
| Anhydrous Na Carbonate | 15.0 | 18.0 | — | 15.0 | 15.0 |
| Sulfate | 5.0 | 12.0 | 5.0 | 17.0 | 3.0 |
| Silicate | — | 1.0 | — | — | 8.0 |
| nprE (optional) | 0.03 | — | 0.1 | 0.06 | — |
| PMN | — | 0.05 | — | — | 0.1 |
| Protease B (optional) | — | 0.01 | — | — | — |
| Protease C (optional) | — | — | — | 0.01 | — |
| Lipase | — | 0.008 | — | — | — |
| Amylase | 0.001 | — | — | — | 0.001 |
| Cellulase | — | 0.0014 | — | — | — |
| Pectin Lyase | 0.001 | 0.001 | 0.001 | 0.001 | 0.001 |
| Aldose Oxidase | 0.03 | — | 0.05 | — | — |
| PAAC | — | 0.01 | — | — | 0.05 |
| Balance to 100% Moisture and/or Minors* | | | | | |

*Perfume, dye, brightener/SRP1/Na carboxymethylcellulose/photobleach/MgSO$_4$/PVPVI/suds suppressor/high molecular PEG/clay.

Example 15

Tablet Detergent Compositions

This Example provides various tablet detergent formulations. The following tablet detergent compositions of the present invention are prepared by compression of a granular dishwashing detergent composition at a pressure of 13 KN/cm$^2$ using a standard 12 head rotary press. In each of these formulations, at least one protease variant provided herein is included at a concentration of from about 0.0001 to about 10 weight percent. In some alternative embodiments, other concentrations will find use, as determined by the formulator, based on their needs.

TABLE 15-1

Tablet Detergent Compositions

| Compound | I | II | III | IV | V | VI | VII | VIII |
|---|---|---|---|---|---|---|---|---|
| STPP | — | 48.8 | 44.7 | 38.2 | — | 42.4 | 46.1 | 46.0 |
| 3Na Citrate 2H$_2$O | 20.0 | — | — | — | 35.9 | — | — | — |
| Na Carbonate | 20.0 | 5.0 | 14.0 | 15.4 | 8.0 | 23.0 | 20.0 | — |
| Silicate | 15.0 | 14.8 | 15.0 | 12.6 | 23.4 | 2.9 | 4.3 | 4.2 |
| Lipase | 0.001 | — | 0.01 | — | 0.02 | — | — | — |
| Protease B (optional) | 0.01 | — | — | — | — | — | — | — |
| Protease C (optional) | — | — | — | — | — | 0.01 | — | — |
| nprE (optional) | 0.01 | 0.08 | — | 0.04 | — | 0.023 | — | 0.05 |
| PMN | — | — | 0.05 | — | 0.052 | — | 0.023 | — |
| Amylase | 0.012 | 0.012 | 0.012 | — | 0.015 | — | 0.017 | 0.002 |
| Pectin Lyase | 0.005 | — | — | 0.002 | — | — | — | — |
| Aldose Oxidase | — | 0.03 | — | 0.02 | 0.02 | — | 0.03 | — |
| PB1 | — | — | 3.8 | — | 7.8 | — | — | 4.5 |
| Percarbonate | 6.0 | — | — | 6.0 | — | 5.0 | — | — |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| PAAC | 0.01 | 0.01 | 0.02 | — | — | — | — | — |
| DETBCHD | — | — | — | 0.02 | 0.02 | — | — | — |
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |
| Glycerol | — | — | — | — | — | 0.4 | — | 0.5 |
| Perfume | — | — | — | 0.05 | 0.2 | 0.2 | 0.2 | 0.2 |
| Balance to 100% Moisture and/or Minors* | | | | | | | | |

*Brightener/SRP1/Na carboxymethylcellulose/photobleach/MgSO$_4$/PVPVI/suds suppressor/high molecular PEG/clay.

The pH of Examples 15(I) through 15(VII) is from about 10 to about 11.5; pH of 15(VIII) is from 8-10. The tablet weight of Examples 15(I) through 15(VIII) is from about 20 grams to about 30 grams.

Example 16

Liquid Laundry Detergent Compositions

In this Example, various formulations for liquid laundry detergent compositions are provided. The following liquid laundry detergent compositions of the present invention are prepared as shown below. In each of these formulations, at least one protease variant provided herein is included at a concentration of from about 0.0001 to about 10 weight percent. In some alternative embodiments, other concentrations will find use, as determined by the formulator, based on their needs.

TABLE 16-1

Liquid Laundry Detergent Compositions

| Compound | I | II | III | IV | V |
|---|---|---|---|---|---|
| LAS | 24.0 | 32.0 | 6.0 | 3.0 | 6.0 |
| NaC$_{16}$-C$_{17}$ HSAS | — | — | — | 5.0 | — |
| C$_{12}$-C$_{15}$ AE$_{1.8}$S | — | — | 8.0 | 7.0 | 5.0 |
| C$_8$-C$_{10}$ propyl dimethyl amine | 2.0 | 2.0 | 2.0 | 2.0 | 1.0 |
| C$_{12}$-C$_{14}$ alkyl dimethyl amine oxide | — | — | — | — | 2.0 |
| C$_{12}$-C$_{15}$ AS | — | — | 17.0 | — | 8.0 |
| CFAA | — | 5.0 | 4.0 | 4.0 | 3.0 |

TABLE 16-1-continued

Liquid Laundry Detergent Compositions

| Compound | I | II | III | IV | V |
|---|---|---|---|---|---|
| $C_{12}$-$C_{14}$ Fatty alcohol ethoxylate | 12.0 | 6.0 | 1.0 | 1.0 | 1.0 |
| $C_{12}$-$C_{18}$ Fatty acid | 3.0 | — | 4.0 | 2.0 | 3.0 |
| Citric acid (anhydrous) | 4.5 | 5.0 | 3.0 | 2.0 | 1.0 |
| DETPMP | — | — | 1.0 | 1.0 | 0.5 |
| Monoethanolamine | 5.0 | 5.0 | 5.0 | 5.0 | 2.0 |
| Sodium hydroxide | — | — | 2.5 | 1.0 | 1.5 |
| 1N HCl aqueous solution | #1 | #1 | — | — | — |
| Propanediol | 12.7 | 14.5 | 13.1 | 10. | 8.0 |
| Ethanol | 1.8 | 2.4 | 4.7 | 5.4 | 1.0 |
| DTPA | 0.5 | 0.4 | 0.3 | 0.4 | 0.5 |
| Pectin Lyase | — | — | — | 0.005 | — |
| Amylase | 0.001 | 0.002 | — | — | — |
| Cellulase | — | — | 0.0002 | — | 0.0001 |
| Lipase | 0.1 | — | 0.1 | — | 0.1 |
| NprE (optional) | 0.05 | 0.3 | — | 0.5 | 0.2 |
| PMN | — | — | 0.08 | — | — |
| Protease A (optional) | — | — | — | — | 0.1 |
| Aldose Oxidase | — | — | 0.3 | — | 0.003 |
| ZnCl2 | 0.1 | 0.05 | 0.05 | 0.05 | 0.02 |
| Ca formate | 0.05 | 0.07 | 0.05 | 0.06 | 0.07 |
| DETBCHD | — | — | 0.02 | 0.01 | — |
| SRP1 | 0.5 | 0.5 | — | 0.3 | 0.3 |
| Boric acid | — | — | — | — | 2.4 |
| Sodium xylene sulfonate | — | — | 3.0 | — | — |
| Sodium cumene sulfonate | — | — | — | 0.3 | 0.5 |
| DC 3225C | 1.0 | 1.0 | 1.0 | 1.0 | 1.0 |
| 2-butyl-octanol | 0.03 | 0.04 | 0.04 | 0.03 | 0.03 |
| Brightener 1 | 0.12 | 0.10 | 0.18 | 0.08 | 0.10 |
| Balance to 100% perfume/dye and/or water | | | | | |

1: Add 1N HCl aq. soln to adjust the neat pH of the formula in the range from about 3 to about 5.

The pH of Examples above 16(I)-(II) is about 5 to about 7, and of 16(III)-(V) is about 7.5 to about 8.5.

TABLE 16-2

Liquid Laundry Detergents

| Compound | I | II | III | IV | V | VI |
|---|---|---|---|---|---|---|
| LAS | 11.5 | 11.5 | 9.0 | — | 4.0 | — |
| $C_{12}$-$C_{15}AE_{2.85}$S | — | — | 3.0 | 18.0 | — | 16.0 |
| $C_{14}$-$C_{15}E_{2.5}$ S | 11.5 | 11.5 | 3.0 | — | 16.0 | — |
| $C_{12}$-$C_{13}E_9$ | — | — | 3.0 | 2.0 | 2.0 | 1.0 |
| $C_{12}$-$C_{13}E_7$ | 3.2 | 3.2 | — | — | — | — |
| CFAA | — | — | — | 5.0 | — | 3.0 |
| TPKFA | 2.0 | 2.0 | — | 2.0 | 0.5 | 2.0 |
| Citric Acid (Anhydrous) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| ZnCl2 | 0.1 | 0.05 | 0.06 | 0.03 | 0.05 | 0.05 |
| Na Culmene Sulfonate | 4.0 | 4.0 | 1.0 | 3.0 | 1.2 | — |
| Borate | 0.6 | 0.6 | 1.5 | — | — | — |
| Na Hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Monoethanolamine | 3.0 | 3.0 | 1.5 | 1.0 | 2.5 | 1.0 |
| TEPAE | 2.0 | 2.0 | — | 1.0 | 1.0 | 1.0 |
| nprE (optional) | 0.03 | 0.05 | — | 0.03 | — | 0.02 |
| PMN | — | — | 0.01 | — | 0.08 | — |
| Protease A (optional) | — | — | 0.01 | — | — | — |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | — | — | — |
| Aldose Oxidase | 0.05 | — | — | 0.05 | — | 0.02 |
| Galactose oxidase | — | 0.04 | — | — | — | — |
| PAAC | 0.03 | 0.03 | 0.02 | — | — | — |
| DETBCHD | — | — | — | 0.02 | 0.01 | — |
| SRP 1 | 0.2 | 0.2 | — | 0.1 | — | — |
| DTPA | — | — | — | 0.3 | — | — |
| PVNO | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |
| Balance to 100% perfume/dye and/or water | | | | | | |

Example 17

Hand Dish Liquid Detergent Compositions

In this Example, various hand dish liquid detergent formulations are provided. The following hand dish liquid detergent compositions of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

TABLE 17-1

Hand Dish Liquid Detergent Compositions

| Compound | I | II | III | IV | V | VI |
|---|---|---|---|---|---|---|
| $C_{12}$-$C_{15}AE_{1.8}S$ | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| $C_{10}$-$C_{18}$ Alkyl Dimethyl Amine Oxide | 5.0 | 3.0 | 7.0 | — | — | — |
| Betaine | 3.0 | — | 1.0 | 3.0 | 1.0 | — |
| $C_{12}$ poly-OH fatty acid amide | — | — | — | 3.0 | — | 1.0 |
| $C_{14}$ poly-OH fatty acid amide | — | 1.5 | — | — | — | — |
| $C_{11}E_9$ | 2.0 | — | 4.0 | — | — | 20.0 |
| DTPA | — | — | — | — | 0.2 | — |
| Tri-sodium Citrate dehydrate | 0.25 | — | — | 0.7 | — | — |
| Diamine | 1.0 | 5.0 | 7.0 | 1.0 | 5.0 | 7.0 |
| $MgCl_2$ | 0.25 | — | — | 1.0 | — | — |
| nprE (optional) | 0.02 | 0.01 | — | 0.01 | — | 0.05 |
| PMN | — | — | 0.03 | — | 0.02 | — |
| Protease A (optional) | — | 0.01 | — | — | — | — |
| Amylase | 0.001 | — | — | 0.002 | — | 0.001 |
| Aldose Oxidase | 0.03 | — | 0.02 | — | 0.05 | — |
| Sodium Cumene Sulphonate | — | — | — | 2.0 | 1.5 | 3.0 |
| PAAC | 0.01 | 0.01 | 0.02 | — | — | — |
| DETBCHD | — | — | — | 0.01 | 0.02 | 0.01 |
| Balance to 100% perfume/dye and/or water | | | | | | |

The pH of Examples 17(I)-(VI) is about 8 to about 11

Example 18

Liquid Automatic Dishwashing Detergent Compositions

In this Example, various liquid automatic dishwashing detergent formulations are provided. The following hand dish liquid detergent compositions of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

TABLE 18-1

Liquid Automatic Dishwashing Detergent Compositions

| Compound | I | II | III | IV | V |
|---|---|---|---|---|---|
| STPP | 16 | 16 | 18 | 16 | 16 |
| Potassium Sulfate | — | 10 | 8 | — | 10 |
| 1,2 propanediol | 6.0 | 0.5 | 2.0 | 6.0 | 0.5 |
| Boric Acid | — | — | — | 4.0 | 3.0 |
| $CaCl_2$ dihydrate | 0.04 | 0.04 | 0.04 | 0.04 | 0.04 |
| Nonionic | 0.5 | 0.5 | 0.5 | 0.5 | 0.5 |
| nprE (optional) | 0.1 | 0.03 | — | 0.03 | — |
| PMN | — | — | 0.05 | — | 0.06 |
| Protease B (optional) | — | — | — | 0.01 | — |
| Amylase | 0.02 | — | 0.02 | 0.02 | — |
| Aldose Oxidase | — | 0.15 | 0.02 | — | 0.01 |
| Galactose Oxidase | — | — | 0.01 | — | 0.01 |
| PAAC | 0.01 | — | — | 0.01 | — |
| DETBCHD | — | 0.01 | — | — | 0.01 |
| Balance to 100% perfume/dye and/or water | | | | | |

Example 19

High Density Dishwashing Detergents

This Example provides various formulations for high density dishwashing detergents. The following compact high density dishwashing detergents of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

TABLE 19-1

High Density Dishwashing Detergents

| Compound | I | II | III | IV | V | VI |
|---|---|---|---|---|---|---|
| STPP | — | 45.0 | 45.0 | — | — | 40.0 |
| 3Na Citrate $2H_2O$ | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |
| PB1 | — | — | 4.5 | — | — | — |
| PB4 | — | — | — | 5.0 | — | — |
| Percarbonate | — | — | — | — | — | 4.8 |
| BB1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| PAAC | 0.03 | 0.05 | 0.02 | — | — | — |
| Paraffin | 0.5 | 0.4 | 0.4 | 0.6 | — | — |
| nprE (optional) | 0.072 | 0.053 | — | 0.026 | — | 0.01 |
| PMN | — | — | 0.053 | — | 0.059 | — |
| ProteaseB (optional) | — | — | — | — | — | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| BTA | 0.3 | 0.2 | 0.2 | 0.3 | 0.3 | 0.3 |
| Polycarboxylate | 6.0 | — | — | — | 4.0 | 0.9 |
| Perfume | 0.2 | 0.1 | 0.1 | 0.2 | 0.2 | 0.2 |
| Balance to 100% Moisture and/or Minors* | | | | | | |

*Brightener/dye/SRP1/Na carboxymethylcellulose/photobleach/$MgSO_4$/PVPVI/suds suppressor/high molecular PEG/clay.
The pH of Examples 19(I) through (VI) is from about 9.6 to about 11.3.

Example 20

Liquid Hard Surface Cleaning Detergents

This Example provides various formulations for liquid hard surface cleaning detergents. The following liquid hard surface cleaning detergent compositions of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

TABLE 20-1

Liquid Hard Surface Cleaning Detergents

| Compound | I | II | III | IV | V | VI | VII |
|---|---|---|---|---|---|---|---|
| $C_9$-$C_{11}E_5$ | 2.4 | 1.9 | 2.5 | 2.5 | 2.5 | 2.4 | 2.5 |
| $C_{12}$-$C_{14}E_5$ | 3.6 | 2.9 | 2.5 | 2.5 | 2.5 | 3.6 | 2.5 |
| $C_7$-$C_9E_6$ | — | — | — | — | 8.0 | — | — |
| $C_{12}$-$C_{14}E_{21}$ | 1.0 | 0.8 | 4.0 | 2.0 | 2.0 | 1.0 | 2.0 |
| LAS | — | — | — | 0.8 | 0.8 | — | 0.8 |
| Sodium culmene sulfonate | 1.5 | 2.6 | — | 1.5 | 1.5 | 1.5 | 1.5 |
| Isachem ® | 0.6 | 0.6 | — | — | — | 0.6 | — |
| $Na_2CO_3$ | 0.6 | 0.13 | 0.6 | 0.1 | 0.2 | 0.6 | 0.2 |
| 3Na Citrate $2H_2O$ | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | — | 0.5 | — | — |
| PAAC | — | — | — | 0.03 | 0.03 | 0.03 | — |
| DETBCHD | 0.03 | 0.05 | 0.05 | — | — | — | — |
| nprE (optional) | 0.07 | — | 0.08 | 0.03 | — | 0.01 | 0.04 |
| PMN | — | 0.05 | — | — | 0.06 | — | — |
| Protease B (optional) | — | — | — | — | — | 0.01 | — |
| Amylase | 0.12 | 0.01 | 0.01 | — | 0.02 | — | 0.01 |
| Lipase | — | 0.001 | — | 0.005 | — | 0.005 | — |
| Pectin Lyase | 0.001 | — | 0.001 | — | — | — | 0.002 |
| ZnCl2 | 0.02 | 0.01 | 0.03 | 0.05 | 0.1 | 0.05 | 0.02 |
| Calcium Formate | 0.03 | 0.03 | 0.01 | — | — | — | — |
| PB1 | — | 4.6 | — | 3.8 | — | — | — |
| Aldose Oxidase | 0.05 | — | 0.03 | — | 0.02 | 0.02 | 0.05 |
| Balance to 100% perfume/dye and/or water | | | | | | | |

The pH of Examples 20(I) through (VII) is from about 7.4 to about 9.5.

Example 21

Automatic Dishwash Performance Tests

In this Example, methods used to determine the wash performance of protease variants using some commercially available dish detergents are described. These protease variants are tested under various conditions. These detergents are commercially available from WFK and are referred to by the designations provided below. The protocols for each of the stain types (minced meat, egg yolk, and egg yolk with milk) are provided below. Before the individual soil types can be applied to the test dishes, the dishes must be thoroughly ashed. This is particularly necessary, as residues of certain persistent stains may still be present on the dishes from previous tests. New dishes were also subjected to three thorough washes before being used for the first time in a test.

The washing tests are typically performed in an automatic dishwasher (e.g., Miele: G690SC), equipped with soiled dishes and stainless steel sheets, as described above. A defined amount of the detergent is used, as indicated in the tables of results below. In some experiments, the temperatures tested are 45° C., 55° C. and 65° C. In some experiments, the water hardness is 9° or 21° GH (German hardness) (374 ppm Ca).

As indicated above, after washing, the plates soiled with minced meat or pasta/sauce/meat/cheese are visually assessed using a photo rating scale of from 0 to 10, wherein "0" designated a completely dirty plate and "10" designated a clean plate. These values correspond to the stain or soil removal (SR) capability of the enzyme-containing detergent.

The washed stainless steel plates soiled with egg yolk and/or egg yolk milk (are analyzed gravimetrically to determine the amount of residual stain after washing.

Some exemplary detergents are provided below.

TABLE 21-1

Phosphate-Free Detergent IEC-60436
WFK Type B (pH = 10.4 in 3 g/l)

| Component | Wt % |
|---|---|
| Sodium citrate dehydrate | 30.0 |
| Maleic acid/acrylic acid copolymer sodium Salt (SOKALAN ® CP5; BASF) | 12.0 |
| Sodium perborate monohydrate | 5.0 |
| TAED | 2.0 |
| Sodium disilicate: Protil A (Cognis) | 25.0 |
| Linear fatty alcohol ethoxylate | 2.0 |
| Sodium carbonate anhydrous | add to 100 |

TABLE 21-2

Phosphate-Containing Detergent: IEC-60436
WFK Type C (pH = 10.5 in 3 g/l))

| Component | Wt % |
|---|---|
| Sodium tripolyphosphate | 23.0 |
| Sodium citrate dehydrate | 22.3 |
| Maleic acid/Acrylic Acis Copolymer Sodium Salt | 4.0 |
| Sodium perborate monohydrate | 6.0 |
| TAED | 2.0 |
| Sodium disilicate: Protil A (Cognis) | 5.0 |
| Linear Fatty Alcohol Ethoxylate | 2.0 |
| Sodium Carbonate anhydrous | add to 100 |

We claim:

1. An isolated subtilisin variant, wherein said subtilisin variant is a mature form having proteolytic activity and comprises an amino acid sequence comprising the combination of amino acid substitutions S188D-E271F, wherein the total net charge of the variant is 0, +1, +2, +3, +4, +5, −1, −2, −3, −4, or −5 relative to the total net charge of the Bacillus lentus subtilisin GG36 protease, and wherein the total net charge is obtained by one or more substitutions selected from: N43D, R45T, N62E, N76D, S101D, P129E, A158E, G159D, G159E, S166D, S188D, A230E, N18R, G20K, G20R, T22R, S24R, N43R, G118R, Q245R, H249R, N269R, E271F, and E271L, wherein the variant is a variant of a parent protease Bacillus lentus subtilisin GG36 protease comprising the amino acid sequence shown in SEQ ID NO: 2, and wherein amino acid positions of the protease variant are numbered according to the numbering of corresponding amino acid positions in the amino acid sequence of Bacillus amyloliquefaciens subtilisin BPN' shown in SEQ ID NO:1, and wherein the variant has at least 90% amino acid sequence identity over its full length to SEQ ID NO: 2.

2. The isolated subtilisin variant of claim 1 having proteolytic activity comprising an amino acid sequence comprising a combination of amino acid substitutions selected from: T022A-N043R-S101G-S103A-V104I-G159D-S188D-L217E-A232V-Q245R-N248D-E271F, T022A-S101G-S103A-V104I-G159D-S188D-A232V-Q245R-N248D-E271F, T022A-N076D-S101G-S103A-V104I-G159D-S188D-A232V-Q245R-N248D-E271F, and T022A-N043R-N076D-S101G-S103A-V104I-G159D-S188D-A232V-Q245R-N248D-E271F, wherein the amino acid positions of the subtilisin variant are numbered by correspondence with the amino acid sequence of *B. amyloliquefaciens* subtilisin BPN' set forth as SEQ ID NO:1.

3. The subtilisin variant of claim 1, wherein said protease variant comprises an amino acid sequence which differs from the amino acid sequence of SEQ ID NO:2, and wherein the total net charge of the protease variant is 0, +1, +2, +3, +4, +5, −1, −2, −3, −4, or −5 relative to the total net charge of the *Bacillus lentus* subtilisin GG36 protease, wherein the parent protease is GG36, and wherein amino acid positions of the protease variant are numbered according to the numbering of corresponding amino acid positions in the amino acid sequence of *Bacillus amyloliquefaciens* subtilisin BPN' shown in SEQ ID NO:1.

4. The subtilisin variant of claim 1, wherein the variant has at least 95% identity to SEQ ID NO: 2.

5. The subtilisin variant of claim 1, wherein the subtilisin variant has one or more of the following characteristics: a) a Test Method 2 performance index of at least 1.1; b) a Test Method 3 performance index of at least 1.1; c) a Test Method 4 performance index of at least 1.1; and/or d) a Test Method 6 performance index of at least 1.1.

6. A composition comprising at least one subtilisin variant of claim 1, wherein said composition is a fabric and home care product.

7. The composition of claim 6, wherein said composition is a cleaning composition.

8. The composition of claim 6, wherein said cleaning composition is a granular, powder, solid, bar, liquid, tablet, gel, or paste composition.

9. The composition of claim 6, further comprising at least one bleaching agent.

10. The composition of claim 6, wherein said cleaning composition is phosphate-free.

11. The composition of claim 6, wherein said cleaning composition contains phosphate.

12. The composition of claim 6, further comprising at least one additional enzyme.

13. The composition of claim 12, wherein said at least one additional enzyme is selected from hemicellulases, cellulases, peroxidases, proteases, metalloproteases, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidases, chondroitinases, laccases, and amylases, and any combination thereof.

14. A method of cleaning, comprising contacting a surface or an item with a cleaning composition comprising at least one subtilisin variant of claim 1.

* * * * *

SEQUENCE LISTING

<160> NUMBER OF SEQ ID NOS: 82

<210> SEQ ID NO 1
<211> LENGTH: 275
<212> TYPE: PRT
<213> ORGANISM: Bacillus amyloliquefaciens

<400> SEQUENCE: 1

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 2
<211> LENGTH: 269
<212> TYPE: PRT
<213> ORGANISM: Bacillus lentus

<400> SEQUENCE: 2

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
```

```
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 3
<211> LENGTH: 1143
<212> TYPE: DNA
<213> ORGANISM: Bacillus lentus

<400> SEQUENCE: 3
gtgagaagca aaaaattgtg gatcgtcgcg tcgaccgcac tactcatttc tgttgctttc     60
agttcatcga tcgcatcggc tgctgaagaa gcaaaagaaa aatatttaat tggctttaat    120
gagcaggaag ctgtcagtga gtttgtagaa caagtagagg caaatgacga ggtcgccatt    180
ctctctgagg aagaggaagt cgaaattgaa ttgcttcatg aatttgaaac gattcctgtt    240
ttatccgttg agttaagccc agaagatgtg gacgcgcttg agctcgatcc agcgatttct    300
tatattgaag aggatgcaga agtaacgaca atggcgcaat cagtgccatg gggaattagc    360
cgtgtgcaag ccccagctgc ccataaccgt ggattgacag gttctggtgt aaaagttgct    420
gtcctcgata caggtatttc cactcatcca gacttaaata ttcgtggtgg cgctagcttt    480
gtaccagggg aaccatccac tcaagatggg aatgggcatg gcacgcatgt ggccgggacg    540
attgctgctt taaacaattc gattggcgtt cttggcgtag cgccgagcgc ggaactatac    600
gctgttaaag tattaggggc gagcggttca ggttcggtca gctcgattgc ccaaggattg    660
gaatgggcag ggaacaatgg catgcacgtt gctaatttga gtttaggaag cccttcgcca    720
agtgccacac ttgagcaagc tgttaatagc gcgacttcta gaggcgttct tgttgtagcg    780
gcatctggaa attcaggtgc aggctcaatc agctatccgg cccgttatgc gaacgcaatg    840
```

-continued

```
gcagtcggag ctactgacca aaacaacaac cgcgccagct tttcacagta tggcgcaggg      900
cttgacattg tcgcaccagg tgtaaacgtg cagagcacat acccaggttc aacgtatgcc      960
agcttaaacg gtacatcgat ggctactcct catgttgcag gtgcagcagc ccttgttaaa     1020
caaaagaacc catcttggtc caatgtacaa atccgcaatc atctaaagaa tacggcaacg     1080
agcttaggaa gcacgaactt gtatggaagc ggacttgtca atgcagaagc tgcaactcgt     1140
taa                                                                   1143
```

<210> SEQ ID NO 4
<211> LENGTH: 380
<212> TYPE: PRT
<213> ORGANISM: Bacillus lentus

<400> SEQUENCE: 4

```
Val Arg Ser Lys Lys Leu Trp Ile Val Ala Ser Thr Ala Leu Leu Ile
1               5                   10                  15

Ser Val Ala Phe Ser Ser Ser Ile Ala Ser Ala Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
        195                 200                 205

Gly Ser Gly Ser Val Ser Ser Ile Ala Gln Gly Leu Glu Trp Ala Gly
    210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Gly Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
```

```
305                 310                 315                 320
Ser Leu Asn Gly Thr Ser Met Ala Thr Pro His Val Ala Gly Ala Ala
                325                 330                 335

Ala Leu Val Lys Gln Lys Asn Pro Ser Trp Ser Asn Val Gln Ile Arg
            340                 345                 350

Asn His Leu Lys Asn Thr Ala Thr Ser Leu Gly Ser Thr Asn Leu Tyr
        355                 360                 365

Gly Ser Gly Leu Val Asn Ala Glu Ala Ala Thr Arg
    370                 375                 380

<210> SEQ ID NO 5
<211> LENGTH: 1143
<212> TYPE: DNA
<213> ORGANISM: Artificial Sequence
<220> FEATURE:
<223> OTHER INFORMATION: synthetic GG36-9 variant

<400> SEQUENCE: 5
gtgagaagca aaaaattgtg atcgtcgcg tcgaccgcac tactcatttc tgttgctttt      60
agttcatcga tcgcatcggc tgctgaagaa gcaaaagaaa aatatttaat tggctttaat    120
gagcaggaag ctgtcagtga gtttgtgaaa caagtagagg caaatgacga ggtcgccatt    180
ctctctgagg aagaggaagt cgaaattgaa ttgcttcatg aatttgaaac gattcctgtt    240
ttatccgttg agttaagccc agaagatgtg acgcgcttg aactcgatcc agcgatttct    300
tatattgaag aggatgcaga agtaacgaca atggcgcaat cagtgccatg gggaattagc    360
cgtgtgcaag ccccggctgc ccataaccgt ggattgacag gttctggtgt aaaagttgct    420
gtcctcgata caggtatttc cactcatcca gacttaaata ttcgtggtgg cgctagcttt    480
gtaccagggg aaccatccac tcaagatggg aatgggcatg gcacgcatgt ggcccgggacg   540 attgctgctc taaacaattc gattggcgta cttggcgtag cgccgagcgc ggaactatac    600
gctgttaaag tattaggggc gagcggtggg gcgccatca gctcgattgc ccaaggattg      660
gaatgggcag ggaacaatgg catgcacgtt gctaatttga gtttaggaag cccttcgcca    720
agtgccacac ttgagcaagc tgttaatagc gcgacttcta ggggcgttct tgttgtagcg    780
gcatctggaa attcgggtgc agactcaatc agctatccgg cccgttatgc gaacgcaatg    840
gcagtcggag ctactgacca aaacaacaac cgcgccagct tttcacagta tggcgcaggg    900
cttgacatcg tcgcaccagg tgtaaacgtg cagagcacat acccaggttc aacgtatgcc    960
agcttaaacg gtacatcgat ggctactcct catgttgcag gtgcagcagt ccttgttaaa   1020
cataagaacc catcttggtc caatgtacga atccgcgatc atctaaagaa aacggcaacg   1080
agcttaggaa gcacgaactt gtatggaagc ggacttgtca atgccgaagc tgcaactcgt   1140
taa                                                                 1143

<210> SEQ ID NO 6
<211> LENGTH: 380
<212> TYPE: PRT
<213> ORGANISM: Artificial Sequence
<220> FEATURE:
<223> OTHER INFORMATION: synthetic GG36-9 variant

<400> SEQUENCE: 6

Val Arg Ser Lys Lys Leu Trp Ile Val Ala Ser Thr Ala Leu Leu Ile
1               5                   10                  15

Ser Val Ala Phe Ser Ser Ser Ile Ala Ser Ala Ala Glu Glu Ala Lys
            20                  25                  30
```

```
Glu Lys Tyr Leu Ile Gly Phe Asn Glu Gln Glu Ala Val Ser Glu Phe
            35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
                100                 105                 110

Gln Ser Val Pro Trp Gly Ile Ser Arg Val Gln Ala Pro Ala Ala His
            115                 120                 125

Asn Arg Gly Leu Thr Gly Ser Gly Val Lys Val Ala Val Leu Asp Thr
130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
            195                 200                 205

Gly Gly Gly Ala Ile Ser Ser Ile Ala Gln Gly Leu Glu Trp Ala Gly
        210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Asp Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
                325                 330                 335

Val Leu Val Lys His Lys Asn Pro Ser Trp Ser Asn Val Arg Ile Arg
            340                 345                 350

Asp His Leu Lys Lys Thr Ala Thr Ser Leu Gly Ser Thr Asn Leu Tyr
            355                 360                 365

Gly Ser Gly Leu Val Asn Ala Glu Ala Ala Thr Arg
370                 375                 380
```

<210> SEQ ID NO 7
<211> LENGTH: 1140
<212> TYPE: DNA
<213> ORGANISM: Artificial Sequence
<220> FEATURE:
<223> OTHER INFORMATION: synthetic GG36-7 variant

<400> SEQUENCE: 7
gtgagaagca aaaaattgtg gatcgtcgcg tcgaccgcac tactcatttc tgttgctttt    60

```
agttcatcga tcgcatcggc tgctgaagaa gcaaagaaa aatatttaat tggcttttaat      120 gagcaggaag ctgtcagtga gtttgtagaa caagtagagg caaatgacga ggtcgccatt      180
ctctctgagg aagaggaagt cgaaattgaa ttgcttcatg aatttgaaac gattcctgtt      240
ttatccgttg agttaagccc agaagatgtg gacgcgcttg aactcgatcc agcgatttct      300
tatattgaag aggatgcaga agtaacgaca atggcgcaat cagtgccatg gggaattagc      360
cgtgtgcaag ccccggctgc ccataaccgt ggattgacag gttctggtgt aaaagttgct      420
gtcctcgata caggtatttc cactcatcca gacttaaata ttcgtggtgg cgctagcttt      480
gtaccagggg aaccatccac tcaagatggg aatgggcatg gcacgcatgt ggccgggacg      540
attgctgctc taaacaattc gattggcgta cttggcgtag cgccgagcgc ggaactatac      600
gctgttaaag tattaggggc gagcggtggg ggcgccatca gctcgattgc ccaaggattg      660
gaatgggcag ggaacaatgg catgcacgtt gctaatttga gtttaggaag cccttcgcca      720
agtgccacac ttgagcaagc tgttaatagc gcgacttcta ggggcgttct tgttgtagcg      780
gcatctggaa attcgggtgc agactcaatc agctatccgg cccgttatgc gaacgcaatg      840
gcagtcggag ctactgacca aaacaacaac cgcgccagct tttcacagta tggcgcaggg      900
cttgacatcg tcgcaccagg tgtaaacgtg cagagcacat acccaggttc aacgtatgcc      960
agcttaaacg gtacatcgat ggctactcct catgttgcag gtgcagcagt ccttgttaaa     1020
caaaagaacc catcttggtc caatgtacga atccgcgatc atctaaagaa tacggcaacg     1080
agcttaggaa gcacgaactt gtatggaagc ggacttgtca atgccgaagc tgcaactcgt     1140
```

<210> SEQ ID NO 8
<211> LENGTH: 380
<212> TYPE: PRT
<213> ORGANISM: Artificial Sequence
<220> FEATURE:
<223> OTHER INFORMATION: synthetic GG36-7 variant

<400> SEQUENCE: 8

```
Val Arg Ser Lys Lys Leu Trp Ile Val Ala Ser Thr Ala Leu Leu Ile
1               5                   10                  15

Ser Val Ala Phe Ser Ser Ile Ala Ser Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175
```

```
Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
        195                 200                 205

Gly Gly Gly Ala Ile Ser Ser Ile Ala Gln Gly Leu Glu Trp Ala Gly
    210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Asp Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
                325                 330                 335

Val Leu Val Lys Gln Lys Asn Pro Ser Trp Ser Asn Val Arg Ile Arg
            340                 345                 350

Asp His Leu Lys Asn Thr Ala Thr Ser Leu Gly Ser Thr Asn Leu Tyr
        355                 360                 365

Gly Ser Gly Leu Val Asn Ala Glu Ala Ala Thr Arg
    370                 375                 380

<210> SEQ ID NO 9
<211> LENGTH: 27
<212> TYPE: DNA
<213> ORGANISM: Artificial Sequence
<220> FEATURE:
<223> OTHER INFORMATION: synthetic primer

<400> SEQUENCE: 9
cgcgcttgag ctcgatccag cgatttc                                      27

<210> SEQ ID NO 10
<211> LENGTH: 25
<212> TYPE: DNA
<213> ORGANISM: Artificial Sequence
<220> FEATURE:
<223> OTHER INFORMATION: synthetic primer

<400> SEQUENCE: 10
gtctccaagc tttaacgagt tgcag                                        25

<210> SEQ ID NO 11
<211> LENGTH: 30
<212> TYPE: DNA
<213> ORGANISM: Artificial Sequence
<220> FEATURE:
<223> OTHER INFORMATION: synthetic primer

<400> SEQUENCE: 11
gcaattcaga tcttccttca ggttatgacc                                   30

<210> SEQ ID NO 12
<211> LENGTH: 30
<212> TYPE: DNA
```

<213> ORGANISM: Artificial Sequence
<220> FEATURE:
<223> OTHER INFORMATION: synthetic primer

<400> SEQUENCE: 12
gcatcgaaga tctgattgct taactgcttc                              30

<210> SEQ ID NO 13
<211> LENGTH: 54
<212> TYPE: DNA
<213> ORGANISM: Artificial Sequence
<220> FEATURE:
<223> OTHER INFORMATION: synthetic primer

<400> SEQUENCE: 13
aaagtattag gggcgagcgg tgcaggtgga cttagctcga ttgcccaagg attg    54

<210> SEQ ID NO 14
<211> LENGTH: 46
<212> TYPE: DNA
<213> ORGANISM: Artificial Sequence
<220> FEATURE:
<223> OTHER INFORMATION: synthetic primer

<400> SEQUENCE: 14
catctggaaa ttcaggtgca gaatcaatca gctatccggc ccgtta            46

<210> SEQ ID NO 15
<211> LENGTH: 45
<212> TYPE: DNA
<213> ORGANISM: Artificial Sequence
<220> FEATURE:
<223> OTHER INFORMATION: synthetic primer

<400> SEQUENCE: 15
ctgcccataa ccgtggattg gcaggttctg gtgtaaaagt tgctg              45

<210> SEQ ID NO 16
<211> LENGTH: 45
<212> TYPE: DNA
<213> ORGANISM: Artificial Sequence
<220> FEATURE:
<223> OTHER INFORMATION: synthetic primer

<400> SEQUENCE: 16
aggtgtaaac gtgcagagca cagaaccagg ttcaacgtat gccag              45

<210> SEQ ID NO 17
<211> LENGTH: 44
<212> TYPE: DNA
<213> ORGANISM: Artificial Sequence
<220> FEATURE:
<223> OTHER INFORMATION: synthetic primer

<400> SEQUENCE: 17
gaagcggact tgtcaatgca ttcgctgcaa ctcgttaaag cttg               44

<210> SEQ ID NO 18
<211> LENGTH: 48
<212> TYPE: DNA
<213> ORGANISM: Artificial Sequence
<220> FEATURE:
<223> OTHER INFORMATION: synthetic primer

<400> SEQUENCE: 18
aaagtattag gggcgagcgg tgcaggttcg gtcagctcga ttgcccaa           48

```
<210> SEQ ID NO 19
<211> LENGTH: 47
<212> TYPE: DNA
<213> ORGANISM: Artificial Sequence
<220> FEATURE:
<223> OTHER INFORMATION: synthetic primer

<400> SEQUENCE: 19
tattaggggc gagcggttca ggtggagtca gctcgattgc ccaagga        47

<210> SEQ ID NO 20
<211> LENGTH: 46
<212> TYPE: DNA
<213> ORGANISM: Artificial Sequence
<220> FEATURE:
<223> OTHER INFORMATION: synthetic primer

<400> SEQUENCE: 20
gtcagctcga ttgcccaagg agtagaatgg gcagggaaca atggca         46

<210> SEQ ID NO 21
<211> LENGTH: 48
<212> TYPE: DNA
<213> ORGANISM: Artificial Sequence
<220> FEATURE:
<223> OTHER INFORMATION: synthetic primer

<400> SEQUENCE: 21
cgttgctaat ttgagtttag gaaacccttc gccaagtgcc acacttga       48

<210> SEQ ID NO 22
<211> LENGTH: 42
<212> TYPE: DNA
<213> ORGANISM: Artificial Sequence
<220> FEATURE:
<223> OTHER INFORMATION: synthetic primer

<400> SEQUENCE: 22
gaaccatcca ctcaagatgg ggaagggcat ggcacgcatg tg             42

<210> SEQ ID NO 23
<211> LENGTH: 47
<212> TYPE: DNA
<213> ORGANISM: Artificial Sequence
<220> FEATURE:
<223> OTHER INFORMATION: synthetic primer

<400> SEQUENCE: 23
accaaaacaa caaccgcgcc gacttttcac agtatggcgc agggctt        47

<210> SEQ ID NO 24
<211> LENGTH: 23
<212> TYPE: DNA
<213> ORGANISM: Artificial Sequence
<220> FEATURE:
<223> OTHER INFORMATION: synthetic primer

<400> SEQUENCE: 24
catatgagtt atgcagtttg tag                                  23

<210> SEQ ID NO 25
<211> LENGTH: 23
<212> TYPE: DNA
<213> ORGANISM: Artificial Sequence
<220> FEATURE:
```

<223> OTHER INFORMATION: synthetic primer

<400> SEQUENCE: 25
tgtttttctt ggaattgtgc tgt                                              23

<210> SEQ ID NO 26
<211> LENGTH: 23
<212> TYPE: DNA
<213> ORGANISM: Artificial Sequence
<220> FEATURE:
<223> OTHER INFORMATION: synthetic primer

<400> SEQUENCE: 26
cagtttgtag aatgcaaaaa gtg                                              23

<210> SEQ ID NO 27
<211> LENGTH: 23
<212> TYPE: DNA
<213> ORGANISM: Artificial Sequence
<220> FEATURE:
<223> OTHER INFORMATION: synthetic primer

<400> SEQUENCE: 27
gacaaggtaa aggataaaac agc                                              23

<210> SEQ ID NO 28
<211> LENGTH: 40
<212> TYPE: DNA
<213> ORGANISM: Artificial Sequence
<220> FEATURE:
<223> OTHER INFORMATION: synthetic primer

<400> SEQUENCE: 28
cataaccgtg gattggcagg ttctggtgta aaagttgctg                            40

<210> SEQ ID NO 29
<211> LENGTH: 40
<212> TYPE: DNA
<213> ORGANISM: Artificial Sequence
<220> FEATURE:
<223> OTHER INFORMATION: synthetic primer

<400> SEQUENCE: 29
acttttacac cagaacctgc caatccacgg ttatgggcag                            40

<210> SEQ ID NO 30
<211> LENGTH: 35
<212> TYPE: DNA
<213> ORGANISM: Artificial Sequence
<220> FEATURE:
<223> OTHER INFORMATION: synthetic primer

<400> SEQUENCE: 30
cactcaagat ggggaagggc atggcacgca tgtgg                                 35

<210> SEQ ID NO 31
<211> LENGTH: 39
<212> TYPE: DNA
<213> ORGANISM: Artificial Sequence
<220> FEATURE:
<223> OTHER INFORMATION: synthetic primer

<400> SEQUENCE: 31
atgcgtgcca tgcccttccc catcttgagt ggatggttc                             39

```
<210> SEQ ID NO 32
<211> LENGTH: 39
<212> TYPE: DNA
<213> ORGANISM: Artificial Sequence
<220> FEATURE:
<223> OTHER INFORMATION: synthetic primer

<400> SEQUENCE: 32
gcgagcggtt caggtggagt cagctcgatt gcccaagga                          39

<210> SEQ ID NO 33
<211> LENGTH: 40
<212> TYPE: DNA
<213> ORGANISM: Artificial Sequence
<220> FEATURE:
<223> OTHER INFORMATION: synthetic primer

<400> SEQUENCE: 33
tgggcaatcg agctgactcc acctgaaccg ctcgcccta                          40

<210> SEQ ID NO 34
<211> LENGTH: 52
<212> TYPE: DNA
<213> ORGANISM: Artificial Sequence
<220> FEATURE:
<223> OTHER INFORMATION: synthetic primer

<400> SEQUENCE: 34
gtggagtcag ctcgattgcc caaggagtag aatgggcagg aacaatggc at            52

<210> SEQ ID NO 35
<211> LENGTH: 52
<212> TYPE: DNA
<213> ORGANISM: Artificial Sequence
<220> FEATURE:
<223> OTHER INFORMATION: synthetic primer

<400> SEQUENCE: 35
cattctactc cttgggcaat cgagctgact ccacctgaac cgctcgcccc ta           52

<210> SEQ ID NO 36
<211> LENGTH: 42
<212> TYPE: DNA
<213> ORGANISM: Artificial Sequence
<220> FEATURE:
<223> OTHER INFORMATION: synthetic primer

<400> SEQUENCE: 36
gcgagcggtg gaggtgcgat cagctcgatt gcccaaggat tg                      42

<210> SEQ ID NO 37
<211> LENGTH: 50
<212> TYPE: DNA
<213> ORGANISM: Artificial Sequence
<220> FEATURE:
<223> OTHER INFORMATION: synthetic primer

<400> SEQUENCE: 37
cttgggcaat cgagctgatc gcacctccac cgctcgcccc taatacttta              50

<210> SEQ ID NO 38
<211> LENGTH: 42
<212> TYPE: DNA
<213> ORGANISM: Artificial Sequence
<220> FEATURE:
<223> OTHER INFORMATION: synthetic primer
```

<400> SEQUENCE: 38
gcgagcggtg caggtggact tagctcgatt gcccaaggat tg                           42

<210> SEQ ID NO 39
<211> LENGTH: 50
<212> TYPE: DNA
<213> ORGANISM: Artificial Sequence
<220> FEATURE:
<223> OTHER INFORMATION: synthetic primer

<400> SEQUENCE: 39
cttgggcaat cgagctaagt ccacctgcac cgctcgcccc taatacttta                  50

<210> SEQ ID NO 40
<211> LENGTH: 40
<212> TYPE: DNA
<213> ORGANISM: Artificial Sequence
<220> FEATURE:
<223> OTHER INFORMATION: synthetic primer

<400> SEQUENCE: 40
tattaggggc gagcggtgca ggttcggtca gctcgattgc                             40

<210> SEQ ID NO 41
<211> LENGTH: 42
<212> TYPE: DNA
<213> ORGANISM: Artificial Sequence
<220> FEATURE:
<223> OTHER INFORMATION: synthetic primer

<400> SEQUENCE: 41
atcgagctga ccgaacctgc accgctcgcc cctaatactt ta                          42

<210> SEQ ID NO 42
<211> LENGTH: 41
<212> TYPE: DNA
<213> ORGANISM: Artificial Sequence
<220> FEATURE:
<223> OTHER INFORMATION: synthetic primer

<400> SEQUENCE: 42
ctaatttgag tttaggaaac ccttcgccaa gtgccacact t                           41

<210> SEQ ID NO 43
<211> LENGTH: 41
<212> TYPE: DNA
<213> ORGANISM: Artificial Sequence
<220> FEATURE:
<223> OTHER INFORMATION: synthetic primer

<400> SEQUENCE: 43
gcacttggcg aagggtttcc taaactcaaa ttagcaacgt g                           41

<210> SEQ ID NO 44
<211> LENGTH: 39
<212> TYPE: DNA
<213> ORGANISM: Artificial Sequence
<220> FEATURE:
<223> OTHER INFORMATION: synthetic primer

<400> SEQUENCE: 44
gaaattcagg tgcagactca atcagctatc cggcccgtt                              39

<210> SEQ ID NO 45
<211> LENGTH: 38

```
<212> TYPE: DNA
<213> ORGANISM: Artificial Sequence
<220> FEATURE:
<223> OTHER INFORMATION: synthetic primer

<400> SEQUENCE: 45
ggatagctga ttgagtctgc acctgaattt ccagatgc                        38

<210> SEQ ID NO 46
<211> LENGTH: 39
<212> TYPE: DNA
<213> ORGANISM: Artificial Sequence
<220> FEATURE:
<223> OTHER INFORMATION: synthetic primer

<400> SEQUENCE: 46
gaaattcagg tgcagaatca atcagctatc cggcccgtt                       39

<210> SEQ ID NO 47
<211> LENGTH: 38
<212> TYPE: DNA
<213> ORGANISM: Artificial Sequence
<220> FEATURE:
<223> OTHER INFORMATION: synthetic primer

<400> SEQUENCE: 47
ggatagctga ttgattctgc acctgaattt ccagatgc                        38

<210> SEQ ID NO 48
<211> LENGTH: 41
<212> TYPE: DNA
<213> ORGANISM: Artificial Sequence
<220> FEATURE:
<223> OTHER INFORMATION: synthetic primer

<400> SEQUENCE: 48
aacgtgcaga gcacagaacc aggttcaacg tatgccagct t                    41

<210> SEQ ID NO 49
<211> LENGTH: 40
<212> TYPE: DNA
<213> ORGANISM: Artificial Sequence
<220> FEATURE:
<223> OTHER INFORMATION: synthetic primer

<400> SEQUENCE: 49
catacgttga acctggttct gtgctctgca cgtttacacc                      40

<210> SEQ ID NO 50
<211> LENGTH: 41
<212> TYPE: DNA
<213> ORGANISM: Artificial Sequence
<220> FEATURE:
<223> OTHER INFORMATION: synthetic primer

<400> SEQUENCE: 50
tcgattgccc aaggagtaga atgggcaggg aacaatggca t                    41

<210> SEQ ID NO 51
<211> LENGTH: 43
<212> TYPE: DNA
<213> ORGANISM: Artificial Sequence
<220> FEATURE:
<223> OTHER INFORMATION: synthetic primer

<400> SEQUENCE: 51
```
cattgttccc tgcccattct actccttggg caatcgagct gac					43

<210> SEQ ID NO 52
<211> LENGTH: 4
<212> TYPE: PRT
<213> ORGANISM: Artificial Sequence
<220> FEATURE:
<223> OTHER INFORMATION: synthetic substrate

<400> SEQUENCE: 52

Ala Ala Pro Phe
1

<210> SEQ ID NO 53
<211> LENGTH: 48
<212> TYPE: DNA
<213> ORGANISM: Artificial Sequence
<220> FEATURE:
<223> OTHER INFORMATION: synthetic primer

<400> SEQUENCE: 53
gttaaagtat tagggggcgag cggtagcggc gccatcagct cgattgcc					48

<210> SEQ ID NO 54
<211> LENGTH: 48
<212> TYPE: DNA
<213> ORGANISM: Artificial Sequence
<220> FEATURE:
<223> OTHER INFORMATION: synthetic primer

<400> SEQUENCE: 54
ggcaatcgag ctgatggcgc cgctaccgct cgcccctaat actttaac					48

<210> SEQ ID NO 55
<211> LENGTH: 51
<212> TYPE: DNA
<213> ORGANISM: Artificial Sequence
<220> FEATURE:
<223> OTHER INFORMATION: synthetic primer

<400> SEQUENCE: 55
gtattagggg cgagcggtgg gggcagcatc agctcgattg cccaaggatt g					51

<210> SEQ ID NO 56
<211> LENGTH: 51
<212> TYPE: DNA
<213> ORGANISM: Artificial Sequence
<220> FEATURE:
<223> OTHER INFORMATION: synthetic primer

<400> SEQUENCE: 56
caatccttgg gcaatcgagc tgatgctgcc cccaccgctc gcccctaata c					51

<210> SEQ ID NO 57
<211> LENGTH: 44
<212> TYPE: DNA
<213> ORGANISM: Artificial Sequence
<220> FEATURE:
<223> OTHER INFORMATION: synthetic primer

<400> SEQUENCE: 57
gggcgagcgg tgggggcgcc gttagctcga ttgcccaagg attg					44

<210> SEQ ID NO 58
<211> LENGTH: 44
<212> TYPE: DNA

```
<213> ORGANISM: Artificial Sequence
<220> FEATURE:
<223> OTHER INFORMATION: synthetic primer

<400> SEQUENCE: 58
caatccttgg gcaatcgagc taacggcgcc cccaccgctc gccc                    44

<210> SEQ ID NO 59
<211> LENGTH: 45
<212> TYPE: DNA
<213> ORGANISM: Artificial Sequence
<220> FEATURE:
<223> OTHER INFORMATION: synthetic primer

<400> SEQUENCE: 59
gcatctggaa attcgggtgc aggctcaatc agctatccgg cccgt                   45

<210> SEQ ID NO 60
<211> LENGTH: 45
<212> TYPE: DNA
<213> ORGANISM: Artificial Sequence
<220> FEATURE:
<223> OTHER INFORMATION: synthetic primer

<400> SEQUENCE: 60
acgggccgga tagctgattg agcctgcacc cgaatttcca gatgc                   45

<210> SEQ ID NO 61
<211> LENGTH: 43
<212> TYPE: DNA
<213> ORGANISM: Artificial Sequence
<220> FEATURE:
<223> OTHER INFORMATION: synthetic primer

<400> SEQUENCE: 61
ctcatgttgc aggtgcagca gcacttgtta aacataagaa ccc                     43

<210> SEQ ID NO 62
<211> LENGTH: 43
<212> TYPE: DNA
<213> ORGANISM: Artificial Sequence
<220> FEATURE:
<223> OTHER INFORMATION: synthetic primer

<400> SEQUENCE: 62
gggttcttat gtttaacaag tgctgctgca cctgcaacat gag                     43

<210> SEQ ID NO 63
<211> LENGTH: 44
<212> TYPE: DNA
<213> ORGANISM: Artificial Sequence
<220> FEATURE:
<223> OTHER INFORMATION: synthetic primer

<400> SEQUENCE: 63
gtgcagcagt ccttgttaaa caaaagaacc catcttggtc caat                    44

<210> SEQ ID NO 64
<211> LENGTH: 44
<212> TYPE: DNA
<213> ORGANISM: Artificial Sequence
<220> FEATURE:
<223> OTHER INFORMATION: synthetic primer

<400> SEQUENCE: 64
attggaccaa gatgggttct tttgtttaac aaggactgct gcac                    44
```

<210> SEQ ID NO 65
<211> LENGTH: 44
<212> TYPE: DNA
<213> ORGANISM: Artificial Sequence
<220> FEATURE:
<223> OTHER INFORMATION: synthetic primer

<400> SEQUENCE: 65
ccatcttggt ccaatgtaca atccgcgat catctaaaga aaac          44

<210> SEQ ID NO 66
<211> LENGTH: 44
<212> TYPE: DNA
<213> ORGANISM: Artificial Sequence
<220> FEATURE:
<223> OTHER INFORMATION: synthetic primer

<400> SEQUENCE: 66
gttttcttta gatgatcgcg gatttgtaca ttggaccaag atgg          44

<210> SEQ ID NO 67
<211> LENGTH: 43
<212> TYPE: DNA
<213> ORGANISM: Artificial Sequence
<220> FEATURE:
<223> OTHER INFORMATION: synthetic primer

<400> SEQUENCE: 67
ggtccaatgt acgaatccgc aatcatctaa agaaaacggc aac          43

<210> SEQ ID NO 68
<211> LENGTH: 43
<212> TYPE: DNA
<213> ORGANISM: Artificial Sequence
<220> FEATURE:
<223> OTHER INFORMATION: synthetic primer

<400> SEQUENCE: 68
gttgccgttt tctttagatg attgcggatt cgtacattgg acc          43

<210> SEQ ID NO 69
<211> LENGTH: 43
<212> TYPE: DNA
<213> ORGANISM: Artificial Sequence
<220> FEATURE:
<223> OTHER INFORMATION: synthetic primer

<400> SEQUENCE: 69
gaatccgcga tcatctaaag aatacggcaa cgagcttagg aag          43

<210> SEQ ID NO 70
<211> LENGTH: 43
<212> TYPE: DNA
<213> ORGANISM: Artificial Sequence
<220> FEATURE:
<223> OTHER INFORMATION: synthetic primer

<400> SEQUENCE: 70
cttcctaagc tcgttgccgt attctttaga tgatcgcgga ttc          43

<210> SEQ ID NO 71
<211> LENGTH: 38
<212> TYPE: DNA
<213> ORGANISM: Artificial Sequence
<220> FEATURE:

<223> OTHER INFORMATION: synthetic primer

<400> SEQUENCE: 71
gtacgaatcc gcgatagact aaagaatacg gcaacgag                    38

<210> SEQ ID NO 72
<211> LENGTH: 44
<212> TYPE: DNA
<213> ORGANISM: Artificial Sequence
<220> FEATURE:
<223> OTHER INFORMATION: synthetic primer

<400> SEQUENCE: 72
gcggacttgt caatgccttt gctgcaactc gttaaagctt acat              44

<210> SEQ ID NO 73
<211> LENGTH: 41
<212> TYPE: DNA
<213> ORGANISM: Artificial Sequence
<220> FEATURE:
<223> OTHER INFORMATION: synthetic primer

<400> SEQUENCE: 73
ggaaattcgg gtgcagaatc aatcagctat ccggcccgtt a                41

<210> SEQ ID NO 74
<211> LENGTH: 38
<212> TYPE: DNA
<213> ORGANISM: Artificial Sequence
<220> FEATURE:
<223> OTHER INFORMATION: synthetic primer

<400> SEQUENCE: 74
ctggaaattc gggtgaagac tcaatcagct atccggcc                    38

<210> SEQ ID NO 75
<211> LENGTH: 51
<212> TYPE: DNA
<213> ORGANISM: Artificial Sequence
<220> FEATURE:
<223> OTHER INFORMATION: synthetic primer

<400> SEQUENCE: 75
cggcatctgg aaattcgggt gaaggctcaa tcagctatcc ggcccgttat g      51

<210> SEQ ID NO 76
<211> LENGTH: 42
<212> TYPE: DNA
<213> ORGANISM: Artificial Sequence
<220> FEATURE:
<223> OTHER INFORMATION: synthetic primer

<400> SEQUENCE: 76
cataaccgtg gattggcagg ttctggtgta aaagttgctg tc                42

<210> SEQ ID NO 77
<211> LENGTH: 38
<212> TYPE: DNA
<213> ORGANISM: Artificial Sequence
<220> FEATURE:
<223> OTHER INFORMATION: synthetic primer

<400> SEQUENCE: 77
tccactcaag atggggaagg gcatggcacg catgtggc                    38

```
<210> SEQ ID NO 78
<211> LENGTH: 42
<212> TYPE: DNA
<213> ORGANISM: Artificial Sequence
<220> FEATURE:
<223> OTHER INFORMATION: synthetic primer

<400> SEQUENCE: 78
cttgttaaac aaaagagacc atcttggtcc aatgtacgaa tc                              42

<210> SEQ ID NO 79
<211> LENGTH: 42
<212> TYPE: DNA
<213> ORGANISM: Artificial Sequence
<220> FEATURE:
<223> OTHER INFORMATION: synthetic primer

<400> SEQUENCE: 79
aatgtacgaa tccgcagaca tctaaagaat acggcaacga gc                              42

<210> SEQ ID NO 80
<211> LENGTH: 43
<212> TYPE: DNA
<213> ORGANISM: Artificial Sequence
<220> FEATURE:
<223> OTHER INFORMATION: synthetic primer

<400> SEQUENCE: 80
cgatcatcta aagaatagag caacgagctt aggaagcacg aac                             43

<210> SEQ ID NO 81
<211> LENGTH: 42
<212> TYPE: DNA
<213> ORGANISM: Artificial Sequence
<220> FEATURE:
<223> OTHER INFORMATION: synthetic primer

<400> SEQUENCE: 81
gtggattgac aggtagaggt gtaaaagttg ctgtcctcga ta                              42

<210> SEQ ID NO 82
<211> LENGTH: 43
<212> TYPE: DNA
<213> ORGANISM: Artificial Sequence
<220> FEATURE:
<223> OTHER INFORMATION: synthetic primer

<400> SEQUENCE: 82
acgattgctg ctctagataa ttcgattggc gtacttggcg tag                             43
```